US012486253B2

(12) United States Patent
Nasveschuk et al.

(10) Patent No.: US 12,486,253 B2
(45) Date of Patent: *Dec. 2, 2025

(54) THERAPEUTICS FOR THE DEGRADATION OF MUTANT BRAF

(71) Applicant: C4 THERAPEUTICS, INC., Watertown, MA (US)

(72) Inventors: Christopher G. Nasveschuk, Stoneham, MA (US); Katrina L. Jackson, Weston, MA (US); Yanke Liang, Belmont, MA (US); Martin Duplessis, Somerville, MA (US); Mark E. Fitzgerald, Newton, MA (US); Cosimo Dolente, Allschwil (CH); David Stephen Hewings, Basel (CH); Daniel Hunziker, Möhlin (CH); Daniela Krummenacher, Zurich (CH); Piergiorgio Francesco Tommaso Pettazzoni, Regensdorf (CH); Juergen Wichmann, Steinen (DE)

(73) Assignee: C4 THERAPEUTICS, INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/980,700

(22) Filed: Dec. 13, 2024

(65) Prior Publication Data

US 2025/0115580 A1 Apr. 10, 2025

Related U.S. Application Data

(63) Continuation of application No. 18/534,395, filed on Dec. 8, 2023, which is a continuation of application No. PCT/US2022/032729, filed on Jun. 8, 2022.

(60) Provisional application No. 63/277,973, filed on Nov. 10, 2021.

(30) Foreign Application Priority Data

Jun. 8, 2021 (EP) .................................... 21178145
Jun. 8, 2021 (EP) .................................... 21178150
Jun. 8, 2021 (EP) .................................... 21178152

(51) Int. Cl.

| | |
|---|---|
| ***C07D 239/72*** | (2006.01) |
| ***A61P 35/00*** | (2006.01) |
| ***C07D 401/14*** | (2006.01) |
| ***C07D 405/14*** | (2006.01) |
| ***C07D 471/10*** | (2006.01) |
| ***C07D 491/107*** | (2006.01) |
| ***C07D 495/10*** | (2006.01) |

(52) U.S. Cl.

CPC ............ *C07D 401/14* (2013.01); *A61P 35/00* (2018.01); *C07D 405/14* (2013.01); *C07D 471/10* (2013.01); *C07D 491/107* (2013.01); *C07D 495/10* (2013.01)

(58) Field of Classification Search

CPC .................................................. C07D 239/72
USPC ........................................................ 544/284
See application file for complete search history.

(56) References Cited

U.S. PATENT DOCUMENTS

| | | | |
|---|---|---|---|
| 5,635,517 | A | 6/1997 | Muller et al. |
| 6,306,663 | B1 | 10/2001 | Kenten et al. |
| 8,008,332 | B2 | 8/2011 | Cao et al. |
| 2014/0302523 | A1 | 10/2014 | Crews et al. |
| 2014/0356322 | A1 | 12/2014 | Crews et al. |
| 2015/0291562 | A1 | 10/2015 | Crew et al. |
| 2016/0022642 | A1 | 1/2016 | Crews et al. |
| 2016/0045607 | A1 | 2/2016 | Crew et al. |
| 2016/0046661 | A1 | 2/2016 | Gray et al. |
| 2016/0058872 | A1 | 3/2016 | Crew et al. |
| 2016/0176916 | A1 | 6/2016 | Bradner et al. |
| 2016/0272639 | A1 | 9/2016 | Crew et al. |
| 2018/0085465 | A1 | 3/2018 | Bradner et al. |
| 2019/0233433 | A1 | 8/2019 | Crews et al. |

FOREIGN PATENT DOCUMENTS

| | | | |
|---|---|---|---|
| WO | WO 2009/011283 | A1 | 1/2009 |
| WO | WO 2012/118492 | A1 | 9/2012 |
| WO | WO 2016/010662 | A1 | 1/2016 |
| WO | WO 2016/065139 | A1 | 4/2016 |
| WO | WO 2016/105518 | A1 | 6/2016 |
| WO | WO 2016/197032 | A1 | 12/2016 |
| WO | WO 2017/024317 | A2 | 2/2017 |
| WO | WO 2017/079267 | A1 | 5/2017 |
| WO | WO 2017/161119 | A1 | 9/2017 |
| WO | WO 2017/197046 | A1 | 11/2017 |
| WO | WO 2017/197051 | A1 | 11/2017 |
| WO | WO 2017/197055 | A1 | 11/2017 |
| WO | WO 2017/201069 | A1 | 11/2017 |

(Continued)

OTHER PUBLICATIONS

Zhifang, C. et al.: Research progress of PROTACs for neurodegenerative diseases therapy. Bioorganic Chem., vol. 147 (107386), pp. 1-14, 2024.*

(Continued)

*Primary Examiner* — Charanjit Aulakh

(74) *Attorney, Agent, or Firm* — Knowles Intellectual Property Strategies, LLC

(57) ABSTRACT

The present invention provides compounds or their pharmaceutically acceptable salts and their pharmaceutical compositions that can be administered to a host such as a human in need thereof for the treatment of a disorder, such as cancer, mediated by mutant BRAF. The compounds efficiently degrade Class I, II and III mutant BRAF proteins.

4 Claims, 20 Drawing Sheets

(56) References Cited

FOREIGN PATENT DOCUMENTS

| | | | |
|---|---|---|---|
| WO | WO 2018/118947 | A1 | 6/2018 |
| WO | WO 2018/119448 | A1 | 6/2018 |
| WO | WO 2018/144649 | A1 | 8/2018 |
| WO | WO 2018/237026 | A1 | 12/2018 |
| WO | WO 2019/060742 | A1 | 3/2019 |
| WO | WO 2019/140387 | A1 | 7/2019 |
| WO | WO 2019/199816 | A1 | 10/2019 |
| WO | WO 2020/051564 | A1 | 3/2020 |
| WO | WO 2020/142612 | A1 | 7/2020 |
| WO | WO 2020/261156 | A1 | 12/2020 |
| WO | WO 2021/250521 | A1 | 12/2021 |
| WO | WO 2022/047145 | A1 | 3/2022 |
| WO | WO 2022/129259 | A1 | 6/2022 |
| WO | WO 2022/129260 | A1 | 6/2022 |
| WO | WO 2022/258584 | A1 | 12/2022 |
| WO | WO 2022/258600 | A1 | 12/2022 |
| WO | WO 2022/258612 | A1 | 12/2022 |
| WO | WO 2023/078881 | A1 | 5/2023 |
| WO | WO 2023/105371 | A1 | 6/2023 |

OTHER PUBLICATIONS

Bartlett, et al. "The evolution of thalidomide and its IMiD derivatives as anticancer agents," Nat Rev Cancer, 4(4), 314-322, Apr. 1, 2004.

Berndsen et al. "New insights into ubiquitin E3 ligase mechanism" Nature structural & molecular biology, 21(4), 301-307, Apr. 4, 2014.

Bondeson et al. "Catalytic in vivo protein knockdown by small-molecule PROTACs" Nature Chemical Biology, 11(8), 611-617, Jun. 10, 2015.

C4 Therapeutics Presentation Phillips—"Small Molecule Driven Targeted Protein Degradation", ChemBio in the Hub 47, Cambridge, MA, 47 pages, Oct. 22, 2018.

C4 Therapeutics Presentation Fisher—"Targeted Protein Degradation", Targeted Protein Degradation Summit, Boston, MA, 39 pages, Oct. 24-25, 2018.

C4 Therapeutics Presentation Fisher—"Degrader Drugs: From cellular activity to in vivo pharmacology Discovery on Target," Boston, MA, 21 pages, Sep. 18, 2019.

C4 Therapeutics Presentation Nasveschuk—"Degrader Drug Space: What Rules?" HT-ADME Conference Cambridge, MA, 20 pages, Jun. 20, 2019.

Chamberlain et al. "Structure of the human cereblon-DDB1-lenalidomide complex reveals basis for responsiveness to thalidomide analogs" Nature Structural and Molecule Biology, 21(9), 803-809, Aug. 10, 2014.

Corson et al. "Design and applications of bifunctional small molecules: Why two heads are better than one" ACS Chemical Biology, 3(11), 677-692, Oct. 23, 2008.

Fischer et al. "Structure of the DDB1-CRBN E3 ubiquitin ligase in complex with thalidomide" Nature, 512(7512), 49-53, Jul. 16, 2014.

Fischer et al. "The Molecular Basis of CRL4DDB2/CSA Ubiquitin Ligase Architecture, Targeting, and Activation," Cell, 147:1024-1039, Nov. 23, 2011.

Li, Ren et al. "The discovery of potent and selective pyridopyrimidine-7-one based inhibitors of B-Raf$^{V600E}$ kinase" Biorganic & Medicinal Chemistry Letters, 22(10), 3387-3391, Apr. 10, 2012.

Wang, Xiaolun et al. "Conformation-Specific Effects of Raf Kinase Inhibitors" J. Med. Chem. 55(17), 7332-7341, Jul. 18, 2012.

Wenglowsky, Steve, et al. "Highly potent and selective 3-N-methylquinazoline-4 (3H)-one based inhibitors of B-Raf$^{V600E}$ kinase" Bioorganic & Medicinal Chemistry Letters 24(8), 1923-1927, Apr. 15, 2014.

International search report and written opinion for PCT/US22/32729, mailed on Sep. 6, 2022, 7 pages.

U.S. Pat. No. 11,802,131 B2, U.S. Appl. No. 16/809,336, Norcross et al., Oct. 31, 2023.

U.S. Pat. No. 12,227,504 B2, U.S. Appl. No. 18/100,992, Nasveschuk et al., Feb. 18, 2025.

US, 2023/0024096, A1, U.S. Appl. No. 17/771,204, Duplessis et al., Jan. 26, 2023.

US, 2025/0057957, A1, U.S. Appl. No. 18/774,801, Phillips et al., Feb. 20, 2025.

US, 2025/0084055, A1, U.S. Appl. No. 18/806,363, Norcross et al., Mar. 13, 2025.

US, 2025/0084081, A1, U.S. Appl. No. 18/945,284, Nasveschuk et al., Mar. 13, 2025.

US, 2025/0101037, A1, U.S. Appl. No. 18/973,867, Phillips et al., Mar. 27, 2025.

US, 2025/0121069, A1, U.S. Appl. No. 18/775,662, Phillips et al., Apr. 17, 2025.

US, 2025/0121070, A1, U.S. Appl. No. 18/979,247, Nasveschuk et al., Apr. 17, 2025.

US, 2025/0122179, A1, U.S. Appl. No. 18/972,557, Nasveschuk et al., Apr. 17, 2025.

US, 2025/0127903, A1, U.S. Appl. No. 18/774,794, Phillips et al., Apr. 24, 2025.

U.S. Appl. No. 19/053,297, Nasveschuk et al., filed Feb. 13, 2025.

U.S. Appl. No. 19/205,510, Nasveschuk et al., filed May 12, 2025.

U.S. Appl. No. 19/224,081, Yu et al., filed May 30, 2025.

Han, X.-R. et al. "Discovery of Selective Small Molecule Degraders of BRAF-V600E." J. Med. Chem. vol. 63, 8, pp. 4069-4080, Mar. 30, 2020.

U.S. Pat. No. 11,802,131 A1, U.S. Appl. No. 16/809,336, Norcross et al., Mar. 4, 2020.

U.S. Pat. No. 10,646,575 B2, U.S. Appl. No. 16/186,339, Phillips et al., May 12, 2020.

U.S. Pat. No. 10,660,968 B2, U.S. Appl. No. 16/186,334, Phillips et al., May 26, 2020.

U.S. Pat. No. 10,849,982 B2, U.S. Appl. No. 16/186,341, Phillips et al., Dec. 1, 2020.

U.S. Pat. No. 10,905,768 B1, U.S. Appl. No. 16/872,225, Phillips et al., Feb. 2, 2021.

U.S. Pat. No. 11,185,592 B2, U.S. Appl. No. 16/882,236, Phillips et al., Nov. 30, 2021.

U.S. Pat. No. 11,254,672 B2, U.S. Appl. No. 16/809,325, Norcross et al., Feb. 22, 2022.

U.S. Pat. No. 11,401,256 B2, U.S. Appl. No. 16/809,345, Norcross et al., Jul. 13, 2022.

U.S. Pat. No. 11,407,732 B1, U.S. Appl. No. 17/498,617, Henderson et al., Aug. 9, 2022.

U.S. Pat. No. 11,459,335 B2, U.S. Appl. No. 16/721,650, Phillips et al., Sep. 14, 2022.

U.S. Pat. No. 11,524,949 B2, U.S. Appl. No. 16/874,475, Phillips et al., Dec. 13, 2022.

U.S. Pat. No. 11,584,748 B2, U.S. Appl. No. 17/072,896, Nasveschuk et al., Feb. 1, 2023.

U.S. Pat. No. 11,623,929 B2, U.S. Appl. No. 17/103,621, Nasveschuk et al., Mar. 22, 2023.

U.S. Pat. No. 11,673,902 B2, U.S. Appl. No. 17/843,769, Nasveschuk et al., Jun. 13, 2023.

U.S. Pat. No. 11,691,972 B2, U.S. Appl. No. 17/541,035, Nasveschuk et al., Jul. 4, 2023.

U.S. Pat. No. 11,787,802 B2, U.S. Appl. No. 17/576,582, Norcross et al., Oct. 17, 2023.

U.S. Pat. No. 11,753,397 A1, U.S. Appl. No. 17/031,550, Henderson et al., Aug. 23, 2023.

U.S. Pat. No. 11,992,531 B2, U.S. Appl. No. 17/107,781, Phillips et al., May 28, 2024.

U.S. Pat. No. 12,048,747 B2, U.S. Appl. No. 17/121,389, Phillips et al., Jul. 30, 2024.

U.S. Pat. No. 12,048,748 B2, U.S. Appl. No. 17/524,558, Phillips et al., Jul. 30, 2024.

U.S. Pat. No. 12,049,464 B2, U.S. Appl. No. 17/901,775, Nasveschuk et al., Jul. 30, 2024.

U.S. Pat. No. 12,076,405 B2, U.S. Appl. No. 17/164,446, Phillips et al., Sep. 3, 2024.

U.S. Pat. No. 12,091,397 B2, U.S. Appl. No. 17/878,753, Norcross et al., Sep. 17, 2024.

(56) References Cited

OTHER PUBLICATIONS

U.S. Pat. No. 12,157,735 B2, U.S. Appl. No. 17/965,569, Nasveschuk et al., Dec. 3, 2024.
U.S. Pat. No. 12,180,225 B2, U.S. Appl. No. 17/959,144, Phillips et al., Dec. 31, 2024.
US, 2022/0372016, A1, U.S. Appl. No. 17/351,935, Phillips et al., Nov. 24, 2022.
US, 2023/0019060, A1, U.S. Appl. No. 17/465,583, Nasveschuk et al., Jan. 19, 2023.
US, 2023/0082430, A1, U.S. Appl. No. 17/723,199, Henderson et al., Mar. 16, 2023.
US, 2023/0145336, A1, U.S. Appl. No. 18/084,380, Nasveschuk et al., May 11, 2023.
US, 2023/0190760, A1, U.S. Appl. No. 18/106,893, Proia et al., Jun. 22, 2023.
US, 2023/0233692, A1, U.S. Appl. No. 18/105,735, Henderson et al., Jul. 27, 2023.
US, 2023/0339902, A1, U.S. Appl. No. 18/134,985, Nasveschuk et al., Oct. 26, 2023.
US, 2023/0357180, A1, U.S. Appl. No. 18/079,815, Phillips et al., Nov. 9, 2023.
US, 2023/0372496, A1, U.S. Appl. No. 18/134,971, Nasveschuk et al., Nov. 23, 2023.
US, 2023/0416251, A1, U.S. Appl. No. 18/100,992, Nasveschuk et al., Dec. 28, 2023.
US, 2024/0018118, A1, U.S. Appl. No. 18/134,990, Nasveschuk et al., Jan. 18, 2024.
US, 2024/0018156, A1, U.S. Appl. No. 18/117,978, Nasveschuk et al., Jan. 18, 2024.
US, 2024/0076300, A1, U.S. Appl. No. 18/144,800, Nasveschuk et al., Mar. 7, 2024.
US, 2024/0109889, A1, U.S. Appl. No. 18/370,186, Norcross et al., Apr. 4, 2024.
US, 2024/0158418, A1, U.S. Appl. No. 18/516,589, Nasveschuk et al., May 16, 2024.
US, 2024/0199581, A1, U.S. Appl. No. 18/534,965, Nasveschuk et al., Dec. 8, 2023.
US, 2024/0199638, A1, U.S. Appl. No. 18/385,277, Norcross et al., Jun. 20, 2024.
US, 2024/0245677, A1, U.S. Appl. No. 18/600,097, Jackson et al., Jul. 25, 2024.
US, 2024/0391912, A1, U.S. Appl. No. 18/797,261, Henderson et al., Nov. 28, 2024.
US, 2024/0398959, A1, U.S. Appl. No. 18/642,602, Phillips et al., Dec. 5, 2024.
U.S. Appl. No. 18/240,231, Henderson et al., filed Aug. 30, 2023.
U.S. Appl. No. 18/774,794, Phillips et al., filed Jul. 16, 2024.
U.S. Appl. No. 18/774,801, Phillips et al., filed Jul. 16, 2024.
U.S. Appl. No. 18/775,662, Phillips et al., filed Jul. 17, 2024.
U.S. Appl. No. 18/806,363, Norcross et al., filed Aug. 15, 2024.
U.S. Appl. No. 18/945,284, Nasveschuk et al., filed Nov. 12, 2024.
U.S. Appl. No. 18/972,557, Nasveschuk et al., filed Dec. 6, 2024.
U.S. Appl. No. 18/973,867, Phillips et al., filed Dec. 9, 2024.
U.S. Appl. No. 18/979,247, Nasveschuk et al., filed Dec. 12, 2024.

* cited by examiner 1000 nM Compound 157

THERAPEUTICS FOR THE DEGRADATION OF MUTANT BRAF

CROSS-REFERENCE TO RELATED APPLICATIONS

This application is a continuation of U.S. patent application Ser. No. 18/534,395, filed on Dec. 8, 2023, which is a continuation of International Patent Application No. PCT/US2022/032729, filed in the U.S. Receiving Office on Jun. 8, 2022, which claims the benefit of European Patent Applications EP21178145.5, EP21178150.5, and EP21178152.1 each of which was filed Jun. 8, 2021, and U.S. Provisional Application 63/277,973, filed Nov. 10, 2021. The entirety of each of these applications is incorporated herein by reference for all purposes.

FIELD OF THE INVENTION

The present invention provides compounds and their pharmaceutically acceptable salts, uses, compositions and manufacture that degrade mutant BRAF, such as Class I, Class II, and/or Class III mutant BRAF. The compounds of the present invention can be administered to a host such as a human in need thereof for the therapeutic and/or prophylactic treatment of a disorder, such as cancer, mediated by mutant BRAF.

BACKGROUND

BRAF is a serine/threonine protein kinase that is a member of the signal transduction protein kinases. BRAF plays a critical role in the MAPK signaling pathway and is mutated in approximately 8% of all human cancers including melanoma (~60%), thyroid (~60%), and lung adenocarcinoma (~10%). BRAF mutations are also observed in thyroid cancer, colorectal cancer, lung cancer and others. The most common mutation in BRAF is V600E (Class I), which occurs in half of malignant melanomas. This mutation hyperactivates ERK and signals as a RAF inhibitor-sensitive monomer. Other common activating mutations include Class II mutations such as G469A and Class III mutations such as G466V. Class II and III mutations activate ERK by promoting RAF homo- or hetero-dimerization.

Despite the therapeutic benefits of available BRAF inhibitors, the duration of the antitumor response to these drugs can be limited by the acquisition of drug resistance.

The BRAF protein presents a mechanism for signaling propagation that requires protein homo-dimerization (BRAF-BRAF) or hetero-dimerization with other RAF proteins (BRAF-RAF1 or BRAF-ARAF). When BRAF is mutated, as observed in oncology indications with BRAF V600E/K substitution, BRAF signaling becomes independent of homodimers and/or heterodimers. The kinase activity becomes hyperactivated as a monomeric protein and drives cellular proliferative signals.

Several BRAF inhibitors have been described that can inhibit monomeric BRAF but not dimeric BRAF including vemurafenib, dabrafenib, and encorafenib, however, resistance usually emerges within a year, including RAS mutation, BRAFV600E amplification, and BRAFV600E intragenic deletion or splice variants. These inhibitors are also ineffective against non-V600 BRAF mutants (Class II & III) that activate ERK by promoting RAF homo- or hetero-dimerization.

Examples of BRAF inhibitors are described in WO2021/116055 and WO2021/116050.

Non-limiting examples of BRAF degrading compounds include those described in WO2018/119448, WO2019/199816, WO2020/051564, and WO2022/047145.

Despite these efforts there remains a need for new therapeutic drugs to treat BRAF mediated cancers, and in particular drugs that treat mutant BRAF mediated cancers.

SUMMARY

The present invention provides compounds and their pharmaceutically acceptable salts, uses, compositions, and manufacture that degrade mutant BRAF, for example a Class I, Class II, and/or Class III mutant BRAF, via the ubiquitin proteasome pathway. The compounds presented herein do not significantly degrade wild-type BRAF. These compounds bind to the ubiquitously expressed E3 ligase protein cereblon (CRBN) and alter the substrate specificity of the CRBN E3 ubiquitin ligase complex, resulting in the recruitment and ubiquitination of mutant BRAF, such as for example BRAF V600. The present compounds are also binders of WT BRAF, RAF1 and ARAF, however more effective targeted degradation is triggered by these compounds for mutant BRAF, such as for example Class I mutant BRAF such as V600E, Class II mutant BRAF such as G469A, Class III mutant BRAF such as G466V mutations, and splice variants such as p61-$BRAF^{V600E}$ (see Example 231).

By degrading mutant BRAF a compound of the present invention can be used to treat a mutant BRAF mediated cancer, for example melanoma, lung cancer including for example non-small cell lung cancer, colorectal cancer including for example microsatellite stable colorectal cancer, thyroid cancer including for example anaplastic thyroid cancer, or ovarian cancer. In certain embodiments a compound of the present invention is used to treat a solid tumor that is mediated by a V600X mutant BRAF. Additional non-limiting examples of disorders that can be treated with the compounds of the present invention include melanoma, non-small cell lung carcinoma, thyroid cancer, colorectal cancer, and other solid tumor malignancies that have a mutant BRAF driver.

In certain embodiments a compound of the present invention, for example Compound 157, has more than about 10-, 100-, or even 1000-fold selectivity for the degradation of mutant BRAF over WT BRAF, KRAS, and/or CRAF (See Example 234). For example, in A375 cells, Compound 157 potently degrades $BRAF^{V600E}$ ($E_{max}$=26% (i.e., 74% of BRAF protein degraded); $DC_{50}$=14 nM at 24 hr), inhibits ERK phosphorylation ($IC_{50}$=11 nM at 24 hr) and cell growth ($GI_{50}$=94 nM at 96 hr) while having no effect in the mutant KRAS driven cell line HCT-116 (see Examples 235 and 236). In A375 xenografts, oral delivery of Compound 157 was more efficacious than a clinically relevant dose of encorafenib and gave profound tumor regressions when dosed at 10 mg/kg BID (see Example 241).

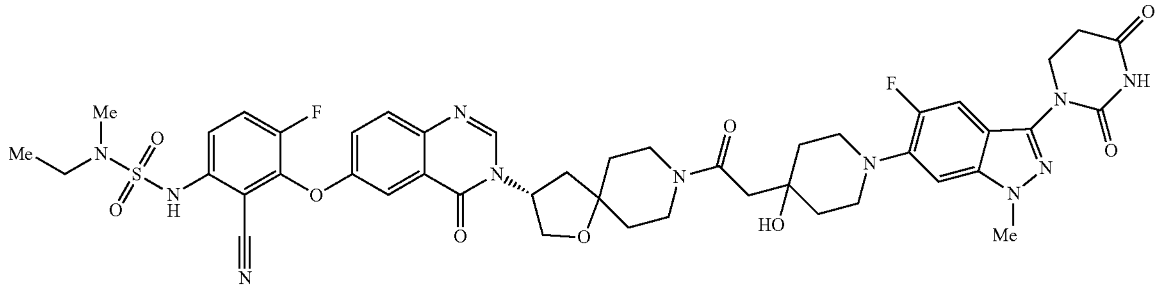 [SMILES: CCN(C)S(=O)(=O)Nc1ccc(F)c(Oc2ccc3ncn([C@H]4COC5(CCN(C(=O)CC6(O)CCN(c7cc8c(cc7F)c(N7CCC(=O)NC7=O)nn8C)CC6)CC5)C4)c(=O)c3c2)c1C#N]

Compound 157/Example 157

A compound of the present invention can be used to treat difficult to treat double mutant cancers wherein one mutation is in BRAF. For example, Compound 157 was much more effective than encorafenib at degrading BRAF in an engineered A375-BRAF$^{V600E}$/NRAS$^{Q61K}$ double mutant model of BRAF inhibitor resistance (see Examples 231 and 241). In this model, in vivo dosing of single agent Compound 157 caused robust tumor growth inhibition and in combination with the MEK inhibitor, trametinib, gave tumor regressions. The combination of encorafenib and trametinib showed no activity in the same model. In certain embodiments a compound of the present invention can be used to degrade BRAF mutants of Class I, Class II, Class III, and splice variants thereof. For example, Compound 157 is able to degrade additional BRAF mutant proteins including G469A (Class II), G466V (Class III), and the p61-BRAF$^{V600E}$ splice variant using heterologous expression in HEK293T cells.

In certain embodiments a compound of the present invention can treat a cancer that has developed resistance to a BRAF inhibitor. For example, Compound 157 is effective in the treatment of a G466V mutant BRAF lung tumor cell line in which encorafenib has no activity (see Example 231). In certain embodiments a compound of the present invention, for example Compound 157, is orally bioavailable.

In certain aspects, a compound of Formula I or Formula II, for example Compound 157, is provided.

(I)

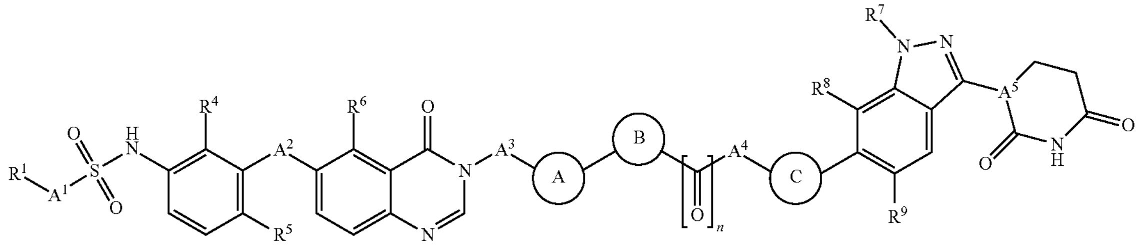

(II)

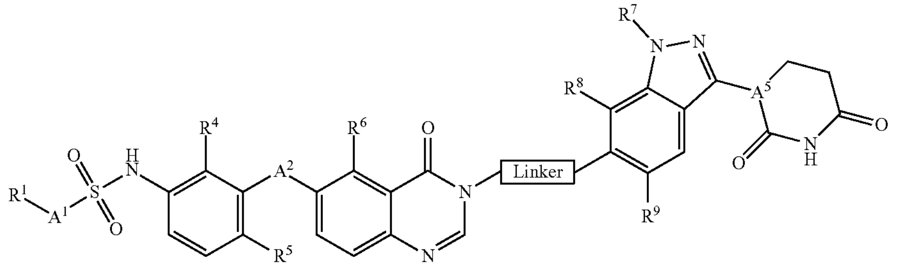

or a pharmaceutically acceptable salt thereof.

In other aspects, a compound of Formula III, Formula IV, Formula V, or Formula VI is provided.

(III)

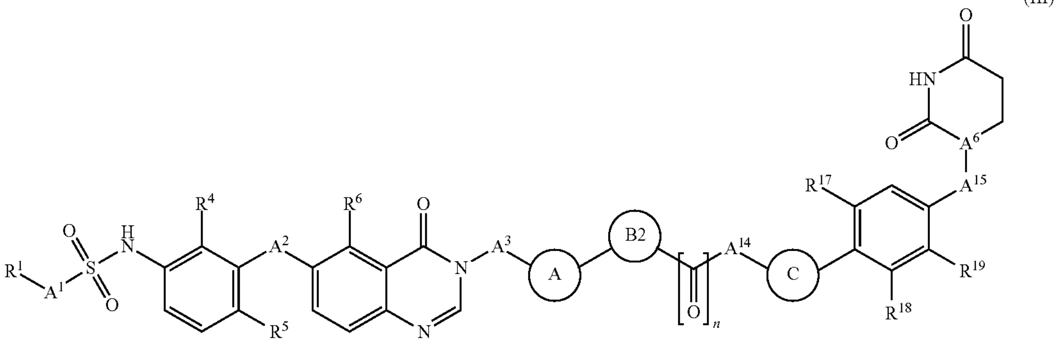

-continued (IV)

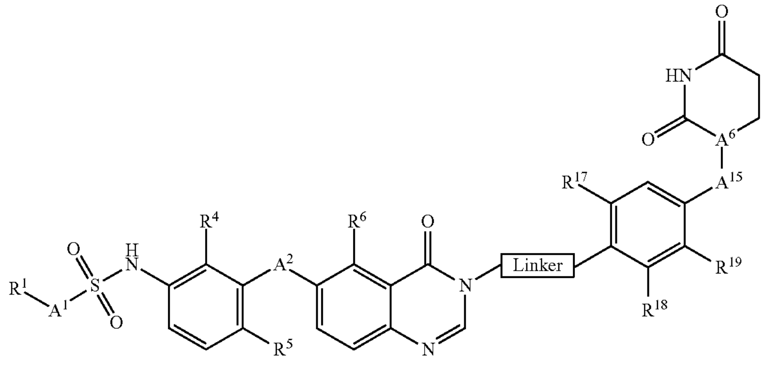

(V)

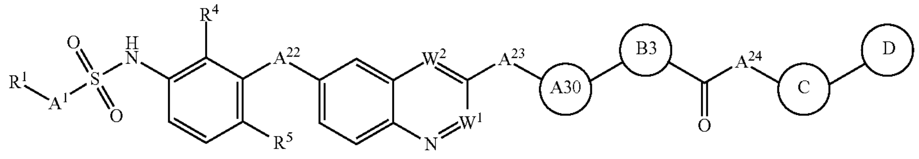

(VI)

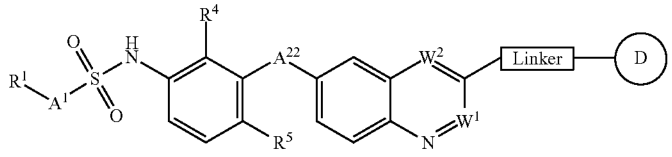

or a pharmaceutically acceptable salt thereof.

wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen (for example F), alkyl, cycloalkyl and alkoxy;

$R^4$ is selected from hydrogen, alkyl, cyano and halogen (for example F);

$R^5$ is selected from hydrogen, alkyl, cyano and halogen (for example F);

$A^2$ is selected from —O—, —NH— and —(C═O)—;

$A^{22}$ is selected from —O—, and —NH—;

$W^1$ is selected from —N— and —CH—;

$W^2$ is selected from —N—, and —$CR^{26}$—;

$R^6$ is selected from hydrogen, halogen (for example F), hydroxy, amino, dialkylamino, alkoxy, alkyl and alkoxyalkyl;

$R^{26}$ is selected from hydrogen, halogen, hydroxy, amino, alkoxy and alkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

$A^{23}$ is selected from a bond, —O— and —$CH_2$—;

A is selected from a bond, pyrimidinyl, pyridinyl, pyrazolyl and 3-azabicyclo[3.1.0]hexyl;

A30 is selected from a bond, —$CH_2$—, pyrimidinyl, pyridinyl, pyrazolyl and 3-azabicyclo[3.1.0]hexyl;

B is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, and 8-azaspiro[4.5]decyl; wherein B is optionally substituted with one or two substituents independently selected from halogen, alkyl and alkoxy;

B2 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl; wherein B2 is optionally substituted with one or two substituents independently selected from halogen, alkyl and alkoxy;

B3 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl and 8-azaspiro[4.5]decyl;

n is 0 or 1;

$A^4$ is selected from a bond, —$CH_2$—, —$(SO_2)$—$CH_2$—, —$CH(CH_2OH)$—, —NH— and —O—;

$A^{14}$ is selected from a bond, —$CH_2$—, —$CH_2$—$CH_2$—, —$CH(CH_2OH)$—, —NH—, —O—, cycloalkyl and alkylamino;

C is selected from azepanyl, azetidinyl, cycloalkyl, piperazinyl and piperidinyl; wherein C is optionally substituted with one or two substituents independently selected from halogen (for example F), hydroxy, alkyl and alkoxy;

D is selected from

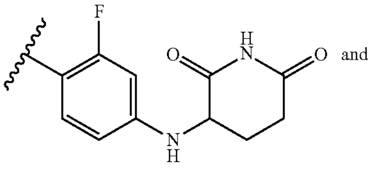

and

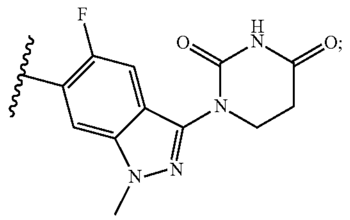

$R^7$ is selected from hydrogen, alkyl, cyano, halogen (for example F) and alkoxy;

$R^8$ is selected from hydrogen, alkyl, cyano, halogen (for example F), and alkoxy;

$R^9$ is selected from hydrogen, alkyl, cyano, halogen (for example F) and alkoxy;

$R^{17}$ is selected from hydrogen, alkyl, cyano, hydroxy, cycloalkyl, halogen and alkoxy;

$R^{18}$ is selected from hydrogen, alkyl, cyano, hydroxy, cycloalkyl, halogen and alkoxy;

$R^{19}$ is selected from hydrogen, alkyl, cyano, hydroxy, cycloalkyl, halogen and alkoxy;

$A^5$ is —CH— or —N—;

$A^{15}$ is selected from a bond, —O— and —NH—;

$A^6$ is —CH— or —N—; and

Linker is a bivalent chemical group.

In certain embodiments Linker is selected from

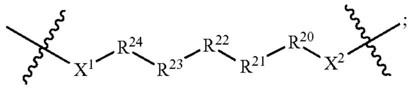

wherein:

$X^1$ and $X^2$ are independently at each occurrence selected from bond, heterocycle, $NR^2$, $C(R^2)_2$, O, C(O), and S;

$R^{20}$, $R^{21}$, $R^{22}$, $R^{23}$, and $R^{24}$ are independently at each occurrence selected from the group consisting of bivalent moieties selected from bond alkyl, —C(O)—, —C(O)O—, —OC(O)—, —$SO_2$—, —S(O)—, —C(S)—, —C(O)$NR^2$—, —$NR^2$C(O)—, —O—, —S—, —$NR^2$—, —C($R^{40}R^{40}$)—, —P(O)($OR^{36}$)O—, —P(O)($OR^{36}$)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;

$R^{36}$ is independently at each occurrence selected from the group consisting of hydrogen, alkyl, arylalkyl, heteroarylalkyl, alkene, alkyne, aryl, heteroaryl, heterocycle, aliphatic and heteroaliphatic; and $R^{40}$ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)$_2$, —$NHSO_2$(aliphatic, including alkyl), —N(aliphatic, including alkyl)$SO_2$alkyl, —$NHSO_2$(aryl, heteroaryl or heterocycle), —N(alkyl)$SO_2$(aryl, heteroaryl or heterocycle), —$NHSO_2$alkenyl, —N(alkyl)$SO_2$alkenyl, —$NHSO_2$alkynyl, —N(alkyl)$SO_2$alkynyl, haloalkyl, aliphatic, heteroaliphatic, aryl, heteroaryl, heterocycle, and cycloalkyl.

In certain embodiments Linker is

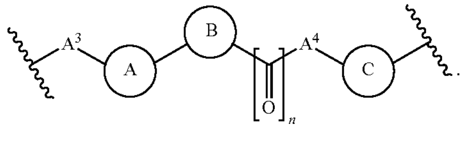

Non-limiting examples of Compounds of Formula I and Formula II include:

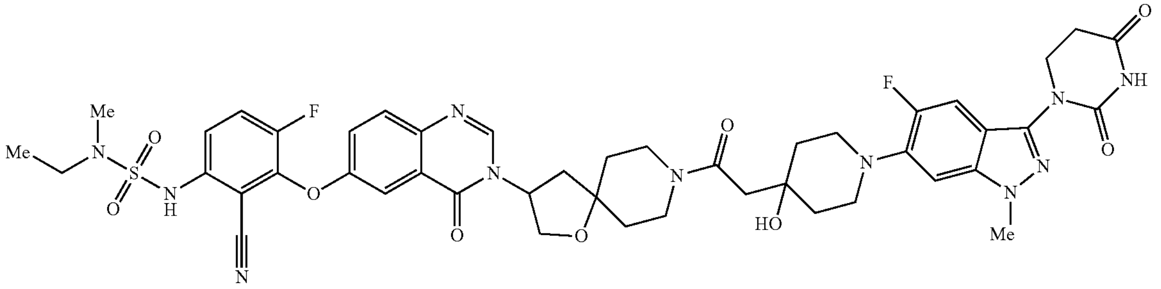

-continued

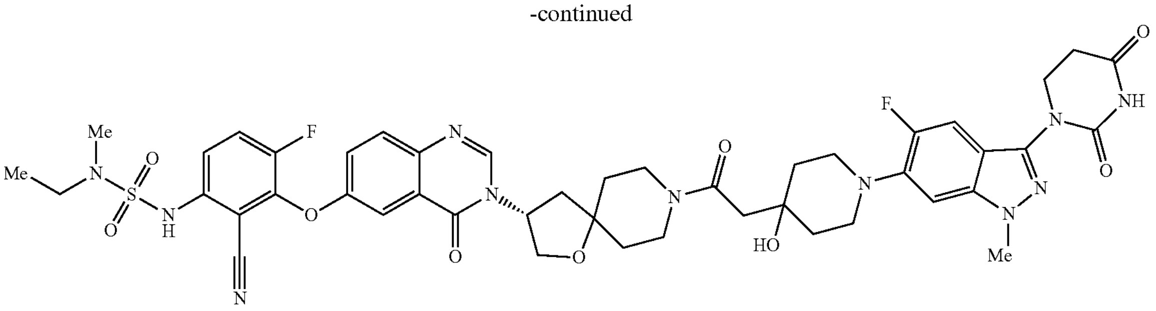

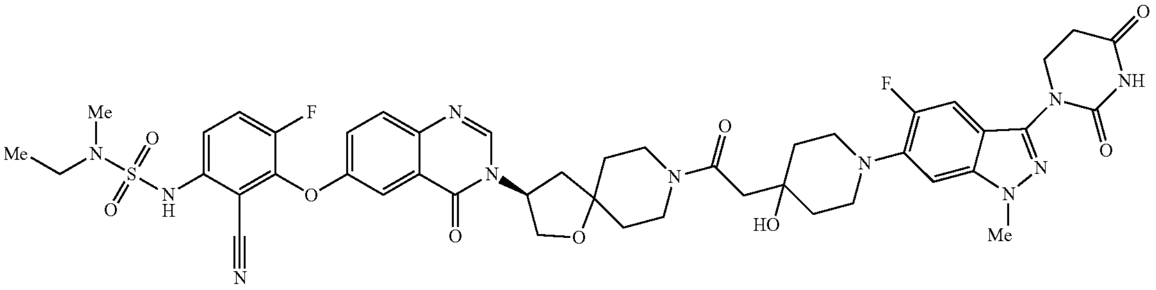

or a pharmaceutically acceptable salt thereof.

The present invention provides compounds that specifically degrade mutant BRAF, such as BRAF presenting with the mutation V600E, via the targeted ubiquitination of the BRAF protein and subsequent proteasomal degradation. The present compounds bind to the ubiquitously expressed E3 ligase protein cereblon (CRBN) and alter the substrate specificity of the CRBN E3 ubiquitin ligase complex, resulting in the recruitment and ubiquitination of mutant BRAF, such as BRAF V600E. The present compounds are also effective binders of WT BRAF, RAF1 and ARAF, however effective targeted degradation is triggered by these compounds for mutant BRAF, such as BRAF V600E.

In certain aspects, a compound of the present invention is used to treat a BRAF mediated cancer, wherein the BRAF has mutated from the wild type. There are a number of possibilities for BRAF mutations. In certain non-limiting embodiments, the mutation is a Class I mutation, a Class II mutation, or a Class III mutation, or any combination thereof. Non-limiting examples of Class I mutations include V600 mutations such as V600E, V600K, V600R, V600D, and V600N. Non-limiting examples of Class II mutations include G469A, G469V, G469L, G469R, L597Q, and K601E. Non-limiting examples of Class III mutations include G466A, G466E, G466R, G466V, S467L, G469E, N581I, D594E, D594G, and D594N.

In certain embodiments a compound of the present invention treats a BRAF mutant mediated disorder wherein the mutation is not a Class I, Class II, or Class III mutation. Non-limiting examples of mutations include G464I, G464R, N581T, L584F, E586K, G593D, G596C, L597R, L597S, S605I, S607F, N684T, E26A, V130M, L745L, and D284E.

In certain embodiments a compound of the present invention treats a BRAF mutant mediated disorder wherein the mutation is a splice variant, for example p61-BRAF$^{V600E}$In certain embodiments a compound of the present invention is used to treat a disorder that is mediated by two or more mutant proteins, for example a cancer mediated by a BRAF$^{V600E}$/NRAS$^{Q61K}$ double mutant.

In certain embodiments, a compound of the present invention is used to treat a cancer that is resistant to at least one BRAF inhibitor, for example a cancer that is resistant to or has acquired resistance to a BRAF inhibitor selected from dabrafenib, trametinib, vemurafenib, and encorafenib.

In certain embodiments a compound described herein is used to treat a cancer that has developed an escape mutation such as BRAF V600E/NRAS$^{Q61K}$ double mutant cancer.

In certain embodiments a compound described herein is used to treat melanoma.

In certain embodiments, a selected compound of the present invention provides an improved efficacy and/or safety profile relative to at least one known BRAF inhibitor. For example, a degrader of the present invention has the efficiency of an inhibitor only protein binding moiety combined with the catalytic degradation activity of the cereblon-activated proteasomal degradation. This provides rapid activity against the mutant BRAF mediated cancer by an active moiety that can quickly "return to action" and repeat the catalytic function. In this way, BRAF is quickly destroyed as done with a covalent suicide inhibitor, but without at the same time destroying the active drug.

In certain embodiments, the degrader compound of the present invention has one or more advantages in the treatment of a BRAF mediated disorder than using an enzyme inhibitor only.

In certain embodiments, less by mole of the compounds described herein is needed for the treatment of a BRAF mediated disorder, than by mole of the BRAF Targeting Ligand portion alone.

In certain embodiments, the compound of the present invention has less of at least one side-effect in the treatment of a BRAF mediated disorder, than by mole of the BRAF Targeting Ligand portion alone.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for inhibiting or preventing a disorder mediated by BRAF or for modulating or decreasing the amount of BRAF.

Another aspect of the present invention provides a compound as described herein, or an enantiomer, diastereomer, or stereoisomer thereof, or pharmaceutically acceptable salt, hydrate, or solvate thereof, or its pharmaceutical composition, for use in the manufacture of a medicament for treating or preventing a disease mediated by BRAF.

In certain embodiments, a selected compound as described herein is useful to treat a disorder comprising an abnormal cellular proliferation, such as a tumor or cancer, wherein BRAF is an oncogenic protein or a signaling mediator of the abnormal cellular proliferative pathway and its degradation decreases abnormal cell growth.

In certain embodiments, a compound of the present invention has at least one desired isotopic substitution of an atom, at an amount above the natural abundance of the isotope, i.e., enriched.

In certain embodiments, a compound of the present invention includes a deuterium atom or multiple deuterium atoms.

In certain embodiments a compound of the present invention is useful for the therapeutic and/or prophylactic treatment of cancer.

In certain aspects a compound of the present invention is used in combination with a second active agent described herein to treat a mutant BRAF mediated cancer. Non-limiting examples of classes of molecules that can be used in combination with a compound of the present invention include MEK inhibitors, immune checkpoint inhibitors, and EGFR antibodies. In certain embodiments a compound of the present invention is used in combination with trametinib for the treatment of a mutant BRAF mediated cancer, for example melanoma or non-small cell lung cancer. In certain embodiments a compound of the present invention is used in combination with an immune checkpoint inhibitor to treat a mutant BRAF mediated cancer. In certain embodiments a compound of the present invention is used in combination with cetuximab or panitumumab to treat a mutant BRAF mediated cancer, for example colorectal cancer. In certain embodiments a compound of the present invention is used in combination with nivolumab, pembrolizumab, cemiplimab, ipilimumab, relatlimab, atezolizumab, avelumab, or durvalumab to treat a mutant BRAF mediated cancer, for example colorectal cancer, melanoma, or non-small cell lung cancer.

In other aspects a compound of the present invention is used in combination with two or more additional active agents described herein to treat a mutant BRAF mediated cancer. In certain embodiments a compound described herein is used in combination with a MEK inhibitor and an immune checkpoint inhibitor to treat melanoma or non-small cell lung cancer.

Other features and advantages of the present application will be apparent from the following detailed description.

The present invention thus includes at least the following features:

(a) A compound of Formula I, Formula II, Formula III, Formula IV, Formula V, or Formula VI or a pharmaceutically acceptable salt or isotopic derivative (including a deuterated derivative) thereof;

(b) A method for treating a mutant BRAF mediated disorder, such as an abnormal cellular proliferation, including cancer, comprising administering an effective amount of a compound of Formula I, Formula II, Formula III, Formula IV, Formula V, or Formula VI, or pharmaceutically acceptable salt thereof, as described herein, to a patient in need thereof;

(c) A compound of Formula I, Formula II, Formula III, Formula IV, Formula V, or Formula VI, or a pharmaceutically acceptable salt, or isotopic derivative (including a deuterated derivative) thereof for use in the treatment of a disorder that is mediated by mutant BRAF, for example an abnormal cellular proliferation such as a tumor or cancer;

(d) Use of a compound of Formula I, Formula II, Formula III, Formula IV, Formula V, or Formula VI, or a pharmaceutically acceptable salt thereof, in an effective amount in the treatment of a patient in need thereof, typically a human, with a mutant BRAF mediated disorder, for example an abnormal cellular proliferation such as a tumor or cancer;

(e) Use of a compound of Formula I, Formula II, Formula III, Formula IV, Formula V, or Formula VI, or a pharmaceutically acceptable salt or isotopic derivative (including a deuterated derivative) thereof in the manufacture of a medicament for the treatment of a mutant BRAF mediated disorder, for example an abnormal cellular proliferation such as a tumor or cancer;

(f) Use of a compound of Formula I, Formula II, Formula III, Formula IV, Formula V, or Formula VI, or a pharmaceutically acceptable salt thereof, in an effective amount in the treatment of a patient in need thereof, typically a human, with a mutant BRAF mediated disorder, for example an abnormal cellular proliferation such as a tumor or cancer;

(g) A pharmaceutical composition comprising an effective patient-treating amount of a compound of Formula I, Formula II, Formula III, Formula IV, Formula V, or Formula VI, or a pharmaceutically acceptable salt, isotopic derivative thereof; and optionally a pharmaceutically acceptable carrier or diluent;

(h) A compound of Formula I, Formula II, Formula III, Formula IV, Formula V, or Formula VI, as described herein as a mixture of enantiomers or diastereomers (as relevant), including as a racemate;

(i) A compound of Formula I, Formula II, Formula III, Formula IV, Formula V, or Formula VI, as described herein in enantiomerically or diastereomerically (as relevant) enriched form, including an isolated enantiomer or diastereomer (i.e., about greater than 85, 90, 95, 97, or 99% pure); and (j) A process for the preparation of therapeutic products that contain an effective amount of a compound of Formula I, Formula II, Formula III, Formula IV, Formula V, or Formula VI, or a pharmaceutically acceptable salt thereof, as described herein.

BRIEF DESCRIPTION OF THE DRAWINGS

As used in the drawings Compound 157 and Example 157 both refer to

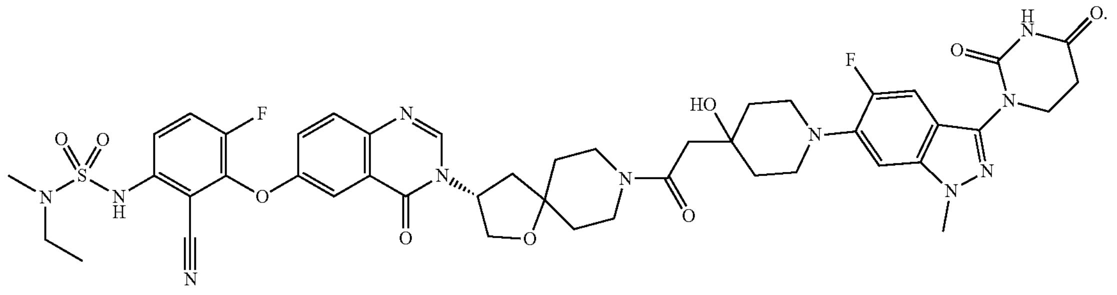 [SMILES: CCN(C)S(=O)(=O)Nc1ccc(F)c(Oc2ccc3ncn([C@H]4COC5(CCN(C(=O)CC6(O)CCN(c7cc8c(cc7F)c(N7CCC(=O)NC7=O)nn8C)CC6)CC5)C4)c(=O)c3c2)c1C#N]

Compound 157 was referred to as Compound 14/Example 14 in U.S. Provisional Application 63/277,973 and European Patent Application 21178150.5.

Figure 1:
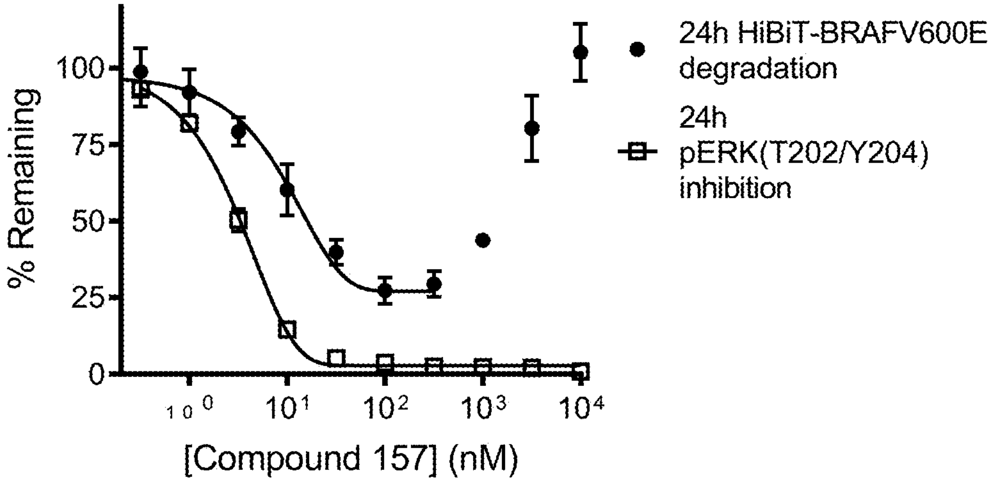

FIG. 1 is a line graph showing HiBiT-BRAF$^{V600E}$ protein levels after 24 hours of treatment with Compound 157. Compound 157 has a $DC_{50}$ of ~100 nM and has a degradation $E_{max}$ of ~25% with concomitant loss of phospho-ERK (pERK), demonstrating blockade of the MAPK pathway with an $IC_{50}$<5 nM. The y-axis is protein remaining measured in %. The x-axis is concentration of Compound 157 measured in nanomolar. The experimental procedures are provided in Example 229 and Example 230.

Figure 2:
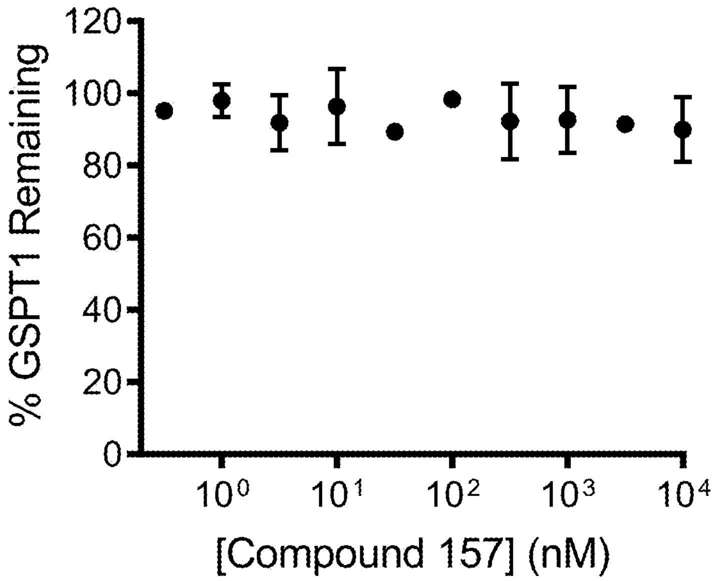

FIG. 2 is a line graph showing steady GSPT1 protein levels after treatment with various concentrations of Compound 157. The y-axis is protein remaining measured in %. The x-axis is concentration of Compound 157 measured in nanomolar. The experimental procedure is provided in Example 229.

Figure 3:
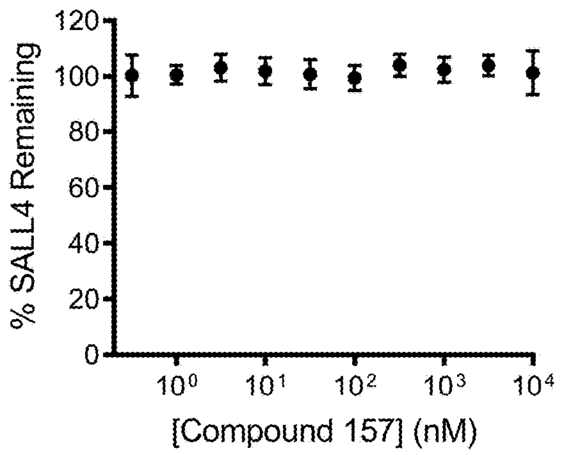

FIG. 3 is a line graph showing steady SALL4 protein levels after treatment with various concentrations of Compound 157. The y-axis is protein remaining measured in %. The x-axis is concentration of Compound 157 measured in nanomolar. The experimental procedure is provided in Example 229.

Figure 4:
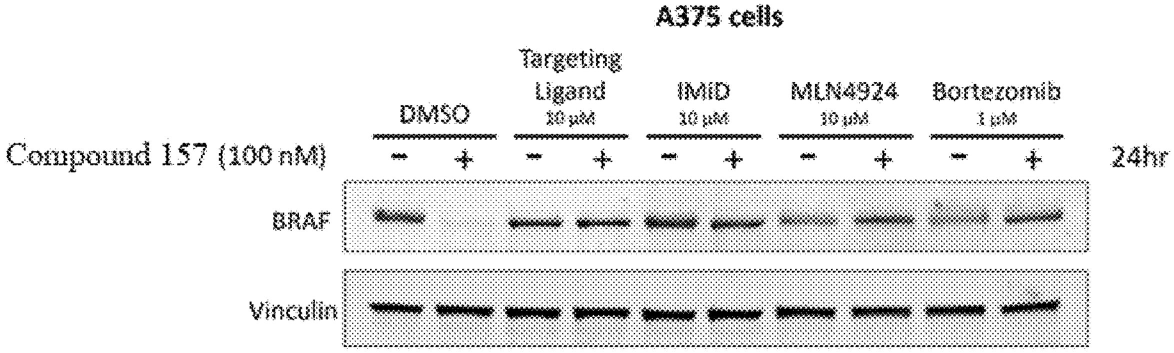

FIG. 4 is a western blot depicting BRAF V600E levels in A375 cells in response to the degrader Compound 157 while being challenged by inhibitors or competitors relevant to the function of a proteasome dependent molecule. The (−/+) indicates presence of Compound 157 in sample. When treated with DMSO alone, BRAF V600E is at a normal level, however after being exposed to Compound 157 for 24 hours the BRAF V600E levels have significantly decreased. This degradation is blocked by addition of an excess of targeting ligand, preventing the degrader from binding to BRAF V600E. The degradation is also blocked when the cells are pretreated with a compound specific to the binding site on cereblon (IMID). Taken together, this suggests that the degrader must bind to both BRAF and CRBN simultaneously to degrade BRAF V600E. Additionally, when the cells are treated with the neddylation inhibitor MLN4962 or the proteasome inhibitor bortezomib in combination with Compound 157, degradation is blocked, indicating that this loss of BRAF V600E with Compound 157 is dependent on neddylation and the proteasome system. The experimental procedure is provided in Example 231.

Figure 5:
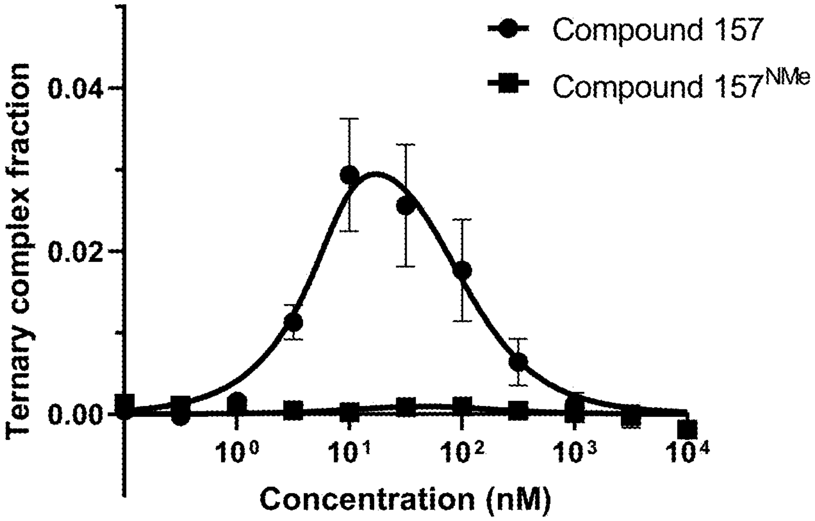

FIG. 5 is a line graph showing the ternary complex formation of BRAF V600E and cereblon with Compound 157 or Compound 157$^{NMe}$ at various concentrations. The y-axis is the fraction of ternary complex. The x-axis is concentration of Compound 157 measured in nanomolar. Compound 157$^{NMe}$ is an analog of Compound 157 that has minimal or no interaction with cereblon, and therefore not a functional degrader. The experimental procedure is provided in Example 232.

Figure 6:
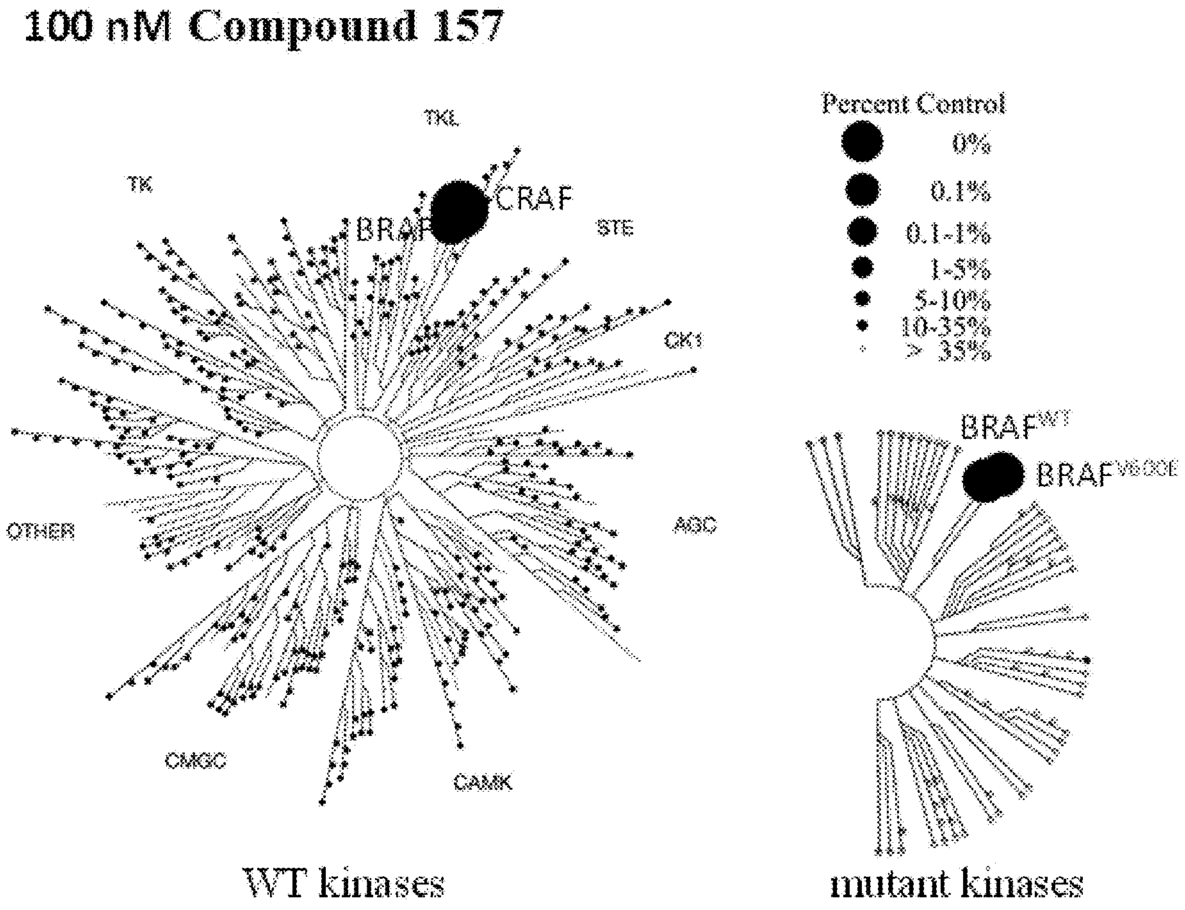

FIG. 6 is a TREEspot™ Interaction Map showing the relative amount of 10 nM Compound 157 binding to several proteins. Kinases that show binding to Compound 157 are highlighted with black circles. Size of the circle reflects % inhibition. The experimental procedure is provided in Example 233.

Figure 7:
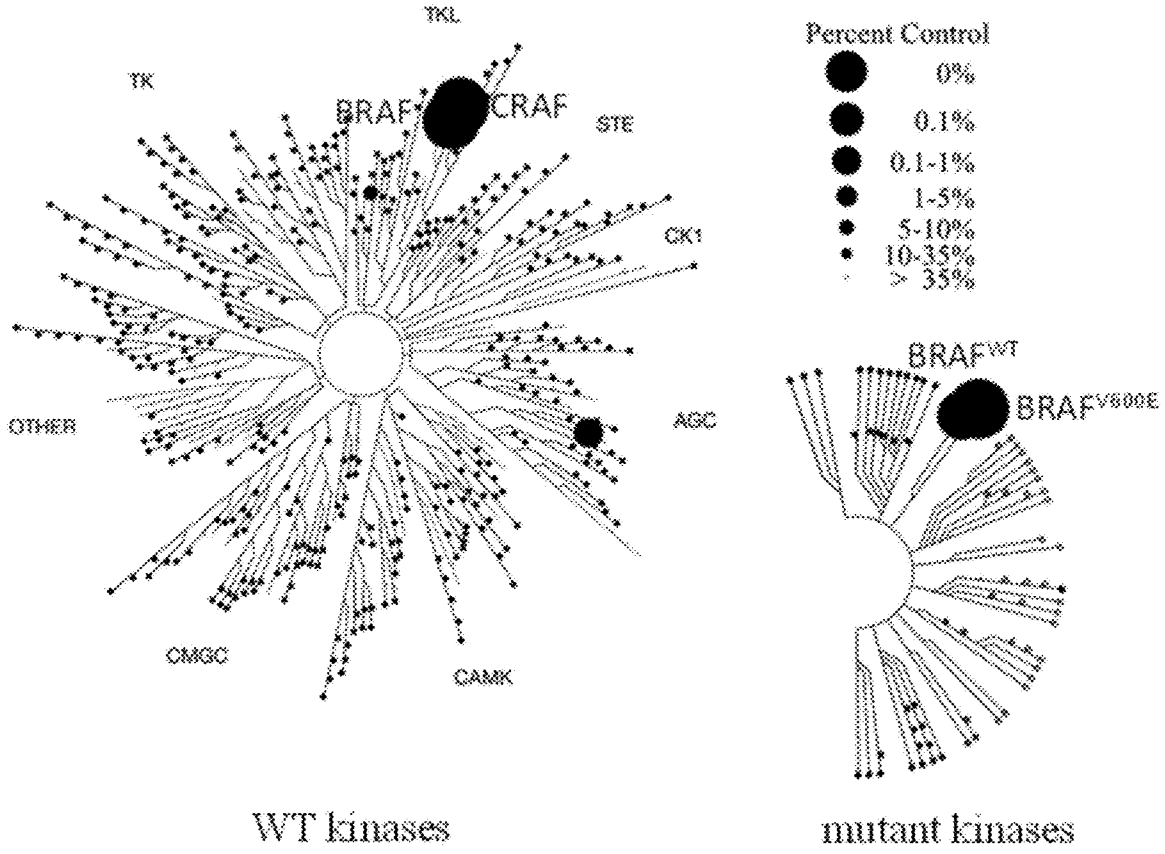

FIG. 7 is a TREEspot™ Interaction Map showing the relative amount of 1,000 nM Compound 157 binding to several proteins. Kinases that show binding to Compound 157 are highlighted with black circles. Size of the circle reflects % inhibition. The experimental procedure is provided in Example 233.

Figure 8:
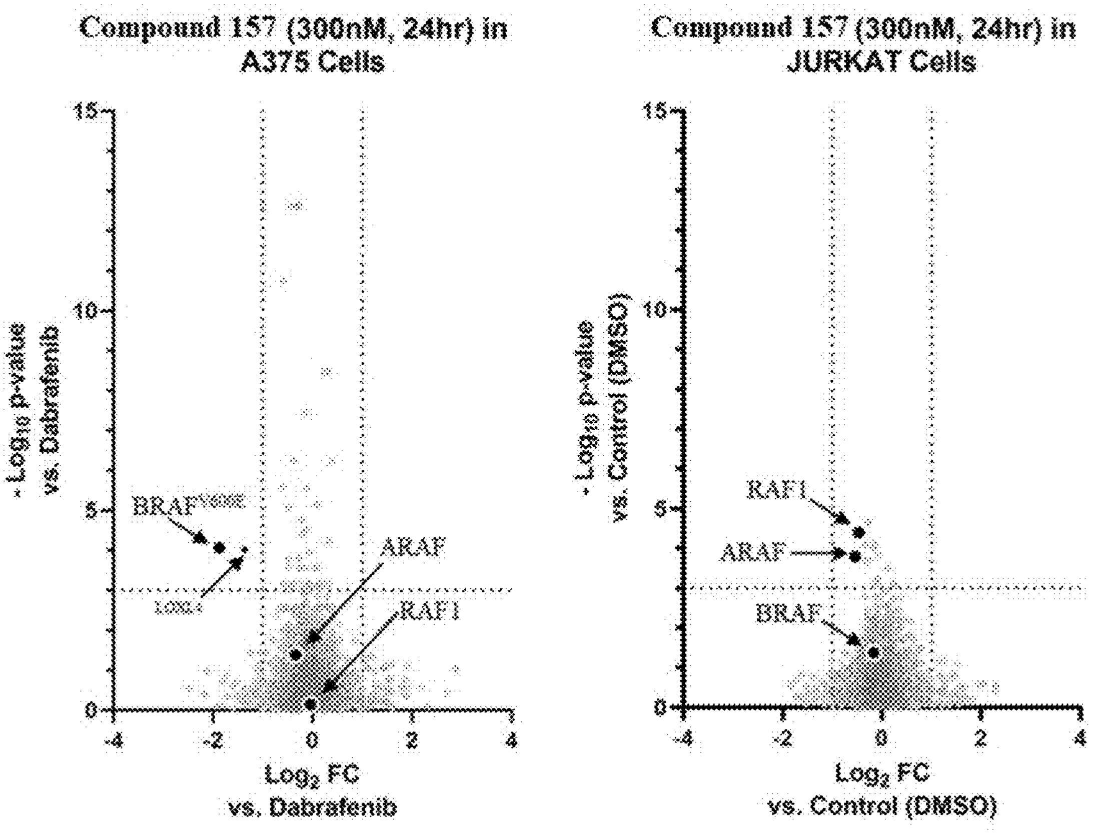

FIG. 8 is a scatter plot showing data from cell lysates analyzed by multiplexed quantitative proteomics of either A375 or JURKAT cells treated with 300 nM Compound 157 for 24 hours (see below for experimental methods). For each experiment data were analyzed by comparing the Compound 157 treated samples (biological duplicates) to the control samples treated with 300 nM dabrafenib (A375 cells) or DMSO (JURKAT cells) and fold changes in relative abundance are depicted in a resulting scatter plot. $Log_2$ fold changes are shown on the x axis and negative $Log_{10}$ adjusted p-values (T-test of Compound 157 vs. DMSO control, adjusted via Benjamini-Hochberg correction) are shown on the y axis. The horizontal dashed line marks the statistical significance (p-value≤0.001) and the vertical line marks fold change cut-off of ≥2. The experimental procedure is provided in Example 234.

Figure 9:
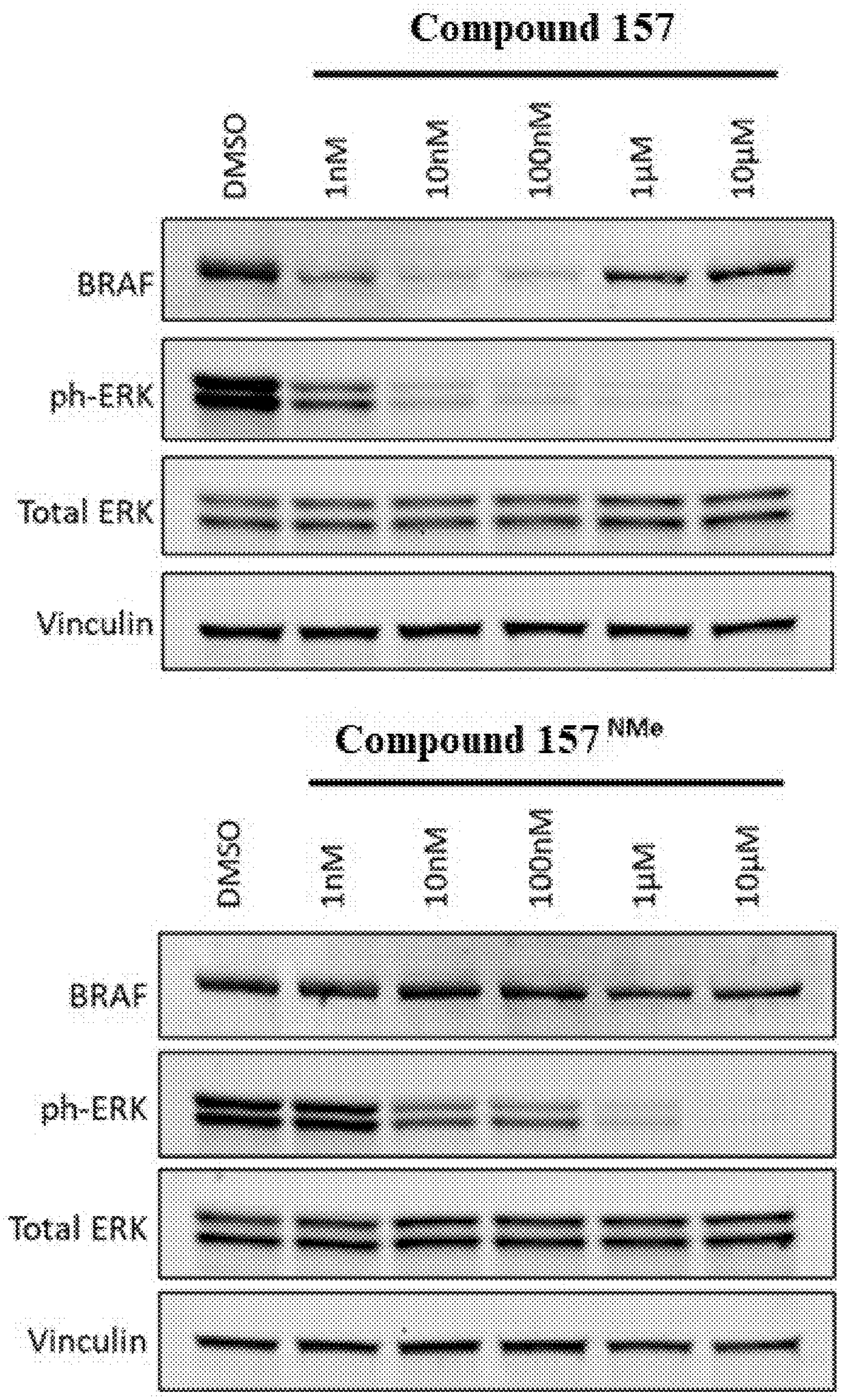

FIG. 9 is a Western blot depicting BRAF V600E and pERK levels in A375 cells in response to the degrader Compound 157 and null degrader Compound 157$^{NMe}$. BRAF V600E levels decrease in a dose dependent manner with Compound 157 until reaching the hook at 1 μM, as is characteristic of bifunctional degraders. MAPK signaling, as read out by ERK phosphorylation significantly drops off after treatment with Compound 157. Compound 157$^{NMe}$ is an analog of Compound 157 that has minimal binding to cereblon, and therefore not a functional degrader. As expected BRAF V600E levels remain unchanged and the loss of ERK phosphorylation is not as pronounced as with the functional degrader. The impact on ERK phosphorylation seen with the null degrader is due to the inhibitory contribution of the ligand targeting side of the bifunctional degrader. The experimental procedure is provided in Example 231.

Figure 10:
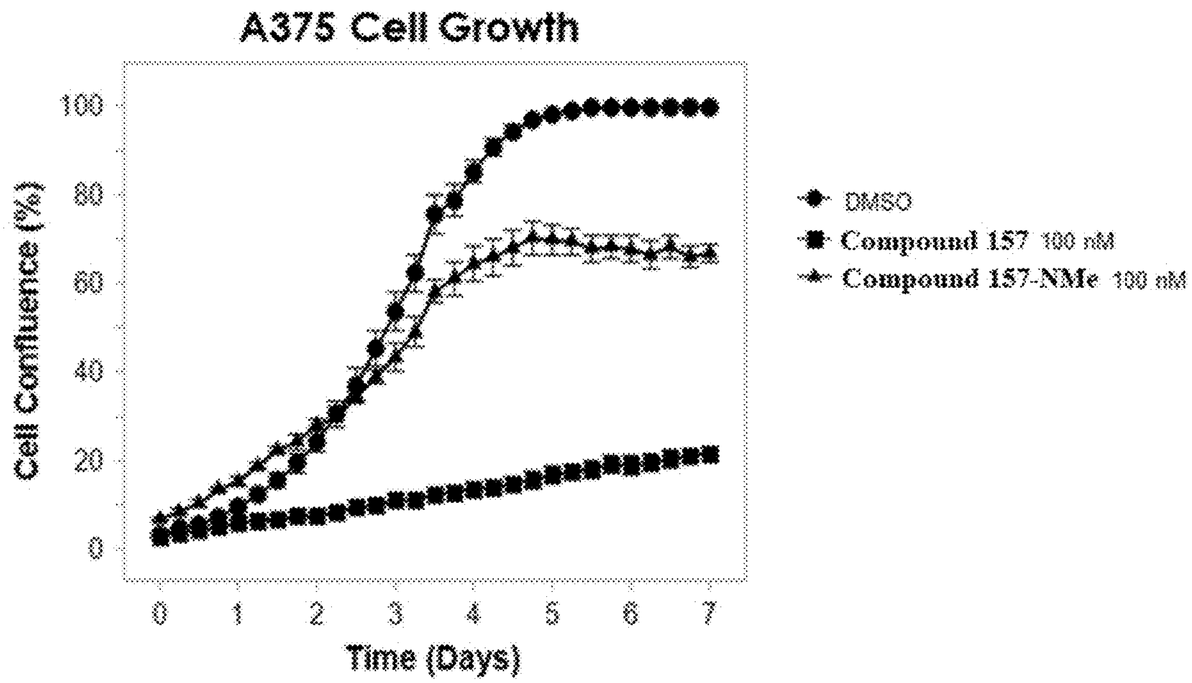

FIG. 10 is a line graph that depicts cellular confluence of A375 cells cultured with Compound 157 and Compound 157$^{NMe}$ by live cell imaging over the course of 7 days. DMSO treated cells grow quickly with expected doubling time and reach 100% confluence around day 5. Upon treatment with the BRAF degrader Compound 157, the cells have notably stunted growth and barely reach 20% confluent by the end of the 7-day experiment. Cells treated with the cereblon null Compound $157^{NMe}$ grow at a normal rate initially, but growth is inhibited to approximately 70% confluency. The shift between the two compounds demonstrates the contribution that BRAF V600E degradation has on inhibition of cell growth compared to an equivalent BRAF V600E inhibition alone. The experimental procedure is provided in Example 231.

Figure 11:
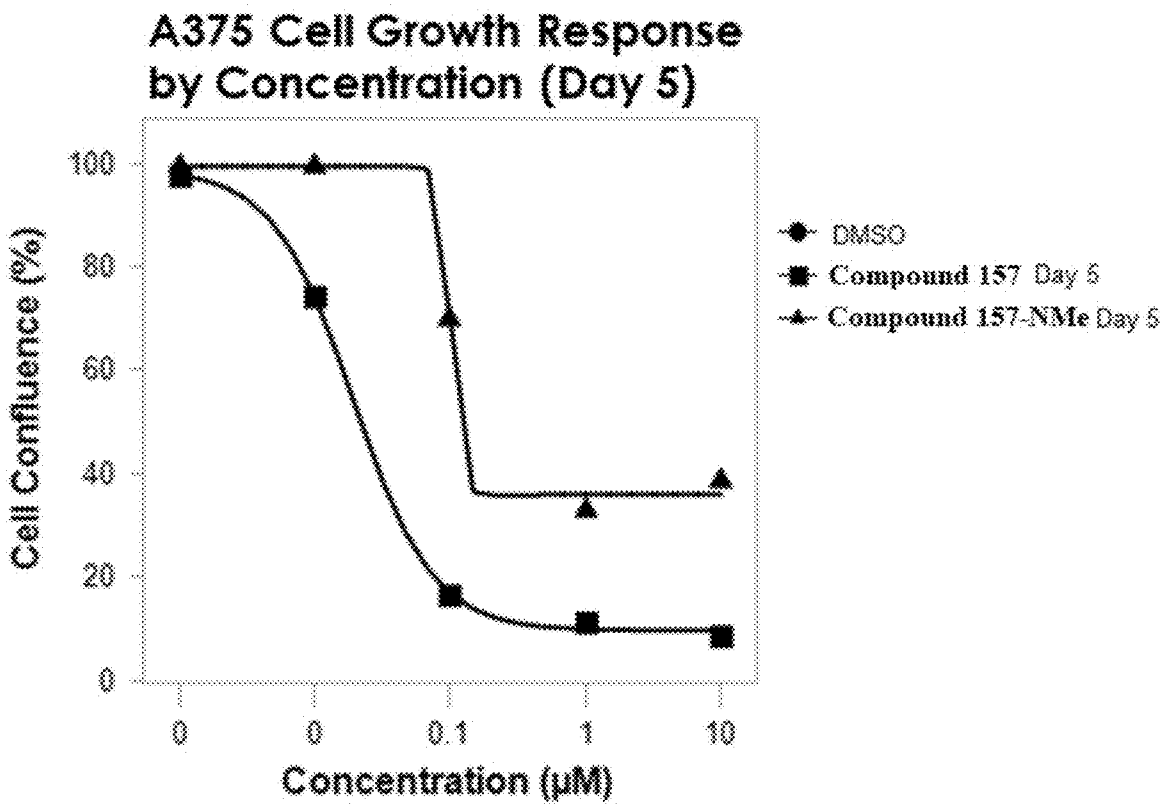

FIG. 11 is a line graph that depicts cellular confluence of A375 cells cultured with Compound 157 and Compound $157^{NMe}$ by live cell imaging at day 5. The contribution that BRAF V600E degradation has on inhibition of cell growth compared to an equivalent BRAF V600E inhibition alone at cell growth is further demonstrated observing cell growth by concentration at a fixed timepoint (day 5), note the degrader is right shifted from its cereblon null counterpart. The experimental procedure is provided in Example 231.

Figure 12:
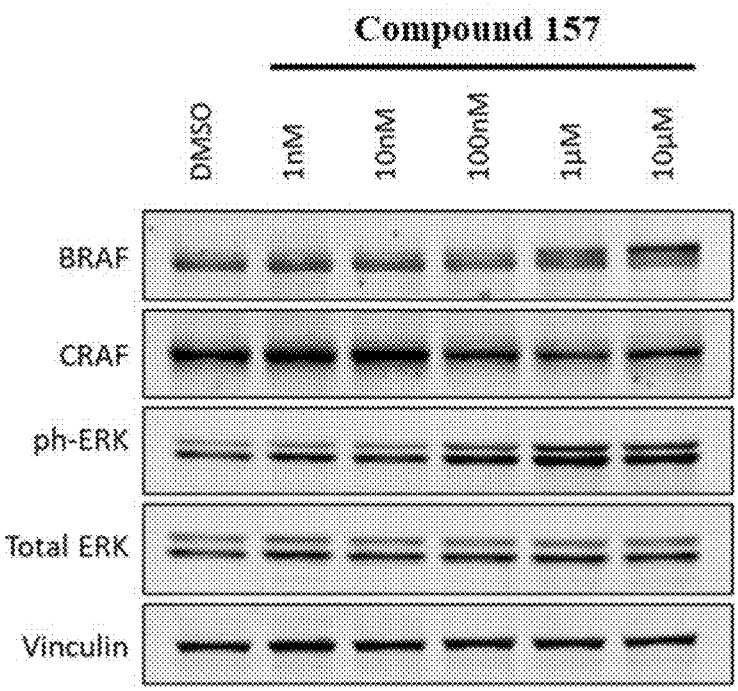

FIG. 12 is a Western blot depicting WT BRAF and pERK levels in HCT-116 cells with endogenous WT BRAF in response to the degrader Compound 157. As expected, there is minimal impact on WT BRAF levels and phosphorylation of ERK. The experimental procedure is provided in Example 231.

Figure 13:
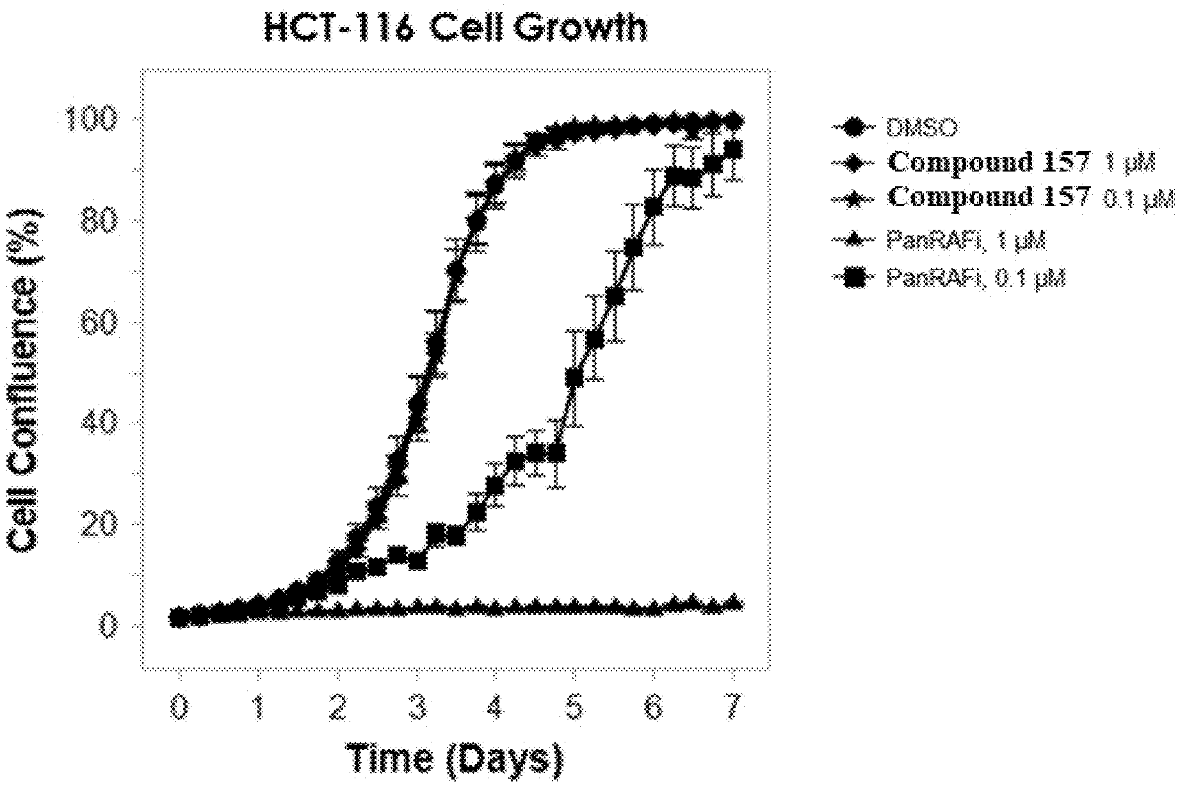

FIG. 13 is a growth over time experiment illustrating HCT-116 WT BRAF cells after treatment with Compound 157 or a pan RAF inhibitor. This cell line has been described in literature to be dependent on RAF signaling and cell growth is significantly hindered by treatment with a pan RAF inhibitor. Compound 157 has no impact on cell growth as the curve for the treated cells overlays directly with the DMSO treated cells, supporting the hypothesis that the phenotypic consequences of Compound 157 are specific to mutant BRAF. The experimental procedure is provided in Example 236.

Figure 14:
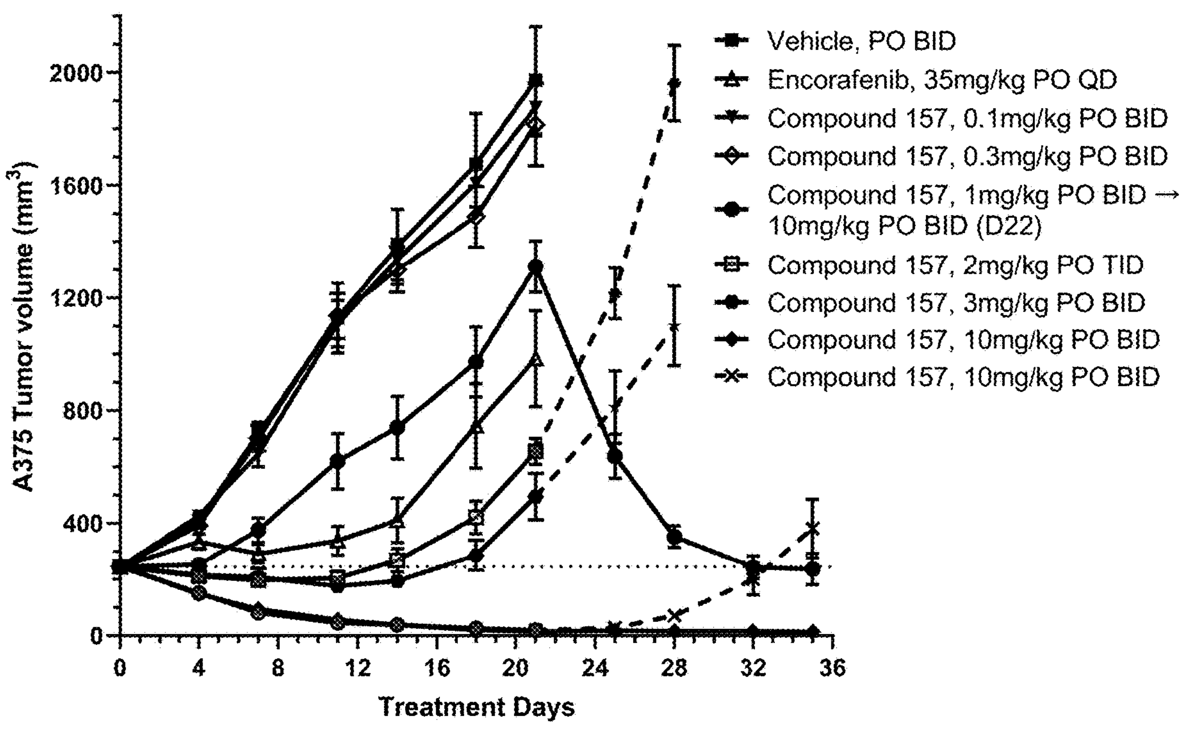

FIG. 14 is a line graph showing the in vivo efficacy of Compound 157 and encorafenib in the treatment of female BALB/c nude mice bearing A375 tumors. Mice were treated with the vehicle control, encorafenib (35 mg/kg) or Compound 157 (0.1, 0.3, 1, 2, 3, or 10 mg/kg) by oral gavage (PO), once (QD), twice (BID) or three times a day (TID), as indicated. Efficacy data are represented as Mean±SEM. Dashed lines represent dosing-free progression. The x-axis is the time measured in days and the y-axis is A375 tumor volume measures in $mm^3$. The experimental procedure is provided in Example 238.

Figure 15:
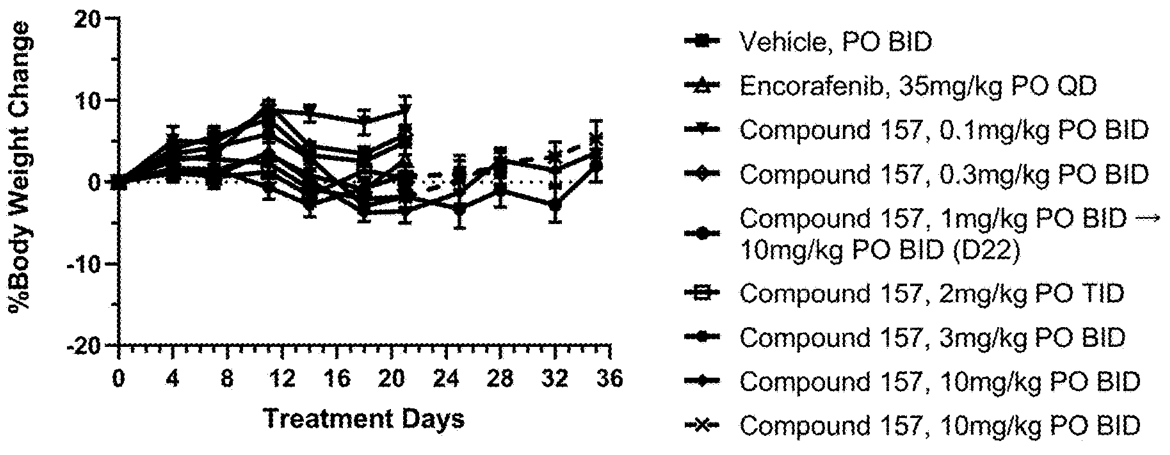

FIG. 15 is a line graph showing body weight change of Compound 157 and encorafenib in the treatment of female BALB/c nude mice bearing A375 tumors. Mice were treated with the vehicle control, encorafenib (35 mg/kg) or Compound 157 (0.1, 0.3, 1, 2, 3, or 10 mg/kg) by oral gavage (PO), once (QD), twice (BID) or three times a day (TID), as indicated. Efficacy data are represented as Mean±SEM. Dashed lines represent dosing-free progression. The x-axis is the time measured in days and the y-axis is body weight change in percent. The experimental procedure is provided in Example 238.

Figure 16:
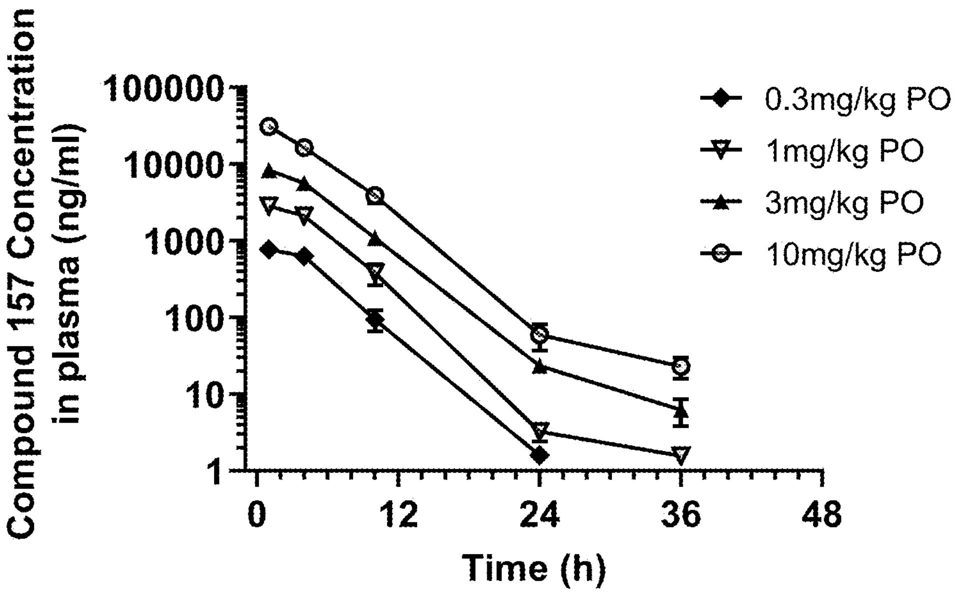

FIG. 16 is a line graph showing the in vivo pharmacokinetic activity of Compound 157 in plasma following a single oral (PO) dose at 0.3, 1, 3 or 10 mg/kg. Plasma and tumors were harvested at the indicated timepoints and injected into the LC/MS/MS system for quantitative analysis. Compound 157 concentration in plasma (ng/ml) and tumor (ng/g) represented as Mean±SEM. The experimental procedure is provided in Example 239.

Figure 17:
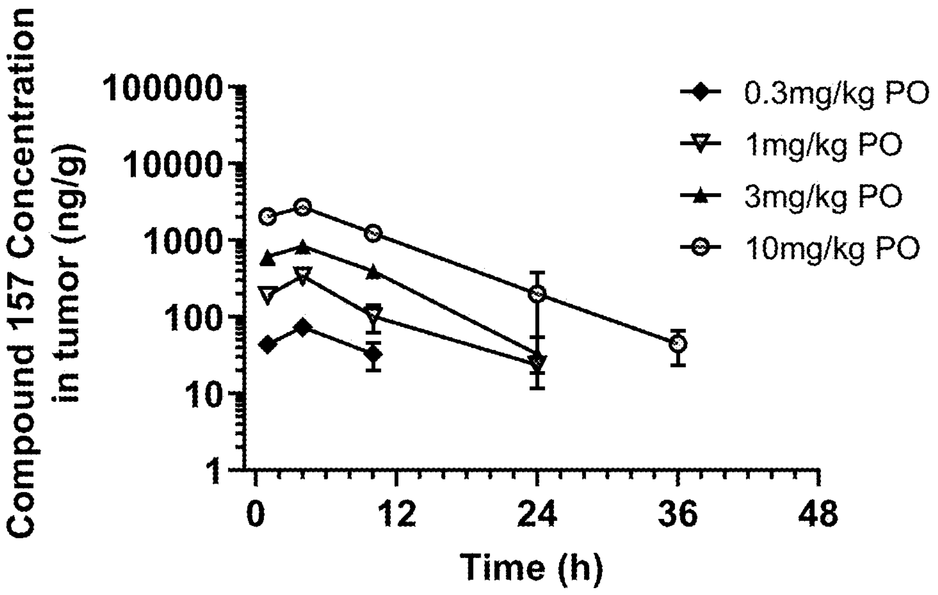

FIG. 17 is a line graph showing the in vivo pharmacokinetic activity of Compound 157 in A375 xenograft tumor following a single oral (PO) dose at 0.3, 1, 3 or 10 mg/kg. Plasma and tumors were harvested at the indicated timepoints and injected into the LC/MS/MS system for quantitative analysis. Compound 157 concentration in plasma (ng/ml) and tumor (ng/g) represented as Mean±SEM. The experimental procedure is provided in Example 239.

Figure 18:
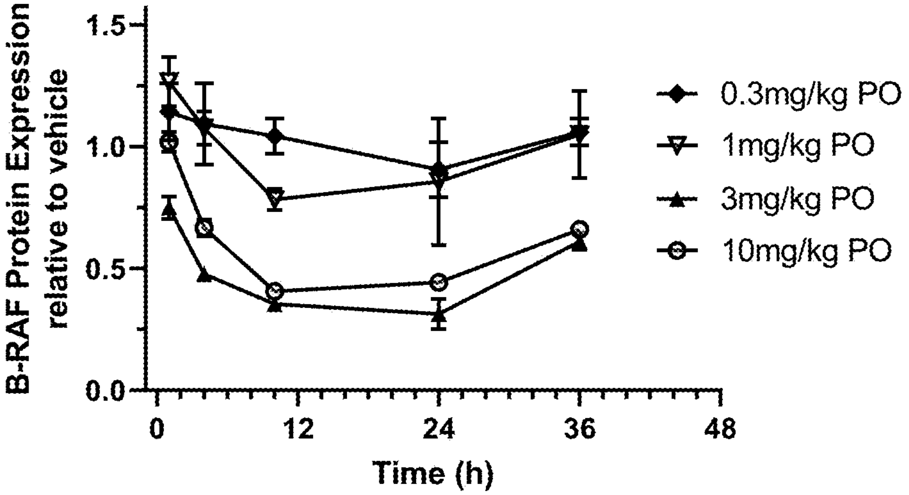

FIG. 18 is a line graph showing the relative protein expression of B-RAF in A375 xenograft tumors. BALB/c nude mice were injected into the right flank with A375 tumor cells. Compound 157 was administered as a single oral (PO) dose at 0.3, 1, 3, or 10 mg/kg and A375 tumors were harvested at the indicated timepoints and protein expression of B-RAF was measured by western blot. The x-axis is time measured in hours post-single dose administration and the y-axis is the percent of protein relative to the vehicle-treated tumors. Data is represented as Mean±SEM. The experimental procedure is provided in Example 239.

Figure 19:
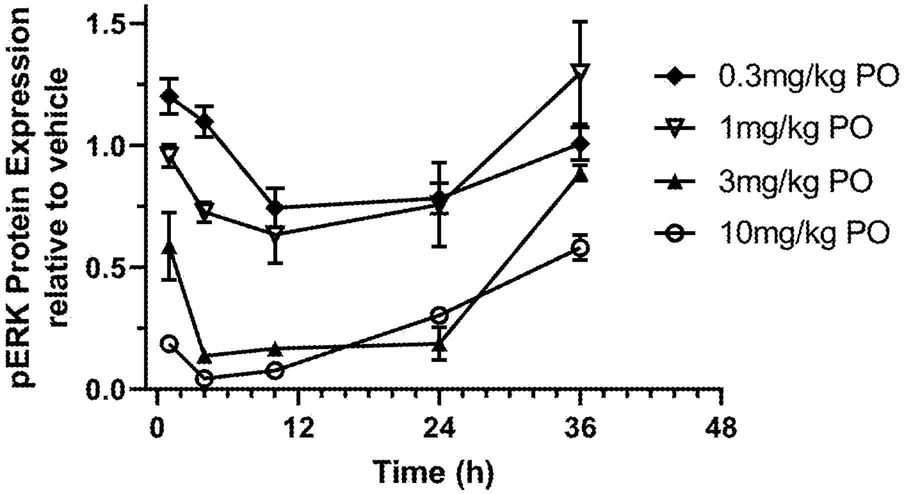

FIG. 19 is a line graph showing the relative protein expression of phospho-ERK in A375 xenograft tumors. BALB/c nude mice were injected into the right flank with A375 tumor cells. Compound 157 was administered as a single oral (PO) dose at 0.3, 1, 3, or 10 mg/kg and A375 tumors were harvested at the indicated timepoints and protein expression of pERK was measured by western blot. The x-axis is time measured in hours post-single dose administration and the y-axis is the percent of protein relative to the vehicle-treated tumors. Data is represented as Mean±SEM. The experimental procedure is provided in Example 239.

Figure 20:
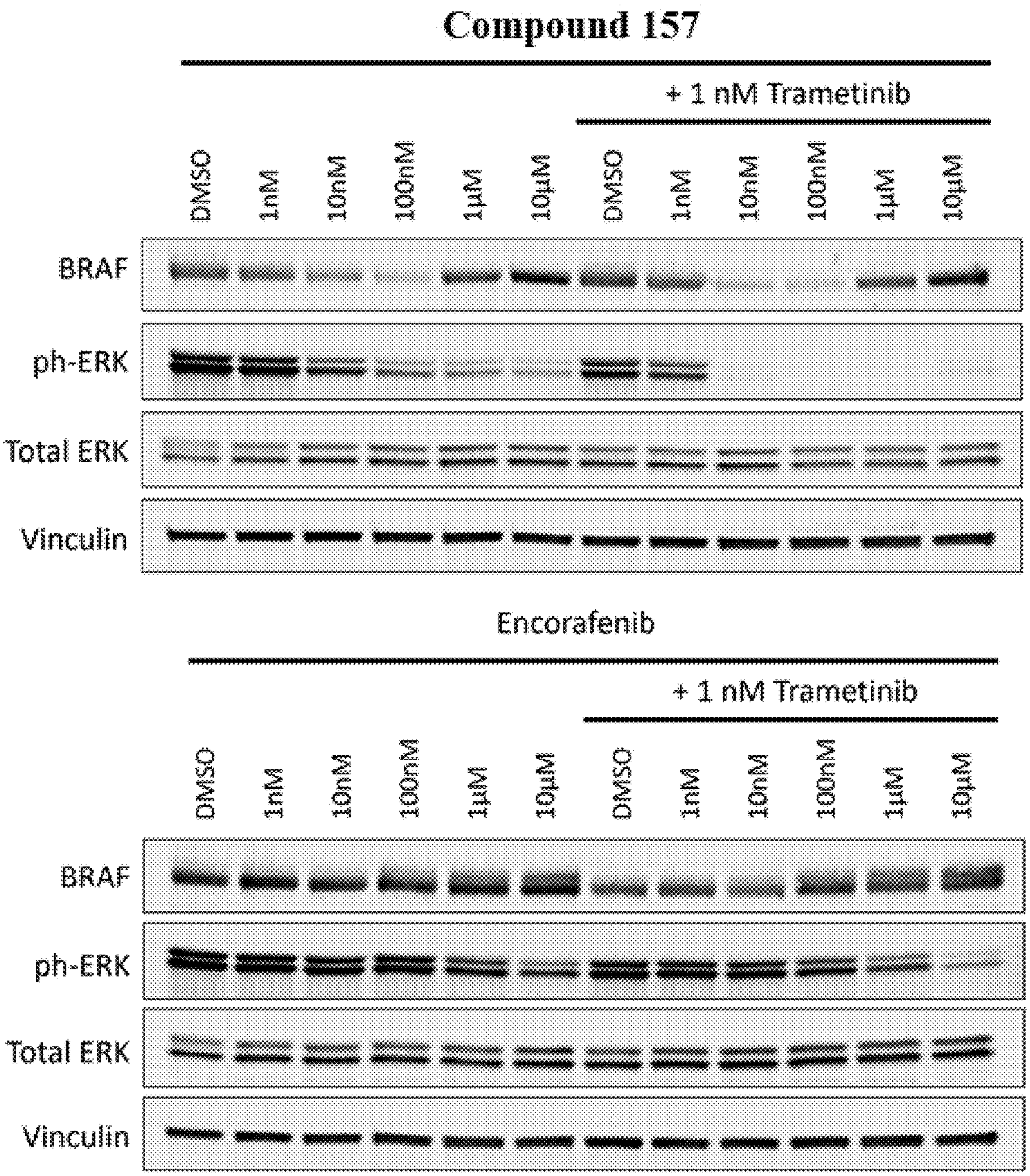

FIG. 20 is a Western Blot of A375 cells expressing the oncogenic $NRAS^{Q61K}$ mutant treated with Compound 157 or encorafenib in a 5-point dose response with or without the addition of 1 nM trametinib for 24 hours. Expressing $NRAS^{Q61K}$ in addition to BRAF V600E represents a resistance mechanism that has been seen in patients and presents a greater challenge to overcome for suppressing MAPK signaling. The degrader, Compound 157 alone can suppress MAPK signaling, as read out by ERK phosphorylation. In combination with the MEK inhibitor trametinib, the ERK activation is completely suppressed by 10 nM of Compound 157. In comparison, the BRAF V600E inhibitor encorafenib is unable to significantly suppress ERK phosphorylation levels with or without a combination with trametinib. This data shows that Compound 157 may be is advantageous for controlling MAPK signaling in in BRAF V600E resistance settings. The experimental procedure is provided in Example 231.

Figure 21:
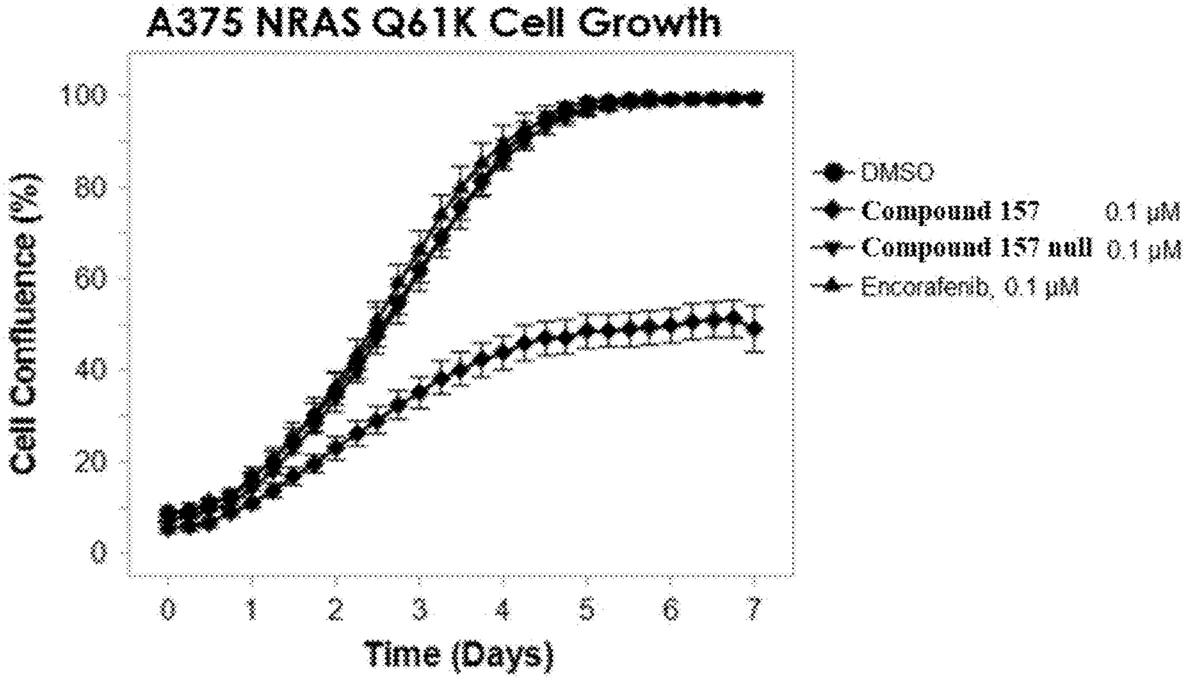

FIG. 21 is a line graph depicting the cellular growth over time of A375 cells expressing the oncogenic $NRAS^{Q61K}$ mutation. Cells treated with DMSO alone exhibit a normal doubling time. When treated with the BRAF V600E degrader Compound 157, the cell growth is inhibited and cells are not capable of achieving more than 50% confluency. When treated with the match pair Compound $157^{NMe}$ that has minimal or no binding to cereblon, the cellular growth is not inhibited. Encorafenib does not inhibit cell growth in the resistance model cell line. The experimental procedure is provided in Example 235.

Figure 22:
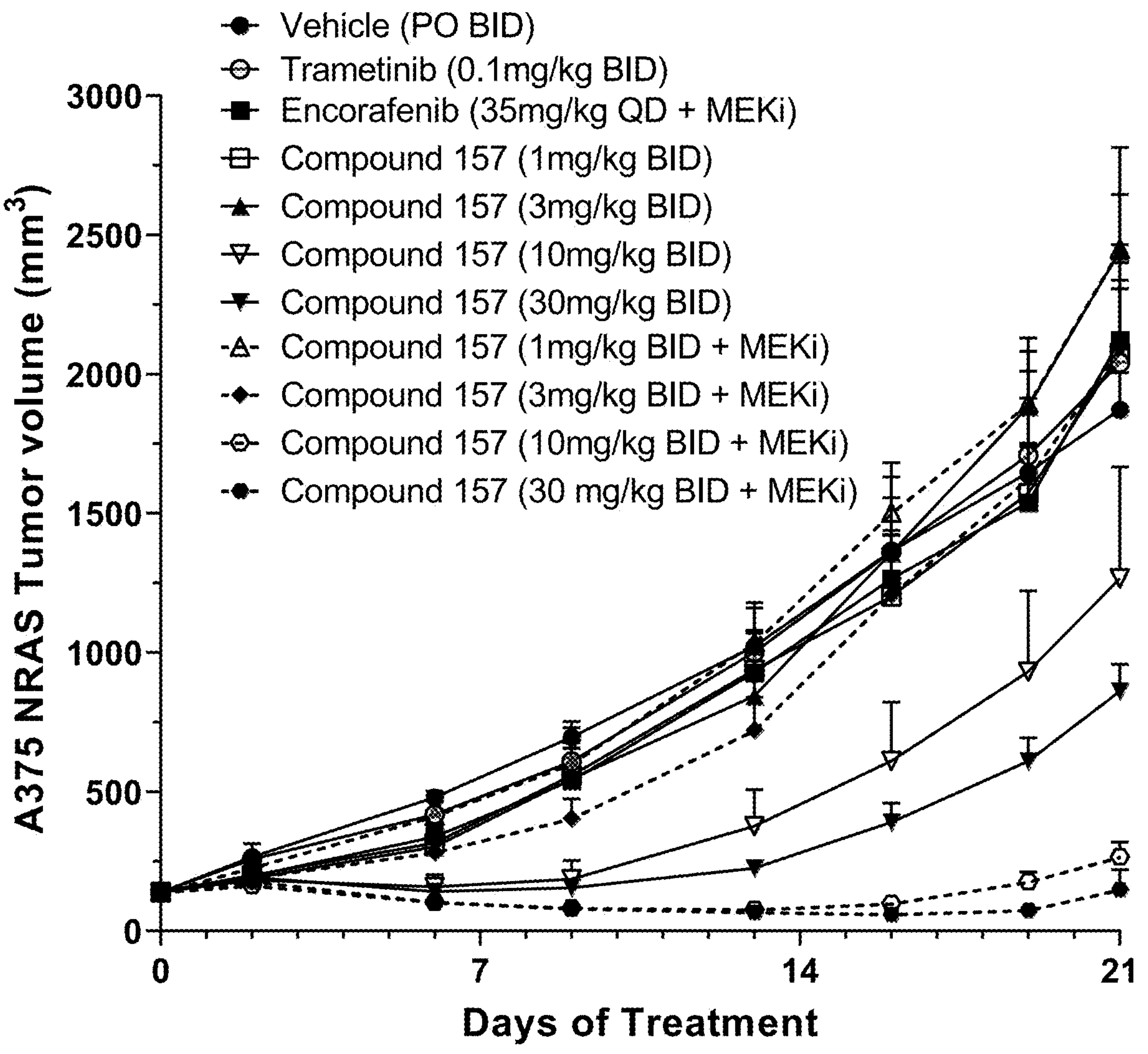

FIG. 22 is a line graph demonstrating the effect of compounds at various concentrations on tumors in Female BALBc/Nude mice bearing an A375 $NRAS^{Q61K}$ mutant melanoma cell line xenograft. Mice were administered vehicle, trametinib (MEK inhibitor (MEKi) 0.1 mg/kg twice daily (BID)), encorafenib (35 mg/kg once daily (QD)+MEKi), Compound 157 (1, 3, 10, or 30 mg/kg BID), or Compound 157 at same doses in combination with MEKi at 0.1 mg/kg BID by oral gavage. Compound 157 was efficacious as a single agent at 10 and 30 mg/kg BID doses and resulted in regressions when dosed in combination with MEKi at 0.1 mg/kg BID. Efficacy data are expressed as mean tumor volumes±SEM. All doses were well tolerated as no group showed more than mean 4.5% body weight loss throughout the study. The experimental procedure is provided in Example 241.

Figure 23:
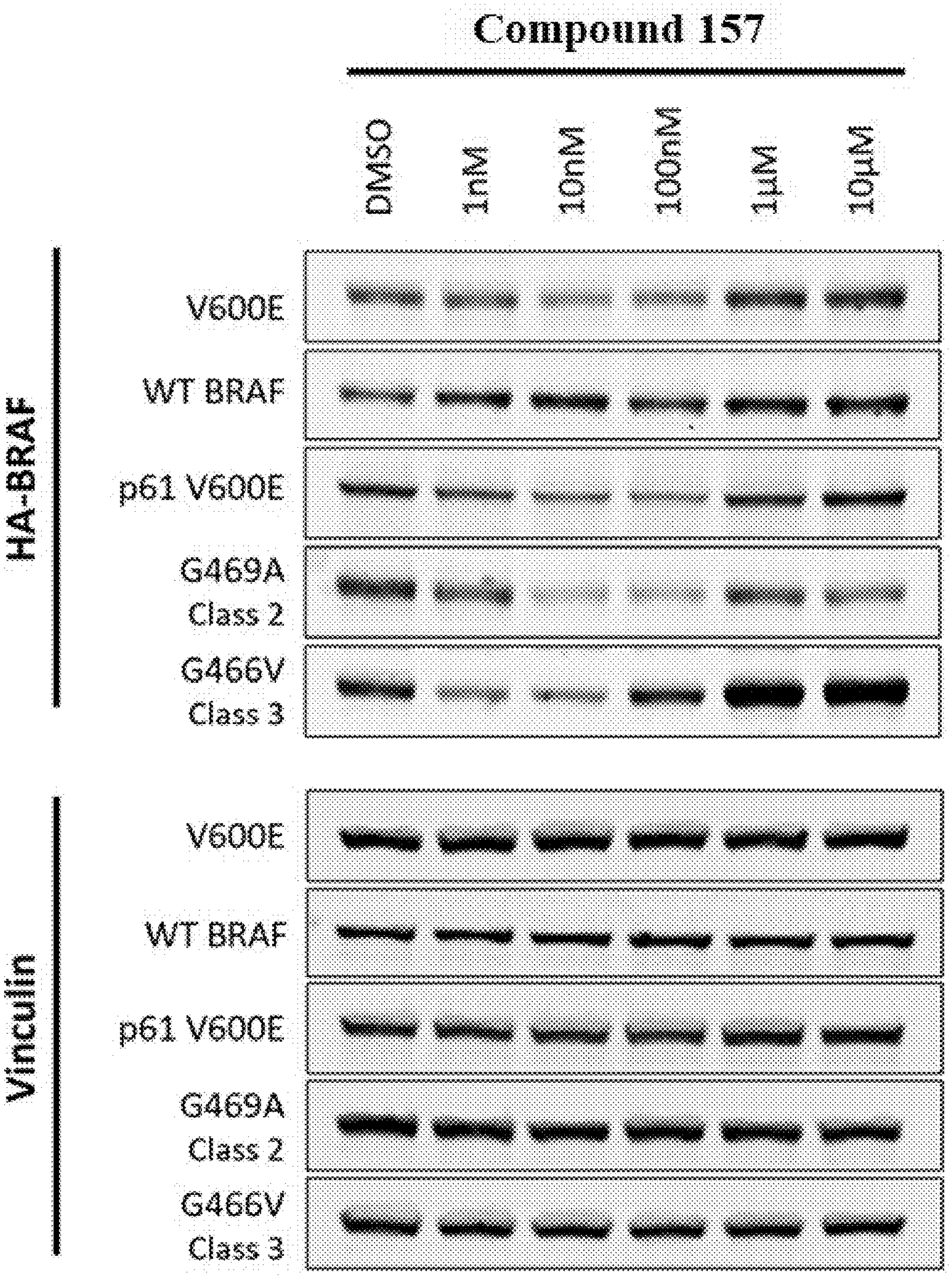

FIG. 23 is a Western Blot that demonstrates the degradation potential of Compound 157 beyond BRAF V600E. HEK-293T (ATCC, CRL-3216) cells were engineered using lentivirus to express BRAF V600E, WT, the p61 splice variant, class II mutant G469A and class III mutant G466V. Compound 157 is capable of degrading all mutants with the exception of WT BRAF. The experimental procedure is provided in Example 231.

Figure 24:
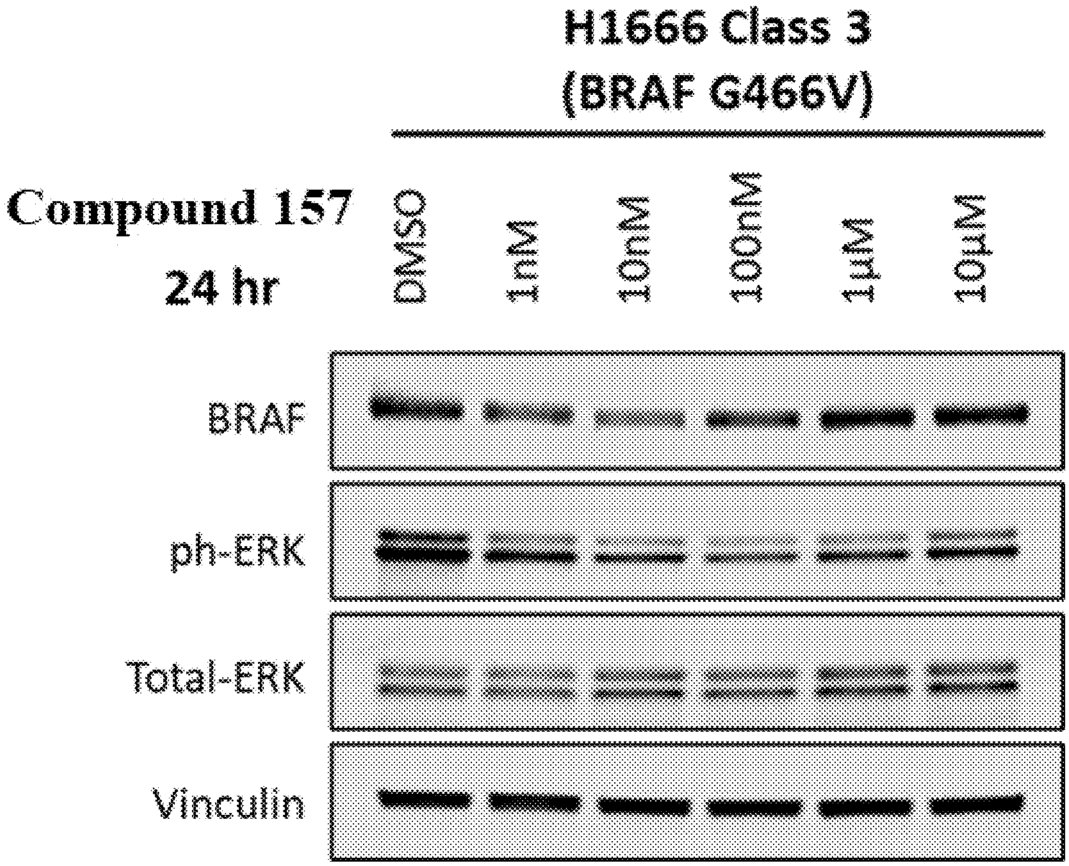

FIG. 24 is a Western Blot of the cell line H1666 (ATCC, CRL-5885) that endogenously expresses the class III mutation G466V. H1666 cells were treated with Compound 157 for 24 hours. Treating H1666 cells with Compound 157 lead to a 53% reduction in BRAF signal, including any WT BRAF that might be present due to the cells being heterozygous for the mutation and that Compound 157 does not degrade WT BRAF. There was also a decrease in phosphorylated ERK signal, indicating the suppression of the MAPK pathway. The experimental procedure is provided in Example 231.

Figure 25:
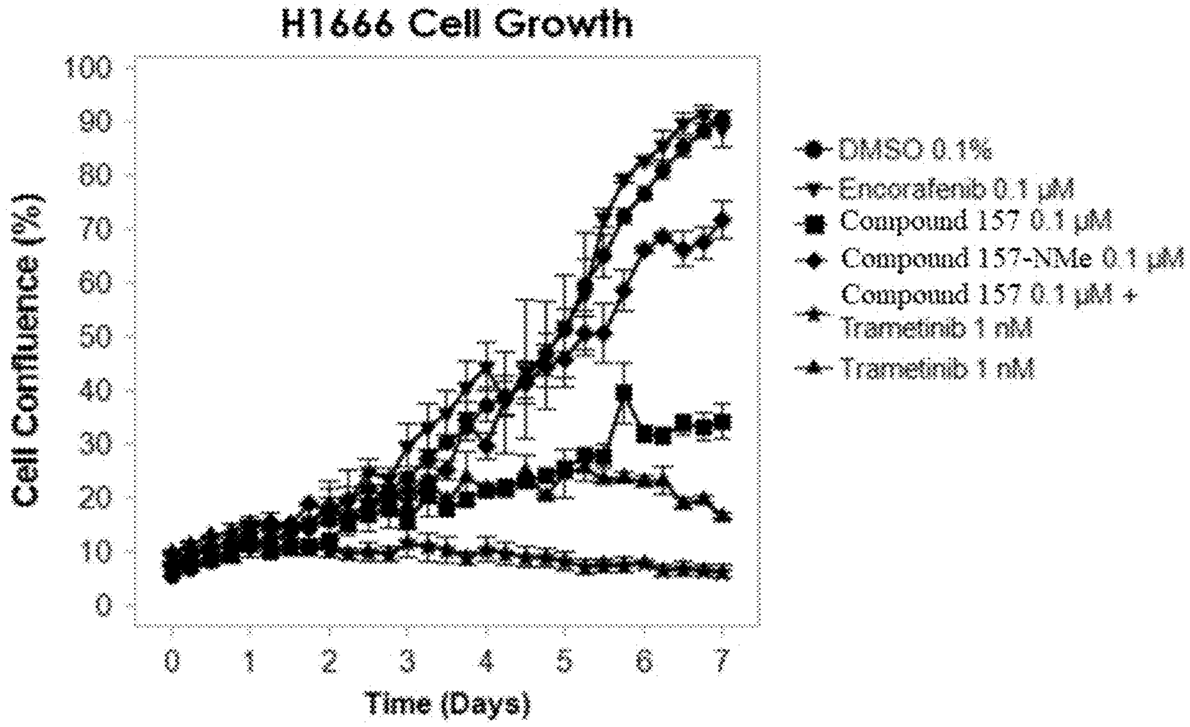

FIG. 25 is a line graph demonstrating cellular growth over time in H1666 cells endogenously expressing the class III BRAF mutation G466V. Cells treated with DMSO alone exhibit a normal doubling time. When treated with the BRAF degrader Compound 157, the cell growth is inhibited, and cells are not capable of achieving more than 30% confluency over the course of 7 days. When treated with the match pair Compound $157^{NMe}$ that has minimal or no binding to cereblon, the cellular growth is not inhibited as significantly. Additionally, encorafenib does not inhibit cell growth in the BRAF class III mutant cell line. The most significant disruption to cell growth was Compound 157 in combination with 1 nM dose of the MEK inhibitor trametinib. The cells failed to expand, and proliferation was severely compromised. The experimental procedure is provided in Example 242.

DETAILED DESCRIPTION

In certain embodiments, the present invention provides a compound of Formula I (I)

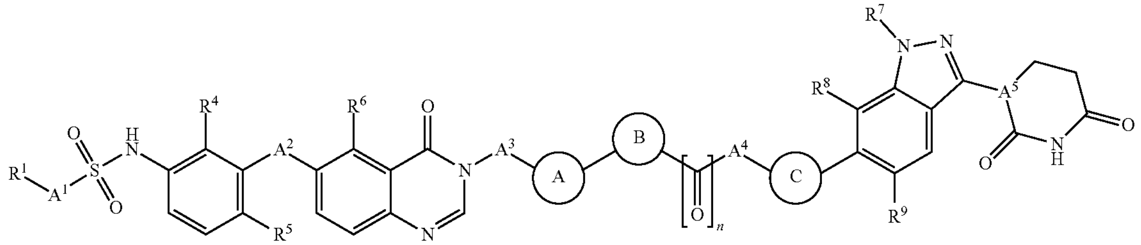

wherein the substituents and variables are as described herein, or a pharmaceutically acceptable salt thereof.

In certain embodiments the compound of Formula I is a compound of Formula I-A (I-A)

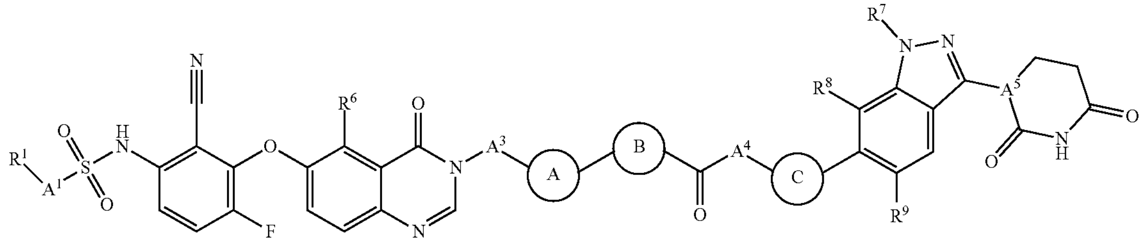

wherein $A^2$ is —O—, n is 1, $R^4$ is cyano, $R^5$ is fluoro and the remaining substituents and variables are as described herein, or a pharmaceutically acceptable salt thereof.

In certain embodiments the compound of Formula I is a compound of Formula I-B (I-B)

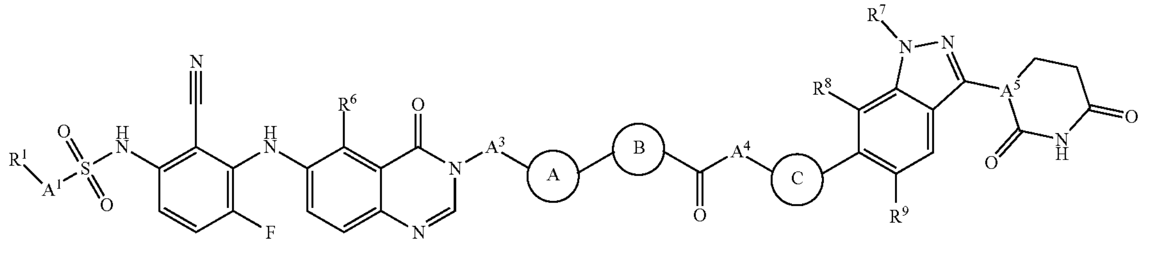

wherein $A^2$ is —NH—, n is 1, $R^4$ is cyano, $R^5$ is fluoro and the remaining substituents and variables are as described herein, or a pharmaceutically acceptable salt thereof.

In certain embodiments the compound of Formula I is a compound of Formula I-C (I-C)

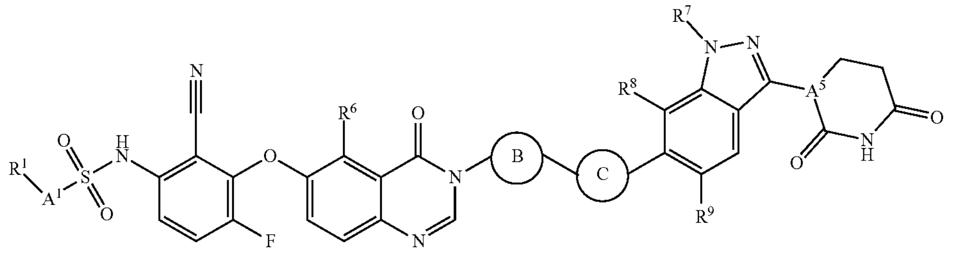

wherein $A^2$ is —O—, $A^3$ is a bond, A is a bond, n is 0, $A^4$ is a bond, $R^4$ is cyano, $R^5$ is fluoro and the remaining substituents and variables are as described herein, or a pharmaceutically acceptable salt thereof.

In certain embodiments the compound of Formula I is a compound of Formula I-D (I-D)

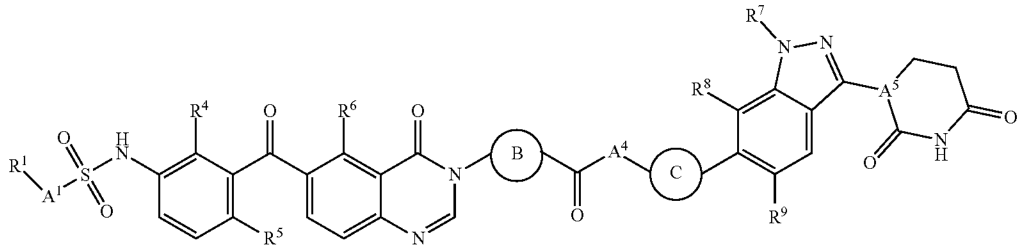

wherein $A^2$ is —(C═O)—, $A^3$ is a bond, A is a bond and the remaining substituents and variables are as described herein, or a pharmaceutically acceptable salt thereof.

The present compounds are useful for the therapeutic and/or prophylactic treatment of cancer.

The present invention provides a compound of Formula I, Formula II, Formula III, Formula IV, Formula V, or Formula VI or a pharmaceutically acceptable salt thereof, the preparation of the above-mentioned compounds, medicaments containing them and their manufacture as well as the use of the above-mentioned compounds in the therapeutic and/or prophylactic treatment of cancer.

Terminology

The following definitions of the general terms used in the present description apply irrespectively of whether the terms in question appear alone or in combination with other terms.

Unless otherwise stated, the following terms used in this application, including the specification and claims, have the definitions given below. It must be noted that, as used in the specification and the appended claims, the singular forms "a" "an," and "the" include plural referents unless the context clearly dictates otherwise.

The term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert-butyl, the isomeric pentyls, the isomeric hexyls, the isomeric heptyls and the isomeric octyls, particularly methyl, ethyl, propyl, butyl and pentyl. Examples of straight-chain and branched-chain C1-C6 alkyl are methyl, ethyl, isopropyl, butyl, isobutyl, tert-butyl, pentyl and hexyl. Methyl and ethyl are particular examples of "alkyl".

The term "cyano", alone or in combination with other groups, denotes the group —C≡N.

The terms "halogen" or "halo", signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e., one, two, three or four halogens.

The term "haloalkyl", alone or in combination with other groups, denotes an alkyl group wherein at least one of the hydrogen atoms of the alkyl group has been replaced by the same or different halogen atoms. Examples of haloalkyl include fluoromethyl, difluoromethyl, trifluoromethyl, fluoroethyl, difluoroethyl and trifluoroethyl. Particular haloalkyl groups include fluoroethyl and difluoroethyl.

The terms "hydroxyl" and "hydroxy", alone or in combination, signify the —OH group.

The term "amino", alone or in combination, signifies the primary amino group (—$NH_2$), the secondary amino group (—NH—), or the tertiary amino group (—N—).

The term "carbonyl", alone or in combination, signifies the —(C═O)— group.

The term "alkylamino" is alkyl group linked to a —NH— group. The term "dialkylamino" denotes two alkyl groups linked to a —N— atom.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. A particular example of "alkoxy" is methoxy.

The term "cycloalkyl", alone or in combination with other groups, denotes a monovalent saturated monocyclic or bicyclic hydrocarbon group of 3 to 8 ring carbon atoms, in particular 3 to 6 ring carbon atoms. Bicyclic means a ring system consisting of two saturated carbocycles having one or two carbon atoms in common. Examples of monocyclic "cycloalkyl" are cyclopropyl, cyclobutanyl, cyclopentyl, cyclohexyl, cycloheptyl and cyclooctyl. An example of bicyclic " " is spiro[3.3]heptanyl. More particular examples of monocyclic "cycloalkyl" are cyclopropyl, cyclobutyl, cyclopentyl and cyclohexyl.

The term "heterocycloalkyl", alone or in combination with other groups, denotes a monovalent saturated or partly unsaturated mono- or bicyclic ring system of 4 to 10 ring atoms, comprising 1, 2, or 3 ring heteroatoms selected from N, O and S, the remaining ring atoms being carbon which is optionally substituted with oxo. Bicyclic means consisting of two cycles having one or two ring atoms in common. The heterocycloalkyl is preferably a monovalent saturated or partly unsaturated monocyclic ring system of 4 to 7 ring atoms, comprising 1 or 2 ring heteroatoms selected from N, O and S (4- to 7-membered heterocycloalkyl). Examples of monocyclic saturated heterocycloalkyl include 4,5-dihydro-oxazolyl, oxetanyl, azetidinyl, pyrrolidinyl, 2-oxo-pyrrolidin-4-yl, 3-oxo-morpholin-6-yl, tetrahydrofuranyl, tetrahydrothiophenyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, 1,4-diazacycloheptyl, diazepanyl, homopiperazinyl and oxazepanyl. Examples of bicyclic saturated heterocycloalkyl include 3-azabicyclo[3.1.0]hexyl, oxabicyclo[2.2.1]heptanyl, oxaspiro[3.3]heptanyl, 8-aza-bicyclo[3.2.1]octyl, quinuclidinyl, 8-oxa-3-aza-bicyclo[3.2.1]octyl, 7-azaspiro[3.5]nonyl, 9-aza-bicyclo[3.3.1]nonyl, 3-oxa-9-aza-bicyclo[3.3.1]nonyl, 3-thia-9-aza-bicyclo[3.3.1]nonyl, 2,8-diazaspiro[4.5]decyl, 2-azaspiro[4.5]decyl, 1-oxa-8-azaspiro[4.5]decyl, 8-azaspiro[4.5]decyl 1-oxa-9-azaspiro[5.5]undecyl and 3-azaspiro[5.5]undecyl. Examples for partly unsaturated heterocycloalkyl include dihydrofuryl, imidazolinyl, dihydro-oxazolyl, tetrahydro-pyridinyl and dihydropyranyl. Particular examples of "heterocycloalkyl" are azetidinyl, pyrrolidinyl, piperazinyl, piperidinyl and 3-azabicyclo[3.1.0]hexyl.

The term "sulfonyl", alone or in combination with other groups, is the group —$SO_2$—.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids include, but are not limited to acetic acid, citric acid, formic acid, fumaric acid, hydrochloric acid, lactic acid, maleic acid, malic acid, methane-sulfonic acid, nitric acid, phosphoric acid, p-toluene sulphonic acid, succinic acid, sulfuric acid (sulphuric acid), tartaric acid, trifluoroacetic acid and the like. Particular acids are formic acid, trifluoroacetic acid and hydrochloric acid.

The term "pharmaceutically acceptable auxiliary substance" refers to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to affect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "inhibitor" denotes a compound which competes with, reduces or prevents the binding of a particular ligand to particular receptor, or which reduces or prevents the function of a particular protein.

If one of the starting materials or compounds of Formula I, Formula II, Formula III, Formula IV, Formula V, or Formula VI contain one or more functional groups which are not stable or are reactive under the reaction conditions of one or more reaction steps, appropriate protecting groups (as described e.g., in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of Formula I, Formula II, Formula III, Formula IV, Formula V, and Formula VI can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

Whenever a chiral carbon is present in a chemical structure, it is intended that all stereoisomers associated with that chiral carbon are encompassed by the structure as pure stereoisomers as well as mixtures thereof.

The compounds of the invention can exist as a tautomer, i.e., a structural isomer which interconverts with the compound of Formula I, Formula II, Formula III, Formula IV, Formula V, or Formula VI as drawn herein, in particular in solution. It is intended that the compound of Formula I, Formula II, Formula III, Formula IV, Formula V, or Formula VI encompasses all existing tautomeric forms thereof.

The compounds of the invention can exist as a solvate. It is intended that the compound of Formula I, Formula II, Formula III, Formula IV, Formula V, or Formula VI encompasses all existing solvates thereof.

The invention also provides pharmaceutical compositions, methods of using, and methods of preparing the aforementioned compounds.

The compounds of the invention may contain one or more asymmetric centers and can therefore occur as racemates, mixtures of enantiomers, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains greater than 90% of the desired isomer by weight, particularly greater than 95% of the desired isomer by weight, or more particularly greater than 99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

Embodiments of Formula I and Formula II

In certain embodiments the compound of Formula I is selected from (I-A)

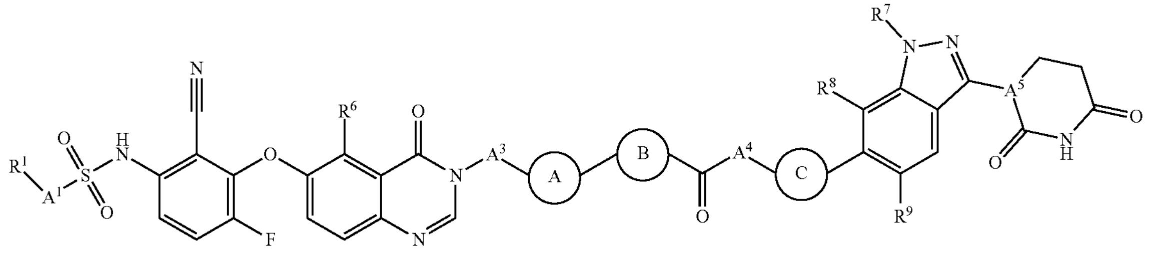

-continued
(I-B)
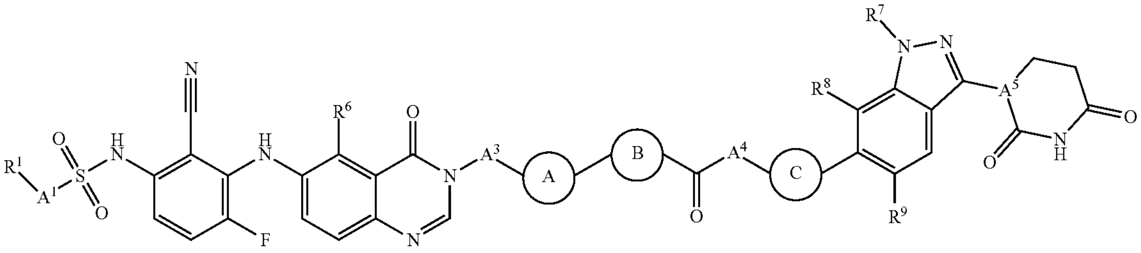
(I-C)
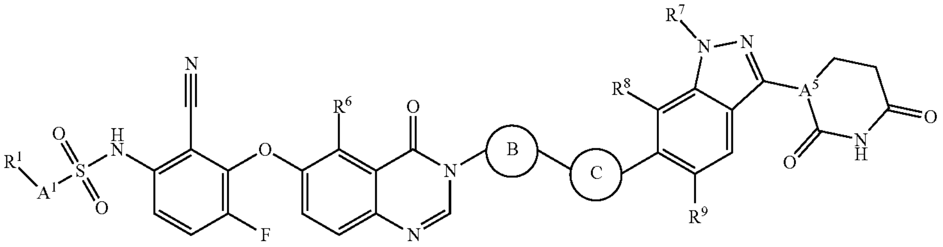
(I-D)
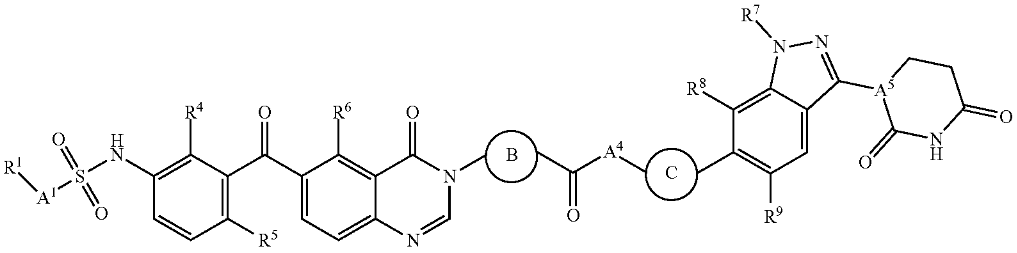
or a pharmaceutically acceptable salt thereof.
In certain embodiments the compound of Formula II is selected from
(II-A)
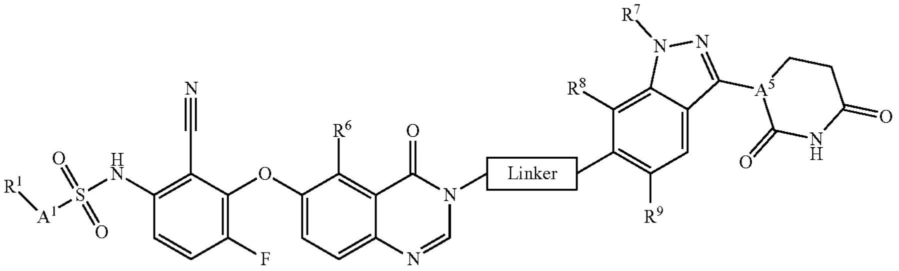
(II-B)
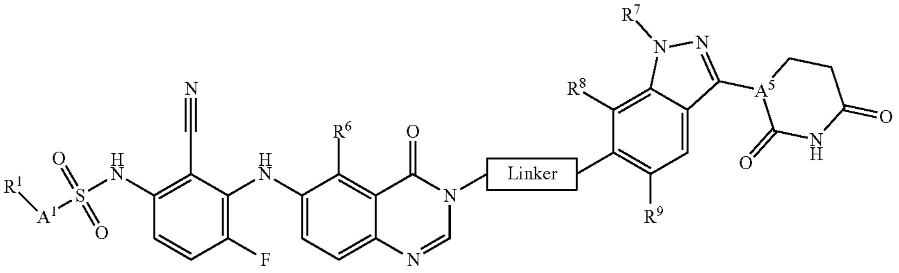

-continued
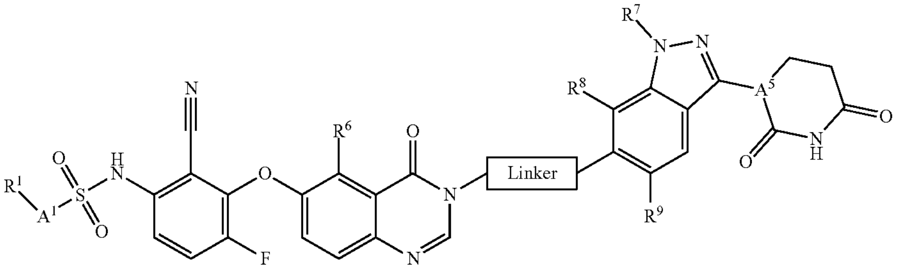
(II-C)
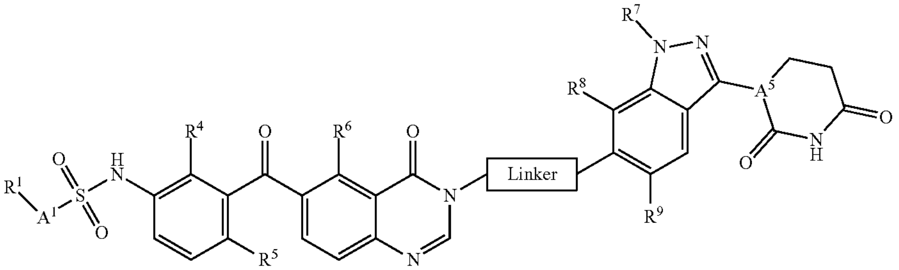
(II-D)
or a pharmaceutically acceptable salt thereof.
In certain embodiments the compound of the present invention is selected from:
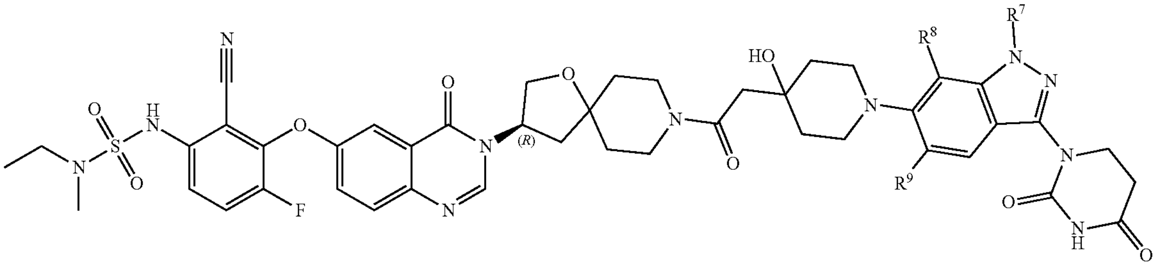
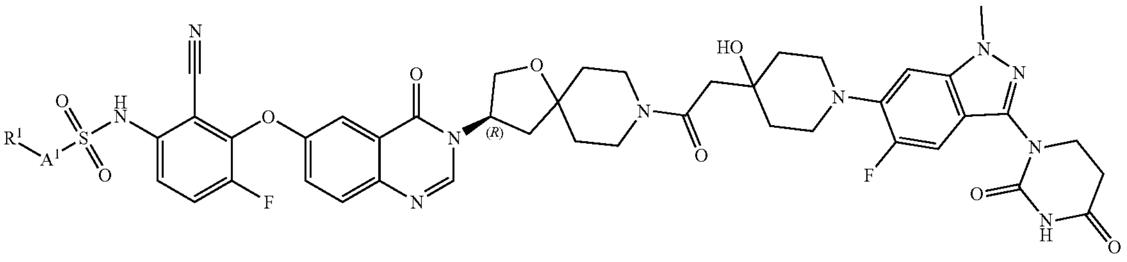
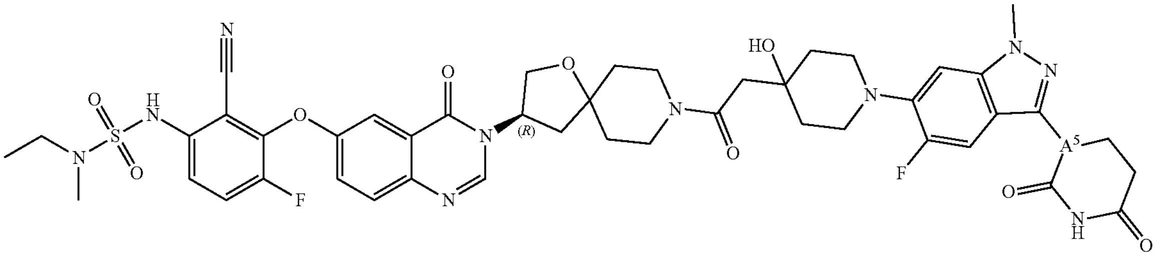

-continued
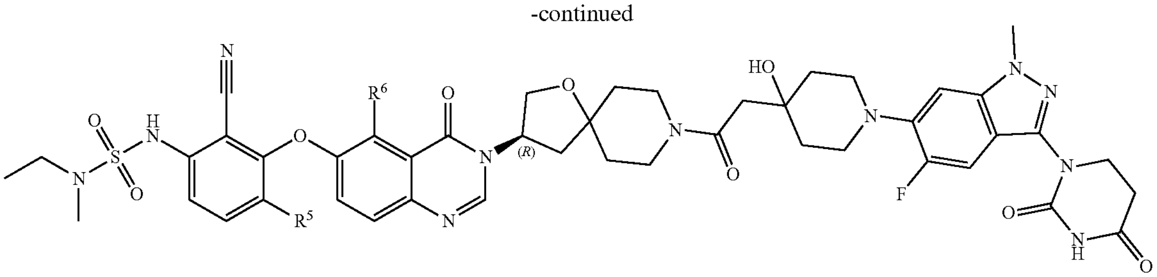
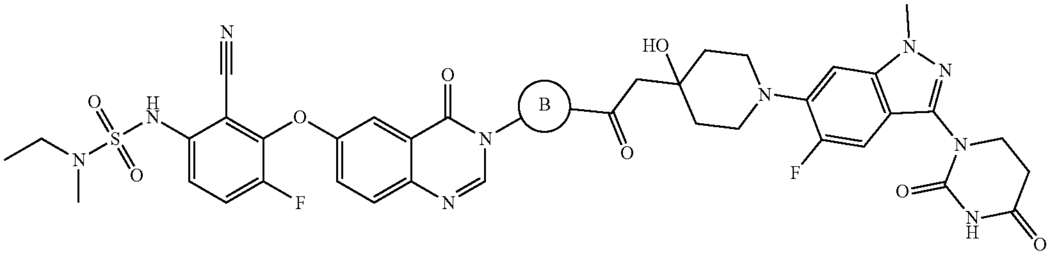
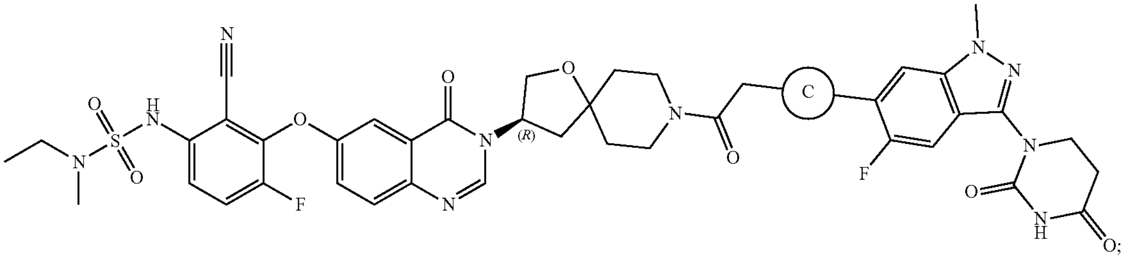
or a pharmaceutically acceptable salt thereof.
In certain embodiments the compound of the present invention is selected from:
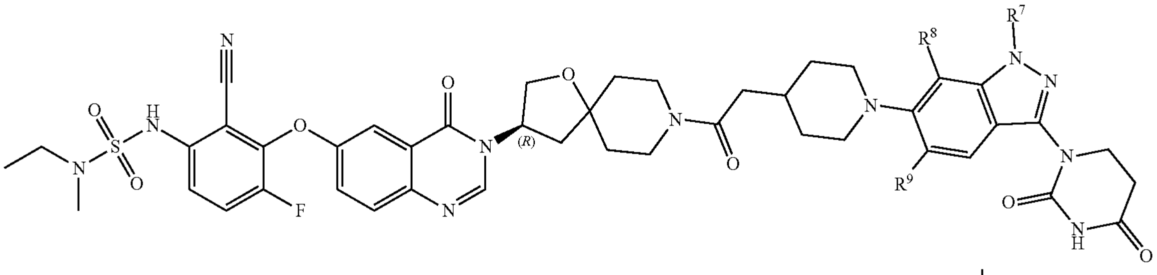
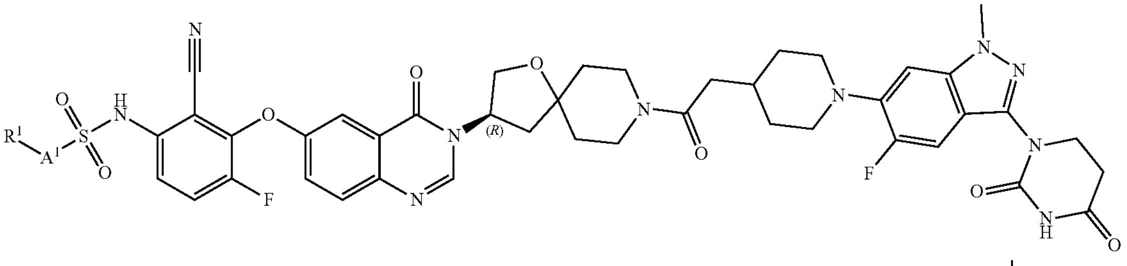
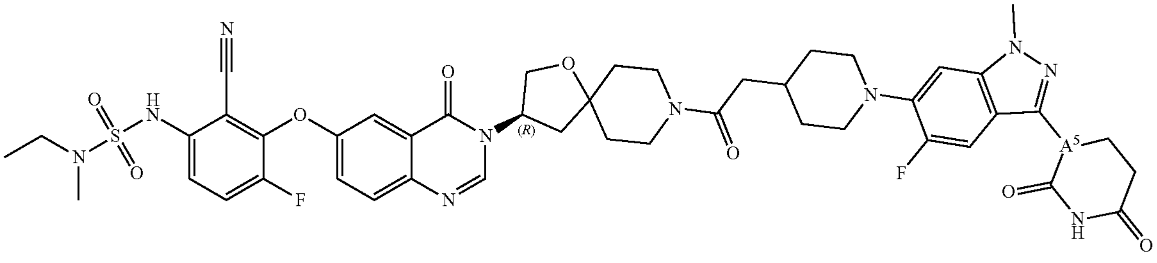

-continued
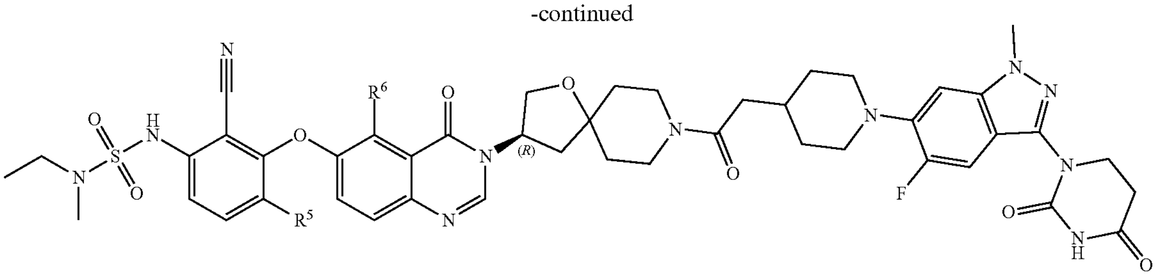
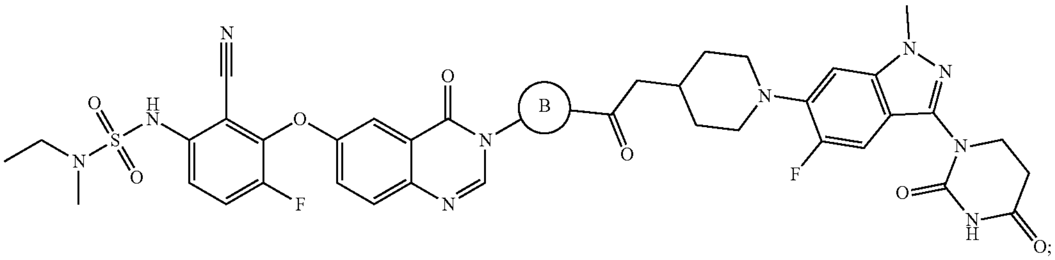
or a pharmaceutically acceptable salt thereof.
In certain embodiments the compound of the present invention is selected from:
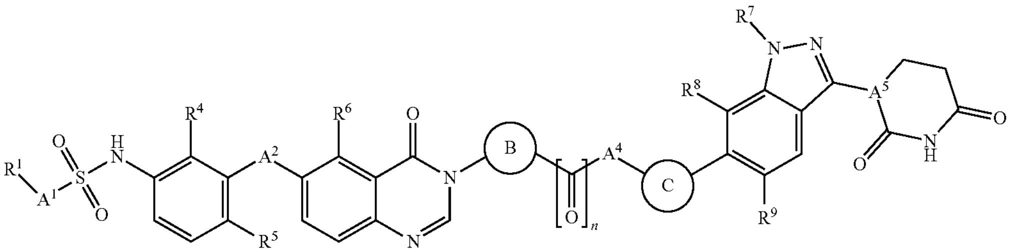
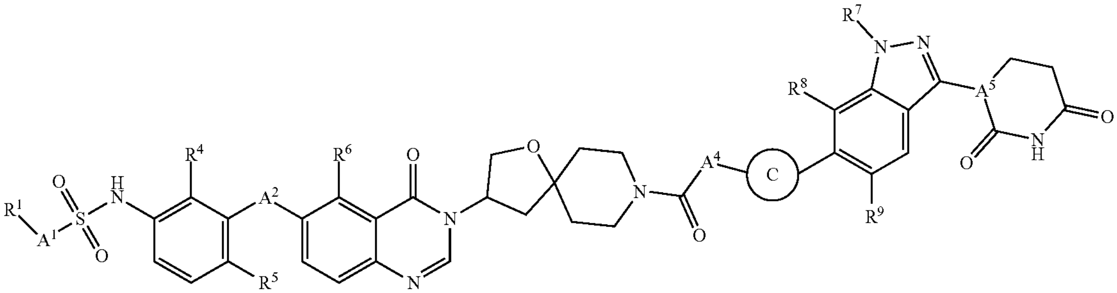
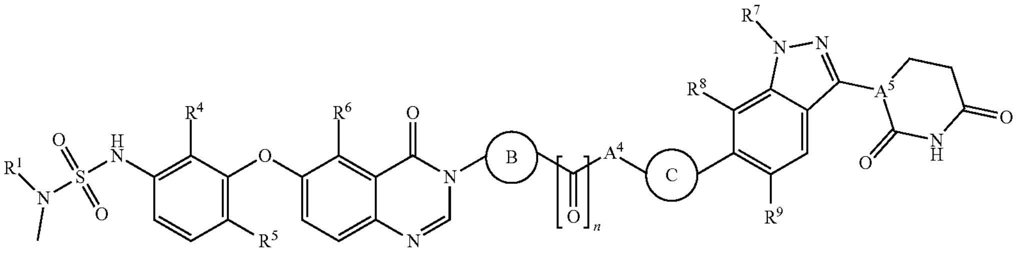

-continued
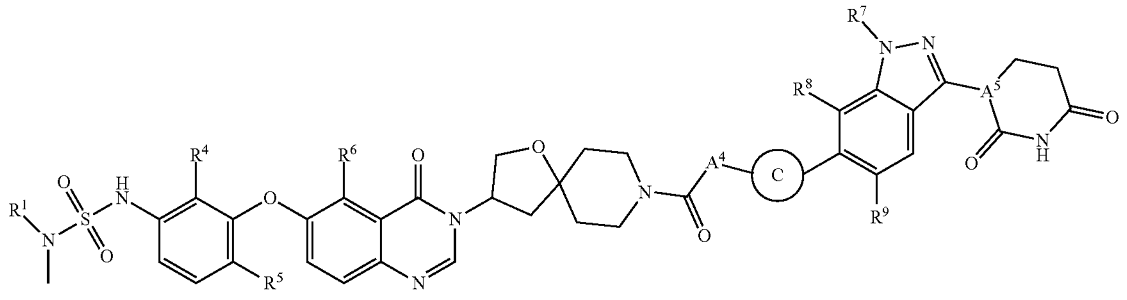
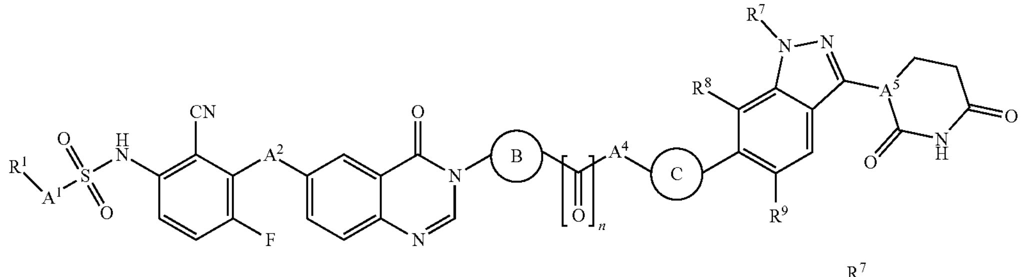
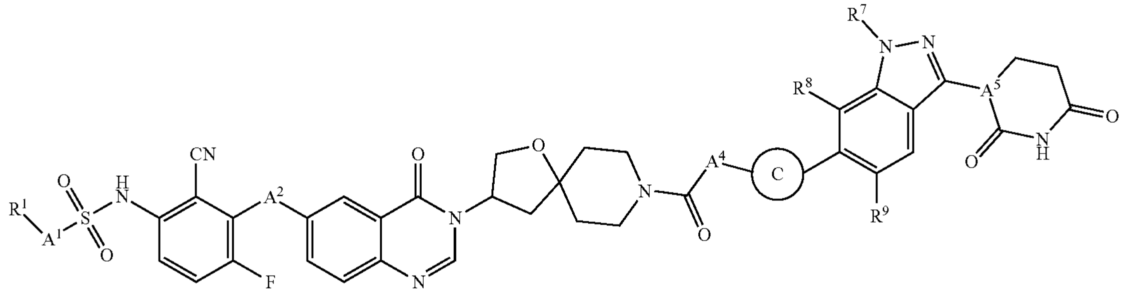
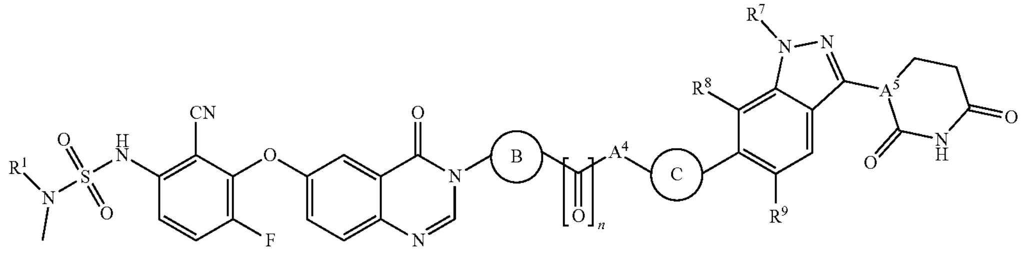
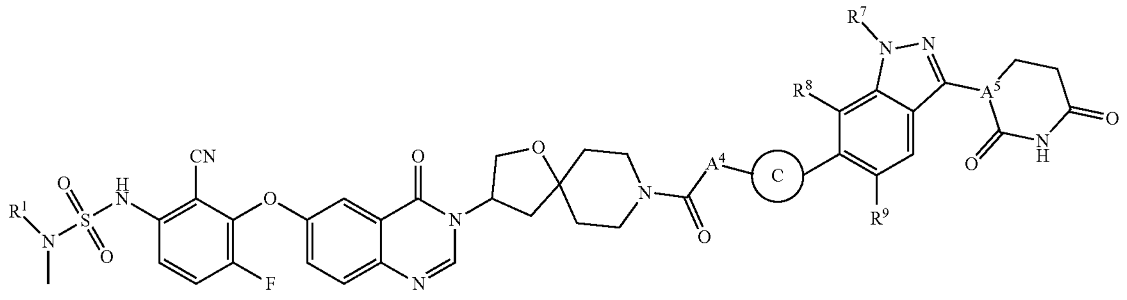
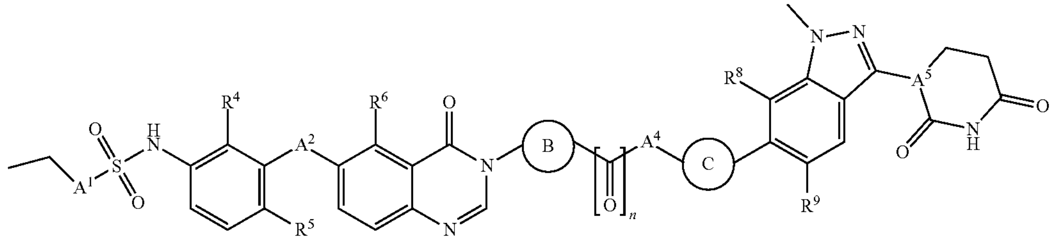

-continued
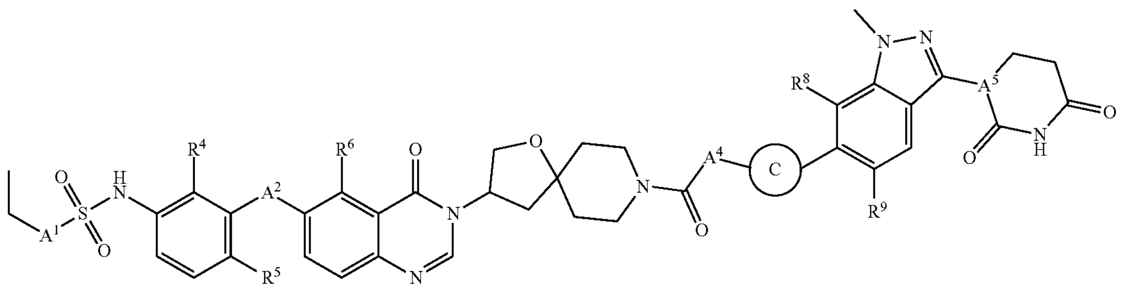
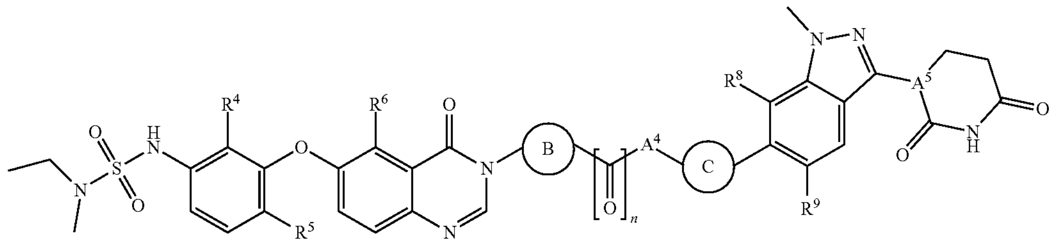
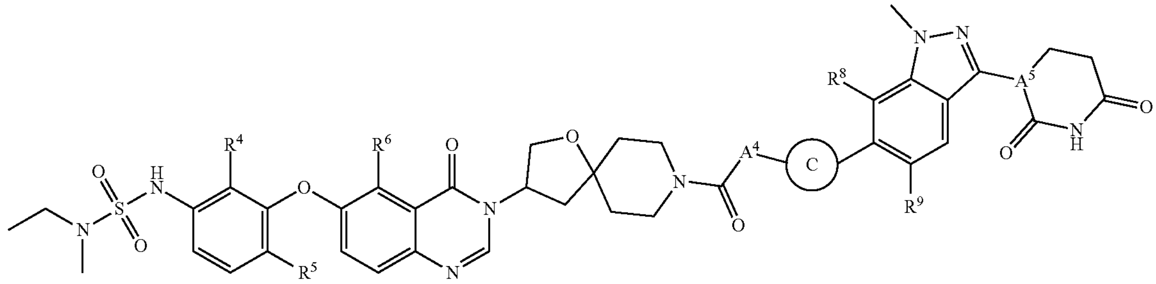
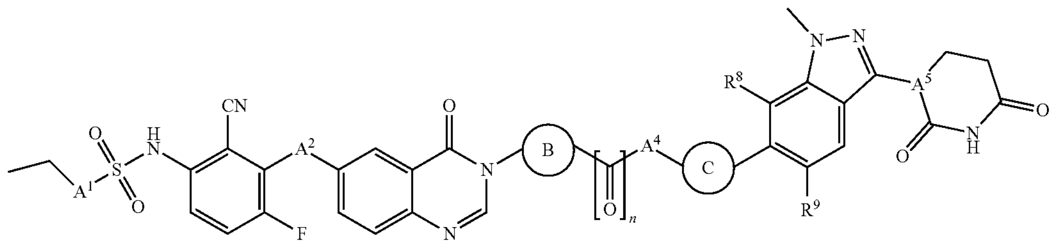
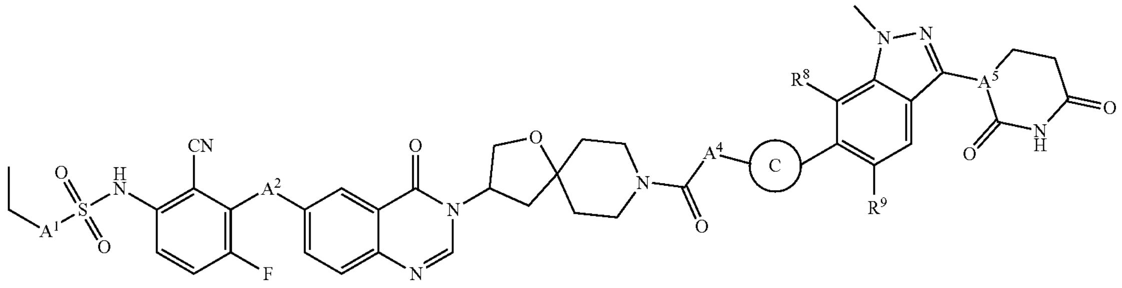
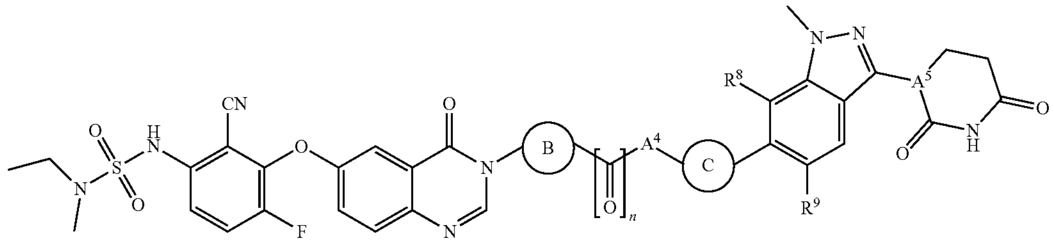

-continued
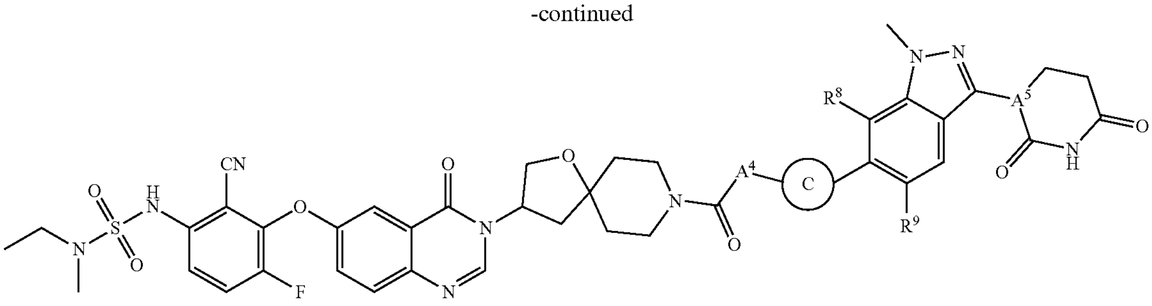
or a pharmaceutically acceptable salt thereof.
In certain embodiments the compound of the present invention is selected from:
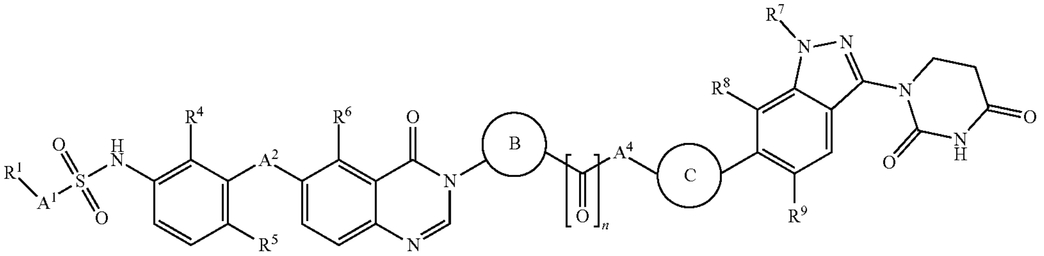
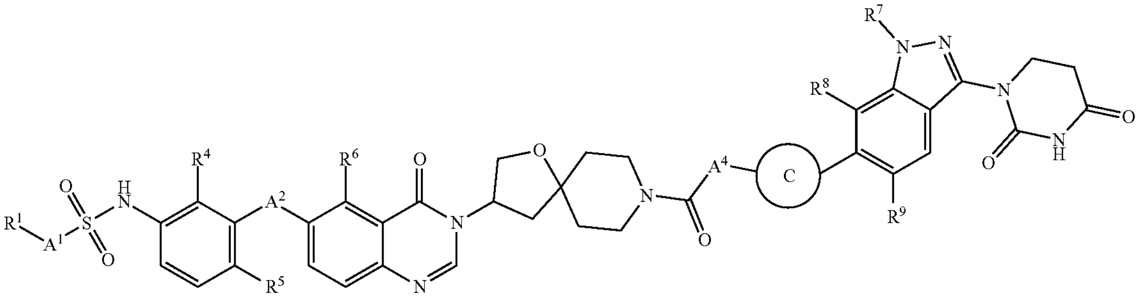
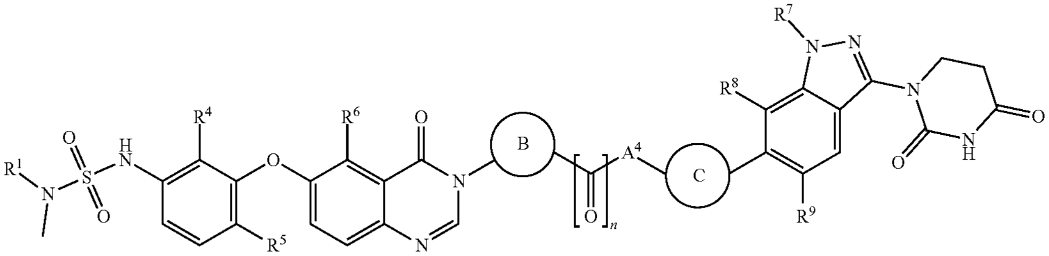
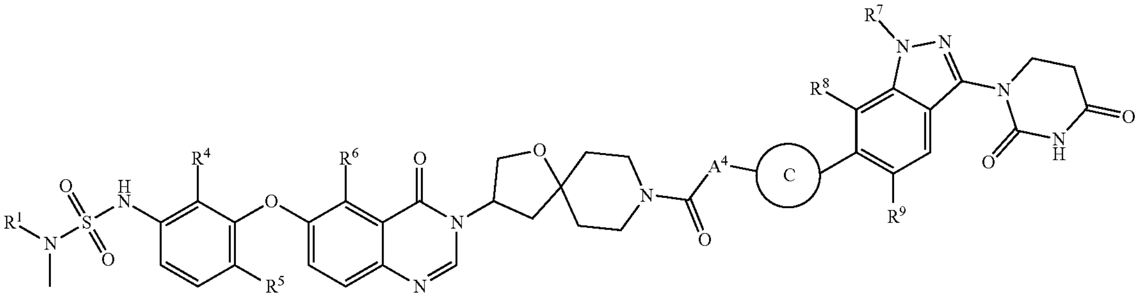

-continued
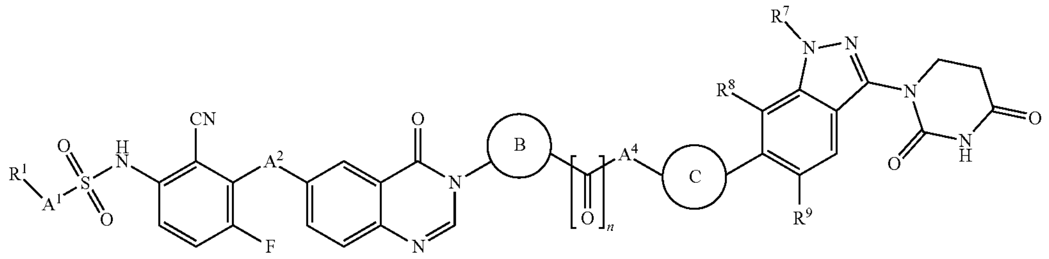
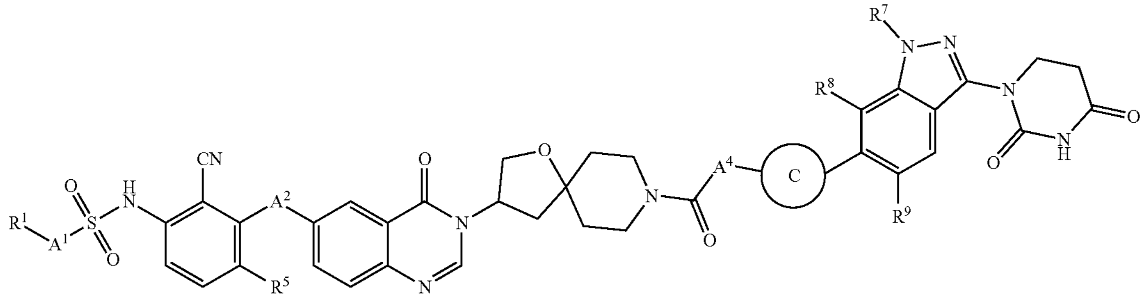
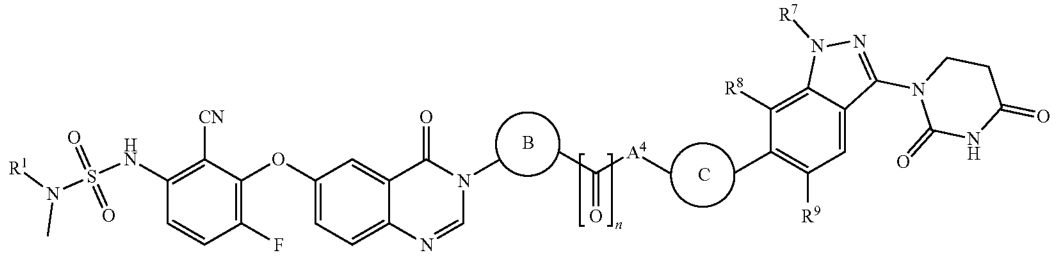
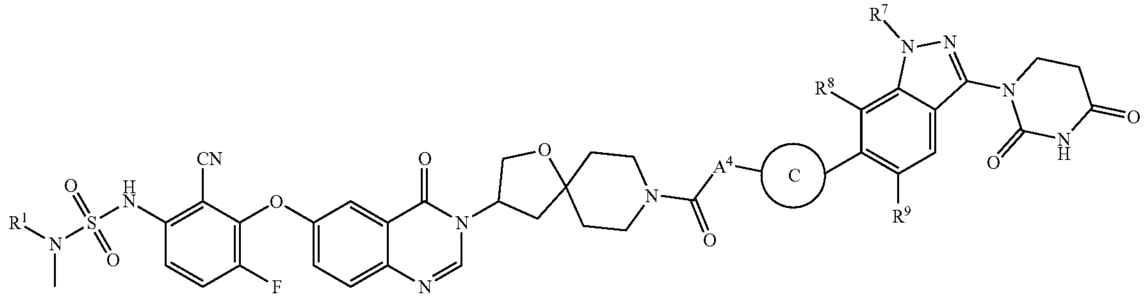
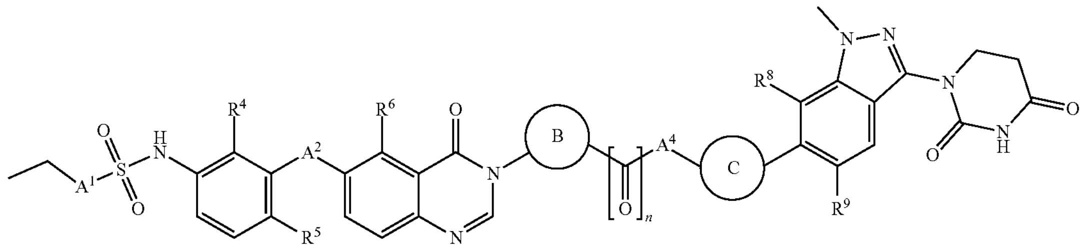
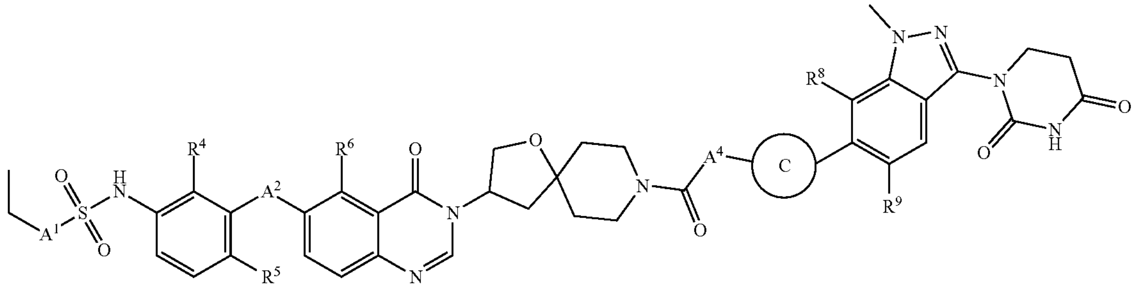

-continued
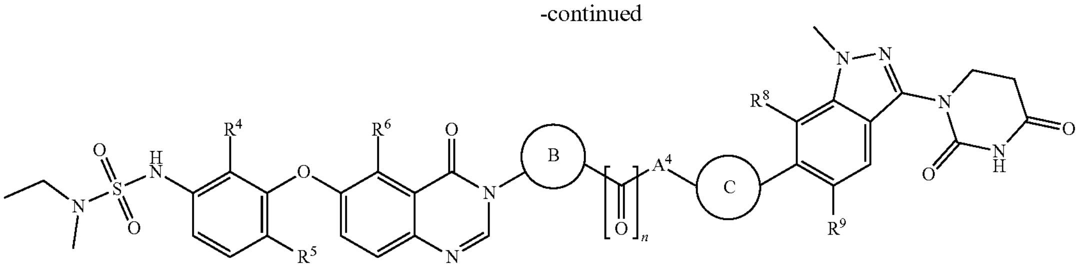
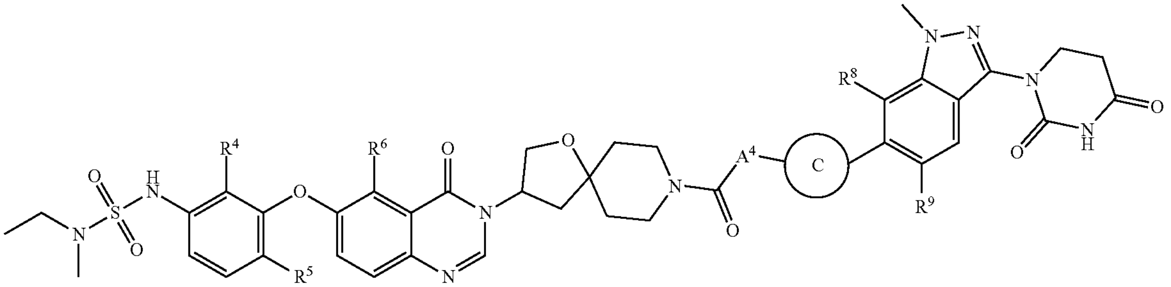
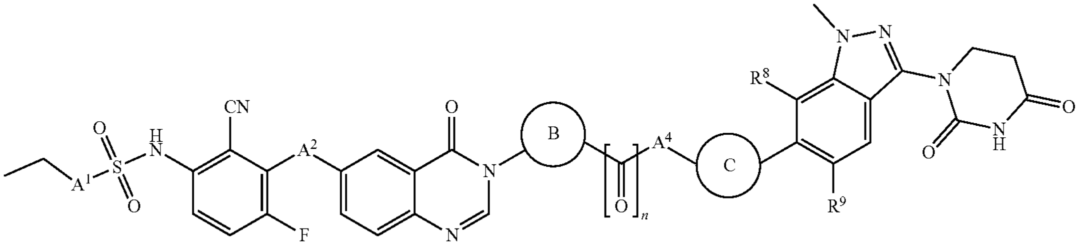
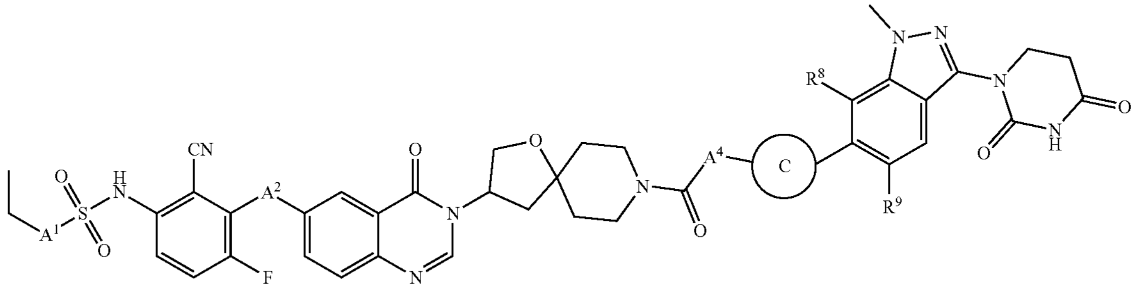
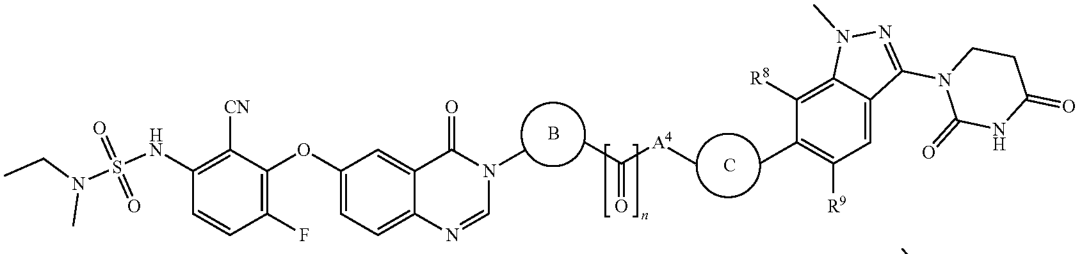
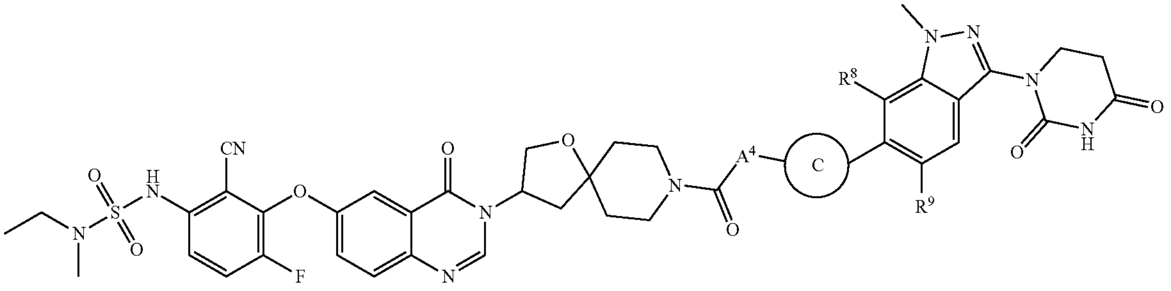
or a pharmaceutically acceptable salt thereof.
In certain embodiments the compound of the present invention is selected from:

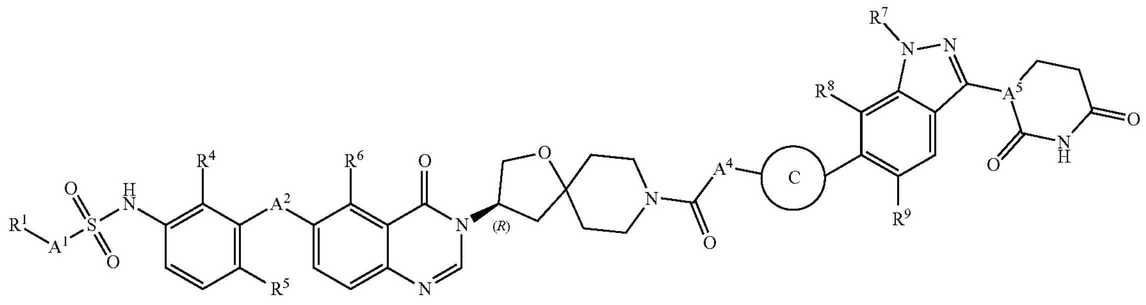
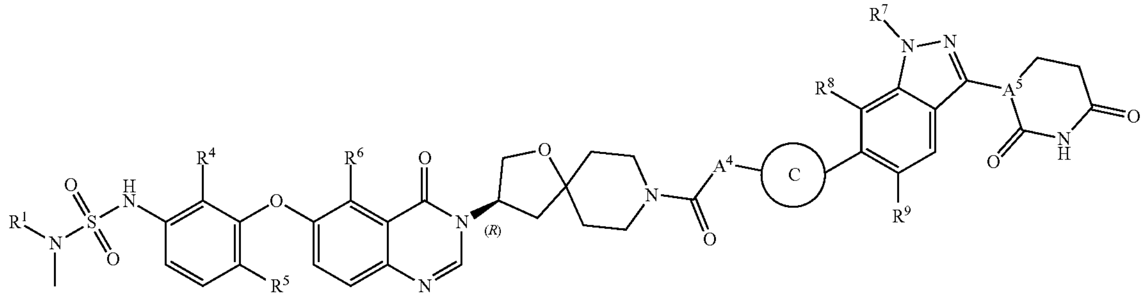
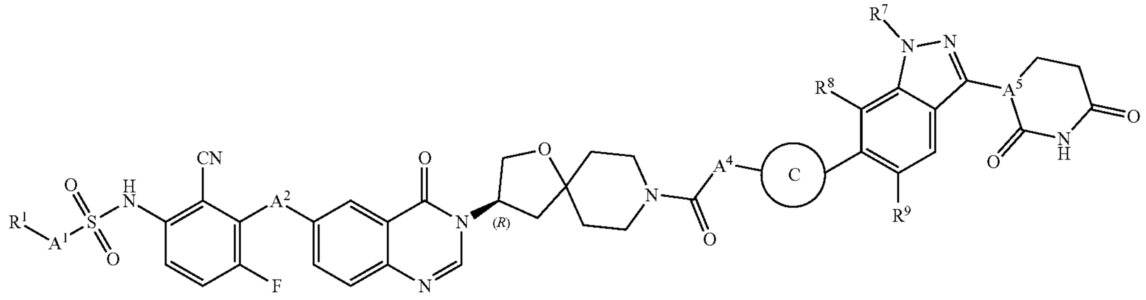
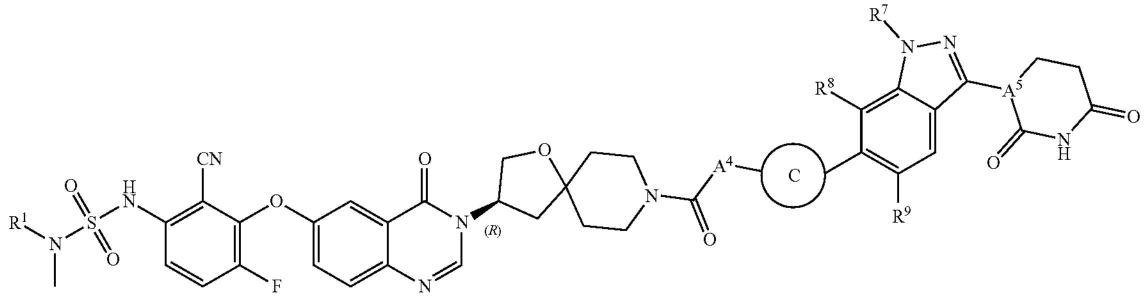
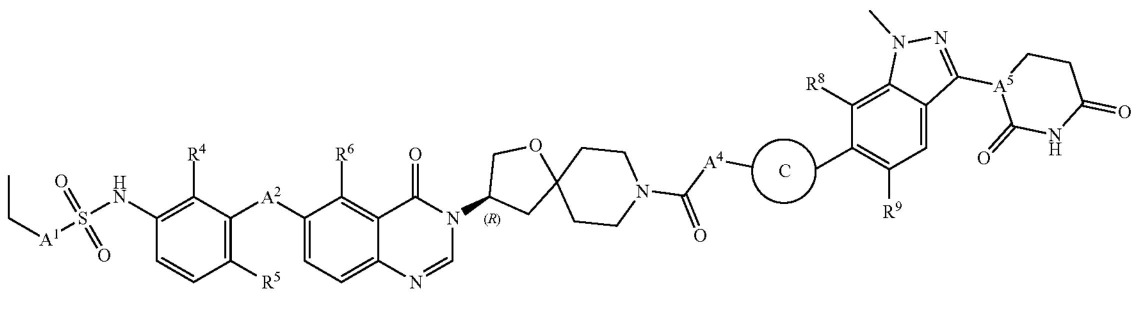

-continued
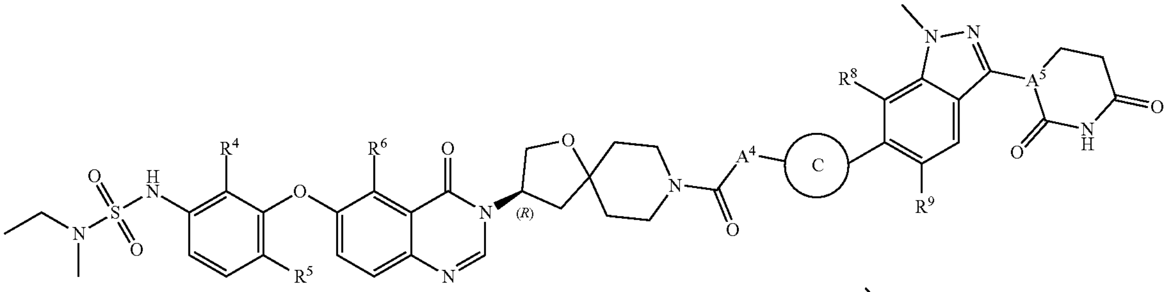
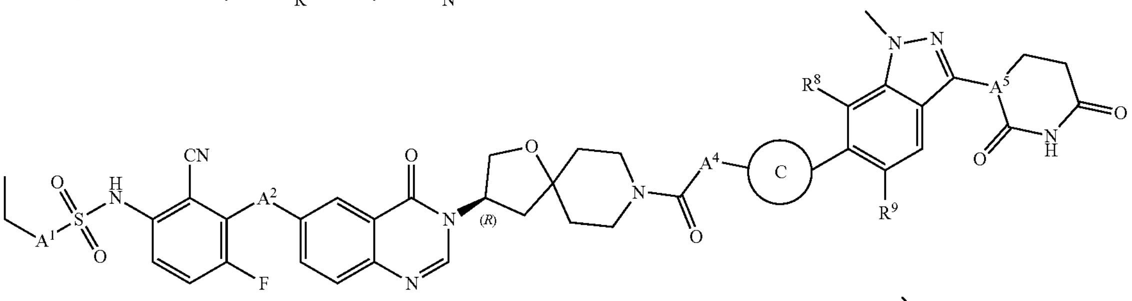
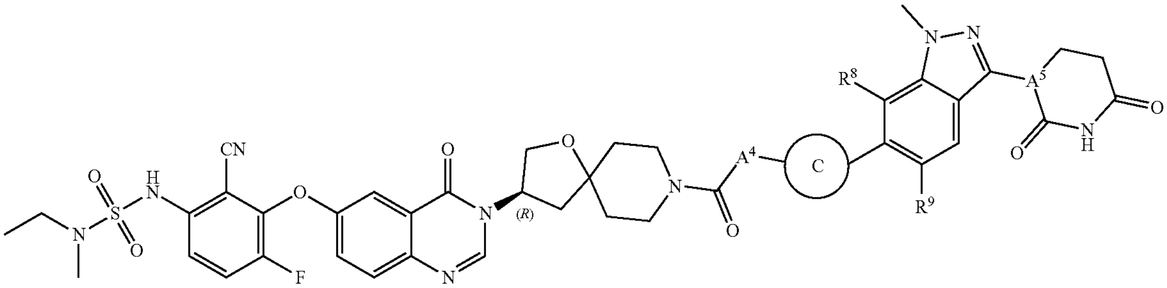
or a pharmaceutically acceptable salt thereof.
In certain embodiments the compound of the present invention is selected from:
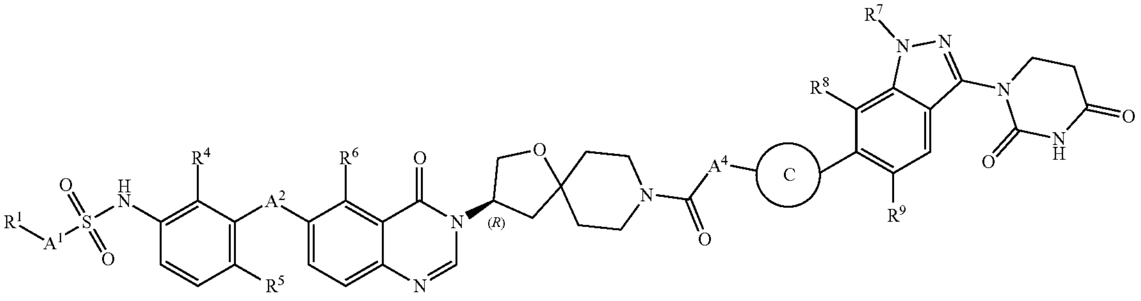
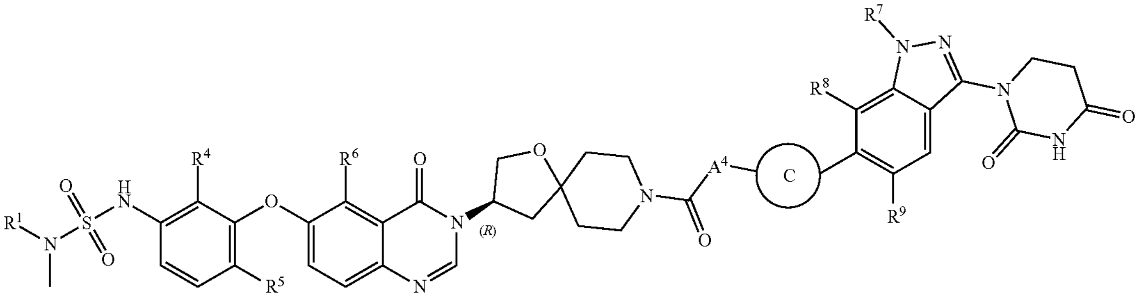

-continued
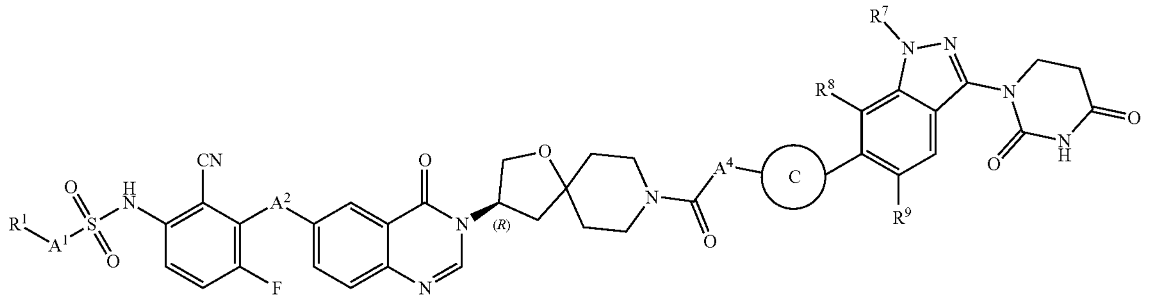
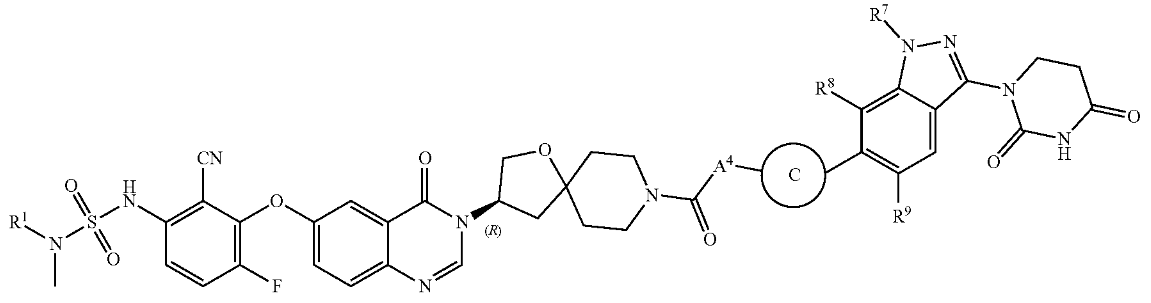
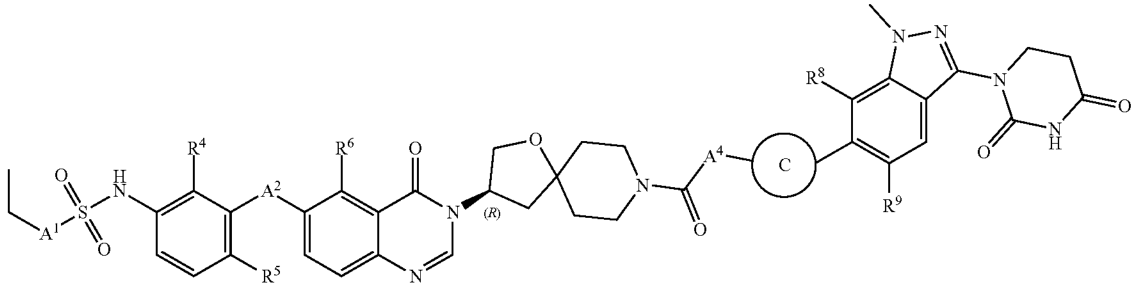
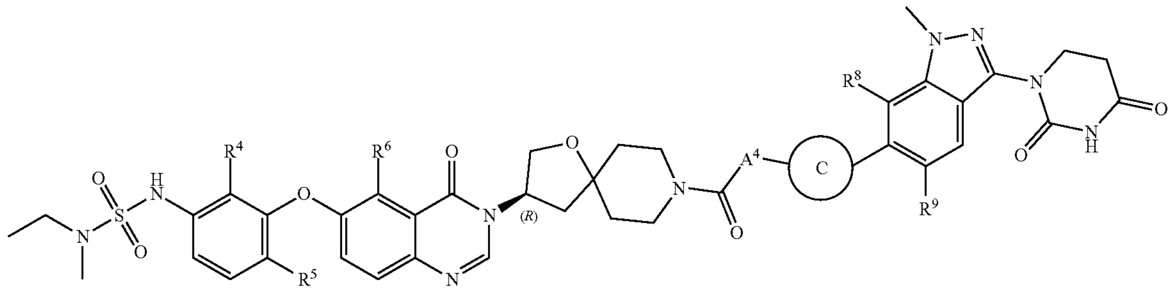
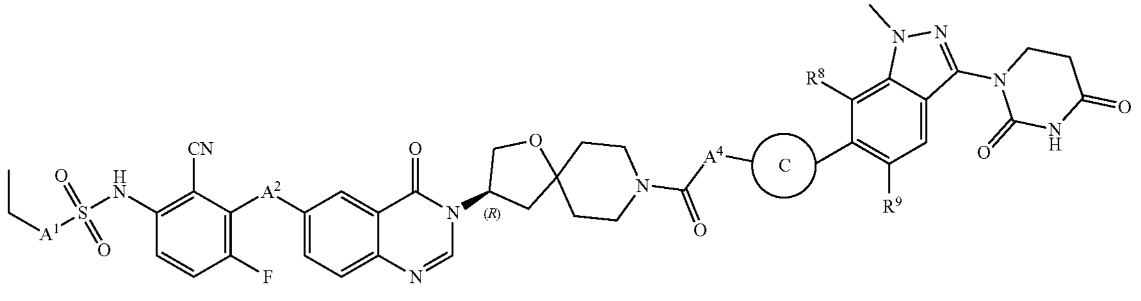

-continued
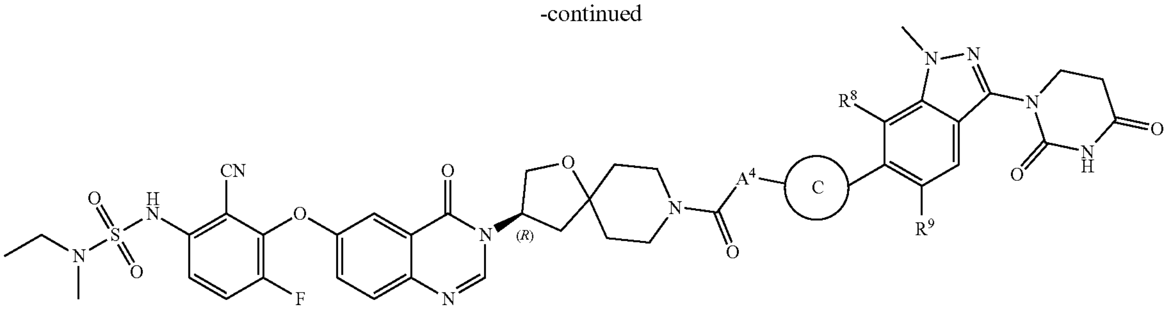
or a pharmaceutically acceptable salt thereof.
In certain embodiments the compound of the present invention is selected from:
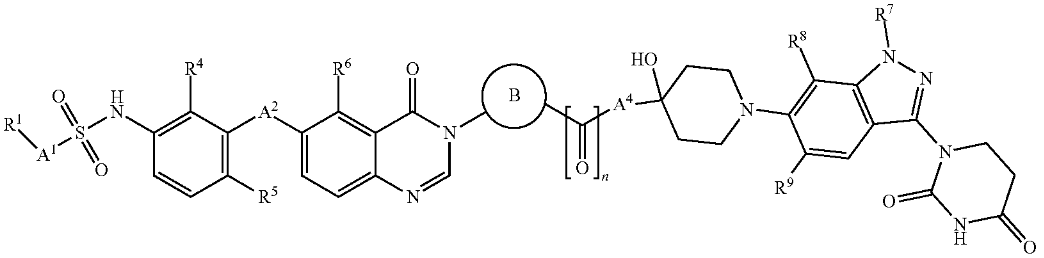
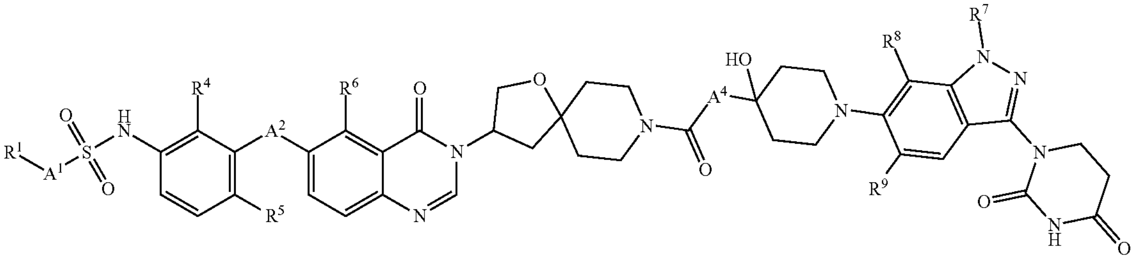
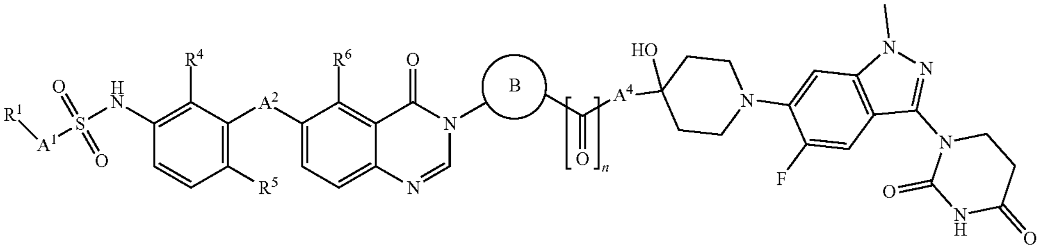
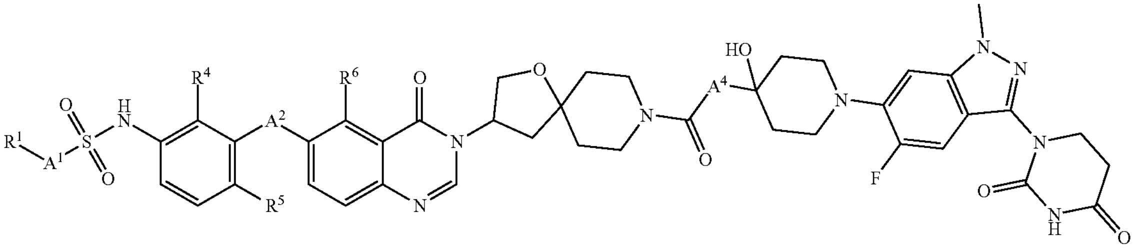

-continued
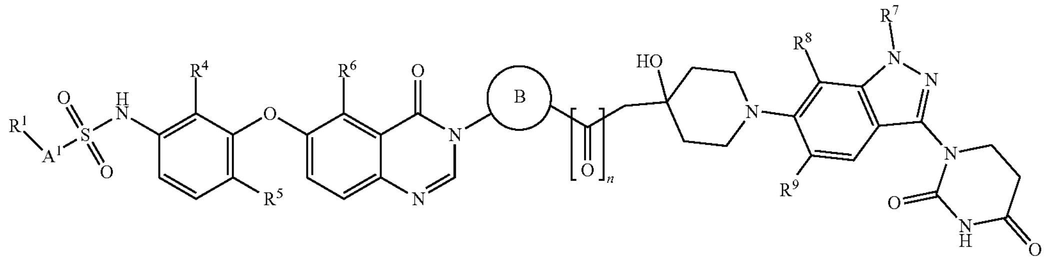
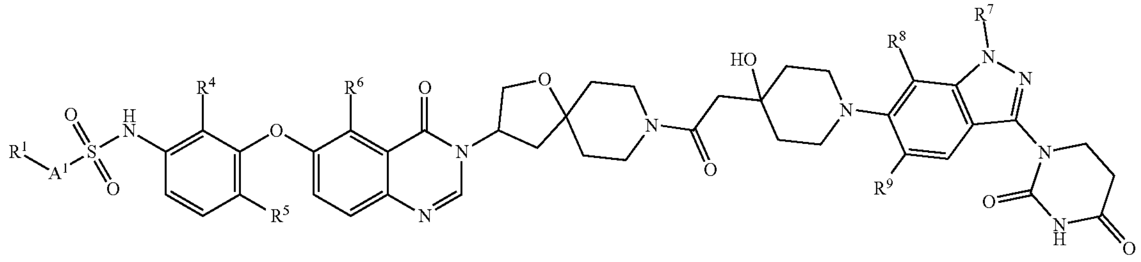
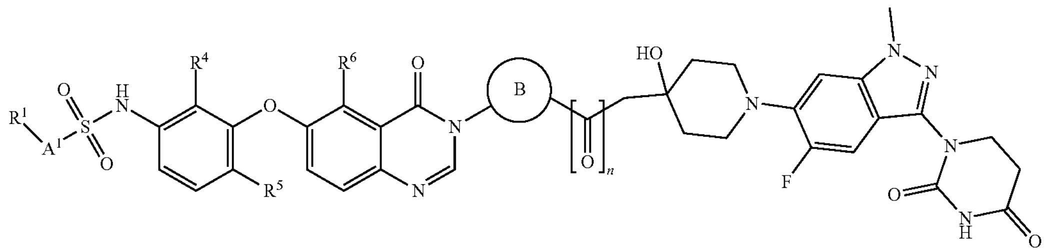
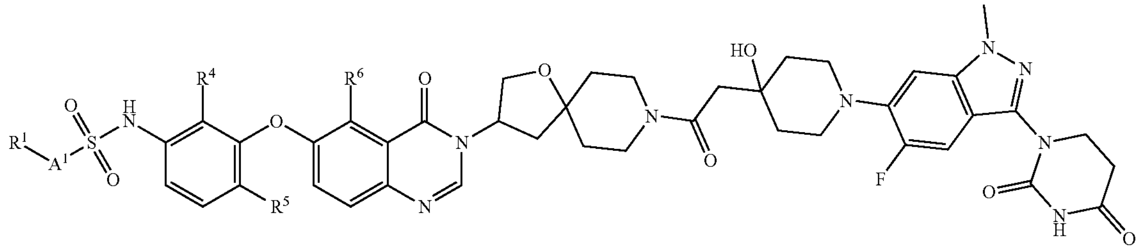
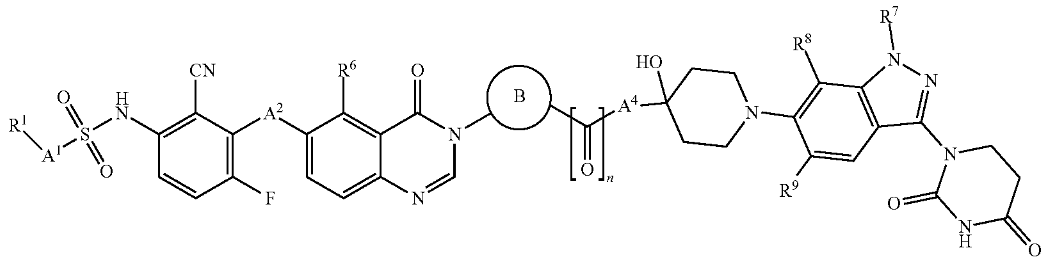
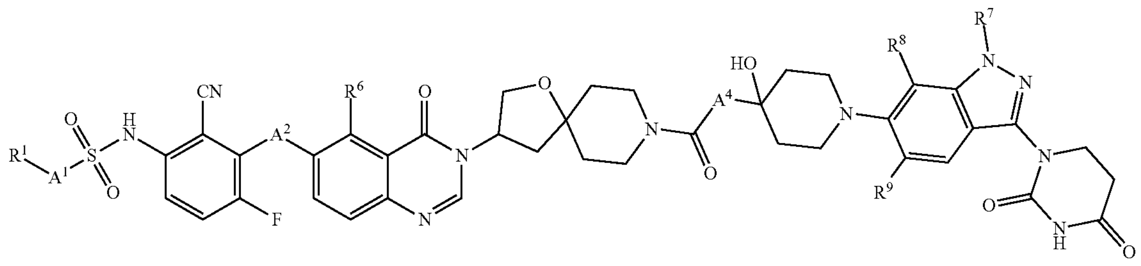

-continued
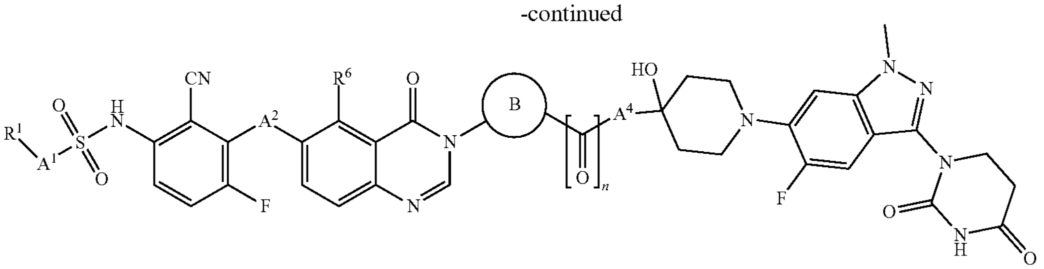
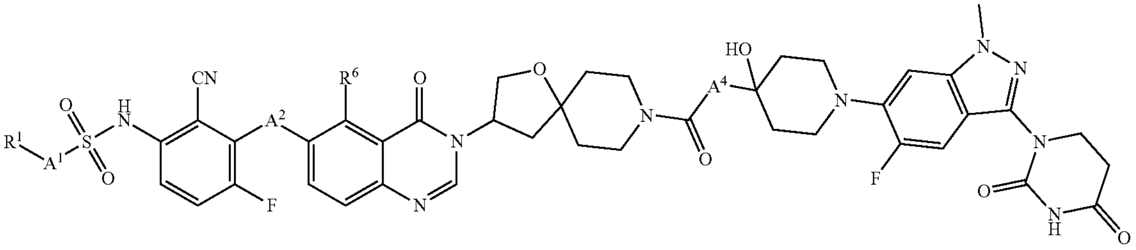
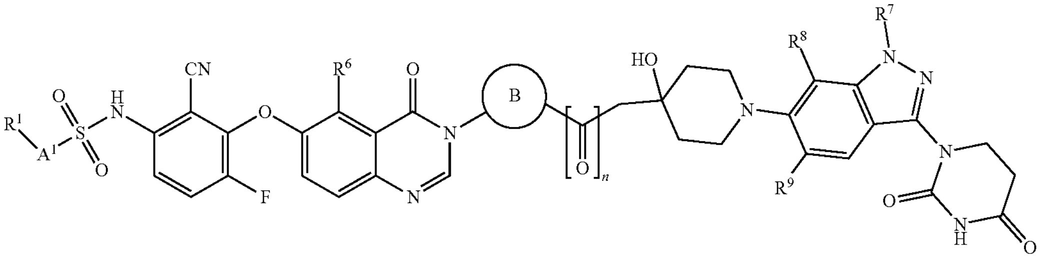
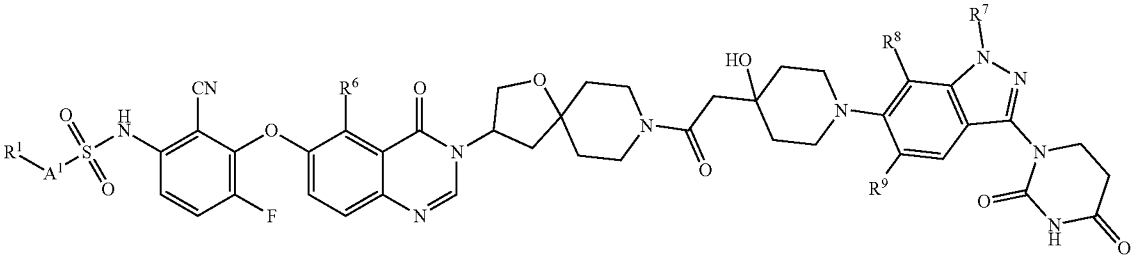
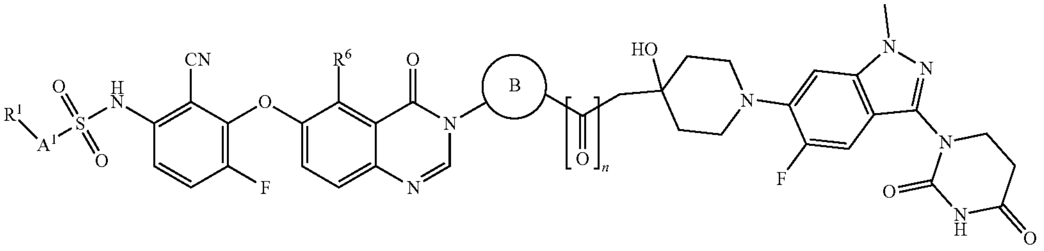
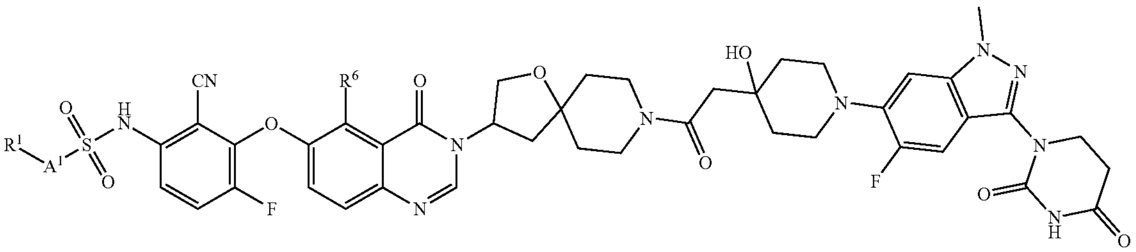
or a pharmaceutically acceptable salt thereof.
In certain embodiments the compound of the present invention is selected from:

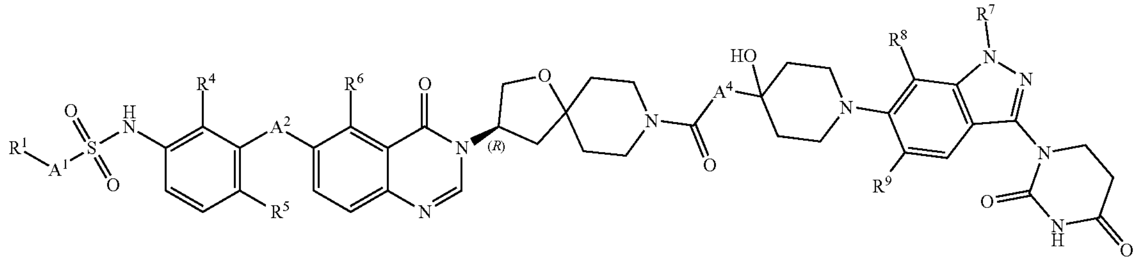
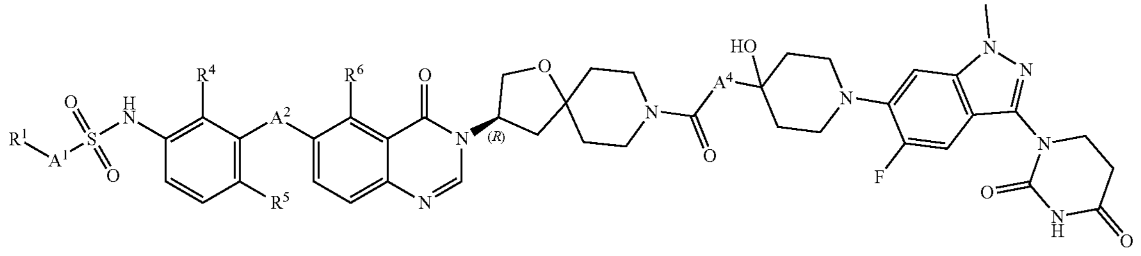
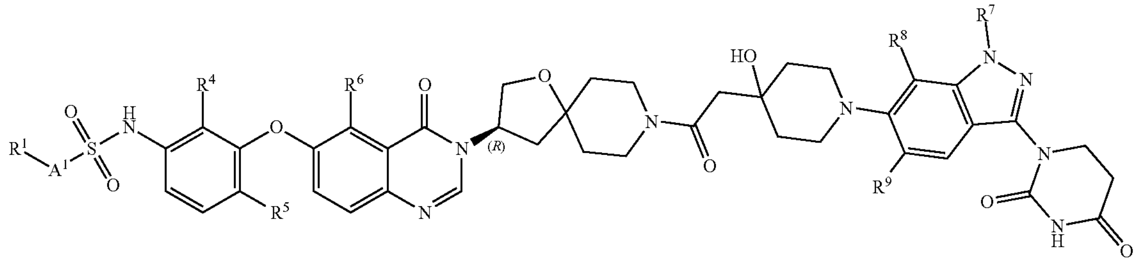
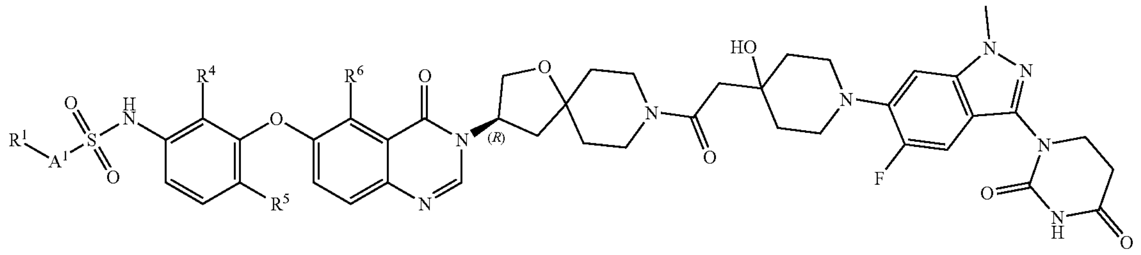
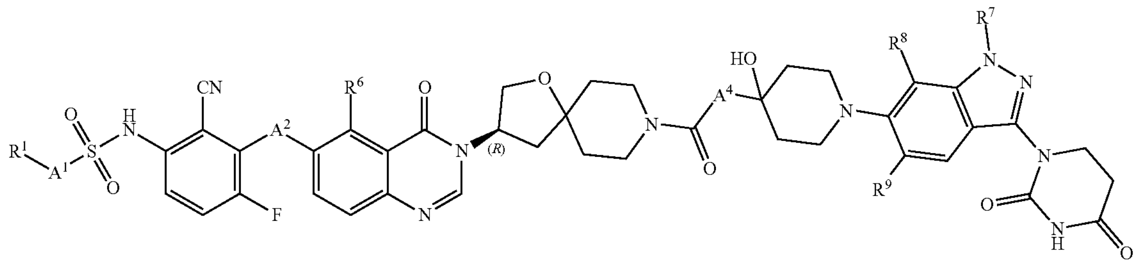
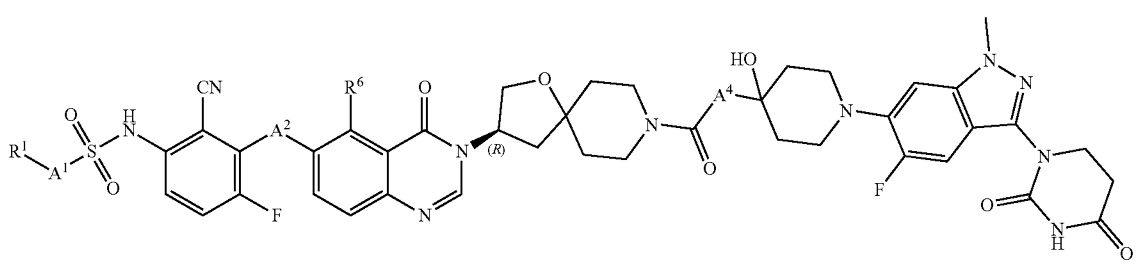

-continued

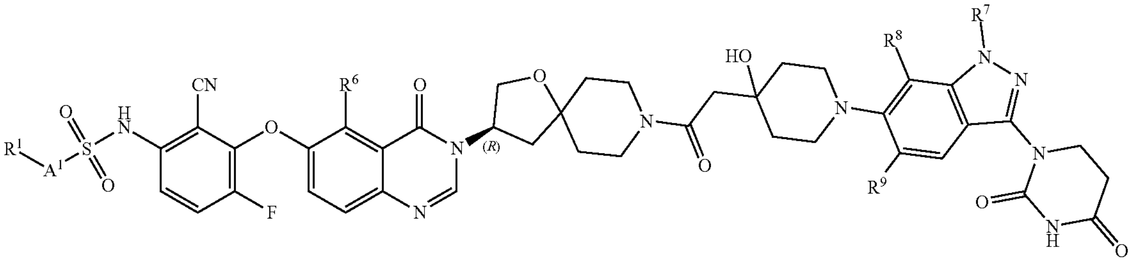

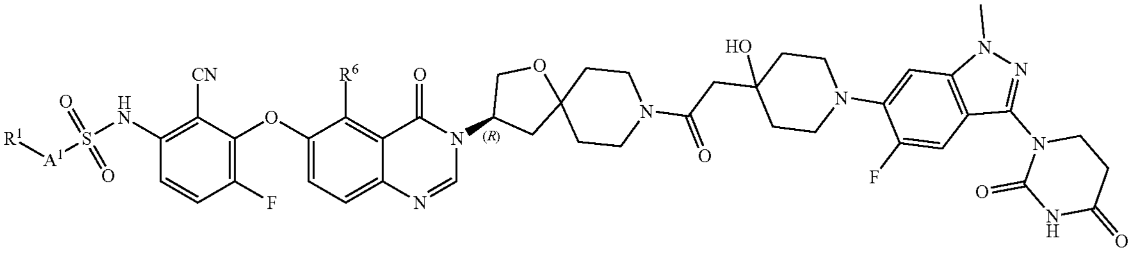

or a pharmaceutically acceptable salt thereof.

In certain embodiments a compound of Formula I is provided (I)

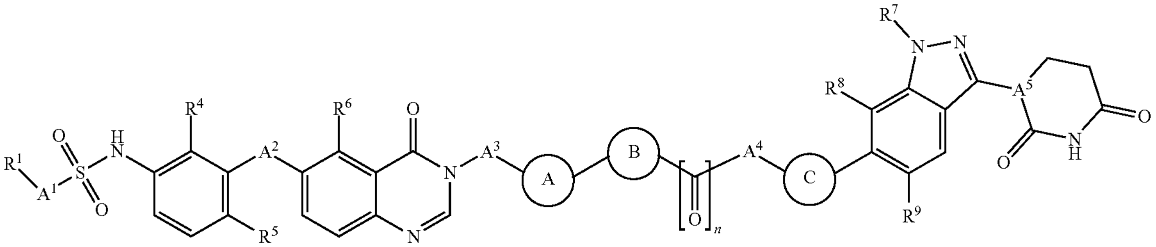

wherein $A^1$ is selected from —$NR^2$— and —$CHR^{2'}$;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C=O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

A is selected from a bond, pyrimidinyl, pyridinyl, pyrazolyl and 3-azabicyclo[3.1.0]hexyl;

B is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, and 8-azaspiro[4.5]decyl; wherein B is optionally substituted with one or two substituents independently selected from halogen, alkyl and alkoxy;

n is 0 or 1;

$A^4$ is selected from a bond, —$CH_2$—, —$(SO_2)$—$CH_2$—, —$CH(CH_2OH)$—, —NH— and —O—;

C is selected from azepanyl, azetidinyl, cycloalkyl, piperazinyl and piperidinyl; wherein C is optionally substituted with one or two substituents independently selected from halogen, hydroxy, alkyl and alkoxy;

$R^7$ is selected from hydrogen, alkyl, cyano, halogen and alkoxy;

$R^8$ is selected from hydrogen, alkyl, cyano, halogen and alkoxy;

$R^9$ is selected from hydrogen, alkyl, cyano, halogen and alkoxy; and $A^5$ is —CH— or —N—;

or a pharmaceutically acceptable salt thereof.

One embodiment of the invention provides a compound of Formula I wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C═O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, and —$CH_2$—$CH_2$—$CH_2$—;

A is selected from a bond, pyrimidinyl, pyridinyl, pyrazolyl and 3-azabicyclo[3.1.0]hexyl;

B is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, and 8-azaspiro[4.5]decyl;

n is 0 or 1;

$A^4$ is selected from a bond, —$CH_2$—, —$(SO_2)$—$CH_2$—, —$CH(CH_2OH)$—, —NH— and —O—;

C is selected from azetidinyl, cycloalkyl, piperazinyl, halopiperidinyl, hydroxypiperidinyl and piperidinyl;

$R^7$ is selected from hydrogen, alkyl, cyano, halogen and alkoxy;

$R^8$ is selected from hydrogen, alkyl, cyano, halogen and alkoxy;

$R^9$ is selected from hydrogen, alkyl, cyano, halogen and alkoxy; and $A^5$ is —CH— or —N—;

or a pharmaceutically acceptable salt thereof.

One embodiment of the invention provides a compound of Formula I wherein $A^1$ is selected from —$NR^2$— and —$CHR^{2'}$—;

$R^1$ is alkyl;

$R^2$ is selected from alkyl and cycloalkyl;

or $R^1$ and $R^2$ together with the nitrogen atom to which they are attached form heterocycloalkyl optionally substituted with one or two $R^3$;

$R^{2'}$ is alkyl;

or $R^1$ and $R^{2'}$ together with the carbon atom to which they are attached form cycloalkyl;

each $R^3$ is independently selected from halogen and alkoxy.

One embodiment of the invention provides a compound of Formula I wherein $A^1$ is selected from —$NR^2$— and —$CHR^{2'}$—;

$R^1$ is methyl;

$R^2$ is selected from ethyl, tert-butyl and cyclopropyl;

or $R^1$ and $R^2$ together with the nitrogen atom to which they are attached form heterocycloalkyl optionally substituted with one or two $R^3$;

$R^{2'}$ is methyl;

or $R^1$ and $R^{2'}$ together with the carbon atom to which they are attached form cycloalkyl;

each $R^3$ is independently selected from fluoro and methoxy.

The invention further provides:

A compound of Formula I wherein $R^1$ is methyl, or a pharmaceutically acceptable salt thereof;

A compound of Formula I wherein $R^2$ is selected from ethyl, tert-butyl and cyclopropyl, or a pharmaceutically acceptable salt thereof;

A compound of Formula I wherein $A^1$ is —$NR^2$—, or a pharmaceutically acceptable salt thereof;

A compound of Formula I wherein $A^1$ is —$CHR^{2'}$—, or a pharmaceutically acceptable salt thereof;

A compound of Formula I wherein the heterocycloalkyl which is formed by $R^1$ and $R^2$ together with the nitrogen atom to which they are attached is selected from pyrrolidinyl, piperidinyl, azetidinyl and 3-azabicyclo[3.1.0]hexyl, and wherein the heterocycloalkyl is in each instance optionally substituted with one or two $R^3$ independently selected from fluoro and methoxy, or a pharmaceutically acceptable salt thereof;

A compound of Formula I wherein the cycloalkyl which is formed by $R^1$ and $R^{2'}$ together with the carbon atom to which they are attached is selected from cyclopropyl, cyclobutyl, cyclopentyl and cyclohexyl, or a pharmaceutically acceptable salt thereof;

A compound of Formula I wherein each $R^3$ is independently selected from fluoro and methoxy, or a pharmaceutically acceptable salt thereof;

A compound of Formula I wherein $R^4$ is cyano, or a pharmaceutically acceptable salt thereof;

A compound of Formula I wherein $R^4$ is fluoro, or a pharmaceutically acceptable salt thereof;

A compound of Formula I wherein $R^5$ is halogen, or a pharmaceutically acceptable salt thereof;

A compound of Formula I wherein $R^5$ is fluoro, or a pharmaceutically acceptable salt thereof;

A compound of Formula I wherein $A^2$ is selected from —O— and —NH—, or a pharmaceutically acceptable salt thereof;

A compound of Formula I wherein $A^2$ is —O—, or a pharmaceutically acceptable salt thereof;

A compound of Formula I wherein $A^2$ is —NH—, or a pharmaceutically acceptable salt thereof; A compound of Formula I wherein $R^6$ is selected from hydrogen, halogen, hydroxy, amino, alkoxy and dialkylamino, or a pharmaceutically acceptable salt thereof;

A compound of Formula I wherein $R^6$ is selected from hydrogen, fluoro, chloro, hydroxy, amino, methoxy and dimethylamino, or a pharmaceutically acceptable salt thereof;

A compound of Formula I wherein $A^3$ is selected from a bond, —$CH_2$—$CH_2$— and —$CH_2$—$CH_2$—$CH_2$—, or a pharmaceutically acceptable salt thereof;

A compound of Formula I wherein $A^3$ is a bond, or a pharmaceutically acceptable salt thereof;

A compound of Formula I wherein A is selected from a bond and pyrimidinyl, or a pharmaceutically acceptable salt thereof;

A compound of Formula I wherein A is a bond, or a pharmaceutically acceptable salt thereof;

A compound of Formula I wherein A is pyrimidinyl, or a pharmaceutically acceptable salt thereof;

A compound of Formula I wherein B is selected from piperidinyl, piperazinyl, 1-oxa-8-azaspiro[4.5]decyl, 3-azaspiro[5.5]undecyl, 7-azaspiro[3.5]nonyl, 1,1-di-oxo-1lambda6-thia-8-azaspiro[4.5]decyl, 1-oxaspiro[4.5]decyl, 1-methyl-1,8-diazaspiro[4.5]decyl and 8-azaspiro[4.5]decyl, or a pharmaceutically acceptable salt thereof;

A compound of Formula I wherein B is selected from piperidin-4-yl, piperazin-1-yl, 1-oxa-8-azaspiro[4.5]decyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl and 8-azaspiro[4.5]decyl, or a pharmaceutically acceptable salt thereof;

A compound of Formula I wherein B is selected from 1-oxa-8-azaspiro[4.5]decyl and 8-azaspiro[4.5]decyl, or a pharmaceutically acceptable salt thereof;

A compound of Formula I wherein B is 8-azaspiro[4.5]decyl, or a pharmaceutically acceptable salt thereof;

A compound of Formula I wherein $A^4$ is selected from a bond, $—CH_2—$ and $—(SO_2)—CH_2—$, or a pharmaceutically acceptable salt thereof;

A compound of Formula I wherein $A^4$ is $—CH_2—$, or a pharmaceutically acceptable salt thereof;

A compound of Formula I wherein C is selected from azetidinyl, cyclohexyl, piperazinyl, difluoropiperidinyl, hydroxypiperidinyl, phosphatepiperidinyl and piperidinyl, or a pharmaceutically acceptable salt thereof;

A compound of Formula I wherein C is selected from azetidinyl, cyclohexyl, piperazinyl, difluoropiperidinyl, hydroxypiperidinyl and piperidinyl, or a pharmaceutically acceptable salt thereof;

A compound of Formula I wherein C is selected from azetidin-1-yl, cyclohexyl, piperazin-1-yl, 3,3-difluoropiperidin-1-yl, 4-hydroxypiperidin-4-yl, piperidin-1-yl and piperidin-4-yl, or a pharmaceutically acceptable salt thereof;

A compound of Formula I wherein C is selected from hydroxypiperidinyl and piperidinyl, or a pharmaceutically acceptable salt thereof;

A compound of Formula I wherein C is selected from hydroxypiperidin-4-yl, piperidin-1-yl and piperidin-4-yl, or a pharmaceutically acceptable salt thereof;

A compound of Formula I wherein $R^7$ is alkyl, or a pharmaceutically acceptable salt thereof;

A compound of Formula I wherein $R^7$ is methyl, or a pharmaceutically acceptable salt thereof;

A compound of Formula I wherein $R^8$ is selected from hydrogen and halogen, or a pharmaceutically acceptable salt thereof;

A compound of Formula I wherein $R^8$ is selected from hydrogen and fluoro, or a pharmaceutically acceptable salt thereof;

A compound of Formula I wherein $R^9$ is selected from hydrogen and halogen, or a pharmaceutically acceptable salt thereof;

A compound of Formula I wherein $R^9$ is selected from hydrogen and fluoro, or a pharmaceutically acceptable salt thereof;

A compound of Formula I wherein $A^5$ is —NH—, or a pharmaceutically acceptable salt thereof;

A compound of Formula I wherein $A^5$ is —CH—, or a pharmaceutically acceptable salt thereof;

A compound of Formula I wherein n is 1, or a pharmaceutically acceptable salt thereof; and A compound of Formula I wherein n is 0, or a pharmaceutically acceptable salt thereof.

The invention further provides a compound of Formula I selected from

6-[2-cyano-3-[[ethyl(methyl)sulfamoyl]amino]-6-fluoro-phenoxy]-3-[2-[1-[2-[4-[3-(2,6-dioxopiperidin-3-yl)-1-methylindazol-6-yl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[3-[1-[2-[4-[3-(2,6-dioxopiperidin-3-yl)-1-methylindazol-6-yl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[1-[l-[2-[4-[3-(2,6-dioxopiperidin-3-yl)-1-methylindazol-6-yl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[7-[2-[4-[3-(2,4-dioxo-1,3-diazinan-1-yl)-1-methylindazol-6-yl]piperidin-1-yl]acetyl]-7-azaspiro[3.5]nonan-2-yl]-4-oxoquinazoline;

3-[6-[2-cyano-3-[[ethyl(methyl)sulfamoyl]amino]-6-fluoro-phenoxy]-4-oxoquinazolin-3-yl]-8-[2-[4-[3-(2,4-dioxo-1,3-diazinan-1-yl)-1-methylindazol-6-yl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[7-[2-[4-[3-(2,6-dioxopiperidin-3-yl)-1-methylindazol-6-yl]piperidin-1-yl]acetyl]-7-azaspiro[3.5]nonan-2-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,6-dioxopiperidin-3-yl)-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,6-dioxopiperidin-3-yl)-1-methylindazol-6-yl]-4-hydroxypiperidin-4-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[4-[3-(2,6-dioxopiperidin-3-yl)-1-methylindazol-6-yl]piperidin-1-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3S)-8-[2-[4-[3-(2,4-dioxo-1,3-diazinan-1-yl)-1-methylindazol-6-yl]piperidin-1-yl]acetyl]-8-azaspiro[4.5]decan-3-yl]-4-oxoquinazoline;

9-[6-[2-cyano-3-[[ethyl(methyl)sulfamoyl]amino]-6-fluoro-phenoxy]-4-oxoquinazolin-3-yl]-3-[2-[4-[3-(2,4-dioxo-1,3-diazinan-1-yl)-1-methylindazol-6-yl]piperidin-1-yl]acetyl]-3-azaspiro[5.5]undecane;

9-[6-[2-cyano-3-[[ethyl(methyl)sulfamoyl]amino]-6-fluoro-phenoxy]-4-oxoquinazolin-3-yl]-3-[2-[4-[3-(2,6-dioxopiperidin-3-yl)-1-methylindazol-6-yl]piperidin-1-yl]acetyl]-3-azaspiro[5.5]undecane;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane; 9-[6-[2-cyano-3-[[ethyl(methyl)sulfamoyl]amino]-6-fluorophenoxy]-4-oxoquinazolin-3-yl]-3-[2-[1-[3-(2,4-dioxo-1,3-diazinan-1-yl)-5-fluoro-1-methylindazol-6-yl]-4-hydroxypiperidin-4-yl]acetyl]-3-azaspiro[5.5]undecane;

6-[2-cyano-3-[[ethyl(methyl)sulfamoyl]amino]-6-fluoro-phenoxy]-3-[(3S)-8-[2-[1-[3-(2,4-dioxo-1,3-diazinan-1-yl)-5-fluoro-1-methylindazol-6-yl]-4-hydroxypiperidin-4-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3S)-8-[2-[4-[3-(2,6-dioxopiperidin-3-yl)-1-methylindazol-6-yl]-3,3-difluoropiperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]-3,3-difluoropiperidin-1-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[4-[3-(2,4-dioxo-1,3-diazinan-1-yl)-5-fluoro-1-methylindazol-6-yl]piperazin-1-yl]acetyl]-8-azaspiro[4.5]decan-3-yl]-4-oxoquinazoline; 9-[6-[2-cyano-3-[[ethyl(methyl)sulfamoyl]amino]-6-fluorophenoxy]-4-oxoquinazolin-3-yl]-3-[2-[4-[3-(2,4-dioxo-1,3-diazinan-1-yl)-5-fluoro-1-methylindazol-6-yl]piperazin-1-yl]acetyl]-3-azaspiro[5.5]undecane;

(3R)-3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-5-fluoro-1-methylindazol-6-yl]piperazin-1-yl]acetyl]-1-oxa-8-azaspiro[4.5]decane;

(3R)—N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

6-[2-chloro-3-[[ethyl(methyl)sulfamoyl]amino]-6-fluoro-phenoxy]-3-[(3S)-8-[2-[4-[3-(2,6-dioxopiperidin-3-yl)-1-methylindazol-6-yl]piperidin-1-yl]acetyl]-8-azaspiro[4.5]decan-3-yl]-4-oxoquinazoline;

N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]cyclopentanesulfonamide;

N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]propane-2-sulfonamide;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]cyclohexyl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]cyclohexyl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[3-[3-(2,6-dioxopiperidin-3-yl)-1-methylindazol-6-yl]azetidin-1-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[1-[3-(2,4-dioxo-1,3-diazinan-1-yl)-7-fluoro-1-methylindazol-6-yl]-4-hydroxypiperidin-4-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-7-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3S)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)-3-[6-[2-cyano-3-[[ethyl(methyl)sulfamoyl]amino]-6-fluoroanilino]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

3-[6-[2-cyano-3-[[ethyl(methyl)sulfamoyl]amino]-6-fluoro-phenoxy]-5-(dimethylamino)-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-5-methoxy-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[5-amino-6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-5-fluoro-1-methylindazol-6-yl]piperidin-1-yl]acetyl]-1-oxa-8-azaspiro[4.5]decane;

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[5-chloro-6-[2-cyano-3-[[ethyl(methyl)sulfamoyl]amino]-6-fluoroanilino]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-5-hydroxy-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]piperidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclohexanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]propane-2-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopentanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopropanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxyazetidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-azabicyclo[3.1.0]hexane-3-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]pyrrolidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]azetidine-1-sulfonamide;

(3R)-3-[6-[2-cyano-3-[[cyclopropyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclobutanesulfonamide;

6-[2-cyano-3-[[ethyl(methyl)sulfamoyl]amino]-6-fluorophenoxy]-3-[2-[4-[2-[1-[3-(2,4-dioxo-1,3-diazinan-1-yl)-5-fluoro-1-methylindazol-6-yl]-4-hydroxypiperidin-4-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[(3R)-8-[4-[3-(2,4-dioxo-1,3-diazinan-1-yl)-5-fluoro-1-methylindazol-6-yl]piperidin-1-yl]-1-oxaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-fluoropiperidin-4-yl]acetyl]-1-oxa-8-azaspiro[4.5]decane;

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[(4R)-4-[3-(2,4-dioxo-1,3-diazinan-1-yl)-5-fluoro-1-methylindazol-6-yl]-3,3-difluoropiperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[(4S)-4-[3-(2,4-dioxo-1,3-diazinan-1-yl)-5-fluoro-1-methylindazol-6-yl]-3,3-difluoropiperidin-1-yl]acetyl]-1-oxa-8-azaspiro[4.5]decane;

(3R)-8-[2-[1-[5-chloro-3-(2,4-dioxo-1,3-diazinan-1-yl)-1-methylindazol-6-yl]-4-hydroxypiperidin-4-yl]acetyl]-3-[6-[2-cyano-3-[[ethyl(methyl)sulfamoyl]amino]-6-fluorophenoxy]-4-oxoquinazolin-3-yl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1,1-dioxo-1lambda6-thia-8-azaspiro[4.5]decane;

6-[2-cyano-3-[[ethyl(methyl)sulfamoyl]amino]-6-fluorophenoxy]-3-[(3R)-8-[[1-[3-(2,4-dioxo-1,3-diazinan-1-yl)-5-fluoro-1-methylindazol-6-yl]-4-hydroxypiperidin-4-yl]methylsulfonyl]-1-oxaspiro[4.5]decan-3-yl]-4-oxoquinazoline;

6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1,8-diazaspiro[4.5]decan-3-yl]-4-oxoquinazoline;

6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-methyl-1,8-diazaspiro[4.5]decan-3-yl]-4-oxoquinazoline;

(3R)-8-[2-[1-[3-(2,4-dioxo-1,3-diazinan-1-yl)-5-fluoro-1-methylindazol-6-yl]-4-hydroxypiperidin-4-yl]acetyl]-3-[6-[3-[[ethyl(methyl)sulfamoyl]amino]-2,6-difluorobenzoyl]-4-oxoquinazolin-3-yl]-1-oxa-8-azaspiro[4.5]decane;

(3R)-3-[6-[3-[[tert-butyl(methyl)sulfamoyl]amino]-2-cyano-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[4-[3-(2,4-dioxo-1,3-diazinan-1-yl)-5-fluoro-1-methylindazol-6-yl]cyclohexyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[4-[3-(2,4-dioxo-1,3-diazinan-1-yl)-5-fluoro-1-methylindazol-6-yl]cyclohexyl]-1-oxa-8-azaspiro[4.5]decane; and (3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-propan-2-ylindazol-6-yl]-4-hydroxypiperidin-4-yl]acetyl]-1-oxa-8-azaspiro[4.5]decane;

or a pharmaceutically acceptable salt thereof.

The invention further provides a compound of Formula I selected from (3R)-3-[6-[2-cyano-3-[[ethyl(methyl)sulfamoyl]amino]-6-fluorophenoxy]-4-oxoquinazolin-3-yl]-8-[2-[4-[3-(2,6-diox; opiperidin-3-yl)-1-methylindazol-6-yl]piperidin-1-yl]acetyl]-1-oxa-8-azaspiro[4.5]decane (3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]piperidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclohexanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]propane-2-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopentanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopropanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]pyrrolidine-1-sulfonamide;

(3R)-3-[6-[2-cyano-3-[[cyclopropyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane; and N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclobutanesulfonamide;

or a pharmaceutically acceptable salt thereof.

The invention further provides:

A compound of Formula I or a pharmaceutically acceptable salt thereof, for use as therapeutically active substance.

A pharmaceutical composition comprising a compound of Formula I or a pharmaceutically acceptable salt thereof, and a pharmaceutically acceptable carrier;

The use of a compound of Formula I or a pharmaceutically acceptable salt thereof, for the therapeutic and/or prophylactic treatment of cancer;

A compound of Formula I or a pharmaceutically acceptable salt thereof, for use in the treatment and/or prophylaxis of cancer;

The use of a compound of Formula I or a pharmaceutically acceptable salt thereof, for the preparation of a medicament for the therapeutic and/or prophylactic treatment of cancer;

A method for the therapeutic and/or prophylactic treatment of cancer, which method comprises administering an effective amount of a compound of Formula I or a pharmaceutically acceptable salt thereof, to a patient in need thereof;

In some embodiments the cancer is a BRAF V600X mutated tumor;

In some embodiments the cancer is a BRAF V600E/K mutated tumor;

In some embodiments the cancer is targeted therapy naïve; and

In some embodiments the cancer is selected from melanoma, colorectal cancer and lung cancer, in particular non-small cell lung cancer.

In certain embodiments the compound of the present invention is

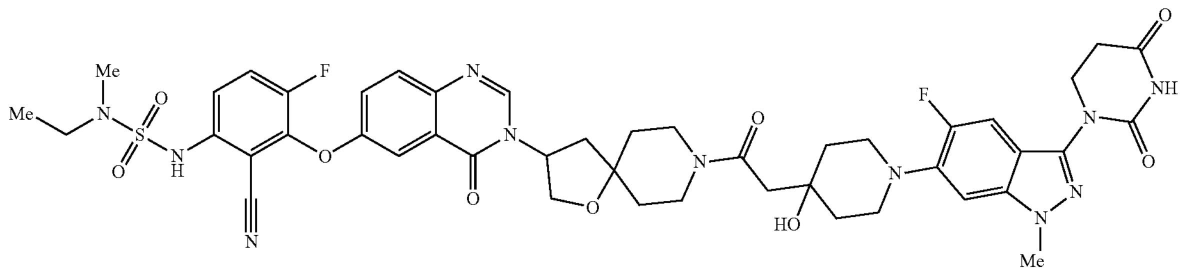 [SMILES: CCN(C)S(=O)(=O)Nc1ccc(F)c(Oc2ccc3ncn(C4COC5(CCN(C(=O)CC6(O)CCN(c7cc8c(cc7F)c(N7CCC(=O)NC7=O)nn8C)CC6)CC5)C4)c(=O)c3c2)c1C#N]

or a pharmaceutically acceptable salt thereof.

In certain embodiments the compound of the present invention is

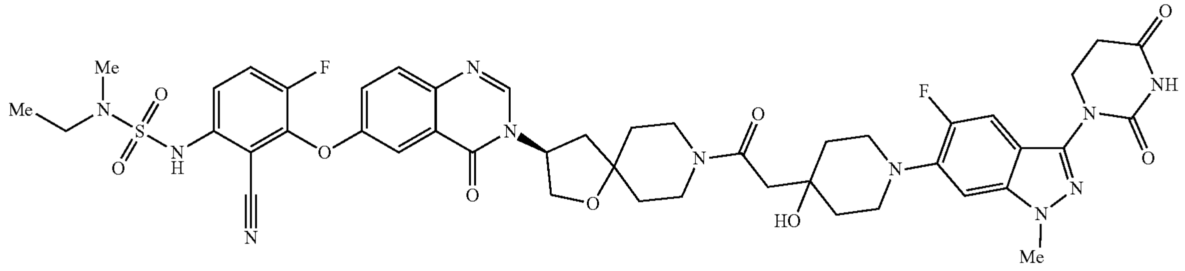 [SMILES: CCN(C)S(=O)(=O)Nc1ccc(F)c(Oc2ccc3ncn([C@@H]4COC5(CCN(C(=O)CC6(O)CCN(c7cc8c(cc7F)c(N7CCC(=O)NC7=O)nn8C)CC6)CC5)C4)c(=O)c3c2)c1C#N]

or a pharmaceutically acceptable salt thereof.

Additional Embodiments of Formula I

1. A compound of Formula I (I)

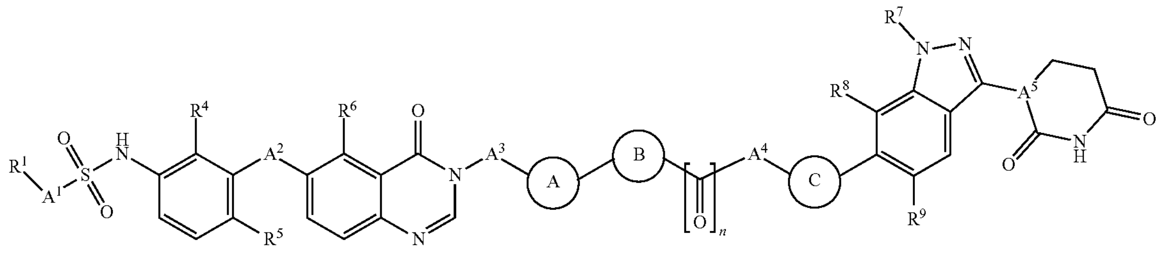

wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C═O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

A is selected from a bond, pyrimidinyl, pyridinyl, pyrazolyl and 3-azabicyclo[3.1.0]hexyl;

B is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, and 8-azaspiro[4.5]decyl; wherein B is optionally substituted with one or two substituents independently selected from halogen, alkyl and alkoxy;

n is 0 or 1;

$A^4$ is selected from a bond, —$CH_2$—, —$(SO_2)$—$CH_2$—, —$CH(CH_2OH)$—, —NH— and —O—;

C is selected from azepanyl, azetidinyl, cycloalkyl, piperazinyl and piperidinyl; wherein C is optionally substituted with one or two substituents independently selected from halogen, hydroxy, alkyl and alkoxy;

$R^7$ is selected from hydrogen, alkyl, cyano, halogen and alkoxy;

$R^8$ is selected from hydrogen, alkyl, cyano, halogen and alkoxy;

$R^9$ is selected from hydrogen, alkyl, cyano, halogen and alkoxy; and $A^5$ is —CH— or —N—;

or a pharmaceutically acceptable salt thereof.

2. A compound according to embodiment 1, wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C=O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, and —$CH_2$—$CH_2$—$CH_2$—;

A is selected from a bond, pyrimidinyl, pyridinyl, pyrazolyl and 3-azabicyclo[3.1.0]hexyl;

B is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, and 8-azaspiro[4.5]decyl;

n is 0 or 1;

$A^4$ is selected from a bond, —$CH_2$—, —($SO_2$)—$CH_2$—, —CH($CH_2$OH)—, —NH— and —O—;

C is selected from azetidinyl, cycloalkyl, piperazinyl, halopiperidinyl, hydroxypiperidinyl and piperidinyl;

$R^7$ is selected from hydrogen, alkyl, cyano, halogen and alkoxy;

$R^8$ is selected from hydrogen, alkyl, cyano, halogen and alkoxy;

$R^9$ is selected from hydrogen, alkyl, cyano, halogen and alkoxy; and $A^5$ is —CH— or —N—;

or a pharmaceutically acceptable salt thereof.

3. A compound according to embodiment 1 or 2, wherein $A^1$ is selected from —$NR^2$— and —$CHR^{2'}$—;

$R^8$ is alkyl;

$R^2$ is selected from alkyl and cycloalkyl;

or $R^1$ and $R^2$ together with the nitrogen atom to which they are attached form heterocycloalkyl optionally substituted with one or two $R^3$;

$R^{2'}$ is alkyl;

or $R^1$ and $R^{2'}$ together with the carbon atom to which they are attached form cycloalkyl;

each $R^3$ is independently selected from halogen and alkoxy.

4. A compound according to any one of embodiments 1 to 3, wherein $A^1$ is selected from —$NR^2$— and —$CHR^{2'}$—;

$R^1$ is methyl;

$R^2$ is selected from ethyl, tert-butyl and cyclopropyl;

or $R^1$ and $R^2$ together with the nitrogen atom to which they are attached form heterocycloalkyl optionally substituted with one or two $R^3$;

$R^{2'}$ is methyl;

or $R^1$ and $R^{2'}$ together with the carbon atom to which they are attached form cycloalkyl;

each $R^3$ is independently selected from fluoro and methoxy.

5. A compound according to any one of embodiments 1 to 4, wherein $R^1$ is methyl.

6. A compound according to any one of embodiments 1 to 5, wherein $R^2$ is selected from ethyl, tert-butyl and cyclopropyl.

7. A compound according to any one of embodiments 1 to 6, wherein $A^1$ is —$NR^2$—.

8. A compound according to any one of embodiments 1 to 6, wherein $A^1$ is —$CHR^{2'}$—.

9. A compound according to any one of embodiments 1 to 8, wherein the heterocycloalkyl which is formed by $R^1$ and $R^2$ together with the nitrogen atom to which they are attached is selected from pyrrolidinyl, piperidinyl, azetidinyl and 3-azabicyclo[3.1.0]hexyl, and wherein the heterocycloalkyl is in each instance optionally substituted with one or two $R^3$ independently selected from fluoro and methoxy.

10. A compound according to any one of embodiments 1 to 9, wherein the cycloalkyl which is formed by $R^1$ and $R^{2'}$ together with the carbon atom to which they are attached is selected from cyclopropyl, cyclobutyl, cyclopentyl and cyclohexyl.

11. A compound according to any one of embodiments 1 to 10, wherein each $R^3$ is independently selected from fluoro and methoxy.

12. A compound according to any one of embodiments 1 to 11, wherein $R^4$ is cyano.

13. A compound according to any one of embodiments 1 to 12, wherein $R^5$ is halogen.

14. A compound according to any one of embodiments 1 to 13, wherein $R^5$ is fluoro.

15. A compound according to any one of embodiments 1 to 14, wherein $A^2$ is selected from —O— and —NH—.

16. A compound according to any one of embodiments 1 to 15, wherein $A^2$ is —O—.

17. A compound according to any one of embodiments 1 to 16, wherein $R^6$ is selected from hydrogen, halogen, hydroxy, amino, alkoxy and dialkylamino.

18. A compound according to any one of embodiments 1 to 17, wherein $R^6$ is selected from hydrogen, fluoro, chloro, hydroxy, amino, methoxy and dimethylamino.

19. A compound according to any one of embodiments 1 to 18, wherein $A^3$ is selected from a bond, —$CH_2$—$CH_2$— and —$CH_2$—$CH_2$—$CH_2$—, 20. A compound according to any one of embodiments 1 to 19, wherein $A^3$ is a bond.

21. A compound according to any one of embodiments 1 to 20, wherein A is selected from a bond and pyrimidinyl.

22. A compound according to any one of embodiments 1 to 21, wherein A is a bond.

23. A compound according to any one of embodiments 1 to 22, wherein B is selected from piperidinyl, piperazinyl, 1-oxa-8-azaspiro[4.5]decyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl and 8-azaspiro[4.5]decyl.

24. A compound according to any one of embodiments 1 to 23, wherein B is selected from 1-oxa-8-azaspiro[4.5]decyl and 8-azaspiro[4.5]decyl.

25. A compound according to any one of embodiments 1 to 24, wherein $A^4$ is selected from a bond, —$CH_2$— and —($SO_2$)—$CH_2$—.

26. A compound according to any one of embodiments 1 to 25, wherein $A^4$ is —$CH_2$—.

27. A compound according to any one of embodiments 1 to 26, wherein C is selected from azetidinyl, cyclohexyl, piperazinyl, difluoropiperidinyl, hydroxypiperidinyl and piperidinyl.

28. A compound according to any one of embodiments 1 to 27, wherein C is selected from hydroxypiperidinyl and piperidinyl.

29. A compound according to any one of embodiments 1 to 28, wherein $R^7$ is alkyl.

30. A compound according to any one of embodiments 1 to 29, wherein $R^7$ is methyl.

31. A compound according to any one of embodiments 1 to 30, wherein $R^8$ is selected from hydrogen and halogen.
32. A compound according to any one of embodiments 1 to 31, wherein $R^8$ is selected from hydrogen and fluoro.
33. A compound according to any one of embodiments 1 to 32, wherein $R^9$ is selected from hydrogen and halogen.
34. A compound according to any one of embodiments 1 to 33, wherein $R^9$ is selected from hydrogen and fluoro.
35. A compound according to any one of embodiments 1 to 34, wherein $A^5$ is —NH—.
36. A compound according to any one of embodiments 1 to 34, wherein $A^5$ is —CH—.
37. A compound according to any one of embodiments 1 to 36, wherein n is 1.
38. A compound according to any of embodiments 1 to 37 selected from 6-[2-cyano-3-[[ethyl(methyl)sulfamoyl]amino]-6-fluoro-phenoxy]-3-[2-[1-[2-[4-[3-(2,6-dioxopiperidin-3-yl)-1-methylindazol-6-yl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[3-[1-[2-[4-[3-(2,6-dioxopiperidin-3-yl)-1-methylindazol-6-yl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[1-[l-[2-[4-[3-(2,6-dioxopiperidin-3-yl)-1-methylindazol-6-yl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[7-[2-[4-[3-(2,4-dioxo-1,3-diazinan-1-yl)-1-methylindazol-6-yl]piperidin-1-yl]acetyl]-7-azaspiro[3.5]nonan-2-yl]-4-oxoquinazoline;

3-[6-[2-cyano-3-[[ethyl(methyl)sulfamoyl]amino]-6-fluoro-phenoxy]-4-oxoquinazolin-3-yl]-8-[2-[4-[3-(2,4-dioxo-1,3-diazinan-1-yl)-1-methylindazol-6-yl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[7-[2-[4-[3-(2,6-dioxopiperidin-3-yl)-1-methylindazol-6-yl]piperidin-1-yl]acetyl]-7-azaspiro[3.5]nonan-2-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,6-dioxopiperidin-3-yl)-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,6-dioxopiperidin-3-yl)-1-methylindazol-6-yl]-4-hydroxypiperidin-4-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[4-[3-(2,6-dioxopiperidin-3-yl)-1-methylindazol-6-yl]piperidin-1-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3S)-8-[2-[4-[3-(2,4-dioxo-1,3-diazinan-1-yl)-1-methylindazol-6-yl]piperidin-1-yl]acetyl]-8-azaspiro[4.5]decan-3-yl]-4-oxoquinazoline;

9-[6-[2-cyano-3-[[ethyl(methyl)sulfamoyl]amino]-6-fluoro-phenoxy]-4-oxoquinazolin-3-yl]-3-[2-[4-[3-(2,4-dioxo-1,3-diazinan-1-yl)-1-methylindazol-6-yl]piperidin-1-yl]acetyl]-3-azaspiro[5.5]undecane;

9-[6-[2-cyano-3-[[ethyl(methyl)sulfamoyl]amino]-6-fluoro-phenoxy]-4-oxoquinazolin-3-yl]-3-[2-[4-[3-(2,6-dioxopiperidin-3-yl)-1-methylindazol-6-yl]piperidin-1-yl]acetyl]-3-azaspiro[5.5]undecane;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

9-[6-[2-cyano-3-[[ethyl(methyl)sulfamoyl]amino]-6-fluoro-phenoxy]-4-oxoquinazolin-3-yl]-3-[2-[1-[3-(2,4-dioxo-1,3-diazinan-1-yl)-5-fluoro-1-methylindazol-6-yl]-4-hydroxypiperidin-4-yl]acetyl]-3-azaspiro[5.5]undecane;

6-[2-cyano-3-[[ethyl(methyl)sulfamoyl]amino]-6-fluoro-phenoxy]-3-[(3S)-8-[2-[1-[3-(2,4-dioxo-1,3-diazinan-1-yl)-5-fluoro-1-methylindazol-6-yl]-4-hydroxypiperidin-4-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3S)-8-[2-[4-[3-(2,6-dioxopiperidin-3-yl)-1-methylindazol-6-yl]-3,3-difluoropiperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]-3,3-difluoropiperidin-1-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[4-[3-(2,4-dioxo-1,3-diazinan-1-yl)-5-fluoro-1-methylindazol-6-yl]piperazin-1-yl]acetyl]-8-azaspiro[4.5]decan-3-yl]-4-oxoquinazoline;

9-[6-[2-cyano-3-[[ethyl(methyl)sulfamoyl]amino]-6-fluoro-phenoxy]-4-oxoquinazolin-3-yl]-3-[2-[4-[3-(2,4-dioxo-1,3-diazinan-1-yl)-5-fluoro-1-methylindazol-6-yl]piperazin-1-yl]acetyl]-3-azaspiro[5.5]undecane;

(3R)-3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-5-fluoro-1-methylindazol-6-yl]piperazin-1-yl]acetyl]-1-oxa-8-azaspiro[4.5]decane;

(3R)—N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

6-[2-chloro-3-[[ethyl(methyl)sulfamoyl]amino]-6-fluoro-phenoxy]-3-[(3S)-8-[2-[4-[3-(2,6-dioxopiperidin-3-yl)-1-methylindazol-6-yl]piperidin-1-yl]acetyl]-8-azaspiro[4.5]decan-3-yl]-4-oxoquinazoline;

N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]cyclopentanesulfonamide;

N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]propane-2-sulfonamide;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]cyclohexyl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]cyclohexyl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[3-[3-(2,6-dioxopiperidin-3-yl)-1-methylindazol-6-yl]azetidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[1-[3-(2,4-dioxo-1,3-diazinan-1-yl)-7-fluoro-1-methylindazol-6-yl]-4-hydroxypiperidin-4-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-7-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3S)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)-3-[6-[2-cyano-3-[[ethyl(methyl)sulfamoyl]amino]-6-fluoroanilino]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

3-[6-[2-cyano-3-[[ethyl(methyl)sulfamoyl]amino]-6-fluorophenoxy]-5-(dimethylamino)-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-5-methoxy-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[5-amino-6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-5-fluoro-1-methylindazol-6-yl]piperidin-1-yl]acetyl]-1-oxa-8-azaspiro[4.5]decane;

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[5-chloro-6-[2-cyano-3-[[ethyl(methyl)sulfamoyl]amino]-6-fluoroanilino]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-5-hydroxy-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]piperidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclohexanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]propane-2-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopentanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopropanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxyazetidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-azabicyclo[3.1.0]hexane-3-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]pyrrolidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]azetidine-1-sulfonamide;

(3R)-3-[6-[2-cyano-3-[[cyclopropyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclobutanesulfonamide;

6-[2-cyano-3-[[ethyl(methyl)sulfamoyl]amino]-6-fluorophenoxy]-3-[2-[4-[2-[1-[3-(2,4-dioxo-1,3-diazinan-1-yl)-5-fluoro-1-methylindazol-6-yl]-4-hydroxypiperidin-4-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[(3R)-8-[4-[3-(2,4-dioxo-1,3-diazinan-1-yl)-5-fluoro-1-methylindazol-6-yl]piperidin-1-yl]-1-oxaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-fluoropiperidin-4-yl]acetyl]-1-oxa-8-azaspiro[4.5]decane;

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[(4R)-4-[3-(2,4-dioxo-1,3-diazinan-1-yl)-5-fluoro-1-methylindazol-6-yl]-3,3-difluoropiperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[(4S)-4-[3-(2,4-dioxo-1,3-diazinan-1-yl)-5-fluoro-1-methylindazol-6-yl]-3,3-difluoropiperidin-1-yl]acetyl]-1-oxa-8-azaspiro[4.5]decane;

(3R)-8-[2-[1-[5-chloro-3-(2,4-dioxo-1,3-diazinan-1-yl)-1-methylindazol-6-yl]-4-hydroxypiperidin-4-yl]acetyl]-3-[6-[2-cyano-3-[[ethyl(methyl)sulfamoyl]amino]-6-fluorophenoxy]-4-oxoquinazolin-3-yl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1,1-dioxo-1lambda6-thia-8-azaspiro[4.5]decane;

6-[2-cyano-3-[[ethyl(methyl)sulfamoyl]amino]-6-fluorophenoxy]-3-[(3R)-8-[[1-[3-(2,4-dioxo-1,3-diazinan-1-yl)-5-fluoro-1-methylindazol-6-yl]-4-hydroxypiperidin-4-yl]methylsulfonyl]-1-oxaspiro[4.5]decan-3-yl]-4-oxoquinazoline;

6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1,8-diazaspiro[4.5]decan-3-yl]-4-oxoquinazoline;

6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-methyl-1,8-diazaspiro[4.5]decan-3-yl]-4-oxoquinazoline;

(3R)-8-[2-[1-[3-(2,4-dioxo-1,3-diazinan-1-yl)-5-fluoro-1-methylindazol-6-yl]-4-hydroxypiperidin-4-yl]acetyl]-3-[6-[3-[[ethyl(methyl)sulfamoyl]amino]-2,6-difluorobenzoyl]-4-oxoquinazolin-3-yl]-1-oxa-8-azaspiro[4.5]decane;

(3R)-3-[6-[3-[[tert-butyl(methyl)sulfamoyl]amino]-2-cyano-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[4-[3-(2,4-dioxo-1,3-diazinan-1-yl)-5-fluoro-1-methylindazol-6-yl]cyclohexyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[4-[3-(2,4-dioxo-1,3-diazinan-1-yl)-5-fluoro-1-methylindazol-6-yl]cyclohexyl]-1-oxa-8-azaspiro[4.5]decane; and (3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-propan-2-ylindazol-6-yl]-4-hydroxypiperidin-4-yl]acetyl]-1-oxa-8-azaspiro[4.5]decane;

or a pharmaceutically acceptable salt thereof.

39. A compound according to any of embodiments 1 to 38 selected from (3R)-3-[6-[2-cyano-3-[[ethyl(methyl)sulfamoyl]amino]-6-fluorophenoxy]-4-oxoquinazolin-3-yl]-8-[2-[4-[3-(2,6-diox; opiperidin-3-yl)-1-methylindazol-6-yl]piperidin-1-yl]acetyl]-1-oxa-8-azaspiro[4.5]decane (3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide;

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane;

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]piperidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclohexanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]propane-2-sulfonamide;

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopentanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopropanesulfonamide;

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]pyrrolidine-1-sulfonamide;

(3R)-3-[6-[2-cyano-3-[[cyclopropyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane; and N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclobutanesulfonamide;

or a pharmaceutically acceptable salt thereof.

40. A compound according to any one of embodiments 1 to 39, or a pharmaceutically acceptable salt thereof, for use as therapeutically active substance.

41. A pharmaceutical composition comprising a compound according to any one of embodiments 1 to 39, or a pharmaceutically acceptable salt thereof, and a pharmaceutically acceptable carrier.

42. The use of a compound according to any one of embodiments 1 to 39, or a pharmaceutically acceptable salt thereof, for the therapeutic and/or prophylactic treatment of cancer.

43. A compound according to any one of embodiments 1 to 39, or a pharmaceutically acceptable salt thereof, for use in the treatment and/or prophylaxis of cancer.

44. The use of a compound according to any one of embodiments 1 to 39, or a pharmaceutically acceptable salt thereof, for the preparation of a medicament for the therapeutic and/or prophylactic treatment of cancer.

45. A method for the therapeutic and/or prophylactic treatment of cancer, which method comprises administering an effective amount of a compound according to any one of embodiments 1 to 39, or a pharmaceutically acceptable salt thereof, to a patient in need thereof.

46. The invention as herein described.

Embodiments of Formula III and Formula IV

In certain embodiments the compound of Formula III is a compound of Formula III-A (III-A)

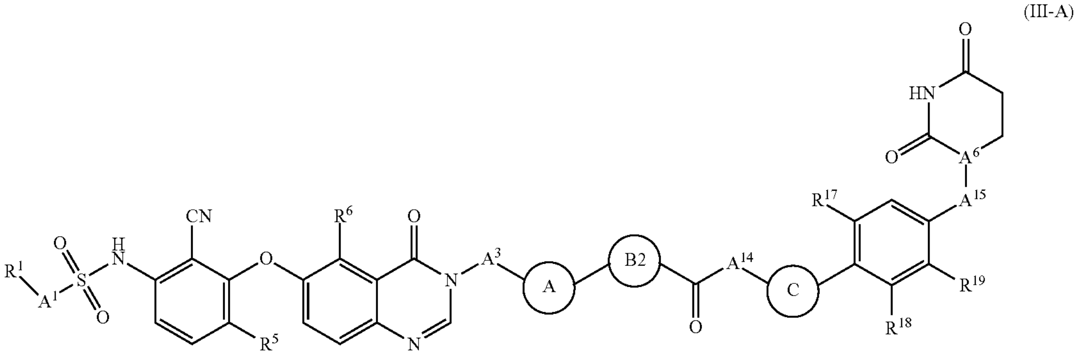

wherein $A^2$ is —O—, n is 1, $R^4$ is cyano, and the remaining substituents and variables are as described herein, or a pharmaceutically acceptable salt thereof.

In certain embodiments the compound of Formula III is a compound of Formula III-B (III-B)

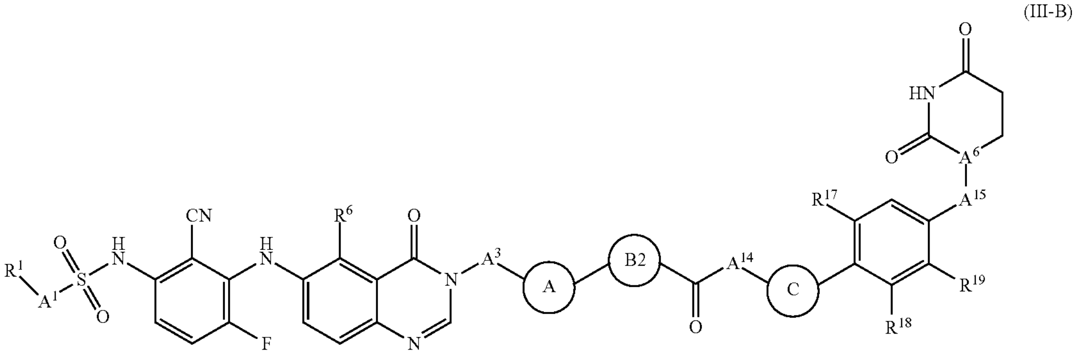

wherein $A^2$ is —NH—, n is 1, $R^4$ is cyano, $R^5$ is fluoro, and the remaining substituents and variables are as described herein, or a pharmaceutically acceptable salt thereof.

In certain embodiments the compound of Formula III is a compound of Formula III-C (III-C)

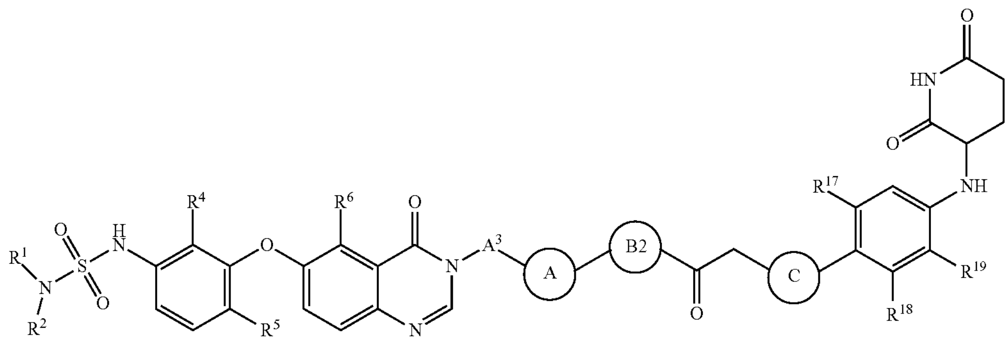

wherein $A^1$ is —$NR^2$—, $A^2$ is —O—, n is 1, $A^{14}$ is —$CH_2$—, $A^{15}$ is —NH—, $A^6$ is —CH—, and the remaining substituents and variables are as described herein, or a pharmaceutically acceptable salt thereof.

In certain embodiments the compound of Formula IV is selected from:

(IV-A)

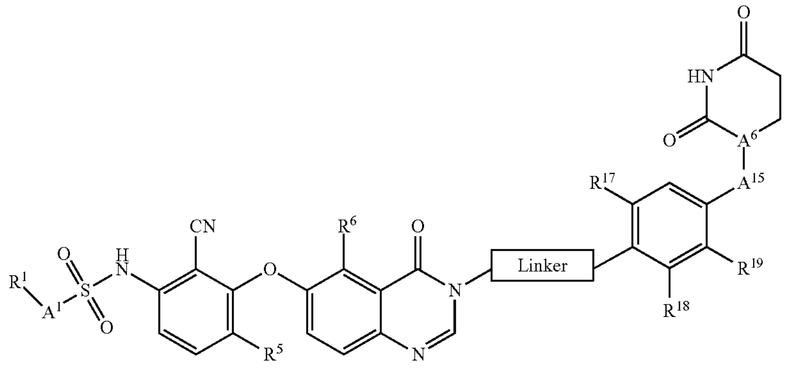

(IV-B)

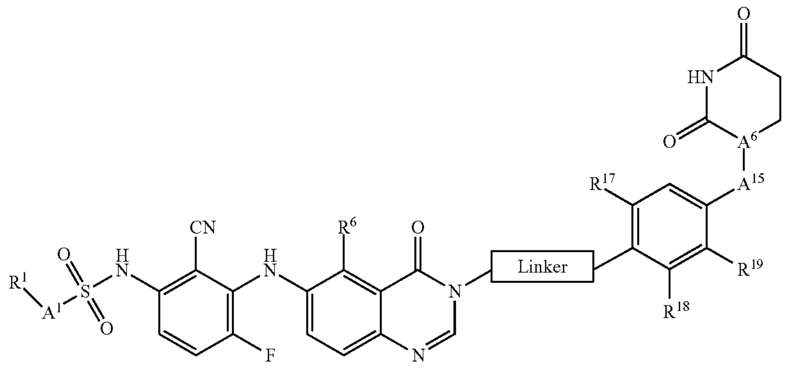

-continued (IV-C)

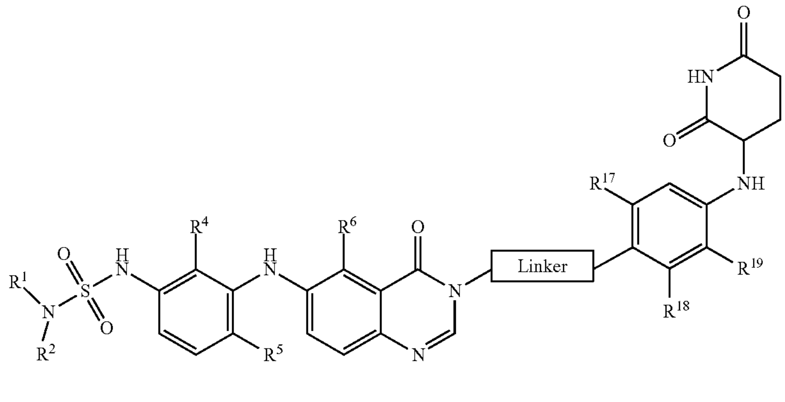

or a pharmaceutically acceptable salt thereof.

In certain aspects a compound of Formula III (III)

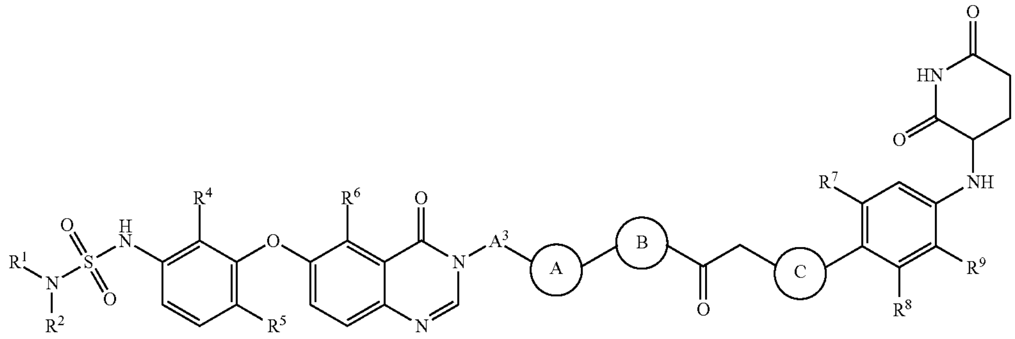

is provided, wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C═O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

A is selected from a bond, pyrimidinyl, pyridinyl, pyrazolyl and 3-azabicyclo[3.1.0]hexyl;

B2 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl; wherein B2 is optionally substituted with one or two substituents independently selected from halogen, alkyl and alkoxy;

n is 0 or 1;

$A^{14}$ is selected from a bond, —$CH_2$—, —$CH_2$—$CH_2$—, —$CH(CH_2OH)$—, —NH—, —O—, cycloalkyl and alkylamino;

C is selected from azepanyl, azetidinyl, cycloalkyl, piperazinyl and piperidinyl; wherein C is optionally substituted with one or two substituents independently selected from halogen, hydroxy, alkyl and alkoxy;

$R^{17}$ is selected from hydrogen, alkyl, cyano, hydroxy, cycloalkyl, halogen and alkoxy;

$R^{18}$ is selected from hydrogen, alkyl, cyano, hydroxy, cycloalkyl, halogen and alkoxy;

$R^{19}$ is selected from hydrogen, alkyl, cyano, hydroxy, cycloalkyl, halogen and alkoxy;

$A^{15}$ is selected from a bond, —O— and —NH—; and $A^6$ is —CH— or —N—;

or a pharmaceutically acceptable salt thereof.

In certain embodiments the invention is a compound of Formula III wherein $A^1$ is selected from —$NR^2$— and —$CHR^{2'}$—;

$R^1$ is selected from hydrogen, alkyl and cycloalkyl;

$R^2$ is selected from alkyl, cycloalkyl and haloalkyl;

or $R^1$ and $R^2$ together with the nitrogen atom to which they are attached form heterocycloalkyl optionally substituted with one or two $R^3$;

$R^{2'}$, is selected from alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C═O)—;

$R^6$ is selected from hydrogen, halogen, hydroxy, amino, dialkylamino, alkoxy, alkyl and alkoxyalkyl;

$A^3$ is selected from a bond, $—CH_2—$, $—CH_2—CH_2—$, $—CH_2—CH_2—CH_2—$, $—CH(CH_3)—CH_2—CH_2—$, $—CH_2—CH(CH_3)—CH_2—$, $—CH_2—CH_2—CH(CH_3)—$, $—CH_2—CH_2—CH_2—CH_2—$ and $—CH_2—CH_2—CH_2—CH_2—CH_2—$;

A is selected from a bond, pyrimidinyl, pyridinyl, pyrazolyl and 3-azabicyclo[3.1.0]hexyl;

B2 is selected from phenyl, piperidinyl, piperazinyl, halopiperidinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl;

n is 0 or 1;

$A^{14}$ is selected from a bond, $—CH_2—$, $—CH_2—CH_2—$, $—CH(CH_2OH)—$, —NH—, —O—, cycloalkyl and alkylamino;

C is selected from azepanyl, azetidinyl, cycloalkyl, halopiperidinyl, hydroxypiperidinyl, alkoxypiperidinyl, piperazinyl and piperidinyl;

$R^{17}$ is selected from hydrogen, halogen and alkoxy;

$R^{18}$ is selected from hydrogen, halogen and alkoxy;

$R^{19}$ is selected from hydrogen, halogen and alkoxy;

$A^{15}$ is selected from a bond, —O— and —NH—; and $A^6$ is —CH— or —N—;

or a pharmaceutically acceptable salt thereof.

In other embodiments of the invention is a compound of Formula III wherein $A^1$ is selected from $—NR^2—$ and $—CHR^{2'}—$;

$R^1$ is alkyl;

$R^2$ is selected from alkyl, cycloalkyl and haloalkyl;

or $R^1$ and $R^2$ together with the nitrogen atom to which they are attached form heterocycloalkyl optionally substituted with one or two $R^3$;

$R^{2'}$ is alkyl;

or $R^1$ and $R^{2'}$ together with the carbon atom to which they are attached form cycloalkyl;

each $R^3$ is independently selected from halogen and alkoxy.

One embodiment of the invention is a compound of Formula III wherein $A^1$ is selected from $—NR^2—$ and $—CHR^{2'}—$;

$R^1$ is methyl;

$R^2$ is selected from ethyl, fluoroethyl, difluoroethyl and cyclopropyl;

or $R^1$ and $R^2$ together with the nitrogen atom to which they are attached form heterocycloalkyl optionally substituted with one or two $R^3$;

$R^{2'}$ is alkyl;

or $R^1$ and $R^{2'}$ together with the carbon atom to which they are attached form cycloalkyl;

each $R^3$ is independently selected from fluoro and methoxy.

Additional embodiments of the invention include:

A compound of Formula III wherein $R^1$ is methyl, or a pharmaceutically acceptable salt thereof;

A compound of Formula III wherein $R^2$ is selected from ethyl, fluoroethyl, difluoroethyl and cyclopropyl, or a pharmaceutically acceptable salt thereof;

A compound of Formula III wherein $A^1$ is $—NR^2—$, or a pharmaceutically acceptable salt thereof;

A compound of Formula III wherein $A^1$ is $—CHR^{2'}—$, or a pharmaceutically acceptable salt thereof;

A compound of Formula III wherein the heterocycloalkyl which is formed by $R^1$ and $R^2$ together with the nitrogen atom to which they are attached is selected from pyrrolidinyl, piperidinyl, azetidinyl and 3-azabicyclo[3.1.0]hexyl, and wherein the heterocycloalkyl is in each instance optionally substituted with one or two $R^3$ independently selected from fluoro and methoxy, or a pharmaceutically acceptable salt thereof;

A compound of Formula III wherein the cycloalkyl which is formed by $R^1$ and $R^{2'}$ together with the carbon atom to which they are attached is selected from cyclopropyl, cyclobutyl, cyclopentyl and cyclohexyl, or a pharmaceutically acceptable salt thereof;

A compound of Formula III wherein each $R^3$ is independently selected from fluoro and methoxy, or a pharmaceutically acceptable salt thereof;

A compound of Formula III wherein $R^4$ is cyano, or a pharmaceutically acceptable salt thereof;

A compound of Formula III wherein $R^5$ is selected from cyano and halogen, or a pharmaceutically acceptable salt thereof;

A compound of Formula III wherein $R^5$ is selected from cyano and fluoro, or a pharmaceutically acceptable salt thereof;

A compound of Formula III wherein $R^5$ is selected from hydrogen and halogen, or a pharmaceutically acceptable salt thereof;

A compound of Formula III wherein $R^5$ is selected from hydrogen and fluoro, or a pharmaceutically acceptable salt thereof;

A compound of Formula III wherein $R^5$ is halogen, or a pharmaceutically acceptable salt thereof;

A compound of Formula III wherein $R^5$ is fluoro, or a pharmaceutically acceptable salt thereof;

A compound of Formula III wherein $R^5$ is cyano, or a pharmaceutically acceptable salt thereof;

A compound of Formula III wherein $A^2$ is selected from —O— and —NH—, or a pharmaceutically acceptable salt thereof;

A compound of Formula III wherein $A^2$ is —O—, or a pharmaceutically acceptable salt thereof;

A compound of Formula III wherein $R^6$ is selected from hydrogen, fluoro, chloro, bromo, hydroxy, amino, methoxy, methyl and methoxymethyl, or a pharmaceutically acceptable salt thereof;

A compound of Formula III wherein $R^6$ is hydrogen, or a pharmaceutically acceptable salt thereof;

A compound of Formula III wherein $A^3$ is selected from a bond, $—CH_2—$, $—CH_2—CH_2—$, $—CH_2—CH_2—CH_2—$, $—CH(CH_3)—CH_2—CH_2—$, $—CH_2—CH(CH_3)—CH_2—$ and $—CH_2—CH_2—CH(CH_3)—$, or a pharmaceutically acceptable salt thereof;

A compound of Formula III wherein $A^3$ is a bond, or a pharmaceutically acceptable salt thereof;

A compound of Formula III wherein A is selected from a bond, pyridinyl and pyrimidinyl, or a pharmaceutically acceptable salt thereof;

A compound of Formula III wherein B2 is selected from phenyl, piperidin-4-yl, 4-fluoro-piperidin-4-yl, piperazin-1-yl, 1,4-diazacycloheptyl, 1-oxa-8-azaspiro[4.5]

decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl, or a pharmaceutically acceptable salt thereof;

A compound of Formula III wherein B2 is selected from phenyl, piperidinyl, piperazinyl, 1-oxa-8-azaspiro[4.5]decyl, 7-azaspiro[3.5]nonyl and 8-azaspiro[4.5]decyl, or a pharmaceutically acceptable salt thereof;

A compound of Formula III wherein B2 is selected from phenyl, piperidin-4-yl, piperazin-1-yl, 1-oxa-8-azaspiro[4.5]decyl, 7-azaspiro[3.5]nonyl and 8-azaspiro[4.5]decyl, or a pharmaceutically acceptable salt thereof;

A compound of Formula III wherein B2 is selected from piperazinyl and 1-oxa-8-azaspiro[4.5]decyl, or a pharmaceutically acceptable salt thereof;

A compound of Formula III wherein B2 is selected from piperazin-1-yl and 1-oxa-8-azaspiro[4.5]decyl, or a pharmaceutically acceptable salt thereof;

A compound of Formula III wherein $A^{14}$ is $—CH_2—$, or a pharmaceutically acceptable salt thereof;

A compound of Formula III wherein C is selected from azepan-1-yl, azetidin-1-yl, cycloalkyl, piperazin-1-yl, piperazin-1-yl, piperidin-4-yl, 4-hydroxypiperidin-4-yl, 3,3-difluoropiperidin-1-yl and 3-methoxypiperidin-1-yl, or a pharmaceutically acceptable salt thereof;

A compound of Formula III wherein C is selected from difluoropiperidinyl, hydroxypiperidinyl, methoxypiperidinyl, piperazinyl and piperidinyl, or a pharmaceutically acceptable salt thereof;

A compound of Formula III wherein C is selected from difluoropiperidinyl, hydroxypiperidinyl, methoxypiperidinyl, piperazinyl and piperidinyl, or a pharmaceutically acceptable salt thereof;

A compound of Formula III wherein C is piperidin-1-yl, or a pharmaceutically acceptable salt thereof;

A compound of Formula III wherein $R^{17}$ is selected from hydrogen, fluoro and methoxy, or a pharmaceutically acceptable salt thereof;

A compound of Formula III wherein $R^{17}$ is fluoro, or a pharmaceutically acceptable salt thereof;

A compound of Formula III wherein $R^{18}$ is selected from hydrogen and fluoro, or a pharmaceutically acceptable salt thereof;

A compound of Formula III wherein $R^{18}$ is hydrogen, or a pharmaceutically acceptable salt thereof;

A compound of Formula III wherein $R^{19}$ is selected from hydrogen, fluoro and methoxy, or a pharmaceutically acceptable salt thereof;

A compound of Formula III wherein $R^{19}$ is hydrogen, or a pharmaceutically acceptable salt thereof;

A compound of Formula III wherein $A^{15}$ is —NH—, or a pharmaceutically acceptable salt thereof;

A compound of Formula III wherein $A^{15}$ is —CH—, or a pharmaceutically acceptable salt thereof;

A compound of Formula III wherein n is 1, or a pharmaceutically acceptable salt thereof; and A compound of Formula III wherein n is 0, or a pharmaceutically acceptable salt thereof.

One embodiment is a compound of Formula III selected from

6-[2-cyano-3-[[ethyl(methyl)sulfamoyl]amino]-6-fluoro-phenoxy]-3-[2-[1-[2-[4-[4-[(2,6-dioxopiperidin-3-yl)amino]-2-fluorophenyl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[2-[1-[2-[4-[4-(2,6-dioxopiperidin-3-yl)-2-fluorophenyl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[2-[1-[2-[4-[4-[(2,6-dioxopiperidin-3-yl)amino]-3-fluorophenyl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]phenyl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[3-[1-[2-[4-[4-(2,6-dioxopiperidin-3-yl)-2-fluorophenyl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]phenyl]piperidin-1-yl]-2-oxoethyl]piperidin-4-yl]propyl]-4-oxoquinazoline;

6-[2-cyano-3-[[ethyl(methyl)sulfamoyl]amino]-6-fluoro-phenoxy]-3-[2-[4-[2-[4-[4-[(2,6-dioxopiperidin-3-yl)amino]-2-fluorophenyl]piperidin-1-yl]acetyl]piperazin-1-yl]ethyl]-4-oxoquinazoline;

6-[2-cyano-3-[[ethyl(methyl)sulfamoyl]amino]-6-fluoro-phenoxy]-3-[2-[4-[2-[4-[4-[(2,6-dioxopiperidin-3-yl)amino]phenyl]piperidin-1-yl]acetyl]piperazin-1-yl]ethyl]-4-oxoquinazoline;

6-[2-cyano-3-[[ethyl(methyl)sulfamoyl]amino]-6-fluoro-phenoxy]-3-[4-[1-[2-[4-[4-[(2,6-dioxopiperidin-3-yl)amino]-2-fluorophenyl]piperidin-1-yl]acetyl]piperidin-4-yl]butan-2-yl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]piperidin-4-yl]butyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]-4-methylpiperidin-4-yl]propyl]-4-oxoquinazoline;

6-[2-cyano-3-[[ethyl(methyl)sulfamoyl]amino]-6-fluoro-phenoxy]-3-[2-[1-[2-[4-[4-[(2,6-dioxopiperidin-3-yl)amino]-2-fluorophenyl]piperidin-1-yl]acetyl]-4-fluoropiperidin-4-yl]ethyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]piperidin-4-yl]-2-methylpropyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]-4-fluoropiperidin-4-yl]propyl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]-2-fluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-(2,6-dioxopiperidin-3-yl)-2-fluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]phenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]-3-fluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]-2,6-difluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]phenyl]piperidin-1-yl]-2-oxoethyl]piperidin-4-yl]pyrazol-4-yl]-4-oxoquinazoline;

6-[2-cyano-3-[[ethyl(methyl)sulfamoyl]amino]-6-fluoro-phenoxy]-3-[7-[2-[4-[4-[(2,6-dioxopiperidin-3-yl)amino]-2-fluorophenyl]piperidin-1-yl]acetyl]-7-azaspiro[3.5]nonan-2-yl]-4-oxoquinazoline;

6-[2-cyano-3-[[ethyl(methyl)sulfamoyl]amino]-6-fluoro-phenoxy]-3-[7-[2-[1-[4-[(2,6-dioxopiperidin-3-yl)amino]-2-fluorophenyl]-4-hydroxypiperidin-4-yl]acetyl]-7-azaspiro[3.5]nonan-2-yl]-4-oxoquinazoline;

3-[6-[2-cyano-3-[[ethyl(methyl)sulfamoyl]amino]-6-fluoro-phenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[3-[2-[4-[4-[(2,6-dioxopiperidin-3-yl)amino]-2-fluorophenyl]piperidin-1-yl]acetyl]-3-azabicyclo[3.1.0]hexan-6-yl]-4-oxoquinazoline;

6-[2-cyano-3-[[ethyl(methyl)sulfamoyl]amino]phenoxy]-3-[7-[2-[4-[4-[(2,6-dioxopiperidin-3-yl)amino]-2-fluoro-phenyl]piperidin-1-yl]acetyl]-7-azaspiro[3.5]nonan-2-yl]-4-oxoquinazoline;

3-[6-[2-cyano-3-[[ethyl(methyl)sulfamoyl]amino]-6-fluoro-phenoxy]-4-oxoquinazolin-3-yl]-8-[2-[1-[4-[(2,6-dioxopiperidin-3-yl)amino]-2-fluorophenyl]-4-hydroxypiperidin-4-yl]acetyl]-1-oxa-8-azaspiro[4.5]decane;

6-[2-cyano-3-[[ethyl(methyl)sulfamoyl]amino]-6-fluoro-phenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

4-[6-[2-cyano-3-[[ethyl(methyl)sulfamoyl]amino]-6-fluoro-phenoxy]-4-oxoquinazolin-3-yl]-9-[2-[4-[4-[(2,6-dioxopiperidin-3-yl)amino]-2-fluorophenyl]piperidin-1-yl]acetyl]-1-oxa-9-azaspiro[5.5]undecane;

9-[6-[2-cyano-3-[[ethyl(methyl)sulfamoyl]amino]-6-fluoro-phenoxy]-4-oxoquinazolin-3-yl]-3-[2-[4-[4-[(2,6-dioxopiperidin-3-yl)amino]-2-fluorophenyl]piperidin-1-yl]acetyl]-3-azaspiro[5.5]undecane;

6-[2-cyano-3-[[ethyl(methyl)sulfamoyl]amino]-6-fluoro-phenoxy]-3-[[7-[2-[4-[4-[(2,6-dioxopiperidin-3-yl)amino]-2-fluorophenyl]piperidin-1-yl]acetyl]-7-azaspiro[3.5]nonan-2-yl]methyl]-4-oxoquinazoline;

6-[2-cyano-3-[[ethyl(methyl)sulfamoyl]amino]-6-fluoro-phenoxy]-3-[2-[2-[4-[4-[(2,6-dioxopiperidin-3-yl)amino]-2-fluorophenyl]piperidin-1-yl]acetyl]-2-azaspiro[4.5]decan-8-yl]-4-oxoquinazoline;

(3S)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

4-[6-[6-[2-cyano-3-[[ethyl(methyl)sulfamoyl]amino]-6-fluorophenoxy]-4-oxoquinazolin-3-yl]-3-azabicyclo[3.1.0]hexan-3-yl]-N-[1-[4-[(2,6-dioxopiperidin-3-yl)amino]-2-fluorophenyl]piperidin-4-yl]benzamide;

3-[[6-[2-cyano-3-[[ethyl(methyl)sulfamoyl]amino]-6-fluorophenoxy]-4-oxoquinazolin-3-yl]methyl]-8-[2-[4-[4-[(2,6-dioxopiperidin-3-yl)amino]-2-fluorophenyl]piperidin-1-yl]acetyl]-1-oxa-8-azaspiro[4.5]decane;

2-[6-[2-cyano-3-[[ethyl(methyl)sulfamoyl]amino]-6-fluoro-phenoxy]-4-oxoquinazolin-3-yl]-N-[1-[4-[(2,6-dioxopiperidin-3-yl)amino]-2-fluorophenyl]piperidin-4-yl]-7-azaspiro[3.5]nonane-7-carboxamide;

3-[6-[2-cyano-3-[[ethyl(methyl)sulfamoyl]amino]-6-fluoro-phenoxy]-4-oxoquinazolin-3-yl]-N-[1-[4-[(2,6-dioxopiperidin-3-yl)amino]-2-fluorophenyl]piperidin-4-yl]-1-oxa-8-azaspiro[4.5]decane-8-carboxamide;

6-[2-cyano-3-[[ethyl(methyl)sulfamoyl]amino]-6-fluoro-phenoxy]-3-[7-[3-[3-[4-[(2,6-dioxopiperidin-3-yl)amino]-2-fluorophenyl]azetidin-1-yl]cyclobutanecarbonyl]-7-azaspiro[3.5]nonan-2-yl]-4-oxoquinazoline;

6-[2-cyano-3-[[ethyl(methyl)sulfamoyl]amino]-6-fluoro-phenoxy]-3-[(3S)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3R)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[[(3R)-2,6-dioxopiperidin-3-yl]amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[[(3S)-2,6-dioxopiperidin-3-yl]amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[(3R)-8-[2-[4-[4-[[(3R)-2,6-dioxopiperidin-3-yl]amino]-2-fluorophenyl]piperidin-1-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3R)-8-[2-[4-[4-[[(3S)-2,6-dioxopiperidin-3-yl]amino]-2-fluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[4-[(2,6-dioxopiperidin-3-yl)amino]-2-fluorophenyl]piperidin-4-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[4-[4-[(2,6-dioxopiperidin-3-yl)amino]-2-fluorophenyl]piperazin-1-yl]acetyl]-8-azaspiro[4.5]decan-3-yl]-4-oxoquinazoline;

(3R)—N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperazin-1-yl]acetyl]-1-oxa-8-azaspiro[4.5]decane;

3-[6-[2-cyano-3-[[ethyl(methyl)sulfamoyl]amino]-6-fluorophenoxy]-5-fluoro-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-5-fluoro-4-oxoquinazoline;

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-3-fluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-3-fluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[4-[4-(2,6-dioxopiperidin-3-yl)-2-fluorophenyl]piperazin-1-yl]acetyl]-8-azaspiro[4.5]decan-3-yl]-4-oxoquinazoline;

N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]cyclopentanesulfonamide;

6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-5-methyl-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]-3,3-difluoropiperidin-1-yl]acetyl]-1-oxa-8-azaspiro[4.5]decane;

3-[6-[2-cyano-3-[[ethyl(methyl)sulfamoyl]amino]-6-fluorophenoxy]-5-methyl-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]piperazin-1-yl]acetyl]-1-oxa-8-azaspiro[4.5]decane;

N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]propane-2-sulfonamide;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2,5-difluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2,3-difluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2,3-difluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]-3,3-difluoropiperidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[4-[4-(2,6-dioxopiperidin-3-yl)-2-fluorophenyl]-3,3-difluoropiperidin-1-yl]acetyl]-8-azaspiro[4.5]decan-3-yl]-4-oxoquinazoline;

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2,5-difluorophenyl]piperidin-1-yl]acetyl]-8-azaspiro[4.5]decan-3-yl]-4-oxoquinazoline;

3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

5-bromo-6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

5-chloro-6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-5-fluoro-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluoro-5-methoxyphenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]azepan-1-yl]acetyl]-1-oxa-8-azaspiro[4.5]decane;

(3R)-3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

5-chloro-6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

5-chloro-6-[2-cyano-3-[[ethyl(methyl)sulfamoyl]amino]-6-fluorophenoxy]-3-[(3R)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

3-[5-amino-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluoroanilino]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[4-[4-[(2,6-dioxopiperidin-3-yl)amino]-2-fluorophenyl]cyclohexyl]-1-oxa-8-azaspiro[4.5]decane;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluorophenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-5-fluoro-4-oxoquinazoline;

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluoro-6-methoxyphenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluoro-5-methoxyphenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluoro-6-methoxyphenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluoro-5-methoxyphenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]-3-hydroxypropanoyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[6-[4-[2-[4-[4-[[(3R)-2,6-dioxopiperidin-3-yl]amino]-2-fluorophenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[6-[4-[2-[4-[4-[[(3S)-2,6-dioxopiperidin-3-yl]amino]-2-fluorophenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

(3R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

6-[2-cyano-3-[[ethyl(methyl)sulfamoyl]amino]-6-fluorophenoxy]-3-[2-[4-[(2S)-2-[4-[4-[[(3S)-2,6-dioxopiperidin-3-yl]amino]-2-fluorophenyl]piperidin-1-yl]-3-hydroxypropanoyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-methoxy-4-oxoquinazoline;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-methoxy-4-oxoquinazoline;

5-amino-6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

5-amino-6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[(3R,4R)-4-[4-[[(3R)-2,6-dioxopiperidin-3-yl]amino]-2-fluorophenyl]-3-methoxypiperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[(3S,4S)-4-[4-[[(3S)-2,6-dioxopiperidin-3-yl]amino]-2-fluorophenyl]-3-methoxypiperidin-1-yl]acetyl]piperazin-1-yl]pyrimidin-5-yl]-4-oxoquinazoline;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclohexanesulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]piperidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]pyrrolidine-1-sulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide;

(3S)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

(3S)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]piperidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide;

(3R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-fluoropyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxyazetidine-1-sulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide;

6-[2-cyano-3-[[2,2-difluoroethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-6-fluoro-3-[[2-fluoroethyl(methyl)sulfamoyl]amino]phenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-6-fluoro-3-[[2-fluoroethyl(methyl)sulfamoyl]amino]phenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[2,2-difluoroethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3,3-difluoropyrrolidine-1-sulfonamide;

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-fluoropyrrolidine-1-sulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]azetidine-1-sulfonamide;

6-[2-cyano-3-[[cyclopropyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[cyclopropyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

(1S,5R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-azabicyclo[3.1.0]hexane-3-sulfonamide;

(3R,4R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3,4-difluoropyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]azetidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclobutanesulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclobutanesulfonamide;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-(methoxymethyl)-4-oxoquinazoline;

(3R)-3-[6-[2-cyano-3-[[ethyl(methyl)sulfamoyl]amino]-6-fluorophenoxy]-4-oxoquinazolin-3-yl]-8-[4-[4-[(2,6-dioxopiperidin-3-yl)amino]-2-fluorophenyl]cyclohexyl]-1-oxa-8-azaspiro[4.5]decane;

N-[3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-2,4-difluorophenyl]cyclopentanesulfonamide;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-(methoxymethyl)-4-oxoquinazoline;

3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorophenoxy]-4-oxoquinazoline;

3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorophenoxy]-4-oxoquinazoline;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-hydroxy-4-oxoquinazoline;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-hydroxy-4-oxoquinazoline;

3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorobenzoyl]-4-oxoquinazoline;

6-[2-cyano-3-[[ethyl(methyl)sulfamoyl]amino]-6-fluorophenoxy]-3-[2-[1-[2-[4-[4-[(2,6-dioxo-3-piperidyl)amino]phenyl]-1-piperidyl]acetyl]-4-piperidyl]ethyl]-4-oxo-quinazoline;

6-[2-cyano-3-[[ethyl(methyl)sulfamoyl]amino]-6-fluorophenoxy]-3-[2-[1-[2-[4-[4-[(2,6-dioxo-3-piperidyl)amino]phenyl]-1-piperidyl]-2-oxo-ethyl]-4-piperidyl]ethyl]-4-oxo-quinazoline;

N-[2-cyano-3-[3-[2-[1-[2-[4-[4-[(2,6-dioxo-3-piperidyl)amino]phenyl]-1-piperidyl]acetyl]-4-piperidyl]ethyl]-4-oxo-quinazolin-6-yl]oxy-4-fluoro-phenyl]cyclopentanesulfonamide;

6-[3-[[tert-butyl(methyl)sulfamoyl]amino]-2-cyano-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline; and 6-[3-[[tert-butyl(methyl)sulfamoyl]amino]-2-cyano-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

or a pharmaceutically acceptable salt thereof.

One embodiment of the invention is a compound of Formula III selected from (3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[[(3R)-2,6-dioxopiperidin-3-yl]amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[[(3S)-2,6-dioxopiperidin-3-yl]amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-4-oxoquinazoline;

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]pyrrolidine-1-sulfonamide;

A compound of Formula III or a pharmaceutically acceptable salt thereof, for use in the treatment and/or prophylaxis of cancer;

The use of a compound of Formula III or a pharmaceutically acceptable salt thereof, for the preparation of a medicament for the therapeutic and/or prophylactic treatment of cancer;

A method for the therapeutic and/or prophylactic treatment of cancer, which method comprises administering an effective amount of a compound of Formula III or a pharmaceutically acceptable salt thereof, to a patient in need thereof;

In some embodiments the cancer is a BRAF V600X mutated tumor;

In some embodiments the cancer is a BRAF V600E/K mutated tumor;

In some embodiments the cancer is targeted therapy naïve; and

In some embodiments the cancer is selected from melanoma, colorectal cancer and lung cancer, in particular non-small cell lung cancer.

Additional Embodiments of Formula III

1. A compound of Formula III (III)

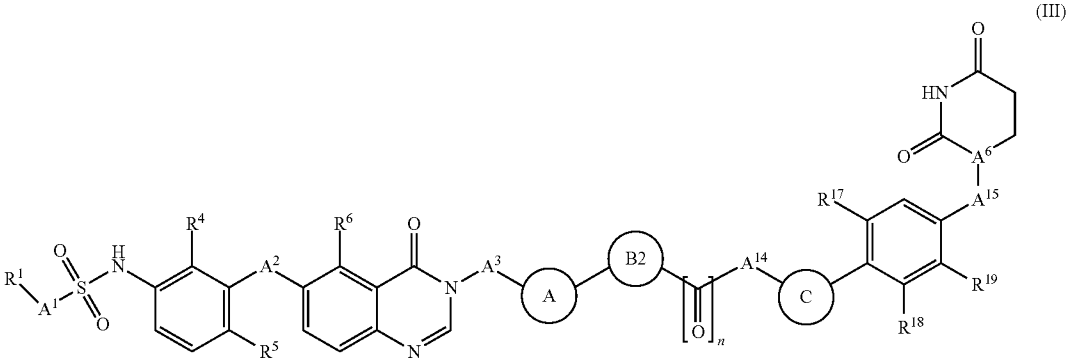

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide; and N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide;

or a pharmaceutically acceptable salt thereof.

The invention further relates to

A compound of Formula III or a pharmaceutically acceptable salt thereof, for use as therapeutically active substance.

A pharmaceutical composition comprising a compound of Formula III or a pharmaceutically acceptable salt thereof, and a pharmaceutically acceptable carrier;

The use of a compound of Formula III or a pharmaceutically acceptable salt thereof, for the therapeutic and/or prophylactic treatment of cancer;

wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C═O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

A is selected from a bond, pyrimidinyl, pyridinyl, pyrazolyl and 3-azabicyclo[3.1.0]hexyl;

B2 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl; wherein B2 is optionally substituted with one or two substituents independently selected from halogen, alkyl and alkoxy;

n is 0 or 1;

$A^{14}$ is selected from a bond, —$CH_2$—, —$CH_2$—$CH_2$—, —$CH(CH_2OH)$—, —NH—, —O—, cycloalkyl and alkylamino;

C is selected from azepanyl, azetidinyl, cycloalkyl, piperazinyl and piperidinyl; wherein C is optionally substituted with one or two substituents independently selected from halogen, hydroxy, alkyl and alkoxy;

$R^{17}$ is selected from hydrogen, alkyl, cyano, hydroxy, cycloalkyl, halogen and alkoxy;

$R^{18}$ is selected from hydrogen, alkyl, cyano, hydroxy, cycloalkyl, halogen and alkoxy;

$R^{19}$ is selected from hydrogen, alkyl, cyano, hydroxy, cycloalkyl, halogen and alkoxy;

$A^{15}$ is selected from a bond, —O— and —NH—; and $A^6$ is —CH— or —N—;

or a pharmaceutically acceptable salt thereof.

2. A compound according to embodiment 1, wherein $A^1$ is selected from —$NR^2$— and —$CHR^{2'}$—;

$R^1$ is selected from hydrogen, alkyl and cycloalkyl;

$R^2$ is selected from alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C═O)—;

$R^6$ is selected from hydrogen, halogen, hydroxy, amino, dialkylamino, alkoxy, alkyl and alkoxyalkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

A is selected from a bond, pyrimidinyl, pyridinyl, pyrazolyl and 3-azabicyclo[3.1.0]hexyl;

B2 is selected from phenyl, piperidinyl, piperazinyl, halopiperidinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl;

n is 0 or 1;

$A^{14}$ is selected from a bond, —$CH_2$—, —$CH_2$—$CH_2$—, —$CH(CH_2OH)$—, —NH—, —O—, cycloalkyl and alkylamino;

C is selected from azepanyl, azetidinyl, cycloalkyl, halopiperidinyl, hydroxypiperidinyl, alkoxypiperidinyl, piperazinyl and piperidinyl;

$R^{17}$ is selected from hydrogen, halogen and alkoxy;

$R^{18}$ is selected from hydrogen, halogen and alkoxy;

$R^{19}$ is selected from hydrogen, halogen and alkoxy;

$A^{15}$ is selected from a bond, —O— and —NH—; and $A^6$ is —CH— or —N—;

or a pharmaceutically acceptable salt thereof.

3. A compound according to embodiment 1 or 2, wherein $A^1$ is selected from —$NR^2$— and —$CHR^{2'}$—;

$R^8$ is alkyl;

$R^2$ is selected from alkyl, cycloalkyl and haloalkyl;

or $R^1$ and $R^2$ together with the nitrogen atom to which they are attached form heterocycloalkyl optionally substituted with one or two $R^3$;

$R^{2'}$ is alkyl;

or $R^1$ and $R^{2'}$ together with the carbon atom to which they are attached form cycloalkyl;

each $R^3$ is independently selected from halogen and alkoxy.

4. A compound according to any one of embodiments 1 to 3, wherein $A^1$ is selected from —$NR^2$— and —$CHR^{2'}$—;

$R^1$ is methyl;

$R^2$ is selected from ethyl, fluoroethyl, difluoroethyl and cyclopropyl;

or $R^1$ and $R^2$ together with the nitrogen atom to which they are attached form heterocycloalkyl optionally substituted with one or two $R^3$;

$R^{2'}$ is alkyl;

or $R^1$ and $R^{2'}$ together with the carbon atom to which they are attached form cycloalkyl;

each $R^3$ is independently selected from fluoro and methoxy.

5. A compound according to any one of embodiments 1 to 4, wherein $R^1$ is methyl.

6. A compound according to any one of embodiments 1 to 5, wherein $R^2$ is selected from ethyl, fluoroethyl, difluoroethyl and cyclopropyl.

7. A compound according to any one of embodiments 1 to 6, wherein $A^1$ is —$NR^2$_.

8. A compound according to any one of embodiments 1 to 6, wherein $A^1$ is —$CHR^{2'}$—.

9. A compound according to any one of embodiments 1 to 8, wherein the heterocycloalkyl which is formed by $R^1$ and $R^2$ together with the nitrogen atom to which they are attached is selected from pyrrolidinyl, piperidinyl, azetidinyl and 3-azabicyclo[3.1.0]hexyl, and wherein the heterocycloalkyl is in each instance optionally substituted with one or two $R^3$ independently selected from fluoro and methoxy.

10. A compound according to any one of embodiments 1 to 9, wherein the cycloalkyl which is formed by $R^1$ and $R^{2'}$ together with the carbon atom to which they are attached is selected from cyclopropyl, cyclobutyl, cyclopentyl and cyclohexyl.

11. A compound according to any one of embodiments 1 to 10, wherein each $R^3$ is independently selected from fluoro and methoxy.

12. A compound according to any one of embodiments 1 to 11, wherein $R^4$ is cyano.

13. A compound according to any one of embodiments 1 to 12, wherein $R^5$ is selected from hydrogen and halogen.

14. A compound according to any one of embodiments 1 to 13, wherein $R^5$ is selected from hydrogen and fluoro.

15. A compound according to any one of embodiments 1 to 14, wherein $A^2$ is selected from —O— and —NH—.

16. A compound according to any one of embodiments 1 to 15, wherein $A^2$ is —O—.

17. A compound according to any one of embodiments 1 to 16, wherein $R^6$ is selected from hydrogen, fluoro, chloro, bromo, hydroxy, amino, methoxy, methyl and methoxymethyl.
18. A compound according to any one of embodiments 1 to 17, wherein $R^6$ is hydrogen.
19. A compound according to any one of embodiments 1 to 18, wherein $A^3$ is selected from a bond, $—CH_2—$, $—CH_2—CH_2—$, $—CH_2—CH_2—CH_2—$, $—CH(CH_3)—CH_2—CH_2—$, $—CH_2—CH(CH_3)—CH_2—$ and $—CH_2—CH_2—CH(CH_3)—$.
20. A compound according to any one of embodiments 1 to 19, wherein $A^3$ is a bond.
21. A compound according to any one of embodiments 1 to 20, wherein A is selected from a bond, pyridinyl and pyrimidinyl.
22. A compound according to any one of embodiments 1 to 21, wherein B2 is selected from phenyl, piperidinyl, piperazinyl, 1-oxa-8-azaspiro[4.5]decyl, 7-azaspiro[3.5]nonyl and 8-azaspiro[4.5]decyl.
23. A compound according to any one of embodiments 1 to 22, wherein B2 is selected from piperazinyl and 1-oxa-8-azaspiro[4.5]decyl.
24. A compound according to any one of embodiments 1 to 23, wherein $A^{14}$ is $—CH_2—$.
25. A compound according to any one of embodiments 1 to 24, wherein C is selected from difluoropiperidinyl, hydroxypiperidinyl, methoxypiperidinyl, piperazinyl and piperidinyl.
26. A compound according to any one of embodiments 1 to 25, wherein C is piperidinyl.
27. A compound according to any one of embodiments 1 to 26, wherein $R^{17}$ is selected from hydrogen, fluoro and methoxy.
28. A compound according to any one of embodiments 1 to 27, wherein $R^{18}$ is selected from hydrogen and fluoro.
29. A compound according to any one of embodiments 1 to 28, wherein $R^{19}$ is selected from hydrogen, fluoro and methoxy.
30. A compound according to any one of embodiments 1 to 29, wherein $A^{15}$ is —NH—.
31. A compound according to any one of embodiments 1 to 29, wherein $A^{15}$ is —CH—.
32. A compound according to any one of embodiments 1 to 31, wherein n is 1.
33. A compound according to any of embodiments 1 to 32 selected from 6-[2-cyano-3-[[ethyl(methyl)sulfamoyl]amino]-6-fluoro-phenoxy]-3-[2-[1-[2-[4-[4-[(2,6-dioxopiperidin-3-yl)amino]-2-fluorophenyl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[2-[1-[2-[4-[4-(2,6-dioxopiperidin-3-yl)-2-fluorophenyl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[2-[1-[2-[4-[4-[(2,6-dioxopiperidin-3-yl)amino]-3-fluorophenyl]piperidin-1-yl]acetyl]piperidin-4-yl]ethyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]phenyl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[3-[1-[2-[4-[4-(2,6-dioxopiperidin-3-yl)-2-fluorophenyl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]piperidin-4-yl]propyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]phenyl]piperidin-1-yl]-2-oxoethyl]piperidin-4-yl]propyl]-4-oxoquinazoline;

6-[2-cyano-3-[[ethyl(methyl)sulfamoyl]amino]-6-fluoro-phenoxy]-3-[2-[4-[2-[4-[4-[(2,6-dioxopiperidin-3-yl)amino]-2-fluorophenyl]piperidin-1-yl]acetyl]piperazin-1-yl]ethyl]-4-oxoquinazoline;

6-[2-cyano-3-[[ethyl(methyl)sulfamoyl]amino]-6-fluoro-phenoxy]-3-[2-[4-[2-[4-[4-[(2,6-dioxopiperidin-3-yl)amino]phenyl]piperidin-1-yl]acetyl]piperazin-1-yl]ethyl]-4-oxoquinazoline;

6-[2-cyano-3-[[ethyl(methyl)sulfamoyl]amino]-6-fluoro-phenoxy]-3-[4-[1-[2-[4-[4-[(2,6-dioxopiperidin-3-yl)amino]-2-fluorophenyl]piperidin-1-yl]acetyl]piperidin-4-yl]butan-2-yl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]piperidin-4-yl]butyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]-4-methylpiperidin-4-yl]propyl]-4-oxoquinazoline;

6-[2-cyano-3-[[ethyl(methyl)sulfamoyl]amino]-6-fluoro-phenoxy]-3-[2-[1-[2-[4-[4-[(2,6-dioxopiperidin-3-yl)amino]-2-fluorophenyl]piperidin-1-yl]acetyl]-4-fluoropiperidin-4-yl]ethyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]piperidin-4-yl]-2-methylpropyl]-4-oxoquinazoline;

6-[2-cyano-3-[[ethyl(methyl)sulfamoyl]amino]-6-fluoro-phenoxy]-3-[3-[1-[2-[4-[4-[(2,6-dioxopiperidin-3-yl)amino]-2-fluorophenyl]piperidin-1-yl]acetyl]-4-fluoropiperidin-4-yl]propyl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]-2-fluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-(2,6-dioxopiperidin-3-yl)-2-fluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]phenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]-3-fluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)amino]-2,6-difluorophenyl]piperidin-1-yl]acetyl]piperidin-4-yl]pyrazol-4-yl]-4-oxoquinazoline;

6-[2-cyano-3-[[ethyl(methyl)sulfamoyl]amino]-6-fluoro-phenoxy]-3-[1-[1-[2-[4-[4-[(2,6-dioxopiperidin-3-yl)

amino]phenyl]piperidin-1-yl]-2-oxoethyl]piperidin-4-yl]pyrazol-4-yl]-4-oxoquinazoline;

6-[2-cyano-3-[[ethyl(methyl)sulfamoyl]amino]-6-fluoro-phenoxy]-3-[7-[2-[4-[4-[(2,6-dioxopiperidin-3-yl)amino]-2-fluorophenyl]piperidin-1-yl]acetyl]-7-azaspiro[3.5]nonan-2-yl]-4-oxoquinazoline;

6-[2-cyano-3-[[ethyl(methyl)sulfamoyl]amino]-6-fluoro-phenoxy]-3-[7-[2-[1-[4-[(2,6-dioxopiperidin-3-yl)amino]-2-fluorophenyl]-4-hydroxypiperidin-4-yl]acetyl]-7-azaspiro[3.5]nonan-2-yl]-4-oxoquinazoline;

3-[6-[2-cyano-3-[[ethyl(methyl)sulfamoyl]amino]-6-fluoro-phenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[3-[2-[4-[4-[(2,6-dioxopiperidin-3-yl)amino]-2-fluorophenyl]piperidin-1-yl]acetyl]-3-azabicyclo[3.1.0]hexan-6-yl]-4-oxoquinazoline;

6-[2-cyano-3-[[ethyl(methyl)sulfamoyl]amino]phenoxy]-3-[7-[2-[4-[4-[(2,6-dioxopiperidin-3-yl)amino]-2-fluoro-phenyl]piperidin-1-yl]acetyl]-7-azaspiro[3.5]nonan-2-yl]-4-oxoquinazoline;

3-[6-[2-cyano-3-[[ethyl(methyl)sulfamoyl]amino]-6-fluoro-phenoxy]-4-oxoquinazolin-3-yl]-8-[2-[1-[4-[(2,6-dioxopiperidin-3-yl)amino]-2-fluorophenyl]-4-hydroxypiperidin-4-yl]acetyl]-1-oxa-8-azaspiro[4.5]decane;

6-[2-cyano-3-[[ethyl(methyl)sulfamoyl]amino]-6-fluoro-phenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

4-[6-[2-cyano-3-[[ethyl(methyl)sulfamoyl]amino]-6-fluoro-phenoxy]-4-oxoquinazolin-3-yl]-9-[2-[4-[4-[(2,6-dioxopiperidin-3-yl)amino]-2-fluorophenyl]piperidin-1-yl]acetyl]-1-oxa-9-azaspiro[5.5]undecane;

9-[6-[2-cyano-3-[[ethyl(methyl)sulfamoyl]amino]-6-fluoro-phenoxy]-4-oxoquinazolin-3-yl]-3-[2-[4-[4-[(2,6-dioxopiperidin-3-yl)amino]-2-fluorophenyl]piperidin-1-yl]acetyl]-3-azaspiro[5.5]undecane;

6-[2-cyano-3-[[ethyl(methyl)sulfamoyl]amino]-6-fluoro-phenoxy]-3-[[7-[2-[4-[4-[(2,6-dioxopiperidin-3-yl)amino]-2-fluorophenyl]piperidin-1-yl]acetyl]-7-azaspiro[3.5]nonan-2-yl]methyl]-4-oxoquinazoline;

6-[2-cyano-3-[[ethyl(methyl)sulfamoyl]amino]-6-fluoro-phenoxy]-3-[2-[2-[4-[4-[(2,6-dioxopiperidin-3-yl)amino]-2-fluorophenyl]piperidin-1-yl]acetyl]-2-azaspiro[4.5]decan-8-yl]-4-oxoquinazoline;

(3S)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

4-[6-[6-[2-cyano-3-[[ethyl(methyl)sulfamoyl]amino]-6-fluorophenoxy]-4-oxoquinazolin-3-yl]-3-azabicyclo[3.1.0]hexan-3-yl]-N-[1-[4-[(2,6-dioxopiperidin-3-yl)amino]-2-fluorophenyl]piperidin-4-yl]benzamide;

3-[[6-[2-cyano-3-[[ethyl(methyl)sulfamoyl]amino]-6-fluorophenoxy]-4-oxoquinazolin-3-yl]methyl]-8-[2-[4-[4-[(2,6-dioxopiperidin-3-yl)amino]-2-fluorophenyl]piperidin-1-yl]acetyl]-1-oxa-8-azaspiro[4.5]decane;

2-[6-[2-cyano-3-[[ethyl(methyl)sulfamoyl]amino]-6-fluoro-phenoxy]-4-oxoquinazolin-3-yl]-N-[1-[4-[(2,6-dioxopiperidin-3-yl)amino]-2-fluorophenyl]piperidin-4-yl]-7-azaspiro[3.5]nonane-7-carboxamide;

3-[6-[2-cyano-3-[[ethyl(methyl)sulfamoyl]amino]-6-fluoro-phenoxy]-4-oxoquinazolin-3-yl]-N-[1-[4-[(2,6-dioxopiperidin-3-yl)amino]-2-fluorophenyl]piperidin-4-yl]-1-oxa-8-azaspiro[4.5]decane-8-carboxamide;

6-[2-cyano-3-[[ethyl(methyl)sulfamoyl]amino]-6-fluoro-phenoxy]-3-[7-[3-[3-[4-[(2,6-dioxopiperidin-3-yl)amino]-2-fluorophenyl]azetidin-1-yl]cyclobutanecarbonyl]-7-azaspiro[3.5]nonan-2-yl]-4-oxoquinazoline;

6-[2-cyano-3-[[ethyl(methyl)sulfamoyl]amino]-6-fluoro-phenoxy]-3-[(3S)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3R)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[[(3R)-2,6-dioxopiperidin-3-yl]amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[[(3S)-2,6-dioxopiperidin-3-yl]amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[(3R)-8-[2-[4-[4-[[(3R)-2,6-dioxopiperidin-3-yl]amino]-2-fluorophenyl]piperidin-1-yl]acetyl]-8-azaspiro[4.5]decan-3-yl]-4-oxoquinazoline;

6-[2-cyano-3-[[ethyl(methyl)sulfamoyl]amino]-6-fluoro-phenoxy]-3-[(3R)-8-[2-[4-[4-[[(3S)-2,6-dioxopiperidin-3-yl]amino]-2-fluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[1-[4-[(2,6-dioxopiperidin-3-yl)amino]-2-fluorophenyl]piperidin-4-yl]acetyl]-1-oxa-8-azaspiro[4.5]decane;

6-[2-cyano-3-[[ethyl(methyl)sulfamoyl]amino]-6-fluoro-phenoxy]-3-[(3S)-8-[2-[4-[4-[(2,6-dioxopiperidin-3-yl)amino]-2-fluorophenyl]piperazin-1-yl]acetyl]-8-azaspiro[4.5]decan-3-yl]-4-oxoquinazoline;

(3R)—N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]-3-fluoropyrrolidine-1-sulfonamide;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperazin-1-yl]acetyl]-1-oxa-8-azaspiro[4.5]decane;

3-[6-[2-cyano-3-[[ethyl(methyl)sulfamoyl]amino]-6-fluoro-phenoxy]-5-fluoro-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluoro-phenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-5-fluoro-4-oxoquinazoline;

6-[2-cyano-3-[[ethyl(methyl)sulfamoyl]amino]-6-fluoro-phenoxy]-3-[(3S)-8-[2-[4-[4-[(2,6-dioxopiperidin-3-yl)amino]-3-fluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-3-fluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[4-[4-(2,6-dioxopiperidin-3-yl)-2-fluorophenyl]piperazin-1-yl]acetyl]-8-azaspiro[4.5]decan-3-yl]-4-oxoquinazoline;

N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]cyclopentanesulfonamide;

6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-5-methyl-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]-3,3-difluoropiperidin-1-yl]acetyl]-1-oxa-8-azaspiro[4.5]decane;

3-[6-[2-cyano-3-[[ethyl(methyl)sulfamoyl]amino]-6-fluorophenoxy]-5-methyl-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]piperazin-1-yl]acetyl]-1-oxa-8-azaspiro[4.5]decane;

N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]propane-2-sulfonamide;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2,5-difluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2,3-difluorophenyl]piperidin-1-yl]acetyl]-8-azaspiro[4.5]decan-3-yl]-4-oxoquinazoline;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2,3-difluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]-3,3-difluoropiperidin-1-yl]acetyl]-1-oxa-8-azaspiro[4.5]decane;

6-[2-cyano-3-[[ethyl(methyl)sulfamoyl]amino]-6-fluorophenoxy]-3-[(3S)-8-[2-[4-[4-(2,6-dioxopiperidin-3-yl)-2-fluorophenyl]-3,3-difluoropiperidin-1-yl]acetyl]-8-azaspiro[4.5]decan-3-yl]-4-oxoquinazoline;

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2,5-difluorophenyl]piperidin-1-yl]acetyl]-8-azaspiro[4.5]decan-3-yl]-4-oxoquinazoline;

3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

5-bromo-6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

5-chloro-6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-5-fluoro-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluoro-5-methoxyphenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]azepan-1-yl]acetyl]-1-oxa-8-azaspiro[4.5]decane;

(3R)-3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

5-chloro-6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

5-chloro-6-[2-cyano-3-[[ethyl(methyl)sulfamoyl]amino]-6-fluorophenoxy]-3-[(3R)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline;

3-[5-amino-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluoroanilino]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[4-[4-[(2,6-dioxopiperidin-3-yl)amino]-2-fluorophenyl]cyclohexyl]-1-oxa-8-azaspiro[4.5]decane;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluorophenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-5-fluoro-4-oxoquinazoline;

6-[2-cyano-3-[[ethyl(methyl)sulfamoyl]amino]-6-fluorophenoxy]-3-[6-[4-[2-[4-[4-[(2,6-dioxopiperidin-3-yl)

amino]-2-fluoro-6-methoxyphenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluoro-5-methoxyphenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluoro-6-methoxyphenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluoro-5-methoxyphenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]-3-hydroxypropanoyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[6-[4-[2-[4-[4-[[(3R)-2,6-dioxopiperidin-3-yl]amino]-2-fluorophenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[6-[4-[2-[4-[4-[[(3S)-2,6-dioxopiperidin-3-yl]amino]-2-fluorophenyl]piperidin-1-yl]acetyl]piperazin-1-yl]pyridin-3-yl]-4-oxoquinazoline;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

(3R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

6-[2-cyano-3-[[ethyl(methyl)sulfamoyl]amino]-6-fluorophenoxy]-3-[2-[4-[(2S)-2-[4-[4-[[(3S)-2,6-dioxopiperidin-3-yl]amino]-2-fluorophenyl]piperidin-1-yl]-3-hydroxypropanoyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-methoxy-4-oxoquinazoline;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-methoxy-4-oxoquinazoline;

5-amino-6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

5-amino-6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[(3R,4R)-4-[4-[[(3R)-2,6-dioxopiperidin-3-yl]amino]-2-fluorophenyl]-3-methoxypiperidin-1-yl]acetyl]piperazin-1-yl]pyrimidin-5-yl]-4-oxoquinazoline;

6-[2-cyano-3-[[ethyl(methyl)sulfamoyl]amino]-6-fluorophenoxy]-3-[2-[4-[2-[(3S,4S)-4-[4-[[(3S)-2,6-dioxopiperidin-3-yl]amino]-2-fluorophenyl]-3-methoxypiperidin-1-yl]acetyl]piperazin-1-yl]pyrimidin-5-yl]-4-oxoquinazoline;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclohexanesulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]piperidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]pyrrolidine-1-sulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide;

(3S)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

(3S)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]piperidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide;

(3R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-fluoropyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxyazetidine-1-sulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide;

6-[2-cyano-3-[[2,2-difluoroethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-6-fluoro-3-[[2-fluoroethyl(methyl)sulfamoyl]amino]phenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-6-fluoro-3-[[2-fluoroethyl(methyl)sulfamoyl]amino]phenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[2,2-difluoroethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3,3-difluoropyrrolidine-1-sulfonamide;

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-fluoropyrrolidine-1-sulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]azetidine-1-sulfonamide;

6-[2-cyano-3-[[cyclopropyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline;

6-[2-cyano-3-[[cyclopropyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

(1S,5R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-azabicyclo[3.1.0]hexane-3-sulfonamide;

(3R,4R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3,4-difluoropyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]azetidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclobutanesulfonamide;

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclobutanesulfonamide;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-(methoxymethyl)-4-oxoquinazoline;

(3R)-3-[6-[2-cyano-3-[[ethyl(methyl)sulfamoyl]amino]-6-fluorophenoxy]-4-oxoquinazolin-3-yl]-8-[4-[4-[(2,6-dioxopiperidin-3-yl)amino]-2-fluorophenyl]cyclohexyl]-1-oxa-8-azaspiro[4.5]decane;

N-[3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-2,4-difluorophenyl]cyclopentanesulfonamide;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-(methoxymethyl)-4-oxoquinazoline;

3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorophenoxy]-4-oxoquinazoline;

3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorophenoxy]-4-oxoquinazoline;

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-hydroxy-4-oxoquinazoline;

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-hydroxy-4-oxoquinazoline;

3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorobenzoyl]-4-oxoquinazoline;

6-[2-cyano-3-[[ethyl(methyl)sulfamoyl]amino]-6-fluorophenoxy]-3-[2-[1-[2-[4-[4-[(2,6-dioxo-3-piperidyl)amino]phenyl]-1-piperidyl]acetyl]-4-piperidyl]ethyl]-4-oxo-quinazoline;

6-[2-cyano-3-[[ethyl(methyl)sulfamoyl]amino]-6-fluorophenoxy]-3-[2-[1-[2-[4-[4-[(2,6-dioxo-3-piperidyl)amino]phenyl]-1-piperidyl]-2-oxo-ethyl]-4-piperidyl]ethyl]-4-oxo-quinazoline;

N-[2-cyano-3-[3-[2-[1-[2-[4-[4-[(2,6-dioxo-3-piperidyl)amino]phenyl]-1-piperidyl]acetyl]-4-piperidyl]ethyl]-4-oxo-quinazolin-6-yl]oxy-4-fluoro-phenyl]cyclopentanesulfonamide;

6-[3-[[tert-butyl(methyl)sulfamoyl]amino]-2-cyano-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline; and 6-[3-[[tert-butyl(methyl)sulfamoyl]amino]-2-cyano-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline;

or a pharmaceutically acceptable salt thereof.

34. A compound according to any of embodiments 1 to 33 selected from (3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[[(3R)-2,6-dioxopiperidin-3-yl]amino]-2-fluorophenyl]piperidin-1-yl]acetyl]-1-oxa-8-azaspiro[4.5]decane;

(3R)-3-[6-[2-cyano-3-[[ethyl(methyl)sulfamoyl]amino]-6-fluorophenoxy]-4-oxoquinazolin-3-yl]-8-[2-[4-[4-[[(3S)-2,6-dioxopiperidin-3-yl]amino]-2-fluorophenyl]piperidin-1-yl]acetyl]-1-oxa-8-azaspiro[4.5]decane;

6-[2-cyano-3-[[ethyl(methyl)sulfamoyl]amino]-6-fluorophenoxy]-3-[2-[4-[2-[4-[4-[(2,6-dioxopiperidin-3-yl)

amino]-2-fluorophenyl]piperidin-1-yl]acetyl]piperazin-1-yl]pyrimidin-5-yl]-4-oxoquinazoline;

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]pyrrolidine-1-sulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide;

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide; and N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide;

or a pharmaceutically acceptable salt thereof.

35. A compound according to any one of embodiments 1 to 34, or a pharmaceutically acceptable salt thereof, for use as therapeutically active substance.

36. A pharmaceutical composition comprising a compound according to any one of embodiments 1 to 34, or a pharmaceutically acceptable salt thereof, and a pharmaceutically acceptable carrier.

37. The use of a compound according to any one of embodiments 1 to 34, or a pharmaceutically acceptable salt thereof, for the therapeutic and/or prophylactic treatment of cancer.

38. A compound according to any one of embodiments 1 to 34, or a pharmaceutically acceptable salt thereof, for use in the treatment and/or prophylaxis of cancer.

39. The use of a compound according to any one of embodiments 1 to 34, or a pharmaceutically acceptable salt thereof, for the preparation of a medicament for the therapeutic and/or prophylactic treatment of cancer.

40. A method for the therapeutic and/or prophylactic treatment of cancer, which method comprises administering an effective amount of a compound according to any one of embodiments 1 to 34, or a pharmaceutically acceptable salt thereof, to a patient in need thereof.

Embodiments of Formula V and Formula VI

In certain embodiments the compound of Formula V is a compound of Formula V-A (V-A)

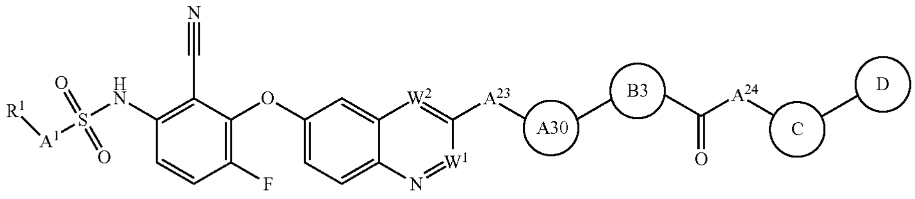

wherein the substituents and variables are as described herein, or a pharmaceutically acceptable salt thereof.

In certain embodiments the compound of Formula V is a compound of Formula V-B (V-B)

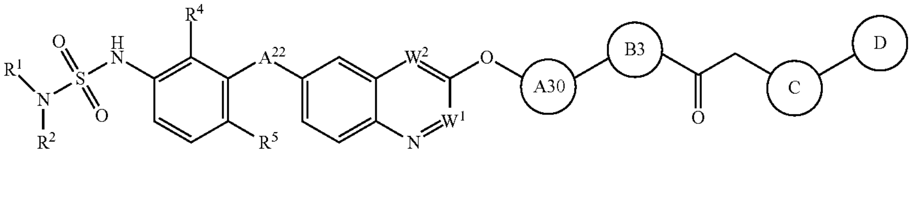

wherein the substituents and variables are as described herein, or a pharmaceutically acceptable salt thereof.

In certain embodiments the compound of Formula V is a compound of Formula V-C (V-C)

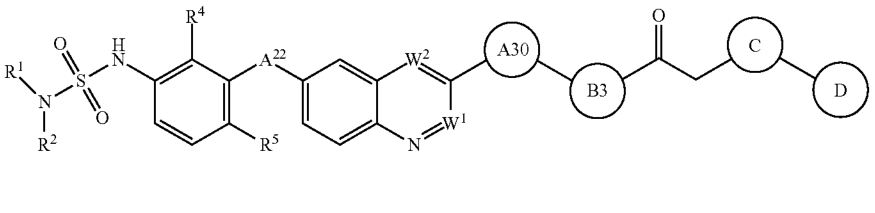

wherein the substituents and variables are as described herein, or a pharmaceutically acceptable salt thereof.

In certain embodiments the compound of Formula V is a compound of Formula V-D (V-D)

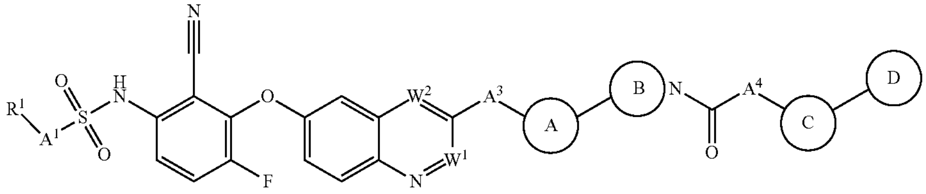

wherein the substituents and variables are as described herein, or a pharmaceutically acceptable salt thereof.

In certain embodiments the compound of Formula V is a compound of Formula V-E (V-E)

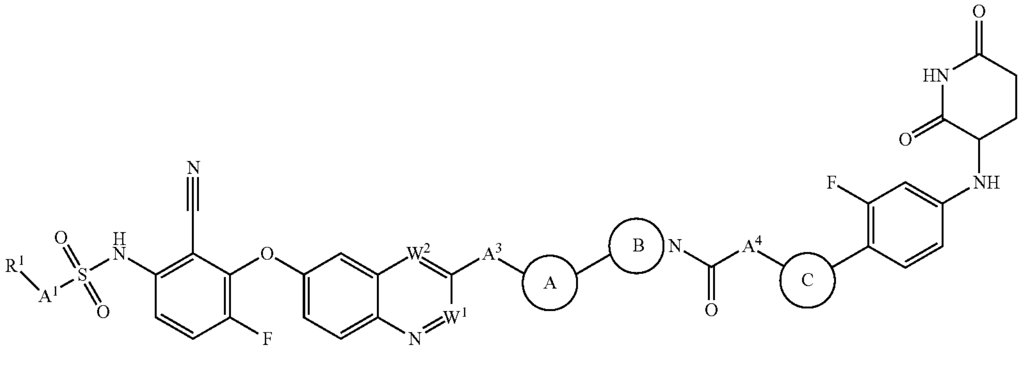

wherein the substituents and variables are as described herein, or a pharmaceutically acceptable salt thereof.

In certain embodiments the compound of Formula V is a compound of Formula V-F (V-F)

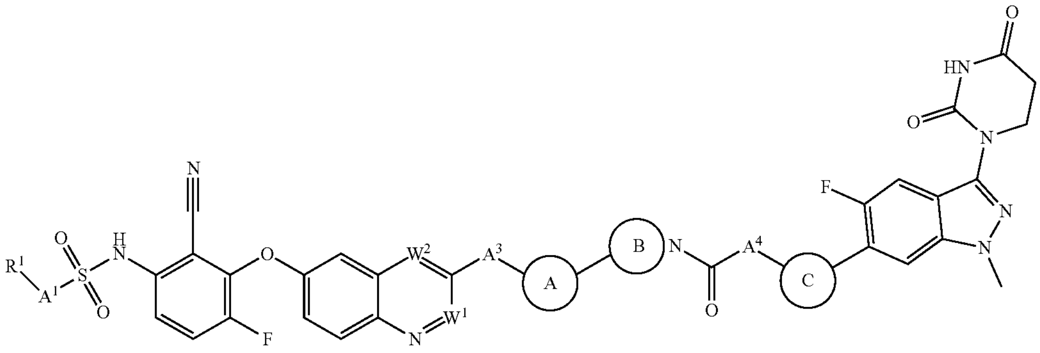

wherein the substituents and variables are as described herein, or a pharmaceutically acceptable salt thereof.

In certain embodiments the compound of Formula VI is selected from:

(VI-A)

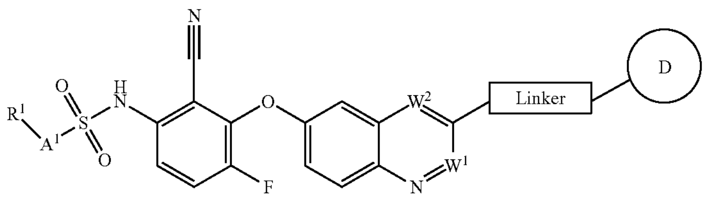

-continued
(VI-B)
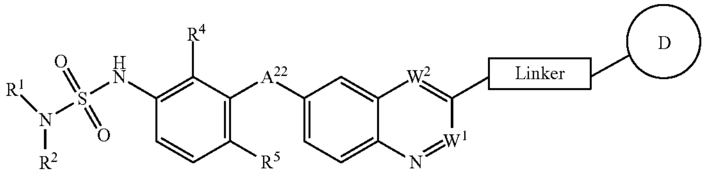
(VI-C)
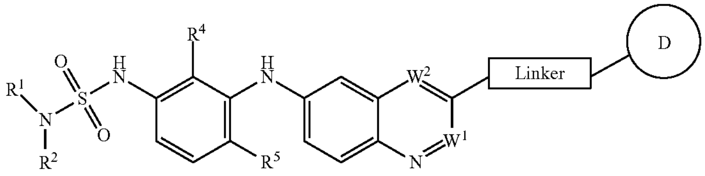
(VI-D)
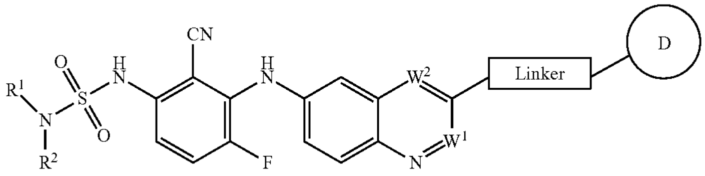
(VI-E)
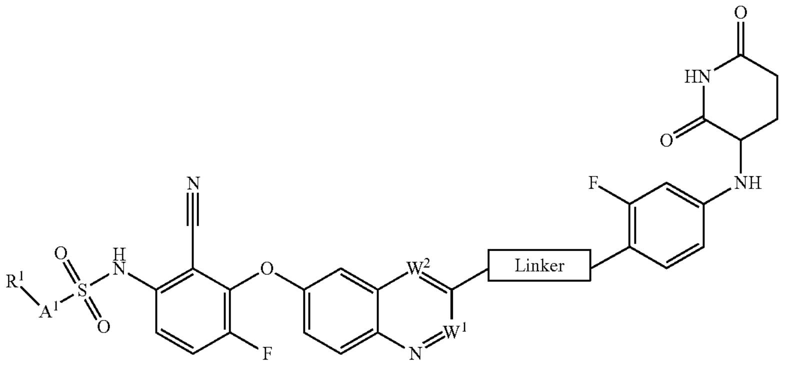
(VI-F)
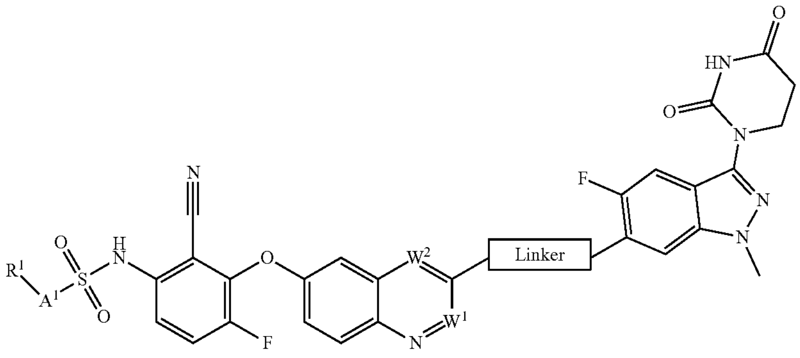
or a pharmaceutically acceptable salt thereof.
A compound of Formula V
(V)
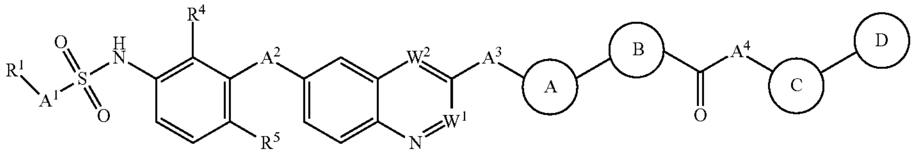

wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^{22}$ is selected from —O—, and —NH—;

$W^1$ is selected from —N— and —CH—;

$W^2$ is selected from —N—, and —$CR^{26}$—;

$R^{26}$ is selected from hydrogen, halogen, hydroxy, amino, alkoxy and alkyl;

$A^{23}$ is selected from a bond, —O— and —$CH_2$—;

A30 is selected from a bond, —$CH_2$—, pyrimidinyl, pyridinyl, pyrazolyl and 3-azabicyclo[3.1.0]hexyl;

B3 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl and 8-azaspiro[4.5]decyl;

$A^{24}$ is selected from a bond, —$CH_2$—, —NH— and —O—;

C is selected from azepanyl, azetidinyl, cycloalkyl, piperazinyl and piperidinyl; wherein C is optionally substituted with one or two substituents independently selected from halogen, hydroxy, alkyl and alkoxy; and D is selected from

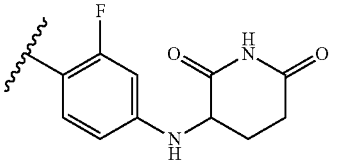

and

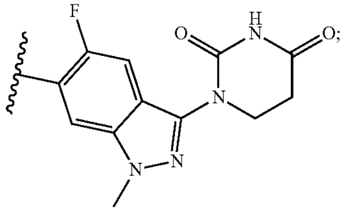

;

or a pharmaceutically acceptable salt thereof.

One embodiment of the invention relates to compound of Formula V wherein $A^1$ is —$NR^2$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

each $R^3$ is independently selected from halogen and alkoxy;

$R^4$ is selected from hydrogen, alkyl, cyano and halogen;

$R^5$ is selected from hydrogen, alkyl, cyano and halogen;

$A^{22}$ is selected from —O—, and —NH—;

$W^1$ is selected from —N— and —CH—;

$W^2$ is selected from —N—, and —$CR^{26}$—;

$R^{26}$ is selected from hydrogen, halogen, hydroxy, amino, alkoxy and alkyl;

$A^{23}$ is selected from a bond, —O— and —$CH_2$—;

A30 is selected from a bond, —$CH_2$—, pyrimidinyl, pyridinyl, pyrazolyl and 3-azabicyclo[3.1.0]hexyl;

B3 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl and 8-azaspiro[4.5]decyl;

$A^{24}$ is selected from a bond, —$CH_2$—, —NH— and —O—;

C is selected from hydroxypiperidinyl and piperidinyl; and

D is selected from

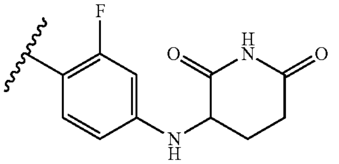

and

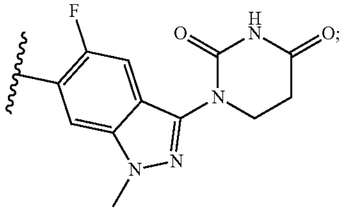

;

or a pharmaceutically acceptable salt thereof.

One embodiment of the invention relates to compound of Formula V wherein $A^1$ is —$NR^2$—;

$R^1$ is alkyl; and $R^2$ is alkyl.

One embodiment of the invention relates to compound of Formula V wherein $A^1$ is —$NR^2$—;

$R^1$ is methyl; and $R^2$ is selected from ethyl, tert-butyl and cyclopropyl.

The invention further relates to:

A compound of Formula V wherein $R^1$ is methyl, or a pharmaceutically acceptable salt thereof;

A compound of Formula V wherein $R^2$ is ethyl or a pharmaceutically acceptable salt thereof;

A compound of Formula V wherein $A^1$ is —$NR^2$—, or a pharmaceutically acceptable salt thereof;

A compound of Formula V wherein the heterocycloalkyl which is formed by $R^1$ and $R^2$ together with the nitrogen atom to which they are attached is selected from pyrrolidinyl, piperidinyl, azetidinyl and 3-azabicyclo[3.1.0]hexyl, and wherein the heterocycloalkyl is in each instance optionally substituted with one or two $R^3$ independently selected from fluoro and methoxy, or a pharmaceutically acceptable salt thereof;

A compound of Formula V wherein the cycloalkyl which is formed by $R^1$ and $R^{2'}$ together with the carbon atom to which they are attached is selected from cyclopropyl, cyclobutyl, cyclopentyl and cyclohexyl, or a pharmaceutically acceptable salt thereof;

A compound of Formula V wherein each $R^3$ is independently selected from fluoro and methoxy, or a pharmaceutically acceptable salt thereof;

A compound of Formula V wherein $R^4$ is cyano, or a pharmaceutically acceptable salt thereof;

A compound of Formula V wherein $R^5$ is halogen, or a pharmaceutically acceptable salt thereof;

A compound of Formula V wherein $R^5$ is fluoro, or a pharmaceutically acceptable salt thereof;

A compound of Formula V wherein $A^{22}$ is —O—, or a pharmaceutically acceptable salt thereof;

A compound of Formula V wherein $W^1$ is —CH—, or a pharmaceutically acceptable salt thereof;

A compound of Formula V wherein $W^2$ is —N—, or a pharmaceutically acceptable salt thereof;

A compound of Formula V wherein $W^2$ is —$CR^{26}$—, or a pharmaceutically acceptable salt thereof;

A compound of Formula V wherein $R^{26}$ is selected from hydrogen and alkoxy, or a pharmaceutically acceptable salt thereof;

A compound of Formula V wherein $R^{26}$ is selected from hydrogen and methoxy, or a pharmaceutically acceptable salt thereof;

A compound of Formula V wherein $A^{23}$ is selected from a bond and —O—, or a pharmaceutically acceptable salt thereof;

A compound of Formula V wherein $A^{23}$ is a bond, or a pharmaceutically acceptable salt thereof;

A compound of Formula V wherein A30 is selected from a bond, —$CH_2$— and pyrazolyl, or a pharmaceutically acceptable salt thereof;

A compound of Formula V wherein A30 is a bond, or a pharmaceutically acceptable salt thereof;

A compound of Formula V wherein A30 is —$CH_2$—, or a pharmaceutically acceptable salt thereof;

A compound of Formula V wherein A30 is pyrazolyl, or a pharmaceutically acceptable salt thereof;

A compound of Formula V wherein B3 is selected from piperidinyl, 1,4-diazacycloheptyl, 1-oxa-8-azaspiro[4.5]decyl, 2,8-diazaspiro[4.5]decyl, 3-azabicyclo[3.1.0]hexyl, and 8-azaspiro[4.5]decyl, or a pharmaceutically acceptable salt thereof;

A compound of Formula V wherein B3 is 1-oxa-8-azaspiro[4.5]decyl, or a pharmaceutically acceptable salt thereof;

A compound of Formula V wherein $A^{24}$ is —$CH_2$—, or a pharmaceutically acceptable salt thereof;

A compound of Formula V wherein C is selected from hydroxypiperidinyl and piperidinyl.

A compound of Formula V wherein D is

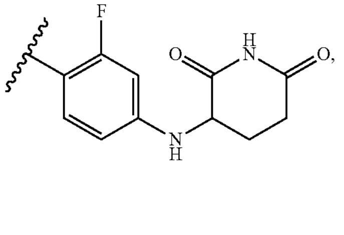 [SMILES: *c1ccc(NC2CCC(=O)NC2=O)cc1F]

or a pharmaceutically acceptable salt thereof; and

A compound of Formula V wherein D is

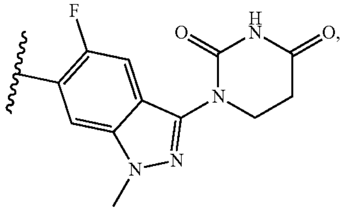

or a pharmaceutically acceptable salt thereof.

The invention further relates to a compound of Formula V selected from

7-[2-cyano-3-[[ethyl(methyl)sulfamoyl]amino]-6-fluorophenoxy]-2-[4-[4-[2-[4-[4-[(2,6-dioxopiperidin-3-yl)amino]-2-fluorophenyl]piperidin-1-yl]acetyl]-1,4-diazepan-1-yl]pyrazol-1-yl]quinoxaline;

7-[2-cyano-3-[[ethyl(methyl)sulfamoyl]amino]-6-fluorophenoxy]-2-[[1-[2-[4-[4-[(2,6-dioxopiperidin-3-yl)amino]-2-fluorophenyl]piperidin-1-yl]acetyl]piperidin-4-yl]methoxy]quinoxaline;

7-[2-cyano-3-[[ethyl(methyl)sulfamoyl]amino]-6-fluorophenoxy]-2-[[(1R,5S)-3-[2-[4-[4-[(2,6-dioxopiperidin-3-yl)amino]-2-fluorophenyl]piperidin-1-yl]acetyl]-3-azabicyclo[3.1.0]hexan-6-yl]methoxy]quinoxaline;

3-[6-[2-cyano-3-[[ethyl(methyl)sulfamoyl]amino]-6-fluorophenoxy]quinolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

7-[2-cyano-3-[[ethyl(methyl)sulfamoyl]amino]-6-fluorophenoxy]-2-[8-[2-[4-[4-[(2,6-dioxopiperidin-3-yl)amino]-2-fluorophenyl]piperidin-1-yl]acetyl]-2,8-diazaspiro[4.5]decan-2-yl]quinoxaline;

7-[2-cyano-3-[[ethyl(methyl)sulfamoyl]amino]-6-fluorophenoxy]-2-[8-[2-[4-[4-[(2,6-dioxopiperidin-3-yl)amino]-2-fluorophenyl]piperidin-1-yl]acetyl]-8-azaspiro[4.5]decan-3-yl]quinoxaline;

3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[7-[2-cyano-3-[[ethyl(methyl)sulfamoyl]amino]-6-fluorophenoxy]quinoxalin-2-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[6-[2-cyano-3-[[ethyl(methyl)sulfamoyl]amino]-6-fluorophenoxy]-4-methoxyquinolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-methoxyquinolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane; and (3S)-3-[6-[2-cyano-3-[[ethyl(methyl)sulfamoyl]amino]-6-fluorophenoxy]cinnolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

or a pharmaceutically acceptable salt thereof.

The invention further relates to

A compound of Formula V or a pharmaceutically acceptable salt thereof, for use as therapeutically active substance.

A pharmaceutical composition comprising a compound of Formula V or a pharmaceutically acceptable salt thereof, and a pharmaceutically acceptable carrier;

The use of a compound of Formula V or a pharmaceutically acceptable salt thereof, for the therapeutic and/or prophylactic treatment of cancer;

A compound of Formula V or a pharmaceutically acceptable salt thereof, for use in the treatment and/or prophylaxis of cancer;

The use of a compound of Formula V or a pharmaceutically acceptable salt thereof, for the preparation of a medicament for the therapeutic and/or prophylactic treatment of cancer;

A method for the therapeutic and/or prophylactic treatment of cancer, which method comprises administering an effective amount of a compound of Formula V or a pharmaceutically acceptable salt thereof, to a patient in need thereof;

In some embodiments the cancer is a BRAF V600X mutated tumor;

In some embodiments the cancer is a BRAF V600E/K mutated tumor;

In some embodiments the cancer is targeted therapy naïve; and

In some embodiments the cancer is selected from melanoma, colorectal cancer and lung cancer, in particular non-small cell lung cancer.

Additional Embodiments of Formula V

1. A compound of Formula V

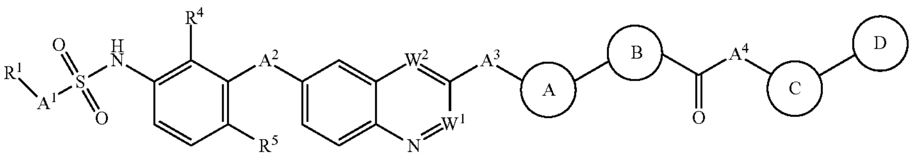

(V)

wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^{22}$ is selected from —O—, and —NH—;

$W^1$ is selected from —N— and —CH—;

$W^2$ is selected from —N—, and —$CR^{26}$—;

$R^{26}$ is selected from hydrogen, halogen, hydroxy, amino, alkoxy and alkyl;

$A^{23}$ is selected from a bond, —O— and —$CH_2$—;

A30 is selected from a bond, —$CH_2$—, pyrimidinyl, pyridinyl, pyrazolyl and 3-azabicyclo[3.1.0]hexyl;

B3 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl and 8-azaspiro[4.5]decyl;

$A^{24}$ is selected from a bond, —$CH_2$—, —NH— and —O—;

C is selected from azepanyl, azetidinyl, cycloalkyl, piperazinyl and piperidinyl; wherein C is optionally substituted with one or two substituents independently selected from halogen, hydroxy, alkyl and alkoxy; and D is selected from

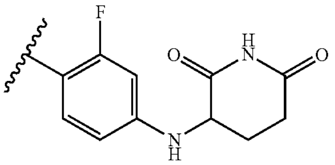

and

-continued

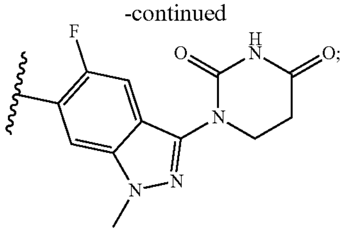

;

or a pharmaceutically acceptable salt thereof.

2. A compound according to embodiment 1, wherein $A^1$ is —$NR^2$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

each $R^3$ is independently selected from halogen and alkoxy;

$R^4$ is selected from hydrogen, alkyl, cyano and halogen;

$R^5$ is selected from hydrogen, alkyl, cyano and halogen;

$A^{22}$ is selected from —O—, and —NH—;

$W^1$ is selected from —N— and —CH—;

$W^2$ is selected from —N—, and —$CR^{26}$—;

$R^{26}$ is selected from hydrogen, halogen, hydroxy, amino, alkoxy and alkyl;

$A^{23}$ is selected from a bond, —O— and —$CH_2$—;

A30 is selected from a bond, —$CH_2$—, pyrimidinyl, pyridinyl, pyrazolyl and 3-azabicyclo[3.1.0]hexyl;

B3 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl and 8-azaspiro[4.5]decyl;

$A^{24}$ is selected from a bond, —$CH_2$—, —NH— and —O—;

C is selected from hydroxypiperidinyl and piperidinyl; and

D is selected from

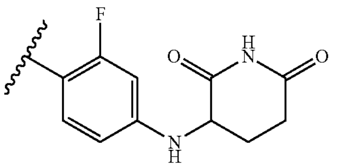

and

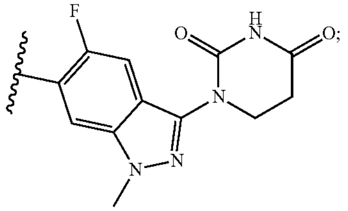 [SMILES: *c1cc2c(cc1F)c(N1CCC(=O)NC1=O)nn2C]

or a pharmaceutically acceptable salt thereof.

3. A compound according to embodiment 1 or 2, wherein
$A^1$ is —$NR^2$—;
$R^1$ is alkyl; and
$R^2$ is alkyl.

4. A compound according to any one of embodiments 1 to 3, wherein
$A^1$ is —$NR^2$—;
$R^1$ is methyl; and
$R^2$ is ethyl.

5. A compound according to any one of embodiments 1 to 4, wherein $R^4$ is cyano.

6. A compound according to any one of embodiments 1 to 5, wherein $R^5$ is halogen.

7. A compound according to any one of embodiments 1 to 6, wherein $R^5$ is fluoro.

8. A compound according to any one of embodiments 1 to 7, wherein $A^{22}$ is —O—.

9. A compound according to any one of embodiments 1 to 8, wherein $W^1$ is —CH—.

10. A compound according to any one of embodiments 1 to 9, wherein $W^2$ is —N—.

11. A compound according to any one of embodiments 1 to 10, wherein $W^2$ is —$CR^{26}$—.

12. A compound according to any one of embodiments 1 to 11, wherein $R^{26}$ is selected from hydrogen and alkoxy.

13. A compound according to any one of embodiments 1 to 12, wherein $R^{26}$ is selected from hydrogen and methoxy.

14. A compound according to any one of embodiments 1 to 13, wherein $A^{23}$ is selected from a bond and —O—.

15. A compound according to any one of embodiments 1 to 14, wherein $A^{23}$ is a bond.

16. A compound according to any one of embodiments 1 to 15, wherein A30 is selected from a bond, —$CH_2$— and pyrazolyl.

17. A compound according to any one of embodiments 1 to 16, wherein A30 is a bond.

18. A compound according to any one of embodiments 1 to 17, wherein B3 is selected from piperidinyl, 1,4-diazacycloheptyl, 1-oxa-8-azaspiro[4.5]decyl, 2,8-diazaspiro[4.5]decyl, 3-azabicyclo[3.1.0]hexyl, and 8-azaspiro[4.5]decyl.

19. A compound according to any one of embodiments 1 to 18, wherein $A^{24}$ is —$CH_2$—.

20. A compound according to any one of embodiments 1 to 19, wherein C is selected from hydroxypiperidinyl and piperidinyl.

21. A compound according to any one of embodiments 1 to 20,
wherein D is

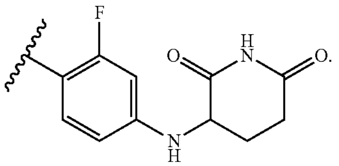 [SMILES: *c1ccc(NC2CCC(=O)NC2=O)cc1F]

22. A compound according to any one of embodiments 1 to 20,
wherein D is

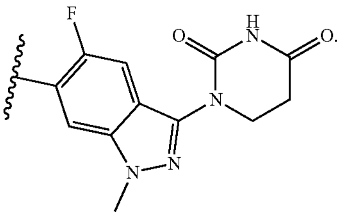

23. A compound according to any of embodiments 1 to 22 selected from

7-[2-cyano-3-[[ethyl(methyl)sulfamoyl]amino]-6-fluoro-phenoxy]-2-[4-[4-[2-[4-[4-[(2,6-dioxopiperidin-3-yl)amino]-2-fluorophenyl]piperidin-1-yl]acetyl]-1,4-diazepan-1-yl]pyrazol-1-yl]quinoxaline;

7-[2-cyano-3-[[ethyl(methyl)sulfamoyl]amino]-6-fluoro-phenoxy]-2-[[1-[2-[4-[4-[(2,6-dioxopiperidin-3-yl)amino]-2-fluorophenyl]piperidin-1-yl]acetyl]piperidin-4-yl]methoxy]quinoxaline;

7-[2-cyano-3-[[ethyl(methyl)sulfamoyl]amino]-6-fluoro-phenoxy]-2-[[(1R,5S)-3-[2-[4-[4-[(2,6-dioxopiperidin-3-yl)amino]-2-fluorophenyl]piperidin-1-yl]acetyl]-3-azabicyclo[3.1.0]hexan-6-yl]methoxy]quinoxaline;

3-[6-[2-cyano-3-[[ethyl(methyl)sulfamoyl]amino]-6-fluoro-phenoxy]quinolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane;

7-[2-cyano-3-[[ethyl(methyl)sulfamoyl]amino]-6-fluoro-phenoxy]-2-[8-[2-[4-[4-[(2,6-dioxopiperidin-3-yl)amino]-2-fluorophenyl]piperidin-1-yl]acetyl]-2,8-diazaspiro[4.5]decan-2-yl]quinoxaline;

7-[2-cyano-3-[[ethyl(methyl)sulfamoyl]amino]-6-fluoro-phenoxy]-2-[8-[2-[4-[4-[(2,6-dioxopiperidin-3-yl)amino]-2-fluorophenyl]piperidin-1-yl]acetyl]-8-azaspiro[4.5]decan-3-yl]quinoxaline;

3-[7-[2-cyano-3-[[ethyl(methyl)sulfamoyl]amino]-6-fluoro-phenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[7-[2-cyano-3-[[ethyl(methyl)sulfamoyl]amino]-6-fluorophenoxy]quinoxalin-2-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane;

(3S)-3-[6-[2-cyano-3-[[ethyl(methyl)sulfamoyl]amino]-6-fluorophenoxy]-4-methoxyquinolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

(3R)-3-[6-[2-cyano-3-[[ethyl(methyl)sulfamoyl]amino]-6-fluorophenoxy]-4-methoxyquinolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane; and (3S)-3-[6-[2-cyano-3-[[ethyl(methyl)sulfamoyl]amino]-6-fluorophenoxy]cinnolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane;

or a pharmaceutically acceptable salt thereof.

24. A compound according to any one of embodiments 1 to 23, or a pharmaceutically acceptable salt thereof, for use as therapeutically active substance.

25. A pharmaceutical composition comprising a compound according to any one of embodiments 1 to 23, or a pharmaceutically acceptable salt thereof, and a pharmaceutically acceptable carrier.

26. The use of a compound according to any one of embodiments 1 to 23, or a pharmaceutically acceptable salt thereof, for the therapeutic and/or prophylactic treatment of cancer.

27. A compound according to any one of embodiments 1 to 23, or a pharmaceutically acceptable salt thereof, for use in the treatment and/or prophylaxis of cancer.

28. The use of a compound according to any one of embodiments 1 to 23, or a pharmaceutically acceptable salt thereof, for the preparation of a medicament for the therapeutic and/or prophylactic treatment of cancer.

29. A method for the therapeutic and/or prophylactic treatment of cancer, which method comprises administering an effective amount of a compound according to any one of embodiments 1 to 23, or a pharmaceutically acceptable salt thereof, to a patient in need thereof.

Embodiments of Formula I, Formula II, Formula III, Formula IV, Formula V, and Formula VI 1. A compound of Formula I, Formula II, Formula III, Formula IV, Formula V, or Formula VI:

(I)

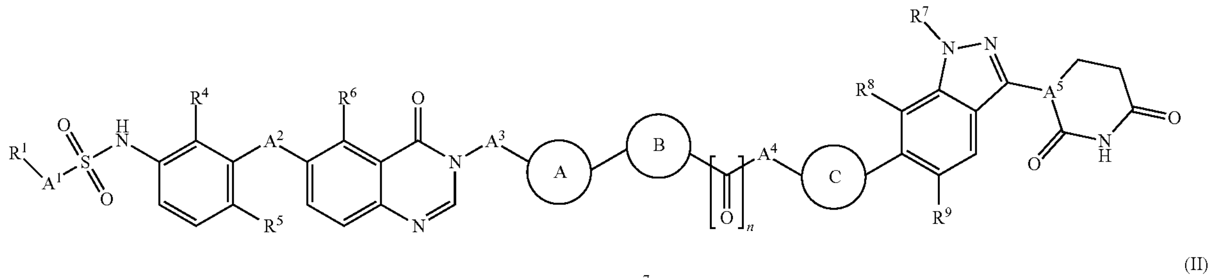

(II)

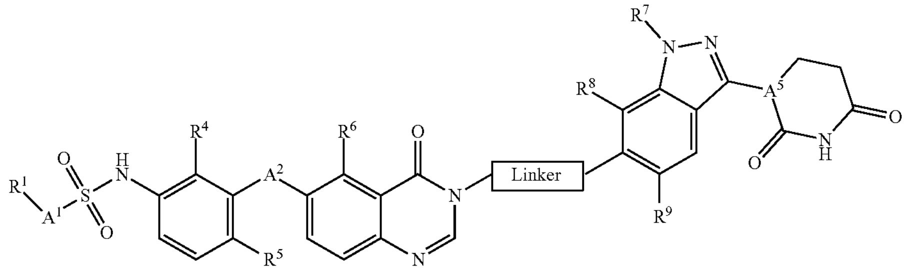

-continued (III)

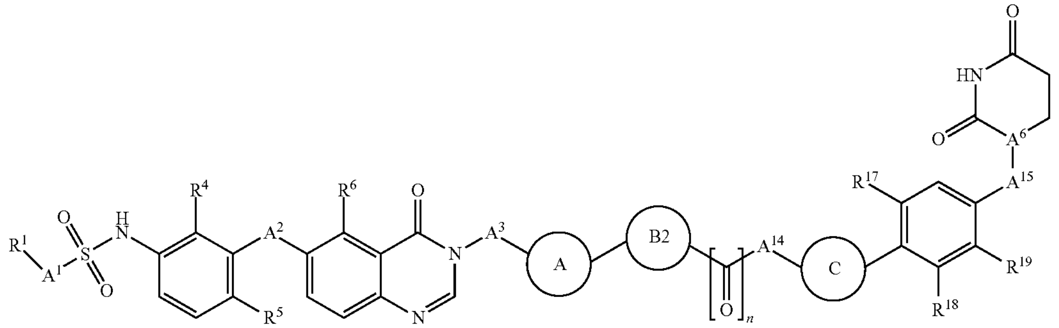

(IV)

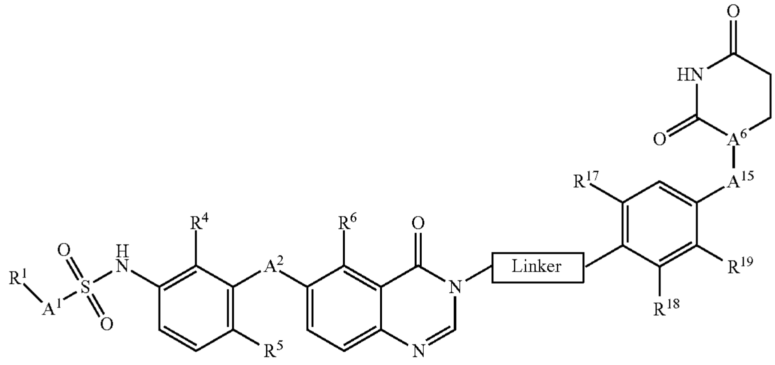

(V)

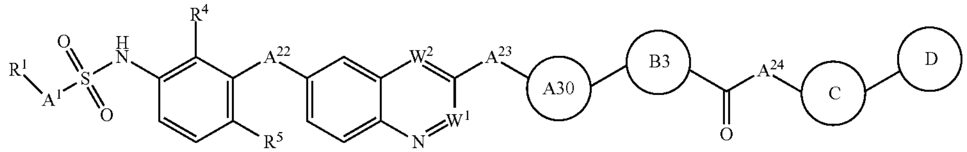

(VI)

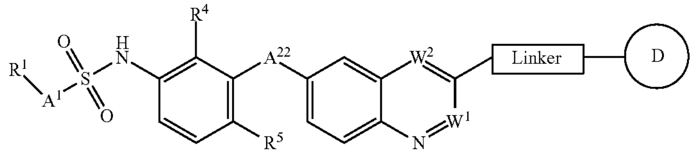

or a pharmaceutically acceptable salt thereof;

wherein $A^1$ is selected from —$NR^2$— and —$CHR^{2'}$—;

$R^1$ is selected from hydrogen, alkyl and cycloalkyl;

$R^2$ is selected from hydrogen, alkyl, cycloalkyl and haloalkyl;

or $R^1$ and $R^2$ together with the nitrogen atom to which they are attached form heterocycloalkyl optionally substituted with one or two $R^3$;

$R^{2'}$ is selected from hydrogen, alkyl, cycloalkyl and haloalkyl;

or $R^1$ and $R^{2'}$ together with the carbon atom to which they are attached form cycloalkyl optionally substituted with one or two $R^3$;

each $R^3$ is independently selected from hydrogen, halogen, alkyl, cycloalkyl and alkoxy;

$R^4$ is selected from hydrogen, alkyl, cyano and halogen;

$R^5$ is selected from hydrogen, alkyl, cyano and halogen;

$A^2$ is selected from —O—, —NH— and —(C=O)—;

$A^{22}$ is selected from —O—, and —NH—;

$W^1$ is selected from —N— and —CH—;

$W^2$ is selected from —N—, and —$CR^{26}$—;

$R^6$ is selected from hydrogen, halogen, hydroxy, amino, dialkylamino, alkoxy, alkyl and alkoxyalkyl;

$R^{26}$ is selected from hydrogen, halogen, hydroxy, amino, alkoxy and alkyl;

$A^3$ is selected from a bond, —$CH_2$—, —$CH_2$—$CH_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$— and —$CH_2$—$CH_2$—$CH_2$—$CH_2$—$CH_2$—;

$A^{23}$ is selected from a bond, —O— and —$CH_2$—;

A is selected from a bond, pyrimidinyl, pyridinyl, pyrazolyl and 3-azabicyclo[3.1.0]hexyl;

A30 is selected from a bond, —$CH_2$—, pyrimidinyl, pyridinyl, pyrazolyl and 3-azabicyclo[3.1.0]hexyl;

B is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, and 8-azaspiro[4.5]

decyl; wherein B is optionally substituted with one or two substituents independently selected from halogen, alkyl and alkoxy;

B2 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl and 8-azaspiro[4.5]decyl; wherein B2 is optionally substituted with one or two substituents independently selected from halogen, alkyl and alkoxy;

B3 is selected from phenyl, piperidinyl, piperazinyl, 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl and 8-azaspiro[4.5]decyl;

n is 0 or 1;

$A^4$ is selected from a bond, —$CH_2$—, —($SO_2$)—$CH_2$—, —CH($CH_2$OH)—, —NH— and —O—;

$A^{14}$ is selected from a bond, —$CH_2$—, —$CH_2$—$CH_2$—, —CH($CH_2$OH)—, —NH—, —O—, cycloalkyl and alkylamino;

C is selected from azepanyl, azetidinyl, cycloalkyl, piperazinyl and piperidinyl; wherein C is optionally substituted with one or two substituents independently selected from, hydroxy, alkyl and alkoxy;

D is selected from

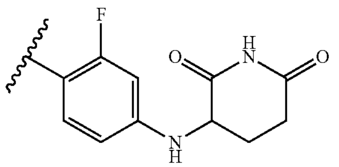

and

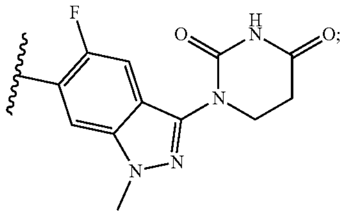 [SMILES: *c1cc2c(cc1F)c(N1CCC(=O)NC1=O)nn2C]

;

$R^7$ is selected from hydrogen, alkyl, cyano, halogen, and alkoxy;

$R^8$ is selected from hydrogen, alkyl, cyano, halogen, and alkoxy;

$R^9$ is selected from hydrogen, alkyl, cyano, halogen, and alkoxy;

$R^{17}$ is selected from hydrogen, alkyl, cyano, hydroxy, cycloalkyl, halogen and alkoxy;

$R^{18}$ is selected from hydrogen, alkyl, cyano, hydroxy, cycloalkyl, halogen and alkoxy;

$R^{19}$ is selected from hydrogen, alkyl, cyano, hydroxy, cycloalkyl, halogen and alkoxy;

$A^5$ is —CH— or —N—;

$A^{15}$ is selected from a bond, —O— and —NH—;

$A^6$ is —CH— or —N—; and

Linker is a bivalent chemical group.

2. The compound of embodiment 1, wherein the compound is of Formula:

(I)

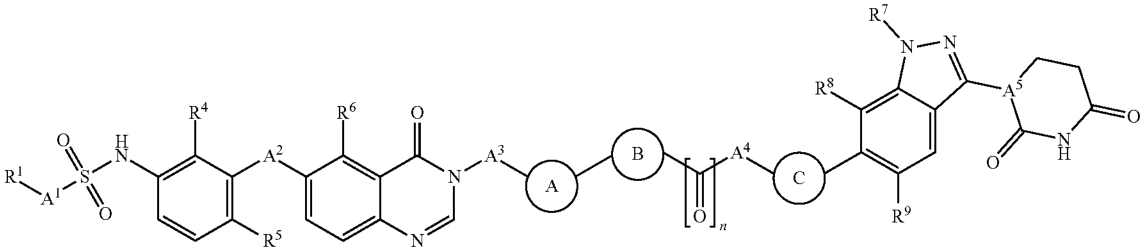

or a pharmaceutically acceptable salt thereof.

3. The compound of embodiment 1 or 2, wherein $A^4$ is bond.

4. The compound of embodiment 1 or 2, wherein $A^4$ is —NH—.

5. The compound of embodiment 1 or 2, wherein $A^4$ is —O—.

6. The compound of any one of embodiments 1-5, wherein $A^5$ is —CH—.

7. The compound of any one of embodiments 1-5, wherein $A^5$ is —N—.

8. The compound of any one of embodiments 1-7, wherein $R^7$ is hydrogen.

9. The compound of any one of embodiments 1-7, wherein $R^7$ is alkyl.

10. The compound of any one of embodiments 1-7, wherein $R^7$ is methyl.

11. The compound of any one of embodiments 1-10, wherein $R^8$ is hydrogen.

12. The compound of any one of embodiments 1-10, wherein $R^8$ is alkyl.

13. The compound of any one of embodiments 1-10, wherein $R^8$ is halogen.

14. The compound of any one of embodiments 1-13, wherein $R^9$ is hydrogen.

15. The compound of any one of embodiments 1-13, wherein $R^9$ is alkyl.

16. The compound of any one of embodiments 1-13, wherein $R^9$ is halogen.

17. The compound of any one of embodiments 1-13, wherein $R^9$ is fluorine.

18. The compound of any one of embodiments 1-17, wherein B is

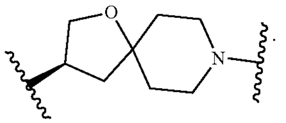 [SMILES: *[C@H]1COC2(CCN(*)CC2)C1]

19. The compound of any one of embodiments 1-17, wherein B is

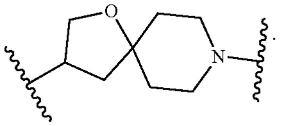 [SMILES: *C1COC2(CCN(*)CC2)C1]

20. The compound of any one of embodiments 1-17, wherein B is phenyl, piperidinyl, or piperazinyl optionally substituted with one or two substituents independently selected from halogen, alkyl and alkoxy.

21. The compound of any one of embodiments 1-17, wherein B is phenyl, piperidinyl, or piperazinyl.

22. The compound of any one of embodiments 1-17, wherein B is 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl, or 8-azaspiro[4.5]decyl.

23. The compound of embodiment 1, wherein the compound is of Formula:

30. The compound of any one of embodiments 23-25, wherein $A^{14}$ is cycloalkyl.

31. The compound of any one of embodiments 23-25, wherein $A^{14}$ is alkylamino.

32. The compound of any one of embodiments 23-31, wherein $R^{17}$ is hydrogen.

33. The compound of any one of embodiments 23-31, wherein $R^{17}$ is alkyl.

34. The compound of any one of embodiments 23-31, wherein $R^{17}$ is halogen.

35. The compound of any one of embodiments 23-31, wherein $R^{17}$ is fluorine.

36. The compound of any one of embodiments 23-35, wherein $R^{18}$ is hydrogen.

37. The compound of any one of embodiments 23-35, wherein $R^{18}$ is alkyl.

38. The compound of any one of embodiments 23-35, wherein $R^{18}$ is halogen.

39. The compound of any one of embodiments 23-35, wherein $R^{18}$ is fluorine.

40. The compound of any one of embodiments 23-39, wherein $R^{19}$ is hydrogen.

41. The compound of any one of embodiments 23-39, wherein $R^{19}$ is alkyl.

42. The compound of any one of embodiments 23-39, wherein $R^{19}$ is halogen.

43. The compound of any one of embodiments 23-39, wherein $R^{19}$ is fluorine.

44. The compound of any one of embodiments 1-43, wherein $A^2$ is —O—.

45. The compound of any one of embodiments 1-43, wherein $A^2$ is —NH—.

46. The compound of any one of embodiments 1-43, wherein $A^2$ is —(C═O)—.

(III)

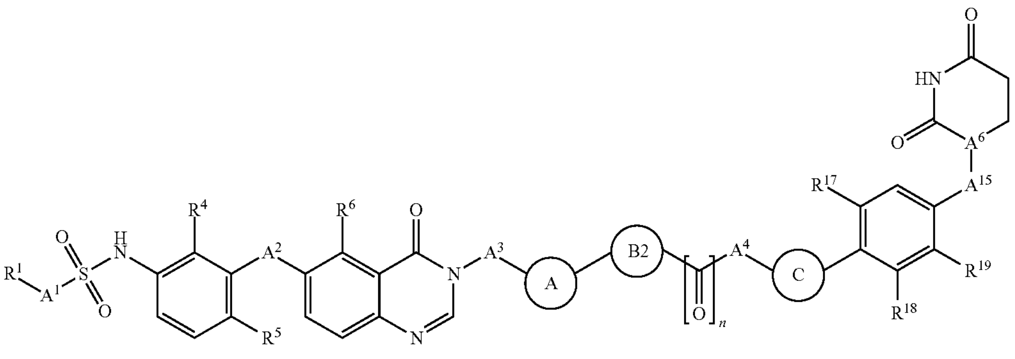

or a pharmaceutically acceptable salt thereof.

24. The compound of embodiment 1 or embodiment 23, wherein $A^6$ is —CH—.

25. The compound of embodiment 1 or embodiment 23, wherein $A^6$ is —N—.

26. The compound of any one of embodiments 23-25, wherein $A^{14}$ is bond.

27. The compound of any one of embodiments 23-25, wherein $A^{14}$ is $—CH_2—$, $—CH_2—CH_2—$, or $—CH(CH_2OH)—$.

28. The compound of any one of embodiments 23-25, wherein $A^{14}$ is —NH—.

29. The compound of any one of embodiments 23-25, wherein $A^{14}$ is —O—.

47. The compound of any one of embodiments 1-46, wherein $A^3$ is bond.

48. The compound of any one of embodiments 1-46, wherein $A^3$ is $—CH_2—$.

49. The compound of any one of embodiments 1-46, wherein $A^3$ is $—CH_2—CH_2—$, $—CH_2—CH_2—CH_2—$, $—CH(CH_3)—CH_2—CH_2—$, $—CH_2—CH(CH_3)—CH_2—$, $—CH_2—CH_2—CH(CH_3)—$, $—CH_2—CH_2—CH_2—CH_2—$ or $—CH_2—CH_2—CH_2—CH_2—CH_2—$.

50. The compound of any one of embodiments 1-49, wherein n is 0.

51. The compound of any one of embodiments 1-49, wherein n is 1.

52. The compound of any one of embodiments 1-51, wherein $R^6$ is hydrogen.

53. The compound of any one of embodiments 1-51, wherein $R^6$ is halogen.

54. The compound of any one of embodiments 1-51, wherein $R^6$ is amino or dialkylamino.

55. The compound of any one of embodiments 1-51, wherein $R^6$ is hydroxy or alkoxy.

56. The compound of embodiment 1, wherein the compound is of Formula:

65. The compound of any one of embodiments 56-64, wherein $A^{23}$ is bond.

66. The compound of any one of embodiments 56-64, wherein $A^{23}$ is —O—.

67. The compound of any one of embodiments 56-64, wherein $A^{23}$ is —$CH_2$—.

68. The compound of any one of embodiments 56-67, wherein A30 is bond.

(V)

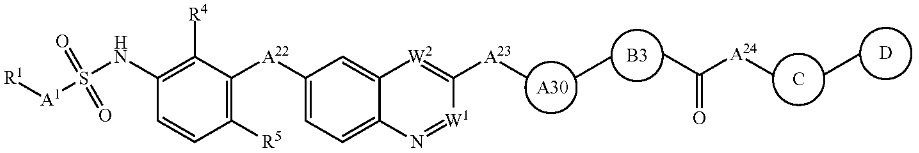

or a pharmaceutically acceptable salt thereof.

57. The compound of embodiment 56, wherein D is

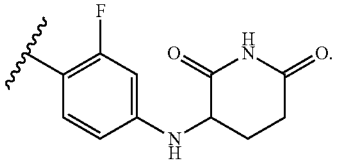 [SMILES: *c1ccc(NC2CCC(=O)NC2=O)cc1F]

58. The compound of embodiment 56, wherein D is

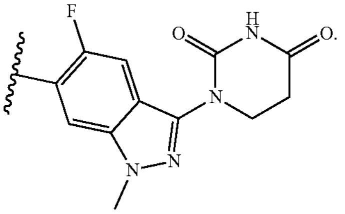 [SMILES: *c1cc2c(cc1F)c(N1CCC(=O)NC1=O)nn2C]

59. The compound of any one of embodiments 56-58, wherein $W^1$ is —N—.

60. The compound of any one of embodiments 56-58, wherein $W^1$ is —CH—.

61. The compound of any one of embodiments 56-60, wherein $W^2$ is —N—.

69. The compound of any one of embodiments 56-67, wherein A30 is —$CH_2$—.

70. The compound of any one of embodiments 56-67, wherein A30 is pyrimidinyl or pyridinyl.

71. The compound of any one of embodiments 56-67, wherein A30 is pyrazolyl.

72. The compound of any one of embodiments 56-67, wherein A30 is 3-azabicyclo[3.1.0]hexyl.

73. The compound of any one of embodiments 56-72, wherein B3 is phenyl.

74. The compound of any one of embodiments 56-72, wherein B3 is piperidinyl or piperazinyl.

75. The compound of any one of embodiments 56-72, wherein B3 is 1,4-diazacycloheptyl, 1-oxa-8-azaspiro[4.5]decyl, 1-oxa-9-azaspiro[5.5]undecyl, 2,8-diazaspiro[4.5]decyl, 2-azaspiro[4.5]decyl, 3-azabicyclo[3.1.0]hexyl, 3-azaspiro[5.5]undecyl, 7-azaspiro[3.5]nonyl, 1,1-dioxo-1lambda6-thia-8-azaspiro[4.5]decyl, 1-oxaspiro[4.5]decyl, 1-methyl-1,8-diazaspiro[4.5]decyl, 1,8-diazaspiro[4.5]decyl or 8-azaspiro[4.5]decyl.

76. The compound of any one of embodiments 56-75, wherein $A^{22}$ is —O—.

77. The compound of any one of embodiments 56-75, wherein $A^{22}$ is —NH—.

78. The compound of embodiment 1, wherein the compound is of Formula:

(II)

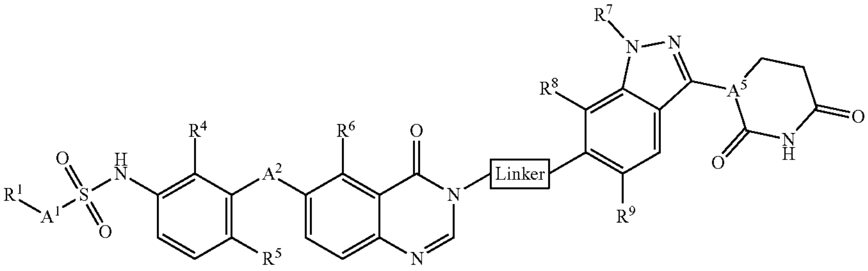

62. The compound of any one of embodiments 56-60, wherein $W^2$ is —$CR^{26}$—.

63. The compound of any one of embodiments 56-62, wherein $R^{26}$ is hydrogen.

64. The compound of any one of embodiments 56-62, wherein $R^{26}$ is halogen.

or a pharmaceutically acceptable salt thereof.

79. The compound of embodiment 78, wherein $A^5$ is —CH—.

80. The compound of embodiment 78, wherein $A^5$ is —N—.

81. The compound of any one of embodiments 78-80, wherein $R^7$ is hydrogen.

82. The compound of any one of embodiments 78-80, wherein $R^7$ is alkyl.

83. The compound of any one of embodiments 78-80, wherein $R^7$ is methyl.

84. The compound of any one of embodiments 78-83, wherein $R^8$ is hydrogen.

85. The compound of any one of embodiments 78-83, wherein $R^8$ is alkyl.

86. The compound of any one of embodiments 78-83, wherein $R^8$ is halogen.

87. The compound of any one of embodiments 78-86, wherein $R^9$ is hydrogen.

88. The compound of any one of embodiments 78-86, wherein $R^9$ is alkyl.

89. The compound of any one of embodiments 78-86, wherein $R^9$ is halogen.

90. The compound of any one of embodiments 78-86, wherein $R^9$ is fluorine.

91. The compound of embodiment 1, wherein the compound is of Formula:

(IV)

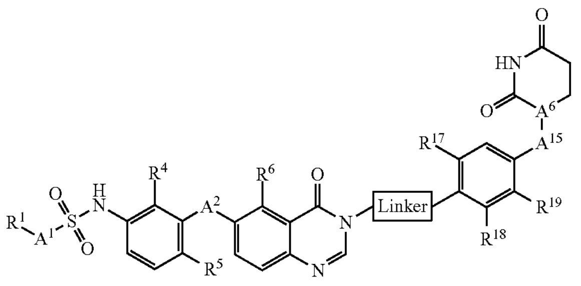

or a pharmaceutically acceptable salt thereof.

92. The compound of embodiment 91, wherein $A^6$ is —CH—

93. The compound of embodiment 91, wherein $A^6$ is —N—.

94. The compound of any one of embodiments 91-93, wherein $R^{17}$ is hydrogen.

95. The compound of any one of embodiments 91-93, wherein $R^{17}$ is alkyl.

96. The compound of any one of embodiments 91-93, wherein $R^{17}$ is halogen.

97. The compound of any one of embodiments 91-93, wherein $R^{17}$ is fluorine.

98. The compound of any one of embodiments 91-97, wherein $R^{18}$ is hydrogen.

99. The compound of any one of embodiments 91-97, wherein $R^{18}$ is alkyl.

100. The compound of any one of embodiments 91-97, wherein $R^{18}$ is halogen.

101. The compound of any one of embodiments 91-97, wherein $R^{18}$ is fluorine.

102. The compound of any one of embodiments 91-101, wherein $R^{19}$ is hydrogen.

103. The compound of any one of embodiments 91-101, wherein $R^{19}$ is alkyl.

104. The compound of any one of embodiments 91-101, wherein $R^{19}$ is halogen.

105. The compound of any one of embodiments 91-101, wherein $R^{19}$ is fluorine.

106. The compound of any one of embodiments 78-105, wherein $A^2$ is —O—.

107. The compound of any one of embodiments 78-105, wherein $A^2$ is —NH—.

108. The compound of any one of embodiments 78-105, wherein $A^2$ is —(C═O)—.

109. The compound of any one of embodiments 78-108, wherein n is 0.

110. The compound of any one of embodiments 78-108, wherein n is 1.

111. The compound of any one of embodiments 78-110, wherein $R^6$ is hydrogen.

112. The compound of any one of embodiments 78-110, wherein $R^6$ is halogen.

113. The compound of any one of embodiments 78-110, wherein $R^6$ is amino or dialkylamino.

114. The compound of any one of embodiments 78-110, wherein $R^6$ is hydroxy or alkoxy.

115. The compound of embodiment 1, wherein the compound is of Formula:

(VI)

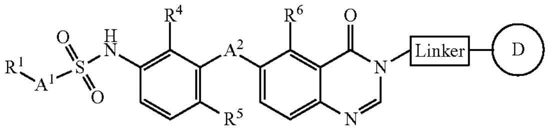

or a pharmaceutically acceptable salt thereof.

116. The compound of embodiment 115, wherein D is

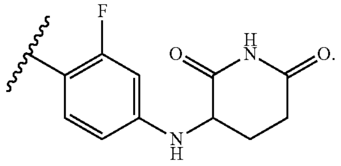 [SMILES: *c1ccc(NC2CCC(=O)NC2=O)cc1F]

117. The compound of embodiment 115, wherein D is

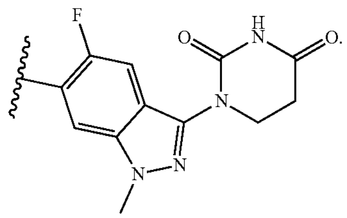 [SMILES: *c1cc2c(cc1F)c(N1CCC(=O)NC1=O)nn2C]

118. The compound of any one of embodiments 115-117, wherein $W^1$ is —N—.

119. The compound of any one of embodiments 115-117, wherein $W^1$ is —CH—.

120. The compound of any one of embodiments 115-119, wherein $W^2$ is —N—.

121. The compound of any one of embodiments 115-119, wherein $W^2$ is —$CR^{26}$—.

122. The compound of any one of embodiments 115-121, wherein $R^{26}$ is hydrogen.

123. The compound of any one of embodiments 115-121, wherein $R^{26}$ is halogen.

124. The compound of any one of embodiments 115-123, wherein $A^{22}$ is —O—.

125. The compound of any one of embodiments 115-123, wherein $A^{22}$ is —NH—.

126. The compound of any one of embodiments 78-125, wherein Linker is selected from

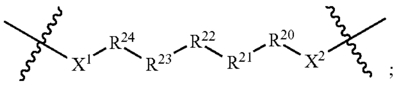

;

wherein:

$X^1$ and $X^2$ are independently at each occurrence selected from bond, heterocycle, $NR^2$, $C(R^2)_2$, O, C(O), and S;

$R^{20}$, $R^{21}$, $R^{22}$, $R^{23}$, and $R^{24}$ are independently at each occurrence selected from the group consisting of bivalent moieties selected from bond alkyl, —C(O)—, —C(O)O—, —OC(O)—, —$SO_2$—, —S(O)—, —C(S)—, —C(O)$NR^2$—, —$NR^2$C(O)—, —O—, —S—, —$NR^2$—, —$C(R^{40}R^{40})$—, —P(O)($OR^{36}$)O—, —P(O)($OR^{36}$)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;

$R^{36}$ is independently at each occurrence selected from the group consisting of hydrogen, alkyl, arylalkyl, heteroarylalkyl, alkene, alkyne, aryl, heteroaryl, heterocycle, aliphatic and heteroaliphatic; and $R^{40}$ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)$_2$, —$NHSO_2$(aliphatic, including alkyl), —N(aliphatic, including alkyl)$SO_2$alkyl, —$NHSO_2$(aryl, heteroaryl or heterocycle), —N(alkyl)$SO_2$(aryl, heteroaryl or heterocycle), —$NHSO_2$alkenyl, —N(alkyl)$SO_2$alkenyl, —$NHSO_2$alkynyl, —N(alkyl)$SO_2$alkynyl, haloalkyl, aliphatic, heteroaliphatic, aryl, heteroaryl, heterocycle, and cycloalkyl.

127. The compound of embodiment 126, wherein linker is of formula:

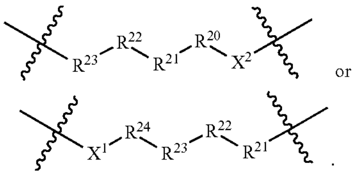

or

.

128. The compound of any one of embodiments 126 and 127, wherein $X^1$ is bond.

129. The compound of any one of embodiments 126 and 127, wherein $X^1$ is heterocycle.

130. The compound of any one of embodiments 126 and 127, wherein $X^1$ is $NR^2$.

131. The compound of any one of embodiments 126 and 127, wherein $X^1$ is C(O).

132. The compound of any one of embodiments 126-131, wherein $X^2$ is bond.

133. The compound of any one of embodiments 126-131, wherein $X^2$ is heterocycle.

134. The compound of any one of embodiments 126-131, wherein $X^2$ is $NR^2$.

135. The compound of any one of embodiments 126-131, wherein $X^2$ is C(O).

136. The compound of any one of embodiments 126-135, wherein $R^{20}$ is bond.

137. The compound of any one of embodiments 126-135, wherein $R^{20}$ is $CH_2$.

138. The compound of any one of embodiments 126-135, wherein $R^{20}$ is heterocycle.

139. The compound of any one of embodiments 126-135, wherein $R^{20}$ is aryl.

140. The compound of any one of embodiments 126-135, wherein $R^{20}$ is phenyl.

141. The compound of any one of embodiments 126-135, wherein $R^{20}$ is bicycle.

142. The compound of any one of embodiments 126-141, wherein $R^{21}$ is bond.

143. The compound of any one of embodiments 126-141, wherein $R^{21}$ is $CH_2$.

144. The compound of any one of embodiments 126-141, wherein $R^{21}$ is heterocycle.

145. The compound of any one of embodiments 126-141, wherein $R^{21}$ is aryl.

146. The compound of any one of embodiments 126-141, wherein $R^{21}$ is.

147. The compound of any one of embodiments 126-141, wherein $R^{21}$ is bicycle.

148. The compound of embodiment 126, wherein Linker is of formula:

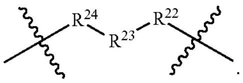

.

149. The compound of any one of embodiments 126-148, wherein $R^{22}$ is bond.

150. The compound of any one of embodiments 126-148, wherein $R^{22}$ is $CH_2$.

151. The compound of any one of embodiments 126-148, wherein $R^{22}$ is heterocycle.

152. The compound of any one of embodiments 126-148, wherein $R^{22}$ is aryl.

153. The compound of any one of embodiments 126-148, wherein $R^{22}$ is phenyl.

154. The compound of any one of embodiments 126-148, wherein $R^{22}$ is bicycle.

155. The compound of any one of embodiments 126-154, wherein $R^{23}$ is bond.

156. The compound of any one of embodiments 126-154, wherein $R^{23}$ is $CH_2$.

157. The compound of any one of embodiments 126-154, wherein $R^{23}$ is heterocycle.

158. The compound of any one of embodiments 126-154, wherein $R^{23}$ is aryl.

159. The compound of any one of embodiments 126-154, wherein $R^{23}$ is phenyl.

160. The compound of any one of embodiments 126-154, wherein $R^{23}$ is bicycle.

161. The compound of any one of embodiments 126-160, wherein $R^{24}$ is bond.

162. The compound of any one of embodiments 126-160, wherein $R^{24}$ is $CH_2$.

163. The compound of any one of embodiments 126-160, wherein $R^{24}$ is heterocycle.

164. The compound of any one of embodiments 126-160, wherein $R^{24}$ is aryl.

165. The compound of any one of embodiments 126-160, wherein $R^{24}$ is phenyl.

166. The compound of any one of embodiments 126-160, wherein $R^{24}$ is bicycle.

167. The compound of any one of embodiments 126-160, wherein $R^{24}$ is C(O).

168. The compound of any one of embodiments 1-167, wherein $A^1$ is —$NR^2$—.

169. The compound of any one of embodiments 1-167, wherein $A^1$ is —$CHR^{2'}$—.

170. The compound of any one of embodiments 1-167, wherein $A^1$ is —NH—.

171. The compound of any one of embodiments 1-167, wherein $A^1$ is —$NCH_3$—.

172. The compound of any one of embodiments 1-167, wherein $A^1$ is —$CH_2$—.

173. The compound of any one of embodiments 1-172, wherein $R^1$ is hydrogen.

174. The compound of any one of embodiments 1-172, wherein $R^1$ is alkyl.

175. The compound of any one of embodiments 1-172, wherein $R^1$ is methyl.

176. The compound of any one of embodiments 1-172, wherein $R^1$ is ethyl.

177. The compound of any one of embodiments 1-176, wherein $R^4$ is hydrogen.

178. The compound of any one of embodiments 1-176, wherein $R^4$ is cyano.

179. The compound of any one of embodiments 1-176, wherein $R^4$ is halogen.

180. The compound of any one of embodiments 1-179, wherein $R^5$ is hydrogen.

181. The compound of any one of embodiments 1-179, wherein $R^5$ is halogen.

182. The compound of any one of embodiments 1-179, wherein $R^5$ is fluorine.

183. The compound of any one of embodiments 1-182, wherein C is

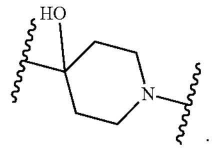 [SMILES: *N1CCC(*)(O)CC1]

184. The compound of any one of embodiments 1-182, wherein C is azepanyl.

185. The compound of any one of embodiments 1-182, wherein C is azetidinyl.

186. The compound of any one of embodiments 1-182, wherein C is piperazinyl.

187. The compound of any one of embodiments 1-182, wherein C is cycloalkyl optionally substituted with one or two substituents independently selected from, hydroxy, alkyl and alkoxy.

188. The compound of any one of embodiments 1-182, wherein C is piperidinyl optionally substituted with one or two substituents independently selected from, hydroxy, alkyl and alkoxy.

189. A compound selected from:

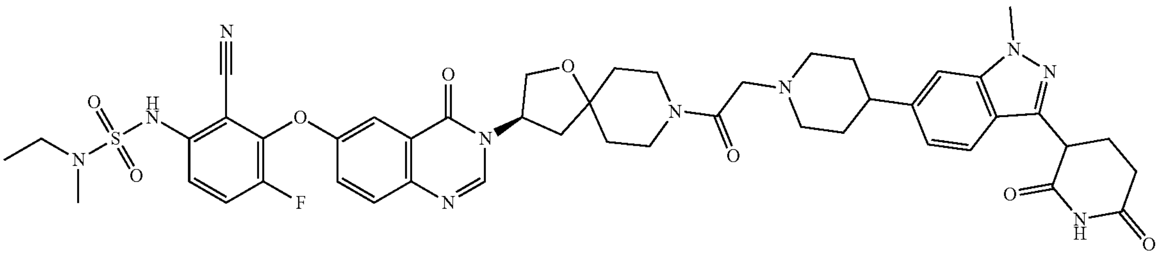

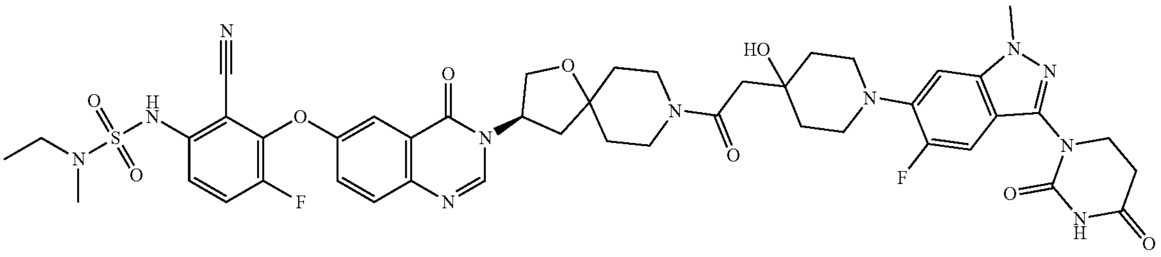

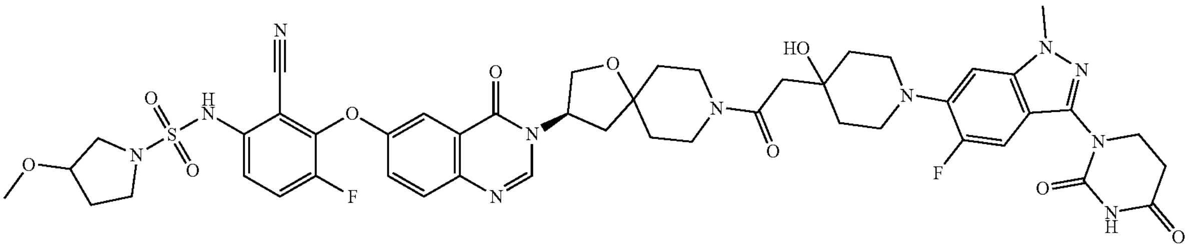

-continued
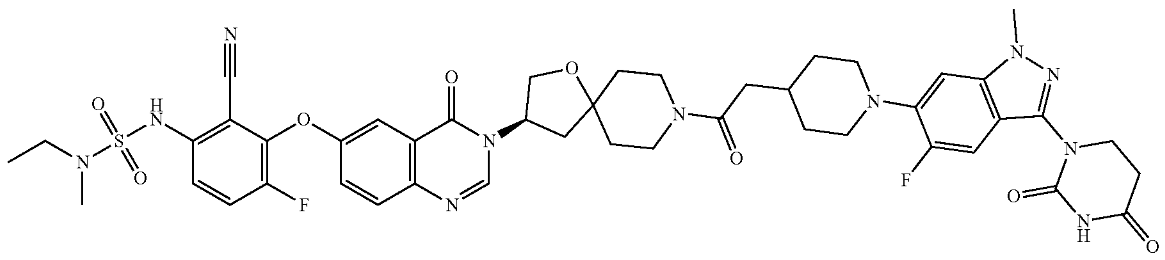
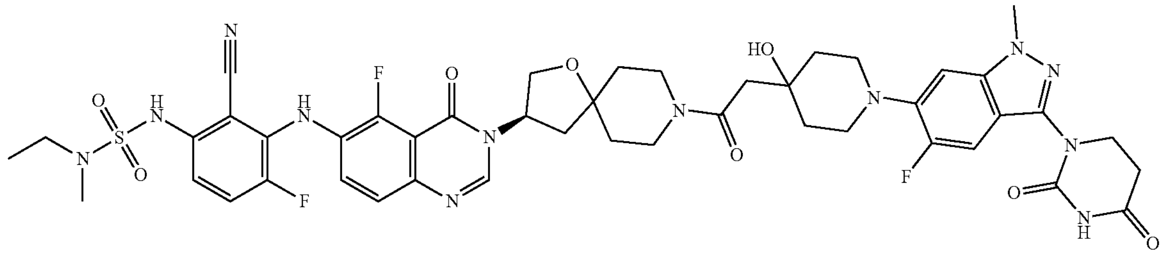
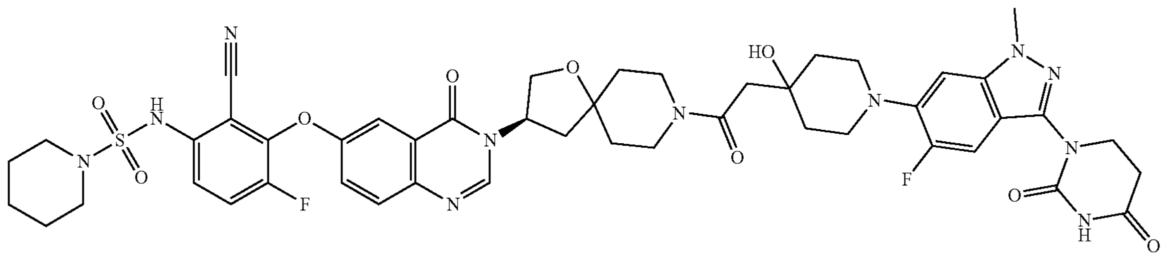
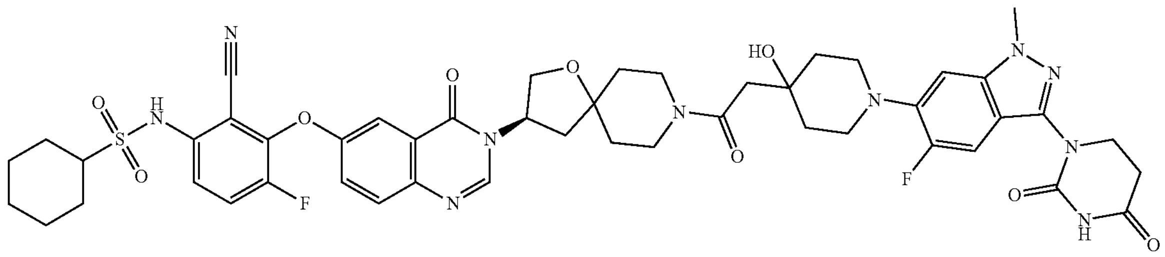
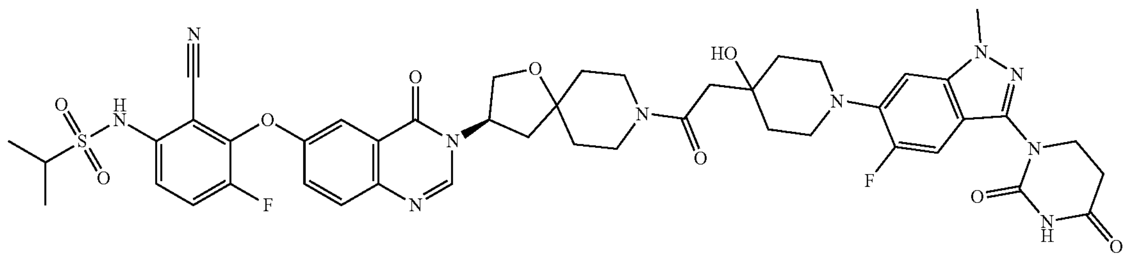
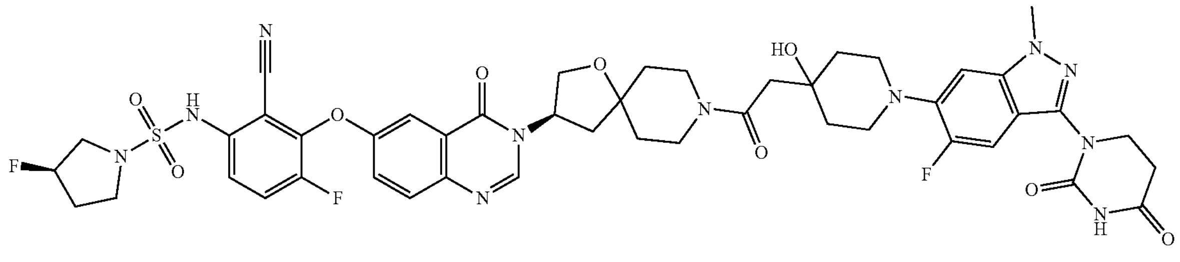

-continued
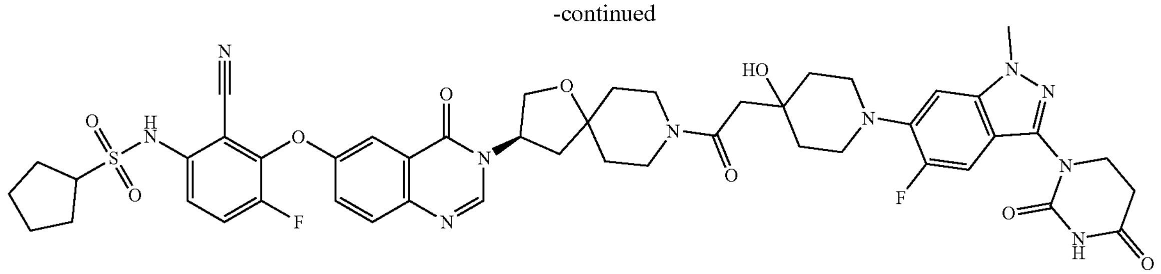
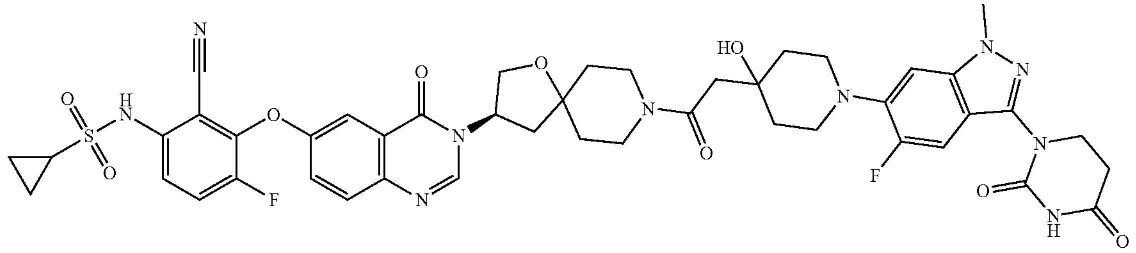
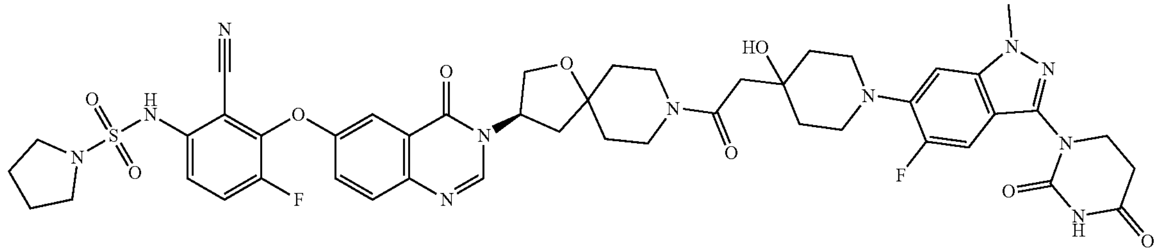
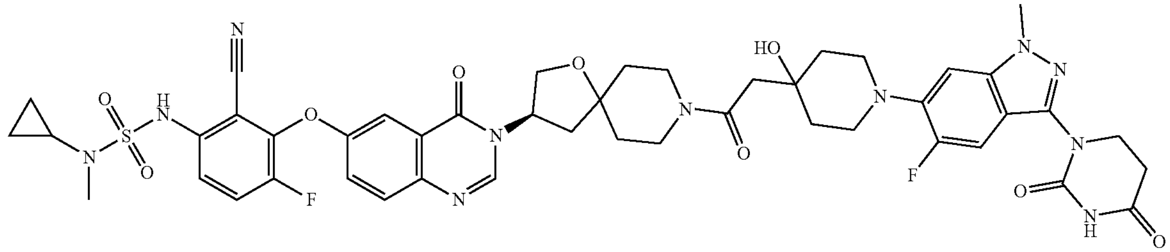
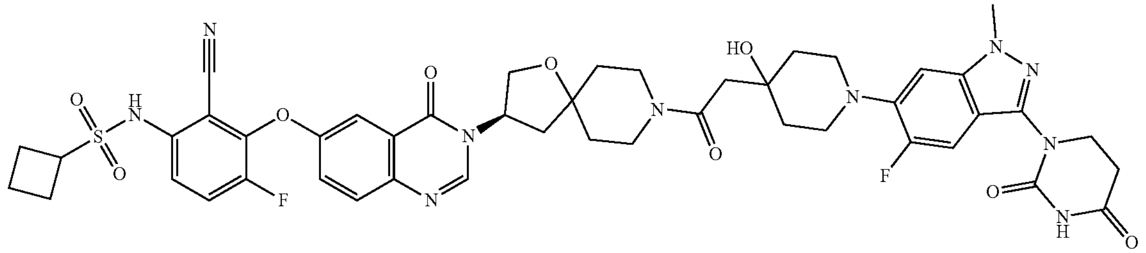 [SMILES: Cn1nc(N2CCC(=O)NC2=O)c2cc(F)c(N3CCC(O)(CC(=O)N4CCC5(CC4)C[C@@H](n4cnc6ccc(Oc7c(F)ccc(NS(=O)(=O)C8CCC8)c7C#N)cc6c4=O)CO5)CC3)cc21]
or a pharmaceutically acceptable salt thereof.
190. The compound of embodiment 189, wherein the compound is of structure
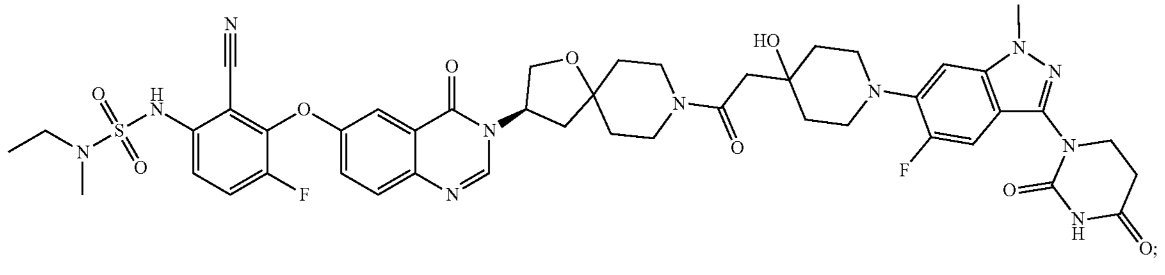 [SMILES: CCN(C)S(=O)(=O)Nc1ccc(F)c(Oc2ccc3ncn([C@H]4COC5(CCN(C(=O)CC6(O)CCN(c7cc8c(cc7F)c(N7CCC(=O)NC7=O)nn8C)CC6)CC5)C4)c(=O)c3c2)c1C#N]
or a pharmaceutically acceptable salt thereof.

191. The compound of embodiment 189, wherein the compound is of structure

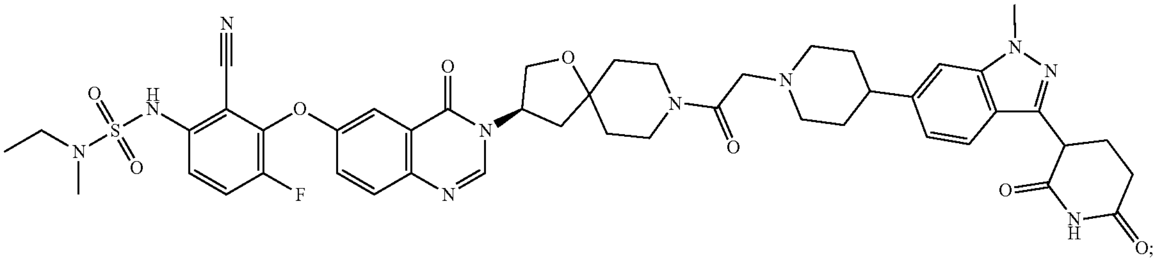 [SMILES: CCN(C)S(=O)(=O)Nc1ccc(F)c(Oc2ccc3ncn([C@H]4COC5(CCN(C(=O)CN6CCC(c7ccc8c(C9CCC(=O)NC9=O)nn(C)c8c7)CC6)CC5)C4)c(=O)c3c2)c1C#N]

or a pharmaceutically acceptable salt thereof.

192. The compound of embodiment 189, wherein the compound is of structure

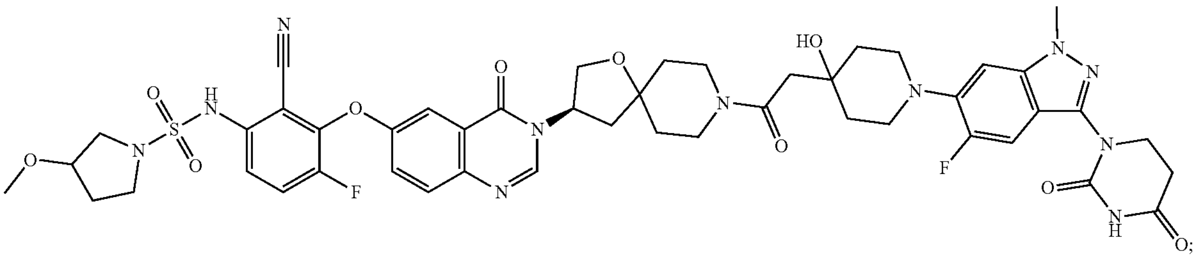 [SMILES: COC1CCN(S(=O)(=O)Nc2ccc(F)c(Oc3ccc4ncn([C@H]5COC6(CCN(C(=O)CC7(O)CCN(c8cc9c(cc8F)c(N8CCC(=O)NC8=O)nn9C)CC7)CC6)C5)c(=O)c4c3)c2C#N)C1]

or a pharmaceutically acceptable salt thereof.

193. The compound of embodiment 189, wherein the compound is of structure

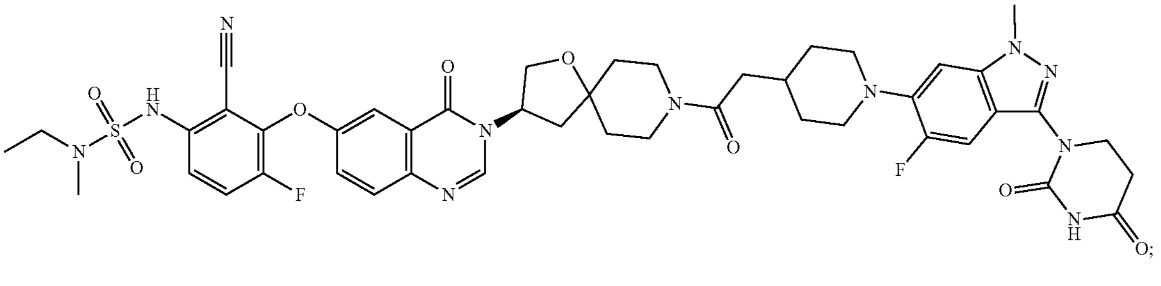 [SMILES: CCN(C)S(=O)(=O)Nc1ccc(F)c(Oc2ccc3ncn([C@H]4COC5(CCN(C(=O)CC6CCN(c7cc8c(cc7F)c(N7CCC(=O)NC7=O)nn8C)CC6)CC5)C4)c(=O)c3c2)c1C#N]

or a pharmaceutically acceptable salt thereof

194. The compound of embodiment 189, wherein the compound is of structure

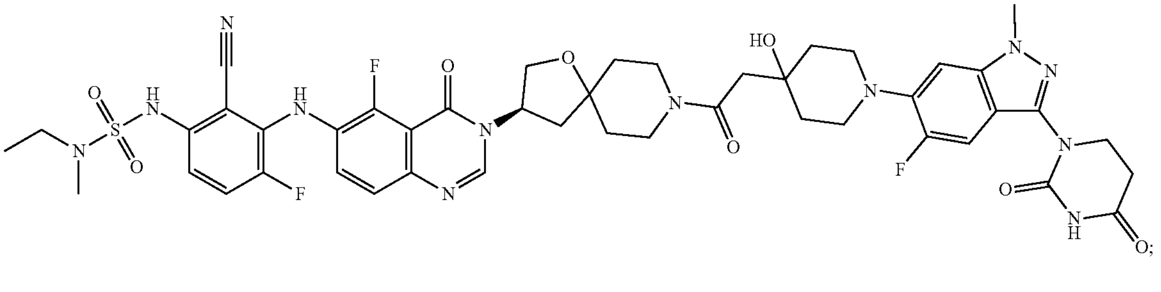 [SMILES: CCN(C)S(=O)(=O)Nc1ccc(F)c(Nc2ccc3ncn([C@H]4COC5(CCN(C(=O)CC6(O)CCN(c7cc8c(cc7F)c(N7CCC(=O)NC7=O)nn8C)CC6)CC5)C4)c(=O)c3c2F)c1C#N]

or a pharmaceutically acceptable salt thereof.

195. The compound of embodiment 189, wherein the compound is of structure

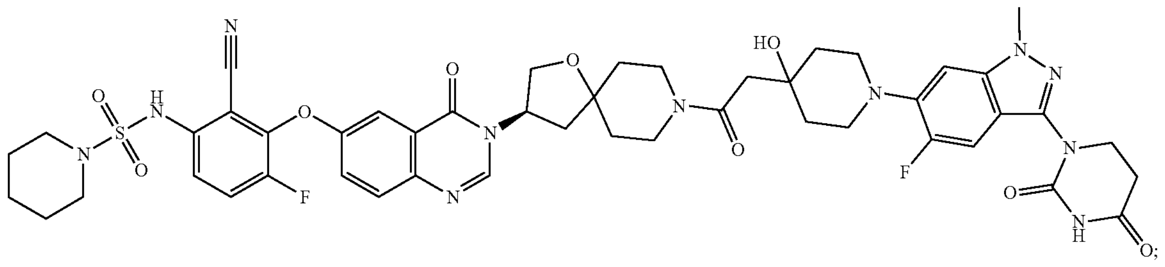 [SMILES: Cn1nc(N2CCC(=O)NC2=O)c2cc(F)c(N3CCC(O)(CC(=O)N4CCC5(CC4)C[C@@H](n4cnc6ccc(Oc7c(F)ccc(NS(=O)(=O)N8CCCCC8)c7C#N)cc6c4=O)CO5)CC3)cc21]

or a pharmaceutically acceptable salt thereof.

196. The compound of embodiment 189, wherein the compound is of structure

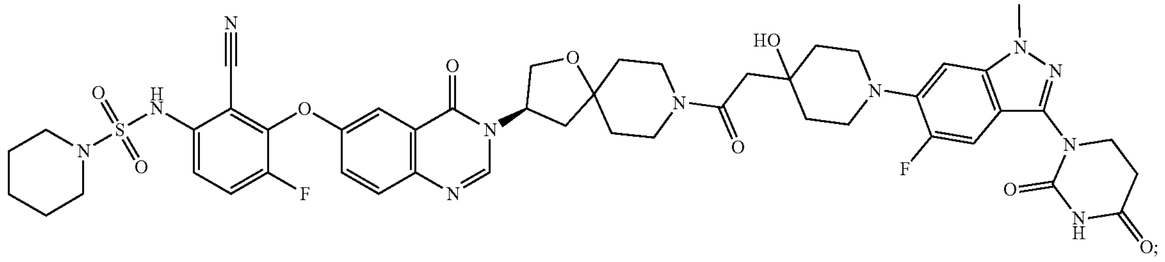 [SMILES: Cn1nc(N2CCC(=O)NC2=O)c2cc(F)c(N3CCC(O)(CC(=O)N4CCC5(CC4)C[C@@H](n4cnc6ccc(Oc7c(F)ccc(NS(=O)(=O)N8CCCCC8)c7C#N)cc6c4=O)CO5)CC3)cc21]

or a pharmaceutically acceptable salt thereof.

197. The compound of embodiment 189, wherein the compound is of structure

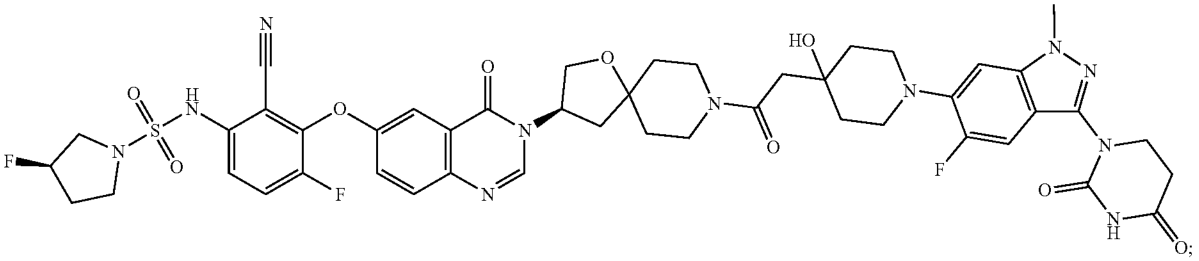 [SMILES: Cn1nc(N2CCC(=O)NC2=O)c2cc(F)c(N3CCC(O)(CC(=O)N4CCC5(CC4)C[C@@H](n4cnc6ccc(Oc7c(F)ccc(NS(=O)(=O)N8CC[C@@H](F)C8)c7C#N)cc6c4=O)CO5)CC3)cc21]

or a pharmaceutically acceptable salt thereof.

198. The compound of embodiment 189, wherein the compound is of structure

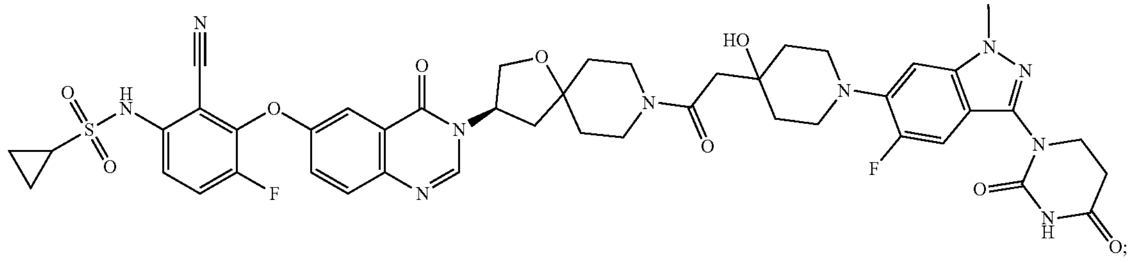 [SMILES: Cn1nc(N2CCC(=O)NC2=O)c2cc(F)c(N3CCC(O)(CC(=O)N4CCC5(CC4)C[C@@H](n4cnc6ccc(Oc7c(F)ccc(NS(=O)(=O)C8CC8)c7C#N)cc6c4=O)CO5)CC3)cc21]

or a pharmaceutically acceptable salt thereof.

199. The compound of embodiment 189, wherein the compound is of structure

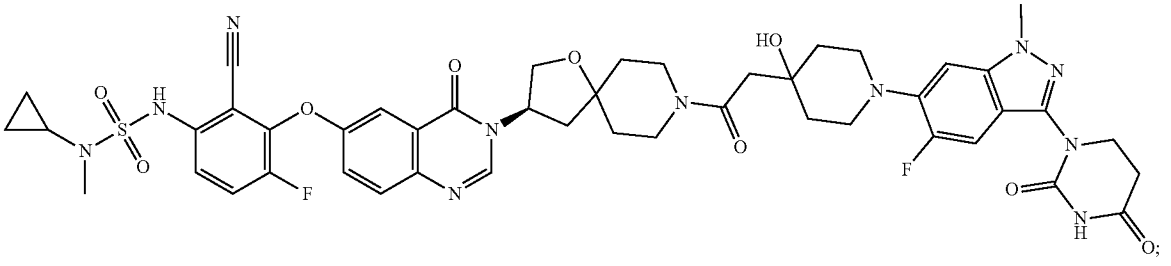 [SMILES: CN(C1CC1)S(=O)(=O)Nc1ccc(F)c(Oc2ccc3ncn([C@H]4COC5(CCN(C(=O)CC6(O)CCN(c7cc8c(cc7F)c(N7CCC(=O)NC7=O)nn8C)CC6)CC5)C4)c(=O)c3c2)c1C#N]

or a pharmaceutically acceptable salt thereof.

200. A pharmaceutical composition comprising a compound according to any one of embodiments 1-199, or a pharmaceutically acceptable salt thereof, and a pharmaceutically acceptable carrier.

201. A method of treating a mutant BRAF mediated disorder comprising administering an effective amount of a compound of any one of embodiments 1-199 or a pharmaceutically acceptable salt thereof or a pharmaceutical composition of embodiment 200 to a patient in need thereof.

202. The method of embodiment 201, wherein the patient is a human.

203. The method of embodiment 201 or 202, wherein the mutant BRAF mediated disorder is a cancer.

204. The method of embodiment 203, wherein the mutant BRAF mediated cancer is melanoma.

205. The method of embodiment 203, wherein the mutant BRAF mediated cancer is lung cancer.

206. The method of embodiment 203, wherein the mutant BRAF mediated cancer is non-small cell lung cancer.

207. The method of embodiment 203, wherein the mutant BRAF mediated cancer is colorectal cancer.

208. The method of embodiment 203, wherein the mutant BRAF mediated cancer is microsatellite stable colorectal cancer.

209. The method of embodiment 203, wherein the mutant BRAF mediated cancer is thyroid cancer.

210. The method of embodiment 203, wherein the mutant BRAF mediated cancer is ovarian cancer.

211. The method of embodiment 201, wherein the mutant BRAF mediated disorder is cholangiocarcinoma, erdeheim-chester disease, langerhans histiocytosis, ganglioglioma, glioma, glioblastoma, hairy cell leukemia, multiple myeloma, non-small-cell lung cancer, ovarian cancer, pilomyxoid astrocytoma, anaplastic pleomorphic xanthoastrocytoma, astrocytoma, papillary thyroid cancer, anaplastic thyroid cancer, pancreatic cancer, thoracic clear cell sarcoma, salivary gland cancer, or microsatellite stable colorectal cancer.

212. The method of any one of embodiments 201-211, wherein the patient also receives an additional active agent.

213. The method of embodiment 212, wherein the additional active agent is a MEK inhibitor.

214. The method of embodiment 213, wherein the MEK inhibitor is trametinib.

215. The method of embodiment 212, wherein the additional active agent is an immune checkpoint inhibitor.

216. The method of embodiment 215, wherein the immune checkpoint inhibitor is selected from nivolumab, pembrolizumab, cemiplimab, ipilimumab, relatlimab, atezolizumab, avelumab, and durvalumab.

217. The method of embodiment 212, wherein the additional active agent is cetuximab or panitumumab.

218. A compound according to any one of embodiments 1-199 or a pharmaceutically acceptable salt thereof or a pharmaceutical composition of embodiment 200 for the therapeutic treatment of a mutant BRAF mediated disorder.

219. The compound of embodiment 218, wherein the mutant BRAF mediated disorder is a cancer.

220. The compound of embodiment 219, wherein the mutant BRAF mediated cancer is melanoma.

221. The compound of embodiment 219, wherein the mutant BRAF mediated cancer is lung cancer.

222. The compound of embodiment 219, wherein the mutant BRAF mediated cancer is non-small cell lung cancer.

223. The compound of embodiment 219, wherein the mutant BRAF mediated cancer is colorectal cancer.

224. The compound of embodiment 219, wherein the mutant BRAF mediated cancer is microsatellite stable colorectal cancer.

225. The compound of embodiment 219, wherein the mutant BRAF mediated cancer is thyroid cancer.

226. The compound of embodiment 219, wherein the mutant BRAF mediated cancer is ovarian cancer.

227. The compound of embodiment 218, wherein the mutant BRAF mediated disorder is cholangiocarcinoma, erdeheim-chester disease, langerhans histiocytosis, ganglioglioma, glioma, glioblastoma, hairy cell leukemia, multiple myeloma, non-small-cell lung cancer, ovarian cancer, pilomyxoid astrocytoma, anaplastic pleomorphic xanthoastrocytoma, astrocytoma, papillary thyroid cancer, anaplastic thyroid cancer, pancreatic cancer, thoracic clear cell sarcoma, salivary gland cancer, or microsatellite stable colorectal cancer.

228. A compound according to any one of embodiments 1-199 or a pharmaceutically acceptable salt thereof or a pharmaceutical composition of embodiment 200 for use in the treatment of a mutant BRAF mediated disorder.

229. The compound of embodiment 228, wherein the mutant BRAF mediated disorder is a cancer.

230. The compound of embodiment 229, wherein the mutant BRAF mediated cancer is melanoma.

231. The compound of embodiment 229, wherein the mutant BRAF mediated cancer is lung cancer.

232. The compound of embodiment 229, wherein the mutant BRAF mediated cancer is non-small cell lung cancer.
233. The compound of embodiment 229, wherein the mutant BRAF mediated cancer is colorectal cancer.
234. The compound of embodiment 229, wherein the mutant BRAF mediated cancer is microsatellite stable colorectal cancer.
235. The compound of embodiment 229, wherein the mutant BRAF mediated cancer is thyroid cancer.
236. The compound of embodiment 229, wherein the mutant BRAF mediated cancer is ovarian cancer.
237. The compound of embodiment 228, wherein the mutant BRAF mediated disorder is cholangiocarcinoma, erdeheim-chester disease, langerhans histiocytosis, ganglioglioma, glioma, glioblastoma, hairy cell leukemia, multiple myeloma, non-small-cell lung cancer, ovarian cancer, pilomyxoid astrocytoma, anaplastic pleomorphic xanthoastrocytoma, astrocytoma, papillary thyroid cancer, anaplastic thyroid cancer, pancreatic cancer, thoracic clear cell sarcoma, salivary gland cancer, or microsatellite stable colorectal cancer.
238. Use of a compound according to any one of embodiments 1-199 or a pharmaceutically acceptable salt thereof or a pharmaceutical composition of embodiment 200 in the manufacture of a medicament for the treatment of a mutant BRAF mediated disorder.
239. The use of embodiment 238, wherein the mutant BRAF mediated disorder is a cancer.
240. The use of embodiment 239, wherein the mutant BRAF mediated cancer is melanoma.
241. The use of embodiment 239, wherein the mutant BRAF mediated cancer is lung cancer.
242. The use of embodiment 239, wherein the mutant BRAF mediated cancer is non-small cell lung cancer.
243. The use of embodiment 239, wherein the mutant BRAF mediated cancer is colorectal cancer.
244. The use of embodiment 239, wherein the mutant BRAF mediated cancer is microsatellite stable colorectal cancer.
245. The use of embodiment 239, wherein the mutant BRAF mediated cancer is thyroid cancer.
246. The use of embodiment 239, wherein the mutant BRAF mediated cancer is ovarian cancer.
247. The use of embodiment 238, wherein the mutant BRAF mediated disorder is cholangiocarcinoma, erdeheim-chester disease, langerhans histiocytosis, ganglioglioma, glioma, glioblastoma, hairy cell leukemia, multiple myeloma, non-small-cell lung cancer, ovarian cancer, pilomyxoid astrocytoma, anaplastic pleomorphic xanthoastrocytoma, astrocytoma, papillary thyroid cancer, anaplastic thyroid cancer, pancreatic cancer, thoracic clear cell sarcoma, salivary gland cancer, or microsatellite stable colorectal cancer.
248. A compound according to any one of embodiments 1 to 199, or a pharmaceutically acceptable salt thereof, for use as therapeutically active substance.

Methods of Treatment

A compound of the present invention or their pharmaceutically acceptable salt or pharmaceutical composition can be used in an effective amount to treat a patient with any disorder mediated by a mutant BRAF.

BRAF is a serine/threonine protein kinase that is a member of the signal transduction protein kinases. BRAF V600X mutations, in particular BRAF V600E/K mutations are often observed in a variety of human tumors including melanoma, thyroid cancer, colorectal cancer, lung cancer and others. Non-limiting examples of V600X mutations include V600E, V600K, V600R, V600D, and V600N. Despite the therapeutic benefits exerted by available BRAF inhibitors in the clinic in many of these indications, the duration of the antitumor response to these drugs is limited by the acquisition of drug resistance.

The BRAF protein presents a mechanism for signaling propagation that requires protein homo-dimerization (BRAF-BRAF) or hetero-dimerization with other RAF proteins (BRAF-RAF1 or BRAF-ARAF). When BRAF is mutated, as observed in oncological indications with BRAF V600X substitution, BRAF signaling becomes independent from the generation of homodimers and/or heterodimers. In this context, the kinase becomes hyperactivated as a monomeric protein and drives cellular proliferative signals.

Because currently available inhibitors only block BRAF activity in its monomeric form and are ineffective on BRAF homodimers or heterodimers, it is not surprising that many BRAF-resistance inducing mechanisms act by restoring RAF homodimerization and heterodimerization mediated signaling.

Targeted protein degradation induces target ubiquitination by recruiting an E3 ligase thus promoting proteasome-mediated disruption of the engaged target. The degradation of BRAF through targeted degradation offers an advantage over conventional inhibition since it eliminates scaffolding activities of BRAF V600E/K and particularly, induces BRAF protein elimination. This activity prevents the dimerization-mediated mechanisms of resistance.

In agreement with this theory, literature reports demonstrated that BRAF protein abrogation may represent a strategy to delay the onset of resistance acquisition as well as potentially targeting tumors that acquired resistance to available inhibitors. This observation offers novel therapeutic opportunities in the treatment of BRAF V600X mutated tumors like melanoma, colorectal cancer, and lung cancer.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing cancer in a patient in need thereof, wherein there is a need of BRAF inhibition for the treatment or prevention of cancer.

In certain aspects, a compound of the present invention is used to treat a BRAF mediated cancer, wherein the BRAF has mutated from the wild type. There are a number of possibilities for BRAF mutations. In certain non-limiting embodiments, the mutation is a Class I mutation, a Class II mutation, or a Class III mutation, or any combination thereof. Non-limiting examples of Class I mutations include V600 mutations such as V600E, V600K, V600R, V600D, and V600N. Non-limiting examples of Class II mutations include G469A, G469V, G469L, G469R, L597Q, and K601E. Non-limiting examples of Class III mutations include G466A, G466E, G466R, G466V, S467L, G469E, N581I, D594E, D594G, and D594N.

In certain embodiments a compound of the present invention treats a BRAF mutant mediated disorder wherein the mutation is not a Class I, Class II, or Class III mutation. Non-limiting examples of mutations include G464I, G464R, N581T, L584F, E586K, G593D, G596C, L597R, L597S, S605I, S607F, N684T, E26A, V130M, L745L, and D284E.

In certain embodiments the BRAF mutation is an exon 11 mutation.

In certain embodiments the BRAF mutation is an exon 15 mutation.

In certain embodiments the BRAF mutation is a G464 mutation.

In certain embodiments the BRAF mutation is a G466 mutation.

In certain embodiments the BRAF mutation is a G466R mutation.

In certain embodiments the BRAF mutation is a G466E mutation.

In certain embodiments the BRAF mutation is a G469 mutation.

In certain embodiments the BRAF mutation is a G469E mutation.

In certain embodiments the BRAF mutation is a D594 mutation.

In certain embodiments the BRAF mutation is a D594A mutation.

In certain embodiments the BRAF mutation is a L597 mutation.

In certain embodiments the BRAF mutation is a L597R mutation.

In certain embodiments the BRAF mutation is a L597S mutation.

In certain embodiments the BRAF mutation is a L597Q mutation.

In certain embodiments the BRAF mutation is a V600 mutation.

In certain embodiments the BRAF mutation is a V600E mutation.

In certain embodiments the BRAF mutation is a V600K mutation.

In certain embodiments the BRAF mutation is a V600R mutation.

In certain embodiments the BRAF mutation is a V600D mutation.

In certain embodiments the BRAF mutation is a K601 mutation.

In certain embodiments the BRAF mutation is a K601E mutation.

In certain embodiments the BRAF mutation is a K601N mutation.

In certain embodiments a compound of the present invention treats a BRAF mutant mediated disorder wherein the mutation is a splice variant, for example p61-BRAF$^{V600E}$.

In certain embodiments a compound of the present invention is used to treat a disorder that is mediated by two or more mutant proteins, for example a cancer mediated by a BRAF$^{V600E}$/NRAS$^{Q61K}$ double mutant.

In certain embodiments, a compound of the present invention is used to treat a cancer that is resistant to at least one BRAF inhibitor, for example a cancer that is resistant to or has acquired resistance to a BRAF inhibitor selected from dabrafenib, trametinib, vemurafenib and encorafenib.

In certain embodiments a compound of the present invention is used to treat a cancer that has developed an escape mutation such as BRAF V600E NRAS$^{Q61K}$ double mutant cancer.

In certain embodiments a compound of the present invention is used to treat melanoma.

Non-limiting examples of melanoma include nonacral cutaneous melanoma, acral melanoma, mucosal melanoma, uveal melanoma, and leptomeningeal melanoma, each of which can be primary or metastatic.

In certain embodiments a compound of the present invention is used to treat triple negative breast cancer, for example triple negative breast cancer with a G464V BRAF mutant.

In certain embodiments a compound of the present invention is used to treat lung cancer, for example lung adenocarcinoma with a G466V BRAF mutant.

In certain embodiments a compound of the present invention is used to treat melanoma with a V600 BRAF mutant.

In certain aspects, Compound 157 is used to treat a BRAF mediated cancer, wherein the BRAF has mutated from the wild type. There are a number of possibilities for BRAF mutations.

In certain non-limiting embodiments, the mutation is a Class I mutation, a Class II mutation, or a Class III mutation, or any combination thereof. Non-limiting examples of Class I mutations include V600 mutations such as V600E, V600K, V600R, V600D, and V600N. Non-limiting examples of Class II mutations include G469A, G469V, G469L, G469R, L597Q, and K601E. Non-limiting examples of Class III mutations include G466A, G466E, G466R, G466V, S467L, G469E, N581I, D594E, D594G, and D594N.

In certain embodiments Compound 157 treats a BRAF mutant mediated disorder wherein the mutation is not a Class I, Class II, or Class III mutation. Non-limiting examples of mutations include G464I, G464R, N581T, L584F, E586K, G593D, G596C, L597R, L597S, S605I, S607F, N684T, E26A, V130M, L745L, and D284E.

In certain embodiments Compound 157 treats a BRAF mutant mediated disorder wherein the mutation is a splice variant, for example p61-BRAF$^{V600E}$.

In certain embodiments Compound 157 is used to treat a disorder that is mediated by two or more mutant proteins, for example a cancer mediated by a BRAF$^{V600E}$/NRAS$^{Q61K}$ double mutant.

In certain embodiments, Compound 157 is used to treat a cancer that is resistant to at least one BRAF inhibitor, for example a cancer that is resistant to or has acquired resistance to a BRAF inhibitor selected from dabrafenib, trametinib, vemurafenib and encorafenib.

In certain embodiments Compound 157 is used to treat a cancer that has developed an escape mutation such as BRAF V600E NRAS$^{Q61K}$ double mutant cancer.

In certain embodiments Compound 157 is used to treat melanoma.

In certain embodiments Compound 157 is used to treat triple negative breast cancer, for example triple negative breast cancer with a G464V BRAF mutant.

In certain embodiments Compound 157 is used to treat lung cancer, for example lung adenocarcinoma with a G466V BRAF mutant.

In certain embodiments Compound 157 is used to treat melanoma with a V600 BRAF mutant.

In certain embodiments Compound 157 is used to treat cholangiocarcinoma.

In certain embodiments Compound 157 is used to treat erdeheim-chester disease.

In certain embodiments Compound 157 is used to treat langerhans histiocytosis.

In certain embodiments Compound 157 is used to treat ganglioglioma.

In certain embodiments Compound 157 is used to treat glioma.

In certain embodiments Compound 157 is used to treat GIST.

In certain embodiments Compound 157 is used to treat glioblastoma.

In certain embodiments Compound 157 is used to treat hairy cell leukemia.

In certain embodiments Compound 157 is used to treat multiple myeloma.

In certain embodiments Compound 157 is used to treat non-small-cell lung cancer.

In certain embodiments Compound 157 is used to treat ovarian cancer.

In certain embodiments Compound 157 is used to treat pilomyxoid astrocytoma.

In certain embodiments Compound 157 is used to treat anaplastic pleomorphic xanthoastrocytoma.

In certain embodiments Compound 157 is used to treat astrocytoma.

In certain embodiments Compound 157 is used to treat thyroid cancer.

In certain embodiments Compound 157 is used to treat papillary thyroid cancer.

In certain embodiments Compound 157 is used to treat anaplastic thyroid cancer.

In certain embodiments Compound 157 is used to treat pancreatic cancer.

In certain embodiments Compound 157 is used to treat thoracic clear cell sarcoma.

In certain embodiments Compound 157 is used to treat salivary gland cancer.

In certain embodiments Compound 157 is used to treat colorectal cancer.

In certain embodiments Compound 157 is used to treat microsatellite stable colorectal cancer.

In certain embodiments a compound of the present invention is used to treat a disorder selected from cholangiocarcinoma, erdeheim-chester disease, langerhans histiocytosis, ganglioglioma, glioma, GIST, glioblastoma, hairy cell leukemia, multiple myeloma, lung cancer, non-small-cell lung cancer, ovarian cancer, pilomyxoid astrocytoma, anaplastic pleomorphic xanthoastrocytoma, astrocytoma, thyroid cancer, papillary thyroid cancer, anaplastic thyroid cancer, pancreatic cancer, thoracic clear cell sarcoma, salivary gland cancer, colorectal cancer, and microsatellite stable colorectal cancer.

Another aspect of the present invention provides a method of treating or preventing a proliferative disease. The method comprises administering an effective amount of a pharmaceutical composition comprising a compound as described herein, or an enantiomer, diastereomer, or stereoisomer thereof, or pharmaceutically acceptable salt, hydrate, or solvate thereof and optionally a pharmaceutically acceptable carrier to a patient in need thereof.

In certain embodiments, the disease or disorder is cancer or a proliferation disease.

In certain embodiments, the BRAF mediated disorder is an abnormal cell proliferation, including, but not limited to, a solid or hematological cancer.

In certain embodiments, the hematological cancer is acute myelogenous leukemia (AML), acute lymphoblastic leukemia (ALL), lymphoblastic T-cell leukemia, chronic myelogenous leukemia (CML), chronic lymphocytic leukemia (CLL), hairy-cell leukemia, chronic neutrophilic leukemia (CNL), acute lymphoblastic T-cell leukemia, acute monocytic leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukemia (MLL), erythroleukemia, malignant lymphoma, Hodgkin's lymphoma, non-Hodgkin's lymphoma, lymphoblastic T-cell lymphoma, Burkitt's lymphoma, follicular lymphoma, B cell acute lymphoblastic leukemia, diffuse large B cell lymphoma, Myc and B-Cell Leukemia (BCL)2 and/or BCL6 rearrangements/overexpression [double- and triple-hit lymphoma], myelodysplastic/myeloproliferative neoplasm, mantle cell lymphoma including bortezomib resistant mantle cell lymphoma.

Solid tumors that can be treated with the compounds described herein include, but are not limited to lung cancers, including small cell lung cancer (SCLC) and non-small cell lung cancer (NSCLC), breast cancers including inflammatory breast cancer, ER-positive breast cancer including tamoxifen resistant ER-positive breast cancer, and triple negative breast cancer, colon cancers, midline carcinomas, liver cancers, renal cancers, prostate cancers including castrate resistant prostate cancer (CRPC), brain cancers including gliomas, glioblastomas, neuroblastoma, and medulloblastoma including MYC-amplified medulloblastoma, colorectal cancers, Wilm's tumor, Ewing's sarcoma, rhabdomyosarcomas, ependymomas, head and neck cancers, melanomas, squamous cell carcinomas, ovarian cancers, pancreatic cancers including pancreatic ductal adenocarcinomas (PDAC) and pancreatic neuroendocrine tumors (PanNET), osteosarcomas, giant cell tumors of bone, thyroid cancers, bladder cancers, urothelial cancers, vulval cancers, cervical cancers, endometrial cancers, mesotheliomas, esophageal cancers, salivary gland cancers, gastric cancers, nasopharyngeal cancers, buccal cancers, cancers of the mouth, GIST (gastrointestinal stromal tumors), NUT-midline carcinomas, testicular cancers, squamous cell carcinomas, hepatocellular carcinomas (HCC), MYCN driven solid tumors, and NUT midline carcinomas (NMC).

In further embodiments, the disease or disorder is sarcoma of the bones, muscles, tendons, cartilage, nerves, fat, or blood vessels.

In further embodiments, the disease or disorder is soft tissue sarcoma, bone sarcoma, or osteosarcoma.

In further embodiments, the disease or disorder is angiosarcoma, fibrosarcoma, liposarcoma, leiomyosarcoma, Kaposi's sarcoma, osteosarcoma, gastrointestinal stromal tumor, synovial sarcoma, pleomorphic sarcoma, chondrosarcoma, Ewing's sarcoma, reticulum cell sarcoma, hemangiosarcoma, botryoid sarcoma, rhabdomyosarcoma, or embryonal rhabdomyosarcoma.

In certain embodiments the disorder is a bone, muscle, tendon, cartilage, nerve, fat, or blood vessel sarcoma.

In other embodiments, the pharmaceutical composition comprising the compound as described herein and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, solid tumors, hematological cancers or solid cancers.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal;

adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colorectum, large intestine, rectum, brain and central nervous system; chronic myeloid leukemia (CML), and leukemia. The term “cancer” includes, but is not limited to, the following cancers: myeloma, lymphoma, or a cancer selected from gastric, renal, or and the following cancers: head and neck, oropharyngeal, non-small cell lung cancer (NSCLC), endometrial, hepatocarcinoma, non-Hodgkin's lymphoma, and pulmonary.

The term “cancer” refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers, such as oral, laryngeal, nasopharyngeal and esophageal, genitourinary cancers, such as prostate, bladder, renal, uterine, ovarian, testicular, lung cancer, such as small-cell and non-small cell, breast cancer, pancreatic cancer, melanoma and other skin cancers, stomach cancer, brain tumors, tumors related to Gorlin's syndrome, such as medulloblastoma or meningioma, and liver cancer.

Additional exemplary forms of cancer include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing sarcoma, and plasmacytoma.

In one aspect of the application, the present application provides for the use of one or more compound as described herein, in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compound as described herein is useful for treating hematopoietic disorders, in particular, acute-myelogenous leukemia (AML), chronic-myelogenous leukemia (CML), acute-promyelocytic leukemia, and acute lymphocytic leukemia (ALL).

In certain embodiments, a compound or it's corresponding pharmaceutically acceptable salt, or isotopic derivative, as described herein can be used in an effective amount to treat a host, for example a human, with a lymphoma or lymphocytic or myelocytic proliferation disorder or abnormality. For example, a compound as described herein can be administered to a host suffering from a Hodgkin's Lymphoma or a Non-Hodgkin's Lymphoma. For example, the host can be suffering from a Non-Hodgkin's Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or it's corresponding pharmaceutically acceptable salt, or isotopic derivative, as described herein can be used in an effective amount to treat a patient, for example a human, with a Hodgkin's lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin's Lymphoma; or Nodular Lymphocyte Predominant HL.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

In accordance with the foregoing, the present application further provides a method for preventing or treating any of the diseases or disorders described above in a patient in need of such treatment, which method comprises administering to said patient a therapeutically effective amount of a compound as described herein, or an enantiomer, diastereomer, or stereoisomer thereof, or pharmaceutically acceptable salt, hydrate, or solvate thereof. For any of the above uses, the required dosage will vary depending on the mode of administration, the particular condition to be treated and the effect desired.

Combination Therapy

The disclosed compounds described herein, or their pharmaceutically acceptable salt or pharmaceutical composition can be used in an effective amount alone or in combination with another compound of the present invention or another bioactive agent or second therapeutic agent to treat a patient such as a human with a mutant BRAF mediated disorder, including but not limited to those described herein.

The term "bioactive agent" or "additional active agent" is used to describe an agent, other than the selected compound according to the present invention, which can be used in combination or alternation with a compound of the present invention to achieve a desired result of therapy. In certain embodiments, the compound of the present invention and the bioactive agent are administered in a manner that they are active in vivo during overlapping time periods, for example, have time-period overlapping Cmax, Tmax, AUC or another pharmacokinetic parameter. In another embodiment, the compound of the present invention and the bioactive agent are administered to a patient in need thereof that do not have overlapping pharmacokinetic parameter, however, one has a therapeutic impact on the therapeutic efficacy of the other.

In some embodiments, a selected compound provided herein, or its pharmaceutically acceptable salt is used in combination with another BRAF inhibitor such as sorafenib, vemurafenib (ZELBORAF®), dabrafenib (TAFINLAR®) or encorafenib (BRAFTOVI®).

In certain embodiments, the bioactive agent is a MEK inhibitor. MEK inhibitors are well known, and include, for example, trametinib/GSK1120212 (N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In certain embodiments the MEK inhibitor is trametinib.

In certain embodiments a compound of the present invention is used in combination with cetuximab or trametinib to treat colorectal cancer. In certain embodiments a compound of the present invention is used in combination with cetuximab and BYL719 to treat colorectal cancer. In certain embodiments a compound of the present invention is used in combination with cetuximab and irinotecan to treat colorectal cancer.

In certain embodiments Compound 157 is used in combination with cetuximab or trametinib to treat colorectal cancer. In certain embodiments Compound 157 is used in combination with cetuximab and BYL719 to treat colorectal cancer. In certain embodiments Compound 157 is used in combination with cetuximab and irinotecan to treat colorectal cancer.

In certain embodiments the bioactive agent is a SHP2 inhibitor. In certain embodiments the SHP2 inhibitor is SHP099.

In certain embodiments the bioactive agent is a RAF inhibitor. Non-limiting examples of Raf inhibitors include, for example, vemurafenib (N-[3-[[5-(4-chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl] pyridin-4-yl]oxy-N-[4-(trifluoromethyl)phenyl] benzimidazol-2-amine), 2-Bromoaldisine (2-bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), sorafenib N-oxide (4-[4-[[[[4-Chloro-3(trifluoroMethyl)phenyl]aMino]carbonyl]aMino] phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (encorafenib (BRAFTOVI®)).

In certain embodiments the RAF inhibitor is encorafenib.

In certain embodiments the RAF inhibitor is vemurafenib.

In certain embodiments the RAF inhibitor is dabrafenib.

In certain embodiments, the bioactive agent is an EGFR inhibitor, including, for example gefitinib (IRESSA®), erlotinib (TARCEVA®), lapatinib (TYKERB®), osimertinib (TAGRISSO®), neratinib (NERLYNX®), vandetanib (CAPRELSA®), dacomitinib (VIZIPRO®), rociletinib (XEGAFRI™), afatinib (GLOTRIF®, GIOTRIFF™, AFANIX™), lazertinib, or nazartib.

Additional examples of EGFR inhibitors include rociletinib (CO-1686), olmutinib (OLITA™), naquotinib (ASP8273), nazartinib (EGF816), PF-06747775, icotinib (BPI-2009), neratinib (HKI-272; PB272); avitinib (AC00010), EAI045, tarloxotinib (TH-4000; PR-610), PF-06459988 (Pfizer), tesevatinib (XL647; EXEL-7647; KD-019), transtinib, WZ-3146, WZ8040, CNX-2006, dacomitinib (PF-00299804; Pfizer), brigatinib (ALUNBRIG®), lorlatinib, and PF-06747775 (PF7775).

In certain embodiments, the bioactive agent is a first-generation EGFR inhibitor such as erlotinib, gefitinib, or lapatinib. In certain embodiments, the bioactive agent is a second-generation EGFR inhibitor such as afatinib and/or dacomitinib. In certain embodiments, the bioactive agent is a third-generation EGFR inhibitor such as osimertinib.

In certain embodiments a compound of the present invention is administered to a patient in need thereof in combination with osimertinib.

In certain embodiments a compound of the present invention is administered to a patient in need thereof in combination with rociletinib.

In certain embodiments a compound of the present invention is administered to a patient in need thereof in combination with avitinib.

In certain embodiments a compound of the present invention is administered to a patient in need thereof in combination with lazertinib.

In certain embodiments a compound of the present invention is administered to a patient in need thereof in combination with nazartinib.

In certain embodiments a compound of the present invention is administered to a patient in need thereof in combination with an EGFR antibody, for example, cetuximab, panitumumab, or necitumumab.

In certain embodiments a compound of the present invention is administered to a patient in need thereof in combination with cetuximab.

In certain embodiments a compound of the present invention is administered to a patient in need thereof in combination with panitumumab.

In certain embodiments a compound of the present invention is administered to a patient in need thereof in combination with necitumumab.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or another inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (OPDIVO®), pembrolizumab (KEYTRUDA®), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (GlaxoSmithKline plc), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (TECENTRIQ®), durvalumab (AstraZeneca and MedImmune), KN035 (Alphamab Co. Ltd.), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors include, but are not limited to, BMS-986016 (Bristol-Myers Squibb), GSK2831781 (GlaxoSmithKline plc), IMP321 (Prima BioMed), LAG525 (Novartis), and the dual PD-1 and LAG-3 inhibitor MGD013 (MacroGenics). An example of a TIM-3 inhibitor is TSR-022 (GlaxoSmithKline plc).

In certain embodiments the checkpoint inhibitor is selected from nivolumab (OPDIVO®); pembrolizumab (KEYTRUDA®); and pidilizumab/CT-011, MPDL3280A/RG7446; MEDI4736; MSB0010718C; BMS 936559, a PDL2/lg fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In yet another embodiment, one or more of the active compounds described herein can be administered in an effective amount for the treatment of abnormal tissue of the female reproductive system such as breast, ovarian, endometrial, or uterine cancer, in combination or alternation with an effective amount of an estrogen inhibitor including, but not limited to, a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, active compounds described herein can be administered in an effective amount for the treatment of abnormal tissue of the male reproductive system such as prostate or testicular cancer, in combination or alternation with an effective amount of an androgen (such as testosterone) inhibitor including, but not limited to a selective androgen receptor modulator, a selective androgen receptor degrader, a complete androgen receptor degrader, or another form of partial or complete androgen antagonist. In certain embodiments, the prostate or testicular cancer is androgen resistant.

Non-limiting examples of anti-androgen compounds are provided in WO 2011/156518 and U.S. Pat. Nos. 8,455,534 and 8,299,112. Additional non-limiting examples of anti-androgen compounds include enzalutamide, apalutamide, cyproterone acetate, chlormadinone acetate, spironolactone, canrenone, drospirenone, ketoconazole, topilutamide, abiraterone acetate, and cimetidine.

In certain embodiments, the bioactive agent is an ALK inhibitor. Examples of ALK inhibitors include but are not limited to crizotinib (XALKORI®), alectinib (ALECENSA®), ceritinib, TAE684 (NVP-TAE684), GSK1838705A, AZD3463, ASP3026, PF-06463922, entrectinib (RXDX-101), and AP26113.

In certain embodiments, the bioactive agent is an HER-2 inhibitor. Examples of HER-2 inhibitors include trastuzumab, lapatinib, ado-trastuzumab emtansine, and pertuzumab.

In certain embodiments, the bioactive agent is a CD20 inhibitor. Examples of CD20 inhibitors include obinutuzumab (GAZYVA®), rituximab (RITUXAN®), ofatumumab, ibritumomab, tositumomab, and ocrelizumab.

In certain embodiments, the bioactive agent is a JAK3 inhibitor. Examples of JAK3 inhibitors include tasocitinib.

In certain embodiments, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (oblimersen).

In certain embodiments, the bioactive agent is a kinase inhibitor. In certain embodiments, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include, but are not limited to, Wortmannin, demethoxyviridin, perifosine, idelalisib, pictilisib, palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl]acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422).

Examples of BTK inhibitors include ibrutinib (also known as PCI-32765) (IMBRUVICA®) (1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-

(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-f{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, but are not limited to, cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (GLEEVEC®; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-amino-tetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In certain embodiments, the bioactive agent is a c-MET inhibitor, for example, crizotinib (XALKORI®, CRIZONIX™), tepotinib (XL880, EXEL-2880, GSK1363089, GSK089), or tivantinib (ARQ 197).

In certain embodiments, the bioactive agent is an AKT inhibitor, including, but not limited to, MK-2206, GSK690693, perifosine, (KRX-0401), GDC-0068, triciribine, AZD5363, honokiol, PF-04691502, and miltefosine, a FLT-3 inhibitor, including, but not limited to, P406, dovitinib, quizartinib (AC220), amuvatinib (MP-470), tandutinib (MHLN518), ENMD-2076, and KW-2449, or a combination thereof.

In certain embodiments, the bioactive agent is an mTOR inhibitor. Examples of mTOR inhibitors include, but are not limited to, rapamycin and its analogs, everolimus (AFINITOR®), temsirolimus, ridaforolimus, sirolimus, and deforolimus.

In certain embodiments, the bioactive agent is a RAS inhibitor. Examples of RAS inhibitors include but are not limited to Reolysin and siG12D LODER.

In certain embodiments, the bioactive agent is a HSP inhibitor. HSP inhibitors include but are not limited to geldanamycin or 17-N-allylamino-17-demethoxygeldanamycin (17AAG), and radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, aFLT-3 inhibitor, a VEGFRinhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase (MEK) inhibitor, a VEGF trap antibody, pemetrexed, panitumumab, amrubicin, oregovomab, Lep-etu, nolatrexed, azd2171, batabulin, of atumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, GLEEVEC®, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In certain embodiments the compound is administered in combination with ifosfamide.

In certain embodiments, the bioactive agent is selected from, but are not limited to, imatinib mesylate (GLEEVEC®), dasatinib (SPRYCEL®), nilotinib (TASIGNA®), bosutinib (BOSULIF®), trastuzumab (HERCEPTIN®), trastuzumab-DM1, pertuzumab (PERJETA®), lapatinib (TYKERB®), gefitinib (IRESSA®), erlotinib (TARCEVA®), cetuximab (ERBITUX®), panitumumab (VECTIBIX®), vandetanib (CAPRELSA®), vemurafenib (ZELBORAF®), vorinostat (ZOLINZA®), romidepsin (ISTODAX®), bexarotene (TAGRETIN®), alitretinoin (PANRETIN®), tretinoin (VESANOID®), carfilizomib (KYPROLIS®), pralatrexate (FOLOTYN®), bevacizumab (AVASTIN®), ziv-aflibercept (ZALTRAP®), sorafenib (NEXAVAR®), sunitinib (SUTENT®), pazopanib (VOTRIENT®), regorafenib (STIVARGA®), and cabozantinib (COMETRIQ®).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: vincristine (ONCOVINE®) or liposomal vincristine (MARQIBO®), daunorubicin (daunomycin or CERUBIDINE®) or doxorubicin (ADRIAMYCIN®), cytarabine (cytosine arabinoside, ara-C, or CYTOSAR®), L-asparaginase (ELSPAR®) or PEG-L-asparaginase (pegaspargase or ONCASPAR®), etoposide (VP-16), teniposide (VUMON®), 6-mercaptopurine (6-MP or PURINETHOL®), methotrexate, cyclophosphamide (CYTOXAN®), prednisone, dexamethasone (DECADRON®), imatinib (GLEEVEC®), dasatinib (SPRYCEL®), nilotinib (TASIGNA®), bosutinib (BOSULIF®), and ponatinib (ICLUSIG®).

Examples of additional suitable chemotherapeutic agents include, but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), chlorambucil, cisplatin, cladribine, colchicin, conjugated estrogens, cyclophosphamide, cyclothosphamide, cytarabine, cytochalasin B, cytoxan, dacarbazine, dactinomycin, dactinomycin (formerly actinomycin), daunirubicin HCL, daunorucbicin citrate, denileukin diftitox, dexrazoxane, dibromomannitol, dihydroxy anthracin dione, docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or other chemical compound useful in the treatment of cancer). Examples of chemotherapeutic agents include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2', 2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example, combination dosing regimes are described in Saltz et al., Proc. Am. Soc. Clin. Oncol. 18:233a (1999) and Douillard et al., Lancet 355(9209): 1041-1047 (2000).

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (ELOXATIN®), PD0332991, ribociclib (LEE011), amebaciclib (LY2835219), HDM201, fulvestrant (FASLODEX®), exemestane (AROMASIN®), PIM447, ruxolitinib (INC424), BGJ398, necitumumab, pemetrexed (ALIMTA®), and ramucirumab (IMC-1121B).

In certain embodiments, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g., a cyclosporin or an ascomycin, e.g., cyclosporin A (NEORAL®), FK506 (tacrolimus), pimecrolimus, a mTOR inhibitor, e.g., rapamycin or a derivative thereof, e.g., sirolimus (RAPAMUNE®), everolimus (CERTICAN®), temsirolimus, zotarolimus, biolimus-7, biolimus-9, a rapalog, e.g., ridaforolimus, azathioprine, campath 1H, a S1P receptor modulator, e.g., fingolimod or an analogue thereof, an anti IL-8 antibody, mycophenolic acid or a salt thereof, e.g., sodium salt, or a prodrug thereof, e.g., mycophenolate mofetil (CELLCEPT®), OKT3 (ORTHOCLONE OKT3®), prednisone, ATGAM®, THYMOGLOBULIN®, brequinar sodium, OKT4, T10B9.A-3A, 33B3.1, 15-deoxyspergualin, tresperimus, leflunomide (ARAVA®), CTLAI-Ig, anti-CD25, anti-IL2R, basiliximab (SIMULECT®), daclizumab (ZENAPAX®), mizorbine, methotrexate, dexamethasone, ISAtx-247, SDZ ASM 981 (pimecrolimus, ELIDEL®), CTLA4lg (abatacept), belatacept, LFA3lg, etanercept (sold as ENBREL® by Immunex), adalimumab (HUMIRA®), infliximab (REMICADE®), an anti-LFA-1 antibody, natalizumab (ANTEGREN®), enlimomab, gavilimomab, antithymocyte immunoglobulin, siplizumab, alefacept, efalizumab, pentasa, mesalazine, asacol, codeine phosphate, benorylate, fenbufen, naprosyn, diclofenac, etodolac and indomethacin, aspirin and ibuprofen.

In some embodiments, the bioactive agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The combination therapy may include a therapeutic agent which is a non-drug treatment. For example, the compound could be administered in addition to radiation therapy, cryotherapy, hyperthermia, and/or surgical excision of tumor tissue.

Linkers

Linker is a bond or a chemically stable bivalent group that covalently attaches the Cereblon Ligand to the BRAF Targeting Ligand.

In certain embodiments, Linker can be any chemically stable group that attaches the Cereblon Ligand to the BRAF Targeting Ligand. In some embodiments, Linker has a chain of 2, 3, 4, 5, 6, 7, 8, 9, 10, 11, 12, 13, 14, 15, 16, 17, 18, 19, or 20 or more carbon atoms of which one or more carbon atoms can be replaced by a heteroatom such as O, N, S, or P, as long as the resulting molecule has a stable shelf life for at least two months, three months, six months, or one year as part of a pharmaceutically acceptable dosage form, and itself is pharmaceutically acceptable. In certain embodiments, the chain has 2, 3, 4, 5, 6, 7, 8, 9, 10, 11, 12, 13, or 14 contiguous atoms in the chain. For example, the chain may include 1 or more ethylene glycol units, and in some embodiments, may have at least 2, 3, 4, 5, 6, 7, 8, 9, or 10 or more contiguous, partially contiguous, or non-contiguous ethylene glycol the Linker. In certain embodiments, the chain has at least 1, 2, 3, 4, 5, 6, 7, or 8 branches which can be independently alkyl, heteroalkyl, aryl, heteroaryl, alkenyl, or alkynyl substituents, which in one embodiment, each branch has 10, 8, 6, 4, 3, 2, or 1 carbon.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocyclic, cycloalkyl, etc., as desired to achieve the appropriate drug properties.

In certain aspects, Linker is selected from

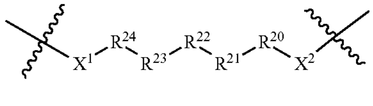

-continued

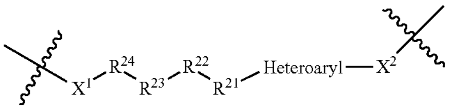

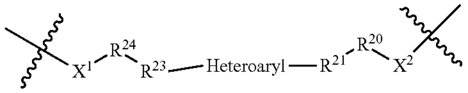

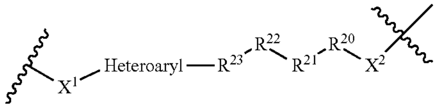

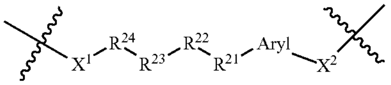

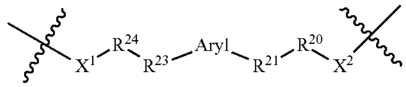

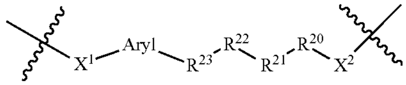

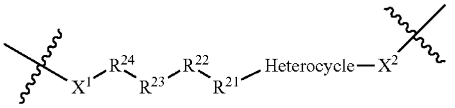

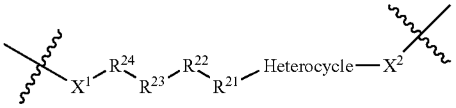

and

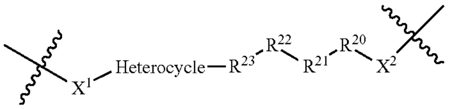

wherein all variables are defined as above.

In certain embodiments the linker includes

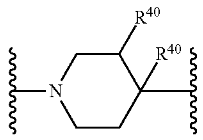

or

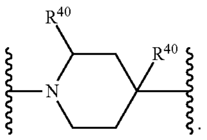

In certain embodiments the linker includes

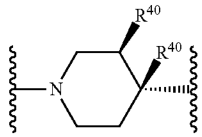

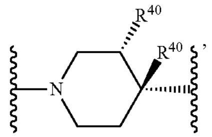

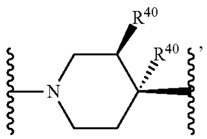

or

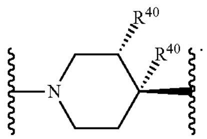

In certain embodiments the linker includes

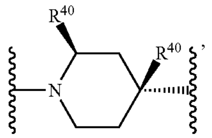

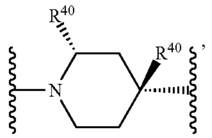

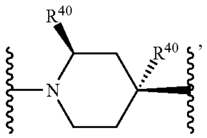

or

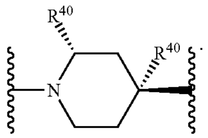

In certain embodiments the linker includes

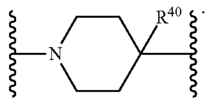

In certain embodiments the linker includes

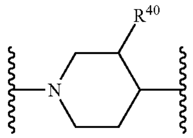

or

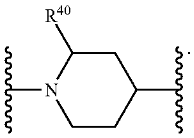

In certain embodiments the linker includes

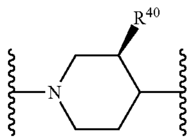

or

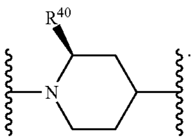

In certain embodiments the linker includes

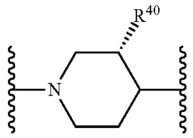

or

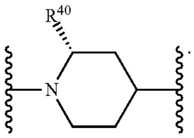

In certain embodiments the linker includes

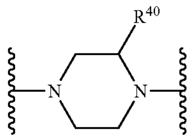

or

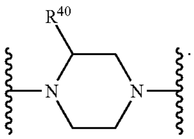

In certain embodiments the linker includes

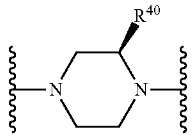
or
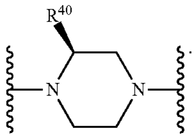
.

In certain embodiments the linker includes

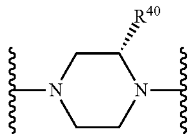
or
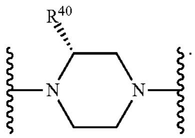
.

In certain embodiments the linker includes

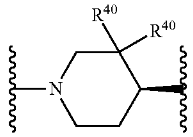
or
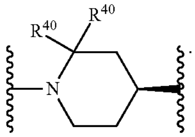
.

In certain embodiments the linker includes

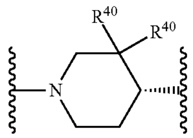
or
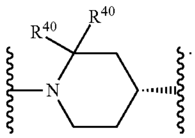
.

In certain embodiments the linker includes

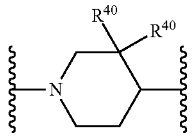
or
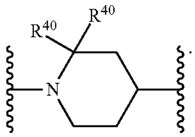
.

The following are non-limiting examples of Linkers that can be used in this invention. Based on this elaboration, those of skill in the art will understand how to use the full breadth of Linkers that will accomplish the goal of the invention.

As certain non-limiting examples, Linker includes:

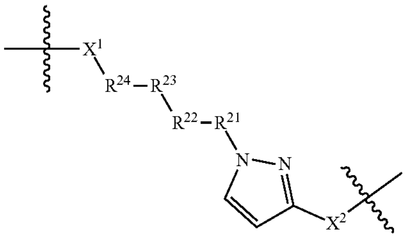
,

-continued

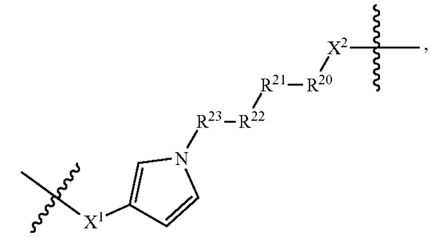
,

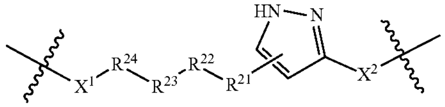
,

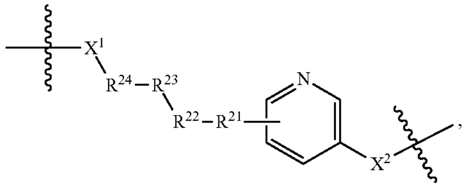
,

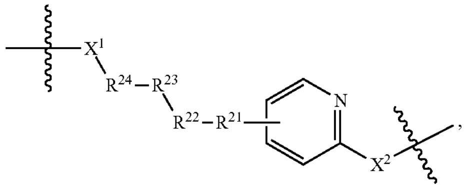
,

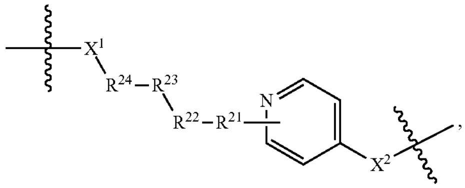
,

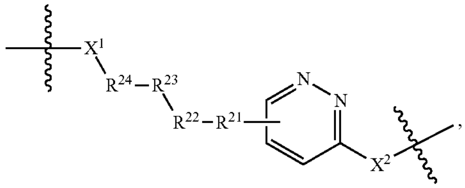
,

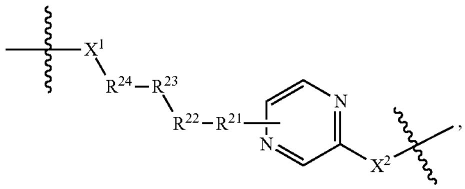
,

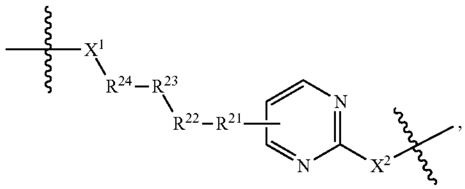
,

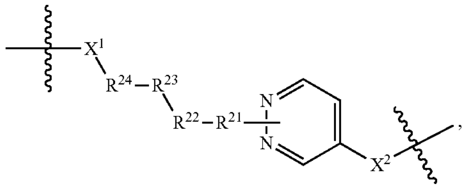
,

-continued
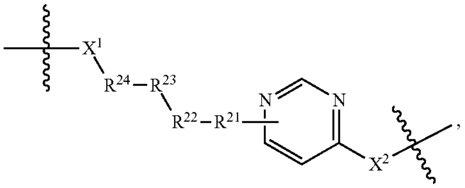
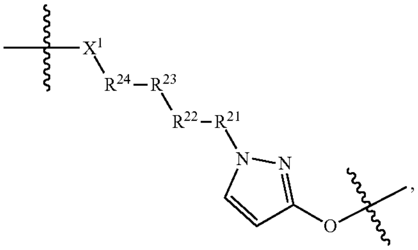
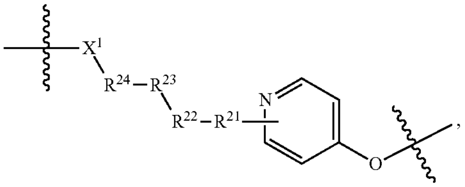
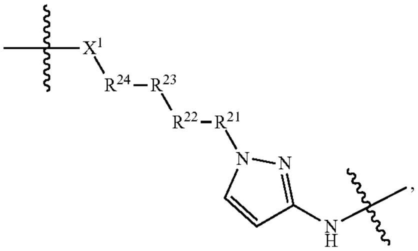
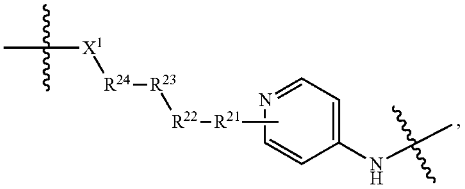
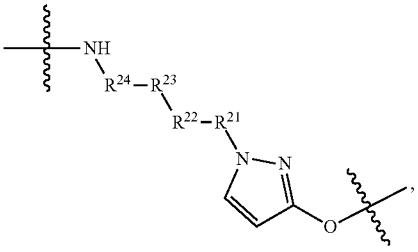
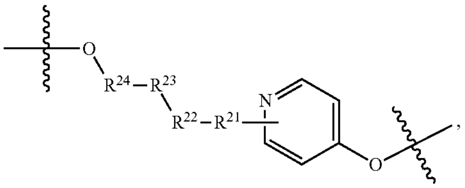
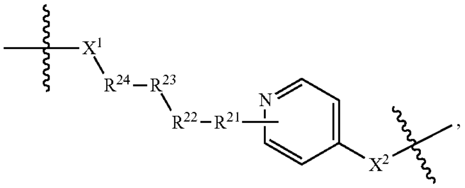
-continued
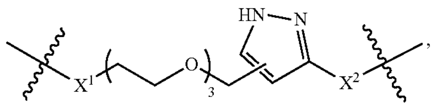
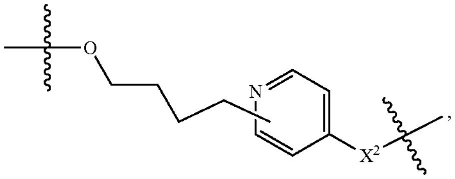
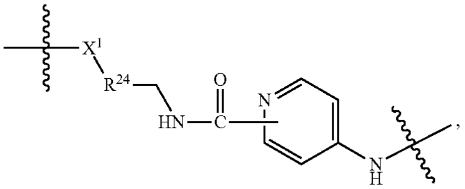
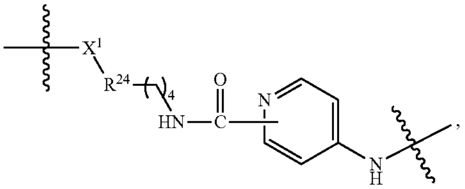
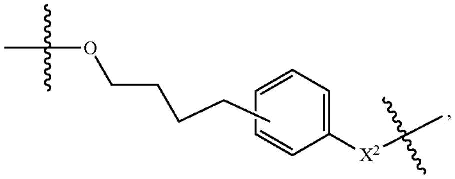
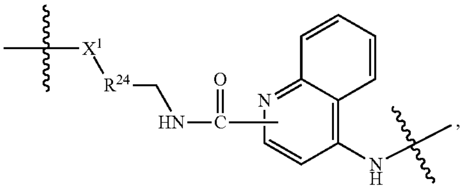
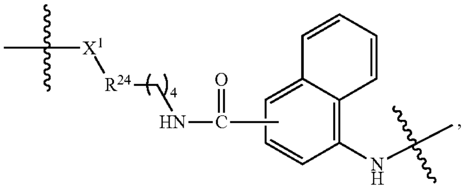
and
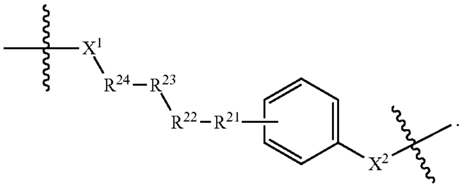

In an additional embodiment Linker is selected from:

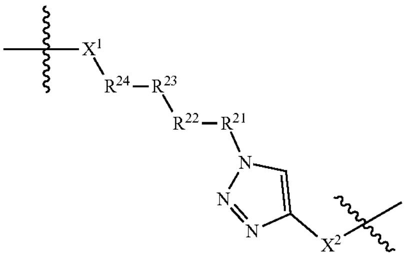

,

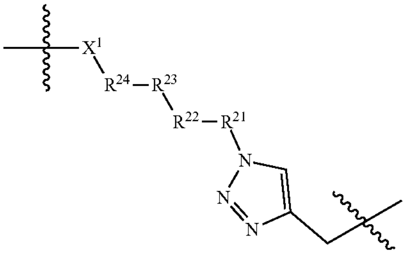

,

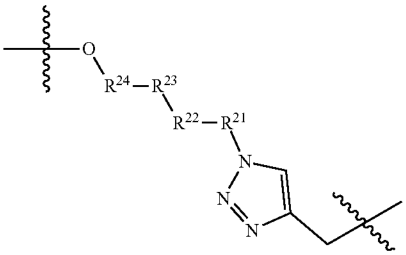

,

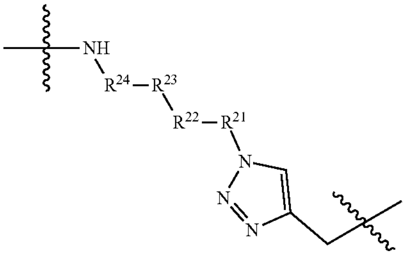

,

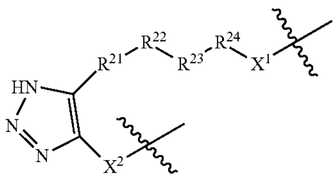

,

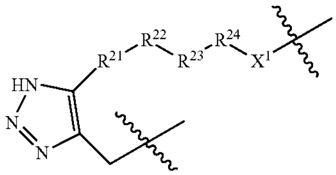

,

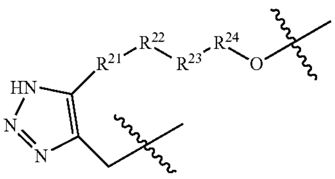

, and

-continued

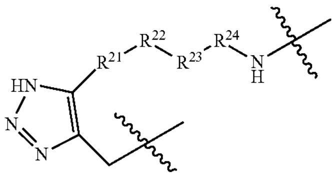

.

In one embodiment $X^1$ is attached to the BRAF Targeting Ligand. In another embodiment $X^2$ is attached to the BRAF Targeting Ligand.

Non-limiting examples of moieties of $R^{20}$, $R^{21}$, $R^{22}$, $R^{23}$, and $R^{24}$ include:

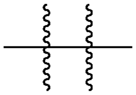

,

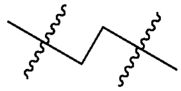

,

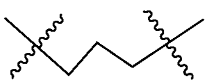

,

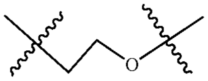

,

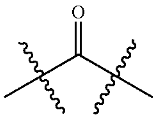

,

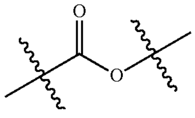

,

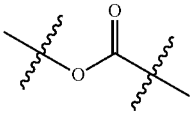

,

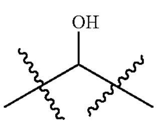

,

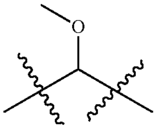

,

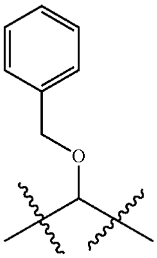

,

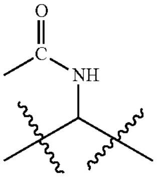

,

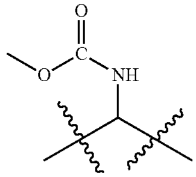

,

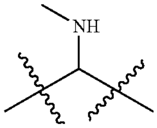

,

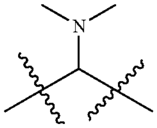

,

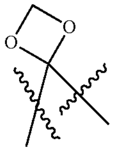

,

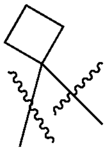

,

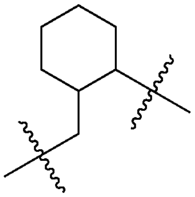

,

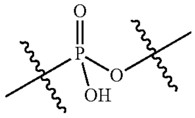

, and

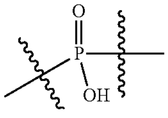

.

Additional non-limiting examples of moieties of $R^{20}$, $R^{21}$, $R^{22}$, $R^{23}$, and $R^{24}$ include:

-continued
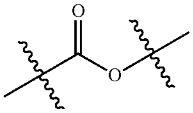,
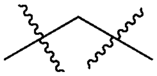,
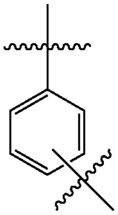,
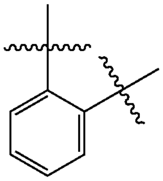,
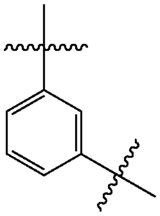,
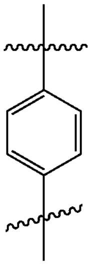,
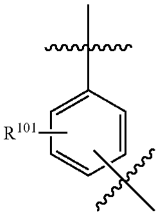,
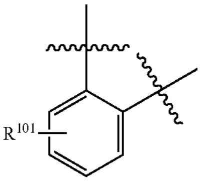,
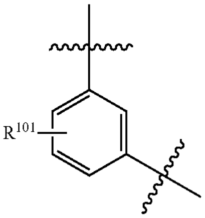,
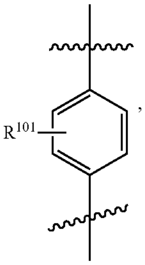,
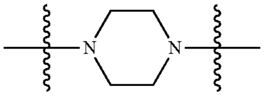,
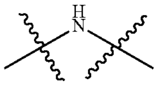,
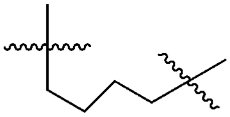,
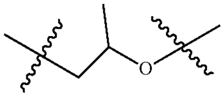,
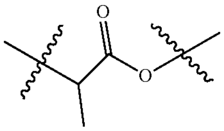,
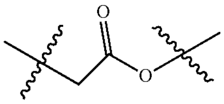,
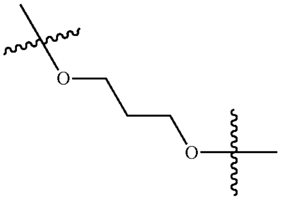,
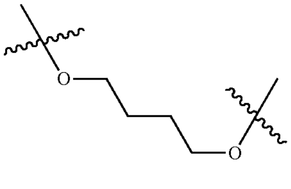,
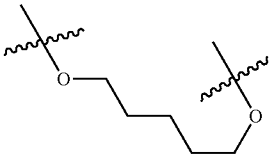,
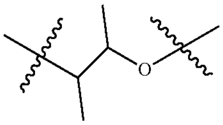,
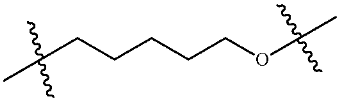,
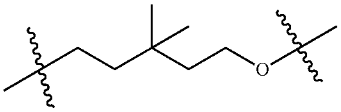,
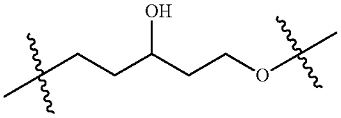,
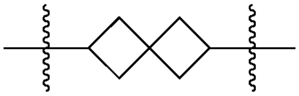,
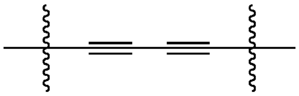,
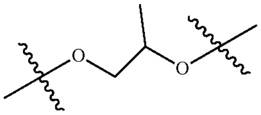,
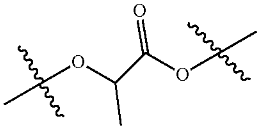,
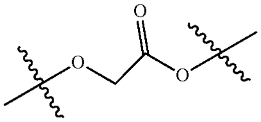,
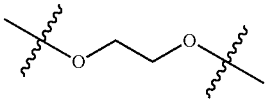, and
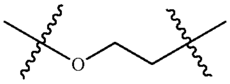.
Additional non-limiting examples of moieties of $R^{20}$, $R^{21}$, $R^{22}$, $R^{23}$, and $R^{24}$ include:
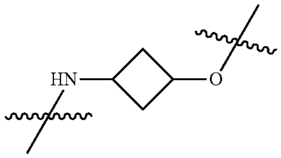,
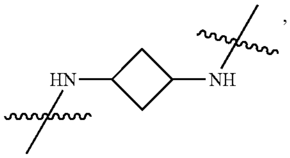, -continued

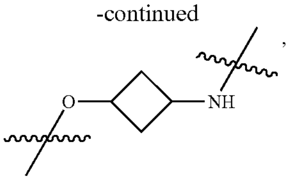
,

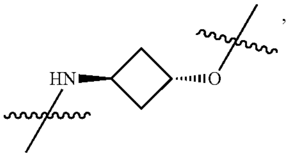
,

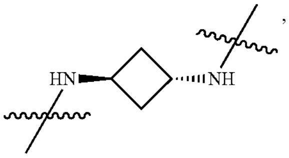
,

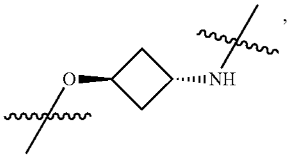
,

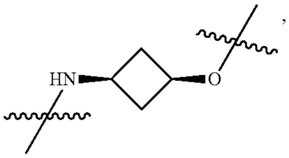
,

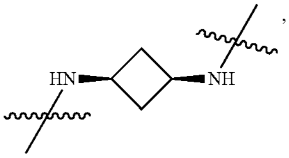
,

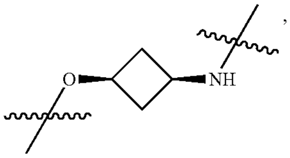
,

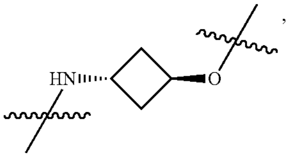
,

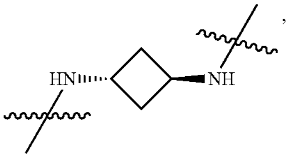
,

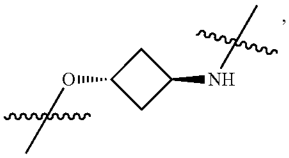
,

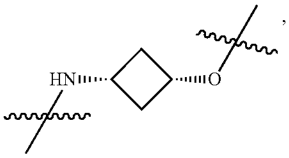
,

-continued

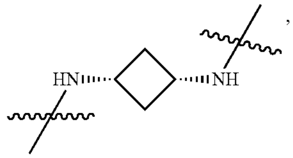
,

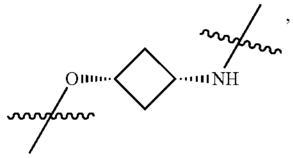
,

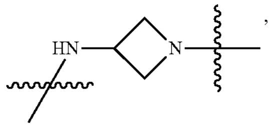
,
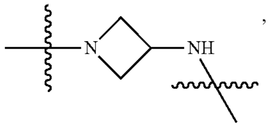
,

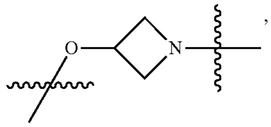
,
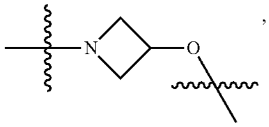
,

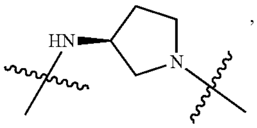
,
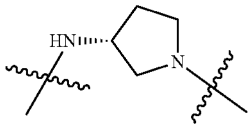
,

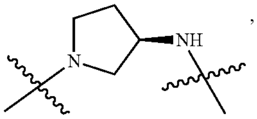
,
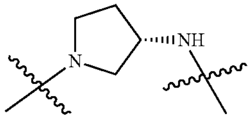
,

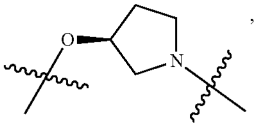
,
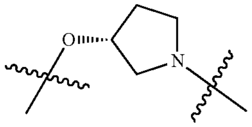
,

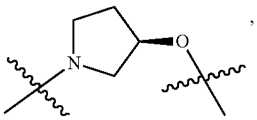
, and

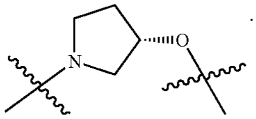
.

In additional embodiments, the Linker is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, Linker is flanked, substituted, or interspersed with an aryl, phenyl, benzyl, alkyl, alkylene, or heterocycle group. In certain embodiments, Linker may be asymmetric or symmetrical. In some embodiments, Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, Linker group may be any suitable moiety as described herein.

In additional embodiments, Linker is selected from:

$—NR^{61}(CH_2)_{n1}$-(lower alkyl)-, $—NR^{61}(CH_2)_{n1}$-(lower alkoxyl)-, $NR^1(CH_2)_{n1}$-(lower alkoxyl)-$OCH_2$—, —$NR^{61}(CH_2)_{n1}$-(lower alkoxyl)-(lower alkyl)-$OCH_2$—, —$NR^{61}(CH_2)_{n1}$-(cycloalkyl)-(lower alkyl)-$OCH_2$—, —$NR^{61}(CH_2)_{n1}$-(heterocycloalkyl)-, —$NR^{61}(CH_2CH_2O)_{n1}$-(lower alkyl)-O—$CH_2$—, —$NR^{61}(CH_2CH_2O)_{n1}$-(heterocycloalkyl)-O—$CH_2$—, —$NR^{61}(CH_2CH_2O)_{n1}$-Aryl-O—$CH_2$—, —$NR^{61}(CH_2CH_2O)_{n1}$-(heteroaryl)-O—$CH_2$—, —$NR^{61}(CH_2CH_2O)_{n1}$-(cycloalkyl)-O-(heteroaryl)-O—$CH_2$—, —$NR^{61}(CH_2CH_2O)_{n1}$-(cycloalkyl)-O-Aryl-O—$CH_2$—, —$NR^{61}(CH_2CH_2O)_{n1}$-(lower alkyl)-NH-Aryl-O—$CH_2$—, —$NR^{61}(CH_2CH_2O)_{n1}$-(lower alkyl)-O-Aryl-$CH_2$, —$NR^{61}(CH_2CH_2O)_{n1}$-cycloalkyl-O-Aryl-, —$NR^{61}(CH_2CH_2O)_{n1}$-cycloalkyl-O-heteroaryl-, —$NR^{61}(CH_2CH_2)_{n1}$-(cycloalkyl)-O-(heterocycle)-$CH_2$, —$NR^{61}(CH_2CH_2)_{n1}$-(heterocycle)-(heterocycle)-$CH_2$, and —$NR^{61}$-(heterocycle)-$CH_2$;

wherein n1 is 0, 1, 2, 3, 4, 5, 6, 7, 8, 9, or 10; and $R^{61}$ is H, methyl, or ethyl.

In additional embodiments, Linker is selected from:

—$N(R^{61})$—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—,

—O—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—,

—O—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—O—;

—$N(R^{61})$—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—O—;

$(CH_2)_{m1}$—$O(CH_2)_{n2}$—$O(CH_2)_{o1}$—$O(CH_2)_{p1}$—$O(CH_2)_{q1}$—$O(CH_2)_{r1}$—O—;

$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—;

—$O(CH_2)_{m1}O(CH_2)_{n2}O(CH_2)_{p1}O(CH_2)_{q1}OCH_2$—;

—$O(CH_2)_{m1}O(CH_2)_{n2}O(CH_2)_{p1}O(CH_2)_{q1}OCH_2$—; wherein m1, n2, o1, p1, q1, and r1 are independently 1, 2, 3, 4, or 5; and $R^{61}$ is H, methyl, or ethyl.

In additional embodiments, Linker is selected from:

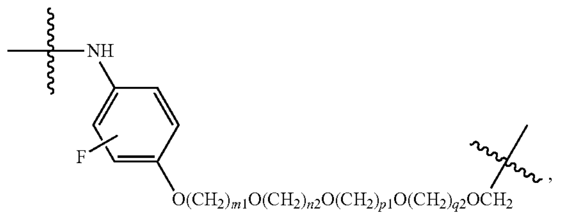

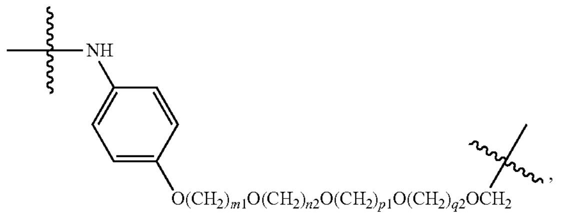

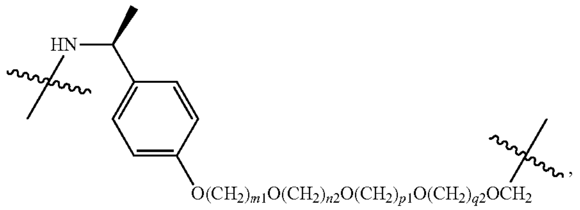

-continued

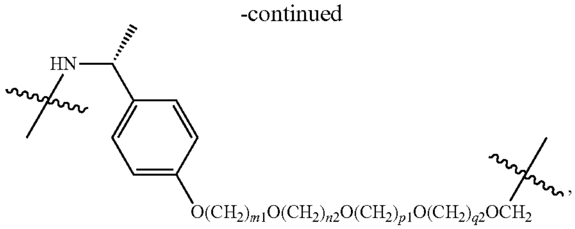

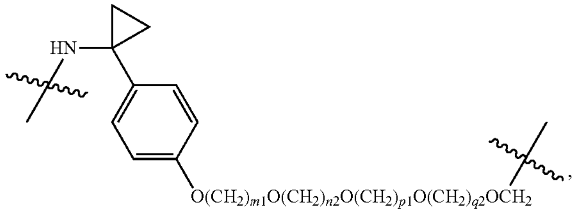

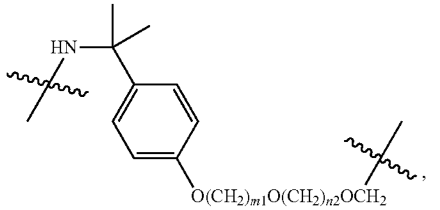

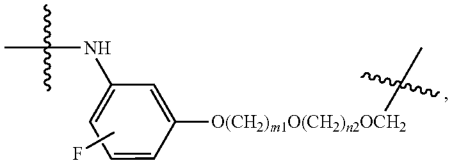

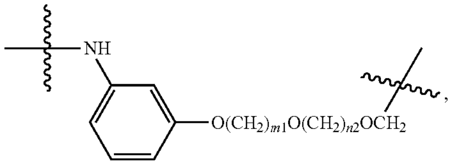

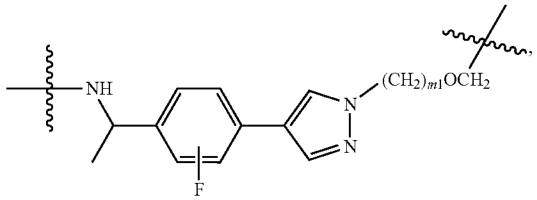

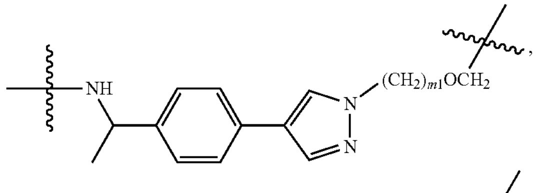

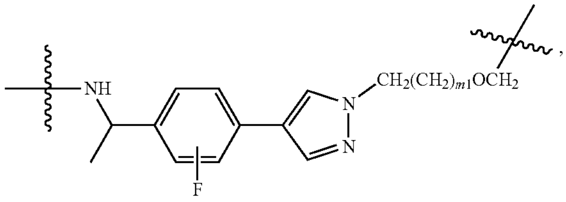

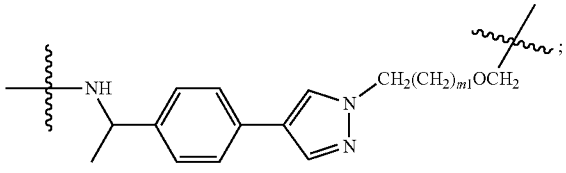

m1, n2, o1, p1, q2, and r1 are independently 1, 2, 3, 4, or 5.

In additional embodiments, Linker is selected from:
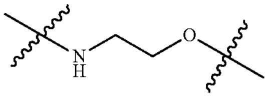,
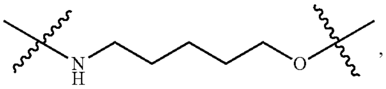,
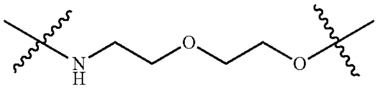,
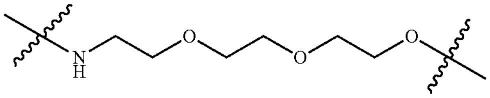,
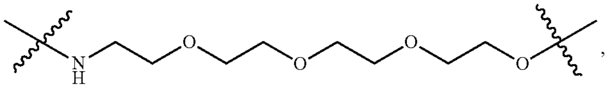,
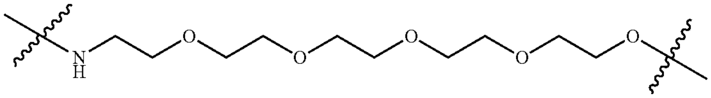,
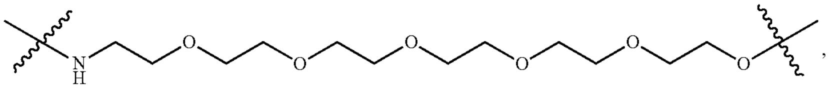,
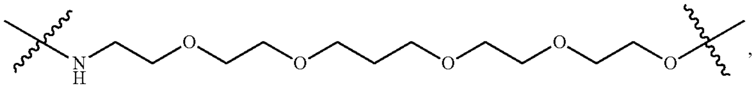,
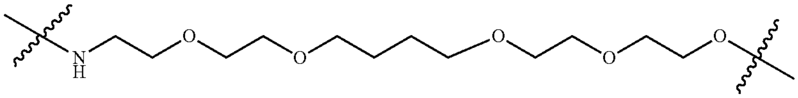,
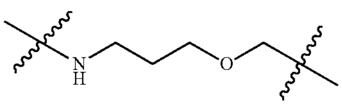,
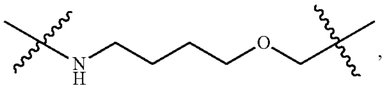,
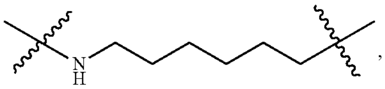,
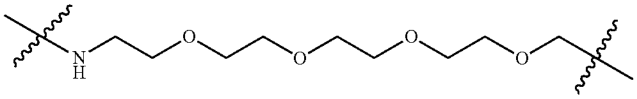,
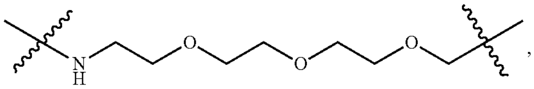,
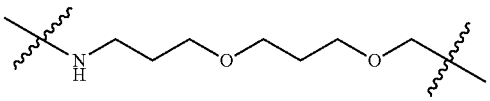,
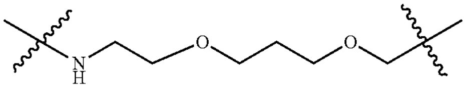,
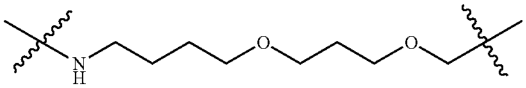,
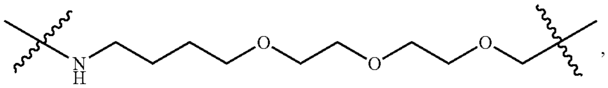,
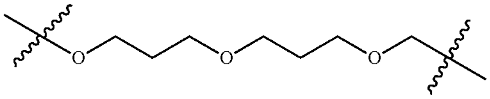,
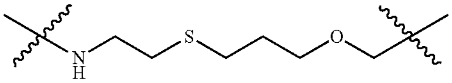,
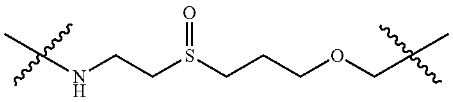,
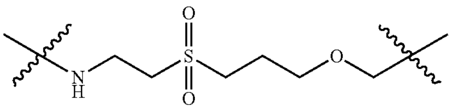,
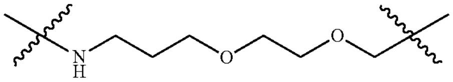,
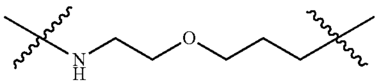,
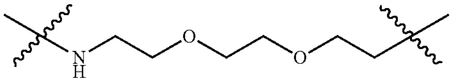,
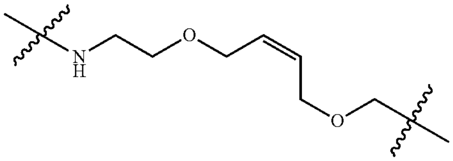,
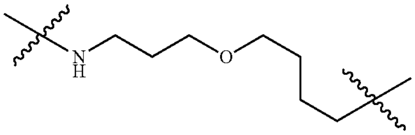,
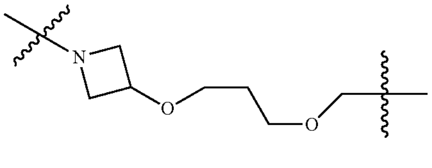,
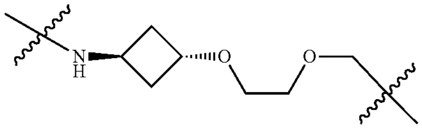, -continued
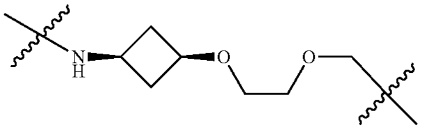,
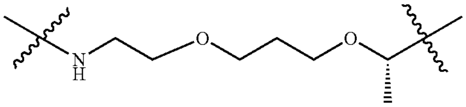,
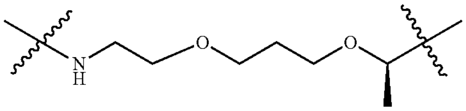,
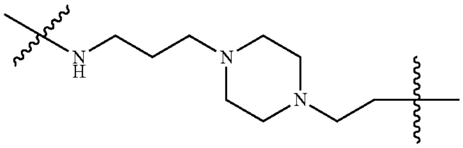,
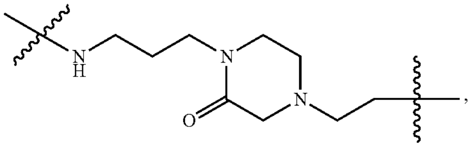,
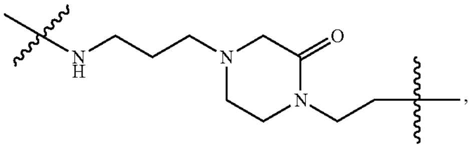,
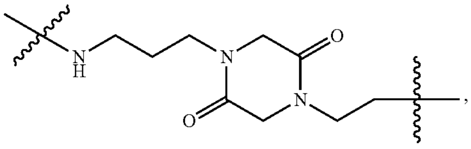,
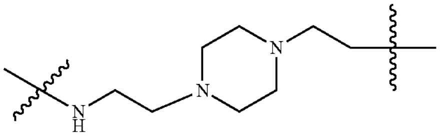,
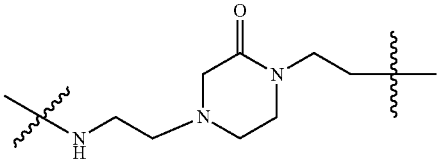,
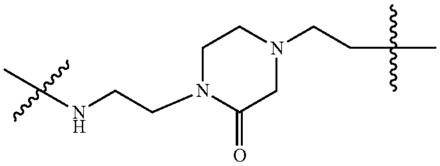,
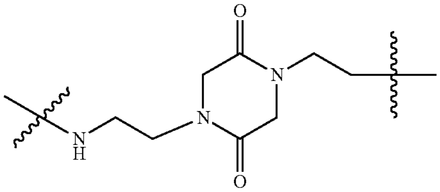
In additional embodiments, Linker is selected from:
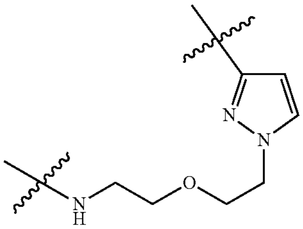,
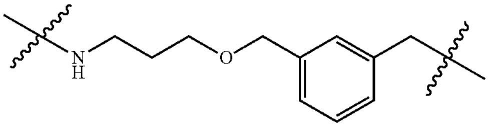,
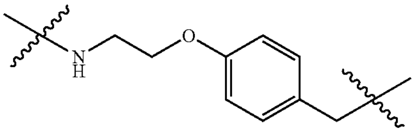,
-continued
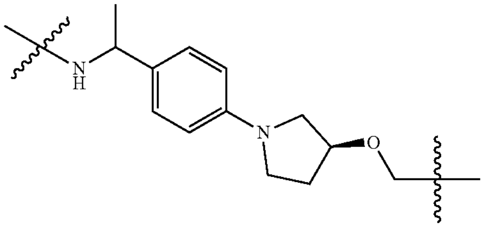,
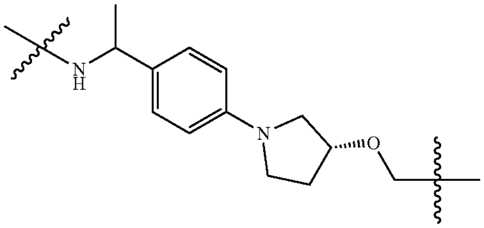, -continued
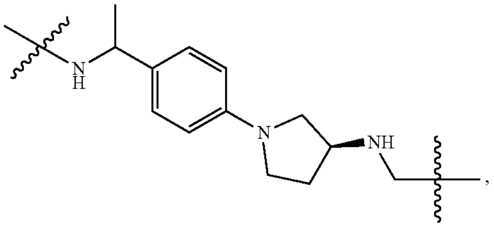
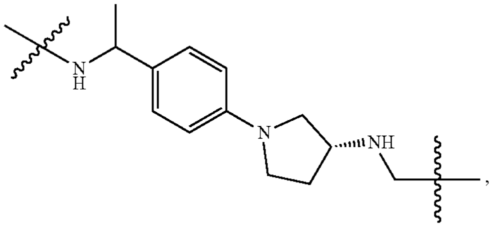
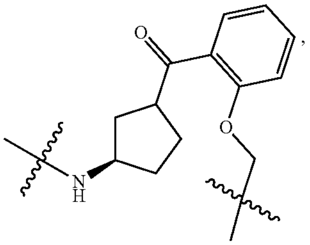
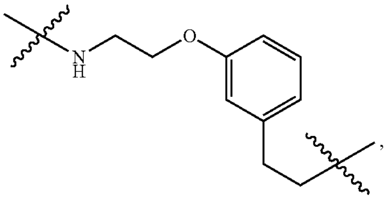
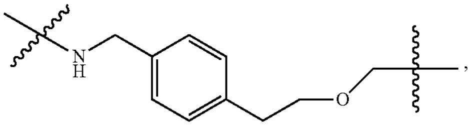
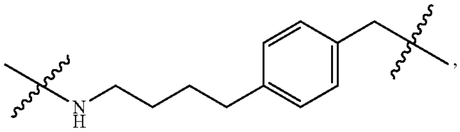
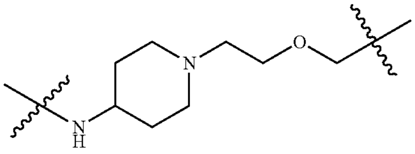
and
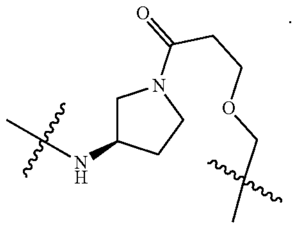
In additional embodiments, Linker is selected from:
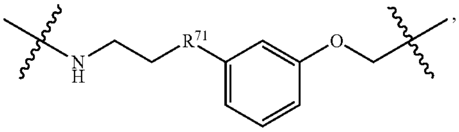
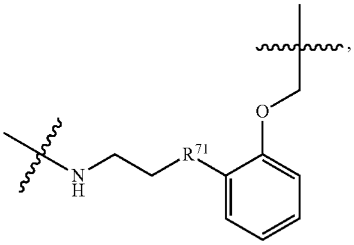
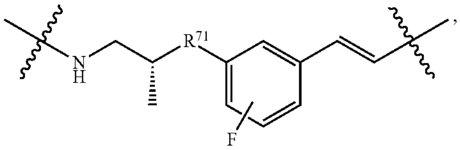
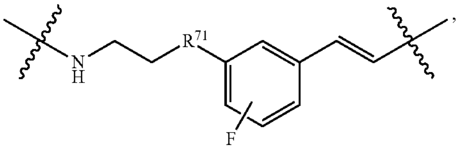
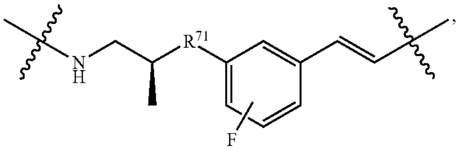
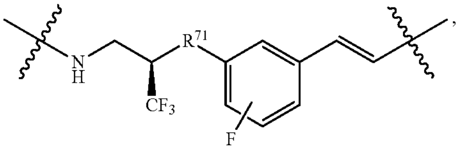
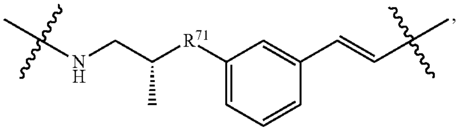
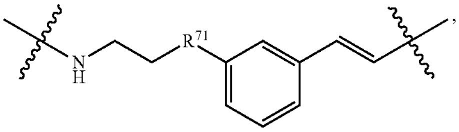
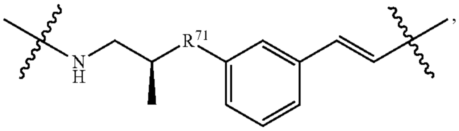
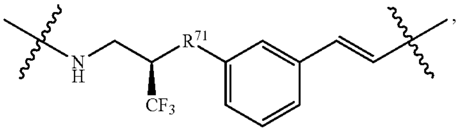
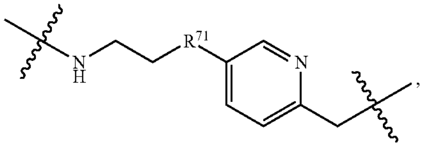

-continued
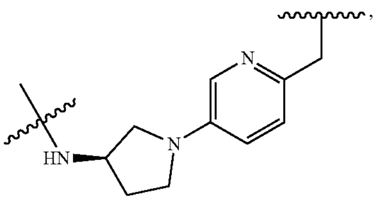,
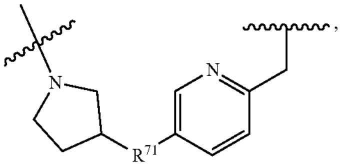,
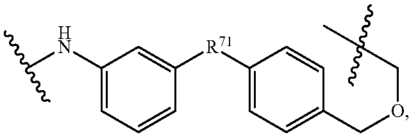,
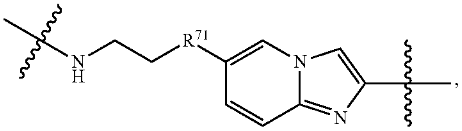,
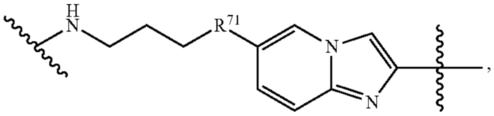,
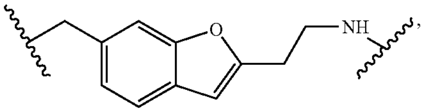,
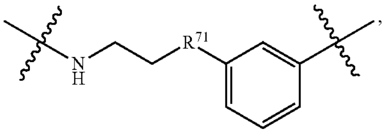,
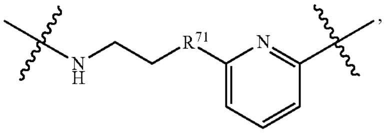,
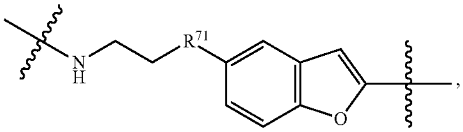,
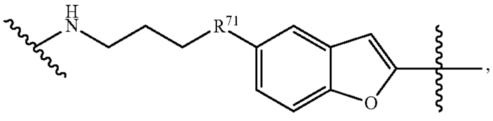,
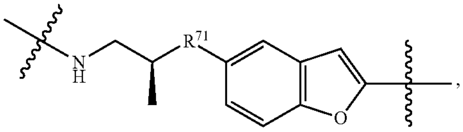,
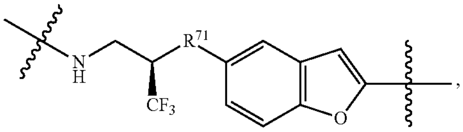,
-continued
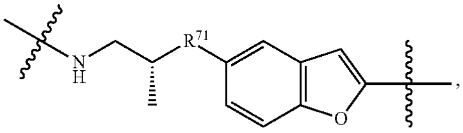,
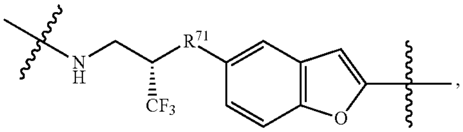,
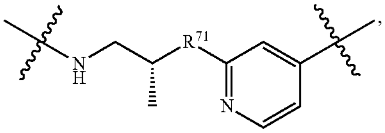,
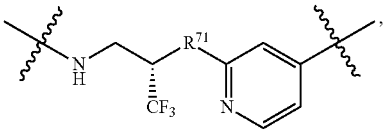,
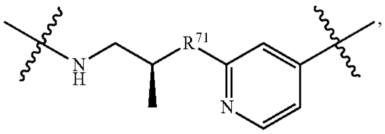,
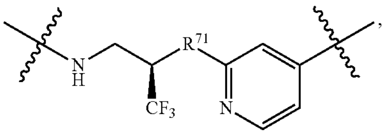,
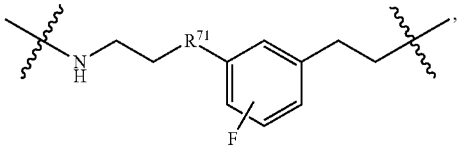,
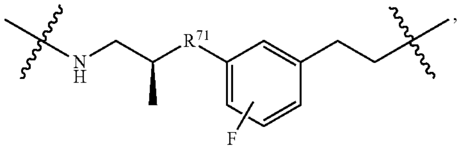,
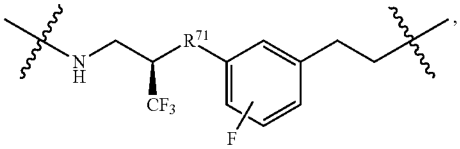,
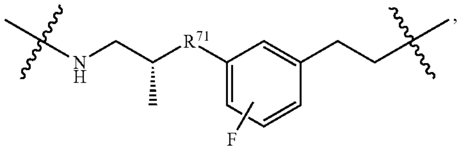,
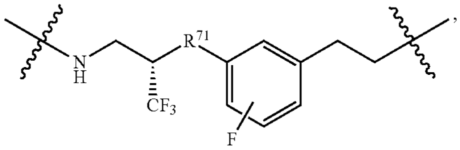,
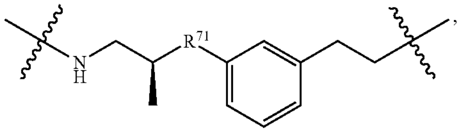, -continued
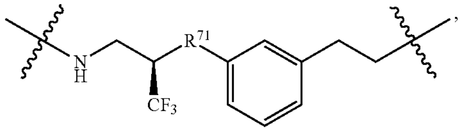
,
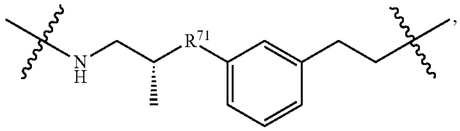
,
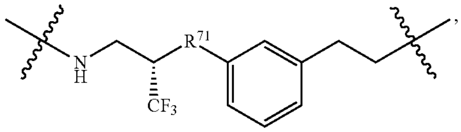
,
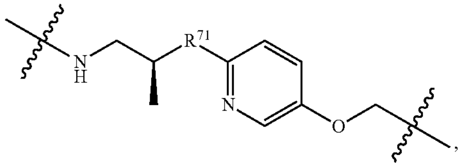
,
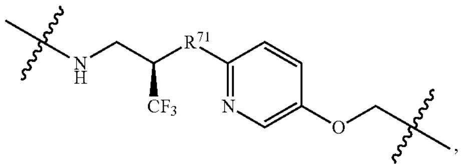
,
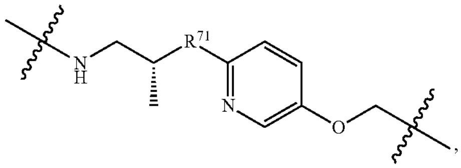
,
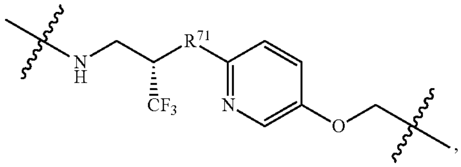
,
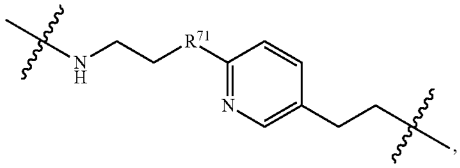
,
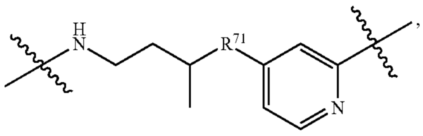
,
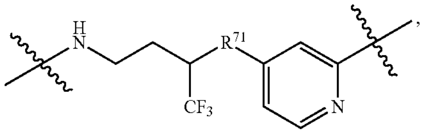
,
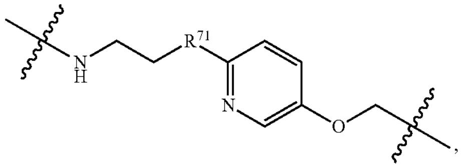
,
-continued
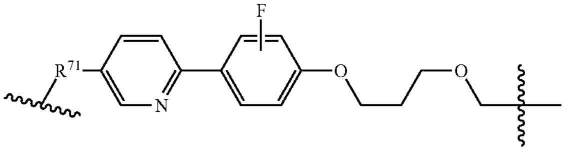
,
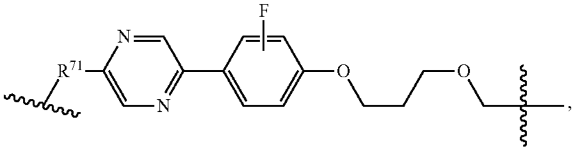
,
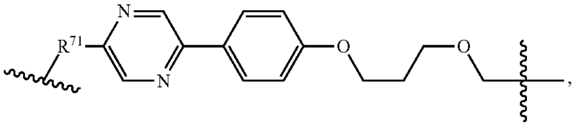
,
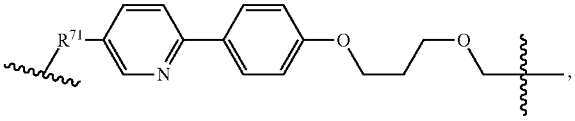
,
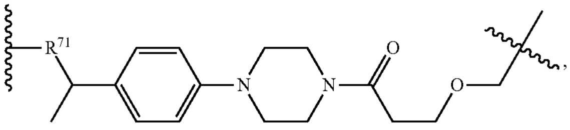
,
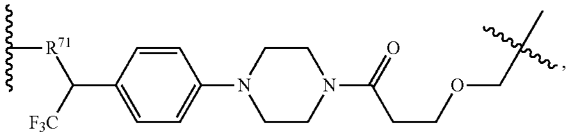
,
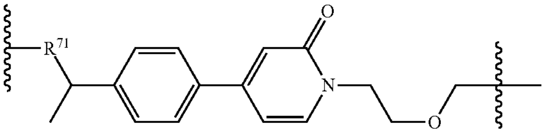
,
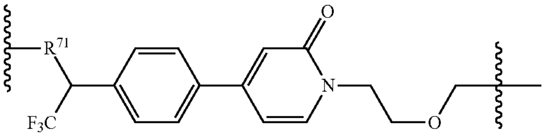
,
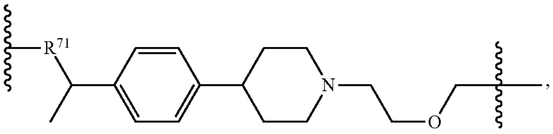
,
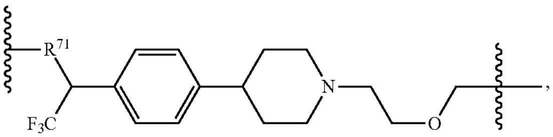
,
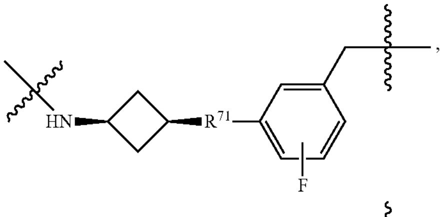
,
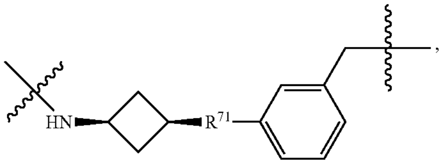

-continued
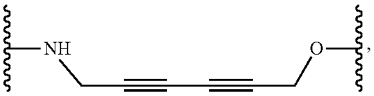
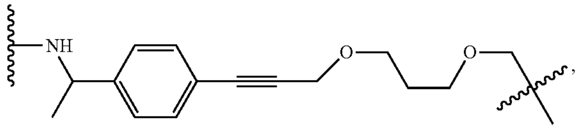
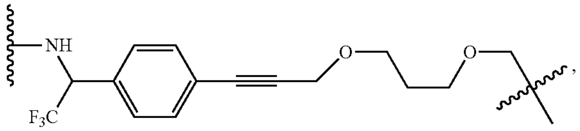
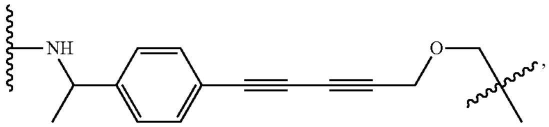
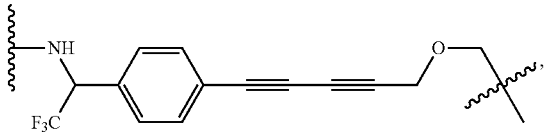
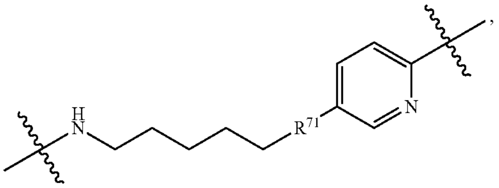
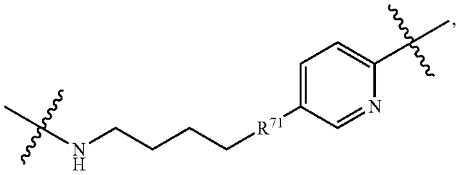
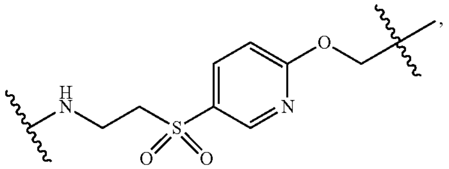
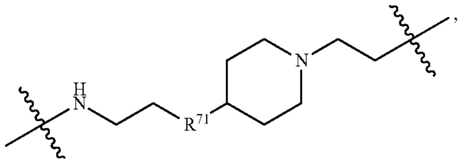
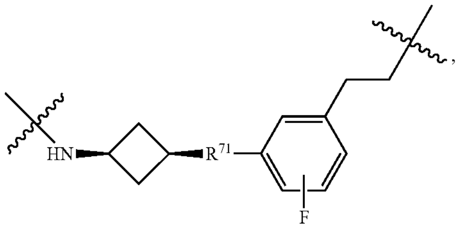
-continued
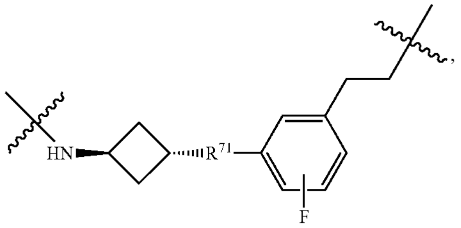
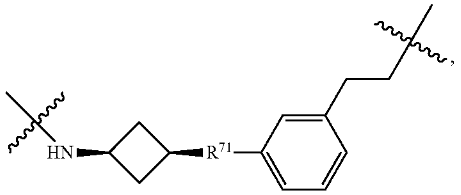
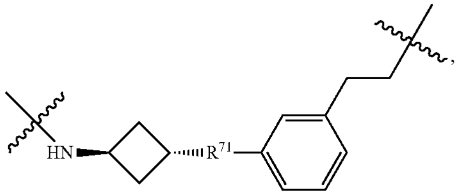
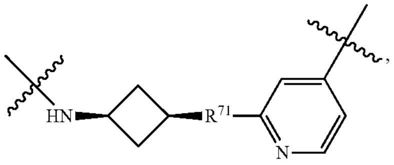
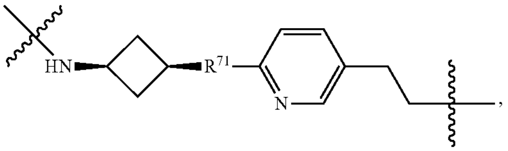
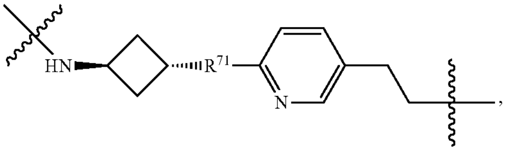
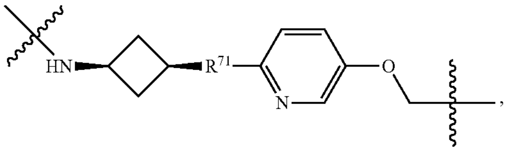
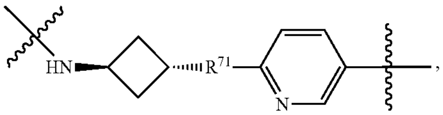
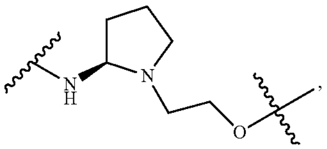
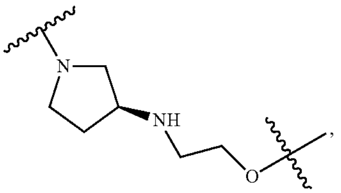

-continued
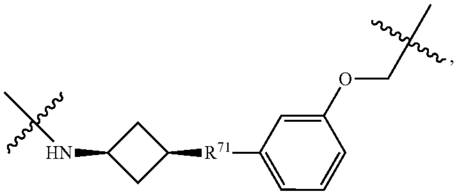
,
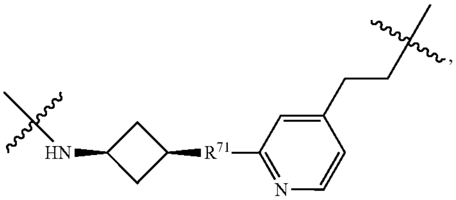
,
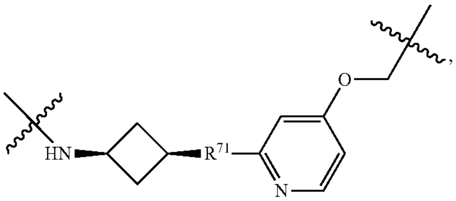
,
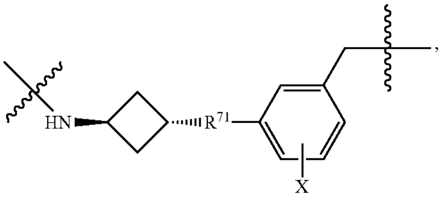
,
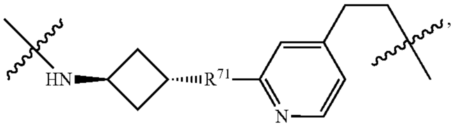
,
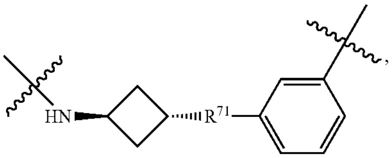
,
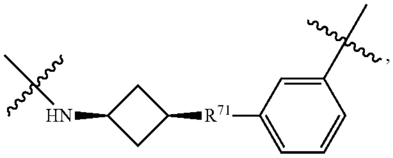
,
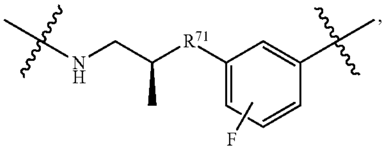
,
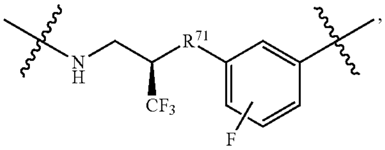
,
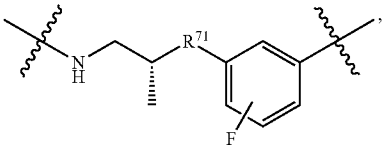
,
-continued
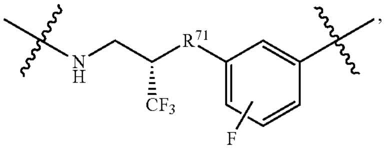
,
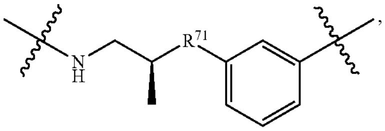
,
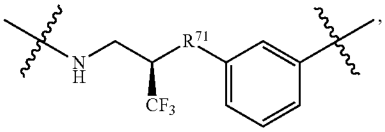
,
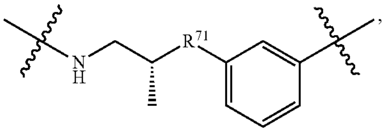
,
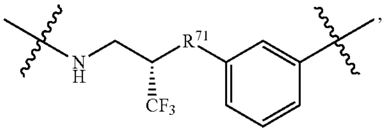
,
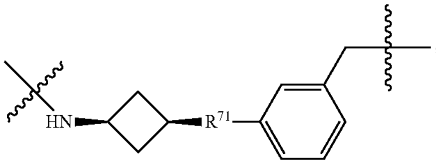
,
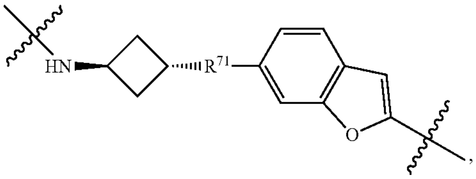
,
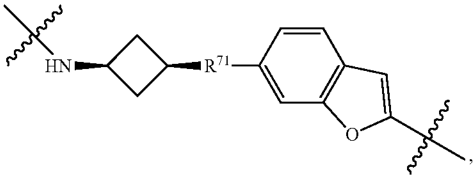
,
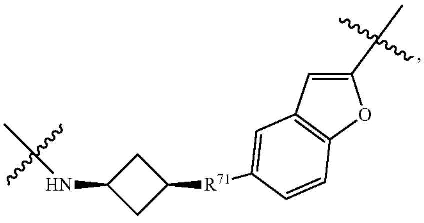
,
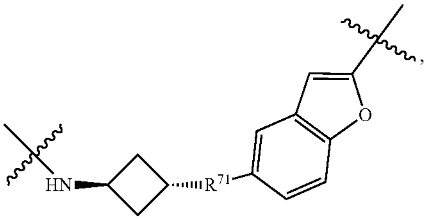
, -continued
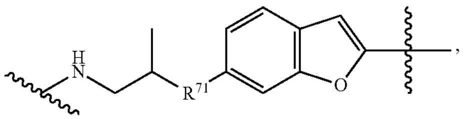
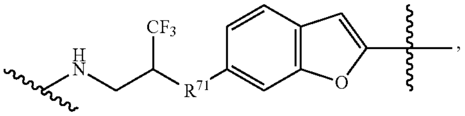
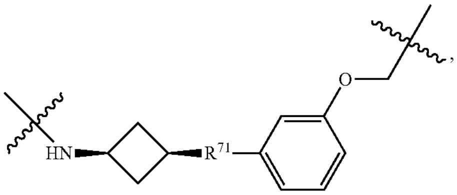
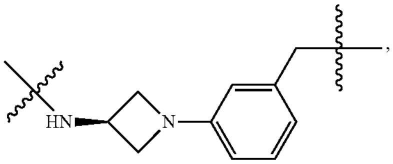
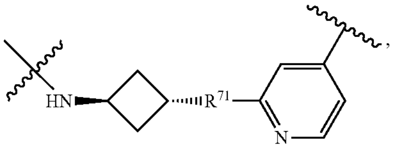
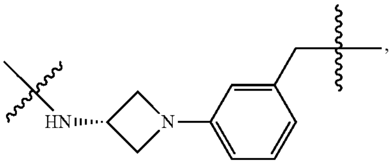
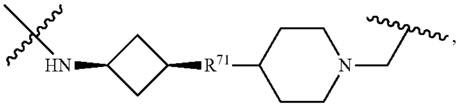
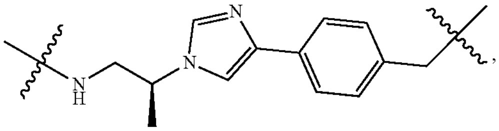
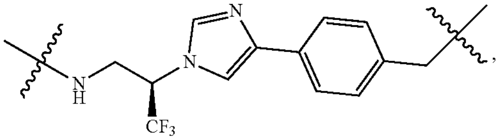
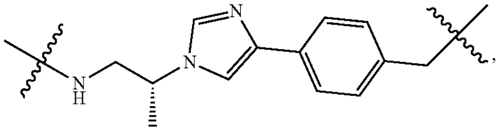
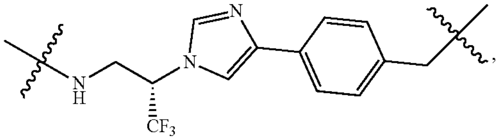
-continued
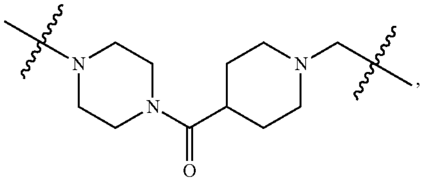
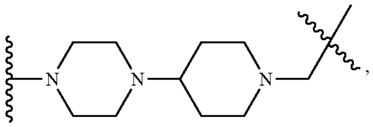
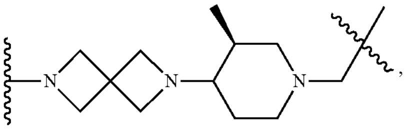
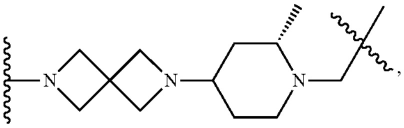
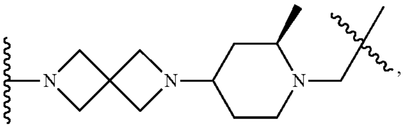
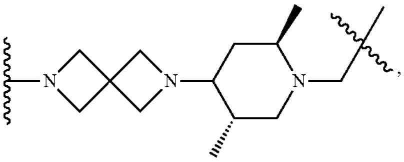
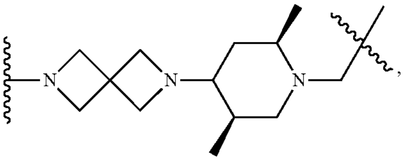
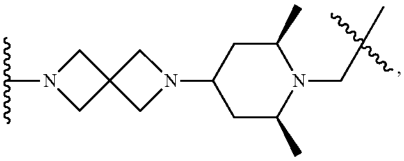
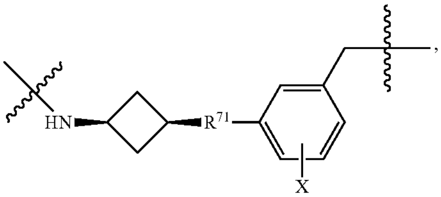
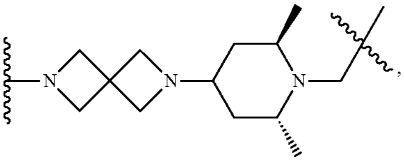
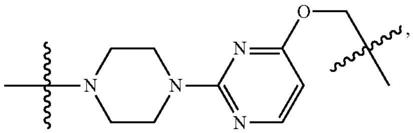

-continued
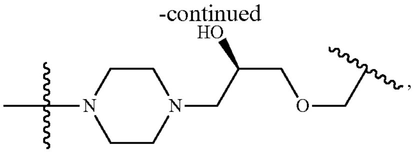
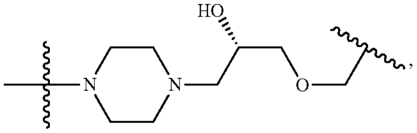
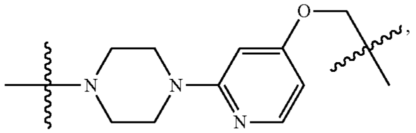
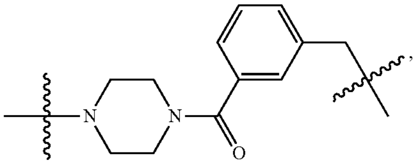
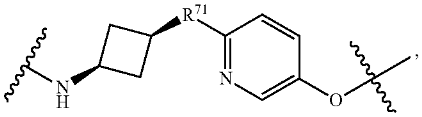
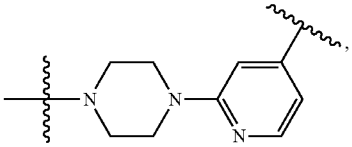
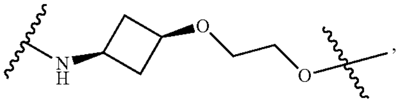
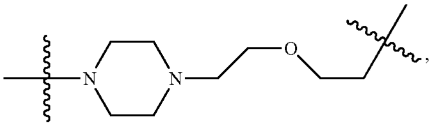
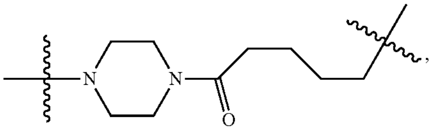
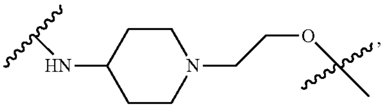
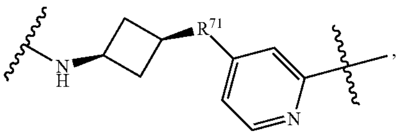
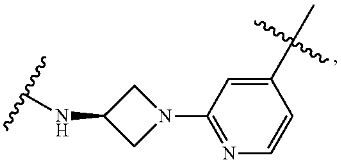
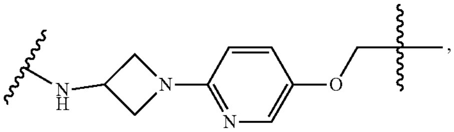
-continued
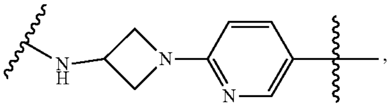
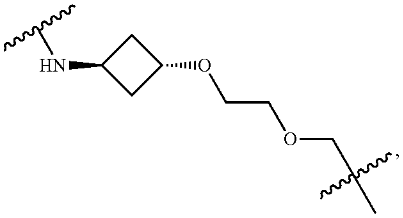
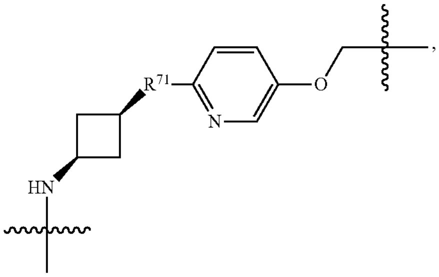
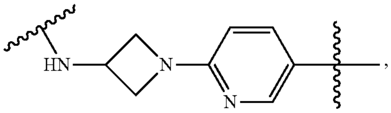
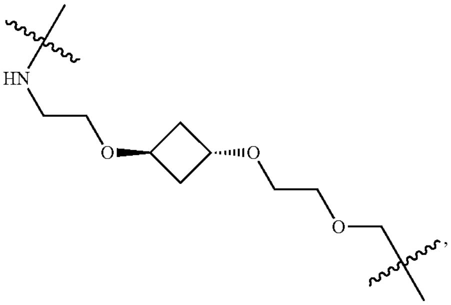
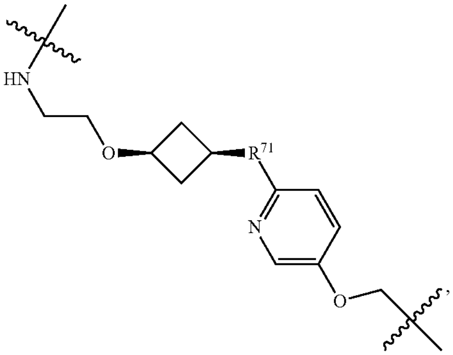
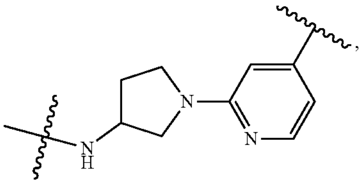

-continued
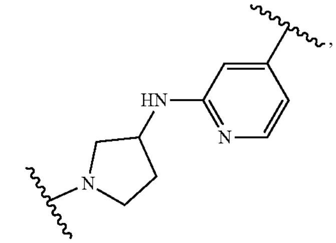
,
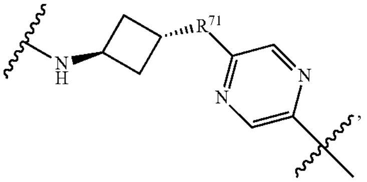
,
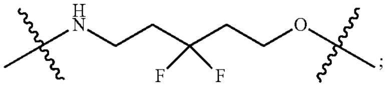
;
wherein $R^{71}$ is —O—, —NH, Nalkyl, heteroaliphatic, aliphatic, or —NMe.
In additional embodiments Linker is selected from:
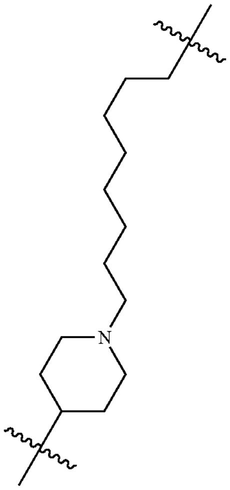
,
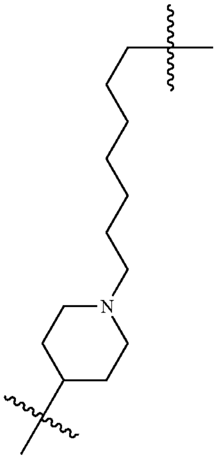
,
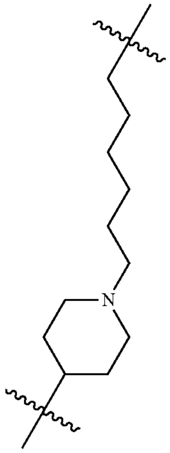
,
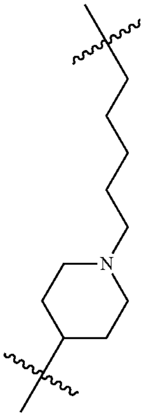
,
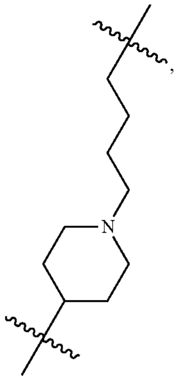
,
-continued
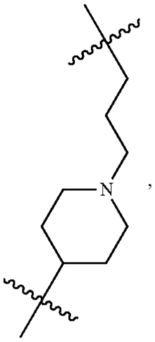
,
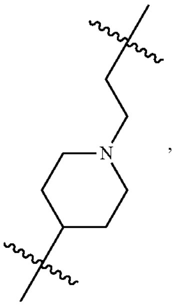
,
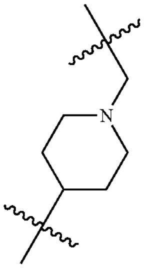
,
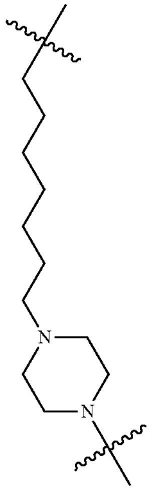
,
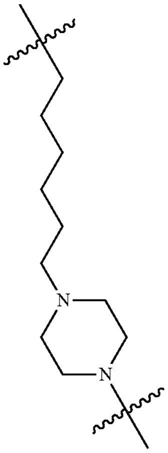
,
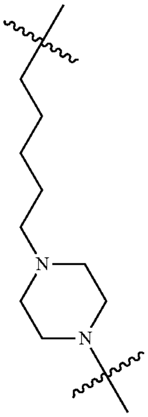
,
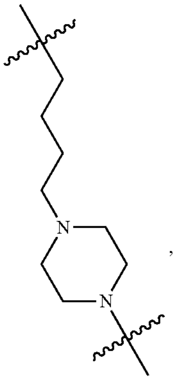
,
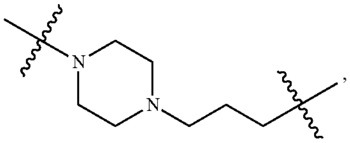
,
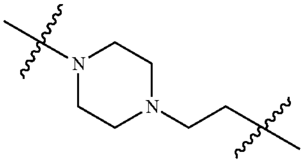
,
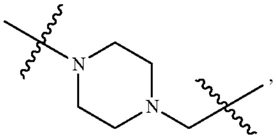
, -continued
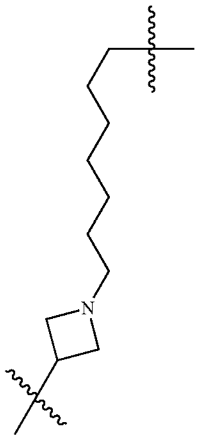,
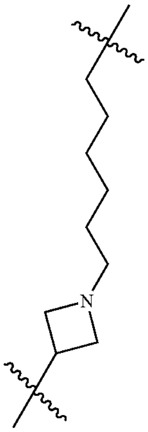,
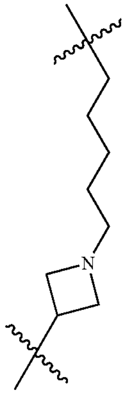,
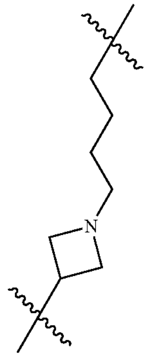,
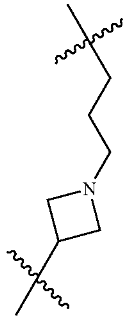,
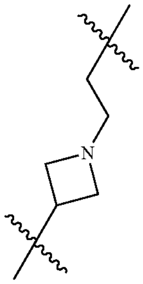,
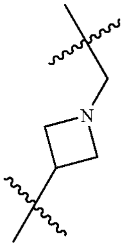,
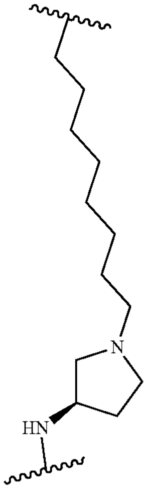,
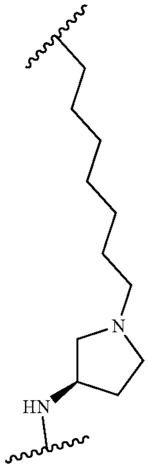,
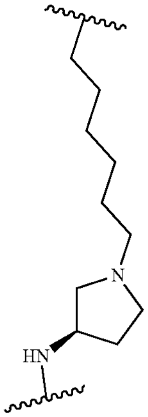,
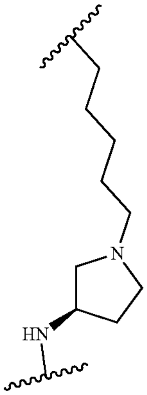,
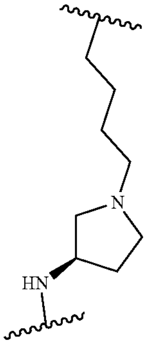,
-continued
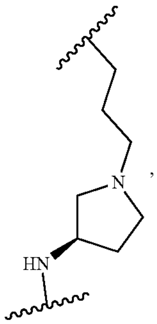,
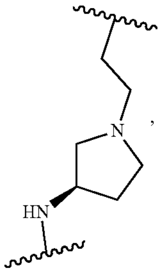,
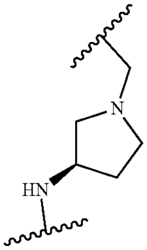,
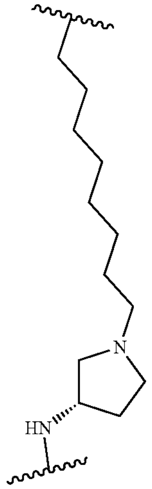,
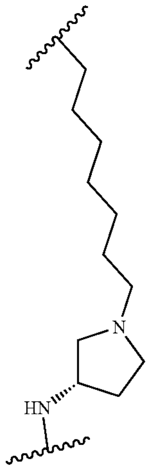,
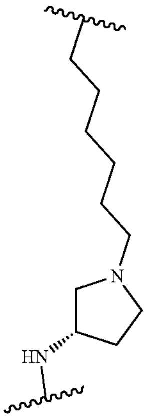,
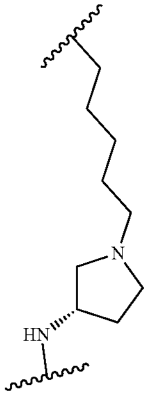,
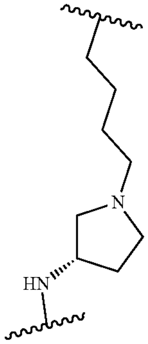,
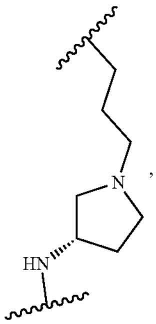,
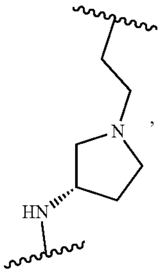, and
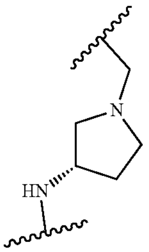.

In additional embodiments, Linker is selected from:
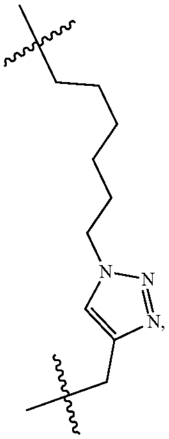
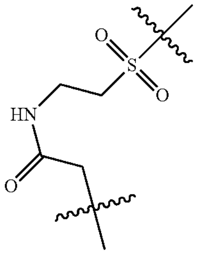
,
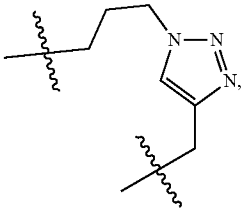
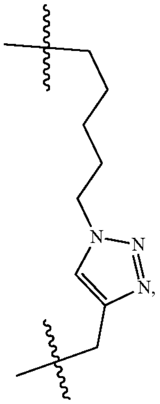
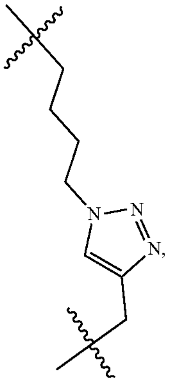
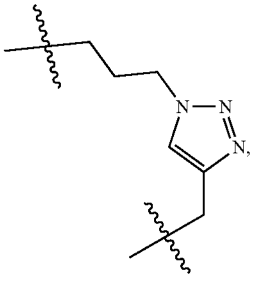
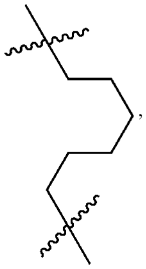
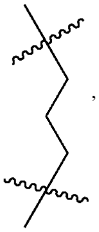
,
-continued
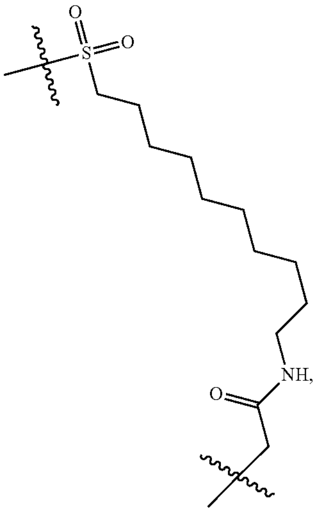
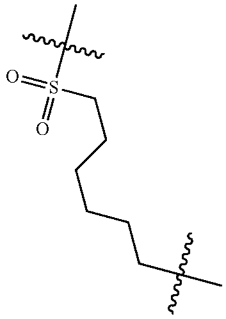
,
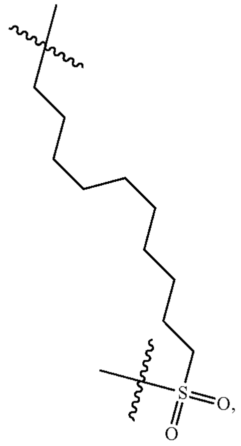
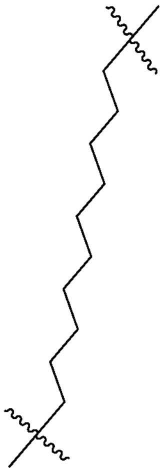
,
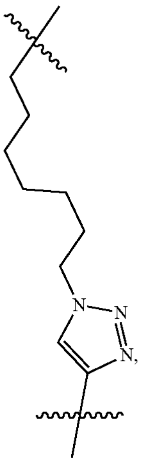
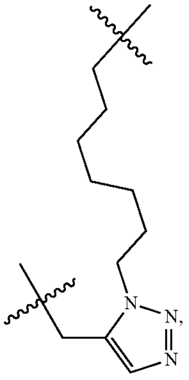
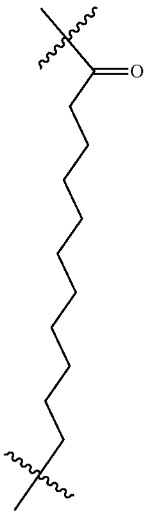
, -continued
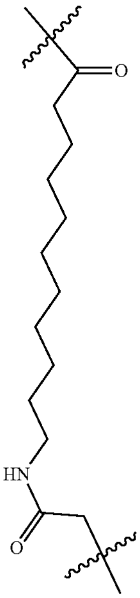
,
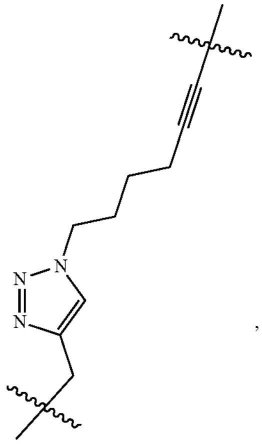
,
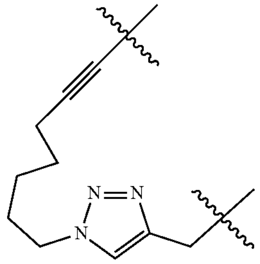
,
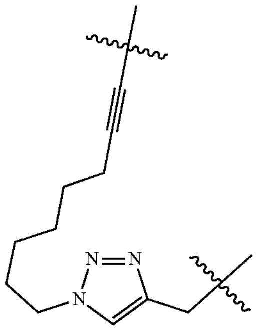
,
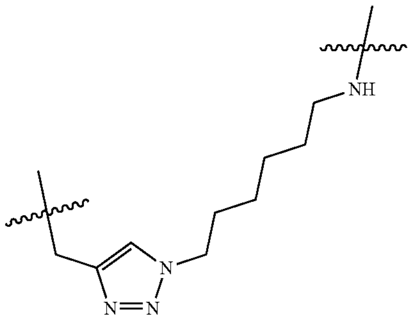
,
-continued
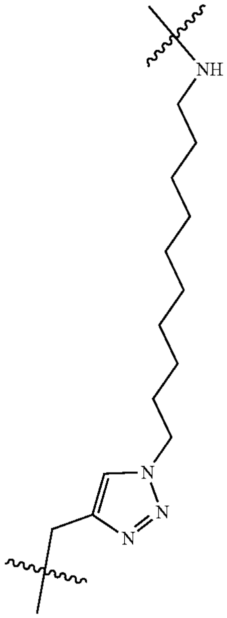
,
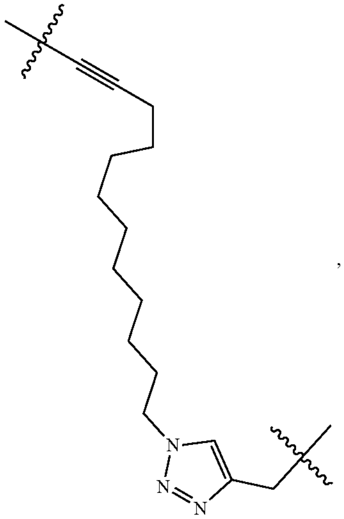
,
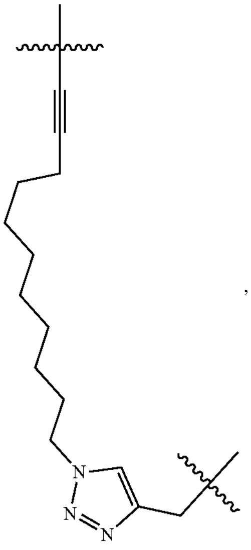
,
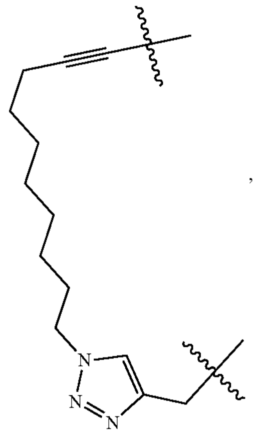
,

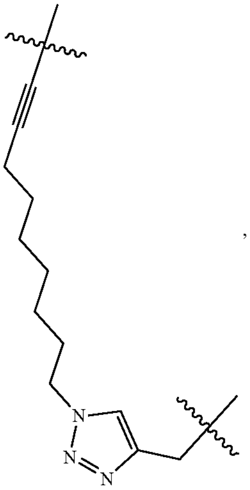
,
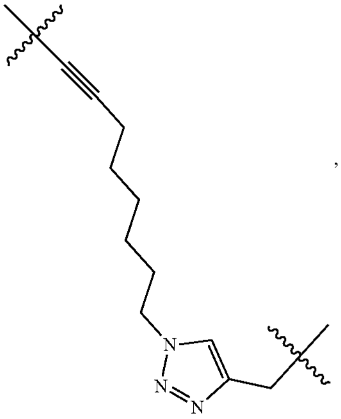
,
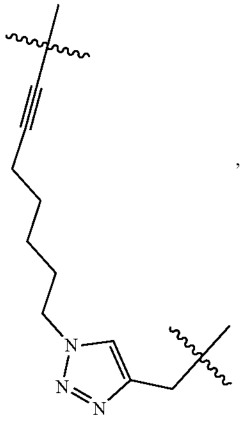
,
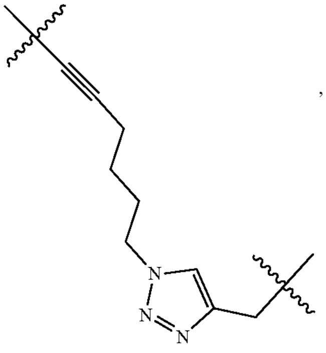
,
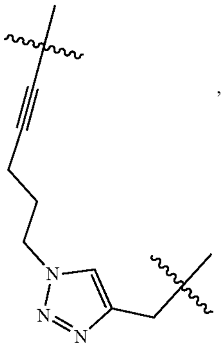
,
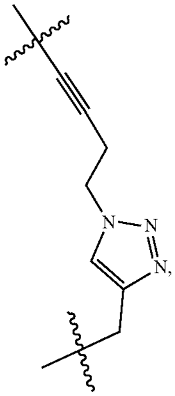
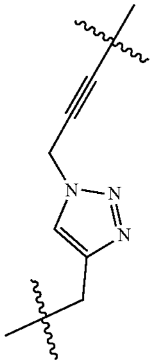
,
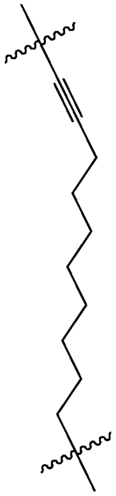
,
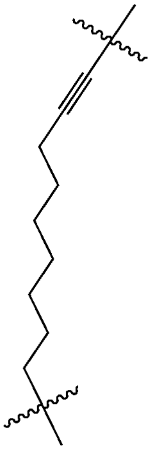
,
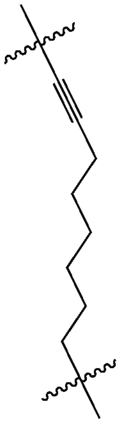
,
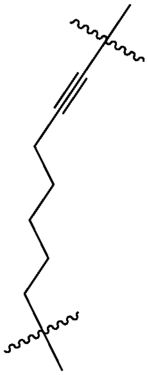
,
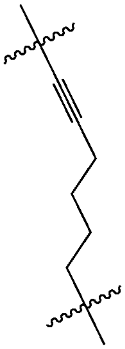
,
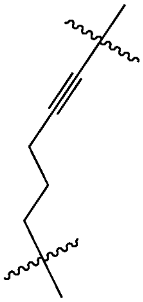
,
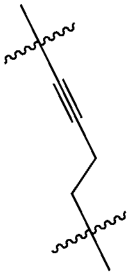
,
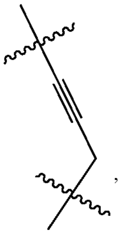
,
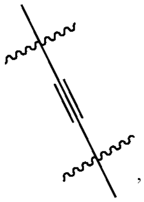
, -continued
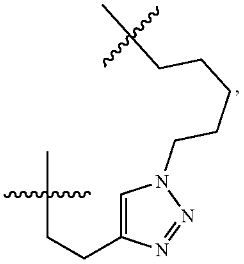
,
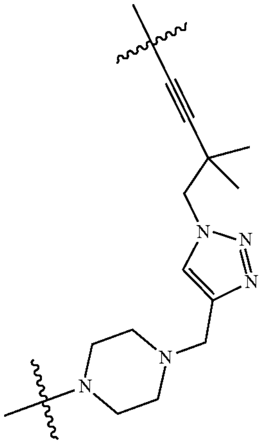
,
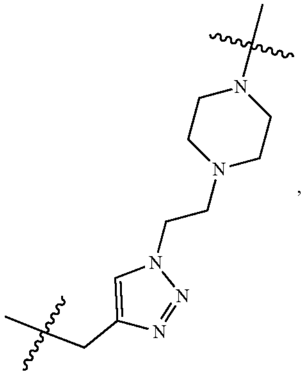
,
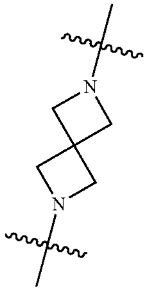
,
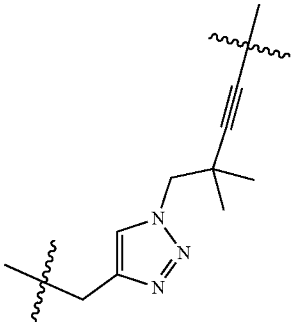
,
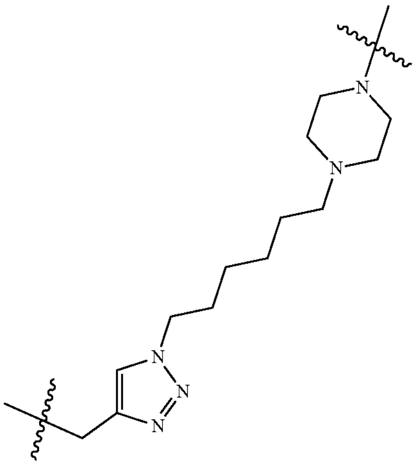
,
-continued
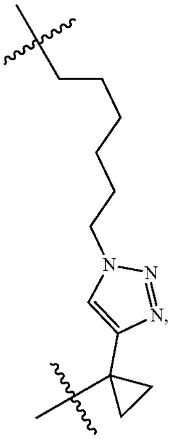
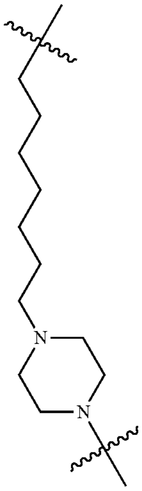
,
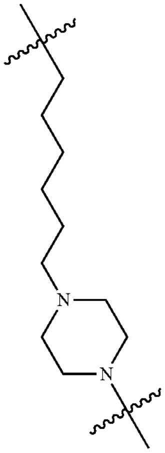
,
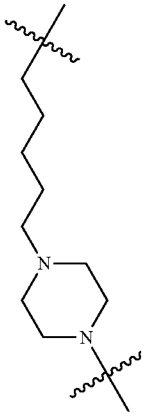
,
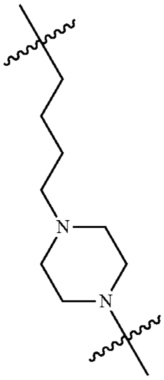
,
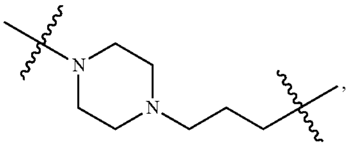
,
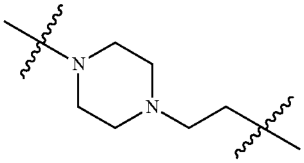
,
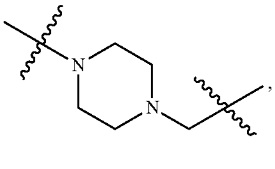
,
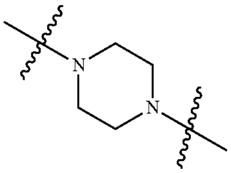
, -continued
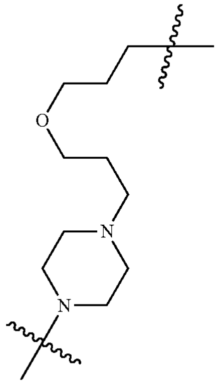
,
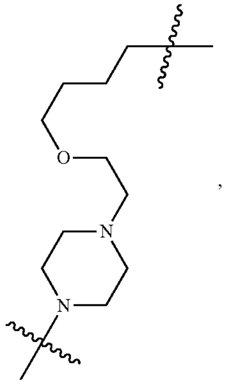
,
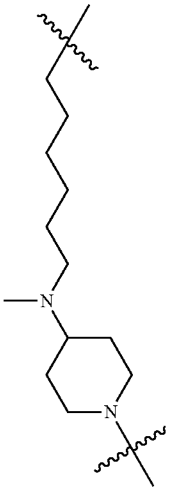
,
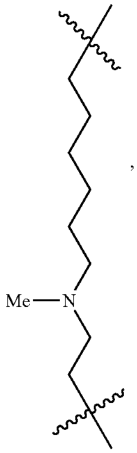
,
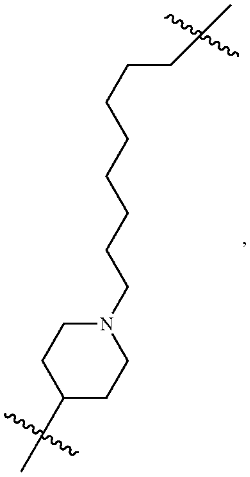
,
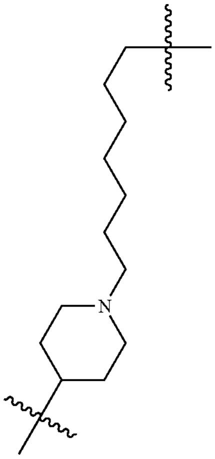
,
-continued
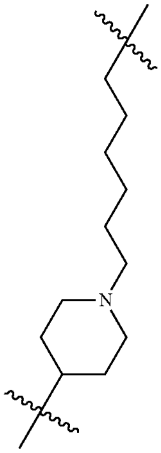
,
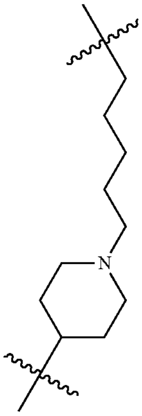
,
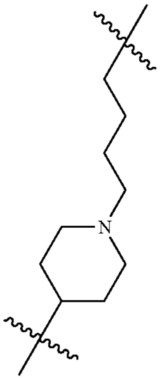
,
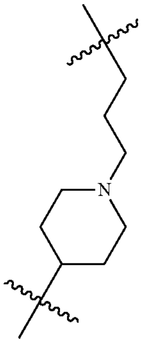
,
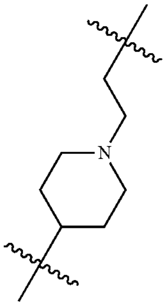
,
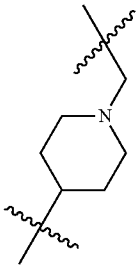
,
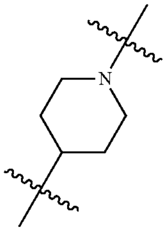
,
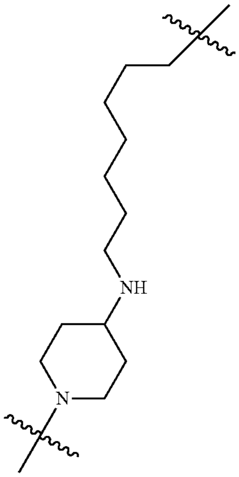
,
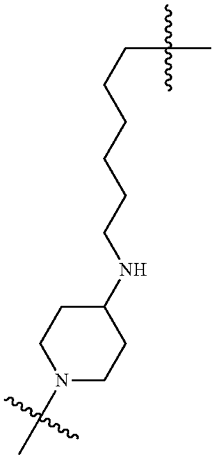
,
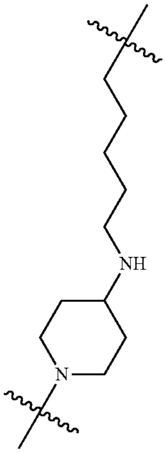
, -continued
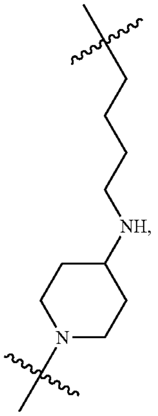
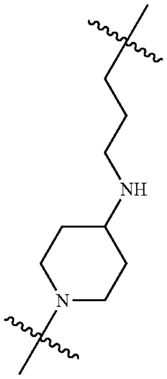
,
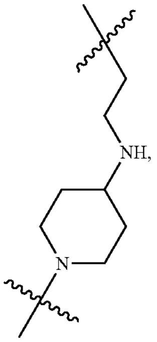
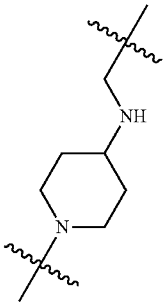
,
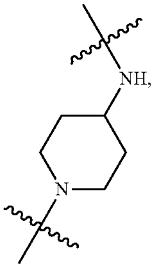
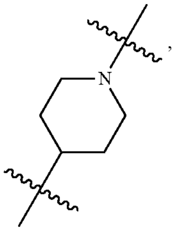
,
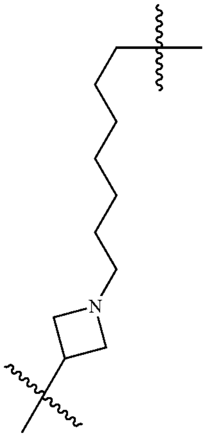
,
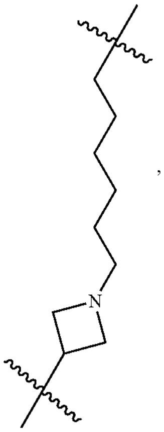
,
-continued
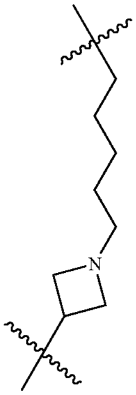
,
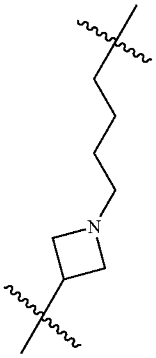
,
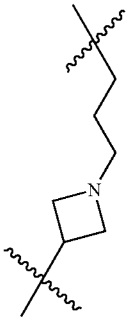
,
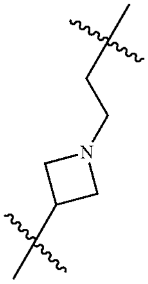
,
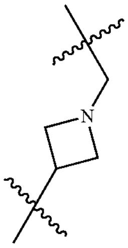
,
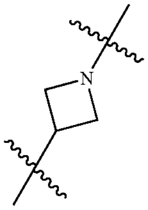
,
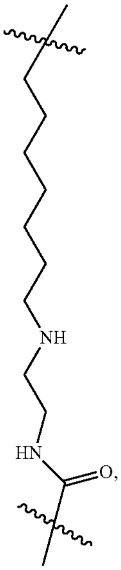
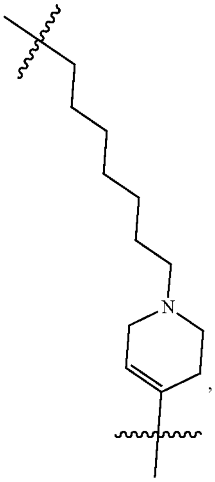
, -continued
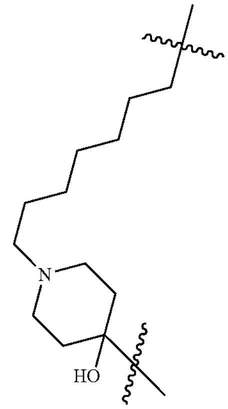
,
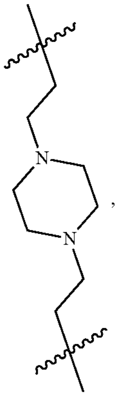
,
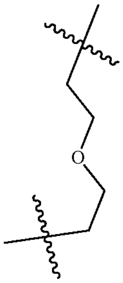
,
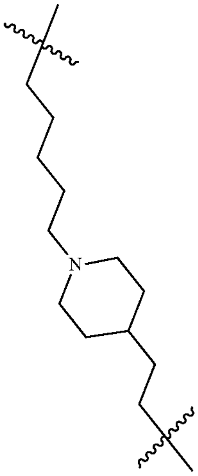
,
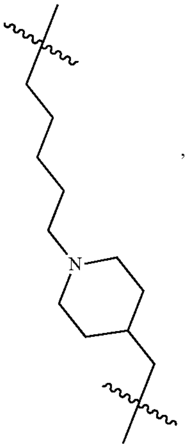
,
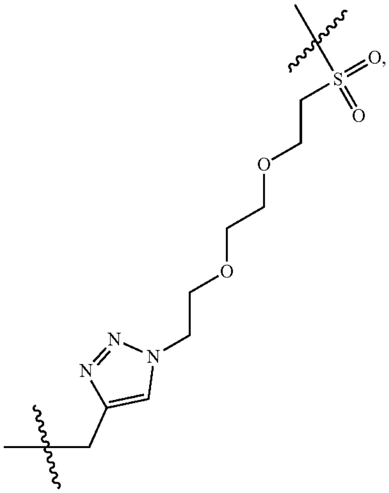
-continued
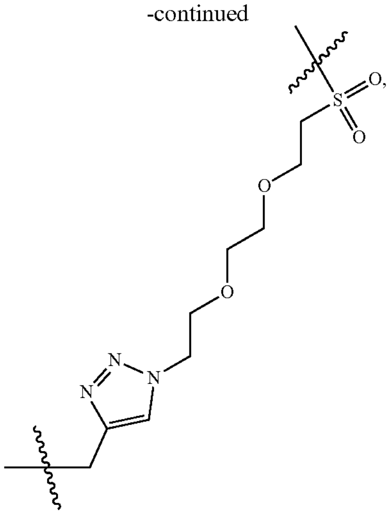
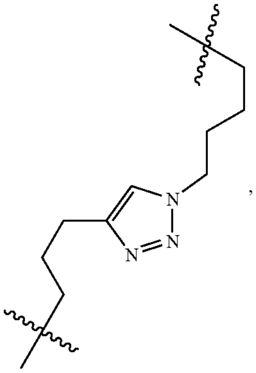
,
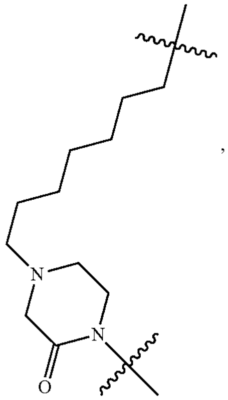
,
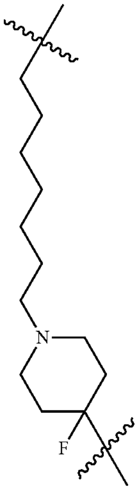
.

In additional embodiments, Linker is selected from:
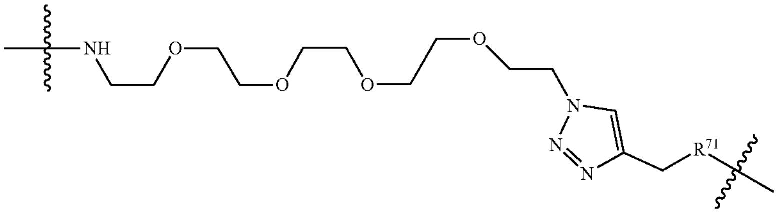
,
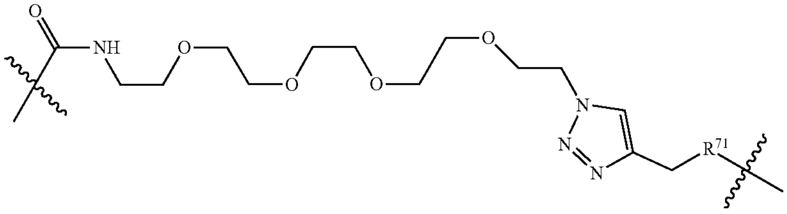
,
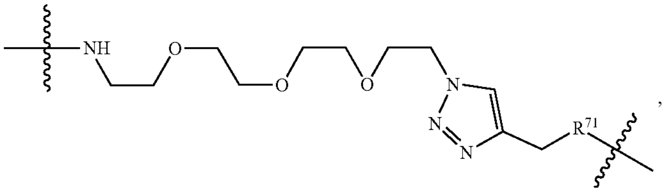
,
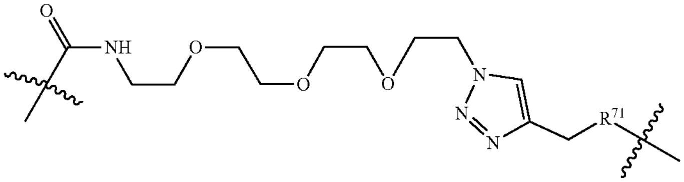
,
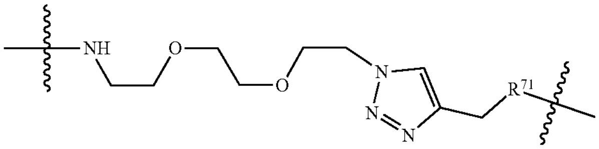
,
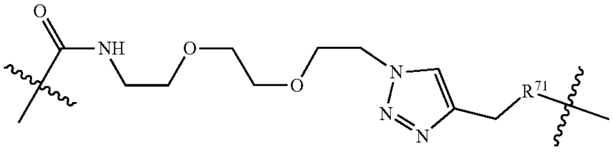
,
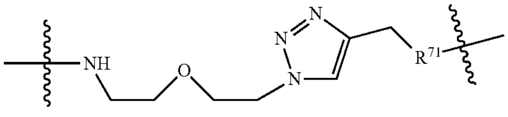
, and
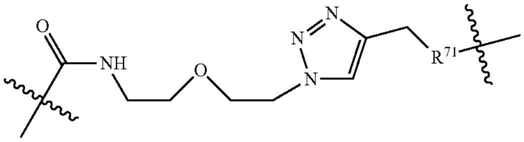
,
In additional embodiments, Linker is selected from:
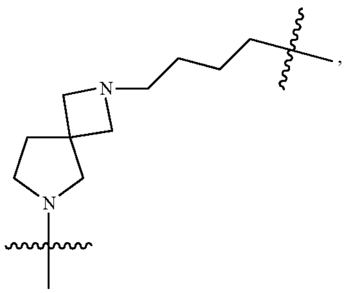
,
-continued
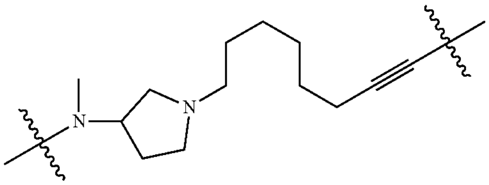
, -continued
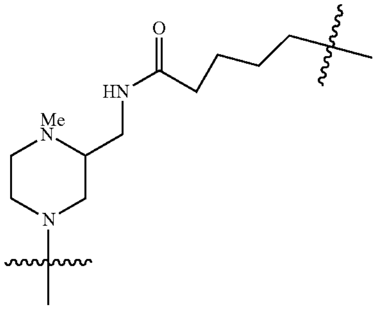
,
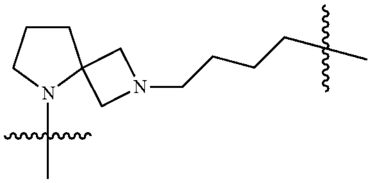
,
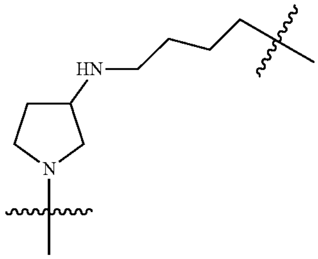
,
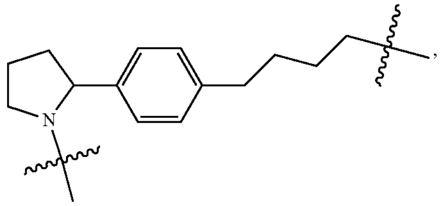
,
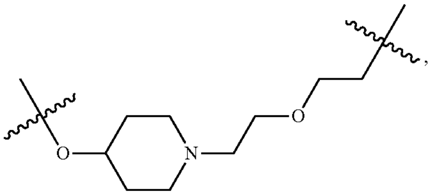
,
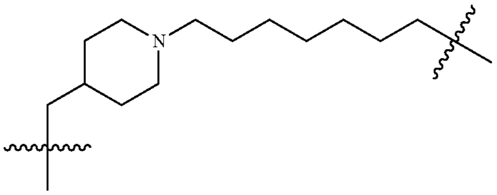
,
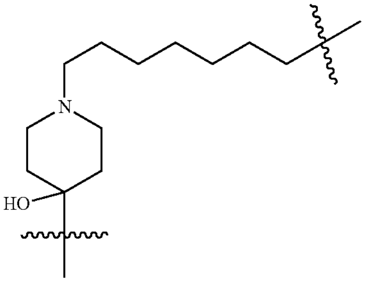
,
-continued
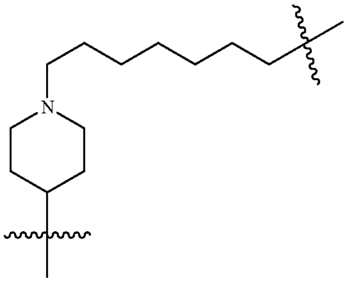
,
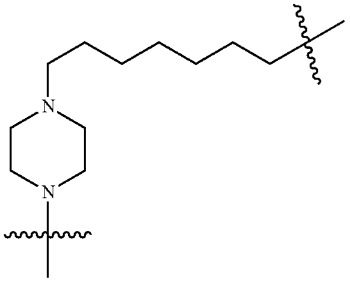
, and
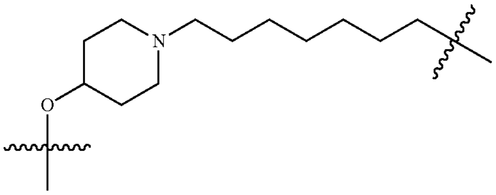
.
In additional embodiments, Linker is selected from:
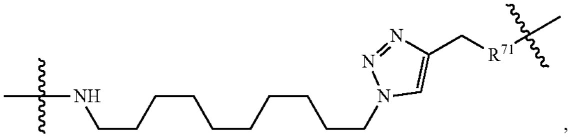
,
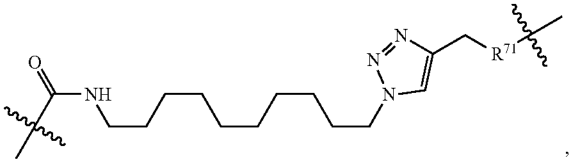
,
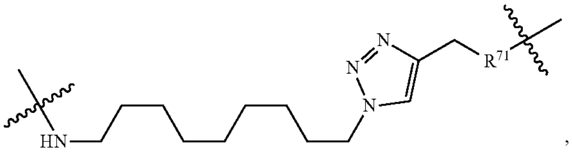
,
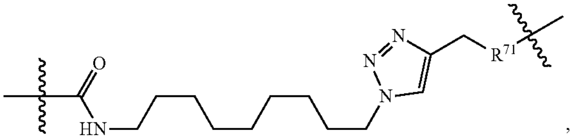
,
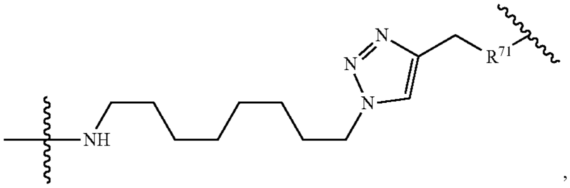
, -continued
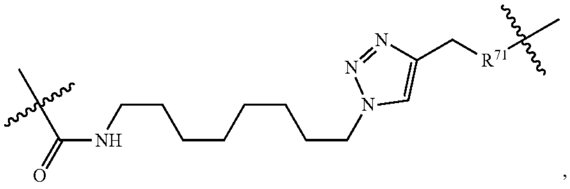
,
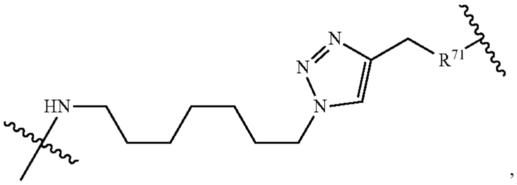
,
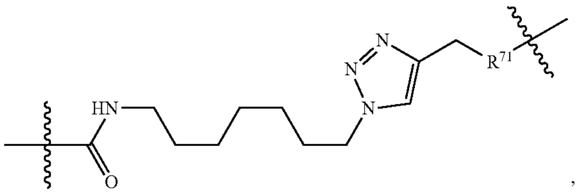
,
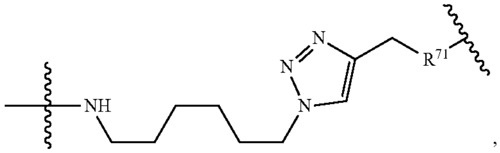
,
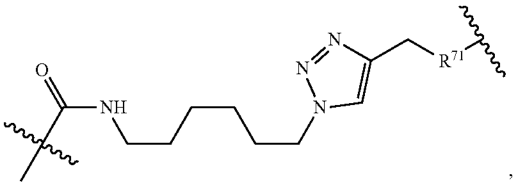
,
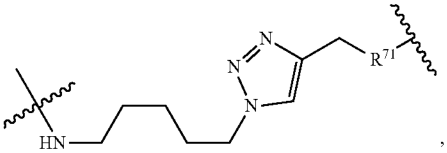
,
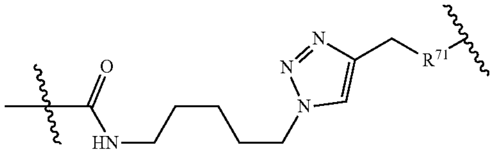
,
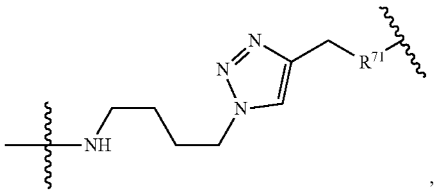
, and
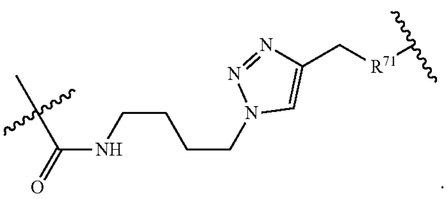
.
In additional embodiments, Linker is selected from:
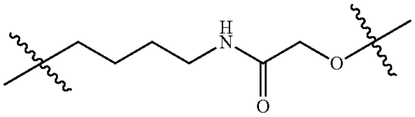
,
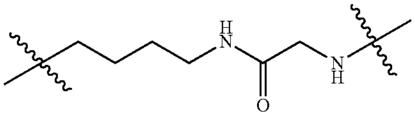
,
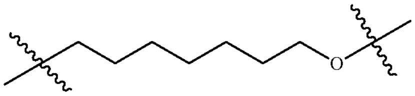
,
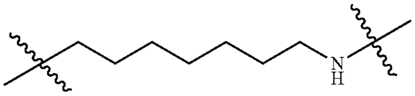
,
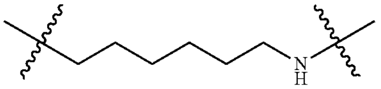
,
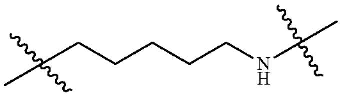
,
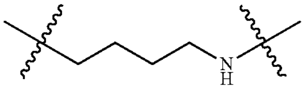
,
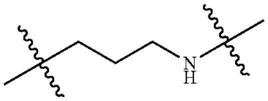
,
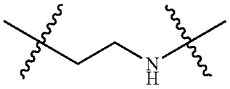
,
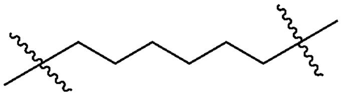
,
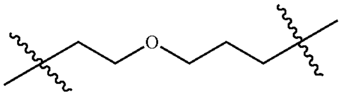
,
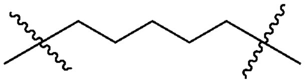
,
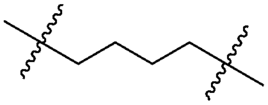
,
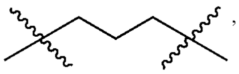
, and
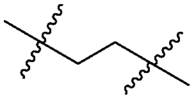
.
In additional embodiments, Linker is selected from:
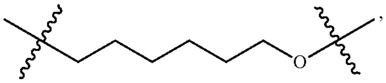
,
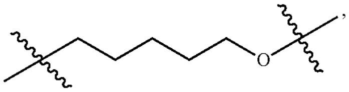
,
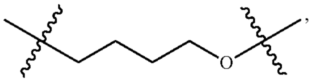
, -continued
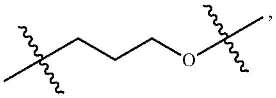
, and
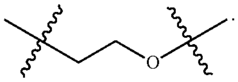
.
In certain embodiments, Linker is selected from:
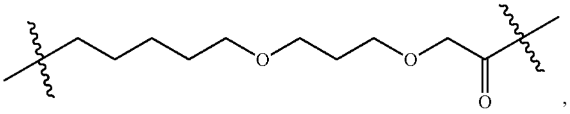
,
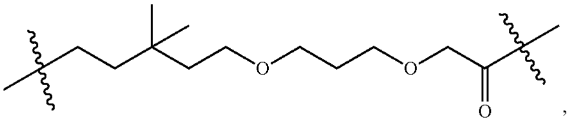
,
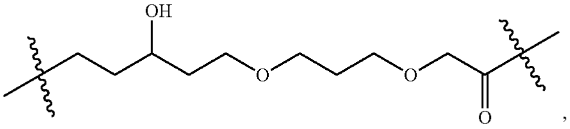
,
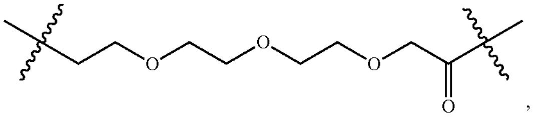
,
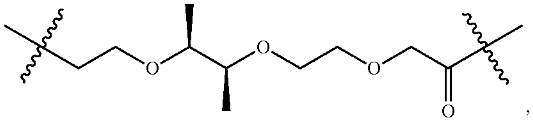
,
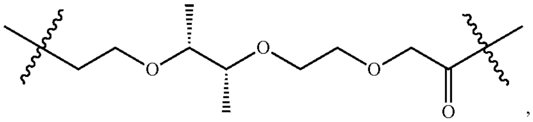
,
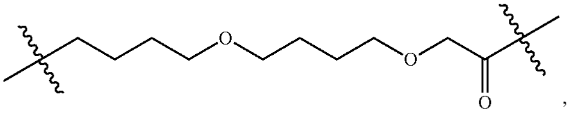
,
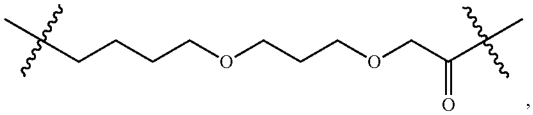
,
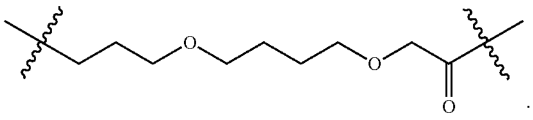
.
In certain embodiments Linker is selected from:
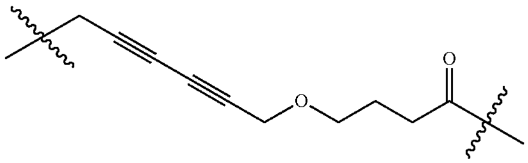
,
-continued
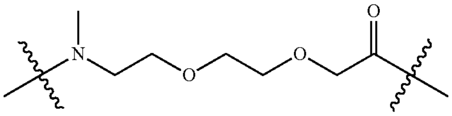
,
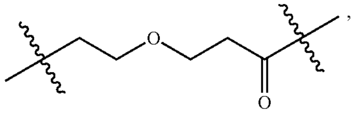
,
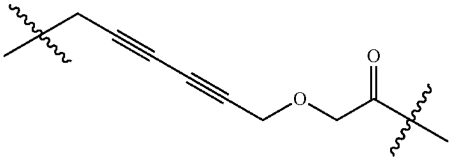
,
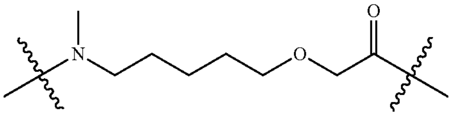
,
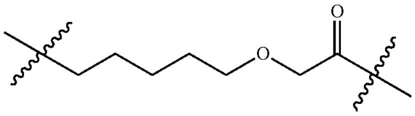
,
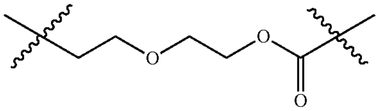
,
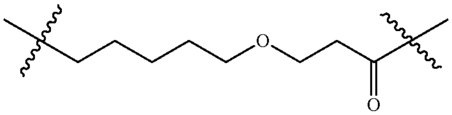
,
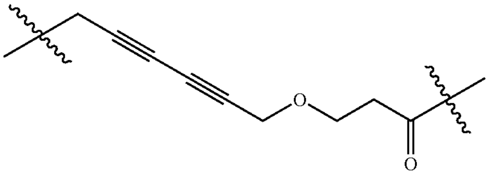
,
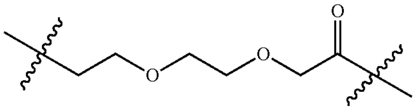
,
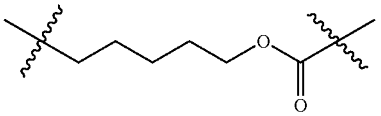
,
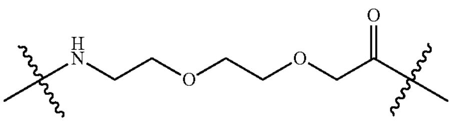
,
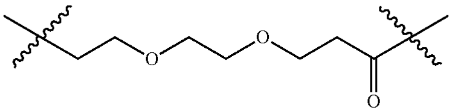
,
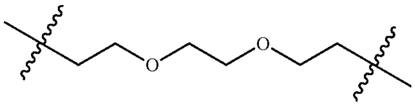
,
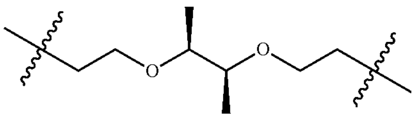
,

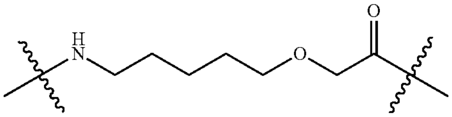
,
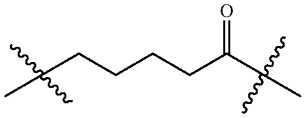
,
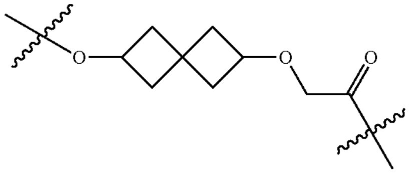
,
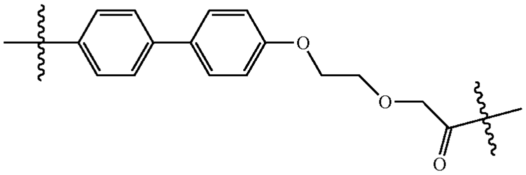
,
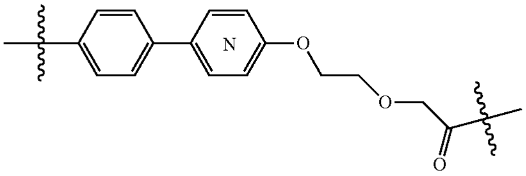
,
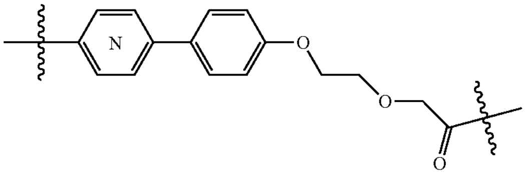
,
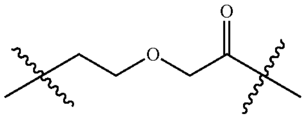
,
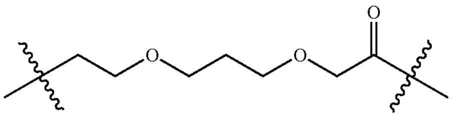
,
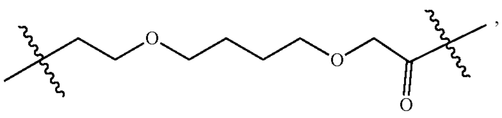
,
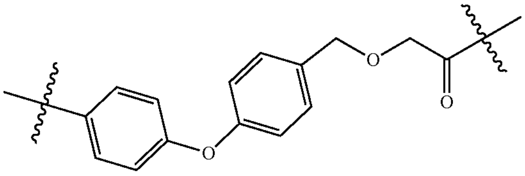
,
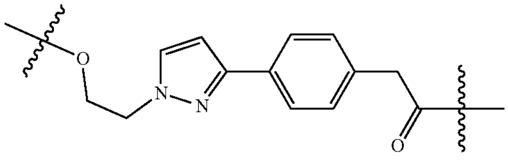
.
In the above structures
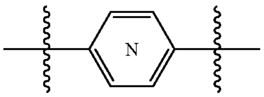
represents
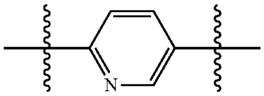
and
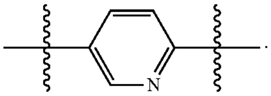
.
In certain embodiments, Linker can be a 4-24 carbon atom linear chains, wherein one or more the carbon atoms in the linear chain can be replaced or substituted with oxygen, nitrogen, amide, fluorinated carbon, etc., such as the following:
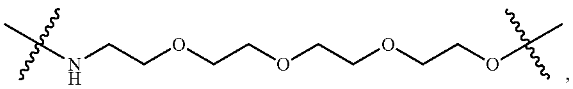
,
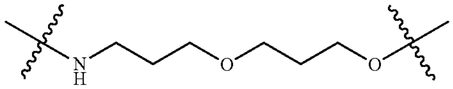
,
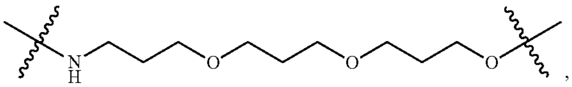
,
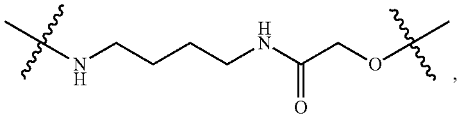
,
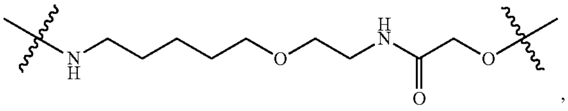
,
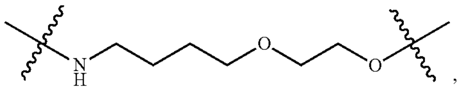
,
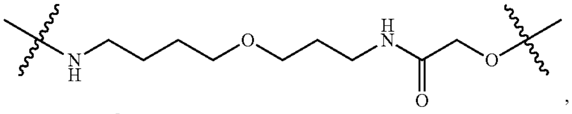
,
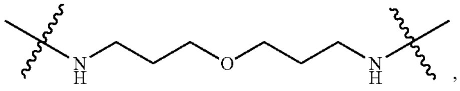
,
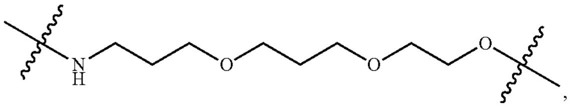
,
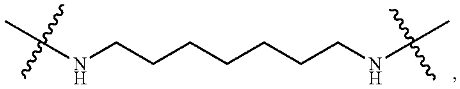
,
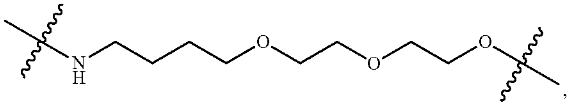
, -continued
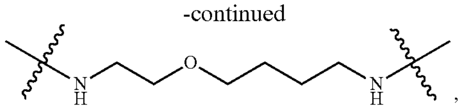,
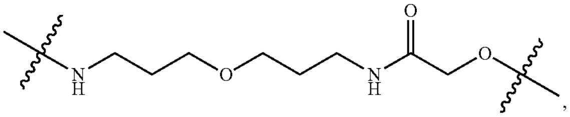,
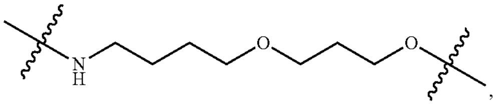,
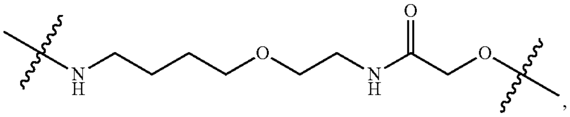,
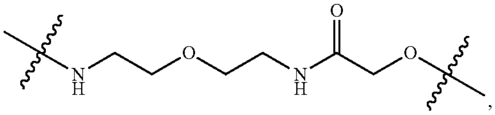,
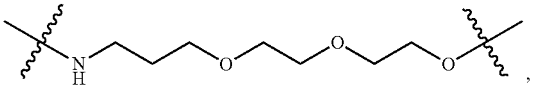,
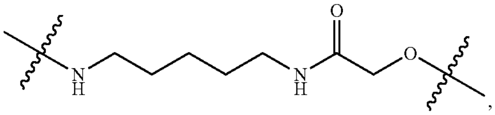,
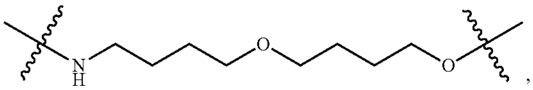,
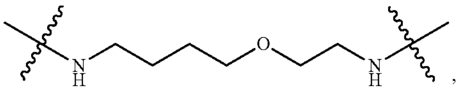,
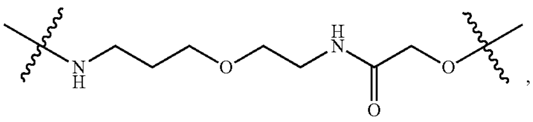,
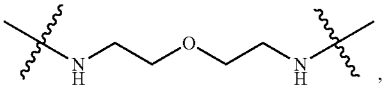,
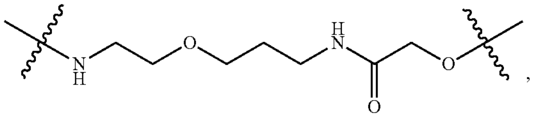,
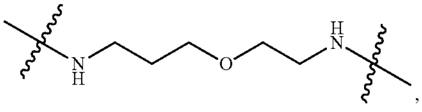,
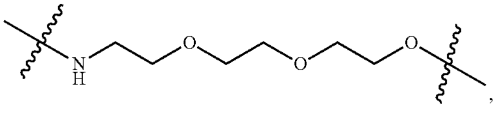,
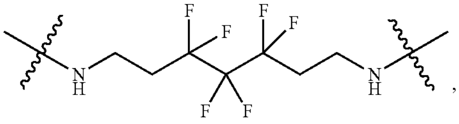,
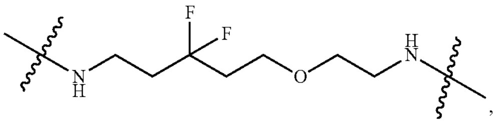,
-continued
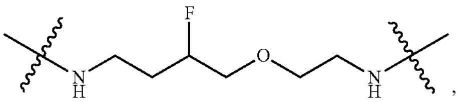,
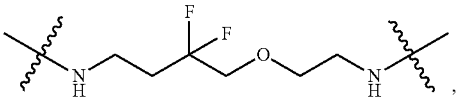,
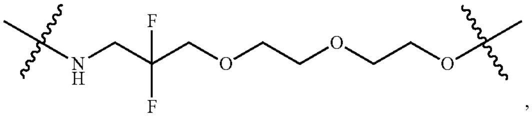,
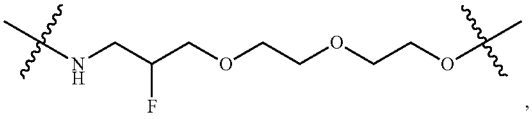,
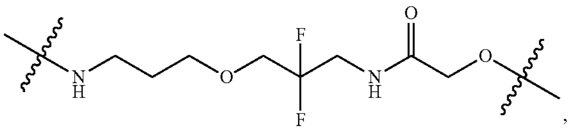,
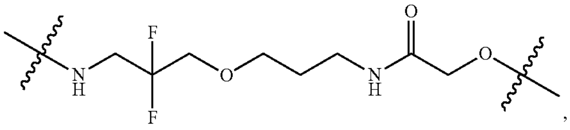,
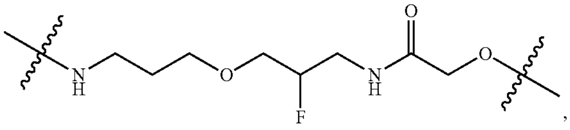,
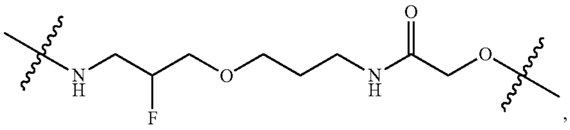,
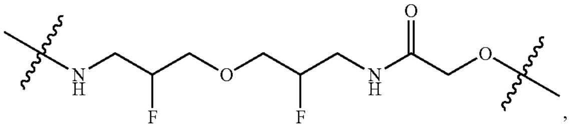,
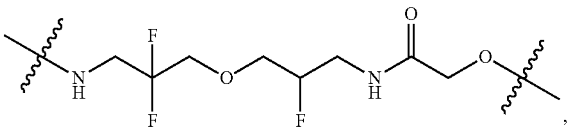,
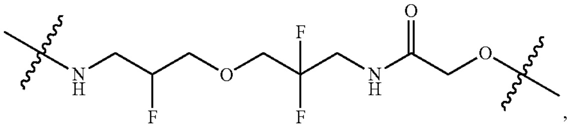,
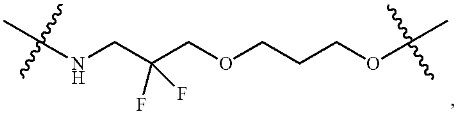,
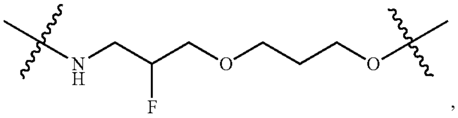,
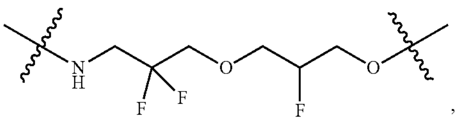, -continued

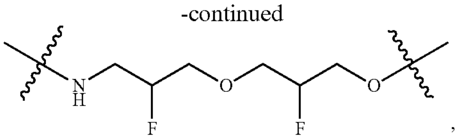

,

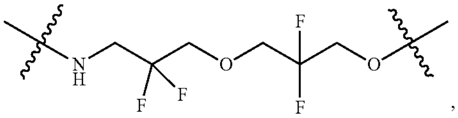

,

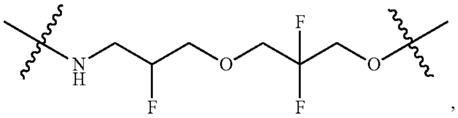

,

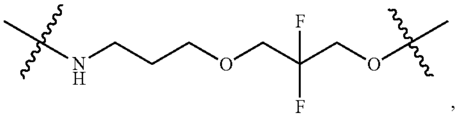

,

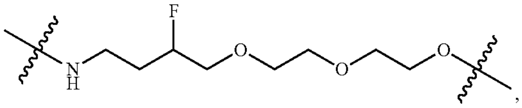

, and

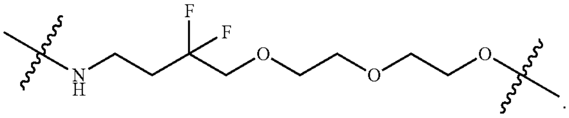

.

In certain embodiments, Linker can be a nonlinear chain, and can be, or include, aliphatic or aromatic or heteroaromatic cyclic moieties.

In certain embodiments, Linker may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, Linker may have 1, 2, 3, 4, 5, 6, 7, 8, 9, 10, 11, 12, 13, 14, or 15 fluorine substituents. In another embodiment Linker is perfluorinated. In yet another embodiment Linker is a partially or fully fluorinated poly ether. Nonlimiting examples of fluorinated Linker moieties include:

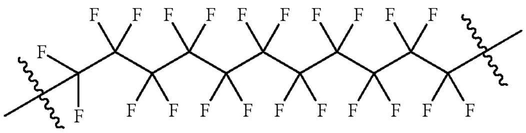

,

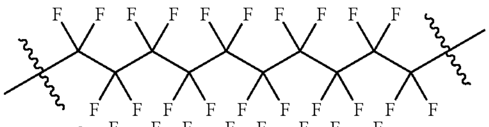

,

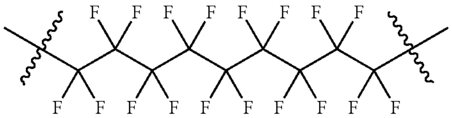

,

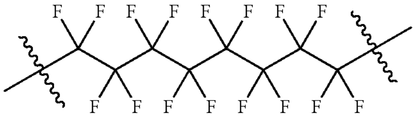

,

-continued

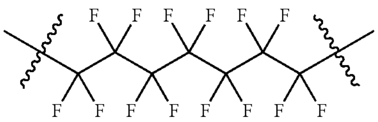

,

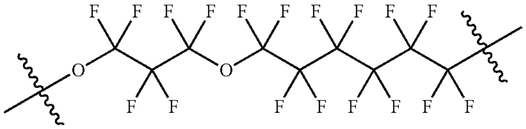

,

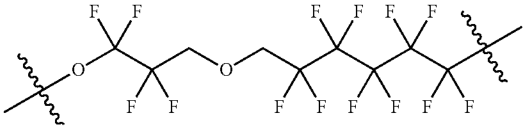

,

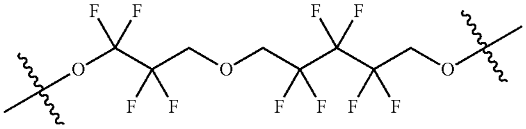

,

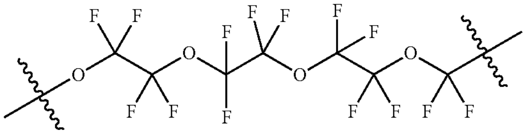

,

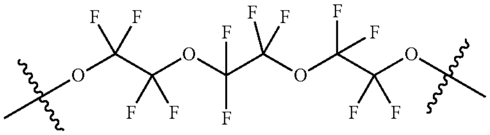

,

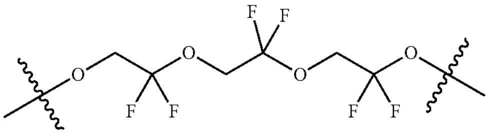

,

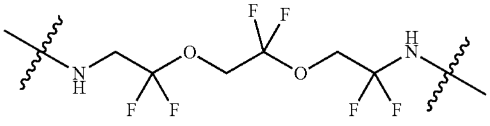

, and

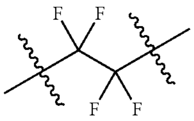

.

Non-limiting examples of moieties of $R^{20}$, $R^{21}$, $R^{22}$, $R^{23}$, and $R^{24}$ include:

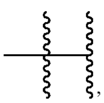

,

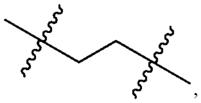

,

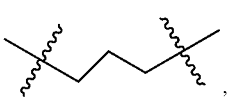

,

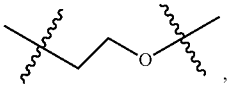

,

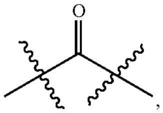

,

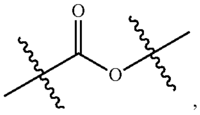

,

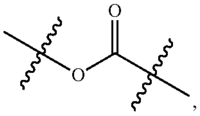

,

-continued
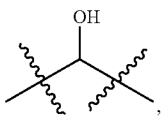, 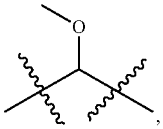, 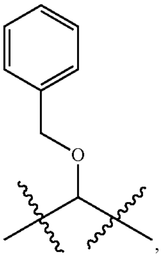,
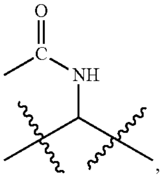, 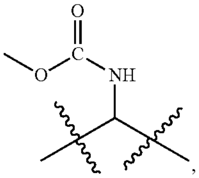, 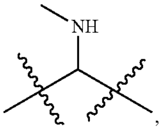,
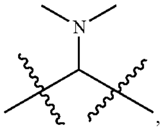, 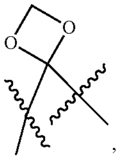, 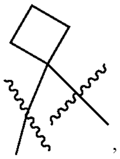,
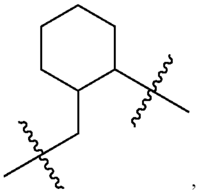, 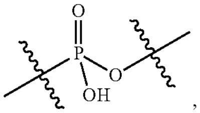, and
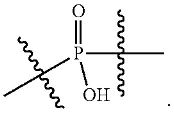.
Additional non-limiting examples of moieties of $R^{20}$, $R^{21}$, $R^{22}$, $R^{23}$, and $R^{24}$ include:
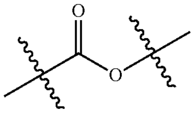, 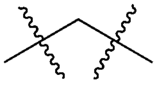, 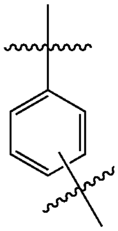,
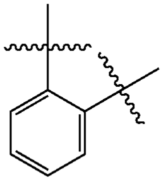, 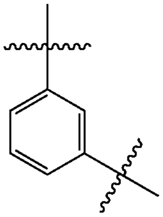, 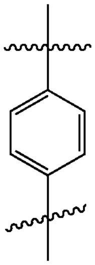,
-continued
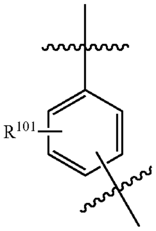, 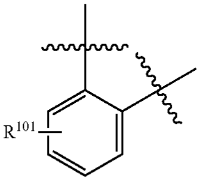,
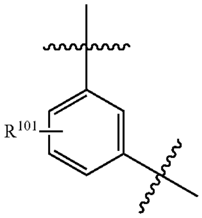, 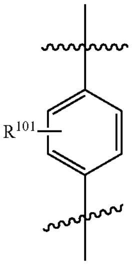,
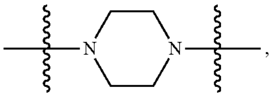, 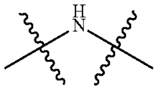,
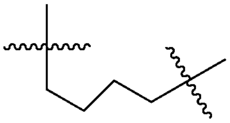, 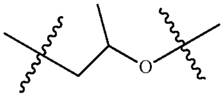,
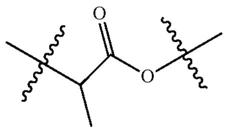, 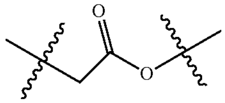,
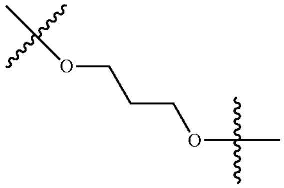,
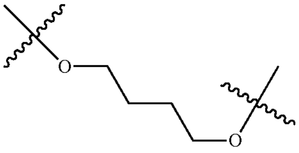,
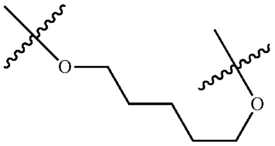, 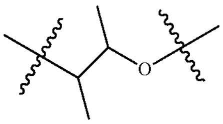,
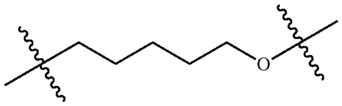,
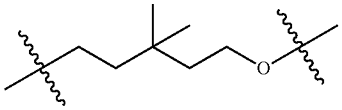,
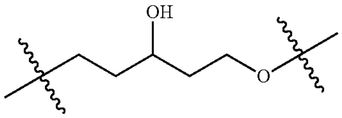, -continued
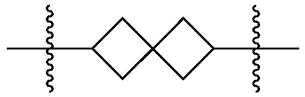
,
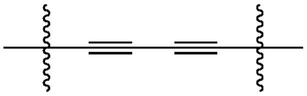
,
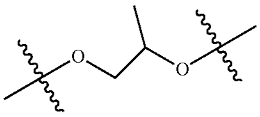
,
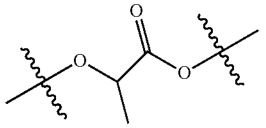
,
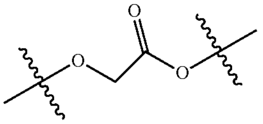
,
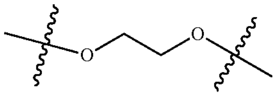
, and
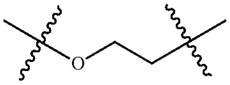
.
Additional non-limiting examples of moieties of $R^{20}$, $R^{21}$, $R^{22}$, $R^{23}$ and $R^{24}$ include:
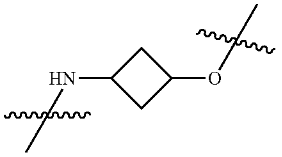
,
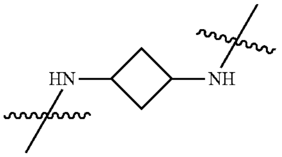
,
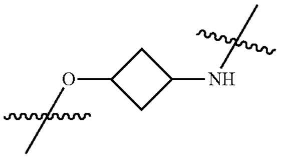
,
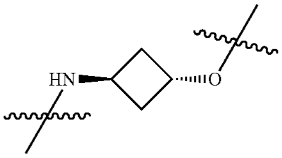
,
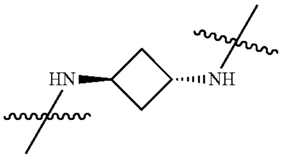
,
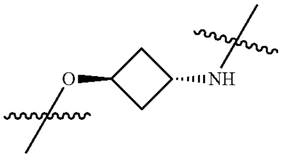
,
-continued
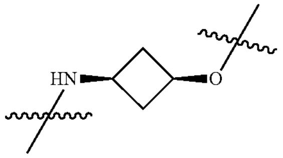
,
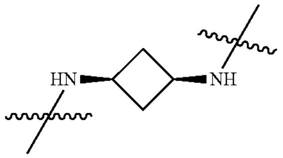
,
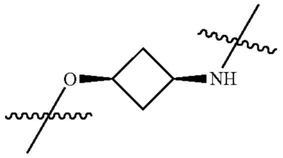
,
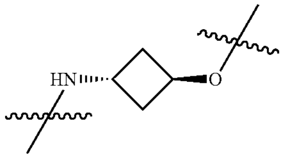
,
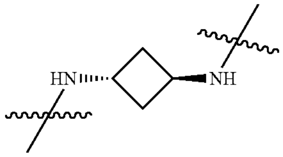
,
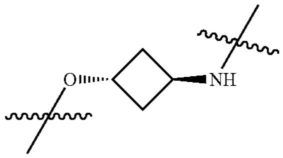
,
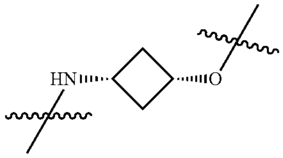
,
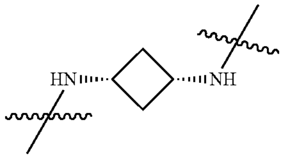
,
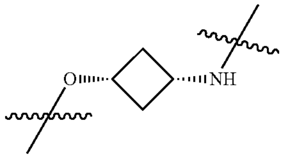
,
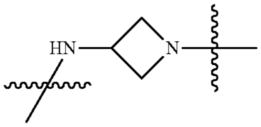
,
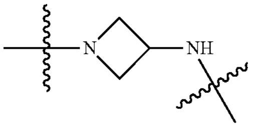
,
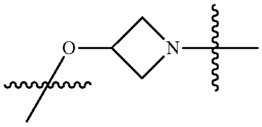
,
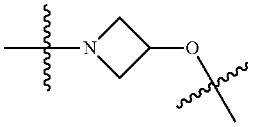
, -continued

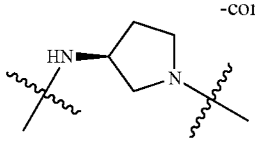, 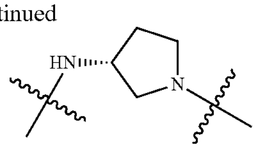,

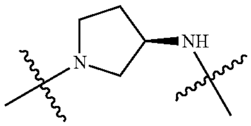, 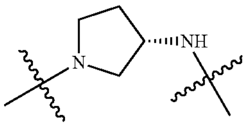,

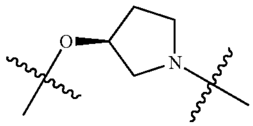, 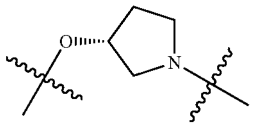,

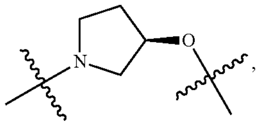, and 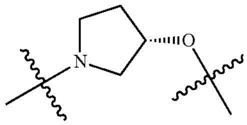.

In certain embodiments, the length can be adjusted as desired or as found necessary for the desired application.

ADDITIONAL EMBODIMENTS OF THE PRESENT INVENTION

All separate embodiments may be combined.

Embodiments of $R^1$

In certain embodiments $R^1$ is hydrogen.

In certain embodiments $R^1$ is alkyl.

In certain embodiments $R^1$ is cycloalkyl.

In certain embodiments $R^1$ is methyl.

In certain embodiments $R^1$ is ethyl.

In certain embodiments $R^1$ is cyclopropyl.

Embodiments of $R^2$

In certain embodiments $R^2$ is hydrogen.

In certain embodiments $R^2$ is alkyl.

In certain embodiments $R^2$ is cycloalkyl.

In certain embodiments $R^2$ is methyl.

In certain embodiments $R^2$ is ethyl.

In certain embodiments $R^2$ is cyclopropyl.

In certain embodiments $R^2$ is haloalkyl.

In certain embodiments $R^2$ is $CF_3$.

In certain embodiments $R^1$ and $R^2$ together with the nitrogen atom to which they are attached form heterocycloalkyl optionally substituted with one or two $R^3$.

Embodiments of $R^{2'}$

In certain embodiments $R^{2'}$ is hydrogen.

In certain embodiments $R^{2'}$ is alkyl.

In certain embodiments $R^{2'}$ is cycloalkyl.

In certain embodiments $R^{2'}$ is methyl.

In certain embodiments $R^{2'}$ is ethyl.

In certain embodiments $R^{2'}$ is cyclopropyl.

In certain embodiments $R^{2'}$ is haloalkyl.

In certain embodiments $R^{2'}$ is $CF_3$.

In certain embodiments $R^1$ and $R^{2'}$ together with the carbon atom to which they are attached form cycloalkyl optionally substituted with one or two $R^3$.

Embodiments of $R^3$

In certain embodiments $R^3$ is hydrogen.

In certain embodiments $R^3$ is alkyl.

In certain embodiments $R^3$ is cycloalkyl.

In certain embodiments $R^3$ is methyl.

In certain embodiments $R^3$ is ethyl.

In certain embodiments $R^3$ is cyclopropyl.

In certain embodiments $R^3$ is alkoxy.

In certain embodiments $R^3$ is methoxy.

In certain embodiments $R^3$ is ethoxy.

In certain embodiments $R^3$ is halogen.

In certain embodiments $R^3$ is F.

Embodiments of $R^4$

In certain embodiments $R^4$ is hydrogen.

In certain embodiments $R^4$ is alkyl.

In certain embodiments $R^4$ is cycloalkyl.

In certain embodiments $R^4$ is methyl.

In certain embodiments $R^4$ is ethyl.

In certain embodiments $R^4$ is cyclopropyl.

In certain embodiments $R^4$ is halogen.

In certain embodiments $R^4$ is F.

In certain embodiments $R^4$ is cyano.

Embodiments of $R^5$

In certain embodiments $R^5$ is hydrogen.

In certain embodiments $R^5$ is alkyl.

In certain embodiments $R^5$ is cycloalkyl.

In certain embodiments $R^5$ is methyl.

In certain embodiments $R^5$ is ethyl.

In certain embodiments $R^5$ is cyclopropyl.

In certain embodiments $R^5$ is halogen.

In certain embodiments $R^5$ is F.

In certain embodiments $R^5$ is cyano.

Embodiments of $W^1$ and $W^2$

In certain embodiments $W^1$ is —N—.

In certain embodiments $W^1$ is —CH—.

In certain embodiments $W^2$ is —N—.

In certain embodiments $W^2$ is —CH—.

In certain embodiments $W^2$ is $—CR^{26}—$.

In certain embodiments $W^2$ is $—CCH_3—$.

In certain embodiments $W^2$ is —CF—.

Embodiments of $R^6$ and $R^{26}$

In certain embodiments $R^6$ is hydrogen.

In certain embodiments $R^6$ is alkyl.

In certain embodiments $R^6$ is cycloalkyl.

In certain embodiments $R^6$ is methyl.

In certain embodiments $R^6$ is ethyl.

In certain embodiments $R^6$ is cyclopropyl.

In certain embodiments $R^6$ is halogen.

In certain embodiments $R^6$ is F.

In certain embodiments $R^6$ is hydroxy.

In certain embodiments $R^6$ is amino.

In certain embodiments $R^6$ is dialkylamino.

In certain embodiments $R^6$ is alkoxy.

In certain embodiments $R^6$ is alkoxyalkyl.

In certain embodiments $R^{26}$ is hydrogen.
In certain embodiments $R^{26}$ is alkyl.
In certain embodiments $R^{26}$ is cycloalkyl.
In certain embodiments $R^{26}$ is methyl.
In certain embodiments $R^{26}$ is ethyl.
In certain embodiments $R^{26}$ is cyclopropyl.
In certain embodiments $R^{26}$ is halogen.
In certain embodiments $R^{26}$ is F.
In certain embodiments $R^{26}$ is hydroxy.
In certain embodiments $R^{26}$ is alkoxy.
In certain embodiments $R^{26}$ is alkoxyalkyl.

Embodiments of $R^7$

In certain embodiments $R^7$ is hydrogen.
In certain embodiments $R^7$ is alkyl.
In certain embodiments $R^7$ is cyano.
In certain embodiments $R^7$ is halogen.
In certain embodiments $R^7$ is alkoxy.
In certain embodiments $R^7$ is fluorine.
In certain embodiments $R^7$ is methoxy.
In certain embodiments $R^7$ is ethoxy.
In certain embodiments $R^7$ is methyl
In certain embodiments $R^7$ is ethyl.

Embodiments of $R^8$

In certain embodiments $R^8$ is hydrogen.
In certain embodiments $R^8$ is alkyl.
In certain embodiments $R^8$ is cyano.
In certain embodiments $R^8$ is halogen.
In certain embodiments $R^8$ is alkoxy.
In certain embodiments $R^8$ is fluorine.
In certain embodiments $R^8$ is methoxy.
In certain embodiments $R^8$ is ethoxy.
In certain embodiments $R^8$ is methyl
In certain embodiments $R^8$ is ethyl.

Embodiments of $R^9$

In certain embodiments $R^9$ is hydrogen.
In certain embodiments $R^9$ is alkyl.
In certain embodiments $R^9$ is cyano.
In certain embodiments $R^9$ is halogen.
In certain embodiments $R^9$ is alkoxy.
In certain embodiments $R^9$ is fluorine.
In certain embodiments $R^9$ is methoxy.
In certain embodiments $R^9$ is ethoxy.
In certain embodiments $R^9$ is methyl
In certain embodiments $R^9$ is ethyl.

Embodiments of $R^{17}$

In certain embodiments $R^{17}$ is hydrogen.
In certain embodiments $R^{17}$ is alkyl.
In certain embodiments $R^{17}$ is cyano.
In certain embodiments $R^{17}$ is halogen.
In certain embodiments $R^{17}$ is alkoxy.
In certain embodiments $R^{17}$ is fluorine.
In certain embodiments $R^{17}$ is methoxy.
In certain embodiments $R^{17}$ is ethoxy.
In certain embodiments $R^{17}$ is methyl
In certain embodiments $R^{17}$ is ethyl.

In certain embodiments $R^{17}$ is hydroxy.
In certain embodiments $R^{17}$ is cycloalkyl.
In certain embodiments $R^{17}$ is cyclopropyl.

Embodiments of $R^{18}$

In certain embodiments $R^{18}$ is hydrogen.
In certain embodiments $R^{18}$ is alkyl.
In certain embodiments $R^{18}$ is cyano.
In certain embodiments $R^{18}$ is halogen.
In certain embodiments $R^{18}$ is alkoxy.
In certain embodiments $R^{18}$ is fluorine.
In certain embodiments $R^{18}$ is methoxy.
In certain embodiments $R^{18}$ is ethoxy.
In certain embodiments $R^{18}$ is methyl
In certain embodiments $R^{18}$ is ethyl.
In certain embodiments $R^{18}$ is hydroxy.
In certain embodiments $R^{18}$ is cycloalkyl.
In certain embodiments $R^{18}$ is cyclopropyl.

Embodiments of $R^{19}$

In certain embodiments $R^{19}$ is hydrogen.
In certain embodiments $R^{19}$ is alkyl.
In certain embodiments $R^{19}$ is cyano.
In certain embodiments $R^{19}$ is halogen.
In certain embodiments $R^{19}$ is alkoxy.
In certain embodiments $R^{19}$ is fluorine.
In certain embodiments $R^{19}$ is methoxy.
In certain embodiments $R^{19}$ is ethoxy.
In certain embodiments $R^{19}$ is methyl
In certain embodiments $R^{19}$ is ethyl.
In certain embodiments $R^{19}$ is hydroxy.
In certain embodiments $R^{19}$ is cycloalkyl.
In certain embodiments $R^{19}$ is cyclopropyl.

Embodiments of $A^1$

In certain embodiments $A^1$ is $NR_2$.
In certain embodiments $A^1$ is $—CHR^{2'}—$.
In certain embodiments $A^1$ is NH.
In certain embodiments $A^1$ is $NCH_3$.
In certain embodiments $A^1$ is $—CH_2—$.

Embodiments of $A^2$ and $A^{22}$

In certain embodiments $A^2$ is —O—.
In certain embodiments $A^2$ is —NH—.
In certain embodiments $A^2$ is —(C═O)—.
In certain embodiments $A^{22}$ is —O—.
In certain embodiments $A^{22}$ is —NH—.

Embodiments of $A^3$ and $A^{23}$

In certain embodiments $A^3$ is bond.
In certain embodiments $A^3$ is $—CH_2—$.
In certain embodiments $A^3$ is $—CH_2—CH_2—$.
In certain embodiments $A^3$ is $—CH_2—CH_2—CH_2—$.
In certain embodiments $A^3$ is $—CH(CH_3)—CH_2—CH_2—$.
In certain embodiments $A^3$ is $—CH_2—CH(CH_3)—CH_2—$.
In certain embodiments $A^3$ is $—CH_2—CH_2—CH(CH_3)—$.
In certain embodiments $A^3$ is $—CH_2—CH_2—CH_2—CH_2—$.
In certain embodiments $A^3$ is $—CH_2—CH_2—CH_2—CH_2—CH_2—$.
In certain embodiments $A^{23}$ is bond.

In certain embodiments $A^{23}$ is —O—.

In certain embodiments $A^{23}$ is —$CH_2$—.

Embodiments of $A^4$ and $A^{14}$

In certain embodiments $A^4$ is bond.

In certain embodiments $A^4$ is —$CH_2$—.

In certain embodiments $A^4$ is —$(SO_2)$—$CH_2$—.

In certain embodiments $A^4$ is —$CH(CH_2OH)$—.

In certain embodiments $A^4$ is —NH—.

In certain embodiments $A^4$ is —O—.

In certain embodiments $A^{14}$ is bond.

In certain embodiments $A^{14}$ is —$CH_2$—.

In certain embodiments $A^{14}$ is —$CH_2$—$CH_2$—.

In certain embodiments $A^{14}$ is —$CH(CH_2OH)$—.

In certain embodiments $A^{14}$ is —NH—.

In certain embodiments $A^{14}$ is —O—.

In certain embodiments $A^{14}$ is cycloalkyl.

In certain embodiments $A^{14}$ is alkylamino.

Embodiments of $A^5$, $A^6$, and $A^{15}$

In certain embodiments $A^5$ is —CH—.

In certain embodiments $A^5$ is —N—.

In certain embodiments $A^6$ is —CH—.

In certain embodiments $A^6$ is —N—.

In certain embodiments $A^{15}$ is —O—.

In certain embodiments $A^{15}$ is —N—.

In certain embodiments $A^{15}$ is bond.

Embodiments of A and $A^{30}$

In certain embodiments A is bond.

In certain embodiments A is pyrimidinyl.

In certain embodiments A is pyridinyl.

In certain embodiments A is pyrazolyl.

In certain embodiments A is 3-azabicyclo[3.1.0]hexyl.

In certain embodiments A30 is bond.

In certain embodiments A30 is pyrimidinyl.

In certain embodiments A30 is pyridinyl.

In certain embodiments A30 is pyrazolyl.

In certain embodiments A30 is —$CH_2$—.

Embodiments of B

1. In certain embodiments B is phenyl wherein B is optionally substituted with one or two substituents independently selected from halogen, alkyl and alkoxy.
2. In certain embodiments B is piperidinyl wherein B is optionally substituted with one or two substituents independently selected from halogen, alkyl and alkoxy.
3. In certain embodiments B is piperazinyl wherein B is optionally substituted with one or two substituents independently selected from halogen, alkyl and alkoxy.
4. In certain embodiments B is 1,4-diazacycloheptyl wherein B is optionally substituted with one or two substituents independently selected from halogen, alkyl and alkoxy.
5. In certain embodiments B is 1-oxa-8-azaspiro[4.5] decyl wherein B is optionally substituted with one or two substituents independently selected from halogen, alkyl and alkoxy.
6. In certain embodiments B is 1-oxa-9-azaspiro[5.5] undecyl wherein B is optionally substituted with one or two substituents independently selected from halogen, alkyl and alkoxy.
7. In certain embodiments B is 2,8-diazaspiro[4.5]decyl wherein B is optionally substituted with one or two substituents independently selected from halogen, alkyl and alkoxy.
8. In certain embodiments B is 2-azaspiro[4.5]decyl wherein B is optionally substituted with one or two substituents independently selected from halogen, alkyl and alkoxy.
9. In certain embodiments B is 3-azabicyclo[3.1.0]hexyl wherein B is optionally substituted with one or two substituents independently selected from halogen, alkyl and alkoxy.
10. In certain embodiments B is 3-azaspiro[5.5]undecyl wherein B is optionally substituted with one or two substituents independently selected from halogen, alkyl and alkoxy.
11. In certain embodiments B is 7-azaspiro[3.5]nonyl wherein B is optionally substituted with one or two substituents independently selected from halogen, alkyl and alkoxy.
12. In certain embodiments B is 1,1-dioxo-1lambda6-thia-8-azaspiro[4.5]decyl wherein B is optionally substituted with one or two substituents independently selected from halogen, alkyl and alkoxy.
13. In certain embodiments B is 1-oxaspiro[4.5]decyl wherein B is optionally substituted with one or two substituents independently selected from halogen, alkyl and alkoxy.
14. In certain embodiments B is 1-methyl-1,8-diazaspiro [4.5]decyl wherein B is optionally substituted with one or two substituents independently selected from halogen, alkyl and alkoxy.
15. In certain embodiments B is 1,8-diazaspiro[4.5]decyl wherein B is optionally substituted with one or two substituents independently selected from halogen, alkyl and alkoxy.
16. In certain embodiments B is 8-azaspiro[4.5]decyl wherein B is optionally substituted with one or two substituents independently selected from halogen, alkyl and alkoxy.
17. Any one of embodiments 1-16, wherein B is substituted with one substituent independently selected from halogen, alkyl and alkoxy.
18. Any one of embodiments 1-16, wherein B is substituted with two substituents independently selected from halogen, alkyl and alkoxy.
19. Any one of embodiments 1-16, wherein B is substituted with halogen.
20. Any one of embodiments 1-16, wherein B is substituted with fluorine.
21. Any one of embodiments 1-16, wherein B is substituted with alkyl.
22. Any one of embodiments 1-16, wherein B is substituted with alkoxy.
23. Any one of embodiments 1-16, wherein B is not substituted.

Embodiments of B2

1. In certain embodiments B2 is phenyl wherein B2 is optionally substituted with one or two substituents independently selected from halogen, alkyl and alkoxy.
2. In certain embodiments B2 is piperidinyl wherein B2 is optionally substituted with one or two substituents independently selected from halogen, alkyl and alkoxy.

3. In certain embodiments B2 is piperazinyl wherein B2 is optionally substituted with one or two substituents independently selected from halogen, alkyl and alkoxy.
4. In certain embodiments B2 is 1,4-diazacycloheptyl wherein B2 is optionally substituted with one or two substituents independently selected from halogen, alkyl and alkoxy.
5. In certain embodiments B2 is 1-oxa-8-azaspiro[4.5] decyl wherein B2 is optionally substituted with one or two substituents independently selected from halogen, alkyl and alkoxy.
6. In certain embodiments B2 is 1-oxa-9-azaspiro[5.5] undecyl wherein B2 is optionally substituted with one or two substituents independently selected from halogen, alkyl and alkoxy.
7. In certain embodiments B2 is 2,8-diazaspiro[4.5]decyl wherein B2 is optionally substituted with one or two substituents independently selected from halogen, alkyl and alkoxy.
8. In certain embodiments B2 is 2-azaspiro[4.5]decyl wherein B2 is optionally substituted with one or two substituents independently selected from halogen, alkyl and alkoxy.
9. In certain embodiments B2 is 3-azabicyclo[3.1.0]hexyl wherein B2 is optionally substituted with one or two substituents independently selected from halogen, alkyl and alkoxy.
10. In certain embodiments B2 is 3-azaspiro[5.5]undecyl wherein B2 is optionally substituted with one or two substituents independently selected from halogen, alkyl and alkoxy.
11. In certain embodiments B2 is 7-azaspiro[3.5]nonyl wherein B2 is optionally substituted with one or two substituents independently selected from halogen, alkyl and alkoxy.
12. In certain embodiments B2 is 8-azaspiro[4.5]decyl wherein B2 is optionally substituted with one or two substituents independently selected from halogen, alkyl and alkoxy.
13. Any one of embodiments 1-12, wherein B2 is substituted with one substituent independently selected from halogen, alkyl and alkoxy.
14. Any one of embodiments 1-12, wherein B2 is substituted with two substituents independently selected from halogen, alkyl and alkoxy.
15. Any one of embodiments 1-12, wherein B2 is substituted with halogen.
16. Any one of embodiments 1-12, wherein B2 is substituted with fluorine.
17. Any one of embodiments 1-12, wherein B2 is substituted with alkyl.
18. Any one of embodiments 1-12, wherein B2 is substituted with alkoxy.
19. Any one of embodiments 1-12, wherein B2 is not substituted.

Embodiments of B3

In certain embodiments B3 is phenyl.

In certain embodiments B3 is piperidinyl.

In certain embodiments B3 is piperazinyl.

In certain embodiments B3 is 1,4-diazacycloheptyl.

In certain embodiments B3 is 1-oxa-8-azaspiro[4.5]decyl.

In certain embodiments B3 is 1-oxa-9-azaspiro[5.5]undecyl.

In certain embodiments B3 is 2,8-diazaspiro[4.5]decyl.

In certain embodiments B3 is 2-azaspiro[4.5]decyl.

In certain embodiments B3 is 3-azabicyclo[3.1.0]hexyl.

In certain embodiments B3 is 3-azaspiro[5.5]undecyl, 7-azaspiro[3.5]nonyl.

In certain embodiments B3 is 1,1-dioxo-1lambda6-thia-8-azaspiro[4.5]decyl.

In certain embodiments B3 is 1-oxaspiro[4.5]decyl.

In certain embodiments B3 is 1-methyl-1,8-diazaspiro[4.5]decyl.

In certain embodiments B3 is 1,8-diazaspiro[4.5]decyl.

In certain embodiments B3 is 8-azaspiro[4.5]decyl.

Embodiments of n

In certain embodiments n is 0.

In certain embodiments n is 1.

Embodiments of C

1. In certain embodiments C is azepanyl optionally substituted with one or two substituents independently selected from halogen (for example F), hydroxy, alkyl and alkoxy.
2. In certain embodiments C is cycloalkyl optionally substituted with one or two substituents independently selected from halogen (for example F), hydroxy, alkyl and alkoxy.
3. In certain embodiments C is piperazinyl optionally substituted with one or two substituents independently selected from halogen (for example F), hydroxy, alkyl and alkoxy.
4. In certain embodiments C is azetidinyl optionally substituted with one or two substituents independently selected from halogen (for example F), hydroxy, alkyl and alkoxy.
5. In certain embodiments C is piperidinyl optionally substituted with one or two substituents independently selected from halogen (for example F), hydroxy, alkyl and alkoxy.
6. Any one of embodiments 1-5, wherein C is substituted with one substituent independently selected from halogen (for example F), hydroxy, alkyl and alkoxy.
7. Any one of embodiments 1-5, wherein C is substituted with two substituents independently selected from halogen (for example F), hydroxy, alkyl and alkoxy.
8. Any one of embodiments 1-7, wherein C is substituted with halogen.
9. Any one of embodiments 1-7, wherein C is substituted with hydroxy.
10. Any one of embodiments 1-7, wherein C is substituted with alkyl.
11. Any one of embodiments 1-7, wherein C is substituted with alkoxy.
12. Any one of embodiments 1-7, wherein C is substituted with fluorine.
13. Any one of embodiments -15, wherein C is not substituted.

Embodiments of D

In certain embodiments D is

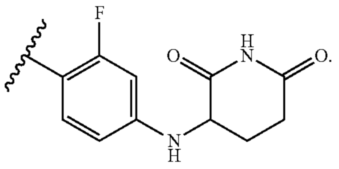 [SMILES: *c1ccc(NC2CCC(=O)NC2=O)cc1F]

In certain embodiments D is

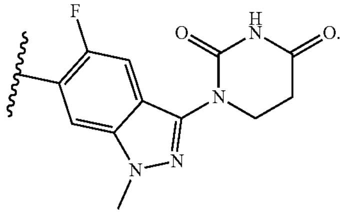 [SMILES: *c1cc2c(cc1F)c(N1CCC(=O)NC1=O)nn2C]

Embodiments of Alkyl

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

Embodiments of Cycloalkyl

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.

In one embodiment "cycloalkyl" has four carbons.

In one embodiment "cycloalkyl" has five carbons.

In one embodiment "cycloalkyl" has six carbons.

In one embodiment "cycloalkyl" has seven carbons.

In one embodiment "cycloalkyl" has eight carbons.

In one embodiment "cycloalkyl" has nine carbons.

In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Embodiments of Haloalkyl

In one embodiment "haloalkyl" is a $C_1$-$C_{10}$haloalkyl, $C_1$-$C_9$haloalkyl, $C_1$-$C_5$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

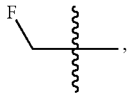, 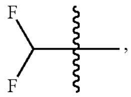, and 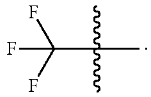.

Additional non-limiting examples of "haloalkyl" include:

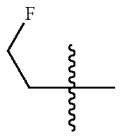, 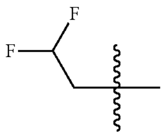, 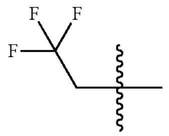, 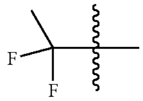, 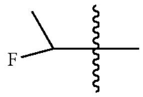, 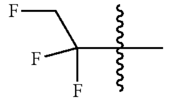, 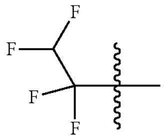, 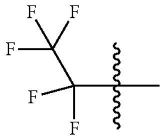, 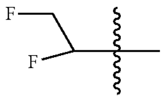, 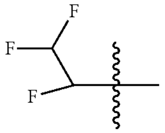, and 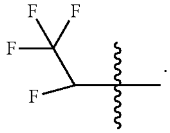.

Additional non-limiting examples of "haloalkyl" include:

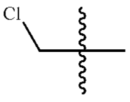, 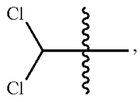, and 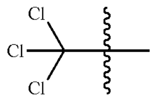.

Additional non-limiting examples of "haloalkyl" include:

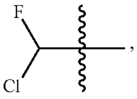, 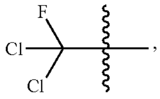, and 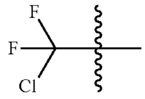.

Embodiments of Aryl

In one embodiment "aryl" is a 6-carbon aromatic group (phenyl).

In one embodiment "aryl" is a 10-carbon aromatic group (napthyl).

In one embodiment "aryl" is a 6-carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

In one embodiment "aryl" is a 6-carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

In one embodiment "heterocycle" refers to a cyclic ring with one nitrogen and 3, 4, 5, 6, 7, or 8 carbon atoms.

Embodiments of Heterocycle

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocycle ring.

Non-limiting examples of "heterocycle" also include:

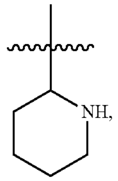,
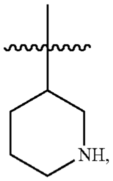,
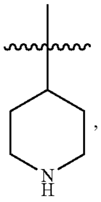,
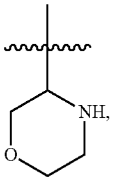,
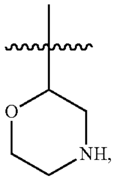,
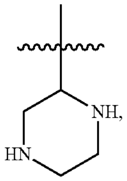,
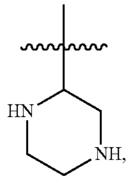,
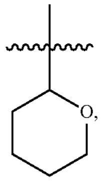,
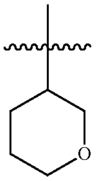, and
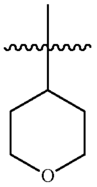.

Additional non-limiting examples of "heterocycle" include:

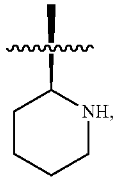,
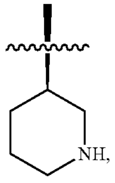,
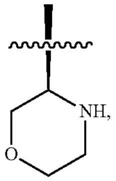,
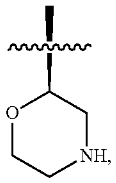,
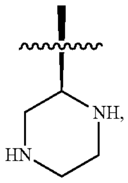,
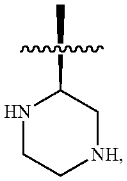,
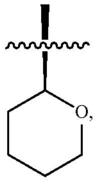, and
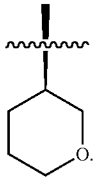.

Additional non-limiting examples of "heterocycle" include:

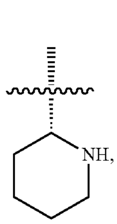,
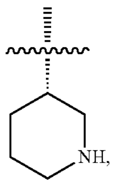,
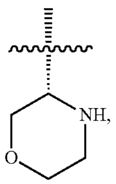,
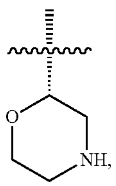,
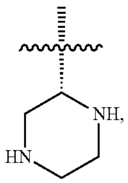,
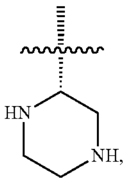,
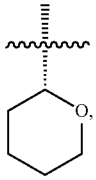, and
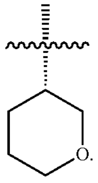.

Non-limiting examples of "heterocycle" also include:

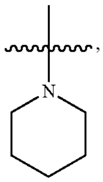,
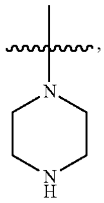, and
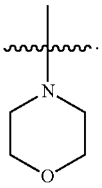.

Non-limiting examples of “heterocycle” also include:

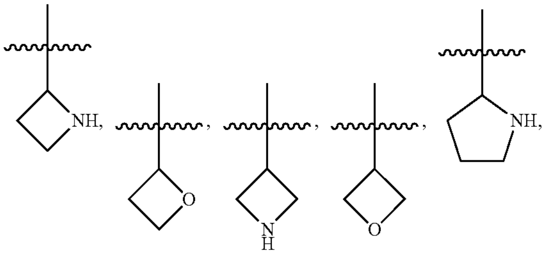

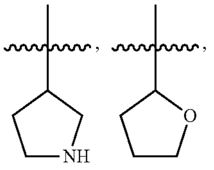

and

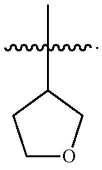

Additional non-limiting examples of “heterocycle” include:

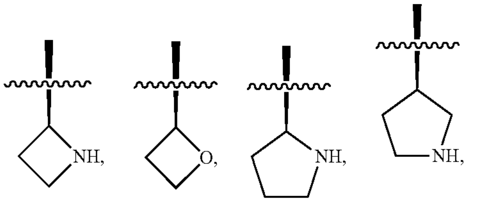

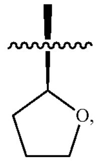

and

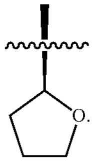

Additional non-limiting examples of “heterocycle” include:

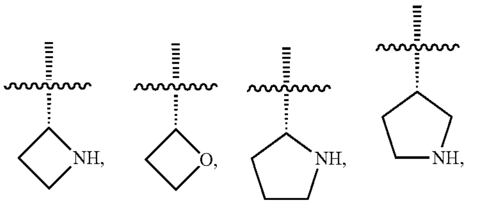

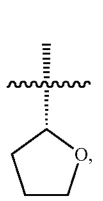

and

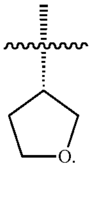

Embodiments of Heteroaryl

In one embodiment “heteroaryl” is a 5 membered aromatic group containing 1, 2, 3, or 4 nitrogen atoms.

Non-limiting examples of 5 membered “heteroaryl” groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered “heteroaryl” groups include:

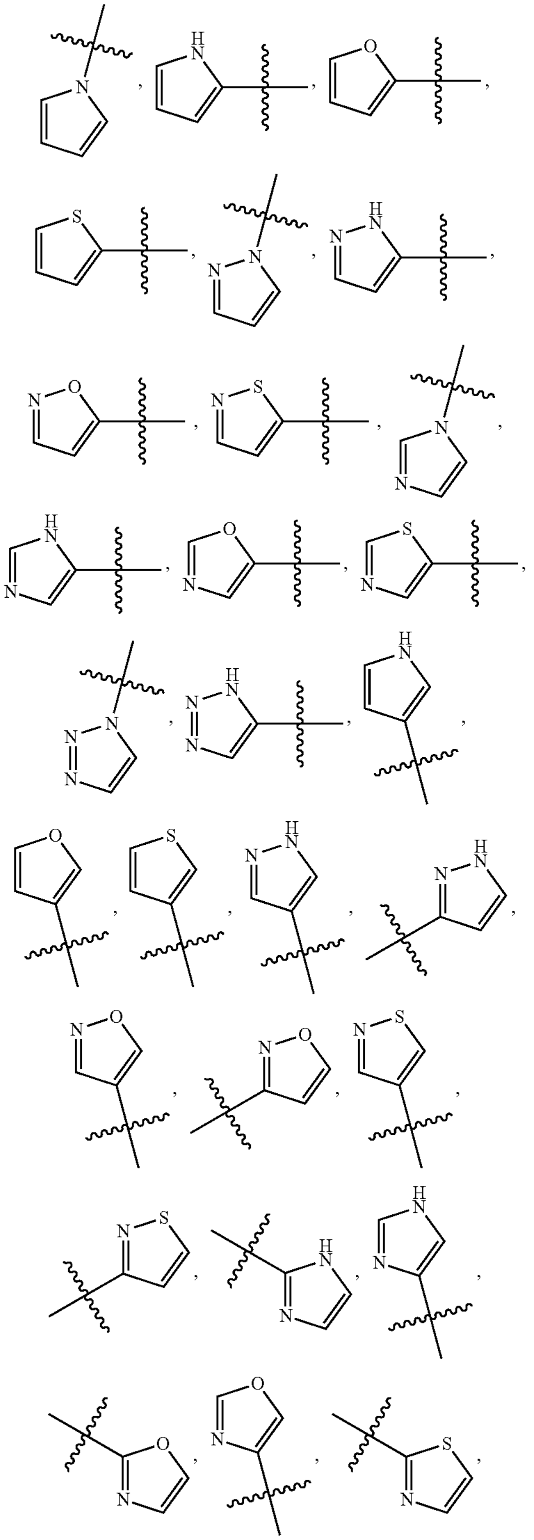

-continued

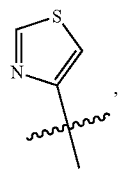, and 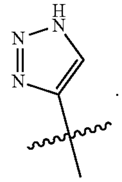.

In one embodiment "heteroaryl" is a 6 membered aromatic group containing 1, 2, or 3 nitrogen atoms (i.e., pyridinyl, pyridazinyl, triazinyl, pyrimidinyl, and pyrazinyl).

Non-limiting examples of 6 membered "heteroaryl" groups with 1 or 2 nitrogen atoms include:

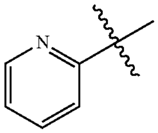, 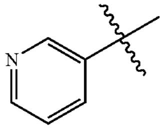, 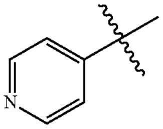,

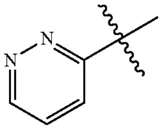, 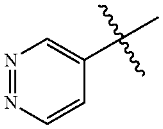, 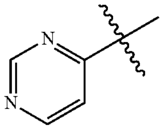,

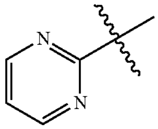, 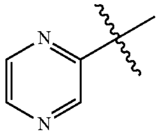,

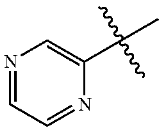, and 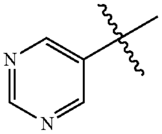.

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

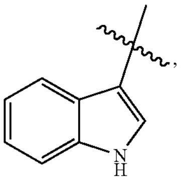, 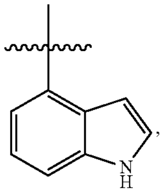, 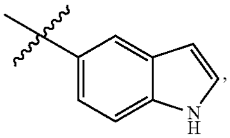,

-continued

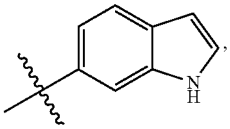, 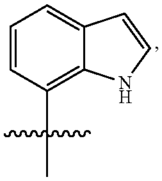,

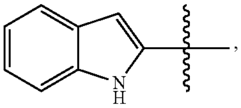, and 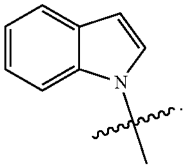.

Additional non-limiting examples of "heteroaryl" groups that are bicyclic include:

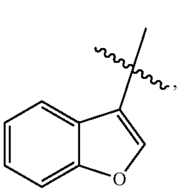, 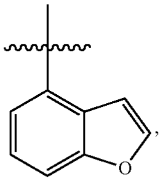, 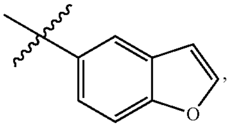,

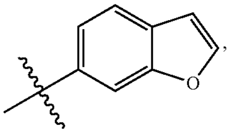, 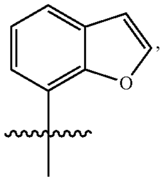, and

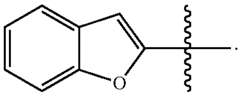.

Additional non-limiting examples of "heteroaryl" groups that are bicyclic include:

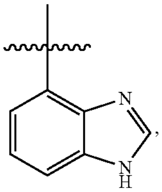, 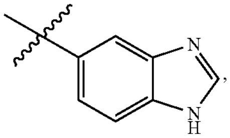,

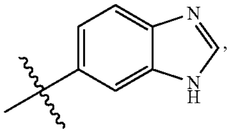, 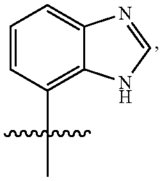,

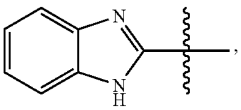, and 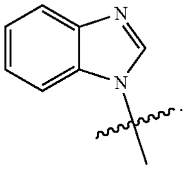.

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

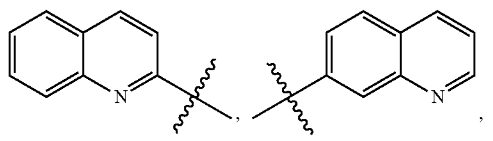

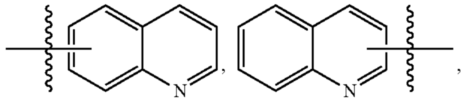

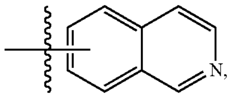

and

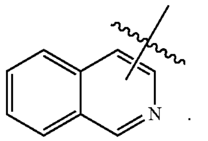

.

In an alternative embodiment "heteroaryl" is "optionally substituted" with 1, 2, 3, or 4 substituents.

Embodiments of Bicycle

In certain embodiments the term "bicycle" refers to a ring system wherein two rings are fused together and each ring is independently selected from carbocycle, heterocycle, aryl, and heteroaryl. Non-limiting examples of bicycle groups include:

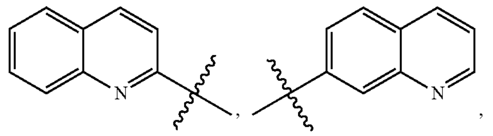

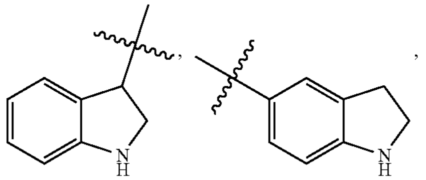

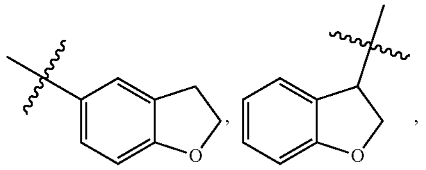

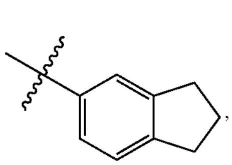

and

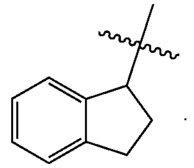

.

When the term "bicycle" is used in the context of a bivalent residue such as Linker the attachment points can be on separate rings or on the same ring. In certain embodiments both attachment points are on the same ring. In certain embodiments both attachment points are on different rings. Non-limiting examples of bivalent bicycle groups include:

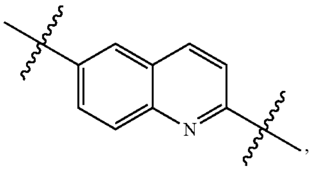

,

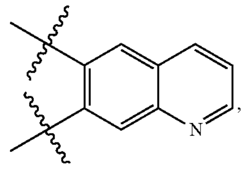

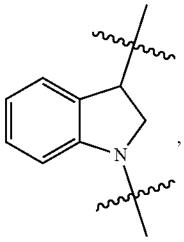

,

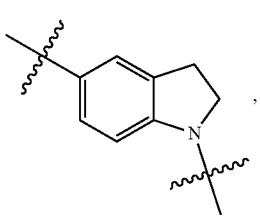

, and

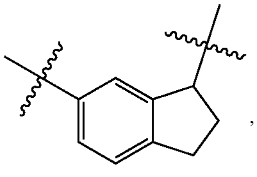

.

In an alternative embodiment "bicycle" is "optionally substituted" with 1, 2, 3, or 4 substituents.

Embodiments of BRAF Targeting Ligand Portion of the Molecule

In certain embodiments $R^1$ is $CH_3$.

In certain embodiments $A^1$ is $—N(CH_2CH_3)—$.

In certain embodiments $R^4$ is cyano.

In certain embodiments $R^5$ is F.

In certain embodiments, $A^2$ is O.

In certain embodiments $R^6$ is hydrogen.

In certain embodiments, the BRAF Targeting Ligand is selected from:

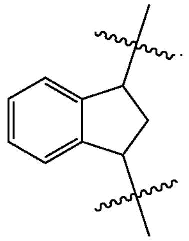

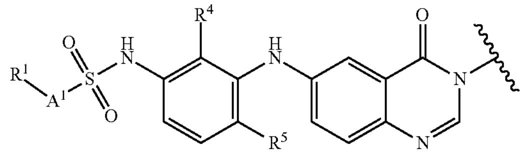

-continued
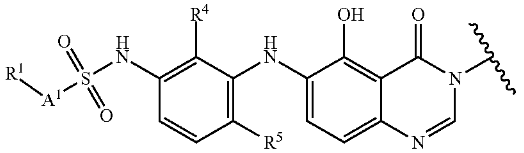
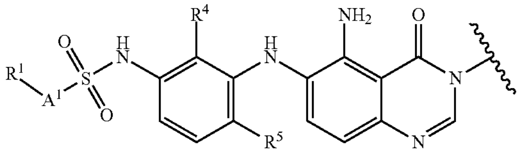
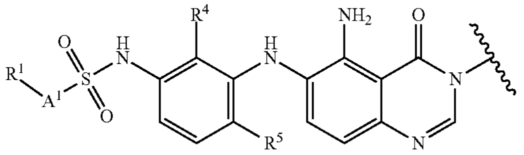
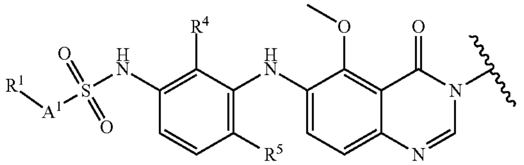
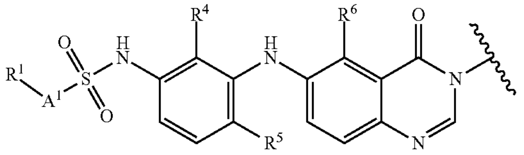
In certain embodiments, the BRAF Targeting Ligand is selected from:
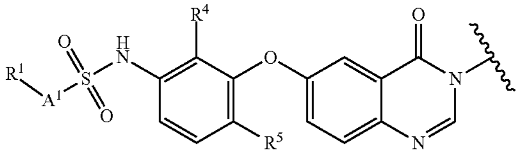
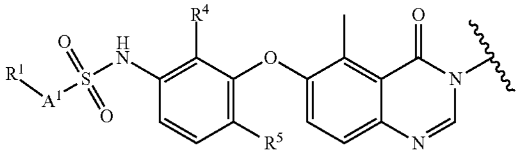
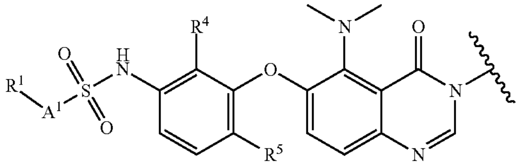
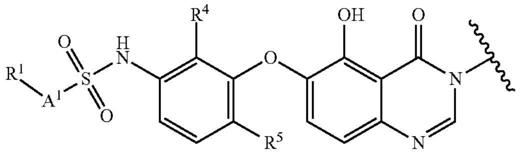
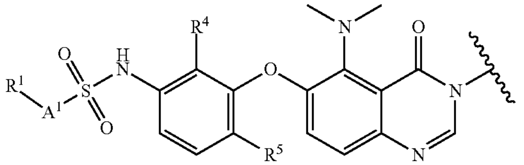
-continued
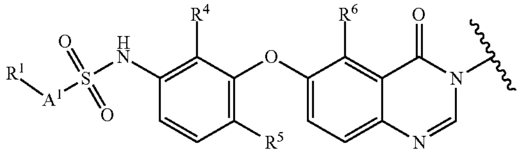
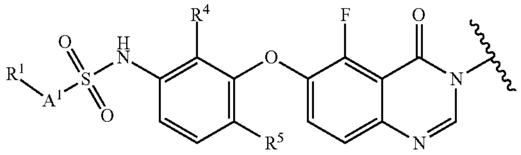
In certain embodiments, the BRAF Targeting Ligand is selected from:
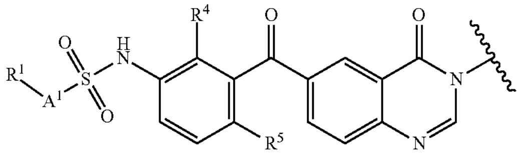
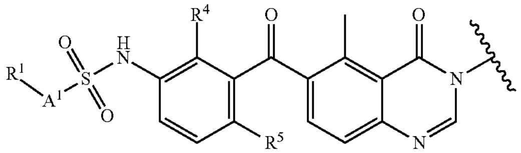
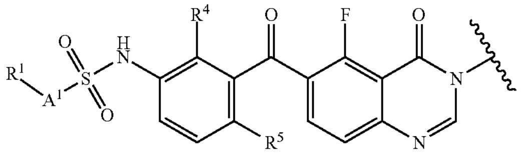
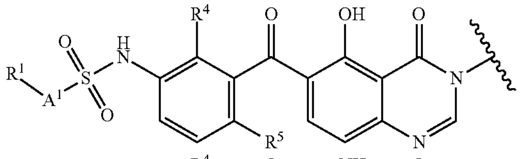
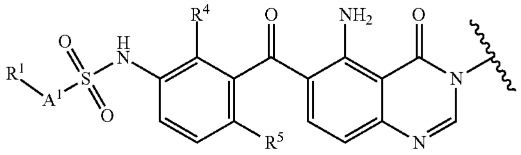
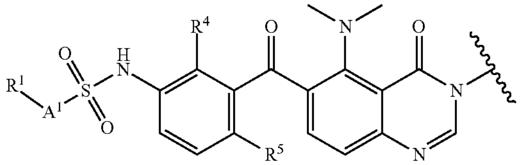
In certain embodiments, the BRAF Targeting Ligand is selected from:
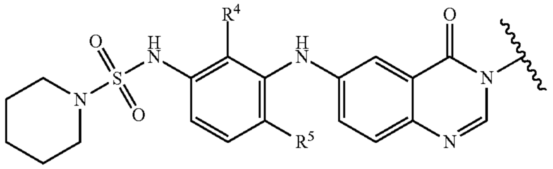

-continued
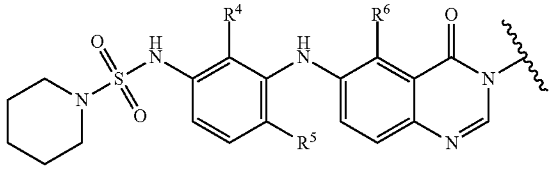
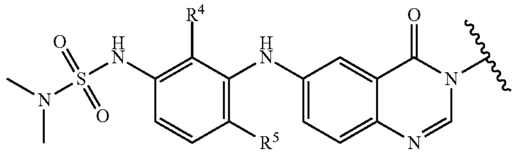
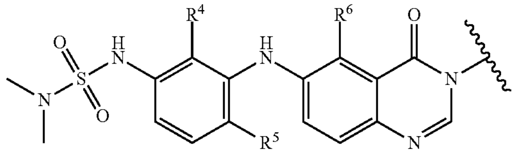
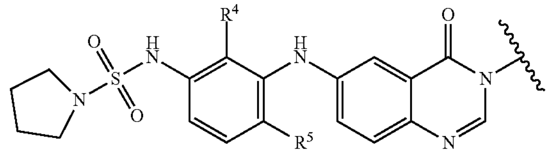
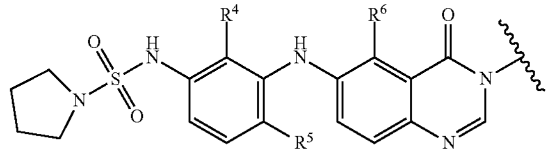
In certain embodiments, the BRAF Targeting Ligand is selected from:
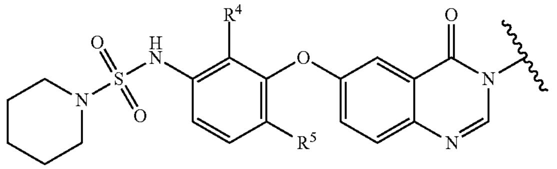
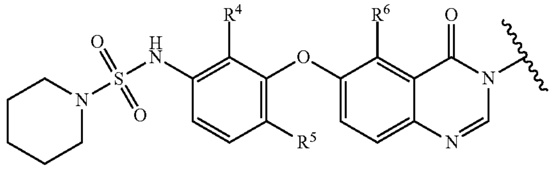
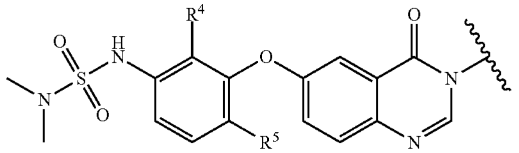
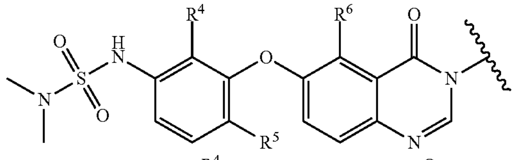
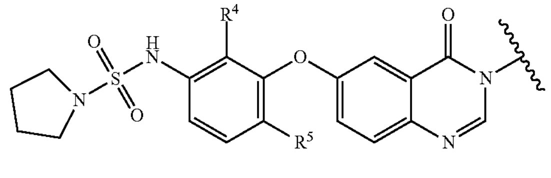
-continued
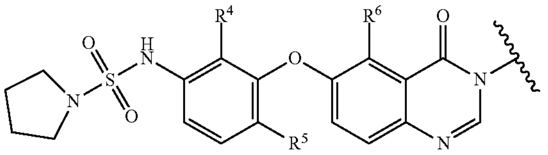
Embodiments of Cereblon Ligand Portion of the Molecule
In certain embodiments, the Cereblon Ligand is selected from
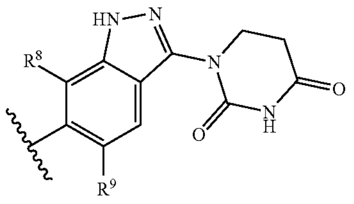
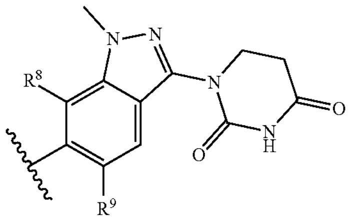
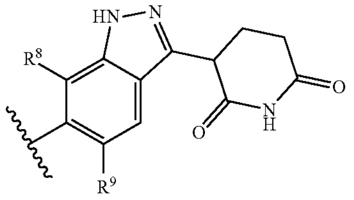
In certain embodiments, the Cereblon Ligand is selected from
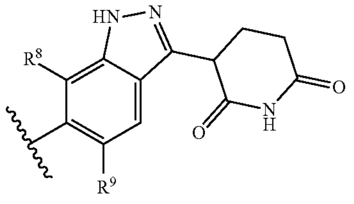
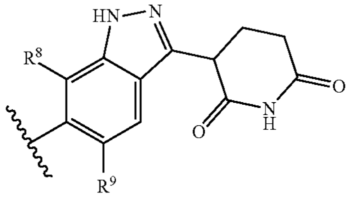

-continued

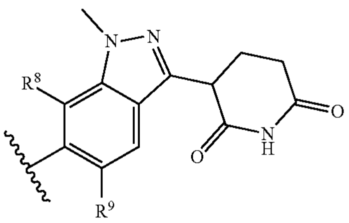

Processes for the manufacture of the compound of the present invention as described herein are also an object of the invention.

Compounds of the present invention can be prepared according to the following processes. As described in the following general schemes 1 to 3 and using method known to the person skilled in the art.

Compounds of the present invention can be prepared according to the following processes. The processes are described in more detail with the following general schemes. Generally speaking, the sequence of steps used to synthesize the compounds of the present invention can also be modified in certain cases.

Scheme 1

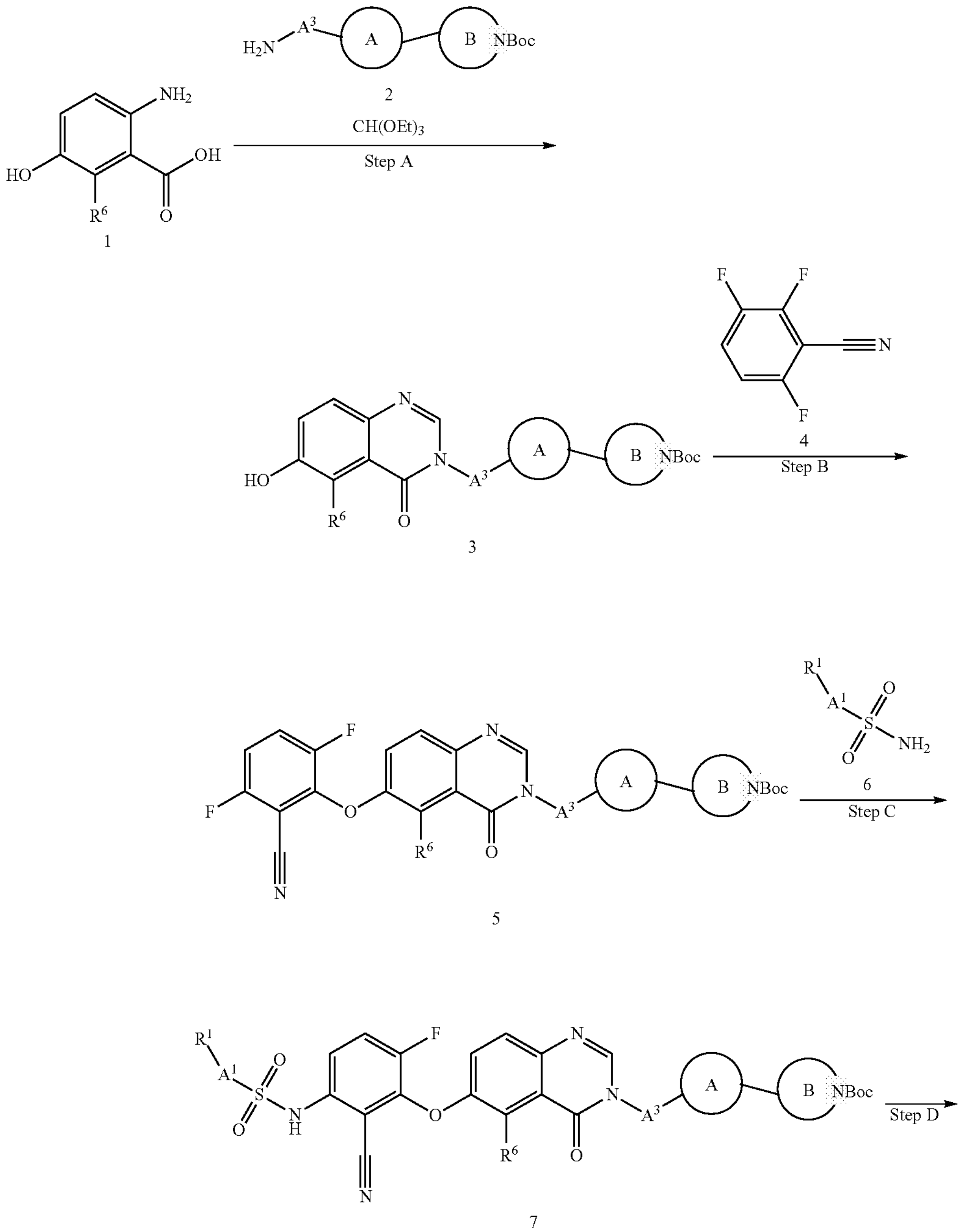

-continued

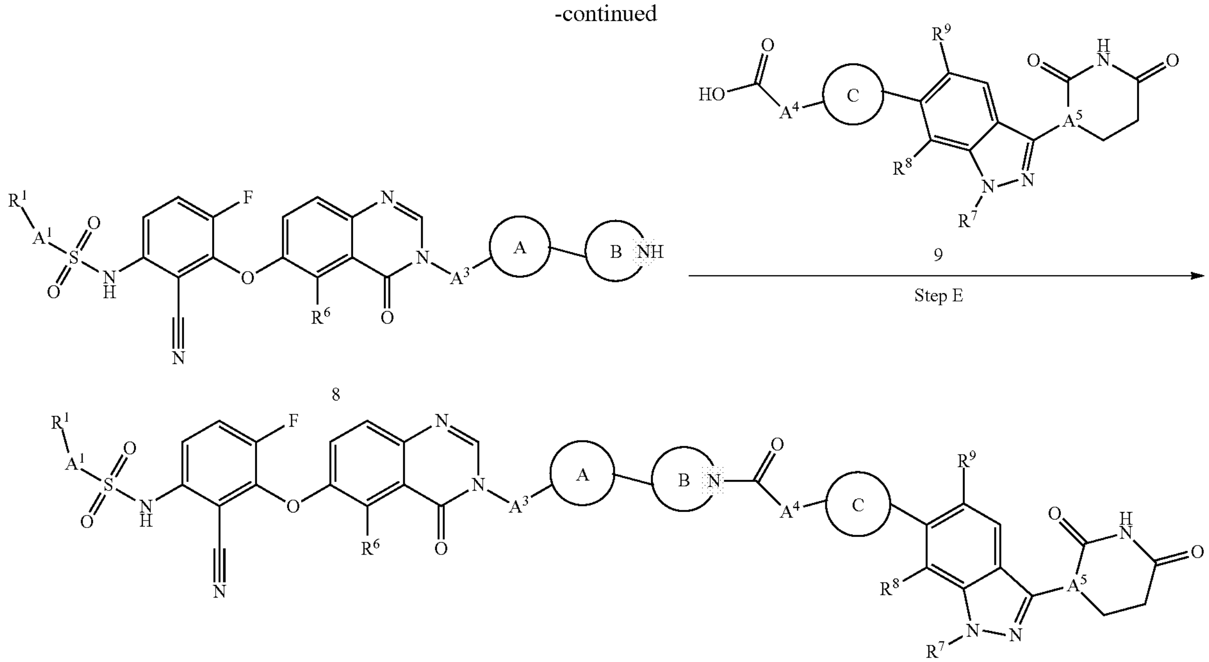

8

9

(Ia)

In the above scheme $A^2$ is —O—, n is 1, $R^4$ is cyano and $R^5$ is fluoro. The remaining substituents and variables are as described herein.

Step A—Cyclization: Cyclization to obtain the quinazolinone intermediate (3) can be achieved by addition of anhydrous triethyl orthoformate and amine (2) to 2-amino-5-hydroxy-benzoic acid or a derivate thereof (1) in a suitable solvent such as toluene, tetrahydrofuran or a mixture thereof at between around 110° C. to around 140° C., and for 12-18 hrs. For cyclization with amine salts (HCl, TFA etc.,), catalytic acetic acid (0.1 eq.) can be used.

Step B—O-arylation: O-arylation to obtain intermediate (5) can be achieved by addition of 2,3,6-trifluorobenzonitrile (4) to the quinazolinone intermediate (3) in presence of a suitable base such as cesium carbonate or potassium tert-butoxide at room temperature in a suitable solvent such as for instance N,N-dimethylformamide, THF or a mixture thereof.

Step C—Sulfomoylation: Addition of the sulfamoyl intermediate (commercially available or as described herein in methods I and II) (6) and a suitable base such as for instance cesium carbonate or the like, to intermediate (5) in a suitable solvent such as N,N-dimethylformamide can provide the sulfonamide intermediate (7) via sulfomoylation. Conveniently conditions are at between around 60° C. to around 70° C. for between around 12 hours to around 18 hrs.

Step D—N-Boc Deprotection: Addition of a suitable acid such as TFA or HCl to sulfonamide intermediate (7) in a suitable solvent at room temperature such as dichloromethane or dioxane can provide the deprotected amine (8).

Step E—Acid-Amine Coupling:

Addition of N,N-diisopropylethylamine and acid (9) to amine (8) in presence of a suitable coupling agent such as HATU or COMU in a suitable solvent such as for instance N,N-dimethylformamide can provide the quinazolinone derivatives (Ia) of the present invention. Convenient conditions for the reaction are between around 0° C. to around 50° C. for between around 2 hrs to around 16 hrs, in particular between around 10° C. to around 40° C. for between around 4 hrs to around 14 hrs.

Scheme 2

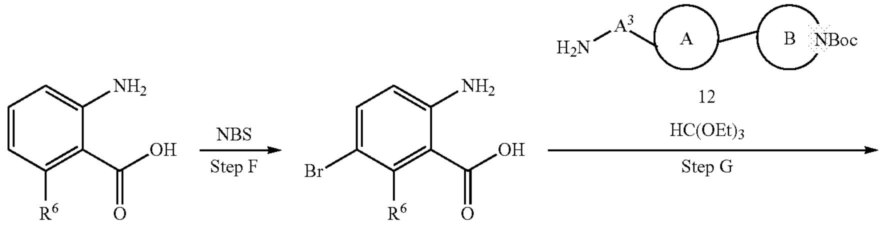

12

10

11

-continued

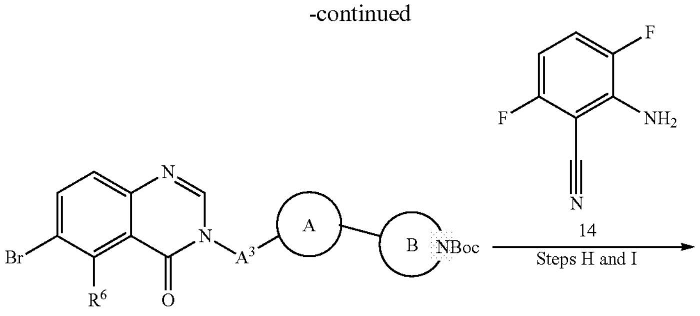

13

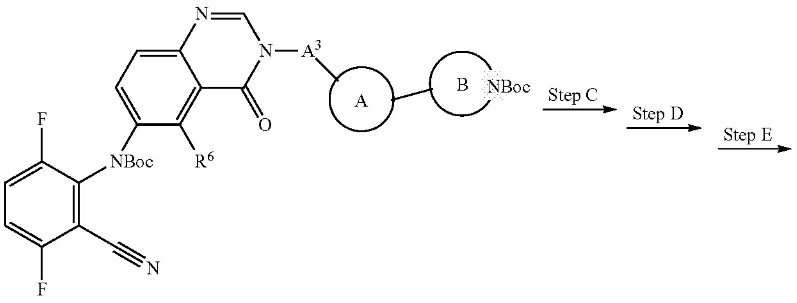

5'

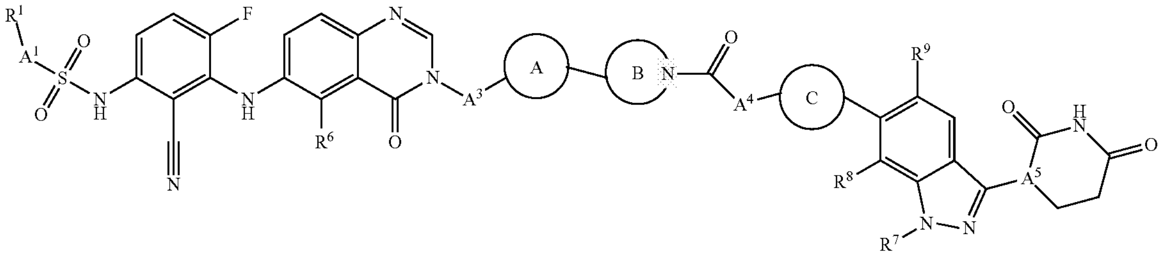

(Ib)

The above scheme provides compounds according to the invention wherein $A^2$ is —NH—, n is 1, $R^4$ is cyano and $R^5$ is fluoro. The remaining substituents and variables are as described herein.

Step F—General Procedure for Bromination: Addition of a bromination agent such as NBS or the like to benzoic acid derivative (11) in a suitable solvent such as for instance DMF can provide the bromobenzyl derivative (12). Conveniently the reaction occurs at room temperature.

Step G—General Procedure for Cyclization: Addition of anhydrous triethyl orthoformate and amine (13) to the bromobenzyl derivative (12) in a suitable solvent such as toluene, tetrahydrofuran or a mixture thereof can provide the quinazolinone intermediate (14) via cyclization. Convenient conditions for the reaction are between around 110° C. to around 140° C. for around 12 hrs to around 18 hrs. For cyclization with amine salts (HCl, TFA etc.,), catalytic acetic acid (0.1 eq.) can be used.

Steps H & I—General Procedure for Amine-Quinazolinone Coupling and Boc Protection: Step H: Pd-PEPPSI-IHept catalyst can be added to the amine (15) and the quinazolinone intermediate (14), in presence of a suitable base such as cesium carbonate or the like in a suitable solvent such as 1,4-dioxane to obtain coupling of (15) and (14). Step I: After the coupling, the quinazolinone intermediate can be Boc protected by the addition of di-tert-butyl dicarbonate and DMAP, in presence of a suitable base such as trimethylamine or DIPEA in a suitable solvent such as acetonitrile to afford the intermediate (5'). Intermediate (5') can further be converted to compounds of formula (Ib) according to the present invention by following analogous steps C, D and E as shown in scheme 1 above.

Scheme 3
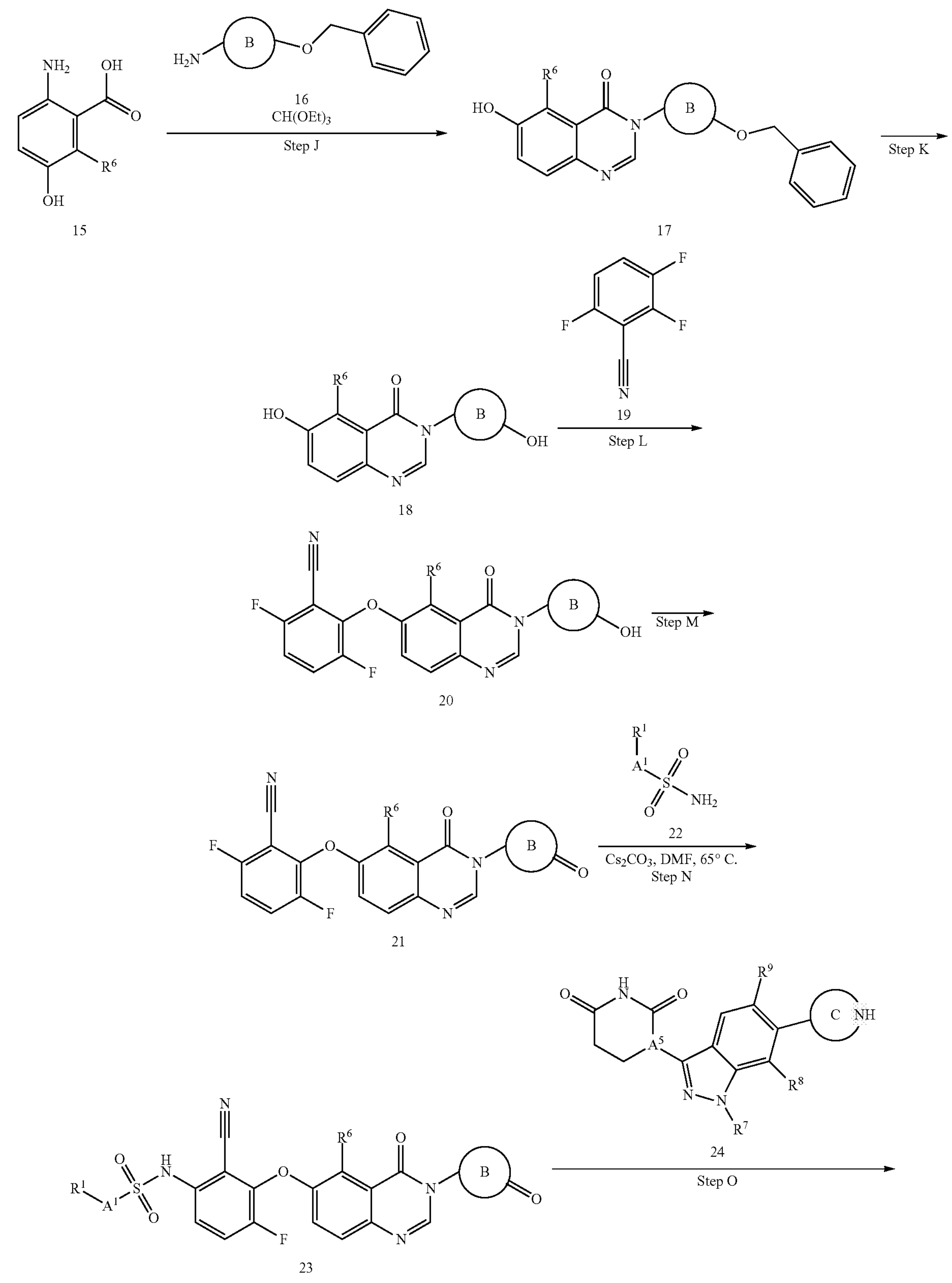

-continued

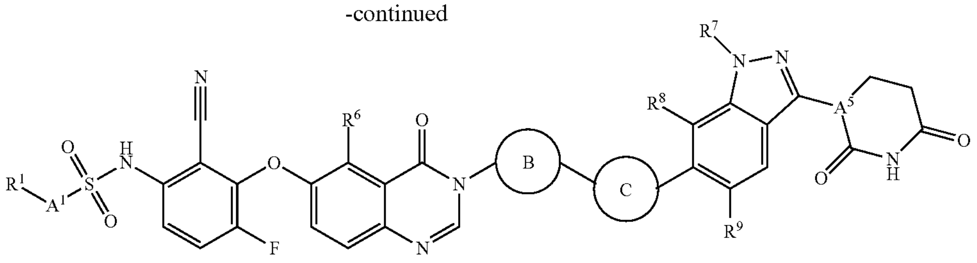

(Ic)

The above scheme provides compounds according to the invention wherein $A^2$ is —O—, A3 is a bond, A is a bond, n is 0, A4 is a bond, $R^4$ is cyano and $R^5$ is fluoro. The remaining substituents and variables are as described herein.

Step J: Addition of 2-amino-5-hydroxy-benzoic acid or a derivative thereof (15) and triethyl orthoformate to amine (16) in a suitable solvent can provide intermediate (17). Conveniently the solvent is toluene, tetrahydrofuran or a mixture thereof. Conveniently the reaction is performed at between around 100° C. to around 140° C. for 12 hrs to 16 hrs.

Step K: The Bn group can be removed from intermediate (17) by addition hydrogen and Pd/C, in a suitable solvent such as methanol at ambient temperature for between around 12 hrs to around 18 hrs to provide intermediate (18).

Step L: Addition of 2,3,6-trifluorobenzonitrile (19) and cesium carbonate to intermediate (18) in a suitable solvent such as for instance THF at ambient temperature under nitrogen atmosphere can provide intermediate (20).

Step M: Addition of pyridinium chlorochromate (PCC) to intermediate (20) in a suitable solvent such as for instance dichloromethane at room temperature under nitrogen atmosphere and for around 12 hrs to 18 hrs can provide ketone intermediate (21).

Step N: Addition of sulfamoyl (22) to intermediate (21) in presence of a suitable base such as cesium carbonate and in a suitable solvent such as for instance DMF at around between around 60° C. to 70° C. can provide ketone intermediate (23).

Step O: Addition of ketone intermediate (23) and Na(CN)$BH_3$ to amine (24) in presence of a suitable base such as DIPEA and in a suitable solvent such as DMAc at between around 60° C. to around 80° C. can provide quinazolinone derivatives (Ic) of the present invention.

Isolation and Purification of the Compounds

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of the present invention can be separated using chiral HPLC and/or chiral SFC. Racemic mixtures of chiral synthetic intermediates may also be separated using chiral HPLC and/or chiral SFC.

Salts of Compounds of the Present Invention

In cases where the compounds of the present invention are basic, they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. A specific salt is the fumarate. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of the present invention as well as all intermediate products can be prepared according to analogous methods or according to the methods set forth herein. Starting materials are commercially available, known in the art or can be prepared by methods known in the art or in analogy thereto.

It will be appreciated that the compounds of the present invention in this invention may be derivatised at functional groups to provide derivatives which are capable of conversion back to the parent compound in vivo.

Pharmacological Tests

The compounds of the present invention and their pharmaceutically acceptable salts possess valuable pharmacological properties. The compounds were investigated in accordance with the test given hereinafter.

Materials

DMEM no-phenol red medium supplemented with L-glutamine was purchased from (Corning). Fetal bovine serum (FBS) was purchased from Gibco (Grand Island, NY, USA). Nano-Glo® HiBiT Lytic Assay Buffer & Reagents were purchased from Promega (Madison, WI, USA). A375 (harboring BRAF homozygous V600E mutation) was purchased from ATCC. A375.10 cell line was generated from A375 cell line from ATCC by knocking-in a HiBiT tag at the N-terminal of $BRAF^{V600E}$ protein via CRISPR technology. Cell culture flasks and 384-well black flat-bottom polystyrene TC-treated microplates were acquired from Corning (Corning, NY, USA).

HiBiT Cellular $BRAF^{V600E}$ Degradation Assay

Prior to the assay, the A375.10 cell line is maintained in DMEM no-phenol red medium supplemented with 10% fetal bovine serum (FBS). Following compound treatment, $BRAF^{V600E}$ degradation was determined based on quantification of HiBiT luminescence signal by lysing the cells followed by addition of Nano-Glo® HiBiT Lytic Assay Reagents. The luminescence signal detected correlates with the total $BRAF^{V600E}$ protein level in cells. Briefly, test compounds were added to the 384-well plate from a top concentration of 10 μM with 11 half log dilutions of compound, plated in duplicate. Then, 30 μL of a suspension of A375.10 cell lines was dispensed into columns 1-24 of the 384-well plates at a cell density of 7500 cells per well. The plates were kept at 37° C. with 5% CO2 for the duration of the assay (6 or 24 hr). After the desired incubation time with compound, 30 μL of Nano-Glo® HiBiT Lytic Buffer containing LgBiT protein (diluted 1:100) and luminescence substrate (diluted 1:50) were added to the cells in columns 1-23 of the assay plate. The plate was the incubated for 30 min on the bench at room temperature. Finally, HiBiT luminescence signal was acquired on EnVision™ Multilabel Reader (PerkinElmer, Santa Clara, CA, USA).

Quantification of luminescence responses measured in the presence of compound were normalized to a high signal/no degradation control (untreated cells+lytic detection reagent) and a low signal/full degradation control (untreated cells, no lytic detection reagent). Data were analyzed with a 4-parameter logistic fit to generate sigmoidal dose-response curves. The DC50 is the concentration of compound at which exactly 50% of the total cellular $BRAF^{V600E}$ has been degraded. The Emax, or maximum effect of each compound, represents the amount of residual protein remaining in the cell following compound treatment is provided in Table 1A, Table 1B, Table 1C, and Table 1D.

TABLE 1A

| DC$_{50}$ value and Emax Value | | |
|---|---|---|
| Ex. | HiBit 24 h DC50 [nM] | HiBit 24 h Emax [%] |
| 1 | 46.87 | 13.91 |
| 2 | 48.57 | 13.54 |
| 3 | 35.9 | 14.68 |
| 4 | 28.55 | 10.84 |
| 5 | 49.29 | 13.07 |
| 6 | 22.74 | 11.48 |
| 7 | 42.16 | 15.19 |
| 8 | 27.95 | 10.04 |
| 9 | 41.91 | 9.87 |
| 10 | 41.91 | 12.64 |
| 11 | 10.05 | 9.52 |
| 12 | 29.18 | 8.33 |
| 13 | 26.24 | 8.27 |
| 14 | 12.53 | 8.11 |
| 15 | 11.1 | 7.29 |
| 16 | 20.52 | 15.46 |
| 17 | 44.01 | 20.67 |
| 18 | 30.66 | 18.52 |
| 19 | 42.31 | 20.64 |
| 20 | 14.43 | 17.67 |
| 21 | 34.32 | 19.62 |
| 22 | 11.17 | 11.53 |
| 23 | 19.3 | 21.69 |
| 24 | 19.52 | 10.85 |
| 25 | 34.83 | 11.94 |
| 26 | 8.49 | 10.01 |
| 27 | 15 | 22.2 |
| 28 | 22.88 | 10.24 |
| 29 | 33.69 | 12.09 |
| 30 | 16.43 | 12.08 |
| 31 | 46.91 | 11.63 |
| 32 | 40.26 | 11.43 |
| 33 | 32.6 | 8.77 |
| 34 | 29.92 | 10.79 |
| 35 | 6.82 | 13.56 |
| 36 | 51.28 | 10.29 |
| 37 | 48.36 | 16.22 |
| 38 | 36.04 | 11.43 |
| 39 | 27.49 | 15.74 |
| 40 | 8.13 | 7.08 |

TABLE 1A-continued

| DC$_{50}$ value and Emax Value | | |
|---|---|---|
| Ex. | HiBit 24 h DC50 [nM] | HiBit 24 h Emax [%] |
| 41 | 16.07 | 9.27 |
| 42 | 22.12 | 8.88 |
| 43 | 23.73 | 9.95 |
| 44 | 25.14 | 14.36 |
| 45 | 18.73 | 11.33 |
| 46 | 29.93 | 13.36 |
| 47 | 25.75 | 19.34 |
| 48 | 34.46 | 15.62 |
| 49 | 147.73 | 10.85 |
| 50 | 127.59 | 13.37 |
| 51 | 29.63 | 10.89 |
| 52 | 20.69 | 11.4 |
| 53 | 14.54 | 11.23 |
| 54 | 15.37 | 12.05 |
| 55 | 30.03 | 14.67 |
| 56 | 31.56 | 11.64 |
| 57 | 20.9 | 11.5 |
| 58 | 45.31 | 13.86 |
| 59 | 55.95 | 10.42 |
| 60 | 40.53 | 13 |
| 61 | 21.06 | 8.44 |
| 62 | 12.98 | 9.04 |
| 63 | 20.37 | 9.52 |
| 64 | 8.05 | 9.88 |
| 65 | 9.48 | 15.38 |
| 66 | 11.31 | 10.25 |
| 67 | 5.31 | 8.05 |
| 68 | 8.77 | 8.05 |
| 69 | 6.63 | 9.52 |
| 70 | 27.66 | 10.71 |
| 71 | 37.65 | 10.53 |
| 72 | 39.86 | 8.63 |
| 73 | 30.68 | 12.02 |
| 74 | 31.55 | 11.58 |
| 75 | 43.15 | 8.31 |
| 76 | 50.11 | 13.19 |
| 77 | 31.78 | 9.51 |
| 78 | 49.67 | 9.7 |
| 79 | 20.06 | 12.88 |
| 80 | 30.51 | 13.8 |
| 81 | 25.43 | 12.19 |
| 82 | 20.67 | 6.45 |
| 83 | 16.28 | 27.77 |
| 84 | 9.97 | 9.26 |
| 85 | 15.81 | 10.99 |
| 86 | 8.28 | 12.93 |
| 87 | 30.33 | 10.07 |
| 88 | 15.14 | 9.01 |
| 89 | 32.99 | 11.53 |
| 90 | 23.46 | 10.67 |
| 91 | 42.44 | 18.42 |
| 92 | 8.71 | 7.37 |
| 93 | 28.01 | 14.14 |
| 94 | 21.48 | 10.46 |
| 95 | 10.71 | 10.38 |
| 96 | 9.91 | 8.43 |
| 97 | 8.41 | 10.57 |
| 98 | 20.14 | 10.11 |
| 99 | 34.22 | 11.41 |
| 100 | 16.36 | 8.4 |
| 101 | 27.67 | 11.62 |
| 102 | 15.01 | 9.75 |
| 103 | 48.26 | 10.83 |
| 104 | 56.26 | 22.27 |
| 105 | 17.72 | 11.78 |
| 106 | 43.59 | 16.71 |
| 107 | 12.93 | 9.8 |
| 108 | 17.77 | 10.94 |
| 109 | 12.55 | 9.04 |
| 110 | 42.55 | 8.22 |
| 111 | 18.62 | 10.27 |
| 112 | 6.47 | 8.79 |
| 113 | 29.66 | 11.1 |
| 114 | 8.33 | 9.6 |
| 115 | 16.09 | 12.79 |

TABLE 1A-continued

| DC$_{50}$ value and Emax Value | | |
|---|---|---|
| Ex. | HiBit 24 h DC50 [nM] | HiBit 24 h Emax [%] |
| 116 | 17.09 | 9.01 |
| 117 | 38.26 | 9.02 |
| 118 | 18.74 | 9.98 |
| 119 | 46.91 | 12.8 |
| 120 | 13.79 | 11.61 |
| 121 | 14.64 | 7.8 |
| 122 | 27.1 | 8.26 |
| 123 | 50.66 | 13.99 |
| 124 | 15.68 | 12.02 |
| 125 | 15.65 | 12.58 |
| 126 | 22.17 | 13.67 |
| 127 | 20.72 | 8.95 |
| 128 | 19.51 | 9.91 |
| 129 | 29.62 | 10.34 |
| 130 | 16.51 | 7.25 |
| 131 | 14.55 | 8.5 |
| 131 | 7.26 | 8.05 |
| 132 | 13.84 | 11.12 |
| 133 | 27.23 | 8.2 |
| 135 | 31.38 | 13.68 |
| 136 | 16.27 | 16.92 |
| 137 | 34.19 | 25.09 |
| 138 | 17.25 | 10.7 |
| 139 | 41.18 | 13.19 |
| 140 | 27.75 | 12.31 |
| 141 | 55.04 | 26.27 |
| A1 | 78 | 23 |
| A2 | 165 | 26 |
| A3 | 242 | 24 |

TABLE 2B

| DC$_{50}$ value and Emax Value | | |
|---|---|---|
| Ex. | HiBit 24 h DC50 [nM] | HiBit 24 h Emax [%] |
| 144 | 28.38 | 16.74 |
| 145 | 10.6 | 14.99 |
| 146 | 22.19 | 16.04 |
| 147 | 26.91 | 9.49 |
| 148 | 18.37 | 8.7 |
| 149 | 10.65 | 11.48 |
| 150 | 12.37 | 11.52 |
| 151 | 18.67 | 24.59 |
| 152 | 27.19 | 25.22 |
| 153 | 28.25 | 14.2 |
| 154 | 24.61 | 11.13 |
| 155 | 23.22 | 9.75 |
| 156 | 26.64 | 20.97 |
| 157 | 14.55 | 27.48 |
| 158 | 25.03 | 30 |
| 159 | 6.98 | 18.8 |
| 160 | 22.19 | 23.85 |
| 162 | 17.29 | 14.52 |
| 163 | 27.55 | 16.24 |
| 164 | 26.62 | 15.57 |
| 165 | 100.2 | 17.78 |
| 166 | 34.46 | 23.51 |
| 167 | 42.57 | 16.48 |
| 168 | 36.5 | 14.13 |
| 169 | 11.93 | 31.49 |
| 170 | 30.85 | 21.23 |
| 171 | 30.67 | 7.11 |
| 172 | 28.92 | 25.06 |
| 173 | 192.22 | 46.03 |
| 174 | 25.55 | 21.18 |
| 175 | 31.22 | 31.11 |
| 176 | 20.54 | 24.76 |
| 177 | 18.04 | 22.3 |
| 178 | 6.13 | 19.07 |
| 179 | 27.81 | 19.28 |

TABLE 2B-continued

| DC$_{50}$ value and Emax Value | | |
|---|---|---|
| Ex. | HiBit 24 h DC50 [nM] | HiBit 24 h Emax [%] |
| 180 | 9.62 | 20.58 |
| 181 | 19.85 | 19.05 |
| 182 | 16.21 | 19.83 |
| 183 | 28.56 | 6.96 |
| 184 | 8.55 | 18.02 |
| 185 | 5.77 | 18.48 |
| 186 | 16.31 | 25.06 |
| 187 | 38.75 | 24.05 |
| 188 | 40.61 | 27.27 |
| 189 | 23.5 | 24.51 |
| 190 | 39.3 | 24.73 |
| 191 | 27.07 | 26.8 |
| 192 | 31.72 | 32.19 |
| 193 | 142.17 | 33.77 |
| 194 | 42.77 | 26.19 |
| 195 | 16.03 | 26.33 |
| 196 | 9990 | 89.38 |
| 197 | 25.7 | 27.76 |
| 198 | 28.69 | 28.11 |
| 199 | 21.72 | 27.85 |
| 200 | 15.94 | 26.86 |
| 201 | 42.51 | 27.16 |
| 202 | 5.17 | 23.85 |
| 203 | 37.53 | 11.27 |
| 204 | 29.77 | 10.86 |

TABLE 3C

| DC$_{50}$ value and Emax Value | | |
|---|---|---|
| Ex. | HiBit 24 h DC50 [nM] | HiBit 24 h Emax [%] |
| 215 | 18.65 | 7.82 |
| 216 | 25.2 | 10.1 |
| 217 | 17.99 | 8.83 |
| 218 | 11.35 | 6.96 |
| 219 | 21.7 | 13.91 |
| 220 | 46.97 | 10.53 |
| 221 | 30.55 | 10.28 |
| 222 | 20.04 | 24.42 |
| 223 | 29.64 | 10.51 |
| 224 | 22.88 | 9.09 |
| 225 | >5000 | 65.26 |
| 226 | 39.42 | 28.17 |

TABLE 4D

| DC$_{50}$ value and Emax Value | | |
|---|---|---|
| Ex. | HiBit 24 h DC50 [nM] | HiBit 24 h Emax [%] |
| 228 | 18.65 | 7.82 |

Pharmaceutical Compositions

A selected compound of the present invention or its pharmaceutically acceptable salt can be administered as the neat chemical, but is often administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.001 mg to about 1000 mg, from about 0.01 mg to about 800 mg, from about 1 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about, or no more than, 0.001, 0.005, 0.010, 0.10, 1, 5, 10, 25, 50, 100, 200, 250, 300, 400, 500, 600, 700, or 750 mg of active compound, or its salt.

In certain embodiments the pharmaceutical composition is in a dosage form that contains about 70 mg of active compound or its salt. In certain embodiments the pharmaceutical composition is in a dosage form that contains about 400 mg of active compound or its salt. In certain embodiments the pharmaceutical composition is in a dosage form that contains about 800 mg of active compound or its salt.

In certain embodiments the compound is administered twice per day to a patient in need thereof.

Compounds disclosed herein may be administered orally, topically, systemically, parenterally, by inhalation or spray, sublingually, via implant, including ocular implant, transdermally, via buccal administration, rectally, as an ophthalmic solution, injection, including intravenous, intra-aortal, intracranial, subdermal, intraperitoneal, subcutaneous, transnasal, sublingual, or rectal or by other means, in dosage unit formulations containing conventional pharmaceutically acceptable carriers.

The pharmaceutical composition may be formulated as any pharmaceutically useful form, e.g., as a solid dosage form, liquid, an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and should be of sufficiently high purity and sufficiently low toxicity to render them suitable for administration in an effective amount to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

In certain embodiments the LNP contains a cationic or ionizable limit. Examples include but are not limited to: U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes.

Formulations suitable for rectal administration are sometimes presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6): 318 (1986)) and sometimes take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional Pharmaceutical Compositions

A compound of Formula I, Formula, Formula III, Formula IV, Formula V, or Formula VI and/or the pharmaceutically acceptable salts thereof can be used as therapeutically active substances, e.g., in the form of pharmaceutical preparations. The pharmaceutical preparations can be administered orally, e.g., in the form of tablets, coated tablets, dragées, hard and soft gelatin capsules, solutions, emulsions or suspensions. The administration can, however, also be affected rectally, e.g., in the form of suppositories, or parenterally, e.g., in the form of injection solutions.

A compound of Formula I, Formula, Formula III, Formula IV, Formula V, or Formula VI and/or the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of Formula I, Formula, Formula III, Formula IV, Formula V, or Formula VI and/or a pharmaceutically acceptable salt thereof and a therapeutically inert carrier are also provided by the present invention, as is a process for their production, which comprises bringing one or more compounds of Formula I, Formula, Formula III, Formula IV, Formula V, or Formula VI, and/or a pharmaceutically acceptable salt thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration, the dosage for adults can vary from about 0.01 mg to about 1000 mg per day of a compound of Formula I, Formula, Formula III, Formula IV, Formula V, or Formula VI or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of Formula I, Formula, Formula III, Formula IV, Formula V, or Formula VI of the corresponding amount of a pharmaceutically acceptable salt thereof.

Examples of compositions according to the invention are:

Example A

Tablets of the following composition are manufactured in the usual manner:

TABLE 5 possible tablet composition

| Ingredient | mg/tablet 5 | 25 | 100 | 500 |
|---|---|---|---|---|
| Compound of formula (I, II, III, IV, V, or VI) | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 6 possible capsule ingredient composition

| Ingredient | mg/capsule 5 | 25 | 100 | 500 |
|---|---|---|---|---|
| Compound of formula (I, II, III, IV, V, or VI) | 5 | 25 | 100 | 500 |
| Hydrous Lactose | 159 | 123 | 148 | — |
| Corn Starch | 25 | 35 | 40 | 70 |
| Talc | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of Formula I, Formula, Formula III, Formula IV, Formula V, or Formula VI, lactose and corn starch are firstly mixed in a mixer and then in a comminuting machine. The mixture is returned to the mixer; the talc is added thereto and mixed thoroughly. The mixture is filled by machine into suitable capsules, e.g., hard gelatin capsules.

Example B-2

Soft Gelatin Capsules of the following composition are manufactured:

TABLE 7 possible soft gelatin capsule ingredient composition

| Ingredient | mg/capsule |
|---|---|
| Compound of formula (I, II, III, IV, V, or VI) | 5 |
| Yellow wax | 8 |
| Hydrogenated Soya bean oil | 8 |
| Partially hydrogenated plant oils | 34 |
| Soya bean oil | 110 |
| Total | 165 |

TABLE 8 possible soft gelatin capsule composition

| Ingredient | mg/capsule |
|---|---|
| Gelatin | 75 |
| Glycerol 85 % | 32 |

TABLE 8-continued

| possible soft gelatin capsule composition | |
|---|---|
| Ingredient | mg/capsule |
| Karion 83 | 8 (dry matter) |
| Titan dioxide | 0.4 |
| Iron oxide yellow | 1.1 |
| Total | 116.5 |

Manufacturing Procedure

The compound of Formula I, Formula, Formula III, Formula IV, Formula V, or Formula VI is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 9

| possible suppository composition | |
|---|---|
| Ingredient | mg/supp. |
| Compound of formula (I, II, III, IV, V, or VI) | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of Formula I, Formula, Formula III, Formula IV, Formula V, or Formula VI is added thereto and stirred until it has dispersed completely. The mixture is poured into suppository molds of suitable size, left to cool; the suppositories are then removed from the molds and packed individually in wax paper or metal foil.

Example D

Injection solutions of the following composition are manufactured:

TABLE 10

| possible injection solution composition | |
|---|---|
| Ingredient | mg/injection solution. |
| Compound of formula (I, II, III, IV, V, or VI) | 3 |
| Polyethylene Glycol 400 | 150 |
| acetic acid | q.s. ad pH 5.0 |
| water for injection solutions | ad 1.0 ml |

Manufacturing Procedure

The compound of Formula I, Formula, Formula III, Formula IV, Formula V, or Formula VI is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 11

| possible sachet composition | |
|---|---|
| Ingredient | mg/sachet |
| Compound of formula (I, II, III, IV, V, or VI) | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of Formula I, Formula, Formula III, Formula IV, Formula V, or Formula VI is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier may separate two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

Synthesis of Representative Compounds of the Present Invention

Abbreviations

ACN=acetonitrile; Boc=tert-butyloxycarbonyl; dba=dibenzylideneacetone; COMU=(1-cyano-2-ethoxy-2-oxoethylidenaminooxy)dimethylamino-morpholino-carbenium hexafluorophosphat, 1-[(1-(cyan-2-ethoxy-2-oxoethylidenaminooxy)-dimethylamino-morpholino)]-uronium-hexafluorophosphat; DBU=1,8-diazabicyclo[5.4.0]undec-7-ene; DCM=dichloromethane; DMAc=dimethylacetamide; DMAP=4-dimethylaminopyridine; DMF=dimethylformamide; DMSO=dimethyl sulfoxide; dppf=1,1'-bis(diphenylphosphino)ferrocene; ESI=electrospray ionization; EtOAc=ethyl acetate; Ex=example; HATU=hexafluorophosphate azabenzotriazole tetramethyl uronium; HPLC=high performance liquid chromatogaphy; IPA=isopropanol; LC-MS=liquid chromatography coupled with mass spectrometry; MS=mass spectrometry; MTBE=methyl tert-butyl ether; NBS=N-bromosuccinimide; NIS=N-iodosuccinimide; NMR=nuclear magnetic resonance; PEPPSI=pyridine-enhanced precatalyst preparation, stabilization, and initiation; PG=protecting group; pin=pinacolato; rt=room temperature; SFC=supercritical fluid chromatography; TEA=triethylamine; Tf=triflate; TFA=trifluoroacetic acid; THF=tetrahydrofuran; TLC=thin layer chromatography; Ts=tosylate; UPLC=ultra performance liquid chromatography.

Synthesis of Intermediates

Scheme I

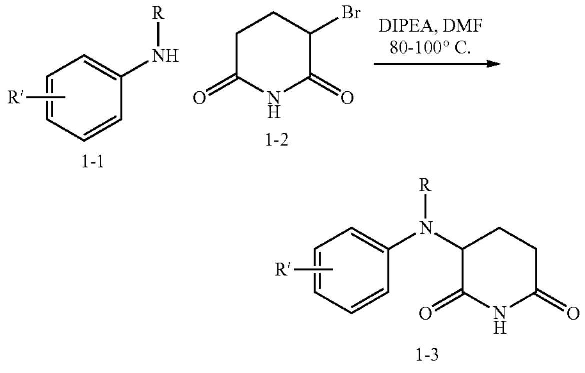

1-1 1-2 1-3

R = H, $CH_3$

General procedure for scheme I: To a mixture of 1-1 (1 mmol) and 1-2 (2 mmol) in dioxane (3 mL) was added N,N-diisopropylethylamine (2 mmol). The resulting solution was heated in a sealed tube at 70-110° C. for 24 hours to produce 1-3. Reaction mixture was then cooled to room temperature, diluted with water, and extracted with Ethyl acetate. The combined Ethyl acetate extract was washed with brine, dried over anhydrous sodium sulfate and concentrated under reduced pressure. The residue was purified by column chromatography (silica, gradient: 0-3% methanol in dichloromethane) to afford 1-3.

Intermediate tert-butyl 4-(4-((2,6-dioxopiperidin-3-yl)amino)phenyl)piperidine-1-carboxylate

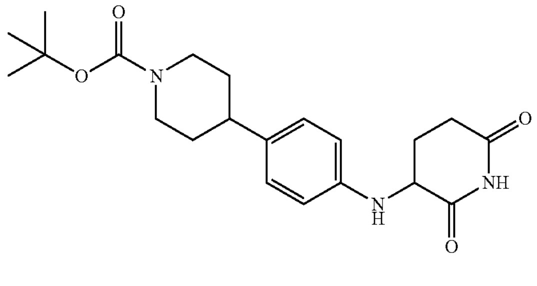 [SMILES: CC(C)(C)OC(=O)N1CCC(c2ccc(NC3CCC(=O)NC3=O)cc2)CC1]

tert-butyl 4-(4-((2,6-dioxopiperidin-3-yl)amino)phenyl)piperidine-1-carboxylate was synthesized from tert-Butyl 4-(4-aminophenyl)-1-piperidinecarboxylate (CAS #170011-57-1) following general procedure (N,N-diisopropylethylamine/Dioxane). Yield-45%; $^1$H NMR (400 MHz, DMSO-$d_6$) δ=10.75 (s, 1H), 6.94 (d, J=8.16 Hz, 2H), 6.60 (d, J=7.88 Hz, 2H), 5.64 (d, J=6.96 Hz, 1H), 4.28-4.24 (m, 1H), 4.07-4.00 (m, 2H), 2.79-2.64 (m, 4H), 2.53-2.48 (m, 2H), 2.11-2.05 (m, 1H), 1.89-1.81 (m, 1H), 1.71-1.64 (m, 2H0, 1.40-1.34 (m, 10H); LC-MS (ES$^-$): m/z 386.3 [M−H]$^-$.

Intermediate tert-butyl 4-(4-((2,6-dioxopiperidin-3-yl)amino)phenyl)piperazine-1-carboxylate

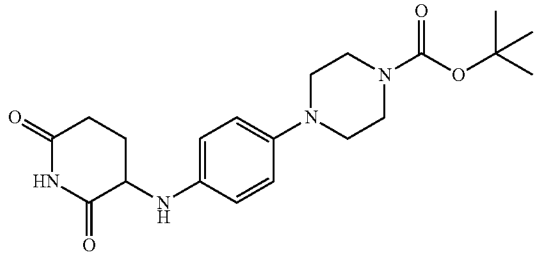 [SMILES: CC(C)(C)OC(=O)N1CCN(c2ccc(NC3CCC(=O)NC3=O)cc2)CC1]

Tert-butyl 4-(4-((2,6-dioxopiperidin-3-yl)amino)phenyl) piperazine-1-carboxylate was synthesized following general procedure (DIPEA/DMF). Yield-50%; LC-MS (ES$^+$): m/z 389.2 [M+H]$^+$.

Scheme II

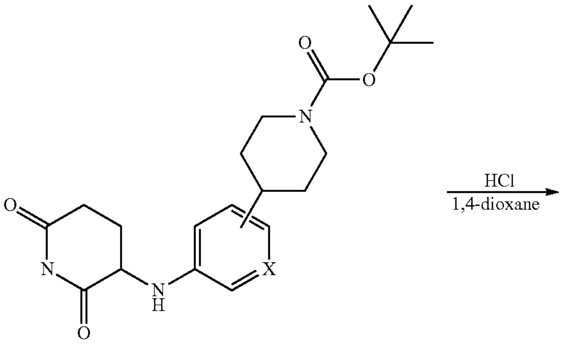

2-1
X = N, CH

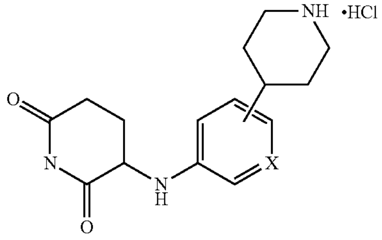

2-2
X = N, CH

General procedure for scheme II: To 2-1 dissolved in methanol (0.1 M) at room temperature was added hydrogen chloride (4M in 1,4-dioxane, 5 equiv.) and the reaction mixture was heated at 40° C. for 2 hours. The volatiles were evaporated under reduced pressure to afford 2-2.

Intermediate 3-((4-(piperidin-4-yl)phenyl)amino) piperidine-2,6-dione hydrochloride

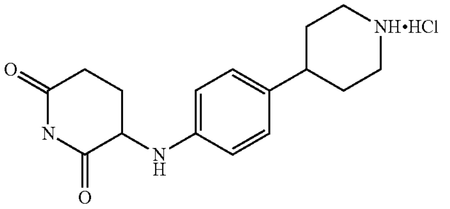

3-((4-(piperidin-4-yl)phenyl)amino)piperidine-2,6-dione hydrochloride was synthesized from tert-butyl 4-(4-((2,6-dioxopiperidin-3-yl)amino)phenyl)piperidine-1-carboxylate following general procedure. Yield-88%; $^1$H NMR (400 MHz, DMSO-$d_6$): δ=10.80 (s, 1H), 8.84 (brs, 1H), 8.77 (brs, 1H), 6.95 (d, J=8.44 Hz, 2H), 6.66 (d, J=8.48 Hz, 2H), 4.29 (dd, J=11.4, 4.72 Hz, 1H), 3.35-3.29 (m, 2H), 2.99-2.91 (m, 2H), 2.71-2.53 (m, 3H), 2.10-2.05 (m, 1H), 1.89-1.71 (m, 5H); LC-MS (ES$^+$): m/z 288.2 [M+H]$^+$.

Intermediate 3-((4-(piperazin-1-yl)phenyl)amino) piperidine-2,6-dione hydrochloride

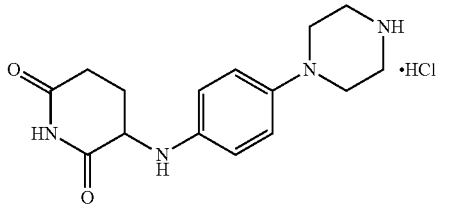 [SMILES: O=C1CCC(Nc2ccc(N3CCNCC3)cc2)C(=O)N1 ; Cl]

3-((4-(piperazin-1-yl)phenyl)amino)piperidine-2,6-dione hydrochloride was synthesized following general procedure (Boc-deprotection). Yield-92%; $^1$H NMR (400 MHz, MeOD): δ=7.38 (d, 8.52 Hz, 2H), 7.21 (d, J=8.6 Hz, 2H), 4.71-4.65 (m, 1H), 3.53 (brs, 4H), 3.40 (brs, 4H), 2.74-2.66 (m, 2H), 2.04 (brs, 2H); LC-MS (ES$^+$): m/z 289.1 [M+H]$^+$.

Synthesis of Intermediate 3-(3-Fluoro-4-piperidin-4-yl-phenylamino)-piperidine-2,6-dione hydrochloride

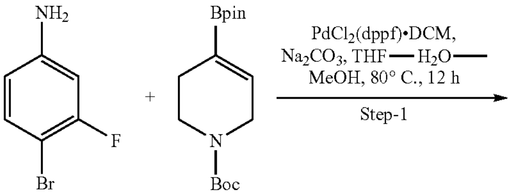

-continued

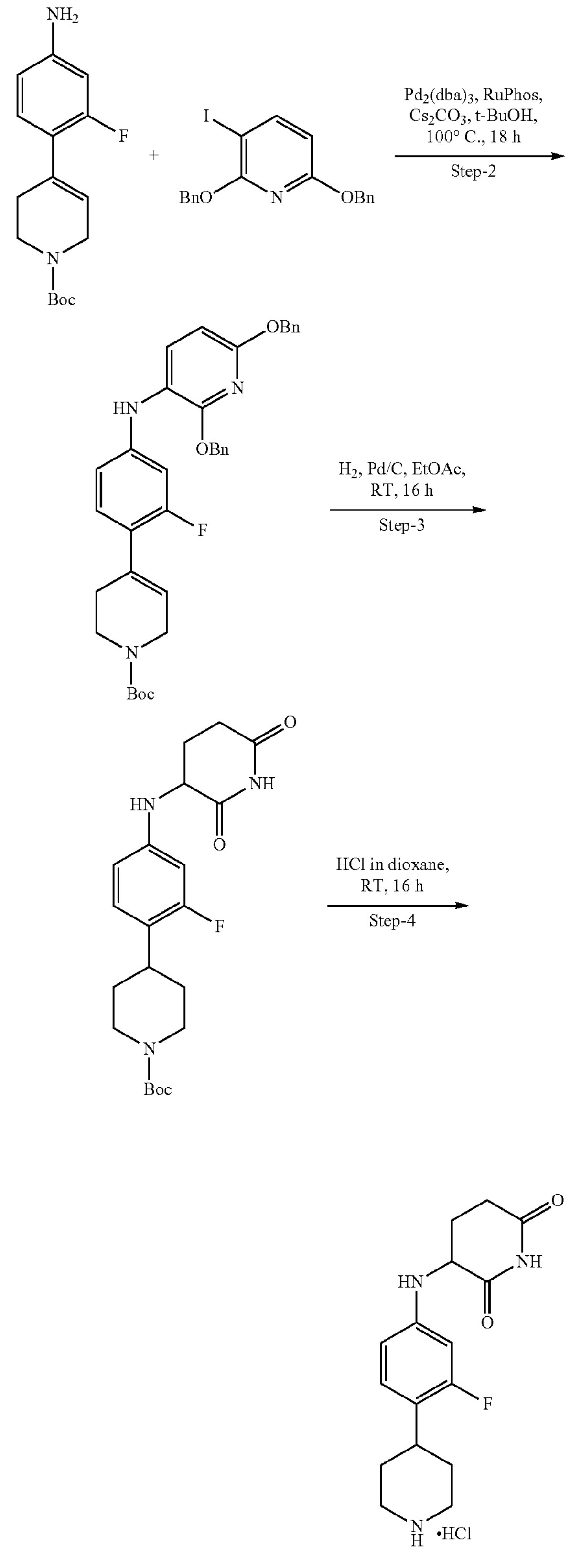

Step-1: Sodium carbonate (6.14 g, 57.89 mmol) was added to a stirred solution of 4-bromo-3-fluoro-aniline (5.00 g, 26.3 mmol) and tert-butyl 4-(4,4,5,5-tetramethyl-1,3,2-dioxaborolan-2-yl)-3,6-dihydro-2H-pyridine-1-carboxylate (8.95 g, 29.0 mmol) in water (12 mL), THF (60 mL) and methanol (24 mL) and the flask was thoroughly purged with argon. $PdCl_2$(dppf)·dichloromethane (430 mg, 526 μmol) was added and the reaction mixture was degassed with nitrogen and then heated at 80° C. for 12 h. The reaction mixture was diluted with ethyl acetate, filtered through a short pad of celite and washed with ethyl acetate. The combined organic extracts were washed with water and brine, dried over anhydrous sodium sulfate, filtered and concentrated under reduced pressure. The residue was purified by column chromatography (15% ethyl acetate-hexane) to get tert-butyl 4-(4-amino-2-fluoro-phenyl)-3,6-dihydro-2H-pyridine-1-carboxylate (6.1 g, 20.9 mmol, 79% yield) as pale-yellow solid. LCMS ($ES^+$): m/z 293 $[M+H]^+$.

Step-2: Cesium carbonate (19.73 g, 60.54 mmol) was added to a stirred solution of tert-butyl 4-(4-amino-2-fluoro-phenyl)-3,6-dihydro-2H-pyridine-1-carboxylate (5.9 g, 20.2 mmol) and 2,6-dibenzyloxy-3-iodo-pyridine (9.26 g, 22.2 mmol) in t-BuOH (60 mL) The resulting mixture was degassed with argon and $Pd_2(dba)_3$ (924 mg, 1.01 mmol), RuPhos (942 mg, 2.02 mmol) were added under inert atmosphere. The resulting mixture was heated at 100° C. for 18 h. The reaction mixture was diluted with ethyl acetate, filtered through a short pad of celite and washed with ethyl acetate. The combined organic extracts were washed with water and brine, dried over anhydrous sodium sulfate, filtered and concentrated under reduced pressure. The residue was purified by column chromatography (15% ethyl acetate-hexane) to get tert-butyl 4-[4-[(2,6-dibenzyloxy-3-pyridyl)amino]-2-fluoro-phenyl]-3,6-dihydro-2H-pyridine-1-carboxylate (5.9 g, 10.1 mmol, 50% yield) as pale-yellow solid. LCMS ($ES^+$): m/z 582 $[M+H]^+$.

Step-3: 10% Pd-C (50% wet, 4.6 g) was added to a stirred nitrogen-degassed solution of tert-butyl 4-[4-[(2,6-dibenzyloxy-3-pyridyl)amino]-2-fluoro-phenyl]-3,6-dihydro-2H-pyridine-1-carboxylate (4.6 g, 7.91 mmol) in ethyl acetate (40 mL). The resulting mixture was stirred at ambient temperature under hydrogen balloon pressure for 20 h. The reaction mixture was filtered through a small pad of celite and washed with ethyl acetate. The combined filtrate was evaporated under reduced pressure and purified by column chromatography (40% ethyl acetate in hexane) to afford tert-butyl 4-[4-[(2,6-dioxo-3-piperidyl)amino]-2-fluoro-phenyl]piperidine-1-carboxylate (2.6 g, 6.41 mmol, 81% yield) as a blue solid. LCMS ($ES^+$): m/z 406 $[M+H]^+$.

Step-4: Dioxane-HCl (4M, 30 mL, 130 mmol) was added to tert-butyl 4-[4-[(2,6-dioxo-3-piperidyl)amino]-2-fluoro-phenyl]piperidine-1-carboxylate (1.3 g, 3.21 mmol) at 10° C. the resulting mixture was warmed to ambient temperature and stirred for 16 h. The reaction mixture was concentrated under reduced pressure, triturated with ether and lyophilized to yield 3-[3-fluoro-4-(4-piperidyl)anilino]piperidine-2,6-dione (840 mg, 2.73 mmol, 85.25% yield) as green solid. LCMS ($ES^+$): m/z 306 $[M+H]^+$. $^1H$ NMR (400 MHz, DMSO-$d_6$): δ=10.79 (s, 1H), 9.00 (br s, 1H), 8.85-8.83 (m, 1H), 6.96-6.91 (m, 1H), 6.50-6.45 (m, 2H), 4.34-4.30 (m, 1H), 3.32-3.29 (m, 2H), 2.98-2.93 (m, 3H), 2.77-2.69 (m, 1H), 2.60-2.56 (m, 1H), 2.08-2.05 (m, 1H), 1.92-1.81 (m, 5H).

Synthesis of 2-[4-[4-[[(3S)-2,6-dioxo-3-piperidyl]amino]-2-fluoro-phenyl]-1-piperidyl]acetic acid and 2-[4-[4-[[(3R)-2,6-dioxo-3-piperidyl]amino]-2-fluoro-phenyl]-1-piperidyl]acetic acid

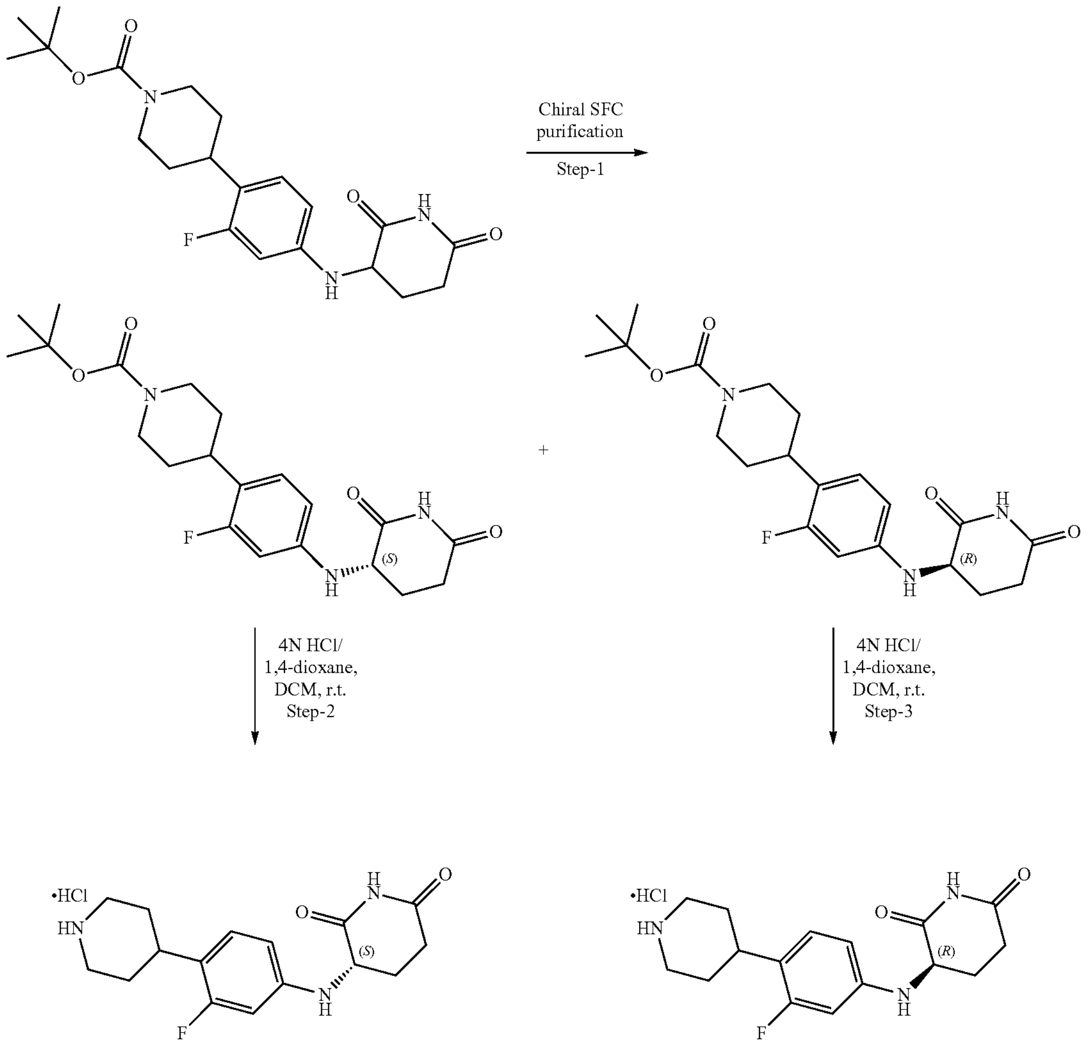

Step-1: The racemic compound tert-butyl 4-[4-[(2,6-dioxo-3-piperidyl)amino]-2-fluoro-phenyl]piperidine-1-carboxylate (10 g, 23.67 mmol) was treated with chiral SFC separation (mobile phase: 40% IPA-$CO_2$; flow rate: 120 mL/min; cycle time: 7.6 min; back pressure: 100 bar; UV: 210 nm) to afford peak 1 (first eluted) tert-butyl 4-[4-[[(3S)-2,6-dioxo-3-piperidyl]amino]-2-fluoro-phenyl]piperidine-1-carboxylate (2.9 g, 7.13 mmol, 29% yield, 99.252% ee) as an off-white solid and peak 2 (second eluted) tert-butyl 4-[4-[[(3R)-2,6-dioxo-3-piperidyl]amino]-2-fluoro-phenyl]piperidine-1-carboxylate (3.1 g, 7.44 mmol, 30% yield, 94.588% ee) as a white solid.

Step-2: To a stirred solution of tert-butyl 4-[4-[[(3S)-2,6-dioxo-3-piperidyl]amino]-2-fluoro-phenyl]piperidine-1-carboxylate (400 mg, 986.53 μmol) in anhydrous dichloromethane (10 mL) was added dropwise 4.0 M HCl in 1,4-dioxane (4 mL) at 0° C. under nitrogen atmosphere. The resulting reaction mixture was stirred at ambient temperature for 2 h. After completion of the reaction, excess solvent was removed from the reaction mixture under reduced pressure to get a crude, which was co-distilled with dichloromethane to afford (3S)-3-[3-fluoro-4-(4-piperidyl)anilino]piperidine-2,6-dione (300 mg, 871.54 μmol, 88% yield) as an off-white solid. LCMS ($ES^+$): m/z 306.2 $[M+H]^+$.

Step-3: To a well-stirred solution of tert-butyl 4-[4-[[(3R)-2,6-dioxo-3-piperidyl]amino]-2-fluoro-phenyl]piperidine-1-carboxylate (300 mg, 739.90 μmol) in dichloromethane (15 mL) was added hydrogen chloride solution 4.0M in dioxane (3 mL) at 0° C. The resulting reaction mixture was stirred at room temperature for 1 h. After completion of the reaction, the reaction mixture was concentrated under vacuum and washed with diethyl ether to afford (3R)-3-[3-fluoro-4-(4-piperidyl)anilino]piperidine-2,6-dione (250 mg, 699.96 μmol, 95% yield) as an off-white solid. LCMS ($ES^+$): m/z 306.2 $[M+H]^+$.

Synthesis of 3-(2-Fluoro-4-piperidin-4-yl-phenylamino)-piperidine-2,6-dione hydrochloride

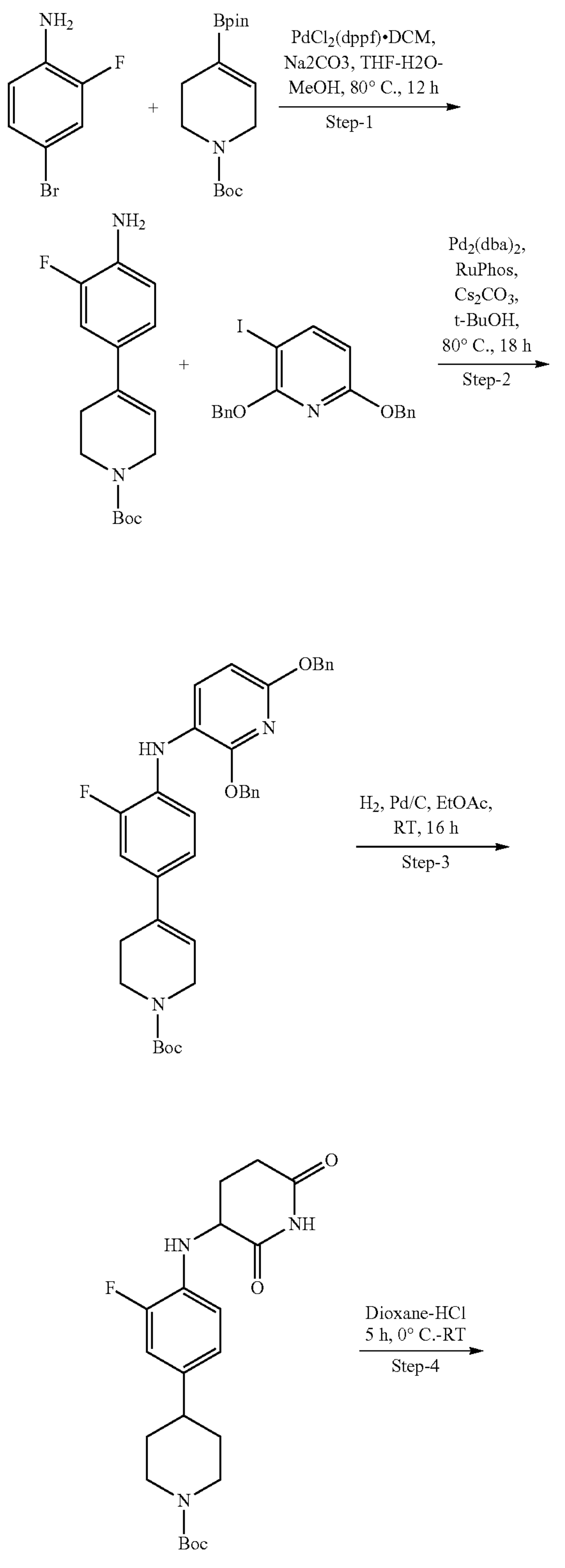

-continued

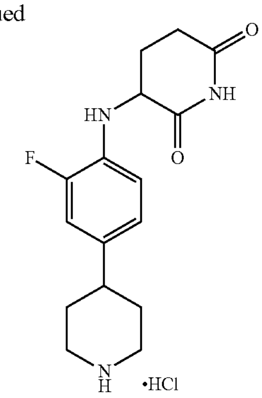

Step-1: Sodium carbonate (6.14 g, 57.89 mmol) was added to a stirred solution of 4-bromo-2-fluoro-aniline (5.00 g, 26.3 mmol) and tert-butyl 4-(4,4,5,5-tetramethyl-1,3,2-dioxaborolan-2-yl)-3,6-dihydro-2H-pyridine-1-carboxylate (8.95 g, 29.0 mmol) in water (12 mL), THF (60 mL) and methanol (24 mL). The resulting mixture was degassed with argon and $PdCl_2$(dppf)·dichloromethane (430 mg, 526 μmol) was added under inert atmosphere. The resulting mixture was heated at 80° C. for 12 h. The reaction mixture was diluted with ethyl acetate, filtered through a short pad of celite and washed with ethyl acetate. The combined organic extracts were washed with water, brine, dried over anhydrous sodium sulfate, filtered and concentrated under reduced pressure. The residue was purified by column chromatography (15% ethyl acetate-hexane) to yield tert-butyl 4-(4-amino-3-fluoro-phenyl)-3,6-dihydro-2H-pyridine-1-carboxylate (6.1 g, 20.9 mmol, 79% yield) as pale-yellow solid. LCMS ($ES^+$): m/z 293 $[M+H]^+$.

Step-2: Cesium carbonate (19.73 g, 60.54 mmol) was added to a stirred solution of tert-butyl 4-(4-amino-3-fluoro-phenyl)-3,6-dihydro-2H-pyridine-1-carboxylate (5.9 g, 20.2 mmol) and 2,6-dibenzyloxy-3-iodo-pyridine (9.26 g, 22.2 mmol) in t-BuOH (60 mL). The resulting mixture was degassed with argon and $Pd_2(dba)_3$ (924 mg, 1.01 mmol) and RuPhos (942 mg, 2.02 mmol) were added under inert atmosphere. The resulting mixture was heated at 100° C. for 18 h. The reaction mixture was diluted with ethyl acetate, filtered through a short pad of celite and washed with ethyl acetate. The combined organic extracts were washed with water, brine, dried over anhydrous sodium sulfate, filtered and concentrated under reduced pressure. The residue was purified by column chromatography (10% ethyl acetate-hexane) to yield tert-butyl 4-[4-[(2,6-dibenzyloxy-3-pyridyl)amino]-3-fluoro-phenyl]-3,6-dihydro-2H-pyridine-1-carboxylate (5.9 g, 10.1 mmol, 50% yield) as pale-yellow solid. LCMS ($ES^+$): m/z 582 $[M+H]^+$.

Step-3: 10% Pd-C (50% wet, 4.6 g) was added to a stirred degassed solution of tert-butyl 4-[4-[(2,6-dibenzyloxy-3-pyridyl)amino]-3-fluoro-phenyl]-3,6-dihydro-2H-pyridine-1-carboxylate (4.6 g, 7.91 mmol) in ethyl acetate (40 mL). The resulting mixture was stirred at ambient temperature under hydrogen balloon pressure for 20 h. The reaction mixture was filtered through a short pad of celite and washed with ethyl acetate. The combined filtrate was evaporated under reduced pressure and purified by column chromatography (40% ethyl acetate-hexane) to yield tert-butyl 4-[4-[(2,6-dioxo-3-piperidyl)amino]-3-fluoro-phenyl]piperidine-1-carboxylate (2.6 g, 6.41 mmol, 81% yield) as a blue solid. LCMS ($ES^+$): m/z 406 $[M+H]^+$.

Step-4: Dioxane HCl (4M, 10 mL, 40 mmol) was added to tert-butyl 4-[4-[(2,6-dioxo-3-piperidyl)amino]-3-fluoro-phenyl]piperidine-1-carboxylate (1.3 g, 3.21 mmol) at 10° C. The resulting mixture was warmed to ambient temperature and stirred for 16 h. The reaction mixture was concentrated under reduced pressure, triturated with ether and lyophilized to yield 3-[2-fluoro-4-(4-piperidyl)anilino]piperidine-2,6-dione hydrochloride (840 mg, 2.73 mmol, 85% yield) as a green solid. LCMS ($ES^+$): m/z 306 $[M+H]^+$. $^1H$ NMR (400 MHz, DMSO-$d_6$): δ=10.82 (s, 1H), 8.85 (br s, 1H), 8.69-8.68 (m, 1H), 6.92-6.89 (m, 1H), 6.83-6.77 (m, 2H), 4.40-4.36 (m, 2H), 3.37-3.31 (m, 2H), 2.98-2.90 (m, 2H), 2.76-2.71 (m, 2H), 2.58-2.56 (m, 1H), 2.05-1.73 (m, 6H).

General Procedure for the Alkylation of Intermediates with Tert-Butyl 2-Bromoacetate:

Synthesis of tert-butyl 2-[4-[4-[(2,6-dioxo-3-piperidyl)amino]phenyl]-1-piperidyl]acetate

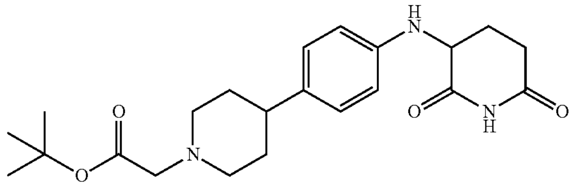 [SMILES: CC(C)(C)OC(=O)CN1CCC(c2ccc(NC3CCC(=O)NC3=O)cc2)CC1]

3-[4-(4-piperidyl)anilino]piperidine-2,6-dione hydrochloride (1 g, 3.09 mmol) was dissolved in N,N-dimethylacetamide (15 mL) and N,N-diisopropylethylamine (1.60 g, 12.4 mmol, 2.15 mL) was added. The mixture was cooled to 0° C., and tert-butyl 2-bromoacetate (663 mg, 3.40 mmol, 498 μL) was added. The mixture was stirred at 0° C. for 4 h. The reaction was diluted with ethyl acetate and washed with saturated sodium bicarbonate and brine. The organic layer was concentrated and purified by silica gel chromatography (0-10% methanol in dichloromethane) to yield tert-butyl 2-[4-[4-[(2,6-dioxo-3-piperidyl)amino]phenyl]-1-piperidyl]acetate (0.84 g, 2.09 mmol, 68% yield) as a white solid. LCMS ($ES^+$): m/z 402.2 $[M+H]^+$.

The following compounds were synthesized using General procedure, as that used for the synthesis of tert-butyl 2-[4-[4-[(2,6-dioxo-3-piperidyl)amino]phenyl]-1-piperidyl]acetate from 3-[14-(4-piperidyl)anilino]piperidine-2,6-di one hydrochloride.

| Starting material | Product | LCMS (ESI+) m/z | % Yield |
|---|---|---|---|
| 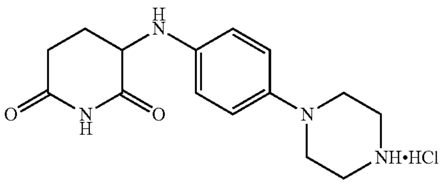 3-((4-(piperazin-1-yl)phenyl)amino)piperidine-2,6-dione hydrochloride | 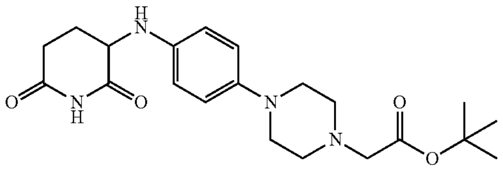 [SMILES: CC(C)(C)OC(=O)CN1CCN(c2ccc(NC3CCC(=O)NC3=O)cc2)CC1] tert-butyl 2-(4-(4-((2,6-dioxopiperidin-3-yl)amino)phenyl)piperazin-1-yl)acetate | 403.2 $[M + H]^+$ | 82% |
| 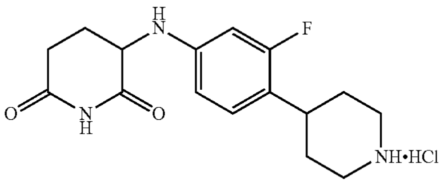 3-((3-fluoro-4-(piperidin-4-yl)phenyl)amino)piperidine-2,6-dione hydrochloride | 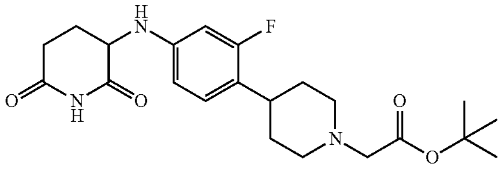 [SMILES: CC(C)(C)OC(=O)CN1CCC(c2ccc(NC3CCC(=O)NC3=O)cc2F)CC1] tert-butyl 2-(4-(4-((2,6-dioxopiperidin-3-yl)amino)-2-fluorophenyl)piperidin-1-yl)acetate | 420.2 $[M + H]^+$ | 72% |
| 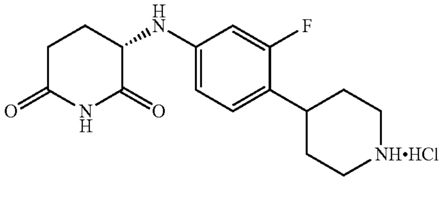 (S)-3-((3-fluoro-4-(piperidin-4-yl)phenyl)amino)piperidine-2,6-dione hydrochloride | 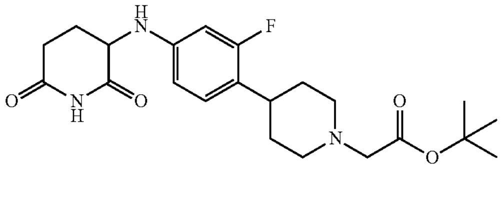 [SMILES: CC(C)(C)OC(=O)CN1CCC(c2ccc(NC3CCC(=O)NC3=O)cc2F)CC1] tert-butyl (S)-2-(4-(4-((2,6-dioxopiperidin-3-yl)amino)-2-fluorophenyl)piperidin-1-yl)acetate | 420.2 $[M + H]^+$ | 69% |

-continued

| Starting material | Product | LCMS (ESI+) m/z | % Yield |
|---|---|---|---|
| 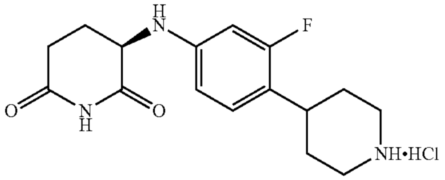 (R)-3-((3-fluoro-4-(piperidin-4-yl)phenyl)amino)piperidine-2,6-dione hydrochloride | 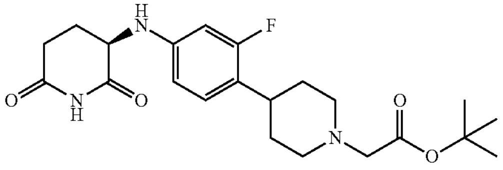 [SMILES: CC(C)(C)OC(=O)CN1CCC(c2ccc(N[C@@H]3CCC(=O)NC3=O)cc2F)CC1] tert-butyl (R)-2-(4-(4-((2,6-dioxopiperidin-3-yl)amino)-2-fluorophenyl)piperidin-1-yl)acetate | 420.2 $[M + H]^+$ | 63% |
| 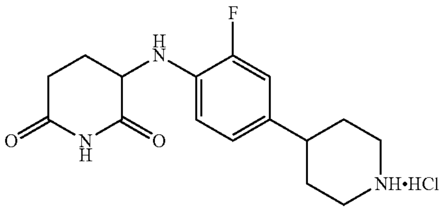 3-((2-fluoro-4-(piperidin-4-yl)phenyl)amino)piperidine-2,6-dione hydrochloride | 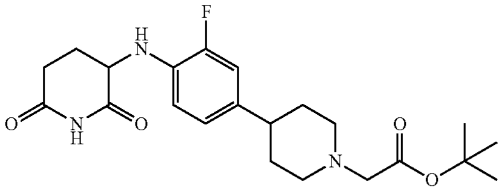 [SMILES: CC(C)(C)OC(=O)CN1CCC(c2ccc(NC3CCC(=O)NC3=O)c(F)c2)CC1] tert-butyl 2-(4-(4-((2,6-dioxopiperidin-3-yl)amino)-3-fluorophenyl)piperidin-1-yl)acetate | 420.2 $[M + H]^+$ | 65% |

General Procedure for the Tert-Butyl Ester Cleavage of Intermediates:

2-[4-[4-[(2,6-dioxo-3-piperidyl)amino]phenyl]-1-piperidyl]acetic acid, trifluoroacetic acid salt

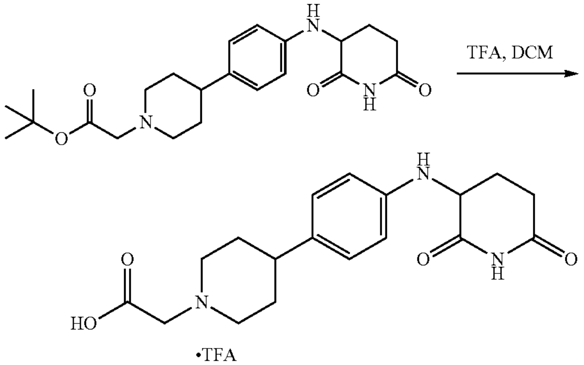

tert-Butyl 2-[4-[4-[(2,6-dioxo-3-piperidyl)amino]phenyl]-1-piperidyl]acetate was dissolved in dichloromethane (5 mL) and TFA (1.61 mL, 20.9 mmol) was added. The reaction mixture was heated at 40° C. for 4 h, and the reaction was complete. The volatiles were evaporated under reduce pressure. The material was frozen to −78° C., submitted to high vacuum, and thawed to afford a dense solid. The solid was re-dissolved in methanol:dichloromethane (1:4), MTBE was added dropwise, until a precipitate formed. The suspension was submitted to sonication, and the solid was filtered under suction. The green solid was collected by filtration to afford 2-[4-[4-[(2,6-dioxo-3-piperidyl)amino]phenyl]-1-piperidyl]acetic acid, trifluoroacetic acid salt (0.95 g, 2.07 mmol, 97% yield). LCMS ($ES^+$): m/z 346.4 $[M+H]^+$.

The following intermediates were synthesized from the appropriate starting materials using general procedure for 2-[4-[4-[(2,6-dioxo-3-piperidyl)amino]phenyl]-1-piperidyl]acetic acid, trifluoroacetic acid salt synthesis.

| Starting material | Product | Yield | LCMS (ESI+) m/z |
|---|---|---|---|
| 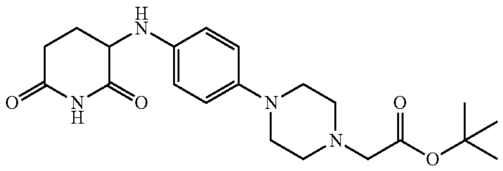 [SMILES: CC(C)(C)OC(=O)CN1CCN(c2ccc(NC3CCC(=O)NC3=O)cc2)CC1] | 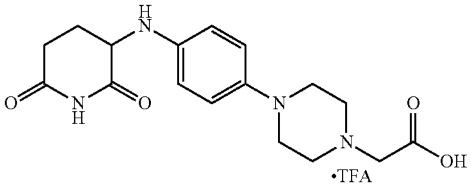 [SMILES: O=C(O)CN1CCN(c2ccc(NC3CCC(=O)NC3=O)cc2)CC1] | 90% | 347.4 $[M + H]^+$ |

-continued

| Starting material | Product | Yield | LCMS (ESI+) m/z |
|---|---|---|---|
| tert-butyl 2-(4-(4-((2,6-dioxopiperidin-3-yl)amino)phenyl)piperazin-1-yl)acetate | 2-(4-(4-((2,6-dioxopiperidin-3-yl)amino)phenyl)piperazin-1-yl)acetic acid | | |
| 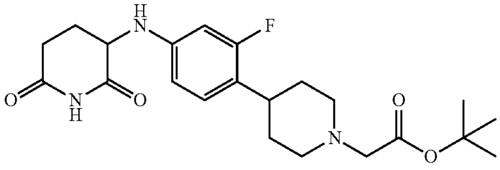 [SMILES: CC(C)(C)OC(=O)CN1CCC(c2ccc(NC3CCC(=O)NC3=O)cc2F)CC1] | 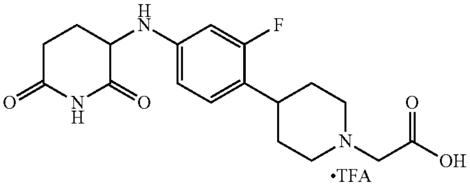 [SMILES: O=C(O)CN1CCC(c2ccc(NC3CCC(=O)NC3=O)cc2F)CC1] •TFA | >98% | 364.2 $[M + H]^+$ |
| tert-butyl 2-(4-(4-((2,6-dioxopiperidin-3-yl)amino)-2-fluorophenyl)piperidin-1-yl)acetate | 2-(4-(5-((2,6-dioxopiperidin-3-yl)amino)pyridin-2-yl)piperidin-1-yl)acetic acid | | |
| 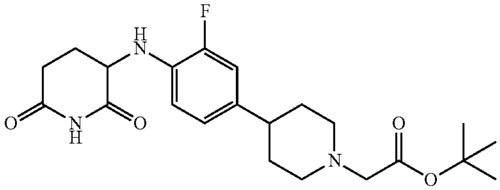 [SMILES: CC(C)(C)OC(=O)CN1CCC(c2ccc(NC3CCC(=O)NC3=O)c(F)c2)CC1] | 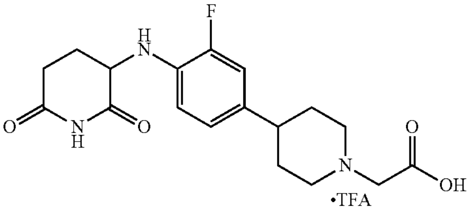 [SMILES: O=C(O)CN1CCC(c2ccc(NC3CCC(=O)NC3=O)c(F)c2)CC1] •TFA | >98% | 364.5 $[M + H]^+$ |
| tert-butyl 2-(4-(4-((2,6-dioxopiperidin-3-yl)amino)-3-fluorophenyl)piperidin-1-yl)acetate | 2-(4-(4-((2,6-dioxopiperidin-3-yl)amino)-3-fluorophenyl)piperidin-1-yl)acetic acid | | |

Synthesis of 2-[4-[4-[[(3S)-2,6-dioxo-3-piperidyl]amino]-2-fluoro-phenyl]-1-piperidyl]acetic acid and 2-[4-[4-[[(3R)-2,6-dioxo-3-piperidyl]amino]-2-fluoro-phenyl]-1-piperidyl]acetic acid

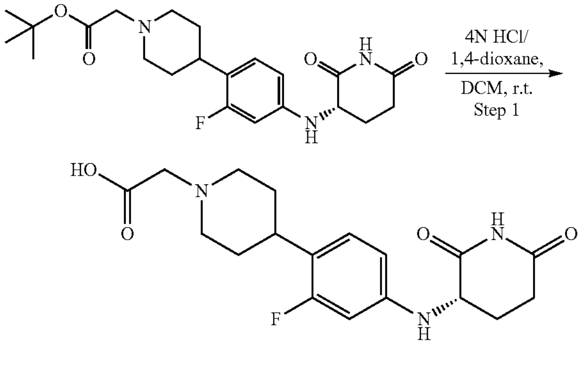

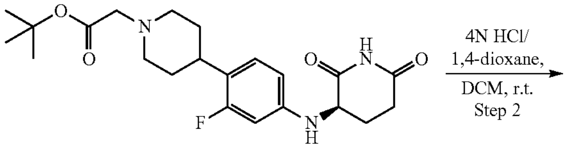

-continued

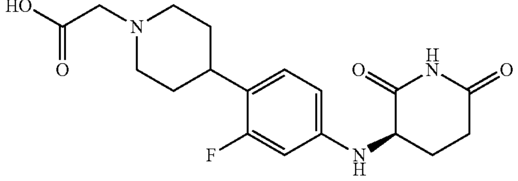

Step 1. To a well-stirred solution of tert-butyl 2-[4-[4-[[(3S)-2,6-dioxo-3-piperidyl]amino]-2-fluoro-phenyl]-1-piperidyl]acetate (330 mg, 786.67 μmol) in dichloromethane (25 mL) was added hydrogen chloride solution 4.0M in dioxane (3 mL) at 0° C., the resulting reaction mixture was stirred at room temperature for 16 h. After completion of the reaction, the reaction mixture was concentrated under vacuum and washed with diethyl ether to afford 2-[4-[4-[[(3S)-2,6-dioxo-3-piperidyl]amino]-2-fluoro-phenyl]-1-piperidyl]acetic acid (300 mg, 750.29 μmol, 95% yield) as an off-white solid. LCMS ($ES^+$): m/z 364.5 $[M+H]^+$.

Step 2. To a well-stirred solution of tert-butyl 2-[4-[4-[[(3R)-2,6-dioxo-3-piperidyl]amino]-2-fluoro-phenyl]-1-piperidyl]acetate (350 mg, 834.35 μmol) in dichloromethane (30 mL) was added hydrogen chloride solution 4.0M in dioxane (3 mL) at 0° C., the resulting reaction mixture was stirred at room temperature for 16 h. After completion of the reaction, the reaction mixture was concentrated under vacuum and washed with diethyl ether to afford 2-[4-[4-[[(3R)-2,6-dioxo-3-piperidyl]amino]-2-fluoro-phenyl]-1-piperidyl]acetic acid (320 mg, 800.31 μmol, 96% yield) as an off-white solid. LCMS ($ES^+$): m/z 364.5 $[M+H]^+$.

Synthesis of 2-[4-[4-[(2,6-dioxo-3-piperidyl)amino]-2-fluoro-phenyl]piperazin-1-yl]acetic acid

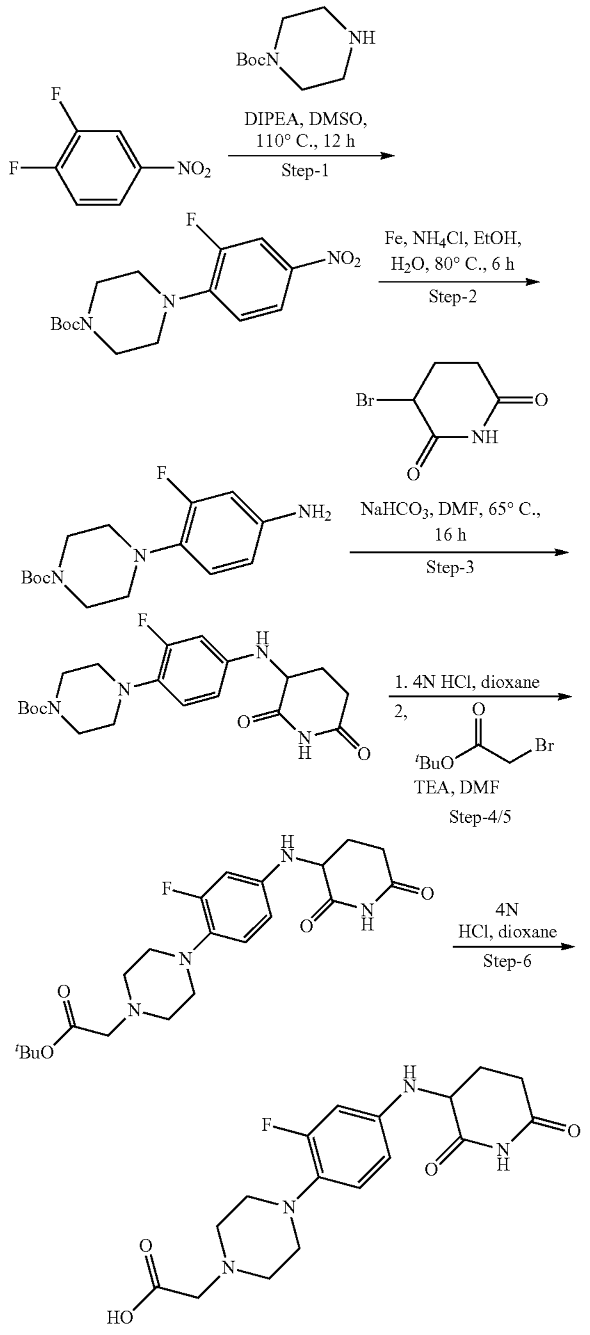

Step-1: To a stirred solution of 1,2-difluoro-4-nitrobenzene (2 g, 12.57 mmol, 1.39 mL), tert-butyl piperazine-1-carboxylate (2.34 g, 12.57 mmol) in N,N-dimethylformamide (20 mL) was added N,N-diisopropylethylamine (8.12 g, 62.86 mmol, 10.95 mL) at room temperature. The reaction mixture was heated to 110° C. for 12 h. The reaction mixture was diluted with water (10 mL) and extracted with ethyl acetate (2×30 mL). The combined organic layers were dried over sodium sulfate, filtered and concentrated under vacuum to get crude compound. The crude compound was purified by silica gel column chromatography eluted with 20-25% ethyl acetate in petroleum ether to afford tert-butyl 4-(2-fluoro-4-nitro-phenyl)piperazine-1-carboxylate (4 g, 12.30 mmol, 98% yield) as a yellow solid. $^1$HNMR (400 MHz, DMSO-$d_6$): δ=8.01-8.07 (m, 2H), 7.19 (t, J=12.80 Hz, 1H), 3.49 (t, J=7.20 Hz, 4H), 3.27 (t, J=6.80 Hz, 4H), 1.43 (s, 9H).

Step-2: To a solution of tert-butyl 4-(2-fluoro-4-nitro-phenyl)piperazine-1-carboxylate (4.1 g, 12.60 mmol) in ethanol (30 mL), water (8 mL) was added iron (3.52 g, 63.01 mmol, 447.70 μL), ammonium chloride (2.02 g, 37.81 mmol, 1.32 mL) and stirred at 70° C. for 4 h. After completion, the reaction mixture was filtered through celite pad and washed with ethyl acetate (200 mL). The filtrate was washed with water (80 mL), $NaHCO_3$ solution (60 mL) and brine (60 mL). The organic layer was dried over sodium sulfate and concentrated under reduced pressure to get crude compound. Crude compound was purified by column chromatography on silica gel eluted with 60% ethyl acetate in petroleum ether to afford tert-butyl 4-(4-amino-2-fluoro-phenyl)piperazine-1-carboxylate (3.7 g, 12.31 mmol, 98% yield). LCMS (ESI): m/z 296.1[M+H]$^+$.

Step-3: To a solution of tert-butyl 4-(4-amino-2-fluoro-phenyl)piperazine-1-carboxylate (2 g, 6.77 mmol) in N,N-dimethylformamide (20 mL) were added sodium bicarbonate (1.99 g, 23.70 mmol, 921.76 μL) followed by 3-bromopiperidine-2,6-dione (3.25 g, 16.93 mmol). The reaction mixture was stirred at 70° C. for 14 h. After completion, the reaction mixture was diluted with water (60 mL) and extracted with ethyl acetate (3×200 mL). The organic layer was washed with brine solution (10 mL), dried over sodium sulfate and concentrated under reduced pressure to get crude which was purified by column chromatography on silica gel eluted with 70% ethyl acetate in petroleum ether to afford tert-butyl 4-[4-[(2,6-dioxo-3-piperidyl)amino]-2-fluoro-phenyl]piperazine-1-carboxylate (2.73 g, 4.96 mmol, 73% yield). LCMS (ESI): m/z 407.1 [M+H]$^+$.

Step-4: To a stirred solution of tert-butyl 4-[4-[(2,6-dioxo-3-piperidyl)amino]-2-fluoro-phenyl]piperazine-1-carboxylate (2.7 g, 6.64 mmol) in 1,4-dioxane (10 mL) was added 4M hydrogen chloride solution in dioxane (4M, 10 mL) at 0° C. The reaction mixture was stirred at room temperature for 2 h. After completion, the reaction mixture was concentrated under vacuum and triturated with diethyl ether to afford 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (1.6 g, 2.38 mmol, 97% yield). LCMS (ESI): m/z 307.0 [M+H]$^+$.

Step-5: 3-(3-fluoro-4-piperazin-1-yl-anilino)piperidine-2,6-dione (2 g, 6.53 mmol) in N,N-dimethylformamide (15 mL) was taken in a seal tube and added triethylamine (2.64 g, 26.12 mmol, 3.64 mL) followed by tert-butyl 2-bromoacetate (1.40 g, 7.18 mmol, 1.05 mL) at room temperature. The reaction mixture was stirred at room temperature for 16 h. After completion of the reaction, water (50 mL) was added to the reaction mixture and extracted with ethyl acetate (2×100 mL). The combined organic layers were dried over $Na_2SO_4$, filtered and concentrated under reduced pressure to get crude product which was washed with diethyl ether to afford tert-butyl 2-[4-[4-[(2,6-dioxo-3-piperidyl)amino]-2-fluoro-phenyl]piperazin-1-yl]acetate (1.7 g, 3.37 mmol, 52% yield). LCMS (ESI): m/z 421.2 [M+H]$^+$.

Step-6: To a stirred solution of tert-butyl 2-[4-[4-[(2,6-dioxo-3-piperidyl)amino]-2-fluoro-phenyl]piperazin-1-yl]acetate (1.7 g, 4.04 mmol) in 1,4-dioxane (10 mL) was added 4M hydrogen chloride solution in dioxane (4M, 20 mL) The reaction mixture was stirred at room temperature for 2 h. The reaction mixture was concentrated under vacuum to afford crude which was triturated with diethyl ether to afford 2-[4-[4-[(2,6-dioxo-3-piperidyl)amino]-2-fluoro-phenyl]piperazin-1-yl]acetic acid (1.5 g, 3.28 mmol, 81% yield). LCMS (ESI): m/z 365.2 $[M+H]^+$.

Synthesis of 2-[4-[4-[(2,6-dioxo-3-piperidyl)amino]-2,6-difluoro-phenyl]-1-piperidyl]acetic acid

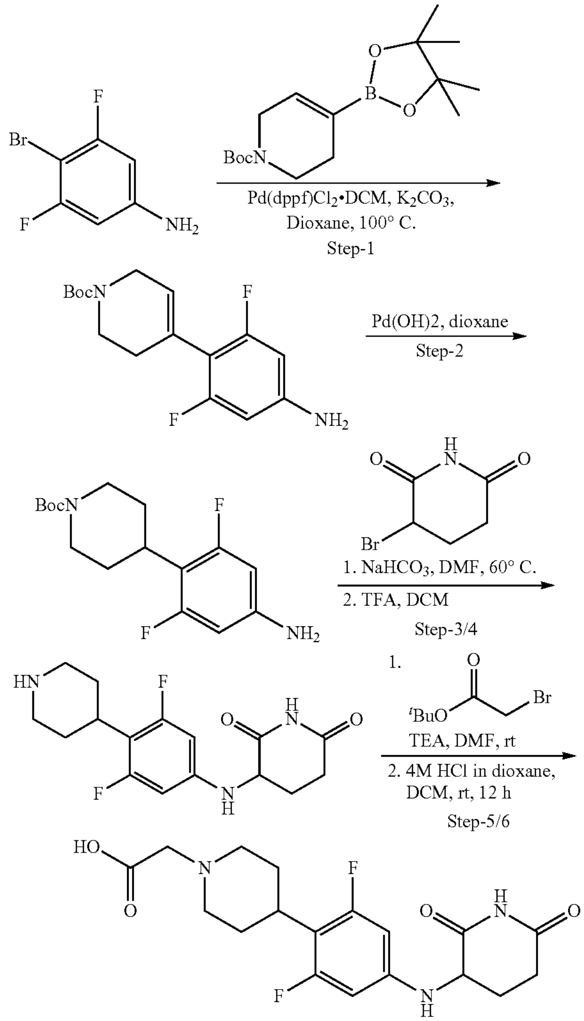

Step-1: To a stirred solution of 4-bromo-3,5-difluoro-aniline (2.49 g, 11.96 mmol) in THF (20 mL), methanol (5 mL) and water (5 mL) was added tert-butyl 4-(4,4,5,5-tetramethyl-1,3,2-dioxaborolan-2-yl)-3,6-dihydro-2H-pyridine-1-carboxylate (5.55 g, 17.94 mmol) and degassed with $N_2$ for 20 minutes. Pd(dppf)$Cl_2$·dichloromethane (0.98 g, 1.20 mmol), sodium carbonate (3.80 g, 35.89 mmol, 1.50 mL) were added to the reaction mixture and heated at 100° C. for 12 h. After completion, the reaction mixture was filtered and concentrated under reduced pressure to get crude which was purified by column chromatography on silica gel eluted with 20% ethyl acetate in petroleum ether to yield tert-butyl 4-(4-amino-2,6-difluoro-phenyl)-3,6-dihydro-2H-pyridine-1-carboxylate (3 g, 7.06 mmol, 59% yield) as an off-white solid. LCMS (ESI): m/z 255.1 $[M-56+H]^+$.

Step-2: A solution of tert-butyl 4-(4-amino-2,6-difluoro-phenyl)-3,6-dihydro-2H-pyridine-1-carboxylate (2.1 g, 6.77 mmol) in 1,4 Dioxane (25 mL) was degassed with $N_2$ for 15 min. $Pd(OH)_2$ (2.1 g, 14.95 mmol) was added to the reaction mixture and stirred under $H_2$ balloon pressure for 24 h. After completion of reaction, the reaction mixture was filtered through celite and concentrated under reduced pressure to afford tert-butyl 4-(4-amino-2,6-difluoro-phenyl)piperidine-1-carboxylate (2 g, 5.51 mmol, 81% yield) as an off-white solid. LCMS (ESI): m/z 257.1 $[M-56+H]^+$.

Step-3: To a stirred solution of tert-butyl 4-(4-amino-2,6-difluoro-phenyl)piperidine-1-carboxylate (500 mg, 1.60 mmol) in N,N-dimethylformamide (20 mL) were added sodium bicarbonate (807 mg, 9.61 mmol, 373.61 μL) and 3-bromopiperidine-2,6-dione (923 mg, 4.81 mmol). The reaction mixture was stirred at 60° C. for 16 h. After completion, the reaction mixture was diluted with ice water (20 mL) and extracted with ethyl acetate (2×50 mL). The combined organic layers were dried over anhydrous sodium sulfate, filtered and concentrated under reduced pressure to get crude which was purified by column chromatography on silica gel eluted with 50% ethyl acetate in petroleum ether to yield tert-butyl 4-[4-[(2,6-dioxo-3-piperidyl)amino]-2,6-difluoro-phenyl]piperidine-1-carboxylate (460 mg, 380.21 μmol, 24% yield) as a viscous liquid. LCMS (ESI): m/z 368.1 $[M-56+H]^+$.

Step-4: To a stirred solution of tert-butyl 4-[4-[(2,6-dioxo-3-piperidyl)amino]-2,6-difluoro-phenyl]piperidine-1-carboxylate (460 mg, 1.09 mmol) in dichloromethane (10 mL) was added hydrogen chloride solution (4M in dioxane, 4.00 g, 109.71 mmol, 5 mL) at 0° C. and the reaction mixture was stirred at room temperature for 12 h. The reaction mixture was concentrated under reduced pressure to get crude which was triturated with diethyl ether to afford 3-[3,5-difluoro-4-(4-piperidyl)anilino]piperidine-2,6-dione (100 mg, 255.53 μmol, 24% yield) as an off-white solid. LCMS (ESI): m/z 324.1 $[M+H]^+$.

Step-5: To a stirred solution of 3-[3,5-difluoro-4-(4-piperidyl)anilino]piperidine-2,6-dione (6, 300 mg, 927.82 μmol) in N,N-dimethylformamide (5 mL) was added TEA (470 mg, 4.64 mmol, 647.38 μL) and tert-butyl 2-bromoacetate (200 mg, 1.03 mmol, 150.38 μL) at 0° C. and the reaction mixture was stirred at room temperature for 12 h. The reaction mixture was diluted with ice water (30 mL) and extracted with ethyl acetate (2×50 mL). The combined organic layers were dried over anhydrous sodium sulfate, filtered and evaporated under reduced pressure to get tert-butyl 2-[4-[4-[(2,6-dioxo-3-piperidyl)amino]-2,6-difluoro-phenyl]-1-piperidyl]acetate (310 mg, 666.09 μmol, 72% yield) as an off-white solid. LCMS (ESI): m/z 438.1 $[M+H]^+$.

Step-6: To a stirred solution of tert-butyl 2-[4-[4-[(2,6-dioxo-3-piperidyl)amino]-2,6-difluoro-phenyl]-1-piperidyl]acetate (250 mg, 571.46 μmol) in dichloromethane (10 mL) was added hydrogen chloride solution (4M in dioxane, 4.00 g, 109.71 mmol, 5 mL) at 0° C. and the reaction mixture was stirred at room temperature for 12 h. The reaction mixture was concentrated under reduced pressure to get crude which was triturated with diethyl ether to afford 2-[4-[4-[(2,6-dioxo-3-piperidyl)amino]-2,6-difluoro-phenyl]-1-piperidyl]acetic acid (200 mg, 459.51 μmol, 80% yield) as an off-white solid. LCMS (ESI): m/z 382.1 $[M+H]^+$.

Synthesis of 2-[1-[4-[(2,6-dioxo-3-piperidyl)amino]-2-fluoro-phenyl]-4-piperidyl]acetic acid

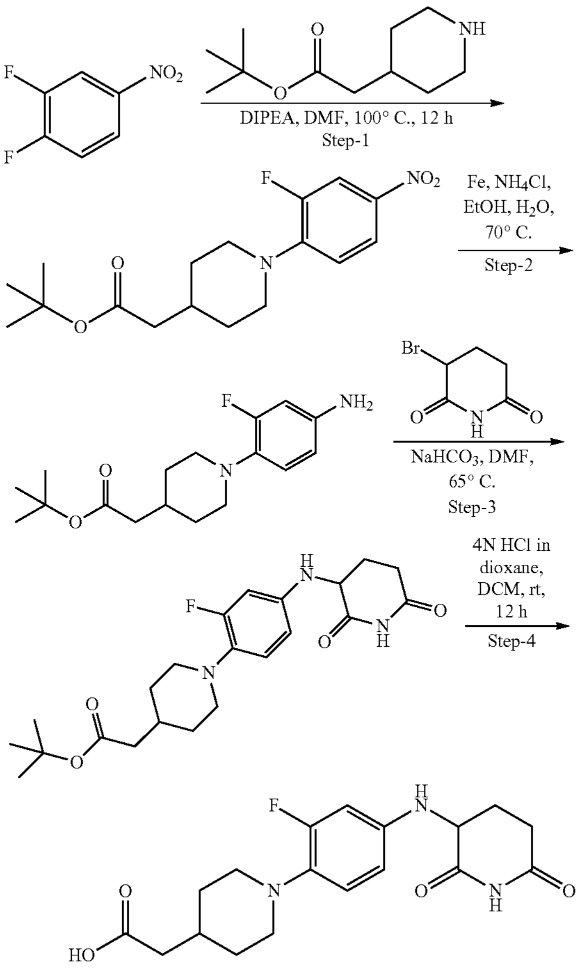

Step-1: To a stirred solution of 1,2-difluoro-4-nitro-benzene (1.5 g, 9.43 mmol, 1.04 mL) and tert-butyl 2-(4-piperidyl)acetate (1.88 g, 9.43 mmol) in N,N-dimethylformamide (15 mL) was added N,N-diisopropylethylamine (6.09 g, 47.14 mmol, 8.21 mL) the reaction mixture was heated at 100° C. for 12 h. After completion, the reaction mixture was added to ice water, then solid was obtained. The solid was filtered, washed with cold water and dried under reduced pressure to get tert-butyl 2-[1-(2-fluoro-4-nitro-phenyl)-4-piperidyl]acetate (2.7 g, 5.67 mmol, 60% yield) as an off-white solid. LCMS (ESI): m/z 339.1 $[M+H]^+$.

Step-2: To a stirred solution of tert-butyl 2-[1-(2-fluoro-4-nitro-phenyl)-4-piperidyl]acetate (2.7 g, 7.98 mmol) in water (10 mL) and ethanol (25 mL) were added Iron powder (2.23 g, 39.90 mmol, 283.47 μL) and ammonium chloride (2.13 g, 39.90 mmol, 1.39 mL) at room temperature under nitrogen atmosphere. Then stirred the reaction at 70° C. for 5 h. After completion of the reaction, reaction mixture was cooled to room temperature, diluted with water (50 mL) and extracted with ethyl acetate (3×70 mL), The combined organic layers were washed with brine solution (100 mL), dried over sodium sulfate, filtered and concentrated under reduced pressure. The crude compound was purified by silica gel column chromatography with 40-50% ethyl acetate in petroleum ether as an eluent to afford tert-butyl 2-[1-(4-amino-2-fluoro-phenyl)-4-piperidyl]acetate (2.5 g, 5.27 mmol, 66% yield) as a yellow solid. LCMS (ESI): m/z 309.1 $[M+H]^+$.

Step-3: To a stirred solution of tert-butyl 2-[1-(4-amino-2-fluoro-phenyl)-4-piperidyl]acetate (1.5 g, 4.86 mmol) in N,N-dimethylformamide (20 mL) were added sodium bicarbonate (1.23 g, 14.59 mmol, 567.51 μL) and 3-bromopiperidine-2,6-dione (2.1 g, 10.94 mmol). The reaction mixture was stirred at 70° C. for 16 h. The reaction mixture was diluted with ice water (20 mL) and extracted with ethyl acetate (2×50 mL). The combined organic layers were dried over anhydrous sodium sulfate, filtered and concentrated under reduced pressure to get crude which was purified by column chromatography on silica gel eluted with 50% ethyl acetate in petroleum ether to yield tert-butyl 2-[1-[4-[(2,6-dioxo-3-piperidyl)amino]-2-fluoro-phenyl]-4-piperidyl]acetate (900 mg, 2.10 mmol, 43% yield) as an off-white solid. LCMS (ESI): m/z 420.2 $[M+H]^+$.

Step-4: To a stirred solution of tert-butyl 2-[1-[4-[(2,6-dioxo-3-piperidyl)amino]-2-fluoro-phenyl]-4-piperidyl]acetate (950 mg, 2.26 mmol) in dichloromethane (10 mL) was added hydrogen chloride solution (4M in dioxane, 2 mL) at 0° C. and the reaction mixture was stirred at room temperature for 12 h. The reaction mixture was concentrated under reduced pressure to get crude which was triturated with diethyl ether to afford 2-[1-[4-[(2,6-dioxo-3-piperidyl)amino]-2-fluoro-phenyl]-4-piperidyl]acetic acid (800 mg, 1.56 mmol, 69% yield) as an off-white solid. LCMS (ESI): m/z 364.2 $[M+H]^+$.

Synthesis of 2-[1-[4-[(2,6-dioxo-3-piperidyl)amino]-2-fluoro-phenyl]-4-hydroxy-4-piperidyl]acetic acid

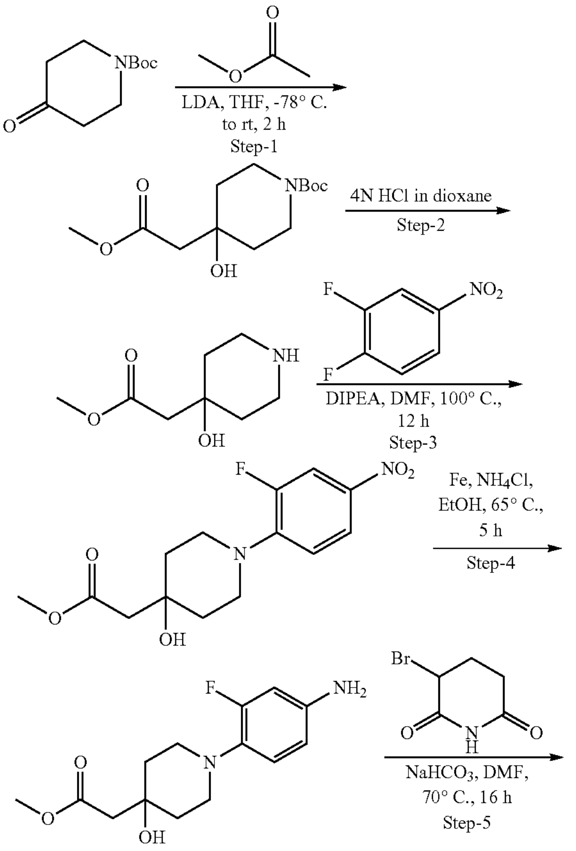

-continued

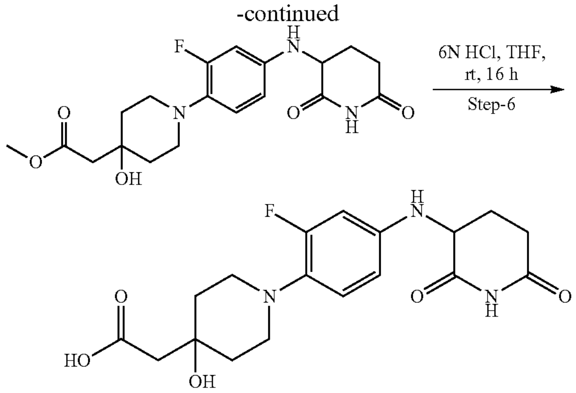

Step-1: To a stirred solution of methyl acetate (4.46 g, 60.23 mmol, 4.78 mL) in dry THF (200 mL), was added lithium diisopropylamide (10.75 g, 100.38 mmol, 50.19 mL) dropwise under nitrogen atmosphere at −78° C. Reaction mixture was stirred at −78° C. for 30 minutes and then tert-butyl 4-oxopiperidine-1-carboxylate (10 g, 50.19 mmol) in THF (50 mL) solution was added dropwise −78° C. and stirred reaction mixture at room temperature for 2 h. After completion, the reaction mixture was quenched with saturated ammonium chloride solution (250 mL) at 0° C. and extracted with ethyl acetate (3×200 mL). Combined organic layers dried over sodium sulfate, filtered and concentrated. crude compound was purified by column chromatography (60-120 silica gel) by using 40-50% ethyl acetate in petroleum ether as eluent to afford tert-butyl 4-hydroxy-4-(2-methoxy-2-oxo-ethyl)piperidine-1-carboxylate (5.6 g, 16.75 mmol, 33% yield) as a yellow liquid. LCMS (ESI): m/z 174.1 $[M-100+H]^+$.

Step-2: To a stirred solution of tert-butyl 4-hydroxy-4-(2-methoxy-2-oxo-ethyl)piperidine-1-carboxylate (5.5 g, 20.12 mmol) in dichloromethane (70 mL), was added hydrogen chloride solution (4M in dioxane, 50 mL) at 5° C. The reaction mixture was stirred at room temperature for 12 h. After completion, the reaction mixture was concentrated under reduced pressure to afford crude methyl 2-(4-hydroxy-4-piperidyl)acetate (5.5 g, 26.23 mmol) as a light-yellow gummy liquid. LCMS (ESI): m/z 174.1 $[M+H]^+$.

Step-3: Methyl 2-(4-hydroxy-4-piperidyl)acetate (5.5 g, 31.75 mmol) in DMSO (70 mL) was taken in a sealed tube and added N,N-diisopropylethylamine (14.36 g, 111.14 mmol, 19.36 mL) and 1,2-difluoro-4-nitrobenzene (6.06 g, 38.10 mmol, 4.21 mL) at room temperature. The reaction mixture was stirred at 100° C. for 12 h. After completion, the reaction mixture was diluted with water (70 mL), extracted with ethyl acetate (3×100 mL). Combined organic layers dried over sodium sulfate, filtered and concentrated under reduced pressure to afford crude. Desired product was purified from crude by column chromatography (60-120 silica gel) by using 40-50% ethyl acetate in petroleum ether as eluent to afford methyl 2-[1-(2-fluoro-4-nitro-phenyl)-4-hydroxy-4-piperidyl]acetate (2.7 g, 7.95 mmol, 25% yield) as a yellow viscous liquid. LCMS (ESI): m/z 313.1 $[M+H]^+$.

Step-4: To a stirred solution of methyl 2-[1-(2-fluoro-4-nitro-phenyl)-4-hydroxy-4-piperidyl]acetate (6.1 g, 19.53 mmol) in ethanol (200 mL) and water (36 mL), were added Iron powder (5.45 g, 97.66 mmol, 693.97 μL) and ammonium chloride (3.13 g, 58.60 mmol, 2.05 mL) at room temperature. The reaction mixture was stirred at 75° C. for 5 h. After completion, the reaction mixture was filtered through celite pad, filtrate was concentrated under reduced pressure, diluted with water (50 mL) and extracted with ethyl acetate (3×70 mL). Combined organic layers dried over sodium sulfate, filtered and concentrated under reduced pressure to afford crude methyl 2-[1-(4-amino-2-fluoro-phenyl)-4-hydroxy-4-piperidyl]acetate (5.5 g, 19.48 mmol, 100% yield) as a light brown liquid. $^1$H-NMR (400 MHz, DMSO-$d_6$): δ=6.75-6.80 (m, 1H), 6.27-6.34 (m, 2H), 4.93 (s, 2H), 4.53 (s, 1H), 3.59 (s, 3H), 2.77-2.89 (m, 4H), 2.50 (s, 2H), 1.75-1.78 (m, 4H).

Step-5: Methyl 2-[1-(4-amino-2-fluoro-phenyl)-4-hydroxy-4-piperidyl]acetate (5.5 g, 19.48 mmol) was taken in a sealed tube and dissolved in N,N-dimethylformamide (70 mL), and added sodium bicarbonate (4.91 g, 58.45 mmol, 2.27 mL) and 3-bromopiperidine-2,6-dione (6.24 g, 48.71 mmol) at room temperature. The reaction mixture was stirred at 75° C. for 16 h. After completion, the reaction mixture was filtered through celite pad, filtrate was concentrated under reduced pressure, diluted with water (100 mL) and extracted with ethyl acetate (3×150 mL). Combined organic layers dried over sodium sulfate, filtered and concentrated under reduced pressure to afford crude. Desired product was purified from crude by column chromatography (60-120 silica gel), by using 80-90% ethyl acetate in petroleum ether as eluent to afford product which was washed with diethyl ether and then with ethyl acetate to afford methyl 2-[1-[4-[(2,6-dioxo-3-piperidyl)amino]-2-fluoro-phenyl]-4-hydroxy-4-piperidyl]acetate (3.8 g, 8.82 mmol, 45% yield) as light green Solid. LCMS (ESI): m/z 394.0 $[M+H]^+$.

Step-6: To a stirred solution of methyl 2-[1-[4-[(2,6-dioxo-3-piperidyl)amino]-2-fluoro-phenyl]-4-hydroxy-4-piperidyl]acetate (3.8 g, 9.66 mmol) in THF (20 mL), was added 6N HCl solution (1.14 mmol, 80 mL) at 5° C. The reaction mixture was stirred at room temperature for 16 h. After completion, the reaction mixture was concentrated under reduced pressure to afford crude. Crude was washed with diethyl ether and then with acetonitrile to afford 2-[1-[4-[(2,6-dioxo-3-piperidyl)amino]-2-fluoro-phenyl]-4-hydroxy-4-piperidyl]acetic acid (4 g, 8.42 mmol, 87% yield) as a yellow solid. LCMS (ESI): m/z 380.1 $[M+H]^+$.

Synthesis of (1r,3r)-3-(3-(4-((2,6-dioxopiperidin-3-yl)amino)-2-fluorophenyl)azetidin-1-yl)cyclobutane-1-carboxylic acid and (1s,3s)-3-(3-(4-((2,6-dioxopiperidin-3-yl)amino)-2-fluorophenyl)azetidin-1-yl)cyclobutane-1-carboxylic acid

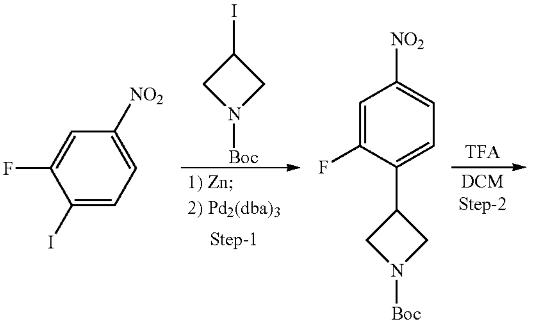

-continued
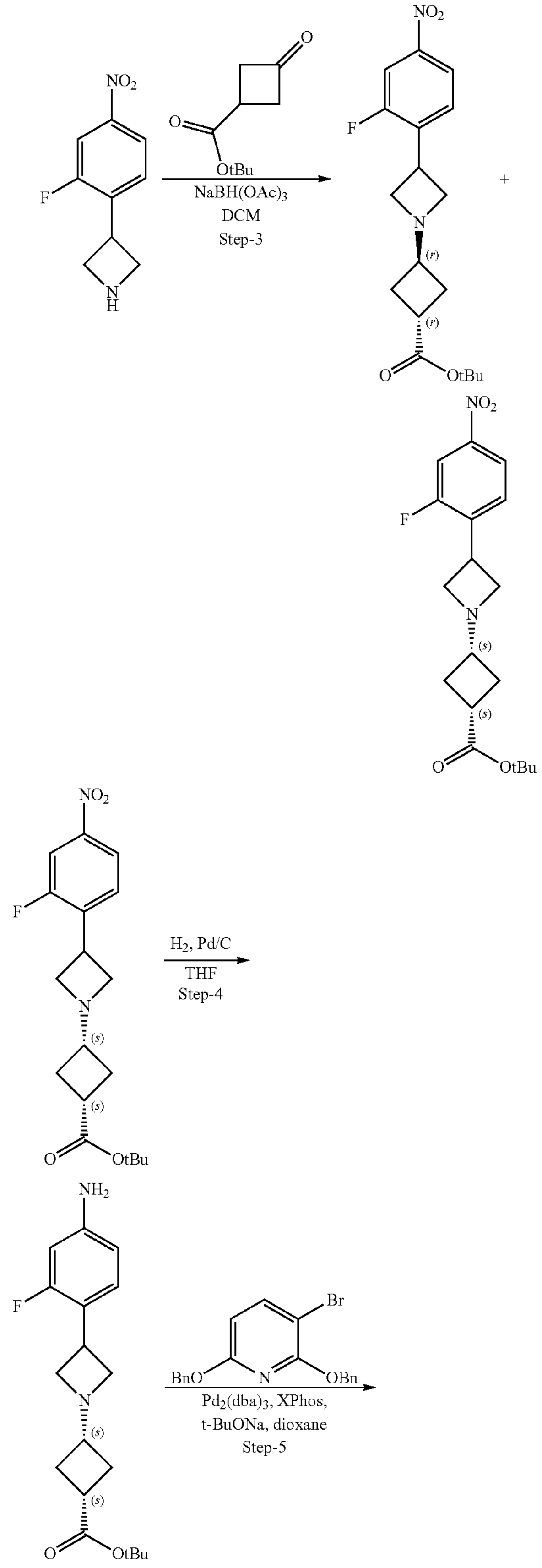
-continued
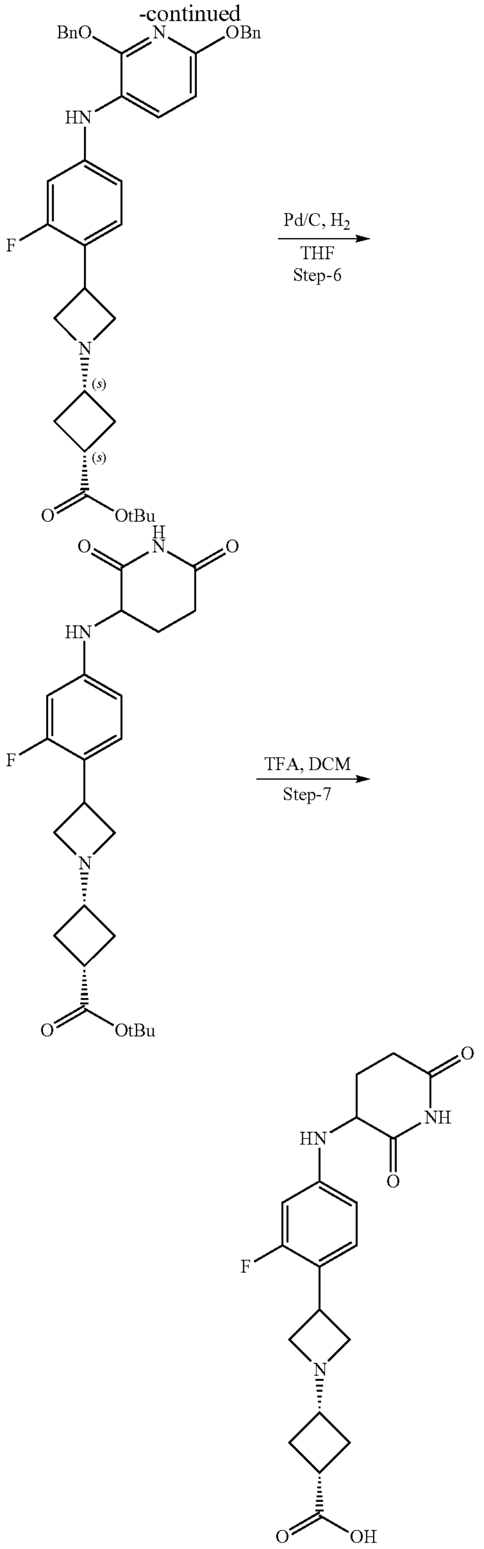
Step-1: 1,2-dibromoethane (5.60 g, 29.8 mmol, 2.25 mL, 1.88e-1 eq) was added to a stirred Zn powder (19.7 g, 301 mmol, 1.90 eq) in THF (49.0 mL) under $N_2$ atmosphere, the resulting mixture was stirred at 80° C. for 10 mins, followed by the addition of a solution of TMSCl (2.57 g, 23.6 mmol, 3.00 mL, 1.49e-1 eq) in THF (18.0 mL) at 25° C. and stirred for 4 mins at that temperature. Then a solution of compound tert-butyl 3-iodoazetidine-1-carboxylate (45.0 g, 158 mmol, 1.00 eq) in THF (102 mL) was added and stirred for 15 mins. The reaction mixture was stirred at 25° C. for 2 hrs then tris(2-furyl)phosphane (2.17 g, 9.37 mmol, 5.89e-2 eq) and $Pd_2(dba)_3$ (2.33 g, 2.54 mmol, 1.60e-2 eq) were added, followed by the addition of a solution of 2-fluoro-1-iodo-4-nitrobenzene (43.9 g, 164 mmol, 1.03 eq) in THF (216 mL), the resulting mixture was stirred at 50° C. for 8 hrs. TLC (petroleum ether/ethyl acetate=10/1) indicated tert-butyl 3-iodoazetidine-1-carboxylate ($R_f$=0.5) was consumed up and one new spot ($R_f$=0.1) formed. The reaction mixture was diluted with ethyl acetate (300 mL) and $H_2O$ (500 mL) was added. The separated organic phase was dried over sodium sulfate, filtered and concentrated under reduced pressure to give a residue, which was purified by flash silica gel chromatography (petroleum ether/ethyl acetate=10/1, $R_f$=0.1) to give tert-butyl 3-(2-fluoro-4-nitrophenyl)azetidine-1-carboxylate (22.0 g, 74.2 mmol, 46.7% yield) as a yellow oil.

Step-2: A mixture of tert-butyl 3-(2-fluoro-4-nitrophenyl) azetidine-1-carboxylate (10.0 g, 33.7 mmol, 1.00 eq) and TFA (19.2 g, 168 mmol, 12.4 mL, 5.00 eq) in DCM (50.0 mL) was stirred at 25° C. for 2 hrs. TLC (petroleum ether/ethyl acetate=0/1) indicated the starting material ($R_f$=0.5) was consumed completely and one new spot ($R_f$=0.1) formed. The reaction mixture was concentrated to give 3-(2-fluoro-4-nitrophenyl)azetidine (10.0 g, crude, TFA salt) as a yellow oil.

Step-3: To a solution of 3-(2-fluoro-4-nitrophenyl)azetidine (10.0 g, 32.2 mmol, 1.00 eq, TFA salt) in DCM (120 mL) was added AcOH (3.48 g, 57.9 mmol, 3.31 mL, 1.80 eq) and tert-butyl 3-oxocyclobutane-1-carboxylate (8 g, 47.00 mmol, 1.46 eq). The resulting mixture was stirred at 25° C. for 15 mins. $NaBH(OAc)_3$ (24.6 g, 116 mmol, 3.60 eq) was added. The reaction mixture was stirred at 30° C. for 6 hrs. TLC (petroleum ether/ethyl acetate=0/1) indicated the starting material ($R_f$~0.1) was consumed completely and two new spots ($R_f$=0.4, $R_f$=0.5) formed. LCMS showed starting material was consumed up and one main peak (RT=0.777 min) with desired mass was detected. The reaction mixture was diluted with DCM (200 mL) and $H_2O$ (300 mL), basified to pH~6 with sat. aq. $NaHCO_3$. The separated organic layer was dried over sodium sulfate, filtered and concentrated to give a residue, which was purified by flash silica gel chromatography (petroleum ether/ethyl acetate=0/1, $R_f$=0.4, $R_f$=0.5) to give tert-butyl (1r,3r)-3-(3-(2-fluoro-4-nitrophenyl)azetidin-1-yl)cyclobutane-1-carboxylate (5.00 g, 14.2 mmol, 98.3% yield) confirmed by HNMR and NOE as a yellow oil. tert-butyl (1s,3s)-3-(3-(2-fluoro-4-nitrophenyl)azetidin-1-yl)cyclobutane-1-carboxylate (6.00 g, 17.1 mmol, 96.5% yield) confirmed by HNMR and NOE was obtained as a yellow oil. LCMS ($ES^+$): m/z 351.1 $[M+H]^+$.

Cis diastereomer $^1$HNMR: δ 8.03 (dd, J=2.1, 8.4 Hz, 1H), 7.88 (dd, J=2.3, 9.7 Hz, 1H), 7.56 (t, J=7.9 Hz, 1H), 3.93 (t, J=7.6 Hz, 1H), 3.66-3.65 (m, 1H), 3.73 (t, J=7.6 Hz, 2H), 3.26 (t, J=7.3 Hz, 2H), 3.17-3.08 (m, 1H), 2.74-2.59 (m, 1H), 2.26-2.18 (m, 2H), 2.16-2.07 (m, 2H), 1.44 (s, 9H).

Step-4: A mixture of tert-butyl (1s,3s)-3-(3-(2-fluoro-4-nitrophenyl)azetidin-1-yl)cyclobutane-1-carboxylate (8.00 g, 24.8 mmol, 1.00 eq) and 10% Pd/C (600 mg, 14.2 mmol, 1.00 eq) in THF (20.0 mL), then the mixture stirred at 25° C. for 2 hrs under $H_2$ (15 psi) atmosphere. TLC (petroleum ether/ethyl acetate=0/1) indicated the starting material ($R_f$=0.5) was consumed up and one new spot ($R_f$=0.3) formed. LCMS showed starting material was consumed up and one main new peak (RT=0.685 min) with desired mass was detected. The reaction mixture was filtered through a celite pad and the filtrate was concentrated under reduced pressure to give tert-butyl (1s,3s)-3-(3-(4-amino-2-fluorophenyl)azetidin-1-yl)cyclobutane-1-carboxylate (7.80 g, 24.3 mmol, 98.0% yield) as a yellow oil.

Step-5: A mixture of tert-butyl (1s,3s)-3-(3-(4-amino-2-fluorophenyl)azetidin-1-yl)cyclobutane-1-carboxylate (20.5 mmol, 1.00 eq), 2,6-bis(benzyloxy)-3-bromopyridine (22.6 mmol, 1.10 eq), $Pd_2(dba)_3$ (600 mg, 655 μmol, 5.25e-2 eq), XPhos (600 mg, 1.26 mmol, 1.01e-1 eq) and t-BuONa (28.6 mmol, 1.40 eq) in dioxane (70.0 mL) was stirred at 100° C. for 8 hrs under $N_2$ atmosphere. TLC (petroleum ether/ethyl acetate=0/1) indicated starting material ($R_f$=0.4) was consumed up and one new spot ($R_f$=0.3) formed. LCMS showed starting material was consumed and one main new peak (RT=1.02 min) with desired mass was detected. The reaction mixture was diluted with ethyl acetate (100 mL), washed with $H_2O$ (200 mL). The combined organic layers were dried over sodium sulfate, filtered and concentrated under reduced pressure to give a residue, which was purified by column chromatography ($SiO_2$, petroleum ether/ethyl acetate=50/1 to 5/1, $R_f$=0.3) to give tert-butyl (1s,3s)-3-(3-(4-((2,6-bis(benzyloxy)pyridin-3-yl)amino)-2-fluorophenyl)azetidin-1-yl)cyclobutane-1-carboxylate (6.30 g, 10.3 mmol, 50.9% yield) as a yellow oil. LCMS ($ES^+$): m/z 610.3 $[M+H]^+$.

Step-6: A mixture of tert-butyl (1s,3s)-3-(3-(4-((2,6-bis(benzyloxy)pyridin-3-yl)amino)-2-fluorophenyl)azetidin-1-yl)cyclobutane-1-carboxylate (10.1 mmol, 1.00 eq) and 10% Pd/C (600 mg, 656 μmol, 0.100 eq) in THF (40.0 mL) was stirred at 25° C. for 24 hrs under $H_2$ (50 psi) atmosphere. TLC (petroleum ether/ethyl acetate=0/1) showed starting material ($R_f$=0.3) was consumed up and one new spot ($R_f$=0.2) formed. The reaction mixture was filtered and the filtrate was concentrated to give a residue, which was purified by column chromatography ($SiO_2$, petroleum ether/ethyl acetate=10/1 to dichloromethane/methanol=10/1) to give tert-butyl (1s,3s)-3-(3-(4-((2,6-dioxopiperidin-3-yl)amino)-2-fluorophenyl)azetidin-1-yl)cyclobutane-1-carboxylate (2.20 g, 5.10 mmol, 51.8 yield) as a blue oil. LCMS ($ES^+$): m/z 493.4 $[M+H]^+$.

Step-7: A mixture of tert-butyl (1s,3s)-3-(3-(4-((2,6-dioxopiperidin-3-yl)amino)-2-fluorophenyl)azetidin-1-yl)cyclobutane-1-carboxylate (5.1 mmol, 1.00 eq) and TFA (15.4 g, 135 mmol, 10.0 mL, 29.1 eq) in DCM (10.0 mL) was stirred at 25° C. for 2 hrs. TLC (dichloromethane/methanol=10/1) indicated the starting material ($R_f$=0.6) was consumed up and one new spot ($R_f$=0.3) formed. The reaction mixture was diluted with $H_2O$ (50 mL), washed with dichloromethane (100 mL). The separated organic layer was discarded, the aqueous was lyophilized and further purified by reversed-phase-HPLC (HPLC:EW20037-26-p1c1, 0.1% TFA condition) to afford (1s,3s)-3-(3-(4-((2,6-dioxopiperidin-3-yl)amino)-2-fluorophenyl)azetidin-1-yl)cyclobutane-1-carboxylic acid (1.35 g, 3.60 mmol, 70.54% yield) as a blue gray solid. $^1$H NMR: (400 MHz, DMSO-$d_6$) δ 12.83-12.11 (m, 1H), 10.80 (s, 1H), 10.73-10.55 (m, 1H), 10.44-10.23 (m, 1H), 7.17 (br t, J=8.4 Hz, 1H), 6.58-6.46 (m, 2H), 6.41-6.14 (m, 1H), 4.37 (br dd, J=4.7, 11.6 Hz, 2H), 4.28-3.86 (m, 5H), 2.87 (quin, J=8.7 Hz, 1H), 2.80-2.68 (m, 1H), 2.58 (td, J=3.8, 17.6 Hz, 1H), 2.46 (br s, 2H), 2.22 (br d, J=9.2 Hz, 2H), 2.12-2.01 (m, 1H), 1.88 (dq, J=4.5, 12.3 Hz, 1H).

Note: the trans diastereomer was prepared with the same manner described above.

Synthesis of 3-((4-(4-aminopiperidin-1-yl)-3-fluorophenyl)amino)piperidine-2,6-dione

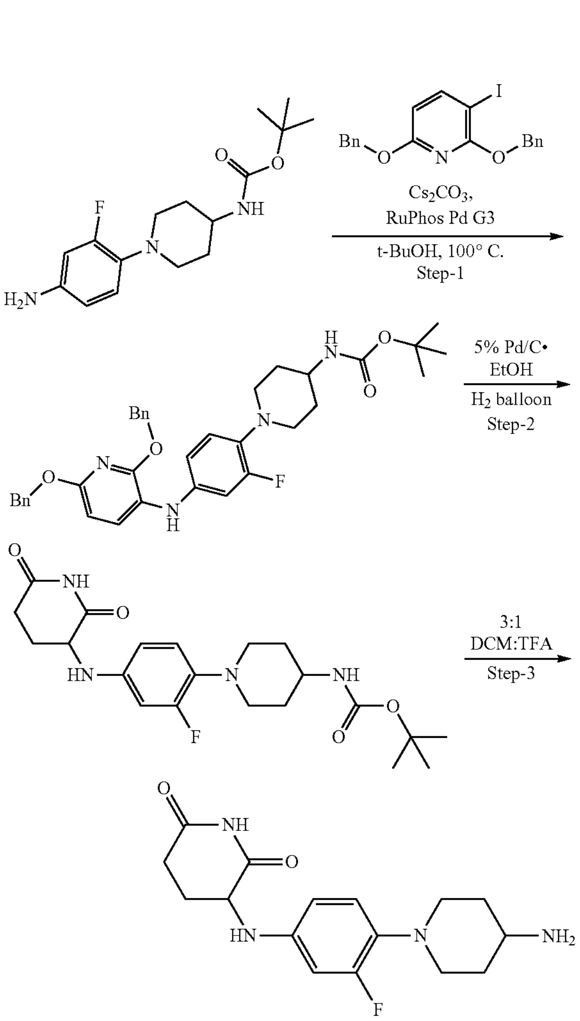

Step-1: To a stirred solution of tert-butyl N-[1-(4-amino-2-fluoro-phenyl)-4-piperidyl]carbamate (150 mg, 484.84 μmol) and 2,6-dibenzyloxy-3-iodo-pyridine (222.53 mg, 533.33 μmol) in t-BuOH (4.85 mL) was added cesium carbonate (473.92 mg, 1.45 mmol) and solution was degassed well by purging with Ar. RuPhos Pd G3 (44.80 mg, 48.48 μmol) was then added and the reaction was degassed again. The reaction mixture was heated at 100° C. for 18 h. The reaction mixture was then diluted with ethyl acetate, filtered over a small pad of celite and washed well with ethyl acetate. The combined organics were washed with water and brine, filtered, dried over anhydrous sodium sulfate and concentrated under reduced pressure to get crude material as an oil which was purified by column chromatography using silica eluted at 40% ethyl acetate in hexane to afford tert-butyl N-[1-[4-[(2,6-dibenzyloxy-3-pyridyl)amino]-2-fluoro-phenyl]-4-piperidyl]carbamate (100 mg, 158.68 μmol, 33% yield) as a pale yellow solid. LCMS ($ES^+$): m/z 600 $[M+H]^+$.

Step-2: To a solution of tert-butyl N-[1-[4-[(2,6-dibenzyloxy-3-pyridyl)amino]-2-fluoro-phenyl]-4-piperidyl]carbamate (75 mg, 125.27 μmol) in EtOH (5 mL) was added Palladium, 5% on activated carbon (4.00 mg, 37.58 μmol) before purging flask with an $H_2$ balloon. The reaction was stirred at rt under a hydrogen atmosphere (balloon pressure) for 16 hours. The reaction was filtered over celite and washed celite pad with 3× EtOH and 3× EtOAc before concentrating to afford crude tert-butyl N-[1-[4-[(2,6-dioxo-3-piperidyl)amino]-2-fluoro-phenyl]-4-piperidyl]carbamate (50 mg, 112.97 μmol, 90% yield) as an oil, which was used without further purification. LCMS ($ES^+$): m/z 421 $[M+H]^+$.

Step-3: To a solution of tert-butyl N-[1-[4-[(2,6-dioxo-3-piperidyl)amino]-2-fluoro-phenyl]-4-piperidyl]carbamate (50 mg, 118.91 μmol) in DCM (2 mL) was added TFA (740.00 mg, 6.49 mmol, 500 μL). The solution was stirred for 3 hours and concentrated from toluene 3× to afford 3-[4-(4-amino-1-piperidyl)-3-fluoro-anilino]piperidine-2,6-dione (45 mg, 98.42 μmol, 83% yield, TFA salt) as a crude oil, which was used without purification for the next step. LCMS ($ES^+$): m/z 321 $[M+H]^+$.

Synthesis of 2-[4-[4-(2,6-dioxo-3-piperidyl)-2-fluoro-phenyl]-3,3-difluoro-1-piperidyl]acetic acid

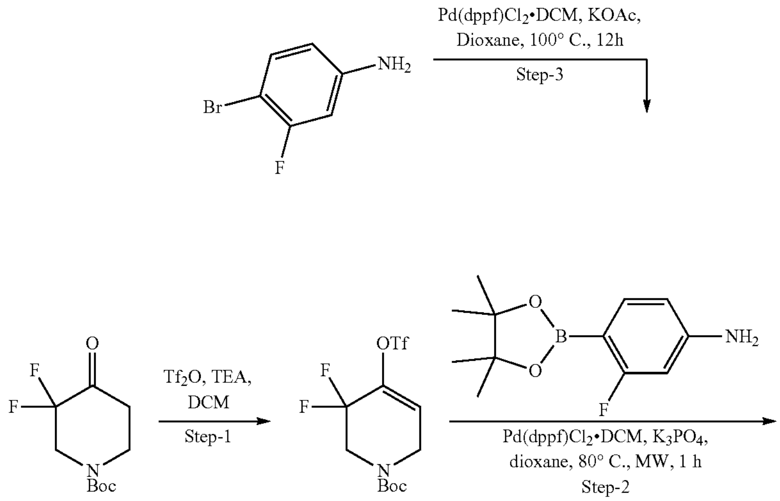

-continued

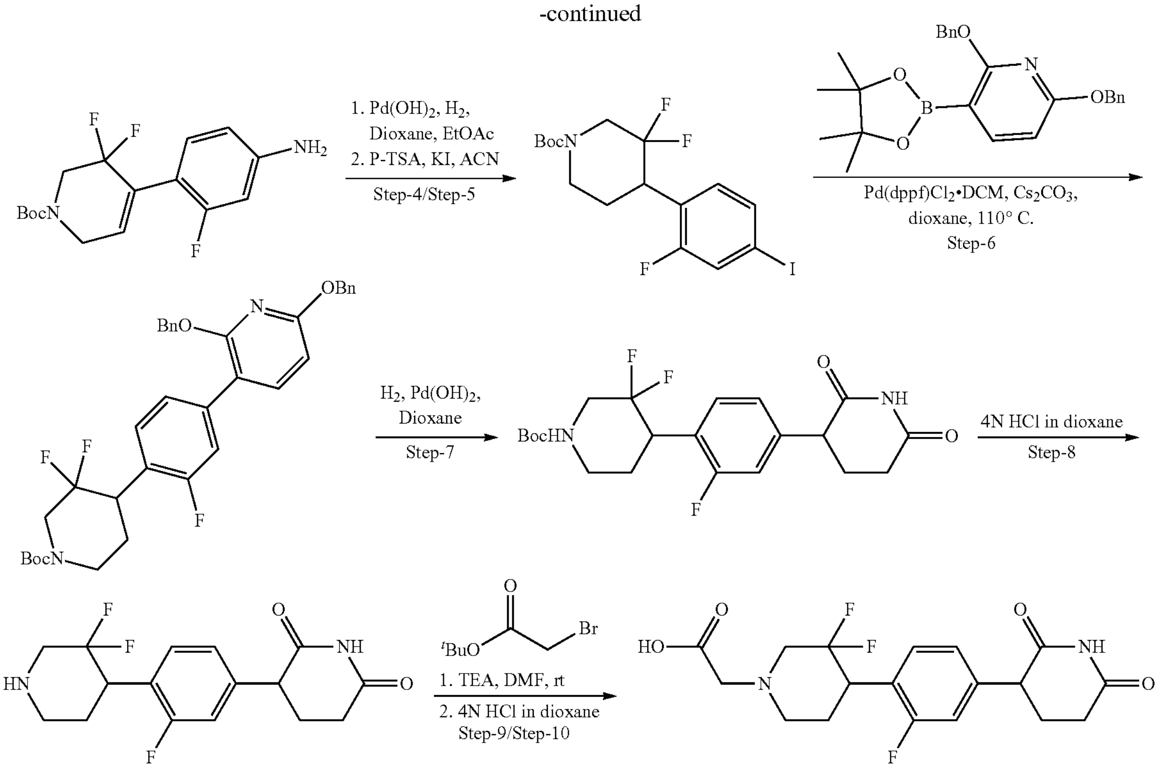

Step-1: To a solution of tert-butyl 3,3-difluoro-4-oxo-piperidine-1-carboxylate (2.5 g, 10.63 mmol) in dichloromethane (30 mL), was added triethylamine (3.23 g, 31.8 mmol, 4.44 mL) and the reaction mixture was cooled to −20° C. The solution of trifluoromethylsulfonyl trifluoromethanesulfonate (4.50 g, 15.94 mmol, 2.68 mL) in dichloromethane (10 mL) was added at −20° C. dropwise under nitrogen atmosphere. The reaction mixture was stirred at room temperature for 16 h. After completion, the reaction was quenched with cold water (70 mL) dropwise at 0° C. and extracted with dichloromethane (3×100 mL). Combined organic layers were dried over sodium sulfate, filtered and concentrated under reduced pressure to afford crude. Desired product was purified from crude by column chromatography (silica gel) by using 5-15% ethyl acetate in pet ether as eluent to afford tert-butyl 3,3-difluoro-4-(trifluoromethylsulfonyloxy)-2,6-dihydropyridine-1-carboxylate (1.3 g, 2.16 mmol, 20% yield) as a light-yellow liquid. LCMS (ES$^+$): m/z 268.0 [M−$CO_2{}^t$Bu+H]$^+$.

Step-2: To a solution of 3-fluoro-4-(4,4,5,5-tetramethyl-1,3,2-dioxaborolan-2-yl)aniline (1.70 g, 7.19 mmol) and tert-butyl 3,3-difluoro-4-(trifluoromethylsulfonyloxy)-2,6-dihydropyridine-1-carboxylate (2.4 g, 6.53 mmol) in 1,4-dioxane (30 mL) and water (3 mL) in sealed tube, were added potassium phosphate tribasic anhydrous (4.16 g, 19.60 mmol). The reaction mixture was degassed with nitrogen gas for 10 mins and then added [1,1'-Bis(diphenylphosphino)ferrocene]dichloropalladium (II), complex with dichloromethane (533.62 mg, 653.44 μmol). The reaction mixture was again purged with nitrogen gas for 5 mins and irradiated under microwave at 80° C. for 1.5 h. After completion, the reaction mixture was diluted with water (50 mL), extracted with ethyl acetate (3×70 mL). Combined organic layers was dried over sodium sulfate, filtered and concentrated under reduced pressure to afford crude. Desired product was purified from crude by silica gel column chromatography by using 15-25% ethyl acetate in petroleum ether as eluent to afford tert-butyl 4-(4-amino-2-fluoro-phenyl)-3,3-difluoro-2,6-dihydropyridine-1-carboxylate (1.6 g, 4.84 mmol, 74% yield) as a light green viscous liquid. LCMS (ES$^+$): m/z 229.2 [M−$CO_2{}^t$Bu+H]$^+$.

Step-3: To a solution of 4-bromo-3-fluoro-aniline (5 g, 26.31 mmol) in 1,4-dioxane (200 mL), was added potassium acetate (7.75 g, 78.94 mmol, 4.93 mL) and 4,4,5,5-tetramethyl-2-(4,4,5,5-tetramethyl-1,3,2-dioxaborolan-2-yl)-1,3,2-dioxaborolane (7.35 g, 28.95 mmol). The reaction mixture was degassed with nitrogen gas for 10 minutes, and then added [1,1'-bis(diphenylphosphino)ferrocene]dichloropalladium (II), complex with dichloromethane (2.15 g, 2.63 mmol). The reaction mixture was stirred at 100° C. for 12 h. After completion, the reaction mixture was diluted with water (100 mL), extracted with ethyl acetate (3×150 mL). Combined organic layers were dried over sodium sulfate, filtered and concentrated to afford crude. Desired product was purified from crude by silica gel column chromatography using 10-20% ethyl acetate in petroleum ether as eluent to afford 3-fluoro-4-(4,4,5,5-tetramethyl-1,3,2-dioxaborolan-2-yl)aniline (5.5 g, 15.96 mmol, 61% yield) as a light yellow viscous solid. LCMS (ES$^+$): m/z 238.2 [M+H]$^+$.

Step-4: To a stirred solution of tert-butyl 4-(4-amino-2-fluoro-phenyl)-3,3-difluoro-2,6-dihydropyridine-1-carboxylate (1.6 g, 4.87 mmol) in methanol (20 mL) and ethyl acetate (20 mL), was charged 20% $Pd(OH)_2$ (2 g, 14.24 mmol) and saturated with hydrogen by bubbling hydrogen gas through for 10 minutes and then subjected to hydrogenation (1 atm) at room temperature for 16 h. After completion, the reaction mixture was purged with nitrogen, catalyst was removed by filtration through celite pad. Celite bed was washed with methanol (200 mL). The filtrate was concentrated under reduced pressure to afford crude tert-butyl 4-(4-amino-2-fluoro-phenyl)-3,3-difluoro-piperidine-1-carboxylate (1.45 g, 4.32 mmol, 89% yield) as an off-white solid. LCMS ($ES^+$): m/z 231.2 $[M+H-CO_2{}^tBu]^+$.

Step-5: To a stirred solution of tert-butyl 4-(4-amino-2-fluoro-phenyl)-3,3-difluoro-piperidine-1-carboxylate (800 mg, 2.42 mmol) in acetonitrile (6 mL) was added 4-methylbenzenesulfonic acid·hydrate (1.40 g, 7.34 mmol, 1.13 mL) at 0-5° C., followed by sodium nitrite (342.53 mg, 4.96 mmol, 157.85 μL) in water (2 mL) at same temperature. The reaction mixture was stirred at 0-5° C. for 1 h and added potassium iodide (848.24 mg, 5.11 mmol, 271.87 μL) in water (2 mL) at same temperature. The reaction mixture was stirred at room temperature for 16 h. After completion, water (8 mL) was added to the reaction mixture and extracted with ethyl acetate (3×8 mL). The combined organic layers were dried over sodium sulfate, filtered, and concentrated under reduced pressure. The crude compound was purified by silica gel column chromatography with 25% ethyl acetate in petroleum ether as eluent to afford tert-butyl 3,3-difluoro-4-(2-fluoro-4-iodo-phenyl)piperidine-1-carboxylate (896 mg, 1.94 mmol, 80% yield) as an orange viscous liquid. LCMS ($ES^+$): m/z 342.0 $[M+H-CO_2{}^tBu]^+$.

Step-6: To a stirred solution of tert-butyl 3,3-difluoro-4-(2-fluoro-4-iodo-phenyl)piperidine-1-carboxylate (800 mg, 1.81 mmol) and 2,6-dibenzyloxy-3-(4,4,5,5-tetramethyl-1,3,2-dioxaborolan-2-yl)pyridine (1.71 g, 2.18 mmol) in 1,4-dioxane (8 mL) and water (2 mL) in microwave vial, were added anhydrous $K_3PO_4$ (962.18 mg, 4.53 mmol). The reaction mixture was purged with nitrogen gas for 10 minutes and then added XPhos-Pd-G2 (142.66 mg, 181.31 μmol). The reaction mixture was again purged with nitrogen gas for 5 minutes and irradiated under microwave at 100° C. for 2 h. After completion, the reaction mixture was diluted with water (15 mL), extracted with ethyl acetate (3×20 mL). Combined organic layers dried over sodium sulfate, filtered, and concentrated under reduced pressure to afford crude. Desired product was purified from crude by silica gel column chromatography using 30-45% ethyl acetate in petroleum ether as eluent to afford tert-butyl 4-[4-(2,6-dibenzyloxy-3-pyridyl)-2-fluoro-phenyl]-3,3-difluoro-piperidine-1-carboxylate (810 mg, 835.91 μmol, 46% yield). LCMS ($ES^+$): m/z 605.2 $[M+H]^+$.

Step-7: To a solution of tert-butyl 4-[4-(2,6-dibenzyloxy-3-pyridyl)-2-fluoro-phenyl]-3,3-difluoro-piperidine-1-carboxylate (810 mg, 1.34 mmol) in ethyl acetate (3 mL) and 1,4-dioxane (3 mL) was added $Pd(OH)_2$ (564.38 mg, 4.02 mmol). The reaction mixture was stirred at room temperature under hydrogen atmosphere for 16 h. After completion of the reaction, the reaction mixture was filtered through celite and washed with ethyl acetate (80 mL). Desired product was purified from crude by silica gel column chromatography using 30-45% ethyl acetate in petroleum ether as eluent to afford tert-butyl 4-[4-(2,6-dioxo-3-piperidyl)-2-fluoro-phenyl]-3,3-difluoro-piperidine-1-carboxylate (420 mg, 927.80 μmol, 69% yield). LCMS ($ES^+$): m/z 327.0 $[M+H-100]^+$.

Step-8: To a stirred solution of tert-butyl 4-[4-(2,6-dioxo-3-piperidyl)-2-fluoro-phenyl]-3,3-difluoro-piperidine-1-carboxylate (420 mg, 984.93 μmol) in 1,4-dioxane (2 mL) was added 4M hydrogen chloride solution in dioxane (4 mL) at 5° C. under nitrogen atmosphere. The reaction mixture was stirred at room temperature for 2 h. After completion, the reaction mixture was concentrated under reduced pressure and washed with the petroleum ether to afford crude 3-[4-(3,3-difluoro-4-piperidyl)-3-fluoro-phenyl]piperidine-2,6-dione (340 mg, 937.22 μmol, 95% yield) as an off-white solid. $^1$HNMR (400 MHz, DMSO-$d_6$): δ=10.90 (s, 1H), 7.35 (t, J=8.00 Hz, 1H), 7.18 (d, J=11.20 Hz, 1H), 7.14 (d, J=8.00 Hz, 1H), 3.80-3.95 (m, 3H), 3.55-3.74 (m, 1H), 3.12-3.45 (m, 2H), 2.41-2.51 (m, 1H), 2.20-2.31 (m, 2H), 1.98-2.15 (m, 3H).

Step-9: To a stirred solution of 3-[4-(3,3-difluoro-4-piperidyl)-3-fluoro-phenyl]piperidine-2,6-dione (340 mg, 1.04 mmol) in N,N-dimethylformamide (2 mL) were added triethylamine (421.74 mg, 4.17 mmol, 580.91 μL) followed by tert-butyl 2-bromoacetate (203.24 mg, 1.04 mmol, 152.81 μL) at room temperature under nitrogen atmosphere. The reaction mixture was stirred at room temperature for 14 h. The reaction mixture was diluted with water (10 mL) and extracted with ethyl acetate (3×10 mL). The organic layer was washed with brine solution (30 mL), dried over sodium sulfate. Then the solution was concentrated under reduced pressure to afford crude tert-butyl 2-[4-[4-(2,6-dioxo-3-piperidyl)-2-fluoro-phenyl]-3,3-difluoro-1-piperidyl]acetate (460 mg, 1.03 mmol, 99% yield) as an off-white solid. LCMS ($ES^+$): m/z 441.2 $[M+H]^+$.

Step-10: To a stirred solution of tert-butyl 2-[4-[4-(2,6-dioxo-3-piperidyl)-2-fluoro-phenyl]-3,3-difluoro-1-piperidyl]acetate (460 mg, 1.04 mmol) in dichloromethane (2 mL) was added 4M hydrogen chloride solution in dioxane (4 M, 5 mL) at 0° C. under nitrogen atmosphere. The reaction mixture was stirred at room temperature for 6 h. The reaction mixture was concentrated under vacuum to afford crude which was washed with the petroleum ether to afford 2-[4-[4-(2,6-dioxo-3-piperidyl)-2-fluoro-phenyl]-3,3-difluoro-1-piperidyl]acetic acid (355 mg, 811.22 μmol, 78% yield) as an off-white solid. LCMS ($ES^+$): m/z 385.2 $[M+H]^+$.

Synthesis of 1-(6-bromo-1-methyl-indazol-3-yl) hexahydropyrimidine-2,4-dione

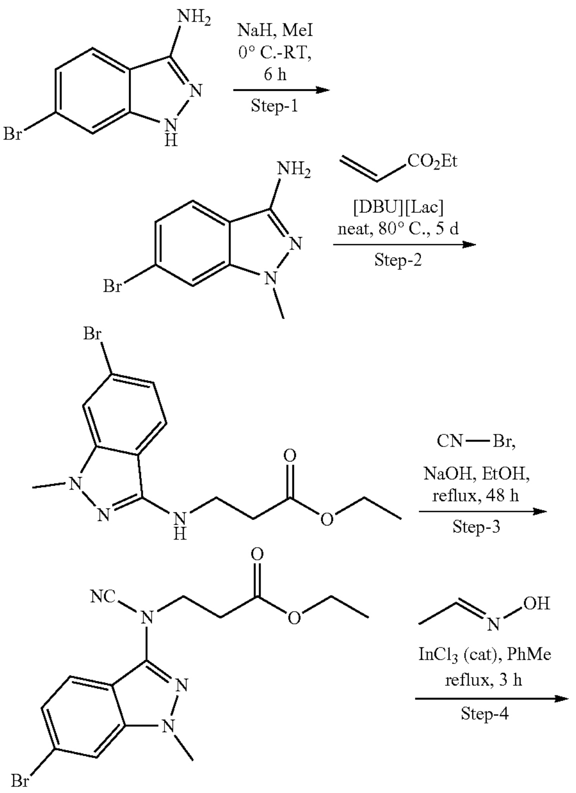

-continued

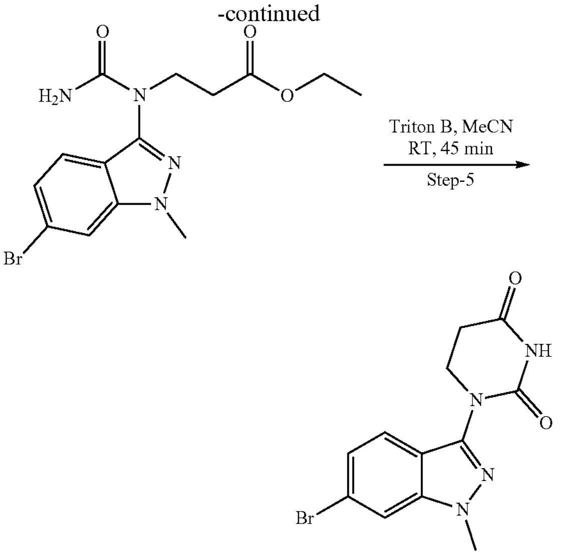

Step-1: Sodium hydride (60% in oil 2.38 g, 59.4 mmol) was added portion wise at 0° C. to a stirred solution of 6-bromo-1H-indazol-3-amine (7 g, 33.0 mmol, 439 μL) in DMF (150 mL) and the mixture was stirred for 40 min. Iodomethane (5.15 g, 36.3 mmol, 2.26 mL) was added drop-wise under cooling and the resulting mixture was warmed to ambient temperature and stirred for 16 h. The reaction mixture was quenched with saturated ammonium chloride solution and extracted with ethyl acetate. The combined organic extracts were washed with water, brine, dried over anhydrous sodium sulphate, filtered and concentrated under reduced pressure. The residue was purified by silica gel chromatography (50% ethyl acetate-hexane) to yield 6-bromo-1-methyl-indazol-3-amine (4.2 g, 18.6 mmol, 56% yield). LCMS ($ES^+$): m/z 227 $[M+H]^+$.

Step-2: Ethyl acrylate (14.0 g, 139 mmol) was added in 5 portions (2.8 g each) over 5 days to a mixture of 6-bromo-1-methyl-indazol-3-amine (4.2 g, 18.6 mmol), [DBU][Lac] (prepared by mixing equimolar mixture of DBU and lactic acid with stirring for 16 h at ambient temperature, 2.09 g, 14.9 mmol) at 80° C. After completion (LCMS), the reaction mixture was quenched with sodium hypochlorite (30% aq, 5 mL) and diluted with ethyl acetate. The combined organics were washed with water, brine, dried over anhydrous sodium sulphate, filtered and concentrated under reduced pressure. The residue was purified by silica gel chromatography (50% ethyl acetate-hexane) to yield ethyl 3-[(6-bromo-1-methyl-indazol-3-yl)amino]propanoate (2.9 g, 8.89 mmol, 48% yield). LCMS ($ES^+$): m/z 327 $[M+H]^+$.

Step-3: Anhydrous sodium acetate (1.46 g, 17.8 mmol), followed by cyanogen bromide (1.41 g, 13.3 mmol) were added to a stirred solution of ethyl 3-[(6-bromo-1-methyl-indazol-3-yl)amino]propanoate (2.9 g, 8.89 mmol) in ethanol (40 mL) at ambient temperature. The resulting mixture was heated to reflux for 48 h. The reaction mixture was concentrated under reduced pressure and diluted with ethyl acetate. The combined organics were washed with water, brine, dried over anhydrous sodium sulphate, filtered and concentrated under reduced pressure. The residue was purified by column chromatography (45% ethyl acetate-hexane) to yield ethyl 3-[(6-bromo-1-methyl-indazol-3-yl)-cyano-amino]propanoate (1.65 g, 4.70 mmol, 53% yield). LCMS ($ES^+$): m/z 352 $[M+H]^+$.

Step-4: (1E)-Acetaldehyde oxime (1.01 g, 17.1 mmol), followed by indium (III) chloride (126 mg, 569 μmol) were added to a stirred solution of ethyl 3-[(6-bromo-1-methyl-indazol-3-yl)-cyano-amino]propanoate (2 g, 5.69 mmol) in toluene (60 mL) at ambient temperature. The resulting mixture was heated to reflux for 1 h. The reaction mixture was diluted with ethyl acetate, washed with water and brine. The organics were dried over anhydrous sodium sulphate, filtered and concentrated under reduced pressure. The residue was purified by column chromatography (60% ethyl acetate-hexane) to yield ethyl 3-[(6-bromo-1-methyl-indazol-3-yl)-carbamoyl-amino]propanoate (1.4 g, 3.79 mmol, 67% yield). LCMS ($ES^+$): m/z 370 $[M+H]^+$.

Step-5: Triton-B (40% in methanol, 2.4 mL, 5.69 mmol) was added drop-wise to a stirred solution of ethyl 3-[(6-bromo-1-methyl-indazol-3-yl)-carbamoyl-amino]propanoate (1.40 g, 3.79 mmol) in MeCN (70 mL) at ambient temperature. The resulting mixture was stirred at ambient temperature for 45 minutes. The reaction mixture was concentrated under vacuum and diluted with ethyl acetate. The organic layer was washed with water, brine, dried over anhydrous sodium sulphate, filtered and concentrated under reduced pressure. The residue was purified by column chromatography (30% ethyl acetate-hexane) to yield 1-(6-bromo-1-methyl-indazol-3-yl)hexahydropyrimidine-2,4-dione (910 mg, 2.81 mmol, 74% yield) as white solid. LCMS ($ES^+$): m/z 324 $[M+H]^+$. $^1H$ NMR (400 MHz, DMSO-$d_6$): δ=10.60 (s, 1H), 7.97 (s, 1H), 7.61 (d, J=8.6 Hz, 1H), 7.26-7.23 (m, 1H), 3.98 (s, 3H), 3.93 (t, J=6.6 Hz, 2H), 2.76 (t, J=6.6 Hz, 2H).

Synthesis of 1-(1-methyl-6-(piperidin-4-yl)-1H-indazol-3-yl)dihydropyrimidine-2,4(1H,3H)-dione hydrochloride

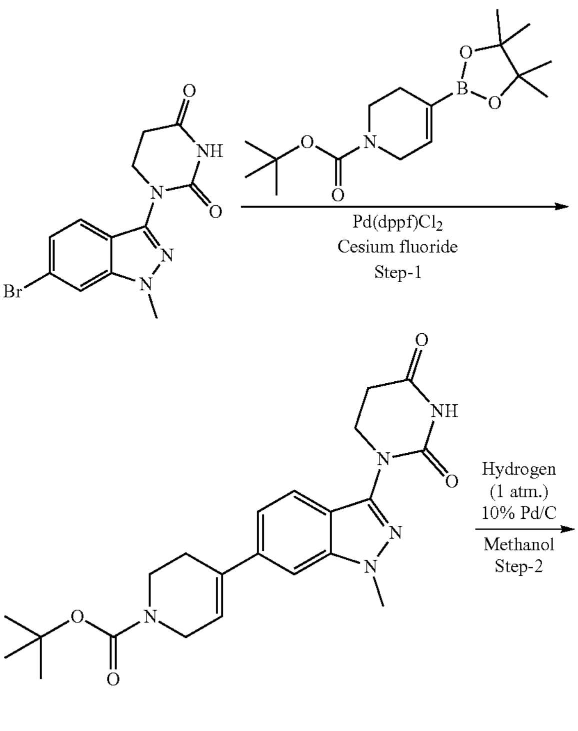

-continued

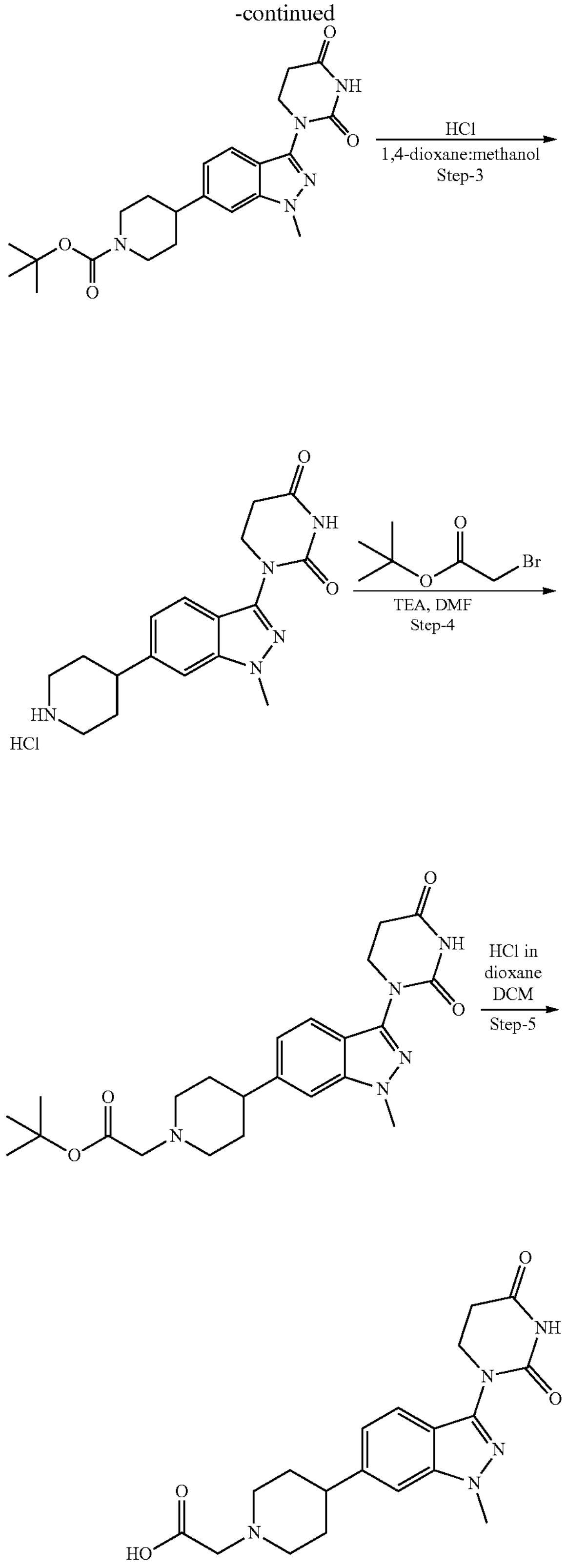

Step 1: A solution of 1-(6-bromo-1-methyl-indazol-3-yl) hexahydropyrimidine-2,4-dione (1.25 g, 3.87 mmol) and tert-butyl 4-(4,4,5,5-tetramethyl-1,3,2-dioxaborolan-2-yl)-3,6-dihydro-2H-pyridine-1-carboxylate (2.39 g, 7.74 mmol) was bubbled with $N_2$ for 10 min. Then, cesium fluoride (1.18 g, 7.74 mmol) and Pd(dppf)$Cl_2$ (566 mg, 774 μmol) were added and the mixture was stirred at 85° C. for 2 h. The mixture was cooled to ambient temperature, diluted with ethyl acetate and filtered through Celite/silica gel. After washing with ethyl acetate, the filtrate was diluted with water and layers were separated, and the organic layer was washed with brine, dried over $Na_2SO_4$, filtered, and concentrated. The residue was purified by normal phase chromatography (5-100% ethyl acetate in hexanes) to afford tert-butyl 4-[3-(2,4-dioxohexahydropyrimidin-1-yl)-1-methyl-indazol-6-yl]-3,6-dihydro-2H-pyridine-1-carboxylate (1.04 g, 2.44 mmol, 63% yield). LCMS ($ES^+$): m/z 426.3 $[M+H]^+$.

Step 2: Palladium (10% on carbon, Type 487, dry, 1.08 g, 1.02 mmol) was added to a solution of tert-butyl 4-[3-(2,4-dioxohexahydropyrimidin-1-yl)-1-methyl-indazol-6-yl]-3,6-dihydro-2H-pyridine-1-carboxylate (1.44 g, 3.38 mmol) in methanol (30 mL) and the mixture was stirred at ambient temperature under a hydrogen balloon atmosphere. After 24 h, the reaction mixture was filtered through a pad of celite, washed with a mixture of dichloromethane/methanol (1:1), and concentrated in vacuo to yield tert-butyl 4-[3-(2,4-dioxohexahydropyrimidin-1-yl)-1-methyl-indazol-6-yl]piperidine-1-carboxylate (1.42 g, 3.32 mmol, 98% yield). LCMS ($ES^+$): m/z 372.3 $[M\text{–tert-butyl}+H]^+$.

Step 3: 1-(1-methyl-6-(piperidin-4-yl)-1H-indazol-3-yl) dihydropyrimidine-2,4(1H,3H)-dione hydrochloride was obtained in quantitative yield from tert-butyl 4-[3-(2,4-dioxohexahydropyrimidin-1-yl)-1-methyl-indazol-6-yl]-3,6-dihydro-2H-pyridine-1-carboxylate using hydrogen chloride (4M in 1,4-dioxane, 5 equiv.) for tert-butoxycarbonyl protecting group deprotection. LCMS ($ES^+$): m/z 328.1 $[M+H]^+$.

Step 4: To a stirred solution of 1-[1-methyl-6-(4-piperidyl)indazol-3-yl]hexahydropyrimidine-2,4-dione hydrochloride (2.8 g, 7.70 mmol) in DMF (30 mL) and triethylamine (3.89 g, 38.48 mmol, 5.36 mL), was added tert-butyl 2-bromoacetate (2.25 g, 11.54 mmol, 1.69 mL) at room temperature. The reaction mixture was stirred at room temperature for 16 h under nitrogen atmosphere. After completion, the reaction mixture was poured into ice water (100 mL) and immediately extracted with ethyl acetate (3×150 mL). Combined organic layers were washed with cold water (3×50 mL), dried over sodium sulfate, filtered and concentrated under reduced pressure to afford tert-butyl 2-[4-[3-(2,4-dioxohexahydropyrimidin-1-yl)-1-methyl-indazol-6-yl]-1-piperidyl]acetate (2.3 g, 4.57 mmol, 59% yield) as a light brown solid. LCMS ($ES^+$): m/z 442.2 $[M+H]^+$.

Step 5: To a stirred solution of tert-butyl 2-[4-[3-(2,4-dioxohexahydropyrimidin-1-yl)-1-methyl-indazol-6-yl]-1-piperidyl]acetate (2.2 g, 4.98 mmol) in DCM (20 mL) was added hydrogen chloride solution 4.0 M in dioxane (4 M, 1.25 mL) at 5° C. under nitrogen atmosphere. The reaction mixture was stirred at room temperature for 6 h. After completion, the reaction mixture was concentrated under reduced pressure to afford 2-[4-[3-(2,4-dioxohexahydropyrimidin-1-yl)-1-methyl-indazol-6-yl]-1-piperidyl]acetic acid (2.5 g, 5.12 mmol, 100% yield) as an off white solid. LCMS ($ES^+$): m/z 386.2 $[M+H]^+$.

Synthesis of 2-[4-[3-(2,6-dioxo-3-piperidyl)-1-methyl-indazol-6-yl]-1-piperidyl]acetic acid
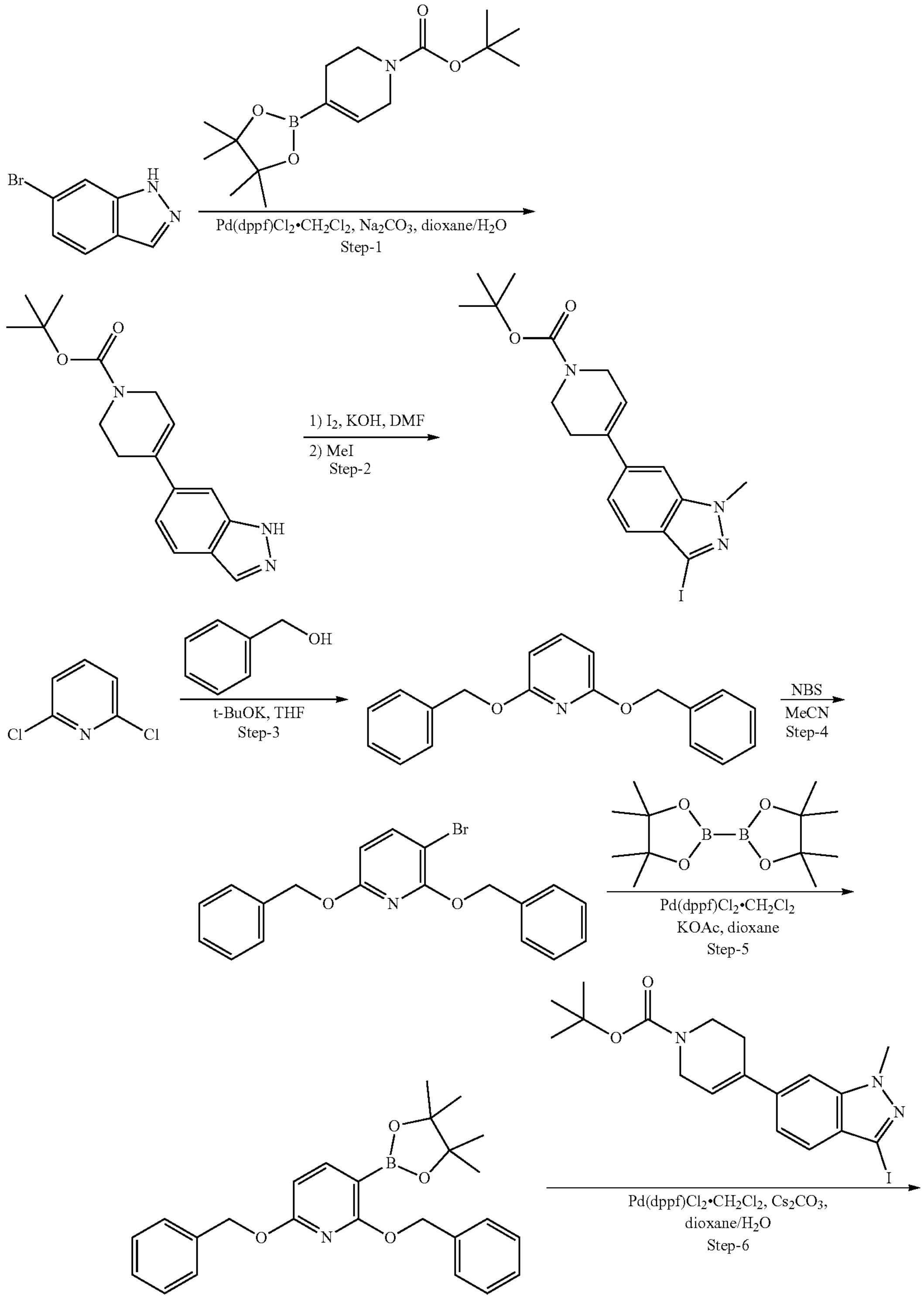

-continued

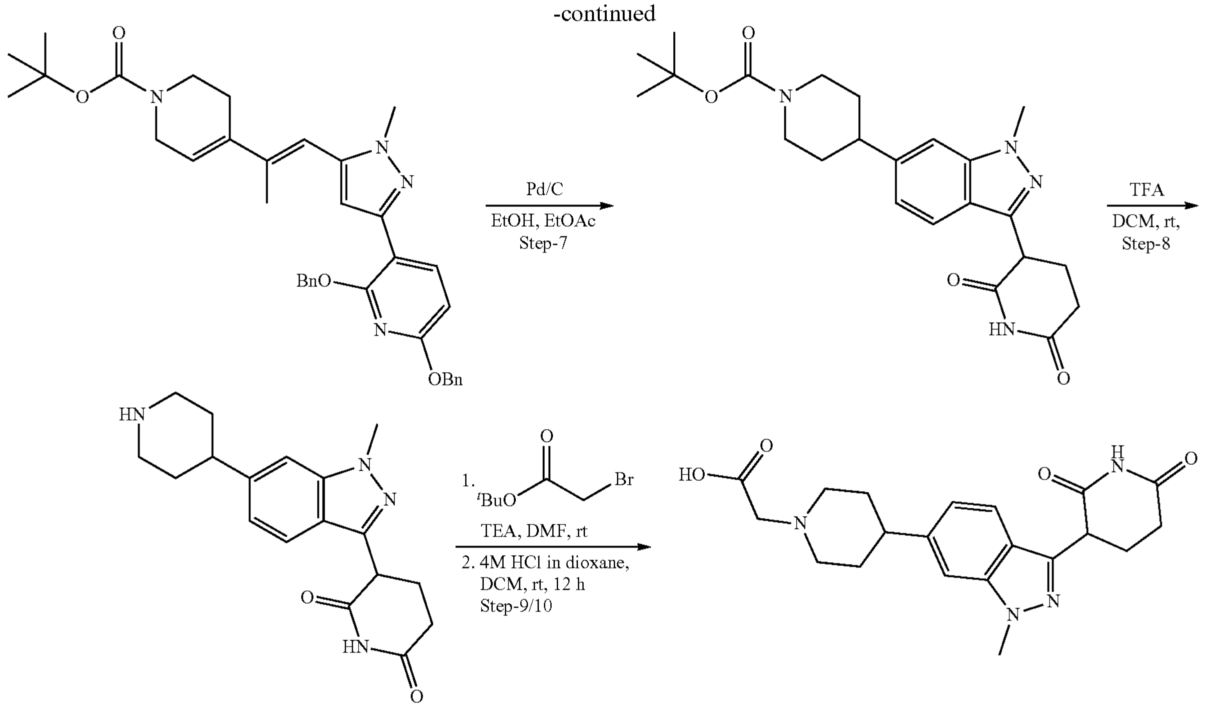

Step-1: A mixture of compound 6-bromo-1H-indazole (57.0 g, 289 mmol), tert-butyl 4-(4,4,5,5-tetramethyl-1,3,2-dioxaborolan-2-yl)-3,6-dihydropyridine-1(2H)-carboxylate (134 g, 433 mmol), $Pd(dppf)Cl_2{\cdot}CH_2Cl_2$ (12.0 g, 14.6 mmol) and $Na_2CO_3$ (100 g, 943 mmol) in dioxane (480 mL) and $H_2O$ (120 mL) was stirred at 105° C. for 12 h. The mixture was filtered through a pad of Celite and washed with ethyl acetate (500 mL). The filtrate was washed with brine (150 mL×3), dried over $Na_2SO_4$, filtered and concentrated under reduced pressure. The residue was purified by silica gel chromatography (0~30% ethyl acetate/petroleum ether) to afford tert-butyl 4-(1H-indazol-6-yl)-3,6-dihydropyridine-1(2H)-carboxylate (80.0 g, 239 mmol, 83% yield) as yellow oil. LCMS ($ES^+$): m/z 300.1 $[M+H]^+$.

Step-2: To a solution of tert-butyl 4-(1H-indazol-6-yl)-3,6-dihydropyridine-1(2H)-carboxylate (75.0 g, 224 mmol) in DMF (700 mL) was added KOH (37.7 g, 672 mmol) and $I_2$ (85.3 g, 336 mmol, 67.7 mL). The mixture was stirred at 25° C. for 12 h and was cooled to 0° C. MeI (44.6 g, 314 mmol, 19.6 mL) was then added. The resulting mixture was stirred at 25° C. for 1 h. The mixture was poured into water (1500 mL) and extracted with ethyl acetate (500 mL×3). The combined organic phase was washed by brine (500 mL×3) and dried over $Na_2SO_4$, filtered and concentrated under vacuum to give a residue, which was purified by silica gel chromatography (0~8% ethyl acetate/petroleum ether) to obtain tert-butyl 4-(3-iodo-1-methyl-1H-indazol-6-yl)-3,6-dihydropyridine-1(2H)-carboxylate (23.0 g, 52.3 mmol, 23% yield) as a yellow oil. LCMS ($ES^+$): m/z 440.1 $[M+H]^+$.

Step-3: To a solution of t-BuOK (190 g, 1.69 mol) in THF (1.00 L) was added phenylmethanol (73.4 g, 679 mmol, 70.6 mL) at 0° C. 2,6-Dichloropyridine (50.0 g, 338 mmol) was added to the mixture at 25° C. and stirred at 75° C. for 12 h. The reaction was quenched with sat. aq. $NH_4Cl$ (200 mL) at 0° C., diluted with ethyl acetate (200 mL), and extracted with ethyl acetate (200 mL×3). The combined organic layers were washed with brine (500 mL), dried over $Na_2SO_4$, filtered, and concentrated under reduced pressure to give a residue. The residue was triturated with petroleum ether (150 mL) to afford 2,6-bis(benzyloxy)pyridine (84.0 g, 85% yield) as a yellow solid. LCMS ($ES^+$): m/z 292.2 $[M+H]^+$ Step-4: To a solution of 2,6-bis(benzyloxy)pyridine (34.0 g, 116 mmol) in acetonitrile (100 mL) was added a solution of NBS (21.0 g, 118 mmol, 1.01 eq) in acetonitrile (200 mL) at 40° C. and the reaction mixture was stirred at 85° C. for 12 h. The reaction mixture was concentrated under reduced pressure, diluted with water (500 mL), and extracted with ethyl acetate (300 mL×3). The combined organic layers were washed with brine (200 mL), dried over $Na_2SO_4$, filtered and concentrated, and the residue triturated with petroleum ether (60 ml) to afford 2,6-bis(benzyloxy)-3-bromopyridine (27.7 g, 64% yield). LCMS ($ES^+$): m/z 371.9 $[M+H]^+$ Step-5: To a solution of 2,6-bis(benzyloxy)-3-bromopyridine (52.4 g, 139 mmol) in dioxane (500 mL) was added 4,4,4',4',5,5,5',5'-octamethyl-2,2'-bi(1,3,2-dioxaborolane) (37.1 g, 146 mmol), KOAc (41.0 g, 418 mmol) and $Pd(dppf)Cl_2{\cdot}CH_2Cl_2$ (5.69 g, 6.97 mmol). The reaction mixture was stirred at 105° C. for 12 h. The reaction mixture was filtered through a pad of Celite. The filtrate was diluted with water (500 mL) and extracted with ethyl acetate (500 mL×2). The extracts were washed with brine (400 mL), dried over $Na_2SO_4$, filtered and concentrated. The residue was purified by silica gel chromatography (0~100% ethyl acetate/petroleum ether) to afford 2,6-bis(benzyloxy)-3-(4,4,5,5-tetramethyl-1,3,2-dioxaborolan-2-yl)pyridine (35.0 g, 60% yield) as yellow oil. LCMS ($ES^+$): m/z 418.3 $[M+H]^+$ Step-6: To a solution of 2,6-bis(benzyloxy)-3-(4,4,5,5-tetramethyl-1,3,2-dioxaborolan-2-yl)pyridine (20.0 g, 45.53 mmol), tert-butyl 4-(1H-indazol-6-yl)-3,6-dihydropyridine-1(2H)-carboxylate (26.6 g, 63.7 mmol) and $Cs_2CO_3$ (44.5 g, 136 mmol) in dioxane (200 mL) and $H_2O$ (40 mL) was added $Pd(dppf)Cl_2{\cdot}CH_2Cl_2$ (3.72 g, 4.55 mmol, 0.10 eq). The reaction mixture was stirred at 100° C. for 2 h. The reaction mixture was filtered through a pad of Celite, and the filtrate was washed with brine (60 mL×3 mL), dried over $Na_2SO_4$, filtered and concentrated. The residue was purified by silica gel chromatography (0-100% ethyl acetate/petroleum ether) to obtain tert-butyl 4-(3-(2,6-bis(benzyloxy)pyridin-3-yl)-1-methyl-1H-indazol-6-yl)-3,6-dihydropyridine-1(2H)-carboxylate (20.0 g, 73% yield) as yellow oil. LCMS ($ES^+$): m/z 603.3 $[M+H]^+$ Step-7: To a solution of tert-butyl 4-(3-(2,6-bis(benzyloxy)pyridin-3-yl)-1-methyl-1H-indazol-6-yl)-3,6-dihydropyridine-1(2H)-carboxylate (18.0 g, 29.8 mmol, 1.00 eq) in EtOH (270 mL) and EtOAc (270 mL) was added 10% Pd/C (4.00 g) under $N_2$ atmosphere. The suspension was degassed and purged with $H_2$ 3 times. The mixture was stirred under $H_2$ (15 psi) at 30° C. for 24 h. The reaction mixture was filtered through a pad of Celite and the filtrate was concentrated. The residue was purified by silica gel chromatography (ethyl acetate/petroleum ether) to afford tert-butyl 4-(3-(2,6-dioxopiperidin-3-yl)-1-methyl-1H-indazol-6-yl) piperidine-1-carboxylate (5.3 g, 41% yield) as a white solid. LCMS ($ES^+$): m/z 427.2 $[M+H]^+$ Step-8: Into a 25 mL single neck round bottom flask containing a well-stirred solution of tert-butyl 4-[3-(2,6-dioxo-3-piperidyl)-1-methyl-indazol-6-yl]piperidine-1-carboxylate (500 mg, 1.17 mmol) in anhydrous DCM (5 mL) was added TFA (668.35 mg, 5.86 mmol, 451.59 µL) at 0° C. After stirring at room temperature for 3 h, the reaction mixture was concentrated under reduced pressure. The residue was azeotroped with toluene (2×15 mL) and triturated with diethyl ether (20 mL) to afford 3-[1-methyl-6-(4-piperidyl)indazol-3-yl]piperidine-2,6-dione (500 mg, 1.12 mmol, 95% yield, TFA salt) as an off-white solid. LCMS ($ES^+$): m/z 326.9 $[M+H]^+$ Step-9: To a stirred solution of 3-[1-methyl-6-(4-piperidyl)indazol-3-yl]piperidine-2,6-dione (230 mg, 704.67 µmol) in N,N-dimethylformamide (4 mL) was added triethylamine (213.92 mg, 2.11 mmol, 294.65 µL) followed by tert-butyl bromoacetate (151.19 mg, 775.14 µmol, 113.68 µL) at room temperature and the resulting reaction mixture was stirred at room temperature for 12 h. The progress of the reaction was monitored by TLC using 5% methanol-dichloromethane as eluent. After completion, water was added and extracted with 5% methanol-dichloromethane (2×30 mL). The combined organic layers were washed with ice cold water (2×30 mL), dried over anhydrous $Na_2SO_4$, filtered and filtrate was evaporated under reduced pressure to get the desired crude compound tert-butyl 2-[4-[3-(2,6-dioxo-3-piperidyl)-1-methyl-indazol-6-yl]-1-piperidyl]acetate (260 mg, 576.44 µmol, 82% yield) as off white solid. LCMS ($ES^+$): m/z 441.4 $[M+H]^+$.

Step-10: To a stirred solution of tert-butyl 2-[4-[3-(2,6-dioxo-3-piperidyl)-1-methyl-indazol-6-yl]-1-piperidyl]acetate (260 mg, 590.19 µmol) in dichloromethane (5 mL) was added hydrogen chloride solution (4.0 M in dioxane, 590.19 µmol, 4 mL) at 0° C. and the resulting reaction mixture was stirred for 12 h at room temperature. The progress of the reaction was monitored by TLC using 5% methanol-dichloromethane as eluent. Reaction mixture was concentrated under reduced pressure. The residue obtained was co-distilled with toluene (2×20 mL) and triturated with diethyl ether (2×5 mL), dried under reduced pressure to afford 2-[4-[3-(2,6-dioxo-3-piperidyl)-1-methyl-indazol-6-yl]-1-piperidyl]acetic acid (230 mg, 545.86 µmol, 92% yield, HCl salt) as off white solid. LCMS ($ES^+$): m/z 385.3 $[M+H]^+$.

Synthesis of 2-[1-[3-(2,6-dioxo-3-piperidyl)-1-methyl-indazol-6-yl]-4-hydroxy-4-piperidyl]acetic acid

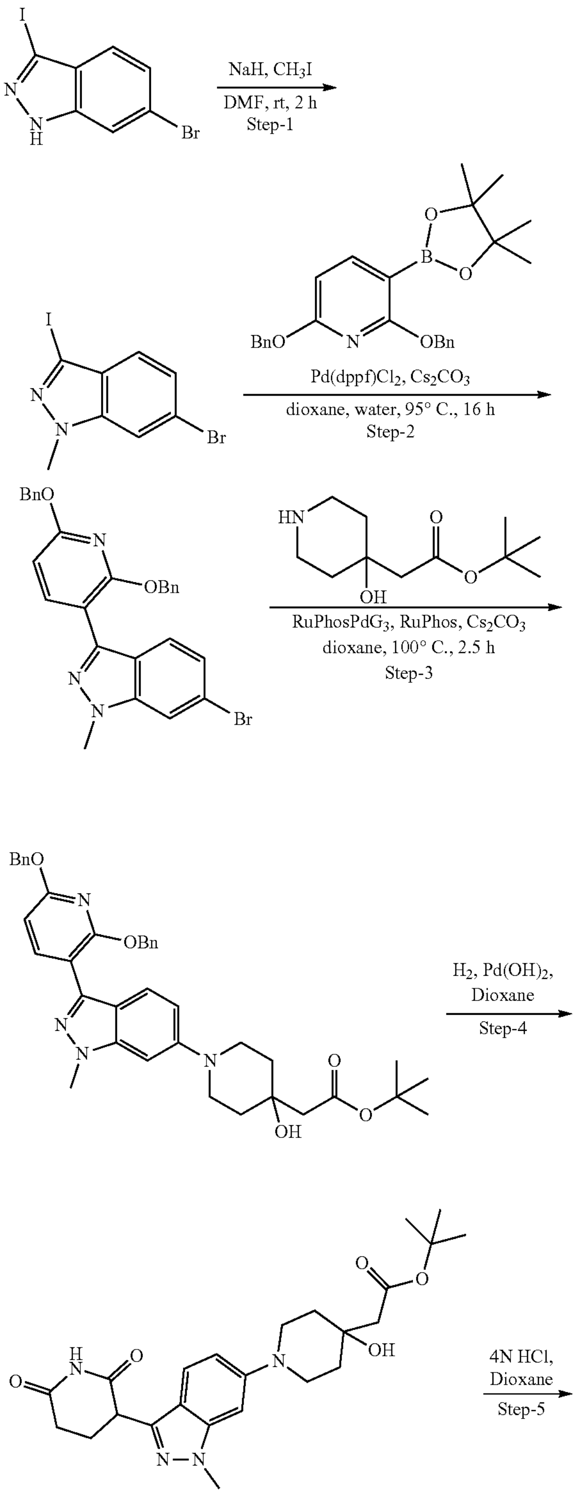

-continued

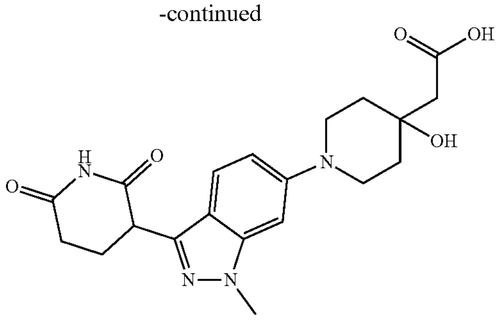

Step-1: To a suspension of sodium hydride (60% dispersion in mineral oil, 557.35 mg, 23.22 mmol) in N,N-dimethylformamide (15 mL) under nitrogen atmosphere was added 6-bromo-3-iodo-1H-indazole (5.0 g, 15.48 mmol) in N,N-dimethylformamide (15 mL) at 0° C. The reaction mixture was stirred at 25° C. for 10 min. Afterwards, the reaction mixture was again cooled 0° C. and iodomethane (4.40 g, 30.97 mmol, 1.93 mL) was added. The reaction mixture was stirred at 25° C. for 2 h. Afterwards, the reaction mixture was quenched with ammonium chloride (20 mL) and extracted with ethyl acetate (2×50 mL). The combined organic layers were washed with ice cold brine solution (2×50 mL), dried over $Na_2SO_4$ and then evaporated to obtain the crude material, which was purified by flash silica gel column chromatography (20% ethyl acetate in petroleum ether) to afford 6-bromo-3-iodo-1-methyl-indazole (4.0 g, 11.79 mmol, 76% yield) as an off-white solid. LCMS ($ES^+$): m/z 339.8 $[M+H]^+$ Step-2: Into a 10 mL sealed-tube containing a well-stirred solution of 6-bromo-3-iodo-1-methyl-indazole (1.56 g, 4.64 mmol) in water (1.8 mL) and dioxane (4.2 mL) was added 2,6-dibenzyloxy-3-(4,4,5,5-tetramethyl-1,3,2-dioxaborolan-2-yl)pyridine (1.5 g, 3.09 mmol) at room temperature under nitrogen. The reaction mixture was degassed by purging nitrogen for 5 mins. Subsequently, Pd(dppf) $Cl_2$·dichloromethane (252.36 mg, 309.02 μmol) and cesium carbonate (2.01 g, 6.18 mmol) were added, and the reaction mixture was heated at 95° C. for 16 h. The reaction mixture was filtered through a pad of Celite bed and washed with ethyl acetate (2×50 mL). The filtrate was concentrated under reduced pressure to get the crude material, which was purified by silica gel flash column chromatography (20% ethyl acetate in petroleum ether) to obtain 6-bromo-3-(2,6-dibenzyloxy-3-pyridyl)-1-methyl-indazole (1.1 g, 1.77 mmol, 57% yield) as a white solid. LCMS ($ES^+$): m/z 502.0 $[M+H]^+$ Step-3: A solution of 6-bromo-3-(2,6-dibenzyloxy-3-pyridyl)-1-methyl-indazole (1.4 g, 2.80 mmol) in 1,4-dioxane (10.0 mL) was taken in a sealed tube and added tert-butyl 2-(4-hydroxy-4-piperidyl)acetate (602.34 mg, 2.80 mmol) and cesium carbonate (2.73 g, 8.39 mmol) at room temperature under nitrogen atmosphere. The reaction mixture was degassed with nitrogen for 15 minutes then RuPhos (130.56 mg, 279.78 μmol), RuPhosPd$G_3$ (234.00 mg, 279.78 μmol) were added to the reaction mixture and again degassed with nitrogen for 5 minutes. The resulting reaction mixture was heated to 100° C. for 2.5 h. After completion, the reaction mixture was diluted with ethyl acetate (50 mL), washed with water (20.0 ml) and brine solution (30.0 mL). The organic layer was dried over sodium sulfate and concentrated under reduced pressure to get crude, which was purified by silica gel column chromatography eluted with 50% ethyl acetate in petroleum ether to afford tert-butyl 2-[1-[3-(2,6-dibenzyloxy-3-pyridyl)-1-methyl-indazol-6-yl]-4-hydroxy-4-piperidyl]acetate (1.1 g, 1.64 mmol, 59% yield) as an off-white solid. LCMS ($ES^+$): m/z 635.2 $[M+H]^+$ Step-4: To a stirred solution of tert-butyl 2-[1-[3-(2,6-dibenzyloxy-3-pyridyl)-1-methyl-indazol-6-yl]-4-hydroxy-4-piperidyl]acetate (2.0 g, 3.15 mmol) in 1,4-dioxane (30 mL) purged with nitrogen gas, then added palladium hydroxide on carbon, 20 wt. % dry basis (442.48 mg, 3.15 mmol) and stirred under hydrogen atmosphere at room temperature for 16 h. After completion of the reaction, the reaction mixture was filtered through celite bed, washed with ethyl acetate (200 mL) and concentrated under reduced pressure to get the crude product, which was purified by silica gel column chromatography eluted with 75% ethyl acetate in petroleum ether to afford tert-butyl 2-[1-[3-(2,6-dioxo-3-piperidyl)-1-methyl-indazol-6-yl]-4-hydroxy-4-piperidyl]acetate (1.2 g, 2.59 mmol, 82% yield) as an off-white solid. LCMS ($ES^+$): m/z 457.2 $[M+H]^+$ Step-5: To a stirred solution of tert-butyl 2-[1-[3-(2,6-dioxo-3-piperidyl)-1-methyl-indazol-6-yl]-4-hydroxy-4-piperidyl]acetate (1.2 g, 2.59 mmol) in 1,4-dioxane (15 mL) was added 4M hydrogen chloride solution in dioxane (30 mL) drop wise at 0° C. and stirred at room temperature for 50 h. After completion of the reaction, the reaction mixture was concentrated and triturated with hexane (100 mL) and dried to afford 2-[1-[3-(2,6-dioxo-3-piperidyl)-1-methyl-indazol-6-yl]-4-hydroxy-4-piperidyl]acetic acid (1.15 g, 2.16 mmol, 83% yield) as an off-white solid. LCMS ($ES^+$): m/z 401.2 $[M+H]^+$ Synthesis of 2-[1-[3-(2,6-dioxo-3-piperidyl)-1-methyl-indazol-6-yl]-4-piperidyl]acetic acid

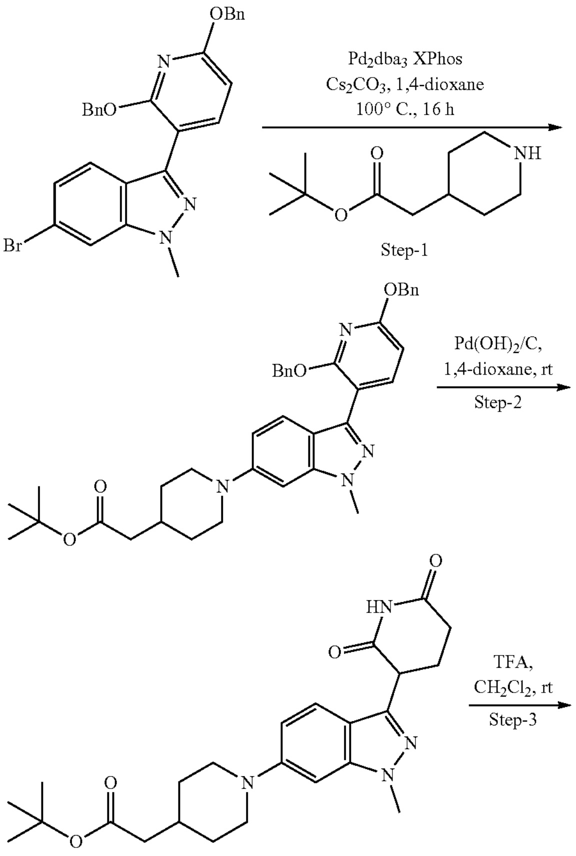

-continued

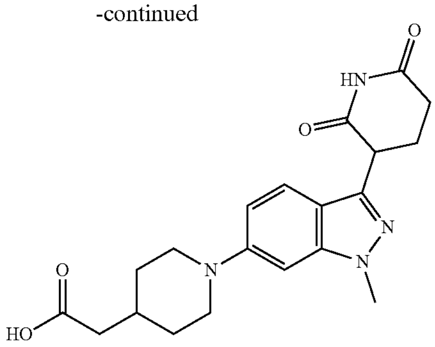

Step-1: To a stirred solution of tert-butyl 2-(4-piperidyl) acetate (50 mg, 250.89 μmol) and 6-bromo-3-(2,6-dibenzyloxy-3-pyridyl)-1-methyl-indazole (125.54 mg, 250.89 μmol) were in 1,4 dioxane (3 mL). The reaction mixture was degassed for 5 minutes, followed by addition of $Cs_2CO_3$ (97.6 mg, 250.89 μmol). Then, XPhos (9.1 mg, 250.89 μmol) was added and followed by addition of Tris(dibenzylideneacetone)dipalladium(0) (9.5 mg, 250.89 μmol). The reaction mixture was stirred for 16 h at 100° C. The reaction mixture was diluted with ethyl acetate (20 mL), washed with cold water (5 mL). The organic layer was washed with brine solution (5 mL), dried over sodium sulphate and concentrated under reduced pressure to get crude, which was purified by column chromatography on silica gel eluted with 30% ethyl acetate in pet ether to afford tert-butyl 2-[1-[3-(2,6-dibenzyloxy-3-pyridyl)-1-methyl-indazol-6-yl]-4-piperidyl]acetate (40 mg, 46.54 μmol, 18.55% yield) as yellow solid. LCMS ($ES^+$): m/z 619.3 $[M+H]^+$.

Step-2: To a stirred solution of tert-butyl 2-[1-[3-(2,6-dibenzyloxy-3-pyridyl)-1-methyl-indazol-6-yl]-4-piperidyl] acetate (500 mg, 808.06 μmol) in 1,4 dioxane (20 mL) was added palladium hydroxide on carbon, 20 wt. % and 50% water (226.97 mg, 1.62 mmol) at 25° C. Total reaction mixture was stirred for 16 h at 25° C. under hydrogen balloon pressure. After completion of reaction, the reaction mixture was filtered through celite bed and washed with 1,4 dioxane (150 mL). The filtrate was concentrated under reduced pressure to yield crude. The crude was washed with diethyl ether (20 mL) to get tert-butyl 2-[1-[3-(2,6-dioxo-3-piperidyl)-1-methyl-indazol-6-yl]-4-piperidyl]acetate (400 mg, 573.85 μmol, 71.02% yield) as brown colour solid. LCMS ($ES^+$): m/z 441.2 $[M+H]^+$.

Step-3: To a stirred solution of tert-butyl 2-[1-[3-(2,6-dioxo-3-piperidyl)-1-methyl-indazol-6-yl]-4-piperidyl]acetate (300 mg, 680.99 μmol) in Dichloromethane (5 mL) was added trifluoroacetic acid (388.24 mg, 3.40 mmol, 262.33 μL) at 0° C. Total reaction mixture was stirred for 2 h at 25° C. Reaction was monitored by LC-MS. After completion of reaction, the reaction mixture was concentrated under reduced pressure to yield crude. The crude was washed with diethyl ether (20 mL) to afford 2-[1-[3-(2,6-dioxo-3-piperidyl)-1-methyl-indazol-6-yl]-4-piperidyl]acetic acid (220 mg, 353.09 μmol, 51.85% yield) as light pink colour solid.

Synthesis of tert-butyl 4-(3-(2,6-dioxopiperidin-3-yl)-1-methyl-1H-indazol-6-yl)-3,3-difluoropiperidine-1-carboxylate

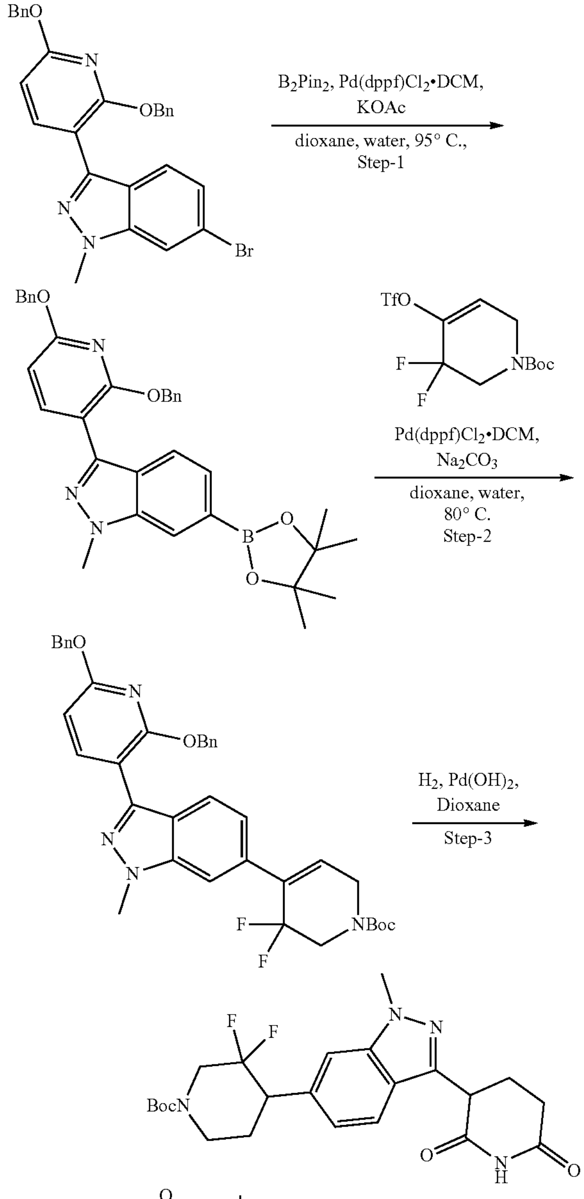

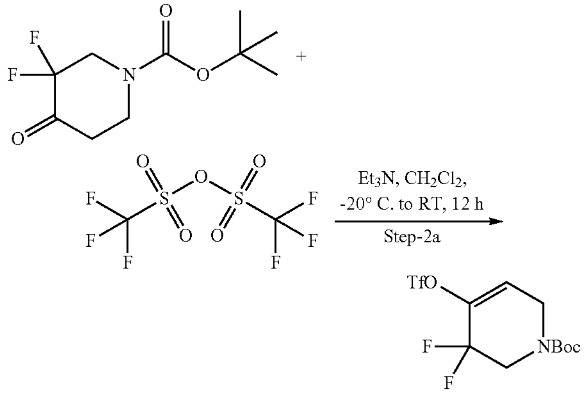

Step-1: In a 100 mL sealed tube containing a well-stirred solution of 6-bromo-3-(2,6-dibenzyloxy-3-pyridyl)-1-methyl-indazole (2 g, 4.00 mmol) in 1,4-dioxane (20 mL), bis(pinacolato)diborane (1.12 g, 4.40 mmol) and potassium acetate (1.18 g, 11.99 mmol, 749.55 μL) was added. The reaction mixture was degassed with nitrogen for 10 minutes. To the reaction mixture Pd(dppf)$Cl_2$·dichloromethane (326.40 mg, 399.69 μmol) was added and degassed again for 5 minutes. The reaction mixture was then stirred at 90° C. for 2 h. After the completion, the reaction mixture was filtered through celite bed and washed with ethyl acetate, and organic layer was concentrated under reduced pressure to get the crude, which was purified by silica gel column chromatography eluted with 20% ethyl acetate in petroleum ether to afford 3-(2,6-dibenzyloxy-3-pyridyl)-1-methyl-6-(4,4,5,5-tetramethyl-1,3,2-dioxaborolan-2-yl)indazole (1.9 g, 3.43 mmol, 86% yield) as a viscous yellow liquid. LCMS ($ES^+$): m/z 548.2 $[M+H]^+$.

Step-2a: To a stirred solution of tert-butyl 3,3-difluoro-4-oxo-piperidine-1-carboxylate (2.5 g, 10.63 mmol) in dichloromethane (25 mL) at −20° C. was added triethyl amine (3.23 g, 31.88 mmol, 4.44 mL) followed by trifluoromethanesulfonic anhydride (4.50 g, 15.94 mmol, 2.68 mL) dropwise. The reaction mass was stirred at RT for 16 h. Then, the reaction was quenched with $NaHCO_3$ (aq), and extracted with dichloromethane, washed with brine, dried over $Na_2SO4$, and concentrated in vacuo. The crude mixture was purified by silica gel column chromatography (0-20% ethyl acetate in petroleum ether) to afford tert-butyl 3,3-difluoro-4-(trifluoromethylsulfonyloxy)-2,6-dihydropyridine-1-carboxylate (1.2 g, 2.29 mmol, 22% yield). $^1H$ NMR (400 MHz, methanol-d4) δ 6.59 (s, 1H), 4.29 (q, J=4.3 Hz, 2H), 4.04 (t, J=11.0 Hz, 2H), 1.51 (s, 9H).

Step-2: Into a 50 ml sealed tube containing a well-stirred solution of 3-(2,6-dibenzyloxy-3-pyridyl)-1-methyl-6-(4,4,5,5-tetramethyl-1,3,2-dioxaborolan-2-yl)indazole (500 mg, 913.32 μmol), tert-butyl 3,3-difluoro-4-(trifluoromethylsulfonyloxy)-2,6-dihydropyridine-1-carboxylate (436.09 mg, 1.19 mmol) in 1,4-dioxane (5 mL) and water (1 mL) were added sodium carbonate (290.41 mg, 2.74 mmol, 114.79 μL). The reaction mixture was purged with nitrogen gas for 15 minutes, then Pd(dppf)$Cl_2$·dichloromethane (111.79 mg, 137.00 μmol) was added and continued for stirring at 80° C. for 2 h. Reaction mixture was passed through celite bed, washed with ethyl acetate (50 mL), filtrate was concentrated under reduced pressure to get the crude, which was purified by flash silica gel column chromatography eluted with 25% ethyl acetate in petroleum ether to afford tert-butyl 4-[3-(2,6-dibenzyloxy-3-pyridyl)-1-methyl-indazol-6-yl]-3,3-difluoro-2,6-dihydropyridine-1-carboxylate (487 mg, 722.00 μmol, 79% yield) as a yellow sticky solid. LCMS ($ES^+$): m/z 639.2 $[M+H]^+$ Step-3: Into a 100 mL single-necked round bottom flask containing a well stirred solution of tert-butyl 4-[3-(2,6-dibenzyloxy-3-pyridyl)-1-methyl-indazol-6-yl]-3,3-difluoro-2,6-dihydropyridine-1-carboxylate (480 mg, 706.43 μmol) in anhydrous 1,4-dioxane (5 mL) was added palladium hydroxide on carbon, 20 wt. % 50% water (545.66 mg, 777.08 μmol) at room temperature. The reaction mixture was stirred under hydrogen bladder for 16 h. After completion of starting material, reaction mixture was filtered through celite bed, washed with 1,4 dioxane (100 mL) and N,N-dimethylformamide (20 mL), and solvent was evaporated under reduced pressure. The crude compound was triturated with diethyl ether (20 mL) and dried under reduced pressure to afford tert-butyl 4-[3-(2,6-dioxo-3-piperidyl)-1-methyl-indazol-6-yl]-3,3-difluoro-piperidine-1-carboxylate (300 mg, 636.15 μmol, 90% yield) as an off-white solid. LCMS ($ES^+$): m/z 463.2 $[M+H]^+$.

Synthesis of 2-[1-[3-(2,4-dioxohexahydropyrimidin-1-yl)-5-fluoro-1-methyl-indazol-6-yl]-4-hydroxy-4-piperidyl]acetic acid

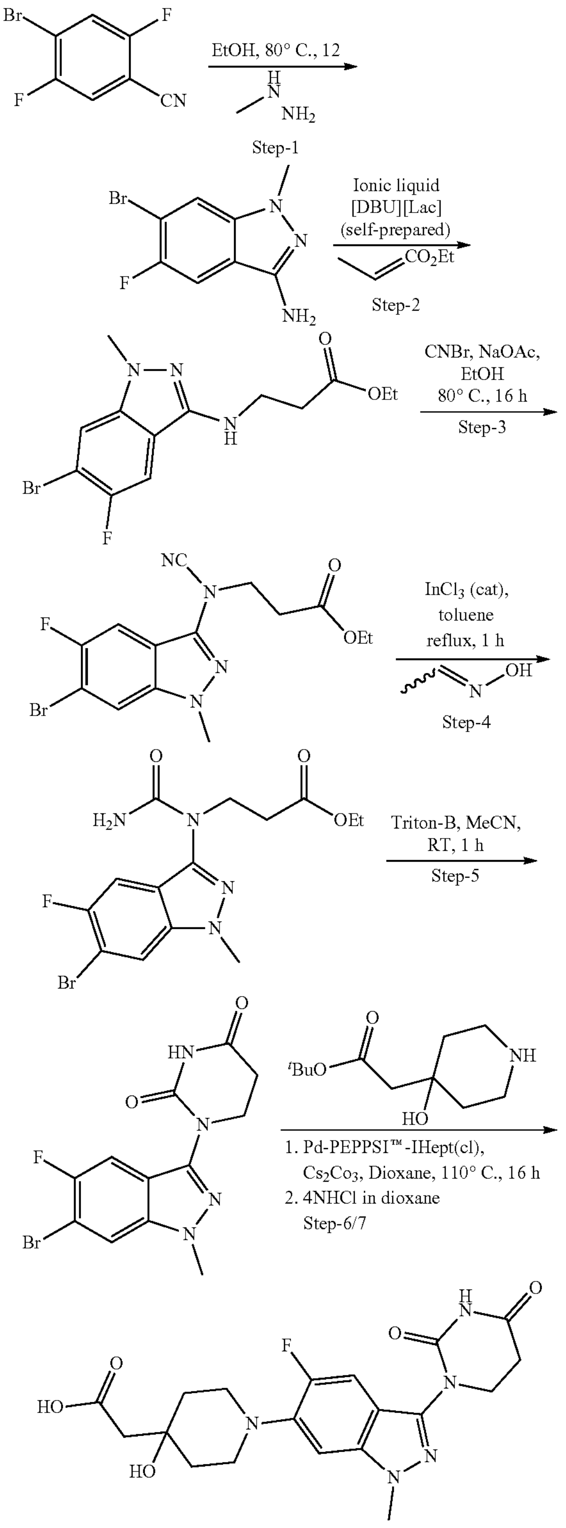

-continued

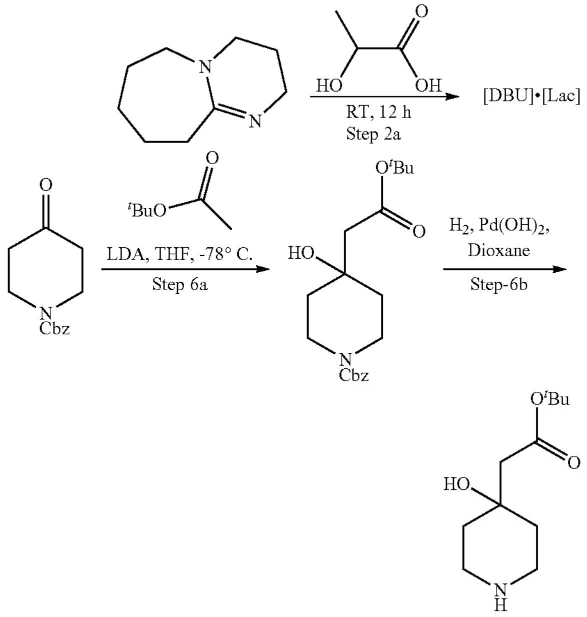

Step-1: To a stirred solution of 4-bromo-2,5-difluoro-benzonitrile (25 g, 114.68 mmol) in ethanol (250 mL) was added methylhydrazine (85% aq. solution, 21.13 g, 458.72 mmol) at room temperature under nitrogen atmosphere. The resulting reaction mixture was heated to 80° C. for 12 h. After completion, the resulting solution was quenched with water (80 ml), and the obtained precipitate was filtered and dried to afford 6-bromo-5-fluoro-1-methyl-indazol-3-amine (17.5 g, 70.71 mmol, 62% yield) as off-white solid, which was carried forward without further purification. LCMS ($ES^+$): m/z 246.0 $[M+H]^+$.

Step-2a: A mixture of DBU (200 g, 1.31 mol, 1.00 eq) and lactic acid (118 g, 1.31 mol, 97.5 mL, 1.00 eq) in a flask (2.00 L) was degassed and purged with $N_2$ for 3 times. The resulting mixture was stirred at 25° C. for 12 h under nitrogen atmosphere to obtain [DBU]. [Lac] ionic liquid (316 g, crude) as a thick solution, which was carried forward without further purification.

Step-2: To a solution of 6-bromo-5-fluoro-1-methyl-indazol-3-amine (17.5 g, 71.70 mmol) in [DBU]·[Lac] ionic liquid (18 g) was added ethyl prop-2-enoate (50.25 g, 501.92 mmol, 54.38 mL) at room temperature under nitrogen atmosphere. The resulting solution was heated to 90° C. for 48 h. After completion, the resulting solution was quenched with water (100 ml) and extracted with ethyl acetate (2×100 mL). The combined organic layer was dried over sodium sulfate and concentrated under reduced pressure. The resulting crude product was purified by silica gel flash column chromatography using ethyl acetate-petroleum ether (0-60%) to afford ethyl 3-[(6-bromo-5-fluoro-1-methyl-indazol-3-yl)amino]propanoate (11.0 g, 30.97 mmol, 43% yield) as red semisolid. LCMS ($ES^+$): m/z 344.4 $[M+H]^+$.

Step-3: A solution of ethyl 3-[(6-bromo-5-fluoro-1-methyl-indazol-3-yl)amino]propanoate (11 g, 31.96 mmol) in ethanol (110 mL) was added sodium acetate (15.73 g, 191.76 mmol, 10.28 mL) and cyanogen bromide (16.93 g, 159.80 mmol, 8.38 mL) at room temperature under nitrogen atmosphere. The reaction mixture was heated to 85° C. for 16 h. The reaction mixture was diluted with water (50 mL) and extracted with ethyl acetate (2×100 mL). The organic layer was washed with brine (30 mL), dried over sodium sulfate and concentrated under reduced pressure to afford ethyl 3-[(6-bromo-5-fluoro-1-methyl-indazol-3-yl)-cyano-amino]propanoate (12 g, 25.98 mmol, 81% yield) as yellow solid, which was carried forward without further purification. LCMS ($ES^+$): m/z 371.0 $[M+H]^+$ Step-4: To a stirred solution of ethyl 3-[(6-bromo-5-fluoro-1-methyl-indazol-3-yl)-cyano-amino]propanoate (12 g, 32.50 mmol) in toluene (120 mL) was added indium (III) chloride (718.91 mg, 3.25 mmol) and acetaldoxime (5.76 g, 97.51 mmol) at room temperature under nitrogen atmosphere. The reaction mixture was heated to 110° C. for 1 h. After completion, the reaction mixture was filtered and concentrated under reduced pressure. The resulting crude product was purified by silica gel flash column chromatography using ethyl acetate-petroleum ether (0-80%) to afford ethyl 3-[(6-bromo-5-fluoro-1-methyl-indazol-3-yl)-carbamoyl-amino]propanoate (8.0 g, 20.33 mmol, 63% yield) as off-white solid. LCMS ($ES^+$): m/z 387.0 $[M+H]^+$.

Step-5: To a stirred solution of ethyl 3-[(6-bromo-5-fluoro-1-methyl-indazol-3-yl)-carbamoyl-amino]propanoate (8.0 g, 20.66 mmol) in acetonitrile (80 mL) was added benzyl trimethylammonium hydroxide (25% solution in methanol, 4.15 g, 6.20 mmol) at room temperature under nitrogen atmosphere. The reaction mixture stirred at room temperature for 1 h. The reaction mixture was diluted with water (50 mL), extracted with ethyl acetate (3×80 mL). The combined organic layer were dried over sodium sulfate and concentrated under reduced pressure to afford 1-(6-bromo-5-fluoro-1-methyl-indazol-3-yl)hexahydropyrimidine-2,4-dione (5.2 g, 15.01 mmol, 73% yield) as off-white solid. LCMS ($ES^+$): m/z 343.0 $[M+H]^+$.

Step-6a: To a well stirred solution of tert-butyl acetate (18.67 g, 160.76 mmol, 160.76 mL) in THF (200 mL) was added lithium di-isopropyl amide (2M in THF, 64.30 mL) at −78° C. and the reaction mixture was stirred at same temperature for 1 h. Then, to the reaction mixture was added the solution of benzyl 4-oxopiperidine-1-carboxylate (15 g, 64.31 mmol, 12.82 mL) slowly at −78° C. before stirred for 1 h. The reaction mixture was quenched with saturated ammonium chloride solution. The reaction mixture was diluted with ethyl acetate (200 mL) and washed with water (40 mL) and brine (40 mL). The organic layer was dried with sodium sulfate, filtered, and concentrated under reduced pressure to afford benzyl 4-(2-tert-butoxy-2-oxo-ethyl)-4-hydroxy-piperidine-1-carboxylate (22.5 g, 64.02 mmol, 100% yield) as colorless oil. LCMS ($ES^+$): m/z 294.2 $[M+H-56]^+$.

Step-6b: To a stirred solution of benzyl 4-(2-tert-butoxy-2-oxo-ethyl)-4-hydroxy-piperidine-1-carboxylate (23 g, 65.82 mmol) in 1,4-dioxane (200 mL) was added palladium (7.00 g, 65.82 mmol), which was saturated with hydrogen by bubbling hydrogen gas through for 10 minutes and then subjected to hydrogenation (1 atm) at room temperature for 20 h. After completion, the reaction mixture was purged with nitrogen and the reaction mixture was filtered through a pad of celite. The filtrate was concentrated under reduced pressure to afford tert-butyl 2-(4-hydroxy-4-piperidyl)acetate (14 g, 64.94 mmol, 99% yield) as off-white solid, which was carried forward without further purification. LCMS ($ES^+$): m/z 216.3 $[M+H]^+$.

Step-6: A solution of 1-(6-bromo-5-fluoro-1-methyl-indazol-3-yl)hexahydropyrimidine-2,4-dione (4.4 g, 12.90 mmol) in 1,4-dioxane (80 mL) was taken in a sealed tube and added cesium carbonate (10.51 g, 32.25 mmol) and tert-butyl 2-(4-hydroxy-4-piperidyl)acetate (5.55 g, 25.80 mmol) at room temperature under nitrogen atmosphere. The reaction mixture was degassed with nitrogen for 10 minutes, then added Pd-PEPPSI-IHept catalyst (626.85 mg, 644.39 μmol) at room temperature. The resulting reaction mixture was heated to 105° C. for 16 h. The reaction mixture was diluted with water (20 mL) and extracted with ethyl acetate (2×50 mL). The combined organic layers were dried over sodium sulfate and concentrated under reduced pressure. The resulting product was purified by silica gel flash column chromatography using ethyl acetate-petroleum ether (0-80%) to afford tert-butyl 2-[1-[3-(2,4-dioxohexahydropyrimidin-1-yl)-5-fluoro-1-methyl-indazol-6-yl]-4-hydroxy-4-piperidyl]acetate (4.0 g, 7.67 mmol, 59% yield) as off-white solid. LCMS ($ES^+$): m/z 476.2 $[M+H]^+$.

Step-7: To a stirred solution of tert-butyl 2-[1-[3-(2,4-dioxohexahydropyrimidin-1-yl)-5-fluoro-1-methyl-indazol-6-yl]-4-hydroxy-4-piperidyl]acetate (0.5 g, 1.05 mmol) in dichloromethane (5 mL) was added hydrogen chloride solution in 1,4-dioxane (4.0 M, 10.51 mL) at 0° C. under nitrogen atmosphere. The resulting solution was stirred at room temperature for 24 h. The resulting solution was concentrated under reduced pressure to afford 2-[1-[3-(2,4-dioxohexahydropyrimidin-1-yl)-5-fluoro-1-methyl-indazol-6-yl]-4-hydroxy-4-piperidyl]acetic acid (0.48 g, 884.68 μmol, 84% yield) as a brownish semisolid, which was carried forward without further purification. LCMS ($ES^+$): m/z 420.2 $[M+H]^+$.

Synthesis of 2-(4-(3-(2,4-dioxotetrahydropyrimidin-1(2H)-yl)-5-fluoro-1-methyl-1H-indazol-6-yl)piperazin-1-yl)acetic acid

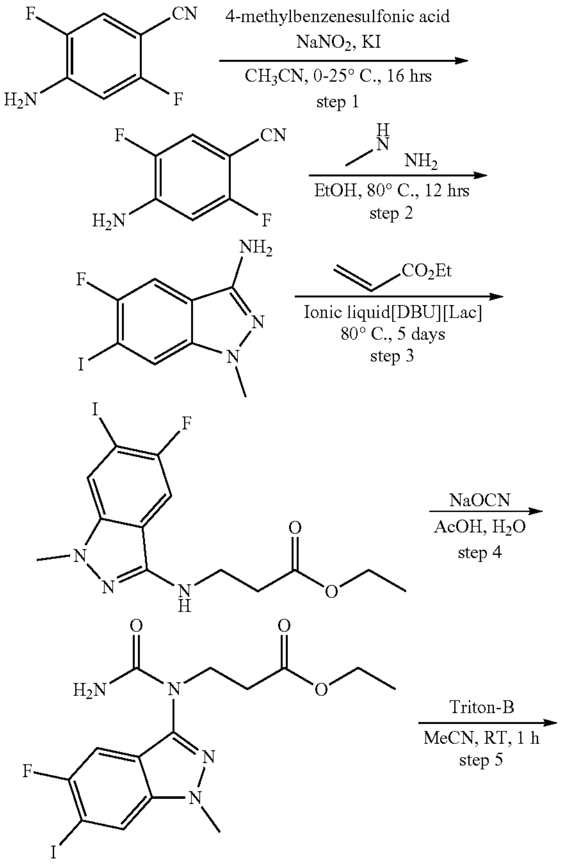

-continued

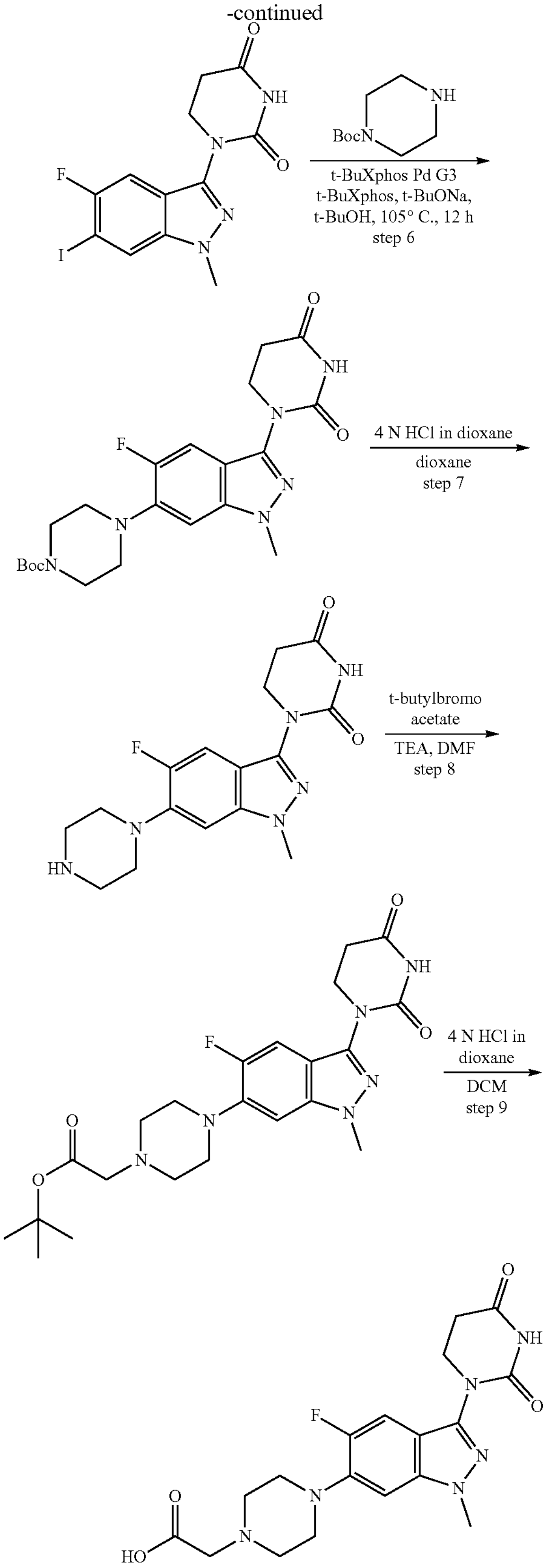

Step-1: A mixture of 4-amino-2,5-difluorobenzonitrile (52.0 g, 0.33 mol), 4-methylbenzenesulfonic acid (208 g, 1.21 mol) in acetonitrile (1.06 L) was stirred for 4 hrs at 15°

C. Then $NaNO_2$ (39.6 g, 0.57 mol) and KI (95.2 g, 0.57 mol) were added into reactor at 0° C. Then the mixture was stirred for 12 h at 15° C. After completion, the mixture was quenched with aq. $NaHSO_3$ (200 mL). The aqueous phase is extracted with ethyl acetate (500 mL). The combined organic phase is washed with brine (200 mL), dried with anhydrous sodium sulfate, filtered and concentrated in vacuum to obtain 2,5-difluoro-4-iodobenzonitrile (120 g, 48% yield) as a white solid. $^1$H NMR (400 MHz, $CDCl_3$): δ=7.39 (s, 1H), 7.12-7.00 (m, 1H).

Step-2: A mixture of 2,5-difluoro-4-iodobenzonitrile (60.0 g, 0.22 mol) and methylhydrazine (59.6 mL, 0.45 mol) in EtOH (600 mL) was degassed and purged with $N_2$ for 3 times at 15° C., and then the mixture was stirred at 80° C. for 16 h under $N_2$ atmosphere. The reaction was concentrated in vacuum under reduced pressure. The residue yellow solid was triturated with EtOH (120 mL) at 15° C. for 5 h and filtered to afford 5-fluoro-6-iodo-1-methyl-1H-indazol-3-amine (109 g, 83% yield) as a white solid.

Step-3: A mixture of 5-fluoro-6-iodo-1-methyl-1H-indazol-3-amine (54.5 g, 220 mmol), ethyl acrylate (142 mL, 1.31 mol) and [DBU]·[Lac](26.4 g, 180 mmol) was degassed and purged with $N_2$ for 3 times, the resulting mixture was stirred at 80° C. for 120 h under $N_2$ atmosphere. The residue was diluted with DCM (500 mL) and $H_2O$ (500 mL), the organic layers were washed with brine (300 mL) dried over $Na_2SO_4$, filtered and filtrate concentrated under reduced pressure to give a residue. The residue was purified by silica gel column chromatography (petroleum ether/ethyl acetate=50/1 to 1/1) to afford ethyl 3-((5-fluoro-6-iodo-1-methyl-1H-indazol-3-yl)amino)propanoate (70.0 g, 48% yield) as a yellow solid.

Step-4: A mixture of ethyl 3-((5-fluoro-6-iodo-1-methyl-1H-indazol-3-yl)amino)propanoate (50.0 g, 0.39 mol), NaOCN (24.9 g, 0.38 mol) in HOAc (225 mL) and water (75.0 mL) was stirred at 15° C. for 3 h. The aqueous phase was extracted with ethyl acetate (150 mL). The combined organic phase was washed with $NaHCO_3$ (150 mL, 3.00× by volume), dried with anhydrous $Na_2SO_4$, filtered and concentrated in vacuum to give ethyl 3-(1-(5-fluoro-6-iodo-1-methyl-1H-indazol-3-yl)ureido)propanoate (32.0 g, 57% yield) as a white solid.

Step-5: A mixture of ethyl 3-(1-(5-fluoro-6-iodo-1-methyl-1H-indazol-3-yl)ureido)propanoate (32.0 g, 73.0 mmol) and Triton B (22.0 mmol, 4.02 mL) in acetonitrile (320 mL) was stirred at 15° C. for 3 h. The reaction mixture was filtered to give cake and the cake was concentrated under reduced pressure to afford 1-(5-fluoro-6-iodo-1-methyl-1H-indazol-3-yl)dihydropyrimidine-2,4(1H,3H)-dione (24.0 g, 84% yield) as an off-white solid. LCMS ($ES^+$): m/z 389.0 $[M+H]^+$. $^1$HNMR (400 MHz, DMSO-$d_6$): δ=10.56 (s, 1H), 8.27-8.01 (m, 1H), 7.51-7.45 (m, 1H), 3.97 (s, 3H), 3.95-3.90 (m, 2H), 2.79-2.73 (m, 2H).

Step-6: To a solution of 1-(5-fluoro-6-iodo-1-methyl-1H-indazol-3-yl)dihydropyrimidine-2,4(1H,3H)-dione (2.5 g, 6.44 mmol) in t-BuOH (50 mL) were added tert-butyl piperazine-1-carboxylate (2.40 g, 12.8 mmol), t-BuONa (1.86 g, 19.3 mmol), t-BuXphos (2.74 g, 6.44 mmol) and t-BuBrettphos Pd G3 (2.56 g, 3.22 mmol). The reaction mixture was stirred at 100° C. for 12 h. The reaction mixture was diluted with water (50 mL), extracted with ethyl acetate (50 mL×3). The combined organic layers were washed by brine (50 mL), dried over $Na_2SO_4$, filtered, concentrated under reduced pressure to give a residue, which was purified by flash silica gel column chromatography (0-100% ethyl acetate in petroleum ether) to afford tert-butyl 4-(3-(2,4-dioxotetrahydropyrimidin-1(2H)-yl)-5-fluoro-1-methyl-1H-indazol-6-yl)piperazine-1-carboxylate (944 mg, 30% yield) as a yellow solid. LCMS ($ES^+$): m/z 447.1 $[M+H]^+$. $^1$HNMR (400 MHz, $CDCl_3$): δ=7.63 (s, 1H), 7.35 (d, J=12.3 Hz, 1H), 6.69 (d, J=6.6 Hz, 1H), 4.08 (t, J=6.7 Hz, 2H), 3.99-3.87 (m, 3H), 3.70-3.60 (m, 4H), 3.14-3.01 (m, 4H), 2.87 (t, J=6.7 Hz, 2H), 1.49 (s, 9H).

Step-7: To a stirred solution of tert-butyl 4-[3-(2,4-dioxohexahydropyrimidin-1-yl)-5-fluoro-1-methyl-indazol-6-yl]piperazine-1-carboxylate (0.15 g, 335.97 μmol) in dioxane (3 mL) was added hydrogen chloride solution 4.0 M in dioxane (4 M, 83.99 μL) at 5° C. under nitrogen atmosphere. The reaction mixture was stirred at room temperature for 6 h. After completion, the reaction mixture was concentrated under reduced pressure to afford 1-(5-fluoro-1-methyl-6-piperazin-1-yl-indazol-3-yl)hexahydropyrimidine-2,4-dione hydrochloride (0.125 g, 309.24 μmol, 92% yield) as an off-white solid. LCMS ($ES^+$): m/z 347.1 $[M+H]^+$.

Step-8: To a solution of 1-(5-fluoro-1-methyl-6-piperazin-1-yl-indazol-3-yl)hexahydropyrimidine-2,4-dione (146 mg, 421.53 μmol), TEA (127.96 mg, 1.26 mmol, 176.26 μL) in DMF (2 mL) was added t-butylbromo acetate (83.07 mg, 421.53 μmol) and stirred at room temperature for 14 h. The reaction mixture was diluted with water (10 mL) and extracted with ethyl acetate (30 mL). The organic layer was washed with brine solution (10 mL), dried over sodium sulfate and concentrated under reduced pressure to afford tert-butyl 2-[4-[3-(2,4-dioxohexahydropyrimidin-1-yl)-5-fluoro-1-methyl-indazol-6-yl]piperazin-1-yl]acetate (130 mg, 271.01 μmol, 64% yield) as a light brown solid. LCMS ($ES^+$): m/z 461.2 $[M+H]^+$.

Step-9: To a solution of tert-butyl 2-[4-[3-(2,4-dioxohexahydropyrimidin-1-yl)-5-fluoro-1-methyl-indazol-6-yl]piperazin-1-yl]acetate (120 mg, 260.59 μmol) in DCM (2 mL) was added hydrogen chloride, 4M in 1,4-dioxane (4 M, 3 mL) at 0° C. and stirred at room temperature for 6 h. The reaction mixture was concentrated under reduced pressure to get crude which was triturated with petroleum ether to afford 2-[4-[3-(2,4-dioxohexahydropyrimidin-1-yl)-5-fluoro-1-methyl-indazol-6-yl]piperazin-1-yl]acetic acid hydrochloride (110 mg, 209.59 μmol, 80% yield) as a brown solid. LCMS ($ES^+$): m/z 405.2 $[M+H]^+$.

Synthesis of 2-(1-(3-(2,4-dioxotetrahydropyrimidin-1(2H)-yl)-7-fluoro-1-methyl-1H-indazol-6-yl)-4-hydroxypiperidin-4-yl)acetic acid

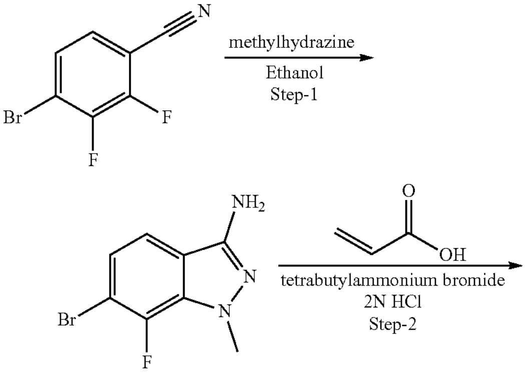

-continued

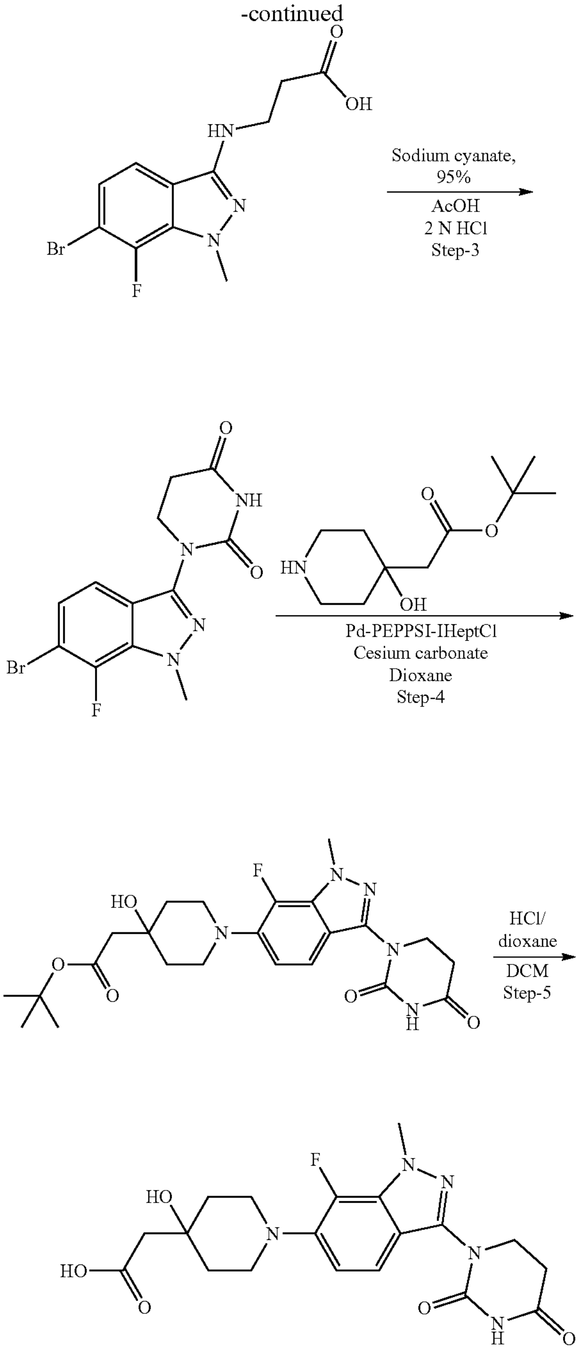

Step-1: To a solution of 4-bromo-2,3-difluoro-benzonitrile (45 g, 206.42 mmol) in ethanol (450 mL) was added 40% methylhydrazine (45.48 g, 412.85 mmol). The mixture was stirred at 80° C. for 12 h. The mixture was cooled down to 30° C. and concentrated under vacuum (40° C.) to removed solvent and filtered. The filter cake was washed with ethanol (5 mL×2) and concentrated at 40° C. under vacuum to give 6-bromo-7-fluoro-1-methyl-indazol-3-amine (44 g, 180.28 mmol, 87% yield) as a yellow solid. $^1$H NMR (400 MHz, DMSO-$d_6$): δ=7.46 (d, J=8.5 Hz, 1H), 7.07 (dd, J=8.5, 5.5 Hz, 1H), 5.68 (s, 2H), 3.84 (s, 3H).

Step-2: To a solution of 6-bromo-7-fluoro-1-methyl-indazol-3-amine (23.5 g, 96.29 mmol) in 2N HCl (230 mL) was added acrylic acid (10.41 g, 144.43 mmol, 9.91 mL) and tetrabutylammonium bromide (3.10 g, 9.63 mmol). The mixture was stirred at 100° C. for 16 h. The reaction mixture was cooled down to rt and stirred overnight, filtered, and washed with water (250 mL). The cake was dried under vacuum to afford 3-[(6-bromo-7-fluoro-1-methyl-indazol-3-yl)amino]propanoic acid (28.5 g, 89.25 mmol, 93% yield) as a white solid. $^1$H NMR (400 MHz, DMSO-$d_6$): δ=7.50 (d, J=8.5 Hz, 1H), 7.09 (dd, J=8.5, 5.6 Hz, 1H), 3.88 (s, 3H), 3.45 (t, J=6.9 Hz, 2H), 2.65-2.51 (m, 2H).

Step-3: A mixture of 3-[(6-bromo-7-fluoro-1-methyl-indazol-3-yl)amino]propanoic acid (28.5 g, 90.15 mmol) and sodium cyanate (11.72 g, 180.31 mmol) in AcOH (280 mL) was stirred at 60° C. for 16 h. To the mixture was added 2 N HCl (280 mL) and stirred at 60° C. for another 6 h. The reaction mixture was cooled down to rt and stirred overnight, filtered and washed with water (250 mL).The cake was dried under vacuum to afford 1-(6-bromo-7-fluoro-1-methyl-indazol-3-yl)hexahydropyrimidine-2,4-dione (16 g, 46.43 mmol, 52% yield) as a white solid. $^1$H NMR (400 MHz, DMSO-$d_6$): δ=10.64 (s, 1H), 7.44 (d, J=8.7 Hz, 1H), 7.30 (dd, J=8.7, 5.7 Hz, 1H), 4.12 (d, J=1.3 Hz, 3H), 3.94 (t, J=6.7 Hz, 2H), 2.77 (t, J=6.7 Hz, 2H).

Step-4: To a solution of 1-(6-bromo-7-fluoro-1-methyl-indazol-3-yl)hexahydropyrimidine-2,4-dione (1 g, 2.93 mmol) and tert-butyl 2-(4-hydroxy-4-piperidyl)acetate (1.58 g, 7.33 mmol) in dioxane (10 mL) was added Pd-PEPPSI-IHeptCl (80 mg, 146.57 μmol) and cesium carbonate (3.34 g, 10.26 mmol). The mixture was stirred at 105° C. for 14 h under $N_2$. The reaction mixture was diluted with water (30 mL) and extracted with ethyl acetate (10 mL×3). The combined organic layers were washed with brine (30 mL), dried over sodium sulfate, filtered and concentrated under reduced pressure. The residue was purified by silica gel column chromatography (petroleum ether/ethyl acetate=1/1 to 0/1) to afford tert-butyl 2-[1-[3-(2,4-dioxohexahydropyrimidin-1-yl)-7-fluoro-1-methyl-indazol-6-yl]-4-hydroxy-4-piperidyl]acetate (0.8 g, 1.67 mmol, 57% yield) as a yellow solid. LCMS ($ES^+$): m/z 420.2 $[M+H]^+$. $^1$H NMR (400 MHz, DMSO-$d_6$): δ=10.57 (s, 1H), 7.33 (d, J=8.9 Hz, 1H), 6.95 (dd, J=8.9, 7.1 Hz, 1H), 4.57 (s, 1H), 4.06 (d, J=1.3 Hz, 3H), 3.90 (t, J=6.7 Hz, 2H), 3.18-3.10 (m, 4H), 2.75 (t, J=6.7 Hz, 2H), 2.38 (s, 2H), 1.90-1.76 (m, 2H), 1.71 (d, J=12.9 Hz, 2H), 1.43 (s, 9H).

Step-5: To a solution of tert-butyl 2-[1-[3-(2,4-dioxohexahydropyrimidin-1-yl)-7-fluoro-1-methyl-indazol-6-yl]-4-hydroxy-4-piperidyl]acetate (800 mg, 1.68 mmol) in DCM (8 mL) was added HCl in dioxane (4 M, 8 mL). The mixture was stirred at 25° C. for 16 h. The reaction mixture was concentrated under reduced pressure to afford 2-[1-[3-(2,4-dioxohexahydropyrimidin-1-yl)-7-fluoro-1-methyl-indazol-6-yl]-4-hydroxy-4-piperidyl]acetic acid hydrochloride (750 mg, 1.58 mmol, 94% yield) as a yellow oil. $^1$H NMR (400 MHz, DMSO-$d_6$): δ=10.58 (s, 1H), 7.37 (d, J=8.9 Hz, 1H), 7.02 (t, J=7.9 Hz, 1H), 4.07 (s, 3H), 3.90 (t, J=6.7 Hz, 2H), 3.29-3.09 (m, 4H), 2.75 (t, J=6.7 Hz, 2H), 2.43 (s, 2H), 1.97-1.85 (m, 2H), 1.75 (d, J=13.1 Hz, 2H).

EXAMPLES

The following examples are provided for illustration of the invention. They should not be considered as limiting the scope of the invention, but merely as being representative thereof.

General scheme for Scaffold A
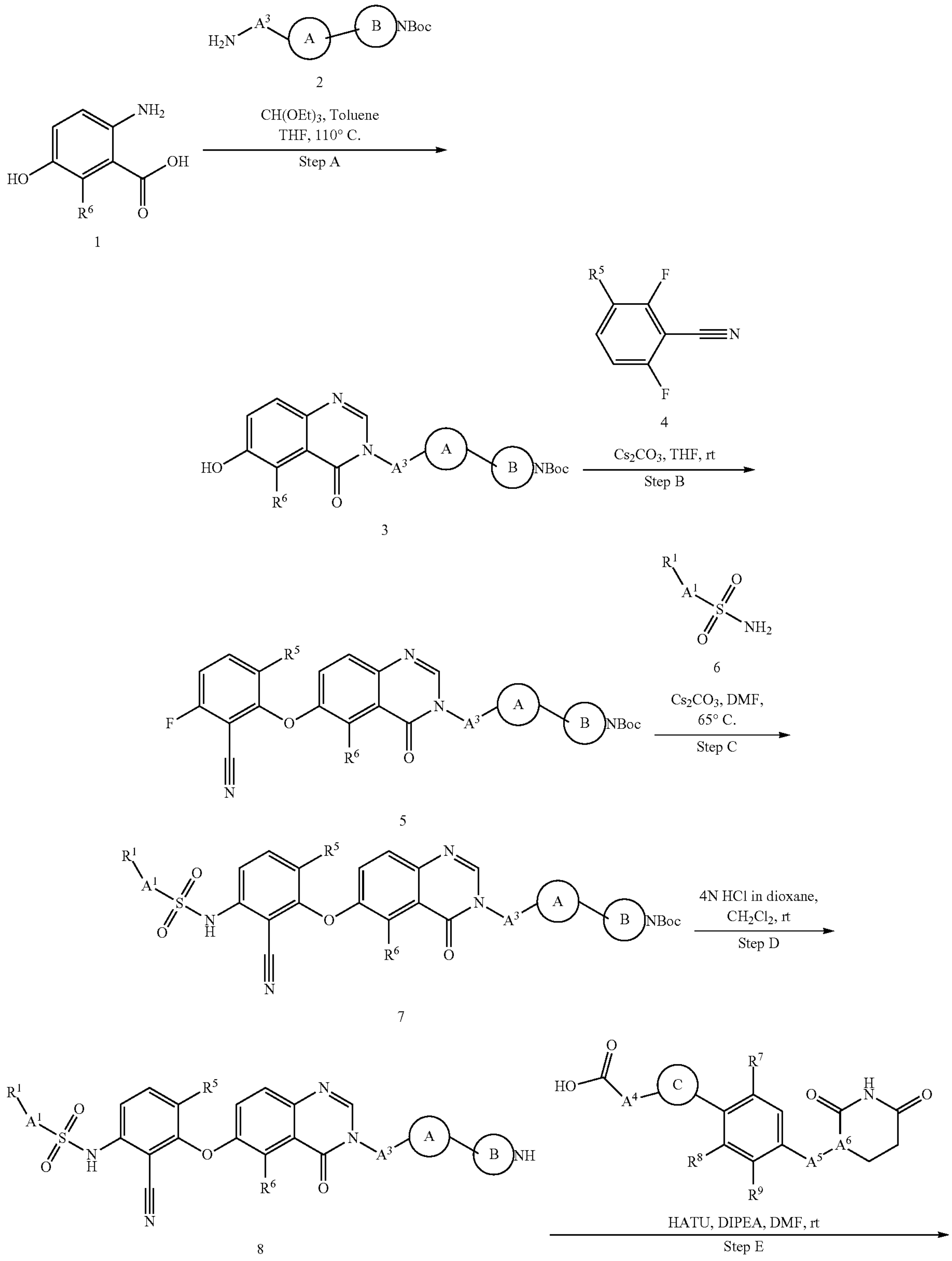

-continued

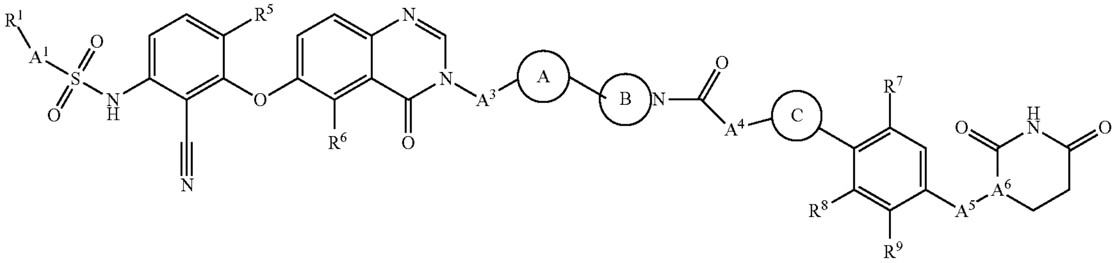

Step A—General Procedure for Cyclization (Procedure A-A): To a stirred solution of 2-amino-5-hydroxy-benzoic acid (1, 1 eq.) in Toluene:Tetrahydrofuran (5:1) was added anhydrous triethyl orthoformate (2 eq.) at room temperature followed by amine (2, 1 eq.) was added and the resulting reaction mixture was heated at 110° C. to 140° C. for 12 to 18 hrs. For cyclization with amine salts (HCl, TFA etc.,), catalytic acetic acid (0.1 eq.) addition gave better conversions. After completion, the reaction mixture was cooled to room temperature. To the reaction mixture was added aqueous sodium bicarbonate solution and the aqueous layers were extracted with ethyl acetate. The combined organic layers were washed with brine, dried over anhydrous sodium sulfate, filtered and filtrate was evaporated under reduced pressure to afford the desired crude product. The crude material was purified by silica gel flash column chromatography using 5% methanol-dichloromethane as eluent to afford quinazolinone intermediate (3).

Step B—General Procedure for O-Arylation (Procedure A-B): To a stirred solution of quinazolinone intermediate (3, 1 eq.) in N,N-Dimethylformamide/THF (10 mL) was added 2,3,6-trifluorobenzonitrile in presence of a base such as cesium carbonate or potassium tert-butoxide (1.1 eq.) and (4, 1.1 eq.) at room temperature. The resulting reaction mixture was stirred at room temperature for around 16 h. After completion, the reaction mixture was quenched with water and extracted with ethyl acetate. Combined organic layers were washed with brine, dried over sodium sulfate, and concentrated under vacuum to yield crude. Crude compound was purified by silica gel flash column chromatography using 50% ethyl acetate in petroleum ether as eluent to yield intermediate (5).

Step C—General Procedure for Sulfomoylation (Procedure A-C): To a solution of intermediate 5 (1 eq.) in N,N-Dimethylformamide was added cesium carbonate (2.5 eq.) and [methyl(sulfamoyl)amino]ethane (2 eq.) at room temperature. The resulting reaction mixture was stirred at between around 60° C. to 70° C. for 12 hrs to 16 hrs. After completion of the reaction, the reaction mixture was cooled to room temperature, diluted with water and extracted with ethyl acetate. The combined organic layers were washed with brine solution, dried over sodium sulfate, filtered, and concentrated under reduced pressure to afford the crude. The crude compound was purified by silica gel flash column chromatography with 20 to 50% ethyl acetate in petroleum ether as eluent to afford sulfonamide intermediate (7).

Note: For majority of reactions, after addition of water, precipitation of solids was observed. These solids were filtered through filter paper. Filtrate was extracted by ethyl acetate. Combined organic layers were washed with brine, dried over sodium sulfate, and concentrated under vacuum to yield sulfonamide intermediate (7) with decent purity.

Step D—General Procedure for N-Boc Deprotection (Procedure A-D): A solution of sulfonamide intermediate (7, 1 eq.) was taken in dichloromethane and added TFA (5 eq.) or 4N HCl in dioxane (10 eq.) at 0° C. The resulted reaction mixture was stirred at room temperature for 2 h. After completion, reaction solvent was removed under reduced pressure get crude product. Crude compound was triturated with methyl t-butyl ether (MTBE) to afford targeting ligand (8).

General Procedure for Acid-Amine Coupling (Procedure A-E): To a stirred solution of intermediate acid (9) (1 eq.) and amine (8) (1 eq.) in N,N-Dimethylformamide (4 mL/mmol) was added N,N-diisopropylethylamine (4 eq.) at room temperature under nitrogen, followed by the addition of HATU (1.1 eq.) at same temperature. The reaction mixture was stirred at room temperature for 12 h. After completion, the reaction mixture was diluted with water and extracted with 10% isopropanol in dichloromethane. Combined organic layers were dried over sodium sulfate, filtered and concentrated under reduced pressure to afford crude compound. The crude compound was purified by reverse phase purification and fractions were lyophilized to afford target compound (10).

General procedure for Acid-Amine coupling (Procedure A-F): To a stirred solution of acid (9) (1 eq.) and amine (8) (1 eq.) in N,N-Dimethylformamide, was added N,N-diisopropylethylamine (4 eq.) and COMU (1.1 eq.) at room temperature under nitrogen atmosphere. The reaction mixture was stirred at room temperature for 6 h. After completion, the reaction mixture was diluted with water (10 mL) and extracted with 10% isopropanol in dichloromethane (3×20 mL). Combined organic layers were dried over sodium sulfate, filtered, and concentrated under reduced pressure to afford crude. The desired product was purified from crude by reverse phase purification and fractions were lyophilized to afford target compound (10).

Examples 1-3
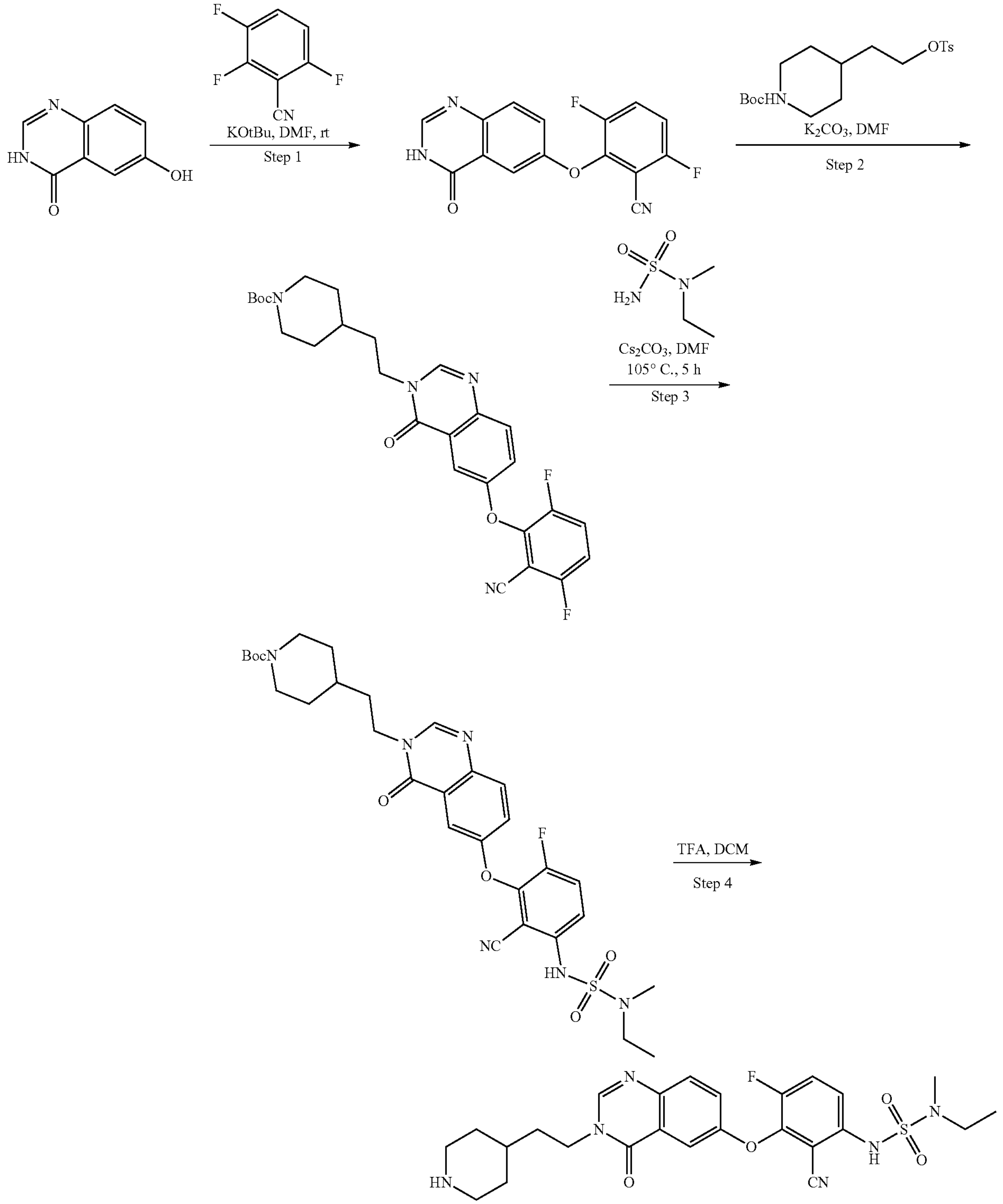
TL28
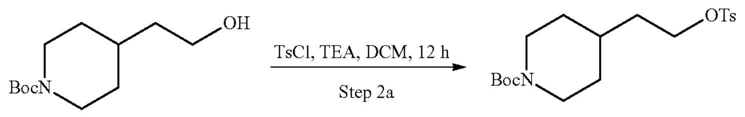 [SMILES: CC(C)(C)OC(=O)N1CCC(CCO)CC1 ; Cc1ccc(S(=O)(=O)OCCC2CCN(C(=O)OC(C)(C)C)CC2)cc1]

Step 1: O-arylated quinazolinone intermediate was synthesized by following general procedure for O-arylation (Procedure A-B) using 6-hydroxy-3H-quinazolin-4-one (5 g, 30.84 mmol), potassium tert-butoxide (3.81 g, 33.92 mmol) and 2,3,6-trifluorobenzonitrile (5.33 g, 33.92 mmol, 3.92 mL) to obtain compound 3,6-difluoro-2-[(4-oxo-3H-quinazolin-6-yl)oxy]benzonitrile (6.8 g, 22.21 mmol, 72% yield) as off-white solid. LCMS m/z (ESI): 300.20 $[M+H]^+$ Step 2a: To a stirred solution of tert-butyl 4-(2-hydroxyethyl)piperidine-1-carboxylate (2 g, 8.72 mmol, 1.92 mL) in dichloromethane (20 mL) was added Triethylamine (882.54 mg, 8.72 mmol, 1.22 mL) at 0° C. followed by p-Toluenesulfonyl chloride (1.83 g, 9.59 mmol) at the same temperature and the resulting reaction mixture was warmed to room temperature for 12 h. After completion, the reaction mixture was diluted with water (40 mL) and extracted with ethyl acetate (2×50 mL). The combined organic layers were dried over sodium sulfate, filtered and concentrated under reduced pressure afford tert-butyl 4-[2-(p-tolylsulfonyloxy)ethyl]piperidine-1-carboxylate (2.8 g, crude) as colorless liquid. LCMS m/z (ESI): 284.30 $[M+H-CO_2{}^tBu]^+$ nazolin-3-yl]ethyl]piperidine-1-carboxylate (180 mg, 242.32 μmol, 25% yield) as pale brown solid. LCMS m/z (ESI): 529.30 $[M+H-CO_2{}^tBu]^+$ Step 4: The requisite amine was synthesized by following Procedure A-D using tert-butyl 4-[2-[6-[2-cyano-3-[[ethyl (methyl)sulfamoyl]amino]-6-fluoro-phenoxy]-4-oxo-quinazolin-3-yl]ethyl]piperidine-1-carboxylate (180 mg, 286.30 μmol) and TFA (592.00 mg, 5.19 mmol, 0.4 mL). The resulted crude compound was triturated with methyl t-butyl ether to afford 6-[2-cyano-3-[[ethyl(methyl)sulfamoyl]amino]-6-fluoro-phenoxy]-4-oxo-3-[2-(4-piperidyl) ethyl]quinazoline (200 mg, crude) as pale brown semisolid. LCMS m/z (ESI): 529.20 $[M+H]^+$ Example 1

6-[2-cyano-3-[[ethyl(methyl)sulfamoyl]amino]-6-fluorophenoxy]-3-[2-[1-[2-[4-[4-[(2,6-dioxopiperidin-3-yl)amino]-2-fluorophenyl]piperidin-1-yl] acetyl]piperidin-4-yl]ethyl]-4-oxoquinazoline

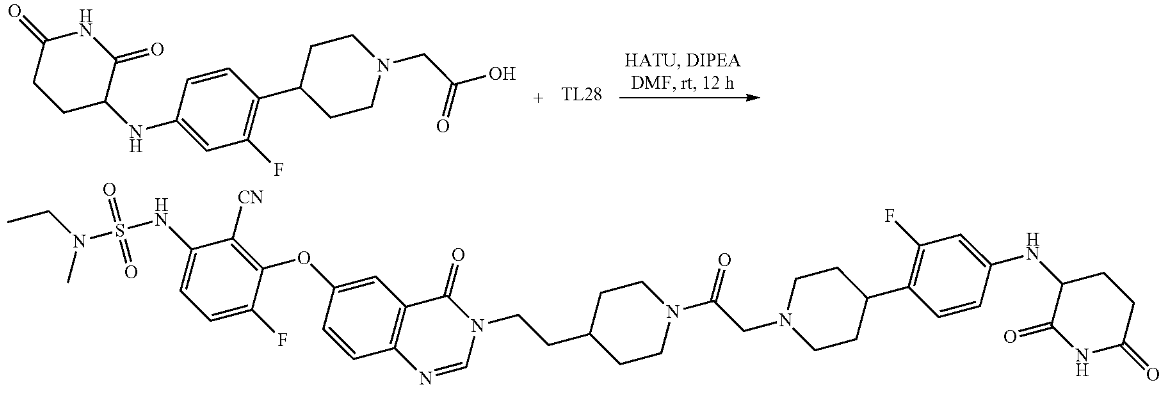

Step 2: To a stirred solution of 3,6-difluoro-2-[(4-oxo-3H-quinazolin-6-yl)oxy]benzonitrile (1.5 g, 5.01 mmol) in N,N-Dimethylformamide (15 mL) was added potassium tert-butoxide (618.75 mg, 5.51 mmol) at room temperature followed by tert-butyl 4-[2-(p-tolylsulfonyloxy)ethyl]piperidine-1-carboxylate (1.92 g, 5.01 mmol) and the resulting reaction mixture was stirred for 12 h at room temperature. After completion of the reaction the reaction mixture was diluted with water (40 mL) and extracted with ethyl acetate (2×50 mL). The combined organic layers were dried over sodium sulfate, filtered and concentrated under reduced pressure to afford crude. The crude compound was purified by silica gel flash column chromatography with 5% methanol in dichloromethane as a eluent to afford tert-butyl 4-[2-[6-(2-cyano-3,6-difluoro-phenoxy)-4-oxo-quinazolin-3-yl]ethyl]piperidine-1-carboxylate (2.4 g, 3.93 mmol, 78% yield) as pale brown liquid. LCMS m/z (ESI): 509.30 $[M-H]^-$ Step 3: Sulfamoylated quinazolinone intermediate was synthesized by following Procedure A-C using tert-butyl 4-[2-[6-(2-cyano-3,6-difluoro-phenoxy)-4-oxo-quinazolin-3-yl]ethyl]piperidine-1-carboxylate (0.5 g, 979.37 μmol), cesium carbonate (797.75 mg, 2.45 mmol) and [methyl (sulfamoyl)amino]ethane (270.68 mg, 1.96 mmol). The crude compound was purified by silica gel flash column chromatography with 5% methanol in dichloromethane as a eluent to afford tert-butyl 4-[2-[6-[2-cyano-3-[[ethyl (methyl)sulfamoyl]amino]-6-fluoro-phenoxy]-4-oxo-qui- Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[2-(4-piperidyl) ethyl]quinazoline (20 mg, 37.84 μmol), HATU (17.26 mg, 45.40 μmol) and N,N-diisopropylethylamine (24.45 mg, 189.18 μmol, 32.95 μL) and 2-[4-[4-[(2,6-dioxo-3-piperidyl) amino]-2-fluoro-phenyl]-1-piperidyl]acetic acid (13.75 mg, 37.84 μmol) to afford crude product. Crude product was purified by Prep HPLC purification method: 10 mm ammonium acetate:acetonitrile and Column: BRIDGE C8(19×150)MM, 5MIC) and pure fractions were lyophilized to afford 6-[2-cyano-3-[[ethyl(methyl)sulfamoyl]amino]-6-fluoro-phenoxy]-3-[2-[1-[2-[4-[4-[(2,6-dioxo-3-piperidyl) amino]-2-fluoro-phenyl]-1-piperidyl]acetyl]-4-piperidyl] ethyl]-4-oxo-quinazoline (9.77 mg, 10.93 μmol, 29% yield) as an off-white solid. LCMS m/z (ESI): 874.50 $[M+H]^+$; $^1$HNMR (400 MHz, DMSO-$d_6$): δ=10.80 (s, 1H), 9.75 (bs, 1H), 8.38 (s, 1H), 7.76 (d, J=9.20 Hz, 1H), 7.63 (dd, J=2.40, 8.80 Hz, 1H), 7.48-7.46 (m, 1H), 7.35-7.29 (m, 2H), 6.99 (t, J=8.40 Hz, 1H), 6.49-6.44 (m, 2H), 6.07 (d, J=7.60 Hz, 1H), 4.33-4.31 (m, 1H), 4.10-4.95 (m, 2H), 3.90-3.75 (m, 2H), 3.25-3.15 (m, 2H), 3.03 (q, J=7.20 Hz, 2H), 2.78-2.67 (m, 7H), 2.62 (s, 3H), 2.10-2.08 (m, 2H), 1.95-1.70 (m, 8H), 1.70-1.50 (m, 4H), 1.25-1.10 (m, 1H), 1.03 (t, J=7.20 Hz, 3H).

Example 2

6-[2-cyano-3-[[ethyl(methyl)sulfamoyl]amino]-6-fluorophenoxy]-3-[2-[1-[2-[4-[4-(2,6-dioxopiperidin-3-yl)-2-fluorophenyl]piperidin-1-yl]acetyl]piperidin-4-yl]ethyl]-4-oxoquinazoline

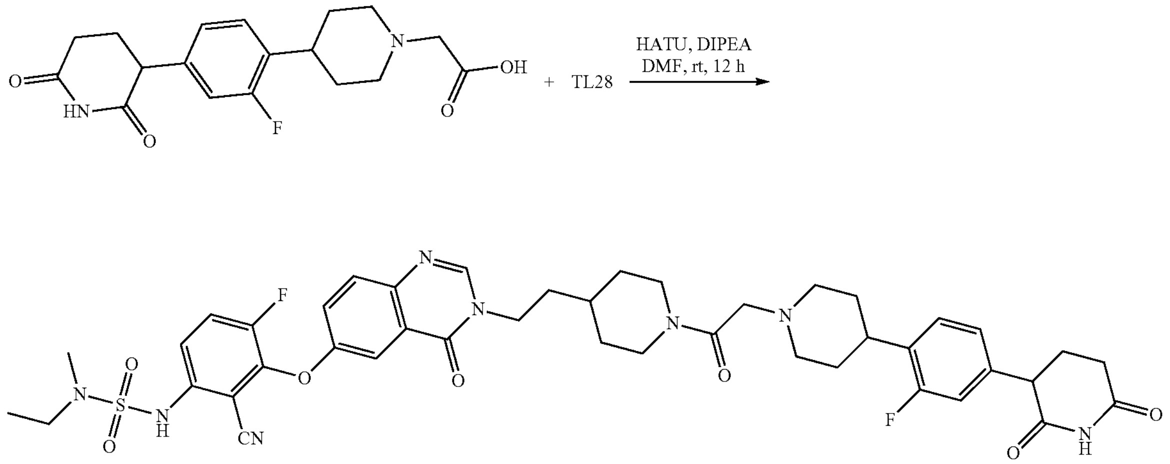

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[2-(4-piperidyl)ethyl]quinazoline (20 mg, 37.84 μmol), HATU (17.26 mg, 45.40 μmol) and N,N-diisopropylethylamine (24.45 mg, 189.18 μmol, 32.95 μL) and 2-[4-[4-(2,6-dioxo-3-piperidyl)-2-fluoro-phenyl]-1-piperidyl]acetic acid (13.18 mg, 37.84 μmol) to afford crude product. Crude product was purified again by Prep HPLC purification (method: 10 mm ammonium acetate:acetonitrile and Column: BRIDGE C8(19×150)MM, 5MIC) and pure fractions were lyophilized to afford 6-[2-cyano-3-[[ethyl(methyl)sulfamoyl]amino]-6-fluoro-phenoxy]-3-[2-[1-[2-[4-[4-(2,6-dioxo-3-piperidyl)-2-fluoro-phenyl]-1-piperidyl]acetyl]-4-piperidyl]ethyl]-4-oxo-quinazoline (10.57 mg, 11.76 μmol, 31% yield) as an off-white solid. LCMS m/z (ESI): 859.40 $[M+H]^+$; $^1$HNMR (400 MHz, DMSO-$d_6$): δ=10.86 (s, 1H), 9.79 (bs, 1H), 8.39 (s, 1H), 7.76 (d, J=8.80 Hz, 1H), 7.65 (d, J=2.80 Hz, 1H), 7.63-7.62 (m, 1H), 7.35-7.27 (m, 3H), 7.07 (t, J=3.20 Hz, 2H), 4.34-4.31 (m, 1H), 4.03-3.99 (m, 2H), 3.95-3.80 (m, 3H), 3.25-3.15 (m, 2H), 3.04 (q, J=7.20 Hz, 2H), 2.97-2.92 (m, 3H), 2.75-2.60 (m, 7H), 2.25-2.21 (m, 1H), 2.10-1.98 (m, 1H), 1.95-1.70 (m, 7H), 1.65-1.50 (m, 4H), 1.25-1.10 (m, 1H), 1.03 (t, J=7.20 Hz, 3H).

Example 3

6-[2-cyano-3-[[ethyl(methyl)sulfamoyl]amino]-6-fluorophenoxy]-3-[2-[1-[2-[4-[4-[(2,6-dioxopiperidin-3-yl)amino]-3-fluorophenyl]piperidin-1-yl]acetyl]piperidin-4-yl]ethyl]-4-oxoquinazoline

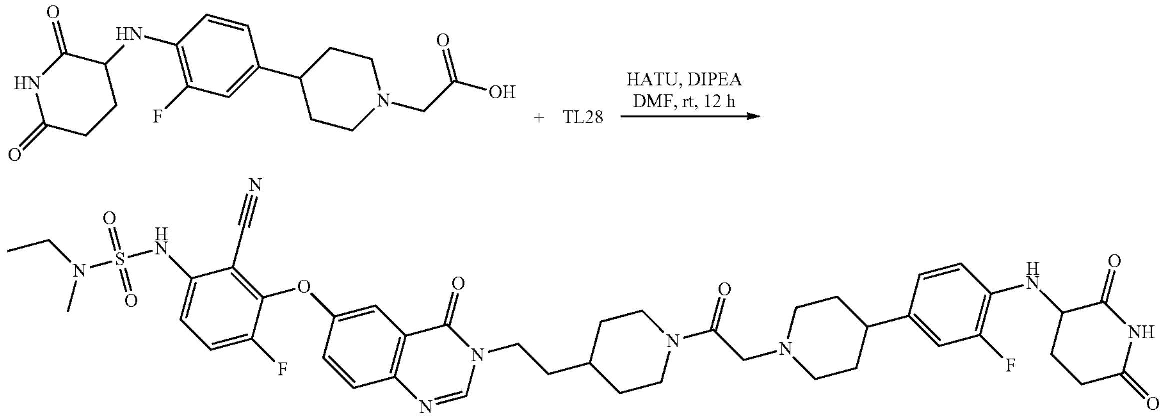

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[2-(4-piperidyl)ethyl]quinazoline (20 mg, 37.84 μmol), HATU (17.26 mg, 45.40 μmol) and N,N-diisopropylethylamine (24.45 mg, 189.18 μmol, 32.95 μL) and 2-[4-[4-[(2,6-dioxo-3-piperidyl)amino]-3-fluoro-phenyl]-1-piperidyl]acetic acid (13.75 mg, 37.84 μmol) to afford crude product. Crude product was purified again by Prep HPLC purification (method: 10 mm ammonium acetate:acetonitrile and Column: BRIDGE C8(19×150)MM, 5MIC) and pure fractions were lyophilized to afford 6-[2-cyano-3-[[ethyl(methyl)sulfamoyl]amino]-6-fluoro-phenoxy]-3-[2-[1-[2-[4-[4-[(2,6-dioxo-3-piperidyl)amino]-3-fluoro-phenyl]-1-piperidyl]acetyl]-4-piperidyl]ethyl]-4-oxo-quinazoline (5.15 mg, 5.81 μmol, 15% yield) as an off-white solid. LCMS m/z (ESI): 874.30 $[M+H]^+$; $^1$HNMR (400 MHz, DMSO-$d_6$): δ=10.80 (s, 1H), 8.40 (s, 1H), 7.76 (d, J=8.80 Hz, 1H), 7.63 (dd, J=2.80, 8.80 Hz, 1H), 7.46-7.44 (m, 1H), 7.35-7.29 (m, 2H), 6.95 (d, J=12.80 Hz, 1H), 6.86-6.84 (m, 1H), 6.80-6.76 (m, 1H), 5.45 (d, J=6.40 Hz, 1H), 4.39-4.31 (m, 2H), 4.31-4.01 (m, 3H), 3.90-3.75 (m, 2H), 3.25-3.15 (m, 3H), 3.02 (q, J=6.80 Hz, 2H), 2.82-2.70 (m, 2H), 2.70-2.55 (m, 6H), 2.08-1.97 (m, 3H), 1.90-1.70 (m, 5H), 1.70-1.50 (m, 4H), 1.24-1.15 (m, 2H), 1.03 (t, J=7.20 Hz, 3H).

Examples 4-6

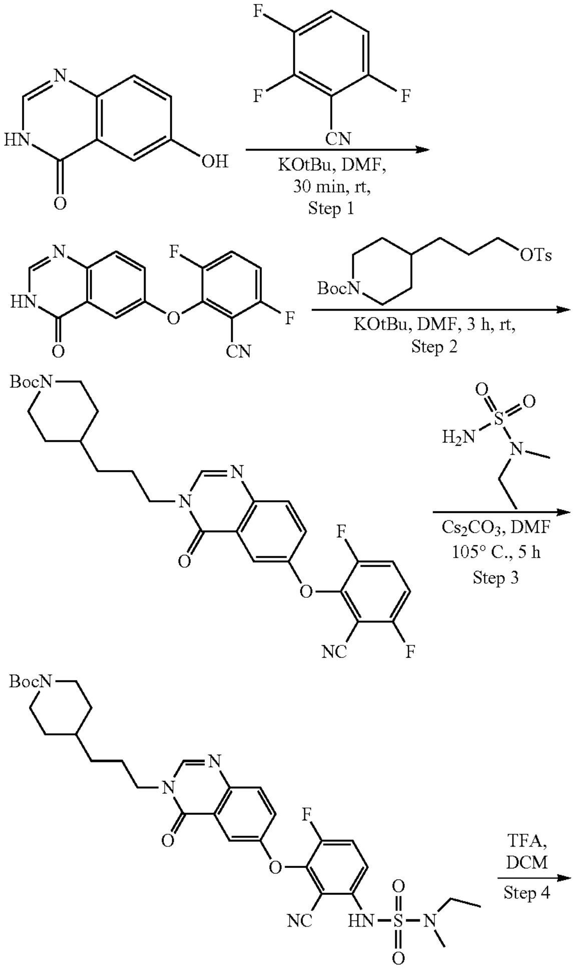

-continued

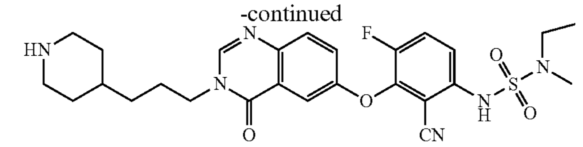

TL30

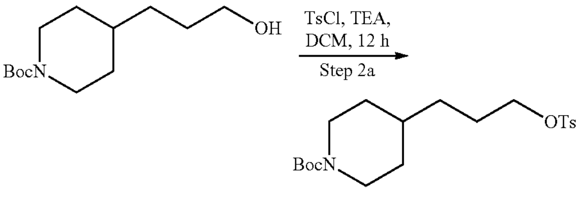

Step 1: O-arylated quinazolinone intermediate was synthesized by following Procedure A-B using 6-hydroxy-3H-quinazolin-4-one (5 g, 30.84 mmol), potassium tert-butoxide (3.81 g, 33.92 mmol) and 2,3,6-trifluorobenzonitrile (5.33 g, 33.92 mmol, 3.92 mL) to obtain compound 3,6-difluoro-2-[(4-oxo-3H-quinazolin-6-yl)oxy]benzonitrile (6.8 g, 22.21 mmol, 72% yield) as off-white solid. LCMS m/z (ESI): 300.20 $[M+H]^+$ Step 2a: To a stirred solution of 4-(3-hydroxypropyl) piperidine-1-carboxylate (2.5 g, 10.27 mmol) in dichloromethane (15 mL) was added Triethylamine (2.60 g, 25.68 mmol, 3.58 mL) at 0° C. followed by p-Toluene sulfonyl chloride (2.15 g, 11.30 mmol) at the same temperature and the resulting reaction mixture was warmed to room temperature for 12 h. After completion of the reaction the reaction mixture was diluted with water (50 mL) and extracted with ethyl acetate (2×70 mL). The combined organic layers were dried over sodium sulfate, filtered, and concentrated under reduced pressure to afford crude product. The crude compound was purified by silica gel flash column chromatography with 15% ethyl acetate in petroleum ether as eluent to afford tert-butyl 4-[3-(p-tolylsulfonyloxy)propyl]piperidine-1-carboxylate (2.2 g, 5.42 mmol, 53% yield) as an off-white solid. LCMS m/z (ESI): 298.30 $[M+H-CO_2{}^tBu]^+$ Step 2: To a stirred solution of 3,6-difluoro-2-[(4-oxo-3H-quinazolin-6-yl)oxy]benzonitrile (1.5 g, 5.01 mmol) in N,N-dimethylformamide (20 mL) was added potassium tert-butoxide (618.75 mg, 5.51 mmol) at room temperature followed by tert-butyl 4-[3-(p-tolylsulfonyloxy)propyl]piperidine-1-carboxylate (2.19 g, 5.51 mmol) and the resulting reaction mixture was stirred for 3 h at room temperature. After completion of the reaction the reaction mixture was diluted with water (50 mL) and extracted with ethyl acetate (2×100 mL). The combined organic layers were dried over sodium sulfate, filtered, and concentrated under reduced pressure to afford crude. The crude compound was purified by silica gel flash column chromatography with 5% methanol in dichloromethane as a eluent to afford tert-butyl 4-[3-[6-(2-cyano-3,6-difluoro-phenoxy)-4-oxo-quinazolin-3-yl]propyl]piperidine-1-carboxylate (2.4 g, 3.66 mmol, 73% yield) as pale brown liquid. LCMS m/z (ESI): 523.30 $[M-H]^-$ Step 3: Sulfamoylated quinazolinone intermediate was synthesized by following Procedure A-C using tert-butyl 4-[3-[6-(2-cyano-3,6-difluoro-phenoxy)-4-oxo-quinazolin-3-yl]propyl]piperidine-1-carboxylate (700 mg, 1.33 mmol), cesium carbonate (1.09 g, 3.34 mmol) and [methyl(sulfamoyl)amino]ethane (368.81 mg, 2.67 mmol). The crude compound was purified by silica gel flash column chromatography with 5% methanol in dichloromethane as a eluent to afford tert-butyl 4-[3-[6-[2-cyano-3-[[ethyl(methyl)sulfamoyl]amino]-6-fluoro-phenoxy]-4-oxo-quinazolin-3-yl]propyl]piperidine-1-carboxylate (260 mg, 355.98 μmol, 27% yield) as pale brown solid. LCMS m/z (ESI): 641.30 $[M-H]^-$ Step 4: The requisite amine was synthesized by following Procedure A-D using tert-butyl 4-[3-[6-[2-cyano-3-[[ethyl(methyl)sulfamoyl]amino]-6-fluoro-phenoxy]-4-oxo-quinazolin-3-yl]propyl]piperidine-1-carboxylate (260 mg, 404.52 μmol) and TFA (740.00 mg, 6.49 mmol, 0.5 mL). The resulted crude compound was triturated with methyl t-butyl ether to afford 6-[2-cyano-3-[[ethyl(methyl)sulfamoyl]amino]-6-fluoro-phenoxy]-4-oxo-3-[3-(4-piperidyl)propyl]quinazoline (280 mg, crude) as pale brown semi-solid. LCMS m/z (ESI): 543.30 $[M+H]^+$

Example 4

6-[2-cyano-3-[[ethyl(methyl)sulfamoyl]amino]-6-fluorophenoxy]-3-[3-[1-[2-[4-[4-[(2,6-dioxopiperidin-3-yl)amino]phenyl]piperidin-1-yl]acetyl]piperidin-4-yl]propyl]-4-oxoquinazoline

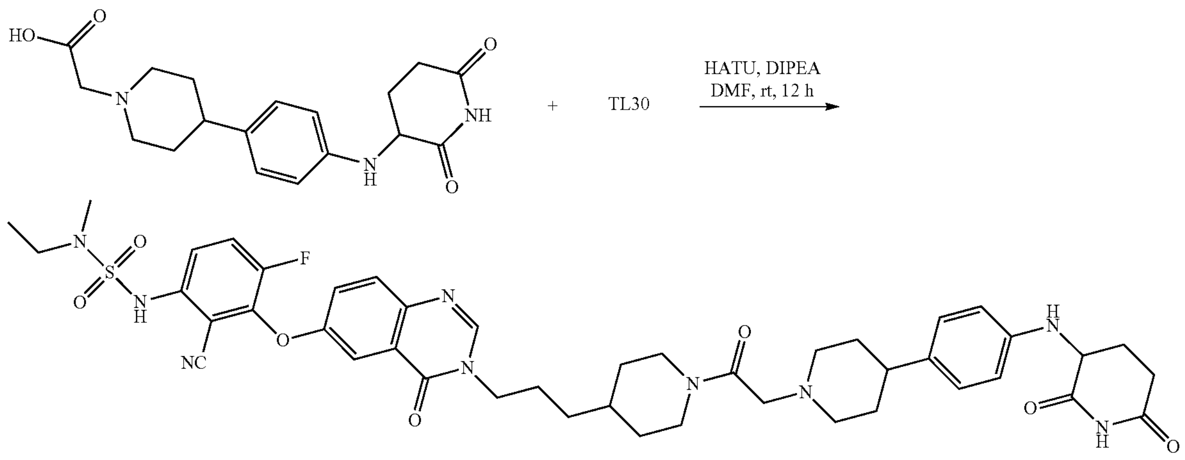

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[3-(4-piperidyl)propyl]quinazoline as its TFA salt (20 mg, 30.46 μmol), 2-[4-[4-[(2,6-dioxo-3-piperidyl)amino]phenyl]-1-piperidyl]acetic acid (14 mg, 30.47 μmol) as its TFA salt, N,N-diisopropylethylamine (371.00 mg, 2.87 mmol, 0.50 mL) and HATU (14 mg, 36.82 μmol) to afford crude product. Crude product was purified by Prep HPLC purification method: 10 mm ammonium acetate:acetonitrile and pure fractions were lyophilized to afford 6-[2-cyano-3-[[ethyl(methyl)sulfamoyl]amino]-6-fluoro-phenoxy]-3-[3-[1-[2-[4-[4-[(2,6-dioxo-3-piperidyl)amino]phenyl]-1-piperidyl]acetyl]-4-piperidyl]propyl]-4-oxo-quinazoline (9.98 mg, 11.08 μmol, 36% yield) as a pale yellow solid. LCMS m/z (ESI): 870.40 $[M+H]^+$; $^1$HNMR (400 MHz, DMSO-$d_6$): δ=10.79 (s, 1H), 9.62 (bs, 1H), 8.38 (s, 1H), 7.78 (d, J=7.20 Hz, 1H), 7.66 (dd, J=4.40, 6.00 Hz, 1H), 7.46 (t, J=10.00 Hz, 1H), 7.37-7.28 (m, 2H), 6.97 (d, J=8.40 Hz, 2H), 6.67 (d, J=10.80 Hz, 2H), 5.73 (d, J=7.60 Hz, 1H), 4.35-4.28 (m, 2H), 4.00-3.75 (m, 5H), 3.35-3.27 (m, 2H), 3.02 (q, J=6.80 Hz, 2H), 2.82-2.65 (m, 3H), 2.65-2.55 (m, 6H), 2.09-2.08 (m, 1H), 1.89-1.72 (m, 9H), 1.60-1.45 (m, 2H), 1.26-1.22 (m, 2H), 1.15-1.05 (m, 1H), 1.03 (t, J=7.20 Hz, 3H), 0.98-0.85 (m, 1H).

Example 5

6-[2-cyano-3-[[ethyl(methyl)sulfamoyl]amino]-6-fluorophenoxy]-3-[3-[1-[2-[4-[4-(2,6-dioxopiperidin-3-yl)-2-fluorophenyl]piperidin-1-yl]acetyl]piperidin-4-yl]propyl]-4-oxoquinazoline

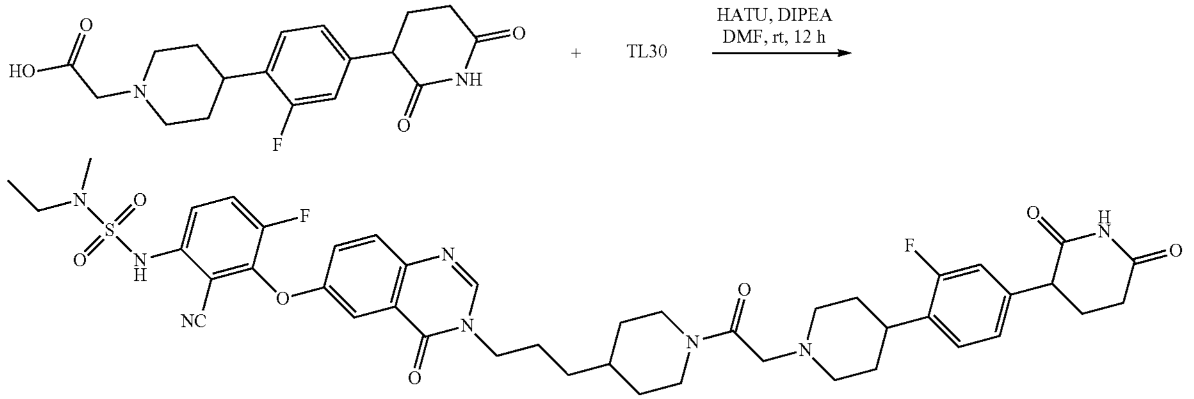

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[3-(4-piperidyl)propyl]quinazoline as its TFA salt (20 mg, 30.46 μmol), 2-[4-[4-(2,6-dioxo-3-piperidyl)-2-fluoro-phenyl]-1-piperidyl]acetic acid as its HCl salt (12 mg, 31.18 μmol), N,N-diisopropylethylamine (371.00 mg, 2.87 mmol, 0.50 mL) and HATU (14 mg, 36.82 μmol) to afford crude product. Crude product was purified by Prep HPLC purification method: 10 mm ammonium acetate:acetonitrile and pure fractions were lyophilized to afford 6-[2-cyano-3-[[ethyl(methyl)sulfamoyl]amino]-6-fluoro-phenoxy]-3-[3-[1-[2-[4-[4-(2,6-dioxo-3-piperidyl)-2-fluoro-phenyl]-1-piperidyl]acetyl]-4-piperidyl]propyl]-4-oxo-quinazoline (11.02 mg, 12.46 μmol, 41% yield) as an off-white solid. LCMS m/z (ESI): 873.40 $[M+H]^+$; $^1$HNMR (400 MHz, DMSO-$d_6$): δ=10.86 (s, 1H), 9.80 (bs, 1H), 8.37 (s, 1H), 7.77 (d, J=8.92 Hz, 1H), 7.65 (dd, J=3.04, 8.90 Hz, 1H), 7.62-7.52 (m, 1H), 7.37-7.34 (m, 2H), 7.29 (t, J=8.16 Hz, 1H), 7.09-7.06 (m, 2H), 4.40-4.30 (m, 1H), 3.95 (t, J=7.16 Hz, 2H), 3.88 (dd, J=4.80, 11.98 Hz, 1H), 3.85-3.75 (m, 1H), 3.30-3.25 (m, 2H), 3.06 (q, J=7.12 Hz, 2H), 3.00-2.85 (m, 2H), 2.80-2.65 (m, 4H), 2.67 (s, 3H), 2.60-2.55 (m, 2H), 2.24-2.21 (m, 1H), 2.08-1.82 (m, 5H), 1.80-1.65 (m, 5H), 1.65-1.50 (m, 1H), 1.27-1.23 (m, 2H), 1.15-1.10 (m, 2H), 1.04 (t, J=7.20 Hz, 3H).

Example 6

6-[2-cyano-3-[[ethyl(methyl)sulfamoyl]amino]-6-fluorophenoxy]-3-[3-[1-[2-[4-[4-[(2,6-dioxopiperidin-3-yl)amino]-2-fluorophenyl]piperidin-1-yl]acetyl]piperidin-4-yl]propyl]-4-oxoquinazoline

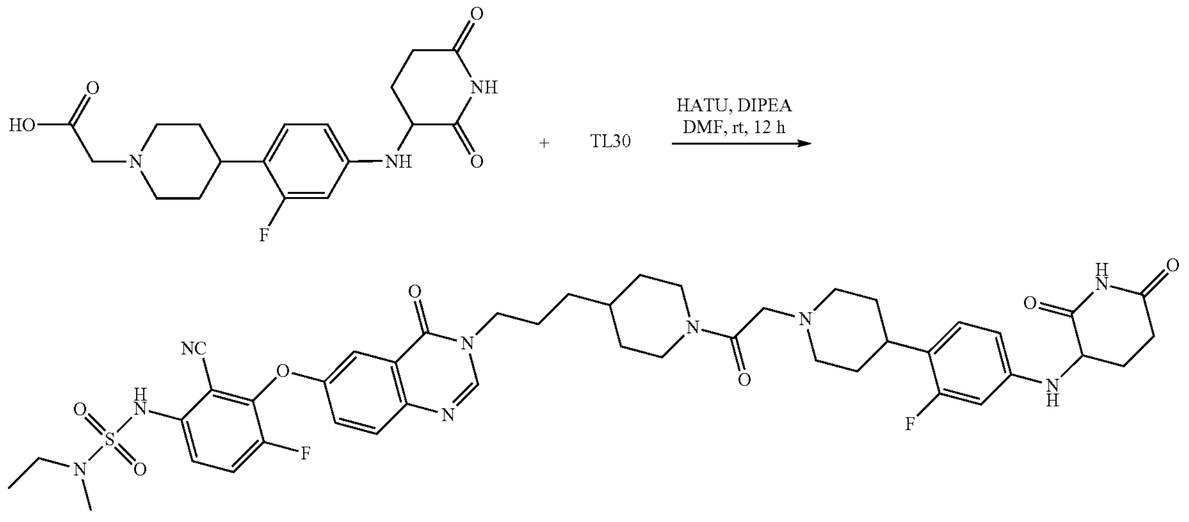

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[3-(4-piperidyl)propyl]quinazoline as its TFA salt (20 mg, 30.46 μmol), 2-[4-[4-[(2,6-dioxo-3-piperidyl)amino]-2-fluoro-phenyl]-1-piperidyl]acetic acid as its HCl salt (13 mg, 32.51 μmol), N,N-diisopropylethylamine (371.00 mg, 2.87 mmol, 0.50 mL) and HATU (14 mg, 36.82 μmol) to afford crude product. Crude product was purified by Prep HPLC purification method: 10 mm ammonium acetate:acetonitrile and pure fractions were lyophilized to afford 6-[2-cyano-3-[[ethyl(methyl)sulfamoyl]amino]-6-fluoro-phenoxy]-3-[3-[1-[2-[4-[4-[(2,6-dioxo-3-piperidyl)amino]-2-fluoro-phenyl]-1-piperidyl]acetyl]-4-piperidyl]propyl]-4-oxo-quinazoline (6.90 mg, 7.20 μmol, 24% yield) as an off-white solid. LCMS m/z (ESI): 887.80 $[M+H]^+$; $^1$HNMR (400 MHz, DMSO-$d_6$): δ=10.80 (s, 1H), 9.69 (bs, 1H), 8.38 (s, 1H), 7.77 (d, J=8.80 Hz, 1H), 7.65 (dd, J=3.20, 9.00 Hz, 1H), 7.60-7.50 (m, 1H), 7.36-7.33 (m, 2H), 7.01-6.97 (m, 1H), 6.50-6.44 (m, 2H), 6.08 (d, J=7.60 Hz, 1H), 4.34-4.31 (m, 2H), 4.00-3.75 (m, 5H), 3.40-3.30 (m, 2H), 3.05 (q, J=7.20 Hz, 2H), 3.00-2.90 (m, 2H), 2.77-2.71 (m, 3H), 2.68 (s, 3H), 2.67-2.59 (m, 2H), 2.08-2.07 (m, 1H), 1.91-1.80 (m, 3H), 1.76-1.72 (m, 6H), 1.60-1.50 (m, 1H), 1.26-1.23 (m, 2H), 1.20-1.05 (m, 1H), 1.10 (t, J=6.80 Hz, 3H), 0.95-0.85 (m, 1H).

Example 7

6-[2-cyano-3-[[ethyl(methyl)sulfamoyl]amino]-6-fluorophenoxy]-3-[3-[1-[2-[4-[4-[(2,6-dioxopiperidin-3-yl)amino]phenyl]piperidin-1-yl]-2-oxoethyl]piperidin-4-yl]propyl]-4-oxoquinazoline

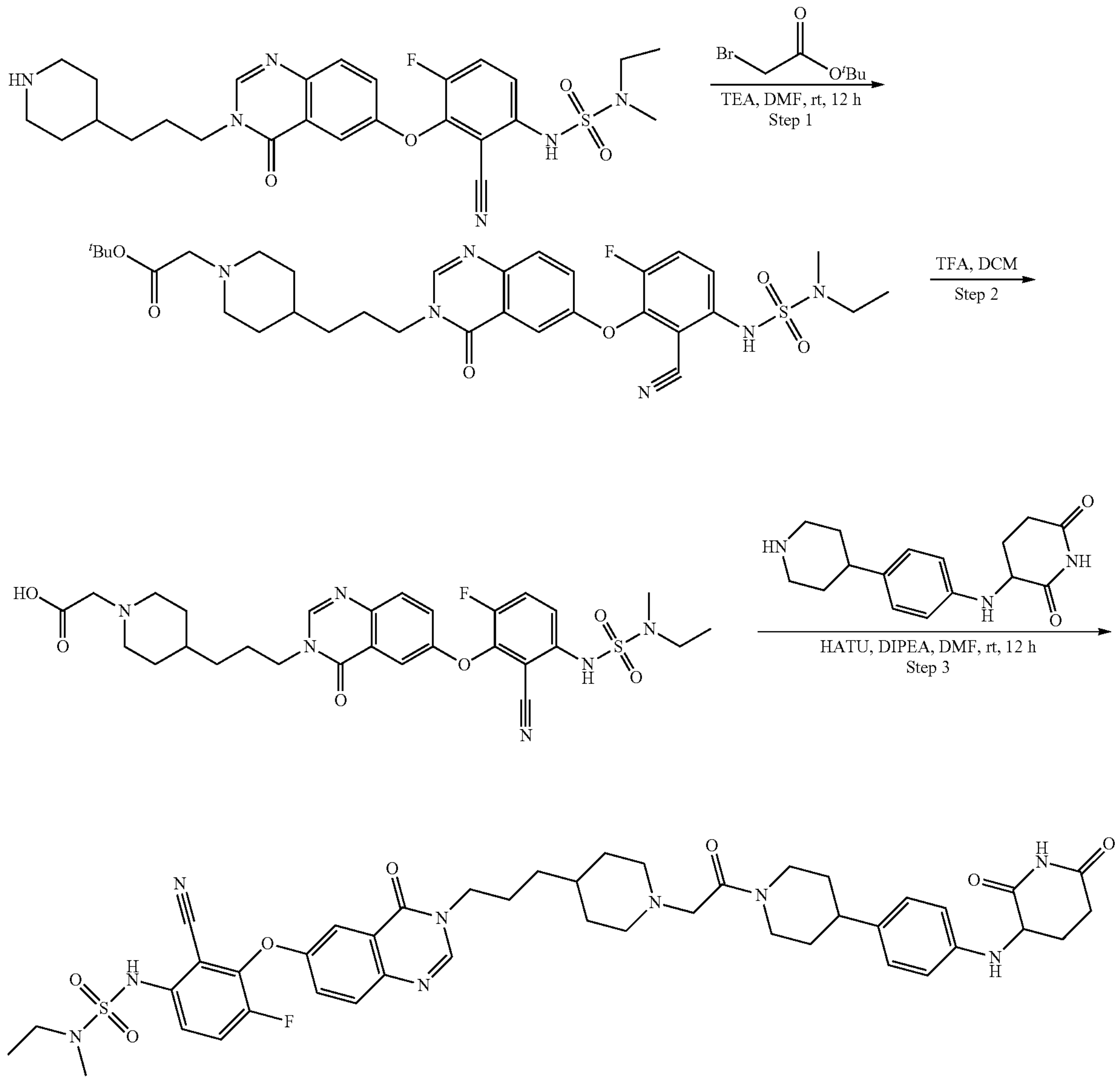

Step 1: To a stirred solution of 6-[2-cyano-3-[[ethyl(methyl)sulfamoyl]amino]-6-fluoro-phenoxy]-4-oxo-3-[3-(4-piperidyl)propyl]quinazoline as its TFA salt (30 mg, 45.69 μmol) in N,N-Dimethylformamide (2 mL) was added Triethylamine (23.12 mg, 228.43 μmol, 31.84 μL) at room temperature followed by tert-butyl 2-bromoacetate (10 mg, 51.27 μmol, 7.52 μL) and the resulting reaction mixture was stirred for 12 h at room temperature. After completion of the reaction the reaction mixture was diluted with water (5 mL) and extracted with ethyl acetate (2×5 mL). The combined organic layers were dried over sodium sulfate, filtered and concentrated under reduced pressure to afford 2-[4-[3-[6-[2-cyano-3-[[ethyl(methyl)sulfamoyl]amino]-6-fluoro-phenoxy]-4-oxo-quinazolin-3-yl]propyl]-1-piperidyl]acetate (25 mg, 31.94 μmol, 70% yield) as a brownish viscous liquid. This crude compound was proceeded to next step without any purification. LCMS m/z (ESI): 657.40 $[M+H]^+$ Step 2: The requisite amine was synthesized by following Procedure A-D using tert-butyl 2-[4-[3-[6-[2-cyano-3-[[ethyl(methyl)sulfamoyl]amino]-6-fluoro-phenoxy]-4-oxo-quinazolin-3-yl]propyl]-1-piperidyl]acetate (25 mg, 38.07 μmol) and TFA (43.40 mg, 380.65 μmol, 29.33 μL). The resulted crude compound was triturated with methyl t-butyl ether to afford 2-[4-[3-[6-[2-cyano-3-[[ethyl(methyl)sulfamoyl]amino]-6-fluoro-phenoxy]-4-oxo-quinazolin-3-yl]propyl]-1-piperidyl]acetic acid as its TFA salt (22 mg, 24.40 μmol, 64% yield) as a brownish viscous liquid. This crude compound was proceeded to next step without any purification LCMS m/z (ESI): 601.40 $[M+H]^+$ Step 3: Target compound was prepared via HATU mediated acid-amine coupling reaction (Procedure A-E). Amide coupling was carried out using 2-[4-[3-[6-[2-cyano-3-[[ethyl(methyl)sulfamoyl]amino]-6-fluoro-phenoxy]-4-oxo-quinazolin-3-yl]propyl]-1-piperidyl]acetic acid as its TFA salt (22 mg, 30.78 μmol), 3-[4-(4-piperidyl)anilino]piperidine-2,6-dione (13 mg, 32.39 μmol), N,N-diisopropylethylamine (371.00 mg, 2.87 mmol, 0.50 mL) and HATU (15 mg, 39.45 μmol) to afford crude product. Crude product was purified by Prep HPLC purification method: 10 mm Ammonium acetate:acetonitrile and pure fractions were lyophilized to afford 6-[2-cyano-3-[[ethyl(methyl)sulfamoyl]amino]-6-fluoro-phenoxy]-3-[3-[1-[2-[4-[4-[(2,6-dioxo-3-piperidyl)amino]phenyl]-1-piperidyl]-2-oxo-ethyl]-4-piperidyl]propyl]-4-oxo-quinazoline (10.56 mg, 11.45 μmol, 37% yield) as a green solid. LCMS m/z (ESI): 870.60 $[M+H]^+$; $^1$HNMR (400 MHz, DMSO-$d_6$): δ=10.78 (s, 1H), 9.60 (bs, 1H), 8.36 (s, 1H), 7.76 (d, J=8.96 Hz, 1H), 7.63 (dd, J=3.00, 8.92 Hz, 1H), 7.46 (t, J=9.76 Hz, 1H), 7.34-7.28 (m, 2H), 6.95 (d, J=8.56 Hz, 2H), 6.62 (d, J=8.60 Hz, 2H), 5.70 (d, J=7.52 Hz, 1H), 5.70 (d, J=7.52 Hz, 1H), 4.55-4.45 (m, 1H), 4.32-4.22 (m, 1H), 4.00-3.80 (m, 5H), 3.34-3.08 (m, 3H), 3.02 (q, J=7.16 Hz, 2H), 2.74-2.67 (m, 5H), 2.64 (s, 3H), 2.09-2.08 (m, 1H), 1.95-1.65 (m, 8H), 1.60-1.45 (m, 1H), 1.39-1.24 (m, 5H), 1.03 (t, J=7.20 Hz, 3H).

Examples 8 and 9

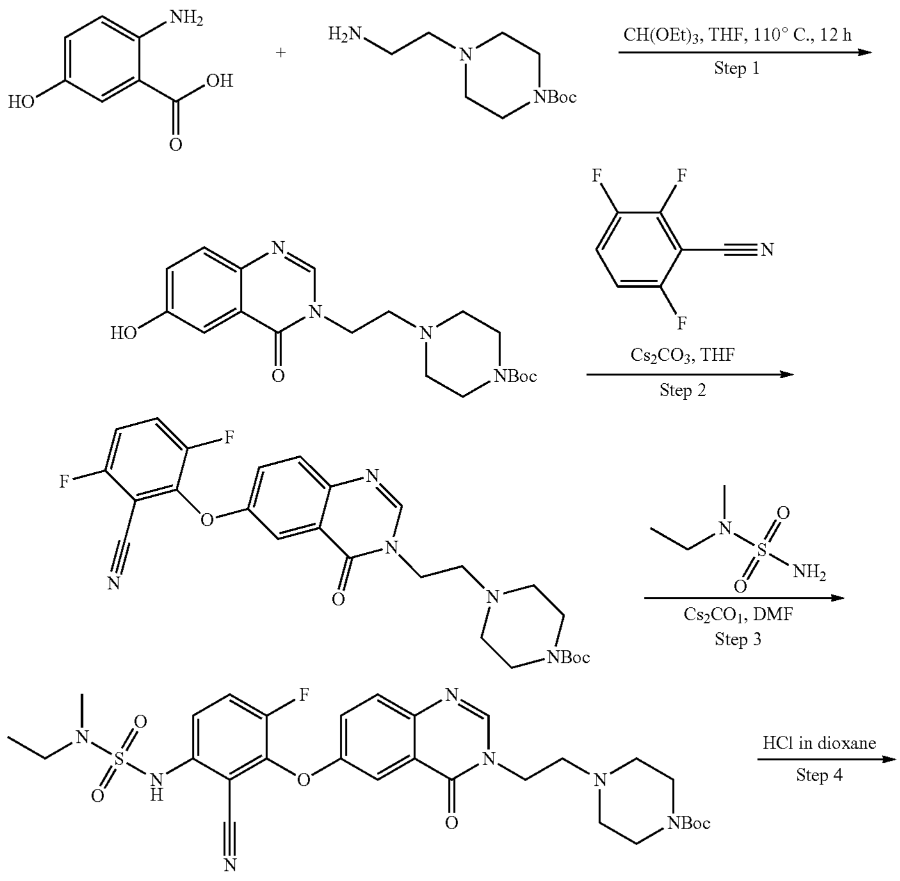

-continued

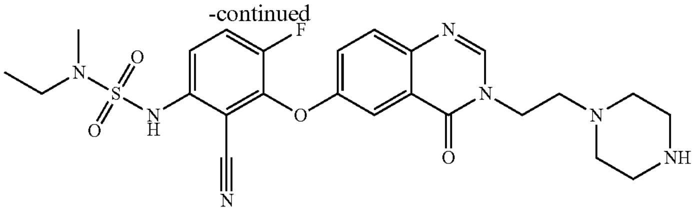

Step 1: Quinazolinone intermediate was synthesized by following Procedure A-A using 2-amino-5-hydroxy-benzoic acid (1 g, 6.53 mmol), Triethyl orthoformate (1.45 g, 9.80 mmol, 1.63 mL) and tert-butyl 4-(2-aminoethyl)piperazine-1-carboxylate (1.65 g, 7.18 mmol). The desired compound was purified from crude by silica gel flash column chromatography using 5% methanol in dichloromethane as eluent to afford tert-butyl 4-[2-(6-hydroxy-4-oxo-quinazolin-3-yl)ethyl]piperazine-1-carboxylate (750 mg, 2.00 mmol, 31% yield) as a brown solid. LCMS m/z (ESI): 375.20 $[M+H]^+$ Step 2: O-arylated quinazolinone intermediate was synthesized by following Procedure A-B using tert-butyl 4-[2-(6-hydroxy-4-oxo-quinazolin-3-yl)ethyl]piperazine-1-carboxylate (750 mg, 2.00 mmol), potassium tert-butoxide (247.24 mg, 2.20 mmol) and 2,3,6-trifluorobenzonitrile (346.13 mg, 2.20 mmol, 254.51 μL) to obtain compound tert-butyl 4-[2-[6-(2-cyano-3,6-difluoro-phenoxy)-4-oxo-quinazolin-3-yl]ethyl]piperazine-1-carboxylate (1 g, 1.80 mmol, 90% yield) as brown solid. LCMS m/z (ESI): 512.20 $[M+H]^+$ Step 3: Sulfamoylated quinazolinone intermediate was synthesized by following Procedure A-C using tert-butyl 4-[2-[6-(2-cyano-3,6-difluoro-phenoxy)-4-oxo-quinazolin-3-yl]ethyl]piperazine-1-carboxylate (1 g, 1.95 mmol), cesium carbonate (1.59 g, 4.89 mmol) and added [methyl(sulfamoyl)amino]ethane (540.31 mg, 3.91 mmol). Crude product was purified by silica gel flash column chromatography using 5% methanol in dichloromethane as eluent to afford tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate (770 mg, 1.10 mmol, 56.02% yield) as a pale brown solid. LCMS m/z (ESI): 630.10 $[M+H]^+$ Step 4: The requisite amine was synthesized by following Procedure A-D using tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate (770 mg, 1.22 mmol) and 4N HCl in dioxane (2.0 mL). The resulted crude compound was triturated with methyl t-butyl ether to afford 6-[2-cyano-3-[[ethyl(methyl)sulfamoyl]amino]-6-fluoro-phenoxy]-4-oxo-3-(2-piperazin-1-ylethyl)quinazoline as its HCl salt (630 mg, 974.42 μmol, 80% yield) as a pale brown solid. LCMS m/z (ESI): 530.20 $[M+H]^+$

Example 8

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]ethyl]-4-oxoquinazoline

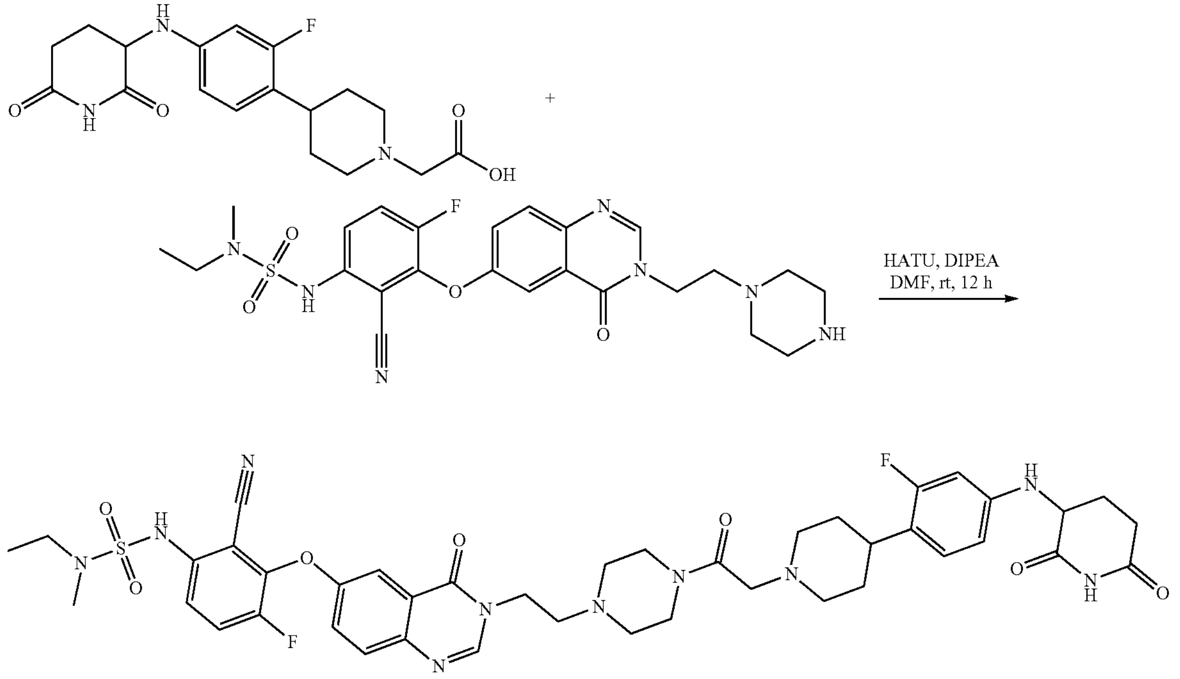

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-yl-ethyl)quinazoline (20 mg, 37.77 μmol), 2-[4-[4-[(2,6-dioxo-3-piperidyl)amino]-2-fluoro-phenyl]-1-piperidyl]acetic acid (13.72 mg, 37.77 μmol), N,N-diisopropylethylamine (24.40 mg, 188.83 μmol, 32.89 μL) and HATU (17.23 mg, 45.32 μmol) to afford crude product. Crude product was purified by Prep HPLC purification method: 10 mm Ammonium acetate:acetonitrile and pure fractions were lyophilized to afford product 6-[2-cyano-3-[[ethyl(methyl)sulfamoyl]amino]-6-fluoro-phenoxy]-3-[2-[4-[2-[4-[4-[(2,6-dioxo-3-piperidyl)amino]-2-fluoro-phenyl]-1-piperidyl]acetyl]piperazin-1-yl]ethyl]-4-oxo-quinazoline (7.34 mg, 8.34 μmol, 22% yield) as an off-white solid. LCMS m/z (ESI): 875.30 $[M+H]^+$; $^1$HNMR (400 MHz, DMSO-$d_6$): δ=10.81 (s, 1H), 9.78 (bs, 1H), 8.32 (s, 1H), 7.76 (d, J=9.20 Hz, 1H), 7.65 (dd, J=3.20, 9.00 Hz, 1H), 7.53 (t, J=10.00 Hz, 1H), 7.35-7.32 (m, 2H), 6.98 (t, J=8.40 Hz, 1H), 6.49-6.44 (m, 2H), 6.07 (d, J=7.60 Hz, 1H), 4.35-4.31 (m, 1H), 4.29-4.09 (m, 2H), 3.85-3.70 (m, 2H), 3.50-3.40 (m, 5H), 3.41-3.22 (m, 3H), 3.04 (q, J=6.80 Hz, 2H), 2.78-2.70 (m, 3H), 2.64 (s, 3H), 2.60-2.55 (m, 4H), 2.48-2.38 (m, 2H), 2.10-2.07 (m, 1H), 1.91-1.76 (m, 5H), 1.03 (t, J=7.20 Hz, 3H).

Example 9

6-[2-cyano-3-[[ethyl(methyl)sulfamoyl]amino]-6-fluorophenoxy]-3-[2-[4-[2-[4-[4-[(2,6-dioxopiperidin-3-yl)amino]phenyl]piperidin-1-yl]acetyl]piperazin-1-yl]ethyl]-4-oxoquinazoline Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-yl-ethyl)quinazoline (20 mg, 37.77 μmol), 2-[4-[4-[(2,6-dioxo-3-piperidyl)amino]phenyl]-1-piperidyl]acetic acid (13.04 mg, 37.77 μmol), N,N-diisopropylethylamine (24.40 mg, 188.83 μmol, 32.89 μL) and HATU (17.23 mg, 45.32 μmol) to afford crude product. Crude product was purified by Prep HPLC purification method: 10 mm 10 mm Ammonium acetate:acetonitrile and pure fractions were lyophilized to afford product 6-[2-cyano-3-[[ethyl(methyl)sulfamoyl]amino]-6-fluoro-phenoxy]-3-[2-[4-[2-[4-[4-[(2,6-dioxo-3-piperidyl)amino]phenyl]-1-piperidyl]acetyl]piperazin-1-yl]ethyl]-4-oxo-quinazoline (7.97 mg, 9.28 μmol, 25% yield) as an off-white solid. LCMS m/z (ESI): 857.20 $[M+H]^+$; $^1$HNMR (400 MHz, DMSO-$d_6$): δ=10.78 (s, 1H), 9.70 (bs, 1H), 8.31 (s, 1H), 7.76 (d, J=8.92 Hz, 1H), 7.64 (dd, J=2.96, 8.92 Hz, 1H), 7.50 (t, J=9.76 Hz, 1H), 7.35-7.30 (m, 2H), 6.96 (d, J=8.32 Hz, 2H), 6.63 (d, J=8.44 Hz, 2H), 5.72 (d, J=7.48 Hz, 1H), 4.30-4.25 (m, 1H), 4.10-4.07 (m, 2H), 3.90-3.78 (m, 2H), 3.45-3.35 (m, 5H), 3.25-3.15 (m, 3H), 3.03 (q, J=7.12 Hz, 2H), 2.80-2.65 (m, 3H), 2.64 (s, 3H), 2.62-2.56 (m, 4H), 2.48-2.38 (m, 2H), 2.12-2.08 (m, 1H), 1.88-1.76 (m, 5H), 1.03 (t, J=7.16 Hz, 3H).

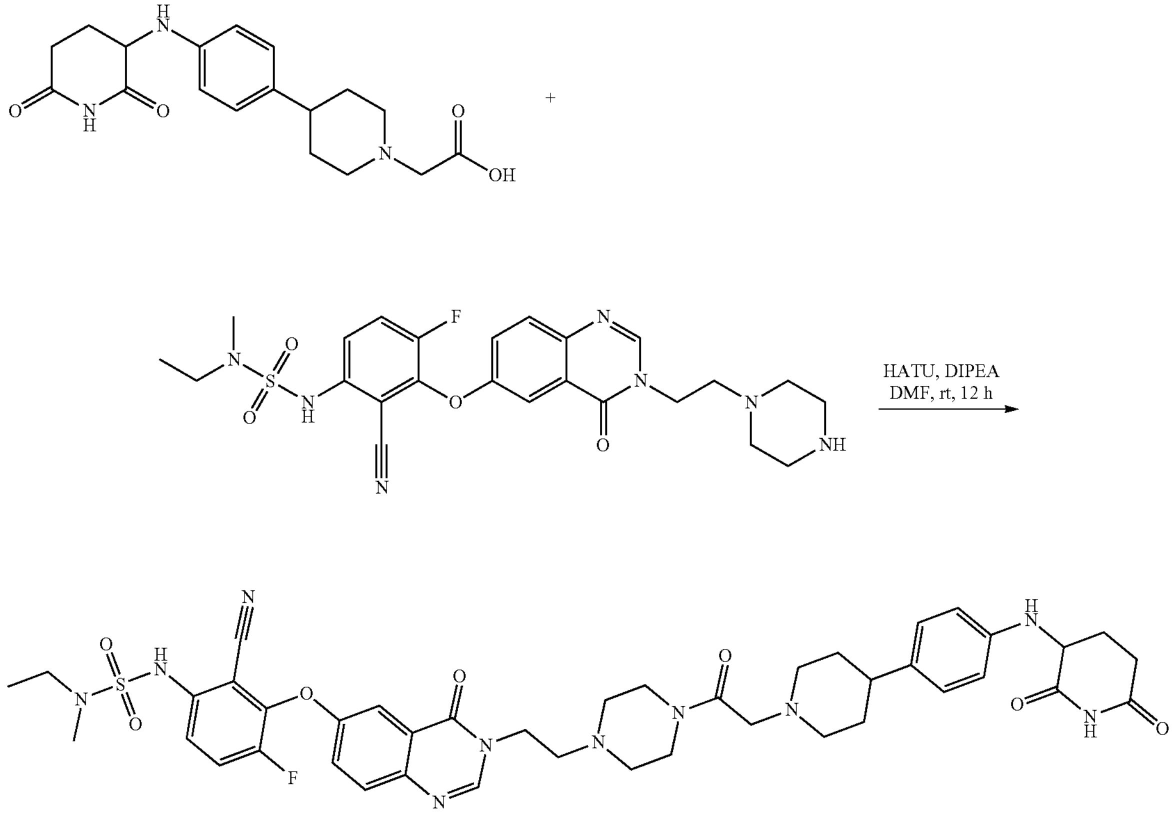

Example 10
6-[2-cyano-3-[[ethyl(methyl)sulfamoyl]amino]-6-fluorophenoxy]-3-[4-[1-[2-[4-[4-[(2,6-dioxopiperidin-3-yl)amino]-2-fluorophenyl]piperidin-1-yl]acetyl]piperidin-4-yl]butan-2-yl]-4-oxoquinazoline
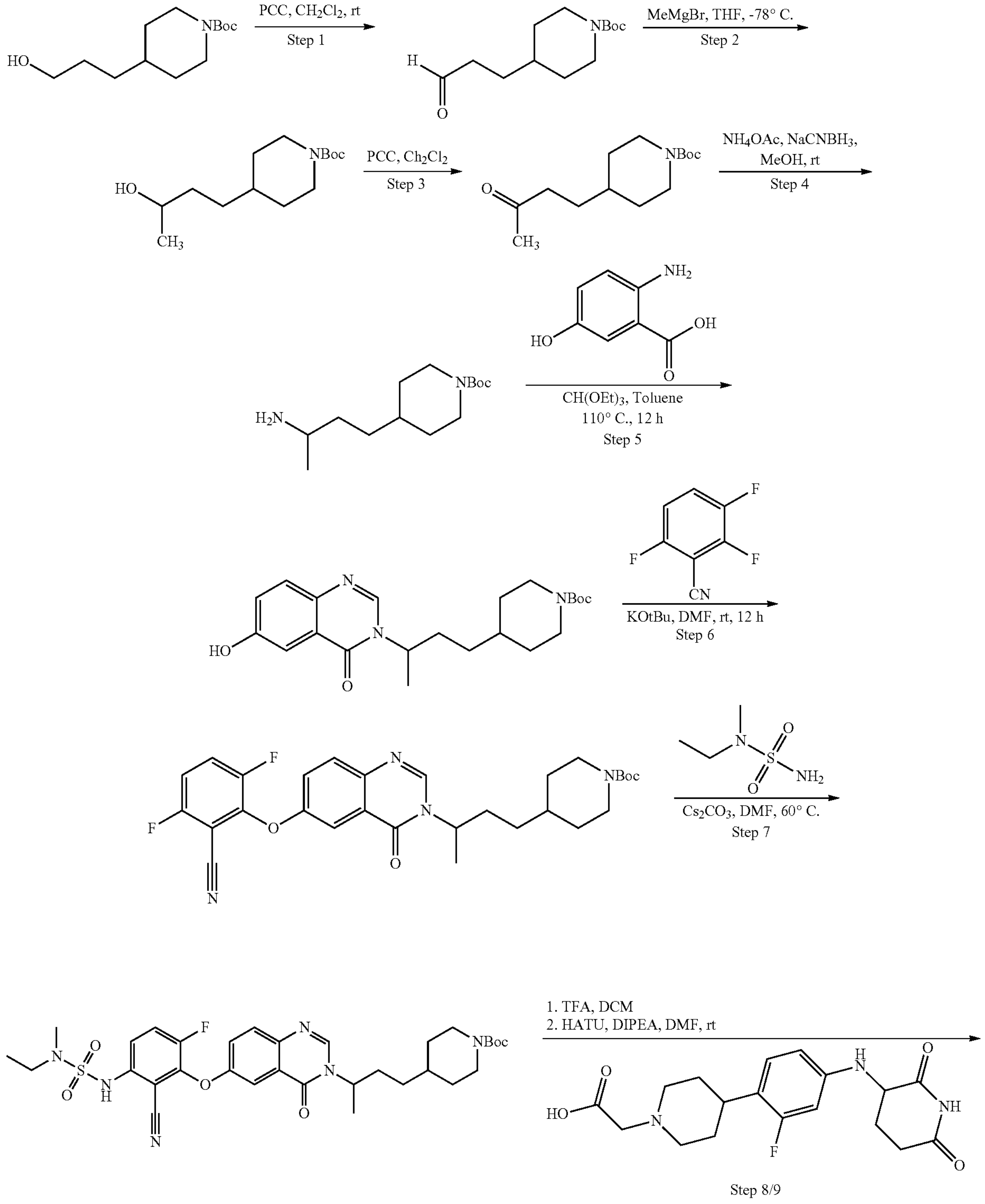

-continued

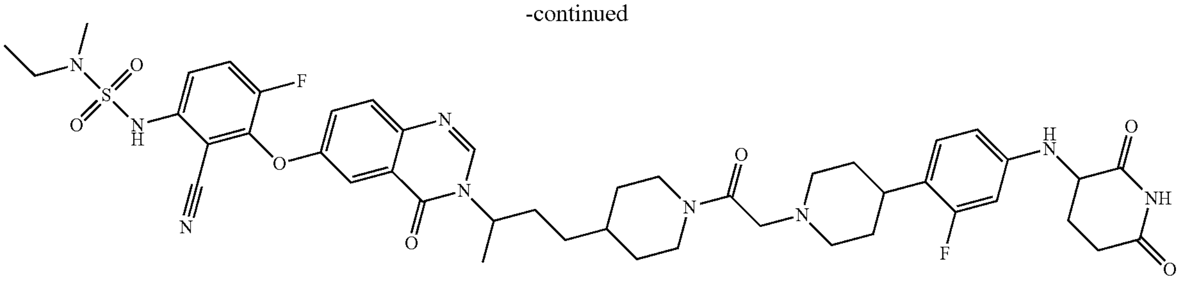

Step 1: To the stirred solution of tert-butyl 4-(3-hydroxypropyl)piperidine-1-carboxylate (100 mg, 410.94 μmol) in dichloromethane (1.6 mL), was added Pyridinium chlorochromate (132.87 mg, 616.41 μmol) at 0° C. and continued the reaction at room temperature for 2 h. After completion, the reaction mixture was quenched with saturated sodium bicarbonate solution (10 mL) and extracted with dichloromethane (2×10 mL). Combined organic layers were washed with brine solution (15 mL) and dried over anhydrous sodium sulfate and concentrated under reduced pressure to afford crude tert-butyl 4-(3-oxopropyl)piperidine-1-carboxylate (0.07 g, 174 μmol, 42.3% yield) as viscous liquid. LCMS m/z (ESI): 186.1 $[M+H-{}^tBu]^+$ Step 2: To a stirred solution of tert-butyl 4-(3-oxopropyl) piperidine-1-carboxylate (3 g, 12.43 mmol) in THF (12 mL), was added methyl magnesium bromide (2.17 g, 18.17 mmol, 2.10 mL) dropwise at −78° C. and continued the reaction at −78° C. for 2 h. After completion, the reaction mixture was quenched by saturated solution of $NH_4Cl$ (50 mL) and extracted with ethyl acetate (2×50 mL) and organic phase was concentrated to afford crude material which was purified using column chromatography eluting with 0-40% ethyl acetate in petroleum ether to afford tert-butyl 4-(3-hydroxybutyl)piperidine-1-carboxylate (2.3 g, 8.49 mmol, 68% yield) as a colorless liquid. LCMS m/z (ESI): 158.2 $[M+H-CO_2{}^tBu]^+$ Step 3: To a stirred solution of tert-butyl 4-(3-hydroxybutyl)piperidine-1-carboxylate (2.2 g, 8.55 mmol) in dichloromethane (30 mL), was added Pyridinium chlorochromate (2.76 g, 12.82 mmol) at 0° C. and continued the reaction at room temperature for 4 h. After completion, the reaction mixture was quenched with saturated sodium bicarbonate (50 mL) solution and extracted with dichloromethane (2×50 mL). The combined organic layers was concentrated to afford crude material which was purified using column chromatography eluting with 0-40% ethyl acetate in petroleum ether to afford tert-butyl 4-(3-oxobutyl)piperidine-1-carboxylate (2 g, 7.60 mmol, 89% yield). LCMS m/z (ESI): 156.1 $[M+H-CO_2{}^tBu]^+$ Step 4: To the stirred solution of tert-butyl 4-(3-oxobutyl) piperidine-1-carboxylate (2 g, 7.83 mmol) in methanol (30 mL) was added ammonium acetate (6.04 g, 78.32 mmol) at room temperature and stirred the reaction mixture at room temperature for 1.5 h. Then sodium cyanoborohydride (738.30 mg, 11.75 mmol) was added to above reaction mixture portion wise at room temperature and refluxed for 16 h. After completion, reaction mixture was concentrated in vacuo to afford crude, which was diluted with water (50 mL) and extracted with ethyl acetate (2×50 mL). The combined organic layers were washed with saturated $NH_4Cl$ solution and dried over sodium sulfate and concentrated in vacuo to afford tert-butyl 4-(3-aminobutyl)piperidine-1-carboxylate (1.4 g, 4.70 mmol, 60% yield). LCMS m/z (ESI): 257.5 $[M+H]^+$ Step 5: The quinazolinone intermediate was synthesized by following the general procedure for cyclization (Procedure A-A) using tert-butyl 4-(3-aminobutyl)piperidine-1-carboxylate (1.3 g, 5.07 mmol), 2-amino-5-hydroxy-benzoic acid (776.48 mg, 5.07 mmol), Triethyl orthoformate (1.88 g, 12.68 mmol, 2.11 mL) to afford tert-butyl 4-[3-(6-hydroxy-4-oxo-quinazolin-3-yl)butyl]piperidine-1-carboxylate (1.6 g, 1.87 mmol, 37% yield). LCMS m/z (ESI): 402.3 $[M+H]^+$ Step 6: O-Arylated quinazolinone intermediate was synthesized by following general procedure for O-arylation (Procedure A-B) using tert-butyl 4-[3-(6-hydroxy-4-oxo-quinazolin-3-yl)butyl]piperidine-1-carboxylate (1.5 g, 3.74 mmol), potassium tert-butoxide (628.84 mg, 5.60 mmol) and 2,3,6-trifluorobenzonitrile (704.28 mg, 4.48 mmol, 517.85 μL). The crude reaction mixture was purified using column chromatography eluting with 0-80% ethyl acetate/petroleum ether to afford pure tert-butyl 4-[3-[6-(2-cyano-3,6-difluoro-phenoxy)-4-oxo-quinazolin-3-yl]butyl]piperidine-1-carboxylate (800 mg, 1.37 mmol, 37% yield) as yellow solid. LCMS m/z (ESI): 483.2 $[M+H-{}^tBu]^+$ Step 7: Sulfamoylated quinazolinone intermediate was synthesized by following Procedure A-C using tert-butyl 4-[3-[6-(2-cyano-3,6-difluoro-phenoxy)-4-oxo-quinazolin-3-yl]butyl]piperidine-1-carboxylate (0.7 g, 1.30 mmol), [methyl(sulfamoyl)amino]ethane (359.21 mg, 2.60 mmol) and cesium carbonate (1.27 g, 3.90 mmol). The resulting crude compound was purified using silica gel flash column chromatography eluting with 0-10% methanol in dichloromethane to afford pure tert-butyl 4-[3-[6-[2-cyano-3-[[ethyl(methyl)sulfamoyl]amino]-6-fluoro-phenoxy]-4-oxo-quinazolin-3-yl]butyl]piperidine-1-carboxylate (560 mg, 596.86 μmol, 46% yield) as off-white solid. LCMS m/z (ESI): 655.1 $[M-H]^-$ Step 8: The requisite amine was synthesized by TFA mediated N-Boc deprotection (Procedure A-D). N-Boc deprotection was performed on tert-butyl 4-[3-[6-[2-cyano-3-[[ethyl(methyl)sulfamoyl]amino]-6-fluoro-phenoxy]-4-oxo-quinazolin-3-yl]butyl]piperidine-1-carboxylate (560 mg, 852.66 μmol) using trifluoroacetic acid (4.44 g, 38.94 mmol, 3 mL) to afford crude 6-[2-cyano-3-[[ethyl(methyl) sulfamoyl]amino]-6-fluoro-phenoxy]-3-[1-methyl-3-(4-piperidyl)propyl]-4-oxo-quinazoline as its TFA salt (430 mg, 702.95 μmol, 82% yield) as a viscous liquid. LCMS m/z (ESI): 557.3 $[M+H]^+$ Step 9: Target compound was prepared via HATU mediated acid-amine coupling reaction (Procedure A-E). Amide coupling was carried out using 6-[2-cyano-3-[[ethyl(methyl) sulfamoyl]amino]-6-fluoro-phenoxy]-3-[1-methyl-3-(4-piperidyl)propyl]-4-oxo-quinazoline (430 mg, 772.48 μmol), 2-[4-[4-[(2,6-dioxo-3-piperidyl)amino]-2-fluoro-phenyl]-1-piperidyl]acetic acid (308.87 mg, 772.48 μmol), HATU (440.58 mg, 1.16 mmol) and N,N-diisopropylethylamine (1.50 g, 11.59 mmol, 2.02 mL). The resulting crude compound was purified by reverse phase column chromatography [Mobile-phase A: 0.1% Ammonium acetate water, Mobile-phase B: acetonitrile; column: 100 g RediSep® Rf C18] to afford the 6-[2-cyano-3-[[ethyl(methyl)sulfamoyl]amino]-6-fluoro-phenoxy]-3-[3-[1-[2-[4-[4-[(2,6-dioxo-3-piperidyl)amino]-2-fluoro-phenyl]-1-piperidyl]acetyl]-4-piperidyl]-1-methyl-propyl]-4-oxo-quinazoline (75 mg, 80.66 μmol, 10% yield) as off-white solid. LCMS m/z (ESI): 902.3 $[M+H]^+$. $^1$HNMR (400 MHz, DMSO-$d_6$): δ=10.81 (s, 1H), 9.66 (s, 1H), 8.41 (s, 1H), 7.76 (d, J=8.80 Hz, 1H), 7.64 (dd, J=2.80, 9.20 Hz, 1H), 7.48-7.57 (m, 1H), 7.33 (d, J=2.80 Hz, 1H), 7.30-7.34 (m, 1H), 6.97-7.02 (m, 1H), 6.48 (d, J=7.60 Hz, 1H), 6.46 (d, J=12.80 Hz, 1H), 6.08 (d, J=7.20 Hz, 1H), 4.85-4.72 (m, 1H), 4.28-4.37 (m, 1H), 3.71-3.82 (m, 1H), 3.20-3.40 (m, 2H), 2.92-3.11 (m, 3H), 2.52-2.81 (m, 6H), 2.62 (s, 3H), 2.05-2.11 (m, 2H), 1.60-1.98 (m, 10H), 1.40-1.52 (m, 2H), 1.42 (d, J=6.80 Hz, 3H), 1.15-1.26 (m, 1H), 1.03 (t, J=7.20 Hz, 3H), 0.82-1.10 (m, 3H).

Example 11

6-[2-cyano-3-[[ethyl(methyl)sulfamoyl]amino]-6-fluorophenoxy]-3-[3-[1-[2-[4-[4-[(2,6-dioxopiperidin-3-yl)amino]-2-fluorophenyl]piperidin-1-yl]acetyl]piperidin-4-yl]butyl]-4-oxoquinazoline

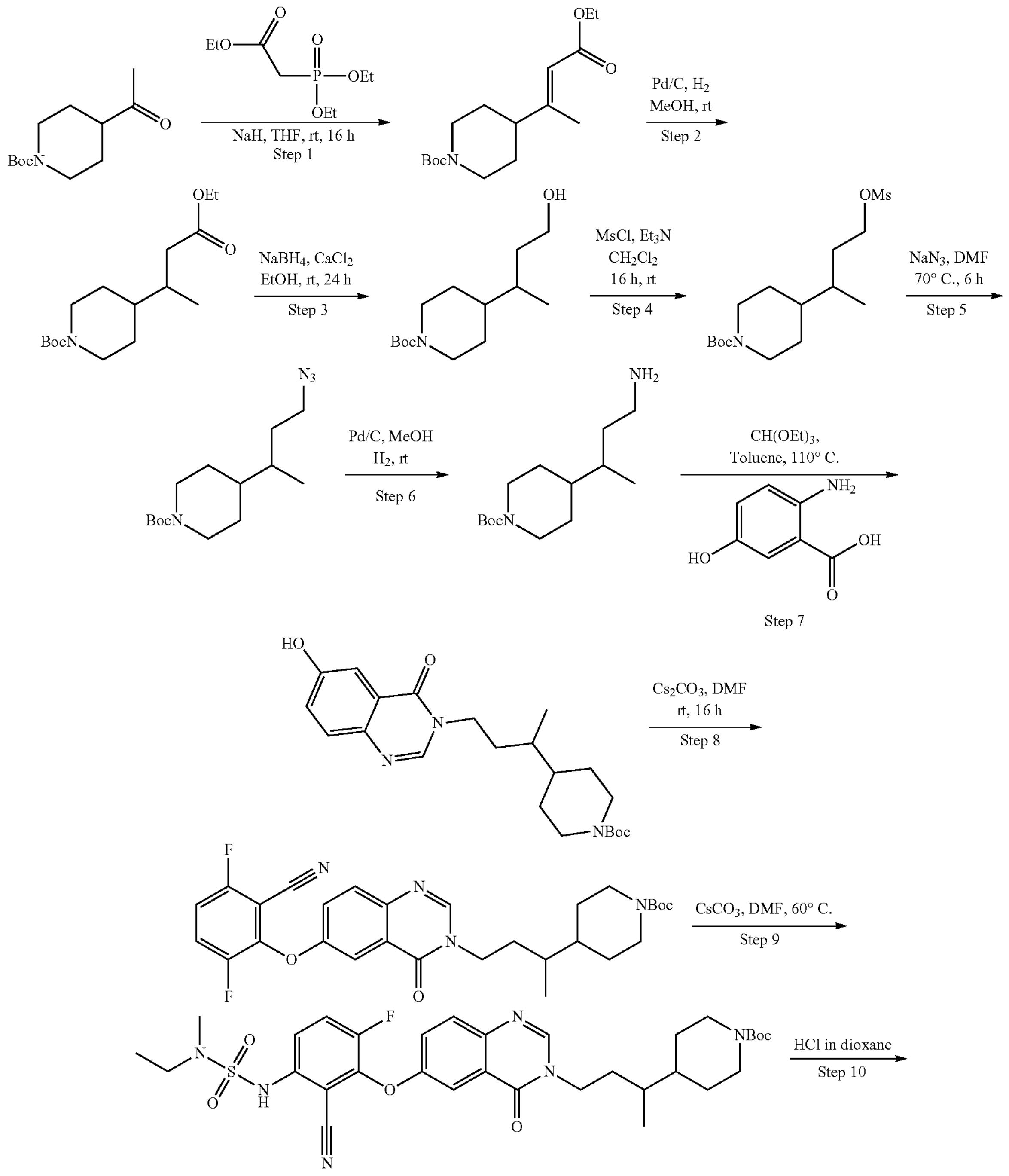

-continued

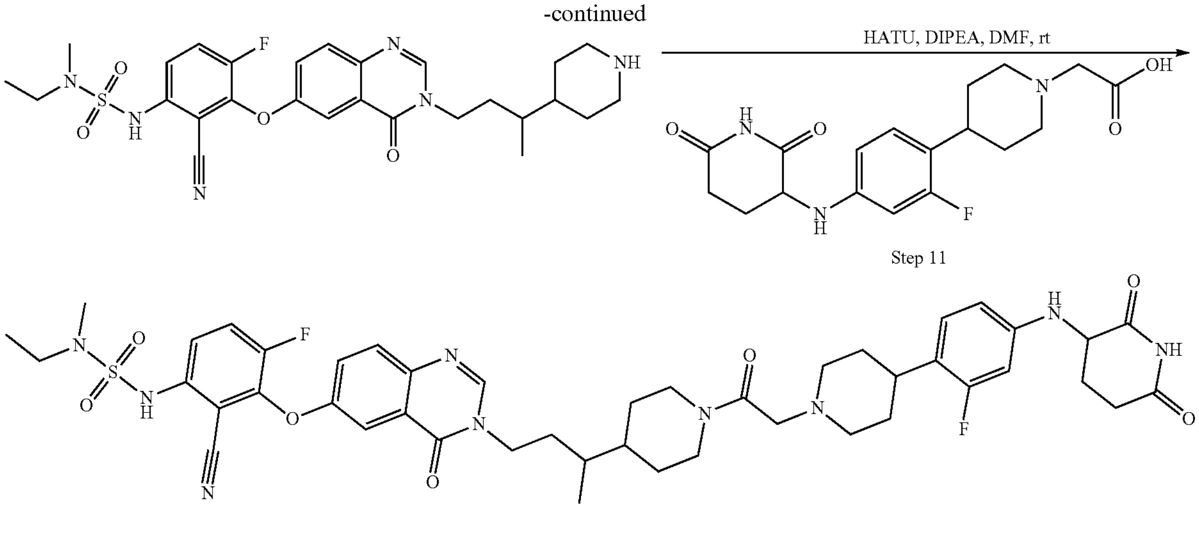

Step 1: To a stirred solution of sodium hydride (60% dispersion in mineral oil, 1.21 g, 52.79 mmol) in Tetrahydrofuran (40 mL) and ethyl 2-diethoxyphosphorylacetate (8.88 g, 39.60 mmol, 7.86 mL) was dissolved in Tetrahydrofuran (10 mL) and added to the reaction mixture at 0° C., the reaction mixture was stirred at room temperature for 2 h. Then tert-butyl 4-acetylpiperidine-1-carboxylate (6 g, 26.40 mmol) was added to the reaction mixture at room temperature. The reaction mixture was stirred at room temperature for 16 h. After completion of the reaction, the reaction mixture was quenched with cold water (50 mL) and extracted with ethyl acetate (2×100 mL). The combined organic layers were dried with anhydrous sodium sulfate and concentrated under reduced pressure to afford crude. The crude compound was purified by silica gel flash column chromatography with 15-25% ethyl acetate in petroleum ether as a eluent to afford tert-butyl 4-[(E)-3-ethoxy-1-methyl-3-oxo-prop-1-enyl]piperidine-1-carboxylate (4 g, 10.76 mmol, 41% yield) as colorless liquid. LCMS m/z (ESI): 198.20 $[M+H-CO_2{}^tBu]^+$ Step 2: To a stirred solution of tert-butyl 4-[(E)-3-ethoxy-1-methyl-3-oxo-prop-1-enyl]piperidine-1-carboxylate (4 g, 13.45 mmol) in degassed, anhydrous methanol (40 mL) was added 10% palladium on carbon dry basis (400 mg, 1.35 mmol) at room temperature. The resulting suspension was stirred at room temperature for 16 h under a hydrogen gas bladder. After completion of the reaction, the reaction mixture was filtered through celite pad, washed with methanol. The filtrate was concentrated under reduced pressure to afford crude mixture of tert-butyl 4-(3-ethoxy-1-methyl-3-oxo-propyl)piperidine-1-carboxylate (3.9 g, 12.24 mmol, 91% yield) as a colorless liquid. LCMS m/z (ESI): 200.1 $[M+H-CO_2{}^tBu]^+$ Step 3: To a stirred solution of tert-butyl 4-(3-ethoxy-1-methyl-3-oxo-propyl)piperidine-1-carboxylate (3 g, 10.02 mmol) in anhydrous ethanol (30 mL) was added calcium chloride (1.11 g, 10.02 mmol) and sodium borohydride (568.58 mg, 15.03 mmol) at 0° C. under nitrogen atmosphere. The resulting suspension was stirred at room temperature for 24 h. After completion of the reaction, the reaction mixture was treated with cold water (50 mL), extracted with ethyl acetate (2×100 mL). The combined organics were washed with brine solution, dried with anhydrous sodium sulfate, filtered and the filtrate was concentrated under reduced pressure to afford the crude product tert-butyl 4-(3-hydroxy-1-methyl-propyl)piperidine-1-carboxylate (2.8 g, 9.79 mmol, 98% yield) as a yellow liquid. LCMS m/z (ESI): 158.1 $[M+H-CO_2{}^tBu]^+$ Step 4: To a stirred solution of tert-butyl 4-(3-hydroxy-1-methyl-propyl)piperidine-1-carboxylate (2.7 g, 10.49 mmol) in anhydrous dichloromethane (30 mL) was added triethylamine (2.65 g, 26.23 mmol, 3.66 mL) followed by mesyl chloride (1.80 g, 15.74 mmol, 1.22 mL) at 0° C. under nitrogen atmosphere. The resulting suspension was stirred at room temperature for 16 h. After completion of the reaction, the reaction mixture was treated with ice-water and extracted with dichloromethane (2×100 mL). The combined organics were washed with brine, dried with anhydrous sodium sulfate, filtered and the filtrate was concentrated under reduced pressure to afford the crude product tert-butyl 4-(1-methyl-3-methylsulfonyloxy-propyl)piperidine-1-carboxylate (2.8 g, 8.26 mmol, 79% yield) as yellow liquid. LCMS m/z (ESI): 236.0 $[M+H-CO_2{}^tBu]^+$ Step 5: To a stirred solution of tert-butyl 4-(1-methyl-3-methylsulfonyloxy-propyl)piperidine-1-carboxylate (2.8 g, 8.35 mmol) in anhydrous N,N-dimethylformamide (30 mL) was added sodium azide (813.94 mg, 12.52 mmol) at room temperature under nitrogen atmosphere. After complete addition, the reaction mixture was stirred at 70° C. for 16 h under nitrogen atmosphere. The reaction mixture was then cooled to room temperature, diluted with ethyl acetate (100 mL) and washed successively with water (2×50 mL) and brine (20 mL). The separated organic layer was dried with anhydrous sodium sulfate, filtered and the filtrate was evaporated to dryness under reduced pressure to obtain crude residue of tert-butyl 4-(3-azido-1-methyl-propyl)piperidine-1-carboxylate (2.35 g, 8.32 mmol, 100% yield) as brown liquid. No ionization was shown by LCMS. This was taken for next step without any purification.

Step 6: To a stirred solution of tert-butyl 4-(3-azido-1-methyl-propyl)piperidine-1-carboxylate (3 g, 10.62 mmol) in methanol (30 mL) was added 10% palladium on carbon (600 mg, 10.62 mmol) at room temperature under nitrogen atmosphere. The resulting suspension was stirred at room temperature under a hydrogen atmosphere bladder for 3 h. After completion of the reaction, reaction mixture was filtered through celite bed which was washed with methanol (100 mL). The combined filtrate was concentrated under reduced pressure to afford a crude product tert-butyl 4-(3-amino-1-methyl-propyl)piperidine-1-carboxylate (2 g, 6.47 mmol, 61% yield) as a pale brown oil. LCMS m/z (ESI): 157.2 [M+H−$CO_2{}^tBu$]$^+$ Step 7: To a stirred solution of tert-butyl 4-(3-amino-1-methyl-propyl)piperidine-1-carboxylate (920.83 mg, 3.59 mmol) and 2-amino-5-hydroxy-benzoic acid (500 mg, 3.27 mmol) in anhydrous Toluene (10 mL) was added triethyl orthoformate (629.05 mg, 4.24 mmol, 706.00 μL) at room temperature under nitrogen atmosphere. The resulting mixture was stirred at 110° C. for 16 h. After completion of the reaction as indicated by TLC, the reaction mixture was cooled to room temperature, diluted with water (70 mL), extracted with ethyl acetate (2×150 mL). The combined organics were washed with brine solution, dried over anhydrous sodium sulfate, filtered and concentrated under reduced pressure to afford tert-butyl 4-[3-(6-hydroxy-4-oxo-quinazolin-3-yl)-1-methyl-propyl]piperidine-1-carboxylate (900 mg, 1.68 mmol, 51% yield) as a pale brown oil. LCMS m/z (ESI): 402.20 [M+H]$^+$ Step 8: O-arylated quinazolinone intermediate was synthesized by following Procedure A-B using tert-butyl 4-[3-(6-hydroxy-4-oxo-quinazolin-3-yl)-1-methyl-propyl]piperidine-1-carboxylate (900 mg, 2.24 mmol), cesium carbonate (1.10 g, 3.36 mmol) and 2,3,6-trifluorobenzonitrile (422.57 mg, 2.69 mmol, 310.71 μL). The crude compound was purified by silica gel flash column chromatography with 70-75% ethyl acetate in petroleum ether as a eluent to afford tert-butyl 4-[3-[6-(2-cyano-3,6-difluoro-phenoxy)-4-oxo-quinazolin-3-yl]-1-methyl-propyl]piperidine-1-carboxylate (800 mg, 1.31 mmol, 58% yield) as yellow viscous liquid. LCMS m/z (ESI): 439.1[M+H−$CO_2{}^tBu$]$^+$ Step 9: Sulfamoylated quinazolinone intermediate was synthesized by following Procedure A-C using tert-butyl 4-[3-[6-(2-cyano-3,6-difluoro-phenoxy)-4-oxo-quinazolin-3-yl]-1-methyl-propyl]piperidine-1-carboxylate (800 mg, 1.49 mmol), cesium carbonate (1.21 g, 3.71 mmol) and [methyl(sulfamoyl)amino]ethane (307.89 mg, 2.23 mmol) to afford crude product tert-butyl 4-[3-[6-[2-cyano-3-[[ethyl(methyl)sulfamoyl]amino]-6-fluoro-phenoxy]-4-oxo-quinazolin-3-yl]-1-methyl-propyl]piperidine-1-carboxylate (800 mg, 682.13 μmol, 46% yield) as a yellow viscous solid. LCMS m/z (ESI): 557.10 [M+H−$CO_2{}^tBu$]$^+$ Step 10: The requisite amine was synthesized by following Procedure A-D using tert-butyl 4-[3-[6-[2-cyano-3-[[ethyl(methyl)sulfamoyl]amino]-6-fluoro-phenoxy]-4-oxo-quinazolin-3-yl]-1-methyl-propyl]piperidine-1-carboxylate (800 mg, 1.22 mmol) and hydrogen chloride solution 4.0 M in dioxane (6 mL). The resulted crude compound was triturated with methyl t-butyl ether to afford 6-[2-cyano-3-[[ethyl(methyl)sulfamoyl]amino]-6-fluoro-phenoxy]-4-oxo-3-[3-(4-piperidyl)butyl]quinazoline as its HCl salt (600 mg, 778.94 μmol, 64% yield) as an off-white solid. LCMS m/z (ESI): 557.20 [M+H]$^+$ Step 11: Target compound was prepared via HATU mediated acid-amine coupling reaction (Procedure A-E). The amide coupling was carried out using 2-[4-[4-[(2,6-dioxo-3-piperidyl)amino]-2-fluoro-phenyl]-1-piperidyl]acetic acid (137.53 mg, 343.95 μmol), 6-[2-cyano-3-[[ethyl(methyl)sulfamoyl]amino]-6-fluoro-phenoxy]-4-oxo-3-[3-(4-piperidyl)butyl]quinazoline (170 mg, 286.62 μmol), N,N-diisopropylethylamine (222.26 mg, 1.72 mmol, 299.54 μL) and HATU (119.88 mg, 315.29 μmol) to afford a crude product. The crude product was purified by C18-reverse phase column chromatography using Isolera (100 g RediSep® Rf C18 (Teledyne ISCO Corp., Thousand Oaks, CA), Method: 10 mM Ammonium acetate in water:acetonitrile) and pure fractions were lyophilized to afford 6-[2-cyano-3-[[ethyl(methyl)sulfamoyl]amino]-6-fluoro-phenoxy]-3-[3-[1-[2-[4-[4-[(2,6-dioxo-3-piperidyl)amino]-2-fluoro-phenyl]-1-piperidyl]acetyl]-4-piperidyl]butyl]-4-oxo-quinazoline (95 mg, 105.10 μmol, 37% yield) as a pale brown solid. LCMS m/z (ESI): 902.30 [M+H]$^+$; $^1$HNMR (400 MHz, DMSO-$d_6$): δ=10.81 (s, 1H), 9.64 (bs, 1H), 8.40 (s, 1H), 7.76 (d, J=9.20 Hz, 1H), 7.64 (dd, J=2.80, 9.00 Hz, 1H), 7.51 (s, 1H), 7.34-7.32 (m, 2H), 7.05-6.90 (m, 1H), 6.47 (t, J=12.00 Hz, 2H), 6.08 (d, J=7.60 Hz, 1H), 4.50-4.40 (m, 1H), 4.45-4.38 (m, 1H), 4.10-3.75 (m, 5H), 3.40-3.20 (m, 2H), 3.03 (q, J=7.20 Hz, 2H), 3.00-2.90 (m, 2H), 2.85-2.70 (m, 3H), 2.63 (s, 3H), 2.60-2.55 (m, 2H), 2.15-2.05 (m, 1H), 1.95-1.70 (m, 7H), 1.70-1.55 (m, 2H), 1.55-1.30 (m, 3H), 1.25-1.10 (m, 1H), 1.03 (t, J=7.20 Hz, 3H), 0.92 (d, J=2.00 Hz, 3H).

Example 12

6-[2-cyano-3-[[ethyl(methyl)sulfamoyl]amino]-6-fluorophenoxy]-3-[3-[1-[2-[4-[4-[(2,6-dioxopiperidin-3-yl)amino]-2-fluorophenyl]piperidin-1-yl]acetyl]-4-methylpiperidin-4-yl]propyl]-4-oxoquinazoline

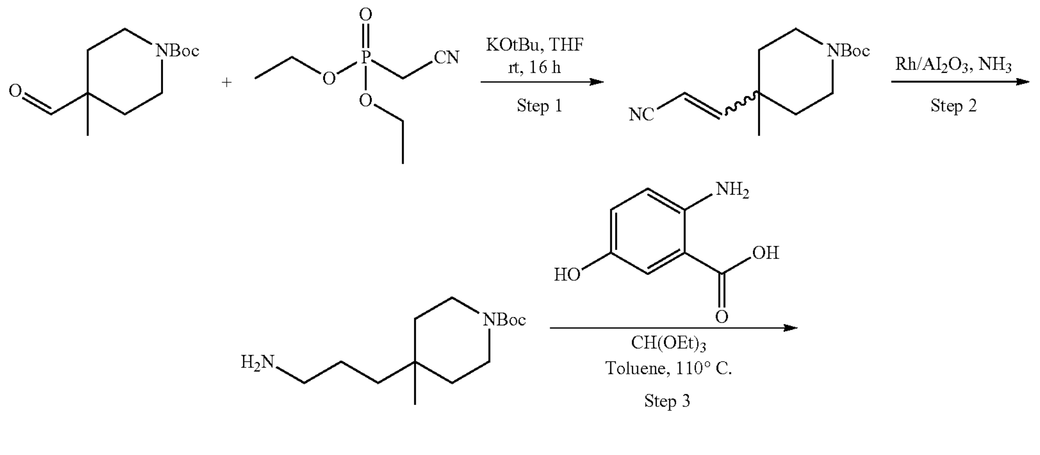

-continued

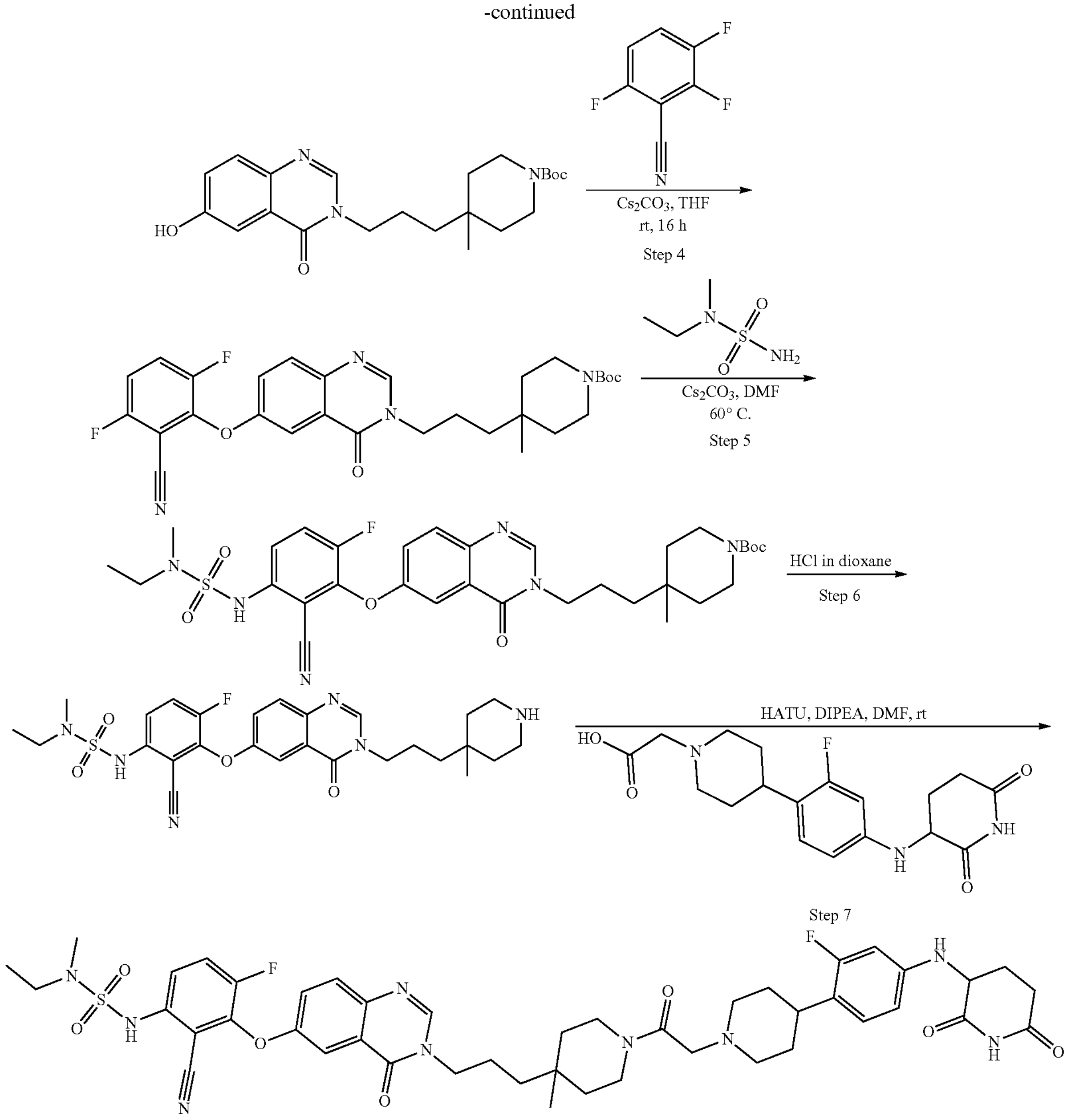

Step 1: To a stirred solution of tert-butyl 4-formyl-4-methyl-piperidine-1-carboxylate (1.9 g, 8.36 mmol) in THF (30 mL) was added 2-diethoxyphosphorylacetonitrile (85.72 mg, 483.94 μmol, 77.93 μL) at room temperature. Then potassium tert-butoxide (1.13 g, 10.03 mmol) was added to the reaction at 0° C. and continued the reaction to stir at room temperature for 16 h. After completion, the reaction mixture was diluted with water (100 mL) and extracted in ethyl acetate (2×100 mL). The combined organic layers were dried over anhydrous sodium sulfate, concentrated under reduced pressure to yield crude. The crude compound was purified by silica gel flash column chromatography eluting with 0-5% ethyl acetate/petroleum ether as eluent to yield tert-butyl 4-[(E)-2-cyanovinyl]-4-methyl-piperidine-1-carboxylate (1 g, 3.79 mmol, 45% yield) as a colorless liquid. $^1$HNMR (400 MHz, $CDCl_3$): δ=6.71 (d, J=16.80 Hz, 1H), 6.38 (d, J=12.40 Hz, 1H), 5.44 (d, J=12.40 Hz, 1H), 5.32 (d, J=−16.80 Hz, 1H), 3.64-3.70 (m, 2H), 3.42-3.47 (m, 4H), 3.17-3.23 (m, 2H), 1.94-1.98 (m, 2H), 1.53-1.62 (m, 4H), 1.49 (s, 18H), 1.28 (s, 3H), 1.10 (s, 3H).

Step 2: To a stirred solution of 3-[1-(2-hydroxyacetyl)-4-methyl-4-piperidyl]propanenitrile (1 g, 4.76 mmol) in ethanol (10 mL) and ammonium hydroxide (10 mL), Rhodium on alumina (489.39 mg, 4.76 mmol) was added and the reaction was heated to 40° C. for 16 h. After completion, the reaction mixture was filtered through a celite bed using ethanol and concentrated to afford crude 1-[4-(3-aminopropyl)-4-methyl-1-piperidyl]-2-hydroxy-ethanone (1 g, 4.67 mmol, 98% yield) which was taken next step without further purification. $^1$HNMR (400 MHz, DMSO-$d_6$): δ=3.41-3.45 (m, 2H), 3.10-3.22 (m, 2H), 2.65-2.80 (m, 2H), 1.49-1.54 (m, 2H), 1.39 (s, 9H), 1.21-1.31 (m, 6H), 0.88 (s, 3H).

Step 3: The quinazolinone intermediate was synthesized by following general procedure for cyclization (Procedure A-A) using tert-butyl 4-(3-aminopropyl)-4-methyl-piperidine-1-carboxylate (1 g, 3.90 mmol), Triethyl orthoformate (578.04 mg, 3.90 mmol, 648.76 μL) and 2-amino-5-hydroxy-benzoic acid (597.29 mg, 3.90 mmol) to afford tert-butyl 4-[3-(6-hydroxy-4-oxo-quinazolin-3-yl)propyl]-4-methyl-piperidine-1-carboxylate (650 mg, 1.30 mmol, 33% yield) as a brownish yellow solid. LCMS m/z (ESI): 402.0 $[M+H]^+$ Step 4: O-arylated quinazolinone intermediate was synthesized by following general procedure for O-arylation (Procedure A-B) using tert-butyl 4-[3-(6-hydroxy-4-oxo-quinazolin-3-yl)propyl]-4-methyl-piperidine-1-carboxylate (600 mg, 1.49 mmol), cesium carbonate (1.46 g, 4.48 mmol) and 2,3,6-trifluorobenzonitrile (234.76 mg, 1.49 mmol, 172.62 μL) to afford tert-butyl 4-[3-[6-(2-cyano-3,6-difluoro-phenoxy)-4-oxo-quinazolin-3-yl]propyl]-4-methyl-piperidine-1-carboxylate (260 mg, 459 μmol, 31% yield) as an off-white solid. LCMS m/z (ESI): 537.2 $[M-H]^-$ Step 5: Sulfamoylated quinazolinone intermediate was synthesized by following Procedure A-C using tert-butyl 4-[3-[6-(2-cyano-3,6-difluoro-phenoxy)-4-oxo-quinazolin-3-yl]propyl]-4-methyl-piperidine-1-carboxylate (260 mg, 482.75 μmol), [methyl(sulfamoyl)amino]ethane (100.06 mg, 724.12 μmol) and cesium carbonate (314.58 mg, 965.49 μmol) to afford the crude residue of tert-butyl 4-[3-[6-[2-cyano-3-[[ethyl(methyl)sulfamoyl]amino]-6-fluoro-phenoxy]-4-oxo-quinazolin-3-yl]propyl]-4-methyl-piperidine-1-carboxylate (200 mg, 267.98 μmol, 56% yield) as an off-white solid. LCMS m/z (ESI): 557.2 $[M+H]^+$ Step 6: The requisite amine was synthesized by TFA mediated N-Boc deprotection (Procedure A-D). N-Boc deprotection was done on tert-butyl 4-[3-[6-[2-cyano-3-[[ethyl(methyl)sulfamoyl]amino]-6-fluoro-phenoxy]-4-oxo-quinazolin-3-yl]propyl]-4-methyl-piperidine-1-carboxylate (200 mg, 304.52 μmol) using TFA (694.45 mg, 6.09 mmol, 469.22 μL) to afford 6-[2-cyano-3-[[ethyl(methyl)sulfamoyl]amino]-6-fluoro-phenoxy]-3-[3-(4-methyl-4-piperidyl)propyl]-4-oxo-quinazoline as its TFA salt (200 mg, 271.37 μmol, 89% yield) as brownish yellow viscous liquid. LCMS m/z (ESI): 556.9$[M+H]^+$ Step 7: Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-3-[3-(4-methyl-4-piperidyl)propyl]-4-oxo-quinazoline (200 mg, 359.29 μmol), 2-[4-[4-[(2,6-dioxo-3-piperidyl)amino]-2-fluoro-phenyl]-1-piperidyl]acetic acid (130.56 mg, 359.29 μmol), HATU (163.94 mg, 431.15 μmol) and N,N-diisopropylethylamine (278.62 mg, 2.16 mmol, 375.49 μL). Crude compound was purified by reverse phase column chromatography eluted with 45% acetonitrile in 0.1% FORMIC ACID in water to afford 6-[2-cyano-3-[[ethyl(methyl)sulfamoyl]amino]-6-fluoro-phenoxy]-3-[3-[1-[2-[4-[4-[(2,6-dioxo-3-piperidyl)amino]-2-fluoro-phenyl]-1-piperidyl]acetyl]-4-methyl-4-piperidyl]propyl]-4-oxo-quinazoline (95 mg, 99.08 μmol, 28% yield) as an off-white solid. LCMS m/z (ESI): 902.3 $[M+H]^+$; $^1$HNMR (400 MHz, DMSO-$d_6$): δ=10.81 (s, 1H), 9.79 (s, 1H), 8.38 (s, 1H), 7.78 (dd, J=3.20, 8.80 Hz, 1H), 7.52-7.69 (m, 2H), 7.34-7.41 (m, 2H), 6.94-7.04 (m, 1H), 6.49 (d, J=7.60 Hz, 1H), 6.46 (d, J=12.40 Hz, 1H), 6.10 (d, J=7.60 Hz, 1H), 4.30-4.36 (m, 1H), 3.91-4.15 (m, 4H), 3.65-3.75 (m, 1H), 3.15-3.41 (m, 3H), 3.02-3.11 (m, 2H), 2.61-2.95 (m, 4H), 2.68 (s, 3H), 2.52-2.61 (m, 2H), 2.02-2.12 (m, 1H), 1.71-2.01 (m, 5H), 1.62-1.71 (m, 2H), 1.21-1.40 (m, 7H), 1.04 (t, J=7.20 Hz, 3H), 0.92 (s, 3H).

Example 13

6-[2-cyano-3-[[ethyl(methyl)sulfamoyl]amino]-6-fluorophenoxy]-3-[2-[1-[2-[4-[4-[(2,6-dioxopiperidin-3-yl)amino]-2-fluorophenyl]piperidin-1-yl]acetyl]-4-fluoropiperidin-4-yl]ethyl]-4-oxoquinazoline

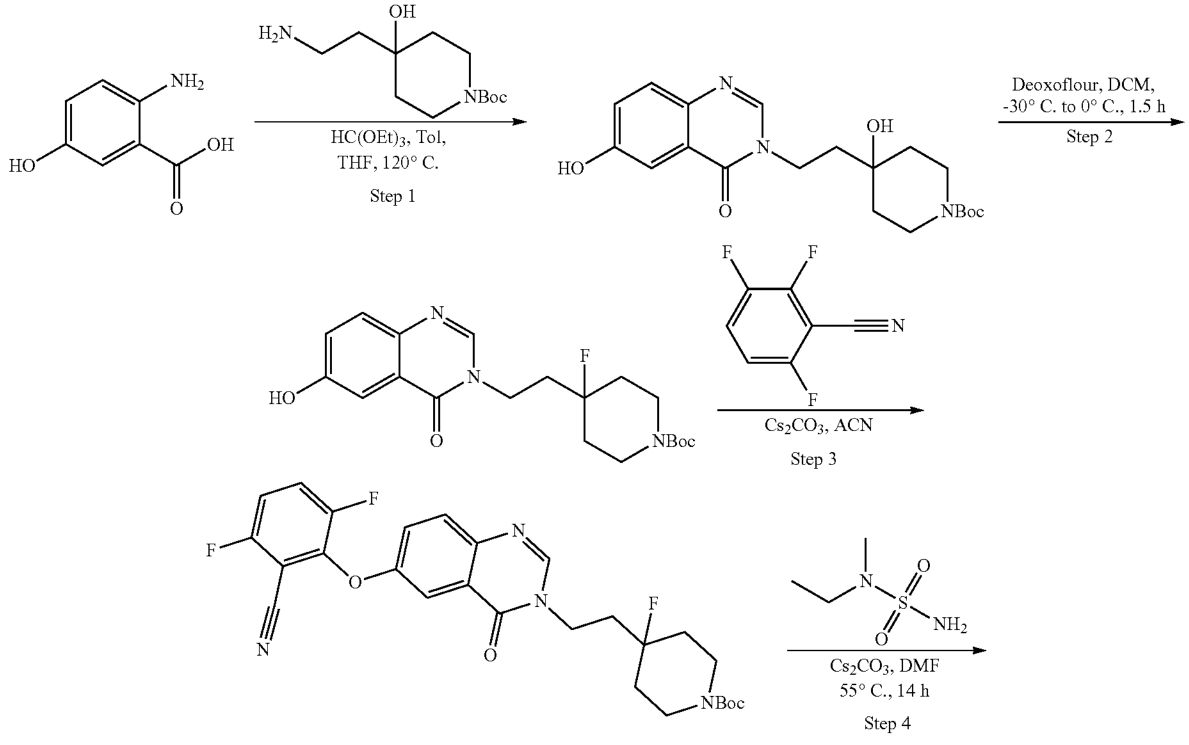

-continued

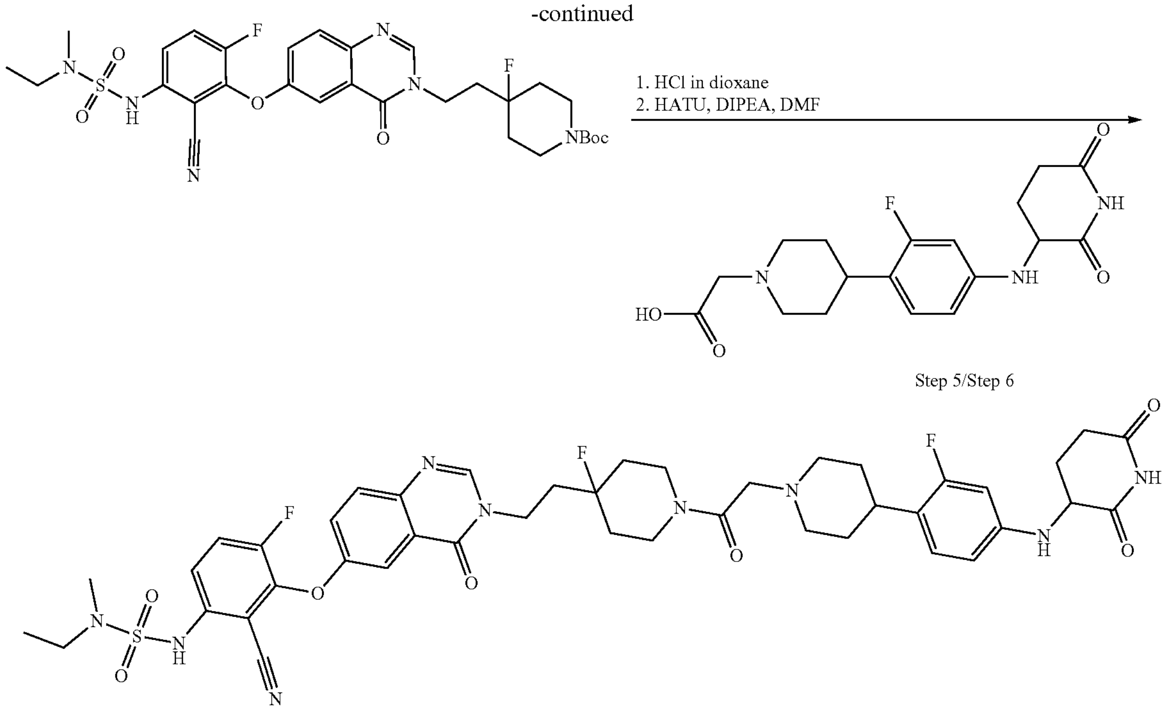

Step 1: The quinazolinone intermediate was synthesized by following general procedure for cyclization (Procedure A-A) using tert-butyl 4-(2-aminoethyl)-4-hydroxy-piperidine-1-carboxylate (1 g, 4.09 mmol), 2-amino-5-hydroxybenzoic acid (752.10 mg, 4.91 mmol) and Triethyl orthoformate (788.52 mg, 5.32 mmol, 884.98 μL). The crude product was triturated with diethyl ether to afford desired tert-butyl 4-hydroxy-4-[2-(6-hydroxy-4-oxo-quinazolin-3-yl)ethyl]piperidine-1-carboxylate (600 mg, 1.53 mmol, 37% yield) as an off-white solid. LCMS m/z (ESI): 388 $[M-H]^-$ Step 2: To a solution of tert-butyl 4-hydroxy-4-[2-(6-hydroxy-4-oxo-quinazolin-3-yl)ethyl]piperidine-1-carboxylate (600 mg, 1.54 mmol) in dichloromethane (5 mL) was added deoxofluor (510.73 mg, 2.31 mmol, 425.61 μL) at −30° C. The reaction mixture was stirred at 0° C. for 1 h. Upon completion, the reaction mixture was quenched with water and extracted with dichloromethane (2×25 mL). The combined organic layers were dried over sodium sulfate and evaporated to dryness to afford desired crude. The crude mixture was purified by using silica gel flash column chromatography eluting with 2% methanol/dichloromethane to afford tert-butyl 4-fluoro-4-[2-(6-hydroxy-4-oxo-quinazolin-3-yl)ethyl]piperidine-1-carboxylate (400 mg, 1.01 mmol, 66% yield) as an off-white solid. LCMS m/z (ESI): 390.2 $[M-H]^-$ Step 3: O-arylated quinazolinone intermediate was synthesized by following general procedure for O-arylation (Procedure A-B) using tert-butyl 4-fluoro-4-[2-(6-hydroxy-4-oxo-quinazolin-3-yl)ethyl]piperidine-1-carboxylate (400 mg, 1.02 mmol), cesium carbonate (998.84 mg, 3.07 mmol) and 2,3,6-trifluorobenzonitrile (192.64 mg, 1.23 mmol, 141.64 μL). The crude product was purified by silica gel flash column chromatography by eluting 1% methanol/dichloromethane to afford tert-butyl 4-[2-[6-(2-cyano-3,6-difluoro-phenoxy)-4-oxo-quinazolin-3-yl]ethyl]-4-fluoro-piperidine-1-carboxylate (430 mg, 724.10 μmol, 71% yield) as off-white solid. LCMS m/z (ESI): 473.1 $[M+H-{}^tBu]^+$ Step 4: Sulfamoylated quinazolinone intermediate was synthesized by following Procedure A-C using tert-butyl 4-[2-[6-(2-cyano-3,6-difluoro-phenoxy)-4-oxo-quinazolin-3-yl]ethyl]-4-fluoro-piperidine-1-carboxylate (400 mg, 756.83 μmol), cesium carbonate (739.77 mg, 2.27 mmol) and [methyl(sulfamoyl)amino]ethane (209.17 mg, 1.51 mmol) to afford tert-butyl 4-[2-[6-[2-cyano-3-[[ethyl(methyl)sulfamoyl]amino]-6-fluoro-phenoxy]-4-oxo-quinazolin-3-yl]ethyl]-4-fluoro-piperidine-1-carboxylate (160 mg, 239.99 μmol, 32% yield) as a viscous liquid. LCMS m/z (ESI): 645.2 $[M+H]^+$ Step 5: The requisite amine was synthesized by HCl mediated N-Boc deprotection (Procedure A-D). N-Boc deprotection was done on tert-butyl 4-[2-[6-[2-cyano-3-[[ethyl(methyl)sulfamoyl]amino]-6-fluoro-phenoxy]-4-oxo-quinazolin-3-yl]ethyl]-4-fluoro-piperidine-1-carboxylate (160 mg, 247.41 μmol) using 4.0 M hydrogen chloride in dioxane (5 mL) to afford 6-[2-cyano-3-[[ethyl(methyl)sulfamoyl]amino]-6-fluoro-phenoxy]-3-[2-(4-fluoro-4-piperidyl)ethyl]-4-oxo-quinazoline as its HCl salt (140 mg, 239.88 μmol, 97% yield) as an off-white solid. LCMS m/z (ESI): 545.1 $[M-H]^-$ Step 6: Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-3-[2-(4-fluoro-4-piperidyl)ethyl]-4-oxo-quinazoline (180 mg, 308.72 μmol), 2-[4-[4-[(2,6-dioxo-3-piperidyl)amino]-2-fluoro-phenyl]-1-piperidyl]acetic acid (123.44 mg, 308.72 μmol), N,N-diisopropylethylamine (159.60 mg, 1.23 mmol, 215.09 μL) and HATU (129.1 mg, 339.59 μmol). The crude compound was purified by reverse phase column chromatography eluting with 40% acetonitrile in 0.1% ammonium acetate in water to afford 6-[2-cyano-3-[[ethyl(methyl)sulfamoyl]amino]-6-fluoro-phenoxy]-3-[2-[1-[2-[4-[4-[(2,6-dioxo-3-piperidyl)amino]-2-fluoro-phenyl]-1-piperidyl]acetyl]-4-fluoro-4-piperidyl]ethyl]-4-oxo-quinazoline (20 mg, 22.27 μmol, 7% yield) as an off-white solid. LCMS m/z (ESI): 890.3 $[M-H]^-$; $^1HNMR$ (400 MHz, DMSO-$d_6$): δ 10.80 (s, 1H), 9.81 (s, 1H), 8.40 (s, 1H), 7.76 (d, J=9.20 Hz, 1H), 7.63 (dd, J=3.20, 9.00 Hz, 1H), 7.40-7.51 (m, 1H), 7.34 (d, J=2.80 Hz, 1H), 7.29-7.34 (m, 1H), 6.99 (t, J=8.00 Hz, 1H), 6.47 (d, J=6.80 Hz, 1H), 6.45 (d, J=12.00 Hz, 1H), 6.06 (d, J=8.00 Hz, 1H), 4.28-4.38 (m, 1H), 4.10-4.17 (m, 3H), 3.75-3.85 (m, 1H), 3.32-3.42 (m, 2H), 3.10-3.21 (m, 1H), 2.92-3.10 (m, 2H), 3.02 (q, J=6.80 Hz, 2H), 2.65-2.81 (m, 2H), 2.61 (s, 3H), 2.51-2.60 (m, 3H), 2.03-2.17 (m, 4H), 1.61-1.98 (m, 9H), 1.03 (t, J=7.20 Hz, 3H).
Example 14
6-[2-cyano-3-[[ethyl(methyl)sulfamoyl]amino]-6-fluorophenoxy]-3-[3-[1-[2-[4-[4-[(2,6-dioxopiperidin-3-yl)amino]-2-fluorophenyl]piperidin-1-yl]acetyl]piperidin-4-yl]-2-methylpropyl]-4-oxoquinazoline
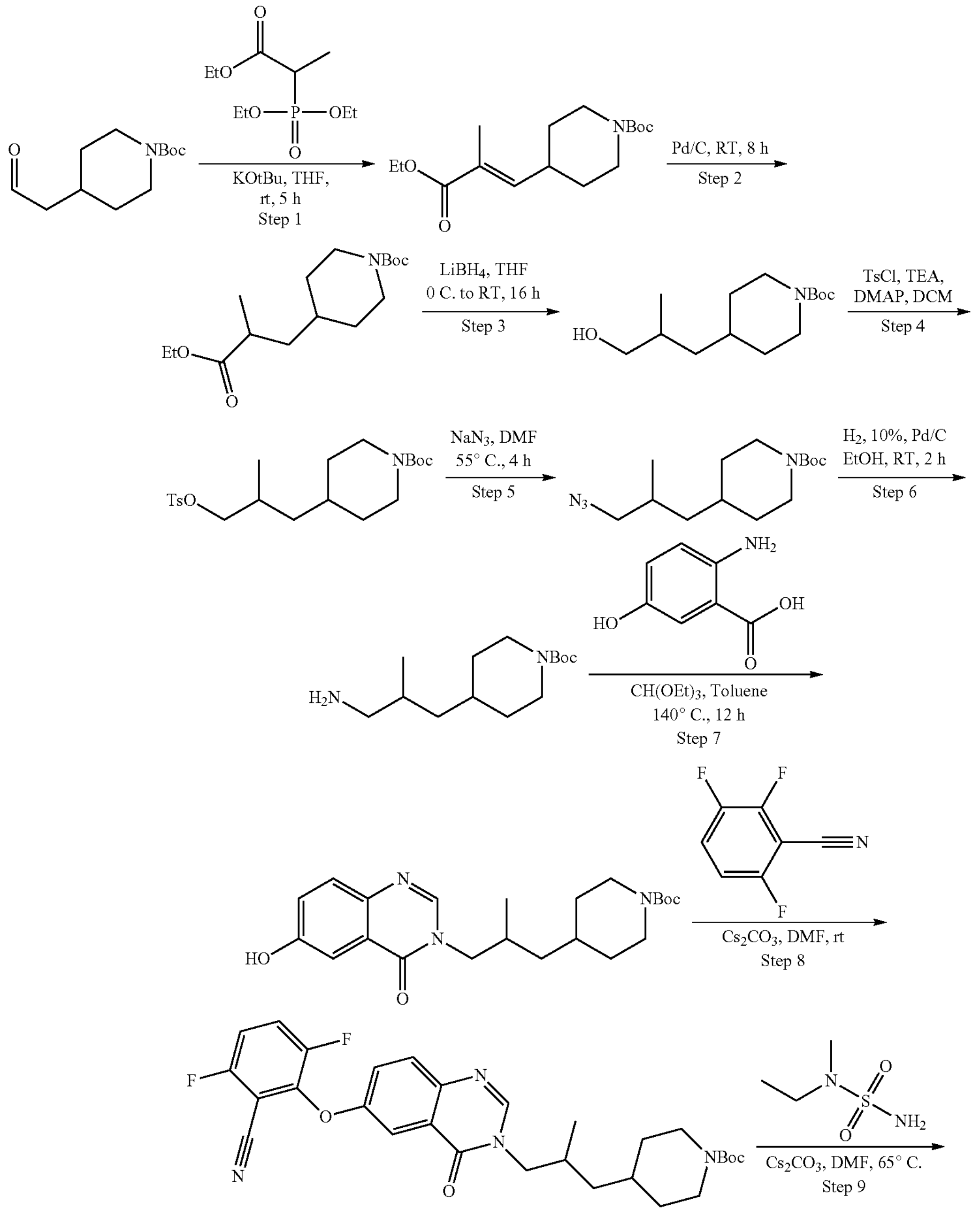

-continued

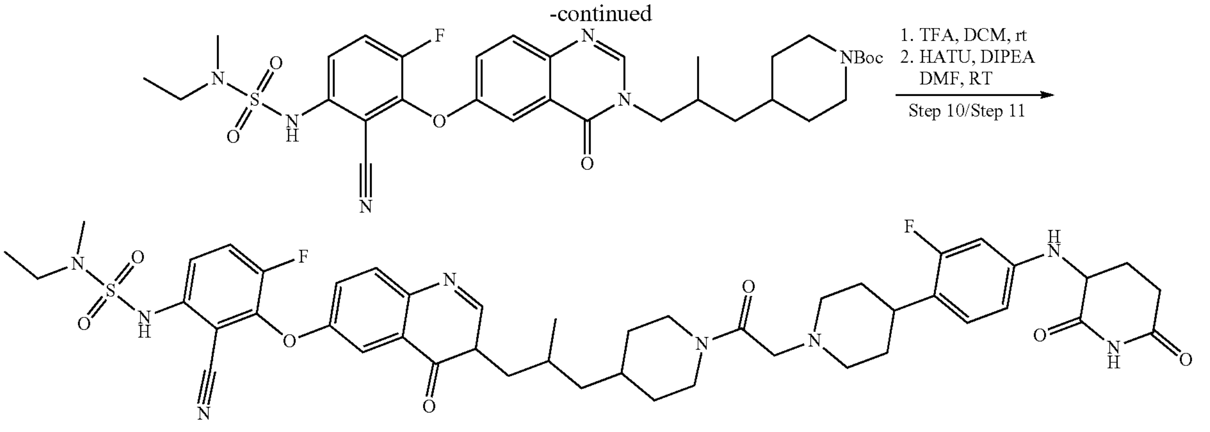

Step 1: To a stirred solution of tert-butyl 4-formylpiperidine-1-carboxylate (3.58 g, 16.79 mmol) in THF (40 mL) was added ethyl 2-diethoxyphosphorylpropanoate (5 g, 20.9 mmol) at 0° C. under a nitrogen atmosphere, stirring at the same temperature for 1 h. KO$^t$Bu (2.36 g, 20.99 mmol) in THF (10 mL) was added to the reaction and stirring was continued for 4 h at room temperature. After completion, the reaction mixture was quenched with saturated ammonium chloride solution (200 mL) and extracted with ethyl acetate (3×150 mL). The combined organic layers were dried over sodium sulfate and concentrated under reduced pressure. The crude material was purified by column chromatography using 30% ethyl acetate-petroleum ether as eluent to afford tert-butyl 4-[(E)-3-ethoxy-2-methyl-3-oxo-prop-1-enyl]piperidine-1-carboxylate (3.5 g, 11.65 mmol, 56% yield) as a colorless liquid. LCMS m/z (ESI): 198.1 $[M+H-CO_2{}^tBu]^+$ Step 2: To a stirred solution of tert-butyl 4-[(E)-3-ethoxy-2-methyl-3-oxo-prop-1-enyl]piperidine-1-carboxylate (3.5 g, 11.77 mmol) in methanol (50 mL) was added 10% Palladium on activated carbon (1.88 g, 17.65 mmol) portion wise and stirring was continued under $H_2$ (1 atm) at room temperature for 16 h. After completion of the reaction, the mixture was filtered through a celite bed and the celite was washed with methanol (100 mL). The filtrate was concentrated under reduced pressure to afford tert-butyl 4-(3-ethoxy-2-methyl-3-oxo-propyl)piperidine-1-carboxylate (3.3 g, 11.01 mmol, 94% yield) as a colorless liquid which was used for next step without any further purification. LCMS m/z (ESI): 200.0 $[M+H]^+$ Step 3: To a stirred solution of tert-butyl 4-(3-ethoxy-2-methyl-3-oxo-propyl)piperidine-1-carboxylate (3.3 g, 11.02 mmol) in THF (30 mL) was added slowly lithium borohydride (360.15 mg, 16.53 mmol) dropwise at 0° C. The reaction mixture was stirred at room temperature for 16 h. After completion, the reaction mixture was quenched with $NH_4Cl$ solution and extracted with ethyl acetate (3×25 mL). The combined organic layers were dried over sodium sulfate and concentrate under reduced pressure to afford tert-butyl 4-(3-hydroxy-2-methyl-propyl)piperidine-1-carboxylate (2.9 g, 10.68 mmol, 97% yield) as a colorless liquid which was taken for next step without any further purification. LCMS m/z (ESI): 158.1 $[M+H-CO_2{}^tBu]^+$ Step 4 To a stirred solution of tert-butyl 4-(3-hydroxy-2-methyl-propyl)piperidine-1-carboxylate (3.1 g, 12.05 mmol) in dichloromethane (30 mL) was added 4-methylbenzenesulfonyl chloride (3.44 g, 18.07 mmol), Triethylamine (3.05 g, 30.11 mmol, 4.20 mL) and N,N-dimethylpyridin-4-amine (735 mg, 6.02 mmol). Stirring was continued at room temperature for 5 h. After completion, reaction mixture was quenched with water (200 mL) and extracted with ethyl acetate (2×150 mL). The combined organic layers were dried over sodium sulfate and concentrated under reduced pressure to afford tert-butyl 4-[2-methyl-3-(p-tolylsulfonyloxy)propyl]piperidine-1-carboxylate (3.5 g, 5.83 mmol, 48% yield, 68.51% pure) as a colorless viscous liquid. LCMS m/z (ESI): 312.0 $[M+H-CO_2{}^tBu]^+$ Step 5: To a stirred solution of tert-butyl 4-[2-methyl-3-(p-tolylsulfonyloxy)propyl]piperidine-1-carboxylate (3.2 g, 7.78 mmol) in N,N-Dimethylformamide (40 mL) was added sodium azide (1.26 g, 19.44 mmol) at room temperature. The resulting reaction mixture was continued stirring at 55° C. for 5 h. After completion, the reaction mixture was quenched with water (500 mL) and extracted with ethyl acetate (3×150 mL). The combined organic layers were dried over sodium sulfate and concentrated under reduced pressure to afford tert-butyl 4-(3-azido-2-methyl-propyl)piperidine-1-carboxylate (2.5 g, 7.57 mmol, 97% yield) as a pale yellow solid. LCMS m/z (ESI): 255.1 $[M+H-N_2]^+$ Step 6: To a stirred solution of tert-butyl 4-(3-azido-2-methyl-propyl)piperidine-1-carboxylate (1.8 g, 6.37 mmol) in ethanol (40 mL) was added 10% Palladium on carbon (1.02 g, 9.56 mmol) and the reaction was stirred under $H_2$ (1 atm) at room temperature for 3 h. The reaction mixture was then filtered through celite pad and the celite was washed with methanol. The filtrate was concentrated under reduced pressure to afford tert-butyl 4-(3-amino-2-methyl-propyl)piperidine-1-carboxylate (1.5 g, 2.16 mmol, 34% yield) as a colorless liquid. LCMS m/z (ESI): 257.1 $[M+H]^+$ Step 7: The quinazolinone intermediate was synthesized by following general procedure for cyclization (Procedure A-A) using tert-butyl 4-(3-amino-2-methyl-propyl)piperidine-1-carboxylate (1.5 g, 5.85 mmol), 2-amino-5-hydroxybenzoic acid (895.93 mg, 5.85 mmol), Triethyl orthoformate (2.17 g, 14.63 mmol, 2.43 mL) and acetic acid (35.13 mg, 585.06 μmol, 33.46 μL). crude material was purified by silica gel flash column chromatography using 0-80% ethyl acetate in petroleum ether to afford tert-butyl 4-[3-(6-hydroxy-4-oxo-quinazolin-3-yl)-2-methyl-propyl]piperidine-1-carboxylate (400 mg, 895.85 μmol, 15% yield) as an off-white solid. LCMS m/z (ESI): 402.2 $[M+H]^+$ Step 8: O-arylated quinazolinone intermediate was synthesized by following the general procedure for O-arylation (Procedure A-B) using tert-butyl 4-[3-(6-hydroxy-4-oxo-quinazolin-3-yl)-2-methyl-propyl]piperidine-1-carboxylate (400 mg, 996.27 μmol), cesium carbonate (649.21 mg, 1.99 mmol) and 2,3,6-trifluorobenzonitrile (187.81 mg, 1.20 mmol, 138.09 μL). The crude material was purified by silica gel flash column chromatography using 0-80% ethyl acetate in petroleum ether to afford tert-butyl 4-[3-(6-hydroxy-4-oxo-quinazolin-3-yl)-2-methyl-propyl]piperidine-1-carboxylate (560 mg, 1.35 mmol, 31% yield) as an off-white solid. LCMS m/z (ESI): 439.1 $[M+H]^+$ Step 9: Sulfamoylated quinazolinone intermediate was synthesized by following Procedure A-C using tert-butyl 4-[3-[6-(2-cyano-3,6-difluoro-phenoxy)-4-oxo-quinazolin-3-yl]-2-methyl-propyl]piperidine-1-carboxylate (370 mg, 686.99 μmol), cesium carbonate (671.50 mg, 2.06 mmol) and [methyl(sulfamoyl)amino]ethane (189.87 mg, 1.37 mmol). Crude compound was purified by silica gel flash column chromatography using 0-80% ethyl acetate in petroleum ether to afford tert-butyl 4-[3-[6-[2-cyano-3-[[ethyl (methyl)sulfamoyl]amino]-6-fluoro-phenoxy]-4-oxo-quinazolin-3-yl]-2-methyl-propyl]piperidine-1-carboxylate (230 mg, 299.14 μmol, 44% yield) as an off-white solid. LCMS m/z (ESI): 557.0 $[M+H-CO_2{}^tBu]^+$ Step 10: The requisite amine was synthesized by HCl mediated N-Boc deprotection (Procedure A-D). N-Boc deprotection was done on tert-butyl 4-[3-[6-[2-cyano-3-[[ethyl(methyl)sulfamoyl]amino]-6-fluoro-phenoxy]-4-oxo-quinazolin-3-yl]-2-methyl-propyl]piperidine-1-carboxylate (230 mg, 350.20 μmol) using 4M hydrogen chloride solution in dioxane (4 M, 2 mL). The crude compound was triturated with diethyl ether to afford (6-[2-cyano-3-[[ethyl(methyl) sulfamoyl]amino]-6-fluoro-phenoxy]-3-[2-methyl-3-(4-piperidyl)propyl]-4-oxo-quinazoline (210 mg, 334.8 μmol, 96% yield) as an off-white solid. LCMS m/z (ESI): 557.2 $[M+H]^+$ Step 11: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (121.35 mg, 303.48 μmol), N,N-diisopropylethylamine (196.11 mg, 1.52 mmol, 264.30 μL) and HATU (174.01 mg, 455.23 μmol) and 6-[2-cyano-3-[[ethyl(methyl)sulfamoyl] amino]-6-fluoro-phenoxy]-3-[2-methyl-3-(4-piperidyl)propyl]-4-oxo-quinazoline (180 mg, 303.5 μmol). Crude compound was purified by reverse phase column chromatography [Mobile-phase A: 0.1% ammonium acetate in water, Mobile-phase B: acetonitrile; column: 100 g RediSep® Rf C18] to afford the 6-[2-cyano-3-[[ethyl (methyl)sulfamoyl]amino]-6-fluoro-phenoxy]-3-[3-[1-[2-[4-[4-[(2,6-dioxo-3-piperidyl)amino]-2-fluoro-phenyl]-1-piperidyl]acetyl]-4-piperidyl]-2-methyl-propyl]-4-oxo-quinazoline (155 mg, 168.13 μmol, 55% yield) as an off-white solid. LCMS m/z (ESI): 902.3 $[M+H]^+$; $^1$HNMR (400 MHz, DMSO-$d_6$): δ=10.81 (s, 1H), 9.67 (s, 1H), 8.33 (s, 1H), 7.77 (d, J=8.80 Hz, 1H), 7.64 (dd, J=2.80, 9.00 Hz, 1H), 7.60-7.42 (m, 1H), 7.33 (s, 1H), 7.30-7.34 (m, 1H), 6.91-7.00 (m, 1H), 6.49 (d, J=7.60 Hz, 1H), 6.46 (d, J=12.40 Hz, 1H), 6.08 (d, J=7.60 Hz, 1H), 4.29-4.40 (m, 2H), 3.61-4.05 (m, 5H), 3.21-3.35 (m, 2H), 3.03 (q, J=7.20 Hz, 2H), 2.92-3.11 (m, 2H), 2.61-2.82 (m, 5H), 2.67 (s, 3H), 2.02-2.16 (m, 2H), 1.55-1.95 (m, 8H), 1.09-1.20 (m, 2H), 1.03 (t, J=7.20 Hz, 3H), 0.81-1.01 (m, 2H), 0.85 (t, J=6.00 Hz, 3H).

Example 15

6-[2-cyano-3-[[ethyl(methyl)sulfamoyl]amino]-6-fluorophenoxy]-3-[3-[1-[2-[4-[4-[(2,6-dioxopiperidin-3-yl)amino]-2-fluorophenyl]piperidin-1-yl] acetyl]-4-fluoropiperidin-4-yl]propyl]-4-oxoquinazoline

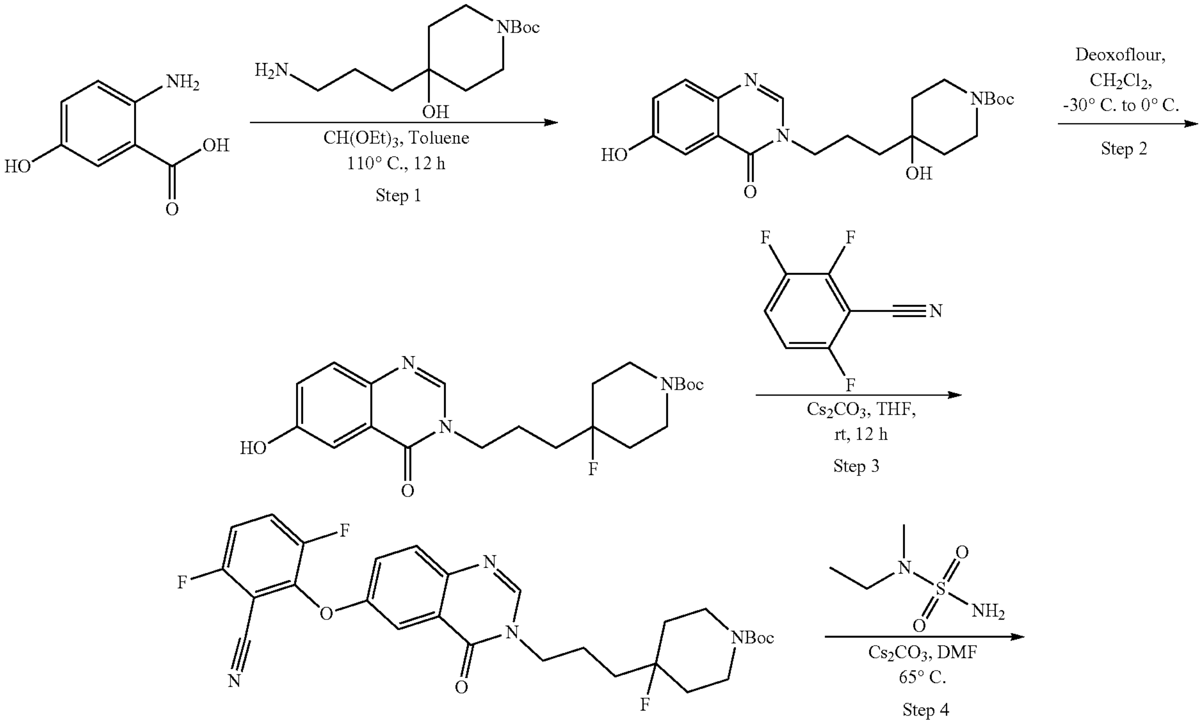

-continued

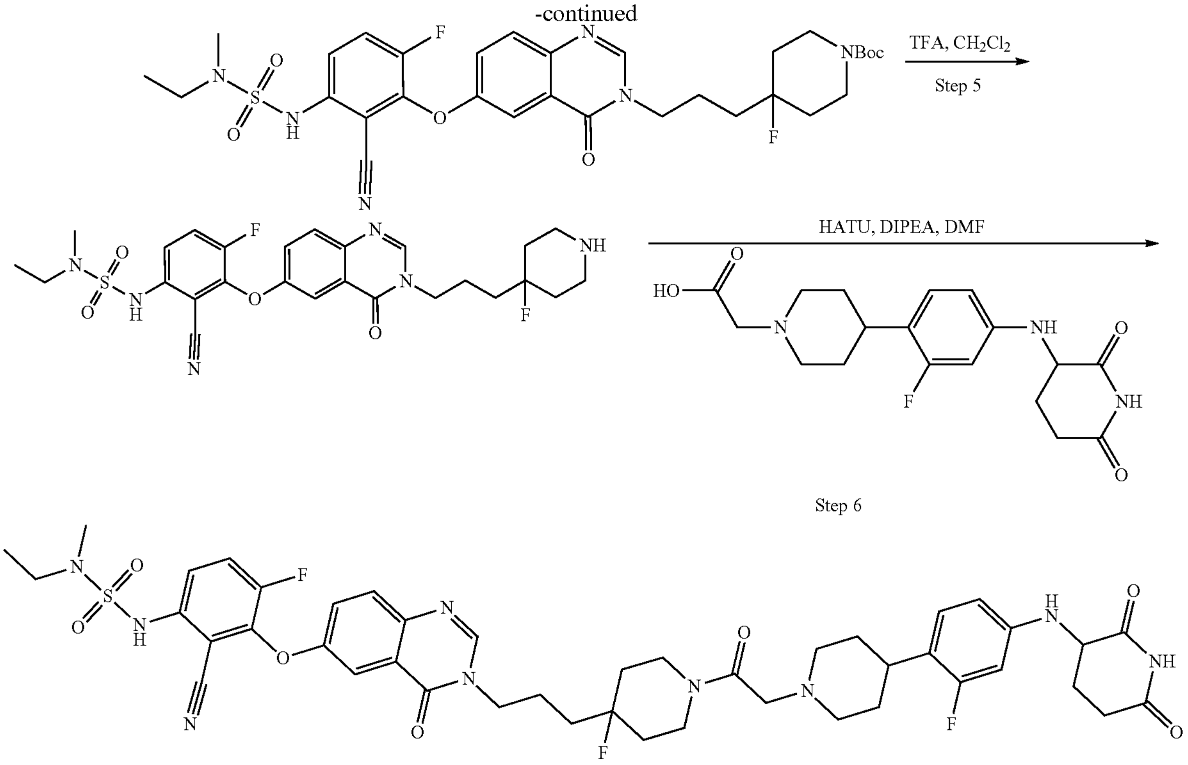

Step 1: The quinazolinone intermediate was synthesized by following general procedure for cyclization (Procedure A-A) using 2-amino-5-hydroxy-benzoic acid (1.30 g, 8.52 mmol), tert-butyl 4-(3-aminopropyl)-4-hydroxy-piperidine-1-carboxylate (2 g, 7.74 mmol) and Triethyl Orthoformate (1.72 g, 11.61 mmol, 1.93 mL) to afford tert-butyl 4-hydroxy-4-[3-(6-hydroxy-4-oxo-quinazolin-3-yl)propyl]piperidine-1-carboxylate (770 mg, 1.76 mmol, 23% yield) as a pale yellow solid. LCMS m/z (ESI): 404.2 $[M+H]^+$ Step 2: To a stirred solution of tert-butyl 4-hydroxy-4-[3-(6-hydroxy-4-oxo-quinazolin-3-yl)propyl]piperidine-1-carboxylate (770 mg, 1.91 mmol) in dichloromethane (15 mL) was added Deoxo-Fluor (633 mg, 2.86 mmol) at −30° C. Stirring of the reaction was continued for 2 h at 0° C. After completion, the reaction mixture was diluted with water (20 mL) and extracted in dichloromethane (2×15 mL). The combined organic layers were dried over anhydrous sodium sulfate and concentrated under reduced pressure to yield crude product. The crude compound was purified by silica gel flash column chromatography eluting with 0-100% ethyl acetate/petroleum ether as eluent system to yield tert-butyl 4-fluoro-4-[3-(6-hydroxy-4-oxo-quinazolin-3-yl)propyl]piperidine-1-carboxylate (440 mg, 965.81 μmol, 51% yield) as a yellow solid. $^1$HNMR (400 MHz, DMSO-$d_6$): δ=10.11 (s, 1H), 8.21 (s, 1H), 7.54 (d, J=11.60 Hz, 1H), 7.44 (s, 1H), 7.27 (dd, J=2.00, 11.80 Hz, 1H), 3.90-3.95 (m, 2H), 3.70-3.77 (m, 2H), 2.80-3.10 (m, 2H), 1.91-2.10 (m, 2H), 1.30-1.85 (m, 6H), 1.39 (s, 9H).

Step 3: O-arylated quinazolinone intermediate was synthesized by following the general procedure for O-arylation (Procedure A-B) using tert-butyl 4-fluoro-4-[3-(6-hydroxy-4-oxo-quinazolin-3-yl)propyl]piperidine-1-carboxylate (500 mg, 1.23 mmol) and 2,3,6-trifluorobenzonitrile (232.47 mg, 1.48 mmol, 170.93 μL) and cesium carbonate (803.57 mg, 2.47 mmol). The crude material was purified by silica gel flash column chromatography eluting with 0-100% ethyl acetate/petroleum ether as eluent system to yield tert-butyl 4-[3-[6-(2-cyano-3,6-difluoro-phenoxy)-4-oxo-quinazolin-3-yl]propyl]-4-fluoro-piperidine-1-carboxylate (600 mg, 1.02 mmol, 83% yield) as a light yellow solid. $^1$HNMR (400 MHz, DMSO-$d_6$): δ=8.39 (s, 1H), 7.96-8.01 (m, 1H), 7.72-7.80 (m, 2H), 7.56-7.62 (m, 2H), 3.97-4.06 (m, 2H), 3.65-3.80 (m, 2H), 2.91-2.98 (m, 2H), 1.91-2.10 (m, 2H), 1.30-1.85 (m, 6H), 1.35 (s, 9H).

Step 4: Sulfamoylated quinazolinone intermediate was synthesized by following Procedure A-C using tert-butyl 4-[3-[6-(2-cyano-3,6-difluoro-phenoxy)-4-oxo-quinazolin-3-yl]propyl]-4-fluoro-piperidine-1-carboxylate (600 mg, 1.11 mmol), [methyl(sulfamoyl)amino]ethane (152.82 mg, 1.11 mmol) and cesium carbonate (720.64 mg, 2.21 mmol). The crude compound was purified by prep HPLC to yield tert-butyl 4-[3-[6-[2-cyano-3-[[ethyl(methyl)sulfamoyl]amino]-6-fluoro-phenoxy]-4-oxo-quinazolin-3-yl]propyl]-4-fluoro-piperidine-1-carboxylate (200 mg, 206.52 μmol, 19% yield) as a white solid. LCMS m/z (ESI): 561 $[M+H-CO_2{}^tBu]^+$ Step 5: The requisite amine was synthesized by TFA mediated N-Boc deprotection (Procedure A-D). N-Boc deprotection was done on tert-butyl 4-[3-[6-[2-cyano-3-[[ethyl(methyl)sulfamoyl]amino]-6-fluoro-phenoxy]-4-oxo-quinazolin-3-yl]propyl]-4-fluoro-piperidine-1-carboxylate (200 mg, 302.70 μmol) using Trifluoroacetic acid (34.51 mg, 302.70 μmol, 23.32 μL) to yield the TFA salt of 6-[2-cyano-3-[[ethyl(methyl)sulfamoyl]amino]-6-fluoro-phenoxy]-3-[3-(4-fluoro-4-piperidyl)propyl]-4-oxo-quinazoline (200 mg, 278.67 μmol, 92% yield) as a white solid. LCMS m/z (ESI): 561.0 $[M+H]^+$ Step 6: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (129.64 mg, 356.75 μmol), N,N-diisopropylethylamine (138.32 mg, 1.07 mmol, 186.41 μL), HATU (203.47 mg, 535.13 μmol) and 6-[2-cyano-3-[[ethyl(methyl)sulfamoyl]amino]-6-fluoro-phenoxy]-3-[3-(4-fluoro-4-piperidyl)propyl]-4-oxo-quinazoline (200 mg, 356.75 μmol). The crude compound was purified by reverse phase HPLC by [Mobile-phase A: 0.1% formic acid in water, Mobile-phase B: acetonitrile; column: 100 g RediSep® Rf C18] to yield 6-[2-cyano-3-[[ethyl(methyl)sulfamoyl]amino]-6-fluoro-phenoxy]-3-5 [3-[1-[2-[4-[4-[(2,6-dioxo-3-piperidyl)amino]-2-fluoro-phenyl]-1-piperidyl]acetyl]-4-fluoro-4-piperidyl]propyl]-4-oxo-quinazoline (70 mg, 72.23 μmol, 20% yield) as an off-white solid. LCMS m/z (ESI): 904.2 $[M-H]^-$; $^1$HNMR (400 MHz, DMSO-$d_6$): δ=10.81 (s, 1H), 10.16 (bs, 1H), 9.51 (bs, 1H), 8.40 (s, 1H), 7.86 (t, J=9.20 Hz, 1H), 7.80 (d, J=8.80 Hz, 1H), 7.70 (dd, J=2.80, 9.00 Hz, 1H), 7.50 (dd, J=4.00, 9.20 Hz, 1H), 7.37 (d, J=3.20 Hz, 1H), 6.92-6.98 (m, 1H), 6.50 (d, J=7.60 Hz, 1H), 6.47 (d, J=12.40 Hz, 1H), 6.12 (d, J=8.00 Hz, 1H), 4.18-4.40 (m, 4H), 3.91-4.05 (m, 2H), 3.45-3.60 (m, 2H), 3.15-3.30 (m, 1H), 3.17 (q, J=7.20 Hz, 2H), 3.00-3.15 (m, 2H), 2.85-2.96 (m, 2H), 2.80 (s, 3H), 2.65-2.79 (m, 1H), 2.51-2.62 (m, 2H), 1.95-2.12 (m, 4H), 1.41-1.94 (m, 10H), 1.06 (t, J=7.20 Hz, 3H).

Example 16-20

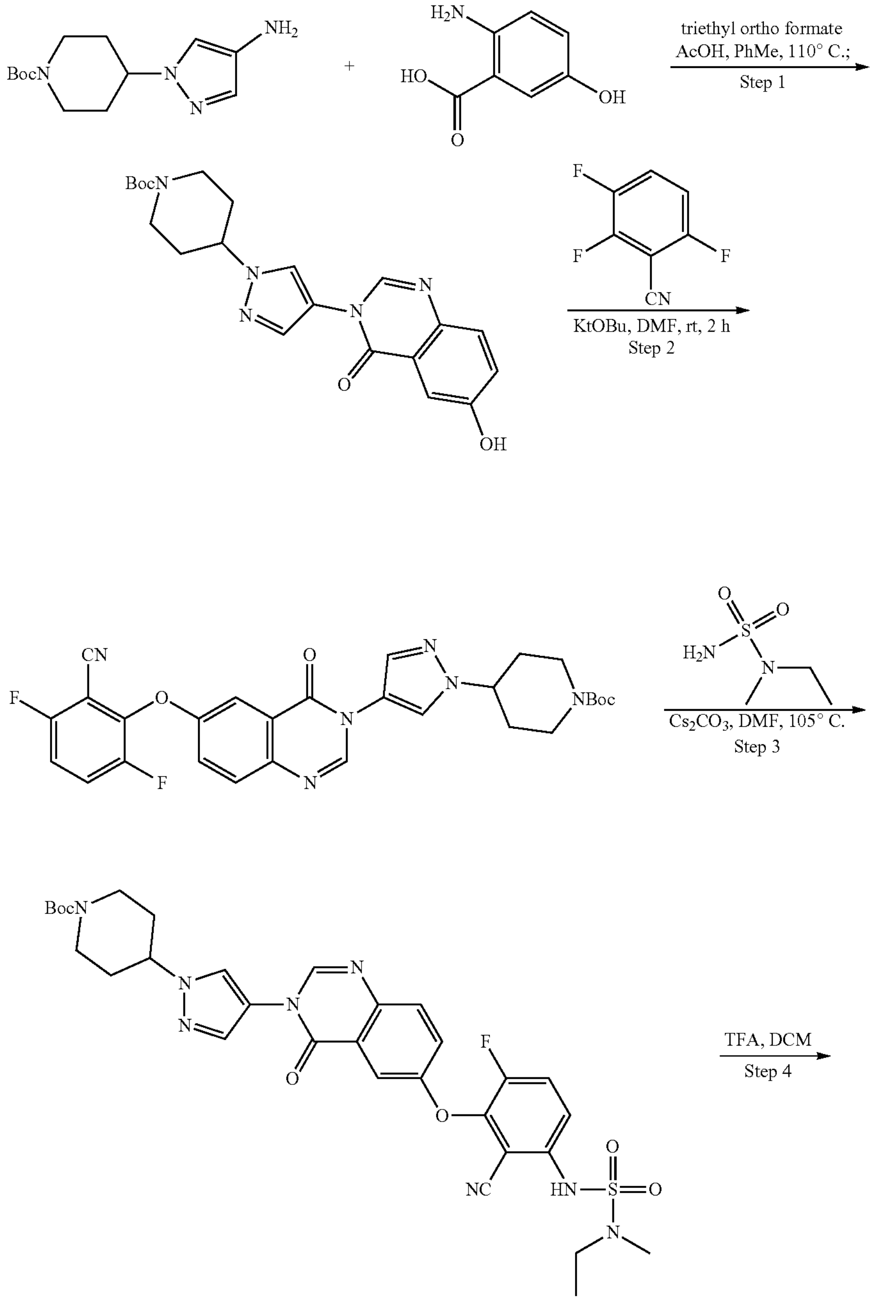

-continued

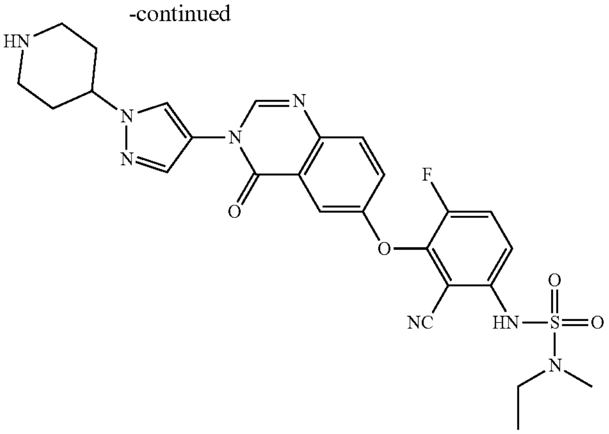

Step 1: The quinazolinone intermediate was synthesized by following general procedure for cyclization (Procedure A-A) using 2-amino-5-hydroxy-benzoic acid (1.5 g, 9.80 mmol), Triethyl orthoformate (2.18 g, 14.69 mmol, 2.44 mL) and tert-butyl 4-(4-aminopyrazol-1-yl)piperidine-1-carboxylate (2.61 g, 9.80 mmol). The desired compound was purified by silica gel flash column chromatography using 3% methanol in dichloromethane as eluent to afford tert-butyl 4-[4-(6-hydroxy-4-oxo-quinazolin-3-yl)pyrazol-1-yl]piperidine-1-carboxylate (1.2 g, 2.53 mmol, 26% yield) as a brown solid. LCMS m/z (ESI): 409.90[M+H]$^+$ Step 2: The O-arylated quinazolinone intermediate was synthesized by following Procedure A-B using tert-butyl 4-[4-(6-hydroxy-4-oxo-quinazolin-3-yl)pyrazol-1-yl]piperidine-1-carboxylate (700 mg, 1.70 mmol), potassium tert-butoxide (210.00 mg, 1.87 mmol) and 2,3,6-trifluorobenzonitrile (293.99 mg, 1.87 mmol, 216.17 μL) to obtain tert-butyl 4-[4-[6-(2-cyano-3,6-difluoro-phenoxy)-4-oxo-quinazolin-3-yl]pyrazol-1-yl]piperidine-1-carboxylate (0.8 g, crude) as an brown solid. LCMS m/z (ESI): 547.20[M+H]$^+$ Step 3: Sulfamoylated quinazolinone intermediate was synthesized by following Procedure A-C using tert-butyl 4-[4-[6-(2-cyano-3,6-difluoro-phenoxy)-4-oxo-quinazolin-3-yl]pyrazol-1-yl]piperidine-1-carboxylate (300 mg, 546.91 μmol), cesium carbonate (445.48 mg, 1.37 mmol) and [methyl(sulfamoyl)amino]ethane (151.15 mg, 1.09 mmol). Crude product purified by silica gel flash column chromatography using 5% methanol in dichloromethane as eluent to afford tert-butyl 4-[4-[6-[2-cyano-3-[[ethyl(methyl)sulfamoyl]amino]-6-fluoro-phenoxy]-4-oxo-quinazolin-3-yl]pyrazol-1-yl]piperidine-1-carboxylate (120 mg, 173.70 μmol, 32% yield) as a pale brown solid. LCMS m/z (ESI): 665.10[M−H]$^+$ Step 4: The requisite amine was synthesized following Procedure A-D using tert-butyl 4-[4-[6-[2-cyano-3-[[ethyl(methyl)sulfamoyl]amino]-6-fluoro-phenoxy]-4-oxo-quinazolin-3-yl]pyrazol-1-yl]piperidine-1-carboxylate (120 mg, 179.99 μmol) and TFA (20.52 mg, 179.99 μmol, 13.87 μL). The resulted crude compound was triturated with methyl t-butyl ether to afford the TFA salt of 6-[2-cyano-3-[[ethyl(methyl)sulfamoyl]amino]-6-fluoro-phenoxy]-4-oxo-3-[1-(4-piperidyl)pyrazol-4-yl]quinazoline (150 mg, crude) as a pale brown semi-solid. LCMS m/z (ESI): [M−H]$^+$ 565.20

Example 16

6-[2-cyano-3-[[ethyl(methyl)sulfamoyl]amino]-6-fluorophenoxy]-3-[1-[1-[2-[4-[4-[(2,6-dioxopiperidin-3-yl)amino]-2-fluorophenyl]piperidin-1-yl]acetyl]piperidin-4-yl]pyrazol-4-yl]-4-oxoquinazoline

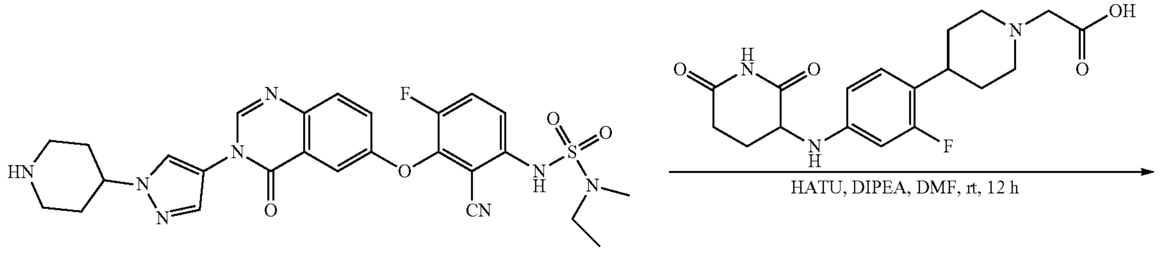

-continued

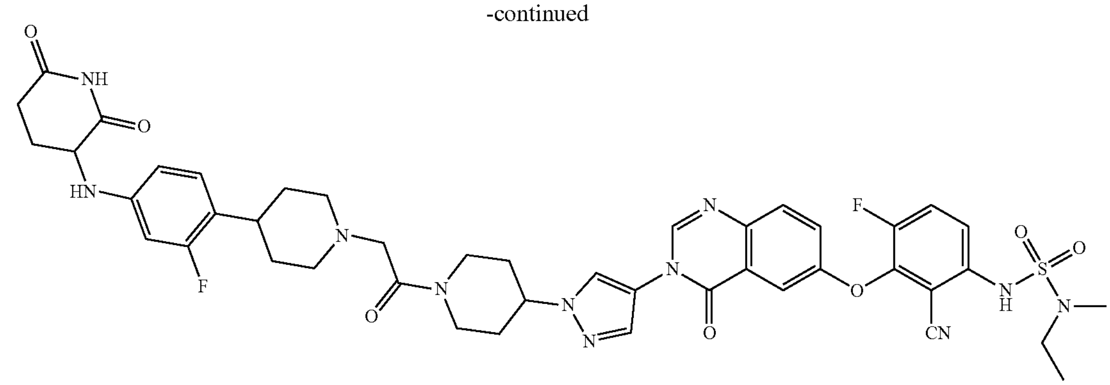

The target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-[1-(4-piperidyl)pyrazol-4-yl]quinazoline (20 mg, 35.30 μmol), 2-[4-[4-[(2,6-dioxo-3-piperidyl)amino]-2-fluoro-phenyl]-1-piperidyl]acetic acid (12.83 mg, 35.30 μmol), N,N-diisopropylethylamine (22.81 mg, 176.49 μmol, 30.74 μL) and HATU (16.11 mg, 42.36 μmol) to afford the crude product. The crude material was purified by Prep HPLC purification method: 10 mm Ammonium acetate:acetonitrile and pure fractions were lyophilized to afford product 6-[2-cyano-3-[[ethyl(methyl)sulfamoyl]amino]-6-fluoro-phenoxy]-3-[1-[1-[2-[4-[4-[(2,6-dioxo-3-piperidyl)amino]-2-fluoro-phenyl]-1-piperidyl]acetyl]-4-piperidyl]pyrazol-4-yl]-4-oxo-quinazoline (10.11 mg, 10.80 μmol, 31% yield) as an off-white solid. LCMS m/z (ESI): 912.20[M+H]$^+$; $^1$HNMR (400 MHz, DMSO-$d_6$): δ=10.80 (s, 1H), 9.90 (bs, 1H), 8.45 (s, 1H), 8.33 (s, 1H), 7.90 (s, 1H), 7.82 (d, J=8.80 Hz, 1H), 7.68 (d, J=2.40 Hz, 1H), 7.60-7.50 (m, 1H), 7.42 (s, 1H), 7.38-7.30 (m, 1H), 7.05-6.95 (m, 1H), 6.52-6.40 (m, 2H), 6.07-6.05 (m, 1H), 4.62-4.42 (m, 2H), 4.35-4.25 (m, 1H), 4.05-3.95 (m, 1H), 3.27-3.15 (m, 3H), 3.04 (q, J=7.20 Hz, 2H), 2.92-2.80 (m, 2H), 2.64 (s, 3H), 2.60-2.51 (m, 5H), 2.20-2.00 (m, 4H), 1.95-1.72 (m, 6H), 1.03 (t, J=7.20 Hz, 3H).

Example 17

6-[2-cyano-3-[[ethyl(methyl)sulfamoyl]amino]-6-fluorophenoxy]-3-[1-[1-[2-[4-[4-(2,6-dioxopiperidin-3-yl)-2-fluorophenyl]piperidin-1-yl]acetyl]piperidin-4-yl]pyrazol-4-yl]-4-oxoquinazoline

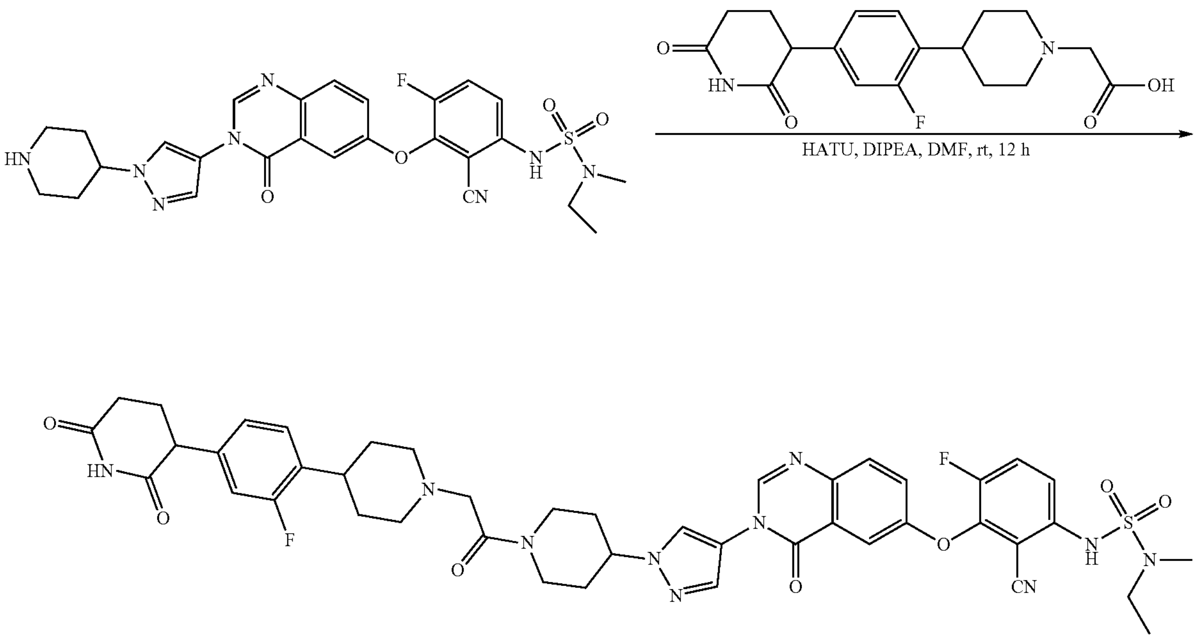

The target compound was prepared via HATU mediated acid-amine coupling reaction (Procedure A-E). The amide coupling was carried out using 6-[2-cyano-3-[[ethyl(methyl)sulfamoyl]amino]-6-fluoro-phenoxy]-4-oxo-3-[1-(4-piperidyl)pyrazol-4-yl]quinazoline (20 mg, 35.30 μmol), 2-[4-[4-(2,6-dioxo-3-piperidyl)-2-fluoro-phenyl]-1-piperidyl] acetic acid (12.30 mg, 35.30 μmol), N,N-diisopropylethylamine (22.81 mg, 176.49 μmol, 30.74 μL) and HATU (16.11 mg, 42.36 μmol) to afford crude product. The crude material was purified by Prep HPLC purification method: 10 mm Ammonium acetate:acetonitrile and pure fractions were lyophilized to afford product 6-[2-cyano-3-[[ethyl(methyl)sulfamoyl]amino]-6-fluoro-phenoxy]-3-[1-[1-[2-[4-[4-(2,6-dioxo-3-piperidyl)-2-fluoro-phenyl]-1-piperidyl]acetyl]-4-piperidyl]pyrazol-4-yl]-4-oxo-quinazoline (9.34 mg, 9.87 μmol, 28% yield) as an off-white solid. LCMS m/z (ESI): 895.60[M−H]$^-$; $^1$HNMR (400 MHz, DMSO-$d_6$): δ=10.86 (s, 1H), 9.90 (bs, 1H), 8.45 (s, 1H), 8.33 (s, 1H), 7.90 (s, 1H), 7.81 (d, J=8.80 Hz, 1H), 7.67 (d, J=2.40 Hz, 1H), 7.53 (t, J=9.60 Hz, 1H), 7.43 (d, J=2.40 Hz, 1H), 7.35-7.27 (m, 2H), 7.05-7.04 (m, 2H), 4.60-4.52 (m, 1H), 4.47 (d, J=12.80 Hz, 1H), 4.08-4.05 (m, 1H), 3.87 (dd, J=4.80, 11.80 Hz, 1H), 3.80-3.60 (m, 2H), 3.34-3.21 (m, 4H), 3.04 (q, J=6.80 Hz, 2H), 2.88-2.72 (m, 2H), 2.71-2.67 (m, 1H), 2.64 (s, 3H), 2.24-2.01 (m, 6H), 1.99-1.84 (m, 6H), 1.03 (t, J=7.20 Hz, 3H).

Example 18

6-[2-cyano-3-[[ethyl(methyl)sulfamoyl]amino]-6-fluorophenoxy]-3-[1-[1-[2-[4-[4-[(2,6-dioxopiperidin-3-yl)amino]phenyl]piperidin-1-yl]acetyl]piperidin-4-yl]pyrazol-4-yl]-4-oxoquinazoline The target compound was prepared via HATU mediated acid-amine coupling reaction (Procedure A-E). The amide coupling was carried out using 6-[2-cyano-3-[[ethyl(methyl)sulfamoyl]amino]-6-fluoro-phenoxy]-4-oxo-3-[1-(4-piperidyl)pyrazol-4-yl]quinazoline (20 mg, 35.30 μmol), 2-[4-[4-[(2,6-dioxo-3-piperidyl)amino]phenyl]-1-piperidyl] acetic acid (14 mg, 30.47 μmol), N,N-diisopropylethylamine (22.81 mg, 176.49 μmol, 30.74 μL) and HATU (16.11 mg, 42.36 μmol) to afford crude product. The crude material was purified by Prep HPLC purification method: 10 mm Ammonium acetate:acetonitrile and pure fractions were lyophilized to afford product 6-[2-cyano-3-[[ethyl(methyl)sulfamoyl]amino]-6-fluoro-phenoxy]-3-[1-[1-[2-[4-[4-[(2,6-dioxo-3-piperidyl)amino]phenyl]-1-piperidyl]acetyl]-4-piperidyl]pyrazol-4-yl]-4-oxo-quinazoline (7.84 mg, 8.14 μmol, 28% yield) as a pale yellow solid. LCMS m/z (ESI): 894.20[M+H]$^+$; $^1$HNMR (400 MHz, DMSO-$d_6$): δ=10.79 (s, 1H), 9.71 (bs, 1H), 8.45 (s, 1H), 8.34 (s, 1H), 7.90 (s, 1H), 7.82 (d, J=9.20 Hz, 1H), 7.67 (dd, J=2.80, 9.00 Hz, 1H), 7.60-7.50 (m, 1H), 7.42 (d, J=3.20 Hz, 1H), 7.42-7.30 (m, 1H), 6.98 (d, J=7.60 Hz, 2H), 6.63 (d, J=8.40 Hz, 2H), 5.72 (d, J=7.20 Hz, 1H), 4.45-4.25 (m, 4H), 4.15-3.95 (m, 2H), 3.03 (q, J=7.20 Hz, 2H), 2.95-2.82 (m, 2H), 2.80-2.65 (m, 6H), 2.63 (s, 3H), 2.12-2.08 (m, 5H), 1.91-1.76 (m, 6H), 1.03 (t, J=7.20 Hz, 3H).

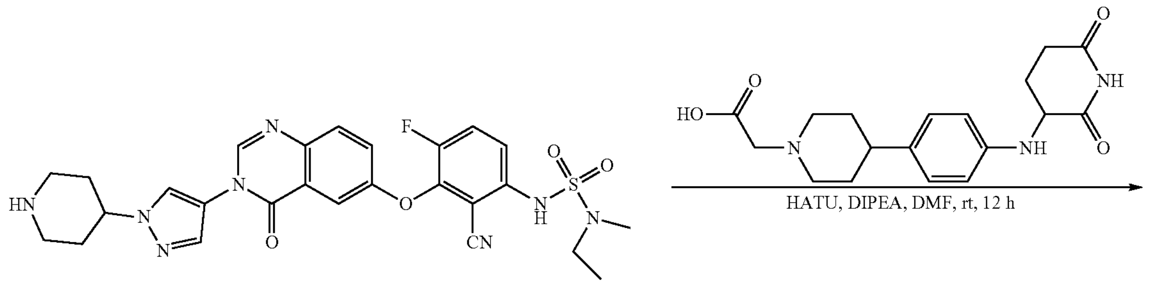

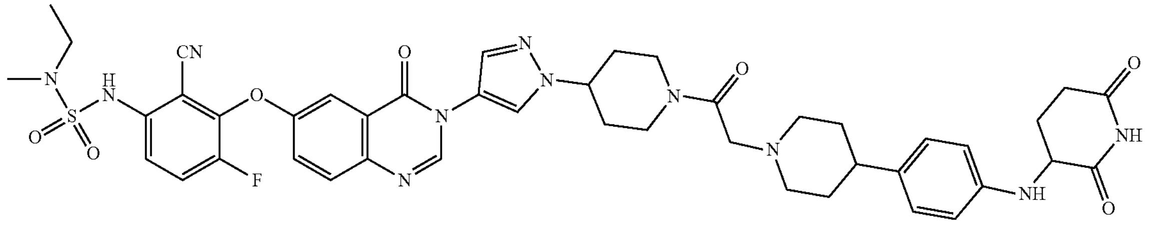

Example 19

6-[2-cyano-3-[[ethyl(methyl)sulfamoyl]amino]-6-fluorophenoxy]-3-[1-[1-[2-[4-[4-[(2,6-dioxopiperidin-3-yl)amino]-3-fluorophenyl]piperidin-1-yl]acetyl]piperidin-4-yl]pyrazol-4-yl]-4-oxoquinazoline

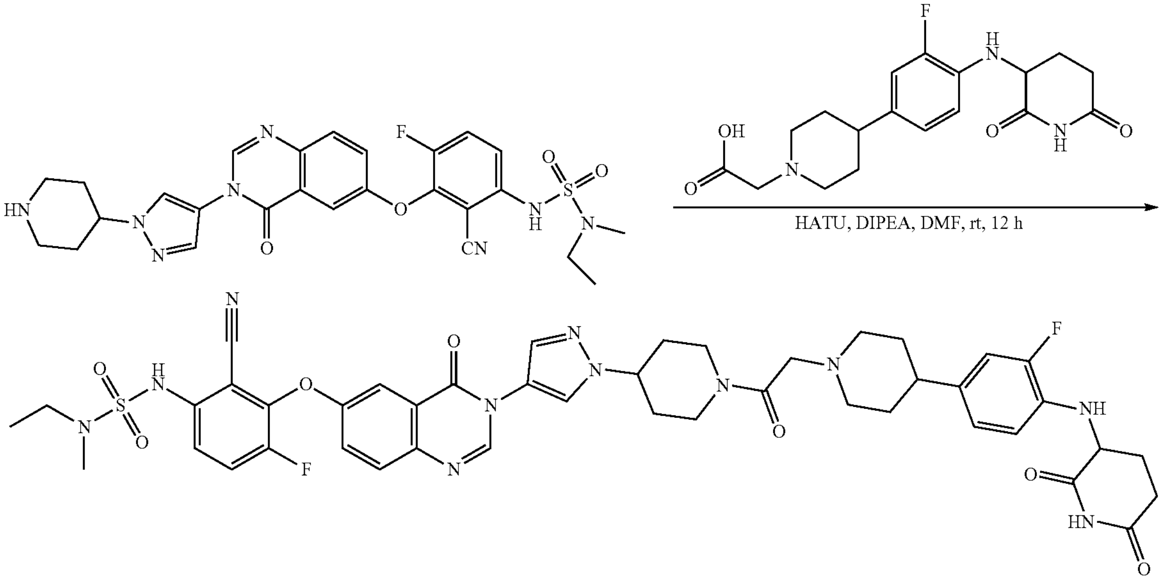

The target compound was prepared via HATU mediated acid-amine coupling reaction (Procedure A-E). The amide coupling was carried out using 6-[2-cyano-3-[[ethyl(methyl)sulfamoyl]amino]-6-fluoro-phenoxy]-4-oxo-3-[1-(4-piperidyl)pyrazol-4-yl]quinazoline (20 mg, 35.30 μmol), 2-[4-[4-[(2,6-dioxo-3-piperidyl)amino]-3-fluoro-phenyl]-1-piperidyl]acetic acid (12.83 mg, 35.30 μmol), N,N-diisopropylethylamine (371.00 mg, 2.87 mmol, 0.50 mL) and HATU (16.11 mg, 42.36 μmol) to afford crude product. The crude material was purified by Prep HPLC purification method: 10 mm A: 0.1% formic acid in water, Mobile-phase B: acetonitrile and pure fractions were lyophilized to afford product 6-[2-cyano-3-[[ethyl(methyl)sulfamoyl]amino]-6-fluoro-phenoxy]-3-[1-[1-[2-[4-[4-[(2,6-dioxo-3-piperidyl)amino]-3-fluoro-phenyl]-1-piperidyl]acetyl]-4-piperidyl]pyrazol-4-yl]-4-oxo-quinazoline (4.42 mg, 4.51 μmol, 13% yield) as an off-white solid. LCMS m/z (ESI): 912.20[M+H]$^+$; $^1$HNMR (400 MHz, DMSO-$d_6$): δ=10.83 (s, 1H), 8.49 (s, 1H), 8.45 (s, 1H), 7.90 (s, 1H), 7.82 (d, J=8.80 Hz, 1H), 7.67 (dd, J=3.20, 9.00 Hz, 1H), 7.65-7.50 (m, 1H), 7.43 (d, J=3.20 Hz, 1H), 7.36-7.33 (m, 1H), 6.97 (d, J=13.20 Hz, 1H), 6.86 (d, J=8.00 Hz, 1H), 6.78 (t, J=8.80 Hz, 1H), 6.55 (s, 1H), 5.47 (d, J=6.80 Hz, 1H), 4.56-4.36 (m, 4H), 4.10-3.90 (m, 2H), 3.20-3.20 (m, 3H), 3.05 (q, J=7.20 Hz, 2H), 2.95-2.80 (m, 1H), 2.80-2.70 (m, 2H), 2.65 (s, 3H), 2.60-2.52 (m, 2H), 2.20-2.00 (m, 6H), 19.00-1.75 (m, 4H), 1.03 (t, J=7.20 Hz, 3H).

Example 20

6-[2-cyano-3-[[ethyl(methyl)sulfamoyl]amino]-6-fluorophenoxy]-3-[1-[1-[2-[4-[4-[(2,6-dioxopiperidin-3-yl)amino]-2,6-difluorophenyl]piperidin-1-yl]acetyl]piperidin-4-yl]pyrazol-4-yl]-4-oxoquinazoline

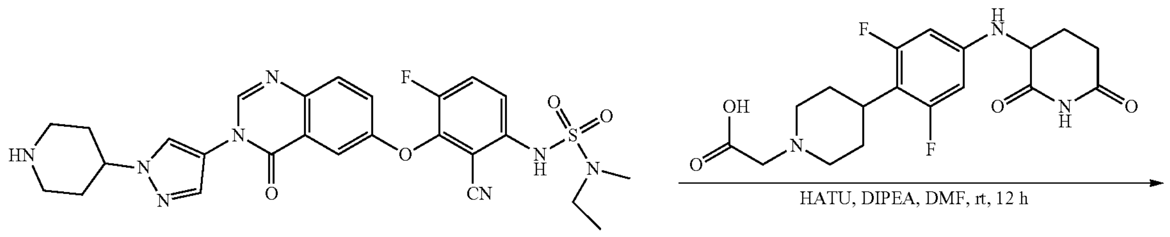

-continued

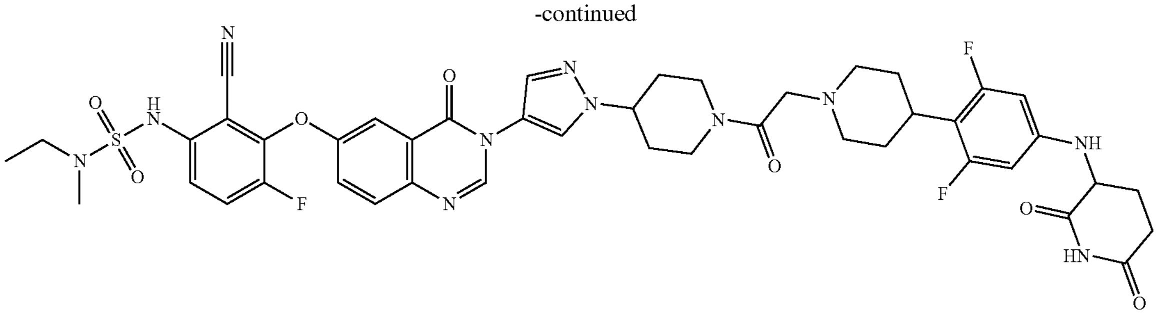

The target compound was prepared via HATU mediated acid-amine coupling reaction (Procedure A-E). The amide coupling was carried out using 6-[2-cyano-3-[[ethyl(methyl)sulfamoyl]amino]-6-fluoro-phenoxy]-4-oxo-3-[1-(4-piperidyl)pyrazol-4-yl]quinazoline (20 mg, 35.30 μmol), 2-[4-[4-[(2,6-dioxo-3-piperidyl)amino]-2,6-difluoro-phenyl]-1-piperidyl]acetic acid (13.46 mg, 35.30 μmol), N,N-diisopropylethylamine (371.00 mg, 2.87 mmol, 0.50 mL) and HATU (16.11 mg, 42.36 μmol) to afford crude product. The crude material was purified by Prep HPLC purification method: 10 mm Ammonium acetate:acetonitrile and pure fractions were lyophilized to afford product 6-[2-cyano-3-[[ethyl(methyl)sulfamoyl]amino]-6-fluoro-phenoxy]-3-[1-[1-[2-[4-[4-[(2,6-dioxo-3-piperidyl)amino]-2,6-difluoro-phenyl]-1-piperidyl]acetyl]-4-piperidyl]pyrazol-4-yl]-4-oxo-quinazoline (5.90 mg, 6.29 μmol, 18% yield) as off-white solid. LCMS m/z (ESI): 930.00[M+H]$^+$; $^1$HNMR (400 MHz, DMSO-$d_6$): δ=10.83 (s, 1H), 9.91 (bs, 1H), 8.45 (s, 1H), 8.33 (s, 1H), 7.90 (s, 1H), 7.82 (d, J=8.80 Hz, 1H), 7.67 (dd, J=3.20, 9.00 Hz, 1H), 7.60-7.50 (m, 1H), 7.43 (d, J=3.20 Hz, 1H), 7.37-7.33 (m, 1H), 6.40-6.32 (m, 3H), 4.55-4.45 (m, 2H), 4.35-4.40 (m, 1H), 4.15-3.95 (m, 1H), 3.29-3.24 (m, 4H), 3.06 (q, J=7.20 Hz, 2H), 2.95-2.80 (m, 2H), 2.80-2.68 (m, 2H), 2.65 (s, 3H), 2.25-2.05 (m, 7H), 1.88-1.82 (m, 3H), 1.73-1.71 (m, 3H), 1.03 (t, J=7.20 Hz, 3H).

Example 21

6-[2-cyano-3-[[ethyl(methyl)sulfamoyl]amino]-6-fluorophenoxy]-3-[1-[1-[2-[4-[4-[(2,6-dioxopiperidin-3-yl)amino]phenyl]piperidin-1-yl]-2-oxoethyl]piperidin-4-yl]pyrazol-4-yl]-4-oxoquinazoline

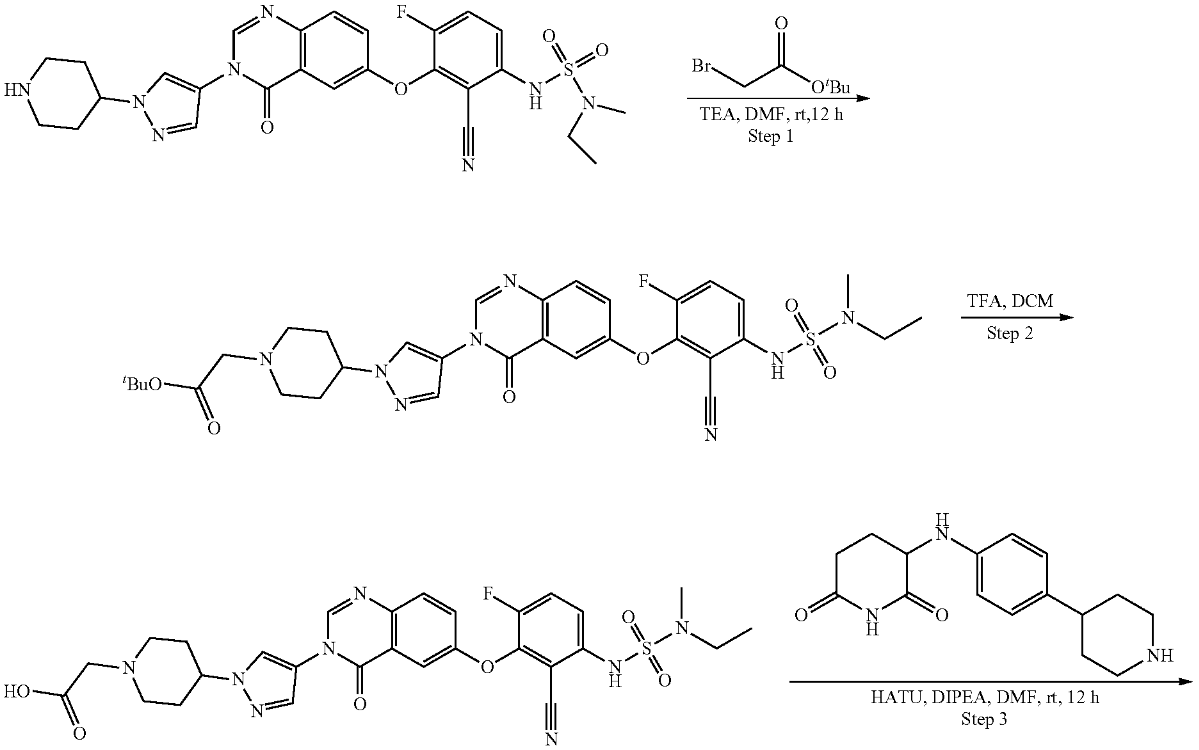

-continued

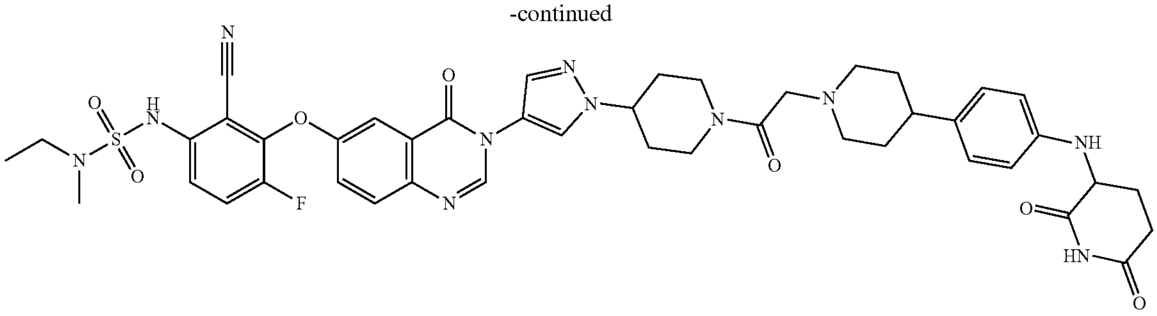

Step 1: To a stirred solution of 6-[2-cyano-3-[[ethyl (methyl)sulfamoyl]amino]-6-fluoro-phenoxy]-4-oxo-3-[1-(4-piperidyl)pyrazol-4-yl]quinazoline as its TFA salt (30 mg, 44.08 μmol) in N,N-dimethylformamide (2 mL) was added Triethylamine (22.30 mg, 220.38 μmol, 30.72 μL) at room temperature followed by tert-butyl 2-bromoacetate (10 mg, 51.27 μmol, 7.52 μL) and the resulting reaction mixture was stirred for 12 h at room temperature. After completion of the reaction the mixture was diluted with water (5 mL) and extracted with ethyl acetate (2×5 mL). The combined organic layers were dried over sodium sulfate, filtered and concentrated under reduced pressure to afford tert-butyl 2-[4-[4-[6-[2-cyano-3-[[ethyl(methyl)sulfamoyl]amino]-6-fluoro-phenoxy]-4-oxo-quinazolin-3-yl]pyrazol-1-yl]-1-piperidyl]acetate (31 mg, 42.23 μmol, 96% yield) as a brownish viscous liquid. This crude compound was proceeded to next step without any purification. LCMS m/z (ESI): 681.40 $[M+H]^+$ Step 2: The requisite amine was synthesized by following Procedure A-D using tert-butyl 2-[4-[4-[6-[2-cyano-3-[[ethyl(methyl)sulfamoyl]amino]-6-fluoro-phenoxy]-4-oxo-quinazolin-3-yl]pyrazol-1-yl]-1-piperidyl]acetate (31 mg, 45.54 μmol) and TFA (51.92 mg, 455.38 μmol, 35.08 μL). The resulting crude compound was triturated with methyl t-butyl ether to afford the TFA salt of 2-[4-[4-[6-[2-cyano-3-[[ethyl(methyl)sulfamoyl]amino]-6-fluoro-phenoxy]-4-oxo-quinazolin-3-yl]pyrazol-1-yl]-1-piperidyl]acetic acid (30 mg, 34.59 μmol, 76% yield) as a brownish viscous liquid. LCMS m/z (ESI): [M+H]625.40

Step 3: The target compound was prepared via HATU mediated acid-amine coupling reaction (Procedure A-E). The amide coupling was carried out using 2-[4-[4-[6-[2-cyano-3-[[ethyl(methyl)sulfamoyl]amino]-6-fluoro-phenoxy]-4-oxo-quinazolin-3-yl]pyrazol-1-yl]-1-piperidyl]acetic acid as its TFA salt (30 mg, 40.61 μmol), 3-[4-(4-piperidyl)anilino]piperidine-2,6-dione (17 mg, 42.35 μmol), N,N-diisopropylethylamine (371.00 mg, 2.87 mmol, 0.50 mL) and HATU (19 mg, 49.97 μmol) to afford crude product. The crude material was purified by Prep HPLC purification method: 10 mm Ammonium acetate:acetonitrile and pure fractions were lyophilized to afford 6-[2-cyano-3-[[ethyl(methyl)sulfamoyl]amino]-6-fluoro-phenoxy]-3-[1-[1-[2-[4-[4-[(2,6-dioxo-3-piperidyl)amino]phenyl]-1-piperidyl]-2-oxo-ethyl]-4-piperidyl]pyrazol-4-yl]-4-oxo-quinazoline (8.56 mg, 9.28 μmol, 23% yield) as an off-white solid. LCMS m/z (ESI): 893.80$[M+H]^+$; $^1$HNMR (400 MHz, DMSO-$d_6$): δ=10.78 (s, 1H), 9.95 (bs, 1H), 8.46 (s, 1H), 8.33 (s, 1H), 7.89 (s, 1H), 7.83 (d, J=8.92 Hz, 1H), 7.70-7.64 (m, 2H), 7.43 (d, J=2.96 Hz, 1H), 7.40-7.37 (m, 1H), 6.96 (d, J=8.52 Hz, 2H), 6.62 (d, J=8.60 Hz, 2H), 5.69 (d, J=7.52 Hz, 1H), 4.52-4.49 (m, 1H), 4.35-4.20 (m, 2H), 4.15-4.05 (m, 1H), 3.75-3.62 (m, 2H), 3.25-3.10 (m, 4H), 3.08 (q, J=7.12 Hz, 2H), 2.74-2.69 (m, 3H), 2.67 (s, 3H), 2.64-2.51 (m, 2H), 2.13-2.08 (m, 5H), 1.88-1.84 (m, 1H), 1.81-1.74 (m, 2H), 1.65-1.50 (m, 1H), 1.45-1.35 (m, 1H), 1.04 (t, J=7.20 Hz, 3H).

Examples 22 and 23

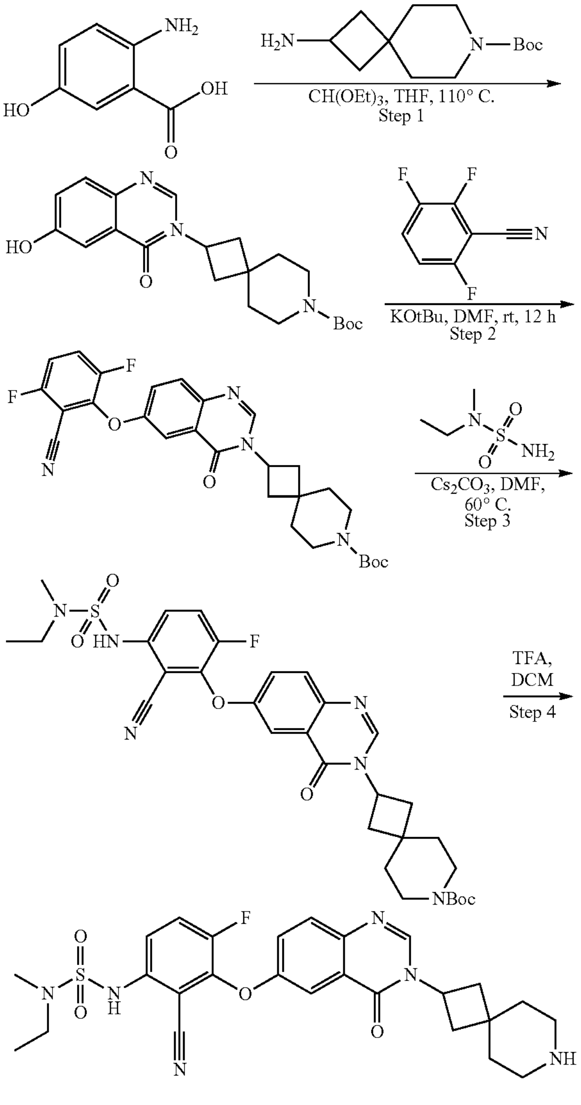

Step 1: The quinazolinone intermediate was synthesized by following general procedure for cyclization (Procedure A-A) using tert-butyl 2-amino-7-azaspiro[3.5]nonane-7-carboxylate (2.0 g, 8.32 mmol), 2-amino-5-hydroxy-benzoic acid (1.53 g, 9.99 mmol), Triethyl orthoformate (1.60 g, 10.82 mmol, 1.80 mL). The crude material was purified by 230-400 silica gel flash column chromatography using 0-100% ethyl acetate in petroleum ether as the eluent yielding tert-butyl 2-(6-hydroxy-4-oxo-quinazolin-3-yl)-7-azaspiro[3.5]nonane-7-carboxylate (1.2 g, 2.46 mmol, 30% yield) as a light brown solid. LCMS m/z (ESI): 386.1 $[M+H]^+$ Step 2: The O-arylated quinazolinone intermediate was synthesized by following general procedure for O-arylation (Procedure A-B) using tert-butyl 2-(6-hydroxy-4-oxo-quinazolin-3-yl)-7-azaspiro[3.5]nonane-7-carboxylate (0.75 g, 1.95 mmol), KO$^t$Bu (436.67 mg, 3.89 mmol) and 2,3,6-trifluorobenzonitrile (305.66 mg, 1.95 mmol, 224.75 μL). The crude compound was purified by silica gel flash column chromatography using 50% ethyl acetate in petroleum ether as the eluent yielding tert-butyl 2-[6-(2-cyano-3,6-difluoro-phenoxy)-4-oxo-quinazolin-3-yl]-7-azaspiro[3.5]nonane-7-carboxylate (0.6 g, 654.49 μmol, 34% yield) as a light brown colored semi solid. LCMS m/z (ESI): 523.1 $[M+H]^+$ Step 3: Sulfamoylated quinazolinone intermediate was synthesized following Procedure A-C using tert-butyl 2-[6-(2-cyano-3,6-difluoro-phenoxy)-4-oxo-quinazolin-3-yl]-7-azaspiro[3.5]nonane-7-carboxylate (0.6 g, 1.15 mmol), cesium carbonate (1.12 g, 3.44 mmol) and [methyl(sulfamoyl)amino]ethane (158.67 mg, 1.15 mmol). The crude material was purified by silica gel flash column chromatography by using 0-100 ethyl acetate in petroleum ether as the eluent yielding tert-butyl 2-[6-[2-cyano-3-[[ethyl(methyl) sulfamoyl]amino]-6-fluoro-phenoxy]-4-oxo-quinazolin-3-yl]-7-azaspiro[3.5]nonane-7-carboxylate (0.45 g, 526.75 μmol, 46% yield) as an orange semi solid. LCMS m/z (ESI): 641.3 $[M+H]^+$ Step 4: The requisite amine was synthesized by TFA mediated N-Boc deprotection (Procedure A-D). N-Boc deprotection was done on tert-butyl 2-[6-[2-cyano-3-[[ethyl (methyl)sulfamoyl]amino]-6-fluoro-phenoxy]-4-oxo-quinazolin-3-yl]-7-azaspiro[3.5]nonane-7-carboxylate (450 mg, 702.33 μmol) using Trifluoroacetic acid (3.70 g, 32.45 mmol, 2.5 mL) to afford the TFA salt of 3-(7-azaspiro[3.5]nonan-2-yl)-6-[2-cyano-3-[[ethyl(methyl)sulfamoyl]amino]-6-fluoro-phenoxy]-4-oxo-quinazoline (0.4 g, 482.71 μmol, 69% yield) as a brown solid. LCMS m/z (ESI): 541.2 $[M+H]^+$ Example 22

6-[2-cyano-3-[[ethyl(methyl)sulfamoyl]amino]-6-fluorophenoxy]-3-[7-[2-[4-[4-[(2,6-dioxopiperidin-3-yl)amino]-2-fluorophenyl]piperidin-1-yl]acetyl]-7-azaspiro[3.5]nonan-2-yl]-4-oxoquinazoline

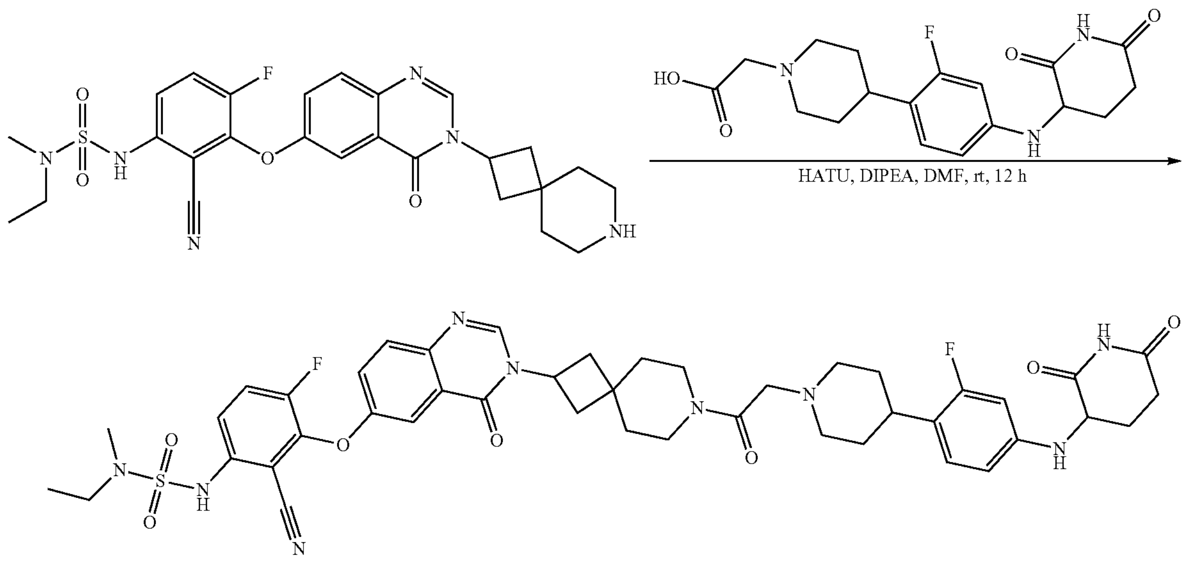

The target compound was prepared via HATU mediated acid-amine coupling reaction (Procedure A-E). The amide coupling was carried out using 2-[4-[4-[(2,6-dioxo-3-piperidyl)amino]-2-fluoro-phenyl]-1-piperidyl]acetic acid (138.77 mg, 347.07 μmol), 3-(7-azaspiro[3.5]nonan-2-yl)-6-[2-cyano-3-[[ethyl(methyl)sulfamoyl]amino]-6-fluoro-phenoxy]-4-oxo-quinazoline (0.25 g, 381.89 μmol), HATU (217.81 mg, 572.84 μmol) and N,N-diisopropylethylamine (246.79 mg, 1.91 mmol, 332.60 μL). The crude compound was purified by reverse phase column chromatography[Mobile-phase A: 0.1% ammonium acetate, Mobile-phase B: acetonitrile] to afford 6-[2-cyano-3-[[ethyl(methyl)sulfamoyl]amino]-6-fluoro-phenoxy]-3-[7-[2-[4-[4-[(2,6-dioxo-3-piperidyl)amino]-2-fluoro-phenyl]-1-piperidyl]acetyl]-7-azaspiro[3.5]nonan-2-yl]-4-oxo-quinazoline (125 mg, 140.23 μmol, 37% yield) as an off-white solid. LCMS m/z (ESI): 886.3 $[M+H]^+$. $^1$HNMR (400 MHz, DMSO-$d_6$): δ=10.81 (s, 1H), 9.77 (bs, 1H), 8.40 (s, 1H), 7.77 (d, J=8.80 Hz, 1H), 7.64 (dd, J=3.20, 8.80 Hz, 1H), 7.51-7.60 (m, 1H), 7.34 (d, J=2.80 Hz, 2H), 6.95-7.05 (m, 1H), 6.49 (d, J=7.60 Hz, 1H), 6.46 (d, J=12.40 Hz, 1H), 6.08 (d, J=7.60 Hz, 1H), 4.95-5.05 (m, 1H), 4.24-4.35 (m, 1H), 3.60-4.10 (m, 2H), 3.46-3.55 (m, 1H), 3.20-3.45 (m, 6H), 3.05 (q, J=6.80 Hz, 2H), 2.60-2.81 (m, 2H), 2.65 (s, 3H), 2.55-2.45 (m, 2H), 2.30-2.45 (m, 5H), 2.05-2.12 (m, 1H), 1.55-1.92 (m, 8H), 1.03 (t, J=7.20 Hz, 3H).

Example 23

6-[2-cyano-3-[[ethyl(methyl)sulfamoyl]amino]-6-fluorophenoxy]-3-[7-[2-[1-[4-[(2,6-dioxopiperidin-3-yl)amino]-2-fluorophenyl]-4-hydroxypiperidin-4-yl]acetyl]-7-azaspiro [3.5]nonan-2-yl]-4-oxoquinazoline

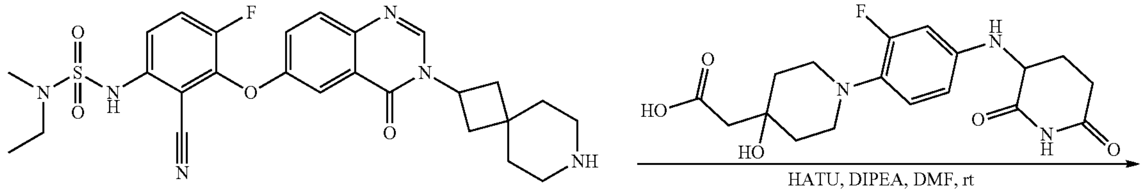

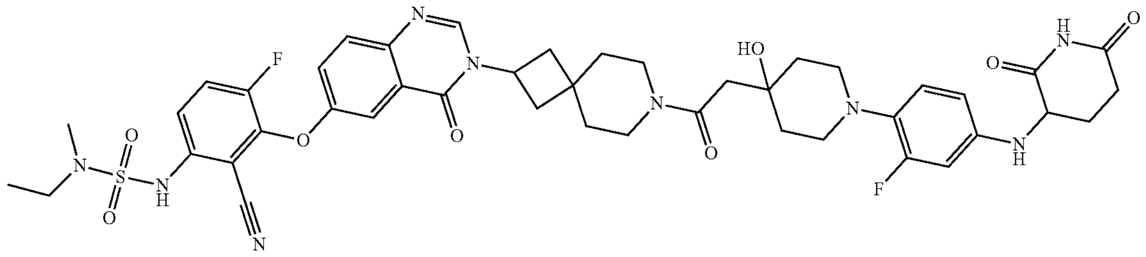

The target compound was prepared via HATU mediated acid-amine coupling reaction (Procedure A-E). The amide coupling was carried out using 3-(7-azaspiro[3.5]nonan-2-yl)-6-[2-cyano-3-[[ethyl(methyl)sulfamoyl]amino]-6-fluoro-phenoxy]-4-oxo-quinazoline (400 mg, 611.03 μmol), 2-[1-[4-[(2,6-dioxo-3-piperidyl)amino]-2-fluoro-phenyl]-4-hydroxy-4-piperidyl]acetic acid (231.81 mg, 557.46 μmol), HATU (302.03 mg, 794.34 μmol) and N,N-diisopropylethylamine (394.86 mg, 3.06 mmol, 532.15 μL). The crude material from the reaction was purified by reverse phase column chromatography [Mobile-phase A: 0.1% formic acid water, Mobile-phase B: acetonitrile; column: 100 g RediSep® Rf C18] column chromatography eluted with 37% acetonitrile in 0.1% formic acid in water to afford 6-[2-cyano-3-[[ethyl(methyl)sulfamoyl]amino]-6-fluoro-phenoxy]-3-[7-[2-[1-[4-[(2,6-dioxo-3-piperidyl)amino]-2-fluoro-phenyl]-4-hydroxy-4-piperidyl]acetyl]-7-azaspiro [3.5]nonan-2-yl]-4-oxo-quinazoline (142 mg, 149.40 μmol, 24% yield) as off-white solid. LCMS m/z (ESI): 902.0 $[M+H]^+$ $^1$HNMR (400 MHz, DMSO-$d_6$): δ=10.79 (s, 1H), 10.20 (s, 1H), 8.42 (d, J=4.00 Hz, 1H), 7.78-7.83 (m, 1H), 7.80 (d, J=8.80 Hz, 1H), 7.68 (dd, J=3.20, 9.00 Hz, 1H), 7.48 (dd, J=3.60, 8.80 Hz, 1H), 7.35 (d, J=2.80 Hz, 1H), 6.85 (t, J=9.20 Hz, 1H), 6.50 (d, J=14.80 Hz, 1H), 6.41 (d, J=8.40 Hz, 1H), 5.78 (d, J=7.60 Hz, 1H), 4.97 (d, J=2.40 Hz, 1H), 4.93-4.96 (m, 1H), 4.23-4.28 (m, 1H), 3.51-3.60 (m, 2H), 3.35-3.42 (m, 2H), 3.15 (q, J=6.80 Hz, 2H), 2.80-2.92 (m, 4H), 2.78 (s, 3H), 2.67-2.77 (m, 1H), 2.46-2.60 (m, 2H), 2.28-2.41 (m, 5H), 2.05-2.12 (m, 1H), 1.80-1.91 (m, 1H), 1.52-1.80 (m, 8H), 1.05 (t, J=7.20 Hz, 3H).

Example 24

3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

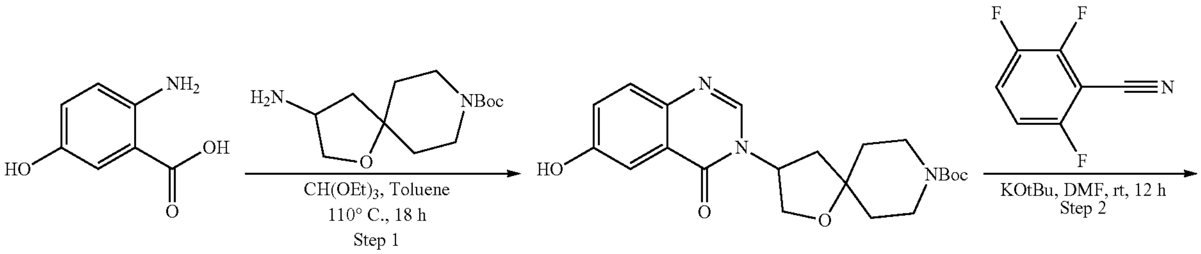

-continued

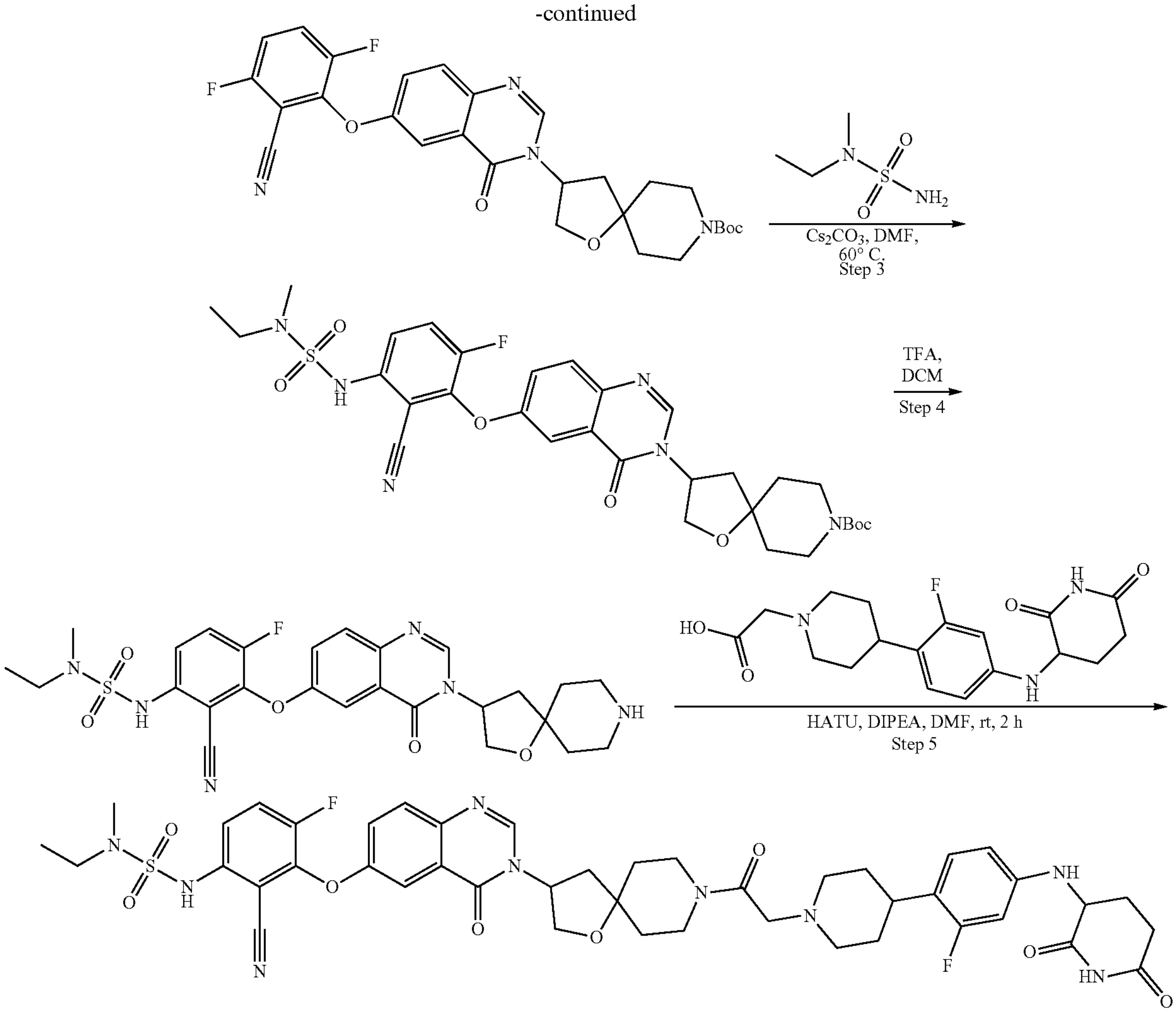

Step 1: The quinazolinone intermediate was synthesized by following general procedure for cyclization (Procedure A-A) using 2-amino-5-hydroxy-benzoic acid (250 mg, 1.63 mmol), Triethyl orthoformate (483.88 mg, 3.27 mmol, 543.08 μL) and tert-butyl 3-amino-1-oxa-8-azaspiro[4.5]decane-8-carboxylate (418.49 mg, 1.63 mmol). The desired compound was purified from the crude reaction mixture by silica gel flash column chromatography using 5% methanol-dichloromethane as eluent to afford tert-butyl 3-(6-hydroxy-4-oxo-quinazolin-3-yl)-1-oxa-8-azaspiro[4.5]decane-8-carboxylate (405 mg, 746.94 μmol, 46% yield) as brown solid. LCMS m/z (ESI): 400.2 $[M-H]^-$ Step 2: The O-arylated quinazolinone intermediate was synthesized by following general procedure for O-arylation (Procedure A-B) using tert-butyl 3-(6-hydroxy-4-oxo-quinazolin-3-yl)-1-oxa-8-azaspiro[4.5]decane-8-carboxylate (999 mg, 2.49 mmol), potassium tert-butoxide (279.23 mg, 2.49 mmol) and 2,3,6-trifluorobenzonitrile (430.01 mg, 2.74 mmol, 316.18 μL) to yield crude tert-butyl 3-[6-(2-cyano-3,6-difluoro-phenoxy)-4-oxo-quinazolin-3-yl]-1-oxa-8-azaspiro[4.5]decane-8-carboxylate (665 mg, 975.51 μmol, 39% yield) as a light brown semi solid. LCMS m/z (ESI): 483.1 $[M+H-{}^{t}Bu]^+$ Step 3: Sulfamoylated quinazolinone intermediate was synthesized by following Procedure A-C using tert-butyl 3-[6-(2-cyano-3,6-difluoro-phenoxy)-4-oxo-quinazolin-3-yl]-1-oxa-8-azaspiro[4.5]decane-8-carboxylate (250 mg, 464.22 μmol), cesium carbonate (378.13 mg, 1.16 mmol) and [methyl(sulfamoyl)amino]ethane (96.22 mg, 696.33 μmol) to afford tert-butyl 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (210 mg, 283.64 μmol, 61% yield) as a pale brown oil. LCMS m/z (ESI): 655.2 $[M-H]^-$ Step 4: The requisite amine was synthesized by TFA mediated N-Boc deprotection (Procedure A-D). N-Boc deprotection was done on tert-butyl 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (210 mg, 319.77 μmol) using TFA (36.46 mg, 319.77 μmol, 24.64 μL) to afford the TFA salt of 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (210 mg, 259.90 μmol, 82% yield) as a pale yellow solid. LCMS m/z (ESI): 557.2 $[M+H]^+$ Step 5: The target compound was prepared via HATU mediated acid-amine coupling reaction (Procedure A-E). The amide coupling was carried out using 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (310 mg, 462.25 μmol), HATU (210.91 mg, 554.70 μmol) and N,N-diisopropylethylamine (298.71 mg, 2.31 mmol, 402.58 μL) and 2-[4-[4-[(2,6-dioxo-3-piperidyl)amino]-2-fluoro-phenyl]-1-piperidyl]acetic acid(203.3 mg, 508.4 μmol). The crude compound was purified by reverse phase column chromatography eluted with 20 to 30% acetonitrile in 0.1% ammonium acetate in water to afford 3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5] decane (106.4 mg, 115.66 μmol, 25% yield) as an off-white solid. LCMS m/z (ESI): 902.2 $[M+H]^+$; $^1$HNMR (400 MHz, DMSO-$d_6$): δ=10.80 (s, 1H), 9.81 (s, 1H), 8.34 (d, J=1.20 Hz, 1H), 7.77 (d, J=8.80 Hz, 1H), 7.65 (dd, J=2.80, 8.80 Hz, 1H), 7.49 (s, 1H), 7.35 (d, J=2.80 Hz, 1H), 7.29-7.34 (m, 1H), 6.99 (s, 1H), 6.48 (d, J=7.20 Hz, 1H), 6.46 (d, J=13.60 Hz, 1H), 6.06 (d, J=7.20 Hz, 1H), 5.31 (s, 1H), 4.32-4.35 (m, 1H), 4.11-4.19 (m, 2H), 3.66-3.75 (m, 1H), 3.41-3.60 (m, 2H), 3.4-3.21 (m, 3H), 3.01-3.10 (m, 2H), 2.62-2.81 (m, 2H), 2.62 (s, 3H), 2.58-2.41 (m, 5H), 2.06-2.10 (m, 2H), 1.60-1.91 (m, 10H), 1.03 (t, J=7.20 Hz, 3H).

Example 25

6-[2-cyano-3-[[ethyl(methyl)sulfamoyl]amino]-6-fluorophenoxy]-3-[3-[2-[4-[4-[(2,6-dioxopiperidin-3-yl)amino]-2-fluorophenyl]piperidin-1-yl]acetyl]-3-azabicyclo[3.1.0]hexan-6-yl]-4-oxoquinazoline

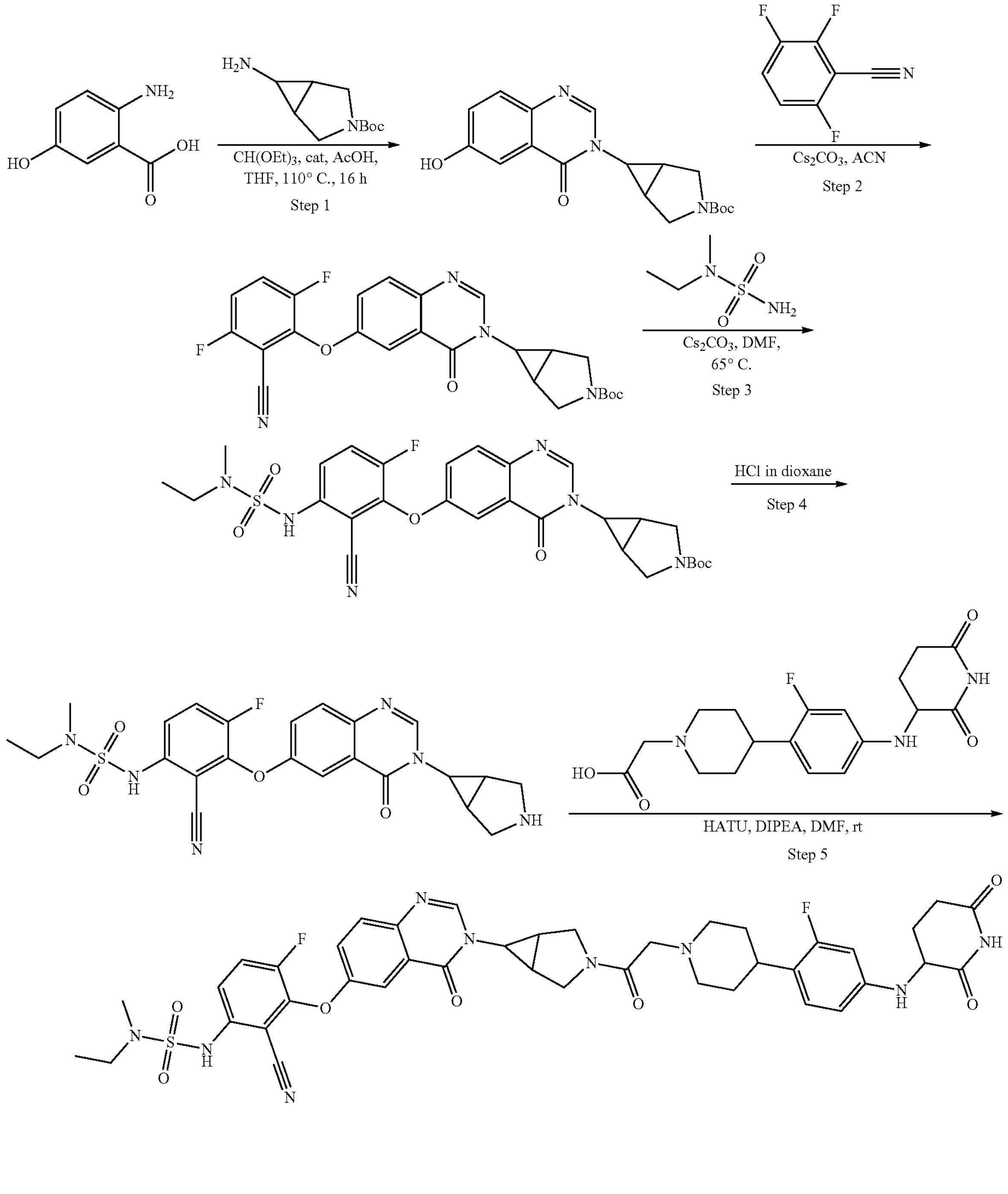

Step 1: The quinazolinone intermediate was synthesized by following the general procedure for cyclization (Procedure A-A) using 2-amino-5-hydroxy-benzoic acid (250 mg, 1.63 mmol), tert-butyl 6-amino-3-azabicyclo[3.1.0]hexane-3-carboxylate (485.51 mg, 2.45 mmol), Triethyl orthoformate (241.94 mg, 1.63 mmol, 271.54 μL) and acetic acid (4.90 mg, 81.63 μmol, 4.67 μL) to afford tert-butyl 6-(6-hydroxy-4-oxo-quinazolin-3-yl)-3-azabicyclo[3.1.0]hexane-3-carboxylate (450 mg, 1.17 mmol, 71% yield) as an off-white solid. LCMS m/z (ESI): 344.1 $[M+H]^+$ Step 2: O-arylated quinazolinone intermediate was synthesized by following general procedure for O-arylation (Procedure A-B) using tert-butyl 6-(6-hydroxy-4-oxo-quinazolin-3-yl)-3-azabicyclo[3.1.0]hexane-3-carboxylate (450 mg, 1.31 mmol), potassium tert-butoxide (161.76 mg, 1.44 mmol) and 2,3,6-trifluorobenzonitrile (226.46 mg, 1.44 mmol, 166.51 μL). The crude compound was purified by silica gel flash column chromatography with 80-90% ethyl acetate in petroleum ether as the eluent to afford tert-butyl 6-[6-(2-cyano-3,6-difluoro-phenoxy)-4-oxo-quinazolin-3-yl]-3-azabicyclo[3.1.0]hexane-3-carboxylate (500 mg, 978.22 μmol, 75% yield) as an off-white solid. LCMS m/z (ESI): 481.1 $[M+H]^+$ Step 3: Sulfamoylated quinazolinone intermediate was synthesized by following Procedure A-C using tert-butyl 6-[6-(2-cyano-3,6-difluoro-phenoxy)-4-oxo-quinazolin-3-yl]-3-azabicyclo[3.1.0]hexane-3-carboxylate (500 mg, 1.04 mmol), cesium carbonate (847.67 mg, 2.60 mmol) and [methyl(sulfamoyl)amino]ethane (316.38 mg, 2.29 mmol). The crude compound was purified by silica gel flash column chromatography with 90-100% ethyl acetate in petroleum ether as the eluent to afford tert-butyl 6-[6-[2-cyano-3-[[ethyl(methyl)sulfamoyl]amino]-6-fluoro-phenoxy]-4-oxo-quinazolin-3-yl]-3-azabicyclo[3.1.0]hexane-3-carboxylate (370 mg, 414.10 μmol, 40% yield) as a pale brown solid. LCMS m/z (ESI): 579.2 $[M-H]^-$ Step 4: The requisite amine was synthesized by HCl mediated N-Boc deprotection (Procedure A-D). N-Boc deprotection was done on tert-butyl 6-[6-[2-cyano-3-[[ethyl(methyl)sulfamoyl]amino]-6-fluoro-phenoxy]-4-oxo-quinazolin-3-yl]-3-azabicyclo[3.1.0]hexane-3-carboxylate (370 mg, 618.06 μmol) using 4M hydrogen chloride solution in dioxane (0.5 mL) to afford the HCl salt of 3-(3-azabicyclo[3.1.0]hexan-6-yl)-6-[2-cyano-3-[[ethyl(methyl)sulfamoyl]amino]-6-fluoro-phenoxy]-4-oxo-quinazoline (320 mg, 466.55 μmol, 75% yield) as a pale brown solid. LCMS m/z (ESI): 499.1 $[M+H]^+$ Step 5: The target compound was prepared via HATU mediated acid-amine coupling reaction (Procedure A-E). The amide coupling was carried out using 3-(3-azabicyclo[3.1.0]hexan-6-yl)-6-[2-cyano-3-[[ethyl(methyl)sulfamoyl]amino]-6-fluoro-phenoxy]-4-oxo-quinazoline (310 mg, 579.45 μmol), N,N-diisopropylethylamine (374.45 mg, 2.90 mmol, 504.65 μL), 2-[4-[4-[(2,6-dioxo-3-piperidyl)amino]-2-fluoro-phenyl]-1-piperidyl]acetic acid (231.69 mg, 579.45 μmol) and HATU (264.39 mg, 695.34 μmol). The crude compound was purified by preparative-HPLC (0.1% formic acid in water:acetonitrile) to afford 6-[2-cyano-3-[[ethyl(methyl)sulfamoyl]amino]-6-fluoro-phenoxy]-3-[3-[2-[4-[4-[(2,6-dioxo-3-piperidyl)amino]-2-fluoro-phenyl]-1-piperidyl]acetyl]-3-azabicyclo[3.1.0]hexan-6-yl]-4-oxo-quinazoline (20.1 mg, 22.13 μmol, 4% yield) as an off-white solid. LCMS m/z (ESI): 844.0 $[M+H]^1$HNMR (400 MHz, DMSO-$d_6$): δ=10.77 (s, 1H), 8.33 (s, 1H), 8.31 (s, 1H), 7.73 (d, J=8.80 Hz, 1H), 7.58 (ddd, J=0.80, 3.00, 8.80 Hz, 1H), 7.35 (d, J=3.20 Hz, 1H), 7.29 (t, J=10.00 Hz, 1H), 7.21-7.24 (m, 1H), 7.00 (t, J=8.40 Hz, 1H), 6.44-6.46 (m, 2H), 5.95-6.05 (m, 1H), 4.25-4.35 (m, 1H), 4.01-4.06 (m, 1H), 3.84 (d, J=11.60 Hz, 2H), 3.70-3.75 (m, 2H), 3.41-3.55 (m, 1H), 3.10 (s, 2H), 2.96 (q, J=7.20 Hz, 2H), 2.85-2.90 (m, 3H), 2.70-2.81 (m, 1H), 2.55 (s, 3H), 2.05-2.25 (m, 5H), 1.80-1.91 (m, 1H), 1.58-1.71 (m, 4H), 1.02 (t, J=7.20 Hz, 3H).

Example 26

6-[2-cyano-3-[[ethyl(methyl)sulfamoyl]amino]phenoxy]-3-[7-[2-[4-[4-[(2,6-dioxopiperidin-3-yl)amino]-2-fluorophenyl]piperidin-1-yl]acetyl]-7-azaspiro[3.5]nonan-2-yl]-4-oxoquinazoline

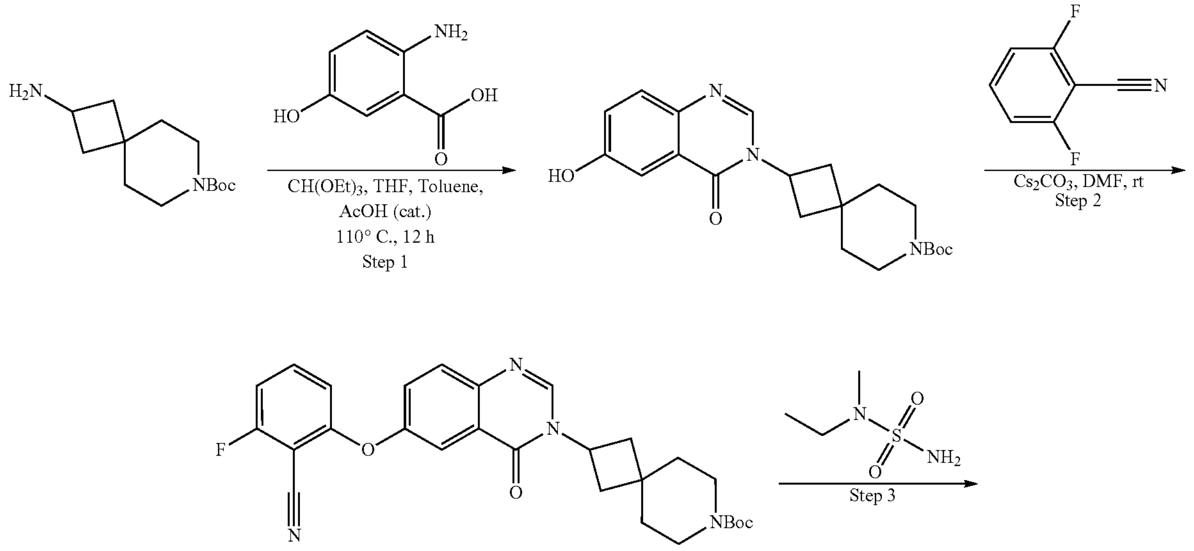

-continued

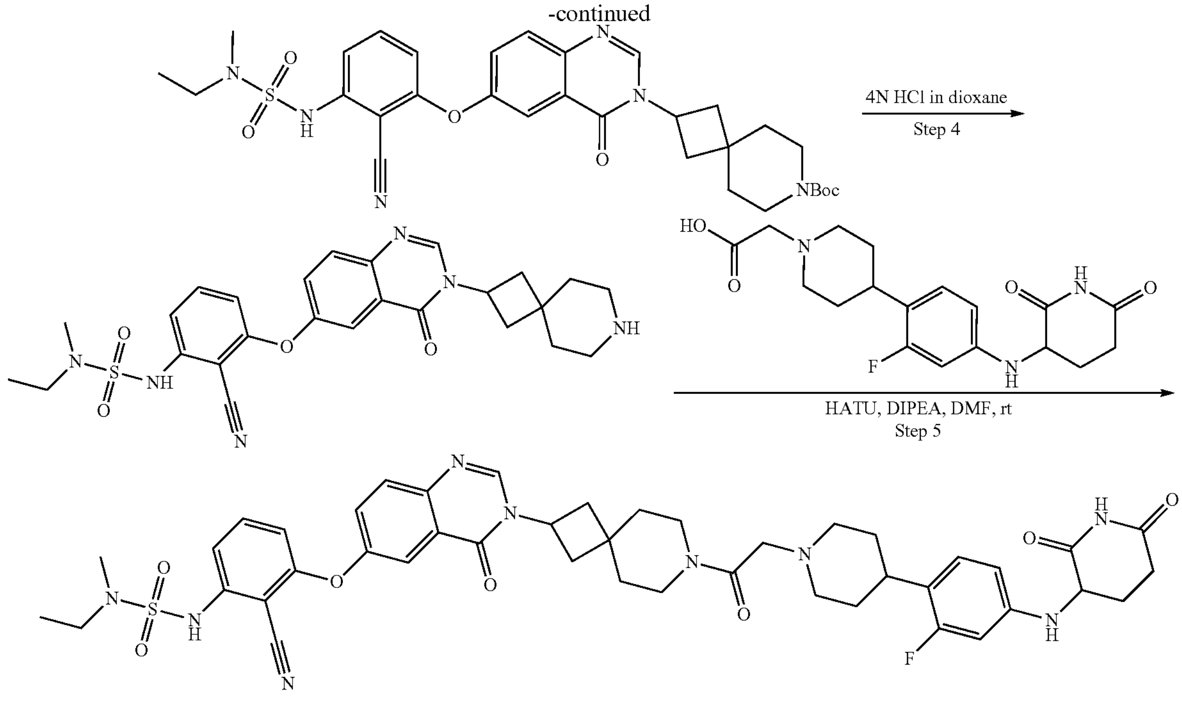

Step 1: The quinazolinone intermediate was synthesized by following general procedure for cyclization (Procedure A-A) using tert-butyl 2-amino-7-azaspiro[3.5]nonane-7-carboxylate (2.0 g, 8.32 mmol), 2-amino-5-hydroxy-benzoic acid (1.53 g, 9.99 mmol), Triethyl orthoformate (1.60 g, 10.82 mmol, 1.80 mL). The crude material was purified by 230-400 silica gel flash column chromatography using 0-100% ethyl acetate in petroleum ether as a eluent yielded tert-butyl 2-(6-hydroxy-4-oxo-quinazolin-3-yl)-7-azaspiro[3.5]nonane-7-carboxylate (1.2 g, 2.46 mmol, 30% yield) as a light brown solid. LCMS m/z (ESI): 386.1 $[M+H]^+$ Step 2: The O-arylated quinazolinone intermediate was synthesized by following general procedure for O-arylation (Procedure A-B) using tert-butyl 2-(6-hydroxy-4-oxo-quinazolin-3-yl)-7-azaspiro[3.5]nonane-7-carboxylate (0.6 g, 1.56 mmol), cesium carbonate (1.52 g, 4.67 mmol) and 2,6-difluorobenzonitrile (259.83 mg, 1.87 mmol, 207.87 μL). The crude compound was purified by silica gel flash column chromatography using 50% ethyl acetate in petroleum ether as the eluent to yield tert-butyl 2-[6-(2-cyano-3-fluoro-phenoxy)-4-oxo-quinazolin-3-yl]-7-azaspiro[3.5]nonane-7-carboxylate (500 mg, 828.46 μmol, 53% yield) as a light brown semi solid. LCMS m/z (ESI): 505.0 $[M+H]^+$ Step 3: The sulfamoylated quinazolinone intermediate was synthesized by following Procedure A-C using tert-butyl 2-[6-(2-cyano-3-fluoro-phenoxy)-4-oxo-quinazolin-3-yl]-7-azaspiro[3.5]nonane-7-carboxylate (300 mg, 594.59 μmol), cesium carbonate (581.18 mg, 1.78 mmol) and [methyl(sulfamoyl)amino]ethane (98.60 mg, 713.50 μmol). The crude material was purified by silica gel flash column chromatography using 0-100 ethyl acetate in petroleum ether as the eluent yielded tert-butyl 2-[6-[2-cyano-3-[[ethyl(methyl)sulfamoyl]amino]phenoxy]-4-oxo-quinazolin-3-yl]-7-azaspiro[3.5]nonane-7-carboxylate (150 mg, 180.66 μmol, 31% yield) as an orange solid. LCMS m/z (ESI): 623.2 $[M+H]^+$ Step 4: The requisite amine was synthesized by TFA mediated N-Boc deprotection (Procedure A-D). N-Boc deprotection was done on tert-butyl 2-[6-[2-cyano-3-[[ethyl(methyl)sulfamoyl]amino]phenoxy]-4-oxo-quinazolin-3-yl]-7-azaspiro[3.5]nonane-7-carboxylate (0.15 g, 240.87 μmol) using Trifluoroacetic acid (1.48 g, 12.98 mmol, 1 mL) to afford the TFA salt of 3-(7-azaspiro[3.5]nonan-2-yl)-6-[2-cyano-3-[[ethyl(methyl)sulfamoyl]amino]phenoxy]-4-oxo-quinazoline (125 mg, 129.59 μmol, 54% yield) as a brown semi solid. LCMS m/z (ESI): 523.2 $[M+H]^+$ Step 5: The target compound was prepared via HATU mediated acid-amine coupling reaction (Procedure A-E). The amide coupling was carried out using 3-(7-azaspiro[3.5]nonan-2-yl)-6-[2-cyano-3-[[ethyl(methyl)sulfamoyl]amino]phenoxy]-4-oxo-quinazoline (125 mg, 196.34 μmol), 2-[4-[4-[(2,6-dioxo-3-piperidyl)amino]-2-fluoro-phenyl]-1-piperidyl]acetic acid (78.48 mg, 196.28 μmol), HATU (111.98 mg, 294.51 μmol) and N,N-diisopropylethylamine (126.88 mg, 981.71 μmol, 171.00 μL). The crude compound was purified by reverse phase column chromatography eluting with 37% acetonitrile in 0.1% formic acid in water to afford 6-[2-cyano-3-[[ethyl(methyl)sulfamoyl]amino]phenoxy]-3-[7-[2-[4-[4-[(2,6-dioxo-3-piperidyl)amino]-2-fluoro-phenyl]-1-piperidyl]acetyl]-7-azaspiro[3.5]nonan-2-yl]-4-oxo-quinazoline (116 mg, 124.43 μmol, 63% yield) as off-white solid. LCMS m/z (ESI): 868.0 $[M+H]^+$ $^1$HNMR (400 MHz, DMSO-$d_6$): δ=10.82 (s, 1H), 10.19 (s, 1H), 9.51 (s, 1H), 8.47 (d, J=4.40 Hz, 1H), 7.82 (d, J=8.80 Hz, 1H), 7.62-7.70 (m, 3H), 7.33 (d, J=8.40 Hz, 1H), 6.93-7.01 (m, 1H), 6.90 (d, J=8.00 Hz, 1H), 6.50 (d, J=7.60 Hz, 1H), 6.48 (d, J=12.80 Hz, 1H), 6.13 (d, J=7.60 Hz, 1H), 4.95-5.08 (m, 1H), 4.23-4.41 (m, 3H), 3.42-3.61 (m, 3H), 3.25-3.35 (m, 3H), 3.19 (q, J=6.80 Hz, 2H), 3.01-3.12 (m, 2H), 2.81-2.92 (m, 1H), 2.80 (s, 3H), 2.67-2.75 (m, 1H), 2.41-2.60 (m, 4H), 1.92-2.10 (m, 4H), 1.58-1.92 (m, 7H), 1.07 (t, J=7.20 Hz, 3H).

Example 27

3-[6-[2-cyano-3-[[ethyl(methyl)sulfamoyl]amino]-6-fluorophenoxy]-4-oxoquinazolin-3-yl]-8-[2-[1-[4-[(2,6-dioxopiperidin-3-yl)amino]-2-fluorophenyl]-4-hydroxypiperidin-4-yl]acetyl]-1-oxa-8-azaspiro[4.5]decane

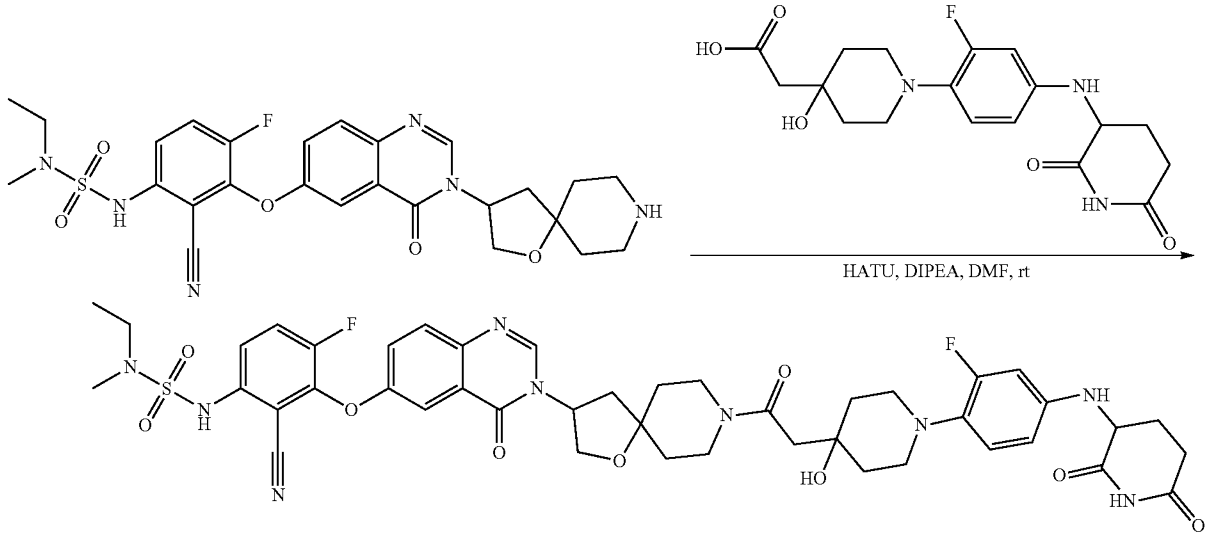

The target compound was prepared via HATU mediated acid-amine coupling reaction (Procedure A-E). The amide coupling was carried out using 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (350 mg, 521.90 μmol), 2-[1-[4-[(2,6-dioxo-3-piperidyl)amino]-2-fluoro-phenyl]-4-hydroxy-4-piperidyl]acetic acid (260.43 mg, 626.28 μmol), N,N-diisopropylethylamine (337.25 mg, 2.61 mmol, 454.51 μL) and HATU (238.13 mg, 626.28 μmol). The crude compound was purified by preparative HPLC (Mobile phase: 10 mM FORMIC ACID in $H_2O$/acetonitrile) to afford the target compound 3-[6-[2-cyano-3-[[ethyl(methyl)sulfamoyl]amino]-6-fluoro-phenoxy]-4-oxo-quinazolin-3-yl]-8-[2-[1-[4-[(2,6-dioxo-3-piperidyl)amino]-2-fluoro-phenyl]-4-hydroxy-4-piperidyl]acetyl]-1-oxa-8-azaspiro[4.5]decane (120 mg, 124.41 μmol, 24% yield) as an off-white solid. LCMS m/z (ESI): 918.4 $[M+H]^+$. $^1$HNMR (400 MHz, DMSO-$d_6$): δ=10.79 (s, 1H), 10.20 (s, 1H), 8.36 (s, 1H), 7.87 (t, J=10.00 Hz, 1H), 7.80 (d, J=9.20 Hz, 1H), 7.71 (dd, J=3.20, 9.00 Hz, 1H), 7.50 (dd, J=4.00, 9.00 Hz, 1H), 7.37 (d, J=3.20 Hz, 1H), 6.85 (t, J=9.20 Hz, 1H), 6.50 (dd, J=2.00, 15.00 Hz, 1H), 6.40-6.45 (m, 1H), 5.78 (d, J=7.20 Hz, 1H), 5.30-5.35 (m, 1H), 4.93 (s, 1H), 4.21-4.31 (m, 1H), 4.05-4.20 (m, 2H), 3.70-3.81 (m, 1H), 3.58-3.67 (m, 1H), 3.44-3.55 (m, 1H), 3.40-3.29 (m, 1H), 3.17 (q, J=7.20 Hz, 2H), 2.65-2.91 (m, 5H), 2.80 (s, 3H), 2.51-2.60 (m, 2H), 2.32-2.41 (m, 1H), 2.02-2.12 (m, 2H), 1.49-1.90 (m, 10H), 1.06 (t, J=6.80 Hz, 3H).

Example 28

6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline

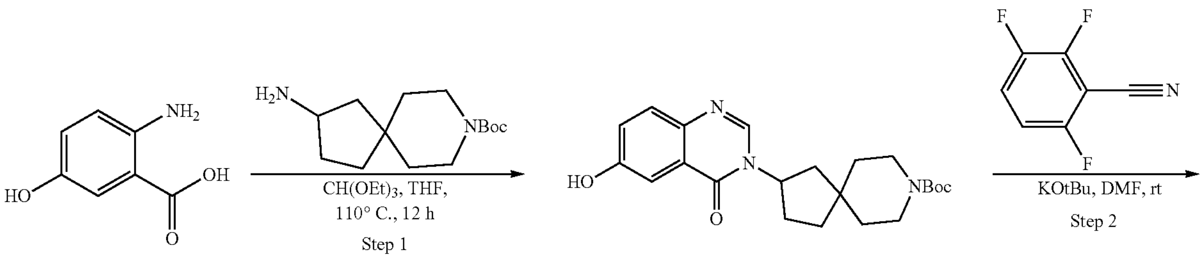

-continued

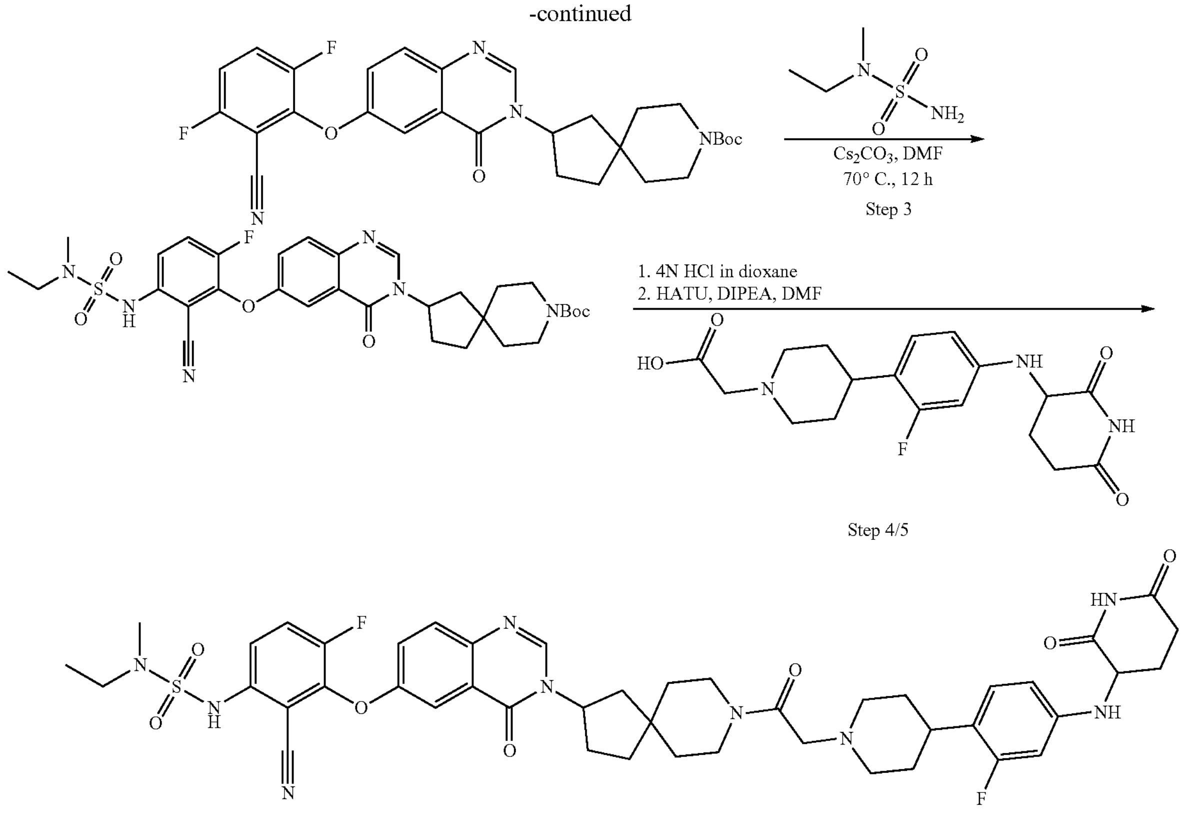

Step 1: The quinazolinone intermediate was synthesized by following general procedure for cyclization (Procedure A-A) using tert-butyl 3-amino-8-azaspiro[4.5]decane-8-carboxylate (4 g, 15.73 mmol), triethyl orthoformate (5,83 g, 39.3 mmol), 2-amino-5-hydroxy-benzoic acid (2.41 g, 15.73 mmol) to afford tert-butyl 3-(6-hydroxy-4-oxo-quinazolin-3-yl)-8-azaspiro[4.5]decane-8-carboxylate (5.8 g, 11.56 mmol, 74% yield) as a pale brown solid. LCMS m/z (ESI): 400.3 $[M+H]^+$ Step 2: The O-arylated quinazolinone intermediate was synthesized by following general procedure for O-arylation (Procedure A-B) using tert-butyl 3-(6-hydroxy-4-oxo-quinazolin-3-yl)-8-azaspiro[4.5]decane-8-carboxylate (5.8 g, 14.52 mmol), potassium tert-butoxide (3.26 g, 29.04 mmol) and 2,3,6-trifluorobenzonitrile (2.74 g, 17.42 mmol, 2.01 mL). The crude compound was purified by silica gel flash column chromatography using 50% ethyl acetate in petroleum ether as the eluent yielding tert-butyl 3-[6-(2-cyano-3,6-difluoro-phenoxy)-4-oxo-quinazolin-3-yl]-8-azaspiro[4.5]decane-8-carboxylate (7.3 g, 6.80 mmol, 47% yield) as a pale yellow liquid. LCMS m/z (ESI): 481.1 $[M+H-{}^tBu]^+$ Step 3: The sulfamoylated quinazolinone intermediate was synthesized by following Procedure A-C using tert-butyl 3-[6-(2-cyano-3,6-difluoro-phenoxy)-4-oxo-quinazolin-3-yl]-8-azaspiro[4.5]decane-8-carboxylate (7.0 g, 13.05 mmol), [methyl(sulfamoyl)amino]ethane (3.61 g, 26.09 mmol) and cesium carbonate (12.75 g, 39.14 mmol). The crude material was purified by silica gel flash column chromatography using 60% ethyl acetate in petroleum ether as the eluent yielding tert-butyl 3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (4.6 g, 4.71 mmol, 36% yield). LCMS m/z (ESI): 653.2$[M-H]^-$ Step 4: The requisite amine was synthesized by HCl mediated N-Boc deprotection (Procedure A-D). N-Boc deprotection was done on tert-butyl 3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (4.1 g, 6.26 mmol) using 4M HCl in 1,4-dioxane (41 mL). The crude compound was triturated with pet ether (2×20 mL) and concentrated to afford the HCl salt of 3-(8-azaspiro[4.5]decan-3-yl)-6-[2-cyano-3-[[ethyl(methyl)sulfamoyl]amino]-6-fluoro-phenoxy]-4-oxo-quinazoline (3.5 g, 5.00 mmol, 80% yield). LCMS m/z (ESI): 555.1 $[M+H]^+$ Step 5: The target compound was prepared via HATU mediated acid-amine coupling reaction (Procedure A-E). The amide coupling was carried out using 3-(8-azaspiro[4.5]decan-3-yl)-6-[2-cyano-3-[[ethyl(methyl)sulfamoyl]amino]-6-fluoro-phenoxy]-4-oxo-quinazoline (1 g, 1.80 mmol), HATU (1.03 g, 2.70 mmol), 2-[4-[4-[(2,6-dioxo-3-piperidyl)amino]-2-fluoro-phenyl]-1-piperidyl]acetic acid (655.17 mg, 1.80 mmol) and N,N-diisopropylethylamine (1.17 g, 9.01 mmol, 1.57 mL). The crude compound was purified by reverse phase column purification using 0.1% Ammonium acetate in acetonitrile as a eluent to afford 6-[2-cyano-3-[[ethyl(methyl)sulfamoyl]amino]-6-fluoro-phenoxy]-3-[8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (505 mg, 553.48 μmol, 31% yield) as an off-white solid. LCMS m/z (ESI): 900.3 $[M+H]^+$; $^1$HNMR (400 MHz, DMSO-$d_6$): δ=10.81 (s, 1H), 9.75 (bs, 1H), 8.43 (d, J=3.60 Hz, 1H), 7.76 (d, J=9.20 Hz, 1H), 7.64 (dd, J=2.80, 8.80 Hz, 1H), 7.41-7.60 (m, 1H), 7.34 (s, 1H), 7.30-7.34 (m, 1H), 6.95-7.08 (m, 1H), 6.48 (d, J=7.20 Hz, 1H), 6.46 (d, J=12.40 Hz, 1H), 6.08 (d, J=7.60 Hz, 1H), 5.01-5.11 (m, 1H), 4.29-4.38 (m, 1H), 3.56-3.66 (m, 1H), 3.18-3.50 (m, 3H), 3.04 (q, J=6.80 Hz, 2H), 2.61-2.85 (m, 5H), 2.67 (s, 3H), 2.46-2.55 (m, 2H), 2.05-2.20 (m, 5H), 1.70-1.95 (m, 8H), 1.40-1.65 (m, 5H), 1.03 (t, J=7.20 Hz, 3H).

Example 29

4-[6-[2-cyano-3-[[ethyl(methyl)sulfamoyl]amino]-6-fluorophenoxy]-4-oxoquinazolin-3-yl]-9-[2-[4-[4-[(2,6-dioxopiperidin-3-yl)amino]-2-fluorophenyl]piperidin-1-yl]acetyl]-1-oxa-9-azaspiro[5.5]undecane

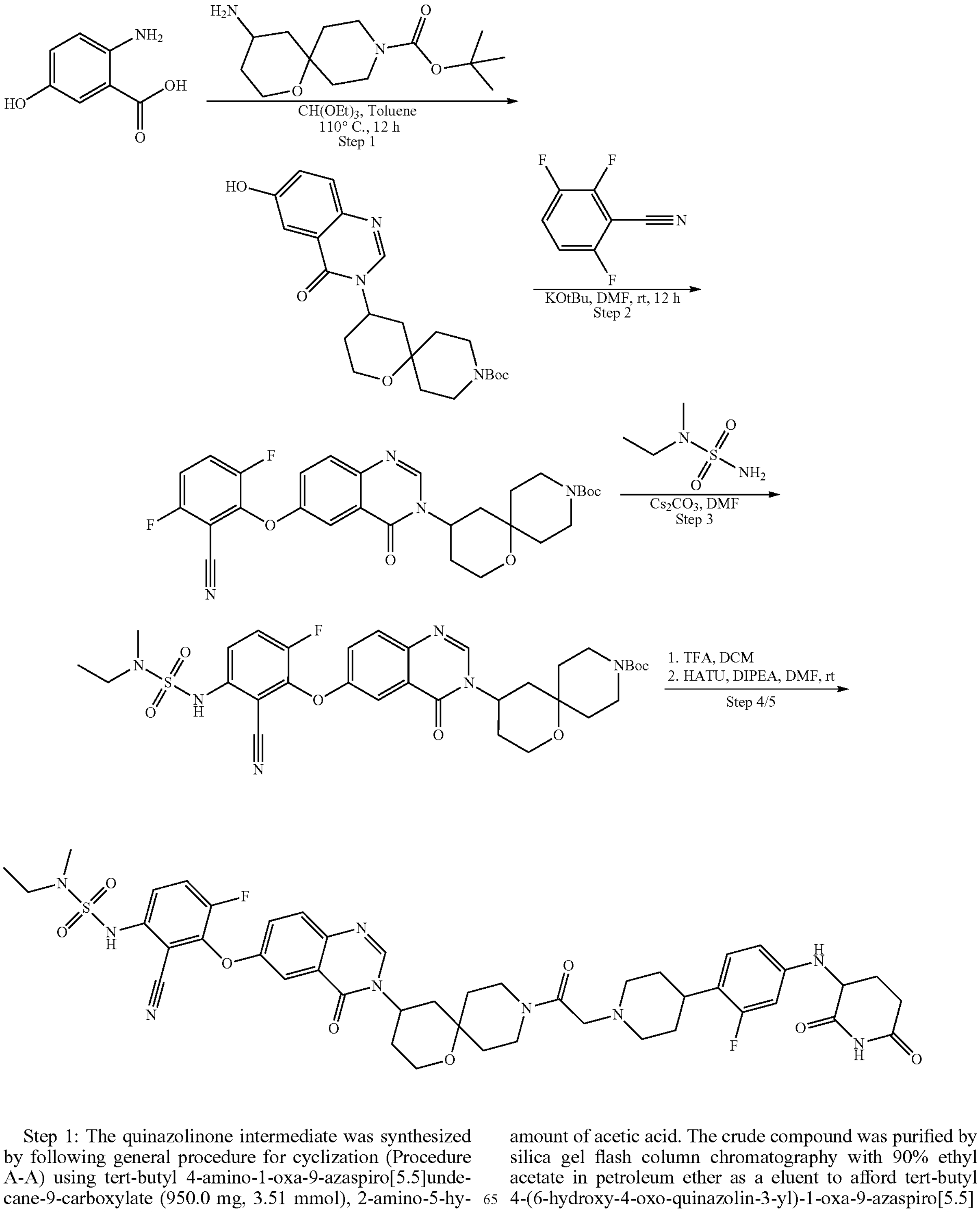

Step 1: The quinazolinone intermediate was synthesized by following general procedure for cyclization (Procedure A-A) using tert-butyl 4-amino-1-oxa-9-azaspiro[5.5]undecane-9-carboxylate (950.0 mg, 3.51 mmol), 2-amino-5-hydroxy-benzoic acid (645.69 mg, 4.22 mmol), Triethyl orthoformate (54.81 mg, 369.87 μmol, 61.52 μL) and a catalytic amount of acetic acid. The crude compound was purified by silica gel flash column chromatography with 90% ethyl acetate in petroleum ether as a eluent to afford tert-butyl 4-(6-hydroxy-4-oxo-quinazolin-3-yl)-1-oxa-9-azaspiro[5.5]undecane-9-carboxylate (700 mg, 1.52 mmol, 43% yield) as a yellow solid. LCMS m/z (ESI): 416.2 $[M+H]^+$ Step 2: The O-arylated quinazolinone intermediate was synthesized by following general procedure for O-arylation (Procedure A-B) using tert-butyl 4-(6-hydroxy-4-oxo-8,8a-dihydroquinazolin-3-yl)-1-oxa-9-azaspiro[5.5]undecane-9-carboxylate (650.0 mg, 1.56 mmol), potassium tert-butoxide (192.17 mg, 1.71 mmol) and 2,3,6-trifluorobenzonitrile (269.03 mg, 1.71 mmol, 197.82 μL). The crude compound was purified by silica gel flash column chromatography with 80% ethyl acetate in petroleum ether as the eluent to afford tert-butyl 4-[6-(2-cyano-3,6-difluoro-phenoxy)-4-oxo-quinazolin-3-yl]-1-oxa-9-azaspiro[5.5]undecane-9-carboxylate (750.0 mg, 997.61 μmol, 64% yield) as a yellow liquid. LCMS m/z (ESI): 497.0 $[M+H]^+$ Step 3: The sulfamoylated quinazolinone intermediate was synthesized by following Procedure A-C using tert-butyl 4-[6-(2-cyano-3,6-difluoro-phenoxy)-4-oxo-quinazolin-3-yl]-1-oxa-9-azaspiro[5.5]undecane-9-carboxylate (700.0 mg, 1.27 mmol), cesium carbonate (1.03 g, 3.17 mmol) and [methyl(sulfamoyl)amino]ethane (350.12 mg, 2.53 mmol) to afford the desired tert-butyl 4-[6-[2-cyano-3-[[ethyl(methyl)sulfamoyl]amino]-6-fluoro-phenoxy]-4-oxo-quinazolin-3-yl]-1-oxa-9-azaspiro[5.5]undecane-9-carboxylate (570.0 mg, 674.74 μmol, 53% yield) as crude product. LCMS m/z (ESI): 669.1 $[M-H]^-$ Step 4: The requisite amine was synthesized by TFA mediated N-Boc deprotection (Procedure A-D). N-Boc deprotection was done on tert-butyl 4-[6-[2-cyano-3-[[ethyl(methyl)sulfamoyl]amino]-6-fluoro-phenoxy]-4-oxo-quinazolin-3-yl]-1-oxa-9-azaspiro[5.5]undecane-9-carboxylate (600.0 mg, 894.52 μmol) and Trifluoroacetic acid (203.99 mg, 1.79 mmol, 137.83 μL). The product obtained was triturated with diethyl ether (2×15 mL), dried under reduced pressure to afford the TFA salt of 4-[6-[2-cyano-3-[[ethyl(methyl)sulfamoyl]amino]-6-fluoro-phenoxy]-4-oxo-quinazolin-3-yl]-1-oxa-9-azaspiro[5.5]undecane (650.0 mg, 652.22 μmol, 73% yield) as a yellow liquid. LCMS m/z (ESI): 571.0 $[M+H]^+$ Step 5: The target compound was prepared via HATU mediated acid-amine coupling reaction (Procedure A-E). The amide coupling was carried out using 4-[6-[2-cyano-3-[[ethyl(methyl)sulfamoyl]amino]-6-fluoro-phenoxy]-4-oxo-quinazolin-3-yl]-1-oxa-9-azaspiro[5.5]undecane (600.0 mg, 1.05 mmol), N,N-diisopropylethylamine (679.47 mg, 5.26 mmol, 915.73 μL), 2-[4-[4-[(2,6-dioxo-3-piperidyl)amino]-2-fluoro-phenyl]-1-piperidyl]acetic acid (382.08 mg, 1.05 mmol) and HATU (1.26 mmol, 479.6 mg). The crude compound was purified by reverse phase column chromatography by using eluted with 37% acetonitrile in 0.1% formic acid in water to afford 4-[6-[2-cyano-3-[[ethyl(methyl)sulfamoyl]amino]-6-fluoro-phenoxy]-4-oxo-quinazolin-3-yl]-9-[2-[4-[4-[(2,6-dioxo-3-piperidyl)amino]-2-fluoro-phenyl]-1-piperidyl]acetyl]-1-oxa-9-azaspiro[5.5]undecane (78.63 mg, 80.29 μmol, 8% yield) as an off-white solid. LCMS m/z (ESI): 916.3 $[M+H]^+$; $^1$HNMR (400 MHz, DMSO-$d_6$): δ=10.81 (s, 1H), 8.47 (d, J=6.00 Hz, 1H), 7.79 (d, J=8.80 Hz, 1H), 7.70-7.81 (m, 1H), 7.68 (dt, J=2.80, 8.80 Hz, 1H), 7.40-7.49 (m, 1H), 7.37 (t, J=3.20 Hz, 1H), 6.93-7.01 (m, 1H), 6.50 (d, J=8.00 Hz, 1H), 6.47 (d, J=14.00 Hz, 1H), 6.11 (d, J=7.60 Hz, 1H), 4.96-5.01 (m, 1H), 3.95-4.35 (m, 4H), 3.78-3.90 (m, 2H), 3.30-3.55 (m, 4H), 3.08 (q, J=6.80 Hz, 2H), 2.85-3.20 (m, 3H), 2.65-2.80 (m, 1H), 2.71 (s, 3H), 2.48-2.60 (m, 2H), 2.20-2.35 (m, 1H), 1.70-2.12 (m, 10H), 1.30-1.65 (m, 3H), 1.00 (t, J=7.20 Hz, 3H)

Example 30

9-[6-[2-cyano-3-[[ethyl(methyl)sulfamoyl]amino]-6-fluorophenoxy]-4-oxoquinazolin-3-yl]-3-[2-[4-[4-[(2,6-dioxopiperidin-3-yl)amino]-2-fluorophenyl]piperidin-1-yl]acetyl]-3-azaspiro[5.5]undecane

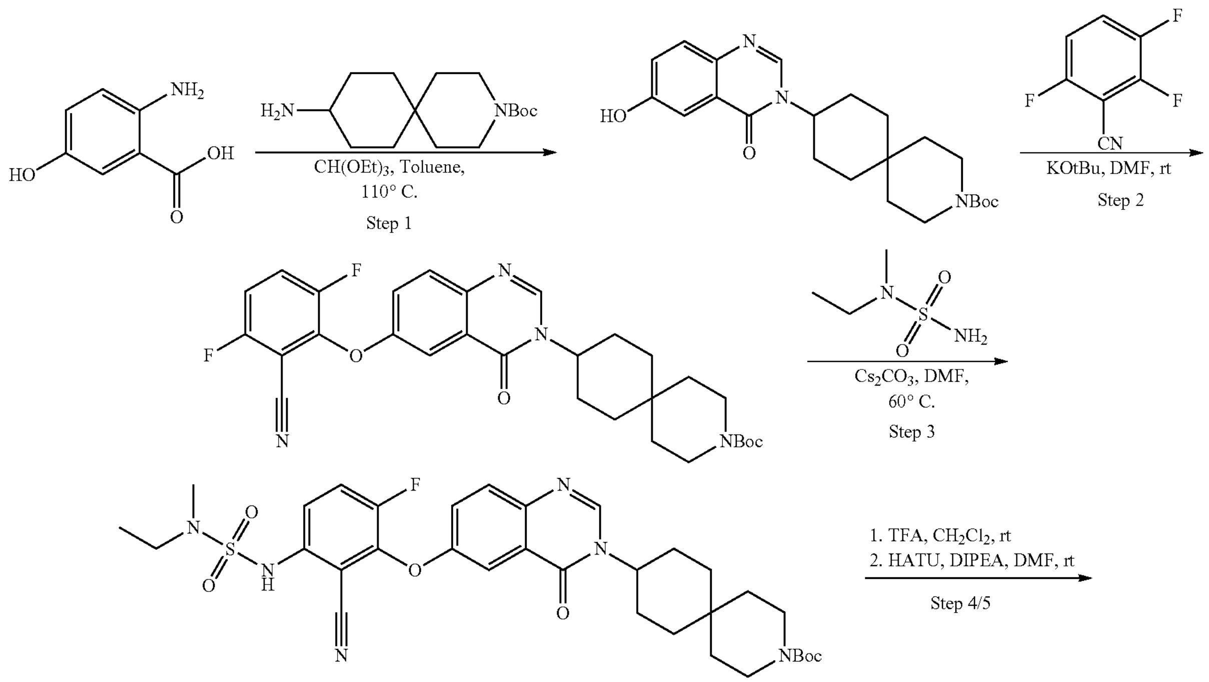

-continued

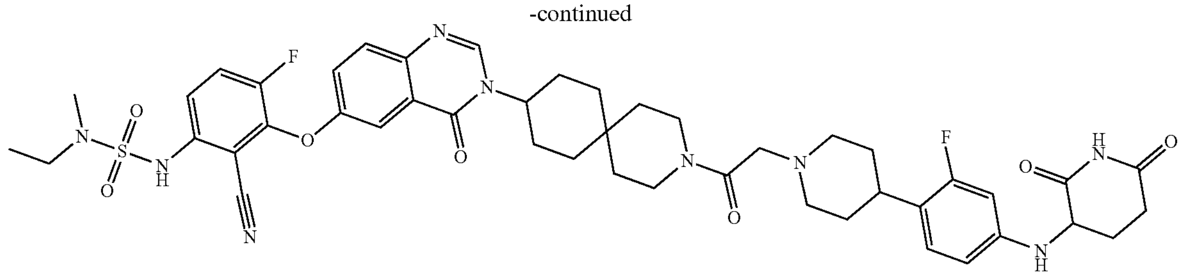

Step 1: The quinazolinone intermediate was synthesized by following general procedure for cyclization (Procedure A-A) using 2-amino-5-hydroxy-benzoic acid (520 mg, 3.40 mmol), tert-butyl 9-amino-3-azaspiro[5.5]undecane-3-carboxylate (911.38 mg, 3.40 mmol) and Triethyl orthoformate (1.26 g, 8.49 mmol, 1.41 mL). The crude product was purified by silica gel flash column chromatography (50 g silica; 0-100% ethyl acetate in petroleum ether) to afford tert-butyl 9-(6-hydroxy-4-oxo-quinazolin-3-yl)-3-azaspiro[5.5]undecane-3-carboxylate (1.05 g, 2.23 mmol, 66% yield) as an off-white solid. LCMS m/z (ESI): 414.3 $[M+H]^+$ Step 2: The O-arylated quinazolinone intermediate was synthesized by following the general procedure for O-arylation (Procedure A-B) using tert-butyl 9-(6-hydroxy-4-oxo-quinazolin-3-yl)-3-azaspiro[5.5]undecane-3-carboxylate (1.05 g, 2.54 mmol), potassium tert-butoxide (341.91 mg, 3.05 mmol), 2,3,6-trifluorobenzonitrile (438.79 mg, 2.79 mmol, 322.64 µL). The crude product was purified by silica gel flash column chromatography (50 g silica; 0-100% ethyl acetate in petroleum ether) to afford tert-butyl 9-[6-(2-cyano-3,6-difluoro-phenoxy)-4-oxo-quinazolin-3-yl]-3-azaspiro[5.5]undecane-3-carboxylate (1.08 g, 1.54 mmol, 61% yield) as a light brown solid. LCMS m/z (ESI): 550.9 $[M+H]^+$ Step 3: The sulfamoylated quinazolinone intermediate was synthesized by following Procedure A-C using tert-butyl 9-[6-(2-cyano-3,6-difluoro-phenoxy)-4-oxo-quinazolin-3-yl]-3-azaspiro[5.5]undecane-3-carboxylate (1.08 g, 1.96 mmol), cesium carbonate (1.92 g, 5.88 mmol), [methyl(sulfamoyl)amino]ethane (542.12 mg, 3.92 mmol). The crude product was purified by silica gel flash column chromatography eluted with 0-100% ethyl acetate in petroleum ether to afford tert-butyl 9-[6-[2-cyano-3-[[ethyl(methyl)sulfamoyl]amino]-6-fluoro-phenoxy]-4-oxo-quinazolin-3-yl]-3-azaspiro[5.5]undecane-3-carboxylate (580 mg, 793.42 µmol, 40% yield) as a light brown solid. LCMS m/z (ESI): 669.0 $[M+H]^+$ Step 4: The requisite amine was synthesized by TFA mediated N-Boc deprotection (Procedure A-D). N-Boc deprotection was done on tert-butyl 9-[6-(2-cyano-3,6-difluoro-phenoxy)-4-oxo-quinazolin-3-yl]-3-azaspiro [5.5]undecane-3-carboxylate (580 mg, 1.05 mmol) using Trifluoroacetic acid (1.20 g, 10.53 mmol, 811.55 µL). The crude compound was triturated with diethyl ether (2×30 mL) and dried to afford the TFA salt of 9-[6-[2-cyano-3-[[ethyl(methyl)sulfamoyl]amino]-6-fluoro-phenoxy]-4-oxo-quinazolin-3-yl]-3-azaspiro[5.5]undecane (570 mg, 655.88 µmol, 62% yield) as a light brown semi solid. LCMS m/z (ESI): 569.2 $[M+H]^+$ Step 5: The target compound was prepared via HATU mediated acid-amine coupling reaction (Procedure A-E). The amide coupling was carried out using 9-[6-[2-cyano-3-[[ethyl(methyl)sulfamoyl]amino]-6-fluoro-phenoxy]-4-oxo-quinazolin-3-yl]-3-azaspiro[5.5]undecane (570 mg, 834.94 µmol), 2-[4-[4-[(2,6-dioxo-3-piperidyl)amino]-2-fluoro-phenyl]-1-piperidyl]acetic acid (333.84 mg, 834.94 µmol), N,N-diisopropylethylamine (539.54 mg, 4.17 mmol, 727.14 µL) and HATU (476.20 mg, 1.25 mmol). The resulting crude compound was purified by reverse phase column chromatography [Mobile-phase A: 0.1% ammonium acetate in water, Mobile-phase B: acetonitrile; column: 100 g RediSep® Rf C18] to afford the 9-[6-[2-cyano-3-[[ethyl(methyl)sulfamoyl]amino]-6-fluoro-phenoxy]-4-oxo-quinazolin-3-yl]-3-[2-[4-[4-[(2,6-dioxo-3-piperidyl)amino]-2-fluoro-phenyl]-1-piperidyl]acetyl]-3-azaspiro[5.5]undecane (287 mg, 312.32 µmol, 37% yield) as an off-white solid. LCMS m/z (ESI): 914.4 $[M+H]^+$; $^1$HNMR (400 MHz, DMSO-$d_6$): δ=10.81 (s, 1H), 9.77 (s, 1H), 8.51 (d, J=6.40 Hz, 1H), 7.76 (d, J=8.80 Hz, 1H), 7.64 (dd, J=2.80, 9.00 Hz, 1H), 7.50-7.58 (m, 1H), 7.35 (s, 1H), 7.31-7.35 (m, 1H), 6.99 (t, J=8.40 Hz, 1H), 6.49 (d, J=7.20 Hz, 1H), 6.46 (d, J=12.00 Hz, 1H), 6.08 (d, J=7.60 Hz, 1H), 4.52-4.60 (m, 1H), 4.30-4.38 (m, 1H), 3.60-3.95 (m, 2H), 3.40-3.51 (m, 4H), 3.21-3.31 (m, 2H), 3.04 (q, J=6.80 Hz, 2H), 2.57-2.79 (m, 3H), 2.64 (s, 3H), 2.48-2.57 (m, 2H), 1.98-2.15 (m, 3H), 1.60-1.95 (m, 11H), 1.22-1.45 (m, 4H), 1.03 (t, J=7.20 Hz, 3H).

Example 31

6-[2-cyano-3-[[ethyl(methyl)sulfamoyl]amino]-6-fluorophenoxy]-3-[[7-[2-[4-[4-[(2,6-dioxopiperidin-3-yl)amino]-2-fluorophenyl]piperidin-1-yl]acetyl]-7-azaspiro[3.5]nonan-2-yl]methyl]-4-oxoquinazoline

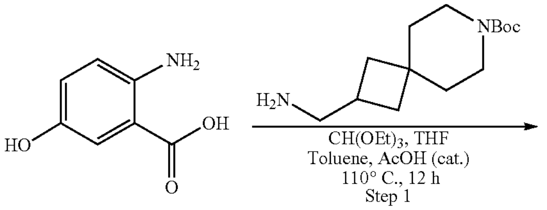

-continued

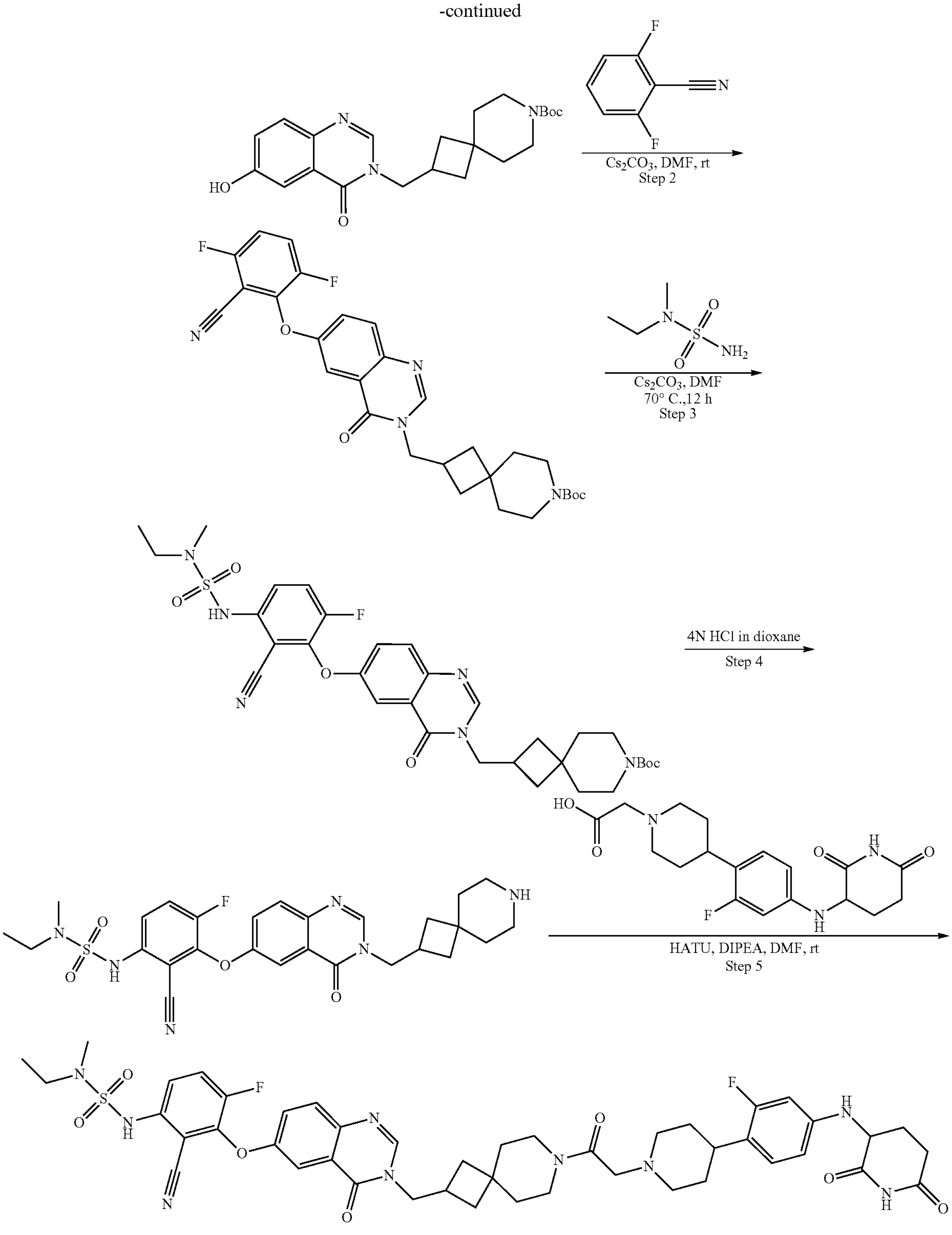

Step 1: The quinazolinone intermediate was synthesized by following general procedure for cyclization (Procedure A-A) using 2-amino-5-hydroxy-benzoic acid (63 mg, 411.40 μmol) in Toluene (30 mL), Triethyl orthoformate (61 mg, 411.61 μmol, 68.46 μL), acetic acid (2.51 mg, 41.75 μmol, 2.39 μL) and tert-butyl 2-(aminomethyl)-7-azaspiro[3.5]nonane-7-carboxylate (104.11 mg, 409.28 μmol). The desired compound was purified from the crude reaction by silica gel flash column chromatography using 50% ethyl acetate in petroleum ether as the eluent to afford tert-butyl 2-[(6-hydroxy-4-oxo-quinazolin-3-yl)methyl]-7-azaspiro[3.5]nonane-7-carboxylate (120 mg, 222.29 μmol, 54% yield) as a brown solid. LCMS m/z (ESI): 398.1 $[M-H]^-$ Step 2: The O-arylated quinazolinone intermediate was synthesized by following general procedure for O-arylation (Procedure A-B) using tert-butyl 2-[(6-hydroxy-4-oxo-quinazolin-3-yl)methyl]-7-azaspiro[3.5]nonane-7-carboxylate (650 mg, 1.63 mmol), cesium carbonate (1.33 g, 4.07 mmol) and 2,3,6-trifluorobenzonitrile (300 mg, 1.91 mmol, 220.59 μL). The desired compound was purified from the crude reaction by silica gel flash column chromatography using 50% ethyl acetate in petroleum ether as the eluent to afford tert-butyl 2-[[6-(2-cyano-3,6-difluoro-phenoxy)-4-oxo-quinazolin-3-yl]methyl]-7-azaspiro[3.5]nonane-7-carboxylate (600 mg, 1.03 mmol, 63% yield) as an off-white solid. LCMS m/z (ESI): 481.0 [M−$^t$Bu+H]$^+$.

Step 3: The sulfamoylated quinazolinone intermediate was synthesized by following Procedure A-C using tert-butyl 2-[[6-(2-cyano-3,6-difluoro-phenoxy)-4-oxo-quinazolin-3-yl]methyl]-7-azaspiro[3.5]nonane-7-carboxylate (600 mg, 1.12 mmol), cesium carbonate (364.34 mg, 1.12 mmol) and [methyl(sulfamoyl)amino]ethane (154.52 mg, 1.12 mmol). The desired compound was purified from the crude mixture by silica gel flash column chromatography using 4% MeOH in dichloromethane as the eluent to afford tert-butyl 2-[[6-[2-cyano-3-[[ethyl(methyl)sulfamoyl]amino]-6-fluoro-phenoxy]-4-oxo-quinazolin-3-yl]methyl]-7-azaspiro[3.5]nonane-7-carboxylate (320 mg, 420.31 μmol, 38% yield) as a light brown solid. LCMS m/z (ESI): 653.1 [M−H]$^-$.

Step 4: The requisite amine was synthesized by 4M HCl in Dioxane mediated N-Boc deprotection (Procedure A-D). N-Boc deprotection was done on tert-butyl 2-[[6-[2-cyano-3-[[ethyl(methyl)sulfamoyl]amino]-6-fluoro-phenoxy]-4-oxo-quinazolin-3-yl]methyl]-7-azaspiro[3.5]nonane-7-carboxylate (320 mg, 488.74 μmol) using hydrogen chloride, 4M in 1,4-dioxane, 99% (4 M, 4 mL) to afford the HCl salt of 3-(7-azaspiro[3.5]nonan-2-ylmethyl)-6-[2-cyano-3-[[ethyl(methyl)sulfamoyl]amino]-6-fluoro-phenoxy]-4-oxo-quinazoline (300 mg, 385.72 μmol, 79% yield) as a light brown solid. LCMS m/z (ESI): 555.3 [M+H]$^+$.

Step 5: The target compound was prepared via HATU mediated acid-amine coupling reaction (Procedure A-E). The amide coupling was carried out using 3-(7-azaspiro[3.5]nonan-2-ylmethyl)-6-[2-cyano-3-[[ethyl(methyl)sulfamoyl]amino]-6-fluoro-phenoxy]-4-oxo-quinazoline (300 mg, 507.53 μmol) and 2-[4-[4-[(2,6-dioxo-3-piperidyl)amino]-2-fluoro-phenyl]-1-piperidyl]acetic acid (184.43 mg, 461.25 μmol), N,N-diisopropylethylamine (262.38 mg, 2.03 mmol, 353.61 μL) and HATU (192.98 mg, 507.53 μmol). The crude compound was purified by reverse phase column chromatography eluted with 45% acetonitrile in 0.1% ammonium acetate in water to afford product 6-[2-cyano-3-[[ethyl(methyl)sulfamoyl]amino]-6-fluoro-phenoxy]-3-[[7-[2-[4-[4-[(2,6-dioxo-3-piperidyl)amino]-2-fluoro-phenyl]-1-piperidyl]acetyl]-7-azaspiro[3.5]nonan-2-yl]methyl]-4-oxo-quinazoline (85 mg, 94.26 μmol, 19% yield) as an off-white solid. LCMS m/z (ESI): 900.3 [M+H]$^+$; $^1$HNMR (400 MHz, DMSO-$d_6$): δ 10.80 (s, 1H), 9.58 (s, 1H), 8.38 (s, 1H), 7.75 (d, J=9.20 Hz, 1H), 7.63 (dd, J=9.00, 3.20 Hz, 1H), 7.40 (bs, 1H), 7.32 (d, J=2.80 Hz, 1H), 7.28 (bs, 1H), 6.97 (s, 1H), 6.45 (d, J=14.80 Hz, 2H), 6.05 (d, J=5.60 Hz, 1H), 4.33-4.30 (m, 1H), 4.02 (d, J=4.40 Hz, 2H), 3.41-3.39 (m, 4H), 3.00 (d, J=7.20 Hz, 3H), 2.74-2.70 (m, 2H), 2.68-2.67 (m, 7H), 2.08-2.07 (m, 1H), 1.87-1.85 (m, 5H), 1.72 (bs, 4H), 1.62-1.54 (m, 4H), 1.52-1.46 (m, 2H), 1.03 (t, J=7.20 Hz, 3H).

Example 32

6-[2-cyano-3-[[ethyl(methyl)sulfamoyl]amino]-6-fluorophenoxy]-3-[2-[2-[4-[4-[(2,6-dioxopiperidin-3-yl)amino]-2-fluorophenyl]piperidin-1-yl]acetyl]-2-azaspiro[4.5]decan-8-yl]-4-oxoquinazoline

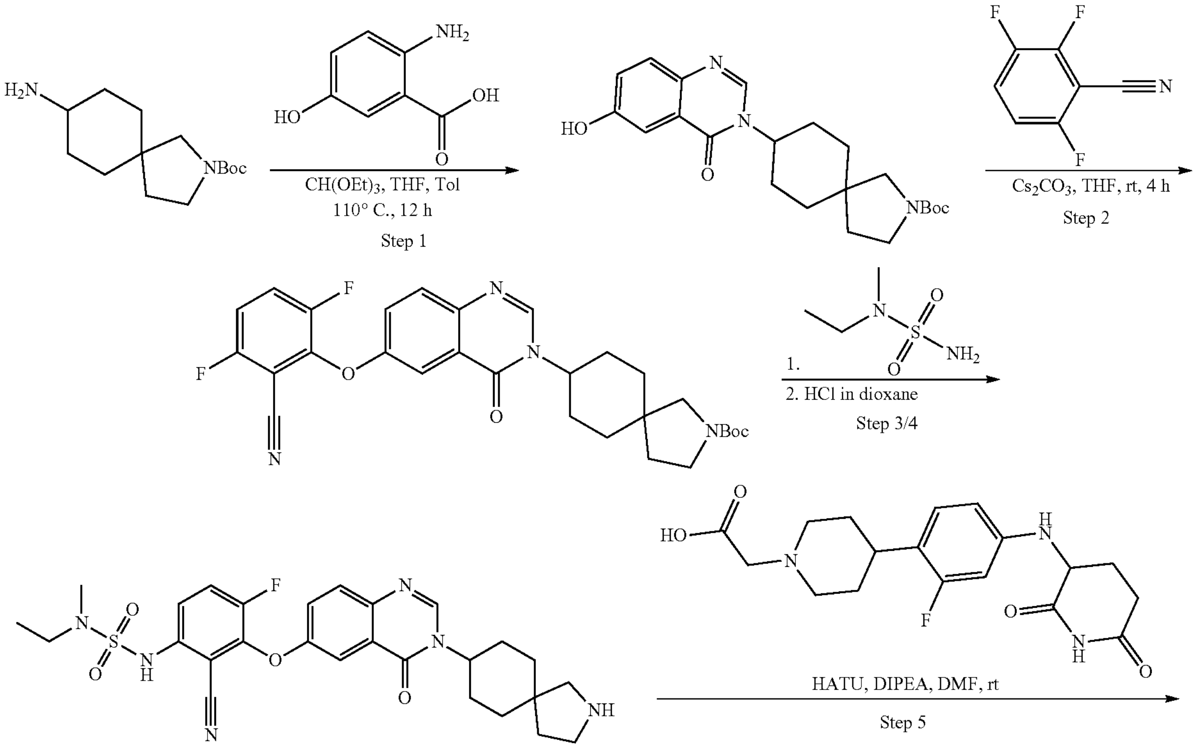

-continued

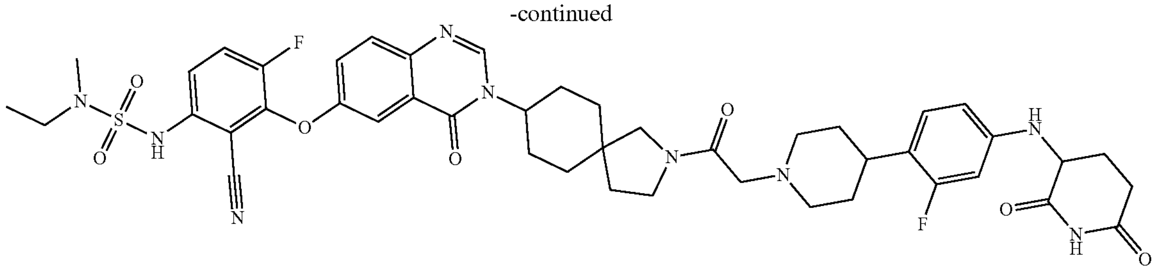

Step 1: The quinazolinone intermediate was synthesized by following the general procedure for cyclization (Procedure A-A) using 2-amino-5-hydroxy-benzoic acid (628.51 mg, 4.10 mmol), Triethyl orthoformate (658.95 mg, 4.45 mmol, 739.56 μL), acetic acid (20.54 mg, 342.02 μmol, 19.56 μL). the desired product was purified from the crude reaction by silica gel flash column chromatography using 40-55% ethyl acetate in petroleum ether as the eluent to afford tert-butyl 8-(6-hydroxy-4-oxo-quinazolin-3-yl)-2-azaspiro[4.5]decane-2-carboxylate (720 mg, 1.50 mmol, 44% yield). LCMS m/z (ESI): 400.2 [M+H]$^+$.

Step 2: The O-arylated quinazolinone intermediate was synthesized by following general procedure for O-arylation (Procedure A-B) using tert-butyl 8-(6-hydroxy-4-oxo-quinazolin-3-yl)-2-azaspiro[4.5]decane-2-carboxylate (720.00 mg, 1.80 mmol), 2,3,6-trifluorobenzonitrile (311.45 mg, 1.98 mmol, 229.01 μL) and cesium carbonate (1.76 g, 5.41 mmol). The desired product was purified from the crude reaction by silica gel flash column chromatography using 30-45% ethyl acetate in petroleum ether as eluent to afford tert-butyl 8-[6-(2-cyano-3,6-difluoro-phenoxy)-4-oxo-quinazolin-3-yl]-2-azaspiro[4.5]decane-2-carboxylate (317 mg, 554.75 μmol, 31% yield). LCMS m/z (ESI): 537.2 [M+H]$^+$.

Step 3: The sulfamoylated quinazolinone intermediate was synthesized by following Procedure A-C using tert-butyl 8-[6-(2-cyano-3,6-difluoro-phenoxy)-4-oxo-quinazolin-3-yl]-2-azaspiro[4.5]decane-2-carboxylate (300 mg, 559.11 μmol), cesium carbonate (546.50 mg, 1.68 mmol) and [methyl(sulfamoyl)amino]ethane (154.52 mg, 1.12 mmol) to afford tert-butyl 8-[6-[2-cyano-3-[[ethyl(methyl)sulfamoyl]amino]-6-fluoro-phenoxy]-4-oxo-quinazolin-3-yl]-2-azaspiro[4.5]decane-2-carboxylate (285 mg, 385.48 μmol, 69% yield). LCMS m/z (ESI): 655.4 [M+H]$^+$.

Step 4: The requisite amine was synthesized by HCl mediated N-Boc deprotection (Procedure A-D). N-Boc deprotection was done on tert-butyl 8-[6-[2-cyano-3-[[ethyl(methyl)sulfamoyl]amino]-6-fluoro-phenoxy]-4-oxo-quinazolin-3-yl]-2-azaspiro[4.5]decane-2-carboxylate (285 mg, 435.28 μmol) using 4.0M in dioxane (99.19 μL) to afford the HCl salt of 3-(2-azaspiro[4.5]decan-8-yl)-6-[2-cyano-3-[[ethyl(methyl)sulfamoyl]amino]-6-fluoro-phenoxy]-4-oxo-quinazoline (300 mg, 407.56 μmol, 94% yield). LCMS m/z (ESI): 555.0 [M+H]$^+$.

Step 5: The target compound was prepared via HATU mediated acid-amine coupling reaction (Procedure A-E). The amide coupling was carried out using 3-(2-azaspiro[4.5]decan-8-yl)-6-[2-cyano-3-[[ethyl(methyl)sulfamoyl]amino]-6-fluoro-phenoxy]-4-oxo-quinazoline (300 mg, 540.90 μmol), 2-[4-[4-[(2,6-dioxo-3-piperidyl)amino]-2-fluoro-phenyl]-1-piperidyl]acetic acid (196.55 mg, 540.90 μmol), N,N-diisopropylethylamine (349.53 mg, 2.70 mmol, 471.06 μL), and HATU (226.23 mg, 594.99 μmol). The resulting crude reaction was purified by reverse phase column chromatography by using 100 g snap column eluting with 37% acetonitrile in 0.1% ammonium acetate in water to afford 6-[2-cyano-3-[[ethyl(methyl)sulfamoyl]amino]-6-fluoro-phenoxy]-3-[2-[2-[4-[4-[(2,6-dioxo-3-piperidyl)amino]-2-fluoro-phenyl]-1-piperidyl]acetyl]-2-azaspiro[4.5]decan-8-yl]-4-oxo-quinazoline (59.64 mg, 65.27 μmol, 12% yield) as an off-white solid. LCMS m/z (ESI): 900.3 [M+H]$^+$. $^1$HNMR (400 MHz, DMSO-$d_6$): δ=10.80 (s, 1H), 9.76 (s, 1H), 8.50 (d, J=2.00 Hz, 1H), 7.77 (d, J=8.80 Hz, 1H), 7.64 (dd, J=2.80, 9.00 Hz, 1H), 7.48-7.60 (m, 1H), 7.35 (s, 1H), 7.31-7.35 (m, 1H), 7.00 (t, J=8.00 Hz, 1H), 6.46 (d, J=12.40 Hz, 1H), 6.43 (d, J=11.60 Hz, 1H), 6.07 (d, J=7.60 Hz, 1H), 4.55-4.65 (m, 1H), 4.25-4.34 (m, 1H), 3.60-3.95 (m, 1H), 3.42-3.61 (m, 4H), 3.12-3.20 (m, 1H), 3.04 (q, J=6.80 Hz, 1H), 2.60-2.81 (m, 6H), 2.63 (s, 3H), 2.51-2.58 (m, 2H), 1.61-2.11 (m, 14H), 1.57 (t, J=12.80 Hz, 2H), 1.03 (t, J=7.20 Hz, 3H).

Example 33

(3S)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluoro-phenyl]piperidin-1-yl]acetyl]-1-oxa-8-azaspiro[4.5]decane

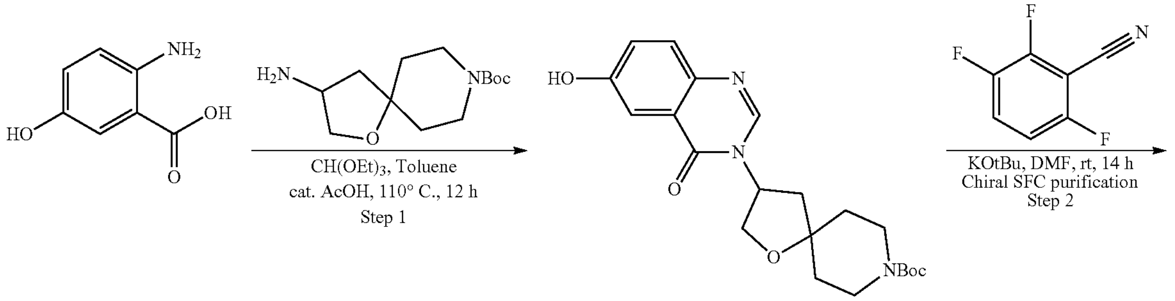

-continued

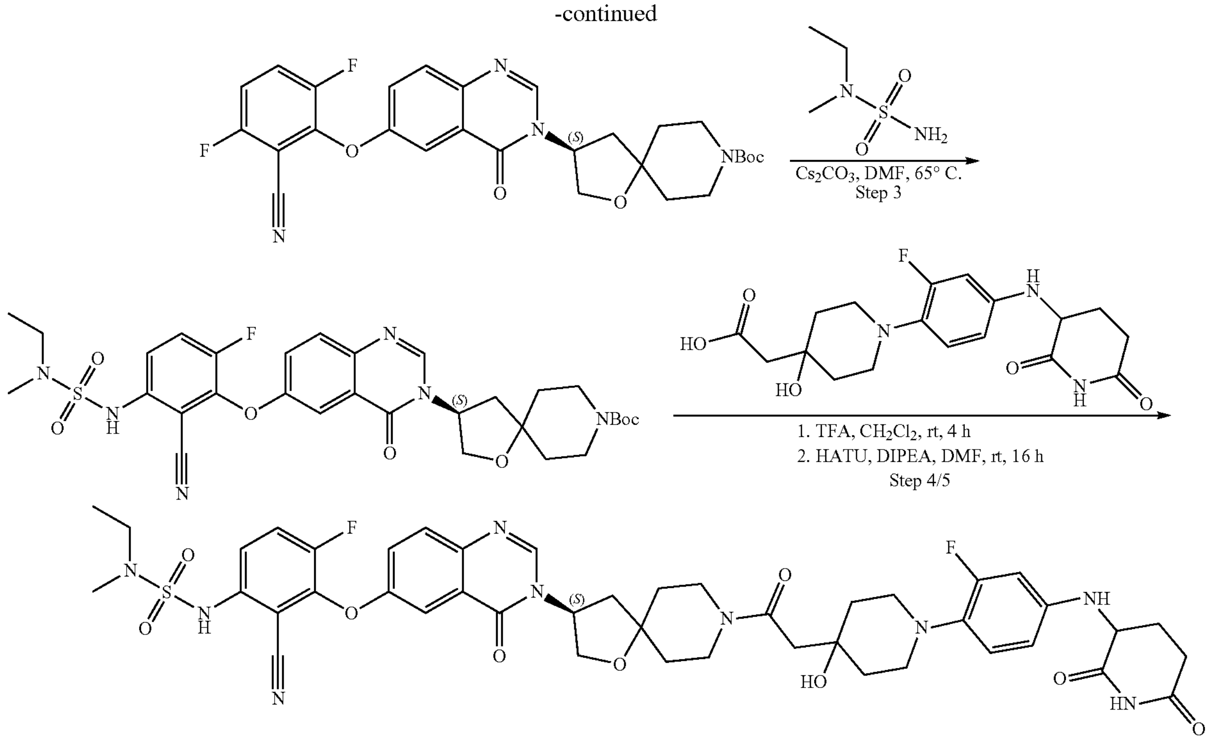

Step 1: The quinazolinone intermediate was synthesized by following general procedure for cyclization (Procedure A-A) using tert-butyl 3-amino-1-oxa-8-azaspiro[4.5]decane-8-carboxylate (2 g, 7.80 mmol), 2-amino-5-hydroxybenzoic acid (1.19 g, 7.80 mmol) and Triethyl orthoformate (1.39 g, 9.36 mmol, 1.56 mL) to afford tert-butyl 3-(6-hydroxy-4-oxo-quinazolin-3-yl)-1-oxa-8-azaspiro[4.5]decane-8-carboxylate (1.5 g, 3.09 mmol, 40% yield) as a pale brown thick oil. LCMS m/z (ESI): 402.3 $[M+H]^+$ Step 2: The O-arylated quinazolinone intermediate was synthesized by following the general procedure for O-arylation (Procedure A-B) using tert-butyl 3-(6-hydroxy-4-oxo-quinazolin-3-yl)-1-oxa-8-azaspiro[4.5]decane-8-carboxylate (1.8 g, 4.48 mmol), potassium tert-butoxide (603.75 mg, 5.38 mmol) and 2,3,6-trifluorobenzonitrile (774.79 mg, 4.93 mmol, 569.70 μL). The crude compound was purified by silica gel flash column chromatography eluting with 80 to 90% of ethyl acetate in petroleum ether to afford racemic tert-butyl 3-[6-(2-cyano-3,6-difluoro-phenoxy)-4-oxo-quinazolin-3-yl]-1-oxa-8-azaspiro[4.5]decane-8-carboxylate. This racemic compound was subjected for chiral SFC method development followed by purification using Lux A1 chiral column(Solvent system-30% of (0.5% Isopropyl amine in Isopropyl alcohol, Temperature—35° C.) to afford tert-butyl (S)-3-(6-(2-cyano-3,6-difluorophenoxy)-4-oxoquinazolin-3(4H)-yl)-1-oxa-8-azaspiro[4.5]decane-8-carboxylate (first eluting isomer, 400 mg, 678.87 μmol, 15% yield) and tert-butyl (R)-3-(6-(2-cyano-3,6-difluorophenoxy)-4-oxoquinazolin-3(4H)-yl)-1-oxa-8-azaspiro[4.5]decane-8-carboxylate(second eluting isomer, 410 mg) as a pale brown solid. LCMS m/z (ESI): 483.1 $[M+H-{}^tBu]^+$ Note: Stereochemistry at the chiral centre after chiral SFC purification was arbitrarily assigned. The First eluted isomer stereochemistry was arbitrary assigned as S-enantiomer and Second eluted isomer stereochemistry was arbitrary assigned as R-enantiomer.

Step 3: The sulfamoylated quinazolinone intermediate was synthesized by following Procedure A-C using tert-butyl (3S)-3-[6-(2-cyano-3,6-difluoro-phenoxy)-4-oxo-quinazolin-3-yl]-1-oxa-8-azaspiro[4.5]decane-8-carboxylate (410 mg, 761.32 μmol), [methyl(sulfamoyl)amino]ethane (157.81 mg, 1.14 mmol) and cesium carbonate (620.1 mg, 1.9 mmol) to afford tert-butyl (3S)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (471 mg, 670.36 μmol, 88% yield) as a pale brown oil. LCMS m/z (ESI): 655.21 $[M-H]^-$ Step 4: The requisite amine was synthesized by TFA mediated N-Boc deprotection (Procedure A-D). N-Boc deprotection was done on tert-butyl (3S)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (470 mg, 715.67 μmol) using TFA (408.02 mg, 3.58 mmol, 275.69 μL) to afford the TFA salt of (3S)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (436 mg, 494.10 μmol, 69% yield). LCMS m/z (ESI): 557.1 $[M+H]^+$ Step 5: The target compound was prepared via HATU mediated acid-amine coupling reaction (Procedure A-E). The amide coupling was carried out using (3S)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (436 mg, 650.13 μmol), 2-[4-[4-[(2,6-dioxo-3-piperidyl)amino]-2-fluoro-phenyl]-1-piperidyl]acetic acid (285.95 mg, 715.15 μmol), N,N-diisopropylethylamine (420.12 mg, 3.25 mmol, 566.19 μL) and HATU (271.92 mg, 715.15 μmol). The crude compound was purified by preparative-HPLC (Mobile phase: 10 mM formic acid in water\acetonitrile) and fractions were lyophilized to afford the (3S)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl] acetyl]-1-oxa-8-azaspiro[4.5]decane (220 mg, 231.12 μmol, 36% yield) as an off-white solid. LCMS m/z (ESI): 902.3 $[M+H]^+$; $^1$HNMR (400 MHz, DMSO-$d_6$): δ=10.82 (s, 1H), 9.52 (bs, 1H), 8.36 (d, J=2.00 Hz, 1H), 7.78-7.81 (m, 1H), 7.80 (d, J=8.80 Hz, 1H), 7.70 (dd, J=2.80, 8.80 Hz, 1H), 7.48 (dd, J=4.00, 9.20 Hz, 1H), 7.37 (d, J=3.20 Hz, 1H), 6.95-7.05 (m, 1H), 6.50 (d, J=7.60 Hz, 1H), 6.47 (d, J=12.80 Hz, 1H), 6.12 (d, J=7.60 Hz, 1H), 5.28-5.38 (m, 1H), 4.10-4.40 (m, 5H), 3.76-3.85 (m, 1H), 3.32-3.61 (m, 5H), 3.15 (q, J=7.20 Hz, 2H), 3.02-3.11 (m, 1H), 2.85-2.95 (m, 1H), 2.65-2.81 (m, 1H), 2.78 (s, 3H), 2.50-2.62 (m, 2H), 2.38-2.48 (m, 1H), 1.96-2.15 (m, 4H), 1.52-1.95 (m, 7H), 1.05 (t, J=7.20 Hz, 3H).

Example 34

(3R)-3-[6-[2-cyano-3-[[ethyl(methyl)sulfamoyl] amino]-6-fluorophenoxy]-4-oxoquinazolin-3-yl]-8-[2-[4-[4-[(2,6-dioxopiperidin-3-yl)amino]-2-fluoro-phenyl]piperidin-1-yl]acetyl]-1-oxa-8-azaspiro [4.5] decane

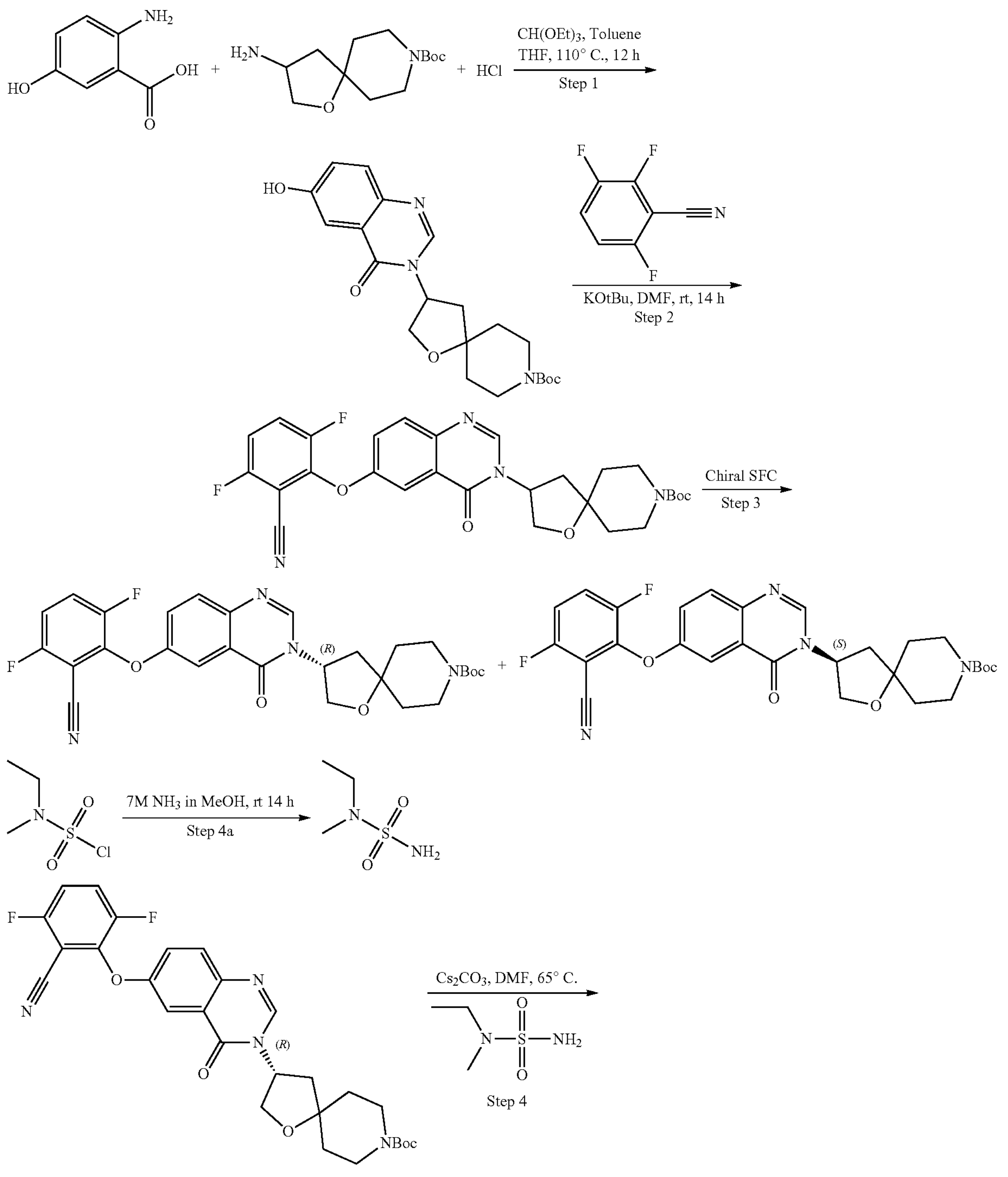

-continued

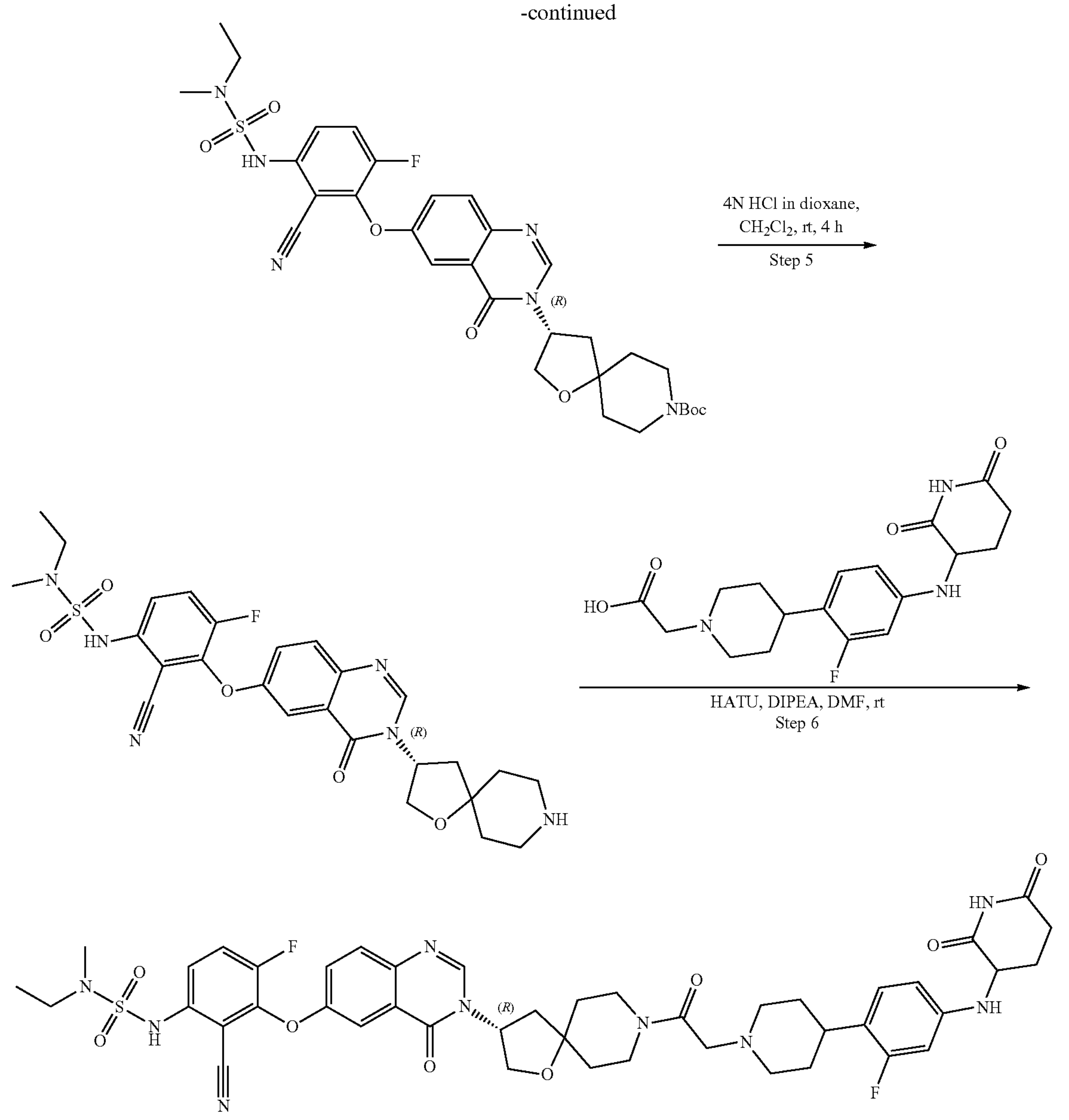

Step 1: The quinazolinone intermediate was synthesized by following the general procedure for cyclization (Procedure A-A) using tert-butyl 3-amino-1-oxa-8-azaspiro[4.5]decane-8-carboxylate·HCl (15 g, 51.23 mmol), 2-amino-5-hydroxy-benzoic acid (7.85 g, 51.23 mmol), Triethyl orthoformate (10.63 g, 71.72 mmol, 11.93 mL). The crude compound was triturated with 20% ethyl acetate in petroleum ether to afford tert-butyl 3-(6-hydroxy-4-oxo-quinazolin-3-yl)-1-oxa-8-azaspiro[4.5]decane-8-carboxylate (12.0 g, 25.29 mmol, 49% yield) as a brown solid. LCMS m/z (ESI): 402.20[M+H]$^+$ Step 2: The O-arylated quinazolinone intermediate was synthesized by following the general procedure for O-arylation (Procedure A-B) using tert-butyl 3-(6-hydroxy-4-oxo-quinazolin-3-yl)-1-oxa-8-azaspiro[4.5]decane-8-carboxylate (12.0 g, 25.11 mmol), cesium carbonate (24.54 g, 75.33 mmol) and 2,3,6-trifluorobenzonitrile (5.13 g, 32.64 mmol, 3.77 mL). The crude compound was purified by column chromatography on silica gel, eluting with 60% ethyl acetate in petroleum ether to afford tert-butyl 3-[6-(2-cyano-3,6-difluoro-phenoxy)-4-oxo-quinazolin-3-yl]-1-oxa-8-azaspiro[4.5]decane-8-carboxylate (9.0 g, 16.54 mmol, 66% yield) as off-white solid along with 1.8 g. LCMS m/z (ESI): 539.2[M+H]$^+$.

Step 3: Tert-butyl 3-[6-(2-cyano-3,6-difluoro-phenoxy)-4-oxo-quinazolin-3-yl]-1-oxa-8-azaspiro[4.5]decane-8-carboxylate (9.0 g, 16.54 mmol) was subjected for chiral SFC purification to resolute the enantiomers. The racemic intermediate was chirally resolved using chiral SFC method using Lux A1 column (250 mm×30 mm; 5 micron) eluting with 40% isopropyl alcohol/$CO_2$ with 0.5% iso-propylamine in methanol as co-solvent (Flow Rate: 4 ml/min; Outlet Pressure: 100 bar) to afford 3.5 g of first eluting isomer and 3.7 g of second eluting isomer.

The configuration of the two isomers is arbitrarily assigned as follows.

Enantiomer 1: First eluting isomer was arbitrarily assigned as tert-butyl (S)-3-(6-(2-cyano-3,6-difluoro-phenoxy)-4-oxoquinazolin-3(4H)-yl)-1-oxa-8-azaspiro[4.5]decane-8-carboxylate Enantiomer 2: Second eluting isomer was arbitrarily assigned as tert-butyl (R)-3-(6-(2-cyano-3,6-difluoro-phenoxy)-4-oxoquinazolin-3(4H)-yl)-1-oxa-8-azaspiro[4.5]decane-8-carboxylate.

Step 4a: To a solution of N-ethyl-N-methyl-sulfamoyl chloride (10 g, 63.44 mmol, 7.81 mL) in MeOH (20 mL) was added 7M ammonia in MeOH (7 M, 30 mL) at 0° C. and stirred the reaction mixture at room temperature for 14 h. The reaction mixture was concentrated under reduced pressure to afford crude product. The crude compound was diluted with water (150 mL), extracted with ethyl acetate (2×150 mL). The combined organic layers were washed with sodium bicarbonate solution (100 ml), brine (100 ml), dried over sodium sulfate and concentrated under reduced pressure to afford crude which was purified by column chromatography on silica gel, eluted with 40% ethyl acetate in petroleum ether to afford [methyl(sulfamoyl)amino]ethane (7.0 g, 48.12 mmol, 76% yield) as colorless liquid. $^1$HNMR (400 MHz, DMSO-$d_6$): δ=6.65 (s, 2H), 2.98 (q, J=7.20 Hz, 2H), 2.61 (s, 3H), 1.09 (t, J=7.20 Hz, 3H).

Step 4: The sulfamoylated quinazolinone intermediate was synthesized by following Procedure A-C using tert-butyl (3R)-3-[6-(2-cyano-3,6-difluoro-phenoxy)-4-oxo-quinazolin-3-yl]-1-oxa-8-azaspiro[4.5]decane-8-carboxylate (3.7 g, 6.87 mmol), cesium carbonate (5.60 g, 17.18 mmol) and [methyl(sulfamoyl)amino]ethane (1.42 g, 10.31 mmol). The crude compound was triturated with 10% dichloromethane in petroleum ether to afford tert-butyl (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (2.8 g, 3.58 mmol, 52% yield) as off-white solid LCMS m/z (ESI): 601.0 $[M+H-{}^tBu]^+$ Step 5: The requisite amine was synthesized by HCl mediated N-Boc deprotection (Procedure A-D). N-Boc deprotection was done on tert-butyl (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (2.7 g, 4.11 mmol) and 4M hydrogen chloride solution in 1,4-dioxane (4M, 36.68 mL). The reaction mixture was concentrated under reduced pressure to afford crude which was triturated with diethyl ether to afford the HCl salt of (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (2.7 g, 3.90 mmol, 95% yield) as a light brown solid. LCMS m/z (ESI): 557.0 $[M+H]^+$ Step 6: Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (800 mg, 1.35 mmol), 2-[4-[4-[(2,6-dioxo-3-piperidyl)amino]-2-fluoro-phenyl]-1-piperidyl]acetic acid (490.17 mg, 1.23 mmol), HATU (512.90 mg, 1.35 mmol) and N,N-diisopropylethylamine (697.35 mg, 5.40 mmol, 939.83 μL). The crude reaction mixture was purified by reverse phase column chromatography by using 30 g snap eluted with 50% acetonitrile in 0.1% formic acid in water to afford (3R)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (400 mg, 0.46 mmol, 33% yield) as off-white solid. LCMS m/z (ESI): 902.2$[M+H]^+$. $^1$HNMR (400 MHz, DMSO-$d_6$): δ=10.82 (s, 1H), 10.20 (bs, 1H), 9.60 (bs, 1H), 8.36 (d, J=2.00 Hz, 1H), 7.79-7.85 (m, 2H), 7.71 (dd, J=3.20, 8.80 Hz, 1H), 7.49 (dd, J=4.00, 9.40 Hz, 1H), 7.37 (d, J=2.80 Hz, 1H), 6.96 (d, J=8.80 Hz, 1H), 6.47-6.51 (m, 1H), 6.48 (d, J=12.40 Hz, 1H), 6.12 (d, J=7.60 Hz, 1H), 5.30-5.40 (m, 1H), 4.10-4.40 (m, 5H), 3.75-3.81 (m, 1H), 3.41-3.51 (m, 2H), 3.35-3.45 (m, 2H), 3.16 (q, J=6.80 Hz, 2H), 3.00-3.10 (m, 1H), 2.85-2.95 (m, 1H), 2.79 (s, 3H), 2.65-2.75 (m, 1H), 2.51-2.61 (m, 2H), 2.50-2.40 (m, 1H), 2.01-2.21 (m, 5H), 1.51-1.95 (m, 7H), 1.05 (t, J=7.20 Hz, 3H).

Example 35

4-[6-[6-[2-cyano-3-[[ethyl(methyl)sulfamoyl]amino]-6-fluorophenoxy]-4-oxoquinazolin-3-yl]-3-azabicyclo[3.1.0]hexan-3-yl]-N-[1-[4-[(2,6-dioxopiperidin-3-yl)amino]-2-fluorophenyl]piperidin-4-yl]benzamide

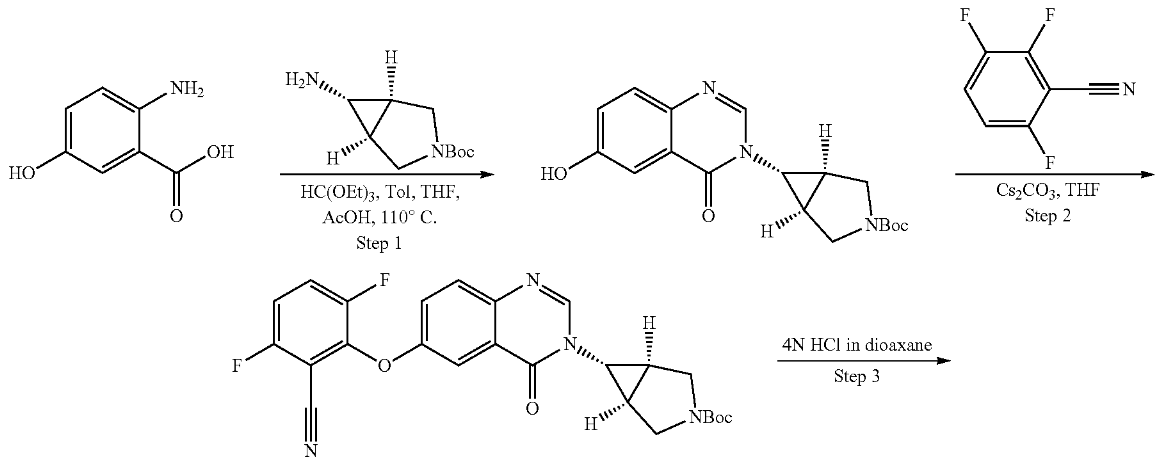

-continued

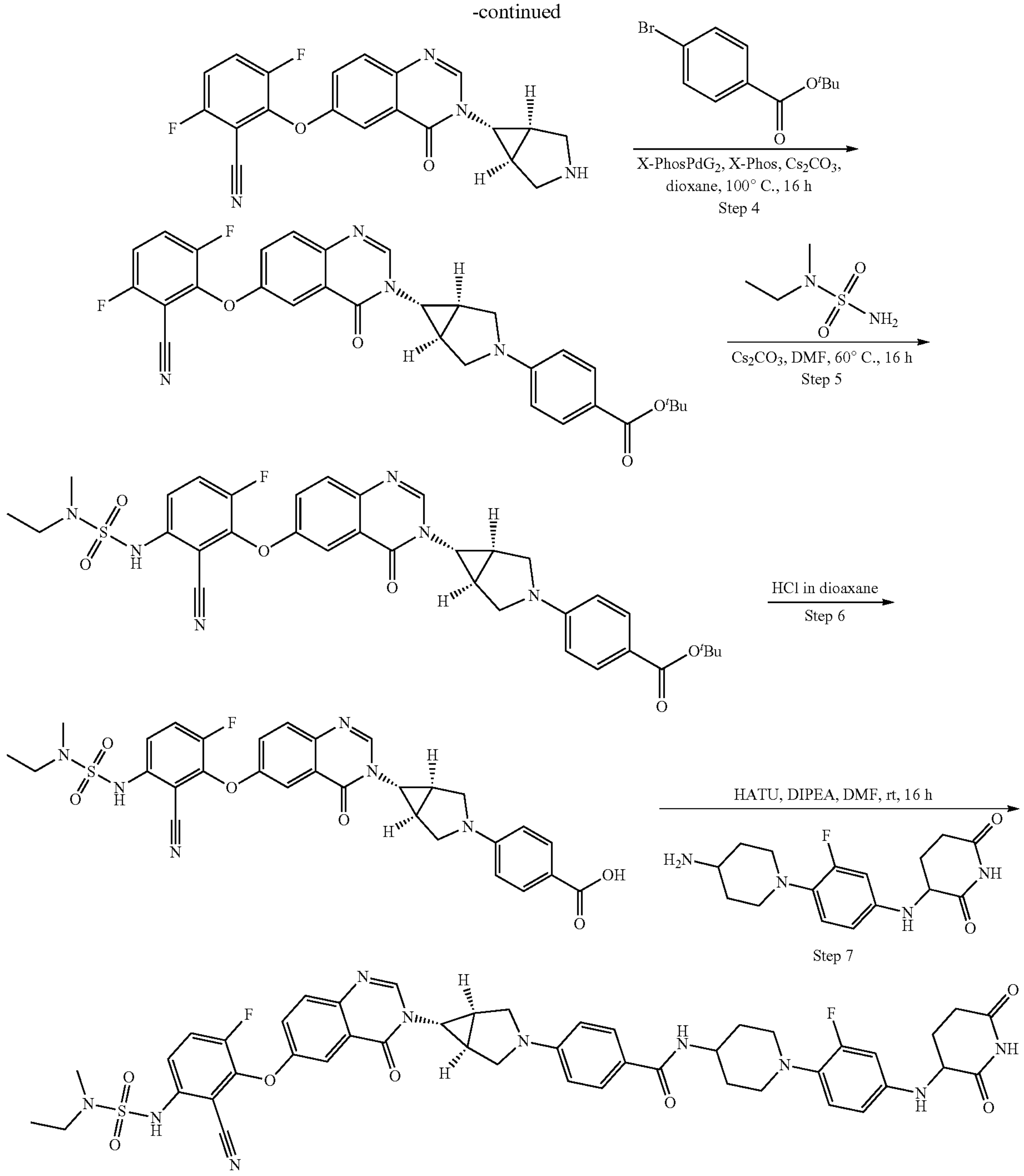

Step 1: quinazolinone intermediate was synthesized by following general procedure for cyclization (Procedure A-A) using tert-butyl (1R,5S)-6-amino-3-azabicyclo[3.1.0]hexane-3-carboxylate (1.10 g, 5.55 mmol), 2-amino-5-hydroxy-benzoic acid (1.02 g, 6.66 mmol) and Triethyl orthoformate (1.07 g, 7.21 mmol, 1.20 mL). The crude product was titrated with diethyl ether to afford desired tert-butyl (1R,5S)-6-(6-hydroxy-4-oxo-quinazolin-3-yl)-3-azabicyclo[3.1.0]hexane-3-carboxylate (1.1 g, 3.12 mmol, 56% yield) as off-white solid. LCMS m/z (ESI): 344.2 $[M+H]^+$ Step 2: O-arylated quinazolinone intermediate was synthesized by following general procedure for O-arylation (Procedure A-B) using tert-butyl (1R,5S)-6-(6-hydroxy-4-oxo-quinazolin-3-yl)-3-azabicyclo[3.1.0]hexane-3-carboxylate (1 g, 2.91 mmol), cesium carbonate (2.85 g, 8.74 mmol) and 2,3,6-trifluorobenzonitrile (548.99 mg, 3.49 mmol, 403.67 μL). The crude product was purified by column chromatography by eluting 1% methanol/dichloromethane to afford tert-butyl (1R,5S)-6-[6-(2-cyano-3,6-difluoro-phenoxy)-4-oxo-quinazolin-3-yl]-3-azabicyclo[3.1.0]hexane-3-carboxylate (1.2 g, 2.46 mmol, 84% yield) as off-white solid. LCMS m/z (ESI): 481.2 $[M+H]^+$ Step 3: To a stirred solution of tert-butyl 6-[6-(2-cyano-3,6-difluoro-phenoxy)-4-oxo-quinazolin-3-yl]-3-azabicyclo[3.1.0]hexane-3-carboxylate (1.1 g, 2.29 mmol) in Dioxane (15 mL) was added 4.0M hydrogen chloride solution in dioxane (1.04 mL) at 0° C. and continued the reaction at room temperature for 3 h. After completion, the reaction mixture was concentrated under reduced pressure to afford the crude compound. This crude compound was triturated with ethyl acetate to afford 2-[3-(3-azabicyclo[3.1.0]hexan-6-yl)-4-oxo-quinazolin-6-yl]oxy-3,6-difluoro-benzonitrile (950 mg, 2.26 mmol, 99% yield) as off-white solid. LCMS m/z (ESI): 381.0 $[M+H]^+$ Step 4: A solution of 2-[3-[(1R,5S)-3-azabicyclo[3.1.0]hexan-6-yl]-4-oxo-quinazolin-6-yl]oxy-3,6-difluoro-benzonitrile (1.0 g, 2.40 mmol) and tert-butyl 4-bromobenzoate (616.89 mg, 2.40 mmol) in dioxane (10 mL) was taken in a seal tube and added cesium carbonate (2.35 g, 7.20 mmol). The resulting reaction mixture was degassed with nitrogen for 10 minutes before X-phos-Pd-$G_2$ (188.74 mg, 239.92 μmol) and X-Phos (114.37 mg, 239.92 μmol) was added to the mixture at room temperature. The reaction mixture was subsequently heated at 100° C. for 16 h. After completion, water (300 mL) was added to the reaction mixture and it was extracted with ethyl acetate (3×200 mL). The combined organic layers were washed with brine solution (200 mL), dried over sodium sulfate, filtered, and concentrated under reduced pressure to afford the crude compound. The crude compound was purified by silica gel flash column chromatography eluting with 50-60% ethyl acetate in petroleum ether as a eluent to afford tert-butyl 4-[(1R,5S)-6-[6-(2-cyano-3,6-difluoro-phenoxy)-4-oxo-quinazolin-3-yl]-3-azabicyclo[3.1.0]hexan-3-yl]benzoate (750 mg, 1.11 mmol, 46.06% yield) as a pale yellow solid. LCMS m/z (ESI): 557.2 $[M+H]^+$ Step 5: The sulfamoylated quinazolinone intermediate was synthesized following Procedure A-C using tert-butyl 4-[(1R,5S)-6-[6-(2-cyano-3,6-difluoro-phenoxy)-4-oxo-quinazolin-3-yl]-3-azabicyclo[3.1.0]hexan-3-yl]benzoate (750 mg, 1.35 mmol), [methyl(sulfamoyl)amino]ethane (409.68 mg, 2.96 mmol) and cesium carbonate (1.10 g, 3.37 mmol). The crude compound was triturated with dichloromethane and petroleum ether to afford tert-butyl 4-[(1R,5S)-6-[6-[2-cyano-3-[[ethyl(methyl)sulfamoyl]amino]-6-fluoro-phenoxy]-4-oxo-quinazolin-3-yl]-3-azabicyclo[3.1.0]hexan-3-yl]benzoate (400 mg, 397.19 μmol, 29% yield) as a pale brown solid. LCMS m/z (ESI): 675.3 $[M+H]^+$ Step 6: The requisite amine was synthesized by HCl mediated N-Boc deprotection (Procedure A-D). N-Boc deprotection was performed on tert-butyl 4-[(1R,5S)-6-[6-(2-cyano-3,6-difluoro-phenoxy)-4-oxo-quinazolin-3-yl]-3-azabicyclo[3.1.0]hexan-3-yl]benzoate (250 mg, 449.19 μmol) in Dioxane (5 mL) using 4M hydrogen chloride in 1,4-dioxane (204.72 μL). The crude compound was triturated with ethyl acetate to afford the HCl salt of 4-[(1R,5S)-6-[6-[2-cyano-3-[[ethyl(methyl)sulfamoyl]amino]-6-fluoro-phenoxy]-4-oxo-quinazolin-3-yl]-3-azabicyclo[3.1.0]hexan-3-yl]benzoic acid (180 mg, 217.35 μmol, 48% yield) as a pale brown solid. LCMS m/z (ESI): 619.2 $[M+H]^+$ Step 7: The target compound was prepared via HATU mediated acid-amine coupling reaction (Procedure A-E). The amide coupling was carried out using 4-[6-[6-[2-cyano-3-[[ethyl(methyl)sulfamoyl]amino]-6-fluoro-phenoxy]-4-oxo-quinazolin-3-yl]-3-azabicyclo[3.1.0]hexan-3-yl]benzoic acid (150 mg, 242.47 μmol), 3-[4-(4-amino-1-piperidyl)-3-fluoro-anilino]piperidine-2,6-dione (103.82 mg, 290.96 μmol), N,N-diisopropylethylamine (156.68 mg, 1.21 mmol, 211.16 μL) and HATU(110.63 mg, 290.96 μmol). The crude compound was purified by reverse phase column chromatography eluting with 40% acetonitrile in 0.1% ammonium acetate in water and the fractions were lyophilized to afford 4-[6-[6-[2-cyano-3-[[ethyl(methyl)sulfamoyl]amino]-6-fluoro-phenoxy]-4-oxo-quinazolin-3-yl]-3-azabicyclo[3.1.0]hexan-3-yl]-N-[1-[4-[(2,6-dioxo-3-piperidyl)amino]-2-fluoro-phenyl]-4-piperidyl]benzamide (33.93 mg, 35.00 μmol, 14% yield) as a pale green solid. LCMS m/z (ESI): 921.4 $[M+H]^+$; $^1$HNMR (400 MHz, DMSO-$d_6$): δ=10.79 (s, 1H), 10.20 (s, 1H), 8.37 (s, 1H), 7.94 (d, J=8.00 Hz, 1H), 7.74-7.80 (m, 4H), 7.68 (dd, J=2.80, 8.80 Hz, 1H), 7.44-7.52 (m, 1H), 7.37 (d, J=2.80 Hz, 1H), 6.87 (t, J=9.60 Hz, 1H), 6.63 (d, J=8.80 Hz, 2H), 6.52 (dd, J=2.40, 15.20 Hz, 1H), 6.43 (d, J=8.80 Hz, 1H), 5.81 (d, J=7.60 Hz, 1H), 4.21-4.31 (m, 1H), 3.80-3.90 (m, 1H), 3.78 (d, J=10.00 Hz, 1H), 3.31-3.48 (m, 4H), 3.11-3.20 (m, 4H), 2.77 (s, 3H), 2.58-2.76 (m, 4H), 2.42 (s, 2H), 2.05-2.15 (m, 1H), 1.81-1.91 (m, 3H), 1.68-1.78 (m, 2H), 1.06 (t, J=6.80 Hz, 3H)ppm.

Example 36

3-[[6-[2-cyano-3-[[ethyl(methyl)sulfamoyl]amino]-6-fluorophenoxy]-4-oxoquinazolin-3-yl]methyl]-8-[2-[4-[4-[(2,6-dioxopiperidin-3-yl)amino]-2-fluoro-phenyl]piperidin-1-yl]acetyl]-1-oxa-8-azaspiro[4.5]decane

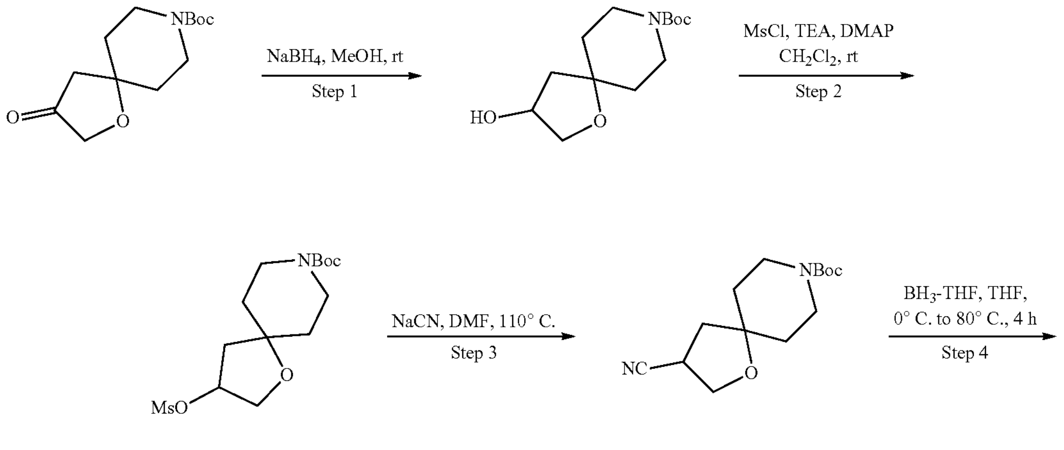

-continued

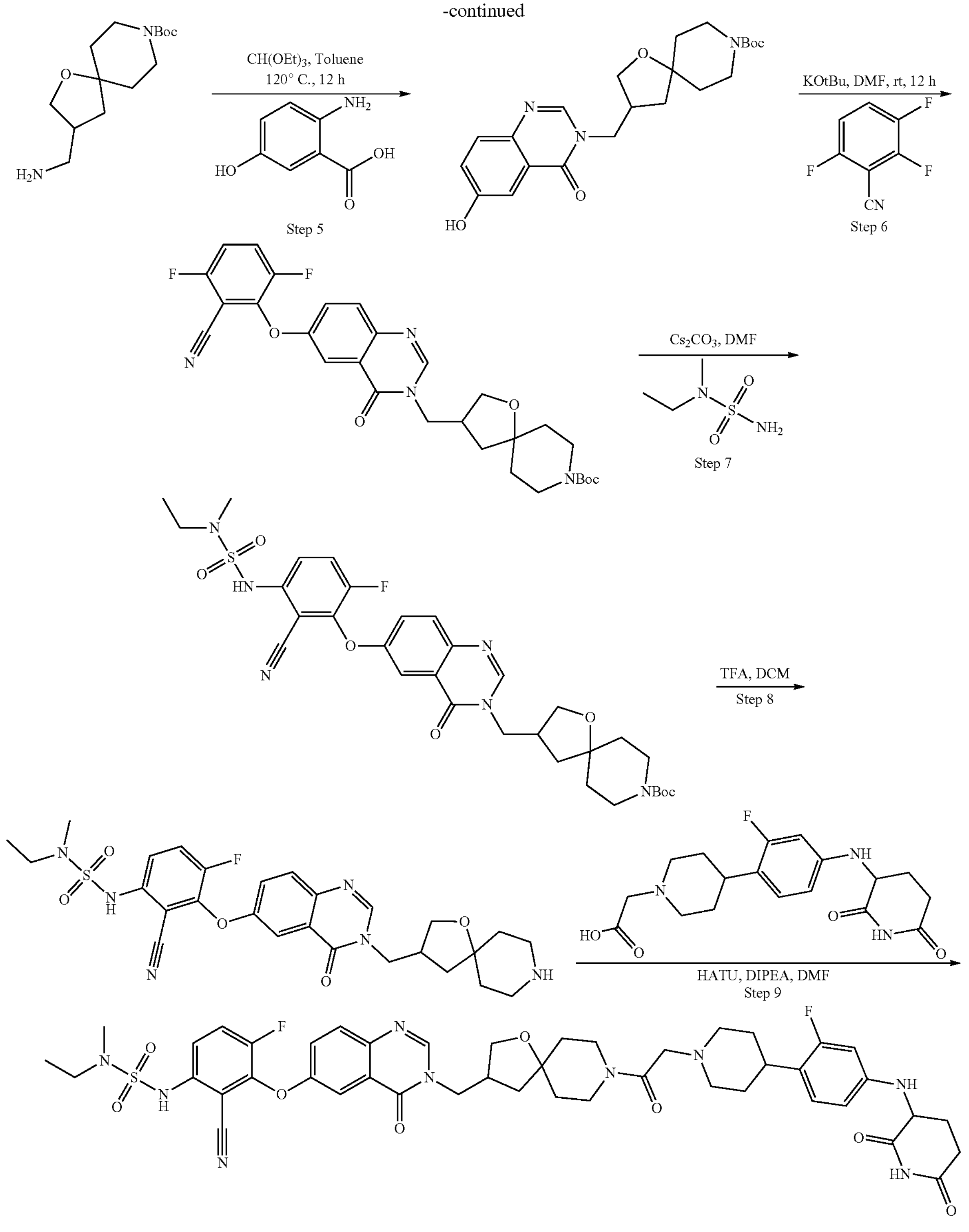

Step 1: To a stirred solution of tert-butyl 3-oxo-1-oxa-8-azaspiro[4.5]decane-8-carboxylate (0.5 g, 1.96 mmol) in methanol (20 mL) was added sodium borohydride (148.18 mg, 3.92 mmol) portion wise at 0° C. and the reaction was stirred at RT for 1 h. After completion, the reaction mixture was concentrated to afford crude material which was partitioned between ethyl acetate and water. The organic layer was dried over sodium sulfate and concentrated in vacuo to afford tert-butyl 3-hydroxy-1-oxa-8-azaspiro [4.5]decane-8-carboxylate (0.4 g, 1.55 mmol, 79% yield) as an off-white solid. LCMS m/z (ESI): 158.1 $[M+H]^+$.

Step 2: To a solution of tert-butyl 3-hydroxy-1-oxa-8-azaspiro[4.5]decane-8-carboxylate (0.4 g, 1.55 mmol) in dichloromethane (6 mL) was added N,N-diethylethanamine (393.24 mg, 3.89 mmol, 541.65 μL) and N,N-dimethylpyridin-4-amine (18.99 mg, 155.44 μmol) and the reaction mixture was cooled to 0° C. Methane sulfonyl chloride (213.68 mg, 1.87 mmol, 144.38 μL) was added dropwise to the reaction mixture at the same temperature and stirring was continued for 45 mins at RT. After completion, the reaction mixture was diluted with dichloromethane (30 mL) and washed with water (100 ml) followed by brine solution (50 mL). The organic phases were separated and dried over sodium sulfate and concentrated in vacuo to afford crude material which was purified using silica gel flash column chromatography (0-60% ethyl acetate/Pet ether) to afford tert-butyl 3-methylsulfonyloxy-1-oxa-8-azaspiro [4.5]decane-8-carboxylate (0.3 g, 885.47 μmol, 57% yield) as a gum. LCMS m/z (ESI): 236.0[M+H]$^+$.

Step 3: A solution of tert-butyl 3-methylsulfonyloxy-1-oxa-8-azaspiro[4.5]decane-8-carboxylate (0.3 g, 894.41 μmol) in N,N-Dimethylformamide (3 mL) was taken up in a sealed tube, and sodium cyanide (65.75 mg, 1.34 mmol) was added in one portion at room temperature. The tube was sealed and the resulting reaction mixture was heated to 110° C. for 16 h. After 16 h, the reaction mixture was cooled to room temperature, diluted with water and extracted with 5% methanol/dichloromethane (100 mL). The organic layer was separated and dried over sodium sulfate, concentrated in vacuo to afford crude material, which was purified using silica gel flash column chromatography (50% ethyl acetate in dichloromethane) to afford tert-butyl 3-cyano-1-oxa-8-azaspiro[4.5]decane-8-carboxylate (0.15 g, 444.93 μmol, 50% yield) as a white solid. LCMS m/z (ESI): 166.9[M+H]$^+$.

Step 4: To a stirred solution of tert-butyl 3-cyano-1-oxa-8-azaspiro[4.5]decane-8-carboxylate (1.40 g, 5.26 mmol) in Tetrahydrofuran (25 mL) at 0° C., was added Borane tetrahydrofuran complex solution (1.13 g, 13.14 mmol, 1M) dropwise and stirring was continued at the same temperature for 10 mins. The reaction mixture was warmed to room temperature and then refluxed at 80° C. for 4 hours under nitrogen atmosphere. The reaction mixture was then quenched with methanol (15 mL) and concentrated in vacuo to afford tert-butyl 3-(aminomethyl)-1-oxa-8-azaspiro[4.5] decane-8-carboxylate (1.40 g, 4.82 mmol, 92% yield) as crude material which was used in next step without further purification. LCMS m/z (ESI): 171.1 [M+H]$^+$.

Step 5: The quinazolinone intermediate was synthesized by following general procedure for cyclization (Procedure A-A) using tert-butyl 3-(aminomethyl)-1-oxa-8-azaspiro [4.5]decane-8-carboxylate (1.4 g, 5.18 mmol), 2-amino-5-hydroxy-benzoic acid (792.96 mg, 5.18 mmol) and Triethyl orthoformate (1.92 g, 12.95 mmol, 2.15 mL). The desired compound was purified from crude material by silica gel flash column chromatography using 0-80% ethyl acetate in petroleum ether as the eluent to afford tert-butyl 3-[(6-hydroxy-4-oxo-quinazolin-3-yl)methyl]-1-oxa-8-azaspiro [4.5]decane-8-carboxylate (1.4 g, 2.92 mmol, 56% yield) as an off-white solid. LCMS m/z (ESI): 360.2[M+H]$^+$.

Step 6: The O-arylated quinazolinone intermediate was synthesized by following general procedure for O-arylation (Procedure A-B) using tert-butyl 3-[(6-hydroxy-4-oxo-quinazolin-3-yl)methyl]-1-oxa-8-azaspiro[4.5]decane-8-carboxylate (1.4 g, 3.37 mmol),cesium carbonate (3.29 g, 10.11 mmol) and 2,3,6-trifluorobenzonitrile (1.06 g, 6.74 mmol, 778.44 μL). The desired compound was purified from the crude mixture by silica gel flash column chromatography using 0-10% methanol in dichloromethane as the eluent to afford tert-butyl 3-[[6-(2-cyano-3,6-difluoro-phenoxy)-4-oxo-quinazolin-3-yl]methyl]-1-oxa-8-azaspiro[4.5]decane-8-carboxylate (1.3 g, 2.12 mmol, 63% yield) as a solid. LCMS m/z (ESI): 453.2 [M+H]$^+$.

Step 7: The sulfamoylated quinazolinone intermediate was synthesized by following Procedure A-C using tert-butyl 3-[[6-(2-cyano-3,6-difluoro-phenoxy)-4-oxo-quinazolin-3-yl]methyl]-1-oxa-8-azaspiro[4.5]decane-8-carboxylate (1.2 g, 2.17 mmol), cesium carbonate (2.12 g, 6.52 mmol) and [methyl(sulfamoyl)amino]ethane (600.20 mg, 4.34 mmol). After completion, the reaction mixture was diluted with water (20 ml) and the solid was filtered off. The filtrate was extracted with ethyl acetate (2×60 ml), and the separated organic layer was dried over sodium sulfate, filtered and concentrated under reduced pressure to afford tert-butyl 3-[[6-[2-cyano-3-[[ethyl(methyl)sulfamoyl] amino]-6-fluoro-phenoxy]-4-oxo-quinazolin-3-yl]methyl]-1-oxa-8-azaspiro[4.5]decane-8-carboxylate (0.7 g, 726.46 μmol, 33% yield) as a liquid. LCMS m/z (ESI): 571.2 [M+H]$^+$.

Step 8: The requisite amine was synthesized by Trifluoroacetic acid mediated N-Boc deprotection (Procedure A-D). N-Boc deprotection was performed on tert-butyl 3-[[6-[2-cyano-3-[[ethyl(methyl)sulfamoyl]amino]-6-fluoro-phenoxy]-4-oxo-quinazolin-3-yl]methyl]-1-oxa-8-azaspiro[4.5]decane-8-carboxylate (0.7 g, 1.04 mmol) using Trifluoroacetic acid (1.19 g, 10.44 mmol, 804.02 μL) at 0° C. under nitrogen atmosphere to afford the TFA salt of 3-[[6-[2-cyano-3-[[ethyl(methyl)sulfamoyl]amino]-6-fluoro-phenoxy]-4-oxo-quinazolin-3-yl]methyl]-1-oxa-8-azaspiro[4.5]decane (0.65 g, 818.46 μmol, 78% yield) as a gum. LCMS m/z (ESI): 571.2 [M+H]$^+$.

Step 9: The target compound was prepared via HATU mediated acid-amine coupling reaction (Procedure A-E). The amide coupling was carried out using 2-[4-[4-[(2,6-dioxo-3-piperidyl)amino]-2-fluoro-phenyl]-1-piperidyl]acetic acid (146.00 mg, 365.15 μmol), 3-[[6-[2-cyano-3-[[ethyl (methyl)sulfamoyl]amino]-6-fluoro-phenoxy]-4-oxo-quinazolin-3-yl]methyl]-1-oxa-8-azaspiro[4.5]decane (0.25 g, 365.15 μmol), N,N-diisopropylethylamine (235.96 mg, 1.83 mmol, 318.00 μL) and HATU (208.26 mg, 547.72 μmol). The crude compound was purified by reverse phase column chromatography eluting with 43% acetonitrile in 0.1% formic acid in water to afford product 3-[[6-[2-cyano-3-[[ethyl(methyl)sulfamoyl]amino]-6-fluoro-phenoxy]-4-oxo-quinazolin-3-yl]methyl]-8-[2-[4-[4-[(2,6-dioxo-3-piperidyl)amino]-2-fluoro-phenyl]-1-piperidyl]acetyl]-1-oxa-8-azaspiro[4.5]decane (98 mg, 101.70 μmol, 28% yield) as an off-white solid. LCMS m/z (ESI): 916.3 [M+H]$^+$. $^1$HNMR (400 MHz, DMSO-$d_6$): δ 10.82 (s, 1H), 9.83 (s, 1H), 8.41 (s, 1H), 7.81 (s, 1H), 7.78 (s, 1H), 7.69 (dd, J=8.80, 2.80 Hz, 1H), 7.48-7.45 (m, 1H), 7.37 (d, J=3.20 Hz, 1H), 6.97 (s, 1H), 6.48 (t, J=13.60 Hz, 2H), 6.12 (d, J=7.60 Hz, 1H), 4.43-4.31 (m, 2H), 4.28-4.19 (m, 2H), 4.02 (d, J=6.80 Hz, 2H), 3.85-3.84 (m, 2H), 3.58-3.51 (m, 2H), 3.38-3.30 (m, 2H), 3.14 (q, J=6.80 Hz, 2H), 3.09-3.01 (m, 2H), 2.76-2.68 (m, 2H), 2.68 (s, 3H), 2.67-2.60 (m, 1H), 2.59-2.53 (m, 1H), 2.11-2.08 (m, 2H), 1.91-0.00 (m, 6H), 1.83-1.71 (m, 1H), 1.52-1.54 (m, 4H), 1.05 (t, J=7.20 Hz, 3H).

Example 37

2-[6-[2-cyano-3-[[ethyl(methyl)sulfamoyl]amino]-6-fluorophenoxy]-4-oxoquinazolin-3-yl]-N-[1-[4-[(2,6-dioxopiperidin-3-yl)amino]-2-fluorophenyl]piperidin-4-yl]-7-azaspiro[3.5]nonane-7-carboxamide

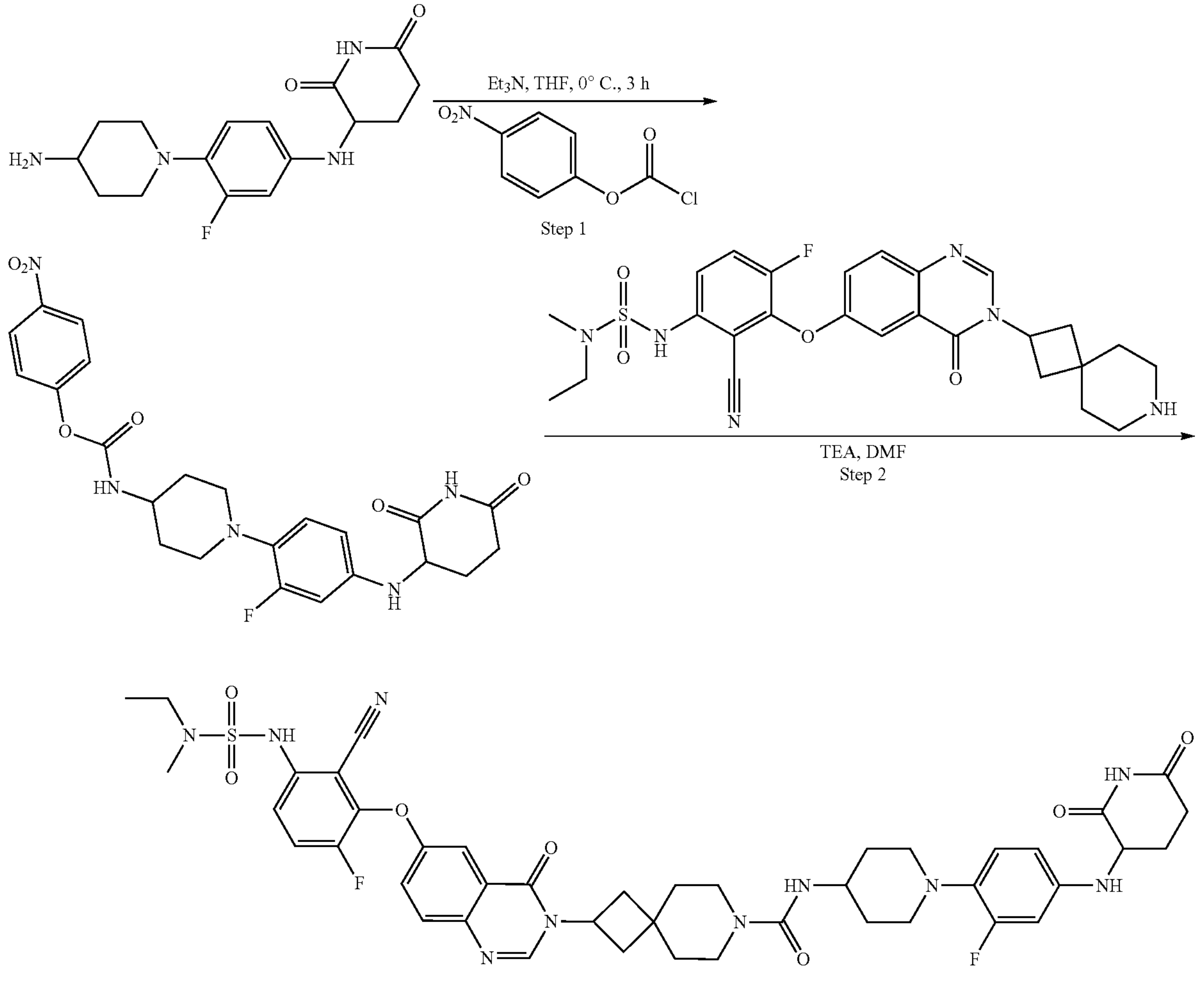

Step 1: To a solution of 3-[4-(4-amino-1-piperidyl)-3-fluoro-anilino]piperidine-2,6-dione (50 mg, 140.13 μmol) in THF (1 mL) was added Triethylamine (70.90 mg, 700.63 μmol, 97.65 μL) and (4-nitrophenyl) carbonochloridate (33.89 mg, 168.15 μmol) at 0° C. The resulting solution was stirred at RT for 3 h. After completion, the solution was concentrated under reduced pressure to afford (4-nitrophenyl)N-[1-[4-[(2,6-dioxo-3-piperidyl)amino]-2-fluoro-phenyl]-4-piperidyl]carbamate (70 mg, 95.11 μmol, 68% yield) as a brown solid. LCMS m/z (ESI): 486.0 $[M+H]^+$ Step 2: To a solution of 3-(7-azaspiro[3.5]nonan-2-yl)-6-[2-cyano-3-[[ethyl(methyl)sulfamoyl]amino]-6-fluoro-phenoxy]-4-oxo-quinazoline (200.45 mg, 306.20 μmol) in N,N-dimethylformamide (4 mL) was added Triethylamine (416.88 mg, 4.12 mmol, 574.21 μL) and (4-nitrophenyl)N-[1-[4-[(2,6-dioxo-3-piperidyl)amino]-2-fluoro-phenyl]-4-piperidyl]carbamate (0.4 g, 823.95 μmol) at −30° C. under nitrogen. The reaction solution was slowly warmed to rt and stirred for 5 h. After completion, the reaction mixture was concentrated under reduced pressure and the crude compound was purified by reverse phase column chromatography, eluting with 45% acetonitrile in 0.1% ammonium acetate, to afford 2-[6-[2-cyano-3-[[ethyl(methyl)sulfamoyl]amino]-6-fluoro-phenoxy]-4-oxo-quinazolin-3-yl]-N-[1-[4-[(2,6-dioxo-3-piperidyl)amino]-2-fluoro-phenyl]-4-piperidyl]-7-azaspiro[3.5]nonane-7-carboxamide (144 mg, 160.27 μmol, 19% yield) as an off-white solid. LCMS m/z (ESI): 887.4 $[M+H]^+$. $^1H$ NMR (400 MHz, DMSO-$d_6$): δ=10.79 (s, 1H), 10.15 (s, 1H), 8.42 (s, 1H), 7.89-7.84 (m, 1H), 7.80 (d, J=9.20 Hz, 1H), 7.69 (dd, J=3.20, 9.00 Hz, 1H), 7.50 (dd, J=4.00, 9.20 Hz, 1H), 7.35 (d, J=2.80 Hz, 1H), 6.85 (t, J=9.60 Hz, 1H), 6.50 (dd, J=15.20, 2.40 Hz, 1H), 6.41 (dd, J=8.80, 2.00 Hz, 1H), 6.23 (d, J=7.20 Hz, 1H), 5.80 (d, J=7.20 Hz, 1H), 4.94 (t, J=8.80 Hz, 1H), 4.40-4.20 (m, 1H), 3.51-3.48 (m, 1H), 3.21-3.16 (m, 4H), 3.11 (t, J=11.20 Hz, 2H), 2.76 (s, 3H), 2.72-2.2.65, (m, 2H), 2.64-2.56 (m, 3H), 2.36 (t, J=8.80 Hz, 3H), 2.27 (t, J=11.60 Hz, 3H), 2.08-1.92 (m, 1H), 1.84-1.77 (m, 3H), 1.61-1.54 (m, 5H), 1.06 (t, J=7.20 Hz, 3H).

Example 38

3-[6-[2-cyano-3-[[ethyl(methyl)sulfamoyl]amino]-6-fluorophenoxy]-4-oxoquinazolin-3-yl]-N-[1-[4-[(2,6-dioxopiperidin-3-yl)amino]-2-fluorophenyl]piperidin-4-yl]-1-oxa-8-azaspiro[4.5]decane-8-carboxamide

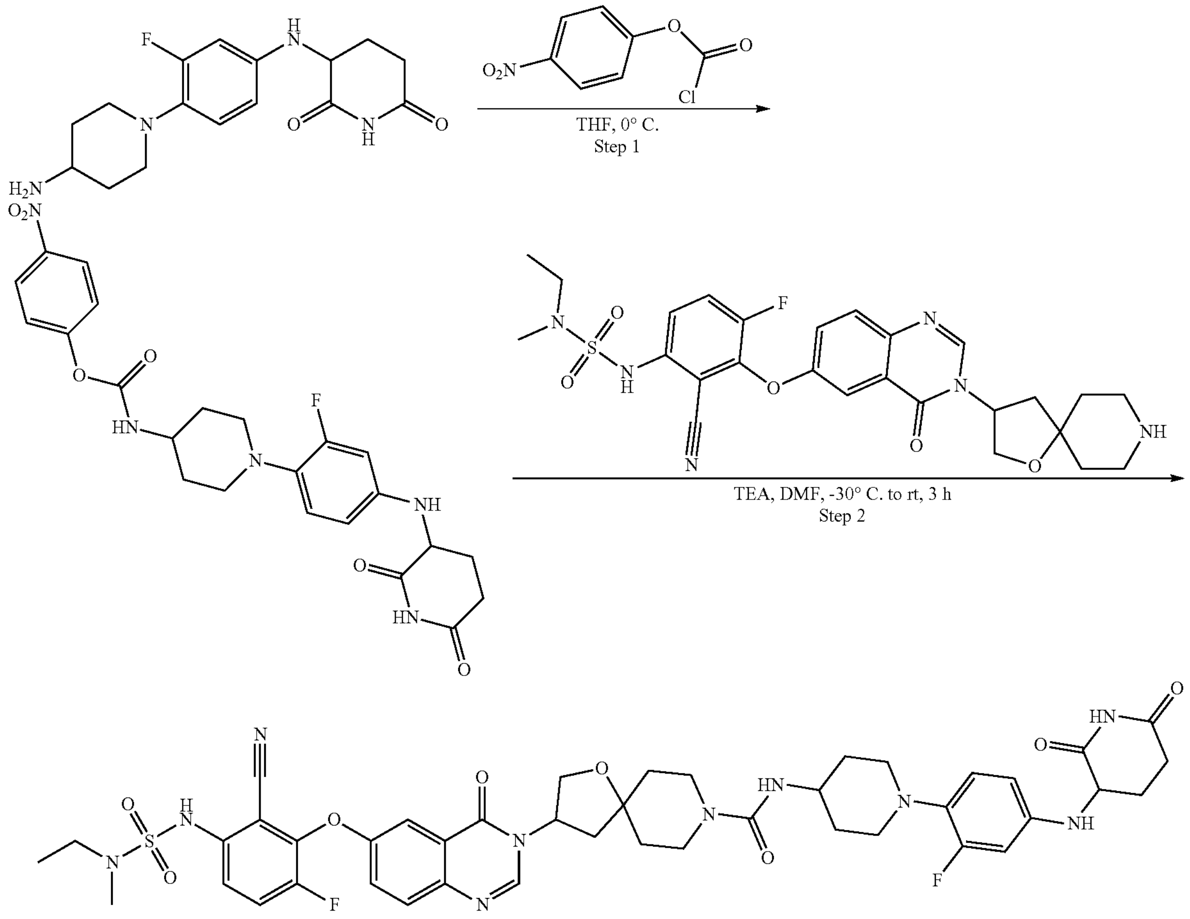

Step 1: To a solution of 3-[4-(4-amino-1-piperidyl)-3-fluoro-anilino]piperidine-2,6-dione (0.7 g, 1.96 mmol) in THF (7 mL) was added triethylamine (992.55 mg, 9.81 mmol, 1.37 mL) and (4-nitrophenyl) carbonochloridate (474.50 mg, 2.35 mmol) at 0° C. under nitrogen. The resulting solution was stirred at 0° C. to room temperature for 3 hours. After completion, the reaction was concentrated under reduced pressure to afford (4-nitrophenyl) N-[1-[4-[(2,6-dioxo-3-piperidyl)amino]-2-fluoro-phenyl]-4-piperidyl]carbamate (1.27 g, 1.95 mmol, 99% yield) as a brown solid, which was carried forward without further purification. LCMS m/z (ESI): 486.2 $[M+H]^+$.

Step 2: To a solution of 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (137.44 mg, 231.74 μmol) in N,N-Dimethylformamide (5 mL), were added Triethylamine (416.88 mg, 4.12 mmol, 574.21 μL) at room temperature under nitrogen atmosphere. The reaction mixture was cooled to −30° C. and stirred for 10 minutes. (4-nitrophenyl) N-[1-[4-[(2,6-dioxo-3-piperidyl)amino]-2-fluoro-phenyl]-4-piperidyl]carbamate (0.25 g, 514.97 μmol) was added at −30° C. and the reaction mixture stirred at room temperature for 3 h. After completion, the reaction mixture was concentrated under vacuum. The crude compound was purified by reverse phase column chromatography, eluting with 40% acetonitrile in 0.1% formic acid in water, to afford 3-[6-[2-cyano-3-[[ethyl(methyl)sulfamoyl]amino]-6-fluoro-phenoxy]-4-oxo-quinazolin-3-yl]-N-[1-[4-[(2,6-dioxo-3-piperidyl)amino]-2-fluoro-phenyl]-4-piperidyl]-1-oxa-8-azaspiro[4.5]decane-8-carboxamide (38.15 mg, 38.83 μmol, 8% yield) as an off-white solid. LCMS m/z (ESI): 901.3 $[M-H]^-$; $^1H$ NMR (400 MHz, DMSO-$d_6$): δ=10.57 (s, 1H), 9.81 (s, 1H), 8.35 (s, 1H), 7.78 (d, J=8.80 Hz, 1H), 7.67 (dd, J=3.20, 9.00 Hz, 1H), 7.60 (d, J=8.00 Hz, 2H), 7.44 (s, 1H), 7.35 (d, J=3.20 Hz, 2H), 7.06 (d, J=8.00 Hz, 1H), 5.32 (s, 1H), 4.20-4.13 (m, 2H), 3.99 (s, 3H), 3.91 (t, J=6.80 Hz, 2H), 3.68-3.59 (m, 1H), 3.50 (m, 2H), 3.06 (d, J=7.20 Hz, 2H), 2.86-2.80 (m, 3H), 2.76 (t, J=6.80 Hz, 3H), 2.67 (d, J=5.60 Hz, 4H), 2.49-2.40 (m, 3H), 2.14-2.07 (m, 1H), 1.96 (s, 4H), 1.83-1.56 (m, 5H), 1.04 (t, J=6.80 Hz, 3H).

Example 39

6-[2-cyano-3-[[ethyl(methyl)sulfamoyl]amino]-6-fluorophenoxy]-3-[7-[3-[3-[4-[(2,6-dioxopiperidin-3-yl)amino]-2-fluorophenyl]azetidin-1-yl]cyclobutanecarbonyl]-7-azaspiro[3.5]nonan-2-yl]-4-oxoquinazoline

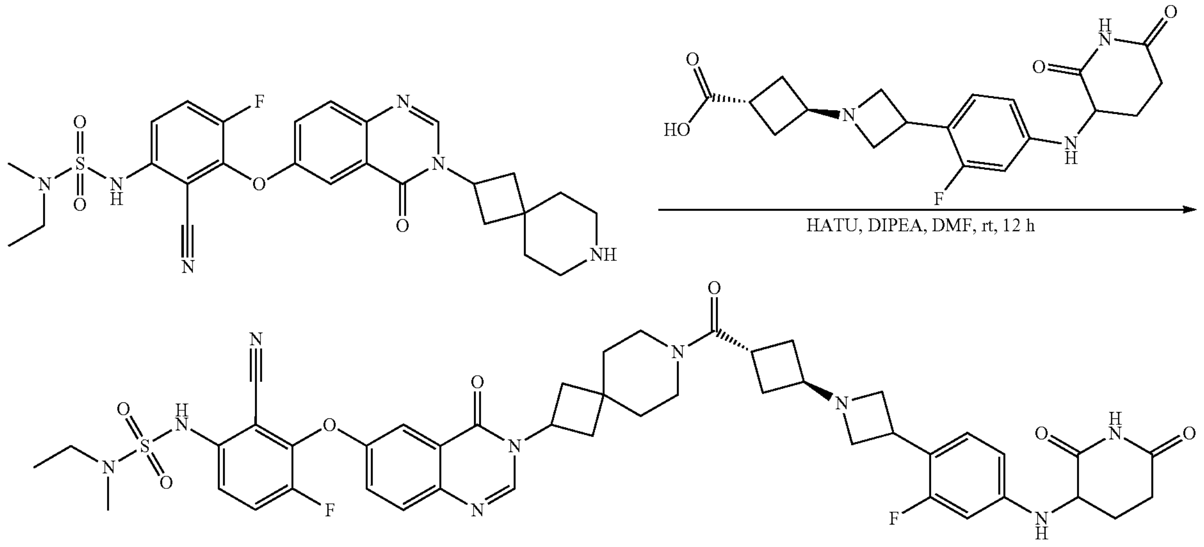

Target compound was prepared via HATU mediated acid-amine coupling reaction (Procedure A-E). Amide coupling was carried out using 3-[3-[4-[(2,6-dioxo-3-piperidyl) amino]-2-fluoro-phenyl]azetidin-1-yl]cyclobutanecarboxylic acid (173.60 mg, 462.44 μmol), 3-(7-azaspiro[3.5] nonan-2-yl)-6-[2-cyano-3-[[ethyl(methyl)sulfamoyl] amino]-6-fluoro-phenoxy]-4-oxo-quinazoline (0.25 g, 462.44 μmol), N,N-diisopropylethylamine (298.84 mg, 2.31 mmol, 402.75 μL) and HATU (263.75 mg, 693.66 μmol). The crude compound was purified by reverse phase column chromatography, eluting with 43% acetonitrile with 0.1% formic acid in water, to afford 6-[2-cyano-3-[[ethyl(methyl) sulfamoyl]amino]-6-fluoro-phenoxy]-3-[7-[3-[3-[4-[(2,6-dioxo-3-piperidyl)amino]-2-fluoro-phenyl]azetidin-1-yl]cyclobutanecarbonyl]-7-azaspiro[3.5]nonan-2-yl]-4-oxo-quinazoline (215 mg, 222.10 μmol, 48% yield) as an off-white solid. LCMS m/z (ESI): 898.3 $[M+H]^+$; $^1H$ NMR (400 MHz, DMSO-$d_6$): δ=10.82 (s, 1H), 10.54 (bs, 1H), 8.40 (d, J=3.20 Hz, 1H), 7.78 (d, J=9.20 Hz, 1H), 7.65 (dd, J=9.00, 3.20 Hz, 2H), 7.40-7.37 (m, 1H), 7.34 (d, J=3.20 Hz, 1H), 7.18 (t, J=8.00 Hz, 1H), 6.51 (t, J=14.00 Hz, 2H), 6.24 (d, J=8.00 Hz, 1H), 6.24 (q, J=8.00 Hz, 1H), 4.37 (q, J=44.00 Hz, 1H), 4.09-0.00 (m, 2H), 3.96-3.71 (m, 4H), 3.51-3.48 (m, 2H), 3.20-3.10 (m, 2H), 3.08 (q, J=7.20 Hz, 3H), 2.78-2.61 (m, 5H), 3.17-3.07 (m, 8H), 2.07-1.91 (m, 1H), 1.91-1.90 (m, 1H), 1.66-1.56 (m, 4H), 1.04 (t, J=7.20 Hz, 3H).

Example 40

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline

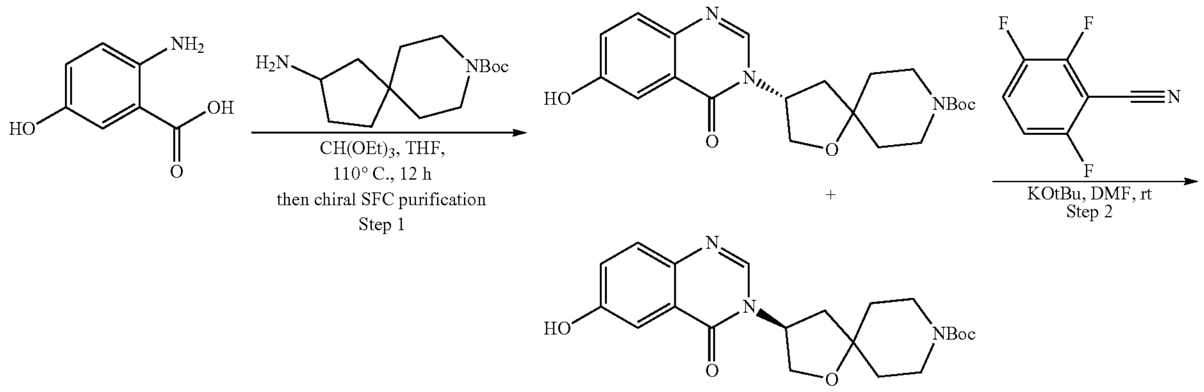

-continued

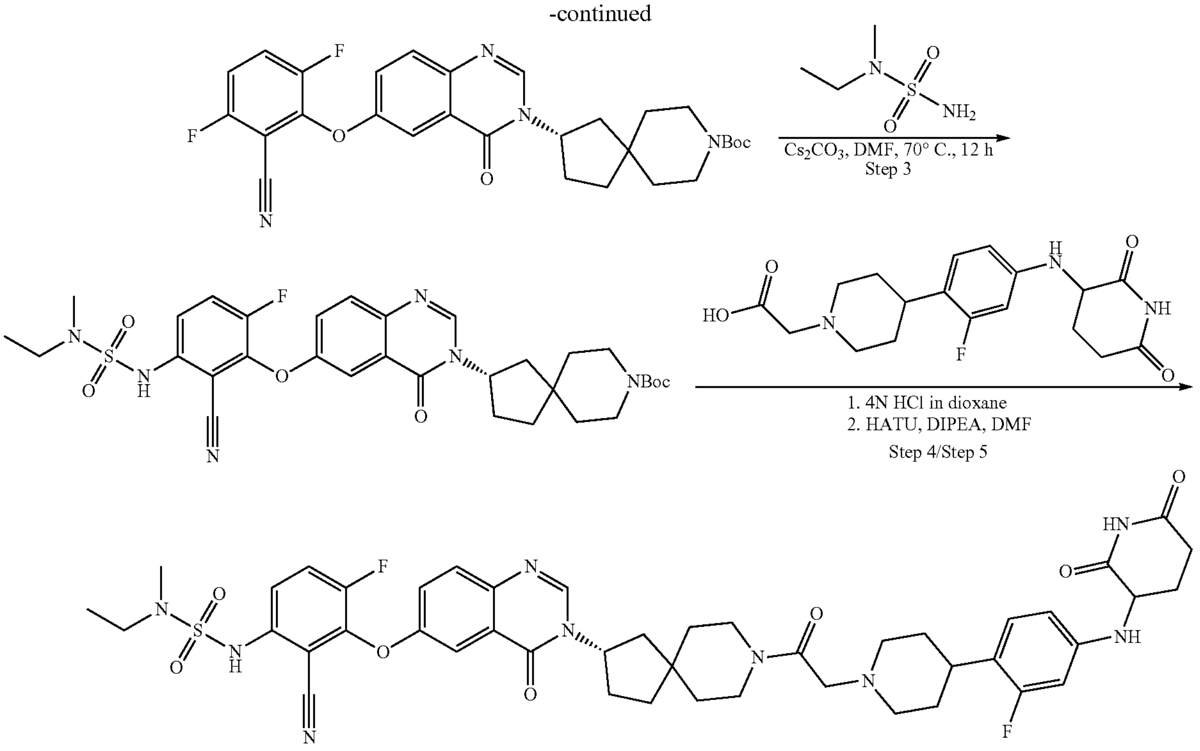

Step 1: Quinazolinone intermediate was synthesized by following general procedure for cyclization (Procedure A-A) using tert-butyl 3-amino-8-azaspiro[4.5]decane-8-carboxylate (5.0 g, 19.66 mmol), 2-amino-5-hydroxy-benzoic acid (3.01 g, 19.66 mmol), triethyl orthoformate (7.28 g, 49.14 mmol, 8.17 mL) and acetic acid (118.04 mg, 1.97 mmol, 112.42 μL). The crude compound was purified by silica gel flash column chromatography with ethyl acetate in petroleum ether to afford tert-butyl 3-(6-hydroxy-4-oxo-quinazolin-3-yl)-8-azaspiro[4.5]decane-8-carboxylate (5.6 g, 13.72 mmol, 70% yield) as a brown solid. The racemic cyclization compound was chirally resolved using chiral SFC purification. 3.0 g of racemic cyclized compound was submitted for SFC Purification using Chiralcel OX—H column (Flowrate: 3 ml/min, Co-Solvent: 30% methanol, Outlet Pressure: 100 bar, Temperature: 35° C.). After SFC purification, 1.3 g of first eluting isomer (Enantiomer 1) and 1.3 g of Second eluting isomer (Enantiomer 2) was obtained. Stereochemistry of the first eluting isomer was arbitrarily assigned as S-enantiomer and second eluting isomer was arbitrarily assigned as R-enantiomer. LCMS m/z (ESI): 400.2 $[M+H]^+$ Please note that, to differentiate two enantiomers and to generate distinct registration numbers, configuration is arbitrarily assigned as follows.

Enantiomer 1: First eluting isomer was arbitrarily assigned as tert-butyl 3-[(3S)-6-hydroxy-4-oxo-quinazolin-3-yl]-8-azaspiro[4.5]decane-8-carboxylate Enantiomer 2: Second eluting isomer was arbitrarily assigned as tert-butyl 3-[(3R)-6-hydroxy-4-oxo-quinazolin-3-yl]-8-azaspiro[4.5]decane-8-carboxylate Step 2: O-arylated quinazolinone intermediate was synthesized by following general procedure for O-arylation (Procedure A-B) using tert-butyl 3-[(3S)-6-hydroxy-4-oxo-quinazolin-3-yl]-8-azaspiro[4.5]decane-8-carboxylate (1.30 g, 3.25 mmol), potassium tert-butoxide (730.32 mg, 6.51 mmol) and 2,3,6-trifluorobenzonitrile (511.21 mg, 3.25 mmol, 375.89 μL). Crude compound was purified by silica gel flash column chromatography, eluting with 60% ethyl acetate in petroleum ether as eluent, to afford tert-butyl (3S)-3-[6-(2-cyano-3,6-difluoro-phenoxy)-4-oxo-quinazolin-3-yl]-8-azaspiro[4.5]decane-8-carboxylate (1.2 g, 1.71 mmol, 53% yield) as an off-white solid. LCMS m/z (ESI): 481.1 $[M+H-{}^tBu]^+$ Step 3: Sulfamoylated quinazolinone intermediate was synthesized by following Procedure A-C using tert-butyl (3S)-3-[6-(2-cyano-3,6-difluoro-phenoxy)-4-oxo-quinazolin-3-yl]-8-azaspiro[4.5]decane-8-carboxylate (1.20 g, 2.24 mmol), cesium carbonate (1.82 g, 5.59 mmol) and [methyl(sulfamoyl)amino]ethane (618.10 mg, 4.47 mmol) to afford tert-butyl (3S)-3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (960.0 mg, 1.01 mmol, 45% yield) as colorless liquid. LCMS m/z (ESI): 653.2 $[M-H]^-$ Step 4: The requisite amine was synthesized by HCl mediated N-Boc deprotection (Procedure A-D). N-Boc deprotection was done on tert-butyl (3S)-3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (400.00 mg, 610.92 μmol) using hydrogen chloride solution in dioxane (4M, 3.0 mL). The residue obtained was triturated with diethyl ether (2×10 mL) and dried under reduced pressure to afford 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (360.0 mg, 542.20 μmol, 89% yield) as yellow solid. LCMS m/z (ESI): 555.2 $[M+H]^+$ Step 5: Target compound was prepared via HATU mediated acid-amine coupling reaction (Procedure A-E). Amide coupling was carried out using 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (400.00 mg, 721.20

μmol), HATU (411.33 mg, 1.08 mmol), N,N-diisopropylethylamine (466.05 mg, 3.61 mmol, 628.10 μL) and 2-[4-[4-[(2,6-dioxo-3-piperidyl)amino]-2-fluoro-phenyl]-1-piperidyl]acetic acid (262.07 mg, 721.20 μmol). The resulting crude was purified by reverse phase column chromatography by using 100 g snap, eluting with 42% acetonitrile in 0.1% Ammonium Acetate in water, to afford 6-[2-cyano-3-[[ethyl(methyl)sulfamoyl]amino]-6-fluoro-phenoxy]-3-[(3S)-8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (230.0 mg, 254.57 μmol, 35% yield) as off-white solid. LCMS m/z (ESI): 900.4 $[M+H]^+$; $^1$H NMR (400 MHz, DMSO-$d_6$): δ=10.80 (s, 1H), 9.74 (s, 1H), 8.43 (d, J=3.60 Hz, 1H), 7.76 (d, J=6.00 Hz, 1H), 7.64 (dd, J=3.20, 8.80 Hz, 1H), 7.45-7.61 (m, 1H), 7.35 (s, 1H), 7.31-7.35 (m, 1H), 6.99 (t, J=8.00 Hz, 1H), 6.49 (d, J=7.60 Hz, 1H), 6.46 (d, J=12.00 Hz, 1H), 6.07 (d, J=8.00 Hz, 1H), 5.01-5.11 (m, 1H), 4.28-4.38 (m, 1H), 3.72-4.01 (m, 1H), 3.53-3.62 (m, 1H), 3.21-3.51 (m, 4H), 3.02-3.07 (m, 2H), 2.60-2.81 (m, 4H), 2.64 (s, 3H), 2.51-2.59 (m, 2H), 2.01-2.18 (m, 4H), 1.70-1.92 (m, 8H), 1.42-1.69 (m, 5H), 1.04 (t, J=7.20 Hz, 3H).

Example 41

6-[2-cyano-3-[[ethyl(methyl)sulfamoyl]amino]-6-fluorophenoxy]-3-[(3R)-8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline

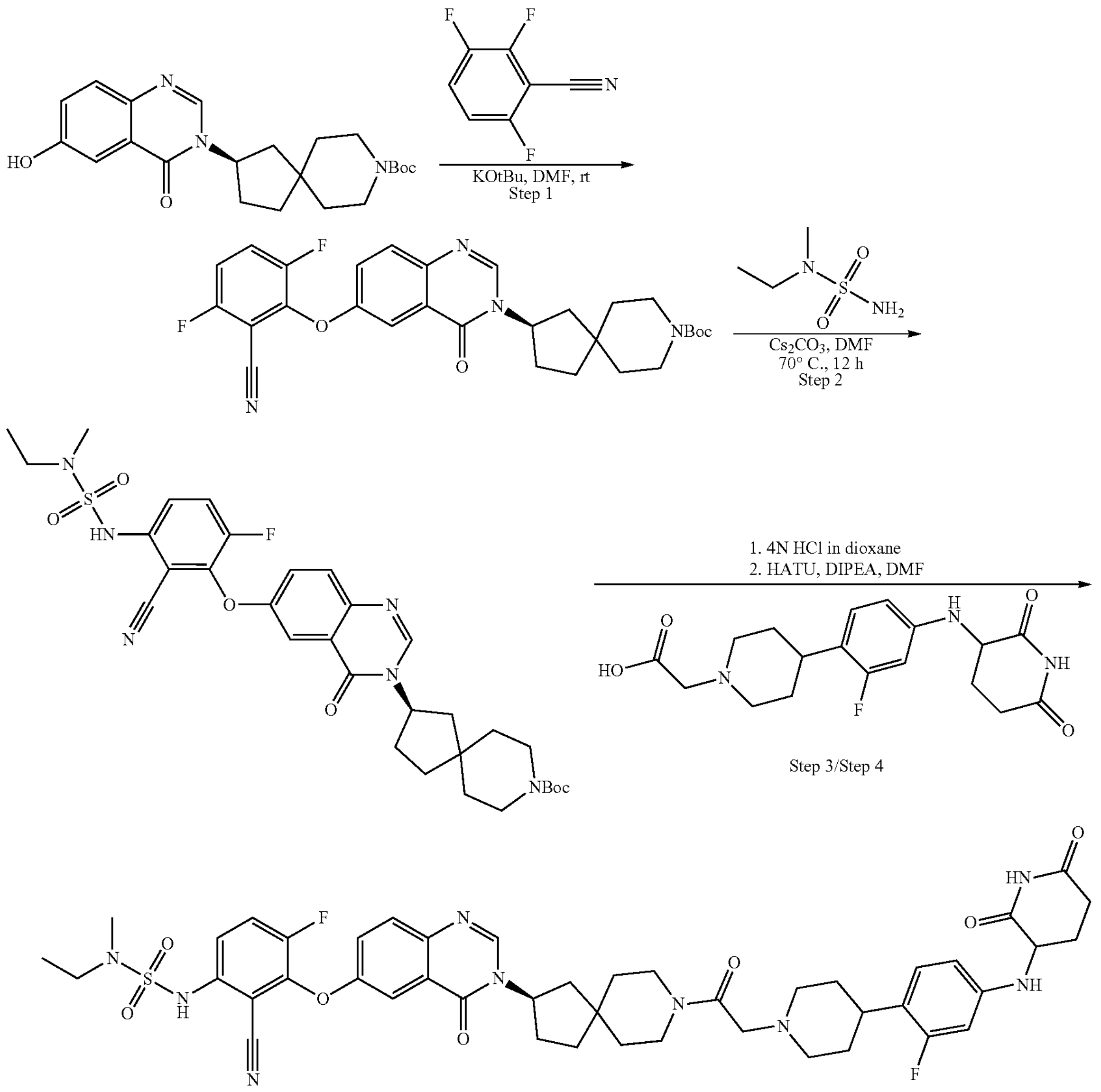

Step 1: O-arylated quinazolinone intermediate was synthesized by following general procedure for O-arylation (Procedure A-B) using tert-butyl (3R)-3-(6-hydroxy-4-oxo-quinazolin-3-yl)-8-azaspiro[4.5]decane-8-carboxylate (1.30 g, 3.25 mmol), potassium tert-butoxide (730.32 mg, 6.51 mmol) and 2,3,6-trifluorobenzonitrile (511.21 mg, 3.25 mmol, 375.89 μL). The crude was purified by 230-400 silica gel flash column chromatography using 60% ethyl acetate in petroleum ether as a eluent to afford tert-butyl (3R)-3-[6-(2-cyano-3,6-difluoro-phenoxy)-4-oxo-quinazolin-3-yl]-8-azaspiro[4.5]decane-8-carboxylate (1.3 g, 1.94 mmol, 60% yield) as off-white solid. LCMS m/z (ESI): 481.3 [M+H−$^{t}$Bu]$^+$ Step 2: Sulfamoylated quinazolinone intermediate was synthesized by following Procedure A-C using tert-butyl (3R)-3-[6-(2-cyano-3,6-difluoro-phenoxy)-4-oxo-quinazolin-3-yl]-8-azaspiro[4.5]decane-8-carboxylate (1.10 g, 2.05 mmol), cesium carbonate (667.95 mg, 2.05 mmol) and [methyl(sulfamoyl)amino]ethane (283.29 mg, 2.05 mmol). The reaction mixture was cooled to room temperature, quenched with water (40 mL), filtered and dried. The filtrate was extracted with ethyl acetate (2×30 mL), and washed with brine (25 mL). The organic layer was dried over sodium sulfate and concentrated to afford tert-butyl (3R)-3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (0.9 g, 934.71 μmol, 46% yield) as a brown liquid. LCMS m/z (ESI): 599.1 [M+H−$^{t}$Bu]$^+$ Step 3: The requisite amine was synthesized by HCl mediated N-Boc deprotection (Procedure A-D). N-Boc deprotection was done on tert-butyl (3R)-3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (400.00 mg, 610.92 μmol) using HCl in dioxane (4.0 M, 4 mL). The obtained crude was triturated with diethyl ether (2×10 mL) and dried to yield 3-[(3R)-8-azaspiro[4.5]decan-3-yl]-6-[2-cyano-3-[[ethyl(methyl)sulfamoyl]amino]-6-fluoro-phenoxy]-4-oxo-quinazoline (0.4 g, 531.89 μmol, 87% yield) as a pale yellow solid. LCMS m/z (ESI): 555.2 [M+H]$^+$ Step 4: Target compound was prepared via HATU mediated acid-amine coupling reaction (Procedure A-E). Amide coupling was carried out using 3-[(3R)-8-azaspiro[4.5]decan-3-yl]-6-[2-cyano-3-[[ethyl(methyl)sulfamoyl]amino]-6-fluoro-phenoxy]-4-oxo-quinazoline (400.00 mg, 721.20 μmol), HATU (411.33 mg, 1.08 mmol), 2-[4-[4-[(2,6-dioxo-3-piperidyl)amino]-2-fluoro-phenyl]-1-piperidyl]acetic acid (262.07 mg, 721.20 μmol) and N,N-diisopropylethylamine (466.05 mg, 3.61 mmol, 628.10 μL). The crude compound was purified by 100 g C18 reverse phase column purification using 0.1% Ammonium acetate in acetonitrile as a eluent to afford 6-[2-cyano-3-[[ethyl(methyl)sulfamoyl]amino]-6-fluoro-phenoxy]-3-[(3R)-8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (130 mg, 140.40 μmol, 19% yield) as off-white solid. LCMS m/z (ESI): 898.3 [M−H]$^-$; $^1$H NMR (400 MHz, DMSO-$d_6$): δ=10.81 (s, 1H), 9.68 (s, 1H), 8.43 (d, J=3.60 Hz, 1H), 7.76 (d, J=8.80 Hz, 1H), 7.64 (dd, J=2.80, 8.80 Hz, 1H), 7.42-7.61 (m, 1H), 7.34 (s, 1H), 7.28-7.34 (m, 1H), 6.91-7.05 (m, 1H), 6.48 (d, J=7.20 Hz, 1H), 6.46 (d, J=12.40 Hz, 1H), 6.08 (d, J=7.20 Hz, 1H), 4.96-5.11 (m, 1H), 4.28-4.35 (m, 1H), 3.55-3.61 (m, 1H), 3.34-3.51 (m, 4H), 3.01-3.08 (m, 2H), 2.72-2.81 (m, 3H), 2.51-2.71 (m, 7H), 2.05-2.16 (m, 4H), 1.71-1.95 (m, 8H), 1.40-1.69 (m, 5H), 1.03 (t, J=7.20 Hz, 3H).

Example 42

(3R)-3-[6-[2-cyano-3-[[ethyl(methyl)sulfamoyl]amino]-6-fluorophenoxy]-4-oxoquinazolin-3-yl]-8-[2-[4-[4-[[(3R)-2,6-dioxopiperidin-3-yl]amino]-2-fluorophenyl]piperidin-1-yl]acetyl]-1-oxa-8-azaspiro[4.5]decane

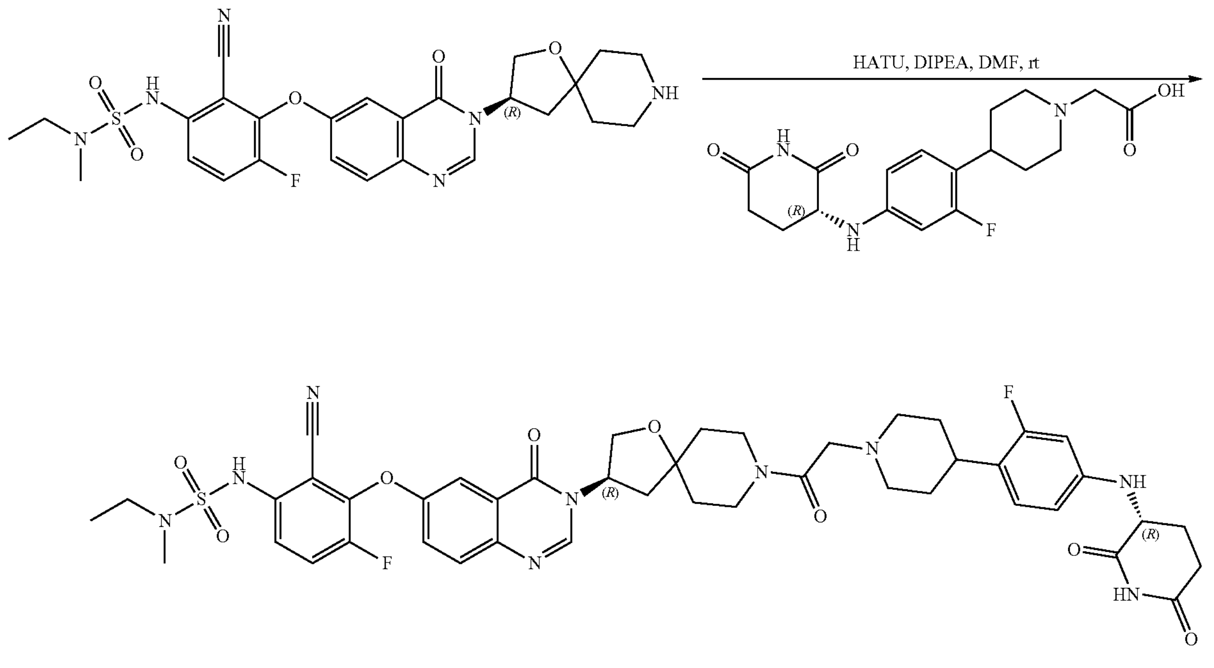

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (800 mg, 1.44 mmol), 2-[4-[4-[[(3R)-2,6-dioxo-3-piperidyl]amino]-2-fluoro-phenyl]-1-piperidyl]acetic acid (548.40 mg, 1.51 mmol), N,N-diisopropylethylamine (928.77 mg, 7.19 mmol, 1.25 mL) and HATU (601.15 mg, 1.58 mmol). The crude compound was purified by reverse phase column chromatography, eluting with 40 to 45% acetonitrile in 0.1% ammonium acetate in water, to afford (3R)-3-[6-[2-cyano-3-[[ethyl(methyl)sulfamoyl]amino]-6-fluoro-phenoxy]-4-oxo-quinazolin-3-yl]-8-[2-[4-[4-[[(3R)-2,6-dioxo-3-piperidyl]amino]-2-fluoro-phenyl]-1-piperidyl]acetyl]-1-oxa-8-azaspiro[4.5]decane (270 mg, 295.42 μmol, 21% yield) as off-white solid. LCMS m/z (ESI): 902.2 $[M+H]^+$; $^1$H NMR (400 MHz, DMSO-$d_6$): δ=10.80 (s, 1H), 9.87 (s, 1H), 8.34 (s, 1H), 7.77 (d, J=8.80 Hz, 1H), 7.66 (dd, J=9.00, 2.80 Hz, 1H), 7.55 (s, 1H), 7.35 (d, J=2.80 Hz, 2H), 6.99 (s, 1H), 6.47 (t, J=12.80 Hz, 2H), 6.07 (d, J=7.60 Hz, 1H), 5.31 (s, 1H), 4.35-4.29 (m, 1H), 4.20-4.11 (m, 2H), 3.70 (d, J=17.20 Hz, 2H), 3.58-3.48 (m, 3H), 3.05 (d, J=7.20 Hz, 2H), 2.74-2.65 (m, 7H), 2.47-2.36 (m, 3H), 2.11-2.06 (m, 3H), 1.92-1.62 (m, 9H), 1.58-1.51 (m, 1H), 1.04 (t, J=6.80 Hz, 3H).

Example 43

(3R)-3-[6-[2-cyano-3-[[ethyl(methyl)sulfamoyl]amino]-6-fluorophenoxy]-4-oxoquinazolin-3-yl]-8-[2-[4-[4-[[(3S)-2,6-dioxopiperidin-3-yl]amino]-2-fluorophenyl]piperidin-1-yl]acetyl]-1-oxa-8-azaspiro[4.5]decane

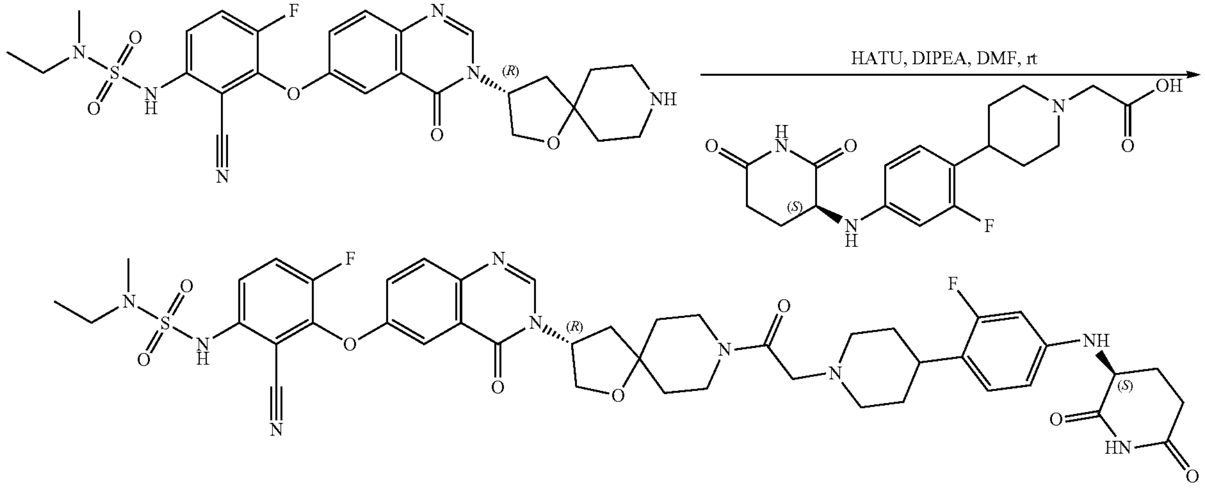

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (0.8 g, 1.35 mmol), 2-[4-[4-[[(3S)-2,6-dioxo-3-piperidyl]amino]-2-fluoro-phenyl]-1-piperidyl]acetic acid (593.29 mg, 1.48 mmol), N,N-diisopropylethylamine (1.74 g, 13.49 mmol, 2.35 mL) and HATU (564.19 mg, 1.48 mmol). The crude compound was purified by reverse phase column chromatography, eluting with 50% acetonitrile in 0.1% ammonium acetate in water, to afford (3R)-3-[6-[2-cyano-3-[[ethyl(methyl)sulfamoyl]amino]-6-fluoro-phenoxy]-4-oxo-quinazolin-3-yl]-8-[2-[4-[4-[[(3S)-2,6-dioxo-3-piperidyl]amino]-2-fluoro-phenyl]-1-piperidyl]acetyl]-1-oxa-8-azaspiro[4.5]decane (307 mg, 336.76 μmol, 25% yield) as off-white solid. LCMS m/z (ESI): 902.2 $[M+H]^+$; $^1$H NMR (400 MHz, DMSO-$d_6$): δ=10.81 (s, 1H), 9.86 (s, 1H), 8.35 (s, 1H), 7.78 (d, J=9.20 Hz, 1H), 7.66 (d, J=8.80 Hz, 1H), 7.55 (s, 1H), 7.35 (s, 2H), 6.99 (s, 1H), 6.47 (t, J=13.60 Hz, 2H), 6.08 (d, J=6.40 Hz, 1H), 5.31 (s, 1H), 4.32 (s, 1H), 4.15 (d, J=12.40 Hz, 3H), 3.72 (s, 1H), 3.47-3.34 (m, 4H), 3.06 (d, J=6.40 Hz, 1H), 2.79-2.66 (m, 5H), 2.42-2.34 (m, 4H), 2.10-2.07 (m, 3H), 1.92-1.55 (m, 11H), 1.04 (t, J=6.80 Hz, 3H).

Example 44

6-[2-cyano-3-[[ethyl(methyl)sulfamoyl]amino]-6-fluorophenoxy]-3-[(3R)-8-[2-[4-[4-[[(3R)-2,6-di-oxopiperidin-3-yl]amino]-2-fluorophenyl]piperidin-1-yl]acetyl]-8-azaspiro[4.5]decan-3-yl]-4-oxoquinazoline

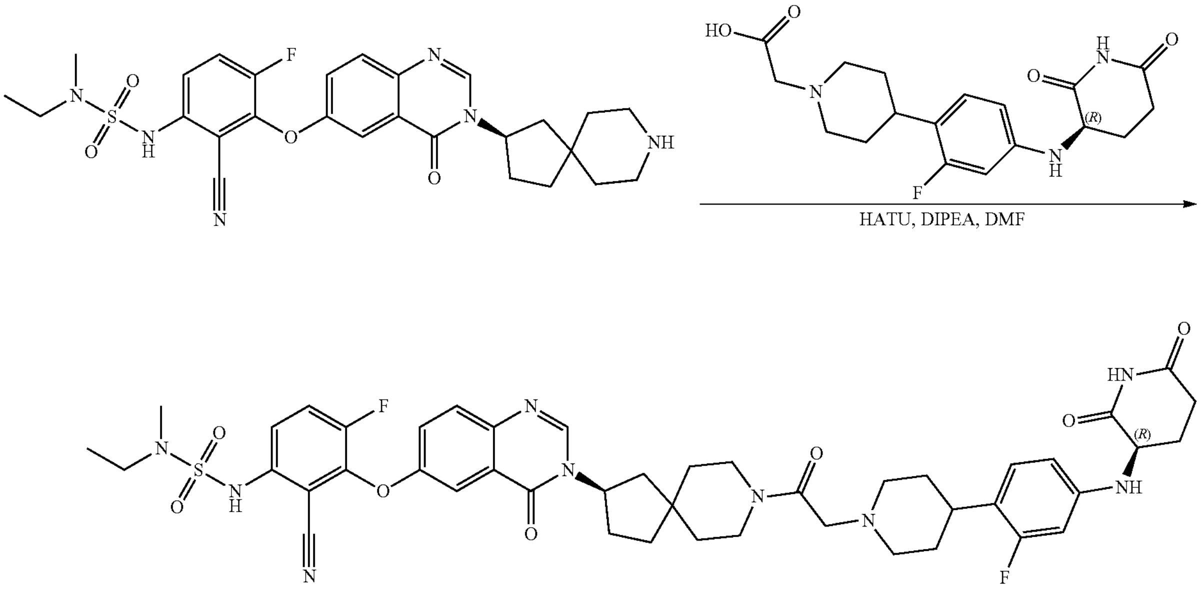

Target compound was prepared via HATU mediated acid-amine coupling reaction (Procedure A-E). Amide coupling was carried out using 3-[(3R)-8-azaspiro[4.5]decan-3-yl]-6-[2-cyano-3-(dimethylsulfamoylamino)-6-fluoro-phenoxy]-4-oxo-quinazoline (0.15 g, 259.93 μmol), HATU (148.25 mg, 389.90 μmol), 2-[4-[4-[[(3R)-2,6-dioxo-3-piperidyl] amino]-2-fluoro-phenyl]-1-piperidyl]acetic acid (94.46 mg, 236.23 μmol) and N,N-diisopropylethyl amine (167.97 mg, 1.30 mmol, 226.38 μL). The crude product was purified by 30 g of C18 reverse phase column chromatography using 0.1% Ammonium acetate in acetonitrile as eluent to yield 6-[2-cyano-3-[[ethyl(methyl)sulfamoyl]amino]-6-fluoro-phenoxy]-3-[(3R)-8-[2-[4-[4-[[(3R)-2,6-di oxo-3-piperidyl] amino]-2-fluoro-phenyl]-1-piperidyl]acetyl]-8-azaspiro [4.5]decan-3-yl]-4-oxo-quinazoline (75 mg, 81.07 μmol, 31% yield) as off-white solid. LCMS m/z (ESI): 900.3 $[M+H]^+$; $^1$H NMR (400 MHz, DMSO-$d_6$): δ=10.81 (s, 1H), 9.70 (s, 1H), 8.43 (d, J=4.00 Hz, 1H), 7.76 (d, J=9.20 Hz, 1H), 7.64 (dd, J=2.80, 9.00 Hz, 1H), 7.45-7.55 (m, 1H), 7.34 (s, 1H), 7.28-7.35 (m, 1H), 6.95-7.02 (m, 1H), 6.48 (d, J=7.20 Hz, 1H), 6.46 (d, J=12.00 Hz, 1H), 6.08 (d, J=7.60 Hz, 1H), 5.01-5.11 (m, 1H), 4.29-4.37 (m, 1H), 3.51-3.61 (m, 1H), 3.35-3.50 (m, 2H), 3.35-3.14 (m, 3H), 3.01-3.07 (m, 2H), 2.70-2.81 (m, 2H), 2.61-2.68 (m, 2H), 2.67 (s, 3H), 2.51-2.58 (m, 2H), 2.02-2.15 (m, 4H), 1.65-1.91 (m, 7H), 1.42-1.68 (m, 5H), 1.03 (t, J=7.20 Hz, 3H).

Example 45

6-[2-cyano-3-[[ethyl(methyl)sulfamoyl]amino]-6-fluorophenoxy]-3-[(3R)-8-[2-[4-[4-[[(3S)-2,6-di-oxopiperidin-3-yl]amino]-2-fluorophenyl]piperidin-1-yl]acetyl]-8-azaspiro[4.5]decan-3-yl]-4-oxoquinazoline

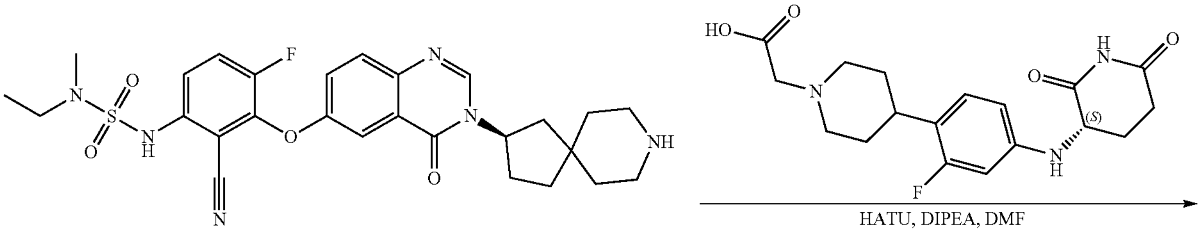

-continued

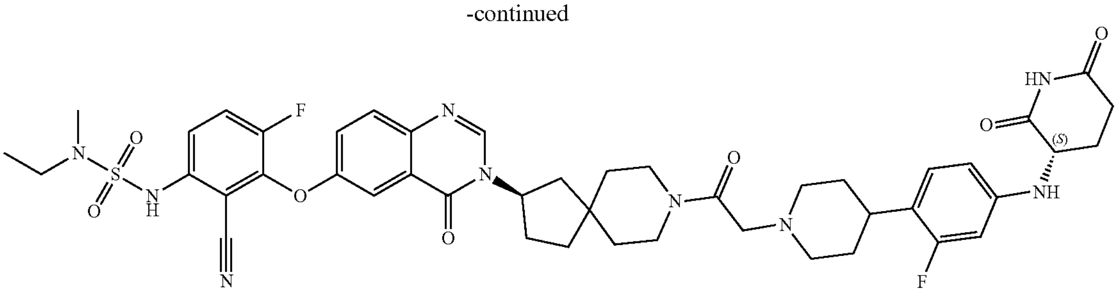

Target compound was prepared via HATU mediated acid-amine coupling reaction (Procedure A-E). Amide coupling was carried out using 2-[4-[4-[[(3S)-2,6-dioxo-3-piperidyl]amino]-2-fluoro-phenyl]-1-piperidyl]acetic acid (101.47 mg, 253.77 μmol), HATU (144.73 mg, 380.65 μmol), N,N-diisopropylethylamine (163.99 mg, 1.27 mmol, 221.01 μL) and 3-[(3R)-8-azaspiro[4.5]decan-3-yl]-6-[2-cyano-3-[[ethyl(methyl)sulfamoyl]amino]-6-fluoro-phenoxy]-4-oxo-quinazoline (150.0 mg, 253.77 μmol). The crude compound was purified by reverse phase column chromatography by using 100 g snap, eluting with 46% acetonitrile in 0.1% Ammonium Acetate in water, to afford 6-[2-cyano-3-[[ethyl(methyl)sulfamoyl]amino]-6-fluoro-phenoxy]-3-[(3R)-8-[2-[4-[4-[[(3S)-2,6-dioxo-3-piperidyl]amino]-2-fluoro-phenyl]-1-piperidyl]acetyl]-8-azaspiro[4.5]decan-3-yl]-4-oxo-quinazoline (35.0 mg, 37.96 μmol, 15% yield) as off-white solid. LCMS m/z (ESI): 900.4 $[M+H]^+$; $^1$H NMR (400 MHz, DMSO-$d_6$): δ=10.80 (s, 1H), 9.69 (s, 1H), 8.43 (d, J=3.60 Hz, 1H), 7.76 (d, J=8.80 Hz, 1H), 7.64 (dd, J=2.80, 8.80 Hz, 1H), 7.42-7.56 (m, 1H), 7.34 (s, 1H), 7.28-7.34 (m, 1H), 6.95-7.02 (m, 1H), 6.48 (d, J=7.20 Hz, 1H), 6.46 (d, J=12.40 Hz, 1H), 6.07 (d, J=7.60 Hz, 1H), 5.01-5.11 (m, 1H), 4.28-4.38 (m, 1H), 3.55-3.62 (m, 1H), 3.11-3.51 (m, 5H), 3.01-3.08 (m, 2H), 2.71-2.81 (m, 3H), 2.51-2.68 (m, 4H), 2.63 (s, 3H), 2.01-2.15 (m, 4H), 1.65-1.95 (m, 7H), 1.40-1.65 (m, 5H), 1.03 (t, J=7.20 Hz, 3H).

Example 46

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]piperidin-1-yl]acetyl]-1-oxa-8-azaspiro[4.5]decane

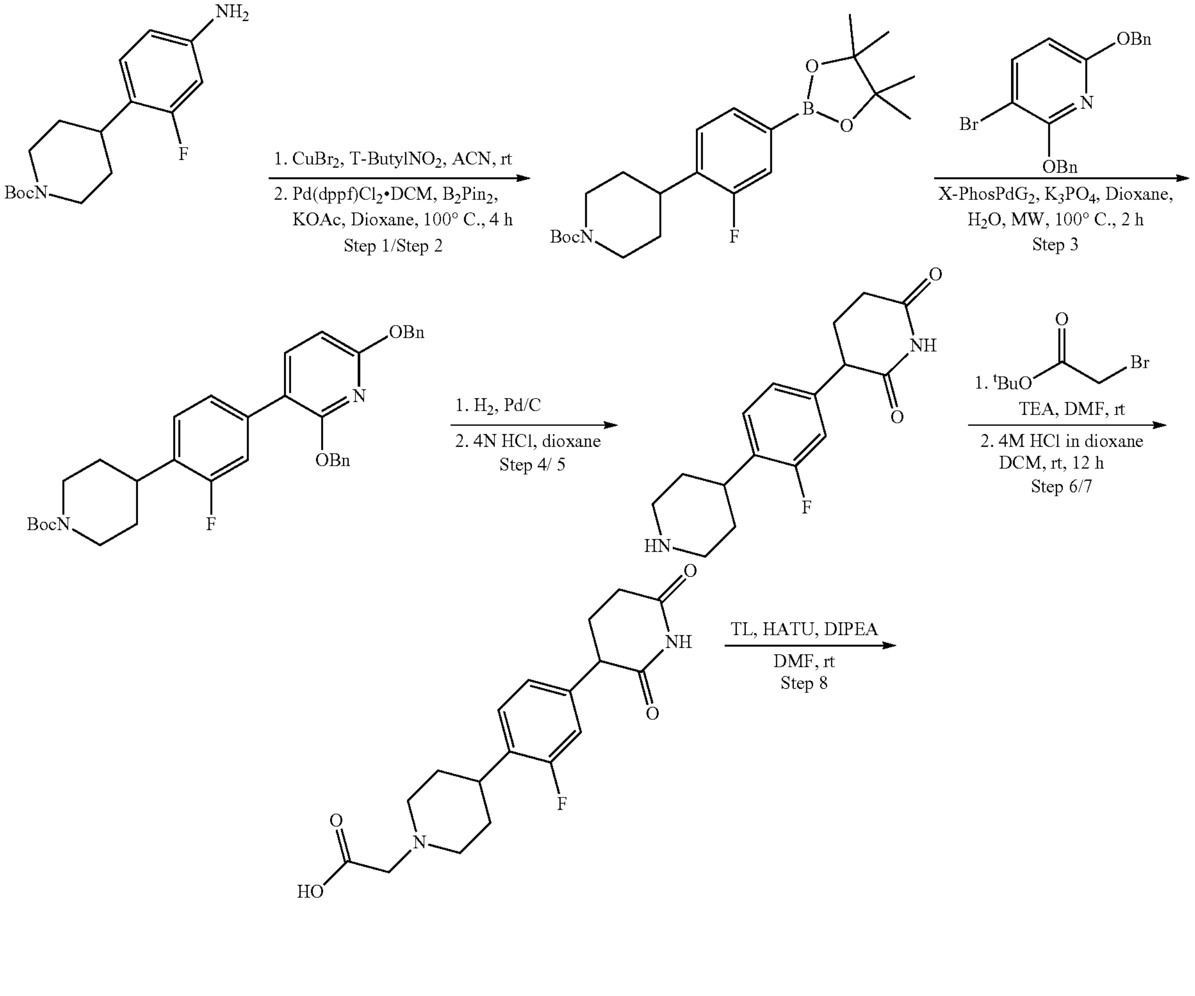

-continued

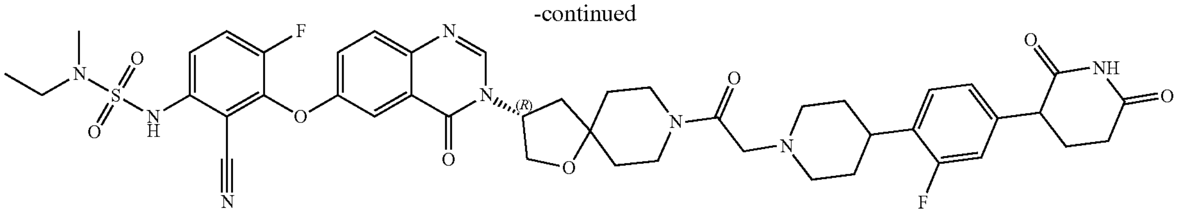

Step 1: To a stirred solution of tert-butyl nitrite (1.58 g, 15.29 mmol, 1.82 mL) and $CuBr_2$ (4.55 g, 20.38 mmol, 966.58 μL) in acetonitrile (30 mL) was added tert-butyl 4-(4-amino-2-fluoro-phenyl)piperidine-1-carboxylate (3 g, 10.19 mmol) at 0-5° C. under nitrogen atmosphere. The reaction mixture was stirred at room temperature for 4 h. After completion of the reaction, the reaction mixture was diluted with water (30 mL) and extracted with ethyl acetate (3×30 mL). The combined organic layer was washed with brine (10 mL), dried over sodium sulfate and concentrated under reduced pressure to afford crude which was purified by column chromatography on silica gel, eluting with 70% ethyl acetate in petroleum ether, to afford tert-butyl 4-(4-bromo-2-fluoro-phenyl)piperidine-1-carboxylate (4.1 g, 4.89 mmol, 48% yield). LCMS m/z (ESI): 304.0 $[M-^tBu+3H]^+$.

Step 2: To a solution of tert-butyl 4-(4-bromo-2-fluoro-phenyl)piperidine-1-carboxylate (3.9 g, 10.89 mmol) in 1,4-dioxane (40 mL) was taken in a sealed tube under nitrogen atmosphere. To the reaction mixture was added potassium acetate (2.14 g, 21.77 mmol, 1.36 mL) and 4,4,5,5-tetramethyl-2-(4,4,5,5-tetramethyl-1,3,2-dioxaborolan-2-yl)-1,3,2-dioxaborolane (4.15 g, 16.33 mmol). The reaction mixture was purged with nitrogen gas for 10 minutes and Pd(dppf) $Cl_2$·dichloromethane (889.02 mg, 1.09 mmol) was added before purging with nitrogen gas for 5 minutes. The reaction mixture was stirred at 100° C. for 16 h. After completion, the reaction mixture was diluted with water (60 mL), extracted with ethyl acetate (3×60 mL). Combined organic layers dried over sodium sulfate, filtered and concentrated under reduced pressure. The resulting crude was purified by column chromatography on silica gel, eluting with 60% ethyl acetate in petroleum ether, to afford tert-butyl 4-[2-fluoro-4-(4,4,5,5-tetramethyl-1,3,2-dioxaborolan-2-yl)phenyl]piperidine-1-carboxylate (4.6 g, 5.33 mmol, 49% yield). LCMS m/z (ESI): 306.2 $[M+H]^+$.

Step 3: To a solution of tert-butyl 4-[2-fluoro-4-(4,4,5,5-tetramethyl-1,3,2-dioxaborolan-2-yl)phenyl]piperidine-1-carboxylate (5 g, 12.34 mmol) in 1,4-dioxane (60 mL) and water (10 mL) in a sealed tube was added $K_3PO_4$ (7.86 g, 37.01 mmol) and 2,6-dibenzyloxy-3-bromo-pyridine (5.02 g, 13.57 mmol). The reaction mixture was purged with nitrogen gas for 10 minutes and Pd(dppf) $Cl_2$·dichloromethane (1.01 g, 1.23 mmol) was added before purging with nitrogen gas for 5 minutes. The reaction mixture was stirred at 110° C. for 12 h. After completion, the reaction mixture was diluted with water (60 mL), extracted with ethyl acetate (3×60 mL). The combined organic layers were dried over sodium sulfate, filtered and concentrated under reduced pressure. The resulting crude was purified by silica gel flash column chromatography, by using 30-45% ethyl acetate in petroleum ether as eluent, to afford tert-butyl 4-[4-(2,6-dibenzyloxy-3-pyridyl)-2-fluoro-phenyl]piperidine-1-carboxylate (2.3 g, 3.79 mmol, 31% yield). LCMS m/z (ESI): 569.3 $[M+H]^+$.

Step 4: To a stirred solution of tert-butyl 4-[4-(2,6-dibenzyloxy-3-pyridyl)-2-fluoro-phenyl]piperidine-1-carboxylate (1 g, 1.76 mmol) in ethyl acetate (3 mL) and 1,4-dioxane (3 mL) was added $Pd(OH)_2$ (493.90 mg, 3.52 mmol). The reaction mixture was stirred at room temperature under hydrogen atmosphere for 6 h. The reaction mixture was filtered through a pad of celite, and the filtrate was concentrated under vacuum to afford tert-butyl 4-[4-(2,6-dioxo-3-piperidyl)-2-fluoro-phenyl]piperidine-1-carboxylate (650 mg, 1.54 mmol, 88% yield) as white solid, which was carried forward without further purification. LCMS m/z (ESI): 389.2 $[M-H]^-$.

Step 5: To a stirred solution of tert-butyl 4-[4-(2,6-dioxo-3-piperidyl)-2-fluoro-phenyl]piperidine-1-carboxylate (500 mg, 1.28 mmol) in 1,4-dioxane (2 mL) was added hydrogen chloride solution in dioxane (4 M, 4 mL) at 0° C. The reaction mixture was stirred at room temperature for 2 h. After completion, the reaction mixture was concentrated under vacuum. The crude compound was washed with diethyl ether to afford 3-[3-fluoro-4-(4-piperidyl)phenyl]piperidine-2,6-dione (490 mg, 1.01 mmol, 79% yield), which was carried forward without further purification. LCMS m/z (ESI): 291.2 $[M+H]^+$.

Step 6: To a solution of 3-[3-fluoro-4-(4-piperidyl)phenyl]piperidine-2,6-dione (490 mg, 1.69 mmol) in N,N-Dimethylformamide (4 mL) was added triethylamine (683.12 mg, 6.75 mmol, 940.94 μL) followed by tert-butyl 2-bromoacetate (362.12 mg, 1.86 mmol, 272.27 μL) at room temperature. The reaction mixture was stirred at room temperature for 16 h. After completion, water (10 mL) was added to the reaction mixture and extracted with ethyl acetate (2×50 mL). The combined organic layers were dried over sodium sulfate, filtered, and concentrated under reduced pressure. The crude product was washed with diethyl ether to afford tert-butyl 2-[4-[4-(2,6-dioxo-3-piperidyl)-2-fluoro-phenyl]-1-piperidyl]acetate (547 mg, 1.22 mmol, 72% yield), which was carried forward without further purification. LCMS m/z (ESI): 405.2 $[M+H]^+$.

Step 7: To a stirred solution of tert-butyl 2-[4-[4-(2,6-dioxo-3-piperidyl)-2-fluoro-phenyl]-1-piperidyl]acetate (547 mg, 1.35 mmol) in 1,4-dioxane (3 mL) was added hydrogen chloride solution in dioxane (4 M, 5 mL) at 0° C. The reaction mixture was stirred at room temperature for 2 h. The reaction mixture was concentrated under vacuum. The crude compound was washed with diethyl ether to afford 2-[4-[4-(2,6-dioxo-3-piperidyl)-2-fluoro-phenyl]-1-piperidyl]acetic acid (800 mg, 1.21 mmol, 89% yield), which was carried forward without further purification. LCMS m/z (ESI): 349.2 $[M+H]^+$.

Step 8: Target compound was prepared via COMU mediated acid-amine coupling reaction (Procedure A-F). Amide coupling was carried out using 3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (300 mg, 538.98 μmol), 2-[4-[4-(2,6-dioxo-3-piperidyl)-2-fluoro-phenyl]-1-piperidyl]acetic acid (206.54 mg, 592.88 μmol), N,N-diisopropylethylamine (348.29 mg, 2.69 mmol, 469.39 μL) followed by COMU (253.91 mg, 592.88 μmol). The crude compound was purified by reverse phase column chromatography, eluting with 40-45% formic acid buffer in acetonitrile, to afford (3R)-3-[6-[2-cyano-3-[[ethyl(methyl)sulfamoyl]amino]-6-fluoro-phenoxy]-4-oxo-quinazolin-3-yl]-8-[2-[4-[4-(2,6-dioxo-3-piperidyl)-2-fluoro-phenyl]-1-piperidyl]acetyl]-1-oxa-8-azaspiro[4.5]decane (10.38 mg, 10.81 μmol, 2% yield) as off-white solid. LCMS m/z (ESI): 887.2 $[M+H]^+$. $^1H$ NMR (400 MHz, DMSO-$d_6$): δ=10.88 (s, 1H), 10.17 (s, 1H), 9.53 (s, 1H), 8.36 (d, J=2.00 Hz, 1H), 7.79-7.89 (m, 1H), 7.80 (d, J=8.80 Hz, 1H), 7.70 (dd, J=2.40, 8.80 Hz, 1H), 7.47 (d, J=6.80 Hz, 1H), 7.37 (d, J=2.80 Hz, 1H), 7.21-7.31 (m, 1H), 7.10 (d, J=11.20 Hz, 2H), 5.29-5.36 (m, 1H), 4.12-4.45 (m, 1H), 4.11-4.18 (m, 2H), 3.89 (dd, J=4.80, 11.80 Hz, 1H), 3.72-3.81 (m, 1H), 3.24-3.65 (m, 4H), 3.02-3.21 (m, 5H), 2.77 (s, 3H), 2.53-2.71 (m, 4H), 2.15-2.27 (m, 1H), 1.60-2.14 (m, 10H), 1.50-1.61 (m, 1H), 1.05 (t, J=7.20 Hz, 3H).

Example 47

(3R)-3-[6-[2-cyano-3-[[ethyl(methyl)sulfamoyl]amino]-6-fluorophenoxy]-4-oxoquinazolin-3-yl]-8-[2-[1-[4-[(2,6-dioxopiperidin-3-yl)amino]-2-fluorophenyl]piperidin-4-yl]acetyl]-1-oxa-8-azaspiro[4.5]decane

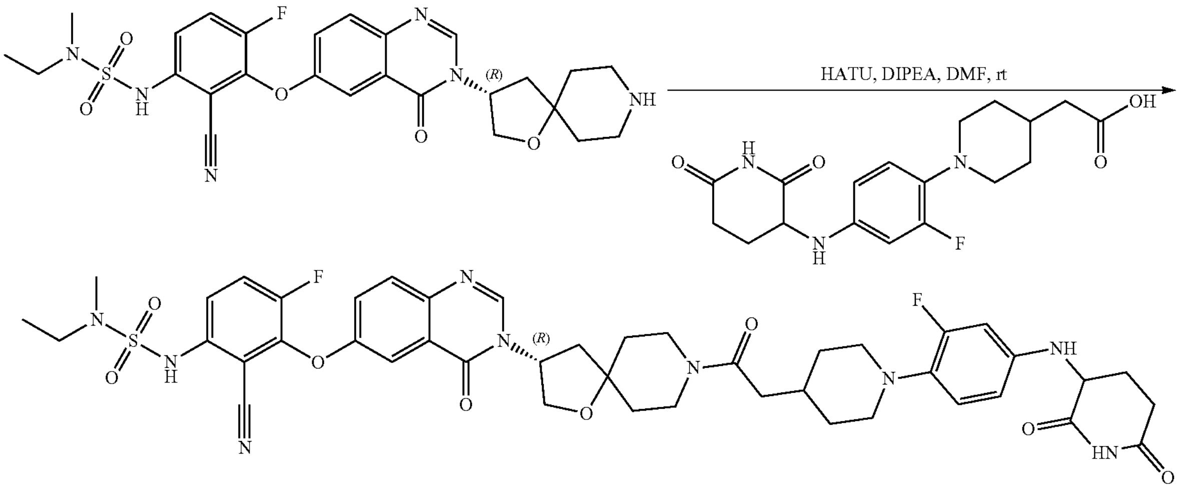

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (230 mg, 352.91 μmol), 2-[1-[4-[(2,6-dioxo-3-piperidyl)amino]-2-fluoro-phenyl]-4-piperidyl]acetic acid (141.11 mg, 352.91 μmol), N,N-diisopropylethylamine (182.44 mg, 1.41 mmol, 245.88 μL) and HATU (134.19 mg, 352.91 μmol). The crude compound was purified by reverse phase column chromatography, eluting with 50% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[1-[4-[(2,6-dioxo-3-piperidyl)amino]-2-fluoro-phenyl]-4-piperidyl]acetyl]-1-oxa-8-azaspiro[4.5]decane (100 mg, 100.94 μmol, 29% yield) as ash solid. LCMS m/z (ESI): 902.2 $[M+H]^+$; $^1H$ NMR (400 MHz, DMSO-$d_6$): δ=10.78 (s, 1H), 10.18 (s, 1H), 8.36 (s, 1H), 7.86 (t, J=10.00 Hz, 1H), 7.80 (d, J=8.80 Hz, 1H), 7.70 (dd, J=9.00, 3.20 Hz, 1H), 7.50 (dd, J=9.20, 4.00 Hz, 1H), 7.37 (d, J=3.20 Hz, 1H), 6.83 (t, J=8.80 Hz, 1H), 6.52 (s, 1H), 6.48 (d, J=2.00 Hz, 1H), 6.41 (d, J=8.80 Hz, 1H), 5.79 (d, J=2.80 Hz, 1H), 4.29-4.21 (m, 1H), 4.15-4.12 (m, 2H), 3.74-3.66 (m, 1H), 3.53-3.42 (m, 3H), 3.18-3.14 (m, 2H), 3.10-3.08 (m, 2H), 2.80 (s, 3H), 2.73-2.68 (m, 2H), 2.60-2.51 (m, 2H), 2.35-2.29 (m, 4H), 2.09-2.07 (m, 2H), 1.79-1.61 (m, 8H), 1.41-1.25 (m, 2H), 1.06 (t, J=7.20 Hz, 3H).

Example 48

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2-fluorophenyl]piperazin-1-yl]acetyl]-8-azaspiro[4.5]decan-3-yl]-4-oxoquinazoline

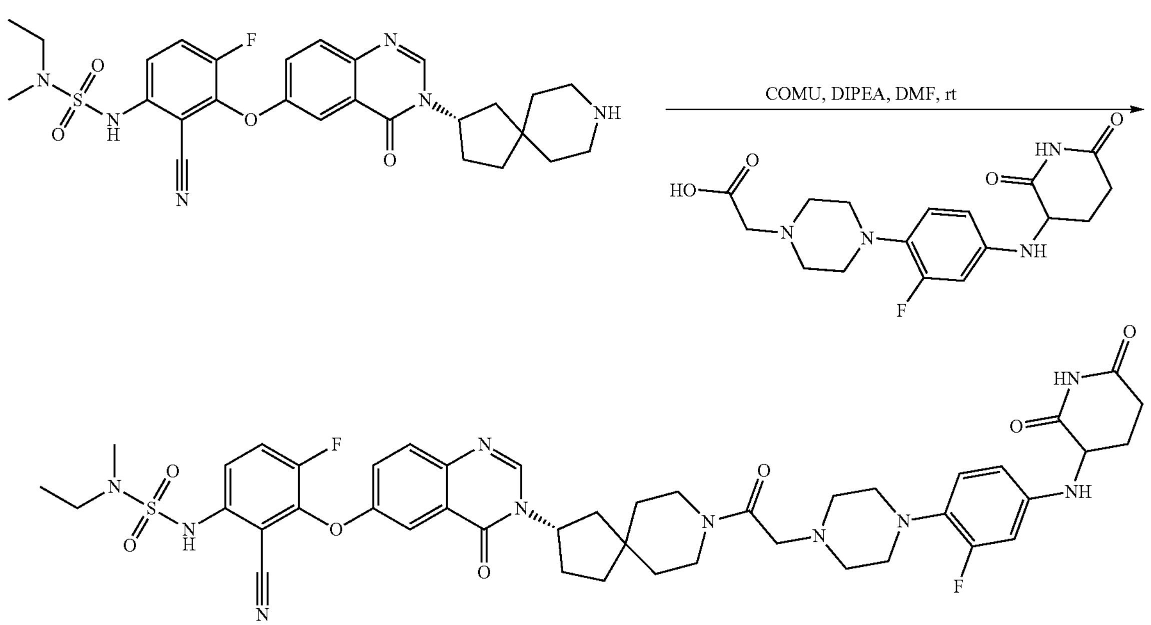

Target compound was prepared via COMU mediated acid-amine coupling reaction (Procedure A-F). Amide coupling was carried out using 2-[4-[4-[(2,6-dioxo-3-piperidyl)amino]-2-fluoro-phenyl]piperazin-1-yl]acetic acid (33.91 mg, 70.87 μmol), 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (50 mg, 84.59 μmol), N,N-diisopropylethylamine (54.66 mg, 422.94 μmol, 73.67 μL) and (1-Cyano-2-ethoxy-2-oxoethylidenaminooxy)dimethyl-amino-morpholino-carbenium hexafluorophosphate (54.34 mg, 126.88 μmol). The crude compound was purified by reverse phase column chromatography, eluting with 35% acetonitrile in 0.1% formic acid in water, to afford product 6-[2-cyano-3-[[ethyl(methyl)sulfamoyl]amino]-6-fluoro-phenoxy]-3-[(3S)-8-[2-[4-[4-[(2,6-dioxo-3-piperidyl)amino]-2-fluoro-phenyl]piperazin-1-yl]acetyl]-8-azaspiro[4.5]decan-3-yl]-4-oxo-quinazoline (40 mg, 40.81 μmol, 48% yield) as an off-white solid. LCMS m/z (ESI): 900.8 $[M+H]^+$; $^1H$ NMR (400 MHz, DMSO-$d_6$): δ=10.78 (s, 1H), 9.98 (bs, 1H), 8.46 (s, 1H), 7.82 (s, 1H), 7.69 (d, J=2.80 Hz, 1H), 7.67 (d, J=2.80 Hz, 1H), 7.48-7.44 (m, 1H), 7.36 (d, J=2.80 Hz, 1H), 6.86 (t, J=9.60 Hz, 1H), 6.53 (dd, J=2.40, 14.80 Hz, 1H), 6.43 (dd, J=2.00, Hz, 1H), 5.87 (d, J=7.60 Hz, 1H), 5.11-4.92 (m, 1H), 4.37-4.22 (m, 1H), 3.55 3.62 (m, 2H), 3.36 (q, J=20.00 Hz, 2H), 3.11-2.74 (m, 9H), 2.60-2.51 (m, 5H), 2.34-2.07 (m, 5H), 1.87-1.82 (m, 3H), 1.65-1.45 (m, 6H), 1.05 (s, 3H).

Example 49

(3R)—N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]-3-fluoropyrrolidine-1-sulfonamide

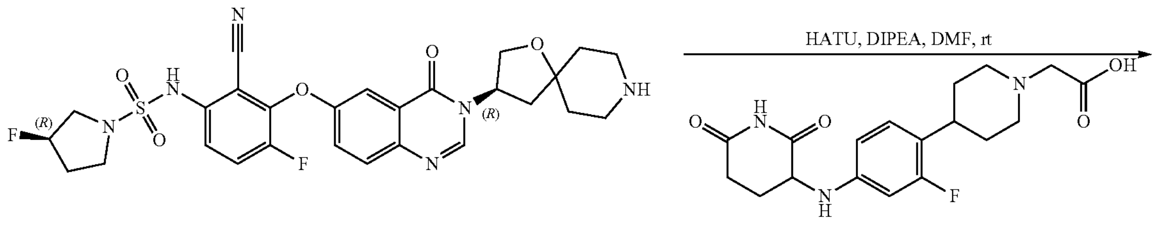

-continued

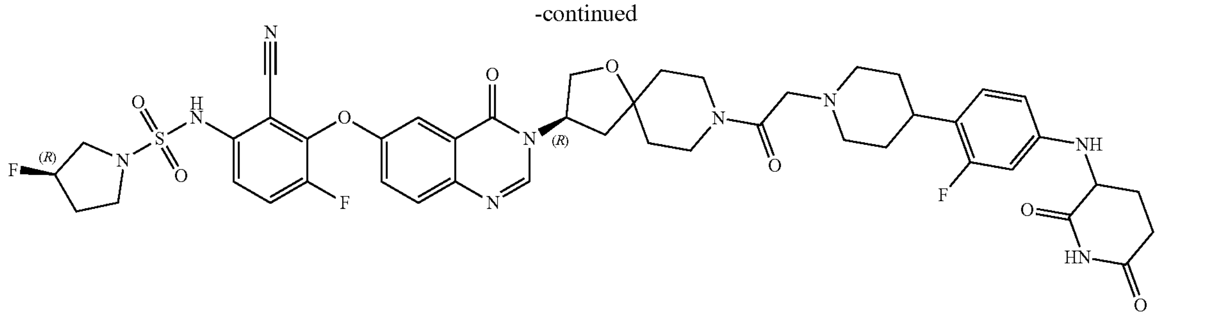

Target compound was prepared via HATU mediated acid-amine coupling reaction (Procedure A-E). Amide coupling was carried out using (3R)—N-[2-cyano-4-fluoro-3-[3-[(3R)-1-oxa-8-azaspiro[4.5]decan-3-yl]-4-oxo-quinazolin-6-yl]oxy-phenyl]-3-fluoro-pyrrolidine-1-sulfonamide (70 mg, 98.87 μmol), 2-[4-[4-[(2,6-dioxo-3-piperidyl)amino]-2-fluoro-phenyl]-1-piperidyl]acetic acid (35.93 mg, 89.85 μmol), N,N-diisopropylethylamine (51.11 mg, 395.46 μmol, 68.88 μL) and HATU (37.59 mg, 98.87 μmol). The crude compound was purified by reverse phase column chromatography, eluting with 50% acetonitrile in 0.1% formic acid in water, to afford product (3R)—N-[2-cyano-3-[3-[(3R)-8-[2-[4-[4-[(2,6-dioxo-3-piperidyl)amino]-2-fluoro-phenyl]-1-piperidyl]acetyl]-1-oxa-8-azaspiro[4.5]decan-3-yl]-4-oxo-quinazolin-6-yl]oxy-4-fluoro-phenyl]-3-fluoro-pyrrolidine-1-sulfonamide (12 mg, 12.01 μmol, 12% yield) as off-white solid. LCMS m/z (ESI): 932.2 $[M+H]^+$; $^1H$ NMR (400 MHz, DMSO-$d_6$): δ=10.81 (s, 1H), 9.47 (s, 1H), 8.35 (s, 1H), 7.79 (d, J=8.80 Hz, 2H), 7.68 (dd, J=2.80, 8.80 Hz, 1H), 7.47 (s, 1H), 7.38 (s, 1H), 6.96 (t, J=8.00 Hz, 1H), 6.49 (t, J=12.40 Hz, 2H), 6.12 (d, J=8.00 Hz, 1H), 5.39-5.25 (m, 2H), 4.36-4.27 (m, 3H), 4.20-4.13 (m, 2H), 3.81-3.78 (m, 1H), 3.51-3.49 (m, 5H), 3.06-2.90 (m, 2H), 2.53-2.51 (m, 7H), 2.14-2.00 (m, 6H), 1.92-1.70 (m, 7H), 1.32-1.20 (m, 1H).

Example 50

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluoro-phenyl]piperazin-1-yl]acetyl]-1-oxa-8-azaspiro[4.5]decane

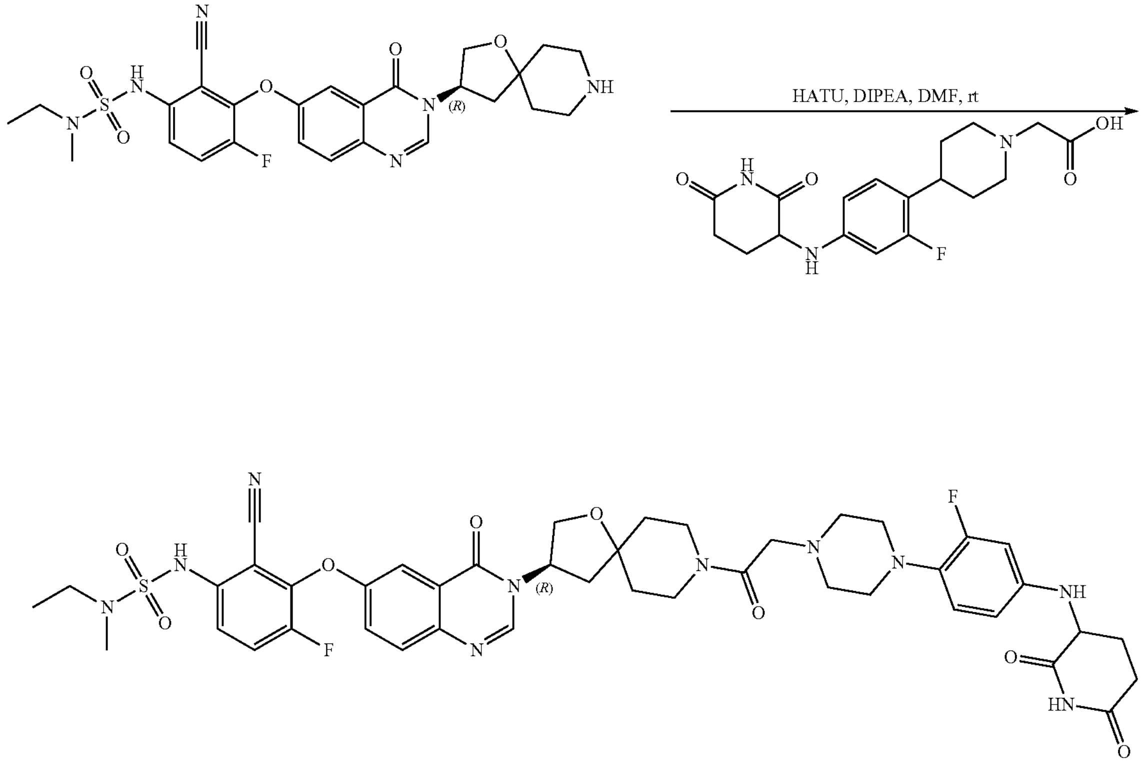

Target compound was prepared via HATU mediated acid-amine coupling reaction (Procedure A-E). Amide coupling was carried out using (3R)-3-[6-[2-cyano-3-[[ethyl(methyl) sulfamoyl]amino]-6-fluoro-phenoxy]-4-oxo-quinazolin-3-yl]-1-oxa-8-azaspiro[4.5]decane (70 mg, 125.76 μmol), 2-[4-[4-[(2,6-dioxo-3-piperidyl)amino]-2-fluoro-phenyl] piperazin-1-yl]acetic acid (45.82 mg, 125.76 μmol), N,N-diisopropylethylamine (65.02 mg, 503.05 μmol, 87.62 μL) and HATU (47.82 mg, 125.76 μmol). The crude compound was purified by reverse phase column chromatography, eluting with 50% acetonitrile in 0.1% formic acid in water, to afford (3R)-3-[6-[2-cyano-3-[[ethyl(methyl)sulfamoyl] amino]-6-fluoro-phenoxy]-4-oxo-quinazolin-3-yl]-8-[2-[4-[4-[(2,6-dioxo-3-piperidyl)amino]-2-fluoro-phenyl]piperazin-1-yl]acetyl]-1-oxa-8-azaspiro[4.5]decane (20 mg, 20.81 μmol, 17% yield) as off-white solid. LCMS m/z (ESI): 903.2 $[M+H]^+$; $^1H$ NMR (400 MHz, DMSO-$d_6$): δ=10.80 (s, 1H), 10.08 (s, 1H), 8.36 (s, 1H), 8.04 (t, J=10.00 Hz, 1H), 7.80 (d, J=8.80 Hz, 1H), 7.71 (dd, J=8.80, 2.80 Hz, 1H), 7.50 (dd, J=9.20, 4.00 Hz, 1H), 7.37 (d, J=2.80 Hz, 1H), 6.88 (t, J=9.20 Hz, 1H), 6.49 (dd, J=35.40, 8.40 Hz, 2H), 5.93 (d, J=7.60 Hz, 1H), 5.31 (s, 1H), 4.27 (t, J=8.40 Hz, 1H), 4.19-4.11 (m, 3H), 3.76 (s, 1H), 3.42-3.34 (m, 3H), 3.19-3.11 (m, 8H), 2.80 (s, 3H), 2.68-2.59 (m, 4H), 2.14-2.06 (m, 3H), 1.95-1.51 (m, 6H), 1.06 (t, J=7.20 Hz, 3H).

Example 51

3-[6-[2-cyano-3-[[ethyl(methyl)sulfamoyl]amino]-6-fluorophenoxy]-5-fluoro-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

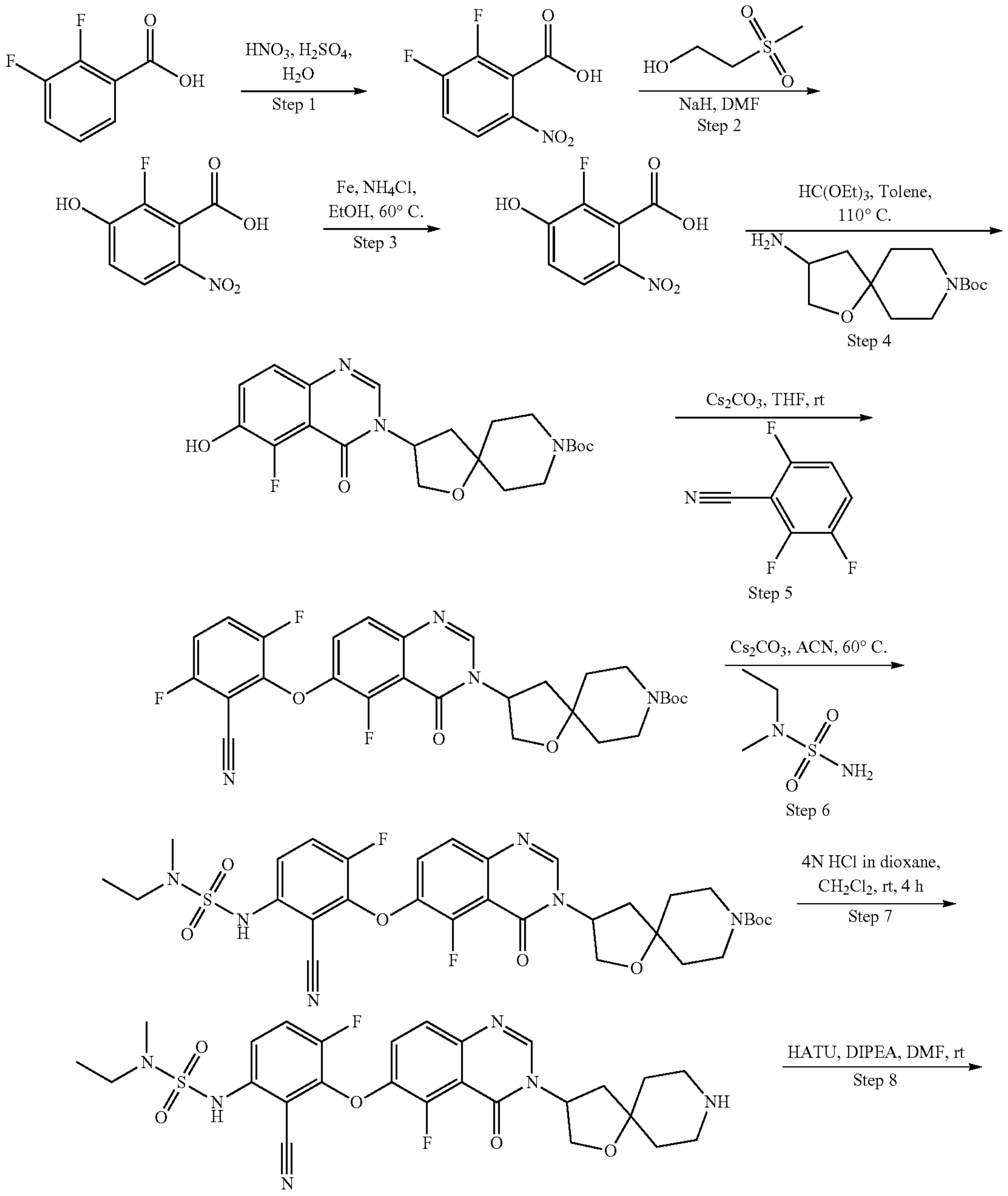

-continued

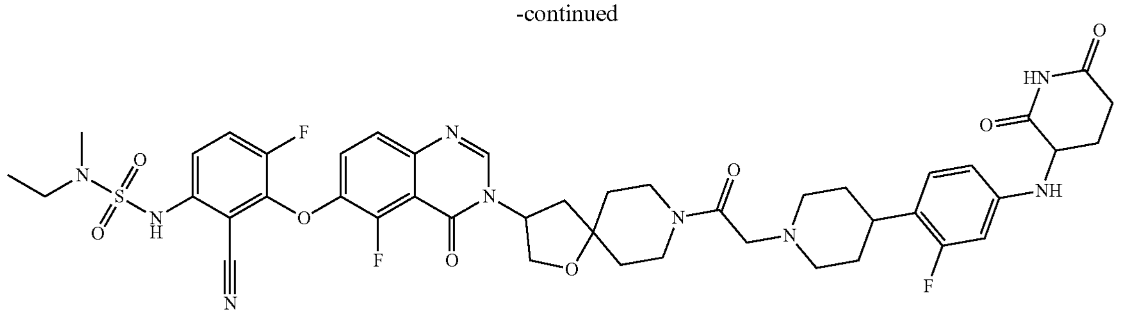

Step 1: To a stirred solution of 2,3-difluorobenzoic acid (10 g, 63.25 mmol) in sulfuric acid (80.52 g, 820.99 mmol, 44.00 mL) was added nitric Acid (4.78 g, 75.90 mmol, 3.17 mL) dropwise at 0° C. under inert condition. The reaction mixture was stirred at 0-5° C. for 2 h. After completion, the reaction mixture was diluted with water (200 mL) and extracted with ethyl acetate (3×100 mL). Combined organic layers washed dried over sodium sulfate, filtered and concentrated under reduced pressure to afford 2,3-difluoro-6-nitro-benzoic acid (9.2 g, 44.39 mmol, 70% yield) as a yellow solid, which was carried forward without further purification. LCMS m/z (ESI): 202.2 $[M-H]^-$ Step 2: To a stirred solution of 2,3-difluoro-6-nitro-benzoic acid (2.7 g, 13.29 mmol) in N,N-dimethylformamide (40 mL) was added sodium hydride (60% dispersion in mineral oil, 2.55 g, 63.68 mmol) The reaction mixture was stirred at 0° C. and stirred for 1 h. After completion, the reaction mixture was quenched dropwise with saturated ammonium chloride solution (50 mL) at 0° C. and extracted with ethyl acetate (3×200 mL). The combined organic layers were washed with cold water (3×100 mL), dried over sodium sulfate, filtered and concentrated under reduced pressure. The crude product was purified by silica gel flash column chromatography using 10-20% ethyl acetate in petroleum ether as eluent to afford 2-fluoro-3-hydroxy-6-nitro-benzoic acid (2.7 g, 10.91 mmol, 82% yield) as a yellow solid. LCMS m/z (ESI): 200.2 $[M-H]^-$ Step 3: To a stirred solution of 2-fluoro-3-hydroxy-6-nitro-benzoic acid (2.7 g, 13.43 mmol) in 1,4-dioxane (30 mL) was added palladium hydroxide on carbon, 20 wt. % (1.89 g, 13.43 mmol) water at room temperature under nitrogen atmosphere. The resulting suspension was stirred at room temperature under hydrogen atmosphere bladder for 16 h. After completion, the reaction mixture was filtered through a pad of celite, washing with methanol (100 mL). The combined filtrate was concentrated under reduced pressure to afford 6-amino-2-fluoro-3-hydroxy-benzoic acid (2.7 g, 7.99 mmol, 60% yield) as a brown viscous solid, which was carried forward without further purification. LCMS m/z (ESI): 170.10 $[M-H]^-$ Step 4: To a stirred solution of 6-amino-2-fluoro-3-hydroxy-benzoic acid (1.2 g, 7.01 mmol) in Toluene (18 mL) and Tetrahydrofuran (3 mL) were added tert-butyl 3-amino-1-oxa-8-azaspiro[4.5]decane-8-carboxylate (1.80 g, 7.01 mmol) and diethoxy methoxy ethane (1.25 g, 8.41 mmol, 1.40 mL) at room temperature under nitrogen atmosphere. The reaction mixture was stirred at 110° C. for 12 h. After completion, the reaction mixture was diluted with water (150 mL) and extracted with ethyl acetate (3×200 mL). The combined organic layers were washed with 10% sodium bicarbonate solution (3×100 mL), dried over sodium sulfate, filtered, and concentrated under reduced pressure. The product was purified by silica gel flash column chromatography by using 70-90% ethyl acetate in petroleum ether as eluent to afford tert-butyl 3-(5-fluoro-6-hydroxy-4-oxo-quinazolin-3-yl)-1-oxa-8-azaspiro[4.5]decane-8-carboxylate (0.460 g, 931.09 μmol, 13% yield). LCMS m/z (ESI): 420.2 $[M+H]^+$ Step 5: O-arylated quinazolinone intermediate was synthesized by following Procedure A-B using tert-butyl 3-(5-fluoro-6-hydroxy-4-oxo-quinazolin-3-yl)-1-oxa-8-azaspiro[4.5]decane-8-carboxylate (0.440 g, 1.05 mmol), cesium carbonate (1.03 g, 3.15 mmol) and 2,3,6-trifluorobenzonitrile (197.75 mg, 1.26 mmol, 145.40 μL). The crude compound was purified by silica gel flash column chromatography with 80-90% ethyl acetate in petroleum ether as a eluent to afford tert-butyl 3-[6-(2-cyano-3,6-difluoro-phenoxy)-5-fluoro-4-oxo-quinazolin-3-yl]-1-oxa-8-azaspiro[4.5]decane-8-carboxylate (0.450 g, 749.43 μmol, 71% yield) as light brown liquid. LCMS m/z (ESI): 501.20 $[M+H-{}^tBu]^+$ Step 6: Sulfamoylated quinazolinone intermediate was synthesized by following Procedure A-C using tert-butyl 3-[6-(2-cyano-3,6-difluoro-phenoxy)-5-fluoro-4-oxo-quinazolin-3-yl]-1-oxa-8-azaspiro[4.5]decane-8-carboxylate (0.430 g, 772.64 μmol), cesium carbonate (629.36 mg, 1.93 mmol) and [methyl(sulfamoyl)amino]ethane (160.16 mg, 1.16 mmol) to afford tert-butyl 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane-8-carboxylate (0.22 g, 292.80 μmol, 38% yield) as a brown solid, which was carried forward without further purification. LCMS m/z (ESI): 673.2 $[M-H]^-$ Step 7: The requisite amine was synthesized by following Procedure A-D using of tert-butyl 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane-8-carboxylate (0.22 g, 326.06 μmol) and hydrogen chloride solution in 1,4-dioxane (4.0 M, 3 mL). The resulted crude compound was triturated with methyl t-butyl ether to afford 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane (0.22 g, 346.01 μmol, 93% yield) as an off-white solid, which was carried forward without further purification. LCMS m/z (ESI): 573.0 $[M-H]^-$ Step 8: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (53.12 mg, 146.19 μmol), 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane (0.07 g, 121.82 μmol), N,N-diisopropylethylamine (61.64 mg, 609.12 μmol, 84.90 μL) and HATU (50.95 mg, 134.01 μmol) to afford crude product. The crude product was purified by C18-reverse phase column chromatography using Isolera (100 g RediSep® Rf C18, Method: 0.1% formic acid in water: acetonitrile) and pure fractions were lyophilized to afford 3-[6-[2-cyano-3-[[ethyl(methyl)sulfamoyl]amino]-6-fluoro-phenoxy]-5-fluoro-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (20.96 mg, 20.43 μmol, 17% yield) as an off-white solid. LCMS m/z (ESI): 920.20 $[M+H]^+$; $^1H$ NMR (400 MHz, DMSO-$d_6$): δ=10.75 (s, 1H), 10.20 (bs, 1H), 9.60 (bs, 1H), 8.35 (s, 1H), 7.74 (m, 1H), 7.61 (d, J=7.20 Hz, 1H), 7.52 (d, J=9.20 Hz, 1H), 7.40 (d, J=6.00 Hz, 1H), 6.98 (m, 1H), 6.55-6.46 (m, 2H), 6.12 (d, J=7.20 Hz, 1H), 5.38-5.27 (m, 1H), 4.40-4.10 (m, 5H), 2.85-2.75 (m, 1H), 3.60-3.40 (m, 2H), 3.30-2.85 (m, 5H), 2.76 (s, 3H), 2.70-2.60 (m, 2H), 2.45-2.35 (m, 2H), 2.20-1.50 (m, 12H), 1.06 (t, J=6.80 Hz, 3H).

Example 52

6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-5-fluoro-4-oxoquinazoline

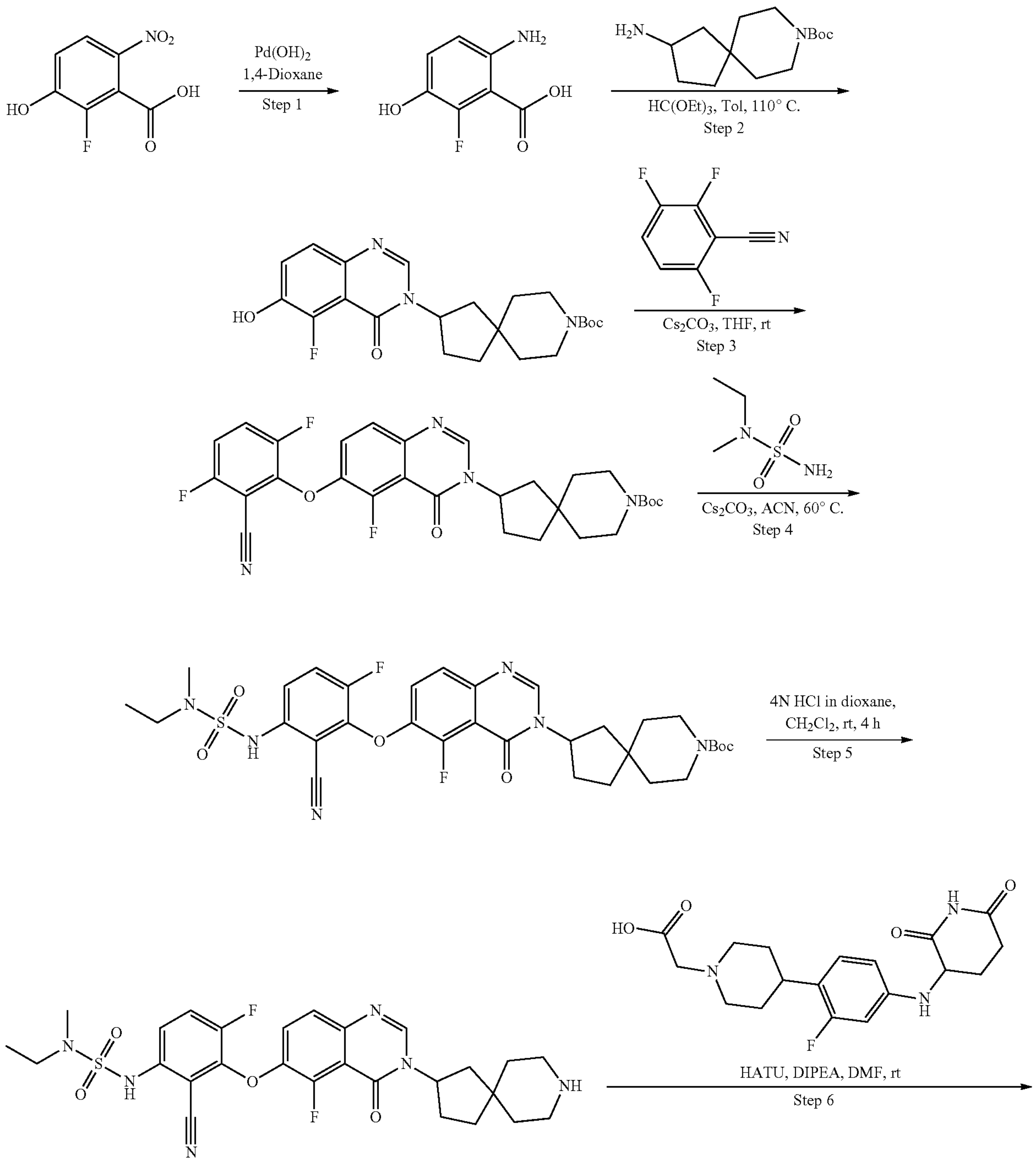

-continued

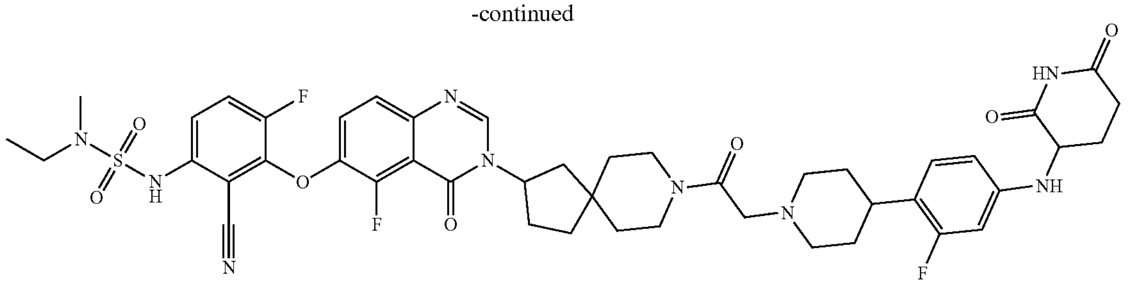

Step 1: To a stirred solution of 2-fluoro-3-hydroxy-6-nitro-benzoic acid (2.7 g, 13.43 mmol) in 1,4-dioxane (30 mL) was added palladium hydroxide on carbon, 20 wt. % (1.89 g, 13.43 mmol) water at room temperature under nitrogen atmosphere. The resulting suspension was stirred at room temperature under hydrogen atmosphere bladder for 16 h. After completion, the reaction mixture was filtered through a pad of celite and was washed with methanol (100 mL). The combined filtrate was concentrated under reduced pressure to afford a crude product 6-amino-2-fluoro-3-hydroxy-benzoic acid (2.7 g, 7.99 mmol, 60% yield) as a brown viscous solid. LCMS m/z (ESI): 170.10 $[M-H]^-$ Step 2: To a stirred solution of 6-amino-2-fluoro-3-hydroxy-benzoic acid (897.00 mg, 2.83 mmol) in toluene (18 mL) and tetrahydrofuran (3 mL) were added tert-butyl 3-amino-8-azaspiro[4.5]decane-8-carboxylate (600 mg, 2.36 mmol) and diethoxymethoxyethane (524.36 mg, 3.54 mmol, 588.51 μL) at room temperature under nitrogen atmosphere. The reaction mixture was stirred at 110° C. for 12 h. After completion, the reaction mixture was diluted with water (75 mL) and extracted with ethyl acetate (3×100 mL). The combined organic layers were washed with 10% sodium bicarbonate solution (3×50 mL), dried over sodium sulfate, filtered and concentrated under reduced pressure. The crude product was purified by silica gel flash column chromatography by using 90-100% ethyl acetate in petroleum ether as eluent to afford tert-butyl 3-(5-fluoro-6-hydroxy-4-oxo-quinazolin-3-yl)-8-azaspiro[4.5]decane-8-carboxylate (0.3 g, 626.57 μmol, 27% yield). LCMS m/z (ESI): 362.20 $[M+H-{}^tBu]^+$ Step 3: O-arylated quinazolinone intermediate was synthesized by following Procedure A-B using tert-butyl 3-(5-fluoro-6-hydroxy-4-oxo-quinazolin-3-yl)-8-azaspiro[4.5]decane-8-carboxylate (0.3 g, 718.61 μmol), cesium carbonate (702.41 mg, 2.16 mmol) and 2,3,6-trifluorobenzonitrile (135.47 mg, 862.33 μmol, 99.61 μL). The crude compound was purified by silica gel flash column chromatography with 80-90% ethyl acetate in petroleum ether as a eluent to afford tert-butyl 3-[6-(2-cyano-3,6-difluoro-phenoxy)-5-fluoro-4-oxo-quinazolin-3-yl]-8-azaspiro[4.5]decane-8-carboxylate (0.190 g, 293.47 μmol, 41% yield) as a brown viscous solid. LCMS m/z (ESI): 554.56 $[M+H]^+$ Step 4: Sulfamoylated quinazolinone intermediate was synthesized by following Procedure A-C using tert-butyl 3-[6-(2-cyano-3,6-difluoro-phenoxy)-5-fluoro-4-oxo-quinazolin-3-yl]-8-azaspiro[4.5]decane-8-carboxylate (0.190 g, 342.61 μmol), cesium carbonate (279.08 mg, 856.54 μmol) and [methyl(sulfamoyl)amino]ethane (71.02 mg, 513.92 μmol) to afford crude product tert-butyl 3-[6-[2-cyano-3-[[ethyl(methyl)sulfamoyl]amino]-6-fluoro-phenoxy]-5-fluoro-4-oxo-quinazolin-3-yl]-8-azaspiro[4.5]decane-8-carboxylate (0.12 g, 126.80 μmol, 37% yield) as brown solid. LCMS m/z (ESI): 671.20 $[M-H]^-$ Step 5: The requisite amine was synthesized by following Procedure A-D using tert-butyl 3-[6-[2-cyano-3-[[ethyl(methyl)sulfamoyl]amino]-6-fluoro-phenoxy]-5-fluoro-4-oxo-quinazolin-3-yl]-8-azaspiro[4.5]decane-8-carboxylate (0.12 g, 178.37 μmol) and hydrogen chloride solution in 1,4-dioxane (4.0 M, 3 mL). The resulted crude compound was triturated with methyl t-butyl ether to afford 3-(8-azaspiro[4.5]decan-3-yl)-6-[2-cyano-3-[[ethyl(methyl)sulfamoyl]amino]-6-fluoro-phenoxy]-5-fluoro-4-oxo-quinazoline (0.11 g, 139.23 μmol, 78% yield) as an off-white solid. LCMS m/z (ESI): 571.0 $[M-H]^-$ Step 6: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (83.77 mg, 230.52 μmol), 3-(8-azaspiro[4.5]decan-3-yl)-6-[2-cyano-3-[[ethyl(methyl)sulfamoyl]amino]-6-fluoro-phenoxy]-5-fluoro-4-oxo-quinazoline (0.110 g, 192.10 μmol), N,N-diisopropylethylamine (97.19 mg, 960.49 μmol, 133.87 μL) and HATU (80.35 mg, 211.31 μmol) to afford crude product. The crude product was purified by C18-reverse phase column chromatography using Isolera (100 g RediSep® Rf C18, Method: 0.1% formic acid in water: acetonitrile) and pure fractions were lyophilized to afford 6-[2-cyano-3-[[ethyl(methyl)sulfamoyl]amino]-6-fluoro-phenoxy]-3-[8-[2-[4-[4-[(2,6-dioxo-3-piperidyl)amino]-2-fluoro-phenyl]-1-piperidyl]acetyl]-8-azaspiro[4.5]decan-3-yl]-5-fluoro-4-oxo-quinazoline (20 mg, 20.11 μmol, 10% yield) as off-white solid. LCMS m/z (ESI): 918.20 $[M+H]^+$; $^1H$ NMR (400 MHz, DMSO-$d_6$): δ=10.70 (s, 1H), 9.50 (bs, 1H), 8.35 (s, 1H), 7.57 (s, 1H), 7.47-7.38 (m, 2H), 7.26 (d, J=5.60 Hz, 1H), 6.90-6.80 (m, 1H), 6.43-6.34 (m, 2H), 6.00 (d, J=7.60 Hz, 1H), 4.95-4.93 (m, 1H), 4.30-4.10 (m, 3H), 3.55-3.45 (m, 2H), 3.45-3.30 (m, 3H), 2.96 (q, J=12.40 Hz, 2H), 2.85-2.70 (m, 3H), 2.67 (s, 3H), 2.60-2.45 (m, 3H), 2.05-1.60 (m, 12H), 1.60-1.32 (m, 4H), 0.93 (t, J=6.80 Hz, 3H).

Example 53
6-[2-cyano-3-[[ethyl(methyl)sulfamoyl]amino]-6-fluorophenoxy]-3-[(3S)-8-[2-[4-[4-[(2,6-dioxopiperidin-3-yl)amino]-3-fluorophenyl]piperidin-1-yl]acetyl]-8-azaspiro[4.5]decan-3-yl]-4-oxoquinazoline
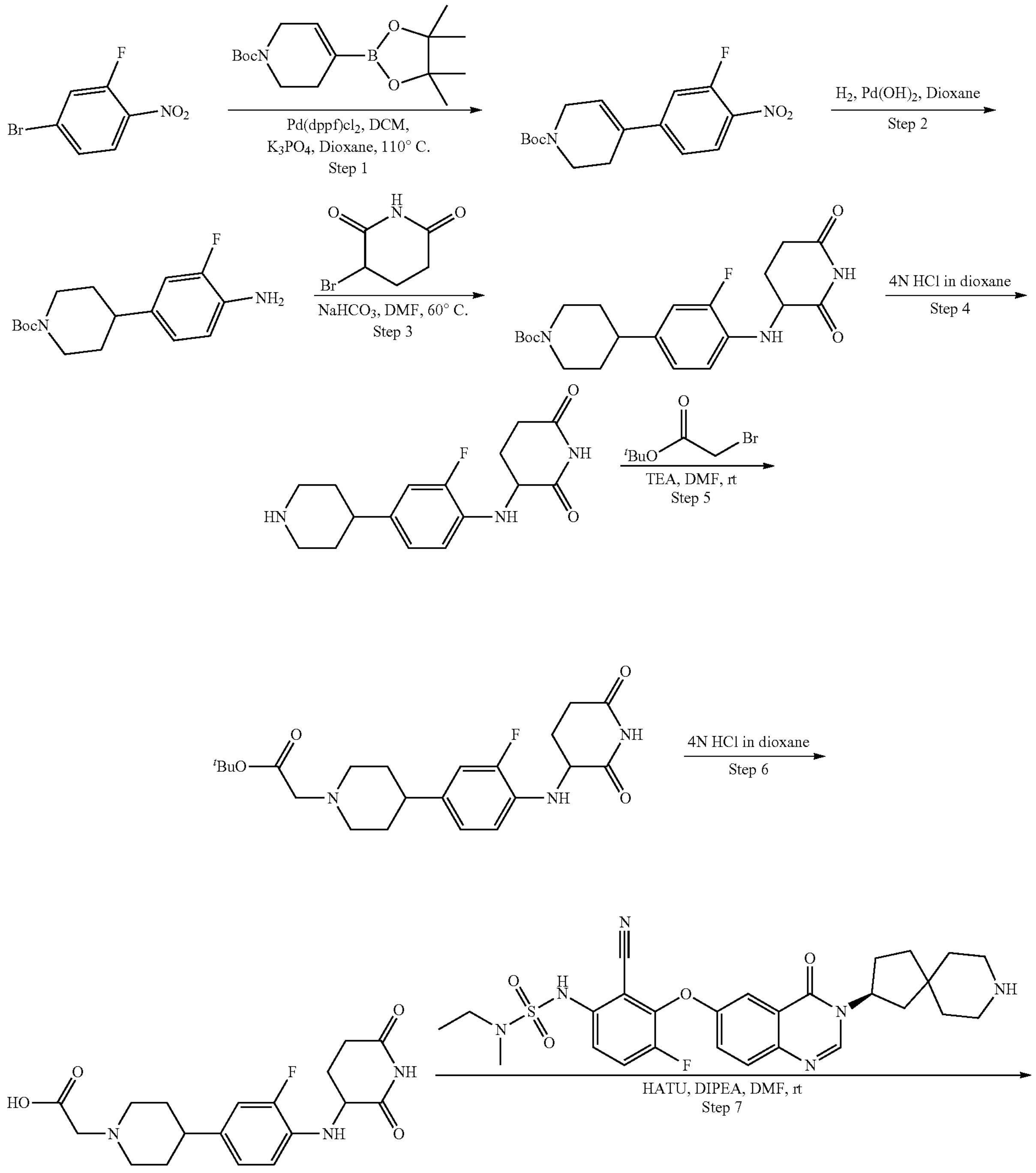

-continued

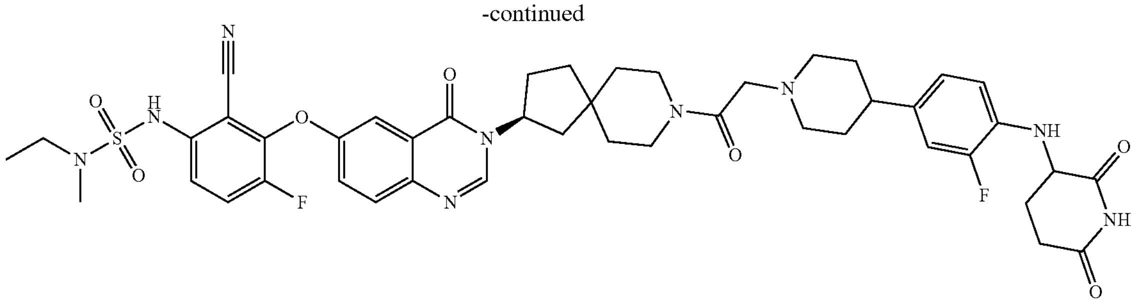

Step 1: To a stirred solution of 4-bromo-2-fluoro-1-nitrobenzene (5.00 g, 22.73 mmol) in Dioxane (50 mL) in sealed tube, were added $K_3PO_4$ (14.47 g, 68.18 mmol) and tert-butyl 4-(4,4,5,5-tetramethyl-1,3,2-dioxaborolan-2-yl)-3,6-dihydro-2H-pyridine-1-carboxylate (7.73 g, 25.00 mmol). The reaction mixture was purged with nitrogen gas for 10 mins, then added $Pd(dppf)Cl_2 \cdot CH_2Cl_2$ (1.86 g, 2.27 mmol), again purged with nitrogen gas for 5 mins and then stirred at 100° C. for 12 h. After completion, the reaction mixture was diluted with water (100 mL) and extracted with ethyl acetate (3×150 mL). Combined organic layers were washed with cold water (3×70 mL), dried over sodium sulfate, filtered, and concentrated. The desired product was purified by silica gel flash column chromatography using 70-80% ethyl acetate in petroleum ether as eluent to afford tert-butyl 4-(3-fluoro-4-nitro-phenyl)-3,6-dihydro-2H-pyridine-1-carboxylate (5.0 g, 14.80 mmol, 65% yield) as an off-white solid. LCMS m/z (ESI): 223.2 $[M+H-CO_2{}^tBu]^+$ Step 2: To a stirred solution of tert-butyl 4-(3-fluoro-4-nitro-phenyl)-3,6-dihydro-2H-pyridine-1-carboxylate (5.00 g, 15.51 mmol) in ethyl acetate (25 mL) and 1,4-dioxane (25 mL) was charged palladium hydroxide on carbon, 20 wt. % (2.18 g, 15.51 mmol). The reaction was saturated with hydrogen by bubbling hydrogen gas through for 10 minutes, and then subjected to hydrogenation (1 atm) at room temperature for 16 h. After completion, the reaction mixture was purged with nitrogen, and catalyst was removed by filtration through a pad of celite. The filtrate was concentrated under reduced pressure to afford tert-butyl 4-(4-amino-3-fluoro-phenyl)piperidine-1-carboxylate (4.2 g, 14.05 mmol, 91% yield) as light brown liquid, which was carried forward without further purification. LCMS m/z (ESI): 195.20 $[M+H-CO_2{}^tBu]^+$ Step 3: To a stirred solution of tert-butyl 4-(4-amino-3-fluoro-phenyl)piperidine-1-carboxylate (1 g, 3.40 mmol) in N,N-dimethylformamide (10 mL) were added sodium bicarbonate (998.84 mg, 11.89 mmol, 462.43 μL) followed by 3-bromopiperidine-2,6-dione (1.63 g, 8.49 mmol) at room temperature under nitrogen atmosphere. The reaction mixture was stirred at 60° C. After completion of the reaction, the reaction mixture was diluted with water (20 mL) and extracted with ethyl acetate (3×30 mL). The organic layer was washed with brine solution (30 mL), dried over sodium sulfate, filtered and concentrated. The crude material was purified by column chromatography on silica gel, eluting with 60% ethyl acetate in petroleum ether, to afford tert-butyl 4-[4-[(2,6-dioxo-3-piperidyl)amino]-3-fluoro-phenyl] piperidine-1-carboxylate (0.6 g, 1.30 mmol, 38% yield) as a yellow solid. LCMS m/z (ESI): 350.20 $[M+H-{}^tBu]^+$ Step 4: To a stirred solution of tert-butyl 4-[4-[(2,6-dioxo-3-piperidyl)amino]-3-fluoro-phenyl]piperidine-1-carboxylate (0.6 g, 1.48 mmol) in 1,4-dioxane (4 mL) was added hydrogen chloride solution in 1,4-dioxane (4.0 M, 3 mL) at 5° C. under nitrogen atmosphere. The reaction mixture was stirred at room temperature for 6 h. After completion, the reaction mixture was concentrated under reduced pressure to afford 3-[2-fluoro-4-(4-piperidyl)anilino]piperidine-2,6-dione (0.5 g, 1.45 mmol, 98% yield) as an off-white solid, which was carried forward without further purification. LCMS m/z (ESI): 306.2 $[M+H]^+$ Step 5: To a stirred solution of 3-[2-fluoro-4-(4-piperidyl)anilino]piperidine-2,6-dione (0.5 g, 1.64 mmol) in N,N-dimethylformamide (5 mL) were added N,N-diethyl ethanamine (662.79 mg, 6.55 mmol, 912.93 μL) followed by tert-butyl 2-bromo acetate (319.40 mg, 1.64 mmol, 240.15 μL) at room temperature under nitrogen atmosphere. The reaction mixture was stirred at room temperature for 12 h. After completion of the reaction, the reaction mixture was diluted with water (10 mL) and extracted with ethyl acetate (3×10 mL). The organic layer was washed with brine solution (30 mL), dried over sodium sulfate, filtered and concentrated under reduced pressure to afford tert-butyl 2-[4-[4-[(2,6-dioxo-3-piperidyl)amino]-3-fluoro-phenyl]-1-piperidyl]acetate (0.120 g, 281.45 μmol, 17% yield), which was carried forward without further purification. LCMS m/z (ESI): 420.2 $[M+H]^+$ Step 6: The requisite amine was synthesized by following Procedure A-D using of tert-butyl 2-[4-[4-[(2,6-dioxo-3-piperidyl)amino]-3-fluoro-phenyl]-1-piperidyl]acetate (0.12 g, 286.06 μmol) and hydrogen chloride solution in 1,4-dioxane (4.0 M, 2 mL). The resulted crude compound was triturated with methyl t-butyl ether to afford 2-[4-[4-[(2,6-dioxo-3-piperidyl)amino]-3-fluoro-phenyl]-1-piperidyl]acetic acid (0.14 g, 350.14 μmol) as an off-white solid, which was carried forward without further purification. LCMS m/z (ESI): 364.20 $[M+H]^+$ Step 7: Target compound was prepared via HATU mediated acid-amine coupling reaction (Procedure A-E). Amide coupling was carried out using 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (0.08 g, 144.24 μmol2-[4-[4-[(2,6-dioxo-3-piperidyl)amino]-3-fluoro-phenyl]-1-piperidyl]acetic acid (52.41 mg, 144.24 μmol), N,N-diisopropylethylamine (93.21 mg, 721.20 μmol, 125.62 μL) and HATU (60.33 mg, 158.66 μmol). The crude product was purified by C18-reverse phase column chromatography using Isolera (100 g RediSep© Rf C18, Method: 0.1% formic acid in water:acetonitrile) and pure fractions were lyophilized to afford 6-[2-cyano-3-[[ethyl(methyl)sulfamoyl]amino]-6-fluoro-phenoxy]-3-[(3S)-8-[2-[4-[4-[(2,6-dioxo-3-piperidyl)amino]-3-fluoro-phenyl]-1-piperidyl] acetyl]-8-azaspiro[4.5]decan-3-yl]-4-oxo-quinazoline (10 mg, 10.48 μmol, 7% yield) as an off-white solid. LCMS m/z (ESI): 900.20 $[M+H]^+$; $^1H$ NMR (400 MHz, DMSO-$d_6$): δ=10.83 (s, 1H), 8.45 (s, 1H), 7.80-7.75 (m, 2H), 7.68 (dd, J=3.20, 9.00 Hz, 1H), 7.46 (s, 1H), 7.37 (s, 1H), 6.95 (d, J=12.80 Hz, 1H), 6.87-6.78 (m, 2H), 5.55-5.45 (m, 1H), 5.15-4.95 (m, 1H), 4.45-4.30 (m, 2H), 4.28-4.15 (m, 1H), 3.65-3.50 (m, 2H), 3.20-3.05 (m, 3H), 2.76 (s, 3H), 2.70-2.60 (m, 2H), 2.20-2.20 (m, 6H), 2.00-1.80 (m, 7H), 1.70-1.40 (m, 6H), 1.27-1.24 (m, 2H), 1.05 (t, J=6.80 Hz, 3H).

Example 54

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-3-fluoro-phenyl]piperidin-1-yl]acetyl]-1-oxa-8-azaspiro[4.5]decane

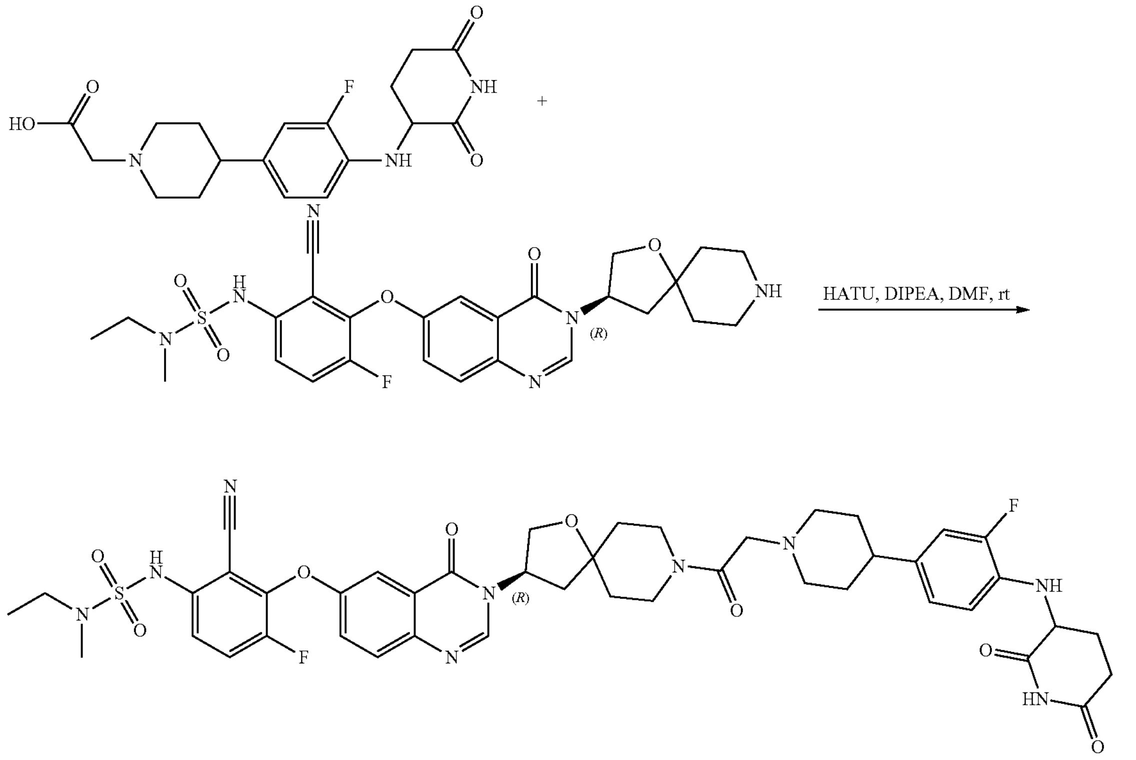

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (70.00 mg, 125.76 μmol), 2-[4-[4-[(2,6-dioxo-3-piperidyl)amino]-3-fluoro-phenyl]-1-piperidyl]acetic acid (45.70 mg, 125.76 μmol), N,N-diisopropylethylamine (81.27 mg, 628.81 μmol, 109.53 μL) and HATU (52.60 mg, 138.34 μmol). The crude product was purified by C18-reverse phase column chromatography using Isolera (100 g RediSep® Rf C18, Method: 0.1% formic acid in water:acetonitrile) and pure fractions were lyophilized to afford (3R)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-3-fluoro-phenyl]-1-piperidyl]acetyl]-1-oxa-8-azaspiro[4.5]decane (10 mg, 10.31 μmol, 8% yield) as an off-white solid. LCMS m/z (ESI): 902.2 $[M+H]^+$; $^1H$ NMR (400 MHz, DMSO-$d_6$): δ=10.82 (s, 1H), 8.34 (s, 1H), 7.77 (d, J=9.20 Hz, 1H), 7.66 (d, J=8.80 Hz, 1H), 7.52 (bs, 1H), 7.35 (s, 2H), 6.96 (d, J=15.20 Hz, 1H), 6.86-6.76 (m, 2H), 5.55-5.40 (m, 1H), 5.35-5.25 (m, 1H), 4.45-4.35 (m, 1H), 4.25-4.10 (m, 2H), 3.75-3.65 (m, 3H), 3.50-3.40 (m, 4H), 3.15-3.00 (m, 3H), 2.85-2.70 (m, 3H), 2.68 (s, 3H), 2.50-2.40 (m, 4H), 2.20-2.00 (m, 3H), 1.90-1.65 (m, 7H), 1.60-1.50 (m, 1H), 1.03 (t, J=7.20 Hz, 3H).

Example 55
6-[2-cyano-3-[[ethyl(methyl)sulfamoyl]amino]-6-fluorophenoxy]-3-[(3S)-8-[2-[4-[4-(2,6-dioxopiperidin-3-yl)-2-fluorophenyl]piperazin-1-yl]acetyl]-8-azaspiro[4.5]decan-3-yl]-4-oxoquinazoline
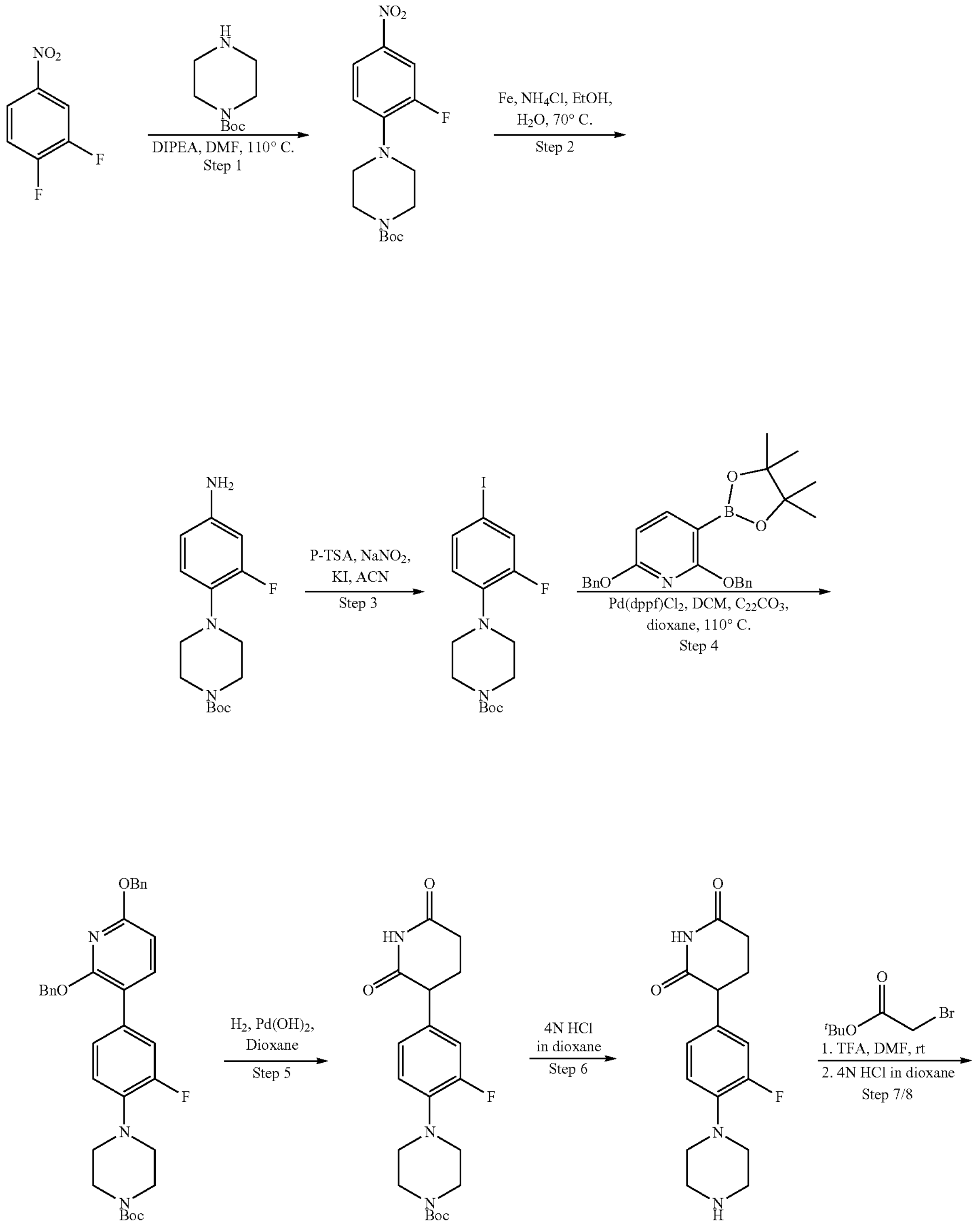

-continued

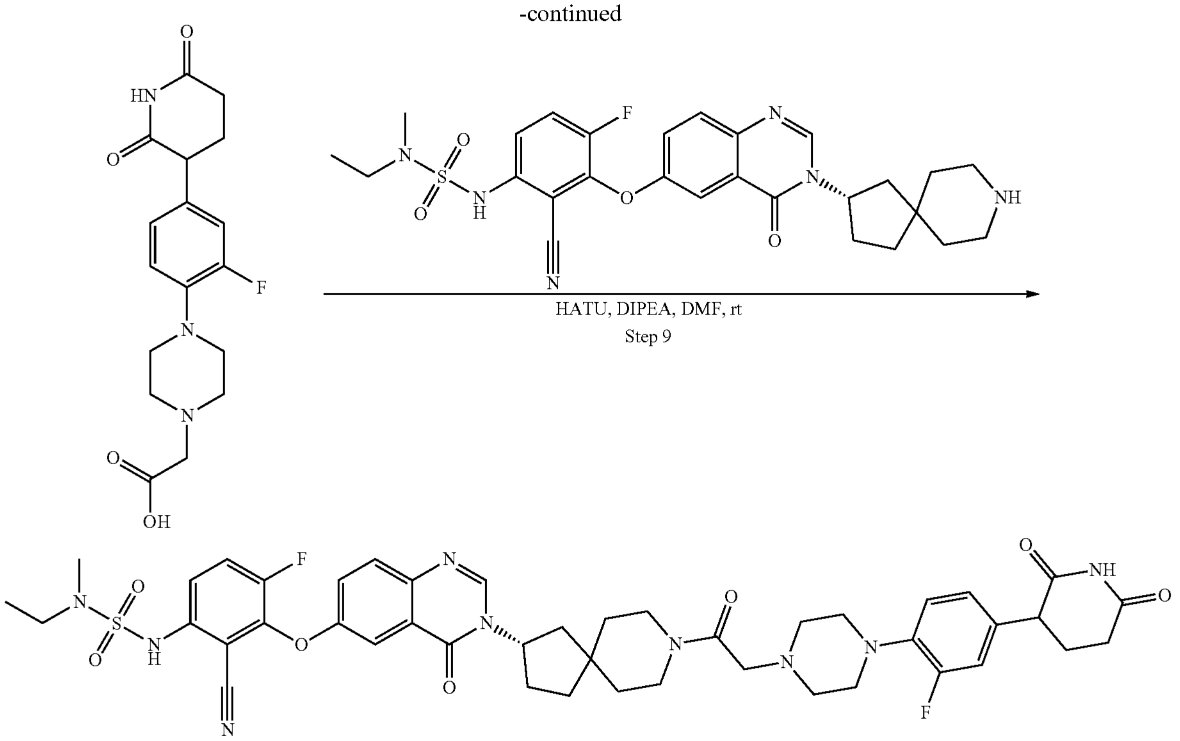

Step 1: A solution of 1,2-difluoro-4-nitro-benzene (5 g, 31.43 mmol, 3.47 mL) in N,N-dimethylformamide (40 mL) was taken in a sealed tube and added N,N-diisopropylethylamine (16.25 g, 125.71 mmol, 21.90 mL) followed by tert-butyl piperazine-1-carboxylate (5.85 g, 31.43 mmol) at room temperature under nitrogen atmosphere. The reaction mixture was heated to 110° C. for 12 h. The reaction mixture was diluted with water (60 mL) and extracted with ethyl acetate (3×100 mL). The combined organic layers were dried over sodium sulfate, filtered, and concentrated under vacuum. The crude compound was purified by silica gel flash column chromatography, eluting with 30-45% ethyl acetate in petroleum ether, to afford tert-butyl 4-(2-fluoro-4-nitro-phenyl)piperazine-1-carboxylate (9.0 g, 27.66 mmol, 88% yield). $^1$H NMR (400 MHz, DMSO-$d_6$): δ=8.01-8.07 (m, 2H), 7.19 (t, J=9.60 Hz, 1H), 3.40-3.51 (m, 4H), 3.27 (t, J=4.80 Hz, 4H), 1.43 (s, 9H).

Step 2: To a solution of tert-butyl 4-(2-fluoro-4-nitro-phenyl)piperazine-1-carboxylate (9.0 g, 27.66 mmol) in ethanol (70 mL), water (20 mL) were added iron powder (7.72 g, 138.32 mmol, 982.75 μL), followed by ammonium hydrochloride (4.44 g, 82.99 mmol) at room temperature and the reaction mixture was stirred at 70° C. for 4 h. After completion, the reaction mixture was filtered through celite and washed with ethyl acetate (250 mL). The filtrate was washed with water (150 mL), saturated sodium bicarbonate solution (50 mL) and brine (50 mL). The organic layer was dried over sodium sulfate and concentrated under reduced pressure. The crude product was purified by column chromatography on silica gel, eluting with 70% ethyl acetate in petroleum ether, to afford [1-(4-amino-2-fluoro-phenyl)-4-piperidyl]methanol (5.8 g, 17.84 mmol, 60% yield) as a light brown solid. LCMS m/z (ESI): 296.2 [M+H]$^+$.

Step 3: To a stirred solution of tert-butyl 4-(4-amino-2-fluoro-phenyl)piperazine-1-carboxylate (2 g, 6.77 mmol) in acetonitrile (20 mL) was added p-TSA·$H_2O$ (3.90 g, 20.52 mmol, 3.15 mL) at 0-5° C., followed by the addition of sodium nitrite (957.77 mg, 13.88 mmol, 441.37 μL) in water (5 mL) at the same temperature. The reaction mixture was stirred at 0-5° C. for 1 h and added potassium iodide (2.37 g, 14.29 mmol, 760.21 μL) in water (5 mL) at the same temperature. The reaction mixture was stirred at room temperature for 16 h. After completion, water (80 mL) was added to the reaction mixture and extracted with ethyl acetate (3×80 mL). The combined organic layers were dried over sodium sulfate, filtered, and concentrated under reduced pressure. The crude compound was purified by silica gel flash column chromatography, eluting with 25% ethyl acetate in petroleum ether as an eluent, to afford tert-butyl 4-(2-fluoro-4-iodo-phenyl)piperazine-1-carboxylate (2.1 g, 4.84 mmol, 71% yield) as a yellow solid. LCMS m/z (ESI): 351.0 [M+H]$^+$.

Step 4: To a stirred solution of tert-butyl 4-(2-fluoro-4-iodo-phenyl)piperazine-1-carboxylate (1 g, 2.46 mmol) and 2,6-dibenzyloxy-3-(4,4,5,5-tetramethyl-1,3,2-dioxaborolan-2-yl)pyridine (2.05 g, 2.95 mmol) in 1,4-dioxane (8 mL) and water (2 mL) in microwave vial, were added anhydrous potassium phosphate (1.31 g, 6.15 mmol). The reaction mixture was purged with nitrogen gas for 10 minutes and then added XPhos-Pd-$G_2$ (193.68 mg, 246.16 μmol). The reaction mixture was again purged with nitrogen gas for 5 minutes and irradiated at 100° C. for 2 h in microwave. After completion, the reaction mixture was diluted with water (40 mL), extracted with ethyl acetate (3×60 mL). Combined organic layers dried over sodium sulfate, filtered, and concentrated under reduced pressure. The desired product was purified from crude by column chromatography using 30-45% ethyl acetate in petroleum ether as eluent to afford tert-butyl 4-[4-(2,6-dibenzyloxy-3-pyridyl)-2-fluoro-phenyl]piperazine-1-carboxylate (1.12 g, 1.67 mmol, 68% yield). LCMS m/z (ESI): 570.2 [M+H]$^+$.

Step 5: To a solution of tert-butyl 4-[4-(2,6-dibenzyloxy-3-pyridyl)-2-fluoro-phenyl]piperazine-1-carboxylate (1.12 g, 1.97 mmol) in 1,4-dioxane (12 mL) was added $Pd(OH)_2$ (700 mg, 4.98 mmol). Then the reaction mixture was stirred at room temperature under hydrogen atmosphere for 16 h. After completion, the reaction mixture was filtered through celite and washed with ethyl acetate (80 mL). The organic layer was concentrated under reduced pressure to afford tert-butyl 4-[4-(2,6-dioxo-3-piperidyl)-2-fluoro-phenyl]piperazine-1-carboxylate (500 mg, 1.25 mmol, 63% yield). LCMS m/z (ESI): 336.2 $[M-{}^{t}Bu+H]^+$.

Step 6: To a stirred solution of tert-butyl 4-[4-(2,6-dioxo-3-piperidyl)-2-fluoro-phenyl]piperazine-1-carboxylate (500 mg, 1.28 mmol) in 1,4-dioxane (4 mL) was added hydrogen chloride solution in 1,4-dioxane (4 M, 4 mL) at 5° C. under nitrogen atmosphere. The reaction mixture was stirred at room temperature for 2 h. After completion, the reaction mixture was concentrated under reduced pressure and washed with petroleum ether to afford 3-(3-fluoro-4-piperazin-1-yl-phenyl)piperidine-2,6-dione (417 mg, 1.27 mmol, 99% yield) as off-white solid. LCMS m/z (ESI): 292.2 $[M+H]^+$.

Step 7: To a stirred solution of 3-(3-fluoro-4-piperazin-1-yl-phenyl)piperidine-2,6-dione (520 mg, 1.78 mmol) in N,N-dimethylformamide (3 mL) were added triethylamine (722.49 mg, 7.14 mmol, 995.16 μL) followed by tert-butyl 2-bromoacetate (348.17 mg, 1.78 mmol, 261.78 μL) at room temperature under nitrogen atmosphere. The reaction mixture was stirred at room temperature for 14 h. The reaction mixture was diluted with water (10 mL) and extracted with ethyl acetate (3×10 mL). The organic layer was washed with brine solution (30 mL), dried over sodium sulfate and concentrated under reduced pressure to afford crude tert-butyl 2-[4-[4-(2,6-dioxo-3-piperidyl)-2-fluoro-phenyl]piperazin-1-yl]acetate (450 mg, 1.09 mmol, 61% yield) as off-white solid. LCMS m/z (ESI): 406.2$[M+H]^+$.

Step 8: To a stirred solution of tert-butyl 2-[4-[4-(2,6-dioxo-3-piperidyl)-2-fluoro-phenyl]piperazin-1-yl]acetate (435 mg, 1.07 mmol) in dichloromethane (3 mL) was added hydrogen chloride solution in 1,4-dioxane (4 M, 5 mL) at 0° C. under nitrogen atmosphere. The reaction mixture was stirred at room temperature for 6 h. The reaction mixture was concentrated under vacuum, and the crude was washed with the petroleum ether to afford 22-[4-[4-(2,6-dioxo-3-piperidyl)-2-fluoro-phenyl]piperazin-1-yl]acetic acid (372 mg, 1.06 mmol, 99% yield) as off-white solid. LCMS m/z (ESI): 350.2 $[M+H]^+$.

Step 9: Target compound was prepared via HATU mediated acid-amine coupling reaction (Procedure A-E). Amide coupling was carried out using 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (80 mg, 144.24 μmol), 2-[4-[4-(2,6-dioxo-3-piperidyl)-2-fluoro-phenyl]piperazin-1-yl]acetic acid (60.47 mg, 173.09 μmol), N,N-diisopropylethylamine (93.21 mg, 721.20 μmol, 125.62 μL) and HATU (60.33 mg, 158.66 μmol). The crude compound was purified by reverse phase column chromatography, eluting with 40 to 45% acetonitrile in 0.1% formic acid in water, to afford 6-[2-cyano-3-[[ethyl(methyl)sulfamoyl]amino]-6-fluoro-phenoxy]-3-[(3S)-8-[2-[4-[4-(2,6-dioxo-3-piperidyl)-2-fluoro-phenyl]piperazin-1-yl]acetyl]-8-azaspiro[4.5]decan-3-yl]-4-oxo-quinazoline (27.35 mg, 28.69 μmol, 20% yield) as off-white solid. LCMS m/z (ESI): 886.2 $[M+H]^+$. $^1H$ NMR (400 MHz, DMSO-$d_6$): δ=10.81 (s, 1H), 10.13 (s, 1H), 8.46 (s, 1H), 7.87 (t, J=10.00 Hz, 1H), 7.80 (d, J=8.80 Hz, 1H), 7.69 (dd, J=2.80, 9.20 Hz, 1H), 7.50 (dd, J=3.60, 9.20 Hz, 1H), 7.37 (s, 1H), 6.99-7.11 (m, 3H), 5.01-5.11 (m, 1H), 4.20-4.55 (m, 2H), 3.83 (dd, J=4.40, 12.00 Hz, 1H), 3.55-3.65 (m, 2H), 3.25-3.52 (m, 3H), 3.12-3.35 (m, 2H), 3.17 (q, J=6.80 Hz, 2H), 2.80 (s, 3H), 2.45-2.65 (m, 7H), 1.95-2.25 (m, 5H), 1.78-1.90 (m, 2H), 1.40-1.75 (m, 5H), 1.06 (t, J=6.80 Hz, 3H).

Example 56

N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]cyclopentanesulfonamide

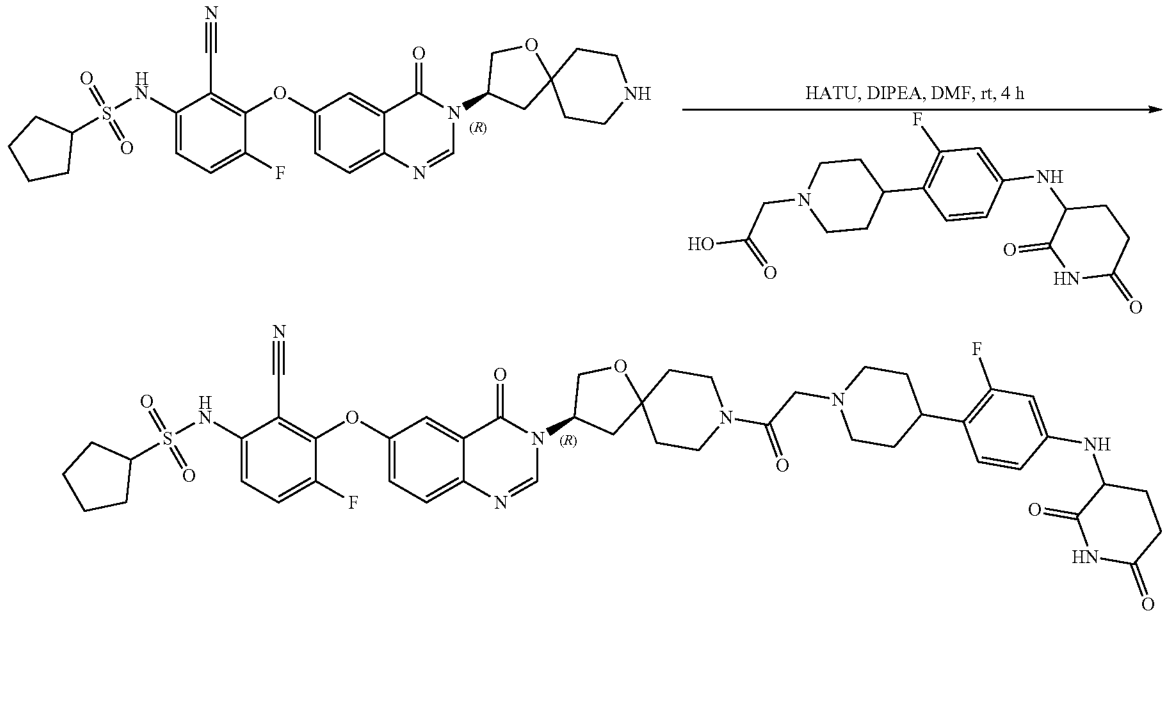

Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (46.33 mg, 115.88 μmol), N-[2-cyano-4-fluoro-3-[3-[(3R)-1-oxa-8-azaspiro[4.5]decan-3-yl]-4-oxo-quinazolin-6-yl]oxy-phenyl]cyclopentanesulfonamide (0.07 g, 115.88 μmol), N,N-diisopropylethylamine (149.76 mg, 1.16 mmol, 201.83 μL) and HATU (48.47 mg, 127.46 μmol). The crude compound was purified by reverse phase column chromatography, eluting with 50% acetonitrile in 0.1% formic acid in water, to afford N-[2-cyano-3-[3-[(3R)-8-[2-[4-[4-[(2,6-dioxo-3-piperidyl)amino]-2-fluoro-phenyl]-1-piperidyl]acetyl]-1-oxa-8-azaspiro[4.5]decan-3-yl]-4-oxo-quinazolin-6-yl]oxy-4-fluoro-phenyl]cyclopentanesulfonamide (34.94 mg, 35.66 μmol, 31% yield) as an off-white solid. LCMS m/z (ESI): 913.2 $[M+H]^+$; $^1H$ NMR (400 MHz, DMSO-$d_6$): δ=10.81 (s, 1H), 10.31 (s, 1H), 8.36 (s, 1H), 7.79 (d, J=8.80 Hz, 1H), 7.69 (dd, J=2.80, 8.80 Hz, 2H), 7.47 (d, J=2.80 Hz, 1H), 7.41 (d, J=2.80 Hz, 1H), 6.97 (s, 1H), 6.51-6.46 (m, 2H), 6.11 (d, J=8.00 Hz, 1H), 5.32 (s, 1H), 4.33 (t, J=4.00 Hz, 2H), 4.20-4.13 (m, 3H), 3.82-3.60 (m, 3H), 3.52-3.40 (m, 4H), 2.91-2.72 (m, 3H), 2.49-2.40 (m, 1H), 2.13-2.06 (m, 3H), 1.95-1.83 (m, 11H), 1.75-1.24 (m, 7H).

Example 57

6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-5-methyl-4-oxoquinazoline

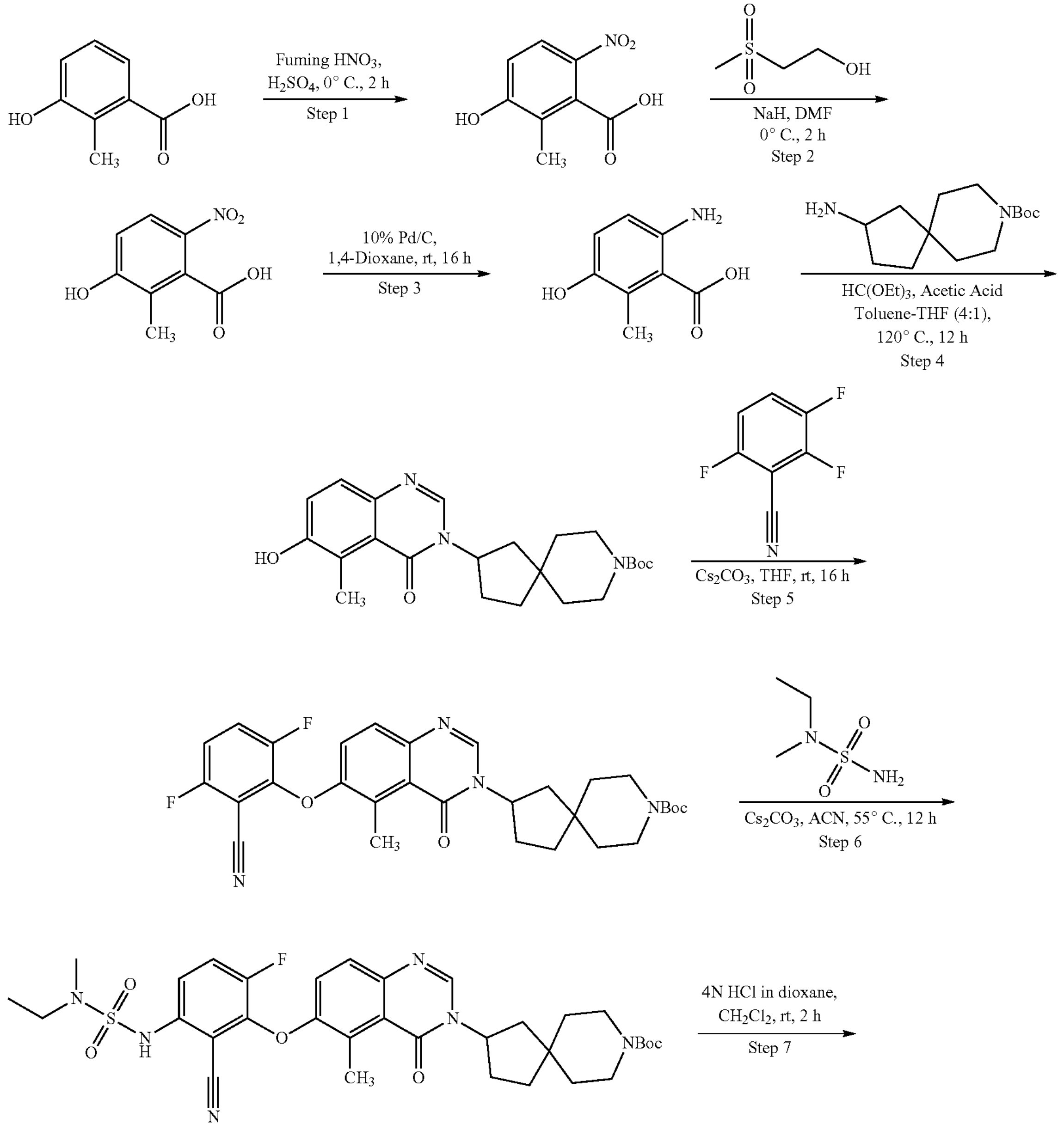

-continued

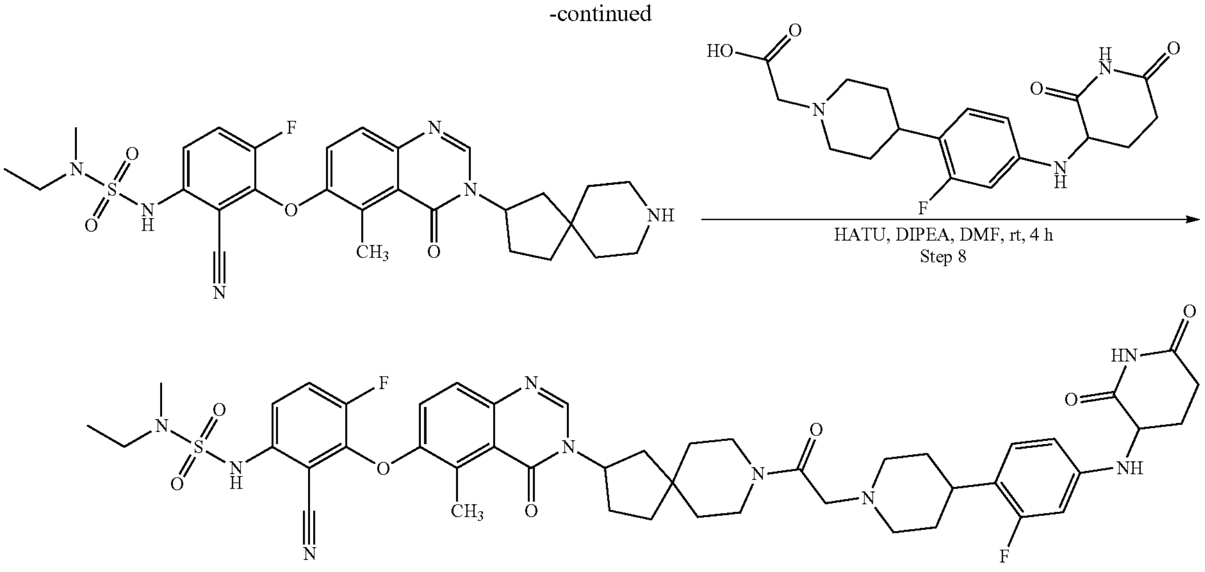

Step 1: To a solution of 3-fluoro-2-methyl-benzoic acid (194.99 mg, 1.27 mmol) in conc·$H_2SO_4$ (2 mL), was added fuming nitric acid (159.42 mg, 2.53 mmol, 0.15 mL) at 0° C. The resulting reaction mass was stirred at 0° C. for 2 h. After completion, the reaction mixture was diluted with cold water (15 mL) and extracted with ethyl acetate (3x30 mL). The combined organic layers were washed with brine solution (20 mL), dried over sodium sulfate, filtered and concentrated to afford 3-fluoro-2-methyl-6-nitro-benzoic acid (0.24 g, 1.03 mmol, 81% yield) as an off-white solid, which was carried forward without further purification. LCMS m/z (ESI): 198.2 $[M-H]^-$.

Step 2: To a solution of 3-fluoro-2-methyl-6-nitro-benzoic acid (5 g, 25.11 mmol) in N,N-dimethylformamide (120 mL), was added 2-methylsulfonylethanol (3.74 g, 30.13 mmol). The reaction mixture was cooled to 0° C., then added sodium hydride (60% dispersion in mineral oil, 8.71 g, 200.87 mmol) portion wise at 0° C. under nitrogen atmosphere. The reaction mixture was stirred at 0° C. for 1 h. The reaction warmed to room temperature and stirred for 1 h. After completion, the reaction mixture was quenched dropwise with 1.5N HCl solution (pH-1) at 0° C. and was extracted with ethyl acetate (3x150 mL). The combined organic layers were washed with cold water (3x100 mL), dried over sodium sulfate, filtered and concentrated under reduced pressure to afford 3-hydroxy-2-methyl-6-nitro-benzoic acid (5 g, 21.54 mmol, 86% yield) as orange solid, which was carried forward without further purification. LCMS m/z (ESI): 196.2 $[M-H]^-$.

Step 3: To a solution of 3-fluoro-2-methyl-6-nitro-benzoic acid (5 g, 25.11 mmol) in 1,4-dioxane (70 mL), was added 10% palladium on carbon wet (2.67 g, 25.11 mmol), saturated with hydrogen by bubbling hydrogen gas through for 10 min and then subjected to hydrogenation (1 atm) at room temperature for 16 h. After completion, the reaction mixture was purged with nitrogen and catalyst was removed by filtration through a pad of celite, washing with methanol (500 mL). The filtrate was concentrated under reduced pressure to afford 6-amino-3-hydroxy-2-methyl-benzoic acid (4.3 g, 16.95 mmol, 68% yield) as dark brown solid, which was carried forward without further purification. LCMS m/z (ESI): 168.2 $[M+H]^+$.

Step 4: Quinazolinone intermediate was synthesized by following general procedure for cyclization (Procedure A-A) using 6-amino-3-hydroxy-2-methyl-benzoic acid (0.6 g, 3.59 mmol), triethyl orthoformate (797.91 mg, 5.38 mmol, 895.52 μL), acetic acid (21.55 mg, 358.93 μmol, 20.53 μL) and tert-butyl 3-amino-8-azaspiro[4.5]decane-8-carboxylate (821.71 mg, 3.23 mmol). The desired compound was purified by silica gel flash column chromatography using 60-70% ethyl acetate in petroleum ether as eluent to afford tert-butyl 3-(6-hydroxy-5-methyl-4-oxo-quinazolin-3-yl)-8-azaspiro[4.5]decane-8-carboxylate (0.4 g, 821.17 μmol, 23% yield) as off-white solid. LCMS m/z (ESI): 414.2 $[M+H]^+$.

Step 5: O-arylated quinazolinone intermediate was synthesized by following general procedure for O-arylation (Procedure A-B) using tert-butyl 3-(6-hydroxy-5-methyl-4-oxo-quinazolin-3-yl)-8-azaspiro[4.5]decane-8-carboxylate (0.4 g, 967.33 μmol), cesium carbonate (945.52 mg, 2.90 mmol) and 2,3,6-trifluorobenzonitrile (303.92 mg, 1.93 mmol, 223.47 μL). The desired compound was purified by silica gel flash column chromatography using 60-70% ethyl acetate in petroleum ether as eluent to afford tert-butyl 3-[6-(2-cyano-3,6-difluoro-phenoxy)-5-methyl-4-oxo-quinazolin-3-yl]-8-azaspiro[4.5]decane-8-carboxylate (0.37 g, 566.83 μmol, 59% yield) as an off-white solid. LCMS m/z (ESI): 551.2 $[M+H]^+$.

Step 6: Sulfamoylated quinazolinone intermediate was synthesized by following Procedure A-C using tert-butyl 3-[6-(2-cyano-3,6-difluoro-phenoxy)-5-methyl-4-oxo-quinazolin-3-yl]-8-azaspiro[4.5]decane-8-carboxylate (280 mg, 508.54 μmol), cesium carbonate (497.08 mg, 1.53 mmol), and [methyl(sulfamoyl)amino]ethane (105.41 mg, 762.81 μmol). After completion, the reaction mixture was diluted with water (5 mL) and the resulting solid was filtered off through filter paper. The aqueous layer was extracted with ethyl acetate (3x8 mL). The organic layer was washed with cold water (3x10 mL), dried over sodium sulfate, filtered and concentrated under reduced pressure to afford crude tert-butyl 3-[6-[2-cyano-3-[[ethyl(methyl)sulfamoyl]amino]-6-fluoro-phenoxy]-5-methyl-4-oxo-quinazolin-3-yl]-8-azaspiro[4.5]decane-8-carboxylate (200 mg, 242.23 μmol, 48% yield) as a light yellow solid. LCMS m/z (ESI): 667.2 $[M-H]^-$.

Step 7: The requisite amine was synthesized by 4M HCl in Dioxane mediated N-Boc deprotection (Procedure A-D). N-Boc deprotection was done on tert-butyl (3S)-3-[6-[2-cyano-3-[[ethyl(methyl)sulfamoyl]amino]-6-fluoro-phenoxy]-5-methyl-4-oxo-quinazolin-3-yl]-8-azaspiro[4.5]decane-8-carboxylate (200 mg, 299.05 μmol) using Hydrogen chloride, 4M in 1,4-dioxane, 99% (4 M, 3 mL) to afford 3-[(3S)-8-azaspiro[4.5]decan-3-yl]-6-[2-cyano-3-[[ethyl(methyl)sulfamoyl]amino]-6-fluoro-phenoxy]-5-methyl-4-oxo-quinazoline (206 mg, 294.81 μmol, 98.58% yield, 87% purity) as a yellow viscous solid. LCMS m/z (ESI): 569.2 $[M+H]^+$.

Step 8: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (58.15 mg, 145.43 μmol), 3-(8-azaspiro[4.5]decan-3-yl)-6-[2-cyano-3-[[ethyl(methyl)sulfamoyl]amino]-6-fluoro-phenoxy]-5-methyl-4-oxo-quinazoline (0.08 g, 132.20 μmol), N,N-Diisopropylethylamine (170.87 mg, 1.32 mmol, 230.28 μL) and HATU (55.29 mg, 145.43 μmol). The crude compound was purified by reverse phase column chromatography eluted with 45% Acetonitrile in 0.1% FORMIC ACID in water to afford product 6-[2-cyano-3-[[ethyl(methyl)sulfamoyl]amino]-6-fluoro-phenoxy]-3-[8-[2-[4-[4-[(2,6-dioxo-3-piperidyl)amino]-2-fluoro-phenyl]-1-piperidyl]acetyl]-8-azaspiro[4.5]decan-3-yl]-5-methyl-4-oxo-quinazoline (11.11 mg, 10.91 μmol, 8% yield, 94.31% purity) as off white solid. LCMS m/z (ESI): 914.2 $[M+H]^+$; $^1$HNMR (400 MHz, DMSO-$d_6$): δ=10.80 (s, 1H), 9.86 (s, 1H), 8.41 (s, 1H), 7.52-7.51 (m, 1H), 7.49 (d, J=9.20 Hz, 1H), 7.30 (d, J=4.40 Hz, 1H), 7.16 (d, J=9.20 Hz, 1H), 6.99 (s, 1H), 6.50-6.45 (m, 2H), 6.08 (d, J=7.60 Hz, 1H), 5.21-5.05 (m, 1H), 4.48-4.29 (m, 1H), 3.62-3.38 (m, 4H), 3.07 (d, J=6.80 Hz, 2H), 2.88 (s, 3H), 2.80-2.65 (m, 3H), 2.50-2.60 (m, 9H), 2.13-2.08 (m, 4H), 1.90-1.78 (m, 7H), 1.67-1.50 (m, 5H), 1.04 (t, J=7.20 Hz, 3H).

Example 58

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]-3,3-difluoropiperidin-1-yl]acetyl]-1-oxa-8-azaspiro[4.5]decane

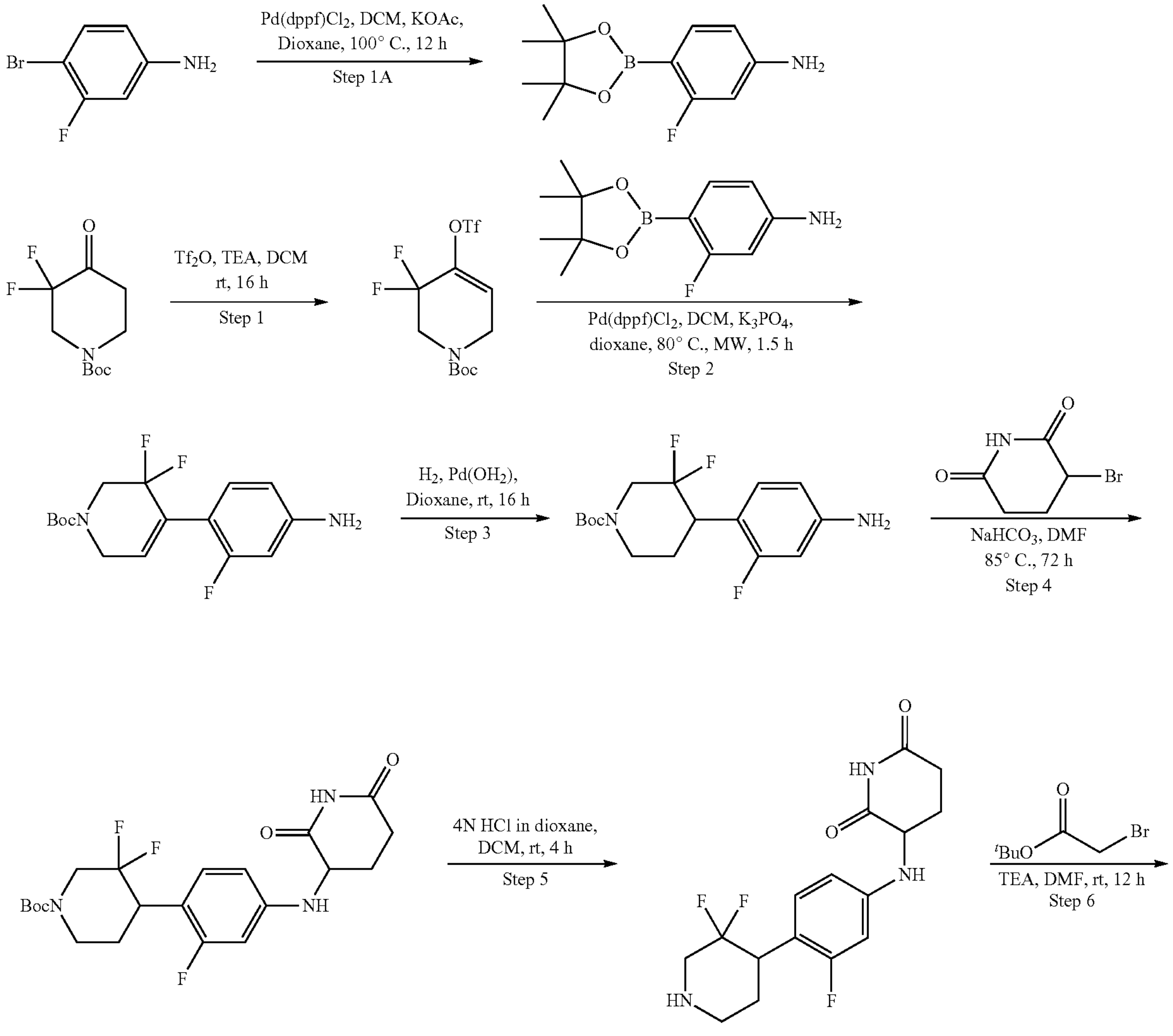

-continued

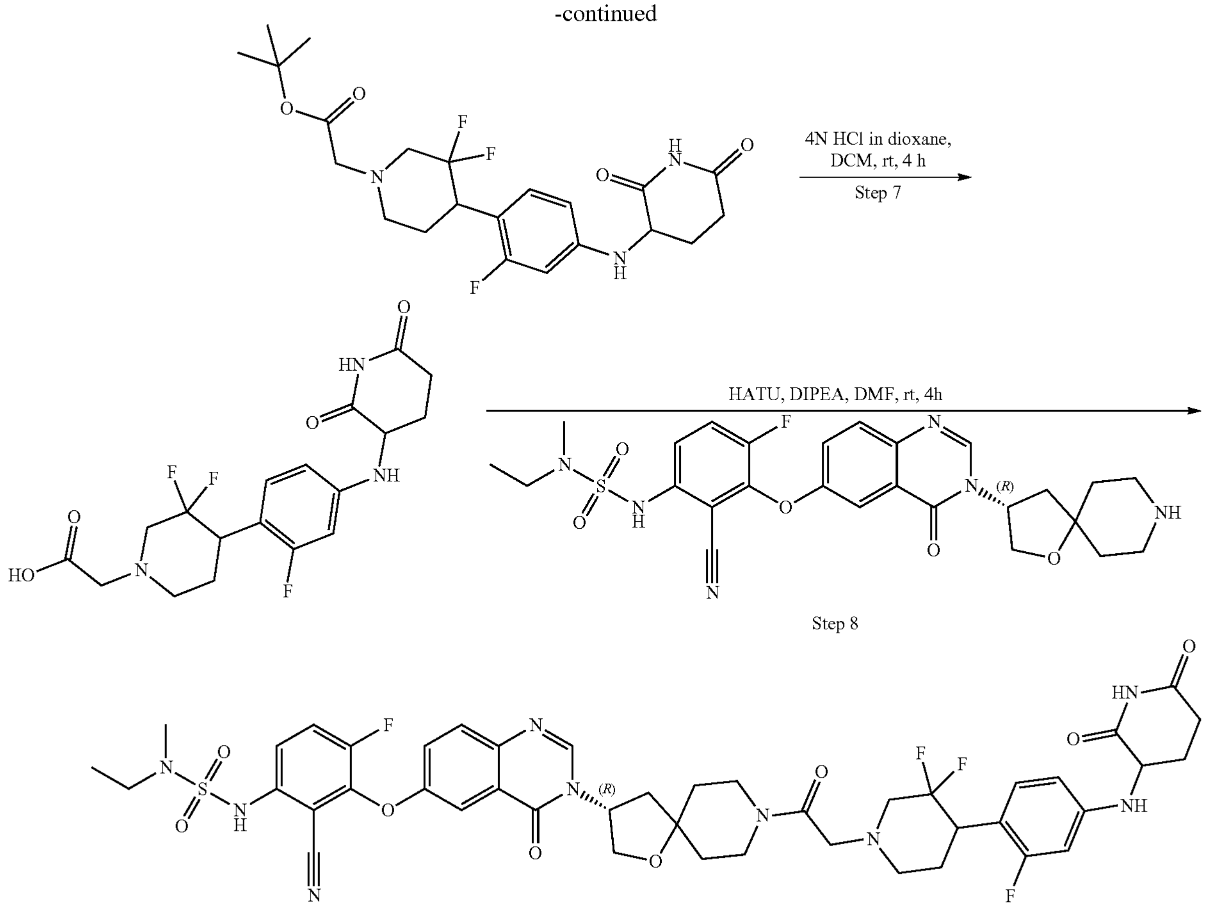

Step 1: To a solution of tert-butyl 3,3-difluoro-4-oxo-piperidine-1-carboxylate (2.5 g, 10.63 mmol) in Dichloromethane (30 mL), was added Triethylamine (3.23 g, 31.8 mmol, 4.44 mL) and the reaction mixture was cooled to −20° C. The solution of Trifluoromethylsulfonyl trifluoromethanesulfonate (4.50 g, 15.94 mmol, 2.68 mL) in Dichloromethane (10 mL) was added at −20° C. dropwise under nitrogen atmosphere. The reaction mixture was stirred at room temperature for 16 h. After completion, the reaction was quenched with cold water (70 mL) dropwise at 0° C. and extracted with Dichloromethane (3×100 mL). Combined organic layers were dried over sodium sulfate, filtered and concentrated under reduced pressure to afford crude. Desired product was purified from crude by column chromatography (silica gel) by using 5-15% ethyl acetate in pet ether as eluent to afford tert-butyl 3,3-difluoro-4-(trifluoromethylsulfonyloxy)-2,6-dihydropyridine-1-carboxylate (1.3 g, 2.16 mmol, 20% yield) as light-yellow liquid. LCMS m/z (ESI). 268.0 $[M-CO_2{}^tBu+H]^+$.

Step 1A: To a solution of 4-bromo-3-fluoro-aniline (5 g, 26.31 mmol) in 1,4-Dioxane (200 mL), was added potassium Acetate (7.75 g, 78.94 mmol, 4.93 mL) and 4,4,5,5-tetramethyl-2-(4,4,5,5-tetramethyl-1,3,2-dioxaborolan-2-yl)-1,3,2-dioxaborolane (7.35 g, 28.95 mmol). The reaction mixture was degassed with nitrogen gas for 10 minutes, and then added [1,1'-Bis(diphenylphosphino)ferrocene]dichloropalladium (II), complex with dichloromethane (2.15 g, 2.63 mmol). The reaction mixture was stirred at 100° C. for 12 h. After completion, the reaction mixture was diluted with water (100 mL) and extracted with ethyl acetate (3×150 mL). The combined organic layers were dried over sodium sulfate, filtered and concentrated. The desired product was purified by column chromatography (silica gel) using 10-20% ethyl acetate in pet ether as eluent to afford 3-fluoro-4-(4,4,5,5-tetramethyl-1,3,2-dioxaborolan-2-yl)aniline (5.5 g, 15.96 mmol, 61% yield) as light yellow viscous solid. LCMS m/z (ESI): 238.2 $[M+H]^+$.

Step 2: To a solution of 3-fluoro-4-(4,4,5,5-tetramethyl-1,3,2-dioxaborolan-2-yl)aniline (1.70 g, 7.19 mmol) and tert-butyl 3,3-difluoro-4-(trifluoromethylsulfonyloxy)-2,6-dihydropyridine-1-carboxylate (2.4 g, 6.53 mmol) in 1,4-dioxane (30 mL) and water (3 mL) in sealed tube, were added potassium phosphate tribasic anhydrous (4.16 g, 19.60 mmol). The reaction mixture was degassed with nitrogen gas for 10 mins and then [1,1'-Bis(diphenylphosphino)ferrocene]dichloropalladium (II), complex with dichloromethane (533.62 mg, 653.44 μmol) was added. The reaction mixture was again purged with nitrogen gas for 5 mins and irradiated under microwave at 80° C. for 1.5 h. After completion, the reaction mixture was diluted with water (50 mL) and extracted with ethyl acetate (3×70 mL). The combined organic layers was dried over sodium sulfate, filtered and concentrated under reduced pressure. The desired product was purified by silica gel flash column chromatography by using 15-25% ethyl acetate in pet ether as eluent to afford tert-butyl 4-(4-amino-2-fluoro-phenyl)-3,3-difluoro-2,6-dihydropyridine-1-carboxylate (1.6 g, 4.84 mmol, 74% yield) as light green liquid. LCMS m/z (ESI): 229.2 $[M-CO_2{}^tBu+H]^+$.

Step 3: To a solution of tert-butyl 4-(4-amino-2-fluoro-phenyl)-3,3-difluoro-2,6-dihydropyridine-1-carboxylate (1.6 g, 4.87 mmol) in methanol (20 mL) and ethyl acetate (20 mL) was added 20% dihydroxypalladium (2 g, 14.24 mmol) and the mixture was saturated with hydrogen by bubbling hydrogen gas through for 10 min. The contents were then subjected to hydrogenation (1 atm) at room temperature for 16 h. After completion, the reaction mixture was filtered through a pad of celite, washing with methanol (200 mL). The filtrate was concentrated under reduced pressure to afford tert-butyl 4-(4-amino-2-fluoro-phenyl)-3,3-difluoro-piperidine-1-carboxylate (1.45 g, 4.32 mmol, 89% yield) as an off-white solid. LCMS m/z (ESI): 231.2 $[M-CO_2{}^tBu+H]^+$.

Step 4: To a solution of tert-butyl 4-(4-amino-2-fluoro-phenyl)-3,3-difluoro-piperidine-1-carboxylate (0.6 g, 1.82 mmol) in N,N-dimethylformamide (8 mL), were added sodium hydrogen carbonate (762.90 mg, 9.08 mmol, 353.19 μL) and 3-bromopiperidine-2,6-dione (2.09 g, 10.90 mmol). 3-bromopiperidine-2,6-dione (2.09 g) was added portion-wise (4×0.52 g) every 12 h. The reaction mixture was stirred at 85° C. for 72 h. After completion, the reaction mixture was diluted with water (70 mL) and extracted with ethyl acetate (3×150 mL). The combined organic layers were washed with cold water (3×70 mL), dried over sodium sulfate, filtered, and concentrated. The desired product was purified by column chromatography (silica gel) by using 40-50% ethyl acetate in pet ether as eluent to afford tert-butyl 4-[4-[(2,6-dioxo-3-piperidyl)amino]-2-fluoro-phenyl]-3,3-difluoro-piperidine-1-carboxylate (0.3 g, 679.59 μmol, 37% yield) as a light blue solid. LCMS m/z (ESI): 386.2 $[M+H]^+$.

Step 5: To a solution of tert-butyl 4-[4-[(2,6-dioxo-3-piperidyl)amino]-2-fluoro-phenyl]-3,3-difluoro-piperidine-1-carboxylate (0.3 g, 679.59 μmol) in dichloromethane (10 mL), was added hydrogen chloride solution in 1,4-dioxane (4 M, 5 mL) at 5° C. under nitrogen atmosphere. The reaction mixture was stirred at room temperature for 4 h. After completion, the reaction mixture was concentrated under reduced pressure to afford 3-[4-(3,3-difluoro-4-piperidyl)-3-fluoro-anilino]piperidine-2,6-dione hydrochloride salt (0.33 g, 873.50 μmol) as light blue viscous solid. $^1$HNMR (400 MHz, DMSO-$d_6$): δ=10.83 (s, 1H), 10.28 (s, 1H), 7.02 (t, J=8.40 Hz, 1H), 6.52 (t, J=14.00 Hz, 2H), 4.38 (d, J=4.80 Hz, 1H), 3.87-3.56 (m, 4H), 3.33 (d, J=11.60 Hz, 1H), 3.22-3.12 (m, 1H), 2.75-2.62 (m, 1H), 2.60-2.56 (m, 2H), 2.43-1.88 (m, 3H)

Step 6: To a solution of 3-[4-(3,3-difluoro-4-piperidyl)-3-fluoro-anilino]piperidine-2,6-dione (0.3 g, 794.10 μmol) in N,N-imethylformamide (5 mL) and triethylamine (401.77 mg, 3.97 mmol, 553.41 μL) was added tert-butyl 2-bromoacetate (232.34 mg, 1.19 mmol, 174.69 μL) at room temperature under nitrogen atmosphere. The reaction mixture was stirred at room temperature for 12 h. After completion, the reaction mixture was diluted with water (30 mL) and extracted with ethyl acetate (3×50 mL). The combined organic layers were washed with cold water (3×30 mL), dried over sodium sulfate, filtered and concentrated under reduced pressure to afford tert-butyl 2-[4-[4-[(2,6-dioxo-3-piperidyl)amino]-2-fluoro-phenyl]-3,3-difluoro-1-piperidyl]acetate (0.23 g, 387.37 μmol, 49% yield) as light brown liquid, which was carried forward without further purification. LCMS m/z (ESI): 456.2 $[M+H]^+$.

Step 7: To a solution of tert-butyl 2-[4-[4-[(2,6-dioxo-3-piperidyl)amino]-2-fluoro-phenyl]-3,3-difluoro-1-piperidyl]acetate (0.23 g, 504.97 μmol) in dichloromethane (10 mL), was added hydrogen chloride solution 4.0M in 1,4-dioxane (5 mL) at 5° C. under nitrogen atmosphere. The reaction mixture was stirred at room temperature for 12 h. After completion, the reaction mixture was concentrated under reduced pressure to afford 2-[4-[4-[(2,6-dioxo-3-piperidyl)amino]-2-fluoro-phenyl]-3,3-difluoro-1-piperidyl] acetic acid (0.23 g, 448.63 μmol, 89% yield) as an off-white solid. LCMS m/z (ESI): 400.2 $[M+H]^+$.

Step 8: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-3,3-difluoro-1-piperidyl] acetic acid (51.68 mg, 118.58 μmol), (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (0.06 g, 101.17 μmol), N,N-diisopropylethylamine (139.32 mg, 1.08 mmol, 187.76 μL) and HATU (45.09 mg, 118.58 μmol). The crude compound was purified by reverse phase column chromatography, eluting with 45% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-3,3-difluoro-1-piperidyl]acetyl]-1-oxa-8-azaspiro[4.5]decane (16 mg, 15.62 μmol, 14% yield) as off-white solid. LCMS m/z (ESI): 938.2 $[M+H]^+$; $^1$H NMR (400 MHz, DMSO-$d_6$): δ=10.81 (s, 1H), 10.20 (s, 1H), 8.36 (s, 1H), 7.80 (t, J=4.40 Hz, 2H), 7.70 (t, J=5.60 Hz, 1H), 7.48 (s, 1H), 7.37 (s, 1H), 7.06 (s, 1H), 6.47 (d, J=14.80 Hz, 2H), 6.18 (d, J=4.40 Hz, 1H), 5.31 (s, 1H), 4.34 (s, 1H), 4.14 (s, 2H), 3.68-3.35 (m, 3H), 3.15 (d, J=6.80 Hz, 4H), 2.92 (s, 1H), 2.77 (s, 3H), 2.59-2.34 (m, 6H), 2.15-2.00 (m, 3H), 1.90-1.49 (m, 8H), 1.05 (t, J=6.80 Hz, 3H).

Example 59

3-[6-[2-cyano-3-[[ethyl(methyl)sulfamoyl]amino]-6-fluorophenoxy]-5-methyl-4-oxoquinazolin-3-yl]-8-[2-[4-[4-[(2,6-dioxopiperidin-3-yl)amino]-2-fluoro-phenyl]piperidin-1-yl]acetyl]-1-oxa-8-azaspiro[4.5]decane

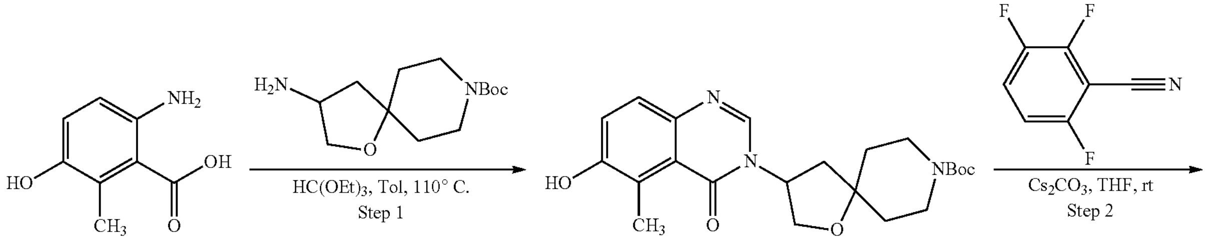

-continued

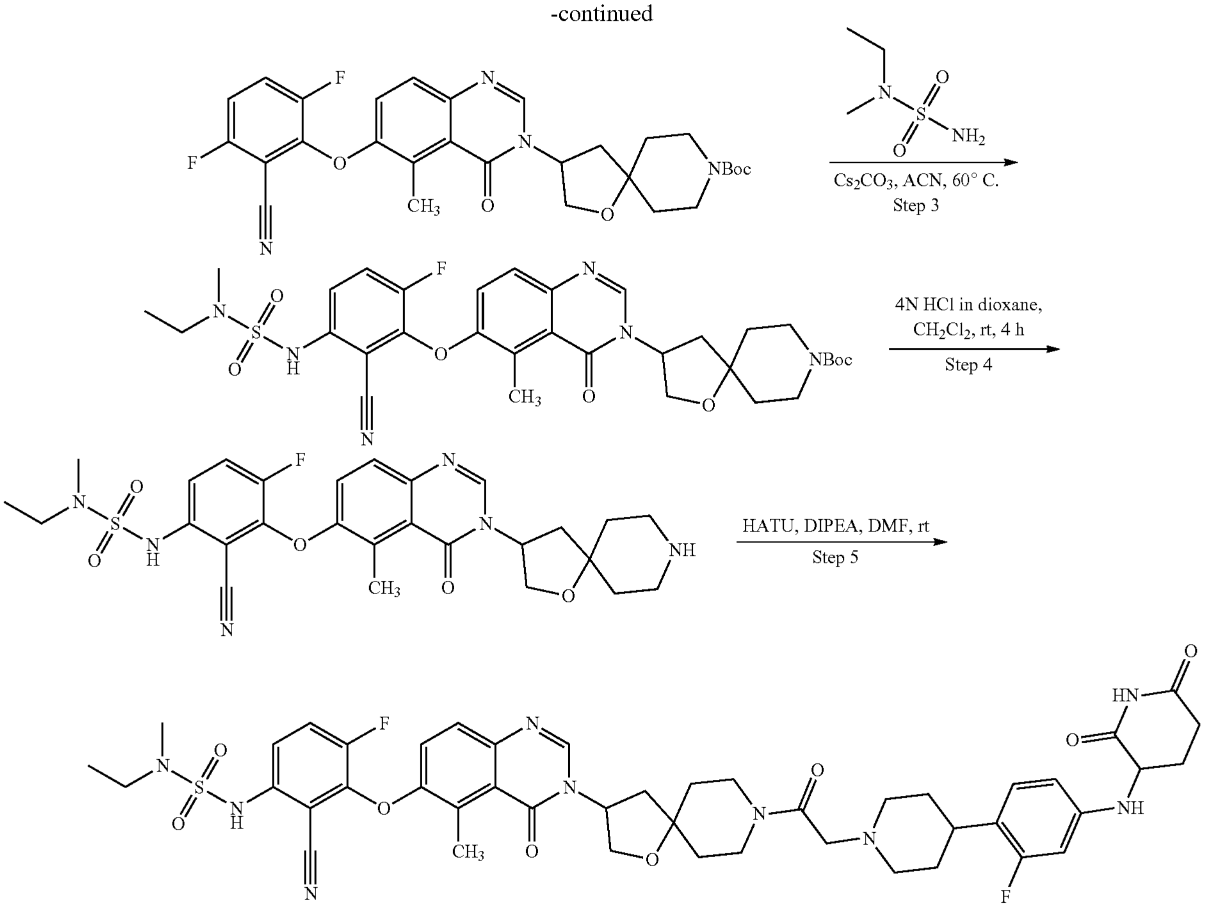

Step 1: Quinazolinone intermediate was synthesized by following general procedure for cyclization (Procedure A-A) using 6-amino-3-hydroxy-2-methyl-benzoic acid (0.8 g, 4.79 mmol), triethyl orthoformate (1.06 g, 7.18 mmol, 1.19 mL), acetic acid (28.74 mg, 478.58 μmol, 27.37 μL) and tert-butyl 3-amino-1-oxa-8-azaspiro[4.5]decane-8-carboxylate (1.10 g, 4.31 mmol). The desired product was purified by column chromatography eluting with 60-80% ethyl acetate in petroleum ether as eluent to afford tert-butyl 3-(6-hydroxy-5-methyl-4-oxo-quinazolin-3-yl)-1-oxa-8-azaspiro[4.5]decane-8-carboxylate (0.73 g, 1.36 mmol, 29% yield) as light yellow solid. LCMS m/z (ESI): 416.2 $[M+H]^+$.

Step 2: O-arylated quinazolinone intermediate was synthesized by following general procedure for O-arylation (Procedure A-B) using tert-butyl 3-(6-hydroxy-5-methyl-4-oxo-quinazolin-3-yl)-1-oxa-8-azaspiro[4.5]decane-8-carboxylate (373 mg, 897.75 μmol), cesium carbonate (877.52 mg, 2.69 mmol) and 2,3,6-trifluorobenzonitrile (211.55 mg, 1.35 mmol, 155.55 μL). The desired product was purified by column chromatography, eluting with 60-80% ethyl acetate in petroleum ether as eluent, to afford tert-butyl 3-[6-(2-cyano-3,6-difluoro-phenoxy)-5-methyl-4-oxo-quinazolin-3-yl]-1-oxa-8-azaspiro[4.5]decane-8-carboxylate (250 mg, 399.95 μmol, 45% yield) as off-white solid. LCMS m/z (ESI): 553.2 $[M+H]^+$.

Step 3: Sulfamoylated quinazolinone intermediate was synthesized by following Procedure A-C using tert-butyl 3-[6-(2-cyano-3,6-difluoro-phenoxy)-5-methyl-4-oxo-quinazolin-3-yl]-1-oxa-8-azaspiro[4.5]decane-8-carboxylate (250 mg, 452.43 μmol), cesium carbonate (442.23 mg, 1.36 mmol) and [methyl(sulfamoyl)amino]ethane (93.78 mg, 678.65 μmol) to afford tert-butyl 3-[6-[2-cyano-3-[[ethyl(methyl)sulfamoyl]amino]-6-fluoro-phenoxy]-5-methyl-4-oxo-quinazolin-3-yl]-1-oxa-8-azaspiro[4.5]decane-8-carboxylate (220 mg, 282.40 μmol, 62% yield) as light brown solid, which was carried forward without further purification. LCMS m/z (ESI): 671.2 $[M+H]^+$.

Step 4: The requisite amine was synthesized by HCl mediated N-Boc deprotection (Procedure A-D). N-Boc deprotection was done on tert-butyl (3R)-3-[6-[2-cyano-3-[[ethyl(methyl)sulfamoyl]amino]-6-fluoro-phenoxy]-5-methyl-4-oxo-quinazolin-3-yl]-1-oxa-8-azaspiro[4.5]decane-8-carboxylate (220 mg, 327.99 μmol) using 4M hydrogen chloride solution in 1,4-dioxane (4 mL) to afford (3R)-3-[6-[2-cyano-3-[[ethyl(methyl)sulfamoyl]amino]-6-fluoro-phenoxy]-5-methyl-4-oxo-quinazolin-3-yl]-1-oxa-8-azaspiro[4.5]decane (215 mg, 325.53 μmol, 99% yield) as a light yellow solid, which was carried forward without further purification. LCMS m/z (ESI): 571.2 $[M+H]^+$.

Step 5: Target compound was prepared via HATU mediated acid-amine coupling reaction (Procedure A-E). Amide coupling was carried out using 3-[6-[2-cyano-3-[[ethyl(methyl)sulfamoyl]amino]-6-fluoro-phenoxy]-5-methyl-4-oxo-quinazolin-3-yl]-1-oxa-8-azaspiro[4.5]decane (80.00 mg, 140.19 μmol) 2-[4-[4-[(2,6-dioxo-3-piperidyl)amino]-2-fluoro-phenyl]-1-piperidyl]acetic acid (61.13 mg, 168.23 μmol), N,N-diisopropylethylamine (90.60 mg, 700.97 μmol, 122.10 μL) and HATU (58.64 mg, 154.21 μmol). The crude compound was purified by reverse phase column chromatography, eluting with 40 to 45% acetonitrile in 0.1% formic acid in water, to afford 3-[6-[2-cyano-3-[[ethyl(methyl)sulfamoyl]amino]-6-fluoro-phenoxy]-5-methyl-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (10.74 mg, 10.96 μmol, 8% yield) as off-white solid. LCMS m/z (ESI): 916.2 $[M+H]^+$. $^1H$ NMR (400 MHz, DMSO-$d_6$): δ=10.80 (s, 1H), 9.90 (s, 1H), 8.32 (s, 1H), 7.59-7.71 (m, 1H), 7.50 (d, J=8.80 Hz, 1H), 7.31-7.39 (m, 1H), 7.19 (d, J=8.80 Hz, 1H), 6.92-7.05 (m, 1H), 6.50 (d, J=7.60 Hz, 1H), 6.47 (d, J=13.60 Hz, 1H), 6.10 (d, J=7.20 Hz, 1H), 5.37 (t, J=6.80 Hz, 1H), 4.31-4.38 (m, 1H), 4.17 (d, J=3.20 Hz, 2H), 3.72-3.81 (m, 1H), 3.25-3.52 (m, 5H), 3.05-3.15 (m, 2H), 2.88 (s, 3H), 2.74 (s, 3H), 2.65-2.74 (m, 1H), 2.41-2.58 (m, 6H), 2.01-2.12 (m, 2H), 1.52-2.01 (m, 10H), 1.05 (t, J=7.20 Hz, 3H).

Example 60

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]piperazin-1-yl]acetyl]-1-oxa-8-azaspiro[4.5]decane

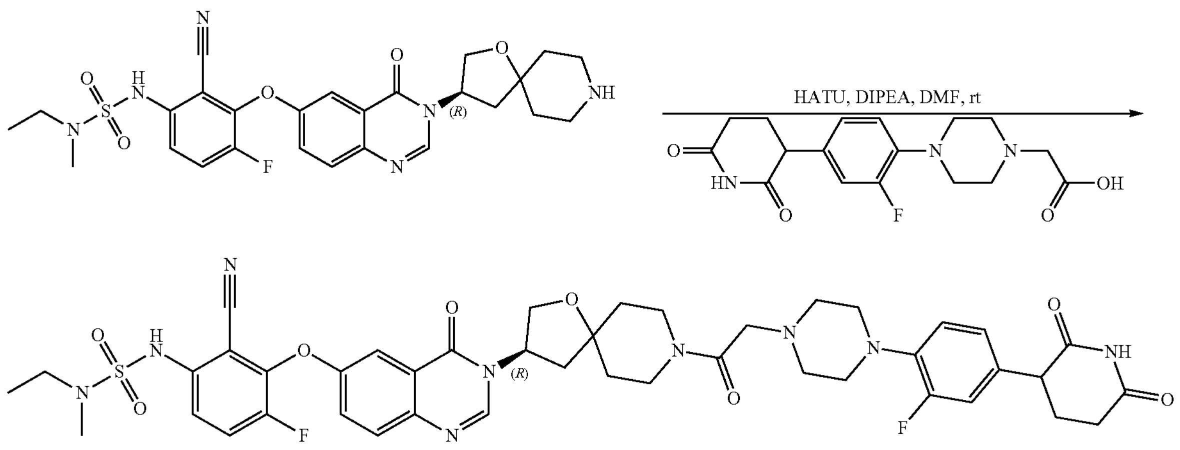

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (70 mg, 118.03 μmol), 2-[4-[4-(2,6-dioxo-3-piperidyl)-2-fluoro-phenyl]piperazin-1-yl]acetic acid (41.23 mg, 106.88 μmol), N,N-diisopropylethylamine (61.02 mg, 472.12 μmol, 82.23 μL) and HATU (44.88 mg, 118.03 μmol). The crude compound was purified by reverse phase column chromatography, eluting with 50% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[4-[4-(2,6-dioxo-3-piperidyl)-2-fluoro-phenyl]piperazin-1-yl]acetyl]-1-oxa-8-azaspiro[4.5]decane (28 mg, 29.51 μmol, 25% yield) as an off-white solid. LCMS m/z (ESI): 888.2 $[M+H]^+$; $^1H$ NMR (400 MHz, DMSO-$d_6$): δ=10.83 (s, 1H), 10.13 (s, 1H), 8.36 (s, 1H), 7.80 (d, J=8.80 Hz, 2H), 7.70 (dd, J=3.20, 8.80 Hz, 1H), 7.47 (dd, J=3.60, 9.40 Hz, 1H), 7.37 (d, J=2.80 Hz, 1H), 7.08-6.97 (m, 3H), 5.30 (s, 1H), 4.16-4.13 (m, 2H), 3.84-3.80 (m, 1H), 3.79-3.70 (m, 1H), 3.52-3.49 (m, 3H), 3.17-3.12 (m, 6H), 2.89-2.79 (m, 2H), 2.77 (s, 3H), 2.69-2.62 (m, 4H), 2.50-2.47 (m, 2H), 2.27-2.20 (m, 1H), 2.15-1.90 (m, 2H), 1.83-1.51 (m, 5H), 1.05 (t, J=6.80 Hz, 3H).

Example 61

N-[2-cyano-3-[3-[(3R)-8-[2-[4-[4-[(2,6-dioxopiperidin-3-yl)amino]-2-fluorophenyl]piperidin-1-yl]acetyl]-1-oxa-8-azaspiro[4.5]decan-3-yl]-4-oxoquinazolin-6-yl]oxy-4-fluorophenyl]propane-2-sulfonamide

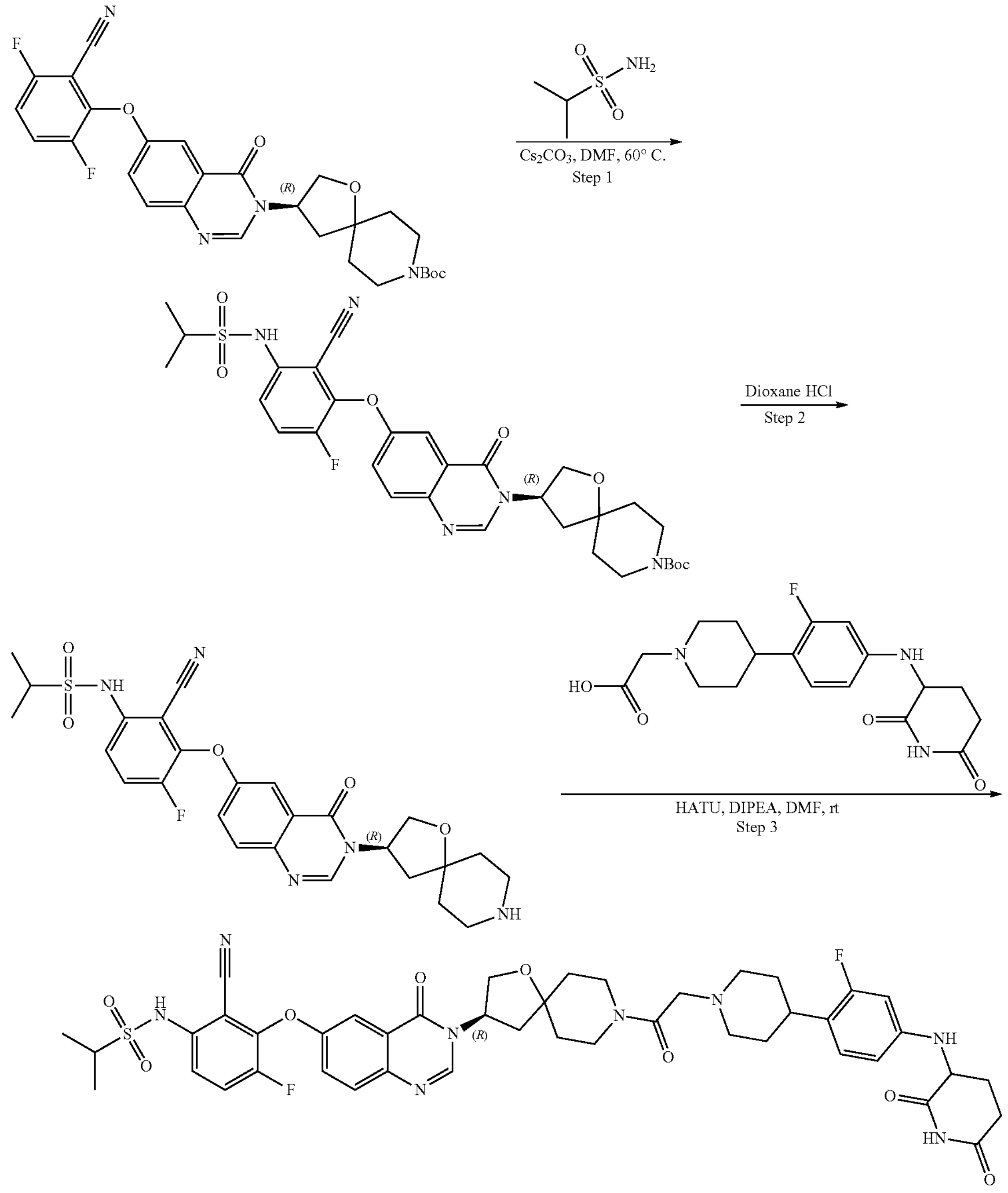

Step 1: Sulfamoylated quinazolinone intermediate was synthesized by following Procedure A-C using tert-butyl (3R)-3-[6-(2-cyano-3,6-difluoro-phenoxy)-4-oxo-quinazolin-3-yl]-1-oxa-8-azaspiro[4.5]decane-8-carboxylate (220 mg, 408.51 μmol), cesium carbonate (332.75 mg, 1.02 mmol) and propane-2-sulfonamide (75.48 mg, 612.77 μmol). The crude compound was purified by silica gel flash column chromatography with 70-75% ethyl acetate in petroleum ether as a eluent to afford tert-butyl (3R)-3-[6-[2-cyano-6-fluoro-3-(isopropylsulfonylamino)phenoxy]-4-oxo-quinazolin-3-yl]-1-oxa-8-azaspiro[4.5]decane-8-carboxylate (230 mg, 320.78 μmol, 79% yield) as a pale yellow solid. LCMS m/z (ESI): 640.20 $[M-H]^-$.

Step 2: The requisite amine was synthesized by following Procedure A-D using of tert-butyl (3R)-3-[6-[2-cyano-6-fluoro-3-(isopropylsulfonylamino)phenoxy]-4-oxo-quinazolin-3-yl]-1-oxa-8-azaspiro[4.5]decane-8-carboxylate (260 mg, 405.17 μmol) and 4M hydrogen chloride solution in 1,4-dioxane (2 mL). The resulting crude compound was triturated with Methyl t-Butyl Ether to afford N-[2-cyano-4-fluoro-3-[3-[(3R)-1-oxa-8-azaspiro[4.5]decan-3-yl]-4-oxo-quinazolin-6-yl]oxy-phenyl]propane-2-sulfonamide (220 mg, 327.34 μmol, 80.79% yield, 86% purity) as an off white solid. LCMS m/z (ESI): 542.20 $[M+H]^+$ Step 3: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (65 mg, 162.56 μmol), N-[2-cyano-4-fluoro-3-[3-[(3R)-1-oxa-8-azaspiro[4.5]decan-3-yl]-4-oxo-quinazolin-6-yl]oxy-phenyl]propane-2-sulfonamide (112.76 mg, 195.08 μmol), N,N-Diisopropylethylamine (126.06 mg, 975.38 μmol, 169.89 μL) and HATU (67.99 mg, 178.82 μmol) to afford crude product. The crude product was purified by C18-reverse phase column chromatography using Isolera (100 g RediSep® Rf C18, Method: 0.1% FORMIC ACID in water: acetonitrile) and pure fractions were lyophilized to afford N-[2-cyano-3-[3-[(3R)-8-[2-[4-[4-[(2,6-dioxo-3-piperidyl)amino]-2-fluoro-phenyl]-1-piperidyl]acetyl]-1-oxa-8-azaspiro[4.5]decan-3-yl]-4-oxo-quinazolin-6-yl]oxy-4-fluoro-phenyl]propane-2-sulfonamide (39 mg, 41.22 μmol, 25.35% yield, 99% purity) as pale brown solid. LCMS m/z (ESI): 887.20 $[M+H]^+$; $^1$HNMR (400 MHz, DMSO-$d_6$): δ=10.81 (s, 1H), 8.35 (s, 1H), 7.77 (d, J=8.80 Hz, 1H), 7.67-7.65 (m, 2H), 7.38 (s, 2H), 6.98 (s, 1H), 6.47 (t, J=12.80 Hz, 2H), 6.09 (d, J=6.80 Hz, 1H), 5.40-5.25 (m, 1H), 4.35-4.29 (m, 1H), 4.20-4.13 (m, 2H), 3.76-3.74 (m, 1H), 3.50-3.40 (m, 2H), 3.15-3.00 (m, 2H), 2.77-2.71 (m, 2H), 2.70-2.68 (m, 2H), 2.42-2.34 (m, 4H), 2.10-2.07 (m, 3H), 1.91-1.69 (m, 9H), 1.58-1.55 (m, 1H), 1.26 (d, J=6.00 Hz, 6H).

Example 62

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2,5-difluorophenyl]piperidin-1-yl]acetyl]-1-oxa-8-azaspiro[4.5]decane

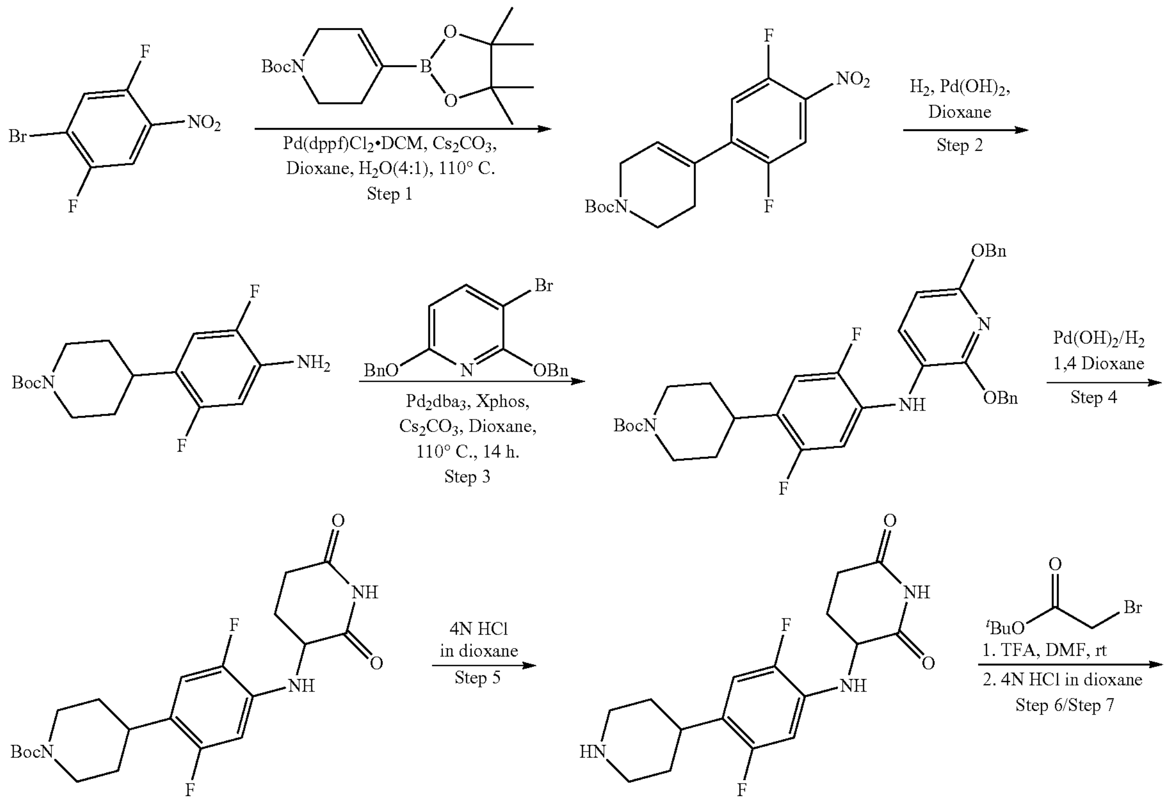

-continued

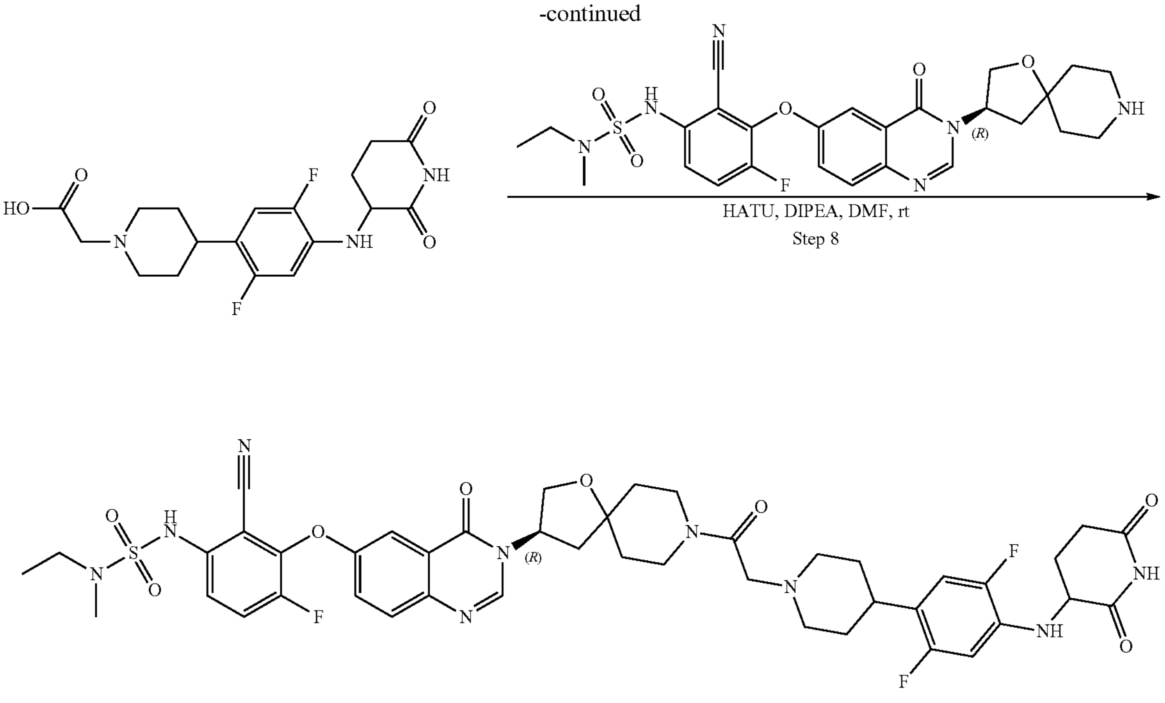

Step 1: A solution of tert-butyl 4-(4,4,5,5-tetramethyl-1,3,2-dioxaborolan-2-yl)-3,6-dihydro-2H-pyridine-1-carboxylate (8.92 g, 28.85 mmol) in 1,4-dioxane (80 mL), water (20 mL) was taken in a sealed tube and added cesium carbonate (23.50 g, 72.11 mmol) at room temperature under nitrogen atmosphere. The reaction mixture was degassed with nitrogen for 10 minutes and Pd(dppf) $Cl_2$·dichloromethane (1.96 g, 2.40 mmol) was added to the reaction mixture. The reaction mixture was stirred at 100° C. After completion, the reaction mixture was diluted with water (60 mL) and extracted with ethyl acetate (2×100 mL). The combined organic layers were dried over sodium sulfate, filtered and concentrated under reduced pressure. The crude compound was purified by silica gel flash column chromatography with 40% ethyl acetate in petroleum ether as a eluent to afford tert-butyl 4-(4-amino-2,5-difluoro-phenyl)-3,6-dihydro-2H-pyridine-1-carboxylate (6 g, 18.61 mmol, 77% yield) as light brown solid. LCMS m/z (ESI): 211.2 $[M+H-CO_2{}^tBu]^+$ Step 2: A solution of tert-butyl 4-(4-amino-2,5-difluoro-phenyl)-3,6-dihydro-2H-pyridine-1-carboxylate (3.5 g, 11.28 mmol) in 1,4-dioxane (20 mL) was degassed for 10 minutes then $Pd(OH)_2$ (3.96 g, 28.20 mmol) was added to the reaction mixture under nitrogen atmosphere. The reaction mixture then stirred under $H_2$ balloon pressure at room temperature for 14 h. The reaction mixture was filtered through celite and concentrated under reduced pressure to afford tert-butyl 4-(4-amino-2,5-difluoro-phenyl)piperidine-1-carboxylate (3 g, 9.41 mmol, 83% yield) as brown solid, which was carried forward without further purification. LCMS m/z (ESI): 213.2 $[M+H-CO_2{}^tBu]^+$ Step 3: A mixture of tert-butyl 4-(4-amino-2,5-difluoro-phenyl)piperidine-1-carboxylate (500 mg, 1.60 mmol), 2,6-dibenzyloxy-3-bromo-pyridine (711.19 mg, 1.92 mmol) and cesium carbonate (1.56 g, 4.80 mmol) in 1,4-dioxane (5 mL) was taken in a sealed tube and the resulting reaction mixture was degassed with $N_2$ for 10 minutes. $Pd_2(dba)_3$(14.66 mg, 16.01 μmol) and X-Phos (7.63 mg, 16.01 μmol) were added to the reaction mixture which was heated at 110° C. for 14 h. The reaction mixture was diluted with water (30 mL) and extracted with ethyl acetate (50 mL). The organic layer was washed with water (50 mL), saturated brine (50 mL), dried over sodium sulfate, and concentrated under reduced pressure. The crude compound was purified by silica gel flash column chromatography, eluting by 70% ethyl acetate in petroleum ether, to afford tert-butyl 4-[4-[(2,6-dibenzyloxy-3-pyridyl)amino]-2,5-difluoro-phenyl]piperidine-1-carboxylate (450 mg, 693.91 μmol, 43% yield) as brown solid. LCMS m/z (ESI): 546 $[M+H-{}^tBu]^+$ Step 4: To a degassed solution of tert-butyl 4-[4-[(2,6-dibenzyloxy-3-pyridyl)amino]-2,5-difluoro-phenyl]piperidine-1-carboxylate (450 mg, 747.90 μmol) in 1,4-dioxane (12 mL) was added Pd(OH)2 (420.13 mg, 2.99 mmol) under $N_2$ atmosphere. The resulting mixture was stirred under $H_2$ bladder pressure at room temperature for 14 h. The reaction mixture was filtered through celite and concentrated under reduced pressure to afford tert-butyl 4-[4-[(2,6-dioxo-3-piperidyl)amino]-2,5-difluoro-phenyl]piperidine-1-carboxylate (300 mg, 658.87 μmol, 88% yield) as light brown solid. LCMS m/z (ESI): 324 $[M+H-CO_2{}^tBu]^+$ Step 5: To a stirred solution of tert-butyl 4-(4-((2,6-dioxopiperidin-3-yl)amino)-2,5-difluorophenyl)piperidine-1-carboxylate (460 mg, 1.09 mmol) in 1,4-dioxane (1.5 mL) was added 4.0M hydrogen chloride solution in dioxane (49.51 μL). The resulting solution was stirred at room temperature for 16 h. The reaction mixture was concentrated under reduced pressure to afford (3-((2,5-difluoro-4-(piperidin-4-yl)phenyl)amino)piperidine-2,6-dione (390 mg, 1.06 mmol, 98% yield) as light brown solid, which was carried forward without further purification. LCMS m/z (ESI): 324.2 [M+H]$^+$ Step 6: To a stirred solution of 3-[2,5-difluoro-4-(4-piperidyl)anilino]piperidine-2,6-dione (520 mg, 1.61 mmol), N,N-diethyl ethanamine (162.74 mg, 1.61 mmol, 224.16 μL) in N,N-dimethylformamide (3 mL) was added tert-butyl 2-bromoacetate (439.17 mg, 2.25 mmol, 330.20 μL) at room temperature under nitrogen atmosphere. The reaction was stirred at room temperature for 14 h. The reaction mixture was diluted with water (10 mL) and extracted with ethyl acetate (30 mL). The organic layer was washed with saturated brine solution (10 mL), dried over sodium sulfate and concentrated under reduced pressure to afford tert-butyl 2-[4-[4-[(2,6-dioxo-3-piperidyl)amino]-2,5-difluoro-phenyl]-1-piperidyl]acetate (390 mg, 797.60 μmol, 50% yield) as light brown solid. LCMS m/z (ESI): 438.2 [M+H]$^+$ Step 7: To a solution of tert-butyl 2-[4-[4-[(2,6-dioxo-3-piperidyl)amino]-2,5-difluoro-phenyl]-1-piperidyl]acetate (390 mg, 891.47 μmol) in dichloromethane (5 mL) was added 4M hydrogen chloride solution in 1,4-dioxane (40.63 μL) at 0° C. and stirred at room temperature for 12 h. The reaction mixture was concentrated under reduced pressure to afford crude which was triturated with petroleum ether to afford 2-[4-[4-[(2,6-dioxo-3-piperidyl)amino]-2,5-difluoro-phenyl]-1-piperidyl]acetic acid (385 mg, 838.49 μmol, 94% yield) as brown solid. LCMS m/z (ESI): 382.2 [M+H]$^+$ Step 8: Target compound was prepared via HATU mediated acid-amine coupling reaction (Procedure A-E). Amide coupling was carried out using 2-[4-[4-[(2,6-dioxo-3-piperidyl)amino]-2,5-difluoro-phenyl]-1-piperidyl]acetic acid (50 mg, 131.11 μmol), (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (72.97 mg, 131.11 μmol), HATU (59.82 mg, 157.33 μmol), N,N-diisopropylethylamine (67.78 mg, 524.42 μmol, 91.34 μL). The crude product was purified by reverse phase column chromatography by using 30 g snap, eluting with 50% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2,5-difluoro-phenyl]-1-piperidyl]acetyl]-1-oxa-8-azaspiro[4.5]decane (5 mg, 5.37 μmol, 4% yield) as off-white solid. LCMS m/z (ESI): 920.2 [M+H]$^+$; $^1$H NMR (400 MHz, DMSO-$d_6$): δ=10.82 (s, 1H), 8.36 (s, 1H), 7.75-7.85 (m, 1H), 7.80 (d, J=9.20 Hz, 1H), 7.70 (dd, J=2.80, 9.00 Hz, 1H), 7.41-7.51 (m, 1H), 7.37 (d, J=2.40 Hz, 1H), 6.92-7.01 (m, 1H), 6.71 (dd, J=7.60, 12.40 Hz, 1H), 5.86 (d, J=8.40 Hz, 1H), 5.38-5.48 (m, 1H), 4.42 (dd, J=8.80, 16.80 Hz, 1H), 4.01-4.38 (m, 4H), 3.75-3.85 (m, 1H), 3.55-3.32 (m, 3H), 3.10-3.18 (m, 2H), 2.85-3.10 (m, 2H), 2.77 (s, 3H), 2.65-2.81 (m, 1H), 2.34-2.65 (m, 4H), 1.92-2.15 (m, 5H), 1.51-1.91 (m, 7H), 1.05 (t, J=7.20 Hz, 3H).

Example 63

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2,3-difluorophenyl]piperidin-1-yl]acetyl]-8-azaspiro[4.5]decan-3-yl]-4-oxoquinazoline

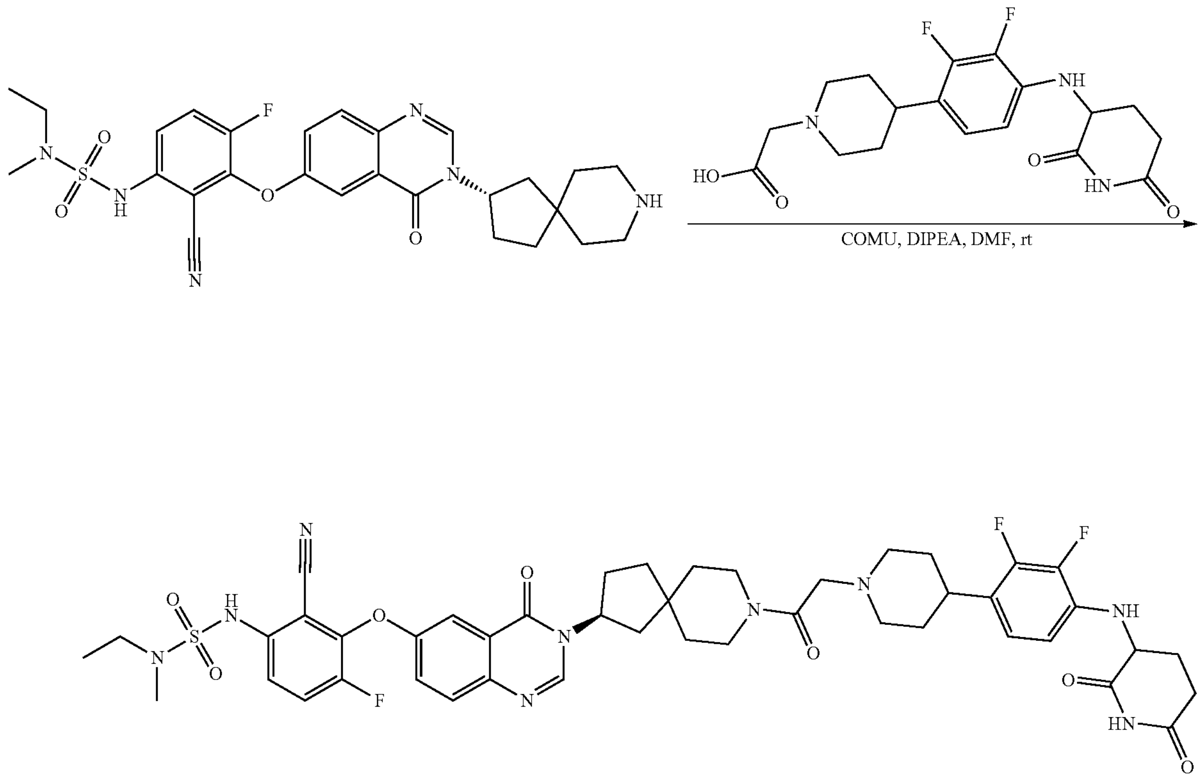

Target compound was prepared via COMU mediated acid-amine coupling reaction (Procedure A-F). Amide coupling was carried out using 2-[4-[4-[(2,6-dioxo-3-piperidyl) amino]-2,3-difluoro-phenyl]-1-piperidyl]acetic acid (70.69 mg, 169.18 μmol), 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (0.1 g, 169.18 μmol) COMU (108.68 mg, 253.77 μmol), N,N-diisopropylethylamine (109.32 mg, 845.89 μmol, 147.34 μL). Crude compound was purified by reverse phase column chromatography by using 30 g snap, eluting with 45% acetonitrile in 0.1% Ammonium acetate in water, to afford 6-[2-cyano-3-[[ethyl(methyl)sulfamoyl]amino]-6-fluoro-phenoxy]-3-[(3S)-8-[2-[4-[4-[(2,6-dioxo-3-piperidyl)amino]-2,3-difluoro-phenyl]-1-piperidyl] acetyl]-8-azaspiro[4.5]decan-3-yl]-4-oxo-quinazoline (52 mg, 55.57 μmol, 33% yield) as light pink solid. LCMS m/z (ESI): 918.2 $[M+H]^+$; $^1$H NMR (400 MHz, DMSO-$d_6$): δ=10.82 (s, 1H), 9.81 (s, 1H), 8.43 (d, J=3.60 Hz, 1H), 7.76 (d, J=8.80 Hz, 1H), 7.64 (dd, J=3.20, 9.00 Hz, 1H), 7.41-7.61 (m, 1H), 7.34 (d, J=6.80 Hz, 1H), 7.29-7.34 (m, 1H), 6.81-6.90 (m, 1H), 6.64 (t, J=8.40 Hz, 1H), 5.75-5.85 (m, 1H), 5.01-5.12 (m, 1H), 4.49-4.40 (m, 1H), 3.32-3.61 (m, 4H), 3.21-3.31 (m, 2H), 3.01-3.09 (m, 2H), 2.60-2.92 (m, 8H), 2.49-2.58 (m, 2H), 2.01-2.20 (m, 5H), 1.68-1.95 (m, 6H), 1.40-1.68 (m, 5H), 1.04 (t, J=7.20 Hz, 3H).

Example 64

(3R)-3-[6-[2-cyano-3-[[ethyl(methyl)sulfamoyl] amino]-6-fluorophenoxy]-4-oxoquinazolin-3-yl]-8-[2-[4-[4-[(2,6-dioxopiperidin-3-yl)amino]-2,3-difluorophenyl]piperidin-1-yl]acetyl]-1-oxa-8-azaspiro [4.5]decane

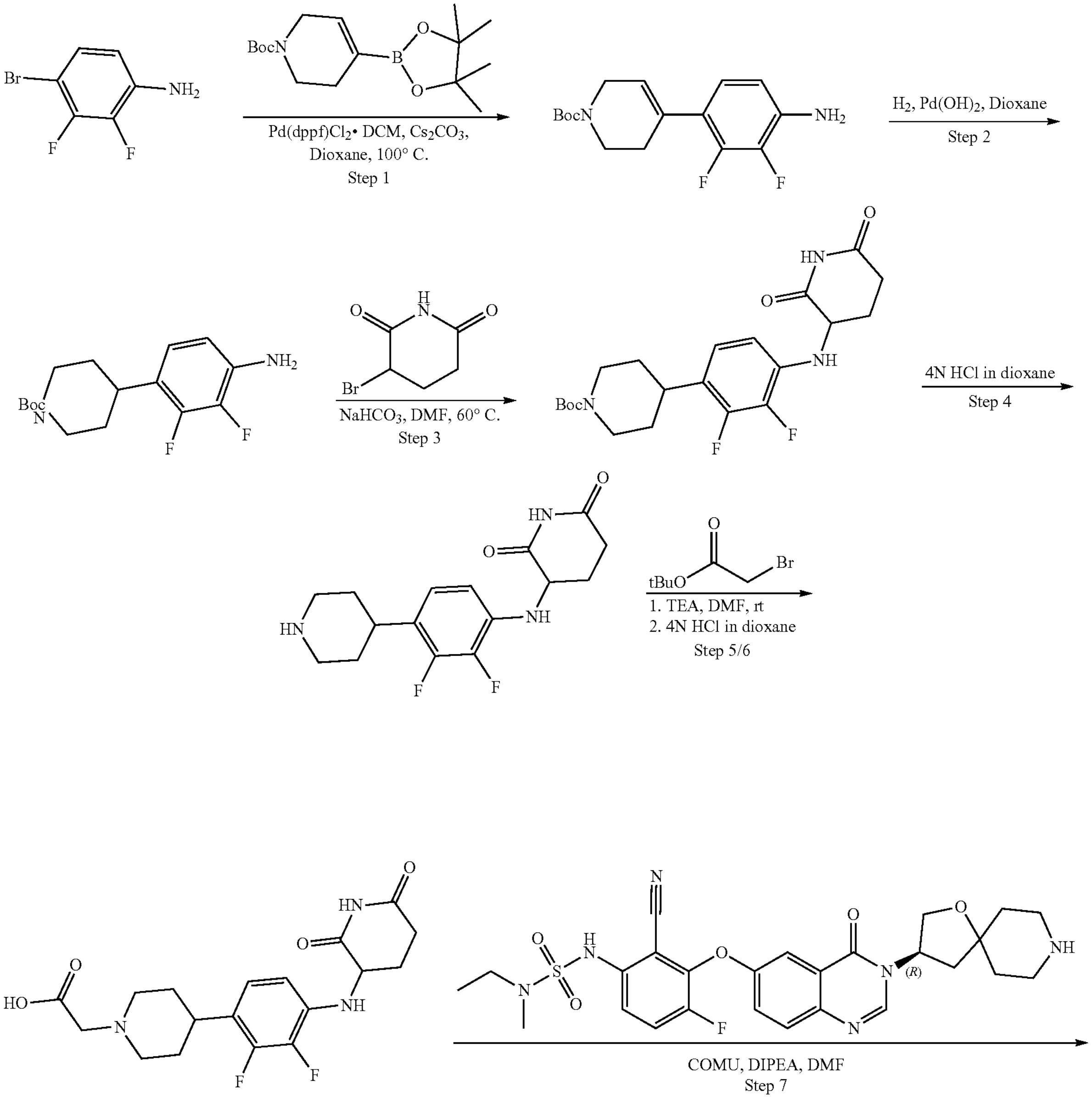

-continued

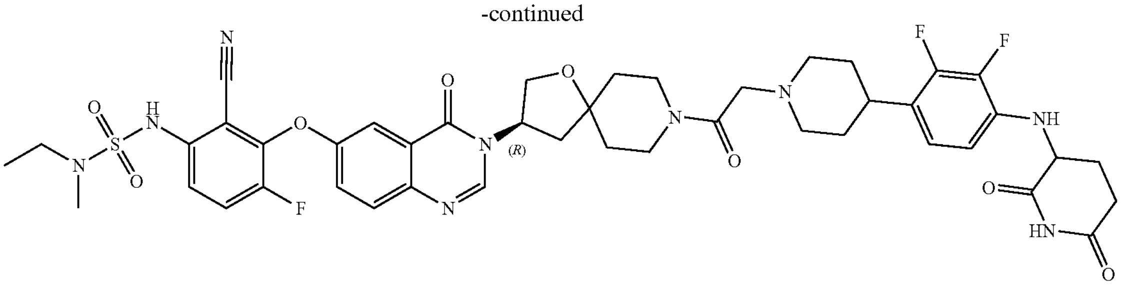

Step 1: To a solution of 4-bromo-2,3-difluoro-aniline (2.0 g, 9.62 mmol) in 1,4-dioxane (30 mL) and water (10 mL) was added cesium carbonate (9.40 g, 28.85 mmol) at rt under nitrogen. The reaction mixture was degassed with nitrogen for 10 min, and then [1,1'-Bis(diphenylphosphino) ferrocene]dichloropalladium (II), complex with dichloromethane (785.21 mg, 961.52 μmol) was added at the same temperature. The resulting solution was heated at 100° C. for 12 h. After completion, the resulting solution was cooled to rt, filtered through a celite bed and washed with ethyl acetate (50 ml). The collected filtrates were concentrated under reduced pressure. The crude compound was purified by silica gel flash column chromatography with 40% ethyl acetate in pet ether as eluent to afford tert-butyl 4-(4-amino-2,3-difluoro-phenyl)-3,6-dihydro-2H-pyridine-1-carboxylate (2.8 g, 8.73 mmol, 91% yield) as an off-white solid. LCMS m/z (ESI): 211.0 $[M+H]^+$.

Step 2: To a solution of tert-butyl 4-(4-amino-2,3-difluoro-phenyl)-3,6-dihydro-2H-pyridine-1-carboxylate (2.8 g, 9.02 mmol) in 1,4-dioxane (30 mL) was added palladium hydroxide on carbon (1.27 g, 9.02 mmol) and the reaction was placed under hydrogen bladder pressure for 12 h. After completion, the reaction mixture was filtered through a pad of Celite and washed with methanol (50 mL). The filtrate was concentrated under reduced pressure to afford the tert-butyl 4-(4-amino-2,3-difluoro-phenyl) piperidine-1-carboxylate (2.8 g, 8.83 mmol, 98% yield) as a liquid, which was carried forward without further purification. LCMS m/z (ESI): 213.2 $[M+H]^+$.

Step 3: To a solution of tert-butyl 4-(4-amino-2,3-difluoro-phenyl)piperidine-1-carboxylate (1.4 g, 4.48 mmol) in N,N-DIMEHTYLFORMAMIDE (14 mL) was added sodium bicarbonate (1.51 g, 17.93 mmol, 697.27 μL) and 3-bromopiperidine-2,6-dione (1.72 g, 8.96 mmol) at rt under nitrogen. Reaction mixture was heated to 80° C. for 20 h. After completion, the reaction mixture was diluted with water (20 mL) and extracted with ethyl acetate (2×50 mL). The organic layer was washed with brine (10 mL), dried over sodium sulfate and concentrated under reduced pressure. The resulting crude product was purified by silica gel (50 g SNAP) column chromatography using ethyl acetate-petroleum ether (0-70%) to afford tert-butyl 4-[4-[(2,6-dioxo-3-piperidyl)amino]-2,3-difluoro-phenyl]piperidine-1-carboxylate (0.23 g, 481.51 μmol, 11% yield) as blue solid. LCMS m/z (ESI): 324.2 $[M+H]^+$.

Step 4: To a solution of tert-butyl 4-[4-[(2,6-dioxo-3-piperidyl)amino]-2,3-difluoro-phenyl]piperidine-1-carboxylate (0.23 g, 543.15 μmol) in dichloromethane (3 mL) was added hydrogen chloride solution in 1,4-dioxane (4.0 M, 2.00 mL) at 0° C. under nitrogen. The resulting solution was stirred at RT for 2 h. After completion, the resulting solution was concentrated under reduced pressure to afford 3-[2,3-difluoro-4-(4-piperidyl) anilino]piperidine-2,6-dione (0.2 g, 507.12 μmol, 93% yield) as a light yellow solid. LCMS m/z (ESI): 324.2 $[M+H]^+$.

Step 5: A solution of 3-[2,3-difluoro-4-(4-piperidyl)anilino]piperidine-2,6-dione (0.20 g, 555.87 μmol) in N,N-DIMEHTYLFORMAMIDE (2 mL) was added triethylamine (140.62 mg, 1.39 mmol, 193.69 μL) and tert-butyl 2-bromoacetate (162.64 mg, 833.80 μmol, 122.28 μL) at rt under nitrogen. The reaction mixture was stirred at rt for 12 h. After completion, the reaction mixture was diluted with water (10 mL) and extracted with ethyl acetate (2×20 mL). The separated organic layer was dried over sodium sulfate and concentrated under reduced pressure. The resulting crude product was purified by silica gel (25 g SNAP) column chromatography using ethyl acetate-petroleum ether (0-80%) to afford tert-butyl 2-[4-[4-[(2,6-dioxo-3-piperidyl) amino]-2,3-difluoro-phenyl]-1-piperidyl]acetate (0.12 g, 246.76 μmol, 44% yield) as green liquid. LCMS m/z (ESI): 438.2 $[M+H]^+$.

Step 6: To a solution of tert-butyl 2-[4-[4-[(2,6-dioxo-3-piperidyl)amino]-2,3-difluoro-phenyl]-1-piperidyl]acetate (0.12 g, 274.30 μmol) in dichloromethane (2 mL) was added hydrogen chloride solution in 1,4-dioxane (4.0 M, 1.37 mL) at 0° C. under nitrogen. The resulting solution was stirred at RT for 12 h. After completion, the resulting solution was concentrated under reduced pressure to afford 2-[4-[4-[(2,6-dioxo-3-piperidyl)amino]-2,3-difluoro-phenyl]-1-piperidyl]acetic acid (0.11 g, 244.99 μmol, 89% yield) as an off-white solid. LCMS m/z (ESI): 382.2 $[M+H]^+$.

Step 7: Target compound was prepared via COMU mediated acid-amine coupling reaction (Procedure A-F). Amide coupling was carried out using 2-[4-[4-[(2,6-dioxo-3-piperidyl)amino]-2,3-difluoro-phenyl]-1-piperidyl]acetic acid (68.52 mg, 179.66 μmol), (3R)-3-[6-[2-cyano-3-[[ethyl (methyl)sulfamoyl]amino]-6-fluoro-phenoxy]-4-oxo-quinazolin-3-yl]-1-oxa-8-azaspiro[4.5]decane (0.1 g, 179.66 μmol), N,N-diisopropylethylamine (116.10 mg, 898.30 μmol, 156.47 μL) and (1-Cyano-2-ethoxy-2-oxoethylidenaminooxy)dimethylamino-morpholino-carbenium hexafluorophosphate (115.41 mg, 269.49 μmol). The crude compound was purified by reverse phase column chromatography, eluting with 45% acetonitrile in 0.1% ammonium acetate in water, to afford (3R)-3-[6-[2-cyano-3-[[ethyl (methyl)sulfamoyl]amino]-6-fluoro-phenoxy]-4-oxo-quinazolin-3-yl]-8-[2-[4-[4-[(2,6-dioxo-3-piperidyl)amino]-2,3-difluoro-phenyl]-1-piperidyl]acetyl]-1-oxa-8-azaspiro [4.5]decane (23 mg, 24.01 μmol, 13% yield) as light pink solid. LCMS m/z (ESI): 920.2 $[M+H]^+$. $^1$H NMR (400 MHz, DMSO-$d_6$): δ=10.82 (s, 1H), 9.86 (bs, 1H), 8.38 (s, 1H), 7.76 (s, 1H), 7.66 (dd, J=9.00, 2.80 Hz, 1H), 7.58 (s, 1H), 7.35 (dd, J=9.00, 2.80 Hz, 2H), 6.89-6.80 (m, 1H), 6.64 (t, J=8.80 Hz, 1H), 6.81 (d, J=8.00 Hz, 1H), 5.32-5.21 (m, 1H), 4.15 (q, J=3.20 Hz, 1H), 4.12-4.09 (m, 2H), 3.51-3.50 (m, 1H), 3.49-3.42 (m, 2H), 3.38-3.33 (m, 3H), 3.06 (q, J=7.20 Hz, 2H), 2.76-2.67 (m, 4H), 2.66 (s, 3H), 2.34-2.33 (m, 2H), 2.08-2.04 (m, 4H), 1.92-1.68 (m, 9H), 1.06 (t, J=7.20 Hz, 3H).

Example 65

(3R)-3-[6-[2-cyano-3-[[ethyl(methyl)sulfamoyl]amino]-6-fluorophenoxy]-4-oxoquinazolin-3-yl]-8-[2-[4-[4-(2,6-dioxopiperidin-3-yl)-2-fluorophenyl]-3,3-difluoropiperidin-1-yl]acetyl]-1-oxa-8-azaspiro[4.5]decane

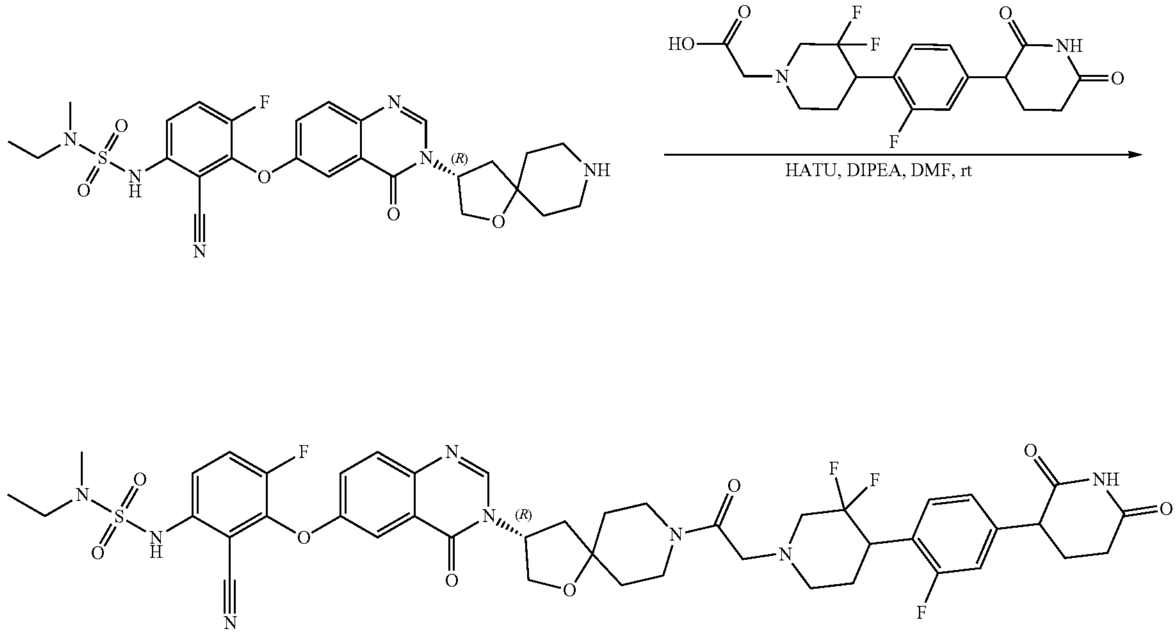

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (80 mg, 143.73 μmol), 2-[4-[4-(2,6-dioxo-3-piperidyl)-2-fluoro-phenyl]-3,3-difluoro-1-piperidyl]acetic acid (66.29 mg, 172.47 μmol), N,N-diisopropylethylamine (92.88 mg, 718.64 μmol, 125.17 μL) and HATU (60.11 mg, 158.10 μmol). The crude compound was purified by reverse phase column chromatography, eluting with 40 to 45% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[4-[4-(2,6-dioxo-3-piperidyl)-2-fluoro-phenyl]-3,3-difluoro-1-piperidyl]acetyl]-1-oxa-8-azaspiro[4.5]decane (17.25 mg, 17.64 μmol, 12% yield) as off-white solid. LCMS m/z (ESI): 923.2 $[M+H]^+$. $^1H$ NMR (400 MHz, DMSO-$d_6$): δ=10.87 (s, 1H), 10.19 (s, 1H), 8.37 (s, 1H), 7.87 (t, J=9.60 Hz, 1H), 7.80 (d, J=8.80 Hz, 1H), 7.70 (dd, J=3.20, 9.00 Hz, 1H), 7.50 (dd, J=4.00, 9.20 Hz, 1H), 7.35-7.41 (m, 1H), 7.37 (d, J=2.80 Hz, 1H), 7.09-7.13 (m, 2H), 5.28-5.38 (m, 1H), 4.11-4.19 (m, 2H), 3.90 (d, J=8.40 Hz, 1H), 3.45-3.75 (m, 4H), 3.25-3.45 (m, 2H), 3.17 (q, J=7.20 Hz, 2H), 2.91-2.99 (m, 1H), 2.80 (s, 3H), 2.59-2.72 (m, 3H), 2.35-2.60 (m, 3H), 2.01-2.31 (m, 5H), 1.45-1.81 (m, 5H), 1.06 (t, J=7.20 Hz, 3H).

Example 66

6-[2-cyano-3-[[ethyl(methyl)sulfamoyl]amino]-6-fluorophenoxy]-3-[(3S)-8-[2-[4-[4-(2,6-dioxopiperidin-3-yl)-2-fluorophenyl]-3,3-difluoropiperidin-1-yl]acetyl]-8-azaspiro [4.5]decan-3-yl]-4-oxoquinazoline

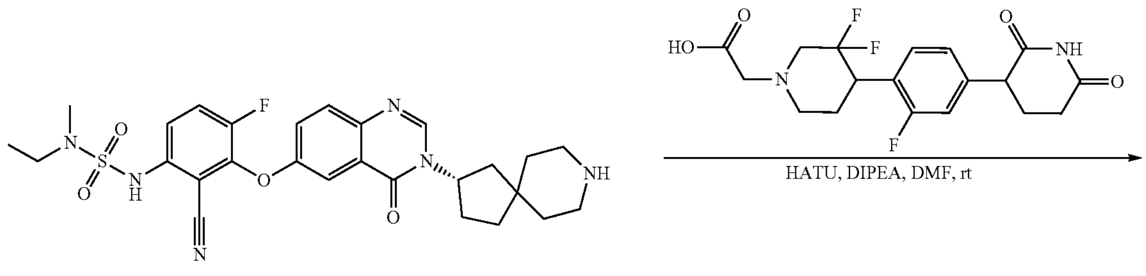

-continued

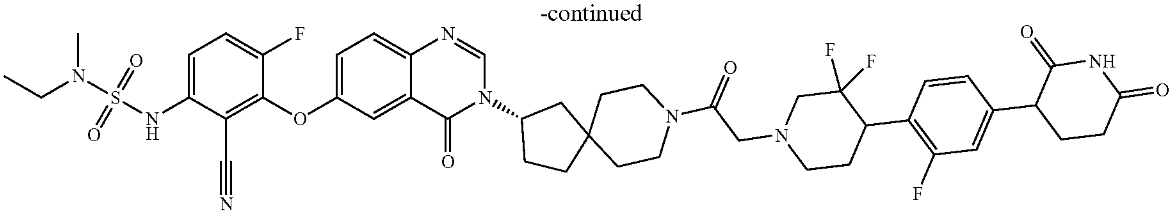

Target compound was prepared via HATU mediated acid-amine coupling reaction (Procedure A-E). Amide coupling was carried out using 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (80 mg, 144.24 μmol), 2-[4-[4-(2,6-dioxo-3-piperidyl)-2-fluoro-phenyl]-3,3-difluoro-1-piperidyl]acetic acid (66.53 mg, 173.09 μmol), N,N-diisopropylethylamine (93.21 mg, 721.20 μmol, 125.62 μL) and HATU (60.33 mg, 158.66 μmol). The crude compound was purified by reverse phase column chromatography, eluting with 40 to 45% acetonitrile in 0.1% formic acid in water, to afford 6-[2-cyano-3-[[ethyl(methyl)sulfamoyl]amino]-6-fluoro-phenoxy]-3-[(3S)-8-[2-[4-[4-(2,6-dioxo-3-piperidyl)-2-fluoro-phenyl]-3,3-difluoro-1-piperidyl]acetyl]-8-azaspiro[4.5]decan-3-yl]-4-oxo-quinazoline (16.73 mg, 17.06 μmol, 12% yield) as off-white solid. LCMS m/z (ESI): 921.2 $[M+H]^+$. $^1H$ NMR (400 MHz, DMSO-$d_6$): δ=10.87 (s, 1H), 10.19 (s, 1H), 8.45 (s, 1H), 7.81-7.90 (m, 1H), 7.80 (d, J=8.80 Hz, 1H), 7.69 (dd, J=2.80, 8.80 Hz, 1H), 7.49 (dd, J=4.00, 9.20 Hz, 1H), 7.37-7.40 (m, 1H), 7.37 (d, J=2.80 Hz, 1H), 7.12 (d, J=11.20 Hz, 1H), 7.09 (d, J=8.40 Hz, 1H), 5.01-5.10 (m, 1H), 3.88-3.95 (m, 1H), 3.48-3.60 (m, 3H), 3.25-3.41 (m, 3H), 3.16 (q, J=6.40 Hz, 2H), 2.91-2.98 (m, 1H), 2.79 (s, 3H), 2.60-2.72 (m, 3H), 2.41-2.60 (m, 3H), 2.18-2.31 (m, 1H), 2.01-2.20 (m, 5H), 1.72-1.91 (m, 3H), 1.41-1.71 (m, 5H), 1.06 (t, J=7.20 Hz, 3H).

Example 67

6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2,5-difluorophenyl]piperidin-1-yl]acetyl]-8-azaspiro[4.5]decan-3-yl]-4-oxoquinazoline

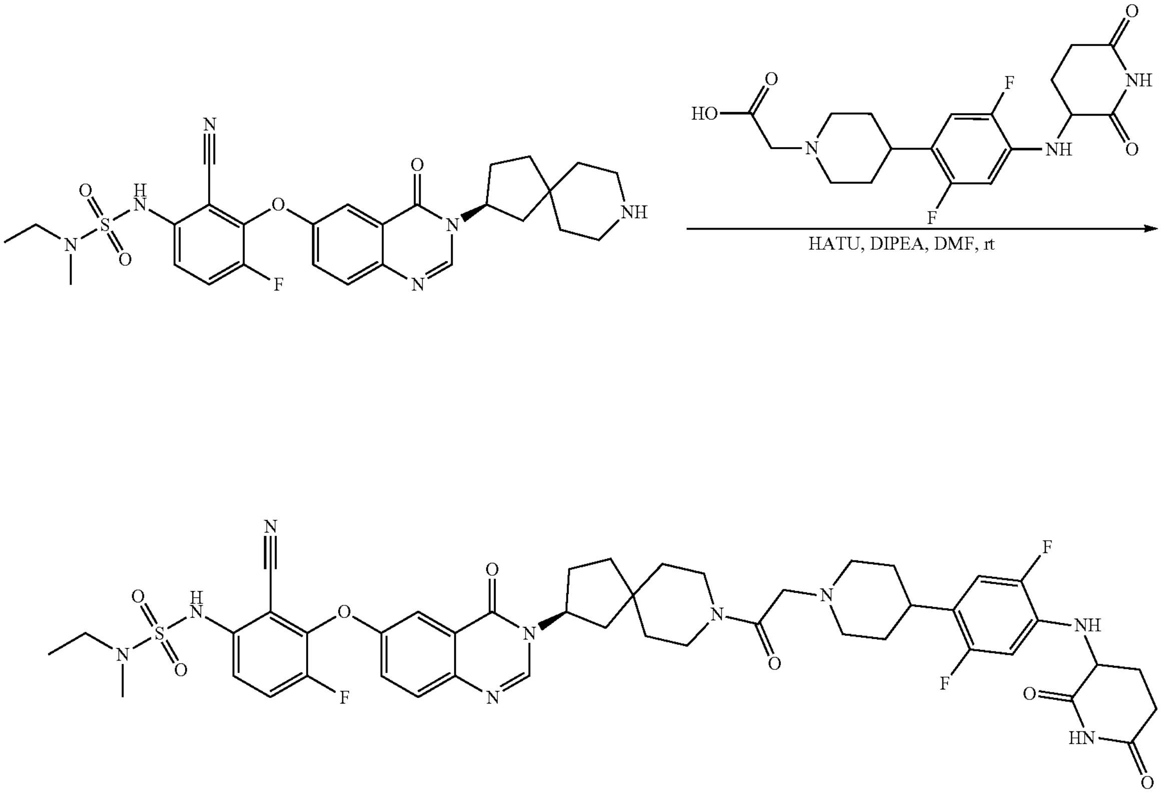

Target compound was prepared via HATU mediated acid-amine coupling reaction (Procedure A-E). Amide coupling was carried out using 2-[4-[4-[(2,6-dioxo-3-piperidyl) amino]-2,5-difluoro-phenyl]-1-piperidyl]acetic acid (50 mg, 119.66 μmol), 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (70.73 mg, 119.66 μmol), HATU (68.25 mg, 179.50 μmol) and N,N-diisopropylethylamine (77.33 mg, 598.32 μmol, 104.21 μL). The crude compound was purified by reverse phase column chromatography by using 30 g snap, eluting with 50% acetonitrile in 0.1% formic acid in water, to afford 6-[2-cyano-3-[[ethyl(methyl) sulfamoyl]amino]-6-fluoro-phenoxy]-3-[(3S)-8-[2-[4-[4-[(2,6-dioxo-3-piperidyl)amino]-2,5-difluoro-phenyl]-1-piperidyl]acetyl]-8-azaspiro[4.5]decan-3-yl]-4-oxo-quinazoline (4.21 mg, 4.17 μmol, 3% yield) as off-white solid. LCMS m/z (ESI): 917.8 $[M+H]^+$; $^1H$ NMR (400 MHz, DMSO-$d_6$): δ=10.84 (s, 1H), 10.20 (s, 1H), 9.45 (s, 1H), 8.46 (s, 1H), 7.78-7.86 (m, 1H), 7.80 (d, J=8.80 Hz, 1H), 7.69 (dd, J=2.40, 9.00 Hz, 1H), 7.48 (d, J=5.20 Hz, 1H), 7.37 (s, 1H), 6.95 (dd, J=6.80, 12.40 Hz, 1H), 6.71 (dd, J=7.60, 13.00 Hz, 1H), 5.87 (d, J=8.00 Hz, 1H), 5.01-5.11 (m, 1H), 4.39-4.48 (m, 1H), 4.21-4.38 (m, 2H), 3.45-3.68 (m, 3H), 3.25-3.43 (m, 2H), 3.15 (q, J=6.40 Hz, 2H), 2.84-3.12 (m, 3H), 2.78 (s, 3H), 2.61-2.77 (m, 1H), 2.53-2.65 (m, 2H), 1.95-2.21 (m, 7H), 1.78-1.92 (m, 3H), 1.45-1.78 (m, 6H), 1.06 (t, J=7.20 Hz, 3H).

Example 68

3-[5-bromo-6-[2-cyano-3-[[ethyl(methyl)sulfamoyl] amino]-6-fluorophenoxy]-4-oxoquinazolin-3-yl]-8-[2-[4-[4-[(2,6-dioxopiperidin-3-yl)amino]-2-fluoro-phenyl]piperidin-1-yl]acetyl]-1-oxa-8-azaspiro[4.5] decane

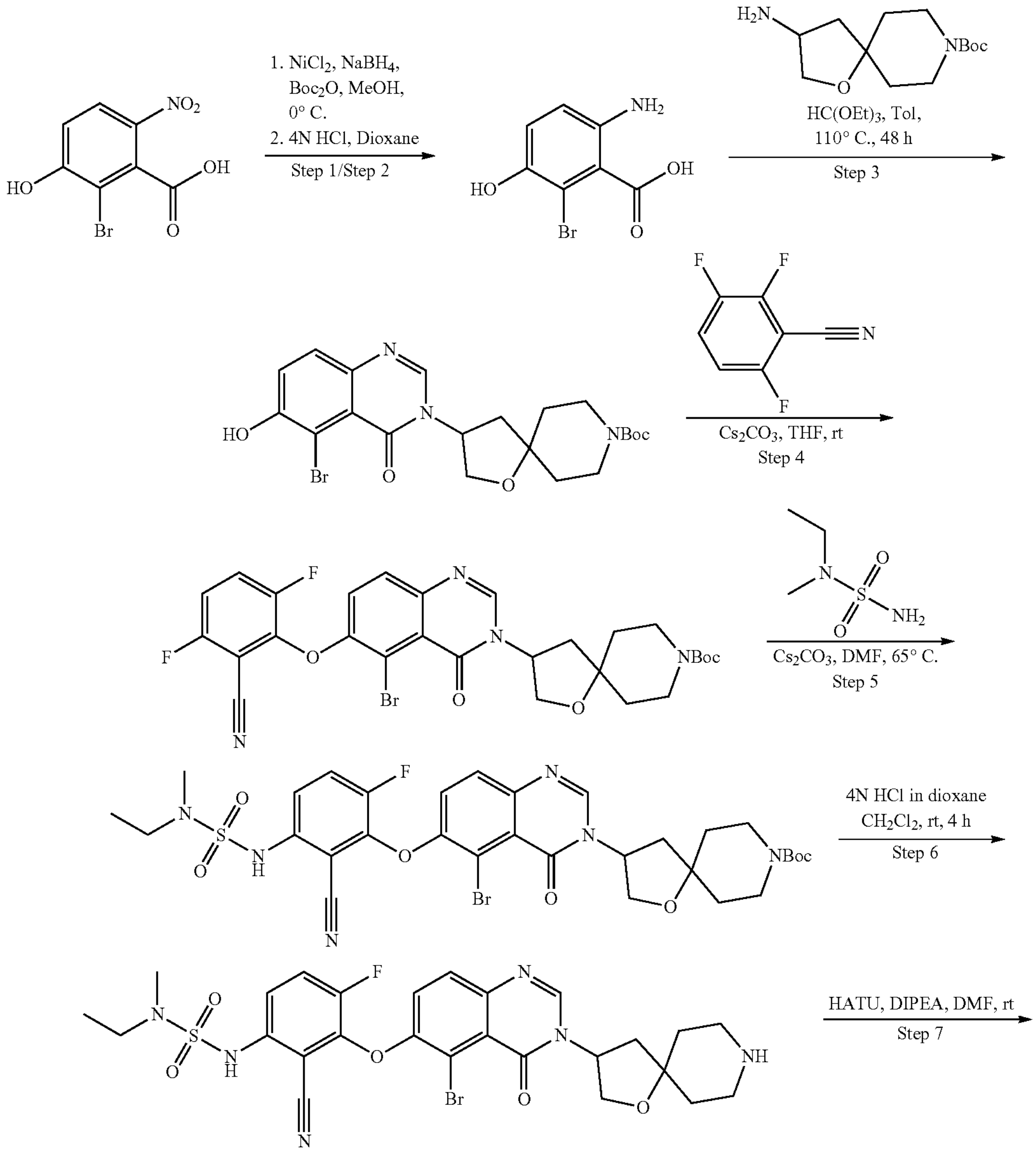

-continued

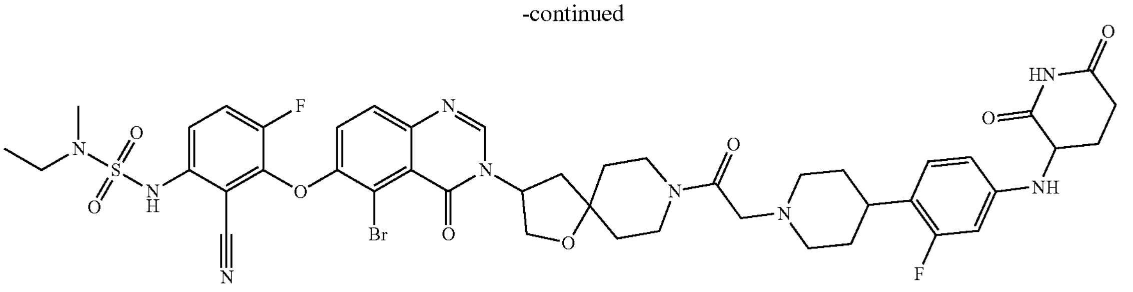

Step 1: Into a stirred solution of 2-bromo-3-hydroxy-6-nitro-benzoic acid (4.00 g, 15.27 mmol) in methanol (50 mL) was added nickel(II) chloride hexahydrate, 98% (434.01 mg, 1.53 mmol, 226.04 μL) at room temperature under nitrogen atmosphere. The resulting mixture was cooled to 0° C. temperature, and sodium borohydride (866.35 mg, 22.90 mmol, 809.67 μL) was added portion wise. The reaction mixture stirred at 0° C. for 30 minutes before warming to room temperature and stirring for 5 h. Di-tert-butyl di-carbonate (10.00 g, 45.80 mmol, 10.51 mL) was added dropwise at 0° C. and stirred for 16 h at room temperature. The reaction mixture was quenched with $NH_4Cl$ solution (40 mL) dropwise at 0° C. The reaction mixture was extracted with ethyl acetate (3×150 mL). The combined organic layers were dried over sodium sulfate, filtered, and concentrated under reduced pressure. The crude compound was purified by silica gel flash column chromatography with 80-100% ethyl acetate in petroleum ether as eluent to afford 2-bromo-6-(tert-butoxycarbonylamino)-3-hydroxy-benzoic acid (1.5 g, 2.89 mmol, 19% yield) as brown solid. LCMS m/z (ESI): 432.0 $[M-H]^-$ Step 2: Into a stirred solution of 2-bromo-6-(tert-butoxycarbonylamino)-3-hydroxy-benzoic acid (1.5 g, 4.52 mmol) in dichloromethane (15 mL) was added hydrogen chloride in 1,4-dioxane (4 M, 10.16 mL) dropwise at 0° C. under nitrogen atmosphere. The reaction mixture was warmed to RT before stirring for 16 h. The reaction mixture was directly concentrated under reduced pressure to afford 6-amino-2-bromo-3-hydroxy-benzoic acid (1.1 g, 1.89 mmol, 42% yield) as brown solid, which was carried forward without further purification. LCMS m/z (ESI): 232.0 $[M+H]^+$.

Step 3: Quinazolinone intermediate was synthesized by following general procedure for cyclization (Procedure A-A) using 6-amino-2-bromo-3-hydroxy-benzoic acid (1. g, 4.31 mmol), triethyl orthoformate (1.60 g, 10.77 mmol, 1.79 mL), acetic acid (25.88 mg, 430.98 μmol, 24.65 μL) and tert-butyl 3-amino-7-oxa-8-azaspiro[4.5]decane-8-carboxylate (1.10 g, 4.31 mmol). The crude product was purified by column chromatography eluting with 70-80% ethyl acetate in petroleum ether as eluent to afford tert-butyl 3-(5-bromo-6-hydroxy-4-oxo-quinazolin-3-yl)-1-oxa-8-azaspiro[4.5]decane-8-carboxylate (480 mg, 770.44 μmol, 18% yield) as brown solid. LCMS m/z (ESI): 480.0 $[M+H]^+$.

Step 4: O-arylated quinazolinone intermediate was synthesized by following general procedure for O-arylation (Procedure A-B) using tert-butyl 3-(5-bromo-6-hydroxy-4-oxo-quinazolin-3-yl)-1-oxa-8-azaspiro[4.5]decane-8-carboxylate (480 mg, 999.27 μmol), 2,3,6-trifluorobenzonitrile (156.98 mg, 999.27 μmol, 115.42 μL) and cesium carbonate (976.75 mg, 3.00 mmol). The crude compound was purified by silica gel flash column chromatography eluting with 70-80% ethyl acetate in petroleum ether to afford tert-butyl 3-[5-bromo-6-(2-cyano-3,6-difluoro-phenoxy)-4-oxo-quinazolin-3-yl]-1-oxa-8-azaspiro[4.5]decane-8-carboxylate (400 mg, 469.04 μmol, 47% yield) as brown solid. LCMS m/z (ESI): 619.3 $[M+H]^+$.

Step 5: Sulfamoylated quinazolinone intermediate was synthesized by following Procedure A-C using tert-butyl 3-[5-bromo-6-(2-cyano-3,6-difluoro-phenoxy)-4-oxo-quinazolin-3-yl]-1-oxa-8-azaspiro[4.5]decane-8-carboxylate (200.00 mg, 323.92 mol), [methyl(sulfamoyl)amino]ethane (89.52 mg, 647.84 μmol) and cesium carbonate (316.62 mg, 971.76 μmol) to afford tert-butyl 3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (170 mg, 171.24 μmol, 53% yield) as brown solid. LCMS m/z (ESI): 735.0 $[M-H]^-$.

Step 6: The requisite amine was synthesized by HCl mediated N-Boc deprotection (Procedure A-D). N-Boc deprotection was done on tert-butyl 3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (80.00 mg, 108.75 μmol) and hydrogen chloride in 1,4-dioxane (4M, 1 mL) to afford 3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane (75 mg, 68.68 μmol, 63% yield) as colorless liquid. LCMS m/z (ESI): 635.0 $[M+H]^+$.

Step 7: Target compound was prepared via HATU mediated acid-amine coupling reaction (Procedure A-E). Amide coupling was carried out using 3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane (75.00 mg, 118.02 μmol), 2-[4-[4-[(2,6-dioxo-3-piperidyl)amino]-2-fluoro-phenyl]-1-piperidyl]acetic acid (42.89 mg, 118.02 μmol), N,N-diisopropylethylamine (76.26 mg, 590.08 μmol, 102.78 μL) and HATU (67.31 mg, 177.02 μmol). The crude reaction mixture was purified by reverse phase column chromatography eluting with 40% acetonitrile in 0.1% formic acid in water to afford 3-[5-bromo-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (13 mg, 12.25 μmol, 10% yield) as off-white solid. LCMS m/z (ESI): 980.2 $[M+H]^+$. $^1H$ NMR (400 MHz, DMSO-$d_6$): δ=10.80 (s, 1H), 9.84 (s, 1H), 8.39 (s, 1H), 7.67 (d, J=8.80 Hz, 1H), 7.60-7.68 (m, 1H), 7.36 (d, J=8.80 Hz, 1H), 6.91-7.11 (m, 1H), 6.45-6.53 (m, 2H), 6.09 (d, J=7.60 Hz, 1H), 7.32-7.41 (m, 1H), 5.32-5.41 (m, 1H), 4.28-4.38 (m, 1H), 4.10-4.21 (m, 2H), 3.92-4.10 (m, 2H), 3.61-3.71 (m, 1H), 3.31-3.52 (m, 3H), 3.04-3.12 (m, 3H), 2.65-2.91 (m, 4H), 2.69 (s, 3H), 2.40-2.58 (m, 2H), 2.02-2.15 (m, 2H), 1.52-2.01 (m, 10H), 1.05 (t, J=7.20 Hz, 3H).

Example 69
5-bromo-6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline
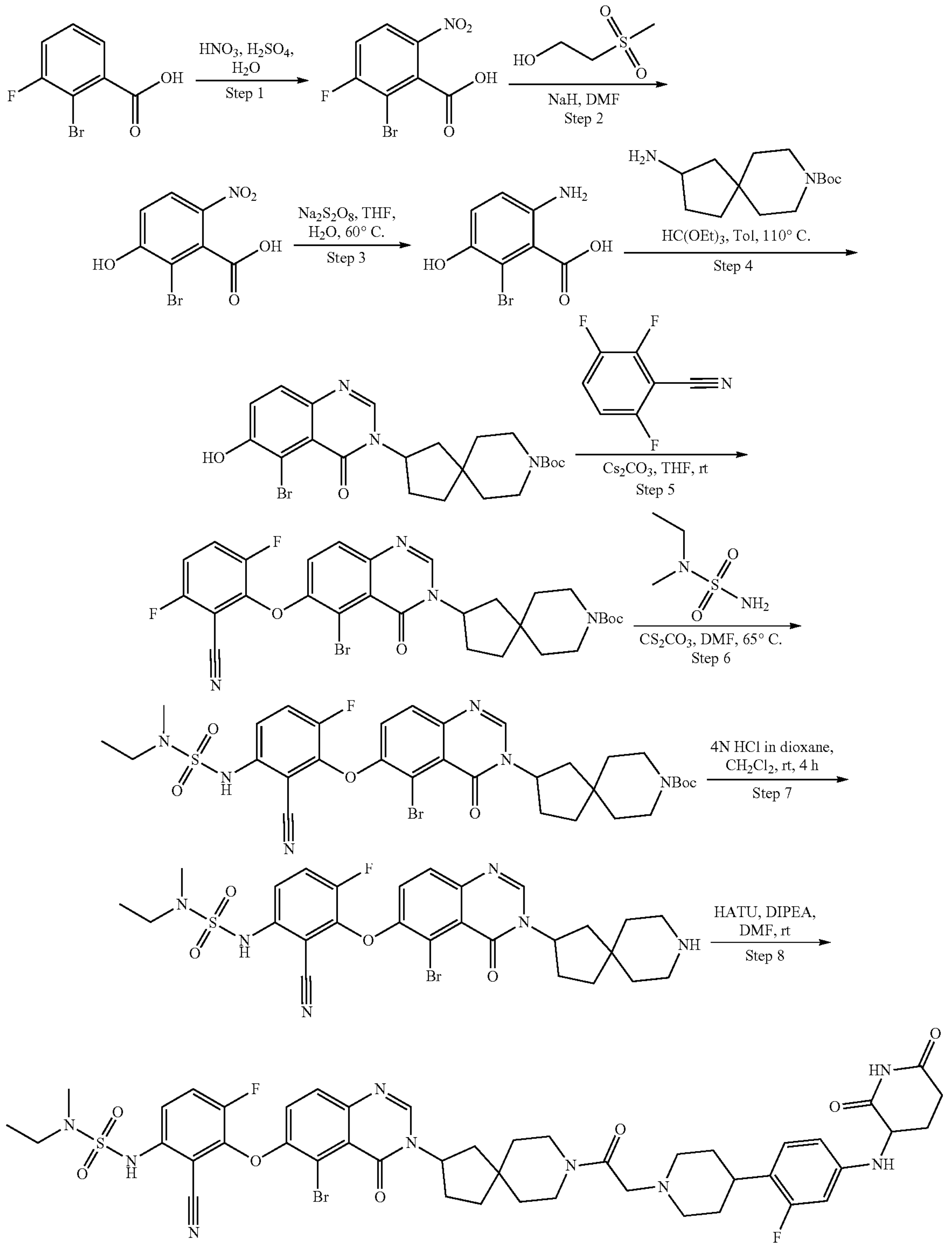

Step 1: To a stirred solution of 2-bromo-3-fluoro-benzoic acid (20.0 g, 91.32 mmol) in sulfuric acid (90 mL) was added nitric acid (5.75 g, 91.32 mmol, 0.35 mL) dropwise at 0° C. temperature under nitrogen condition. The resulting mixture was stirred at 0° C. for 2 h. After completion, the reaction mixture was cooled to 0° C., poured into a beaker containing ice and solid precipitates out. Obtained solid was filtered, washed with water (200 mL) and dried under reduced pressure to afford 2-bromo-3-fluoro-6-nitro-benzoic acid (20 g, 58.41 mmol, 64% yield) as a white solid. LCMS m/z (ESI): 261.0 $[M-2H]^-$ Step 2: To a stirred solution of 2-bromo-3-fluoro-6-nitro-benzoic acid (10.00 g, 37.88 mmol) in N,N-dimethylformamide (400 mL) was added 2-methylsulfonylethanol (5.64 g, 45.45 mmol) at room temperature under nitrogen atmosphere. The reaction mixture was stirred at 0° C., added sodium hydride (60% dispersion in mineral oil, 5.8 g, 151.51 mmol, 2.53 mL) lot wise at 0° C. temperature and allowed the reaction mixture to room temperature and stirred for 2 h. After completion, the reaction mixture was quenched with 1.5N HCl solution (pH-1) by dropwise at 0° C. and extracted with ethyl acetate (3×150 mL). Combined organic layers were washed with cold water (3×50 mL), dried over sodium sulfate, filtered, and concentrated under reduced pressure to afford 2-bromo-3-hydroxy-6-nitro-benzoic acid (7 g, 18.97 mmol, 50% yield) as a brown solid. LCMS m/z (ESI): 260.0 $[M-2H]^-$.

Step 3: To a solution of 2-bromo-3-hydroxy-6-nitro-benzoic acid (2.50 g, 9.54 mmol) in tetrahydrofuran (20 mL) was added sodium dithionite (4.98 g, 28.62 mmol) dissolved in water (6 mL) at room temperature under nitrogen atmosphere. The resulting mixture was stirred at 65° C. temperature for 16 h. After completion, the reaction mixture was diluted water (5 mL), extracted with ethyl acetate (3×50 mL). The organic layer was washed with brine (20 mL), dried over sodium sulfate, and concentrated under reduced pressure to afford 6-amino-2-bromo-3-hydroxy-benzoic acid (850 mg, 2.27 mmol, 24% yield) as a brown solid. LCMS m/z (ESI): 230.0 $[M-2H]^-$.

Step 4: Quinazolinone intermediate was synthesized by following general procedure for cyclization (Procedure A-A) using 6-amino-2-bromo-3-hydroxy-benzoic acid (1.2 g, 5.17 mmol), triethyl orthoformate (1.92 g, 12.93 mmol, 2.15 mL), acetic acid (31.05 mg, 517 μmol, 29.57 μL) and tert-butyl 3-amino-8-azaspiro[4.5]decane-8-carboxylate (1.32 g, 5.17 mmol). The crude product was purified by silica gel flash column chromatography by eluting with 70-80% ethyl acetate in petroleum ether as eluent to afford tert-butyl 3-(5-bromo-6-hydroxy-4-oxo-quinazolin-3-yl)-8-azaspiro[4.5]decane-8-carboxylate (350 mg, 515.07 μmol, 10% yield) as a brown solid. LCMS m/z (ESI): 422.0 $[M-{}^{t}Bu+H]^+$.

Step 5: O-arylated quinazolinone intermediate was synthesized by following general procedure for O-arylation (Procedure A-B) using tert-butyl 3-(5-bromo-6-hydroxy-4-oxo-quinazolin-3-yl)-8-azaspiro[4.5]decane-8-carboxylate (350 mg, 731.64 μmol), 2,3,6-trifluorobenzonitrile (114.94 mg, 731.64 μmol, 84.51 μL) and cesium carbonate (715.15 mg, 2.19 mmol). The crude was purified by silica gel flash column chromatography eluting with 70-80% ethyl acetate in petroleum ether to afford tert-butyl 3-[5-bromo-6-(2-cyano-3,6-difluoro-phenoxy)-4-oxo-quinazolin-3-yl]-8-azaspiro[4.5]decane-8-carboxylate (180 mg, 205.89 μmol, 28 yield) as a brown solid. LCMS m/z (ESI): 599.0 $[M-{}^{t}Bu+H]^+$.

Step 6: Sulfamoylated quinazolinone intermediate was synthesized by following Procedure A-C using tert-butyl (3S)-3-[5-bromo-6-(2-cyano-3,6-difluoro-phenoxy)-4-oxo-quinazolin-3-yl]-8-azaspiro[4.5]decane-8-carboxylate (180 mg, 292.46 μmol), [methyl(sulfamoyl)amino]ethane (80.83 mg, 584.92 μmol) and cesium carbonate (285.87 mg, 877.39 μmol) to afford tert-butyl (3S)-3-[5-bromo-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (115 mg, 82.14 μmol, 28% yield) as a brown solid. LCMS m/z (ESI): 677.0 $[M-{}^{t}Bu+H]^+$.

Step 7: The requisite amine was synthesized by HCl mediated N-Boc deprotection (Procedure A-D). N-Boc deprotection was done on tert-butyl 3-[5-bromo-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (75.00 mg, 102.23 μmol) using 4 M HCl in 1,4-dioxane (4 M, 937.50 μL) to afford 3-(8-azaspiro[4.5]decan-3-yl)-5-bromo-6-[2-cyano-3-[[ethyl(methyl)sulfamoyl]amino]-6-fluoro-phenoxy]-4-oxo-quinazoline (75 mg, 52.27 μmol, 51% yield) as a colorless liquid. LCMS m/z (ESI): 635.0 $[M+2H]^+$.

Step 8: Target compound was prepared via HATU mediated acid-amine coupling reaction (Procedure A-E). Amide coupling was carried out using 3-(8-azaspiro[4.5]decan-3-yl)-5-bromo-6-[2-cyano-3-[[ethyl(methyl)sulfamoyl]amino]-6-fluoro-phenoxy]-4-oxo-quinazoline (75.00 mg, 118.38 μmol), 2-[4-[4-[(2,6-dioxo-3-piperidyl)amino]-2-fluoro-phenyl]-1-piperidyl]acetic acid (43.02 mg, 118.38 μmol), N,N-diisopropylethylamine (76.50 mg, 591.92 μmol, 103.10 μL) and HATU (67.52 mg, 177.58 μmol). The crude reaction mixture was purified by reverse phase column chromatography eluted with 40% acetonitrile in 0.1% formic acid in water to afford 5-bromo-6-[2-cyano-3-[[ethyl(methyl)sulfamoyl]amino]-6-fluoro-phenoxy]-3-[8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (8 mg, 7.54 μmol, 6% yield) as an off-white solid. LCMS m/z (ESI): 978.2 $[M+H]^+$. $^1$HNMR (400 MHz, DMSO-$d_6$): δ=10.81 (s, 1H), 9.61 (s, 1H), 8.51 (d, J=2.40 Hz, 1H), 7.60-7.71 (m, 1H), 7.67 (d, J=8.80 Hz, 1H), 7.39 (d, J=8.00 Hz, 2H), 6.95-7.02 (m, 1H), 6.50 (d, J=8.00 Hz, 1H), 6.48 (d, J=12.40 Hz, 1H), 6.11 (d, J=8.00 Hz, 1H), 5.05-5.15 (m, 1H), 4.02-4.45 (m, 3H), 3.58-3.68 (m, 1H), 3.25-3.35 (m, 3H), 3.09-3.18 (m, 2H), 2.81-3.10 (m, 3H), 2.65-2.82 (m, 2H), 2.74 (s, 3H), 2.45-2.60 (m, 2H), 2.05-2.18 (m, 4H), 1.70-2.05 (m, 7H), 1.48-1.70 (m, 5H), 1.06 (t, J=7.20 Hz, 3H).

Example 70

5-chloro-6-[2-cyano-3-[[ethyl(methyl)sulfamoyl]amino]-6-fluorophenoxy]-3-[8-[2-[4-[4-[(2,6-dioxopiperidin-3-yl)amino]-2-fluorophenyl]piperidin-1-yl]acetyl]-8-azaspiro[4.5]decan-3-yl]-4-oxoquinazoline

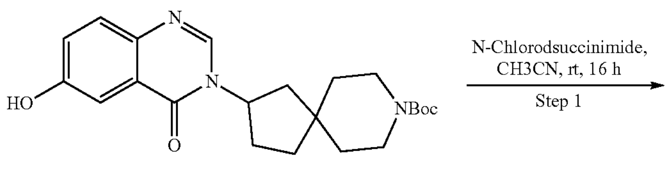

-continued

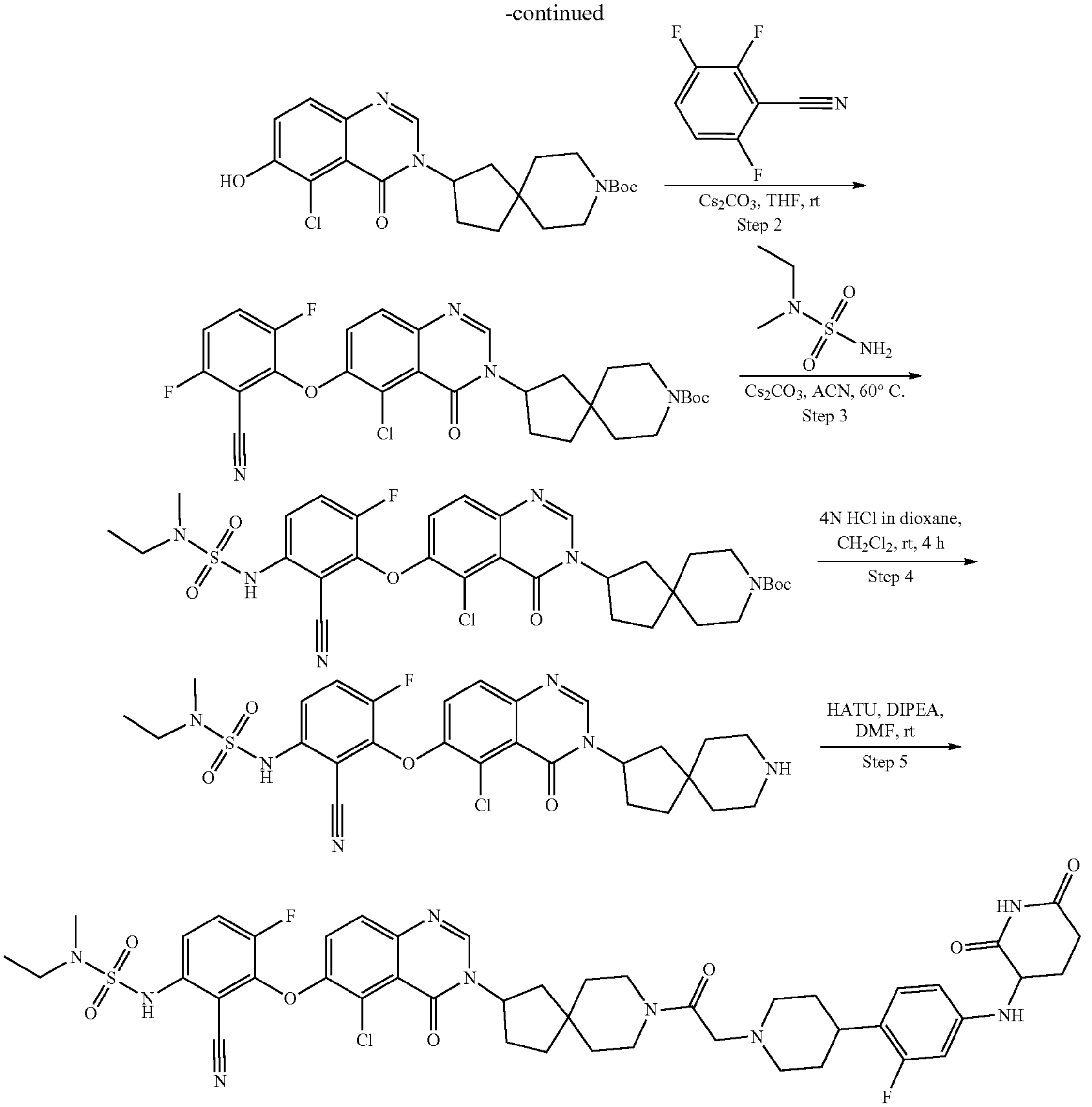

Step 1: To a stirred solution of tert-butyl 3-(6-hydroxy-4-oxo-quinazolin-3-yl)-8-azaspiro[4.5]decane-8-carboxylate (2.2 g, 5.51 mmol) in acetonitrile (30 mL) was added N— chlorosuccinimide (1.47 g, 11.01 mmol, 891.37 μL) at room temperature under nitrogen atmosphere. The reaction mixture was stirred at room temperature for 16 h. After completion, the reaction mixture was diluted with water (30 mL) and extracted with ethyl acetate (3×50 mL). The combined organic layers were dried over sodium sulfate, filtered and concentrated under vacuum to afford crude. Desired product was purified from crude by silica gel flash column chromatography with 20-30% ethyl acetate in petroleum ether as eluent to afford tert-butyl 3-(5-chloro-6-hydroxy-4-oxo-quinazolin-3-yl)-8-azaspiro[4.5]decane-8-carboxylate (1.5 g, 2.06 mmol, 37% yield) as a brown viscous liquid. LCMS m/z (ESI): 378.2 [M−$^t$Bu+H]$^+$.

Step 2: O-arylated quinazolinone intermediate was synthesized by following general procedure for O-arylation (Procedure A-B) using tert-butyl 3-(5-chloro-6-hydroxy-4-oxo-quinazolin-3-yl)-8-azaspiro[4.5]decane-8-carboxylate (190.00 mg, 437.86 μmol), cesium carbonate (427.99 mg, 1.31 mmol) and 2,3,6-trifluorobenzonitrile (82.54 mg, 525.43 μmol, 60.69 μL). The desired compound was purified from crude by silica gel flash column chromatography using 80-90% ethyl acetate in petroleum ether as eluent to afford tert-butyl 3-[5-chloro-6-(2-cyano-3,6-difluoro-phenoxy)-4-oxo-quinazolin-3-yl]-8-azaspiro[4.5]decane-8-carboxylate (0.13 g, 189.10 μmol, 43% yield) as a light brown liquid. LCMS m/z (ESI): 515.0 [M−$^t$Bu+H]$^+$.

Step 3: Sulfamoylated quinazolinone intermediate was synthesized by following Procedure A-C using tert-butyl 3-[5-chloro-6-(2-cyano-3,6-difluoro-phenoxy)-4-oxo-quinazolin-3-yl]-8-azaspiro[4.5]decane-8-carboxylate (160 mg, 280.20 μmol), cesium carbonate (228.24 mg, 700.51 μmol) and [methyl(sulfamoyl)amino]ethane (58.08 mg, 420.31 μmol). The crude compound was triturated with 10% dichloromethane in pet ether to afford tert-butyl 3-[5-chloro-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (150 mg, 154.53 μmol, 55% yield) as alight brown solid. LCMS m/z (ESI): 633.4[M−$^t$Bu+H]$^+$.

Step 4: The requisite amine was synthesized by 4M HCl in Dioxane mediated N-Boc deprotection (Procedure A-D).

N-Boc deprotection was done on tert-butyl 3-[5-chloro-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (155 mg, 159.68 μmol) using hydrogen chloride, 4M in 1,4-dioxane (4 M, 2.20 mL) at 0° C. to afford 3-(8-azaspiro[4.5]decan-3-yl)-5-chloro-6-[2-cyano-3-[[ethyl(methyl)sulfamoyl]amino]-6-fluoro-phenoxy]-4-oxo-quinazoline (130 mg, 155.87 μmol, 98% yield) as a brown solid. LCMS m/z (ESI): 589.2 [M+H]$^+$.

Step 5: The target compound was prepared via HATU mediated acid-amine coupling reaction (Procedure A-E). Amide coupling was carried out using 3-(8-azaspiro[4.5]decan-3-yl)-5-chloro-6-[2-cyano-3-[[ethyl(methyl)sulfamoyl]amino]-6-fluoro-phenoxy]-4-oxo-quinazoline (80 mg, 135.80 μmol), 2-[4-[4-[(2,6-dioxo-3-piperidyl)amino]-2-fluoro-phenyl]-1-piperidyl]acetic acid (49.35 mg, 135.80 μmol), N,N-diisopropylethylamine (70.21 mg, 543.22 μmol, 94.62 μL) and HATU (51.64 mg, 135.80 μmol). The crude compound was purified by reverse phase column chromatography eluted with 50% acetonitrile in 0.1% ammonium acetate in water to afford product 5-chloro-6-[2-cyano-3-[[ethyl(methyl)sulfamoyl]amino]-6-fluoro-phenoxy]-3-[8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (14 mg, 13.76 μmol, 10% yield) as an off-white solid. LCMS m/z (ESI): 934.2 [M+H]$^+$; $^1$HNMR (400 MHz, DMSO-$d_6$): δ=10.80 (s, 1H), 9.80 (s, 1H), 8.49 (s, 1H), 7.70-7.69 (m, 1H), 7.64 (d, J=9.20 Hz, 1H), 7.45 (d, J=8.80 Hz, 1H), 7.39 (dd, J=9.00, 4.00 Hz, 1H), 6.99 (s, 1H), 6.51-6.46 (m, 2H), 6.10 (d, J=8.00 Hz, 1H), 5.18-5.06 (m, 1H), 5.46-4.35 (m, 1H), 4.30-4.21 (m, 1H), 3.64-3.38 (m, 6H), 3.14-3.12 (m, 3H), 3.10-2.81 (m, 2H), 2.75 (s, 3H), 2.70-2.65 (m, 2H), 2.16-2.08 (m, 6H), 2.05-1.80 (m, 6H), 1.68-1.51 (m, 5H), 1.06 (t, J=7.20 Hz, 3H).

Example 71

3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

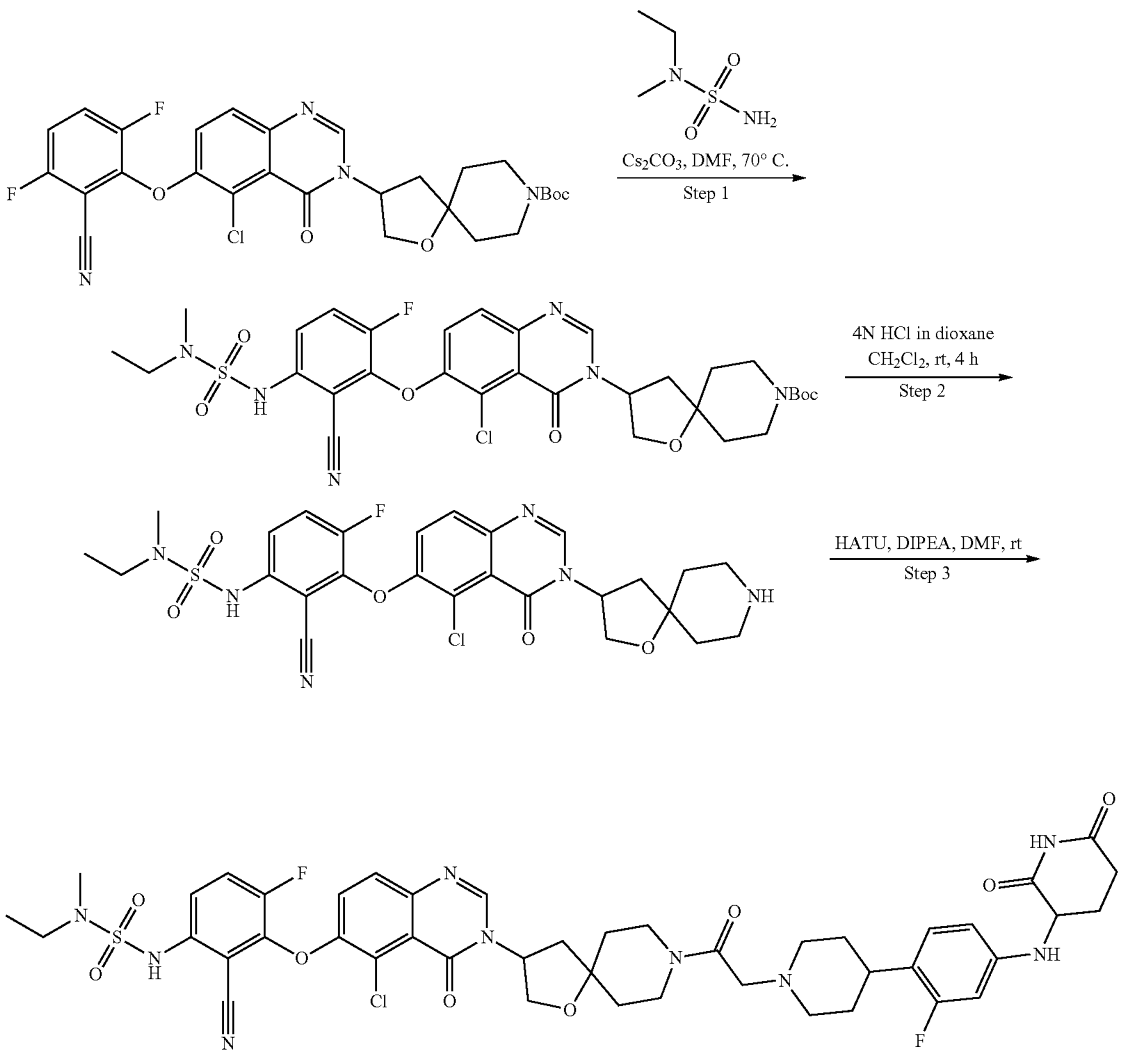

Step 1: Sulfamoylated quinazolinone intermediate was synthesized by following Procedure A-C using tert-butyl 3-[5-chloro-6-(2-cyano-3,6-difluoro-phenoxy)-4-oxo-quinazolin-3-yl]-1-oxa-8-azaspiro[4.5]decane-8-carboxylate (50 mg, 87.26 μmol), cesium carbonate (113.73 mg, 349.05 μmol) and [methyl(sulfamoyl)amino]ethane (36.18 mg, 261.79 μmol) to afford crude tert-butyl 3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (51 mg, 54.80 μmol, 63% yield) as a light yellow solid. LCMS m/z (ESI): 635.0 [M+H-$^{t}$Bu]$^{+}$.

Step 2: The requisite amine was synthesized by HCl mediated N-Boc deprotection (Procedure A-D). N-Boc deprotection was done on tert-butyl 3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (51 mg, 73.79 μmol) using 4M hydrogen chloride solution in dioxane (4 M, 2 mL) to afford crude 3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane (53 mg, 73.48 μmol, 100% yield) as an off-white solid. LCMS m/z (ESI): 591.3 [M+H]$^{+}$.

Step 3: Target compound was prepared via HATU mediated acid-amine coupling reaction (Procedure A-E). Amide coupling was carried out using 3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane (60 mg, 101.51 μmol), 2-[4-[4-[(2,6-dioxo-3-piperidyl)amino]-2-fluoro-phenyl]-1-piperidyl]acetic acid (40.58 mg, 111.67 μmol) N,N-diisopropylethylamine (65.60 mg, 507.57 μmol, 88.41 μL) and HATU (42.46 mg, 111.67 μmol) to afford 3-[5-chloro-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (4 mg, 3.97 μmol, 4% yield) as an off-white solid. LCMS m/z (ESI): 936.2 [M+H]$^{+}$. $^{1}$HNMR (400 MHz, DMSO-$d_6$): δ=10.81 (s, 1H), 10.15 (s, 1H), 9.56 (s, 1H), 8.38 (s, 1H), 7.71 (s, 1H), 7.68 (d, J=4.00 Hz, 1H), 7.45 (d, J=9.20 Hz, 1H), 7.38 (s, 1H), 6.98 (s, 1H), 6.51-6.46 (m, 2H), 6.11 (d, J=7.60 Hz, 1H), 5.34 (m, 1H), 5.34 (m, 1H), 4.32-4.30 (m, 2H), 4.18-4.16 (m, 3H), 3.78 (m, 1H), 3.44-3.41 (m, 3H), 3.13-3.11 (m, 3H), 2.73 (s, 3H), 2.11-2.08 (m, 3H), 2.45-2.38 (m, 4H), 1.96-1.74 (m, 9H), 1.05 (t, J=7.20 Hz, 3H).

Example 72

(3R)-3-[6-[2-cyano-3-[[ethyl(methyl)sulfamoyl]amino]-6-fluorophenoxy]-5-fluoro-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

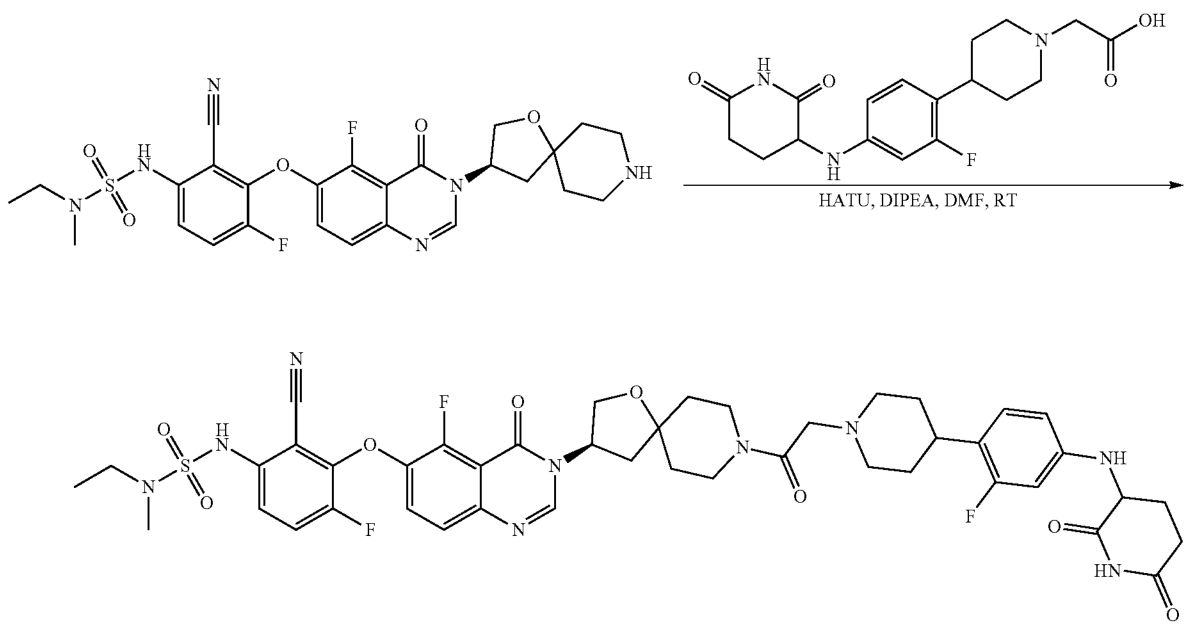 [SMILES: CCN(C)S(=O)(=O)Nc1ccc(F)c(Oc2ccc3ncn([C@H]4COC5(CCNCC5)C4)c(=O)c3c2F)c1C#N ; O=C(O)CN1CCC(c2ccc(NC3CCC(=O)NC3=O)cc2F)CC1 ; CCN(C)S(=O)(=O)Nc1ccc(F)c(Oc2ccc3ncn([C@H]4COC5(CCN(C(=O)CN6CCC(c7ccc(NC8CCC(=O)NC8=O)cc7F)CC6)CC5)C4)c(=O)c3c2F)c1C#N]

Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane HCl salt (17 mg, 27.82 μmol), 2-[4-[4-[(2,6-dioxo-3-piperidyl)amino]-2-fluoro-phenyl]-1-piperidyl]acetic acid (10.11 mg, 25.28 μmol), N,N-diisopropylethylamine (14.38 mg, 111.28 μmol, 19.38 μL) and HATU (10.58 mg, 27.82 μmol) to afford (3R)-3-[6-[2-cyano-3-[[ethyl(methyl)sulfamoyl]amino]-6-fluoro-phenoxy]-5-fluoro-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (3 mg, 3.16 μmol, 11% yield) as off-white solid. LCMS m/z (ESI): 920.2 [M+H]$^{+}$; $^{1}$HNMR (400 MHz, DMSO-$d_6$): δ=10.80 (s, 1H), 9.73 (s, 1H), 8.33 (s, 1H), 7.51-7.40 (m, 3H), 7.29-7.22 (m, 1H), 6.98 (s, 1H), 6.54-6.44 (m, 2H), 6.05 (d, J=12.00 Hz, 1H), 5.35-5.33 (m, 1H), 4.32 (t, J=7.20 Hz, 1H), 4.20-4.14 (m, 2H), 3.72-3.71 (m, 1H), 3.15-2.85 (m, 4H), 2.74 (q, J=16.00 Hz, 2H), 2.46-2.32 (m, 4H), 2.16-2.04 (m, 5H), 1.97-1.72 (m, 9H), 1.03 (t, J=7.20 Hz, 3H).

Example 73

(3R)-3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

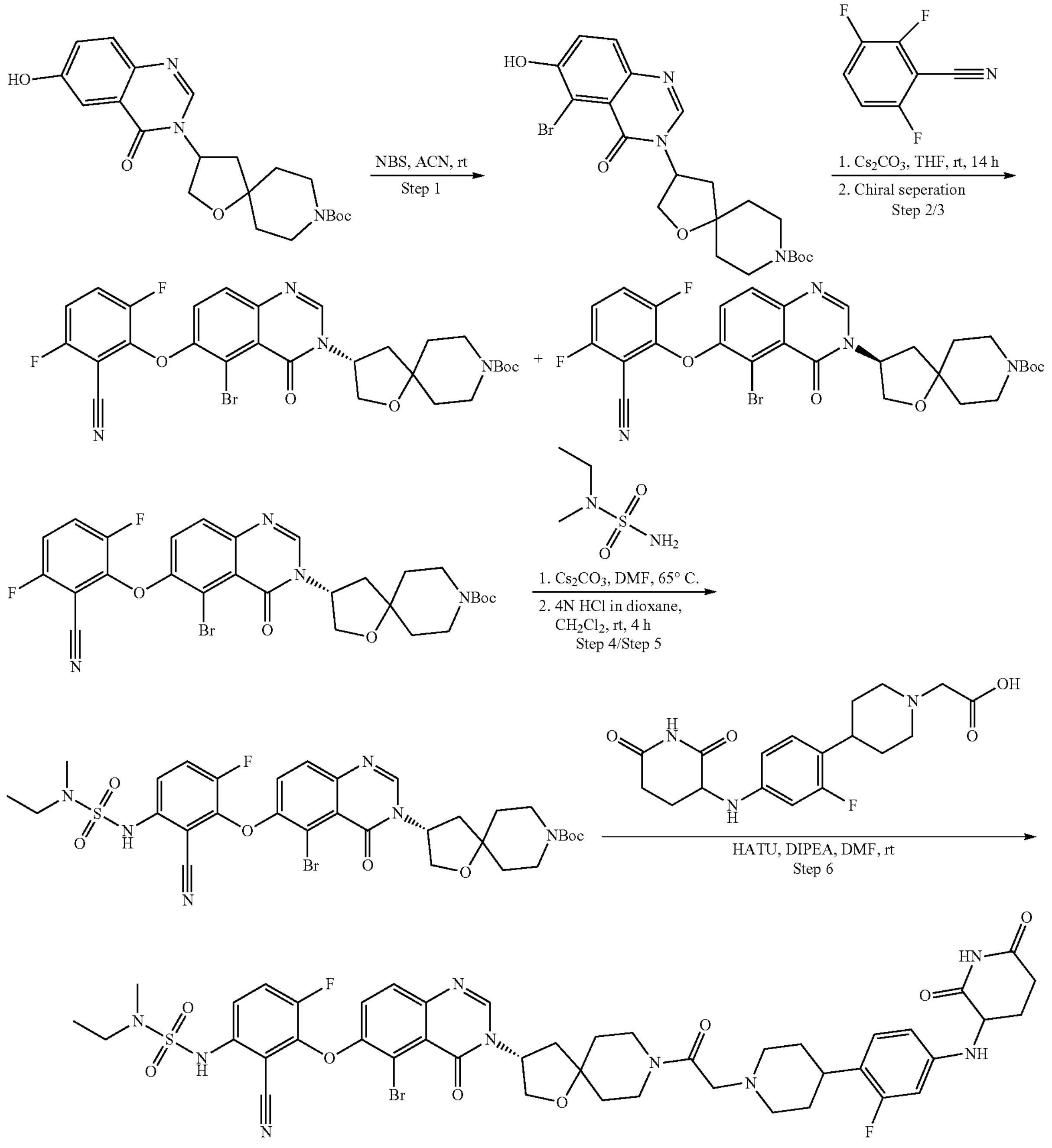

Step 1: Into a stirred solution of tert-butyl 3-(6-hydroxy-4-oxo-quinazolin-3-yl)-1-oxa-8-azaspiro[4.5]decane-8-carboxylate (1.1 g, 2.74 mmol) in acetonitrile (15 mL) was added N— bromosuccinimide (487.68 mg, 2.74 mmol, 232.23 μL) at room temperature under nitrogen atmosphere and the resulting mixture was stirred at room temperature for 1 h. The reaction mixture was diluted water (20 mL) and extracted with ethyl acetate (3×25 mL). Combined organic layers washed brine (15 mL), dried over sodium sulfate, filtered, and concentrated under reduced pressure to afford the crude. The crude product was purified by column chromatography using 230-400 silica gel by eluting with 60-70% ethyl acetate in petroleum ether to afford tert-butyl 3-(5-bromo-6-hydroxy-4-oxo-quinazolin-3-yl)-1-oxa-8-azaspiro[4.5]decane-8-carboxylate (600 mg, 1.19 mmol, 43% yield) as a pale brown solid. LCMS m/z (ESI): 482.0 $[M+H]^+$.

Step 2: O-arylated quinazolinone intermediate was synthesized by following general procedure for O-arylation (Procedure A-B) using tert-butyl 3-(5-bromo-6-hydroxy-4-oxo-quinazolin-3-yl)-1-oxa-8-azaspiro[4.5]decane-8-carboxylate (600 mg, 1.20 mmol), 2,3,6-trifluorobenzonitrile (188.18 mg, 1.20 mmol, 138.37 μL) and cesium carbonate (1.17 g, 3.59 mmol). The crude compound was purified by column chromatography using 230-400 silica gel by eluting with 70-80% ethyl acetate in petroleum ether to afford tert-butyl 3-[5-bromo-6-(2-cyano-3,6-difluoro-phenoxy)-4-oxo-quinazolin-3-yl]-1-oxa-8-azaspiro[4.5]decane-8-carboxylate (400 mg, 638.12 μmol, 53% yield) as a brown solid. LCMS m/z (ESI): 618.0 $[M-H]^-$.

Step 3: 400 mg of the racemic mixture was subjected for chiral SFC purification using (R,R) Whelk-01 column to afford tert-butyl (S)-3-(5-bromo-6-(2-cyano-3,6-difluorophenoxy)-4-oxoquinazolin-3(4H)-yl)-1-oxa-8-azaspiro[4.5]decane-8-carboxylate(160 mg, 99.8% pure) and tert-butyl (R)-3-(5-bromo-6-(2-cyano-3,6-difluorophenoxy)-4-oxo-quinazolin-3(4H)-yl)-1-oxa-8-azaspiro[4.5]decane-8-carboxylate(160 mg, 99.8% pure).

Note: First eluted isomer was arbitrarily assigned as S-isomer and second eluted isomer was arbitrarily assigned as R-isomer.

Step 4: Sulfamoylated quinazolinone intermediate was synthesized by following Procedure A-C using tert-butyl 3-[(3R)-5-bromo-6-(2-cyano-3,6-difluoro-phenoxy)-4-oxo-quinazolin-3-yl]-1-oxa-8-azaspiro[4.5]decane-8-carboxylate (160 mg, 259.14 μmol), [methyl(sulfamoyl)amino]ethane (35.81 mg, 259.14 μmol) and cesium carbonate (211.08 mg, 647.84 μmol) to afford tert-butyl 3-[(3R)-5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (120 mg, 125.89 μmol, 49% yield) as a pale brown solid. LCMS m/z (ESI): 735.0, $[M-H]^-$.

Step 5: The requisite amine was synthesized by HCl mediated N-Boc deprotection (Procedure A-D). N-Boc deprotection was done on tert-butyl (3R)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (120 mg, 163.13 μmol) using 4M HCl in dioxane (4 M, 1.63 mL) to afford (3R)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane (105 mg, 132.35 μmol, 81% yield) as pale brown solid. LCMS m/z (ESI): 637.0 $[M+H]^+$.

Step 6: Target compound was prepared via HATU mediated acid-amine coupling reaction (Procedure A-E). Amide coupling was carried out using (3R)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane (105 mg, 165.22 μmol), 2-[4-[4-[(2,6-dioxo-3-piperidyl)amino]-2-fluoro-phenyl]-1-piperidyl]acetic acid (66.06 mg, 165.22 μmol), N,N-diisopropylethylamine (106.77 mg, 826.12 μmol, 143.89 μL) and HATU (94.23 mg, 247.83 μmol). The crude compound was purified by reverse phase column chromatography by using C18-30 g snap eluted with 50% acetonitrile in 0.1% formic acid in water to afford (3R)-3-[5-bromo-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (27 mg, 25.74 μmol, 16% yield) as beige solid. LCMS m/z (ESI): 980.0 $[M+H]^+$; $^1$HNMR (400 MHz, DMSO-$d_6$): δ=10.81 (s, 1H), 10.15 (bs, 1H), 9.45 (bs, 1H), 8.40 (s, 1H), 7.78 (t, J=10.00 Hz, 1H), 7.68 (d, J=9.20 Hz, 1H), 7.41-7.45 (m, 2H), 6.91-7.02 (m, 1H), 6.50 (d, J=7.60 Hz, 1H), 6.48 (d, J=12.80 Hz, 1H), 6.12 (d, J=7.60 Hz, 1H), 5.31-5.41 (m, 1H), 4.12-4.41 (m, 5H), 3.75-3.85 (m, 1H), 3.31-3.61 (m, 4H), 3.02-3.21 (m, 4H), 2.85-2.95 (m, 1H), 2.78 (s, 3H), 2.68-2.78 (m, 1H), 2.41-2.62 (m, 2H), 1.60-2.15 (m, 12H), 1.07 (t, J=7.20 Hz, 3H).

Example 74

(3S)-3-[5-bromo-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

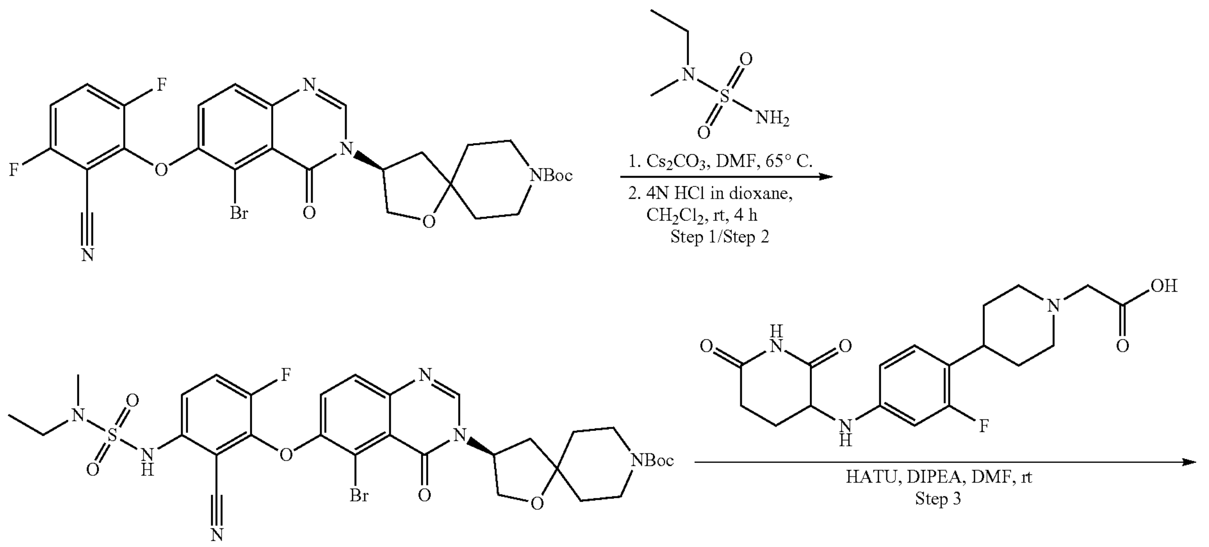

-continued

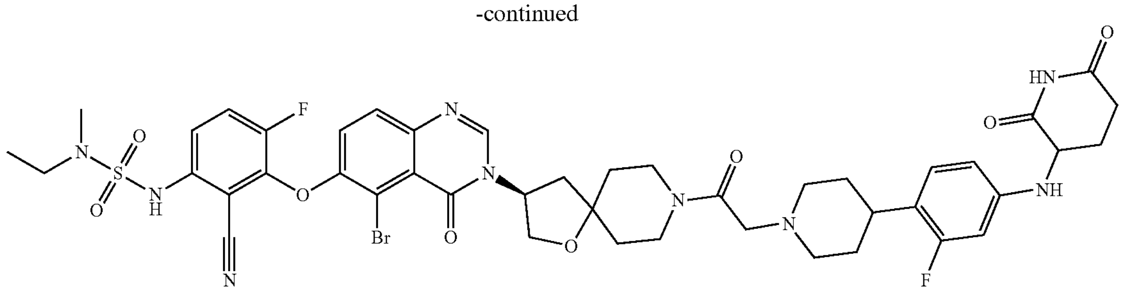

Step 1: Sulfamoylated quinazolinone intermediate was synthesized by following Procedure A-C using tert-butyl (3S)-3-[5-bromo-6-(2-cyano-3,6-difluoro-phenoxy)-4-oxo-quinazolin-3-yl]-1-oxa-8-azaspiro[4.5]decane-8-carboxylate (160 mg, 259.14 [methyl(sulfamoyl)amino]ethane (35.81 mg, 259.13 μmol) and cesium carbonate (211.08 mg, 647.84 μmol) to afford tert-butyl (3R)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (120 mg, 130.34 μmol, 500% yield) as a pale brown solid. LCMS m/z (ESI). 735.0, $[M+H]^+$.

Step 2: The requisite amine was synthesized by HCl mediated N-Boc deprotection (Procedure A-D). N-Boc deprotection was done on tert-butyl (3S)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (120 mg, 163.13 μmol) using 4M HCl in dioxane (4 M, 1.63 mL) to afford (3S)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane (110 mg, 142.01 μmol, 87% yield) as a pale brown solid. LCMS m/z (ESI): 635.0, $[M+H]^+$.

Step 3: Target compound was prepared via HATU mediated acid-amine coupling reaction (Procedure A-E). Amide coupling was carried out using (3S)-3-[5-bromo-6-[2-cyano-3-[[ethyl(methyl)sulfamoyl]amino]-6-fluoro-phenoxy]-4-oxo-quinazolin-3-yl]-1-oxa-8-azaspiro[4.5]decane (110 mg, 163.70 μmol), 2-[4-[4-[(2,6-dioxo-3-piperidyl)amino]-2-fluoro-phenyl]-1-piperidyl]acetic acid (65.45 mg, 163.70 μmol), N,N-diisopropylethylamine (105.78 mg, 818.50 μmol, 142.57 μL) and HATU (93.36 mg, 245.55 μmol). The crude compound was purified by reverse phase column chromatography by using C18-30 g snap eluted with 50% acetonitrile in 0.1% formic acid in water to afford (3S)-3-[5-bromo-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (21 mg, 20.24 μmol, 12% yield) as a beige solid. LCMS m/z (ESI): 980.0 $[M+H]^+$ 1HNMR (400 MHz, DMSO-$d_6$): δ=10.81 (s, 1H), 10.15 (bs, 1H), 9.45 (bs, 1H), 8.40 (s, 1H), 7.71-7.80 (m, 1H), 7.68 (d, J=8.80 Hz, 1H), 7.39-7.43 (m, 2H), 6.91-7.02 (m, 1H), 6.50 (d, J=7.60 Hz, 1H), 6.48 (d, J=13.20 Hz, 1H), 6.12 (d, J=7.60 Hz, 1H), 5.31-5.41 (m, 1H), 4.12-4.41 (m, 5H), 3.75-3.85 (m, 1H), 3.31-3.57 (m, 4H), 3.11-3.21 (m, 2H), 2.98-3.11 (m, 1H), 2.81-2.90 (m, 1H), 2.76 (s, 3H), 2.65-2.76 (m, 1H), 2.40-2.65 (m, 2H), 1.56-2.18 (m, 12H), 1.06 (t, J=6.80 Hz, 3H).

Example 75

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluoro-5-methoxyphenyl]piperidin-1-yl]acetyl]-1-oxa-8-azaspiro[4.5]decane

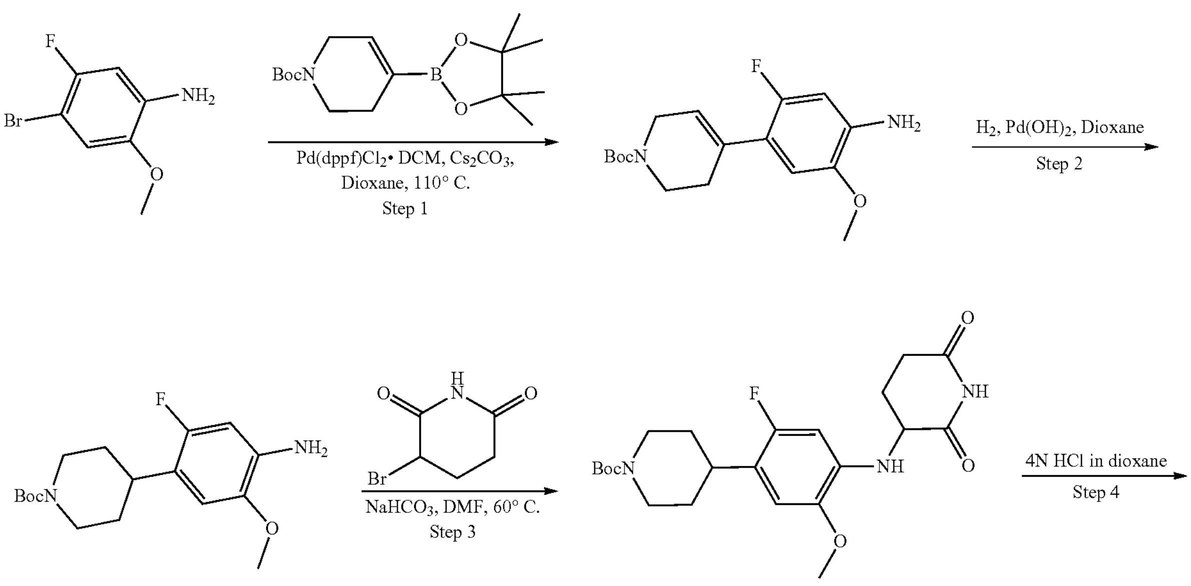

-continued

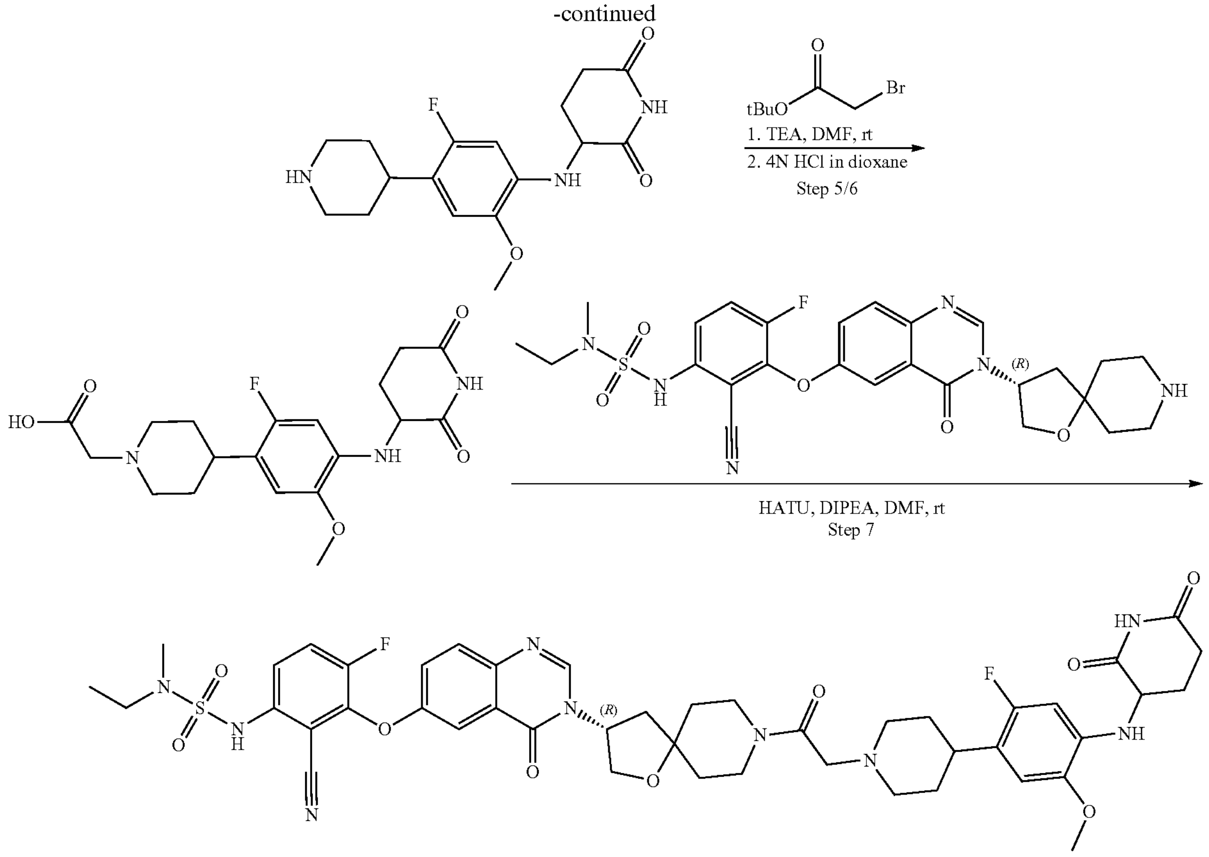

Step 1: A solution of 4-bromo-5-fluoro-2-methoxy-aniline (2 g, 9.09 mmol), tert-butyl 4-(4,4,5,5-tetramethyl-1,3,2-dioxaborolan-2-yl)-3,6-dihydro-2H-pyridine-1-carboxylate (3.37 g, 10.91 mmol) in dioxane (20 mL) was taken in a sealed tube and added cesium carbonate (8.88 g, 27.27 mmol) at room temperature under nitrogen atmosphere. The reaction mixture was degassed with nitrogen for 5 minutes and added Pd(dppf)$Cl_2$·dichloromethane (742.27 mg, 908.93 μmol) at same temperature. Resulting reaction mixture stirred at 110° C. for 16 h. The reaction mixture was diluted with water (50 mL) and extracted by ethyl acetate (2×30 mL). The combined organic layers were washed with brine solution, dried over anhydrous sodium sulfate, filtered and concentrated under reduced pressure to afford crude product. Crude product was purified by column chromatography using silica gel and 0-50% ethyl acetate in Petroleum ether as eluent to afford tert-butyl 4-(4-amino-2-fluoro-5-methoxy-phenyl)-3,6-dihydro-2H-pyridine-1-carboxylate (2.1 g, 6.32 mmol, 70% yield) as a yellow solid. LCMS m/z (ESI): 223.2 $[M+H-100]^+$ Step 2: To a stirred solution of tert-butyl 4-(4-amino-2-fluoro-5-methoxy-phenyl)-3,6-dihydro-2H-pyridine-1-carboxylate (2.1 g, 6.51 mmol) in dioxane (25 mL) was charged palladium hydroxide on carbon (20 wt. % 50% water, 914.82 mg, 6.51 mmol) and saturated with hydrogen by bubbling hydrogen gas through for 10 minutes and then subjected for hydrogenation (1 atm) at room temperature for 16 h. After completion, the reaction mixture was purged with nitrogen, catalyst was removed by filtration through celite pad. The filtrate was concentrated under reduced pressure to afford crude tert-butyl 4-(4-amino-2-fluoro-5-methoxy-phenyl)piperidine-1-carboxylate (2 g, 6.13 mmol, 94% yield) as an off-white solid. LCMS m/z (ESI): 225.2 $[M+H-100]^+$.

Step 3: To a stirred solution of tert-butyl 4-(4-amino-2-fluoro-5-methoxy-phenyl)piperidine-1-carboxylate (337.89 mg, 1.04 mmol) in N,N-Dimethylformamide (10 mL) was added sodium bicarbonate (262.51 mg, 3.12 mmol, 121.53 μL) followed by 3-bromopiperidine-2,6-dione (0.5 g, 2.60 mmol) and reaction was heated to 60° C. for 14 h. The reaction mixture was diluted with water (20 mL) and extracted with ethyl acetate (3×30 mL). The organic layer was washed with brine solution (30 mL), dried over sodium sulfate and concentrated under reduced pressure to afford crude. Desired product was purified from crude by silica gel flash column chromatography eluting with 50-70% ethyl acetate in petroleum ether as eluent to afford tert-butyl 4-[4-[(2,6-dioxo-3-piperidyl)amino]-2-fluoro-5-methoxy-phenyl]piperidine-1-carboxylate (0.4 g, 889.02 μmol, 85% yield) as a light green viscous compound. LCMS m/z (ESI): 380.2 $[M+H-56]^+$.

Step 4: To a stirred solution of tert-butyl 4-[4-[(2,6-dioxo-3-piperidyl)amino]-2-fluoro-3-methoxy-phenyl]piperidine-1-carboxylate (0.225 g, 516.66 μmol) in dioxane (2 mL), was added 4M hydrogen chloride solution in 1,4-dioxane (4M, 2 mL) at 5° C. under nitrogen atmosphere. The reaction mixture was stirred at room temperature for 2 h. After completion, the reaction mixture was concentrated under reduced pressure to afford crude 3-[3-fluoro-2-methoxy-4-(4-piperidyl)anilino]piperidine-2,6-dione (0.17 g, 413.94 μmol, 80% yield) as an off-white solid. LCMS m/z (ESI): 336.2 $[M-H]^-$.

Step 5: To a stirred solution of 3-[5-fluoro-2-methoxy-4-(4-piperidyl)anilino]piperidine-2,6-dione (0.30 g, 894.53

μmol) in N,N-dimethylformamide (3 mL) were added Triethylamine (362.07 mg, 3.58 mmol, 498.72 μL) followed by tert-butyl 2-bromoacetate (174.48 mg, 894.53 μmol, 131.19 μL) at room temperature under nitrogen atmosphere. The reaction mixture was stirred at room temperature for 12 h. The reaction mixture was diluted with water (10 mL) and extracted with ethyl acetate (3×20 mL). The organic layer was washed with brine solution (20 mL), dried over sodium sulfate. Then the solution was concentrated under reduced pressure to afford tert-butyl 2-[4-[4-[(2,6-dioxo-3-piperidyl) amino]-2-fluoro-5-methoxy-phenyl]-1-piperidyl]acetate (0.20 g, 442.96 μmol, 50% yield). LCMS m/z (ESI): 450.2 $[M+H]^+$.

Step 6: To a stirred solution of tert-butyl 2-[4-[4-[(2,6-dioxo-3-piperidyl)amino]-2-fluoro-5-methoxy-phenyl]-1-piperidyl]acetate (0.14 g, 311.45 μmol) in dichloromethane (2 mL) was added 4M hydrogen chloride solution in dioxane (4M, 1.5 mL) at 5° C. under nitrogen atmosphere. The reaction mixture was stirred at room temperature for 16 h. After completion, the reaction mixture was concentrated under reduced pressure to afford crude, which was washed with methyl tert-butyl ether (50 mL) to afford 2-[4-[4-[(2,6-dioxo-3-piperidyl)amino]-2-fluoro-5-methoxy-phenyl]-1-piperidyl]acetic acid (0.130 g, 296.02 μmol, 95% yield) a brown solid. LCMS m/z (ESI): 394.0 $[M+H]^+$.

Step 7: Target compound was prepared via HATU mediated acid-amine coupling reaction (Procedure A-E). Amide coupling was carried out using 2-[4-[4-[(2,6-dioxo-3-piperidyl)amino]-2-fluoro-5-methoxy-phenyl]-1-piperidyl]acetic acid (70.68 mg, 179.66 μmol), N,N-diisopropylethylamine (92.88 mg, 718.64 μmol, 125.17 μL), HATU (68.31 mg, 179.66 μmol) and (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (0.1 g, 179.66 μmol) was added. The desired product was purified from crude by reverse phase column chromatography (0.1% formic acid in water:acetonitrile) and fractions were lyophilized to afford (3R)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-5-methoxy-phenyl]-1-piperidyl]acetyl]-1-oxa-8-azaspiro[4.5]decane (21.34 mg, 21.21 μmol, 12% yield) as an off-white solid. LCMS m/z (ESI): 932.0 $[M+H]^+$. $^1$HNMR (400 MHz, DMSO-$d_6$): δ=10.85 (s, 1H), 10.20 (s, 1H), 9.50 (s, 1H), 8.36 (d, J=1.60 Hz, 1H), 7.78-7.85 (m, 1H), 7.80 (d, J=8.80 Hz, 1H), 7.70 (dd, J=2.80, 8.80 Hz, 1H), 7.42-7.51 (m, 1H), 7.38 (d, J=2.80 Hz, 1H), 6.66 (d, J=6.80 Hz, 1H), 6.52 (d, J=13.20 Hz, 1H), 5.29-5.40 (m, 2H), 4.10-4.40 (m, 4H), 3.82 (s, 3H), 3.75-3.81 (m, 1H), 3.25-3.60 (m, 5H), 3.11-3.21 (m, 2H), 2.91-3.10 (m, 2H), 2.70-2.81 (m, 1H), 2.77 (s, 3H), 2.45-2.61 (m, 4H), 1.92-2.21 (m, 4H), 1.51-1.90 (m, 6H), 1.06 (t, J=7.20 Hz, 3H).

Example 76

(3R)-3-[6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]azepan-1-yl]acetyl]-1-oxa-8-azaspiro[4.5]decane

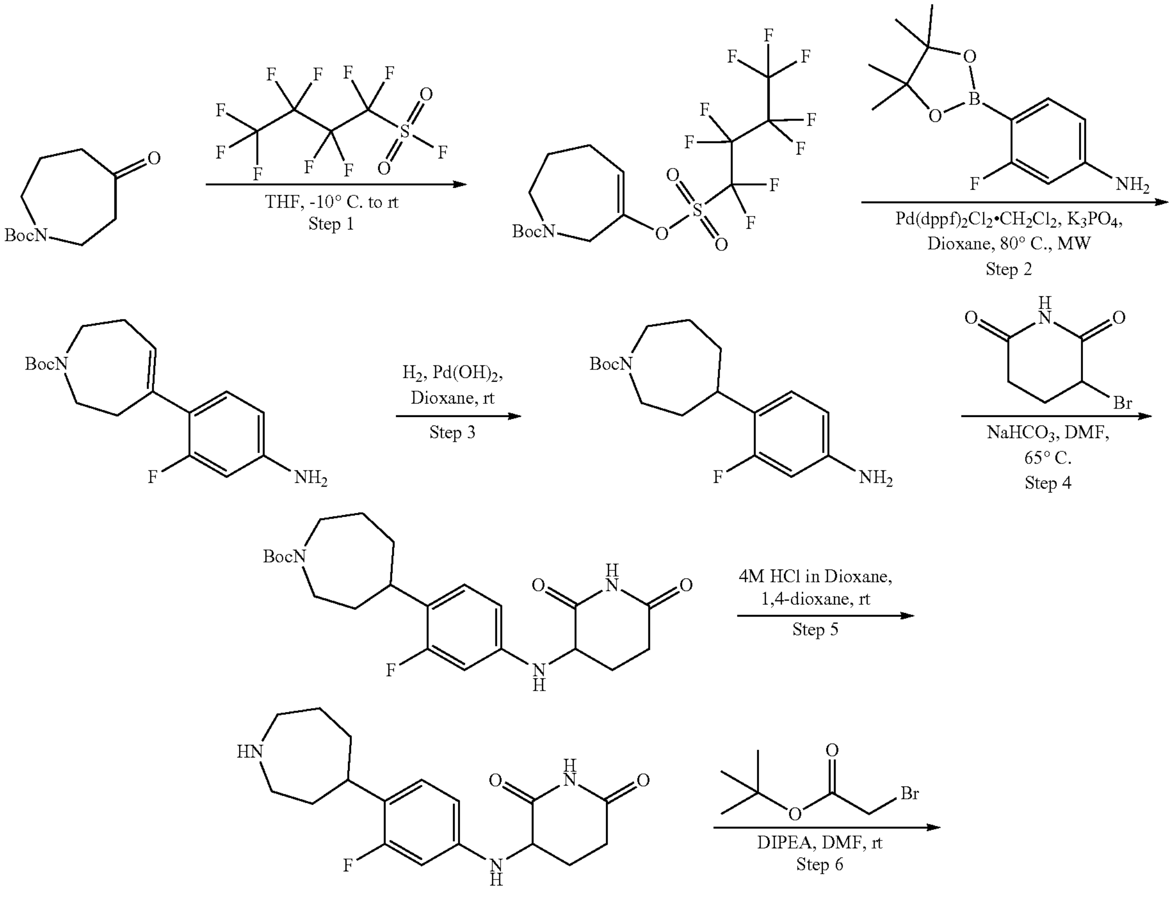

-continued

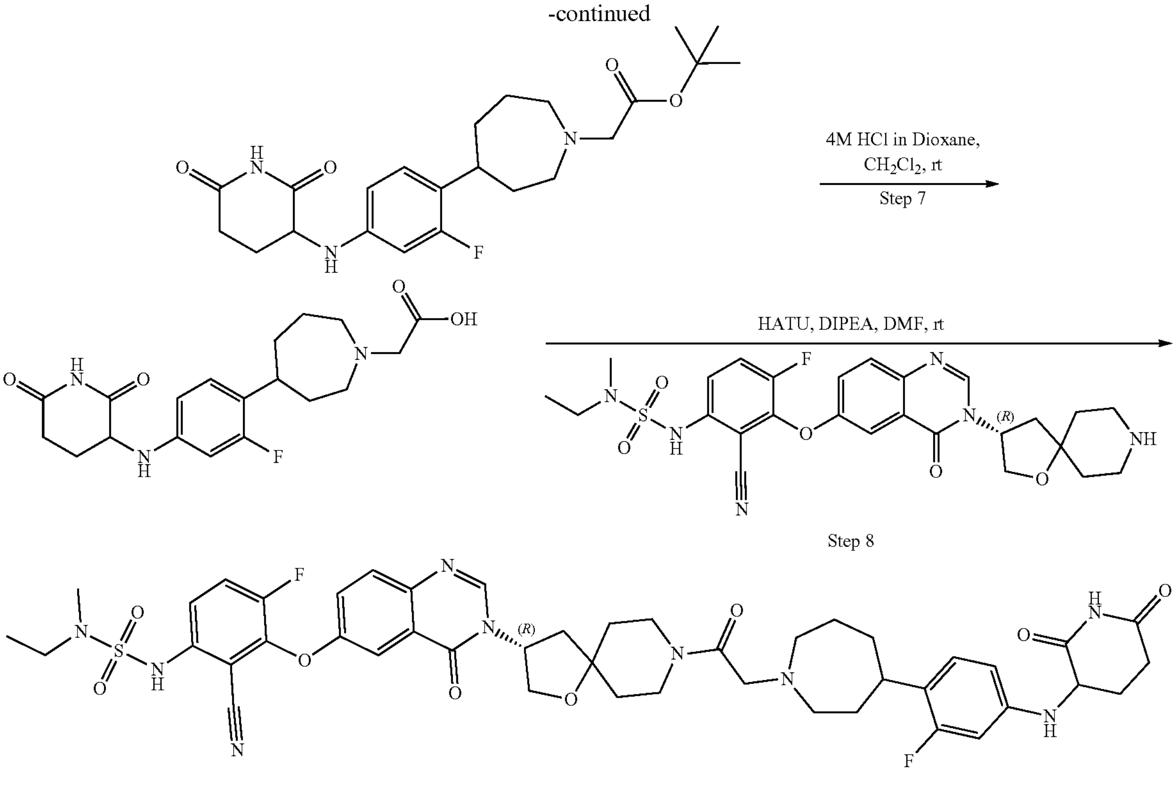

Step 1: To a solution of tert-butyl 4-oxoazepane-1-carboxylate (3 g, 14.07 mmol) in tetrahydrofuran (30 mL) was added 1,8-diazabicyclo[5.4.0]undec-7-ene (6.42 g, 42.20 mmol, 6.30 mL) followed by the addition of nonafluorobutanesulfonyl fluoride (10.62 g, 35.17 mmol, 6.07 mL) at −10° C. The reaction mixture was stirred at room temperature for 5 h. After completion of the reaction the reaction mixture was diluted with water (50 mL) and extracted with ethyl acetate (2×100 mL). The combined organic layers were dried over sodium sulfate, filtered, and concentrated under reduced to afford the crude. The crude compound was purified by silica gel flash column chromatography with 15-20% ethyl acetate in petroleum ether as eluent to afford tert-butyl 4-(1,1,2,2,3,3,4,4,4-nonafluorobutylsulfonyloxy)-2,3,6,7-tetrahydroazepine-1-carboxylate (3.8 g, 7.66 mmol, 54% yield) as a pale oil. LCMS m/z (ESI): 396.0 $[M-CO_2{}^tBu+H]^+$ Step 2: To a stirred solution of tert-butyl 4-(1,1,2,2,3,3,4,4,4-nonafluorobutylsulfonyloxy)-2,3,6,7-tetrahydroazepine-1-carboxylate (1.5 g, 3.03 mmol) and 3-fluoro-4-(4,4,5,5-tetramethyl-1,3,2-dioxaborolan-2-yl)aniline (789.69 mg, 3.33 mmol) in 1,4-dioxane (10 mL) and water (2 mL) was added potassium phosphate tribasic anhydrous (1.93 g, 9.08 mmol) at room temperature under nitrogen atmosphere. The reaction mixture was purged with nitrogen for 15 min followed by the addition of $Pd(dppf)Cl_2{\cdot}CH_2Cl_2$ (247.29 mg, 302.81 μmol). The reaction mixture was stirred at 80° C. for 2 h in microwave. After completion of the reaction, the reaction mixture was cooled to room temperature, filtered through celite and celite bed was washed with ethyl acetate (2×50 mL). The combined filtrate was concentrated under reduced pressure to afford crude. The crude compound was purified by silica gel flash column chromatography with 65-70% ethyl acetate in petroleum ether as eluent to afford tert-butyl 4-(4-amino-2-fluoro-phenyl)-2,3,6,7-tetrahydroazepine-1-carboxylate (610 mg, 1.92 mmol, 63% yield) as a colorless liquid. LCMS m/z (ESI): 207.20 $[M-CO_2{}^tBu+H]^+$ Step 3: To a stirred solution of tert-butyl 4-(4-amino-2-fluoro-phenyl)-2,3,6,7-tetrahydroazepine-1-carboxylate (610 mg, 1.99 mmol) in 1,4-dioxane (7 mL) was added palladium hydroxide on carbon (419.41 mg, 2.99 mmol) under nitrogen atmosphere at room temperature. The reaction mixture stirred under $H_2$ pressure for 12 h. After completion of the reaction, the catalyst was removed by filtration through celite bed. The celite bed was washed with ethyl acetate (3×30 mL) and filtrate was concentrated under reduced pressure to afford tert-butyl 4-(4-amino-2-fluoro-phenyl)azepane-1-carboxylate (560 mg, 1.78 mmol, 89% yield) as a colorless liquid. LCMS m/z (ESI): 209.20 $[M-CO_2{}^tBu+H]^+$ Step 4: To a stirred solution of tert-butyl 4-(4-amino-2-fluoro-phenyl)azepane-1-carboxylate (560 mg, 1.82 mmol) in N,N-dimethylformamide (6 mL) was added sodium bicarbonate (610.18 mg, 7.26 mmol, 282.49 μL) and 3-bromopiperidine-2,6-dione (1.05 g, 5.45 mmol) at room temperature The resulting reaction mixture was stirred for 12 h at 70° C. After completion, the reaction mixture was diluted with water (20 mL) and extracted with ethyl acetate (2×25 mL). The combined organic layers were dried over sodium sulfate, filtered and concentrated under reduced pressure to afford crude. The crude compound was purified by silica gel flash column chromatography with 60-65% ethyl acetate in petroleum ether as a eluent to afford tert-butyl 4-[4-[(2,6-dioxo-3-piperidyl)amino]-2-fluoro-phenyl]azepane-1-carboxylate (380 mg, 878.69 μmol, 48% yield) as an an off-white solid. LCMS m/z (ESI): 418.30 $[M-H]^-$ Step 5: To a stirred solution of tert-butyl 4-[4-[(2,6-dioxo-3-piperidyl)amino]-2-fluoro-phenyl]azepane-1-carboxylate (380 mg, 905.86 μmol) in 1,4-dioxane (4 mL) was added hydrogen chloride solution 4.0M in dioxane (3 mL) at 5° C. under nitrogen atmosphere. The reaction mixture was stirred at room temperature for 6 h. After completion of the reaction, the reaction mixture was concentrated under reduced pressure to afford crude 3-[4-(azepan-4-yl)-3-fluoro-anilino]piperidine-2,6-dione (310 mg, 848.54 μmol, 94% yield) as a yellow solid. LCMS m/z (ESI): 320.20 $[M+H]^+$ Step 6: To a stirred solution of 3-[4-(azepan-4-yl)-3-fluoro-anilino]piperidine-2,6-dione (310 mg, 871.19 μmol) in N,N-dimethylformamide (3 mL) were added N,N-diisopropylethylamine (440.78 mg, 4.36 mmol, 607.13 μL) and tert-butyl bromoacetate (169.93 mg, 871.19 μmol, 127.77 μL) at room temperature under nitrogen atmosphere. The reaction mixture was stirred at room temperature for 12 h. After completion, the reaction mixture was diluted with water (10 mL) and extracted with ethyl acetate (3×10 mL). The organic layer was washed with brine solution (30 mL), dried over sodium sulfate, filtered, and concentrated under reduced pressure to afford crude. The crude compound was purified by reverse phase column chromatography eluted with 50% acetonitrile in 0.1% ammonium acetate in water to afford product tert-butyl 2-[4-[4-[(2,6-dioxo-3-piperidyl)amino]-2-fluoro-phenyl]azepan-1-yl]acetate (216 mg, 496.71 μmol, 57% yield) as an off-white solid. LCMS m/z (ESI): 434.20 $[M+H]^+$ Step 7: To a stirred solution of tert-butyl 2-[4-[4-[(2,6-dioxo-3-piperidyl)amino]-2-fluoro-phenyl]azepan-1-yl]acetate (210 mg, 484.41 μmol) in dichloromethane (5 mL) was added and hydrogen chloride solution 4.0 M in 1,4-dioxane (2 mL). The content was stirred at rt for 6 h. After completion, the resulted crude compound was dried under reduced pressure, triturated with methyl t-butyl ether to afford 2-[4-[4-[(2,6-dioxo-3-piperidyl)amino]-2-fluoro-phenyl]azepan-1-yl]acetic acid (170 mg, 406.65 μmol, 84% yield) as a yellow solid. LCMS m/z (ESI): 378.20 $[M+H]^+$ Step 8: Target compound was prepared via HATU mediated acid-amine coupling reaction (Procedure A-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (90 mg, 151.75 μmol), 2-[4-[4-[(2,6-dioxo-3-piperidyl)amino]-2-fluoro-phenyl]azepan-1-yl]acetic acid (69.09 mg, 166.93 μmol), N,N-diisopropylethylamine (98.07 mg, 758.77 μmol, 132.16 μL) and HATU (69.24 mg, 182.10 μmol). The crude compound was purified by reverse phase column chromatography eluted with 55% acetonitrile in 0.1% ammonium acetate in water to afford product (3R)-3-[6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]azepan-1-yl]acetyl]-1-oxa-8-azaspiro[4.5]decane (9.5 mg, 10.14 μmol, 7% yield) as an off-white solid. LCMS m/z (ESI): 916.30 $[M+H]^+$; $^1$HNMR (400 MHz, DMSO-$d_6$): δ=10.80 (s, 1H), 8.33 (s, 1H), 7.76 (d, J=8.80 Hz, 1H), 7.64 (dd, J=2.80, 9.00 Hz, 1H), 7.39-7.29 (m, 3H), 6.99 (t, J=8.40 Hz, 1H), 6.54-6.42 (m, 2H), 6.02 (d, J=7.60 Hz, 1H), 5.32-5.31 (m, 1H), 4.35-4.25 (m, 1H), 4.22-4.10 (m, 2H), 3.80-3.68 (m, 1H), 3.60-3.40 (m, 2H), 3.05-2.85 (m, 6H), 2.80-2.70 (m, 2H), 2.59 (s, 3H), 2.55-2.53 (m, 1H), 2.45-2.35 (m, 2H), 2.15-2.05 (m, 3H), 1.95-1.50 (m, 12H), 1.03 (t, J=7.20 Hz, 3H).

Example 77

(3R)-3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

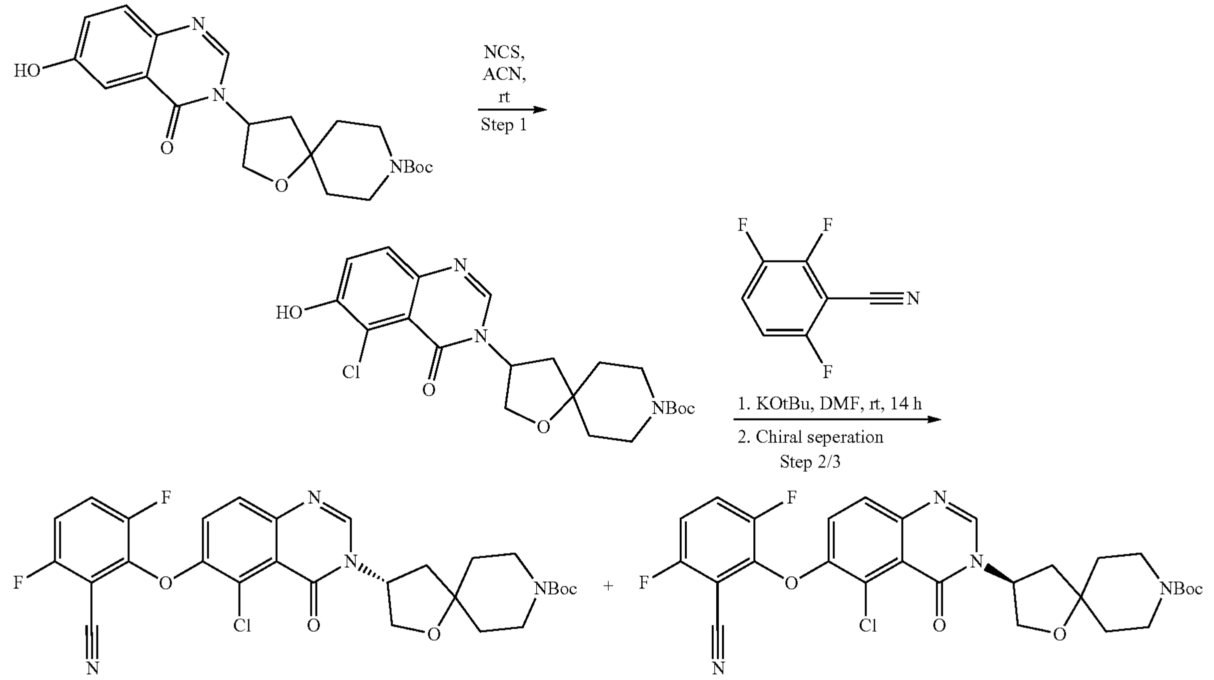

-continued

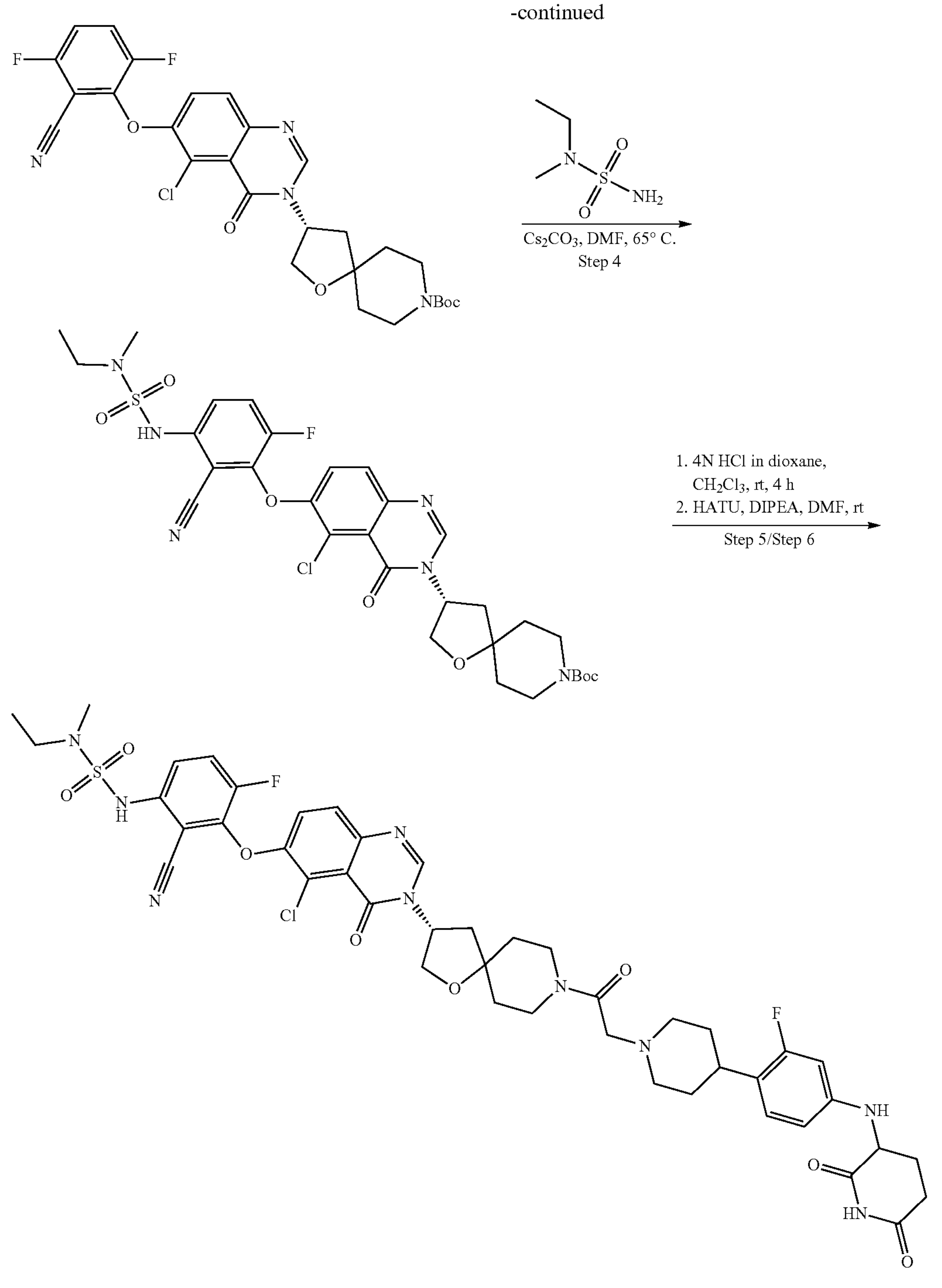

Step 1: To a stirred solution of tert-butyl 3-(6-hydroxy-4-oxo-quinazolin-3-yl)-1-oxa-8-azaspiro[4.5]decane-8-carboxylate (1 g, 2.49 mmol) in acetonitrile (10 mL) was added 1-chloropyrrolidine-2,5-dione (399.15 mg, 2.99 mmol, 241.91 μL) at room temperature under nitrogen atmosphere. The reaction mixture was stirred at room temperature for 14 h. The reaction mixture was diluted with water (10 mL) and extracted with ethyl acetate (40 mL). The organic layer was dried over sodium sulfate, filtered and concentrated under reduced to afford crude tert-butyl 3-(5-chloro-6-hydroxy-4-oxo-quinazolin-3-yl)-1-oxa-8-azaspiro[4.5]decane-8-carboxylate (1.2 g, 2.16 mmol, 87% yield) as a brown solid. LCMS m/z (ESI): 380.2 $[M+H-^{t}Bu]^{+}$.

Step 2: O-arylated quinazolinone intermediate was synthesized by following general procedure for O-arylation (Procedure A-B) using tert-butyl 3-(5-chloro-6-hydroxy-4-oxo-quinazolin-3-yl)-1-oxa-8-azaspiro[4.5]decane-8-carboxylate (1.2 g, 2.15 mmol), cesium carbonate (2.10 g, 6.44 mmol) and 2,3,6-trifluorobenzonitrile (505.98 mg, 3.22 mmol, 372.05 μL) a to afford tert-butyl 3-[5-chloro-6-(2-cyano-3,6-difluoro-phenoxy)-4-oxo-quinazolin-3-yl]-1-oxa-8-azaspiro[4.5]decane-8-carboxylate (140 mg, 239.45 μmol, 11% yield) as an off-white solid. LCMS m/z (ESI): 517.0 [M+H−$^t$Bu]$^+$.

Step 3: Tert-butyl 3-[5-chloro-6-(2-cyano-3,6-difluoro-phenoxy)-4-oxo-quinazolin-3-yl]-1-oxa-8-azaspiro[4.5]decane-8-carboxylate (250 mg, 239.45 μmol, 11.15% yield) was separated by SFC chiral separation using YMC Cellulose-SC column. After the chiral purification the two isomers are reduced under vacuum pressure to afford tert-butyl (3R)-3-[5-chloro-6-(2-cyano-3,6-difluoro-phenoxy)-4-oxo-quinazolin-3-yl]-1-oxa-8-azaspiro[4.5]decane-8-carboxylate (100.00 mg, 174.52 μmol) 71.82% yield) and tert-butyl (3S)-3-[5-chloro-6-(2-cyano-3,6-difluoro-phenoxy)-4-oxo-quinazolin-3-yl]-1-oxa-8-azaspiro[4.5]decane-8-carboxylate (80.00 mg, 139.62 μmol 28% yield).

Note: Chirally pure compounds have checked with the reference column (Lux A1). First eluting peak from the Lux A1 column was arbitrarily assigned as S-isomer and second eluting peak was arbitrarily assigned as R-isomer.

Step 4: Sulfamoylated quinazolinone intermediate was synthesized by following Procedure A-C using tert-butyl (3R)-3-[5-chloro-6-(2-cyano-3,6-difluoro-phenoxy)-4-oxo-quinazolin-3-yl]-1-oxa-8-azaspiro[4.5]decane-8-carboxylate (100.00 mg, 174.52 μmol), cesium carbonate (227.45 mg, 698.10 μmol) and [methyl(sulfamoyl)amino]ethane (72.35 mg, 523.57 μmol) to afford tert-butyl (3R)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (135 mg, 173.84 μmol, 100% yield) as a light yellow solid. LCMS m/z (ESI): 635.7 [M+H−$^t$Bu]$^+$.

Step 5: The requisite amine was synthesized by HCl mediated N-Boc deprotection (Procedure A-D). N-Boc deprotection was done on tert-butyl (3R)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (135 mg, 195.32 μmol) using 4M hydrogen chloride solution in dioxane (4M, 5 mL) to afford crude 3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane (140 mg, 178.48 μmol, 91% yield) as an off-white solid. LCMS m/z (ESI): 591.7 [M+H]$^+$.

Step 6: Target compound was prepared via HATU mediated acid-amine coupling reaction (Procedure A-E). Amide coupling was carried out using (3R)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane (140 mg, 236.87 μmol) 2-[4-[4-[(2,6-dioxo-3-piperidyl)amino]-2-fluoro-phenyl]-1-piperidyl]acetic acid (86.07 mg, 236.87 μmol), N,N-diisopropylethylamine (153.07 mg, 1.18 mmol, 206.29 μL) and HATU (99.07 mg, 260.55 μmol) to afford (3R)-3-[5-chloro-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (27.35 mg, 27.69 μmol, 12% yield) as an off-white solid. LCMS m/z (ESI): 936.2 [M+H]$^+$; $^1$H-NMR (400 MHz, DMSO-$d_6$): δ 10.81 (s, 1H), 10.15 (s, 1H), 9.56 (s, 1H), 8.38 (s, 1H), 7.69 (s, 1H), 7.64 (d, J=9.20 Hz, 1H), 7.46 (d, J=8.80 Hz, 1H), 7.39 (d, J=5.60 Hz, 1H), 6.98 (s, 1H), 6.50 (d, J=6.80 Hz, 1H), 6.46 (s, 1H), 6.11 (d, J=8.00 Hz, 1H), 5.34 (m, 1H), 4.36-4.29 (m, 1H), 4.18-4.16 (m, 2H), 3.51-3.45 (m, 4H), 3.18-3.01 (m, 4H), 2.94-2.82 (m, 1H), 2.75 (s, 3H), 2.71 (m, 1H), 2.45-2.38 (m, 4H), 2.14-1.72 (m, 12H), 1.61-1.53 (m, 1H), 1.07 (t, J=3.60 Hz, 3H).

Example 78

(3S)-3-[5-chloro-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

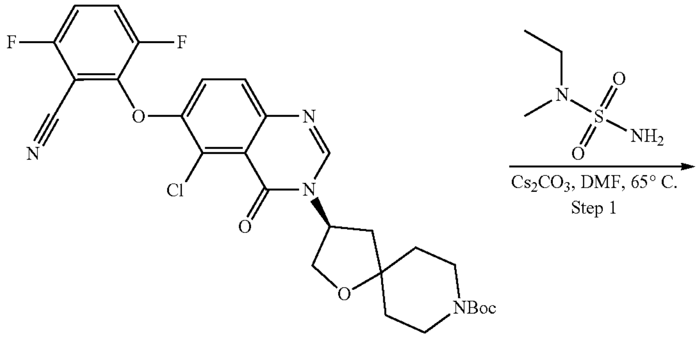

-continued

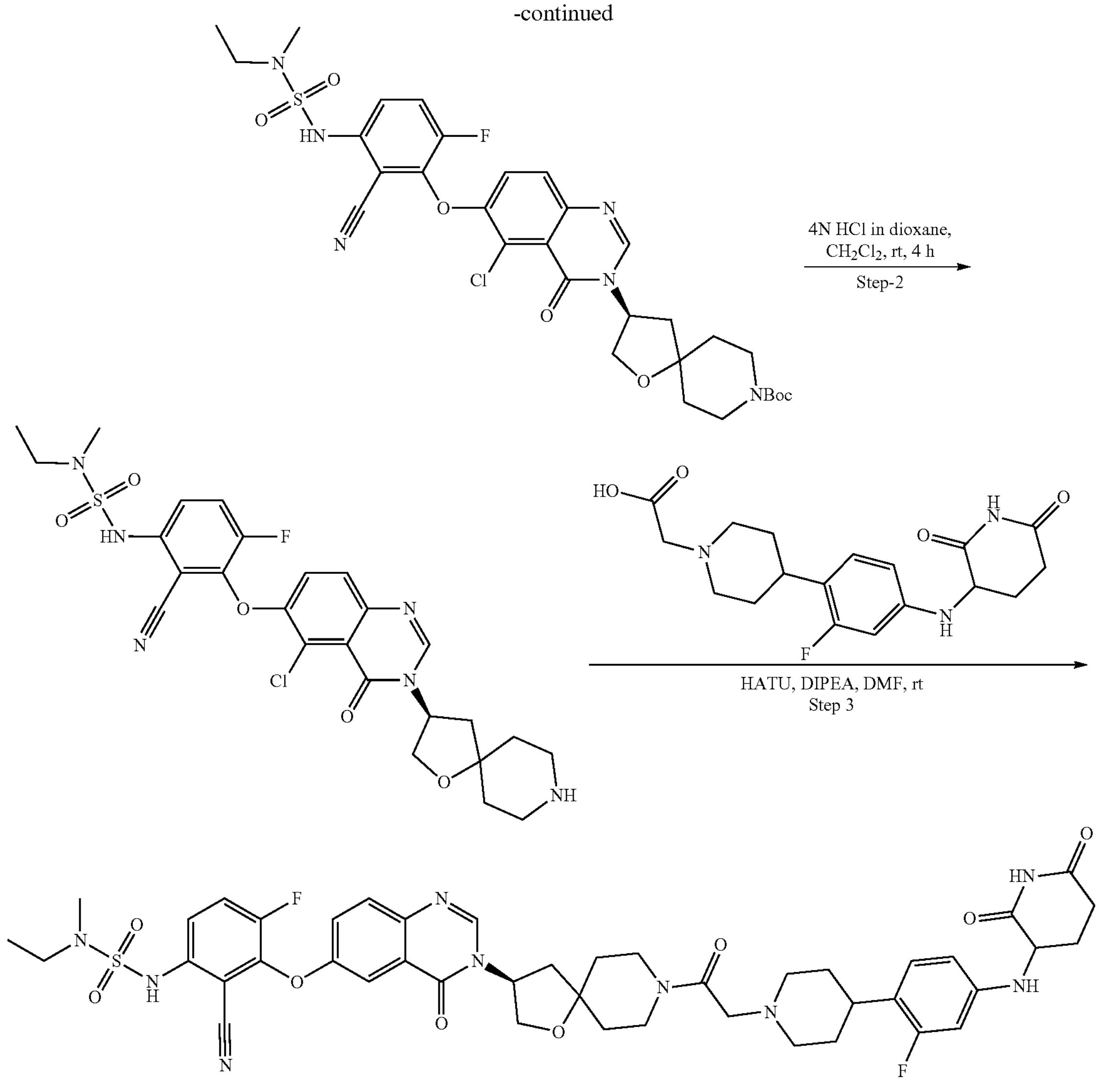

Step 1: Sulfamoylated quinazolinone intermediate was synthesized by following Procedure A-C using tert-butyl (3S)-3-[5-chloro-6-(2-cyano-3,6-difluoro-phenoxy)-4-oxo-quinazolin-3-yl]-1-oxa-8-azaspiro[4.5]decane-8-carboxylate (80.00 mg, 139.62 μmol), cesium carbonate (181.96 mg, 558.48 μmol) and [methyl(sulfamoyl)amino]ethane (57.88 mg, 418.86 μmol) to afford tert-butyl (3S)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (109 mg, 138.78 μmol, 99% yield) as a light yellow solid. LCMS m/z (ESI): 635.7 $[M+H-{}^{t}Bu]^{+}$.

Step 2: The requisite amine was synthesized by HCl mediated N-Boc deprotection (Procedure A-D). N-Boc deprotection was done on tert-butyl (3S)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (120 mg, 173.62 μmol) using 4M hydrogen chloride solution in dioxane (4 M, 43.40 μL) to afford (3S)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane (120 mg, 150.59 μmol, 87% yield) as an off-white solid. LCMS m/z (ESI): 591.7 $[M+H]^{+}$.

Step 3: Target compound was prepared via HATU mediated acid-amine coupling reaction (Procedure A-E). Amide coupling was carried out using (3S)-3-[5-chloro-6-[2-cyano-3-[[ethyl(methyl)sulfamoyl]amino]-6-fluoro-phenoxy]-4-oxo-quinazolin-3-yl]-1-oxa-8-azaspiro[4.5]decane (120 mg, 203.03 μmol), 2-[4-[4-[(2,6-dioxo-3-piperidyl)amino]-2-fluoro-phenyl]-1-piperidyl]acetic acid (73.78 mg, 203.03 μmol), N,N-diisopropylethylamine (26.24 mg, 203.03 μmol, 35.36 μL) and HATU (77.20 mg, 203.03 μmol) to afford (3S)-3-[5-chloro-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (19.28 mg, 19.37 μmol, 10% yield,) as an off-white solid. LCMS m/z (ESI): 936.0 $[M+H]^{+}$. $^{1}$HNMR (400 MHz, DMSO-$d_6$): δ 10.82 (s, 1H), 10.15 (s, 1H), 9.56 (s, 1H), 8.38 (s, 1H), 7.77 (s, 1H), 7.64 (d, J=8.80 Hz, 1H), 7.49 (d, J=9.20 Hz, 1H), 7.42 (dd, J=3.60, 9.00 Hz, 1H), 6.98 (s, 1H), 6.51-6.46 (m, 2H), 6.12 (d, J=8.00 Hz, 1H), 5.35-5.34 (m, 1H), 4.38-4.26 (m, 2H), 4.33-4.30 (m, 3H), 4.18-4.16 (m, 2H), 3.84-3.78 (m, 1H), 3.58-3.49 (m, 1H), 3.47-3.38 (m, 3H), 3.16 (q, J=6.80 Hz, 3H), 3.12-3.03 (m, 2H), 2.93-2.85 (m, 1H), 2.78 (s, 3H), 2.08-2.01 (m, 4H), 1.89-1.76 (m, 7H), 1.64-1.53 (m, 1H), 1.06 (t, J=7.20 Hz, 3H).

Example 79
5-chloro-6-[2-cyano-3-[[ethyl(methyl)sulfamoyl]amino]-6-fluorophenoxy]-3-[(3S)-8-[2-[4-[4-[(2,6-dioxopiperidin-3-yl)amino]-2-fluorophenyl]piperidin-1-yl]acetyl]-8-azaspiro [4.5]decan-3-yl]-4-oxoquinazoline
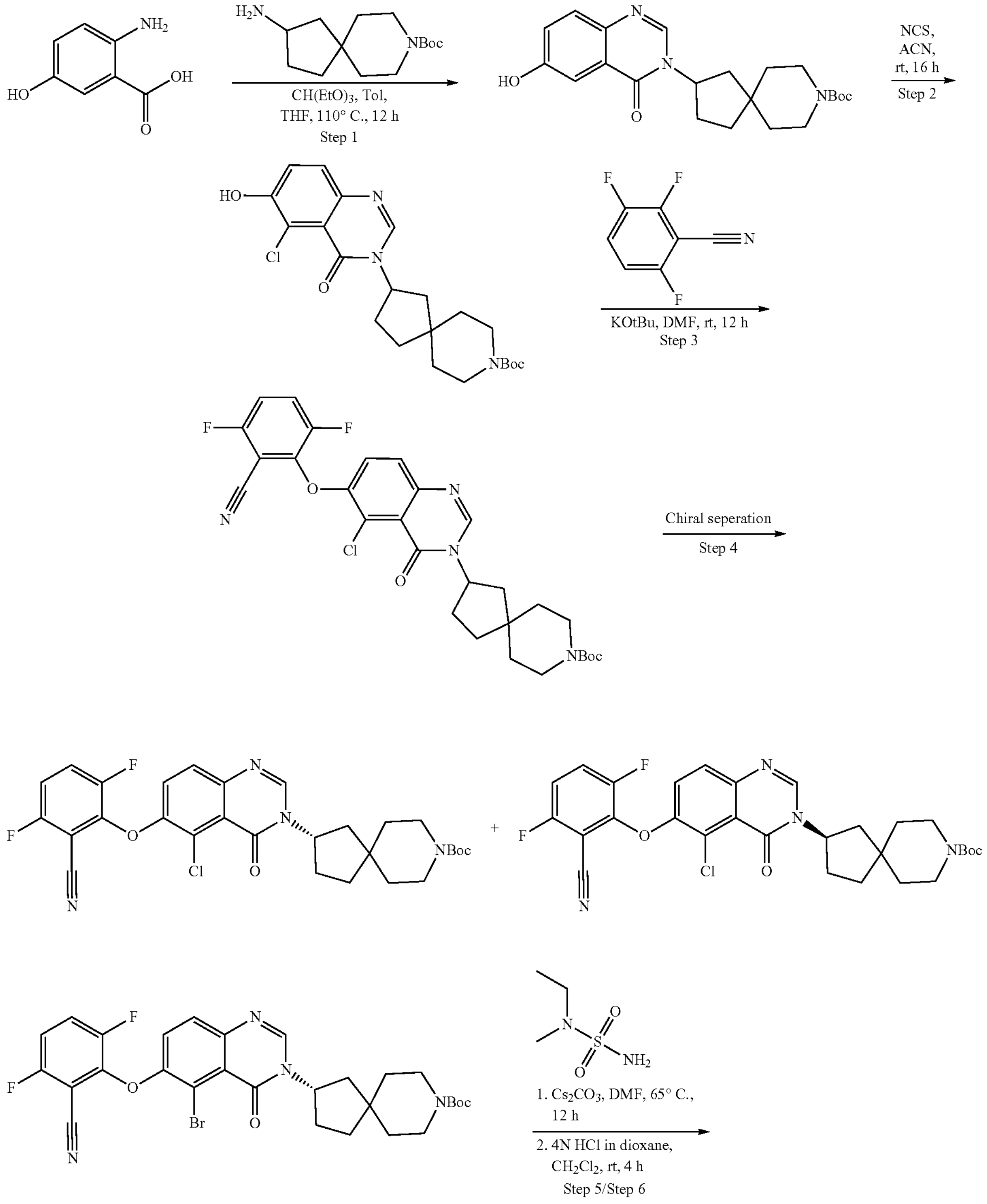

-continued

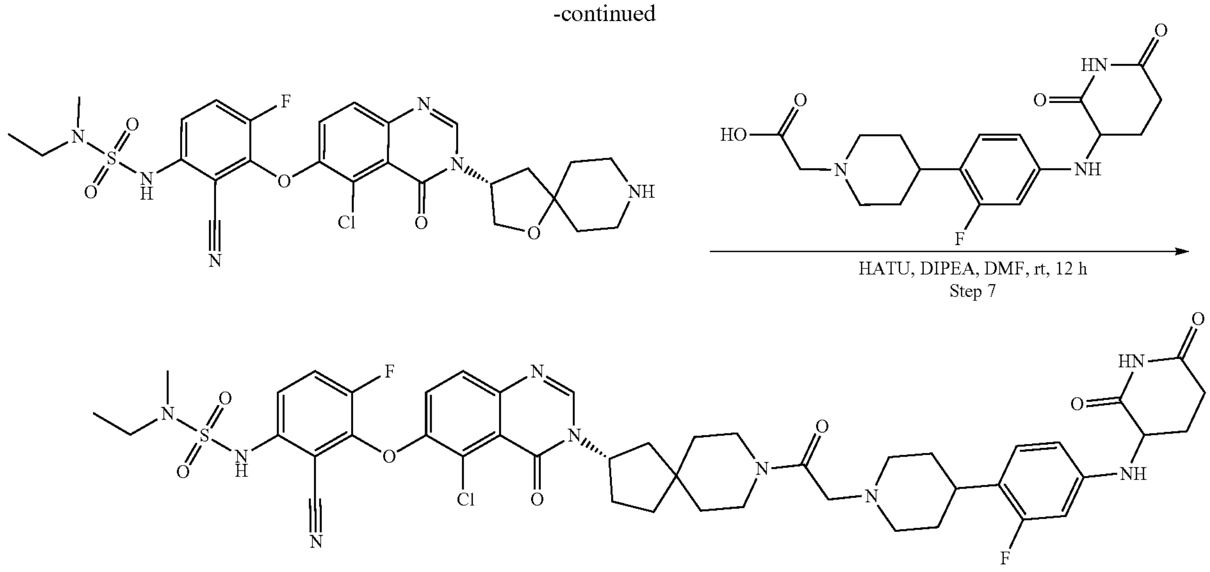

Step 1: To a stirred solution of 2-amino-5-hydroxy-benzoic acid (3.2 g, 20.90 mmol) in toluene (40 mL) and THF (10 mL) in sealed tube, were added diethoxy-methoxy ethane (4.65 g, 31.34 mmol, 5.21 mL), acetic acid (525.00 mg, 8.74 mmol, 0.5 mL) and tert-butyl 3-amino-8-azaspiro[4.5]decane-8-carboxylate (5.32 g, 20.90 mmol) at room temperature under nitrogen atmosphere. The reaction mixture was stirred at 110° C. for 12 h. After completion, the reaction mixture was diluted with water (70 mL) and extracted with ethyl acetate (3×100 mL). Combined organic layers washed with 10% sodium bicarbonate solution (3×30 mL), then washed with water (30 mL), dried over sodium sulfate, filtered and concentrated under reduced pressure to afford crude tert-butyl 3-(6-hydroxy-4-oxo-quinazolin-3-yl)-8-azaspiro[4.5]decane-8-carboxylate (4 g, 8.59 mmol, 41% yield) as a light brown solid. LCMS m/z (ESI): 400.2 $[M+H]^+$.

Step 2: To a Stirred solution of tert-butyl 3-(6-hydroxy-4-oxo-quinazolin-3-yl)-8-azaspiro[4.5]decane-8-carboxylate (2.2 g, 5.51 mmol) in acetonitrile (30 mL), was added N-chlorosuccinimide (1.47 g, 11.01 mmol, 891.37 µL) at room temperature under nitrogen atmosphere. The reaction mixture was stirred at room temperature for 16 h. After completion, the reaction mixture was diluted with water (30 mL) and extracted with ethyl acetate (3×50 mL). The combined organic layers were dried over sodium sulfate, filtered, and concentrated under vacuum to afford crude. Desired product was purified from crude by column chromatography by using 20-30% ethyl acetate in petroleum ether as eluent to afford tert-butyl 3-(5-chloro-6-hydroxy-4-oxo-quinazolin-3-yl)-8-azaspiro[4.5]decane-8-carboxylate (1.5 g, 2.06 mmol, 37% yield) as a brown viscous liquid. LCMS m/z (ESI): 378.2 $[M+H]^+$.

Step 3: O-arylated quinazolinone intermediate was synthesized by following general procedure for O-arylation (Procedure A-B) using tert-butyl 3-(5-chloro-6-hydroxy-4-oxo-quinazolin-3-yl)-8-azaspiro[4.5]decane-8-carboxylate (1.5 g, 3.46 mmol), cesium carbonate (3.38 g, 10.37 mmol) and 2,3,6-trifluorobenzonitrile (1.09 g, 6.91 mmol, 798.59 µL). Desired product was purified from crude by silica gel flash column chromatography using 80-90% ethyl acetate in pet ether as eluent to afford racemic product tert-butyl 3-[5-chloro-6-(2-cyano-3,6-difluoro-phenoxy)-4-oxo-quinazolin-3-yl]-8-azaspiro[4.5]decane-8-carboxylate (0.7 g 80.39% Pure). Racemic product (0.5 g, 80.39% pure) was purified by reverse phase column chromatography (10 mM ammonium acetate in water:acetonitrile) and fractions were concentrated to afford pure product. (0.28 g). LCMS m/z (ESI): 515.0 $[M+H-56]^+$.

Step 4: Racemic product (0.28 g) was purified by Chiral SFC purification to afford tert-butyl (3 S)-3-[5-chloro-6-(2-cyano-3,6-difluoro-phenoxy)-4-oxo-quinazolin-3-yl]-8-azaspiro[4.5]decane-8-carboxylate (0.13 g, 226.66 µmol, 6.56% yield) as an off-white solid and tert-butyl (3R)-3-[5-chloro-6-(2-cyano-3,6-difluoro-phenoxy)-4-oxo-quinazolin-3-yl]-8-azaspiro[4.5]decane-8-carboxylate (0.09 g, 157.61 µmol, 5% yield) as a light brown solid. LCMS m/z (ESI): 515.0 $[M+H-56]^+$.

Note: The absolute stereochemistry for the isomers was arbitrarily assigned as follows: first eluting peak as S-Isomer and second eluting peak as R-Isomer.

Step 5: Sulfamoylated quinazolinone intermediate was synthesized by following Procedure A-C using tert-butyl (3S)-3-[5-chloro-6-(2-cyano-3,6-difluoro-phenoxy)-4-oxo-quinazolin-3-yl]-8-azaspiro[4.5]decane-8-carboxylate (0.13 g, 227.67 µmol), cesium carbonate (222.53 mg, 683.00 µmol) and [methyl(sulfamoyl)amino]ethane (62.92 mg, 455.33 µmol) to afford crude tert-butyl (3S)-3-[5-chloro-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (0.12 g, 165.22 µmol, 73% yield) as a colorless viscous liquid. LCMS m/z (ESI): 687.0 $[M-H]^-$.

Step 6: The requisite amine was synthesized by TFA mediated N-Boc deprotection (Procedure A-D). N-Boc deprotection was done on tert-butyl tert-butyl (3S)-3-[5-chloro-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (120.00 mg, 174.12 µmol) using 4M hydrogen chloride solution in dioxane (4 M, 1.2 mL) to afford crude 33-[(3S)-8-azaspiro[4.5]decan-3-yl]-5-chloro-6-[2-cyano-3-[[ethyl(methyl)sulfamoyl]amino]-6-fluoro-phenoxy]-4-oxo-quinazoline (0.1 g, 145.28 µmol, 83% yield) as a light brown solid. LCMS m/z (ESI): 589.2 $[M+H]^+$.

Step 7: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (70.31 mg, 175.85 μmol), N,N-diisopropylethylamine (206.61 mg, 1.60 mmol, 278.45 μL), HATU (66.86 mg, 175.85 μmol) and 3-[(3S)-8-azaspiro[4.5]decan-3-yl]-5-chloro-6-[2-cyano-3-[[ethyl(methyl)sulfamoyl]amino]-6-fluoro-phenoxy]-4-oxo-quinazoline (0.1 g, 159.86 μmol). The desired product was purified from crude by reverse phase column chromatography (10 mM ammonium acetate in water:acetonitrile) and fractions were lyophilized to afford 5-chloro-6-[2-cyano-3-[[ethyl(methyl)sulfamoyl]amino]-6-fluoro-phenoxy]-3-[(3S)-8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (59 mg, 62.92 μmol, 39% yield) as an off-white solid. LCMS m/z (ESI): 934.0 $[M+H]^+$; $^1$HNMR (400 MHz, DMSO-$d_6$): δ 10.80 (s, 1H), 8.47 (d, J=-2.40 Hz, 1H), 7.62 (d, J=9.20 Hz, 1H), 7.35 (d, J=9.60 Hz, 1H), 7.28 (d, J=5.60 Hz, 1H), 6.47 (t, J=12.80 Hz, 2H), 6.07 (d, J=7.20 Hz, 1H), 5.09 (q, J=52.00 Hz, 1H), 4.36-4.28 (m, 1H), 3.65-3.55 (m, 1H), 3.05 (q, J=36.00 Hz, 2H), 2.78-2.69 (m, 1H), 2.62 (s, 3H), 2.20-2.03 (m, 5H), 1.95-1.70 (m, 8H), 1.70-1.55 (m, 4H), 1.55-1.45 (m, 1H), 1.04 (t, J=7.20 Hz, 3H).

Example 80

5-chloro-6-[2-cyano-3-[[ethyl(methyl)sulfamoyl]amino]-6-fluorophenoxy]-3-[(3R)-8-[2-[4-[4-[(2,6-dioxopiperidin-3-yl)amino]-2-fluorophenyl]piperidin-1-yl]acetyl]-8-azaspiro [4.5]decan-3-yl]-4-oxoquinazoline

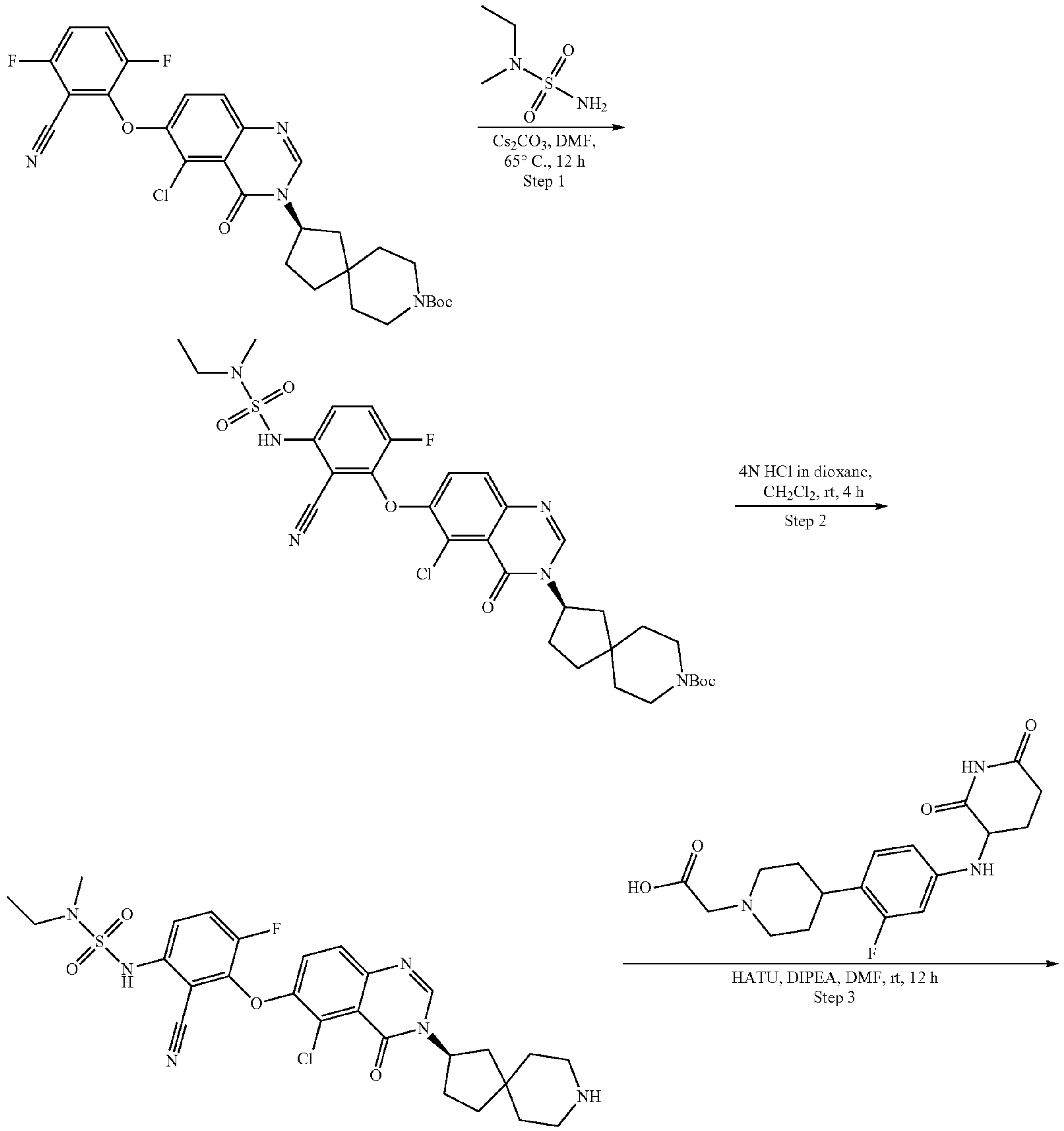

-continued

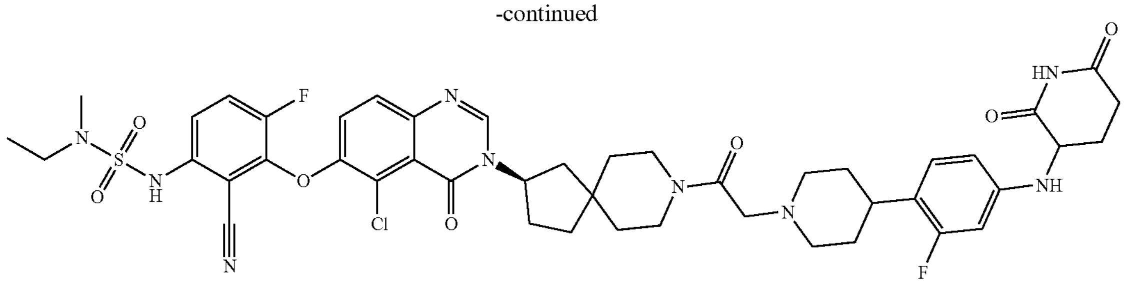

Step 1: Sulfamoylated quinazolinone intermediate was synthesized by following Procedure A-C using tert-butyl (3R)-3-[5-chloro-6-(2-cyano-3,6-difluoro-phenoxy)-4-oxo-quinazolin-3-yl]-8-azaspiro[4.5]decane-8-carboxylate (0.09 g, 157.61 μmol), cesium carbonate (154.06 mg, 472.84 μmol) and [methyl(sulfamoyl)amino]ethane (43.56 mg, 315.23 μmol) to afford crude tert-butyl (3R)-3-[5-chloro-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (0.08 g, 105.94 μmol, 67% yield). LCMS m/z (ESI): 687.0 $[M-H]^-$.

Step 2: The requisite amine was synthesized by HCl mediated N-Boc deprotection (Procedure A-D). N-Boc deprotection was done on tert-butyl (3R)-3-[5-chloro-6-[2-cyano-3-[[ethyl(methyl)sulfamoyl]amino]-6-fluoro-phenoxy]-4-oxo-quinazolin-3-yl]-8-azaspiro[4.5]decane-8-carboxylate (0.09 g, 130.59 μmol) using 4M hydrogen chloride solution in dioxane (4 M, 1.2 mL) to afford crude 3-[(3R)-8-azaspiro[4.5]decan-3-yl]-5-chloro-6-[2-cyano-3-[[ethyl(methyl)sulfamoyl]amino]-6-fluoro-phenoxy]-4-oxo-quinazoline (0.08 g, 119.45 μmol, 91% yield) as a light brown solid. LCMS m/z (ESI): 589.0 $[M+H]^+$.

Step 3: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (56.25 mg, 140.68 μmol), N,N-diisopropylethylamine (165.28 mg, 1.28 mmol, 222.75 μL), HATU (53.49 mg, 140.68 μmol) and 3-[(3R)-8-azaspiro[4.5]decan-3-yl]-5-chloro-6-[2-cyano-3-[[ethyl(methyl)sulfamoyl]amino]-6-fluoro-phenoxy]-4-oxo-quinazoline (0.08 g, 127.89 μmol). The desired product was purified from crude by reverse phase column chromatography (10 mM ammonium acetate in water:acetonitrile) and fractions were lyophilized to afford 5-chloro-6-[2-cyano-3-[[ethyl(methyl)sulfamoyl]amino]-6-fluoro-phenoxy]-3-[(3R)-8-[2-[4-[4-[(2,6-dioxo-3-piperidyl)amino]-2-fluoro-phenyl]-1-piperidyl]acetyl]-8-azaspiro[4.5]decan-3-yl]-4-oxo-quinazoline (36 mg, 37.99 μmol, 30% yield) as an off-white solid. LCMS m/z (ESI): 934.0 $[M+H]^+$; $^1$HNMR (400 MHz, DMSO-$d_6$): δ 10.81 (s, 1H), 8.47 (d, J=2.40 Hz, 1H), 7.61 (d, J=9.20 Hz, 1H), 7.34 (dd, J=20.00, 32.80 Hz, 2H), 7.02-6.92 (m, 1H), 6.47 (t, J=13.20 Hz, 2H), 6.07 (d, J=7.20 Hz, 1H), 5.11 (q, J=48.00 Hz, 1H), 4.38-4.28 (m, 1H), 3.65-3.40 (m, 8H), 3.02 (d, J=7.20 Hz, 2H), 2.78-2.69 (m, 1H), 2.61 (s, 3H), 2.19-2.07 (m, 5H), 1.95-1.72 (m, 8H), 1.69-1.43 (m, 5H), 1.55-1.45 (m, 1H), 1.04 (t, J=7.20 Hz, 3H).

Example 81

3-[5-amino-6-[2-cyano-3-[[ethyl(methyl)sulfamoyl]amino]-6-fluorophenoxy]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

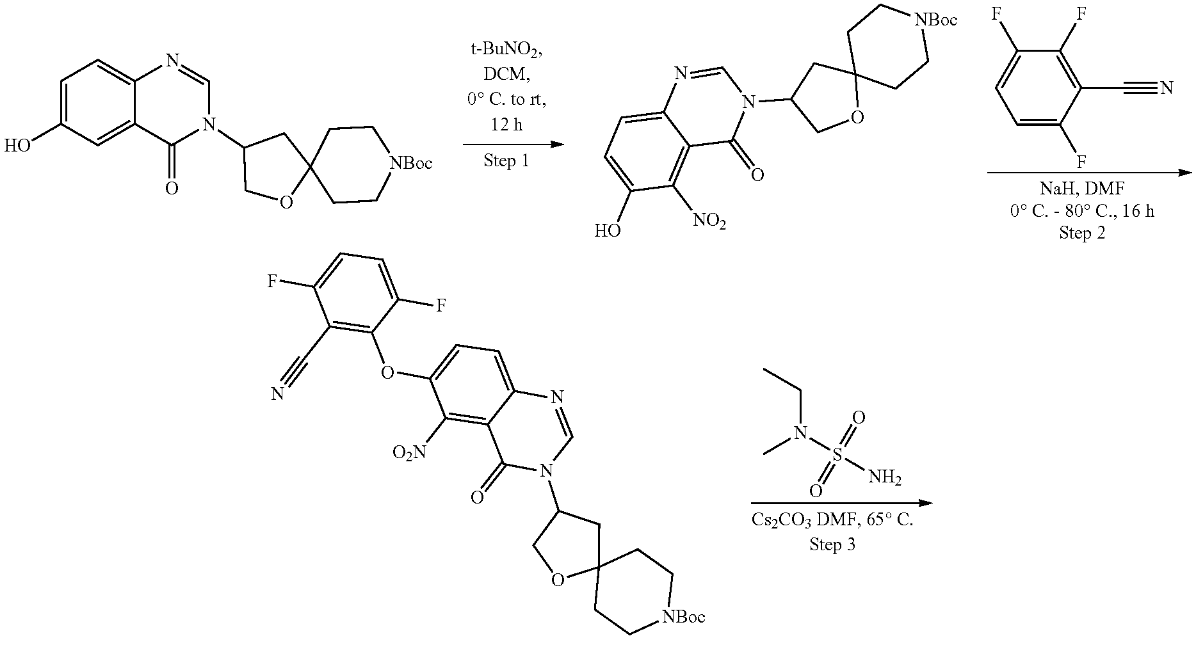

-continued

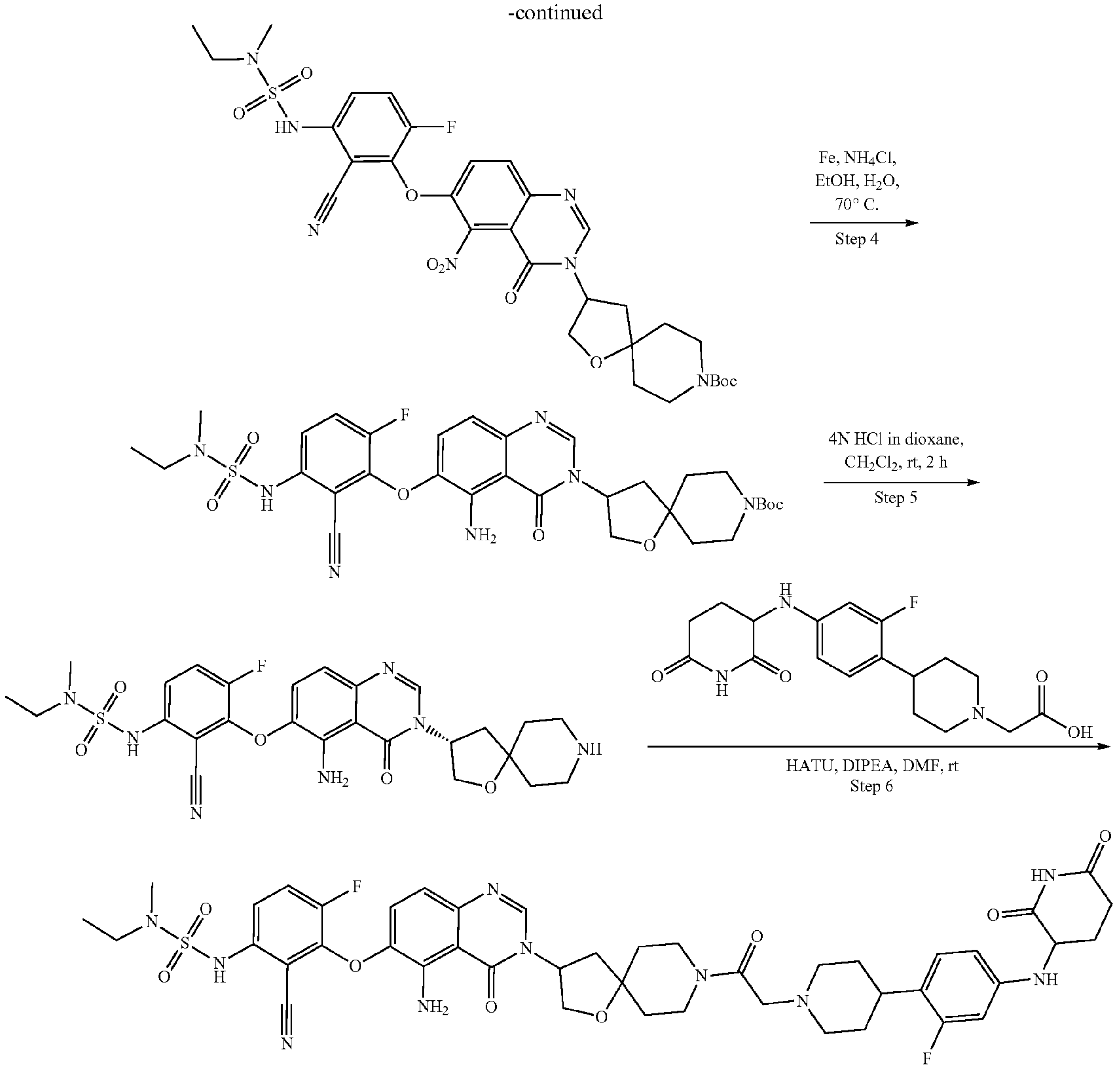

Step 1: To a stirred solution of tert-butyl 3-(6-hydroxy-4-oxo-quinazolin-3-yl)-1-oxa-8-azaspiro[4.5]decane-8-carboxylate (400 mg, 996.38 μmol) in dichloromethane (10 mL) was added tert-butyl nitrite (308.24 mg, 2.99 mmol, 355.52 μL) at 0° C. and the reaction mixture was stirred at room temperature for 12 h under nitrogen atmosphere. After completion of the reaction, the reaction mixture was diluted with water (20 mL) and extracted with dichloromethane (3x30 mL). The combined organic layers were washed with brine solution (50 mL), dried over sodium sulfate, filtered, and concentrated under reduced pressure to afford the crude. The crude compound was purified by silica gel flash column chromatography with 80-85% ethyl acetate in petroleum ether as a eluent to afford tert-butyl 3-(6-hydroxy-5-nitro-4-oxo-quinazolin-3-yl)-1-oxa-8-azaspiro[4.5]decane-8-carboxylate (210 mg, 437.45 μmol, 44% yield) as a brown solid. LCMS m/z (ESI): 445.6 $[M-H]^-$ Step 2: To a stirred solution of sodium hydride (60% dispersion in mineral oil, 33.47 mg, 1.46 mmol) in N,N-Dimethylformamide (2 mL) was added solution of tert-butyl 3-(6-hydroxy-5-nitro-4-oxo-quinazolin-3-yl)-1-oxa-8-azaspiro[4.5]decane-8-carboxylate (130 mg, 291.18 μmol) in N,N-Dimethylformamide (2 mL) at 0° C., and the reaction mixture was stirred at room temperature for 2 h. Then 2,3,6-trifluorobenzonitrile (137.23 mg, 873.55 μmol, 100.90 μL) was added to the reaction mixture and was stirred at 80° C. for 16 h. After completion of the reaction, the reaction mixture was quenched with cold water (10 mL) and extracted with ethyl acetate (2x10 mL). The combined organic layer was dried with anhydrous sodium sulfate and concentrated under reduced pressure to afford crude. The crude compound was purified by silica gel flash column chromatography with 60-70% ethyl acetate in petroleum ether as a eluent to afford tert-butyl 3-[6-(2-cyano-3,6-difluoro-phenoxy)-5-nitro-4-oxo-quinazolin-3-yl]-1-oxa-8-azaspiro[4.5]decane-8-carboxylate (60 mg, 90.48 μmol, 31% yield) as a brown solid. LCMS m/z (ESI): 484.00 $[M+H-CO2tBu]^+$ Step 3: Sulfamoylated quinazolinone intermediate was synthesized by following Procedure A-C using tert-butyl 3-[6-(2-cyano-3,6-difluoro-phenoxy)-5-nitro-4-oxo-quinazolin-3-yl]-1-oxa-8-azaspiro[4.5]decane-8-carboxylate (40 mg, 68.55 μmol), cesium carbonate (67.00 mg, 205.64 μmol) and [methyl(sulfamoyl)amino]ethane 28.42 mg, 205.64 μmol). The crude compound was purified by silica gel flash column chromatography with 70-80% ethyl acetate in petroleum ether as a eluent to afford tert-butyl 3-[6-[2-cyano-3-[[ethyl(methyl)sulfamoyl]amino]-6-fluoro-phenoxy]-5-nitro-4-oxo-quinazolin-3-yl]-1-oxa-8-azaspiro[4.5]decane-8-carboxylate (25 mg, 27.79 μmol, 41% yield) as a brown viscous. LCMS m/z (ESI): 700.00 $[M-H]^-$.

Step 4: To a stirred solution of tert-butyl 3-[6-[2-cyano-3-[[ethyl(methyl)sulfamoyl]amino]-6-fluoro-phenoxy]-5-nitro-4-oxo-quinazolin-3-yl]-1-oxa-8-azaspiro[4.5]decane-8-carboxylate (25 mg, 35.63 μmol) in water (1 mL)/ethanol (3 mL) were added iron powder (9.95 mg, 178.13 μmol) and ammonium chloride (9.53 mg, 178.13 μmol) at room temperature. The reaction mixture was stirred at 80° C. for 3 h. After completion of the reaction, the reaction mixture was filtered and concentrated under vacuum to afford crude. This crude was dissolved in water (5 mL), extracted with ethyl acetate (2×10 mL). The combined organic phases were dried with anhydrous sodium sulfate, filtered and the filtrate was evaporated under reduced pressure to afford crude product, which was purified by silica gel flash column chromatography using 80-90% ethyl acetate in petroleum ether as eluent to afford tert-butyl 3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (20 mg, 21.44 μmol, 60% yield) as a brown viscous. LCMS m/z (ESI): 672.20 $[M+H]^+$ Step 5: The requisite amine was synthesized by following Procedure A-D using tert-butyl 3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (20 mg, 29.77 μmol) and hydrogen chloride solution 4.0 M in dioxane (1 mL). The resulted crude compound was triturated with methyl t-butyl ether to afford 3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane (18 mg, 29.60 μmol, 99% yield) as an off-white solid. LCMS m/z (ESI): 572.40 $[M+H]^+$ Step 6: Target compound was prepared via HATU mediated acid-amine coupling reaction (Procedure A-E). Amide coupling was carried out using 3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane (20 mg, 32.89 μmol), 2-[4-[4-[(2,6-dioxo-3-piperidyl)amino]-2-fluoro-phenyl]-1-piperidyl]acetic acid (19.73 mg, 49.34 μmol), N,N-diisopropylethylamine (42.51 mg, 328.90 μmol, 57.29 μL) and HATU (18.76 mg, 49.34 μmol) to afford crude product. The crude compound was purified by reverse phase column chromatography eluted with 45% acetonitrile in 0.1% formic acid in water to afford product 3-[5-amino-6-[2-cyano-3-[[ethyl(methyl)sulfamoyl]amino]-6-fluoro-phenoxy]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5]decane (8.5 mg, 8.59 μmol, 26% yield) as an off-white solid. LCMS m/z (ESI): 917.00 $[M+H]^+$; $^1$HNMR (400 MHz, DMSO-$d_6$): δ=12.30 (s, 1H), 10.79 (s, 1H), 8.16 (d, J=9.20 Hz, 2H), 7.36 (s, 1H), 7.21 (d, J=5.20 Hz, 2H), 7.01-6.97 (m, 1H), 6.90 (d, J=8.80 Hz, 1H), 6.66 (d, J=8.80 Hz, 1H), 6.49-6.43 (m, 2H), 6.04 (d, J=4.40 Hz, 1H), 5.33 (s, 1H), 4.31 (t, J=3.60 Hz, 1H), 4.14 (d, J=4.80 Hz, 2H), 3.66-3.48 (m, 4H), 3.20-2.92 (m, 5H), 2.72-2.51 (m, 5H), 2.50-2.41 (m, 2H), 2.09-2.05 (m, 3H), 1.81-1.34 (m, 10H), 1.28-1.24 (m, 1H), 1.03 (t, J=7.20 Hz, 3H).

Example 82

(3R)-3-[6-[2-cyano-3-[[ethyl(methyl)sulfamoyl]amino]-6-fluoroanilino]-4-oxoquinazolin-3-yl]-8-[2-[4-[4-[(2,6-dioxopiperidin-3-yl)amino]-2-fluorophenyl]piperidin-1-yl]acetyl]-1-oxa-8-azaspiro[4.5]decane

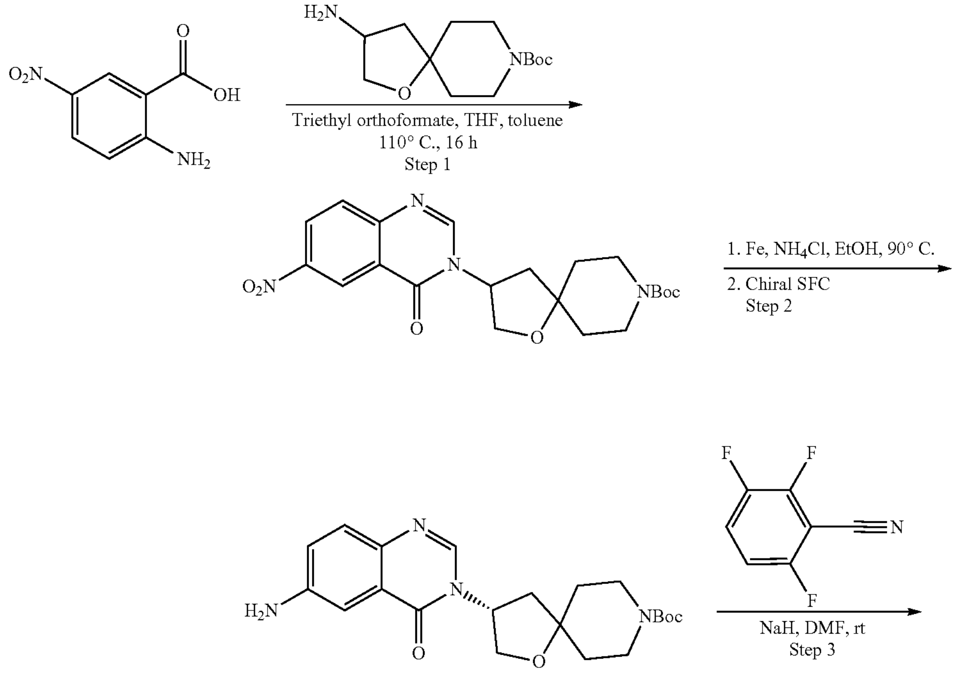

-continued
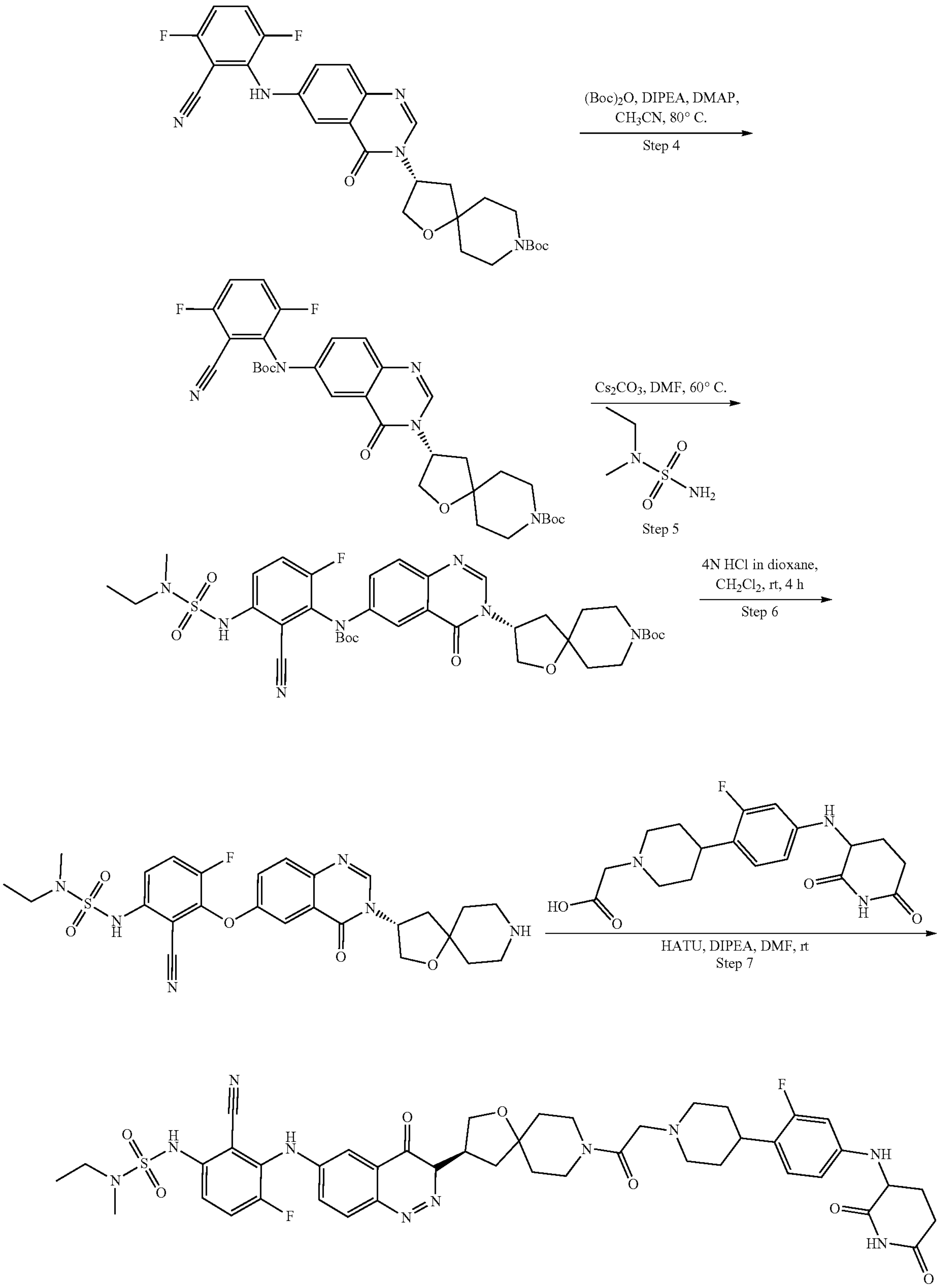

Step 1: Quinazolinone intermediate was synthesized by following general procedure for cyclization (Procedure A-A) using tert-butyl 3-amino-1-oxa-8-azaspiro[4.5]decane-8-carboxylate (2 g, 7.80 mmol), 2-amino-5-nitro-benzoic acid (1.42 g, 7.80 mmol), triethyl orthoformate (3.47 g, 23.41 mmol, 3.89 mL). After reaction completion, the reaction mixture was diluted water (50 mL) and extracted with ethyl acetate (3×50 mL). The organic layer was washed with sodium bicarbonate solution (2×50 mL) and brine (50 mL), dried over sodium sulfate and concentrated under reduced pressure to provide a crude residue, which was triturated with 10% ethyl acetate in petroleum ether to afford tert-butyl 3-(6-nitro-4-oxo-quinazolin-3-yl)-1-oxa-8-azaspiro[4.5]decane-8-carboxylate (3 g, 5.44 mmol, 70% yield) as a brown solid. LCMS m/z (ESI): 375.20 $[M-CO_2{}^tBu+H]^+$ Step 2: To a stirred solution of tert-butyl 3-(6-nitro-4-oxo-quinazolin-3-yl)-1-oxa-8-azaspiro[4.5]decane-8-carboxylate (3 g, 6.97 mmol) in water (5 mL)/ethanol (25 mL) were added iron powder (1.95 g, 34.85 mmol, 247.59 μL) and ammonium chloride (1.86 g, 34.85 mmol, 1.22 mL) at room temperature. The reaction mixture was stirred at 85° C. for 3 h. After completion, the reaction mixture was filtered and concentrated under reduced pressure to provide crude material. The crude was dissolved in water (50 mL) and extracted with ethyl acetate (3×50 mL). The combined organic phases were dried over anhydrous sodium sulfate, filtered, and the filtrate was evaporated under reduced pressure to afford crude product. The crude material was purified by silica gel chromatography using 70-80% ethyl acetate in petroleum ether as eluent to afford tert-butyl 3-(6-amino-4-oxo-quinazolin-3-yl)-1-oxa-8-azaspiro[4.5]decane-8-carboxylate (1.8 g, 4.45 mmol, 630.85% yield) as a brown solid. The racemic compound was chirally resolved by chiral SFC (column Lux-A1 [250*30 mm, 5 micron]; Mobile phase: 50% IPA-$CO_2$+0.5% isopropyl amine in methanol; Flow rate: 120 mL/min; cycle time: 7.6 min; back pressure: 100 bar; UV: 210 nm) to afford peak 1 (first-eluted, arbitrarily assigned as S-isomer) tert-butyl (S)-3-(6-amino-4-oxoquinazolin-3(4H)-yl)-1-oxa-8-azaspiro[4.5]decane-8-carboxylate (610 mg) as off-white solid and the desired peak 2 (second eluted, arbitrarily assigned as R-isomer) tert-butyl (R)-3-(6-amino-4-oxoquinazolin-3(4H)-yl)-1-oxa-8-azaspiro[4.5]decane-8-carboxylate (600 mg, 2.93 mmol, 10% yield) as off-white solid. LCMS m/z (ESI): 401.20 $[M+H]^+$ Step 3: To a stirred solution of sodium hydride (60% dispersion in mineral oil, 172.22 mg, 4.49 mmol) in N,N-dimethylformamide (10 mL) was added tert-butyl (3R)-3-(6-amino-4-oxo-quinazolin-3-yl)-1-oxa-8-azaspiro[4.5]decane-8-carboxylate (600 mg, 1.50 mmol) dissolved in N,N-dimethylformamide (5 mL) at 0° C. The reaction mixture was stirred at room temperature for 2 h. Next, 2,3,6-trifluorobenzonitrile (470.73 mg, 3.00 mmol, 346.12 μL) was added to the reaction mixture at room temperature and stirred for 16 h. After completion, the reaction mixture was quenched with cold water (50 mL) and extracted with ethyl acetate (2×50 mL). The combined organic layer was dried with anhydrous sodium sulfate and concentrated under reduced pressure to afford crude. The crude compound was purified by silica gel flash column chromatography with 70-80% ethyl acetate in petroleum ether as a eluent to afford tert-butyl (3R)-3-[6-(2-cyano-3,6-difluoro-anilino)-4-oxo-quinazolin-3-yl]-1-oxa-8-azaspiro[4.5]decane-8-carboxylate (720 mg, 688.05 μmol, 46% yield) as a brown solid. LCMS m/z (ESI): 538.80 $[M+H]^+$ Step 4: To a solution of tert-butyl(3R)-3-[6-(2-cyano-3,6-difluoro-anilino)-4-oxo-quinazolin-3-yl]-1-oxa-8-azaspiro[4.5]decane-8-carboxylate (700 mg, 1.30 mmol) in anhydrous acetonitrile (8 mL) were added DMAP (79.54 mg, 651.09 μmol) and triethylamine (395.31 mg, 3.91 mmol, 544.50 μL) at room temperature. Di-tert-butyl pyro carbonate (568.40 mg, 2.60 mmol, 597.68 μL) was added dropwise at 0° C., and the contents were allowed to stir at room temperature for 16 h. After completion, the reaction mixture was quenched with water (50 mL), extracted with ethyl acetate (60 mL), dried over sodium sulfate, and filtered. The solvent was evaporated. The crude material was purified by silica gel flash column chromatography with 70-80% ethyl acetate in petroleum ether as a eluent to afford tert-butyl (3R)-3-[6-(N-tert-butoxycarbonyl-2-cyano-3,6-difluoro-anilino)-4-oxo-quinazolin-3-yl]-1-oxa-8-azaspiro[4.5]decane-8-carboxylate (600 mg, 412.59 μmol, 32% yield) as an off-white solid. LCMS m/z (ESI): 638.40 $[M+H]^+$ Step 5: Sulfamoylated quinazolinone intermediate was synthesized by following Procedure A-C using of tert-butyl (3R)-3-[6-(N-tert-butoxycarbonyl-2-cyano-3,6-difluoro-anilino)-4-oxo-quinazolin-3-yl]-1-oxa-8-azaspiro[4.5]decane-8-carboxylate (600 mg, 940.92 μmol), cesium carbonate (919.71 mg, 2.82 mmol) and [methyl(sulfamoyl)amino] ethane (370.77 mg, 2.35 mmol). The crude compound was purified using reverse phase prep HPLC (Column: X-select C18 (150*19) mm 5 micron Prep method: 0.1% ammonium acetate in water/acetonitrile) to afford tert-butyl (3R)-3-[6-[N-tert-butoxycarbonyl-2-cyano-3-[[ethyl(methyl)sulfamoyl]amino]-6-fluoro-anilino]-4-oxo-quinazolin-3-yl]-1-oxa-8-azaspiro[4.5]decane-8-carboxylate (160 mg, 185.75 μmol, 20% yield) as an off-white solid. LCMS m/z (ESI): 754.10 $[M-H]^-$ Step 6: The requisite amine was synthesized by following Procedure A-D using tert-butyl (3R)-3-[6-[N-tert-butoxycarbonyl-2-cyano-3-[[ethyl(methyl)sulfamoyl]amino]-6-fluoro-anilino]-4-oxo-quinazolin-3-yl]-1-oxa-8-azaspiro [4.5]decane-8-carboxylate (160 mg, 211.68 μmol) and hydrogen chloride solution (4.0M in dioxane, 3 mL). The resulted crude compound was triturated with methyl t-butyl ether to afford (3R)-3-[6-[2-cyano-3-[[ethyl(methyl)sulfamoyl]amino]-6-fluoro-anilino]-4-oxo-quinazolin-3-yl]-1-oxa-8-azaspiro[4.5]decane (140 mg, 204.18 μmol, 96% yield) as an off-white solid. LCMS m/z (ESI): 556.70 $[M+H]^+$ Step 7: Target compound was prepared via HATU mediated acid-amine coupling reaction (Procedure A-E). Amide coupling was carried out using (3R)-3-[6-[2-cyano-3-[[ethyl (methyl)sulfamoyl]amino]-6-fluoro-anilino]-4-oxo-quinazolin-3-yl]-1-oxa-8-azaspiro[4.5]decane (70 mg, 102.09 μmol), 2-[4-[4-[(2,6-dioxo-3-piperidyl)amino]-2-fluoro-phenyl]-1-piperidyl]acetic acid (48.98 mg, 122.51 μmol), N,N-diisopropylethylamine (65.97 mg, 510.44 μmol, 88.91 μL) and HATU (58.23 mg, 153.13 μmol). The crude compound was purified by reverse phase column chromatography eluted with 45% acetonitrile in 0.1% ammonium acetate in water to afford product (3R)-3-[6-[2-cyano-3-[[ethyl (methyl)sulfamoyl]amino]-6-fluoro-anilino]-4-oxo-quinazolin-3-yl]-8-[2-[4-[4-[(2,6-dioxo-3-piperidyl)amino]-2-fluoro-phenyl]-1-piperidyl]acetyl]-1-oxa-8-azaspiro[4.5] decane (21 mg, 23.09 μmol, 23% yield) as an off-white solid. LCMS m/z (ESI): 901.20 $[M+H]^+$; $^1$HNMR (400 MHz, DMSO-$d_6$): δ=10.80 (s, 1H), 9.89 (bs, 1H), 8.88 (bs, 1H), 8.22 (s, 1H), 7.84 (d, J=8.80 Hz, 2H), 7.35-7.23 (m, 3H), 6.98 (t, J=8.40 Hz, 1H), 6.44 (s, 2H), 6.04 (s, 1H), 5.34 (s, 1H), 4.32-4.30 (m, 1H), 4.19 (d, J=5.20 Hz, 2H), 3.49-3.68 (m, 4H), 3.10 (s, 5H), 2.85-2.75 (m, 1H), 2.74 (s, 3H), 2.52-2.50 (m, 2H), 2.06 (s, 4H), 1.91-1.53 (m, 11H), 1.04 (t, J=7.20 Hz, 3H).

Example 83
(3R)-3-[6-[2-cyano-3-[[ethyl(methyl)sulfamoyl]amino]-6-fluorophenoxy]-4-oxoquinazolin-3-yl]-8-[4-[4-[(2,6-dioxopiperidin-3-yl)amino]-2-fluorophenyl]cyclohexyl]-1-oxa-8-azaspiro[4.5]decane
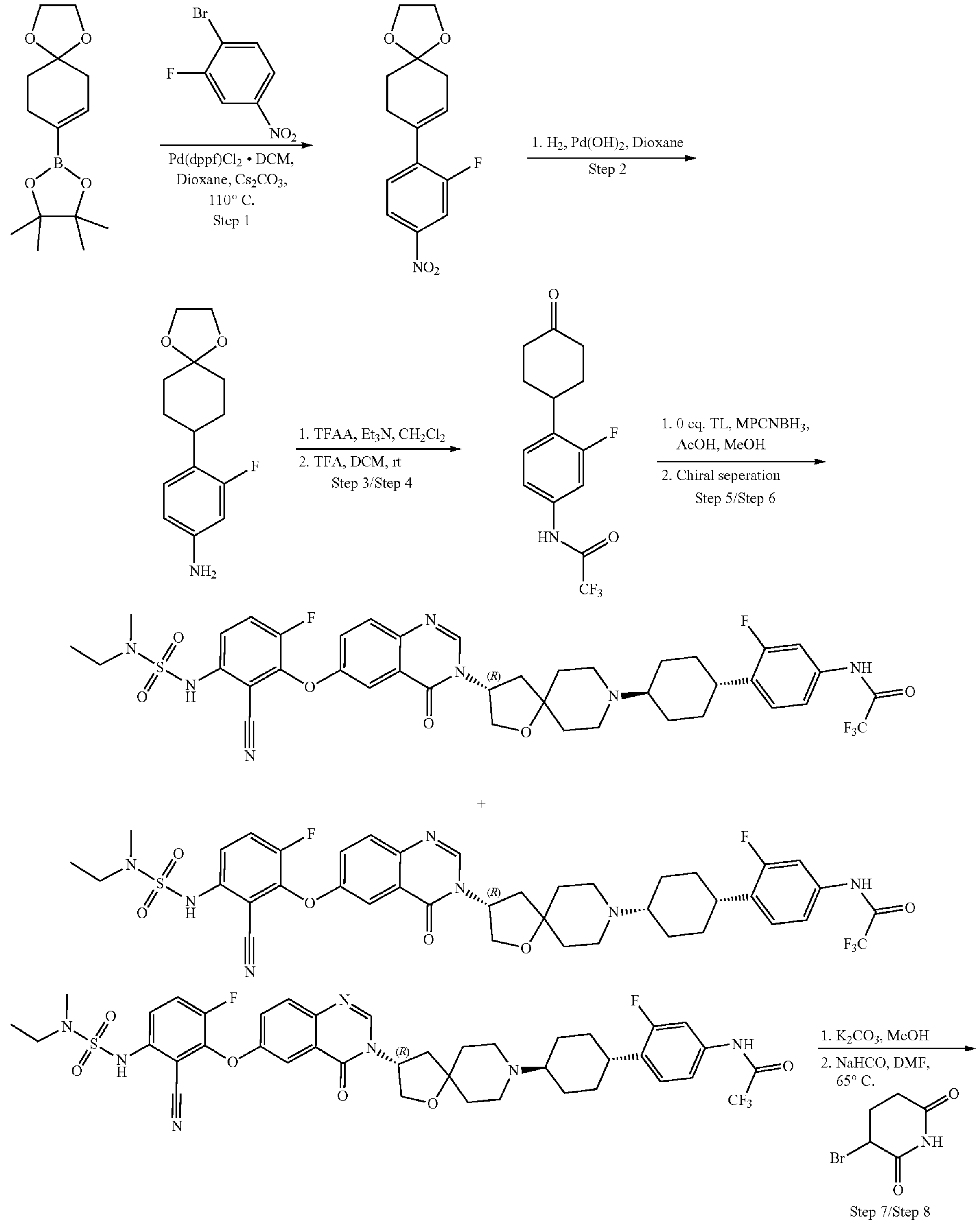

-continued

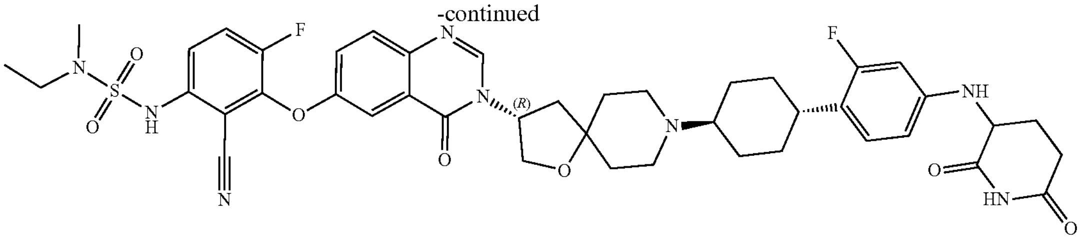

Step 1: To a 250 mL sealed-tube containing a well-stirred solution of 1-bromo-2-fluoro-4-nitro-benzene (4.0 g, 18.18 mmol) and 2-(1,4-dioxaspiro[4.5]dec-7-en-8-yl)-4,4,5,5-tetramethyl-1,3,2-dioxaborolane (5.80 g, 21.79 mmol) in 1,4-dioxane (50 mL) was added sodium carbonate (1.0 M, 55.0 mL) at ambient temperature under nitrogen atmosphere. The resulting mixture was degassed by bubbling nitrogen gas into the reaction mixture for 10 minutes. Subsequently, $Pd(dppf)Cl_2$·dichloromethane (750 mg, 918.40 μmol) was added, and the reaction mixture was heated to 80° C. for 16 h. The reaction mixture was cooled to room temperature, poured into water (100 mL), and extracted with ethyl acetate (3×100 mL). The combined organic phases were dried over anhydrous sodium sulfate, filtered, and the filtrate was concentrated under reduced pressure. The crude product was purified by silica gel flash column chromatography eluting with 30-40% of ethyl acetate in petroleum ether to afford 8-(2-fluoro-4-nitro-phenyl)-1,4-dioxaspiro[4.5]dec-7-ene (4.40 g, 14.97 mmol, 82% yield) as an yellow viscous liquid. $^1$HNMR (400 MHz, DMSO-$d_6$): δ=8.03-8.09 (m, 2H), 7.63 (t, J=8.40 Hz, 1H), 6.05 (s, 1H), 3.94 (s, 4H), 2.52 (t, J=1.60 Hz, 2H), 2.42 (s, 2H), 1.82 (t, J=6.40 Hz, 2H).

Step 2: To a 250 mL single-necked round-bottomed flask containing a well-stirred solution of 8-(2-fluoro-4-nitro-phenyl)-1,4-dioxaspiro[4.5]dec-7-ene (4.40 g, 15.76 mmol) in anhydrous 1,4-dioxane (50 mL) was added palladium hydroxide on carbon, (20 wt. % 50% water, 1.50 g, 2.14 mmol, 20% purity). The resultant mixture was saturated with hydrogen by bubbling hydrogen gas through for 10 min then subjected to hydrogenation (1 atm) at ambient temperature for 32 h. The reaction mixture was purged with nitrogen, and the catalyst was removed by filtration through celite pad. The filtrate was concentrated under reduced pressure to afford 4-(1,4-dioxaspiro[4.5]decan-8-yl)-3-fluoro-aniline (3.70 g, 14.28 mmol, 91% yield) as an off-white solid. LCMS m/z (ESI): 252.2 $[M+H]^+$.

Step 3: To a stirred solution of 4-(1,4-dioxaspiro[4.5]decan-8-yl)-3-fluoro-aniline (3.70 g, 14.72 mmol) in anhydrous dichloromethane (50 mL) was added triethylamine (4.50 g, 44.48 mmol, 6.20 mL) at 0-5° C. under nitrogen atmosphere, followed by the (2,2,2-trifluoroacetyl) 2,2,2-trifluoroacetate (4.77 g, 22.70 mmol, 3.20 mL) at the same temperature. The resulting mixture was stirred at ambient temperature for 16 h. water (100 mL) was added, and the aqueous mixture was extracted with dichloromethane (3×100 mL). The combined organic layers were dried over anhydrous sodium sulfate, filtered, and concentrated under reduced pressure. The crude compound was purified by silica gel flash column chromatography eluting with 50-60% ethyl acetate in petroleum ether to afford N-[4-(1,4-dioxaspiro[4.5]decan-8-yl)-3-fluoro-phenyl]-2,2,2-trifluoro-acetamide (4.40 g, 7.60 mmol, 52% yield) as an off-white solid. LCMS m/z (ESI): 346.2 $[M-H]^-$ Step 4: To a stirred solution of N-[4-(1,4-dioxaspiro[4.5]decan-8-yl)-3-fluoro-phenyl]-2,2,2-trifluoro-acetamide (4.40 g, 12.67 mmol) in anhydrous dichloromethane (30 mL) was added trifluoroacetic acid (14.80 g, 129.80 mmol, 10 mL) at ambient temperature under nitrogen atmosphere. The resulting mixture was stirred at ambient temperature for 16 h. The reaction mixture was concentrated under reduced pressure. Saturated sodium bicarbonate solution was added to the reaction mixture, and the aqeuous mixture was extracted with dichloromethane (3×100 mL). The combined organic layers were dried over sodium sulfate, filtered, and concentrated under reduced pressure. The crude product was purified by silica gel flash column chromatography eluting with ethyl acetate in petroleum ether to afford 2,2,2-trifluoro-N-[3-fluoro-4-(4-oxocyclohexyl)phenyl]acetamide (2.50 g, 8.16 mmol, 64% yield) as an off-white solid. LCMS m/z (ESI): 302.09 $[M-H]^-$.

Step 5/Step 6: To a 25 mL single necked round bottomed flask containing a well-stirred solution of (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (200 mg, 359.32 μmol) and 2,2,2-trifluoro-N-[3-fluoro-4-(4-oxocyclohexyl)phenyl]acetamide (220 mg, 725.47 μmol) in anhydrous methanol (5.0 mL) were added anhydrous sodium acetate(60 mg, 731.41 μmol, 39.22 μL), acetic acid (21.58 mg, 359.32 μmol, 20.55 μL) and MP-$CNBH_3$ (500 mg, 359.32 μmol) at ambient temperature under nitrogen atmosphere. The resulting mixture was stirred at ambient temperature for 32 h. The reaction mixture was filtered through celite, and the filtrate was concentrated under reduced pressure. The crude material was purified by preparative-HPLC using the method: Mobile phase: A: 0.1% formic acid in MQ-water; B: acetonitrile; to afford 260 mg of racemic compound. This racemic compound was purified by SFC-chiral purification (using this method: flow rate: 5 ml/min; column: YMC Cellulose-SC; co-solvent: 0.5% isopropyl amine in isopropyl alcohol; injected volume: 15 μl; outlet pressure: 100 bar; temperature: 35° C.) to afford N-[4-(1s, 4s)-[4-[(3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decan-8-yl]cyclohexyl]-3-fluoro-phenyl]-2,2,2-trifluoro-acetamide (120 mg, 137.94 μmol, 38% yield, $F_1$) as a pale brown viscous liquid and N-[4-(1r, 4r)-[[4-[(3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decan-8-yl]cyclohexyl]-3-fluoro-phenyl]-2,2,2-trifluoro-acetamide (110 mg, 126.18 μmol, 35% yield, $F_2$) as a pale brown solid. LCMS m/z (ESI): 844.0 $[M+H]^+$.

NOTE: First eluting isomer (F1) was arbitrarily assigned as cis isomer and Second eluting isomer (F2) was arbitrarily assigned as trans isomer Step 7: To a 25 mL single-necked round-bottomed flask containing a well-stirred solution of N-[4-(1r, 4r) [4-[(3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decan-8-yl]cyclohexyl]-3-fluoro-phenyl]-2,2,2-trifluoro-acetamide (100 mg, 118.50 μmol) in a mixture of methanol (5.0 mL) and water (1.0 mL) at room temperature was added anhydrous potassium carbonate (85 mg, 615.02 μmol, 37.12 μL). The resulting mixture was heated to 50° C. for 16 h. water (30 ml) was added, and the mixture was extracted with 5% methanol/dichloromethane (3×50 mL). The combined organic layers were dried over sodium sulfate, filtered, and concentrated under reduced pressure. The crude residue was purified by silica gel flash column chromatography eluting with 10-15% methanol in dichloromethane to afford (3R)-8-[4-(1r, 4r)-(4-amino-2-fluoro-phenyl)cyclohexyl]-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (70 mg, 85.18 μmol, 72% yield) as a pale yellow solid. LCMS m/z (ESI): 748.6 $[M+H]^+$.

Step 8: To a 10 mL sealed-tube reactor containing a well-stirred solution of (3R)-8-[4-(1r, 4r) (4-amino-2-fluoro-phenyl)cyclohexyl]-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (60 mg, 80.23 μmol) in anhydrous N,N-dimethylformamide (2.0 mL) were added sodium bicarbonate (42 mg, 499.96 μmol, 19.44 μL) and 3-bromopiperidine-2,6-dione (80 mg, 416.64 μmol) at ambient temperature under nitrogen atmosphere. The resulting mixture was heated to 70° C. for 48 h. The reaction mixture was cooled to room temperature, and water (20 mL) was added. The mixture was extracted with 10% isopropyl alcohol/dichloromethane (3×50 mL). The combined organic layers were dried over anhydrous sodium sulfate, filtered, and the filtrate concentrated under reduced pressure. The crude material was purified by preparative-HPLC (X-SELECT C18 (250*19)MM 5 MICRONS, 10 MM ABC:ACN) to afford (3R)-3-[6-[2-cyano-3-[[ethyl(methyl)sulfamoyl]amino]-6-fluoro-phenoxy]-4-oxo-quinazolin-3-yl]-8-[4-(1r, 4r) [4-[(2,6-dioxo-3-piperidyl)amino]-2-fluoro-phenyl]cyclohexyl]-1-oxa-8-azaspiro[4.5]decane (4.0 mg, 4.40 μmol, 5% yield) as an off-white solid. LCMS m/z (ESI): 859.2 $[M+H]^+$; $^1$HNMR (400 MHz, DMSO-$d_6$): δ=10.80 (s, 1H), 8.31 (s, 1H), 7.76 (d, J=8.80 Hz, 1H), 7.64 (dd, J=3.20, 9.00 Hz, 1H), 7.43-7.33 (m, 1H), 7.33 (d, J=2.80 Hz, 1H), 7.28-7.26 (m, 1H), 6.97 (t, J=8.40 Hz, 1H), 6.46-6.42 (m, 2H), 6.03 (d, J=7.60 Hz, 1H), 5.30-5.27 (m, 1H), 4.33-4.29 (m, 1H), 4.21-4.17 (m, 1H), 4.14-4.09 (m, 1H), 3.20-3.05 (m, 2H), 3.01 (q, J=6.80 Hz, 2H), 2.80-2.60 (m, 10H), 2.20-2.18 (m, 1H), 2.14-2.05 (m, 3H), 2.08-1.91 (m, 2H), 1.91-1.72 (m, 4H), 1.73-1.42 (m, 5H), 1.03 (t, J=7.20 Hz, 3H).

General Procedure for Sulfonamide Synthesis (Method I)

A representative example for the sulfonamide synthesis is described below using (3R)-3-fluoropyrrolidine-1-sulfonamide:

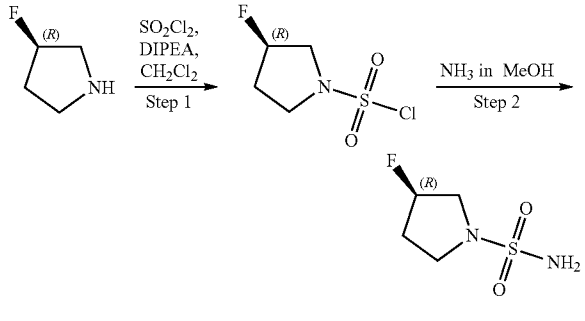

Step 1: To a stirred solution of (R)-3-fluoropyrrolidine hydrochloride(2.0 g, 15.93 mmol) in dichloromethane (3 mL) was added N,N-diisopropylethylamine (3.09 g, 23.89 mol, 4.16 mL) under nitrogen atmosphere at room temperature. Sulfuryl chloride (5.37 g, 39.82 mmol, 3.24 mL) was added at −30° C. and the mixture was stirred at that temperature for 2 h. After completion, the reaction mixture was quenched with water (5 mL) via dropwise addition, extracted with ethyl acetate (2×50 mL). Combined organic layer was washed with 1.5N HCl solution (2×5 mL), dried over sodium sulfate, filtered, and concentrated under reduced pressure to afford crude sulfonyl chloride intermediate (2.1 g, 11.19 mmol, 70% yield), which was used in next step without further purification.

Step 2: To a solution of (3R)-3-fluoropyrrolidine-1-sulfonyl chloride (1.8 g, 9.59 mmol) in methanol (5 mL) was added ammonia (7M in methanol) (163.38 mg, 9.59 mmol, 10 mL) at 0° C. and stirred at room temperature for 14 h. After completion of the reaction, the mixture was concentrated under reduced pressure and the residue was diluted with water (25 mL) and extracted with ethyl acetate (2×50 mL). The organic layer was washed with sodium bicarbonate solution (20 mL), brine (25 mL), dried over sodium sulfate, concentrated under reduced pressure and purified by column chromatography on silica gel; eluted with 40% ethyl acetate in pet ether to afford (3R)-3-fluoropyrrolidine-1-sulfonamide (850 mg, 5.00 mmol, 52% yield) as a light-yellow liquid. LCMS m/z: 169.2 $[M+H]^+$.

The following sulfonamides were synthesized using the general procedure from either Step 1/2 or Step 2 of Method I.

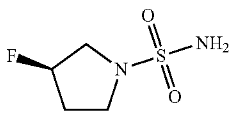

Yield = 52.15%
LC-MS (ESI+)
m/z = 169.2
$[M+H]^+$

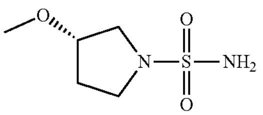

Yield = 16.4%
LC-MS (ESI+)
m/z = 181.2
$[M+H]^+$

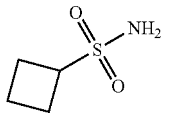

Yield = 75.25%
LC-MS (ESI+)
m/z = 136.1
$[M+H]^+$

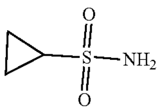

Yield = 17.1%
LC-MS (ESI+)
m/z = 122.2
$[M+H]^+$

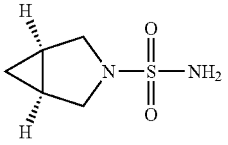

Yield = 29.86%
LC-MS (ESI+)
m/z = 162.0
$[M+H]^+$

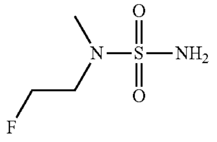

Yield = 31.06%
LC-MS (ESI+)
m/z = 156.2
$[M+H]^+$

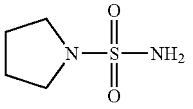

Yield = 50.58%
LC-MS (ESI+)
m/z = 151.1
$[M+H]^+$

-continued

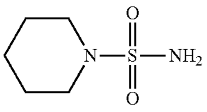

Yield = 66.43%
LC-MS (ESI+)
m/z = 165.20
[M+H]+

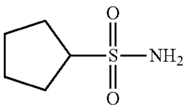

Commercial

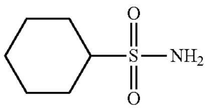

Yield = 64.90%
$^1$H NMR complies

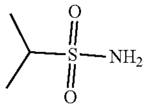

Yield = 34.6%
$^1$H NMR complies

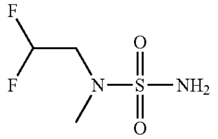

Yield = 32.55%
LC-MS (ESI+)
m/z = 173.0
[M+H]+

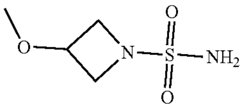

Yield = 33.69%
LC-MS (ESI+)
m/z = 167.0
[M+H]+

General Procedure for Sulfonamide Synthesis (Method II)

A representative example for the sulfonamide synthesis is described below using 3,3-difluoropyrrolidine-1-sulfonamide:

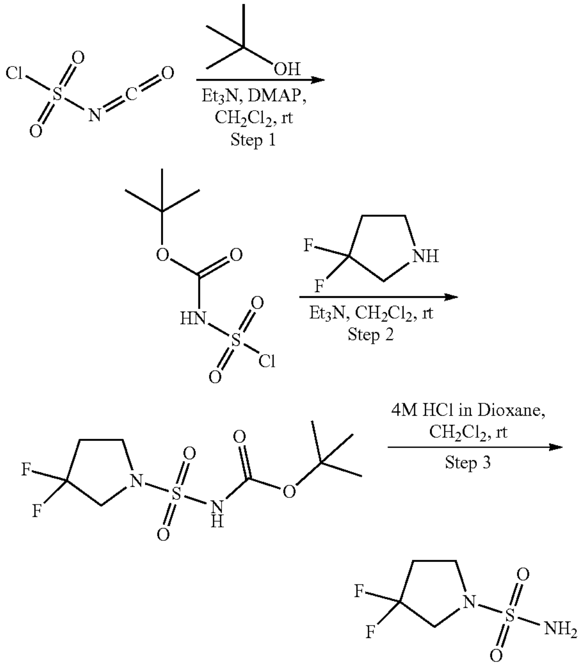

Step 1: To a stirred solution of tert-butyl alcohol (3.14 g, 42.39 mmol, 4.00 mL) and DMAP (7.77 g, 63.59 mmol) in dichloromethane (20 mL) were added N-(oxomethylene) sulfamoyl chloride (3 g, 21.20 mmol, 1.84 mL) at 0° C. dropwise. The resulting mixture was stirred at rt for 2 h. After completion, the mixture was diluted with water (3x20 mL), extracted with dichloromethane (3x50 mL), dried over anhydrous sodium sulfate, and evaporated under reduced pressure to afford crude tert-butyl N-chlorosulfonylcarbamate (3.5 g, 16.09 mmol, 76% yield) as white solid.

Step 2: To a stirred solution of 3,3-difluoropyrrolidine (1.0 g, 9.34 mmol) in dichloromethane (15 mL) under nitrogen atmosphere was added triethyl amine (944.80 mg, 9.34 mmol, 1.30 mL) and tert-butyl N-chlorosulfonylcarbamate (2.01 g, 9.34 mmol) at 0° C. The resulting reaction mixture was stirred at rt for 16 h. After completion, the reaction mixture was water (25 ml) and extracted with ethyl acetate (2x50 mL). The organic phases were combined and washed with brine, dried (anhydrous sodium sulfate), filtered and concentrated under reduced pressure to afford a crude product. The crude product was purified by silica gel flash column chromatography using 1-10% methanol in dichloromethane as eluent to afford tert-butyl N-(3,3-difluoropyrrolidin-1-yl)sulfonyl carbamate (1.5 g, 5.19 mmol, 56% yield) as a white solid. LCMS (ELSD-MS) m/z: 285.20 $[M-H]^-$.

Step 3: To a stirred solution of tert-butyl N-(3,3-difluoropyrrolidin-1-yl) sulfonylcarbamate (1.5 g, 5.24 mmol) in anhydrous 1,4-dioxane (5 mL) was added 4.0M HCl in dioxane (4.0 M, 1.31 mL) at ambient temperature under nitrogen atmosphere. The resulting suspension was stirred at ambient temperature for 16 h. After completion, the reaction mixture was concentrated under reduced pressure to yield a crude product which was triturated with pet ether to afford 3,3-difluoropyrrolidine-1-sulfonamide (0.9 g, 4.03 mmol, 77% yield) as an off-white solid. LCMS m/z: 185.2 $[M-H]^-$.

The following sulfonamides were synthesized using the general procedure of Method II

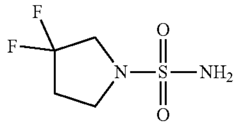

Yield = 76.92%
LC-MS (ESI+) m/z =
187.2 [M+H]+

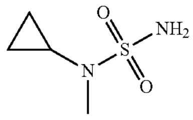

Yield = 97.8%
$^1$H NMR

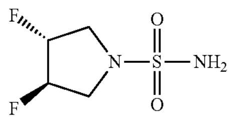

Yield = 33.69%
LC-MS (ESI+) m/z =
187.2 [M+H]+

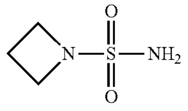

Yield = 65.49%
LC-MS (ESI+) m/z =
137.2 [M+H]+

Example 84
6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-4-oxoquinazoline
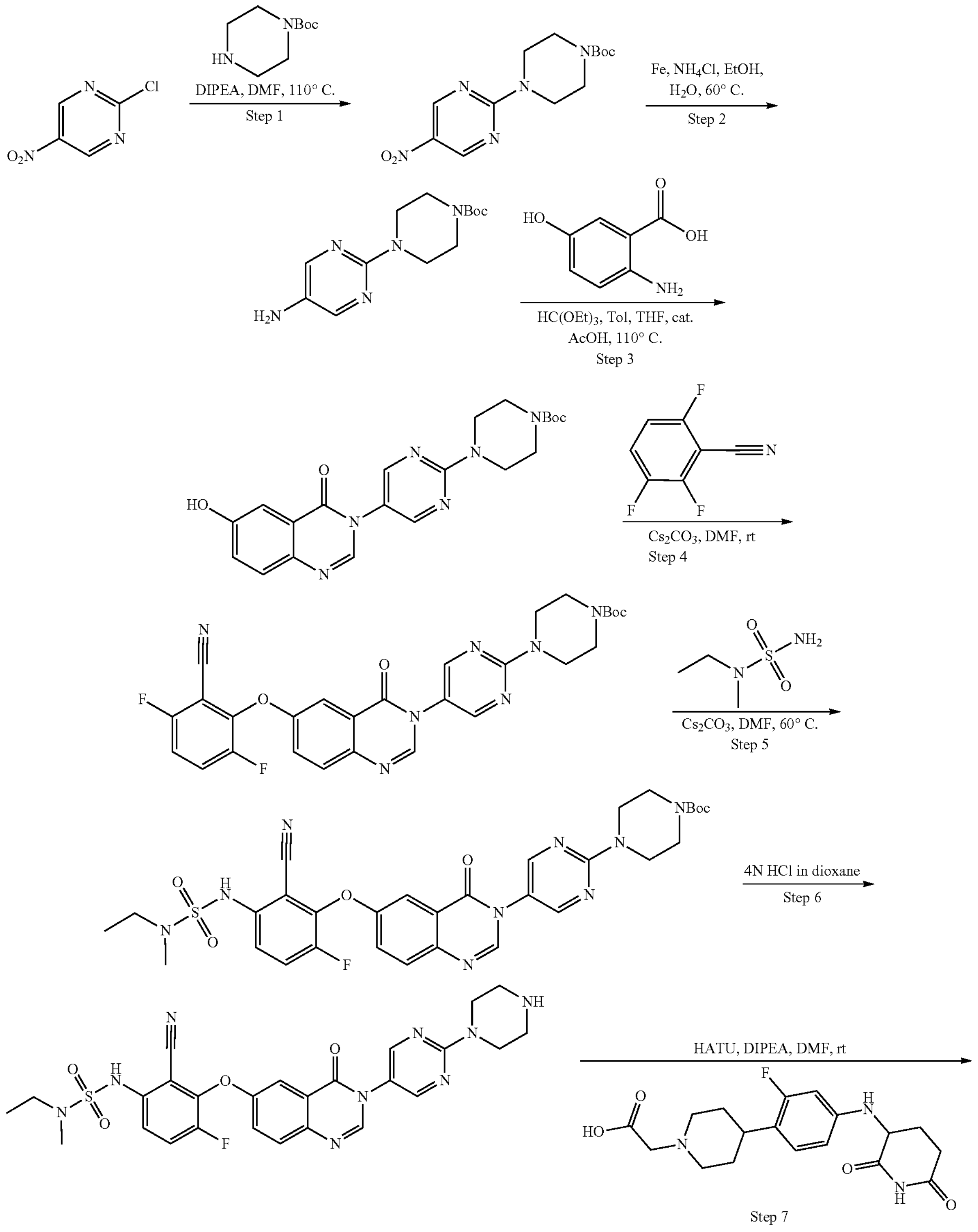

-continued

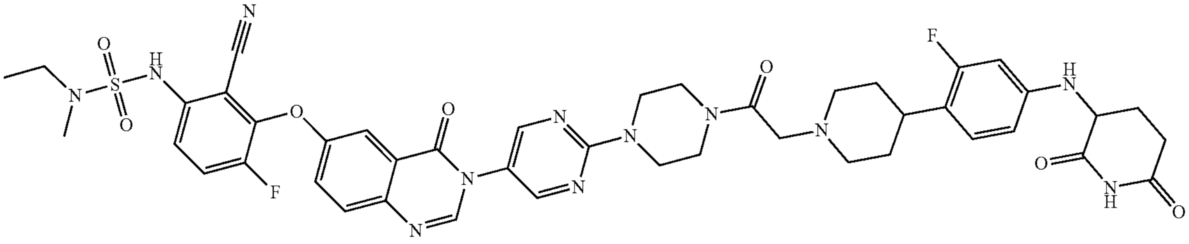 [SMILES: CCN(C)S(=O)(=O)Nc1ccc(F)c(Oc2ccc3ncn(-c4cnc(N5CCN(C(=O)CN6CCC(c7ccc(NC8CCC(=O)NC8=O)cc7F)CC6)CC5)nc4)c(=O)c3c2)c1C#N]

Step 1: To a solution of 2-chloro-5-nitro-pyrimidine (5 g, 31.34 mmol) in NN-dimethylformamide (20 mL) in a sealed tube was added tert-butyl piperazine-1-carboxylate (5.84 g, 31.34 mmol) and N,N-diisopropylethylamine (16.20 g, 125.37 mmol, 21.84 mL) at room temperature under Nitrogen atmosphere. The reaction mixture was stirred at 110° C. for 12 h. After completion of the reaction, the reaction mixture was poured into ice cold water. Obtained solids were filtered through Buchner funnel and dried under reduced pressure to afford tert-butyl 4-(5-nitropyrimidin-2-yl)piperazine-1-carboxylate (3.78 g, 12.15 mmol, 39% yield) as light brown solid crude. LCMS m/z (ESI): 254 $[M+H-{}^{t}Bu]^+$ Step 2: To a solution of tert-butyl 4-(5-nitropyrimidin-2-yl)piperazine-1-carboxylate (3.78 g, 12.22 mmol) in ethanol (32 mL) and water (4 mL) were added iron powder (3.41 g, 61.10 mmol, 434.13 µL) and Ammonium chloride (1.96 g, 36.66 mmol, 1.28 mL) at room temperature under inert atmosphere. The resulting reaction mixture was stirred at 70° C. for 6 h. After completion of the reaction, the reaction mixture was filtered through celite and washed with ethyl acetate (200 mL). The filtrate was washed with water (80 mL), saturated sodium bicarbonate solution (60 mL) and brine (60 mL). The organic layer was dried over sodium sulfate and concentrated under reduced pressure to afford the crude, which was purified by column chromatography on silica gel eluted with 70% ethyl acetate in petroleum ether to afford tert-butyl 4-(5-aminopyrimidin-2-yl)piperazine-1-carboxylate (1.67 g, 4.18 mmol, 34% yield) as a brown solid. LCMS m/z (ESI): 280.2 $[M+H]^+$ Step 3: Quinazolinone intermediate was synthesized by following the general procedure for cyclization (Procedure A-A) using tert-butyl 4-(5-aminopyrimidin-2-yl)piperazine-1-carboxylate (1.4 g, 5.01 mmol), 2-amino-5-hydroxy-benzoic acid (767.49 mg, 5.01 mmol), Triethyl orthoformate (1.49 g, 10.02 mmol, 1.67 mL) and acetic acid (3.01 mg, 50.12 µmol, 2.87 µL). The crude compound was purified by silica gel flash column chromatography with 70% ethyl acetate in petroleum ether as a eluent to afford tert-butyl 4-[5-(6-hydroxy-4-oxo-quinazolin-3-yl)pyrimidin-2-yl]piperazine-1-carboxylate (260 mg, 569.68 µmol, 11% yield) as a light yellow solid LCMS m/z (ESI): 425.2 $[M+H]^+$ Step 4: O-arylated quinazolinone intermediate was synthesized by following the general procedure for O-arylation (Procedure A-B) using tert-butyl 4-[5-(6-hydroxy-4-oxo-quinazolin-3-yl)pyrimidin-2-yl]piperazine-1-carboxylate (280 mg, 659.67 µmol), cesium carbonate (537.34 mg, 1.65 mmol) and 2,3,6-Trifluorobenzonitrile (155.45 mg, 989.51 µmol, 114.30 µL). The resulting crude was purified by silica gel flash column chromatography eluted with 60% ethyl acetate in petroleum ether to afford tert-butyl 4-[5-[6-(2-cyano-3,6-difluoro-phenoxy)-4-oxo-quinazolin-3-yl]pyrimidin-2-yl]piperazine-1-carboxylate (250 mg, 431.85 µmol, 65% yield) as an off-white solid. LCMS m/z (ESI): 562.2 $[M+H]^+$ Step 5: Sulfamoylated quinazolinone intermediate was synthesized by following Procedure A-C using tert-butyl 4-[5-[6-(2-cyano-3,6-difluoro-phenoxy)-4-oxo-quinazolin-3-yl]pyrimidin-2-yl]piperazine-1-carboxylate (220 mg, 391.78 µmol), [methyl(sulfamoyl)amino]ethane (108.28 mg, 783.56 µmol) and cesium carbonate (319.12 mg, 979.4 µmol). The crude compound was purified with 75% ethyl acetate in petroleum ether to afford tert-butyl 4-[5-[6-[2-cyano-3-[[ethyl(methyl)sulfamoyl]amino]-6-fluoro-phenoxy]-4-oxo-quinazolin-3-yl]pyrimidin-2-yl]piperazine-1-carboxylate (120 mg, 155.36 µmol, 40% yield) as an off-white solid. LCMS m/z (ESI): 624.2 $[M+H-{}^{t}Bu]^+$ Step 6: The requisite amine was synthesized by HCl mediated N-Boc deprotection (Procedure A-D). N-Boc deprotection was done on tert-butyl 4-(5-(6-(2-cyano-3-((N-ethyl-N-methylsulfamoyl)amino)-6-fluorophenoxy)-4-oxo-quinazolin-3(4H)-yl)pyrimidin-2-yl)piperazine-1-carboxylate (60 mg, 88.27 µmol), hydrogen chloride solution (4.0M in dioxane, 20 µL) to afford (6-[2-cyano-3-[[ethyl(methyl)sulfamoyl]amino]-6-fluoro-phenoxy]-4-oxo-3-(2-piperazin-1-ylpyrimidin-5-yl)quinazoline (53 mg, 75.71 µmol, 86% yield) as a light brown solid. LCMS m/z (ESI): 580.2 $[M+H]^+$ Step 7: The target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (43 mg, 74.19 µmol), 2-[4-[4-[(2,6-dioxo-3-piperidyl)amino]-2-fluoro-phenyl]-1-piperidyl]acetic acid (26.96 mg, 74.19 µmol), HATU (42.31 mg, 111.28 µmol) and N,N-diisopropylethylamine (47.94 mg, 370.94 µmol, 64.61 µL). The crude compound was purified by reverse phase column chromatography eluted with 64% of acetonitrile in 0.1% formic acid in water to afford 6-[2-cyano-3-[[ethyl(methyl)sulfamoyl]amino]-6-fluoro-phenoxy]-3-[2-[4-[2-[4-[4-[(2,6-dioxo-3-piperidyl)amino]-2-fluoro-phenyl]-1-piperidyl]acetyl]piperazin-1-yl]pyrimidin-5-yl]-4-oxo-quinazoline (3 mg, 2.99 µmol, 4% yield) as off-white solid. LCMS m/z (ESI): 925.2 $[M+H]^+$; $^1$HNMR (400 MHz, DMSO-$d_6$): δ=10.80 (s, 1H), 9.95 (s, 1H), 8.58 (s, 2H), 8.32 (s, 1H), 7.85 (d, J=8.80 Hz, 1H), 7.73 (dd, J=2.80, 8.80 Hz, 1H), 7.36-7.45 (m, 1H), 7.39 (d, J=2.80 Hz, 1H), 6.95-7.05 (m, 1H), 6.49 (d, J=6.80 Hz, 1H), 6.47 (d, J=12.80 Hz, 1H), 6.08 (d, J=6.00 Hz, 1H), 7.61-7.81 (m, 1H), 4.29-4.38 (m, 1H), 3.84-3.95 (m, 4H), 3.57-3.68 (m, 4H), 3.06-3.17 (m, 3H), 2.64-2.75 (m, 3H), 2.51-2.62 (m, 3H), 2.52 (s, 3H), 2.05-2.15 (m, 2H), 1.72-2.01 (m, 6H), 1.03 (t, J=7.20 Hz, 3H).

Example 85
6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluorophenyl]piperidin-1-yl]acetyl]piperazin-1-yl]pyridin-3-yl]-4-oxoquinazoline
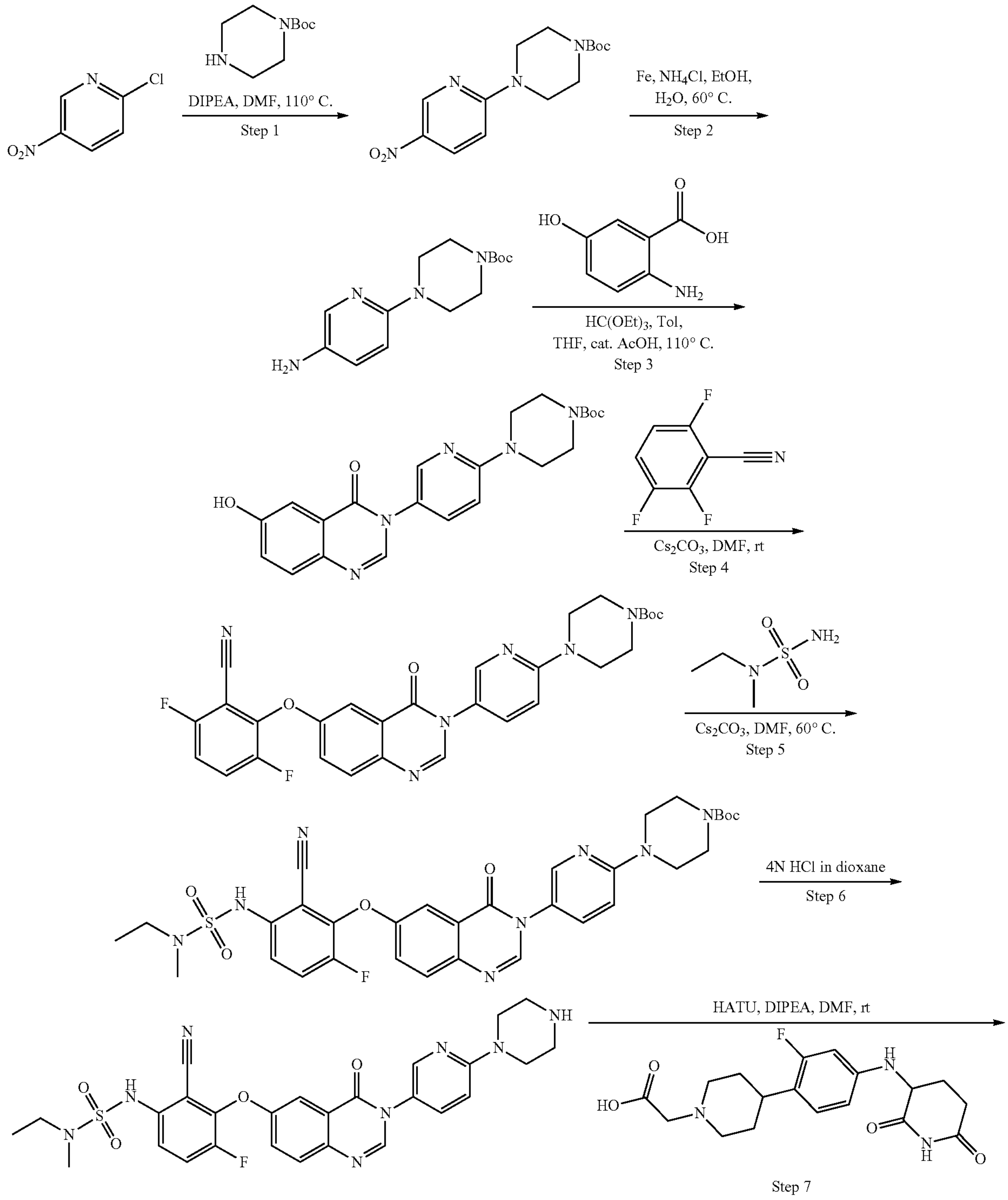

-continued

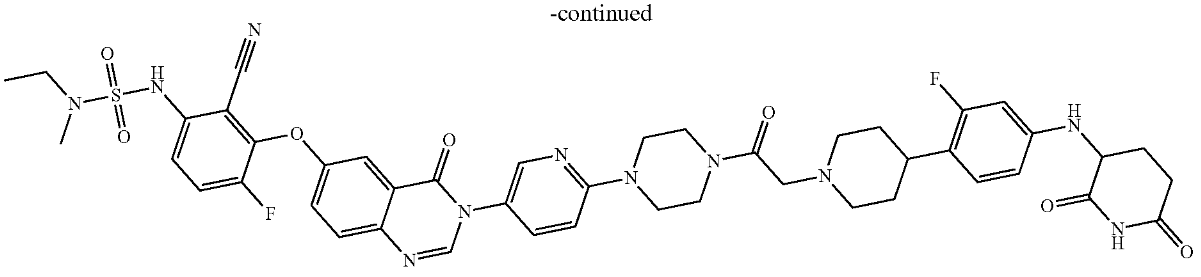

Step 1: To a solution of 2-chloro-5-nitro-pyridine (5 g, 31.54 mmol) in N,N-Dimethylformamide (20 mL) in a sealed tube were added tert-butyl piperazine-1-carboxylate (5.87 g, 31.54 mmol) and N,N-diisopropylethylamine (16.30 g, 126.15 mmol, 21.97 mL) at room temperature under inert atmosphere. The reaction was stirred at 110° C. for 12 h. After completion, the reaction mixture was poured into ice cold water. The resulting solids were filtered in a Buchner funnel and dried under reduced pressure to afford tert-butyl 4-(5-nitro-2-pyridyl)piperazine-1-carboxylate (3.95 g, 12.63 mmol, 40% yield) as a light brown solid crude. LCMS m/z (ESI): 253.2 $[M+H-{}^{t}Bu]^+$ Step 2: To a solution of tert-butyl 4-(5-nitro-2-pyridyl) piperazine-1-carboxylate (3.9 g, 12.65 mmol) in ethanol (32 mL) and water (4 mL) were added iron powder(3.53 g, 63.24 mmol, 449.38 μL) and ammonium chloride (2.03 g, 37.95 mmol, 1.33 mL) at room temperature and the resulting mixture was stirred at 70° C. for 6 h. After completion, the reaction mixture was filtered through celite and washed with ethyl acetate (200 mL). The filtrate was washed with water (80 mL), sodium bicarbonate solution (60 mL) and brine (60 mL). The resulting organic layer was dried over sodium sulfate and concentrated under reduced pressure to afford the crude, which was purified by column chromatography on silica gel eluted with 70% ethyl acetate in petroleum ether to afford tert-butyl 4-(5-amino-2-pyridyl)piperazine-1-carboxylate (3.4 g, 11.85 mmol, 94% yield) as a brown solid. LCMS m/z (ESI): 279 $[M+H]^+$ Step 3: quinazolinone intermediate was synthesized by following general procedure for cyclization (Procedure A-A) using tert-butyl 4-(5-amino-2-pyridyl)piperazine-1-carboxylate (2 g, 7.19 mmol), triethyl orthoformate (2.13 g, 14.37 mmol, 2.39 mL), acetic acid (4.31 mg, 71.85 μmol, 4.11 μL). The crude compound was purified by silica gel flash column chromatography with 40% ethyl acetate in petroleum ether as a eluent to afford tert-butyl 4-[5-(6-hydroxy-4-oxo-quinazolin-3-yl)-2-pyridyl]piperazine-1-carboxylate (460 mg, 1.05 mmol, 15% yield) as a light brown solid LCMS m/z (ESI): 424.2 $[M+H]^+$ Step 4: O-arylated quinazolinone intermediate was synthesized by following general procedure for O-arylation (Procedure A-B) using tert-butyl 4-[5-(6-hydroxy-4-oxo-quinazolin-3-yl)-2-pyridyl]piperazine-1-carboxylate (514 mg, 1.21 mmol), cesium carbonate (988.70 mg, 3.03 mmol) and 2,3,6-trifluorobenzonitrile (286.01 mg, 1.82 mmol, 210.30 μL). The crude compound was purified by silica gel flash column chromatography eluted with 60% ethyl acetate in petroleum ether to afford tert-butyl 4-[5-[6-(2-cyano-3,6-difluoro-phenoxy)-4-oxo-quinazolin-3-yl]-2-pyridyl]piperazine-1-carboxylate (460 mg, 796.00 μmol, 66% yield) as an off-white solid. LCMS m/z (ESI): 505.2 $[M+H-{}^{t}Bu]^+$ Step 5: Sulfamoylated quinazolinone intermediate was synthesized by following Procedure A-C using tert-butyl 4-[5-[6-(2-cyano-3,6-difluoro-phenoxy)-4-oxo-quinazolin-3-yl]-2-pyridyl]piperazine-1-carboxylate (460 mg, 820.62 μmol), [methyl(sulfamoyl)amino]ethane (226.80 mg, 1.64 mmol), cesium carbonate (668.44 mg, 2.05 mmol). The crude compound was purified with 75% ethyl acetate in petroleum ether to afford tert-butyl 4-[5-[6-[2-cyano-3-[[ethyl(methyl)sulfamoyl]amino]-6-fluoro-phenoxy]-4-oxo-quinazolin-3-yl]-2-pyridyl]piperazine-1-carboxylate (110 mg, 115.07 μmol, 14% yield) as light brown solid. LCMS m/z (ESI): 677.2 $[M-H]^-$ Step 6: The requisite amine was synthesized by HCl mediated N-Boc deprotection (Procedure A-D). N-Boc deprotection was done on tert-butyl 4-[5-[6-[2-cyano-3-[[ethyl(methyl)sulfamoyl]amino]-6-fluoro-phenoxy]-4-oxo-quinazolin-3-yl]-2-pyridyl]piperazine-1-carboxylate (110 mg, 162.07 μmol) and hydrogen chloride solution (4.0M in dioxane, 40 μL) to afford crude (6-[2-cyano-3-[[ethyl (methyl)sulfamoyl]amino]-6-fluoro-phenoxy]-4-oxo-3-(6-piperazin-1-yl-3-pyridyl)quinazoline (105 mg, 124.62 μmol, 77% yield) as light brown solid. LCMS m/z (ESI): 579.0 $[M+H]^+$ Step 7: Target compound was prepared via HATU mediated acid-amine coupling reaction (Procedure A-E). Amide coupling was carried out using 6-[2-cyano-3-[[ethyl(methyl) sulfamoyl]amino]-6-fluoro-phenoxy]-4-oxo-3-(6-piperazin-1-yl-3-pyridyl)quinazoline (42.93 mg, 74.19 μmol), 2-[4-[4-[(2,6-dioxo-3-piperidyl)amino]-2-fluoro-phenyl]-1-piperidyl]acetic acid (26.96 mg, 74.19 μmol), HATU (42.31 mg, 111.28 μmol) and N,N-diisopropylethylamine (47.94 mg, 370.94 μmol, 64.61 μL). The crude compound was purified by reverse phase column chromatography eluted with 70% of acetonitrile in 0.1% formic acid in water to afford 6-[2-cyano-3-[[ethyl(methyl)sulfamoyl]amino]-6-fluoro-phenoxy]-3-[6-[4-[2-[4-[4-[(2,6-dioxo-3-piperidyl) amino]-2-fluoro-phenyl]-1-piperidyl]acetyl]piperazin-1-yl]-3-pyridyl]-4-oxo-quinazoline formic acid salt (12 mg, 11.65 μmol, 16% yield) as off-white solid. LCMS m/z (ESI): 924.2 $[M+H]^+$; $^1$HNMR (400 MHz, DMSO-$d_6$): δ=10.81 (s, 1H), 8.28 (s, 1H), 8.25 (s, 1H), 7.83 (d, J=9.20 Hz, 1H), 7.71 (d, J=8.00 Hz, 1H), 7.75 (d, J=9.20 Hz, 1H), 7.53-7.68 (m, 1H), 7.39 (s, 1H), 7.32-7.39 (m, 1H), 7.03 (d, J=8.80 Hz, 1H), 6.96-7.04 (m, 1H), 6.48 (d, J=6.40 Hz, 1H), 6.46 (d, J=12.80 Hz, 1H), 6.07 (d, J=6.00 Hz, 1H), 4.28-4.36 (m, 1H), 4.11 (q, J=4.40 Hz, 1H), 3.61-3.75 (m, 8H), 3.17 (d, J=5.20 Hz, 2H), 3.02-3.12 (m, 2H), 2.61-2.80 (m, 4H), 2.51 (s, 3H), 2.04-2.12 (m, 2H), 1.71-1.95 (m, 6H), 1.02 (t, J=7.20 Hz, 3H).

Example 86
6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]acetyl]piperazin-1-yl]pyrimidin-5-yl]-5-fluoro-4-oxoquinazoline
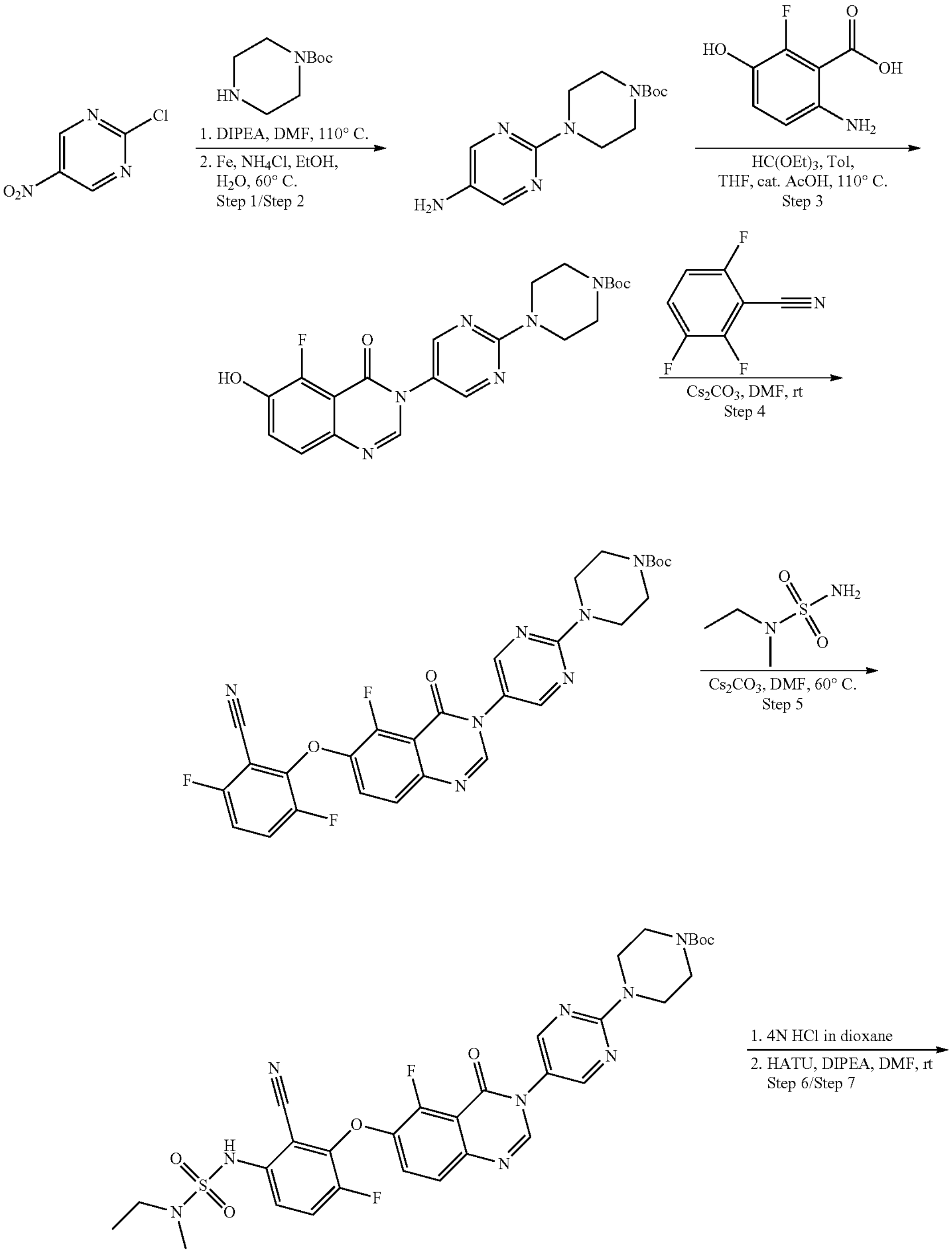

-continued

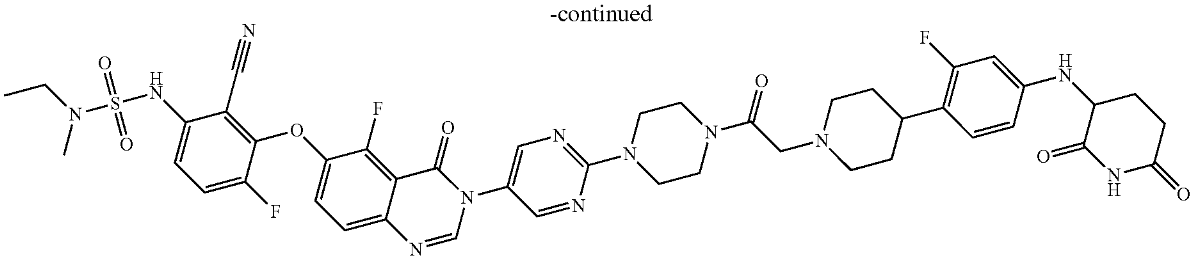

Step 1: Tert-butyl piperazine-1-carboxylate (5.84 g, 31.34 mmol) and N,N-diisopropylethylamine (16.20 g, 125.37 mmol, 21.84 mL) were added to a well-stirred solution of 2-chloro-5-nitro-pyrimidine (5 g, 31.34 mmol) in N,N-dimethylformamide (20 mL) at room temperature under a nitrogen atmosphere. The reaction was stirred at 110° C. for 12 h. After completion of reaction the reaction mixture was poured into ice cold water. The precipitate was filtered off and dried under reduced pressure to afford tert-butyl 4-(5-nitropyrimidin-2-yl)piperazine-1-carboxylate (3.78 g, 12.15 mmol, 39% yield) was get as light brown solid. $^1$HNMR (400 MHz, DMSO-$d_6$): δ=9.14 (s, 2H), 3.92 (t, J=7.20 Hz, 4H), 3.46 (t, J=6.80 Hz, 4H), 1.43 (s, 9H).

Step 2: To a solution of tert-butyl 4-(5-nitropyrimidin-2-yl)piperazine-1-carboxylate (3.78 g, 12.22 mmol) in ethanol (32 mL), water (4 mL) were added iron powder (3.41 g, 61.10 mmol, 434.13 μL), ammonium chloride (1.96 g, 36.66 mmol, 1.28 mL) at room temperature under inert atmosphere. The reaction mixture was stirred at 70° C. for 6 h. After completion, the reaction mixture was filtered through celite and washed with ethyl acetate (200 mL). The filtrate was washed with water (80 mL), sodium bicarbonate solution (60 mL) and brine (60 mL). The organic layer was dried over sodium sulfate and concentrated under reduced pressure to afford crude, which was purified by column chromatography on silica gel eluted with 70% ethyl acetate in petroleum ether to afford tert-butyl 4-(5-aminopyrimidin-2-yl)piperazine-1-carboxylate (1.67 g, 4.18 mmol, 34% yield) as brown solid. LCMS m/z (ESI): 280.2 $[M+H]^+$ Step 3: Quinazolinone intermediate was synthesized by following general procedure for cyclization (Procedure A-A) using tert-butyl 4-(5-aminopyrimidin-2-yl)piperazine-1-carboxylate (1.04 g, 3.73 mmol), 6-amino-2-fluoro-3-hydroxy-benzoic acid (0.58 g, 3.39 mmol) and triethyl orthoformate (753.44 mg, 5.08 mmol, 845.62 μL) to afford tert-butyl 4-[5-(5-fluoro-6-hydroxy-4-oxo-quinazolin-3-yl) pyrimidin-2-yl]piperazine-1-carboxylate (0.950 g, 1.30 mmol, 38% yield) as brown solid. LCMS m/z (ESI−): 441.2 $[M-H]^-$.

Step 4: O-arylated quinazolinone intermediate was synthesized by following general procedure for O-arylation (Procedure A-B) tert-butyl 4-[5-(5-fluoro-6-hydroxy-4-oxo-quinazolin-3-yl)pyrimidin-2-yl]piperazine-1-carboxylate (0.9 g, 2.03 mmol), cesium carbonate (1.99 g, 6.10 mmol) and 2,3,6-trifluorobenzonitrile (319.55 mg, 2.03 mmol). Desired product was purified from crude by column chromatography using 80-90% ethyl acetate in petroleum ether as eluent to afford tert-butyl 4-[5-[6-(2-cyano-3,6-difluoro-phenoxy)-5-fluoro-4-oxo-quinazolin-3-yl]pyrimidin-2-yl] piperazine-1-carboxylate (0.210 g, 362.36 μmol, 18% yield) as light brown liquid. LCMS m/z (ESI): 524.3 $[M+H-56]^+$.

Step 5: Sulfamoylated quinazolinone intermediate was synthesized by following Procedure A-C using tert-butyl 4-[5-[6-(2-cyano-3,6-difluoro-phenoxy)-5-fluoro-4-oxo-quinazolin-3-yl]pyrimidin-2-yl]piperazine-1-carboxylate (0.21 g, 362.36 μmol), cesium carbonate (295.16 mg, 905.91 μmol) and [methyl(sulfamoyl)amino]ethane (75.11 mg, 543.54 μmol) to afford crude tert-butyl 4-[5-[6-[2-cyano-3-[[ethyl(methyl)sulfamoyl]amino]-6-fluoro-phenoxy]-5-fluoro-4-oxo-quinazolin-3-yl]pyrimidin-2-yl]piperazine-1-carboxylate (0.14 g, 162.59 μmol, 45% yield) as brown solid. LCMS m/z (ESI): 696.0 $[M-H]^-$ Step 6: The requisite amine was synthesized by hydrogen chloride-mediated N-Boc deprotection (Procedure A-D). N-tert-butoxycarbamate deprotection was done on tert-butyl 4-[5-[6-[2-cyano-3-[[ethyl(methyl)sulfamoyl]amino]-6-fluoro-phenoxy]-5-fluoro-4-oxo-quinazolin-3-yl]pyrimidin-2-yl]piperazine-1-carboxylate (0.12 g, 171.99 μmol) using a hydrogen chloride solution (4M in 1,4-dioxane, 40 μL,) to afford crude 6-[2-cyano-3-[[ethyl(methyl)sulfamoyl] amino]-6-fluoro-phenoxy]-5-fluoro-4-oxo-3-(2-piperazin-1-ylpyrimidin-5-yl)quinazoline hydrochloride (0.12 g, 169.57 μmol, 99% yield) as a yellow solid. LCMS m/z (ESI): 598.0 $[M+H]^+$.

Step 7: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]acetic acid (87.56 mg, 240.97 μmol), N,N-diisopropylethylamine (129.76 mg, 1.00 mmol, 174.88 μL), HATU (83.99 mg, 220.89 μmol) and 6-[2-cyano-3-[[ethyl(methyl)sulfamoyl] amino]-6-fluoro-phenoxy]-5-fluoro-4-oxo-3-(2-piperazin-1-ylpyrimidin-5-yl)quinazoline (0.12 g, 200.80 μmol). The desired product was purified from crude by reverse phase column chromatography (0.1% formic acid in water:acetonitrile) and fractions were lyophilized to afford 6-[2-cyano-3-[[ethyl(methyl)sulfamoyl]amino]-6-fluoro-phenoxy]-3-[2-[4-[2-[4-[4-[(2,6-dioxo-3-piperidyl)amino]-2-fluoro-phenyl]-1-piperidyl]acetyl]piperazin-1-yl]pyrimidin-5-yl]-5-fluoro-4-oxo-quinazoline (18.26 mg, 18.95 μmol, 9% yield) as an off-white solid. LCMS m/z (ESI): 943.0 $[M+H]^+$; $^1$HNMR (400 MHz, DMSO-$d_6$): δ=10.79 (s, 1H), 9.86 (s, 1H), 8.58 (d, J=5.60 Hz, 2H), 8.31 (s, 1H), 7.57 (s, 2H), 7.45-7.56 (m, 1H), 7.31 (d, J=4.80 Hz, 1H), 7.01 (t, J=7.60 Hz, 1H), 6.49 (d, J=7.20 Hz, 1H), 6.46 (d, J=12.00 Hz, 1H), 6.06 (d, J=7.60 Hz, 1H), 4.28-4.38 (m, 1H), 3.82-3.98 (m, 4H), 3.58-3.70 (m, 4H), 3.15-3.40 (m, 4H), 3.02-3.11 (m, 2H), 2.60-2.82 (m, 3H), 2.66 (s, 3H), 2.48-2.60 (m, 2H), 2.02-2.15 (m, 1H), 1.69-1.91 (m, 5H), 1.04 (t, J=7.20 Hz, 3H).

Example 87

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluoro-6-methoxyphenyl]piperidin-1-yl]acetyl]piperazin-1-yl]pyridin-3-yl]-4-oxoquinazoline

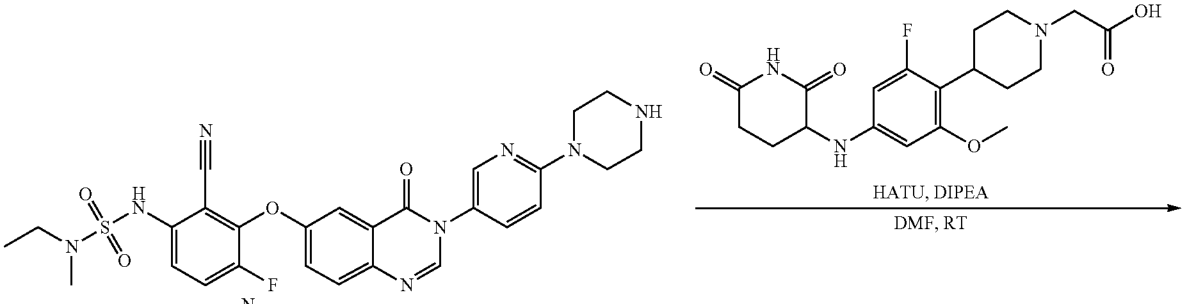

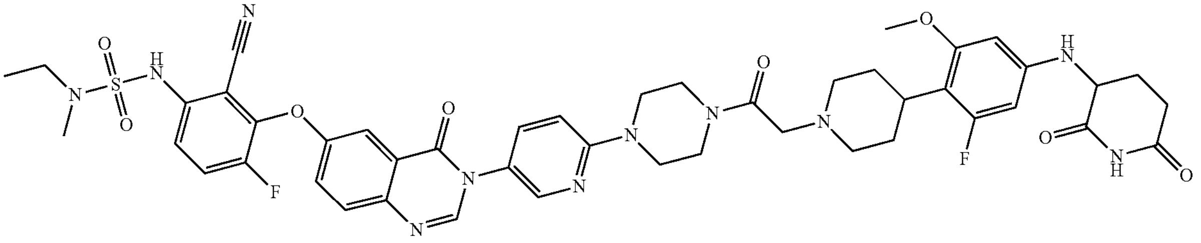

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(6-piperazin-1-yl-3-pyridyl)quinazoline (85 mg, 146.90 μmol), 2-[4-[4-[(2,6-dioxo-3-piperidyl)amino]-2-fluoro-6-methoxy-phenyl]-1-piperidyl]acetic acid (57.79 mg, 146.90 μmol), NN-diisopropylethylamine (75.94 mg, 587.61 μmol, 102.35 μL) and HATU (55.86 mg, 146.90 μmol) to afford 6-[2-cyano-3-[[ethyl(methyl)sulfamoyl]amino]-6-fluoro-phenoxy]-3-[6-[4-[2-[4-[4-[(2,6-dioxo-3-piperidyl)amino]-2-fluoro-6-methoxy-phenyl]-1-piperidyl]acetyl]piperazin-1-yl]-3-pyridyl]-4-oxo-quinazoline (33 mg, 34.56 μmol, 24% yield) as an off-white solid. LCMS m/z (ESI): 954.0 [M+H]; HNMR (400 MHz, DMSO-$d_6$): =10.80 (s, 1H), 9.83 (s, 1H), 8.28 (s, 1H), 8.25 (d, J=2.80 Hz, 3H), 7.83 (d, J=8.80 Hz, 1H), 7.75 (dd, J=2.40, 9.00 Hz, 1H), 7.70 (dd, J=2.80, 9.00 Hz, 1H), 7.57 (s, 1H), 7.39 (d, J=2.80 Hz, 1H), 7.35 (s, 1H), 7.03 (d, J=9.20 Hz, 1H), 6.18-6.05 (m, 2H), 4.45 (t, J=20.00 Hz, 1H), 3.72 (s, 3H), 3.71-3.68 (m, 3H), 3.64-3.61 (m, 6H), 3.07-3.02 (m, 3H), 2.74-2.70 (m, 1H), 2.68 (q, J=2.00 Hz, 2H) 2.60-2.59 (m, 1H), 2.34-2.33 (m, 2H), 2.09-2.06 (m, 2H), 1.60-1.58 (m, 2H), 1.03 (t, J=7.20 Hz, 3H).

Example 88

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluoro-5-methoxyphenyl]piperidin-1-yl]acetyl]piperazin-1-yl]pyrimidin-5-yl]-4-oxoquinazoline

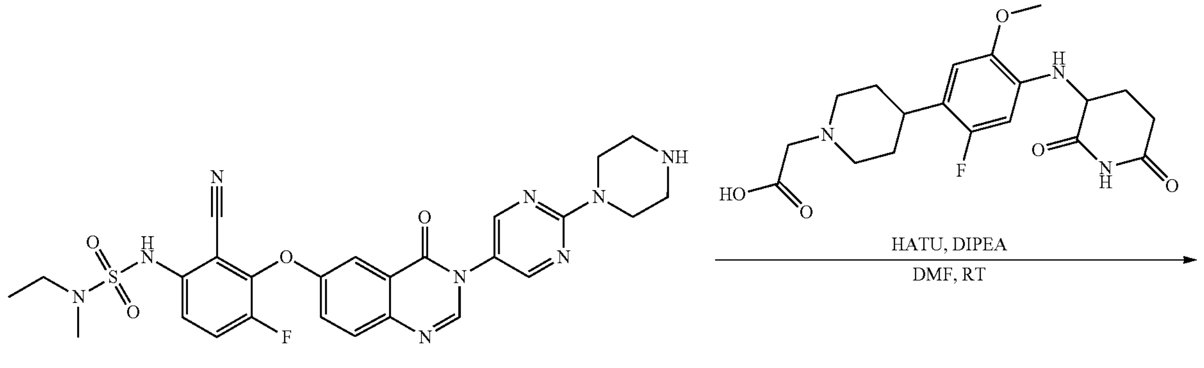

-continued

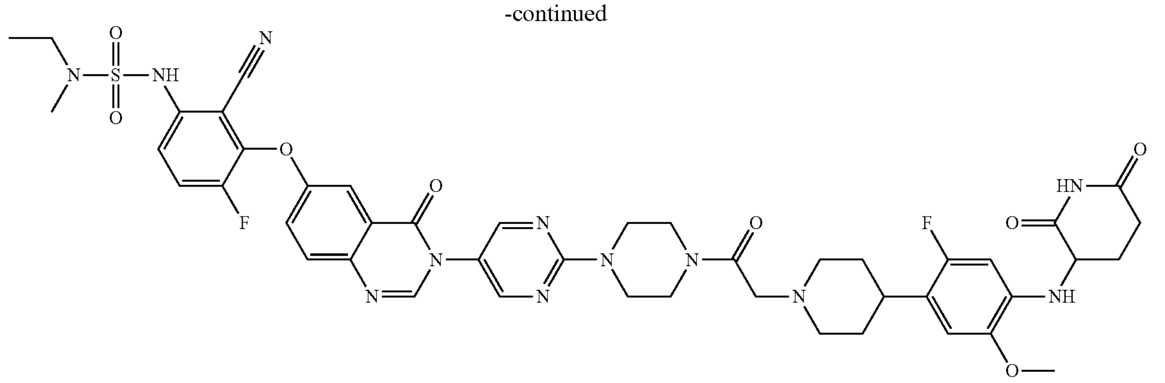

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (100 mg, 172.53 μmol), 2-[4-[4-[(2,6-dioxo-3-piperidyl)amino]-2-fluoro-5-methoxy-phenyl]-1-piperidyl]acetic acid (67.88 mg, 172.53 μmol), N,N-diisopropylethylamine (89.19 mg, 690.13 μmol, 120.21 μL) and HATU (65.60 mg, 172.53 μmol) to afford 6-[2-cyano-3-[[ethyl(methyl)sulfamoyl]amino]-6-fluoro-phenoxy]-3-[2-[4-[2-[4-[4-[(2,6-dioxo-3-piperidyl)amino]-2-fluoro-5-methoxy-phenyl]-1-piperidyl]acetyl]piperazin-1-yl]pyrimidin-5-yl]-4-oxo-quinazoline (35 mg, 36.31 μmol, 21% yield) as an off-white solid. LCMS m/z (ESI): 955.0 $[M+H]^+$; $^1$H-NMR (400 MHz, DMSO-$d_6$): δ=10.87 (s, 1H), 9.84 (s, 1H), 8.57 (s, 2H), 8.30 (s, 1H), 7.82 (d, J=8.80 Hz, 1H), 7.68 (dd, J=2.80, 8.80 Hz, 1H), 7.40 (s, 1H), 7.37 (d, J=2.80 Hz, 1H), 7.27 (s, 1H), 6.70 (d, J=6.80 Hz, 1H), 6.49 (d, J=12.80 Hz, 1H), 5.33-5.32 (m, 1H), 4.31 (q, J=6.40 Hz, 1H), 3.93-3.86 (m, 2H), 3.85-3.79 (m, 2H), 3.81 (s, 3H), 3.68-3.59 (m, 5H), 3.08-3.01 (m, 2H), 2.82-2.76 (m, 2H), 2.68-2.61 (m, 5H), 2.13-2.11 (m, 2H), 1.96-1.92 (m, 4H), 1.77-1.76 (m, 2H), 1.02 (t, J=7.20 Hz, 3H)

Example 89

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluoro-6-methoxyphenyl]piperidin-1-yl]acetyl]piperazin-1-yl]pyrimidin-5-yl]-4-oxoquinazoline

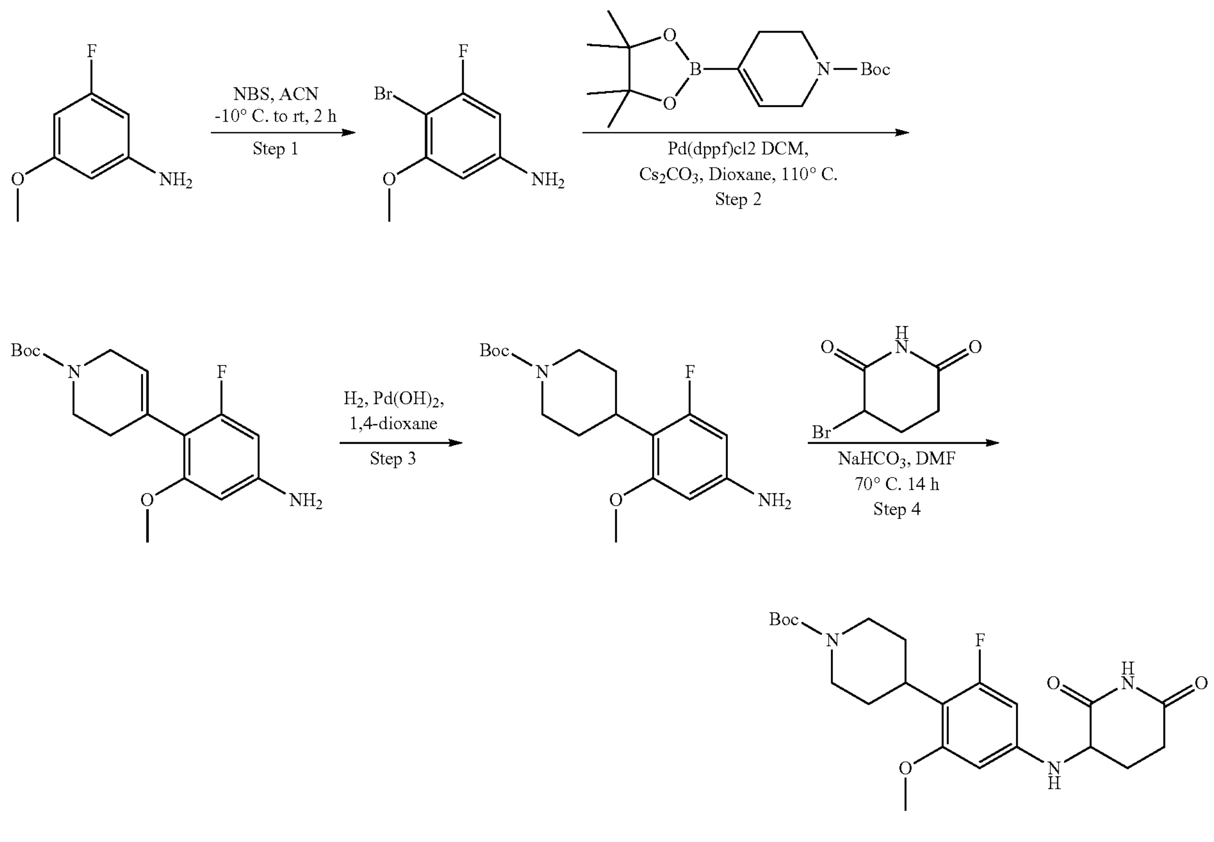

-continued

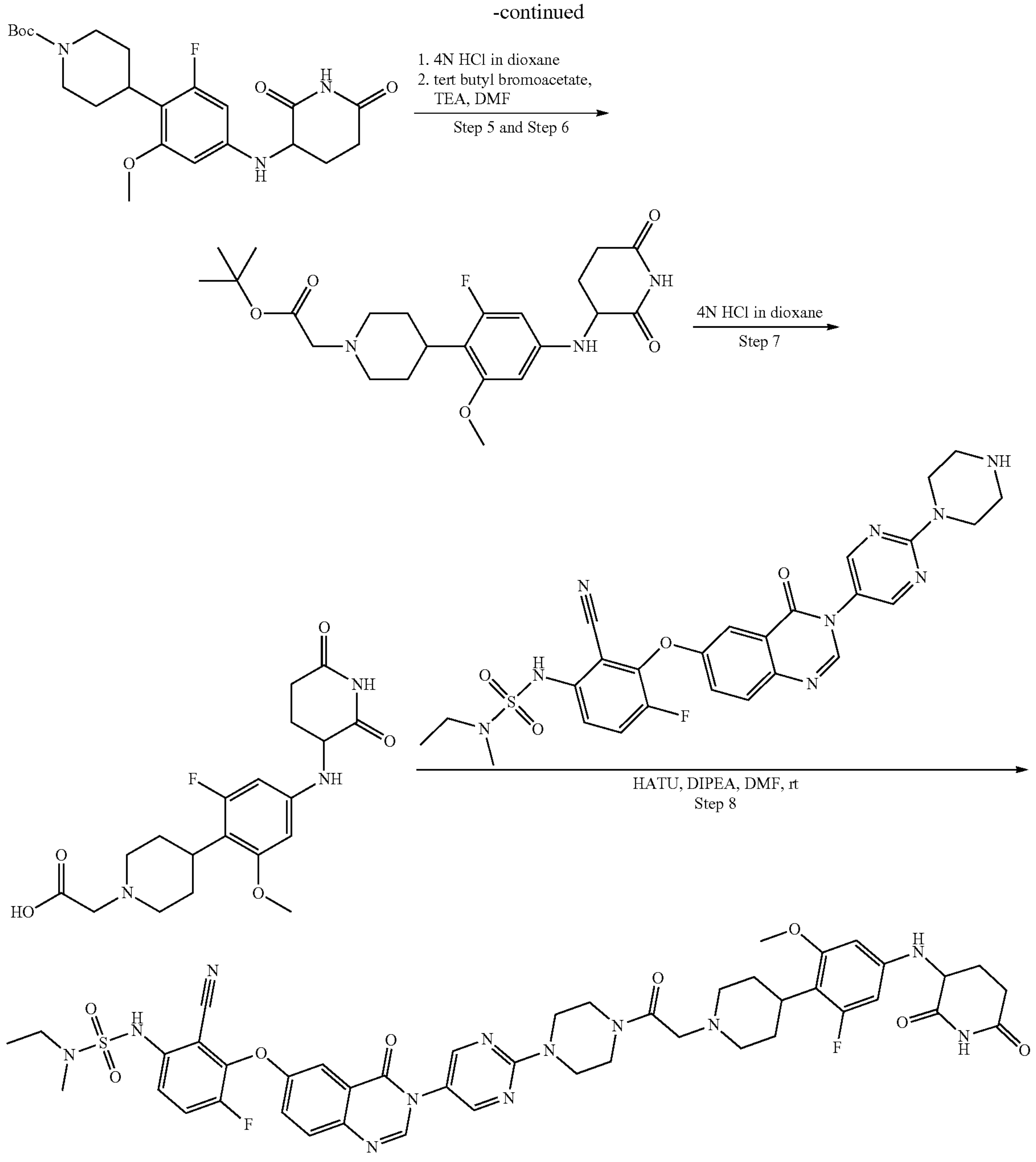

Step 1: To a solution of 3-fluoro-5-methoxy-aniline (2 g, 14.17 mmol) in acetonitrile (20 mL) was added 1-bromopyrrolidine-2,5-dione (2.52 g, 14.17 mmol, 1.20 mL) at −10° C. under a nitrogen atmosphere. The reaction mixture was stirred at room temperature for 2 h. The reaction mixture was diluted with water (70 mL), extracted with ethyl acetate (2×75 mL). The combined organic layers were dried over sodium sulfate and concentrated under reduced pressure to afford crude compound. The resulting crude product was purified by silica gel flash column chromatography eluted with 70% ethyl acetate in petroleum ether to afford 4-bromo-3-fluoro-5-methoxy-aniline (2.2 g, 9.88 mmol, 70% yield) as an off-white solid. LCMS m/z (ESI): 220.0 $[M+H]^+$.

Step 2: To a stirred solution of 4-bromo-3-fluoro-5-methoxy-aniline (2.2 g, 10.00 mmol) in 1,4-dioxane (20 mL) were added tert-butyl 4-(4,4,5,5-tetramethyl-1,3,2-dioxaborolan-2-yl)-3,6-dihydro-2H-pyridine-1-carboxylate (3.71 g, 12.00 mmol), cesium carbonate (9.77 g, 29.99 mmol) and Pd(dppf)$Cl_2$·dichloromethane (816.49 mg, 999.82 μmol). The reaction mixture and stirred at 120° C. for 16 h. The reaction mixture was diluted with water (30 mL) and extracted with ethyl acetate (2×40 mL). The combined organic layer was dried over sodium sulfate, filtered and concentrated under reduced pressure. The obtained crude was purified by silica gel flash column chromatography eluted with 30-45% ethyl acetate in petroleum ether to afford tert-butyl 4-(4-amino-2-fluoro-6-methoxy-phenyl)-3,6-dihydro-2H-pyridine-1-carboxylate (3.0 g, 8.79 mmol, 88% yield) as a light brown solid. LCMS m/z (ESI): 223.2 $[M+H-CO_2{}^tBu]^+$ Step 3: To a degassed solution of tert-butyl 4-(4-amino-2-fluoro-6-methoxy-phenyl)-3,6-dihydro-2H-pyridine-1-carboxylate (3 g, 9.31 mmol) in 1,4-dioxane (30 mL) was added palladium(II) hydroxide (20% on charcoal, wet, 1.31 g, 9.31 mmol) under $N_2$ atmosphere. The resulting mixture was stirred under $H_2$ bladder pressure at room temperature for 14 h. The reaction mixture was filtered through celite and the filtrate was concentrated under reduced pressure to afford tert-butyl 4-(4-amino-2-fluoro-6-methoxy-phenyl)piperidine-1-carboxylate (2.8 g, 8.29 mmol, 89% yield) as a light yellow solid. LCMS m/z (ESI): 225.2[M+H−$CO_2{}^tBu$]$^+$ Step 4: A solution of tert-butyl 4-(4-amino-2-fluoro-6-methoxy-phenyl)piperidine-1-carboxylate (500 mg, 1.54 mmol) in N,N-dimethylformamide (10 mL) was taken in sealed tube and added sodium bicarbonate (453.19 mg, 5.39 mmol, 209.81 μL), 3-bromopiperidine-2,6-dione (739.89 mg, 3.85 mmol) at room temperature. The reaction mixture was stirred at 70° C. for 14 h. The reaction mixture was diluted with water (20 mL) and extracted with ethyl acetate (60 mL). The organic layer was washed with brine solution (30 mL), dried over sodium sulfate, and concentrated under reduced pressure to afford crude. The crude product was purified by silica gel flash column chromatography eluted with 60% ethyl acetate in petroleum ether to afford tert-butyl 4-[4-[(2,6-dioxo-3-piperidyl)amino]-2-fluoro-6-methoxy-phenyl]piperidine-1-carboxylate (520 mg, 1.15 mmol, 74% yield) as a light green solid. LCMS m/z (ESI): 380.5 [M+H−$^t$Bu]$^+$.

Step 5: To a solution of tert-butyl 4-[4-[(2,6-dioxo-3-piperidyl)amino]-2-fluoro-6-methoxy-phenyl]piperidine-1-carboxylate (520 mg, 1.19 mmol) in 1,4-dioxane (5 mL), was added hydrogen chloride solution (4M in dioxane, 6 mL) at 0° C. and stirred at room temperature for 2 h. After completion of the reaction, the reaction mixture was concentrated under reduced pressure to afford 3-[3-fluoro-5-methoxy-4-(4-piperidyl)anilino]piperidine-2,6-dione hydrochloride (410 mg, 1.03 mmol, 86% yield) as an off-white solid. LCMS m/z (ESI): 336.2 [M+H]$^+$.

Step 6: To a solution of 3-[3-fluoro-5-methoxy-4-(4-piperidyl)anilino]piperidine-2,6-dione (470 mg, 1.40 mmol) in N,N-dimethylformamide (3 mL) were added triethylamine (567.24 mg, 5.61 mmol, 781.33 μL), tert-butyl 2-bromoacetate (273.35 mg, 1.40 mmol, 205.53 μL) at 0° C. and stirred at room temperature for 14 h. After completion of the reaction, the reaction mixture was diluted with water (15 mL) and extracted with ethyl acetate (40 mL). The organic layer was washed with brine solution (20 mL), dried over sodium sulfate, filtered and concentrated under reduced pressure to afford crude compound, which was purified by silica gel flash column chromatography eluted with 30-45% ethyl acetate petroleum ether to afford tert-butyl 2-[4-[4-[(2,6-dioxo-3-piperidyl)amino]-2-fluoro-6-methoxy-phenyl]-1-piperidyl]acetate (250 mg, 546.03 μmol, 39% yield) as a light green solid. LCMS m/z (ESI): 450.2 [M+H]$^+$.

Step 7: To a stirred solution of tert-butyl 2-[4-[4-[(2,6-dioxo-3-piperidyl)amino]-2-fluoro-6-methoxy-phenyl]-1-piperidyl]acetate (250 mg, 556.16 μmol) in dichloromethane (5 mL) was added hydrogen chloride solution in dioxane (4M in 1,4-dioxane, 4 mL) at 5° C. under nitrogen atmosphere. The reaction mixture was stirred at room temperature for 12 h. After completion of the reaction, the reaction mixture was concentrated under reduced pressure to afford crude 2-[4-[4-[(2,6-dioxo-3-piperidyl)amino]-2-fluoro-6-methoxy-phenyl]-1-piperidyl]acetic acid (140 mg, 299.63 μmol, 54% yield). LCMS m/z (ESI): 394.7 [M+H]$^+$.

Step 8: Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (90 mg, 155.28 μmol), 2-[4-[4-[(2,6-dioxo-3-piperidyl)amino]-2-fluoro-6-methoxy-phenyl]-1-piperidyl]acetic acid (61.09 mg, 155.28 μmol), N,N-diisopropylethylamine (100.34 mg, 776.39 μmol, 135.23 μL) and HATU (64.95 mg, 170.81 μmol) to afford 6-[2-cyano-3-[[ethyl(methyl)sulfamoyl]amino]-6-fluoro-phenoxy]-3-[2-[4-[2-[4-[4-[(2,6-dioxo-3-piperidyl)amino]-2-fluoro-6-methoxy-phenyl]-1-piperidyl]acetyl]piperazin-1-yl]pyrimidin-5-yl]-4-oxo-quinazoline (17.99 mg, 18.72 μmol, 12% yield) as an off-white solid. LCMS m/z (ESI): 955.0[M+H]$^+$. $^1$HNMR (400 MHz, DMSO-$d_6$): δ=10.81 (s, 1H), 9.86 (s, 1H), 8.58 (s, 2H), 8.31 (s, 1H), 7.83 (d, J=8.80 Hz, 1H), 7.70 (dd, J=2.80, 8.80 Hz, 1H), 7.52-7.31 (m, 2H), 7.38 (d, J=2.80 Hz, 1H), 6.17 (s, 1H), 6.06 (d, J=13.60 Hz, 2H), 4.37-4.29 (m, 1H), 3.91-3.83 (m, 4H), 3.73 (s, 3H), 3.69-3.58 (m, 4H), 3.14-2.93 (m, 4H), 2.76-2.67 (m, 1H), 2.63-2.56 (m, 6H), 2.10-2.07 (m, 4H), 1.89-1.84 (m, 2H), 1.82-1.56 (m, 2H), 1.02 (t, J=7.20 Hz, 3H).

Example 90

6-[2-cyano-3-[[ethyl(methyl)sulfamoyl]amino]-6-fluorophenoxy]-3-[6-[4-[2-[4-[4-[(2,6-dioxopiperidin-3-yl)amino]-2-fluoro-5-methoxyphenyl]piperidin-1-yl]acetyl]piperazin-1-yl]pyridin-3-yl]-4-oxoquinazoline

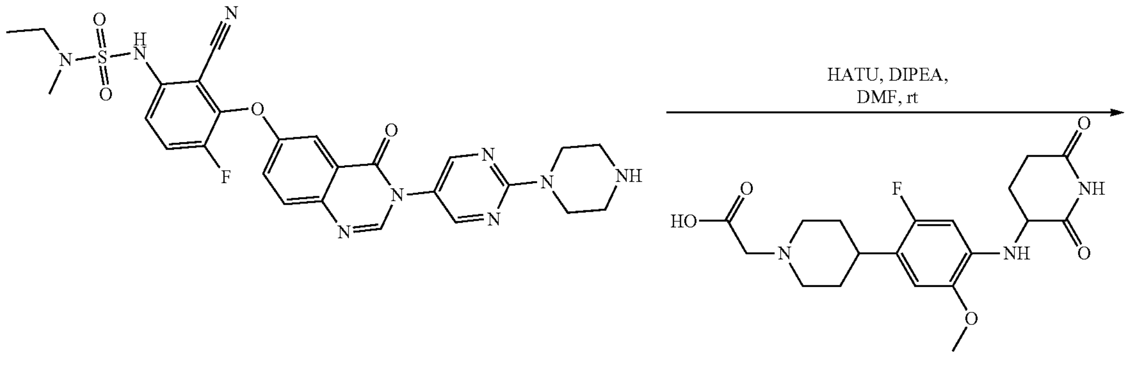

-continued

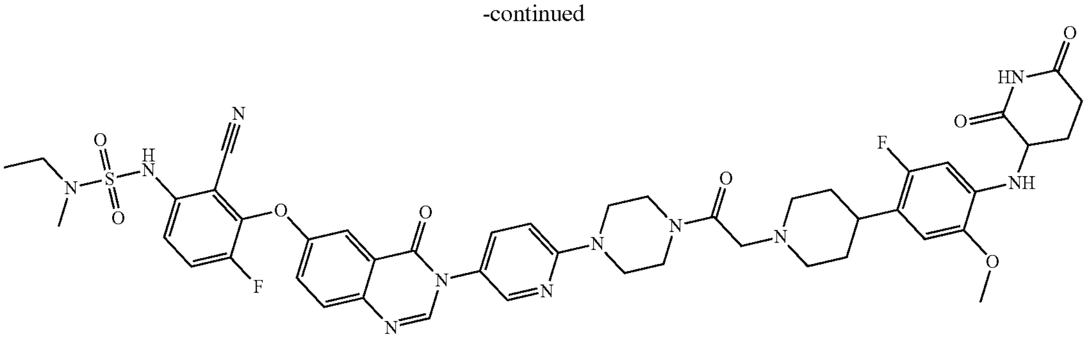

Target compound was prepared via HATU mediated acid-amine coupling reaction (Procedure A-E). Amide coupling was carried out using 2-[4-[4-[(2,6-dioxo-3-piperidyl)amino]-2-fluoro-5-methoxy-phenyl]-1-piperidyl]acetic acid (82.27 mg, 209.12 μmol), N,N-diisopropylethylamine (245.70 mg, 1.90 mmol, 331.13 μL), HATU (79.51 mg, 209.12 μmol) and 6-[2-cyano-3-[[ethyl(methyl)sulfamoyl]amino]-6-fluoro-phenoxy]-4-oxo-3-(6-piperazin-1-yl-3-pyridyl)quinazoline (0.11 g, 190.11 μmol). The desired product was purified from crude by reverse phase column chromatography (0.1% ammonium acetate in water:acetonitrile) and fractions were lyophilized to afford 6-[2-cyano-3-[[ethyl(methyl)sulfamoyl]amino]-6-fluoro-phenoxy]-3-[6-[4-[2-[4-[4-[(2,6-dioxo-3-piperidyl)amino]-2-fluoro-5-methoxy-phenyl]-1-piperidyl]acetyl]piperazin-1-yl]-3-pyridyl]-4-oxo-quinazoline (25.78 mg, 26.53 μmol, 14% yield) as an off-white solid. LCMS m/z (ESI): 954.2 [M+H]; $^1$HNMR (400 MHz, DMSO-$d_6$): δ=10.86 (s, 1H), 8.26 (s, 1H), 8.24 (d, J=2.80 Hz, 1H), 7.81 (d, J=8.80 Hz, 1H), 7.74 (dd, J=2.40, 9.00 Hz, 1H), 7.66 (dd, J=3.20, 9.00 Hz, 1H), 7.38 (d, J=2.80 Hz, 1H), 7.30-7.41 (m, 1H), 7.22-7.28 (m, 1H), 7.02 (d, J=8.80 Hz, 1H), 6.70 (d, J=7.20 Hz, 1H), 6.49 (d, J=12.80 Hz, 1H), 5.29 (d, J=6.40 Hz, 1H), 4.25-4.35 (m, 1H), 3.80 (s, 3H), 3.65-3.75 (m, 4H), 3.58-3.65 (m, 4H), 3.22-3.41 (m, 2H), 2.93-3.10 (m, 4H), 2.70-2.85 (m, 1H), 2.67 (s, 3H), 2.41-2.65 (m, 2H), 2.05-2.31 (m, 2H), 1.85-2.01 (m, 2H), 1.60-1.85 (m, 4H), 1.02 (t, J=7.20 Hz, 3H).

Example 91

6-[2-cyano-3-[[ethyl(methyl)sulfamoyl]amino]-6-fluorophenoxy]-3-[2-[4-[2-[4-[4-[(2,6-dioxopiperidin-3-yl)amino]-2-fluorophenyl]piperidin-1-yl]-3-hydroxypropanoyl]piperazin-1-yl]pyrimidin-5-yl]-4-oxoquinazoline

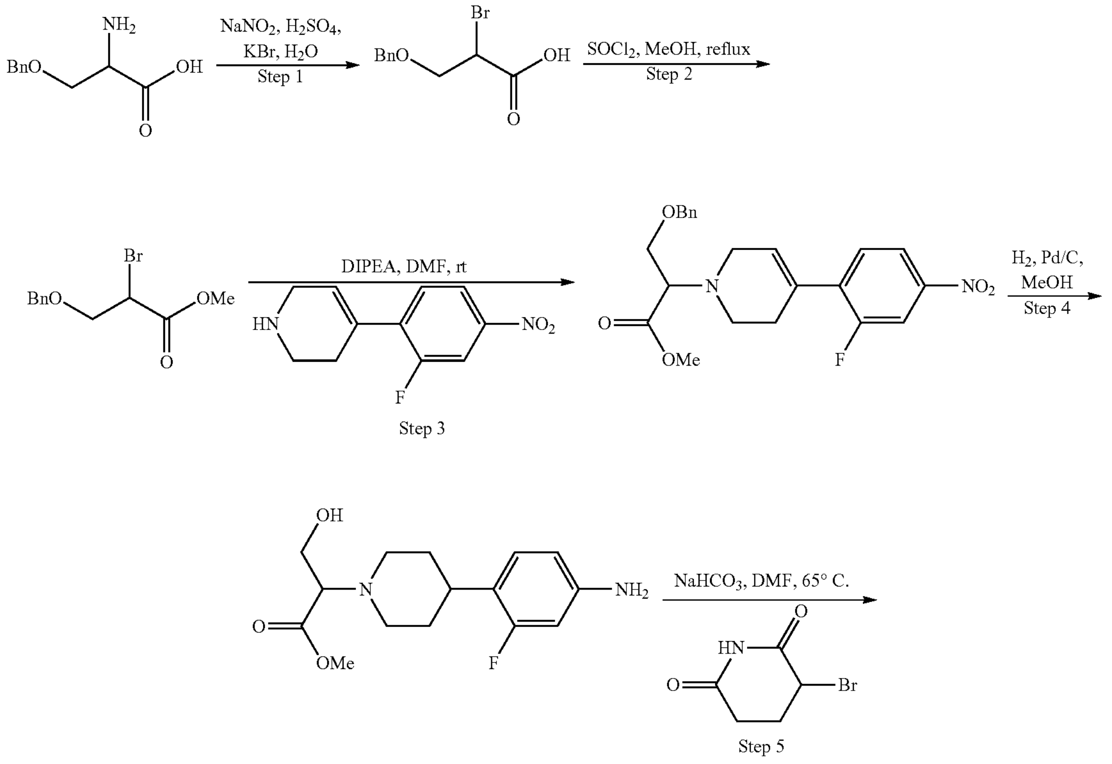

-continued

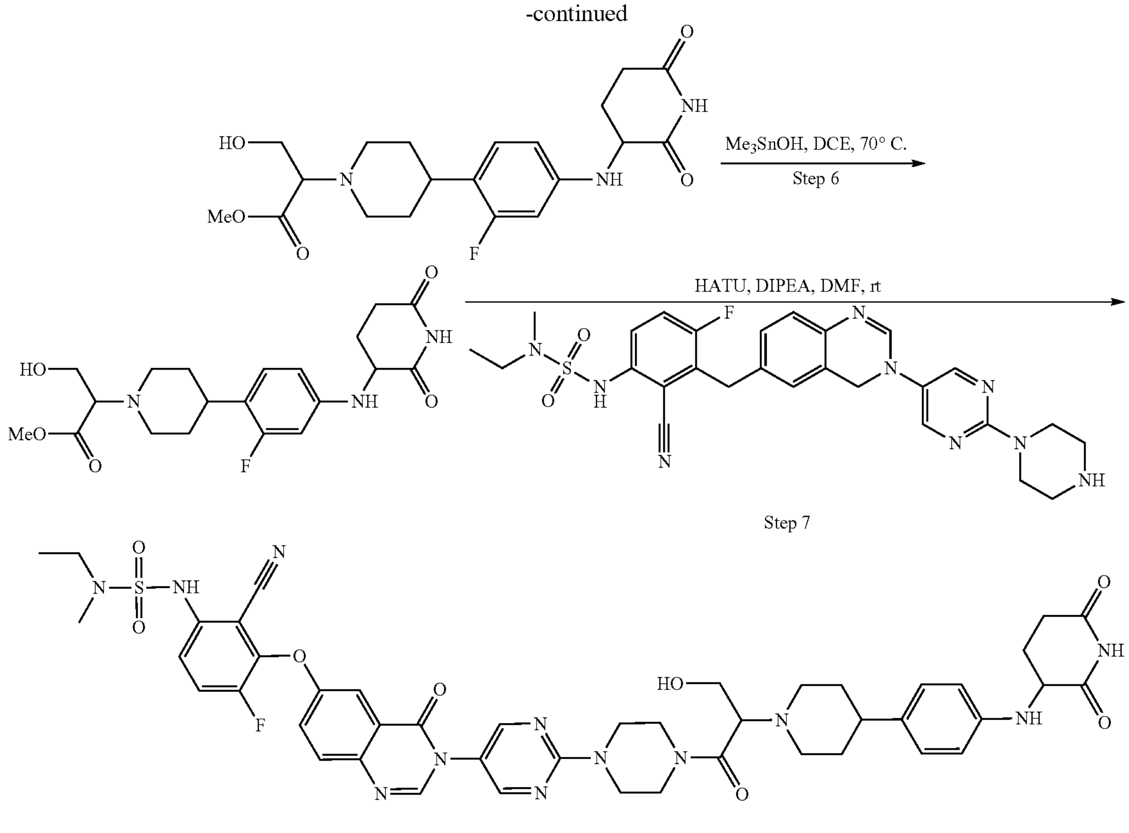

Step 1: To a stirred solution of 2-amino-3-benzyloxy-propanoic acid (3 g, 15.37 mmol) and potassium bromide (6.40 g, 53.79 mmol, 2.33 mL) in ice cold water (15 mL) was added the solution of sodium nitrite (1.59 g, 23.05 mmol, 732.93 μL) in water (15 mL) drop wise at −4° C. under nitrogen atmosphere. The reaction mixture was stirred at 0° C. for about 45 min, and then stirred at room temperature for 1 hr. After the completion, the reaction mixture was diluted with water (50 mL) and extracted with ethyl acetate (3×50 mL). The organic layer was washed with brine solution (20 mL), dried over sodium sulfate, filtered, and concentrated to afford crude. The crude compound was purified by silica gel flash column chromatography, while the desired compound was eluted with 30-45% ethyl acetate in pet ether to afford 3-benzyloxy-2-bromo-propanoic acid (2.3 g, 8.43 mmol, 55% yield) as a brown viscous. LCMS m/z (ESI): 259.20 $[M-H]^-$ Step 2: To a stirred solution of 3-benzyloxy-2-bromo-propanoic acid (1.8 g, 6.95 mmol) in methanol (10 mL) was added thionyl chloride (826.51 mg, 6.95 mmol, 516.57 μL) at 0° C. The reaction mixture was stirred at room temperature under nitrogen atmosphere for 14 h. After completion of the reaction, the reaction mixture was diluted with water (10 mL) and extracted with ethyl acetate (3×20 mL). The combined organic layers were dried over sodium sulfate, filtered, and concentrated under vacuum to afford crude. The crude compound was purified by silica gel flash column chromatography, compound eluted with 30-45% ethyl acetate in pet ether to afford methyl 3-benzyloxy-2-bromo-propanoate (1.8 g, 6.46 mmol, 93% yield) as a brown solid. $^1$HNMR (400 MHz, DMSO-$d_6$): δ=7.37-7.30 (m, 5H), 4.76 (t, J=8.00 Hz, 1H), 4.56 (s, 2H), 3.89 (dd, J=9.60, 14.20 Hz, 1H), 3.77 (dd, J=8.00, 14.00 Hz, 1H), 3.72 (s, 3H).

Step 3: To a stirred solution of methyl 3-benzyloxy-2-bromo-propanoate (1.6 g, 5.86 mmol) in N,N-dimethylformamide (10 mL) was added triethylamine (1.78 g, 17.57 mmol, 2.45 mL) at 0° C. under nitrogen atmosphere. 4-(2-fluoro-4-nitro-phenyl)-1,2,3,6-tetrahydropyridine (1.30 g, 5.86 mmol) was added and stirred at room temperature for 14 h. After completion of the reaction, the reaction mixture was diluted with water (15 mL) and extracted with ethyl acetate (3×15 mL). The organic layer was washed with brine solution (30 mL), dried over sodium sulfate, filtered and concentrated under vacuum to afford crude. The crude compound was purified by silica gel flash column chromatography, compound eluted with 30-45% ethyl acetate in pet ether to afford methyl 3-benzyloxy-2-[4-(2-fluoro-4-nitro-phenyl)-3,6-dihydro-2H-pyridin-1-yl]propanoate (2.0 g, 4.78 mmol, 82% yield) as a yellow solid. LCMS m/z (ESI): 415.6 $[M+H]^+$.

Step 4: To a stirred solution of methyl 3-benzyloxy-2-[4-(2-fluoro-4-nitro-phenyl)-3,6-dihydro-2H-pyridin-1-yl]propanoate (1.00 g, 2.41 mmol) in methanol (15 mL) was added Palladium hydroxide (20 wt. % on carbon, wet, 677.73 mg, 4.83 mmol) at room temperature under nitrogen atmosphere. The resulting suspension was stirred at room temperature under hydrogen atmosphere bladder for 16 h. After completion, reaction mixture was filtered through celite bed and celite bed was washed with methanol (50 mL). The combined filtrate was concentrated under reduced pressure to afford a crude product methyl 2-[4-(4-amino-2-fluoro-phenyl)-1-piperidyl]-3-hydroxy-propanoate (300 mg, 347.24 μmol, 14% yield) as an off-white solid. LCMS m/z (ESI): 297.2 $[M+H]^+$.

Step 5: To a stirred solution of methyl 2-[4-(4-amino-2-fluoro-phenyl)-1-piperidyl]-3-hydroxy-propanoate (500 mg, 1.69 mmol) in N,N-dimethylformamide (5 mL) were added sodium bicarbonate (566.99 mg, 6.75 mmol) and 3-bromopiperidine-2,6-dione (971.92 mg, 5.06 mmol) at room temperature under nitrogen atmosphere. After completion of the reaction, the reaction mixture was diluted with water (20 mL) and extracted with ethyl acetate (3×30 mL). The organic layer was washed with brine solution (30 mL), dried over sodium sulfate, filtered and concentrated to afford crude, which was purified by purified by C18-reverse phase column chromatography (30 g RediSep® Rf C18, Method: 10 mM Ammonium acetate in water:acetonitrile) and pure fractions were lyophilized to afford methyl 2-[4-[4-[(2,6-dioxo-3-piperidyl)amino]-2-fluoro-phenyl]-1-piperidyl]-3-hydroxy-propanoate (450 mg, 1.05 mmol, 62% yield) as an off-white solid. LCMS m/z (ESI): 406.00 $[M-H]^-$.

Step 6: To a stirred solution of methyl 2-[4-[4-[(2,6-dioxo-3-piperidyl)amino]-2-fluoro-phenyl]-1-piperidyl]-3-hydroxy-propanoate (400 mg, 981.75 μmol) in dichloroethane (4 mL) was added trimethyl tin hydroxide (177.52 mg, 981.75 μmol) at 0° C. under nitrogen atmosphere. The reaction mixture was stirred at 80° C. for 12 h. After completion of the reaction, the reaction mixture was concentrated under reduced pressure to afford crude and purified by C18-reverse phase column chromatography (30 g RediSep® Rf C18, Method: 10 mM Ammonium acetate in water:acetonitrile). Pure fractions were lyophilized to afford 2-[4-[4-[(2,6-dioxo-3-piperidyl)amino]-2-fluoro-phenyl]-1-piperidyl]-3-hydroxy-propanoic acid (150 mg, 205.89 μmol, 21% yield) as an off-white solid. LCMS m/z (ESI): 392.20 $[M-H]^-$ Step 7: Target compound was prepared via HATU mediated acid-amine coupling reaction (Procedure A-E). Amide coupling was carried out using 2-[4-[4-[(2,6-dioxo-3-piperidyl)amino]-2-fluoro-phenyl]-1-piperidyl]-3-hydroxy-propanoic acid (50 mg, 127.09 μmol), 6-[2-cyano-3-[[ethyl(methyl)sulfamoyl]amino]-6-fluoro-phenoxy]-4-oxo-3-(2-piperazin-1-ylpyrimidin-5-yl)quinazoline (71.18 mg, 115.54 μmol), N,N-diisopropylethylamine (74.66 mg, 577.70 μmol, 100.62 μL) and HATU (52.72 mg, 138.65 μmol) to afford crude product. The crude compound was purified by reverse phase column chromatography eluted with 43% acetonitrile in 0.1% formic acid in water to afford product 6-[2-cyano-3-[[ethyl(methyl)sulfamoyl]amino]-6-fluoro-phenoxy]-3-[2-[4-[2-[4-[4-[(2,6-dioxo-3-piperidyl)amino]-2-fluoro-phenyl]-1-piperidyl]-3-hydroxy-propanoyl]piperazin-1-yl]pyrimidin-5-yl]-4-oxo-quinazoline (6.13 mg, 6.07 μmol, 5% yield) as an off-white solid. LCMS m/z (ESI): 955.20 $[M+H]^+$; $^1$HNMR (400 MHz, DMSO-$d_6$): δ=12.75 (s, 1H), 10.79 (s, 1H), 10.20 (s, 1H), 8.57 (s, 2H), 8.31 (s, 1H), 7.83 (d, J=8.80 Hz, 1H), 7.70 (d, J=10.00 Hz, 1H), 7.39 (d, J=2.80 Hz, 1H), 7.32-7.30 (m, 1H), 6.97 (t, J=8.80 Hz, 1H), 6.53 (s, 1H), 6.46-6.42 (m, 2H), 6.00 (d, J=6.80 Hz, 1H), 4.49 (s, 1H), 4.31-4.29 (m, 1H), 4.07-3.99 (m, 2H), 3.81-3.76 (m, 6H), 3.65-3.62 (m, 2H), 3.50 (m, 1H), 3.10 (s, 3H), 2.98 (m, 1H), 2.68-2.61 (m, 1H), 2.67-2.59 (m, 4H), 2.50-2.35 (m, 2H), 2.10-2.06 (m, 1H), 1.88-1.84 (m, 1H), 1.50-1.70 (m, 5H) 1.02 (t, J=7.20 Hz, 3H).

Example 92

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline

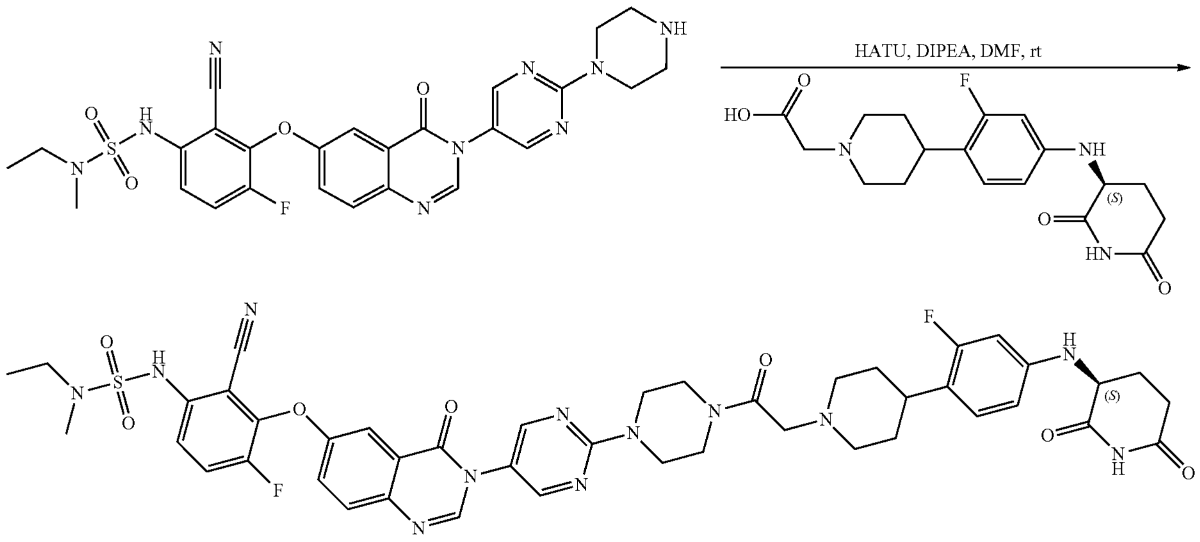

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (300 mg, 486.96 μmol), 2-[4-[4-[[(3S)-2,6-dioxo-3-piperidyl]amino]-2-fluoro-phenyl]-1-piperidyl]acetic acid (292.06 mg, 730.44 μmol), N,N-diisopropylethylamine (1.11 g, 8.61 mmol, 1.5 mL) and HATU (222.19 mg, 584.35 μmol) to afford crude product. The crude compound was purified by reverse phase column chromatography eluted with 45% acetonitrile in 0.1% ammonium acetate in water to afford product 6-[2-cyano-3-[[ethyl(methyl)sulfamoyl]amino]-6-fluoro-phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazoline (132 mg, 137.14 μmol, 28% yield) as an off-white solid. LCMS m/z (ESI): 925.25 $[M+H]^+$; $^1$HNMR (400 MHz, DMSO-$d_6$): δ=10.81 (s, 1H), 9.93 (bs, 1H), 8.62 (s, 2H), 8.35 (s, 1H), 7.84 (dd, J=5.20, 9.20 Hz, 1H), 7.71 (dd, J=3.20, 8.80 Hz, 1H), 7.59 (s, 1H), 7.53-7.38

(m, 2H), 7.00-6.98 (m, 1H), 6.49-6.44 (m, 2H), 6.06 (d, J=7.60 Hz, 1H), 4.35-4.25 (m, 1H), 3.95-3.75 (m, 4H), 3.65-3.55 (m, 4H), 3.25-3.15 (m, 2H), 3.10-3.00 (m, 2H), 2.80-2.70 (m, 2H), 2.68 (s, 3H), 2.62-2.55 (m, 2H), 2.45-2.35 (m, 1H), 2.10-2.06 (m, 2H), 1.91-1.89 (m, 1H), 1.88-1.76 (m, 5H), 1.02 (t, J=7.20 Hz, 3H).

Example 93

6-[2-cyano-3-[[ethyl(methyl)sulfamoyl]amino]-6-fluorophenoxy]-3-[6-[4-[2-[4-[4-[[(3R)-2,6-dioxopiperidin-3-yl]amino]-2-fluorophenyl]piperidin-1-yl]acetyl]piperazin-1-yl]pyridin-3-yl]-4-oxoquinazoline

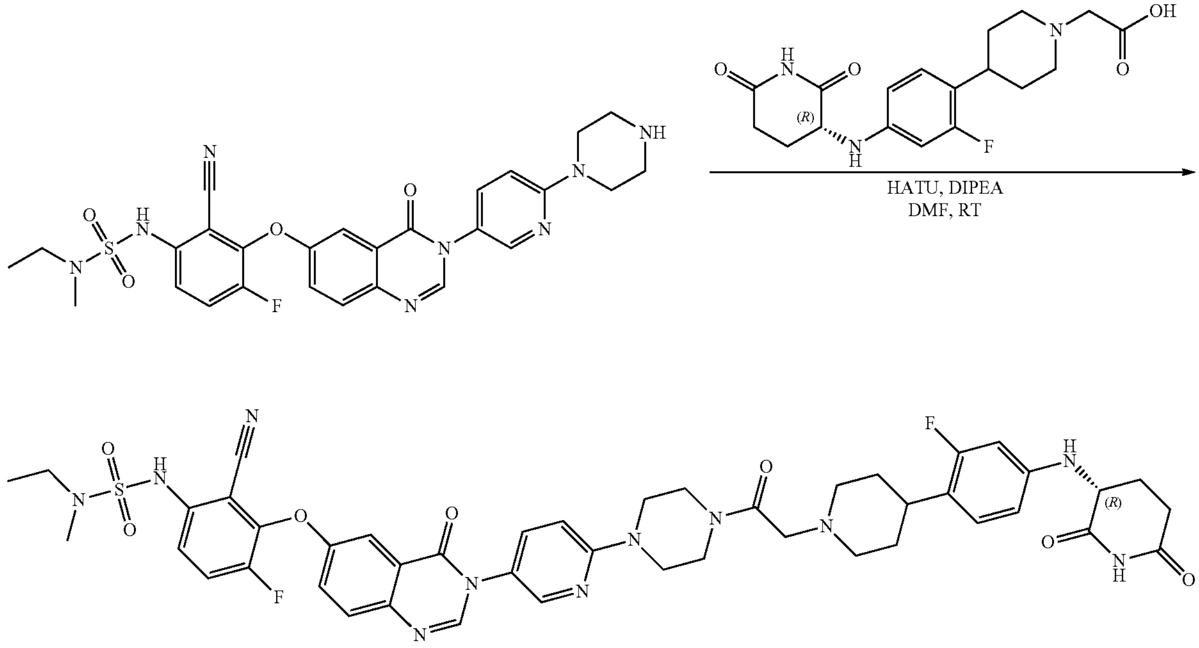

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(6-piperazin-1-yl-3-pyridyl)quinazoline (280 mg, 483.91 μmol), 2-[4-[4-[[(3R)-2,6-dioxo-3-piperidyl]amino]-2-fluoro-phenyl]-1-piperidyl]acetic acid (175.85 mg, 483.91 μmol), N,N-diisopropylethylamine (250.17 mg, 1.94 mmol, 337.16 μL) and HATU (184.00 mg, 483.91 μmol) to afford 6-[2-cyano-3-[[ethyl(methyl)sulfamoyl]amino]-6-fluoro-phenoxy]-3-[6-[4-[2-[4-[4-[[(3R)-2,6-dioxo-3-piperidyl]amino]-2-fluoro-phenyl]-1-piperidyl]acetyl]piperazin-1-yl]-3-pyridyl]-4-oxo-quinazoline (95 mg, 100.79 μmol, 21% yield) as an off-white solid. LCMS m/z (ESI): 924.0 $[M+H]^+$; $^1$HNMR (400 MHz, DMSO-$d_6$): δ=10.80 (s, 1H), 8.26 (s, 1H), 8.24 (d, J=2.80 Hz, 1H), 7.80 (d, J=8.80 Hz, 1H), 7.73 (dd, J=2.40, 9.00 Hz, 1H), 7.65 (dd, J=2.80, 8.80 Hz, 1H), 7.37 (d, J=2.80 Hz, 1H), 7.29 (t, J=10.00 Hz, 1H), 7.21 (dd, J=4.40, 9.60 Hz, 1H), 7.03-6.98 (m, 2H), 6.46-6.45 (m, 2H), 6.01 (dd, J=16.00, Hz, 1H), 4.34-4.28 (m, 1H), 3.72-3.66 (m, 4H), 3.59 (s, 4H), 3.22 (s, 2H), 2.98-2.92 (m, 4H), 2.76-2.70 (m, 1H), 2.69-2.67 (m, 1H), 2.62-2.53 (m, 2H), 2.34-2.33 (m, 4H), 2.10-2.06 (m, 6H), 1.88-1.65 (m, 4H), 1.01 (t, J=7.20 Hz, 3H).

Example 94

6-[2-cyano-3-[[ethyl(methyl)sulfamoyl]amino]-6-fluorophenoxy]-3-[6-[4-[2-[4-[4-[[(3S)-2,6-dioxopiperidin-3-yl]amino]-2-fluorophenyl]piperidin-1-yl]acetyl]piperazin-1-yl]pyridin-3-yl]-4-oxoquinazoline

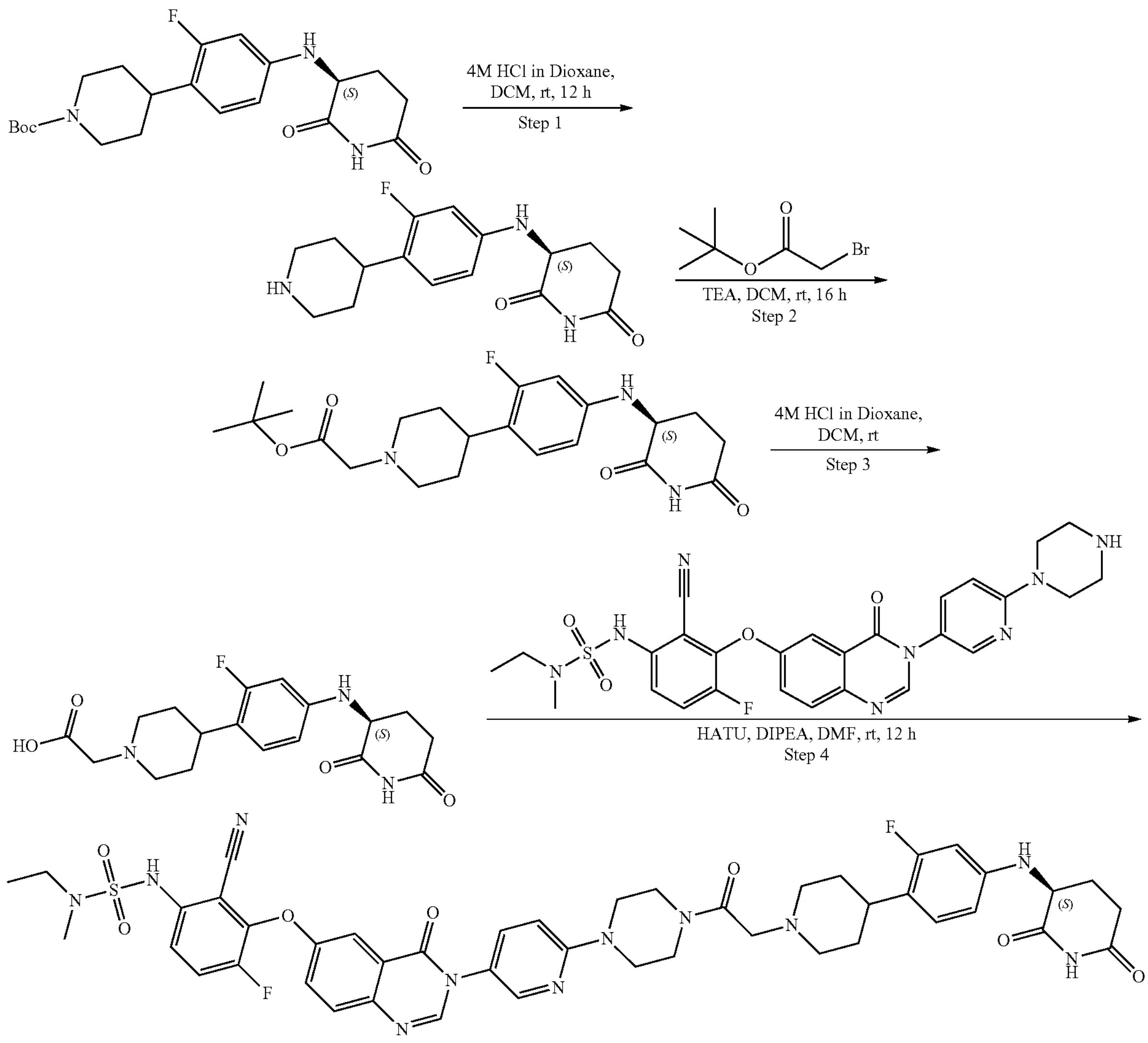

Step 1: To a stirred solution of tert-butyl 4-[4-[[(3S)-2,6-dioxo-3-piperidyl]amino]-2-fluoro-phenyl]piperidine-1-carboxylate (1.2 g, 2.96 mmol) in dichloromethane (20 mL), was added hydrogen chloride solution (4 M in 1,4-dioxane, 15 mL) at 5° C. under nitrogen atmosphere. The reaction mixture was stirred at room temperature for 12 h. After completion, the reaction mixture was concentrated under reduced pressure to afford crude (3S)-3-[3-fluoro-4-(4-piperidyl)anilino]piperidine-2,6-dione hydrochloride (1.2 g, 3.48 mmol) as an off-white solid. LCMS m/z (ESI): 306.2 $[M+H]^+$.

Step 2: To a stirred solution of (3S)-3-[3-fluoro-4-(4-piperidyl)anilino]piperidine-2,6-dione (1.2 g, 3.93 mmol) in N,N-dimethylformamide (15 mL) and triethylamine (1.99 g, 19.65 mmol, 2.74 mL), was added tert-butyl 2-bromoacetate (1.15 g, 5.89 mmol, 864.53 μL) at room temperature under nitrogen atmosphere. The reaction mixture was stirred at room temperature for 16 h. After completion, the reaction mixture was poured into ice water (50 mL), immediately extracted with ethyl acetate (3×70 mL). Combined organic layers washed with cold water (3×30 mL), dried over sodium sulfate, filtered and concentrated under reduced pressure to afford crude tert-butyl 2-[4-[4-[[(3S)-2,6-dioxo-3-piperidyl]amino]-2-fluoro-phenyl]-1-piperidyl]acetate (1.4 g, 3.34 mmol, 85% yield) as an off-white solid. LCMS m/z (ESI): 420.2 $[M+H]^+$.

Step 3: To a stirred solution of tert-butyl 2-[4-[4-[[(3S)-2,6-dioxo-3-piperidyl]amino]-2-fluoro-phenyl]-1-piperidyl]acetate (1.4 g, 3.34 mmol) in dichloromethane (30 mL), was added hydrogen chloride solution (4 M in 1,4-dioxane, 15 mL) at 5° C. under nitrogen atmosphere. The reaction mixture was stirred at room temperature for 16 h. After completion, the reaction mixture was concentrated under reduced pressure to afford crude 2-[4-[4-[[(3 S)-2,6-dioxo-3-piperidyl]amino]-2-fluoro-phenyl]-1-piperidyl]acetic acid hydrochloride (1.3 g, 3.20 mmol, 96% yield) as a brown solid. LCMS m/z (ESI): 364.2 $[M+H]^+$.

Step 4: Target compound was prepared via HATU mediated acid-amine coupling reaction (Procedure A-E). Amide coupling was carried out using 2-[4-[4-[[(3S)-2,6-dioxo-3-piperidyl]amino]-2-fluoro-phenyl]-1-piperidyl]acetic acid (259.95 mg, 650.12 μmol), N,N-diisopropylethylamine (840.50 mg, 6.50 mmol, 1.13 mL), HATU (272.00 mg, 715.36 μmol) and 6-[2-cyano-3-[[ethyl(methyl)sulfamoyl]amino]-6-fluoro-phenoxy]-4-oxo-3-(6-piperazin-1-yl-3-pyridyl)quinazoline (0.4 g, 650.32 μmol) was added. The desired product was purified from crude by reverse phase column chromatography (10 mM ammonium acetate in water acetonitrile) and fractions were lyophilized to afford 6-[2-cyano-3-[[ethyl(methyl)sulfamoyl]amino]-6-fluoro-phenoxy]-3-[6-[4-[2-[4-[4-[[(3S)-2,6-dioxo-3-piperidyl]amino]-2-fluoro-phenyl]-1-piperidyl]acetyl]piperazin-1-yl]-3-pyridyl]-4-oxo-quinazoline (122 mg, 127.07 μmol, 20% yield) as a light green solid. LCMS m/z (ESI): 924.2 $[M+H]^+$ and $^1$HNMR (400 MHz, DMSO-$d_6$): δ=10.80 (s, 1H), 8.26 (d, J=10.00 Hz, 2H), 8.04 (d, J=161.60 Hz, 1H), 7.82-7.69 (m, 2H), 7.39 (s, 1H), 7.02 (d, J=7.20 Hz, 2H), 6.47 (t, J=12.00 Hz, 2H), 6.06 (d, J=8.00 Hz, 1H), 4.35-4.29 (m, 1H), 3.68-3.63 (m, 10H), 3.05 (d, J=6.80 Hz, 2H), 2.85-2.70 (m, 1H), 2.68-2.65 (m, 4H), 2.11-2.06 (m, 1H), 1.95-1.68 (m, 5H), 1.03 (t, J=7.20 Hz, 3H).

Example 95

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (300 mg, 517.59 μmol), 6-[2-cyano-3-[[ethyl(methyl)sulfamoyl]amino]-6-fluoro-phenoxy]-4-oxo-3-(2-piperazin-1-ylpyrimidin-5-yl) quinazoline (300 mg, 517.59 μmol) 2-[4-[4-[[(3R)-2,6-dioxo-3-piperidyl]amino]-2-fluoro-phenyl]-1-piperidyl] acetic acid (188.08 mg, 517.59 μmol), N,N-diisopropylethylamine (334.47 mg, 2.59 mmol, 450.77 μL) and HATU (216.49 mg, 569.35 μmol) to afford 6-[2-cyano-3-[[ethyl(methyl)sulfamoyl]amino]-6-fluoro-phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazoline (80 mg, 81.44 μmol, 16% yield) as an off-white solid. LCMS m/z (ESI): 925.2 $[M+H]^+$. $^1$HNMR (400 MHz, DMSO-$d_6$): δ=10.81 (s, 1H), 9.85 (s, 1H), 8.57 (s, 2H), 8.31 (s, 1H), 7.83 (d, J=8.80 Hz, 1H), 7.69 (dd, J=6.00, 8.80 Hz, 1H), 7.50 (s, 1H), 7.38 (d, J=2.80 Hz, 1H), 7.31 (s, 1H), 7.02-6.98 (m, 1H), 6.48-6.44 (m, 2H), 6.06 (d, J=7.20 Hz, 1H), 4.33-4.30 (m, 1H), 3.90-3.83 (m, 4H), 3.68-3.59 (m, 4H), 3.17 (m, 1H), 3.03-2.91 (m, 3H), 2.77-2.71 (m, 2H), 2.61-2.59 (m, 6H), 2.09-2.06 (m, 1H), 1.89-1.75 (m, 4H), 1.02 (t, J=7.20 Hz, 3H).

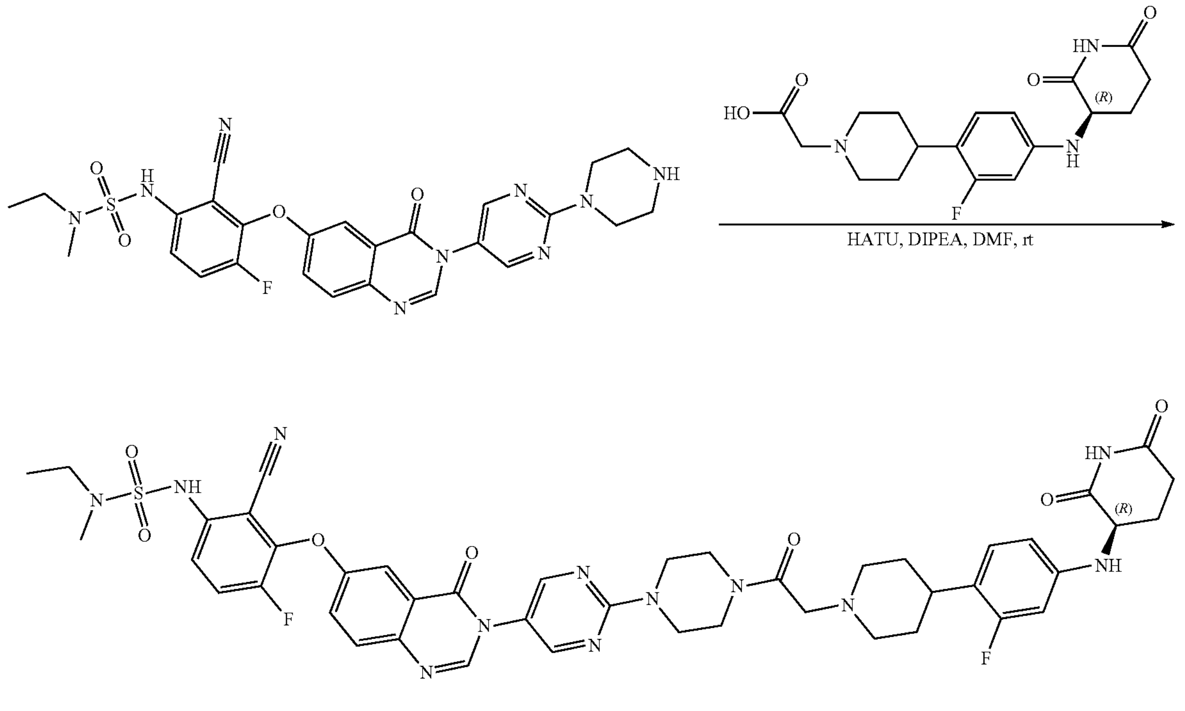

Example 96

(3R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide

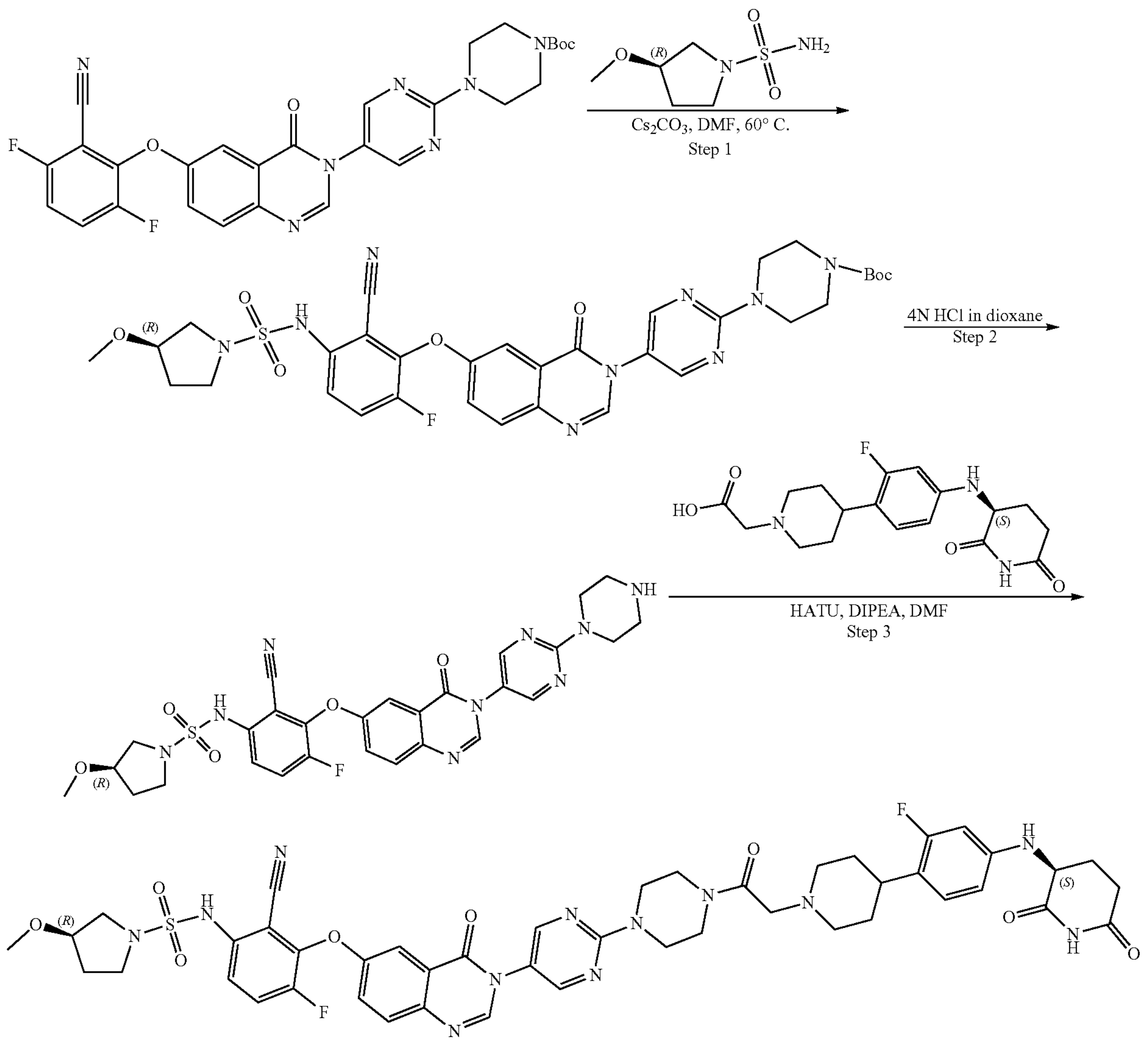

Step 1: Sulfamoylated quinazolinone intermediate was synthesized using Procedure A-C using tert-butyl 4-[5-[6-(2-cyano-3,6-difluoro-phenoxy)-4-oxo-quinazolin-3-yl]pyrimidin-2-yl]piperazine-1-carboxylate (450 mg, 801.37 μmol), cesium carbonate (261.10 mg, 801.37 μmol) and (3R)-3-methoxypyrrolidine-1-sulfonamide (144.43 mg, 801.37 μmol) to afford tert-butyl 4-[5-[6-[2-cyano-6-fluoro-3-[[(3R)-3-methoxypyrrolidin-1-yl]sulfonylamino]phenoxy]-4-oxo-quinazolin-3-yl]pyrimidin-2-yl]piperazine-1-carboxylate (400 mg, 509.87 μmol, 64% yield) as an off-white solid. LCMS m/z (ESI): 666.7 $[M+H-{}^tBu]^+$.

Step 2: The requisite amine was synthesized by hydrogen chloride mediated N-Boc deprotection (Procedure A-D). N-Boc deprotection was done on tert-butyl 4-[5-[6-[2-cyano-6-fluoro-3-[[(3R)-3-methoxypyrrolidin-1-yl]sulfonylamino]phenoxy]-4-oxo-quinazolin-3-yl]pyrimidin-2-yl]piperazine-1-carboxylate (420 mg, 581.91 μmol) using hydrogen chloride solution (4M in 1,4-dioxane, 4 mL) to afford (3R)—N-[2-cyano-4-fluoro-3-[4-oxo-3-(2-piperazin-1-ylpyrimidin-5-yl)quinazolin-6-yl]oxy-phenyl]-3-methoxy-pyrrolidine-1-sulfonamide (380 mg, 551.03 μmol, 95% yield) as a light brown solid. LCMS m/z (ESI): 622.3 $[M+H]^+$).

Step 3: Target compound was prepared via HATU mediated acid-amine coupling reaction (Procedure A-E). Amide coupling was carried out using (3R)—N-[2-cyano-4-fluoro-3-[4-oxo-3-(2-piperazin-1-ylpyrimidin-5-yl)quinazolin-6-yl]oxy-phenyl]-3-methoxy-pyrrolidine-1-sulfonamide HCl salt (120 mg, 182.34 μmol), 2-[4-[4-[[(3S)-2,6-dioxo-3-piperidyl]amino]-2-fluoro-phenyl]-1-piperidyl]acetic acid (66.26 mg, 165.71 μmol), N,N-diisopropylethylamine (94.27 mg, 729.37 μmol, 127.04 μL) and HATU (69.33 mg, 182.34 μmol) to afford (3R)—N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-methoxy-pyrrolidine-1-sulfonamide (35 mg, 34.54 μmol, 19% yield) as an off-white solid. LCMS m/z (ESI): 967.0 $[M+H]^+$; $^1$HNMR (400 MHz, DMSO-$d_6$): δ=10.81 (s, 1H), 10.23 (bs, 1H), 8.59 (s, 2H), 8.33 (s, 1H), 7.84 (dd, J=8.80, 14.40 Hz, 1H), 7.82-7.80 (m, 1H), 7.75 (dd, J=3.20, 8.80 Hz, 1H), 7.52 (dd, J=4.00, 8.80 Hz, 1H), 7.43 (d, J=2.80 Hz, 1H), 6.97 (d, J=6.40 Hz, 1H), 6.52-6.46 (m, 3H), 6.12 (d, J=8.00 Hz, 1H), 4.34-4.32 (m, 1H), 3.97-3.93 (m, 6H), 3.67-3.63 (m, 2H), 3.59-3.51 (m, 4H), 3.29-3.25 (m, 2H), 3.18 (s, 3H), 3.15-3.05 (m, 1H), 2.97-2.85 (m, 1H), 2.75-2.67 (m, 1H), 2.11-1.82 (m, 8H).

Example 97

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide

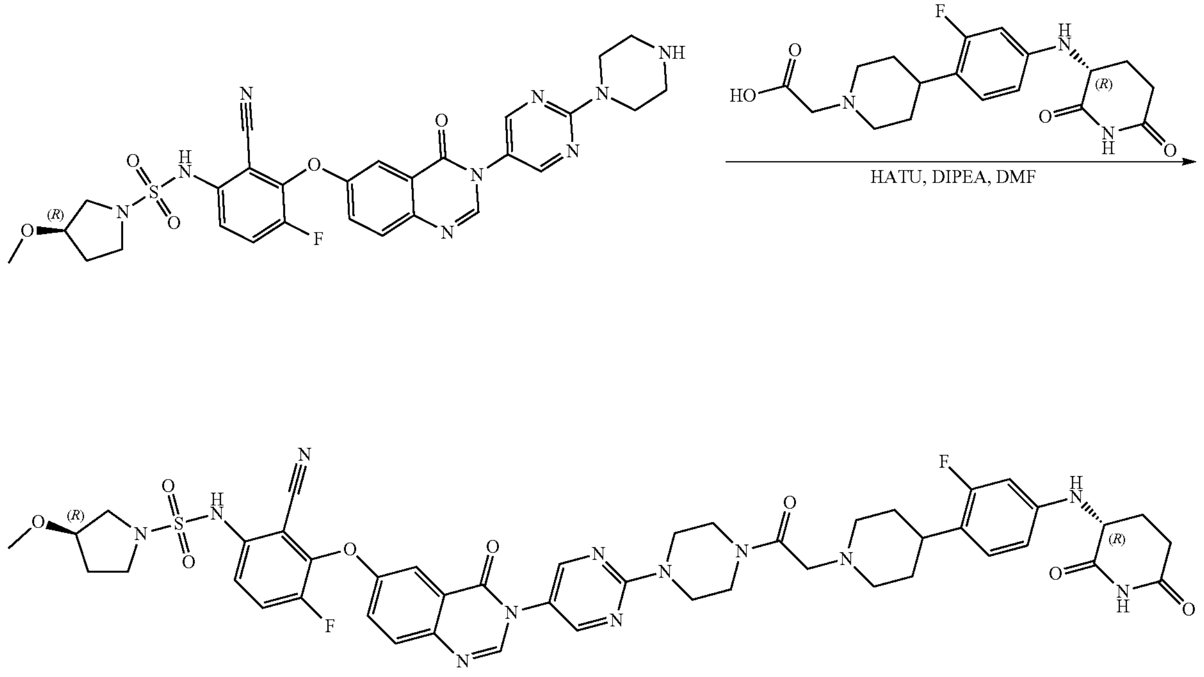

Target compound was prepared via HATU mediated acid-amine coupling reaction (Procedure A-E). Amide coupling was carried out using (3R)—N-[2-cyano-4-fluoro-3-[4-oxo-3-(2-piperazin-1-ylpyrimidin-5-yl)quinazolin-6-yl]oxy-phenyl]-3-methoxy-pyrrolidine-1-sulfonamide HCl salt (130 mg, 197.54 μmol), 2-[4-[4-[[(3R)-2,6-dioxo-3-piperidyl]amino]-2-fluoro-phenyl]-1-piperidyl]acetic acid (71.78 mg, 179.52 μmol), N,N-diisopropylethylamine (102.12 mg, 790.15 μmol, 137.63 μL) and HATU (75.11 mg, 197.54 μmol) to afford (3R)—N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-methoxy-pyrrolidine-1-sulfonamide (43 mg, 42.32 μmol, 21% yield) as an off-white solid. LCMS m/z (ESI): 967.0 $[M+H]^+$; $^1$HNMR (400 MHz, DMSO-$d_6$): δ=10.81 (s, 1H), 10.19 (bs, 1H), 9.59 (bs, 1H), 8.59 (s, 2H), 8.33 (s, 1H), 7.84-7.76 (m, 2H), 7.74 (dd, J=2.80, 9.00 Hz, 1H), 7.51-7.43 (m, 1H), 7.42 (d, J=2.80 Hz, 1H), 6.97 (d, J=8.40 Hz, 1H), 6.51-6.46 (m, 2H), 6.11 (d, J=8.00 Hz, 1H), 4.34-4.30 (m, 2H), 3.95-3.85 (m, 5H), 3.71-3.65 (m, 2H), 3.59-3.48 (m, 3H), 3.28-3.26 (m, 2H), 3.18 (s, 3H), 2.92-2.83 (m, 1H), 2.79-2.71 (m, 1H), 2.61-2.60 (m, 1H), 2.12-1.82 (m, 9H).

Example 98

6-[2-cyano-3-[[ethyl(methyl)sulfamoyl]amino]-6-fluorophenoxy]-3-[2-[4-[(2S)-2-[4-[4-[[(3S)-2,6-dioxopiperidin-3-yl]amino]-2-fluorophenyl]piperidin-1-yl]-3-hydroxypropanoyl]piperazin-1-yl]pyrimidin-5-yl]-4-oxoquinazoline

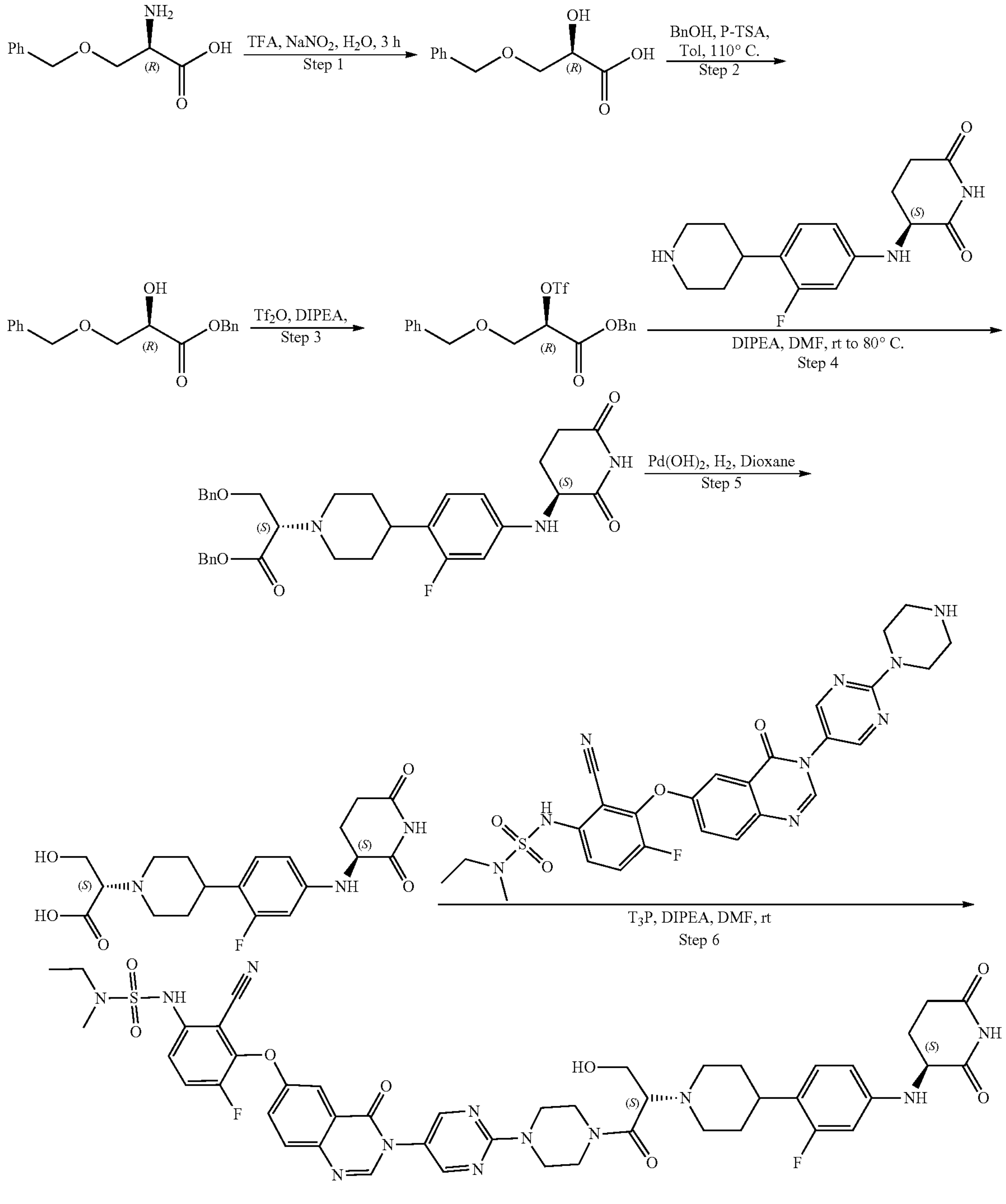

Step 1: To a stirred solution of (2R)-2-amino-3-benzyloxy-propanoic acid (7 g, 35.86 mmol) in trifluoroacetic acid in $H_2O$ (0.7 M, 51.23 mL) was added sodium nitrite (3.71 g, 53.79 mmol, 1.71 mL, dissolved in water (50 mL) at 0° C. The reaction mixture was stirred at room temperature for 5 h. After completion of the reaction, sodium chloride was added to the reaction mixture and extracted with ethyl acetate, the combined organic layer was dried with anhydrous sodium sulfate and concentrated under reduced pressure to afford (2R)-3-benzyloxy-2-hydroxy-propanoic acid (6 g, 28.13 mmol, 78% yield) as a colorless liquid which was used as is in the following step. LCMS m/z (ESI): 195.2 $[M-H]^-$ Step 2: To a stirred solution of (2R)-3-benzyloxy-2-hydroxy-propanoic acid (6 g, 30.58 mmol) in toluene (70 mL) was added benzyl alcohol (16.53 g, 152.91 mmol, 15.75 mL) and p-TSA (526.61 mg, 3.06 mmol) at 0° C. under nitrogen atmosphere. The resulting reaction mixture was stirred at 110° C. for 16 h. After completion, the reaction mixture was diluted with water and extracted with dichloromethane. The combined organic layer was dried with anhydrous sodium sulfate and concentrated under reduced pressure to afford crude product. The crude was purified by reverse phase C-18 chromatography (0.1% Ammonium Acetate in water and acetonitrile), Pure fractions are concentrated under reduced pressure to afford benzyl (2R)-3-benzyloxy-2-hydroxy-propanoate (5.8 g, 16.21 mmol, 53% yield) as a colorless liquid. $^1$HNMR (400 MHz, DMSO-$d_6$): δ=7.27-7.39 (m, 10H), 5.69 (d, J=6.40 Hz, 1H), 5.16 (d, J=5.20 Hz, 2H), 4.52 (t, J=5.60 Hz, 2H), 4.31-4.35 (m, 1H), 3.63-3.70 (m, 2H).

Step 3 and Step 4: To a stirred solution of benzyl (2R)-3-benzyloxy-2-hydroxy-propanoate (562.62 mg, 1.96 mmol) in toluene (3 mL) was added N,N-diisopropylethylamine (253.96 mg, 1.96 mmol, 342.26 μL) followed by dropwise addition of trifluoromethanesulfonic anhydride (554.40 mg, 1.96 mmol, 330.00 μL) at 0° C. under inert atmosphere. The reaction mixture was slowly warmed to room temperature for 1 h. In a separate reaction vessel, a stirred solution of (3S)-3-[3-fluoro-4-(4-piperidyl)anilino] piperidine-2,6-dione (0.3 g, 982.49 μmol) in N,N-dimethylformamide (3 mL) was added N,N-diisopropylethylamine (253.96 mg, 1.96 mmol, 342.26 μL) and dropwise solution of above prepared solution in toluene at 0° C. under nitrogen atmosphere. The reaction mixture was slowly warmed to room temperature and continued the reaction for 12 h. The reaction mixture was diluted with water (10 ml), extracted with ethyl acetate (2×50 mL). the combined organic layer was dried over sodium sulfate and concentrated under reduced pressure to afford crude. The crude compound was purified by silica gel flash column chromatography with 80% ethyl acetate in petroleum ether as a eluent to afford benzyl (2S)-3-benzyloxy-2-[4-[4-[[(3S)-2,6-dioxo-3-piperidyl]amino]-2-fluoro-phenyl]-1-piperidyl]propanoate (0.22 g, 366.13 μmol, 37% yield) as brownish semisolid. LCMS m/z (ESI): 574.2 $[M+H]^+$ Step 5: In to a 50 mL RB flask containing a well-stirred solution of benzyl (2S)-3-benzyloxy-2-[4-[4-[[(3S)-2,6-dioxo-3-piperidyl]amino]-2-fluoro-phenyl]-1-piperidyl]propanoate (220.00 mg, 383.51 μmol) in dioxane (4 mL) was added Palladium hydroxide on carbon (0.22 g, 383.51 μmol) and the reaction was hydrogenated under hydrogen bladder pressure for 16 h. The reaction mixture was filtered through a pad of celite and washed with 5% methanol in dichloromethane (50 mL). The filtrate was concentrated under reduced pressure to afford (2S)-2-[4-[4-[[(3S)-2,6-dioxo-3-piperidyl]amino]-2-fluoro-phenyl]-1-piperidyl]-3-hydroxy-propanoic acid (75 mg, 160.58 μmol, 42% yield) as semi-solid. LCMS m/z (ESI): 394.5 $[M+H]^+$.

Step 6: To a solution of(2S)-2-[4-[4-[[(3S)-2,6-dioxo-3-piperidyl]amino]-2-fluoro-phenyl]-1-piperidyl]-3-hydroxy-propanoic acid (31.93 mg, 81.16 μmol), 6-[2-cyano-3-[[ethyl(methyl)sulfamoyl]amino]-6-fluoro-phenoxy]-4-oxo-3-(2-piperazin-1-ylpyrimidin-5-yl)quinazoline (50 mg, 81.16 μmol) in N,N-Dimethylformamide (1 mL) were added 1-Propanephosphonic anhydride solution (619.76 μg, 97.39 μmol, 50% purity) and N,N-diisopropylethylamine (52.45 mg, 405.80 μmol, 70.68 μL) and stirred at room temperature for 3 h. After completion of the reaction, the reaction mixture was concentrated under reduced pressure to half of its volume, which was purified by reverse phase column chromatography by using 30 g C18 column, eluting with 35% acetonitrile in 0.1% formic acid in water to afford 6-[2-cyano-3-[[ethyl(methyl)sulfamoyl]amino]-6-fluoro-phenoxy]-3-[2-[4-[(2S)-2-[4-[4-[[(3S)-2,6-dioxo-3-piperidyl]amino]-2-fluoro-phenyl]-1-piperidyl]-3-hydroxy-propanoyl]piperazin-1-yl]pyrimidin-5-yl]-4-oxo-quinazoline (26 mg, 25.21 μmol, 31% yield) as an off-white solid. LCMS m/z (ESI): 955.0$[M+H]^+$; $^1$HNMR (400 MHz, DMSO-$d_6$): δ=10.78 (s, 1H), 10.00 (s, 1H), 8.57 (s, 2H), 8.32 (s, 1H), 7.85 (d, J=8.80 Hz, 1H), 7.74 (dd, J=3.20, 8.80 Hz, 2H), 7.55-7.30 (m, 2H), 7.05-6.85 (m, 1H), 6.55-6.35 (m, 2H), 6.03 (s, 1H), 4.32-4.30 (m, 1H), 4.10-3.95 (m, 2H), 3.88-3.78 (m, 4H), 3.75-3.58 (m, 4H), 3.13-3.11 (m, 4H), 2.74-2.67 (m, 4H), 2.62-2.58 (m, 1H), 2.57-2.55 (m, 3H), 2.15-2.05 (m, 1H), 1.89-1.85 (m, 2H), 1.80-1.65 (m, 3H), 1.58-1.45 (m, 2H), 1.04 (t, J=7.20 Hz, 3H).

Example 99

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-methoxy-4-oxoquinazoline

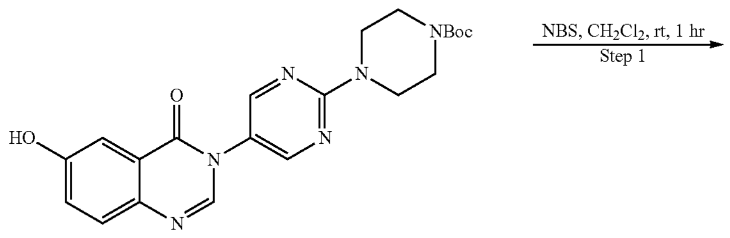

-continued

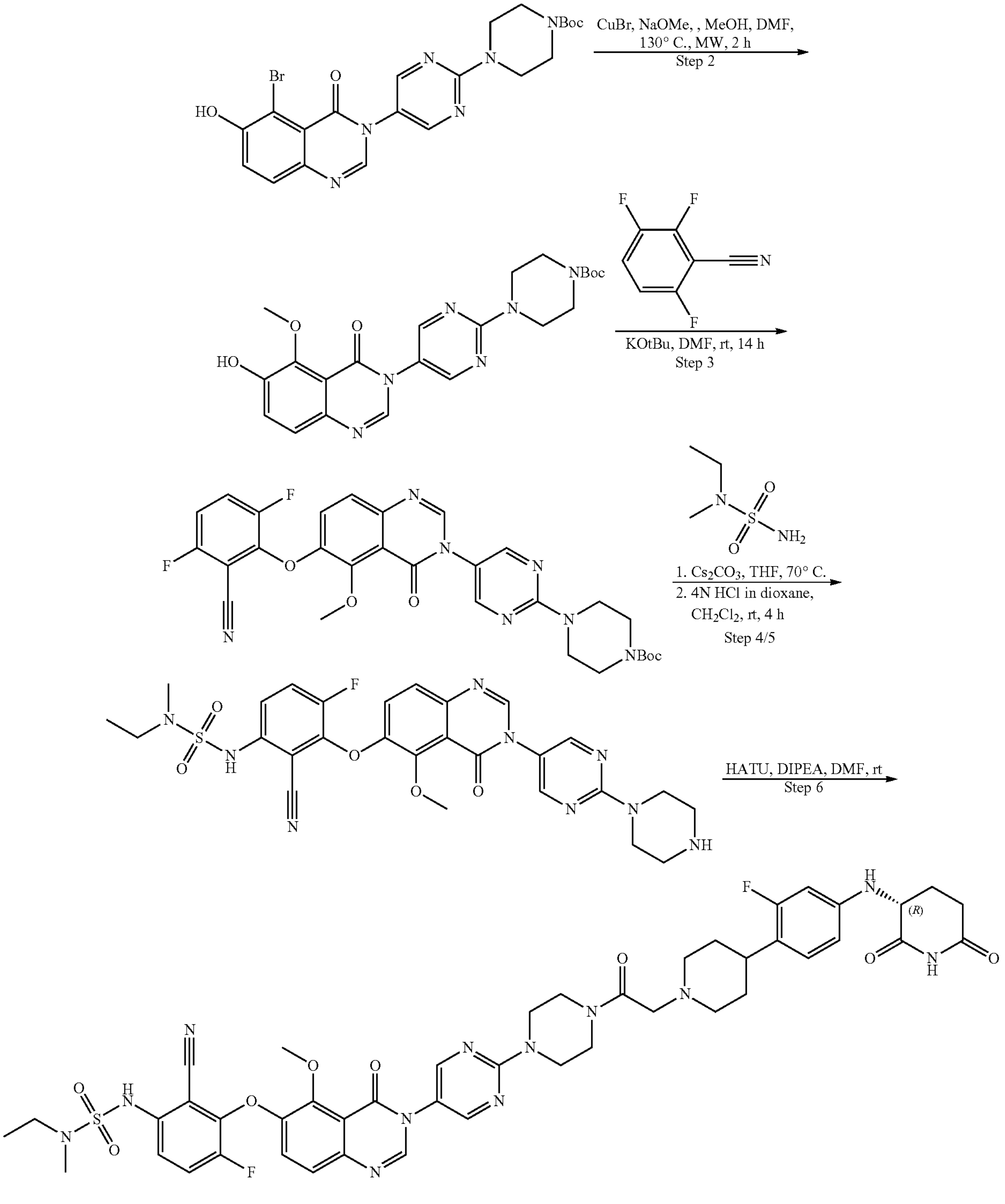

Step 1: To a stirred solution of tert-butyl 4-[5-(6-hydroxy-4-oxo-quinazolin-3-yl)pyrimidin-2-yl]piperazine-1-carboxylate (950 mg, 2.24 mmol) in dichloromethane (30 mL) under nitrogen atmosphere was added N-bromosuccinimide, 99% (398.36 mg, 2.24 mmol, 189.70 μL) at 0° C. The reaction mixture was stirred at 0° C. for 30 minutes. After completion, the reaction mixture was quenched with water (50 ml) and extracted with ethyl acetate (2×100 ml). The organic phases were combined and washed with brine, dried (anhydrous sodium sulfate), filtered and concentrated under reduced pressure to afford a crude product. The crude product was purified by silica gel flash column chromatography using 70-80% ethyl acetate in Petroleum ether as eluent to afford tert-butyl 4-[5-(5-bromo-6-hydroxy-4-oxo-quinazolin-3-yl)pyrimidin-2-yl]piperazine-1-carboxylate (1.0 g, 1.89 mmol, 84% yield) as a yellow solid. LCMS ($ES^+$): m/z 447.0, 449.0 [M+H−$^t$Bu], Bromo-Isotope Pattern).

Step 2: To a stirred solution of tert-butyl 4-[5-(5-bromo-6-hydroxy-4-oxo-quinazolin-3-yl)pyrimidin-2-yl]piperazine-1-carboxylate (400 mg, 794.68 μmol) and copper (I) bromide (57.00 mg, 397.34 μmol, 12.10 μL) in anhydrous methanol (5 mL) and N,N-dimethylformamide (7 mL) was added sodium methoxide (257.59 mg, 4.77 mmol, 265.83 μL) at room temperature under nitrogen atmosphere. The reaction mixture was stirred at 130° C. for 2 h under microwave condition. After completion of reaction, the reaction mixture was quenched with saturated ammonium chloride solution (10 mL), extracted with ethyl acetate (3×30 mL). The combined organic phases were dried with anhydrous sodium sulfate, filtered, and the filtrate was evaporated under reduced pressure to afford crude product, which was purified using silica gel flash column chromatography using 80-90% ethyl acetate in pet ether as eluent to afford tert-butyl 4-[5-(6-hydroxy-5-methoxy-4-oxo-quinazolin-3-yl) pyrimidin-2-yl]piperazine-1-carboxylate (300 mg, 547.88 μmol, 69% yield) as a brown solid. LCMS ($ES^+$): m/z calculated 455.20 $[M+H]^+$ (Br-Isotope pattern).

Step 3: O-arylated quinazolinone intermediate was synthesized by following general procedure for O-arylation (Procedure A-B) using tert-butyl 4-[5-(6-hydroxy-5-methoxy-4-oxo-quinazolin-3-yl)pyrimidin-2-yl]piperazine-1-carboxylate (50 mg, 110.02 μmol), cesium carbonate (107.54 mg, 330.05 μmol) and 2,3,6-trifluorobenzonitrile (22.47 mg, 143.02 μmol, 16.52 μL). The desired compound was purified from crude by silica gel flash column chromatography using 60% ethyl acetate in petroleum ether as eluent to afford tert-butyl 4-[5-[6-(2-cyano-3,6-difluoro-phenoxy)-5-methoxy-4-oxo-quinazolin-3-yl]pyrimidin-2-yl]piperazine-1-carboxylate (40 mg, 64.91 μmol, 59% yield) as a pale yellow solid. LCMS m/z (ESI): 592.2 $[M+H]^+$.

Step 4: Sulfamoylated quinazolinone intermediate was synthesized by following Procedure A-C using tert-butyl 4-[5-[6-(2-cyano-3,6-difluoro-phenoxy)-5-methoxy-4-oxo-quinazolin-3-yl]pyrimidin-2-yl]piperazine-1-carboxylate (0.9 g, 1.52 mmol), cesium carbonate (1.49 g, 4.56 mmol) and [methyl(sulfamoyl)amino]ethane (525.60 mg, 3.80 mmol). The desired compound was purified from crude by silica gel flash column chromatography using 55% ethyl acetate in petroleum ether as eluent to afford tert-butyl 4-[5-[6-[2-cyano-3-[[ethyl(methyl)sulfamoyl]amino]-6-fluoro-phenoxy]-5-methoxy-4-oxo-quinazolin-3-yl]pyrimidin-2-yl]piperazine-1-carboxylate (370 mg, 469.18 μmol, 31% yield) as brown viscous liquid. LCMS m/z (ESI): 708.0 $[M-H]^-$ Step 5: The requisite amine was synthesized hydrogen chloride-mediated N-Boc deprotection (Procedure A-D). N-Boc deprotection was done on tert-butyl 4-[5-[6-[2-cyano-3-[[ethyl(methyl)sulfamoyl]amino]-6-fluoro-phenoxy]-5-methoxy-4-oxo-quinazolin-3-yl]pyrimidin-2-yl] piperazine-1-carboxylate (250 mg, 352.24 μmol) using a hydrogen chloride solution (4M in 1,4-dioxane, 1 mL) to afford 6-[2-cyano-3-[[ethyl(methyl)sulfamoyl]amino]-6-fluoro-phenoxy]-5-methoxy-4-oxo-3-(2-piperazin-1-ylpyrimidin-5-yl)quinazoline (215 mg, 272.21 μmol, 77% yield) as an off-white solid. LCMS m/z (ESI): 610.2 $[M+H]^+$.

Step 6: Target compound was prepared via HATU mediated acid-amine coupling reaction (Procedure A-E). Amide coupling was carried out using 6-[2-cyano-3-[[ethyl(methyl) sulfamoyl]amino]-6-fluoro-phenoxy]-5-methoxy-4-oxo-3-(2-piperazin-1-ylpyrimidin-5-yl)quinazoline (100 mg, 154.78 μmol), 2-[4-[4-[[(3R)-2,6-dioxo-3-piperidyl]amino]-2-fluoro-phenyl]-1-piperidyl]acetic acid (56.24 mg, 154.78 μmol), N,N-diisopropylethylamine (60.01 mg, 464.33 μmol, 80.88 μL) and HATU (88.28 mg, 232.17 μmol). The crude compound was purified by reverse phase column chromatography eluted with 40% acetonitrile in 0.1% ammonium acetate in water to afford product 6-[2-cyano-3-[[ethyl (methyl)sulfamoyl]amino]-6-fluoro-phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-5-methoxy-4-oxo-quinazoline (29 mg, 29.37 μmol, 19% yield) as an off-white solid. LCMS m/z (ESI): 955.0 $[M+H]^+$; $^1$HNMR (400 MHz, DMSO-$d_6$): δ=10.79 (s, 1H), 9.89 (s, 1H), 8.58 (s, 2H), 8.26 (s, 1H), 7.53 (s, 1H), 7.50 (s, 2H), 7.29 (dd, J=4.00, 8.80 Hz, 1H), 7.01 (t, J=8.40 Hz, 1H), 6.49-6.45 (m, 2H), 6.05 (d, J=7.60 Hz, 1H), 4.40-4.30 (m, 1H), 3.88 (d, J=25.60 Hz, 4H), 3.82 (s, 3H), 3.64 (s, 5H), 3.27 (s, 2H), 3.11 (q, J=7.20 Hz, 2H), 2.80-2.60 (m, 6H), 2.49-2.53 (m, 3H), 2.10-2.07 (m, 1H), 1.92-1.77 (m, 5H), 1.05 (t, J=7.20 Hz, 3H).

Example 100

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl] acetyl]piperazin-1-yl]pyrimidin-5-yl]-5-methoxy-4-oxoquinazoline

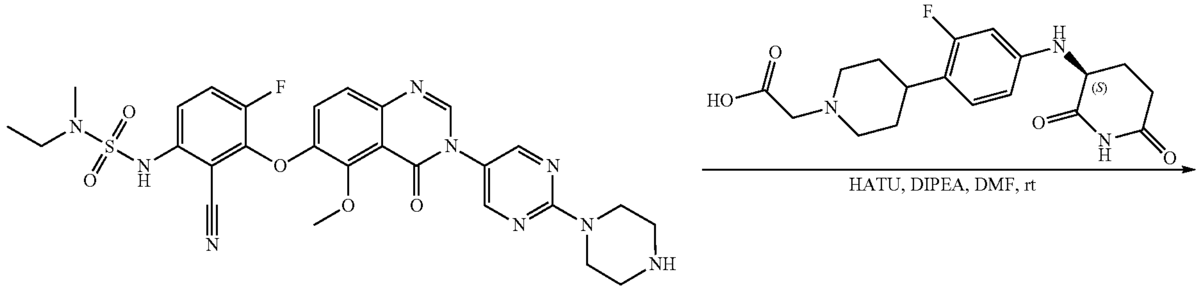

-continued

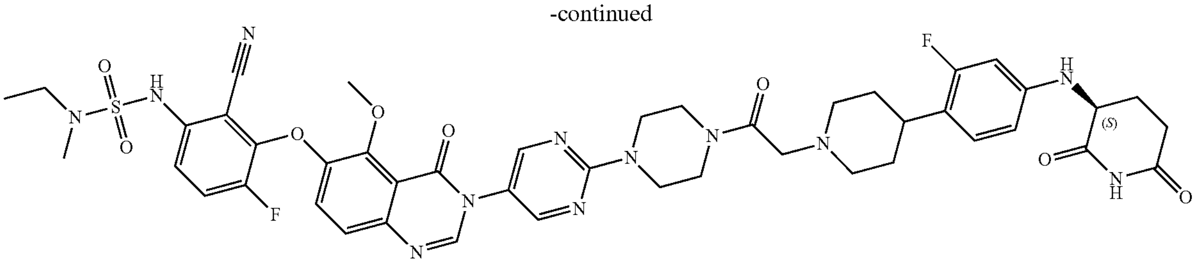

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-5-methoxy-4-oxo-3-(2-piperazin-1-ylpyrimidin-5-yl)quinazoline (80 mg, 123.82 μmol), and 2-[4-[4-[[(3S)-2,6-dioxo-3-piperidyl]amino]-2-fluoro-phenyl]-1-piperidyl]acetic acid (49.51 mg, 123.82 μmol), N,N-diisopropylethylamine (80.01 mg, 619.11 μmol, 107.83 μL) and HATU (94.16 mg, 247.64 μmol). The crude compound was purified by reverse phase column chromatography eluted with 40% acetonitrile in 0.1% ammonium acetate in water to afford product 6-[2-cyano-3-[[ethyl(methyl)sulfamoyl]amino]-6-fluoro-phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-5-methoxy-4-oxo-quinazoline (10 mg, 10.37 μmol, 8% yield) as off-white solid. LCMS m/z (ESI): 955.0 [M+H]; $^1$HNMR (400 MHz, DMSO-$d_6$): δ=10.79 (s, 1H), 9.89 (s, 1H), 8.58 (s, 2H), 8.26 (s, 1H), 7.51-7.46 (m, 3H), 7.50 (s, 2H), 7.27 (d, J=3.20 Hz, 1H), 7.01 (t, J=8.40 Hz, 1H), 6.49-6.45 (m, 2H), 6.05 (d, J=7.60 Hz, 1H), 4.40-4.30 (m, 1H), 3.88 (d, J=25.60 Hz, 4H), 3.83 (s, 3H), 3.64 (d, J=14.40 Hz, 5H), 3.27 (s, 2H), 3.11 (q, J=7.20 Hz, 2H), 2.80-2.50 (m, 6H), 2.10-2.07 (m, 1H), 1.92-1.77 (m, 6H), 1.05 (t, J=7.20 Hz, 3H).

Example 101

5-amino-6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline

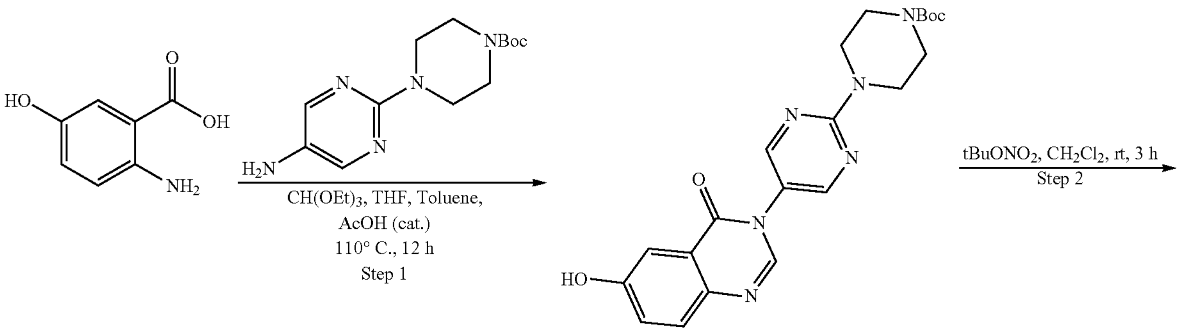

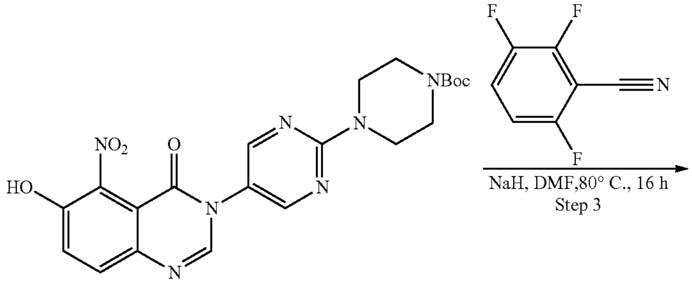

-continued

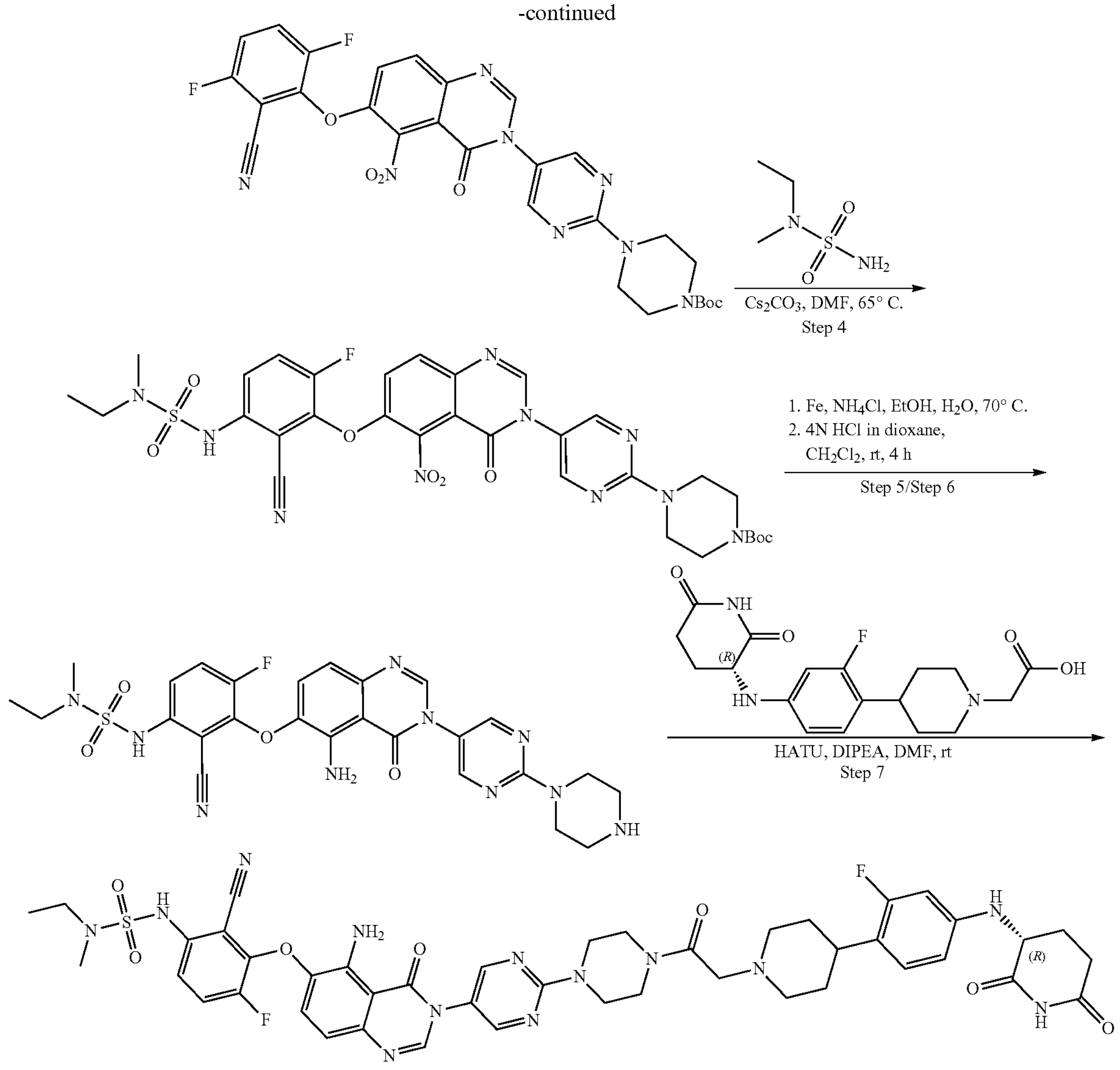

Step 1: Quinazolinone intermediate was synthesized by following general procedure for cyclization (Procedure A-A) using 2-amino-5-hydroxy-benzoic acid (2.19 g, 14.32 mmol) in toluene (35 mL), triethyl orthoformate (4.24 g, 28.64 mmol, 4.76 mL), acetic acid (8.60 mg, 143.20 μmol, 8.19 μL) and tert-butyl 4-(5-aminopyrimidin-2-yl)piperazine-1-carboxylate (4.0 g, 14.32 mmol). The desired compound was purified from crude by silica gel flash column chromatography using 70% ethyl acetate in petroleum ether as eluent to afford tert-butyl 4-[5-(6-hydroxy-4-oxo-quinazolin-3-yl)pyrimidin-2-yl]piperazine-1-carboxylate (1.5 g, 3.53 mmol, 25% yield) as a yellow solid. LCMS m/z (ESI): 425.2 $[M+H]^+$.

Step 2: To a stirred solution of tert-butyl 4-[5-(6-hydroxy-4-oxo-quinazolin-3-yl)pyrimidin-2-yl]piperazine-1-carboxylate (1.5 g, 3.53 mmol) in dichloromethane (100 mL) under nitrogen atmosphere was added tert-Butyl nitrite (1.09 g, 10.60 mmol, 1.26 mL) at 0° C. The reaction mixture was stirred at rt for 3 hr. After completion, the reaction mixture was diluted with water and extracted with dichloromethane (2×50 mL). The organic layer was dried with anhydrous sodium sulfate and concentrated under reduced pressure to afford crude product which was purified by silica gel (230-400 mesh) column chromatography, and the desired product eluted in 0-80% ethyl acetate in Pet ether to afford tert-butyl 4-[5-(6-hydroxy-5-nitro-4-oxo-quinazolin-3-yl)pyrimidin-2-yl]piperazine-1-carboxylate (1 g, 2.02 mmol, 57% yield) as a brown solid. LCMS (ESI): 468.2 $[M-H]^-$.

Step 3: O-arylated quinazolinone intermediate was synthesized by following general procedure for O-arylation (Procedure A-B) using tert-butyl 4-[5-(6-hydroxy-5-nitro-4-oxo-quinazolin-3-yl)pyrimidin-2-yl]piperazine-1-carboxylate (800 mg, 1.70 mmol), sodium hydride (60% dispersion in mineral oil, 156.71 mg, 6.82 mmol) and 2,3,6-trifluorobenzonitrile (535.41 mg, 3.41 mmol, 393.68 μL). The desired compound was purified from crude by silica gel flash column chromatography using 60% ethyl acetate in petroleum ether as eluent to afford tert-butyl 4-[5-[6-(2-cyano-3,6-difluoro-phenoxy)-5-nitro-4-oxo-quinazolin-3-yl]pyrimidin-2-yl]piperazine-1-carboxylate (480 mg, 783.47 μmol, 46% yield) as a pale yellow solid. LCMS m/z (ESI): 551.5 $[M-{}^tBu+H]^+$.

Step 4: Sulfamoylated quinazolinone intermediate was synthesized by following Procedure A-C using tert-butyl 4-[5-[6-(2-cyano-3,6-difluoro-phenoxy)-5-nitro-4-oxo-quinazolin-3-yl]pyrimidin-2-yl]piperazine-1-carboxylate (480 mg, 791.38 μmol), cesium carbonate (773.54 mg, 2.37 mmol) and [methyl(sulfamoyl)amino]ethane (273.40 mg, 1.98 mmol). The desired compound was purified from crude by silica gel flash column chromatography using 80% ethyl acetate in petroleum ether as eluent to afford tert-butyl 4-[5-[6-[2-cyano-3-[[ethyl(methyl)sulfamoyl]amino]-6-fluoro-phenoxy]-5-nitro-4-oxo-quinazolin-3-yl]pyrimidin-2-yl]piperazine-1-carboxylate (240 mg, 271.55 μmol, 34% yield) as brown viscous solid. LCMS m/z (ESI): 723.2 [M−H].

Step 5: To a stirred solution of tert-butyl 4-[5-[6-[2-cyano-3-[[ethyl(methyl)sulfamoyl]amino]-6-fluoro-phenoxy]-5-nitro-4-oxo-quinazolin-3-yl]pyrimidin-2-yl]piperazine-1-carboxylate (210 mg, 289.77 μmol) in ethanol (3 mL) and water (0.5 mL) was added Ammonium Chloride (93.00 mg, 1.74 mmol, 60.78 μL), iron powder (80.92 mg, 1.45 mmol, 10.29 μL) at room temperature. The reaction mixture was heated to 70° C. for 16 h. The reaction mixture was cooled to room temperature, diluted with ethyl acetate, filtered through celite bed and washed with ethyl acetate. Filtrate was concentrated under reduced pressure to afford crude. The crude product was purified by silica gel flash column chromatography 0-100% ethyl acetate in petroleum ether to afford tert-butyl 4-[5-[5-amino-6-[2-cyano-3-[[ethyl(methyl)sulfamoyl]amino]-6-fluoro-phenoxy]-4-oxo-quinazolin-3-yl]pyrimidin-2-yl]piperazine-1-carboxylate (160 mg, 218.79 μmol, 76% yield) as an yellow solid. LCMS ($ES^+$): m/z 639.7 $[M+H-{}^tBu]^+$.

Step 6: The requisite amine was synthesized by 4M HCl in Dioxane mediated N-Boc deprotection (Procedure A-D). N-Boc deprotection was done on tert-butyl 4-[5-[5-amino-6-[2-cyano-3-[[ethyl(methyl)sulfamoyl]amino]-6-fluoro-phenoxy]-4-oxo-quinazolin-3-yl]pyrimidin-2-yl]piperazine-1-carboxylate (160 mg, 230.30 μmol) using hydrogen chloride, 4M in 1,4-dioxane, 99% (167.94 mg, 4.61 mmol, 209.93 μL) to afford 5-amino-6-[2-cyano-3-[[ethyl(methyl)sulfamoyl]amino]-6-fluoro-phenoxy]-4-oxo-3-(2-piperazin-1-ylpyrimidin-5-yl)quinazoline (160 mg, 223.11 μmol, 97% yield) as an off-white solid. LCMS m/z (ESI): 593.7 $[M-H]^-$.

Step 7: Target compound was prepared via HATU mediated acid-amine coupling reaction (Procedure A-E). Amide coupling was carried out using 2-[4-[4-[[(3R)-2,6-dioxo-3-piperidyl]amino]-2-fluoro-phenyl]-1-piperidyl]acetic acid (50.42 mg, 138.74 μmol) and 5-amino-6-[2-cyano-3-[[ethyl(methyl)sulfamoyl]amino]-6-fluoro-phenoxy]-4-oxo-3-(2-piperazin-1-ylpyrimidin-5-yl)quinazoline (75 mg, 126.13 μmol), N,N-diisopropylethylamine (48.90 mg, 378.39 μmol, 65.91 μL) and HATU (71.94 mg, 189.20 μmol). The crude compound was purified by reverse phase column chromatography eluted with 40% acetonitrile in 0.1% ammonium acetate in water to afford product 5-amino-6-[2-cyano-3-[[ethyl(methyl)sulfamoyl]amino]-6-fluoro-phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazoline (18 mg, 17.85 μmol, 14% yield) as an off-white solid. LCMS m/z (ESI): 940.2 $[M+H]^+$; $^1$HNMR (400 MHz, DMSO-$d_6$): δ=10.80 (s, 1H), 9.90 (s, 1H), 8.59 (s, 2H), 8.11 (s, 1H), 7.54 (s, 1H), 7.30 (dd, J=4.00, 9.20 Hz, 1H), 7.18 (s, 1H), 7.01 (dd, J=8.40, 12.20 Hz, 2H), 6.74 (d, J=5.60 Hz, 1H), 6.49-6.44 (m, 2H), 6.05 (d, J=7.60 Hz, 1H), 4.33-4.31 (m, 1H), 3.92-3.85 (m, 5H), 3.64 (s, 5H), 3.33-3.11 (m, 2H), 3.10-3.06 (m, 2H), 2.80-2.50 (m, 7H), 2.10-2.07 (m, 1H), 1.89-1.77 (m, 5H), 1.05 (t, J=7.20 Hz, 3H).

Example 102

5-amino-6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline

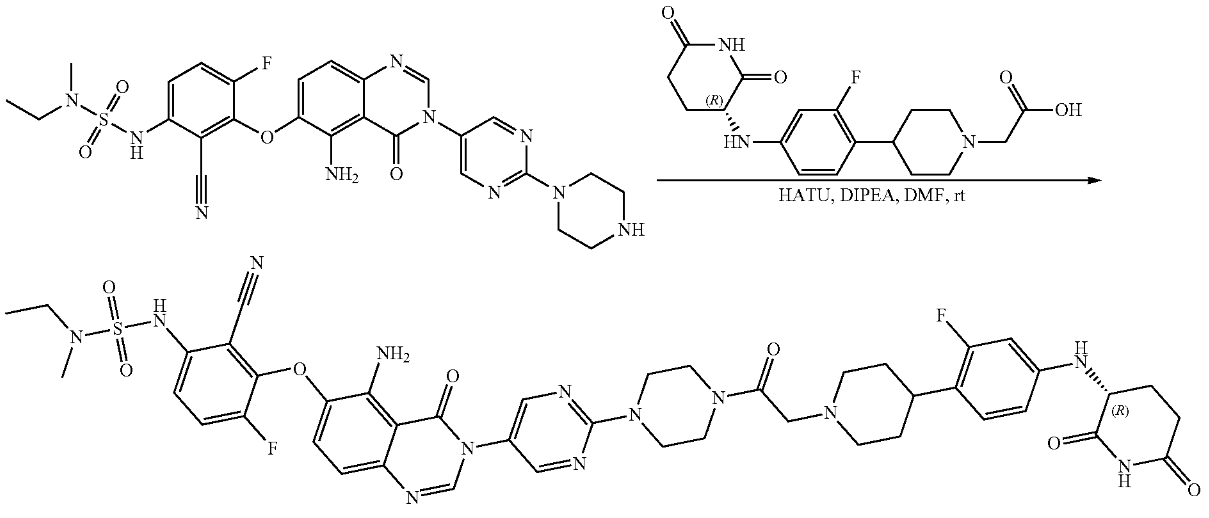

Target compound was prepared via HATU mediated acid-amine coupling reaction (Procedure A-E). Amide coupling was carried out using 5-amino-6-[2-cyano-3-[[ethyl(methyl)sulfamoyl]amino]-6-fluoro-phenoxy]-4-oxo-3-(2-piperazin-1-ylpyrimidin-5-yl)quinazoline (70 mg, 110.92 μmol) and 2-[4-[4-[[(3S)-2,6-dioxo-3-piperidyl]amino]-2-fluoro-phenyl]-1-piperidyl]acetic acid (44.34 mg, 110.89 μmol), N,N-diisopropylethylamine (43.01 mg, 332.76 μmol, 57.96 μL) and HATU (63.26 mg, 166.38 μmol). The crude compound was purified by reverse phase column chromatography eluted with 40% acetonitrile in 0.1% ammonium acetate in water to afford product 5-amino-6-[2-cyano-3-[[ethyl (methyl)sulfamoyl]amino]-6-fluoro-phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazoline (14.5 mg, 14.98 μmol, 14% yield) as an off-white solid. LCMS m/z (ESI): 940.0 [M+H]; $^{1}$HNMR (400 MHz, DMSO-$d_6$): δ=10.80 (s, 1H), 9.89 (s, 1H), 8.61 (s, 1H), 8.11 (s, 1H), 7.55 (s, 1H), 7.55 (s, 1H), 7.31 (t, J=4.80 Hz, 1H), 7.19 (s, 1H), 6.99 (d, J=8.80 Hz, 2H), 6.72 (d, J=8.40 Hz, 1H), 6.49-6.45 (m, 2H), 6.05 (d, J=8.00 Hz, 1H), 4.35-4.30 (m, 1H), 3.88 (d, J=27.20 Hz, 5H), 3.64 (s, 5H), 3.40-3.20 (m, 3H), 2.78-2.59 (m, 11H), 2.11-2.08 (m, 1H), 1.91-1.77 (m, 5H), 1.05 (t, J=7.20 Hz, 3H).

Example 103

6-[2-cyano-3-[[ethyl(methyl)sulfamoyl]amino]-6-fluorophenoxy]-3-[2-[4-[2-[(3R,4R)-4-[4-[[(3R)-2,6-dioxopiperidin-3-yl]amino]-2-fluorophenyl]-3-methoxypiperidin-1-yl]acetyl]piperazin-1-yl]pyrimidin-5-yl]-4-oxoquinazoline

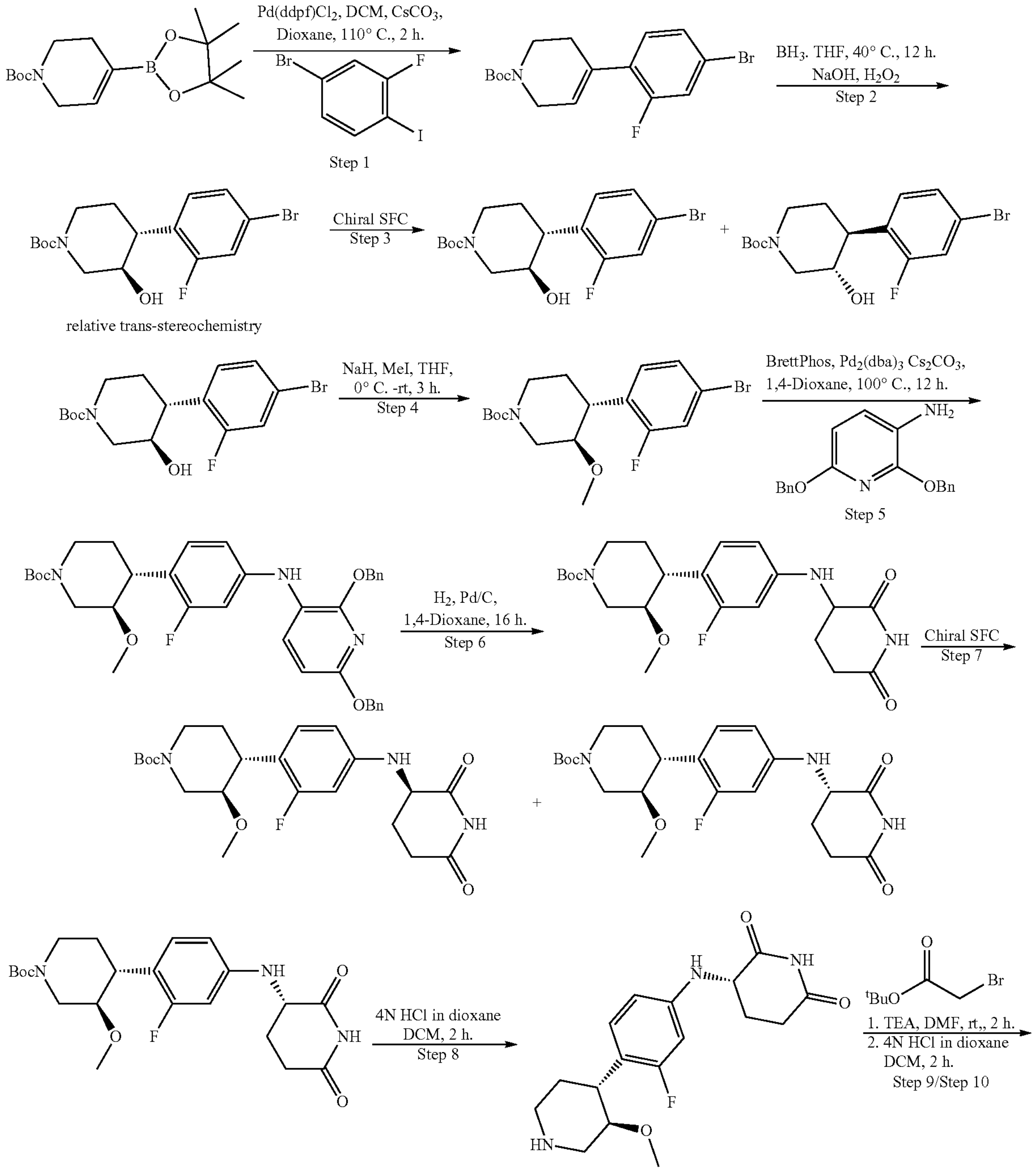

-continued

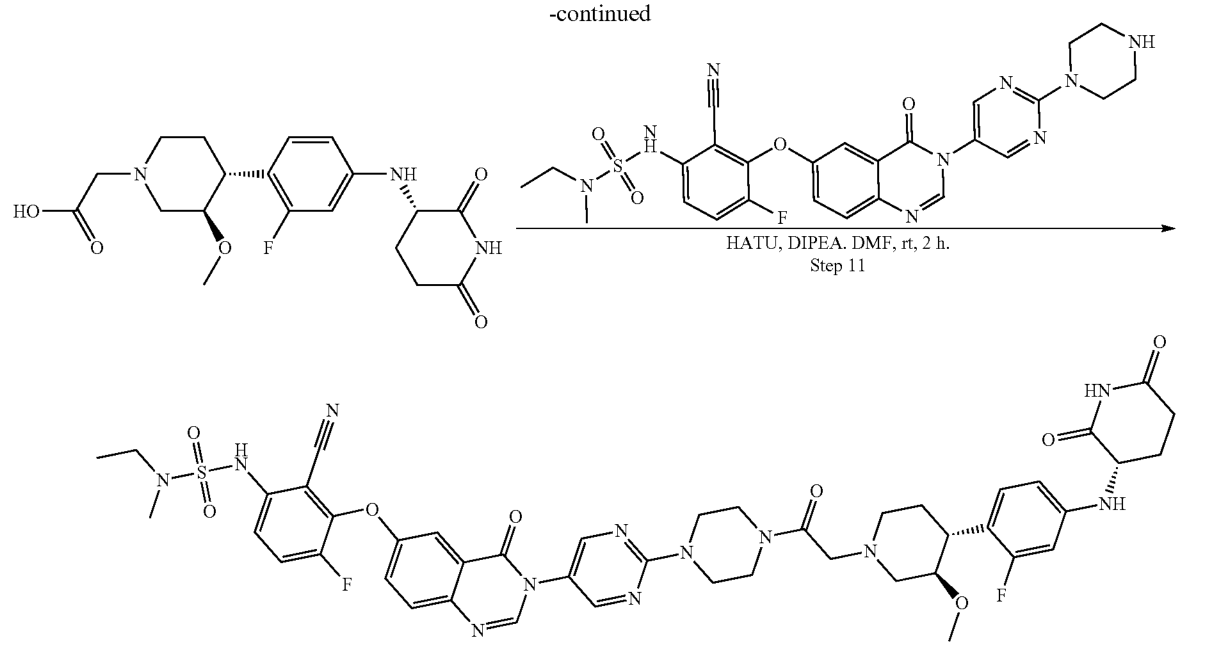

Step 1: Into a 250 mL sealed-tube containing a well-stirred solution of tert-butyl 4-(4,4,5,5-tetramethyl-1,3,2-dioxaborolan-2-yl)-3,6-dihydro-2H-pyridine-1-carboxylate (10 g, 32.34 mmol) and 4-bromo-2-fluoro-1-iodo-benzene (9.73 g, 32.34 mmol, 1.80 mL) in anhydrous 1,4-dioxane (100 mL) was added Pd(dppf)$Cl_2$·dichloromethane (2.64 g, 3.23 mmol) and sodium carbonate (8.57 g, 80.85 mmol, 3.39 mL) in water (20 mL) at ambient temperature under nitrogen atmosphere and the resulting mixture was degassed by bubbling nitrogen gas into the reaction mixture for 10 minutes, the reaction mixture was heated to 110° C. for 2 h. After completion of the reaction, the reaction mixture was quenched with water and extracted with ethyl acetate (2×100 ml). The organic phases were combined and washed with brine, dried over anhydrous sodium sulfate, filtered and concentrated under reduced pressure to afford a crude product, The crude product was purified by silica gel flash column chromatography (90% ethyl acetate in Petroleum ether to afford tert-butyl 4-(4-bromo-2-fluoro-phenyl)-3,6-dihydro-2H-pyridine-1-carboxylate (8.4 g, 22.52 mmol, 70% yield) as an off-white solid. LCMS m/z (ESI): 256.2 $[M+H]^+$.

Step 2: Into a 250 mL two necked round bottomed flask containing a well stirred solution of tert-butyl 4-(4-bromo-2-fluoro-phenyl)-3,6-dihydro-2H-pyridine-1-carboxylate (8.6 g, 21.49 mmol) in Tetrahydrofuran (100 mL) under nitrogen atmosphere was added borane tetrahydrofuran complex solution (1M in THF) (1 M, 35.11 mL) at 0° C. The reaction mixture was heated at 40° C. for 12 h. The reaction mixture was cooled to 0° C. and then added 25% of sodium hydroxide solution (859.45 mg, 21.49 mmol, 403.50 μL) and 35% of Hydrogen peroxide (730.74 mg, 21.49 mmol, 664.31 μL). After completion of the reaction, the reaction mixture was quenched with water and extracted with ethyl acetate (2×100 ml). The organic phases were combined and washed with brine, dried over anhydrous sodium sulfate, filtered and concentrated under reduced pressure to afford a crude product. The crude product was purified by reverse phase preparatory HPLC (Column: Xbridge C-18 20×150 m; mobile phase: A: 0.1% formic acid in water, B: acetonitrile] to afford the purified fraction which was lyophilized to afford tert-butyl 4-(4-bromo-2-fluoro-phenyl)-3-hydroxy-piperidine-1-carboxylate (4.3 g, 11.26 mmol, 52% yield) as a white solid. LCMS m/z (ESI): 274.0 $[M+H-CO_2{}^tBu]^+$ Step 3: tert-butyl 4-(4-bromo-2-fluoro-phenyl)-3-hydroxy-piperidine-1-carboxylate (4.6 g, 12.17 mmol) was purified by chiral SFC (column: Chiralcel OD-H [250*30 mm, 5 μm]; mobile phase: [CO2:MeOH (80:20)]; flow rate: 70 g/min; cycle time: 3.3 min; back pressure: 100 bar; UV: 220 nm) to afford the pure enantiomers tert-butyl (3R,4R)-4-(4-bromo-2-fluoro-phenyl)-3-hydroxy-piperidine-1-carboxylate (2.2 g, 5.82 mmol, 48% yield) and tert-butyl (3S,4S)-4-(4-bromo-2-fluoro-phenyl)-3-hydroxy-piperidine-1-carboxylate (2.3 g, 6.08 mmol, 50% yield) as a white solids. LCMS m/z (ESI): 276.2 $[M-CO_2{}^tBu+2H]^+$ Note: First eluting isomer is arbitrarily assigned as tert-butyl (3R,4R)-4-(4-bromo-2-fluoro-phenyl)-3-hydroxy-piperidine-1-carboxylate and second eluting isomer arbitrarily assigned as tert-butyl (3S,4S)-4-(4-bromo-2-fluoro-phenyl)-3-hydroxy-piperidine-1-carboxylate.

Step 4: Into a 100 mL single necked round bottomed flask containing a well stirred solution of tert-butyl (3R,4R)-4-(4-bromo-2-fluoro-phenyl)-3-hydroxy-piperidine-1-carboxylate (920 mg, 2.43 mmol) in N,N-Dimethylformamide (10 mL) under nitrogen atmosphere was added sodium hydride (60% dispersion in mineral oil, 139.88 mg, 3.65 mmol) at 0° C. The reaction mixture was stirred at 0° C. for 30 minutes and then added methyl iodide (690.88 mg, 4.87 mmol, 303.02 μL). The reaction mixture was stirred at room temperature for 2 h. After completion of the reaction, the reaction mixture was quenched with ammonium chloride solution and extracted with ethyl acetate (2×50 ml).The organic phases were combined and washed with brine, dried (anhydrous sodium sulfate), filtered and concentrated under reduced pressure to afford a crude product tert-butyl (3R,4R)-4-(4-bromo-2-fluoro-phenyl)-3-methoxy-piperidine-1-carboxylate (900 mg, 2.29 mmol, 94% yield) as viscous liquid. LCMS m/z (ESI): 332.0 $[M-{}^tBu+H]^+$.

Step 5: Into a 50 ml sealed-tube containing a well-stirred solution of tert-butyl (3R,4R)-4-(4-bromo-2-fluoro-phenyl)-

3-methoxy-piperidine-1-carboxylate (850 mg, 2.17 mmol) in anhydrous 1,4-dioxane (10 mL) were added 2,6-dibenzyloxypyridin-3-amine (838.70 mg, 2.60 mmol), BrettPhos (232.67 mg, 433.46 μmol) and $Pd(dba)_3$ (396.93 mg, 433.46 μmol) and cesium carbonate (2.12 g, 6.50 mmol) at ambient temperature, and the resulting mixture was degassed by bubbling nitrogen gas into the reaction mixture for 5 minutes, the reaction mixture was heated to 100° C. for 12 h. After completion of the reaction, the reaction mixture was quenched with water and extracted with ethyl acetate (2×100 ml). The organic layers were combined and washed with brine, dried over anhydrous sodium sulfate, filtered and concentrated under reduced pressure to afford a crude product. The crude product was purified by silica gel flash column chromatography eluted with 90% ethyl acetate in Petroleum ether to afford the product tert-butyl (3R,4R)-4-[4-[(2,6-dibenzyloxy-3-pyridyl)amino]-2-fluoro-phenyl]-3-methoxy-piperidine-1-carboxylate (900 mg, 1.10 mmol, 51% yield) as a viscous liquid. LCMS m/z (ESI): 614.8 $[M+H]^+$.

Step 6: Into a 100 mL single-necked round-bottomed flask containing a well-stirred solution of tert-butyl (3R,4R)-4-[4-[(2,6-dibenzyloxy-3-pyridyl)amino]-2-fluoro-phenyl]-3-methoxy-piperidine-1-carboxylate (960 mg, 1.17 mmol) in anhydrous 1,4-dioxane (20 mL) was added Palladium hydroxide on carbon (20 wt. % 50% water, 640.00 mg, 911.42 μmol, 20% purity) at ambient temperature under nitrogen atmosphere. The resulting suspension was stirred at ambient temperature under hydrogen atmosphere (1 atm) for 16 h. After complete consumption of the starting material, the reaction mixture was filtered through a filtered pad and filtered pad was washed with tetrahydrofuran(50 ml) and concentrated under reduced pressure to yield a crude product which was purified by reverse phase preparatory HPLC (Column: Xbridge C-18 20×150 mm mobile phase: A: 0.1% formic acid in water, B: acetonitrile] to afford the purified fraction which was lyophilized to afford the tert-butyl (3R,4R)-4-[4-[(2,6-dioxo-3-piperidyl)amino]-2-fluoro-phenyl]-3-methoxy-piperidine-1-carboxylate (515 mg, 1.17 mmol, 100% yield) as a solid. LCMS m/z (ESI): 336.2 $[M+H-CO_2{}^tBu]^+$ Step 7: tert-butyl (3R,4R)-4-[4-[(2,6-dioxo-3-piperidyl)amino]-2-fluoro-phenyl]-3-methoxy-piperidine-1-carboxylate (520 mg, 1.18 mmol) was purified by chiral SFC (column: YMC Cellulose-SC [250*30 mm, 5 μm]; mobile phase: [$CO_2$:isopropyl alcohol (60:40)]; flow rate: 110 g/min; cycle time: 8 min; back pressure: 100 bar; UV: 210 nm) to afford the pure enantiomers tert-butyl (3R,4R)-4-[4-[[(3S)-2,6-dioxo-3-piperidyl]amino]-2-fluoro-phenyl]-3-methoxy-piperidine-1-carboxylate (230 mg, 512.30 μmol, 43% yield) and tert-butyl (3R,4R)-4-[4-[[(3R)-2,6-dioxo-3-piperidyl]amino]-2-fluoro-phenyl]-3-methoxy-piperidine-1-carboxylate (250 mg, 551.11 μmol, 47% yield) as off-white solids. LCMS m/z (ESI): 336.2 $[M+H-CO_2{}^tBu]^+$.

Note: First eluting isomer is arbitrarily assigned as tert-butyl (3R,4R)-4-[4-[[(3S)-2,6-dioxo-3-piperidyl]amino]-2-fluoro-phenyl]-3-methoxy-piperidine-1-carboxylate and second eluting isomer arbitrarily assigned as tert-butyl (3R,4R)-4-[4-[[(3R)-2,6-dioxo-3-piperidyl]amino]-2-fluoro-phenyl]-3-methoxy-piperidine-1-carboxylate.

Step 8: Into a 50 mL single-necked round-bottomed flask containing a well-stirred solution of tert-butyl (3R,4R)-4-[4-[[(3R)-2,6-dioxo-3-piperidyl]amino]-2-fluoro-phenyl]-3-methoxy-piperidine-1-carboxylate (250 mg, 568.33 μmol) in anhydrous dichloromethane (2 mL) was added 4M hydrogen chloride solution in dioxane (5.38 mL) at ambient temperature under nitrogen atmosphere. The resulting suspension was stirred at ambient temperature for 2 h. After complete consumption of the starting material, the reaction mixture was concentrated under reduced pressure to afford a crude product which was triturated with petroleum ether to afford (3R)-3-[3-fluoro-4-[(3R,4R)-3-methoxy-4-piperidyl]anilino]piperidine-2,6-dione (200 mg, 505.60 μmol, 89% yield) as off-white solid. LCMS m/z (ESI): 336.2 $[M+H]^+$.

Step 9: Into a 50 mL two necked round bottomed flask containing a well stirred solution of (3R)-3-[3-fluoro-4-[(3R,4R)-3-methoxy-4-piperidyl]anilino]piperidine-2,6-dione (180 mg, 515.25 μmol) in N,N-dimethylformamide (5 mL) under nitrogen atmosphere was added tert-butyl bromoacetate (100.50 mg, 515.25 μmol, 75.56 μL) at 0° C. The reaction mixture was stirred at room temperature for 2 h. After completion of the reaction, the reaction mixture was quenched with water and extracted with ethyl acetate (2×100 ml). The organic layers were combined and washed with brine, dried over anhydrous sodium sulfate, filtered and concentrated under reduced pressure to afford tert-butyl 2-[(3R,4R)-4-[4-[[(3R)-2,6-dioxo-3-piperidyl]amino]-2-fluoro-phenyl]-3-methoxy-1-piperidyl]acetate (200 mg, 440.48 μmol, 85% yield) as viscous liquid. LCMS m/z (ESI): 450.2 $[M+H]^+$.

Step 10: To a stirred solution of tert-butyl 2-[(3R,4R)-4-[4-[[(3R)-2,6-dioxo-3-piperidyl]amino]-2-fluoro-phenyl]-3-methoxy-1-piperidyl]acetate (300 mg, 667.39 μmol) in dichloromethane (3 mL) was added 4N HCl in dioxane (2.0 ml) at 0° C. under nitrogen atmosphere. The reaction mixture was stirred at room temperature for 3 h. The reaction mixture was concentrated under reduced pressure to afford crude 2-[(3R,4R)-4-[4-[[(3R)-2,6-dioxo-3-piperidyl]amino]-2-fluoro-phenyl]-3-methoxy-1-piperidyl]acetic acid (220 mg, 509.28 μmol, 76% yield) as a light brown solid. LCMS m/z (ESI): 394.2 $[M+H]^+$ Step 11: Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (169.60 mg, 251.65 μmol), 2-[(3R,4R)-4-[4-[[(3R)-2,6-dioxo-3-piperidyl]amino]-2-fluoro-phenyl]-3-methoxy-1-piperidyl]acetic acid (100 mg, 251.65 μmol), N,N-diisopropylethylamine (162.62 mg, 1.26 mmol, 219.16 μL) and HATU (143.53 mg, 377.47 μmol) to afford crude product. The crude product was purified by reverse phase column chromatography using a pre-packed silica column (100 g C18 packing, Method: 0.1% formic acid in water:acetonitrile) and pure fractions were lyophilized to afford 6-[2-cyano-3-[[ethyl(methyl)sulfamoyl]amino]-6-fluoro-phenoxy]-3-[2-[4-[2-[(3R,4R)-4-[4-[[(3R)-2,6-dioxo-3-piperidyl]amino]-2-fluoro-phenyl]-3-methoxy-1-piperidyl]acetyl]piperazin-1-yl]pyrimidin-5-yl]-4-oxo-quinazoline (70 mg, 69.23 μmol, 28% yield) as a off-white solid. LCMS m/z (ESI): 955.0 $[M+H]^+$; $^1$HNMR (400 MHz, DMSO-$d_6$): δ=10.81 (s, 1H), 10.08 (s, 1H), 8.60 (s, 2H), 8.35 (s, 1H), 7.90-7.85 (m, 2H), 7.76 (dd, J=2.80, 9.00 Hz, 1H), 7.52-7.50 (m, 1H), 7.41 (d, J=2.80 Hz, 1H), 7.09-6.62 (m, 1H), 7.42-7.41 (m, 2H), 6.10 (d, J=12.00 Hz, 1H), 4.34-4.32 (m, 2H), 3.93-3.87 (m, 5H), 3.67-3.57 (m, 6H), 3.19-3.13 (m, 6H), 2.76 (s, 3H), 2.71-2.67 (m, 3H), 2.61-2.60 (m, 2H), 2.12-2.08 (m, 1H), 1.91-1.85 (m, 3H), 1.05 (t, J=6.80 Hz, 3H).

Example 104
6-[2-cyano-3-[[ethyl(methyl)sulfamoyl]amino]-6-fluorophenoxy]-3-[2-[4-[2-[(3S,4S)-4-[4-[[(3S)-2,6-dioxopiperidin-3-yl]amino]-2-fluorophenyl]-3-methoxypiperidin-1-yl]acetyl]piperazin-1-yl]pyrimidin-5-yl]-4-oxoquinazoline
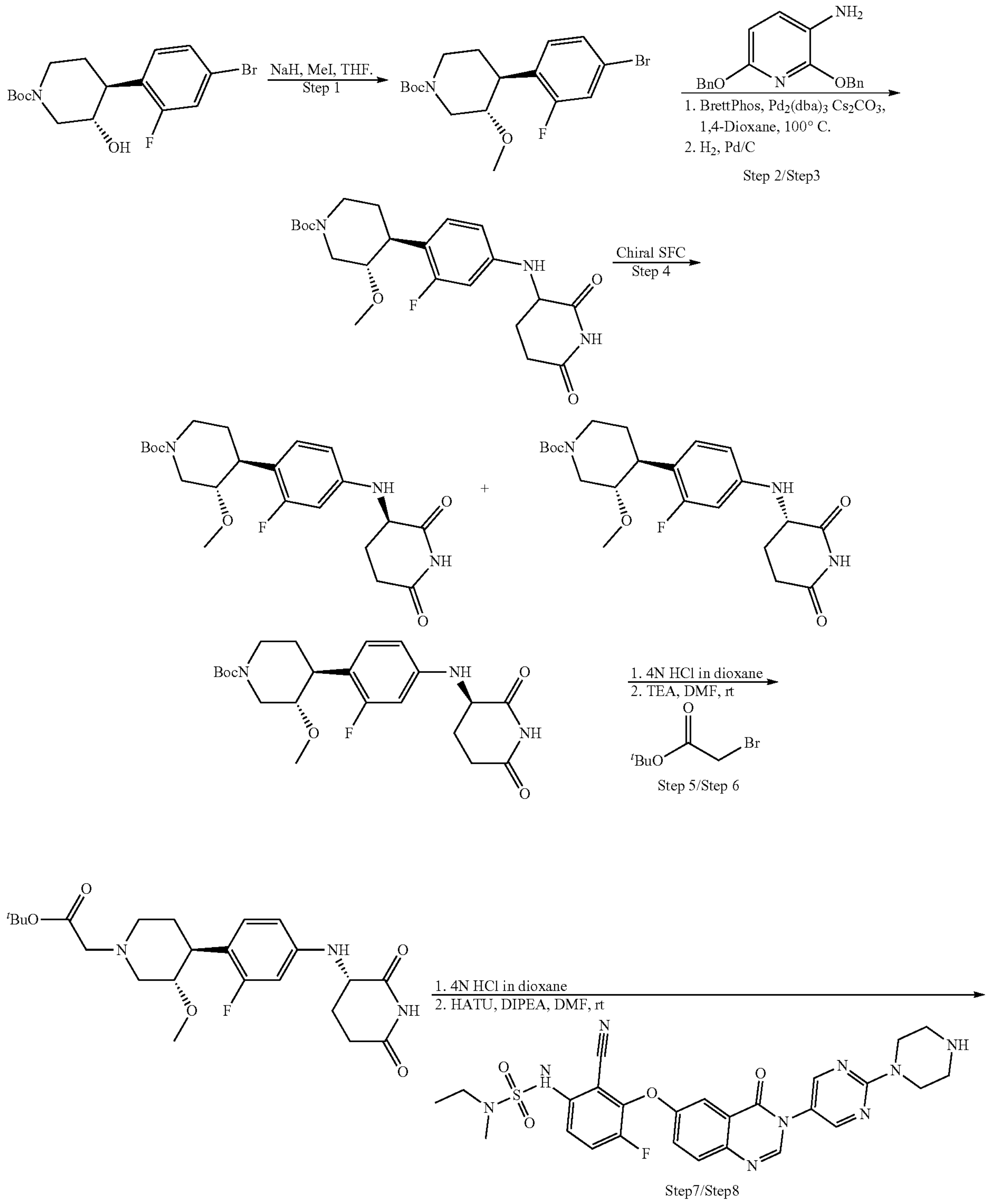

-continued

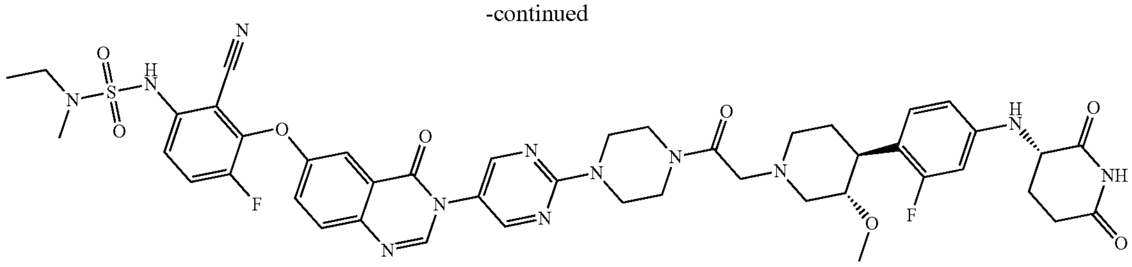

Step 1: To a stirred solution of tert-butyl (3S,4S)-4-(4-bromo-2-fluoro-phenyl)-3-hydroxy-piperidine-1-carboxylate (900 mg, 2.40 mmol) in N,N-dimethylformamide (10 mL) was added sodium hydride (60% dispersion in mineral oil, 138.22 mg, 3.61 mmol) at 0° C. under nitrogen atmosphere and stirred for 30 minutes. Iodomethane (682.68 mg, 4.81 mmol, 299.42 μL) was added to the reaction mixture and stirred at room temperature for 2 h. After completion, the reaction mixture was quenched with saturated ammonium chloride solution (40 mL) and extracted with ethyl acetate (2×50 mL). The combined organic layer was washed with brine (30 mL), dried with anhydrous sodium sulfate and concentrated under reduced pressure to afford tert-butyl (3 S, 4S)-4-(4-bromo-2-fluoro-phenyl)-3-methoxy-piperidine-1-carboxylate (880 mg, 2.27 mmol, 94% yield) as a viscous liquid. LCMS m/z (ESI). 332.0 $[M+H-{}^tBu]^+$.

Step 2: Into a 50-ml sealed-tube containing a well-stirred solution of tert-butyl (3S,4S)-4-(4-bromo-2-fluoro-phenyl)-3-methoxy-piperidine-1-carboxylate (880 mg, 2.27 mmol) in anhydrous 1,4-dioxane (10 mL) were added 2,6-dibenzyloxypyridin-3-amine(1.04 g, 3.40 mmol), cesium carbonate (2.22 g, 6.80 mmol) followed by Brett-Phos(243.33 mg, 453.29 μmol) and $Pd_2(dba)_3$ (415.09 mg, 453.29 μmol) at ambient temperature, and the resulting mixture was degassed by bubbling nitrogen gas into the reaction mixture for 5 minutes, the reaction mixture was heated to 100° C. for 12 h. After completion of the reaction, the reaction mixture was quenched with water and extracted with ethyl acetate (2×100 ml). The organic phases were combined and washed with brine, dried over anhydrous sodium sulfate, filtered and concentrated under reduced pressure to afford a crude product. The crude product was purified by silica gel flash column chromatography eluting with 90% ethyl acetate in petroleum ether to afford the product tert-butyl (3S,4S)-4-[4-[(2,6-dibenzyloxy-3-pyridyl)amino]-2-fluoro-phenyl]-3-methoxy-piperidine-1-carboxylate (730 mg, 689.89 μmol, 30% yield) as a viscous liquid. LCMS m/z (ESI): 612.83 $[M-H]^-$ Step 3: To a solution of tert-butyl (3S,4S)-4-[4-[(2,6-dibenzyloxy-3-pyridyl)amino]-2-fluoro-phenyl]-3-methoxy-piperidine-1-carboxylate (1 g, 1.63 mmol) in 1,4-dioxane (10 mL) was added Palladium hydroxide on carbon (457.65 mg, 3.26 mmol) at room temperature. Then the reaction mixture was stirred at room temperature under hydrogen atmosphere for 16 h. After completion of the reaction, the reaction mixture was filtered through celite and washed with ethyl acetate (80 mL) and dried through a vacuum to afford tert-butyl (3S,4S)-4-[4-[(2,6-dioxo-3-piperidyl)amino]-2-fluoro-phenyl]-3-methoxy-piperidine-1-carboxylate (665 mg, 1.53 mmol, 94% yield). LCMS m/z (ESI): 336.2 $[M+H-CO_2{}^tBu]^+$ Step 4: tert-butyl (3S,4S)-4-[4-[(2,6-dioxo-3-piperidyl)amino]-2-fluoro-phenyl]-3-methoxy-piperidine-1-carboxylate (665 mg, 1.53 mmol) was purified by chiral SFC (column: YMC Cellulose-SC [250*30 mm, 5 μm]; mobile phase: [$CO_2$:isopropyl alcohol (60:40)]; flow rate: 100 g/min; back pressure: 100 bar; wave length: 210 nm; cycle time: 9.0 min) to afford tert-butyl (3S,4S)-4-[4-[[(3S)-2,6-dioxo-3-piperidyl]amino]-2-fluoro-phenyl]-3-methoxy-piperidine-1-carboxylate (260 mg, 593.39 μmol, 36% yield) and tert-butyl (3S,4S)-4-[4-[[(3R)-2,6-dioxo-3-piperidyl]amino]-2-fluoro-phenyl]-3-methoxy-piperidine-1-carboxylate (260 mg, 593.39 μmol, 36% yield).

Note: First eluting isomer from chiral SFC purification was arbitrarily assigned as tert-butyl (3S,4S)-4-[4-[[(3S)-2,6-dioxo-3-piperidyl]amino]-2-fluoro-phenyl]-3-methoxy-piperidine-1-carboxylate and second eluting isomer was arbitrarily assigned as tert-butyl (3S,4S)-4-[4-[[(3R)-2,6-dioxo-3-piperidyl]amino]-2-fluoro-phenyl]-3-methoxy-piperidine-1-carboxylate.

Step 5: To a stirred solution of tert-butyl (3S,4S)-4-[4-[[(3S)-2,6-dioxo-3-piperidyl]amino]-2-fluoro-phenyl]-3-methoxy-piperidine-1-carboxylate (260 mg, 597.03 μmol) in 1,4-dioxane (2 mL) was added 4M hydrogen chloride solution in dioxane (4M, 3.00 mL) at 0° C. under nitrogen atmosphere. The reaction mixture was stirred at room temperature for 2 h. After completion, the reaction mixture was concentrated under reduced pressure to afford crude (3S)-3-[3-fluoro-4-[(3S,4S)-3-methoxy-4-piperidyl]anilino]piperidine-2,6-dione (220 mg, 580.89 μmol, 97% yield) as a grey solid. LCMS m/z (ESI): 336.2 $[M+H]^+$.

Step 6: To a stirred solution of (3S)-3-[3-fluoro-4-[(3S, 4S)-3-methoxy-4-piperidyl]anilino]piperidine-2,6-dione (220 mg, 655.99 μmol) in N,N-Dimethylformamide (3 mL) were added Triethylamine (66.38 mg, 655.99 μmol, 91.43 μL) followed by tert-butyl 2-bromoacetate (127.95 mg, 655.99 μmol, 96.21 μL) at room temperature under nitrogen atmosphere. The reaction mixture was stirred at room temperature for 12 h. The reaction mixture was diluted with water (10 mL) and extracted with ethyl acetate (3×10 mL). The organic layer was washed with brine solution (30 mL), dried over sodium sulfate and concentrated under reduced pressure to afford crude tert-butyl 2-[(3S,4S)-4-[4-[[(3S)-2,6-dioxo-3-piperidyl]amino]-2-fluoro-phenyl]-3-methoxy-1-piperidyl]acetate (230 mg, 510.64 μmol, 78% yield). LCMS m/z (ESI): 450.2 $[M+H]^+$.

Step 7: To a stirred solution of tert-butyl 2-[(3S,4S)-4-[4-[[(3S)-2,6-dioxo-3-piperidyl]amino]-2-fluoro-phenyl]-3-methoxy-1-piperidyl]acetate (230 mg, 511.66 μmol) in dichloromethane (4 mL) was added 4M hydrogen chloride solution in dioxane (4 M, 127.92 μL) at 0° C. under nitrogen atmosphere. The reaction mixture was stirred at room temperature for 12 h. After completion, the reaction mixture was concentrated under reduced pressure to afford crude 2-[(3S, 4S)-4-[4-[[(3S)-2,6-dioxo-3-piperidyl]amino]-2-fluoro-phenyl]-3-methoxy-1-piperidyl]acetic acid (200 mg, 459.53 μmol, 90% yield). LCMS m/z (ESI): 394.5 $[M+H]^+$.

Step 8: Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (120 mg, 207.04 μmol), 2-[(3S,4S)-4-[4-[[(3S)-2,6-dioxo-3-piperidyl]amino]-2-fluoro-phenyl]-3-methoxy-1-piperidyl]acetic acid (81.45 mg, 207.04 μmol), N,N-diisopropylethylamine (133.79 mg, 1.04 mmol, 180.31 μL) followed by HATU (86.59 mg, 227.74 μmol). The crude compound was purified by reverse phase column chromatography, eluted with 40-45% formic acid buffer in acetonitrile to afford 6-[2-cyano-3-[[ethyl(methyl)sulfamoyl]amino]-6-fluoro-phenoxy]-3-[2-[4-[2-[(3S,4S)-4-[4-[[(3S)-2,6-dioxo-3-piperidyl]amino]-2-fluoro-phenyl]-3-methoxy-1-piperidyl]acetyl]piperazin-1-yl]pyrimidin-5-yl]-4-oxo-quinazoline (37.16 mg, 37.08 μmol, 18% yield) as an off-white solid. LCMS m/z (ESI): 955.0 $[M+H]^+$. $^1$H-NMR (400 MHz, DMSO-$d_6$): δ=10.82 (s, 1H), 9.93 (s, 2H), 8.60 (s, 2H), 8.39 (s, 1H), 7.88 (d, J=8.80 Hz, 2H), 7.76 (dd, J=3.20, 8.80 Hz, 1H), 7.50 (dd, J=4.00, 9.00 Hz, 1H), 7.41 (d, J=2.80 Hz, 1H), 7.02 (s, 1H), 0.00-6.53 (m, 2H), 5.92 (d, J=6.40 Hz, 1H), 4.37-4.29 (m, 1H), 4.19-4.05 (m, 6H), 3.93-3.87 (m, 3H), 3.75-3.73 (m, 3H), 3.17-3.12 (m, 6H), 2.79 (s, 3H), 2.75-2.61 (m, 3H), 2.09-2.08 (m, 2H), 1.90-1.84 (m, 3H), 1.05 (t, J=7.20 Hz, 3H).

Example 105

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclohexanesulfonamide

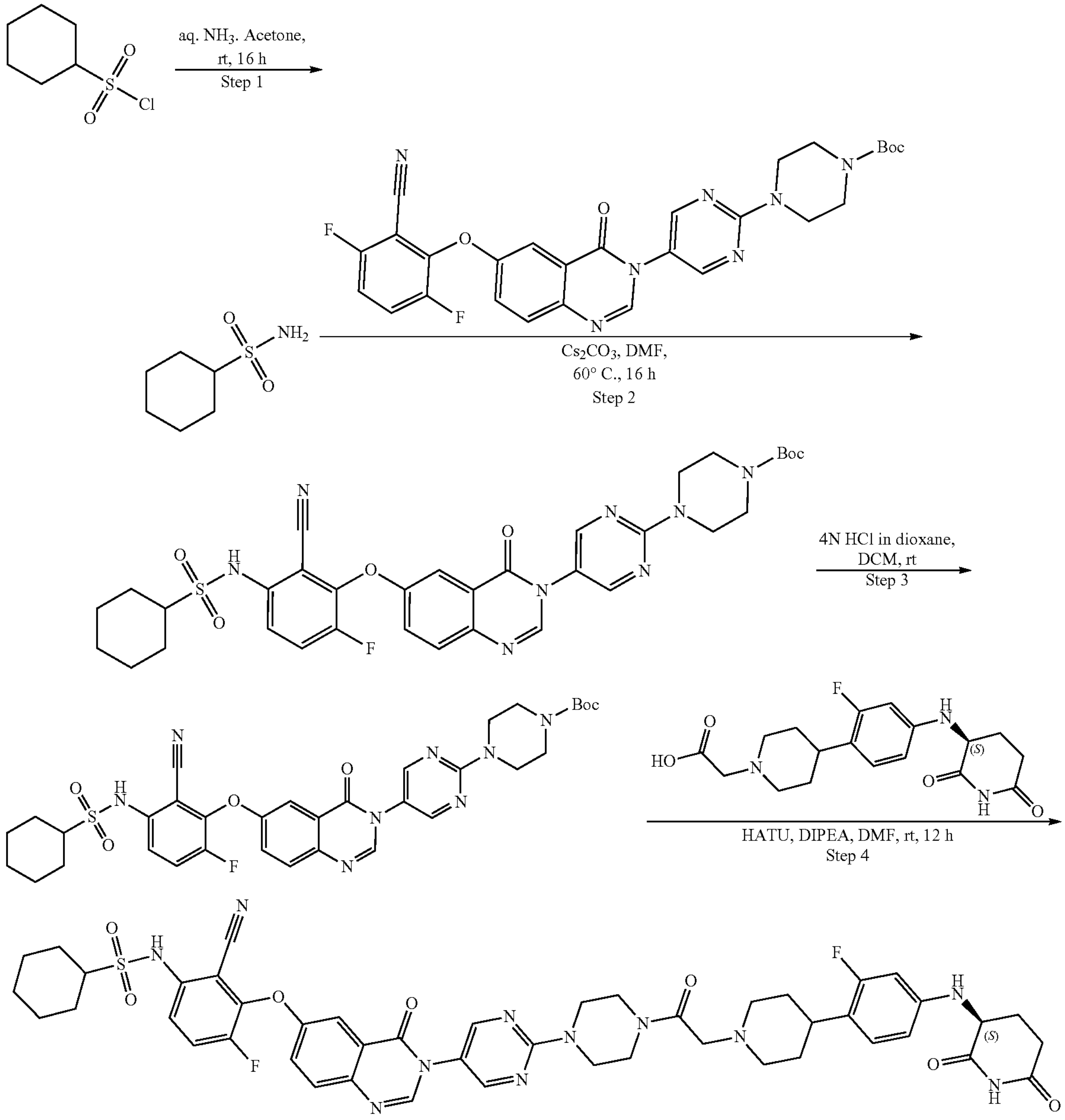

Step 1: To a stirred solution of cyclohexane sulfonyl chloride (1 g, 5.47 mmol) in Acetone (5 mL), was added Aqueous ammonia (30% aqueous, 10 mL, 5.47 mmol) slowly at 5° C. The reaction mixture was stirred at room temperature for 16 h under nitrogen atmosphere. After completion, the reaction mixture was concentrated under reduced pressure, diluted with water (30 mL) and extracted with ethyl acetate (3×50 mL). Combined organic layers dried over sodium sulfate, filtered, and concentrated under reduced pressure to afford crude. Desired crude was purified by silica gel flash column chromatography using 30-50% ethyl acetate in petroleum ether as eluent to afford cyclohexane sulfonamide (0.58 g, 3.55 mmol, 65% yield) as off-white solid. $^1$HNMR (400 MHz, DMSO-$d_6$): δ=6.61 (s, 2H), 2.74 (t, J=9.60 Hz, 1H), 2.02-2.12 (m, 2H), 1.79 (d, J=10.40 Hz, 2H), 1.64 (d, J=11.60 Hz, 1H), 1.21-1.38 (m, 4H), 1.05-1.17 (m, 1H).

Step 2: tert-butyl 4-[5-[6-(2-cyano-3,6-difluoro-phenoxy)-4-oxo-quinazolin-3-yl]pyrimidin-2-yl]piperazine-1-carboxylate (0.5 g, 890.41 μmol) was dissolved in N,N-Dimethylformamide (10 mL) in a sealed tube, and cesium carbonate (870.34 mg, 2.67 mmol) and cyclohexane sulfonamide (363.37 mg, 2.23 mmol) at room temperature. The reaction mixture was stirred at 65° C. for 16 h. After completion, the reaction mixture was diluted with water (30 mL). The reaction mixture was filtered through a paper filter. The filtrate was extracted with ethyl acetate (3×50 mL). Combined organic layers washed with cold water (3×50 mL), dried over sodium sulfate, filtered and concentrated under reduced pressure to afford crude tert-butyl 4-[5-[6-[2-cyano-3-(cyclohexylsulfonylamino)-6-fluoro-phenoxy]-4-oxo-quinazolin-3-yl]pyrimidin-2-yl]piperazine-1-carboxylate (0.45 g, 557.22 μmol, 63% yield) as a brown viscous liquid. LCMS m/z (ESI): 703.4 [M−H]$^-$.

Step 3: To a stirred solution of tert-butyl 4-[5-[6-[2-cyano-3-(cyclohexylsulfonylamino)-6-fluoro-phenoxy]-4-oxo-quinazolin-3-yl]pyrimidin-2-yl]piperazine-1-carboxylate (0.44 g, 624.32 μmol) in dichloromethane (10 mL), was added hydrogen chloride (4 M solution in 1,4-dioxane, 4 mL) at 5° C. under nitrogen atmosphere. The reaction mixture was stirred at room temperature for 12 h. After completion, the reaction mixture was concentrated under reduced pressure to afford crude N-[2-cyano-4-fluoro-3-[4-oxo-3-(2-piperazin-1-ylpyrimidin-5-yl)quinazolin-6-yl]oxy-phenyl]cyclohexanesulfonamide (0.44 g, 585.07 μmol, 94% yield) as a light brown solid. LCMS m/z (ESI): 605.2 [M+H]$^+$.

Step 4: Target compound was prepared via HATU mediated acid-amine coupling reaction (Procedure A-E). Amide coupling was carried out using 2-[4-[4-[[(3S)-2,6-dioxo-3-piperidyl]amino]-2-fluoro-phenyl]-1-piperidyl]acetic acid (143.44 mg, 358.75 μmol), N,N-diisopropylethylamine (463.66 mg, 3.59 mmol, 624.88 μL), HATU (150.05 mg, 394.62 μmol) and N-[2-cyano-4-fluoro-3-[4-oxo-3-(2-piperazin-1-ylpyrimidin-5-yl)quinazolin-6-yl]oxy-phenyl]cyclohexanesulfonamide (0.23 g, 358.75 μmol). The desired product was purified from crude by reverse phase column chromatography (10 mM ammonium acetate in water:acetonitrile) and fractions were lyophilized to afford N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]cyclohexanesulfonamide (108 mg, 112.53 μmol, 31% yield) as an off-white solid. LCMS m/z (ESI): 950.0 [M+H]$^+$. $^1$H NMR (400 MHz, DMSO-$d_6$): δ=10.79 (s, 1H), 10.02 (s, 1H), 8.58 (s, 2H), 8.31 (s, 1H), 7.83 (d, J=8.80 Hz, 1H), 7.71 (d, J=2.80 Hz, 1H), 7.41 (t, J=8.80 Hz, 3H), 7.00 (s, 1H), 6.47 (t, J=12.00 Hz, 2H), 6.06 (d, J=8.00 Hz, 1H), 4.32 (s, 1H), 3.88 (d, J=26.00 Hz, 4H), 3.63 (s, 4H), 2.72 (d, J=42.80 Hz, 3H), 2.12-2.07 (m, 4H), 1.89-1.76 (m, 8H), 1.56 (d, J=43.60 Hz, 2H), 1.42-1.39 (m, 2H), 1.24-1.12 (m, 4H).

Example 106

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]piperidine-1-sulfonamide

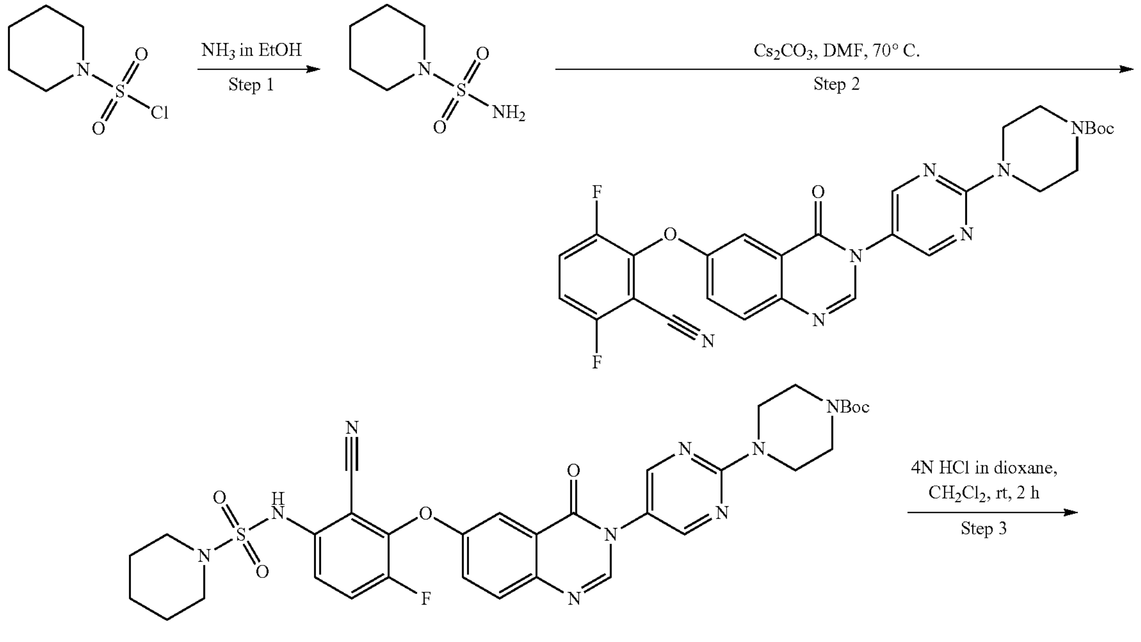

-continued

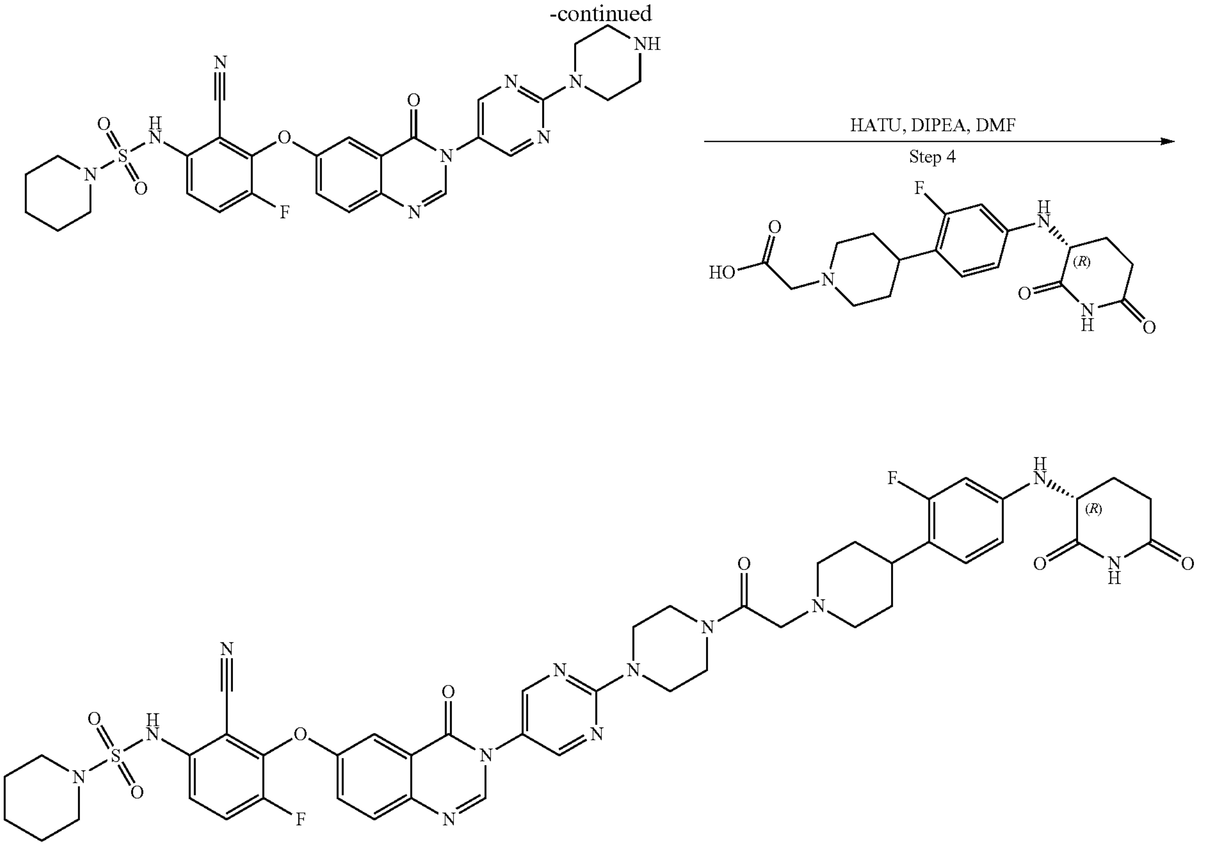

Step 1: To a stirred solution of piperidine-1-sulfonyl chloride (2 g, 10.89 mmol, 1.53 mL) in methanol (20 mL) was added an ammonia solution (7N methanolic ammonia) (10.89 mmol, 10 mL) at 0° C. The reaction mixture was stirred at room temperature for 16 h. After completion of the reaction, the reaction mixture was quenched with ice water (50 mL) and extracted with ethyl acetate (2×50 mL). The combined organic phases were dried with anhydrous sodium sulfate, filtered and the filtrate was evaporated under reduced pressure to afford crude productpiperidine-1-sulfonamide (1.2 g, 7.23 mmol, 66% yield) as an off-white solid. LCMS m/z (ESI): 165.20 $[M+H]^+$.

Step 2: Sulfamoylated quinazolinone intermediate was synthesized by following Procedure A-C using tert-butyl 4-[5-[6-(2-cyano-3,6-difluoro-phenoxy)-4-oxo-quinazolin-3-yl]pyrimidin-2-yl]piperazine-1-carboxylate (500 mg, 890.41 μmol), cesium carbonate (1.02 g, 3.12 mmol) and piperidine-1-sulfonamide (365.57 mg, 2.23 mmol) to afford crude product tert-butyl 4-[5-[6-[2-cyano-6-fluoro-3-(1-piperidylsulfonylamino)phenoxy]-4-oxo-quinazolin-3-yl]pyrimidin-2-yl]piperazine-1-carboxylate (400 mg, 498.75 μmol, 56% yield) as a brown solid. LCMS m/z (ESI): 704.0 $[M-H]^-$.

Step 3: The requisite amine was synthesized by following Procedure A-D using tert-butyl 4-[5-[6-[2-cyano-6-fluoro-3-(1-piperidylsulfonylamino)phenoxy]-4-oxo-quinazolin-3-yl]pyrimidin-2-yl]piperazine-1-carboxylate (400 mg, 566.77 μmol) and hydrogen chloride solution 4.0M in dioxane (3 mL). The resulted crude compound was triturated with methyl t-butyl ether to afford N-[2-cyano-4-fluoro-3-[4-oxo-3-(2-piperazin-1-ylpyrimidin-5-yl)quinazolin-6-yl]oxy-phenyl]piperidine-1-sulfonamide (400 mg, 517.05 μmol, 91% yield) as an off-white solid. LCMS m/z (ESI): 606.2 $[M+H]^+$ Step 4: Target compound was prepared via HATU mediated acid-amine coupling reaction (Procedure A-E). Amide coupling was carried out using N-[2-cyano-4-fluoro-3-[4-oxo-3-(2-piperazin-1-ylpyrimidin-5-yl)quinazolin-6-yl]oxy-phenyl]piperidine-1-sulfonamide (200 mg, 330.23 μmol), 2-[4-[4-[[(3R)-2,6-dioxo-3-piperidyl]amino]-2-fluoro-phenyl]-1-piperidyl]acetic acid (132.00 mg, 363.25 μmol), N,N-diisopropylethylamine (213.40 mg, 1.65 mmol, 287.60 μL) and HATU (150.68 mg, 396.27 μmol) to afford crude product. The crude compound was purified by reverse phase column chromatography eluted with 45% acetonitrile in 0.1% ammonium acetate in water to afford product N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]piperidine-1-sulfonamide (72.14 mg, 71.44 μmol, 22% yield) as an off-white solid. LCMS m/z (ESI): 951.0 $[M+H]^+$; $^1$HNMR (400 MHz, DMSO-$d_6$): δ=10.79 (s, 1H), 9.85 (bs, 1H), 8.57 (s, 2H), 8.30 (s, 1H), 7.82 (d, J=8.80 Hz, 1H), 7.69 (dd, J=3.20, 9.00 Hz, 1H), 7.38 (d, J=24.80 Hz, 3H), 7.00 (s, 1H), 6.48 (d, J=6.80 Hz, 1H), 6.44 (s, 1H), 6.04 (d, J=7.20 Hz, 1H), 4.33-4.30 (m, 1H), 3.87 (d, J=27.20 Hz, 4H), 3.66-3.61 (m, 4H), 3.20-3.18 (m, 1H), 3.05-2.95 (m, 4H), 2.85-2.70 (m, 2H), 2.65-2.60 (m, 1H), 2.59-2.55 (m, 1H), 2.50-2.45 (m, 1H), 2.25-2.15 (m, 2H), 1.95-1.85 (m, 3H), 1.82-1.60 (m, 4H), 1.35-1.59 (m, 6H)

Example 107

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]pyrrolidine-1-sulfonamide

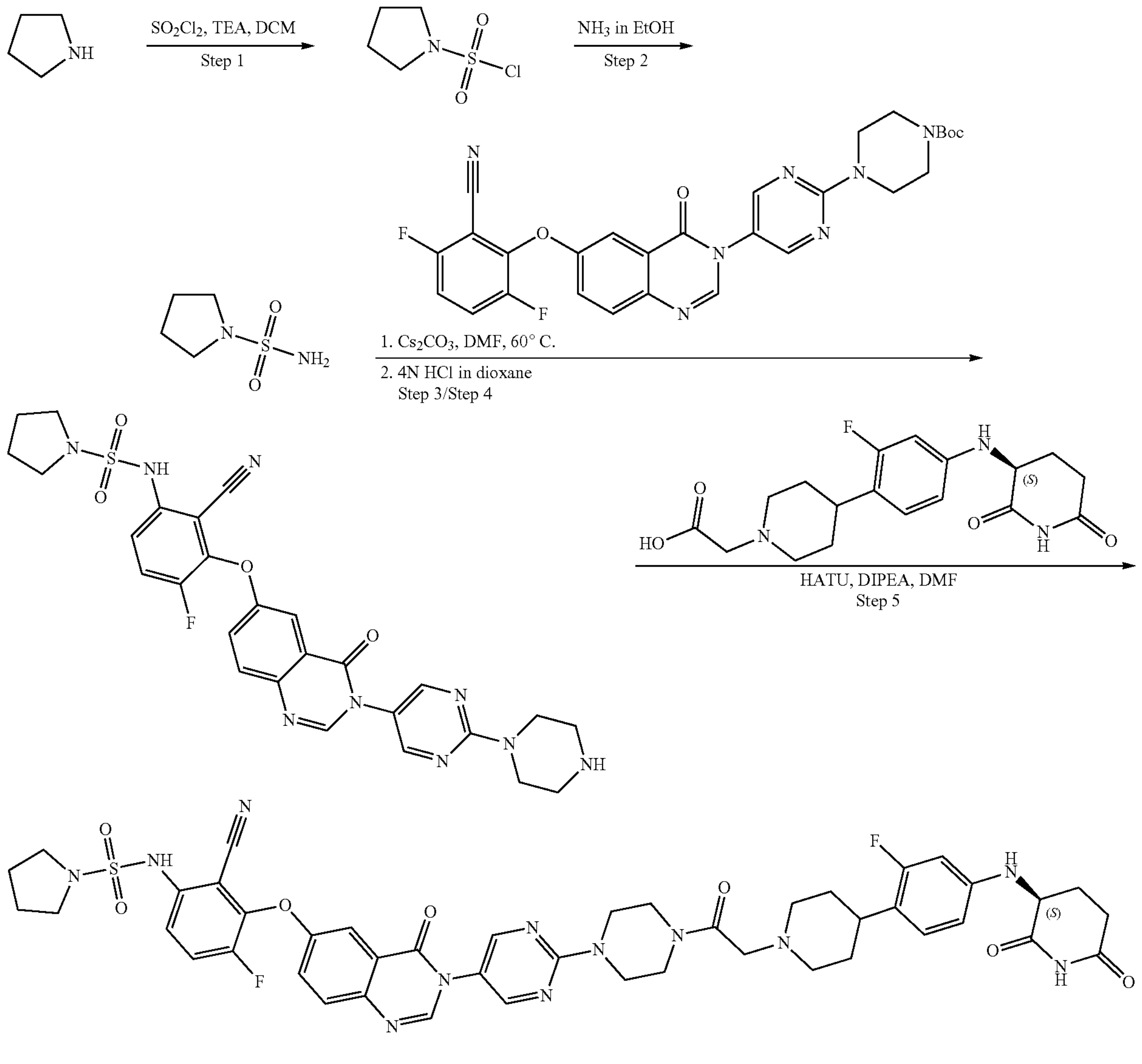

Step 1/Step 2: To a stirred solution of pyrrolidine (5 g, 70.30 mmol, 5.84 mL) in dichloromethane (5 mL) were added N,N-diisopropylethylamine (13.63 g, 105.45 mmol, 18.37 mL), sulfuryl chloride (18.98 g, 140.61 mmol, 11.43 mL) at −30° C., and the reaction mixture was stirred at the same temperature for 2 h. After completion, the reaction mixture was quenched with water (60 mL) dropwise, extracted with ethyl acetate (2×100 mL). Combined organic layers were washed with 1.5N hydrochloric acid (2×50 mL), dried over sodium sulfate, filtered, and concentrated under reduced pressure to afford crude pyrrolidine-1-sulfonyl chloride (10 g, 44.21 mmol, 63% yield) as a light brown solid. To a solution of pyrrolidine-1-sulfonyl chloride (10 g, 58.95 mmol) in methanol (30 mL) was added 7N Ammonia in methanol (1.00 g, 58.95 mmol) at 0° C. and stirred at room temperature for 14 h. The reaction mixture was concentrated under reduced pressure to afford crude, which was diluted with water (30 mL), extracted with ethyl acetate (50 mL). The organic layer was washed with sodium bicarbonate solution (20 ml), brine (20 ml), dried over sodium sulfate and concentrated under reduced pressure to afford crude which was purified by silica gel flash column chromatography eluted with 40% ethyl acetate in petroleum ether to afford pyrrolidine-1-sulfonamide (4.5 g, 29.82 mmol, 51% yield) as an off-white solid. LCMS m/z (ESI): 151.2 $[M+H]^+$.

Step 3: Sulfamoylated quinazolinone intermediate was synthesized following Procedure A-C using tert-butyl 4-[5-

[6-(2-cyano-3,6-difluoro-phenoxy)-4-oxo-quinazolin-3-yl] pyrimidin-2-yl]piperazine-1-carboxylate (500 mg, 890.41 μmol), cesium carbonate (870.34 mg, 2.67 mmol) and pyrrolidine-1-sulfonamide (267.48 mg, 1.78 mmol) to afford crude tert-butyl 4-[5-[6-[2-cyano-6-fluoro-3-(576yrrolidine-1-ylsulfonylamino)phenoxy]-4-oxo-quinazolin-3-yl]pyrimidin-2-yl]piperazine-1-carboxylate (440 mg, 535.62 μmol, 60% yield) as brown viscous compound. LCMS m/z (ESI): 690.0 $[M-H]^-$ Step 4: The requisite amine was synthesized by trifluoracetic acid mediated N-Boc deprotection (Procedure A-D). N-Boc deprotection was done on tert-butyl 4-[5-[6-[2-cyano-6-fluoro-3-(576yrrolidine-1-ylsulfonylamino)phenoxy]-4-oxo-quinazolin-3-yl]pyrimidin-2-yl]piperazine-1-carboxylate (440 mg, 636.09 μmol) using -trifluoroacetic acid (72.53 mg, 636.09 μmol, 49.00 L) to afford N-[2-cyano-4-fluoro-3-[4-oxo-3-(2-piperazin-1-ylpyrimidin-5-yl)quinazolin-6-yl]oxy-phenyl]pyrrolidine-1-sulfonamide (370 mg, 442.35 μmol, 70% yield) as brown viscous compound. LCMS m/z (ESI): 592.2 $[M+H]^+$.

Step 5: Target compound was prepared via HATU mediated acid-amine coupling reaction (Procedure A-E). Amide coupling was carried out using N-[2-cyano-4-fluoro-3-[4-oxo-3-(2-piperazin-1-ylpyrimidin-5-yl)quinazolin-6-yl] oxy-phenyl]pyrrolidine-1-sulfonamide (185 mg, 312.70 μmol), N,N-diisopropylethylamine (202.07 mg, 1.56 mmol, 272.33 μL) and 2-[4-[4-[[(3 S)-2,6-dioxo-3-piperidyl] amino]-2-fluoro-phenyl]-1-piperidyl]acetic acid (113.63 mg, 312.70 μmol) and HATU (130.79 mg, 343.97 μmol). The desired product was purified from crude by reverse phase column chromatography (0.1% formic acid in water: acetonitrile) and fractions were lyophilized to afford N-[2-cyano-3-[3-[2-[4-[2-[4-[4-[[(3 S)-2,6-dioxo-3-piperidyl] amino]-2-fluoro-phenyl]-1-piperidyl]acetyl]piperazin-1-yl] pyrimidin-5-yl]-4-oxo-quinazolin-6-yl]oxy-4-fluoro-phenyl]pyrrolidine-1-sulfonamide (74.82 mg, 74.34 μmol, 24% yield) as an off-white solid. LCMS m/z (ESI): 937.0 $[M+H]^+$; $^1$H-NMR (400 MHz, DMSO-$d_6$): δ=10.81 (s, 1H), 10.20 (s, 1H), 9.61 (s, 1H), 8.59 (s, 2H), 8.33 (s, 1H), 7.89-7.84 (m, 2H), 7.76 (dd, J=3.20, 8.80 Hz, 1H), 7.53 (dd, J=4.00, 9.20 Hz, 1H), 7.41 (d, J=2.80 Hz, 1H), 6.98 (t, J=8.00 Hz, 1H), 6.51 (d, J=7.60 Hz, 1H), 6.48 (d, J=12.80 Hz, H), 6.12 (d, J=7.60 Hz, 1H), 4.38-4.50 (m, 3H), 3.82-3.95 (m, 4H), 3.65-3.71 (m, 2H), 3.49-3.62 (m, 4H), 3.21-3.31 (m, 4H), 3.05-3.18 (m, 1H), 2.82-2.92 (m, 1H), 2.71-2.81 (m, 1H), 2.50-2.65 (m, 2H), 1.95-2.15 (m, 3H), 1.75-1.92 (m, 7H).

Examples 108 and 109

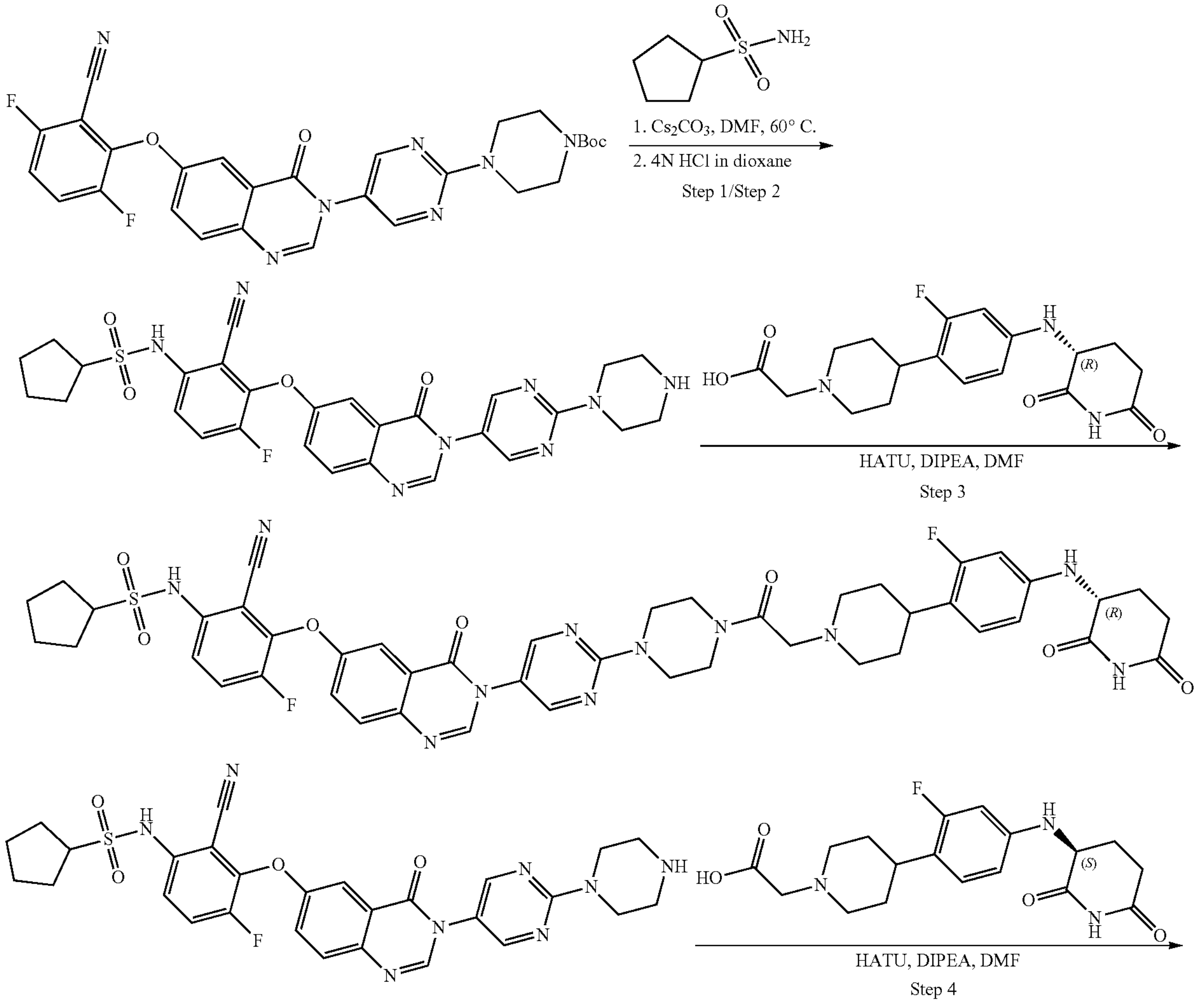

-continued

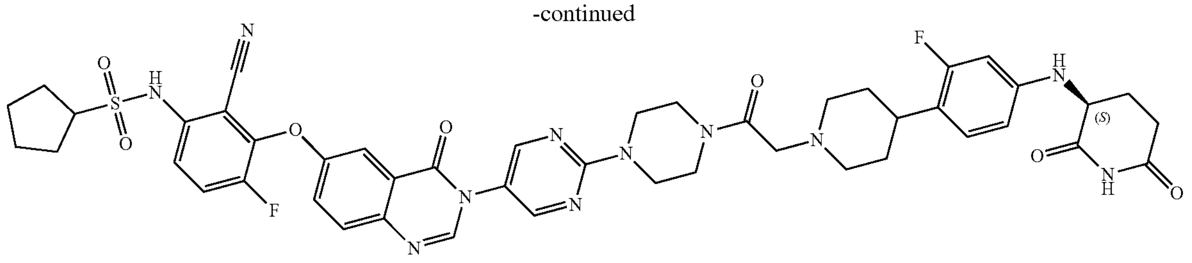

Step 1: Sulfamoylated quinazolinone intermediate was synthesized by following Procedure A-C using tert-butyl 4-[5-[6-(2-cyano-3,6-difluoro-phenoxy)-4-oxo-quinazolin-3-yl]pyrimidin-2-yl]piperazine-1-carboxylate (0.5 g, 890.41 μmol), cesium carbonate (725.28 mg, 2.23 mmol) and cyclopentane sulfonamide (199.29 mg, 1.34 mmol) to afford crude tert-butyl 4-[5-[6-[2-cyano-3-(cyclopentylsulfonylamino)-6-fluoro-phenoxy]-4-oxo-quinazolin-3-yl]pyrimidin-2-yl]piperazine-1-carboxylate (0.47 g, 574.55 μmol, 65% yield) as a colorless liquid, which was carried forward without further purification. LCMS m/z (ESI): 689.4 $[M-H]^-$ Step 2: The requisite amine was synthesized by HCl mediated N-Boc deprotection (Procedure A-D). N-Boc deprotection was done on tert-butyl 4-[5-[6-[2-cyano-3-(cyclopentylsulfonylamino)-6-fluoro-phenoxy]-4-oxo-quinazolin-3-yl]pyrimidin-2-yl]piperazine-1-carboxylate (0.47 g, 680.43 μmol) using hydrogen chloride solution in 1,4-dioxane (4M, 5 mL) to afford N-[2-cyano-4-fluoro-3-[4-oxo-3-(2-piperazin-1-ylpyrimidin-5-yl)quinazolin-6-yl]oxy-phenyl]cyclopentanesulfonamide (0.42 g, 669.76 μmol, 98% yield) as a brown solid, which was carried forward without further purification. LCMS m/z (ESI): 591.6 $[M+H]^+$ Example 108

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide Step 3: Target compound was prepared via HATU mediated acid-amine coupling reaction (Procedure A-E). Amide coupling was carried out using 2-[4-[4-[[(3R)-2,6-dioxo-3-piperidyl]amino]-2-fluoro-phenyl]-1-piperidyl]acetic acid (110.74 mg, 304.76 μmol), N-[2-cyano-4-fluoro-3-[4-oxo-3-(2-piperazin-1-ylpyrimidin-5-yl)quinazolin-6-yl]oxy-phenyl]cyclopentanesulfonamide (0.18 g, 304.76 μmol), HATU (115.88 mg, 304.76 μmol) and N,N-diisopropylethylamine (196.94 mg, 1.52 mmol, 265.42 μL). The crude compound was purified by reverse phase column chromatography by using 30 g snap, eluting with 35% acetonitrile in 0.1% formic acid in water, to afford N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]cyclopentanesulfonamide (90 mg, 88.45 μmol, 29% yield) as an off-white solid. LCMS m/z (ESI): 936.0 $[M+H]^+$; $^1H$ NMR (400 MHz, DMSO-$d_6$): δ=10.79 (s, 1H), 9.98 (s, 1H), 8.58 (s, 2H), 8.32 (s, 1H), 7.86-7.84 (m, 1H), 7.74 (dd, J=3.20, 9.00 Hz, 2H), 7.48-7.45 (m, 2H), 7.10-6.90 (m, 1H), 6.51-6.46 (m, 2H), 6.08 (d, J=7.60 Hz, 1H), 4.32-4.31 (m, 1H), 4.22-4.15 (m, 1H), 3.96-3.82 (m, 5H), 3.70-3.55 (m, 6H), 3.50-3.35 (m, 2H), 2.96-2.82 (m, 2H), 2.78-2.71 (m, 1H), 2.59-2.55 (m, 1H), 2.14-2.05 (m, 1H), 2.02-1.89 (m, 7H), 1.88-1.80 (m, 2H), 1.70-1.67 (m, 2H), 1.58-1.55 (m, 2H).

Example 109

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopentanesulfonamide Step 4: Target compound was prepared via HATU mediated acid-amine coupling reaction (Procedure A-E). Amide coupling was carried out using N-[2-cyano-4-fluoro-3-[4-oxo-3-(2-piperazin-1-ylpyrimidin-5-yl)quinazolin-6-yl]oxy-phenyl]cyclopentanesulfonamide (180 mg, 287.04 μmol), 2-[4-[4-[[(3S)-2,6-dioxo-3-piperidyl]amino]-2-fluoro-phenyl]-1-piperidyl]acetic acid (104.31 mg, 260.87 μmol), HATU (109.14 mg, 287.04 μmol) and N,N-diisopropylethylamine (37.10 mg, 287.04 μmol, 50.00 μL). The crude compound was purified by reverse phase column chromatography by using 30 g snap, eluting with 35% acetonitrile in 0.1% formic acid in water, to afford N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]cyclopentanesulfonamide (73 mg, 73.43 μmol, 26% yield) as an off-white solid. LCMS m/z (ESI): 937 $[M+H]^+$; $^1H$ NMR (400 MHz, DMSO-$d_6$): δ=10.79 (s, 1H), 10.10 (s, 1H), 8.58 (s, 2H), 8.32 (s, 1H), 7.85-7.83 (m, 1H), 7.72 (dd, J=2.80, 9.00 Hz, 1H), 7.64 (s, 1H), 7.43 (d, J=2.80 Hz, 2H), 7.07-6.98 (m, 1H), 6.52-6.45 (m, 2H), 6.06 (d, J=7.60 Hz, 1H), 4.38-4.30 (m, 1H), 3.98-3.90 (m, 2H), 3.90-3.82 (m, 2H), 3.68-3.58 (m, 4H), 3.58-3.47 (m, 1H), 3.29-3.10 (m, 2H), 2.95-2.70 (m, 3H), 2.62-2.58 (m, 1H), 2.57-2.55 (m, 1H), 2.54 (m, 2H), 2.15-2.05 (m, 1H), 1.85-1.98 (m, 7H), 1.83-1.75 (m, 2H), 1.72-1.63 (m, 2H), 1.60-1.49 (m, 2H).

Examples 110-130

Examples 110-130 were synthesized using corresponding sulfonamides in the same manner as examples 105-109 using Method I and II above and the general procedures from C to E.

Example 110

(3S)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide

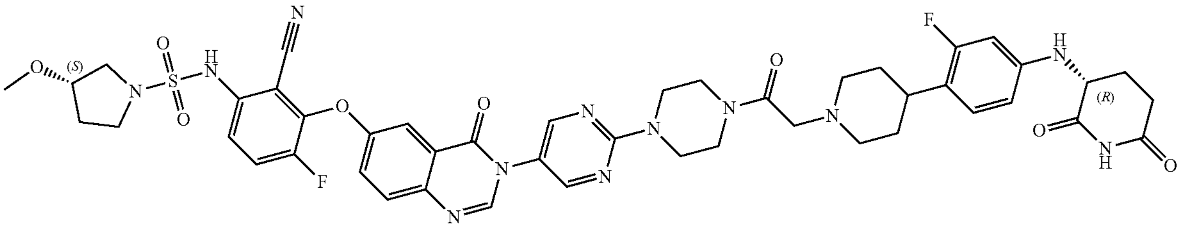

The title compound was purified by reverse phase column chromatography eluting with 45% acetonitrile in 0.1% formic acid in water to afford (3S)—N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-methoxy-pyrrolidine-1-sulfonamide (33 mg, 30.71 μmol, 17% yield) as an off-white solid. LCMS m/z (ESI): 967.20 $[M+H]^+$. $^1H$ NMR (400 MHz, DMSO-$d_6$): δ=10.81 (s, 1H), 10.18 (bs, 1H), 8.60 (s, 2H), 8.33 (s, 1H), 7.76 (dd, J=2.80, 8.80 Hz, 3H), 7.50 (dd, J=5.20, Hz, 1H), 7.42 (d, J=3.20 Hz, 1H), 6.99 (s, 1H), 6.50 (d, J=7.60 Hz, 1H), 6.46 (s, 1H), 6.11 (s, 1H), 4.35-4.30 (m, 4H), 3.96-3.87 (m, 5H), 3.67 (s, 3H), 3.55-3.43 (m, 4H), 3.28-3.23 (m, 3H), 3.22-3.20 (m, 3H), 3.18-3.02 (m, 1H), 2.98-2.92 (m, 2H), 2.80-2.70 (m, 1H), 2.65-2.60 (m, 1H), 2.58-2.55 (m, 1H), 2.15-2.05 (m, 2H), 2.10-1.95 (m, 1H), 1.80-0.30 (m, 5H).

Example 111

(3S)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxypyrrolidine-1-sulfonamide

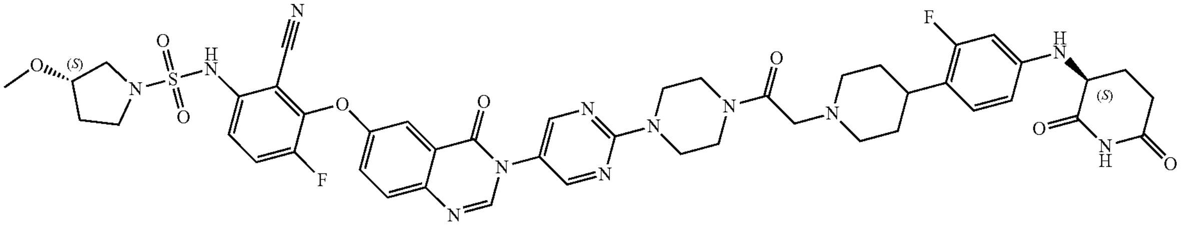

The title compound was purified by reverse phase column chromatography, eluting with 45% acetonitrile in 0.1% ammonium acetate in water, to afford (3S)—N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-methoxy-pyrrolidine-1-sulfonamide (20 mg, 20.21 μmol, 11% yield) as an off-white solid. LCMS m/z (ESI): 967.0 $[M+H]^+$. $^1H$ NMR (400 MHz, DMSO-$d_6$): δ=10.79 (s, 1H), 9.90 (s, 1H), 8.57 (s, 2H), 8.30 (s, 1H), 7.82 (d, J=8.80 Hz, 1H), 7.69 (dd, J=3.20, 9.00 Hz, 1H), 7.39 (d, J=2.80 Hz, 2H), 7.33 (s, 1H), 7.00 (d, J=8.40 Hz, 1H), 6.51 (d, J=18.40 Hz, 1H), 6.44 (s, 1H), 6.04 (d, J=7.60 Hz, 1H), 4.31 (m, 1H), 3.93-3.91 (m, 3H), 3.91-3.83 (m, 2H), 3.61 (m, 4H), 3.30-3.20 (m, 2H), 3.20-3.15 (m, 4H), 3.15-3.00 (m, 4H), 2.74-2.71 (m, 2H), 2.53-2.50 (m, 2H), 2.08-2.07 (m, 2H), 1.93-1.85 (m, 3H), 1.76-1.74 (m, 4H).

Example 112

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide

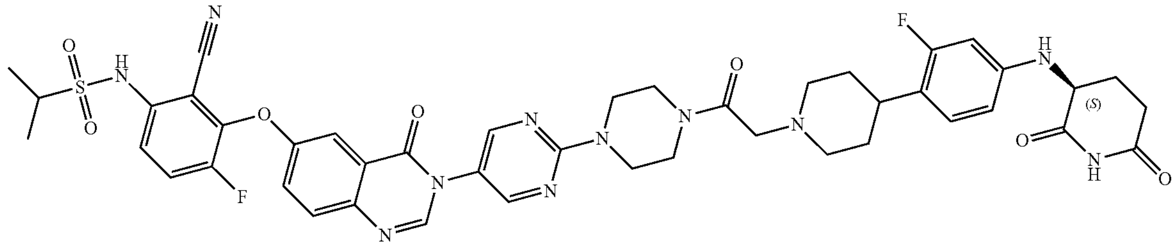

The crude compound was purified by reverse phase column chromatography, eluting with 50% acetonitrile in 0.1% ammonium bicarbonate in water, to afford product N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]propane-2-sulfonamide (57 mg, 62.45 μmol, 21% yield) as a light green solid. LCMS m/z (ESI): 910.0 $[M+H]^+$; $^1$H NMR (400 MHz, DMSO-$d_6$): δ=10.75 (s, 1H), 8.51 (s, 2H), 8.24 (s, 1H), 7.76 (d, J=8.80 Hz, 1H), 7.64 (dd, J=3.20, 8.80 Hz, 1H), 7.34 (d, J=2.80 Hz, 2H), 7.32-7.29 (m, 1H), 7.95-6.89 (m, 1H), 6.46-6.37 (m, 2H), 5.99 (d, J=7.60 Hz, 1H), 4.29-4.20 (m, 1H), 3.80 (d, J=25.60 Hz, 4H), 3.60 (d, J=36.80 Hz, 4H), 2.75 (t, J=5.20 Hz, 4H), 2.36-2.08 (m, 4H), 2.72-2.61 (m, 5H), 2.02 (d, J=40.00 Hz, 6H).

Example 113

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]piperidine-1-sulfonamide

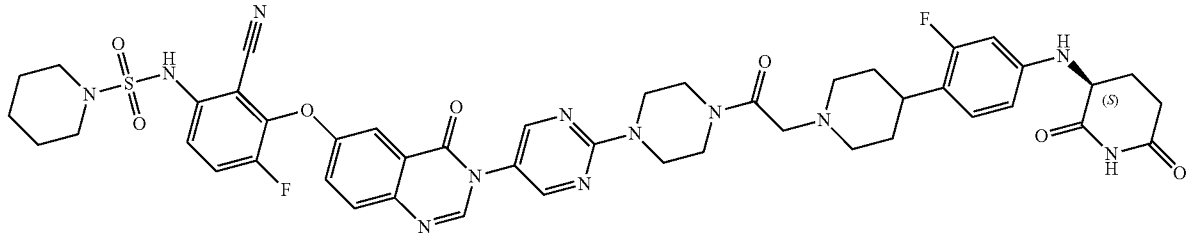

The titled compound was purified by reverse phase column chromatography, eluting with 45% acetonitrile in 0.1% ammonium acetate in water, to afford product N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]piperidine-1-sulfonamide (60.25 mg, 60.10 μmol, 18% yield) as an off-white solid. LCMS m/z (ESI): 951.0 $[M+H]^+$. $^1$H NMR (400 MHz, DMSO-$d_6$): δ=10.80 (s, 1H), 9.88 (bs, 1H), 8.58 (s, 2H), 8.31 (s, 1H), 7.84 (d, J=8.80 Hz, 1H), 7.71 (dd, J=3.20, 9.00 Hz, 1H), 7.55 (s, 1H), 7.39 (d, J=2.80 Hz, 2H), 7.00 (s, 1H), 6.47 (t, J=12.00 Hz, 2H), 6.07 (d, J=7.60 Hz, 1H), 4.33-4.30 (m, 1H), 3.91-3.84 (m, 4H), 3.70-3.55 (m, 4H), 3.29-3.15 (m, 2H), 3.09-3.03 (m, 4H), 2.79-2.71 (m, 2H), 2.70-2.59 (m, 3H), 2.34 (t, J=2.00 Hz, 1H), 2.11-2.06 (m, 2H), 1.92-1.79 (m, 5H), 1.50-1.41 (m, 6H).

Example 114

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide

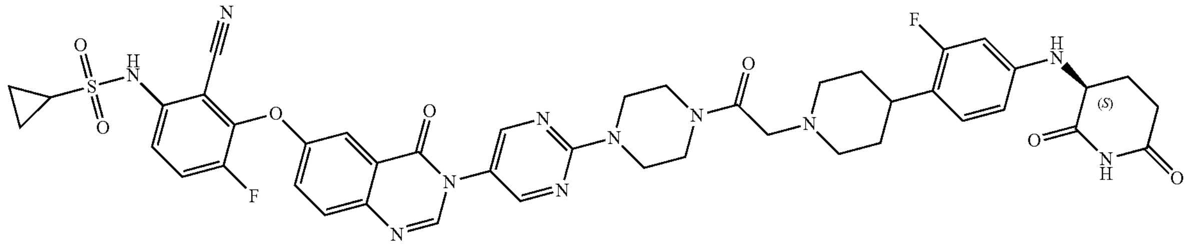

The crude product was purified by reverse phase preparatory HPLC (Column: Xbridge C-18 20×150 m mobile phase: A: 0.1% Ammonium bicarbonate in water, B: acetonitrile] to afford to afford product N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl] cyclopropanesulfonamide (80 mg, 82.56 μmol, 19% yield) as an off-white solid. LCMS m/z (ESI): 908.0 $[M+H]^+$; $^1H$ NMR (400 MHz, DMSO-$d_6$): δ=10.79 (s, 1H), 9.99 (bs, 1H), 8.58 (s, 2H), 8.31 (s, 1H), 7.84 (d, J=9.20 Hz, 1H), 7.72 (dd, J=2.80, 9.00 Hz, 1H), 7.59-7.50 (m, 1H), 7.42-7.38 (m, 2H), 7.01 (t, J=8.00 Hz, 1H), 6.49-6.45 (m, 2H), 6.05 (d, J=7.60 Hz, 1H), 4.33-4.30 (m, 1H), 4.30-3.84 (m, 5H), 3.71-3.63 (m, 5H), 3.22-3.17 (m, 2H), 3.22-3.17 (m, 3H), 2.60-2.59 (m, 2H), 2.09-2.07 (m, 1H), 1.90-1.86 (m, 3H), 1.85-1.77 (m, 3H), 0.87-0.85 (m, 4H).

Example 115

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclopropanesulfonamide

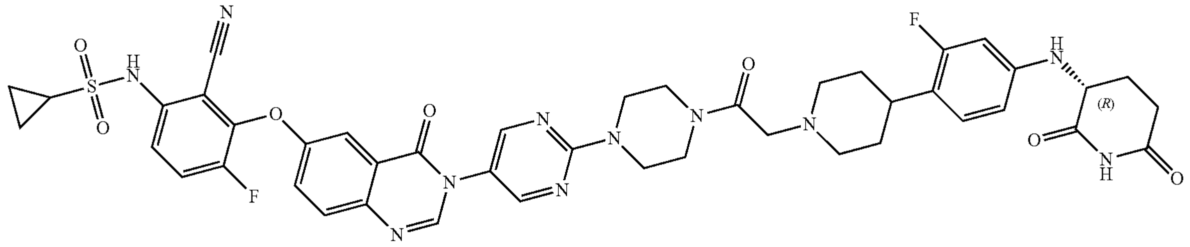

The titled compound was purified by reverse phase preparatory HPLC (Column: Xbridge C-18 20×150 m mobile phase: A: 0.1% Ammonium bicarbonate in water, B: acetonitrile] to afford to afford product N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl] cyclopropanesulfonamide (50 mg, 53.00 μmol, 15% yield) as an off-white solid. LCMS m/z (ESI): 908.0 $[M+H]^+$; $^1H$ NMR (400 MHz, DMSO-$d_6$): δ=10.80 (s, 1H), 9.90 (s, 1H), 8.58 (s, 2H), 8.32 (s, 1H), 7.84 (d, J=8.80 Hz, 1H), 7.74 (d, J=1.60 Hz, 1H), 7.58 (s, 1H), 7.41 (s, 2H), 7.01 (s, 1H), 6.49 (d, J=6.40 Hz, 1H), 6.45 (s, 1H), 6.06 (d, J=6.80 Hz, 1H), 4.32-4.31 (m, 1H), 3.91-3.85 (m, 5H), 3.63 (m, 5H), 3.24-3.23 (m, 2H), 2.79-2.70 (m, 3H), 2.51 (m, 3H), 2.10-2.08 (m, 1H), 1.89-1.84 (m, 4H), 1.78 (m, 1H), 0.87-0.85 (m, 4H).

Example 116

(3R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-fluoropyrrolidine-1-sulfonamide

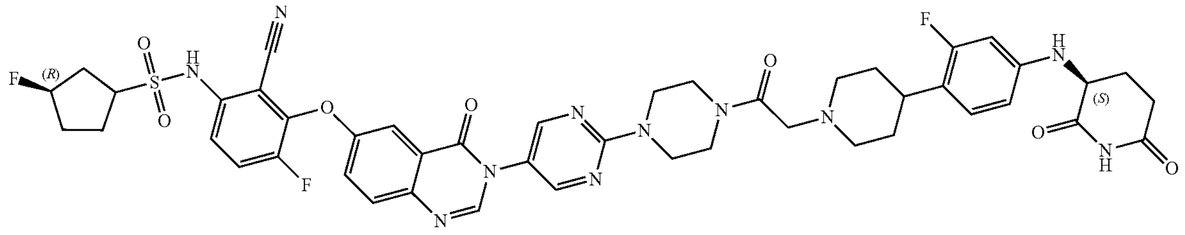

The titled compound was purified by reverse phase column chromatography, eluting with 45% acetonitrile in 0.1% formic acid in water to afford (3R)—N-[2-cyano-3-[3-[2-[4-[2-[4-[4-[[(3 S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-fluoro-pyrrolidine-1-sulfonamide (59.79 mg, 57.83 μmol, 22% yield) as an off-white solid. LCMS m/z (ESI): 955.0 $[M+H]^+$; $^1H$ NMR (400 MHz, DMSO-$d_6$): δ=10.82 (s, 1H), 10.34 (s, 1H), 8.59 (s, 2H), 8.32 (s, 1H), 7.86 (d, J=9.20 Hz, 1H), 7.83 (s, 1H), 7.75 (dd, J=3.20, 8.80 Hz, 1H), 7.52 (dd, J=3.60, 9.00 Hz, 1H), 7.43 (d, J=2.80 Hz, 1H), 6.98 (t, J=8.40 Hz, 1H), 6.52-6.46 (m, 2H), 6.13 (d, J=7.60 Hz, 1H), 5.39-5.26 (m, 1H), 4.44-4.32 (m, 3H), 3.97-3.85 (m, 4H), 3.68 (s, 2H), 3.70-3.39 (m, 8H), 3.19-3.09 (m, 1H), 23.01-2.89 (m, 1H), 2.78-2.69 (m, 1H), 2.61-2.50 (m, 2H), 2.15-2.03 (m, 5H), 1.91-1.87 (m, 3H).

Example 117

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-methoxyazetidine-1-sulfonamide

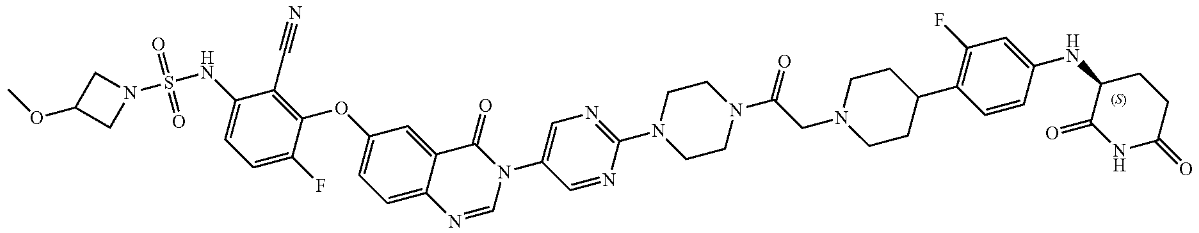

The titled compound was purified by reverse phase column chromatography, eluting with 45% acetonitrile in 0.1% ammonium bicarbonate in water, to afford N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-methoxy-azetidine-1-sulfonamide (89.43 mg, 92.81 μmol, 23% yield) as an off-white solid. LCMS m/z (ESI): 953.2 $[M+H]^+$; $^1H$ NMR (400 MHz, DMSO-$d_6$): δ=10.81 (s, 1H), 9.62 (s, 1H), 8.58 (s, 2H), 8.30 (s, 1H), 7.83 (d, J=8.80 Hz, 1H), 7.70 (dd, J=3.20, 8.80 Hz, 1H), 7.50-7.30 (m, 3H), 6.99 (s, 1H), 6.48 (t, J=12.40 Hz, 2H), 6.09 (d, J=7.20 Hz, 1H), 4.35-4.31 (m, 1H), 4.03 (t, J=5.60 Hz, 1H), 3.89 (d, J=25.20 Hz, 4H), 3.80-3.50 (m, 9H), 3.15 (s, 4H), 3.00-2.65 (m, 3H), 2.56 (t, J=11.20 Hz, 2H), 2.11-1.83 (m, 6H).

Example 118

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]propane-2-sulfonamide

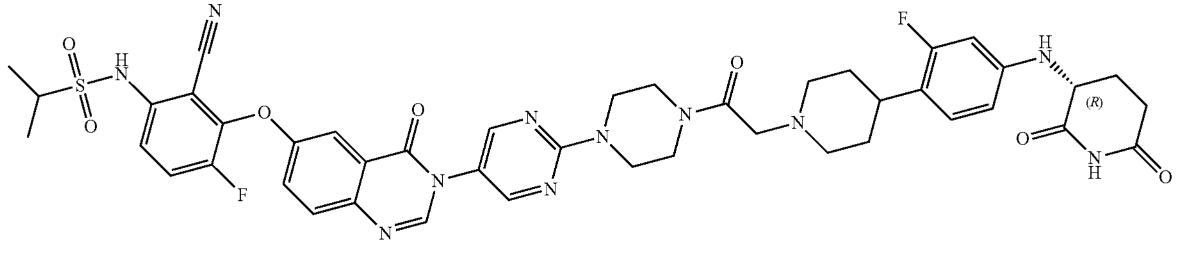

The title compound was purified by reverse phase column chromatography, eluting with 35% acetonitrile in 0.1% ammonium acetate in water, to afford N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]propane-2-sulfonamide (97 mg, 104.46 μmol, 35% yield) as an off-white solid. LCMS m/z (ESI): 910.2 $[M+H]^+$; $^1H$ NMR (400 MHz, DMSO-$d_6$): δ=10.80 (s, 1H), 10.00 (s, 1H), 8.58 (s, 2H), 8.31 (s, 1H), 7.84-7.82 (m, 1H), 7.71-7.68 (m, 1H), 7.47-7.34 (m, 3H), 7.36 (t, J=5.60 Hz, 1H), 6.49-6.44 (m, 2H), 6.05 (d, J=7.60 Hz, 1H), 4.31-4.30 (m, 1H), 3.95-3.80 (m, 4H), 3.76-3.58 (m, 5H), 3.24-3.15 (m, 1H), 3.14-3.00 (m, 2H), 2.80-2.68 (m, 2H), 2.64-2.56 (m, 2H), 2.15-2.06 (m, 1H), 1.91-1.76 (m, 7H), 1.24 (d, J=6.80 Hz, 6H).

Example 119

6-[2-cyano-3-[[2,2-difluoroethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline

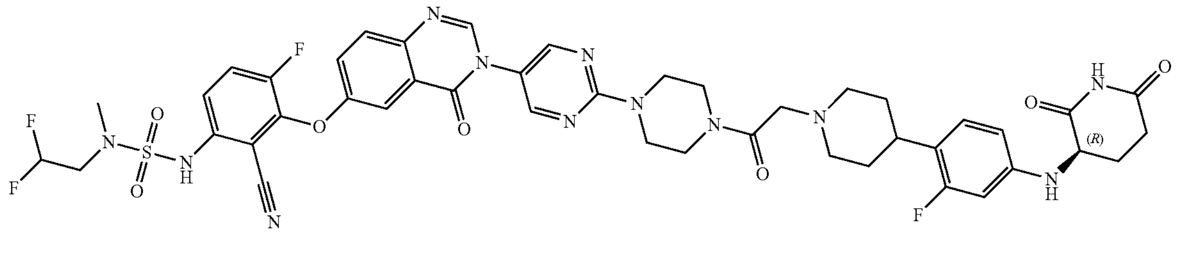

The titled compound was purified by reverse phase column chromatography, eluting with 40% acetonitrile in 0.1% ammonium bicarbonate in water, to afford 6-[2-cyano-3-[[2,2-difluoroethyl(methyl)sulfamoyl]amino]-6-fluoro-phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazoline (41.5 mg, 42.89 μmol, 47% yield) as an off-white solid. LCMS m/z (ESI): 961.0 $[M+H]^+$; $^1H$ NMR (400 MHz, DMSO-$d_6$): δ=10.81 (s, 1H), 9.62 (s, 1H), 8.58 (s, 2H), 8.30 (s, 1H), 7.82 (d, J=8.80 Hz, 1H), 7.69 (dd, J=3.20, 8.80 Hz, 1H), 7.38 (d, J=2.80 Hz, 2H), 7.26 (d, J=4.40 Hz, 1H), 6.99 (s, 1H), 6.48 (d, J=12.40 Hz, 2H), 6.15 (t, J=4.40 Hz, 2H), 4.36-4.30 (m, 1H), 3.93-3.86 (m, 4H), 3.66-3.58 (m, 5H), 3.30 (t, J=Hz, 2H), 3.28 (t, J=Hz, 2H), 3.10 (s, 1H), 2.90 (s, 1H), 2.79-2.73 (m, 1H), 2.68 (s, 3H), 2.60 (d, J=4.00 Hz, 2H), 2.56-2.53 (m, 2H), 2.10-2.07 (m, 1H), 1.92-1.83 (m, 4H).

Example 120

6-[2-cyano-6-fluoro-3-[[2-fluoroethyl(methyl)sulfamoyl]amino]phenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline

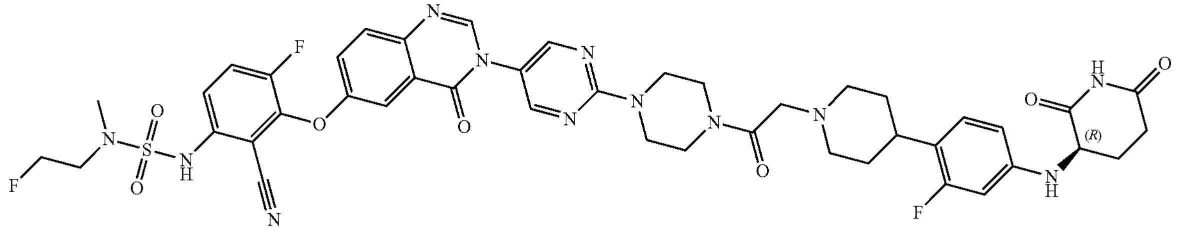

The titled compound was purified by reverse phase column chromatography, eluting with 40% acetonitrile in 0.1% ammonium bicarbonate in water, to afford 6-[2-cyano-6-fluoro-3-[[2-fluoroethyl(methyl)sulfamoyl]amino]phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazoline (45.42 mg, 47.57 μmol, 18% yield) as an off-white solid. LCMS m/z (ESI): 943.0 $[M+H]^+$; $^1H$ NMR (400 MHz, DMSO-$d_6$): δ=10.80 (s, 1H), 9.76 (s, 1H), 8.58 (s, 2H), 8.30 (s, 1H), 7.83 (d, J=8.80 Hz, 1H), 7.69 (dd, J=3.20, 9.00 Hz, 1H), 7.38 (d, J=2.80 Hz, 2H), 7.30 (s, 1H), 7.00 (s, 1H), 6.49 (d, J=7.20 Hz, 2H), 6.45 (s, 2H), 6.07 (t, J=7.20 Hz, 1H), 4.59 (t, J=4.80 Hz, 1H), 4.49-4.31 (m, 1H), 3.89 (d, J=17.60 Hz, 4H), 3.70-3.63 (m, 5H), 3.93-3.86 (m, 2H), 3.30-3.28 (m, 2H), 3.15 (s, 1H), 3.31-3.28 (m, 1H), 2.98-2.85 (m, 1H), 2.78-2.70 (m, 3H), 2.62-2.58 (m, 2H), 2.50-2.42 (m, 2H), 2.15-2.05 (m, 1H), 1.90-1.83 (m, 2H).

Example 121

6-[2-cyano-6-fluoro-3-[[2-fluoroethyl(methyl)sulfamoyl]amino]phenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline

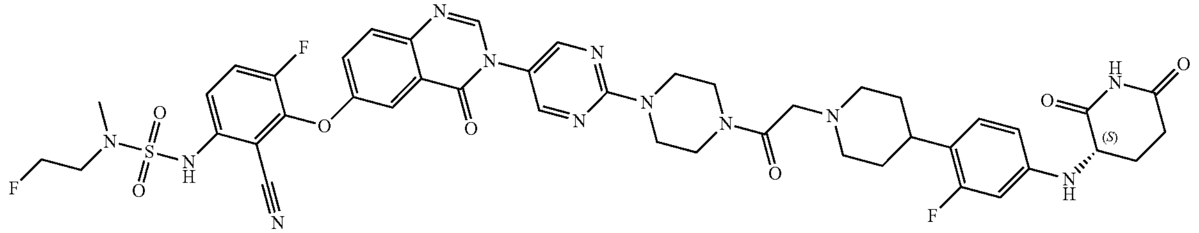

The title compound was purified by reverse phase column chromatography, eluting with 40% acetonitrile in 0.1% formic acid in water, to afford 6-[2-cyano-6-fluoro-3-[[2-fluoroethyl(methyl)sulfamoyl]amino]phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazoline (51.25 mg, 49.89 μmol, 19% yield) as an off-white solid. LCMS m/z (ESI): 943.0 $[M+H]^+$; $^1H$ NMR (400 MHz, DMSO-$d_6$): δ=10.81 (s, 1H), 10.11 (bs, 1H), 8.59 (s, 2H), 8.32 (s, 1H), 7.85 (d, J=9.20 Hz, 1H), 7.73 (dd, J=2.80, 8.80 Hz, 2H), 7.40 (d, J=2.80 Hz, 2H), 6.99 (bs, 1H), 6.54-6.46 (m, 2H), 6.11 (d, J=7.60 Hz, 1H), 4.58 (t, J=4.80 Hz, 1H), 4.46 (t, J=5.20 Hz, 1H), 4.35-4.30 (m, 2H), 3.92-3.85 (m, 4H), 3.69-3.52 (m, 6H), 3.37-3.35 (m, 1H), 3.30-3.28 (m, 1H), 2.95-2.85 (m, 3H), 2.78-2.70 (m, 4H), 2.69-2.57 (m, 2H), 2.11-2.07 (m, 2H), 1.90-1.89 (m, 1H), 1.87-1.83 (m, 3H).

Example 122

6-[2-cyano-3-[[2,2-difluoroethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline

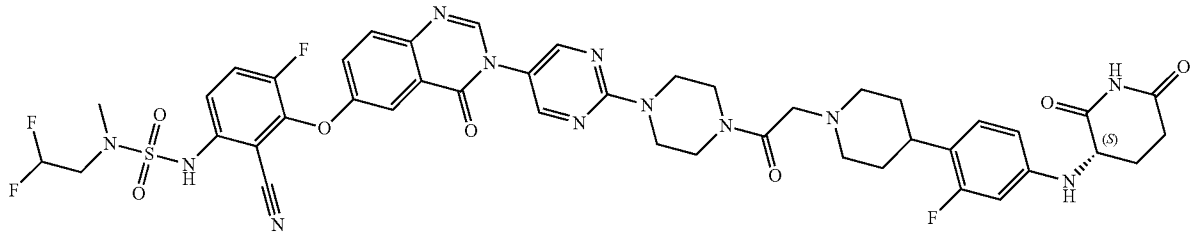

The title compound was purified by reverse phase column chromatography, eluting with 40% acetonitrile in 0.1% ammonium bicarbonate in water, to afford 6-[2-cyano-3-[[2,2-difluoroethyl(methyl)sulfamoyl]amino]-6-fluoro-phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazoline (42.24 mg, 42.93 μmol, 47% yield) as an off-white solid. LCMS m/z (ESI): 961.2 $[M+H]^+$; $^1H$ NMR (400 MHz, DMSO-$d_6$): δ=10.80 (s, 1H), 9.64 (bs, 1H), 8.58 (s, 2H), 8.30 (s, 1H), 7.82 (d, J=8.80 Hz, 1H), 7.69 (dd, J=3.20, 9.00 Hz, 1H), 7.38 (d, J=2.80 Hz, 2H), 7.27-7.23 (m, 1H), 7.00 (bs, 1H), 6.50-6.45 (m, 2H), 6.16 (t, J=4.40 Hz, 2H), 4.36-4.30 (m, 1H), 3.89 (d, J=25.20 Hz, 4H), 3.65-3.60 (m, 4H), 3.43-3.38 (m, 1H), 3.28-3.27 (m, 3H), 2.78-2.73 (m, 2H), 2.71-2.68 (m, 1H), 2.67 (s, 3H), 2.60-2.56 (m, 3H), 2.51-2.50 (m, 2H), 2.11-2.07 (m, 1H), 1.90-1.83 (m, 4H).

Example 123

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3,3-difluoropyrrolidine-1-sulfonamide

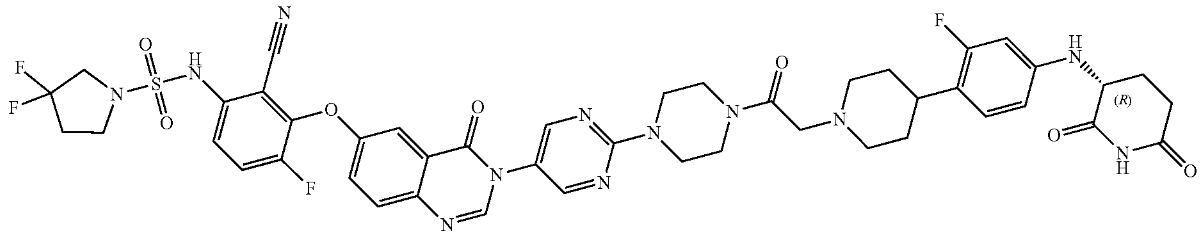

The title compound was purified by reverse phase column chromatography, eluting with 40% acetonitrile in 0.1% ammonium acetate in water, to afford N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3,3-difluoro-pyrrolidine-1-sulfonamide (30 mg, 30.74 μmol, 19% yield) as an off-white solid. LCMS m/z (ESI): 973.0 $[M+H]^+$; $^1H$ NMR (400 MHz, DMSO-$d_6$): δ=10.80 (s, 1H), 9.55 (s, 1H), 8.59 (s, 2H), 8.30 (s, 1H), 7.82 (d, J=8.80 Hz, 1H), 7.69 (dd, J=3.20, 9.00 Hz, 1H), 7.41 (s, 1H), 7.39 (d, J=3.20 Hz, 1H), 7.32-7.29 (m, 1H), 6.99 (s, 1H), 6.51 (s, 1H), 6.48 (d, J=12.80 Hz, 1H), 6.10 (d, J=8.00 Hz, 1H), 4.35-4.31 (m, 2H), 3.93 (s, 2H), 3.87 (s, 2H), 3.67 (s, 2H), 3.57 (s, 2H), 3.39 (t, J=24.00 Hz, 3H), 3.26 (t, J=7.20 Hz, 3H), 3.12 (m, 1H), 2.87 (m, 1H), 2.76-2.72 (m, 1H), 2.68-2.61 (m, 2H), 2.38-2.32 (m, 3H), 2.11-2.10 (m, 1H), 2.09-2.07 (m, 1H), 1.87-1.83 (m, 3H).

Example 124

(3R)—N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-fluoropyrrolidine-1-sulfonamide

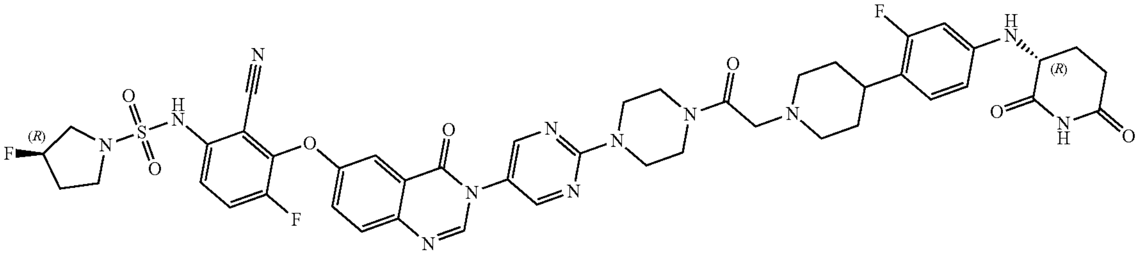

The title compound was purified by reverse phase column chromatography, eluting with 40% acetonitrile in 0.1% formic acid in water, to afford (3R)—N-[2-cyano-3-[3-[2-[4-[2-[4-[4-[[(3R)-2,6-dioxo-3-piperidyl]amino]-2-fluorophenyl]-1-piperidyl]acetyl]piperazin-1-yl]pyrimidin-5-yl]-4-oxo-quinazolin-6-yl]oxy-4-fluoro-phenyl]-3-fluoro-pyrrolidine-1-sulfonamide (48.54 mg, 47.81 μmol, 16% yield) as off-white solid. LCMS m/z (ESI): 955.0 $[M+H]^+$; $^1H$ NMR (400 MHz, DMSO-$d_6$): δ=10.80 (s, 1H), 9.56 (s, 1H), 8.59 (s, 2H), 8.33 (s, 1H), 7.86 (d, J=9.20 Hz, 1H), 7.74 (dd, J=2.80, 9.00 Hz, 2H), 7.51-7.50 (m, 1H), 7.43 (d, J=3.20 Hz, 1H), 6.99 (s, 1H), 6.51 (d, J=8.00 Hz, 1H), 6.47 (s, 1H), 6.11 (d, J=8.00 Hz, 1H), 5.39 (s, 1H), 5.26 (s, 1H), 4.36-4.30 (m, 3H), 3.94 (s, 2H), 3.94 (s, 2H), 3.68 (s, 2H), 3.52 (m, 4H), 3.41 (s, 2H), 3.27-3.26 (m, 2H), 2.93-2.90 (m, 1H), 2.78-2.72 (m, 1H), 2.15-2.07 (m, 6H), 1.91-1.87 (m, 4H).

Example 125

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]azetidine-1-sulfonamide

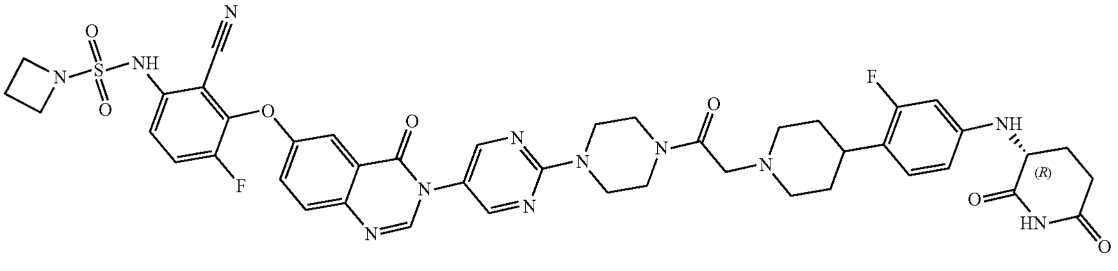

The title compound was purified by reverse phase column chromatography, eluting with 35% acetonitrile in 0.1% formic acid in water, to afford N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]azetidine-1-sulfonamide (19 mg, 19.14 μmol, 15% yield) as an off-white solid. LCMS m/z (ESI): 923.2 $[M+H]^+$; $^1H$ NMR (400 MHz, DMSO-$d_6$): δ=10.80 (s, 1H), 10.40 (s, 1H), 8.59 (s, 2H), 8.33 (s, 1H), 7.86 (d, J=8.80 Hz, 1H), 7.75 (dd, J=3.20, 9.00 Hz, 2H), 7.52-7.50 (m, 1H), 7.43 (d, J=2.80 Hz, 1H), 7.03-6.99 (m, 1H), 6.50 (t, J=12.80 Hz, 2H), 6.11 (d, J=7.60 Hz, 1H), 4.34-4.30 (m, 2H), 3.98-3.90 (m, 2H), 3.93-3.83 (m, 2H), 3.81 (t, J=7.20 Hz, 3H), 3.70-3.60 (m, 2H), 3.60-3.45 (m, 4H), 3.08 (s, 1H), 2.89-2.82 (m, 1H), 2.80-2.72 (m, 1H), 2.62-2.58 (m, 1H), 2.57-2.53 (m, 3H), 2.15-2.06 (m, 5H), 1.91-1.87 (m, 3H).

Example 126

6-[2-cyano-3-[[cyclopropyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline

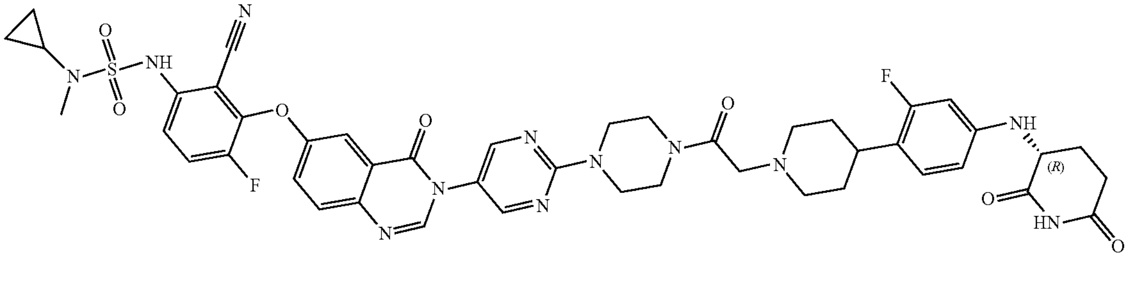

The title compound was purified by reverse phase column chromatography, eluting with 40% acetonitrile in 0.1% formic acid in water, to afford 6-[2-cyano-3-[[cyclopropyl(methyl)sulfamoyl]amino]-6-fluoro-phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazoline (73 mg, 72.72 μmol, 38% yield) as off-white solid. LCMS m/z (ESI): 937.0 $[M+H]^+$; $^1H$ NMR (400 MHz, DMSO-$d_6$): δ=10.82 (s, 1H), 9.90 (s, 1H), 8.58 (s, 2H), 8.34 (s, 1H), 7.86-7.84 (m, 1H), 7.74 (d, J=2.80 Hz, 2H), 7.47-7.41 (m, 1H), 7.39 (d, J=2.80 Hz, 1H), 7.04-6.95 (m, 1H), 6.51-6.46 (m, 2H), 6.11 (d, J=7.60 Hz, 1H), 4.39-4.32 (m, 2H), 3.87-3.93 (m, 4H) 3.70-3.55 (m, 6H), 3.08-2.70 (m, 7H), 2.63-2.58 (m, 2H), 2.37-2.27 (m, 1H), 2.18-1.80 (m, 6H), 0.60 (d, J=18.00 Hz, 4H).

Example 127

6-[2-cyano-3-[[cyclopropyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline

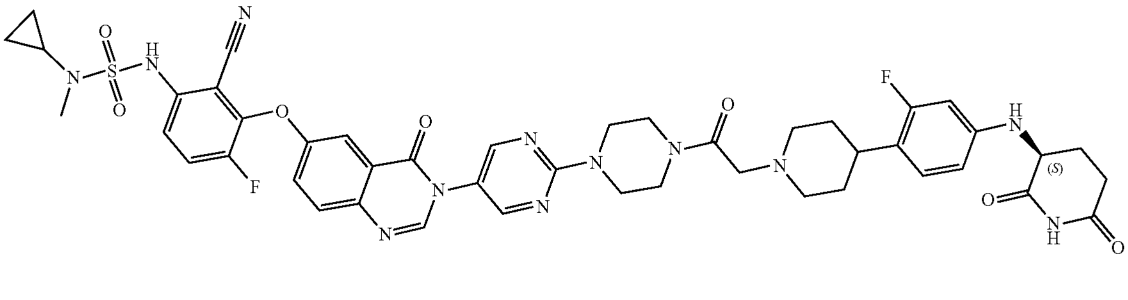

The title compound was purified by reverse phase column chromatography, eluting with 40% acetonitrile in 0.1% formic acid in water, to afford product 6-[2-cyano-3-[[cyclopropyl(methyl)sulfamoyl]amino]-6-fluoro-phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazoline (15 mg, 14.52 μmol, 7% yield) as pale yellow solid. LCMS m/z (ESI): 937.2 $[M+H]^+$; $^1H$ NMR (400 MHz, DMSO-$d_6$): δ=10.99 (s, 1H), 9.99 (s, 1H), 8.58 (s, 2H), 8.32 (s, 1H), 7.86 (d, J=9.20 Hz, 1H), 7.76-7.73 (m, 2H), 7.47-7.46 (m, 1H), 7.39 (t, J=2.80 Hz, 1H), 6.99 (m, 1H), 6.52-6.50 (m, 1H), 6.47-6.46 (m, 1H), 6.11 (d, J=7.60 Hz, 1H), 4.33-4.31 (m, 2H), 3.95-3.92 (m, 2H), 3.90-3.86 (m, 2H), 3.69-3.65 (m, 2H), 3.59-3.55 (m, 2H), 3.52-3.49 (m, 2H), 3.15-2.98 (m, 2H), 2.95-2.85 (m, 2H), 2.78 (s, 3H), 2.75-2.73 (m, 1H), 2.68-2.67 (m, 1H), 2.61-2.60 (m, 1H), 2.09-2.01 (m, 3H), 2.09-2.01 (m, 3H).

Example 128

(1S,5R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3-azabicyclo[3.1.0]hexane-3-sulfonamide

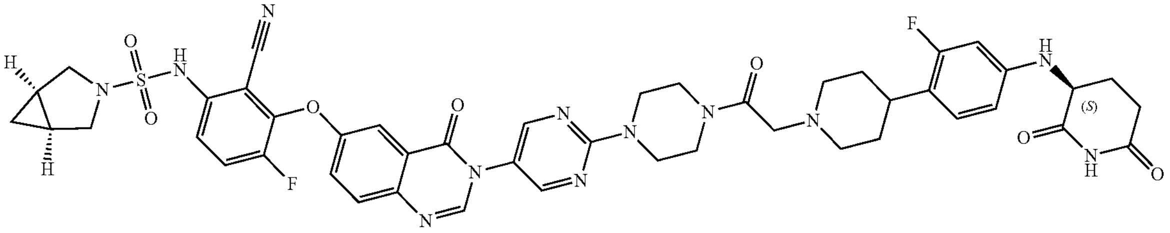

The title compound was purified by reverse phase column chromatography, eluting with 45% acetonitrile in 0.1% ammonium bicarbonate in water, to afford (1S,5R)—N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3-azabicyclo[3.1.0]hexane-3-sulfonamide (67.69 mg, 69.16 μmol, 25% yield) as an off-white solid. LCMS m/z (ESI): 949.2 $[M+H]^+$; $^1H$ NMR (400 MHz, DMSO-$d_6$): δ=10.79 (s, 1H), 9.58 (s, 1H), 8.58 (d, J=5.20 Hz, 2H), 8.30 (s, 1H), 7.83 (d, J=8.80 Hz, 1H), 7.70 (dd, J=3.20, 9.00 Hz, 1H), 7.48 (s, 1H), 7.39 (d, J=2.80 Hz, 1H), 7.28 (s, 1H), 7.01 (t, J=8.00 Hz, 1H), 6.49-6.44 (m, 2H), 6.05 (d, J=7.60 Hz, 1H), 4.33-4.32 (m, 1H), 3.87 (d, J=26.40 Hz, 5H), 3.64 (s, 4H), 3.17 (s, 5H), 2.77-2.71 (m, 2H), 2.10-2.08 (m, 1H), 1.90-1.74 (m, 5H), 1.47-1.46 (m, 2H), 0.48-0.47 (m, 1H), 0.33-0.32 (m, 1H).

Example 129

(3R,4R)—N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]-3,4-difluoropyrrolidine-1-sulfonamide

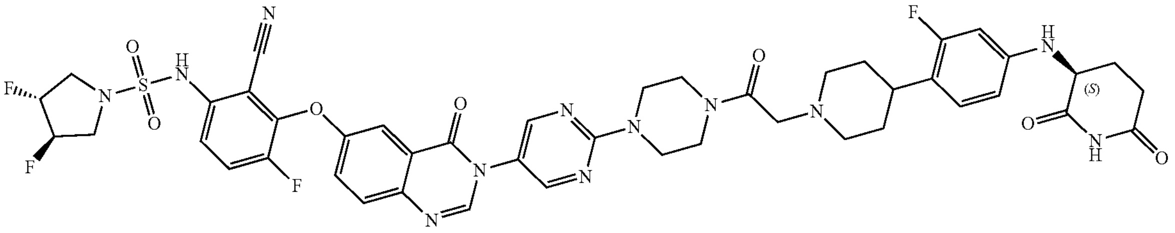

The title compound was purified by reverse phase column chromatography, eluting with 40% acetonitrile in 0.1% ammonium bicarbonate in water, to afford (3R,4R)—N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]-3,4-difluoro-pyrrolidine-1-sulfonamide (52 mg, 53.21 μmol, 21% yield) as an off-white solid. LCMS m/z (ESI): 973.2 $[M+H]^+$; $^1H$ NMR (400 MHz, DMSO-$d_6$): δ=10.81 (s, 1H), 9.59 (s, 2H), 8.59 (s, 1H), 7.82 (d, J=9.20 Hz, 1H), 7.69 (dd, J=3.20, 9.00 Hz, 1H), 7.38 (d, J=2.40 Hz, 1H), 7.48-7.38 (m, 1H), 7.00 (t, J=15.20 Hz, 1H), 6.51-6.46 (m, 2H), 6.20 (d, J=40.00 Hz, 1H), 5.34-5.32 (m, 1H), 5.22-5.20 (m, 1H), 4.33-4.29 (m, 2H), 3.89 (d, J=26.00 Hz, 4H), 3.66 (s, 3H), 3.59-3.50 (m, 4H), 3.35-3.21 (m, 4H), 2.70-2.60 (m, 2H), 2.60 (d, J=16.00 Hz, 2H), 2.10-2.07 (m, 3H), 1.90-1.86 (m, 4H).

Example 130

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]azetidine-1-sulfonamide

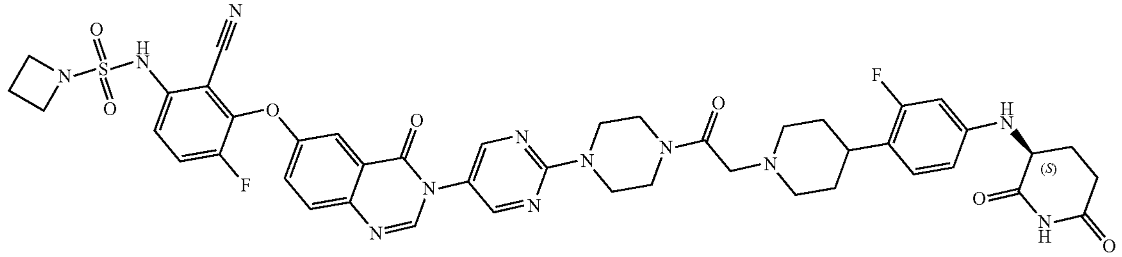

The title compound was purified by reverse phase column chromatography, eluting with 35% acetonitrile in 0.1% FORMIC ACID in water, to afford N-[2-cyano-3-[3-[2-[4-[2-[4-[4-[[(3 S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]azetidine-1-sulfonamide (35 mg, 35.56 μmol, 21% yield) as an off-white solid. LCMS m/z (ESI): 923.2 $[M+H]^+$; $^1$H NMR (400 MHz, DMSO-$d_6$): δ=10.80 (s, 1H), 9.75 (s, 1H), 8.58 (s, 2H), 8.30 (s, 1H), 7.83 (d, J=8.80 Hz, 1H), 7.70 (dd, J=2.80, 8.80 Hz, 1H), 7.50-7.40 (m, 1H), 7.39 (d, J=2.80 Hz, 1H), 7.38-7.30 (m, 1H), 7.30-6.92 (m, 1H), 6.48 (t, J=12.40 Hz, 2H), 6.08 (d, J=7.20 Hz, 1H), 4.33-4.31 (m, 1H), 3.91-3.85 (m, 5H), 3.70-3.50 (m, 9H), 2.79-2.70 (m, 3H), 2.60-2.52 (m, 2H), 2.10-1.99 (m, 4H), 1.93-1.80 (m, 6H).

Example 131

(3R)-3-[6-[2-cyano-3-[[ethyl(methyl)sulfamoyl]amino]-6-fluorophenoxy]-4-oxoquinazolin-3-yl]-8-[4-[4-[(2,6-dioxopiperidin-3-yl)amino]-2-fluorophenyl]cyclohexyl]-1-oxa-8-azaspiro[4.5]decane

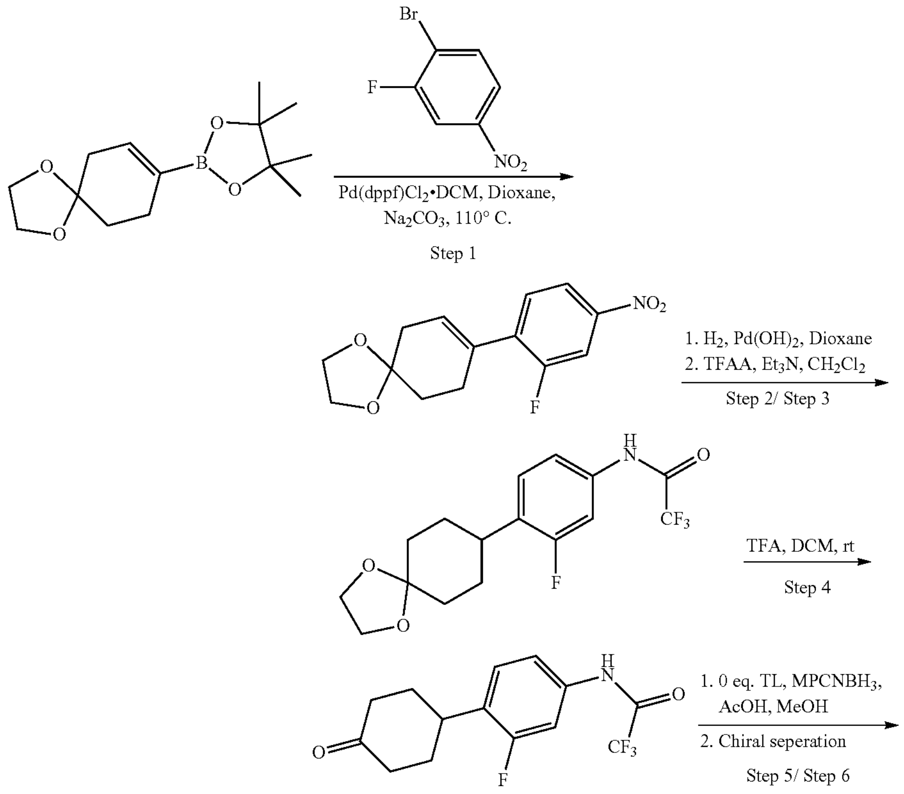

-continued

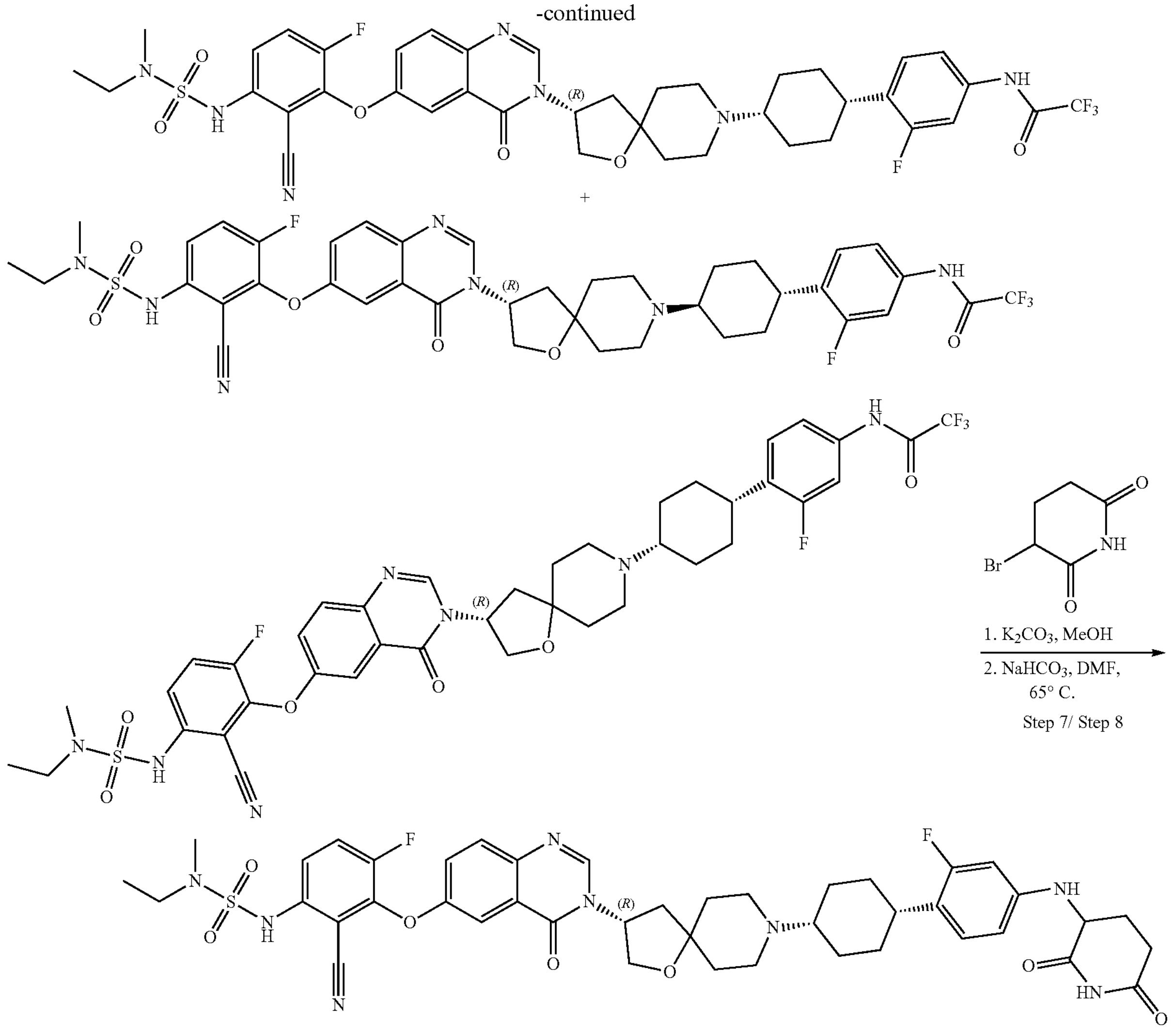

Step 1: Into a 250 mL sealed-tube containing a well-stirred solution of 1-bromo-2-fluoro-4-nitro-benzene (4.0 g, 18.18 mmol) and 2-(1,4-dioxaspiro[4.5]dec-7-en-8-yl)-4,4,5,5-tetramethyl-1,3,2-dioxaborolane (5.80 g, 21.79 mmol) in 1,4-dioxane (50 mL) was added sodium carbonate (1.0 M, 55.0 mL) at ambient temperature under nitrogen atmosphere. The resulting mixture was degassed by bubbling nitrogen gas into the reaction mixture for 10 minutes. Subsequently, Pd(dppf)$Cl_2$·dichloromethane (750 mg, 918.40 μmol) was added to the reaction mixture and heated to 80° C. for 16 h. After completion of the reaction, the reaction mixture was cooled to room temperature and poured into water (100 mL) and extracted with ethyl acetate (3×100 mL). The combined organic phases were dried over anhydrous sodium sulfate, filtered and the filtrate was concentrated under reduced pressure to afford a crude residue. The crude product purified by flash silica gel column chromatography eluting with 30-40% of ethyl acetate in petroleum ether to afford 8-(2-fluoro-4-nitro-phenyl)-1,4-dioxaspiro[4.5]dec-7-ene (4.40 g, 14.97 mmol, 82% yield) as a yellowish viscous liquid. $^1$HNMR (400 MHz, DMSO-$d_6$): δ=8.03-8.09 (m, 2H), 7.63 (t, J=8.40 Hz, 1H), 6.05 (s, 1H), 3.94 (s, 4H), 2.51-2.55 (m, 2H), 2.42 (s, 2H), 1.82 (t, J=6.40 Hz, 2H).

Step 2: Into a 250 mL single-necked round-bottomed flask containing a well-stirred solution of 8-(2-fluoro-4-nitro-phenyl)-1,4-dioxaspiro[4.5]dec-7-ene (4.40 g, 15.76 mmol) in anhydrous 1,4-dioxane (50 mL) was charged palladium hydroxide on carbon (20 wt. % 50% water, 1.50 g, 2.14 mmol), saturated with hydrogen by bubbling hydrogen gas through for 10 minutes and subjected to hydrogenation (1 atm) at ambient temperature for 32 h. After completion, the reaction mixture was purged with nitrogen, catalyst was removed by filtration through celite pad. The filtrate was concentrated under reduced pressure to afford 4-(1,4-dioxaspiro[4.5]decan-8-yl)-3-fluoro-aniline (3.70 g, 14.28 mmol, 91% yield) as an off-white solid. This crude product was taken to the next step without purification. LCMS m/z (ESI): 252.2 $[M+H]^+$ Step 3: To a stirred solution of 4-(1,4-dioxaspiro[4.5]decan-8-yl)-3-fluoro-aniline (3.70 g, 14.72 mmol) in anhydrous dichloromethane (50 mL) was added triethylamine (4.50 g, 44.48 mmol, 6.20 mL) at 0-5° C. under nitrogen atmosphere, followed by the addition of (2,2,2-trifluoroacetyl) 2,2,2-trifluoroacetate (4.77 g, 22.70 mmol, 3.20 mL) at same temperature. The resulting mixture was stirred at ambient temperature for 16 h. After completion of the reaction, water (100 mL) was added to the reaction mixture and extracted with dichloromethane (3×100 mL). The combined organic layers were dried over anhydrous sodium sulfate, filtered and the filtrate was concentrated under reduced pressure to afford crude residue. The crude compound was purified by flash silica gel column chromatography eluting with 50-60% ethyl acetate in petroleum ether to afford N-[4-(1,4-dioxaspiro[4.5]decan-8-yl)-3-fluoro-phenyl]-2,2,2-trifluoro-acetamide (4.40 g, 7.60 mmol, 52% yield) as an off-white solid. LCMS m/z (ESI): 346.2 $[M-H]^-$ Step 4: Into a 250 mL single-necked round-bottomed flask containing a well-stirred solution of N— [4-(1,4-dioxaspiro[4.5]decan-8-yl)-3-fluoro-phenyl]-2,2,2-trifluoro-acetamide (4.40 g, 12.67 mmol, 000) in anhydrous dichloromethane (30 mL) was added trifluoroacetic acid (14.80 g, 129.80 mmol, 10 mL) at ambient temperature under nitrogen atmosphere. The resulting mixture was stirred at ambient temperature for 16 h. After completion, the reaction mixture was concentrated under reduced pressure. Saturated sodium bicarbonate solution was added to the reaction mixture and extracted with dichloromethane (3×100 mL). The combined organic layers were dried over sodium sulfate, filtered, and concentrated under reduced pressure. The crude product was purified by flash silica gel column chromatography eluted with 40-50% of ethyl acetate in petroleum ether to afford 2,2,2-trifluoro-N-[3-fluoro-4-(4-oxocyclohexyl)phenyl]acetamide (2.50 g, 8.16 mmol, 64% yield) as an off-white solid. LCMS m/z (ESI): 302.3 $[M-H]^-$.

Step 5/Step 6: Into a 25 mL single necked round bottomed flask containing a well-stirred solution of (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (200 mg, 359.32 μmol) and 2,2,2-trifluoro-N-[3-fluoro-4-(4-oxocyclohexyl)phenyl]acetamide (220 mg, 725.47 μmol) in anhydrous methanol (5.0 mL) were added sodium acetate, anhydrous (60 mg, 731.41 μmol, 39.22 μL), acetic acid (21.58 mg, 359.32 μmol, 20.55 μL) and MP-$CNBH_3$ (500 mg, 359.32 μmol) at ambient temperature under nitrogen atmosphere. The resulting mixture was stirred at ambient temperature for 32 h. After completion, the reaction mixture was filtered through celite and filtrate was concentrated under reduced pressure. Reaction crude was purified by preparative-HPLC using acetonitrile in 0.1% formic acid in water to afford 260 mg of racemic compound. This racemic compound was purified by SFC-chiral purification (column: YMC Cellulose-SC [(250*30) mm, 5μ ]; mobile Phase: $CO_2$. 0.5% isopropylamine in IPA (50:50); total flow: 110 g/min; back pressure: 100 bar; wavelength: 254 nm; cycle time: 11.0 min) to afford N-(4-((1S,4s)-4-((R)-3-(6-(2-cyano-3-((N-ethyl-N— methylsulfamoyl)amino)-6-fluorophenoxy)-4-oxoquinazolin-3(4H)-yl)-1-oxa-8-azaspiro[4.5]decan-8-yl)cyclohexyl)-3-fluorophenyl)-2,2,2-trifluoroacetamide (first eluting isomer, 120 mg, 137.94 μmol, 38% yield) as a pale brown viscous liquid and N-(4-((1R,4r)-4-((R)-3-(6-(2-cyano-3-((N-ethyl-N-methylsulfamoyl)amino)-6-fluorophenoxy)-4-oxoquinazolin-3(4H)-yl)-1-oxa-8-azaspiro[4.5]decan-8-yl)cyclohexyl)-3-fluorophenyl)-2,2,2-trifluoroacetamide (second eluting isomer, 110 mg, 126.18 μmol, 35% yield) as a pale brown solid. LCMS (ESI): m/z 844.29 $[M+H]^+$.

NOTE: first eluting isomer was arbitrarily assigned as -cis isomer and second eluting isomer was arbitrarily assigned as -trans isomer.

Step 7: Into a 25 mL single-necked round-bottomed flask containing a well-stirred solution of N— (4-((1S,4s)-4-((R)-3-(6-(2-cyano-3-((N-ethyl-N-methylsulfamoyl)amino)-6-fluorophenoxy)-4-oxoquinazolin-3(4H)-yl)-1-oxa-8-azaspiro[4.5]decan-8-yl)cyclohexyl)-3-fluorophenyl)-2,2,2-trifluoroacetamide (120 mg, 142.20 μmol) in a mixture of methanol (5.0 mL) and water (2.0 mL) was added anhydrous potassium carbonate (100 mg, 723.56 μmol, 43.67 μL) at ambient temperature. The resulting mixture was heated to 50° C. for 16 h. After completion of the reaction, water (30 ml) was added to the reaction mixture and extracted with 5% methanol/dichloromethane (3×50 mL). The combined organic layers were dried over sodium sulfate, filtered, and concentrated under reduced pressure to afford crude residue. The crude residue was purified by flash silica gel column chromatography eluted with 10-15% of methanol in dichloromethane to afford (3R)-8-[4-(4-amino-2-fluoro-phenyl)cyclohexyl]-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (70 mg, 84.24 μmol, 59% yield) as a pale yellow solid. LCMS m/z (ESI): 748.7 $[M+H]^+$ Step 8: Into a 10 mL sealed-tube reactor containing a well-stirred solution of (3R)-8-[4-(4-amino-2-fluoro-phenyl)cyclohexyl]-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (70 mg, 93.60 μmol) in anhydrous N,N-dimethylformamide (3.0 mL) were added sodium bicarbonate (50 mg, 595.19 μmol, 23.15 L) and 3-bromopiperidine-2,6-dione (90 mg, 468.72 μmol) at ambient temperature under nitrogen atmosphere. The resulting mixture was heated to 70° C. for 48 h. After completion, the reaction mixture was cooled to room temperature and water (20 mL) was added and extracted with 10% isopropanol in dichloromethane (3×50 mL). The combined organic layers were dried over anhydrous sodium sulfate, filtered and the filtrate was concentrated under reduced pressure to afford crude residue. The crude compound was purified by preparative-HPLC (X-BRIDGE C8(150*19)MM 5 MICRONS, 0.1% formic acid in water:acetonitrile) to afford (3R)-3-[6-[2-cyano-3-[[ethyl(methyl)sulfamoyl]amino]-6-fluoro-phenoxy]-4-oxo-quinazolin-3-yl]-8-[4-[4-[(2,6-dioxo-3-piperidyl)amino]-2-fluoro-phenyl]cyclohexyl]-1-oxa-8-azaspiro[4.5]decane (840.00 g, 0.895 μmol, 1% yield) as a yellow solid. LCMS m/z (ESI): 859.2$[M+H]^+$. $^1$HNMR (400 MHz, DMSO-$d_6$): δ=10.80 (s, 1H), 8.32 (s, 1H), 7.76 (d, J=8.80 Hz, 1H), 7.64 (dd, J=2.80, 8.80 Hz, 1H), 7.47-7.36 (m, 1H), 7.33 (d, J=9.20 Hz, 1H), 7.29-7.23 (m, 1H), 7.12-7.08 (m, 1H), 6.46 (t, J=14.40 Hz, 2H), 6.03 (d, J=8.00 Hz, 1H), 5.32-5.22 (m, 1H), 4.35-4.25 (m, 1H), 4.17-4.11 (m, 1H), 4.13-4.07 (m, 1H), 2.98 (q, J=32.00 Hz, 3H), 2.92-2.81 (m, 2H), 2.67-2.51 (m, 5H), 2.50-2.35 (m, 2H), 2.14-2.07 (m, 3H), 1.95-1.73 (m, 11H), 1.59 (s, 3H), 1.03 (t, J=7.20 Hz, 3H).

Example 132

N-[2-cyano-3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclobutanesulfonamide

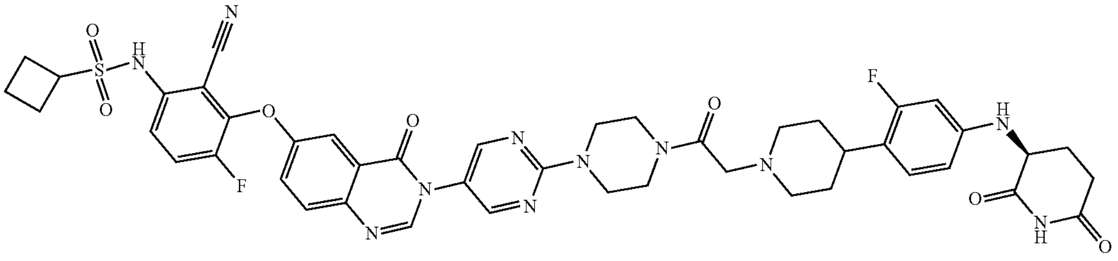

The titled compound was synthesized in the same fashion as examples 105-130 using cyclobutanesulfonamide as starting material. The titled compound was purified by reverse phase preparatory HPLC (column: X-bridge C18 20×150 m; mobile phase: A: 0.1% formic acid in water, B: acetonitrile] to give N-[2-cyano-3-[3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]cyclobutanesulfonamide (60 mg, 60.99 μmol, 18% yield) as an off-white solid. LCMS m/z (ESI): 922.2 $[M+H]^+$; $^1$HNMR (400 MHz, DMSO-$d_6$): δ=10.81 (s, 1H), 10.01 (s, 1H), 8.59 (s, 2H), 8.33 (s, 1H), 7.86 (d, J=9.20 Hz, 1H), 7.73-7.87 (m, 1H), 7.75 (dd, J=2.80, 8.80 Hz, 1H), 7.42-7.46 (m, 2H), 6.95-7.05 (m, 1H), 6.51 (d, J=8.00 Hz, 1H), 6.48 (d, J=12.80 Hz, 1H), 6.11 (d, J=7.60 Hz, 1H), 4.01-4.39 (m, 3H), 4.02 (t, J=7.60 Hz, 1H), 3.87-3.93 (m, 4H), 3.67 (m, 2H), 3.42-3.61 (m, 2H), 3.57 (m, 2H), 2.81-3.20 (m, 3H), 2.64-2.80 (m, 2H), 2.20-2.41 (m, 4H), 1.75-2.12 (m, 8H).

Example 133

N-[2-cyano-3-[3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-4-fluorophenyl]cyclobutanesulfonamide

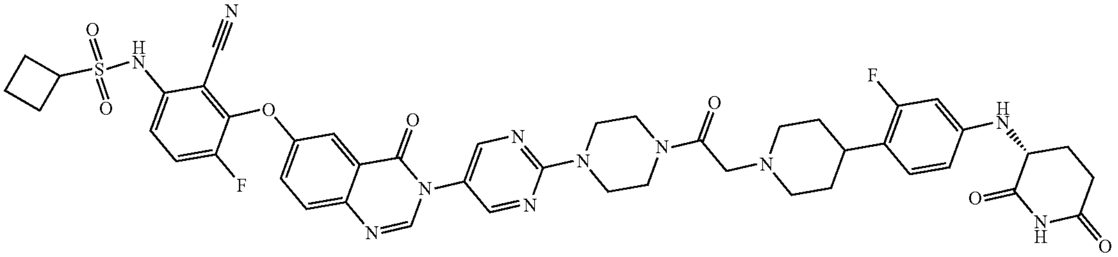 [SMILES: N#Cc1c(NS(=O)(=O)C2CCC2)ccc(F)c1Oc1ccc2ncn(-c3cnc(N4CCN(C(=O)CN5CCC(c6ccc(N[C@@H]7CCC(=O)NC7=O)cc6F)CC5)CC4)nc3)c(=O)c2c1]

The titled compound was synthesized in the same fashion as examples 105-130 using cyclobutanesulfonamide as starting material. The titled compound was purified by reverse phase preparatory HPLC (Column: X-bridge C18 20×150 m; mobile phase: A: 0.1% ammonium bicarbonate in water, B: acetonitrile] to give N-[2-cyano-3-[3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-4-oxo-quinazolin-6-yl]oxy-4-fluoro-phenyl]cyclobutanesulfonamide (55 mg, 58.77 μmol, 34% yield) as an off-white solid. LCMS m/z (ESI): 922.2 $[M+H]^+$; $^1$HNMR (400 MHz, DMSO-$d_6$): δ=10.79 (s, 1H), 10.05 (bs, 1H), 8.57 (s, 2H), 8.30 (s, 1H), 7.82 (d, J=8.80 Hz, 1H), 7.69 (dd, J=2.80, 8.80 Hz, 1H), 7.46 (bs, 1H), 7.41 (d, J=2.80 Hz, 1H), 7.32 (dd, J=4.00, 9.20 Hz, 1H), 7.03-6.98 (m, 1H), 6.48 (d, J=6.40 Hz, 1H), 6.45 (d, J=12.00 Hz, 1H), 6.04 (d, J=7.60 Hz, 1H), 4.34-4.30 (m, 1H), 3.90-3.83 (m, 3H), 3.82-3.74 (m, 2H), 3.72-3.63 (m, 4H), 3.63-3.35 (m, 4H), 3.33-3.14 (m, 2H), 2.77-2.71 (m, 2H), 2.34-2.25 (m, 3H), 2.16-2.07 (m, 3H), 1.91-1.71 (m, 7H).

Examples 134 and 135
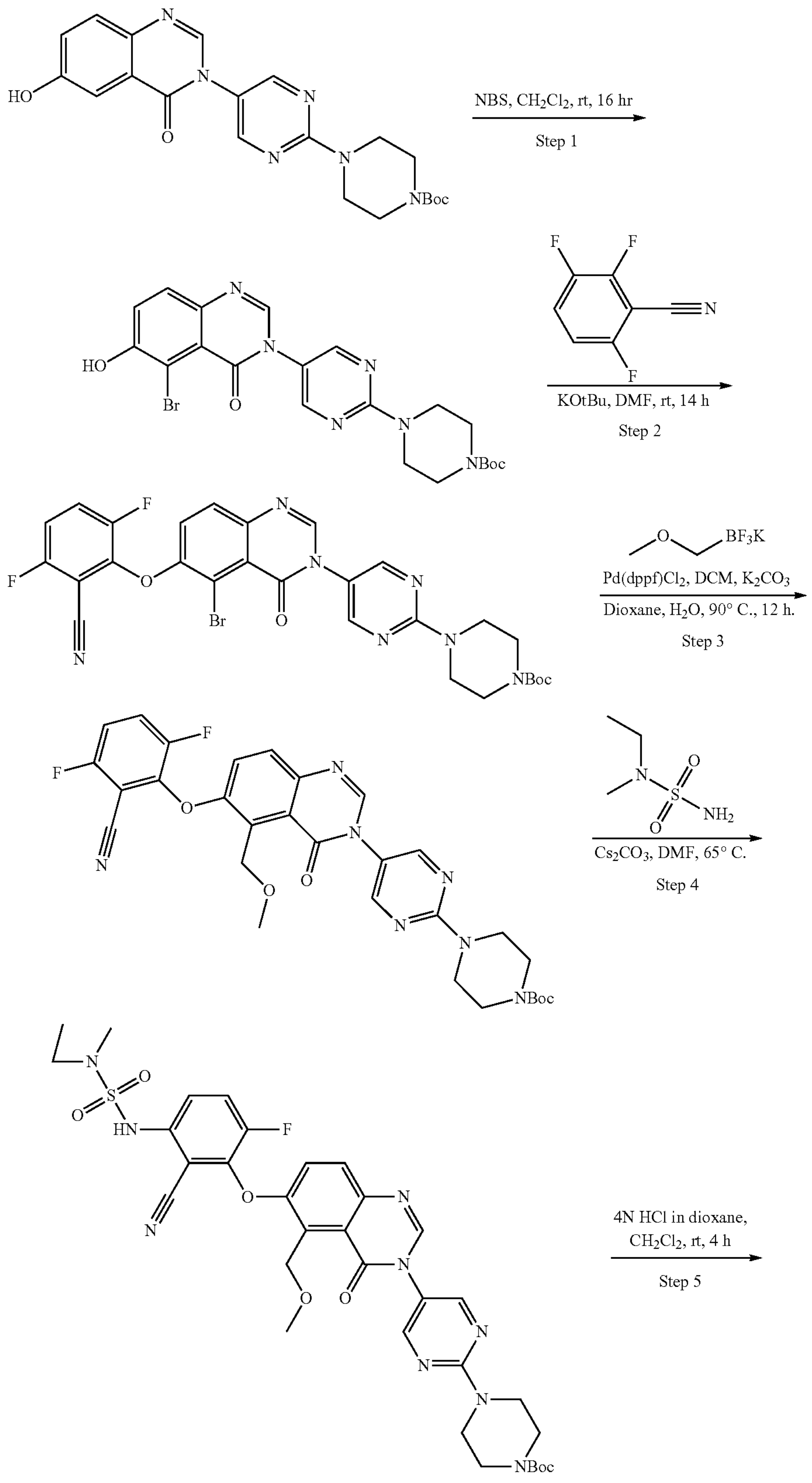

-continued

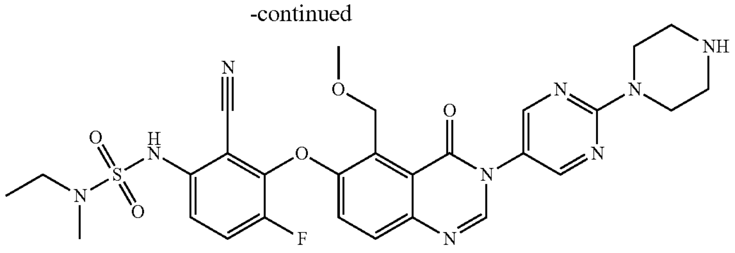

Step 1: Into a 100 mL single necked round bottomed flask containing a well stirred solution of tert-butyl 4-[5-(6-hydroxy-4-oxo-quinazolin-3-yl)pyrimidin-2-yl]piperazine-1-carboxylate (3.0 g, 5.51 mmol) in dichloromethane (50.12 mL) under nitrogen atmosphere was added N-bromosuccinimide(883.10 mg, 4.96 mmol, 420.93 μL) at 0° C. The reaction mixture was stirred at 0° C. for 30 minutes. After completion, the reaction mixture was quenched with water and extracted with dichloromethane (2×100 mL). The organic phases were combined and washed with brine, dried over anhydrous sodium sulfate, filtered and concentrated under reduced pressure to afford a crude product. The crude product was triturated with 10% of ethyl acetate in petroleum ether to afford the tert-butyl 4-[5-(5-bromo-6-hydroxy-4-oxo-quinazolin-3-yl)pyrimidin-2-yl]piperazine-1-carboxylate (2.5 g, 3.97 mmol, 72% yield) as yellow solid. LCMS m/z (ESI): 503.0 $[M+H]^+$.

Step 2: To a stirred solution of tert-butyl 4-[5-(5-bromo-6-hydroxy-4-oxo-quinazolin-3-yl)pyrimidin-2-yl]piperazine-1-carboxylate (2 g, 3.97 mmol) in N,N-dimethylformamide (40 mL), were added potassium tert-butoxide (3.88 g, 34.61 mmol) and 2,3,6-trifluorobenzonitrile (1.25 g, 7.95 mmol, 917.93 μL) at room temperature under nitrogen atmosphere. The reaction mixture was stirred at room temperature for 12 h. After completion, the reaction mixture was diluted with water (50 mL), extracted with ethyl acetate (3×170 mL). Combined organic layers washed with cold water (3×50 mL), dried over sodium sulfate, filtered and concentrated under reduced pressure to afford crude. Desired product was purified from crude by silica gel column chromatography by using 70-90% ethyl acetate in petroleum ether as eluent to afford tert-butyl 4-[5-[5-bromo-6-(2-cyano-3,6-difluoro-phenoxy)-4-oxo-quinazolin-3-yl]pyrimidin-2-yl]piperazine-1-carboxylate (1.7 g, 2.17 mmol, 55% yield) as a light brown solid. LCMS m/z (ESI): 584.4$[M+H-{}^tBu]^+$ Step 3: To a stirred solution of tert-butyl 4-[5-[5-bromo-6-(2-cyano-3,6-difluoro-phenoxy)-4-oxo-quinazolin-3-yl]pyrimidin-2-yl]piperazine-1-carboxylate (0.8 g, 1.25 mmol) in 1,4-dioxane (10 mL) and water (1 mL) in sealed tube, were added potassium carbonate (517.92 mg, 3.75 mmol, 226.17 μL) and potassium (methoxymethyl)trifluoroborate (474.57 mg, 3.12 mmol). The reaction mixture was purged with nitrogen gas for 10 minutes, then added Pd(dppf) $Cl_2$·dichloromethane (102.01 mg, 124.92 μmol), again purged with nitrogen gas for 5 minutes and then stirred at 90° C. for 12 h. After completion, the reaction mixture was diluted with water (10 mL), extracted with ethyl acetate (3×20 mL). Combined organic layers dried over sodium sulfate, filtered and concentrated to afford crude. The desired product was purified from crude by reverse phase column chromatography (10 mM ammonium bicarbonate in water: acetonitrile) to afford tert-butyl 4-[5-[6-(2-cyano-3,6-difluoro-phenoxy)-5-(methoxymethyl)-4-oxo-quinazolin-3-yl]pyrimidin-2-yl]piperazine-1-carboxylate (0.22 g, 340.58 μmol, 27% yield) as an off-white solid. LCMS m/z (ESI): 506.5$[M+H-CO_2{}^tBu]^+$ Step 4: To a stirred solution of tert-butyl 4-[5-[6-(2-cyano-3,6-difluoro-phenoxy)-5-(methoxymethyl)-4-oxo-quinazolin-3-yl]pyrimidin-2-yl]piperazine-1-carboxylate (0.22 g, 363.28 μmol) in N,N-dimethylformamide (10 mL) in sealed tube, were added cesium carbonate (355.09 mg, 1.09 mmol) and [methyl(sulfamoyl)amino]ethane (125.50 mg, 908.20 μmol) at room temperature. The reaction mixture was stirred at 65° C. for 12 h. After completion, the reaction mixture was diluted with water (20 mL). The reaction mixture was filtered through filter paper to remove the fluorescent impurity. The filtrate was extracted with ethyl acetate (3×30 mL). Combined organic layers washed with cold water (3×20 mL), dried over sodium sulfate, filtered and concentrated under reduced pressure to afford crude tert-butyl 4-[5-[6-[2-cyano-3-[[ethyl(methyl)sulfamoyl]amino]-6-fluoro-phenoxy]-5-(methoxymethyl)-4-oxo-quinazolin-3-yl]pyrimidin-2-yl]piperazine-1-carboxylate (0.2 g, 255.47 μmol, 70% yield) as an off-white solid. LCMS m/z (ESI): 624.6$[M+H-CO_2{}^tBu]^+$ Step 5: To a stirred solution of tert-butyl 4-[5-[6-[2-cyano-3-[[ethyl(methyl)sulfamoyl]amino]-6-fluoro-phenoxy]-5-(methoxymethyl)-4-oxo-quinazolin-3-yl]pyrimidin-2-yl]piperazine-1-carboxylate (0.2 g, 276.33 μmol) in dichloromethane (4 mL), was added 4M hydrogen chloride solution in dioxane (2 mL) at 5° C. under nitrogen atmosphere. The reaction mixture was stirred at room temperature for 3 h. After completion, the reaction mixture was concentrated under reduced pressure to afford 6-[2-cyano-3-[[ethyl(methyl)sulfamoyl]amino]-6-fluoro-phenoxy]-5-(methoxymethyl)-4-oxo-3-(2-piperazin-1-ylpyrimidin-5-yl)quinazoline (0.19 g, 112.54 μmol, 41% yield) as an off-white solid. LCMS m/z (ESI): 624.7 $[M+H]^+$ Example 134

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-(methoxymethyl)-4-oxoquinazoline

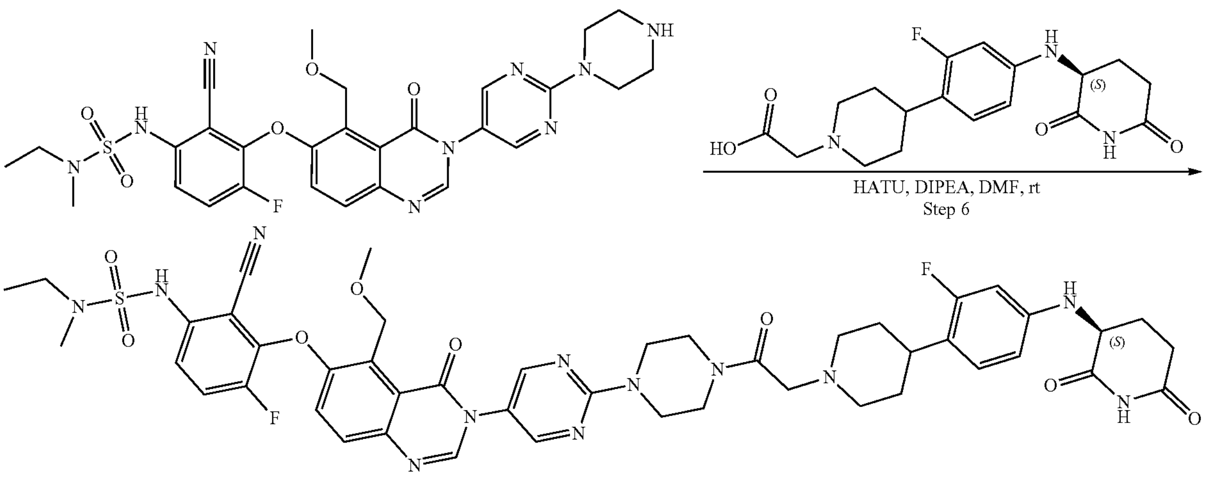

Step 6: Target compound was prepared via HATU mediated acid-amine coupling reaction (Procedure A-E). Amide coupling was carried out using 2-[4-[4-[[(3S)-2,6-dioxo-3-piperidyl]amino]-2-fluoro-phenyl]-1-piperidyl]acetic acid (54.50 mg, 136.30 μmol), N-ethyl-N-isopropyl-propan-2-amine (176.21 mg, 1.36 mmol, 237.48 μL), HATU (57.02 mg, 149.97 μmol) and 6-[2-cyano-3-[[ethyl(methyl)sulfamoyl]amino]-6-fluoro-phenoxy]-5-(methoxymethyl)-4-oxo-3-(2-piperazin-1-ylpyrimidin-5-yl)quinazoline (0.09 g, 136.34 μmol). The desired product was purified by reverse phase column chromatography (0.1% formic acid in water: acetonitrile) to afford 6-[2-cyano-3-[[ethyl(methyl)sulfamoyl]amino]-6-fluoro-phenoxy]-3-[2-[4-[2-[4-[4-[[(3S)-2,6-dioxo-3-piperidyl]amino]-2-fluoro-phenyl]-1-piperidyl]acetyl]piperazin-1-yl]pyrimidin-5-yl]-5-(methoxymethyl)-4-oxo-quinazoline (7 mg, 6.55 μmol, 5% yield) as an off-white solid. LCMS m/z (ESI): 969.0[M+H]$^+$; $^1$HNMR (400 MHz, DMSO-$d_6$): δ=10.79 (s, 1H), 8.60 (s, 2H), 8.30 (s, 1H), 7.72 (d, J=8.80 Hz, 1H), 7.30 (t, J=8.80 Hz, 1H), 7.01 (d, J=16.00 Hz, 1H), 6.05 (d, J=7.60 Hz, 1H), 5.20 (s, 2H), 4.33-4.28 (m, 1H), 3.89 (d, J=26.80 Hz, 5H), 3.71-3.66 (m, 5H), 3.06 (d, J=6.40 Hz, 3H), 2.66 (d, J=20.00 Hz, 4H), 2.10-2.05 (m, 2H), 1.87-1.82 (m, 2H), 1.82-1.68 (m, 3H), 1.04 (t, J=7.20 Hz, 3H).

Example 135

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-(methoxymethyl)-4-oxoquinazoline

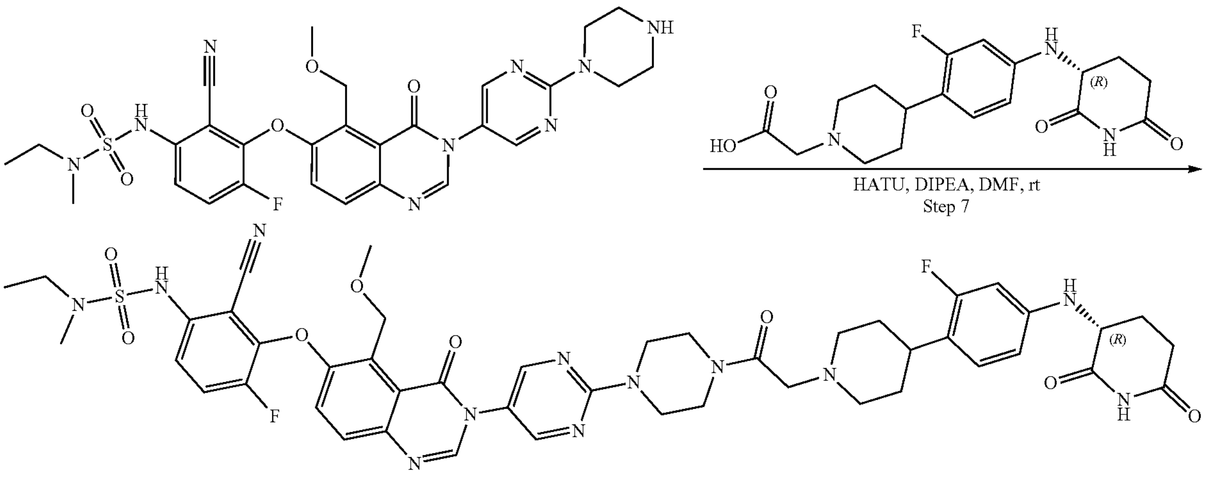

Step 7: Target compound was prepared via HATU mediated acid-amine coupling reaction (Procedure A-E). Amide coupling was carried out using 2-[4-[2-fluoro-4-[[(3R)-2,6-dioxo-3-piperidyl]amino]phenyl]-1-piperidyl]acetic acid (54.50 mg, 136.30 μmol), N-ethyl-N-isopropyl-propan-2-amine (176.21 mg, 1.36 mmol, 237.48 μL), HATU (57.02 mg, 149.97 μmol) and 6-[2-cyano-3-[[ethyl(methyl)sulfamoyl]amino]-6-fluoro-phenoxy]-5-(methoxymethyl)-4-oxo-3-(2-piperazin-1-ylpyrimidin-5-yl)quinazoline (0.09 g, 136.34 μmol). The desired product was purified by reverse phase column chromatography (0.1% formic acid in water: acetonitrile) to afford 6-[2-cyano-3-[[ethyl(methyl)sulfamoyl]amino]-6-fluoro-phenoxy]-3-[2-[4-[2-[4-[4-[[(3R)-2,6-dioxo-3-piperidyl]amino]-2-fluoro-phenyl]-1-piperidyl]acetyl]piperazin-1-yl]pyrimidin-5-yl]-5-(methoxymethyl)-4-oxo-quinazoline (11 mg, 10.16 μmol, 7% yield) as a light green solid. LCMS m/z (ESI): 969.2[M+H]$^+$; $^1$HNMR (400 MHz, DMSO-$d_6$): δ=10.80 (s, 1H), 9.90 (bs, 1H), 8.60 (s, 2H), 8.30 (s, 1H), 7.73 (d, J=8.80 Hz, 1H), 7.59 (bs, 1H), 7.33 (d, J=8.00 Hz, 2H), 7.01 (s, 1H), 6.49 (d, J=6.40 Hz, 1H), 6.45 (s, 1H), 6.07 (d, J=8.00 Hz, 1H), 5.20 (s, 2H), 4.32 (s, 1H), 3.93-3.87 (m, 5H), 3.64-3.51 (m, 4H), 2.99 (d, J=13.20 Hz, 3H), 2.77-2.68 (m, 7H), 2.09 (d, J=8.80 Hz, 1H), 1.89-1.80 (m, 6H), 1.05 (t, J=6.80 Hz, 3H).

Example 136

6-[2-cyano-3-[[ethyl(methyl)sulfamoyl]amino]-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-5-hydroxy-4-oxoquinazoline

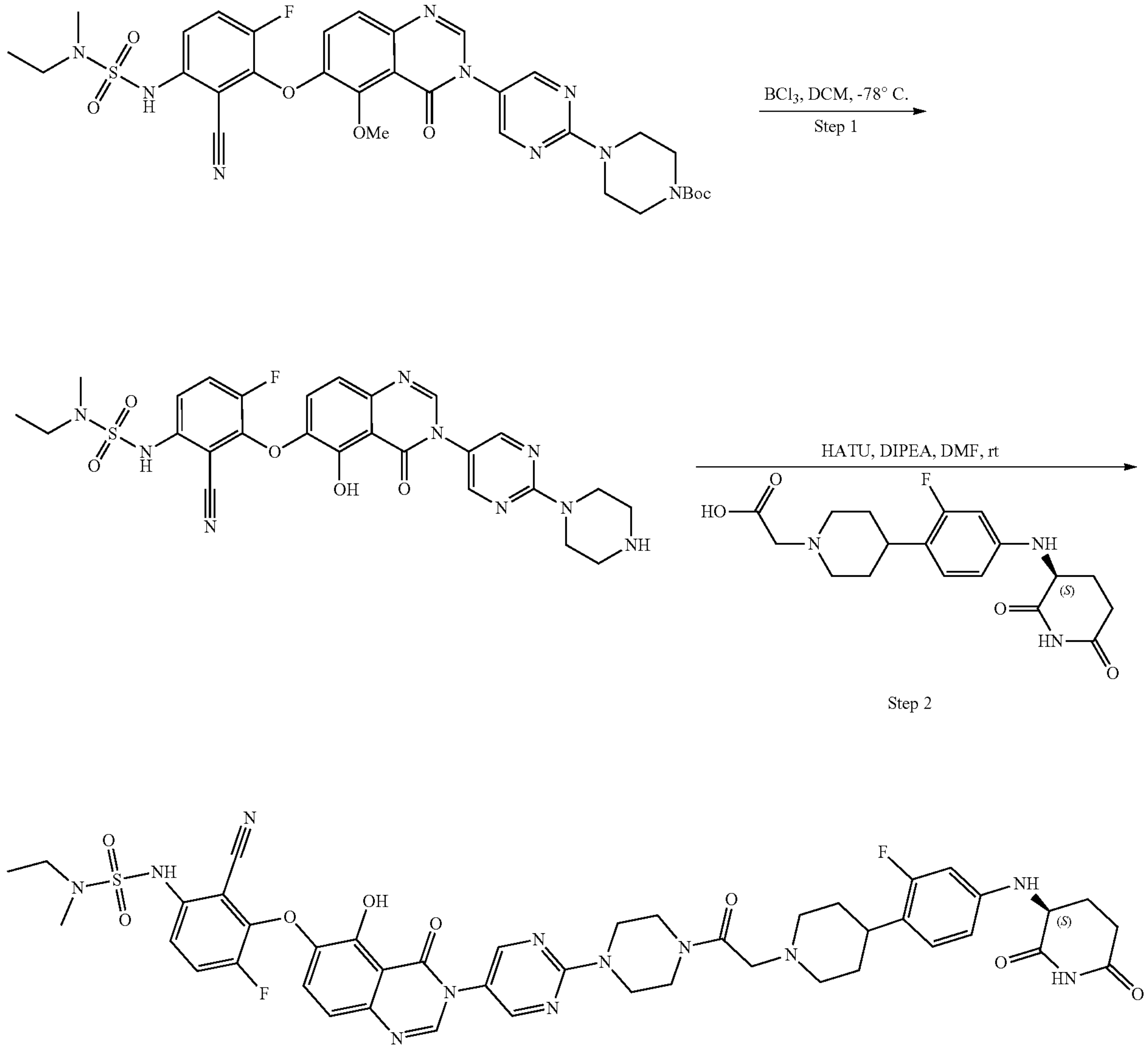

Step 1: To a stirred solution of tert-butyl 4-[5-[6-[2-cyano-3-[[ethyl(methyl)sulfamoyl]amino]-6-fluoro-phenoxy]-5-methoxy-4-oxo-quinazolin-3-yl]pyrimidin-2-yl]piperazine-1-carboxylate (250 mg, 352.24 μmol) in anhydrous dichloromethane (4 mL) at −78° C. and was added boron trichloride solution 1.0 M methylene chloride (3.52 mmol, 15 mL) dropwise. The resulting contents were stirred at room temperature for 36 h. After completion, the reaction mixture was concentrated under reduced pressure to afford a crude and purified by reverse phase column chromatography eluting with 40% acetonitrile in 0.1% formic acid in water to afford 6-[2-cyano-3-[[ethyl(methyl)sulfamoyl]amino]-6-fluoro-phenoxy]-5-hydroxy-4-oxo-3-(2-piperazin-1-ylpyrimidin-5-yl)quinazoline (200 mg, 246.25 μmol, 70% yield) as an off-white solid. LCMS m/z (ESI): 596.3 $[M+H]^+$.

Step 2: Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-5-hydroxy-4-oxo-3-(2-piperazin-1-ylpyrimidin-5-yl)quinazoline (100 mg, 167.90 μmol), 2-[4-[2-fluoro-4-[[(3S)-2,6-dioxo-3-piperidyl]amino]phenyl]-1-piperidyl]acetic acid (61.01 mg, 167.90 μmol), N,N-diisopropylethylamine (108.49 mg, 839.48 μmol, 146.22 μL) and HATU (82.99 mg, 218.27 μmol). The crude compound was purified by prep-HPLC (method: 0.1% formic acid in water:acetonitrile; column: X SELECT C18 (19×150) mm, 5 micron) to afford 6-[2-cyano-3-[[ethyl(methyl)sulfamoyl]amino]-6-fluoro-phenoxy]-3-[2-[4-[2-[4-[2-fluoro-4-[[(3S)-2,6-dioxo-3-piperidyl]amino]phenyl]-1-piperidyl]acetyl]piperazin-1-yl]pyrimidin-5-yl]-5-hydroxy-4-oxo-quinazoline (7 mg, 6.76 μmol, 4% yield) as a brown solid. LCMS m/z (ESI): 941.2 $[M+H]^+$. $^1$H-NMR (400 MHz, DMSO-$d_6$): δ=11.73 (s, 1H), 10.81 (s, 1H), 8.63 (s, 2H), 8.31 (s, 1H), 7.51-7.46 (m, 2H), 7.27-7.24 (m, 1H), 7.20 (d, J=6.80 Hz, 1H), 7.00 (s, 1H), 6.47 (t, J=12.00 Hz, 2H), 6.05 (s, 1H), 4.32-4.31 (m, 1H), 3.92-3.85 (m, 5H), 3.64-3.63 (m, 5H), 3.30-3.41 (m, 2H), 3.08 (s, 4H), 2.81-2.50 (m, 4H), 2.08-2.06 (m, 3H), 1.89-1.74 (m, 6H), 1.06-1.02 (m, 3H).

Example 137

6-[2-cyano-3-[[ethyl(methyl)sulfamoyl]amino]-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-5-hydroxy-4-oxoquinazoline

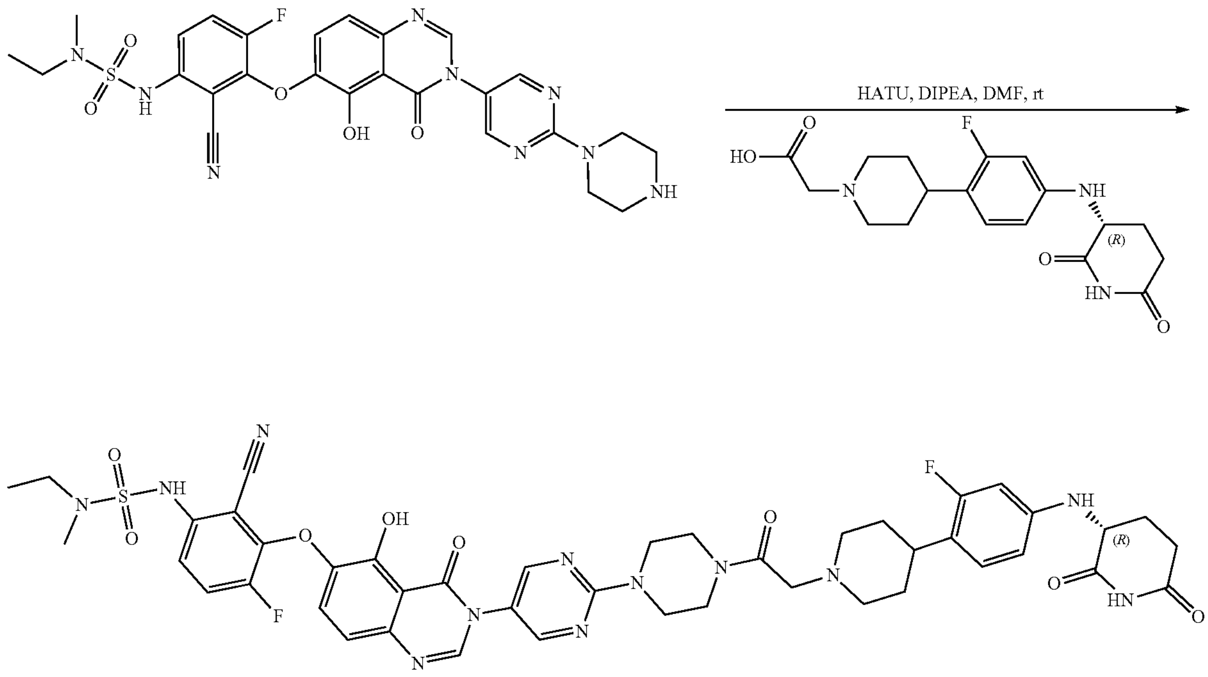

Target compound was prepared via HATU mediated acid-amine coupling reaction (Procedure A-E). Amide coupling was carried out using 6-[2-cyano-3-[[ethyl(methyl)sulfamoyl]amino]-6-fluoro-phenoxy]-5-hydroxy-4-oxo-3-(2-piperazin-1-ylpyrimidin-5-yl)quinazoline (70 mg, 117.53 μmol), 2-[4-[2-fluoro-4-[[(3R)-2,6-dioxo-3-piperidyl]amino]phenyl]-1-piperidyl]acetic acid (42.71 mg, 117.53 μmol), N,N-diisopropylethylamine 75.95 mg, 587.64 μmol, 102.35 μL) and HATU (58.09 mg, 152.79 μmol). The crude compound was purified by prep-HPLC (method: 0.1% formic acid in water:acetonitrile; column: X SELECT C18 (19×150) mm, 5 micron) to afford 6-[2-cyano-3-[[ethyl(methyl)sulfamoyl]amino]-6-fluoro-phenoxy]-3-[2-[4-[2-[4-[2-fluoro-4-[[(3R)-2,6-dioxo-3-piperidyl]amino]phenyl]-1-piperidyl]acetyl]piperazin-1-yl]pyrimidin-5-yl]-5-hydroxy-4-oxo-quinazoline (6 mg, 5.91 μmol, 5% yield) as a brown solid. LCMS m/z (ESI): 941.2 $[M+H]^+$. $^1$HNMR (400 MHz, DMSO-$d_6$): δ=11.73 (s, 1H), 10.81 (s, 1H), 9.92 (s, 1H), 8.63 (s, 2H), 8.31 (s, 1H), 7.48 (t, J=16.80 Hz, 2H), 7.27-7.20 (m, 2H), 7.01 (s, 1H), 6.46 (d, J=12.00 Hz, 1H), 6.06 (d, J=7.60 Hz, 1H), 4.35-4.29 (m, 1H), 3.91-3.85 (m, 5H), 3.64 (s, 5H), 3.30-3.41 (m, 1H), 3.08 (d, J=7.20 Hz, 3H), 2.69-2.52 (m, 9H), 2.08 (t, J=3.60 Hz, 1H), 1.91-1.76 (m, 5H), 1.02 (t, J=5.20 Hz, 3H).

Example 138
N-[3-[3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazolin-6-yl]oxy-2,4-difluorophenyl]cyclopentanesulfonamide
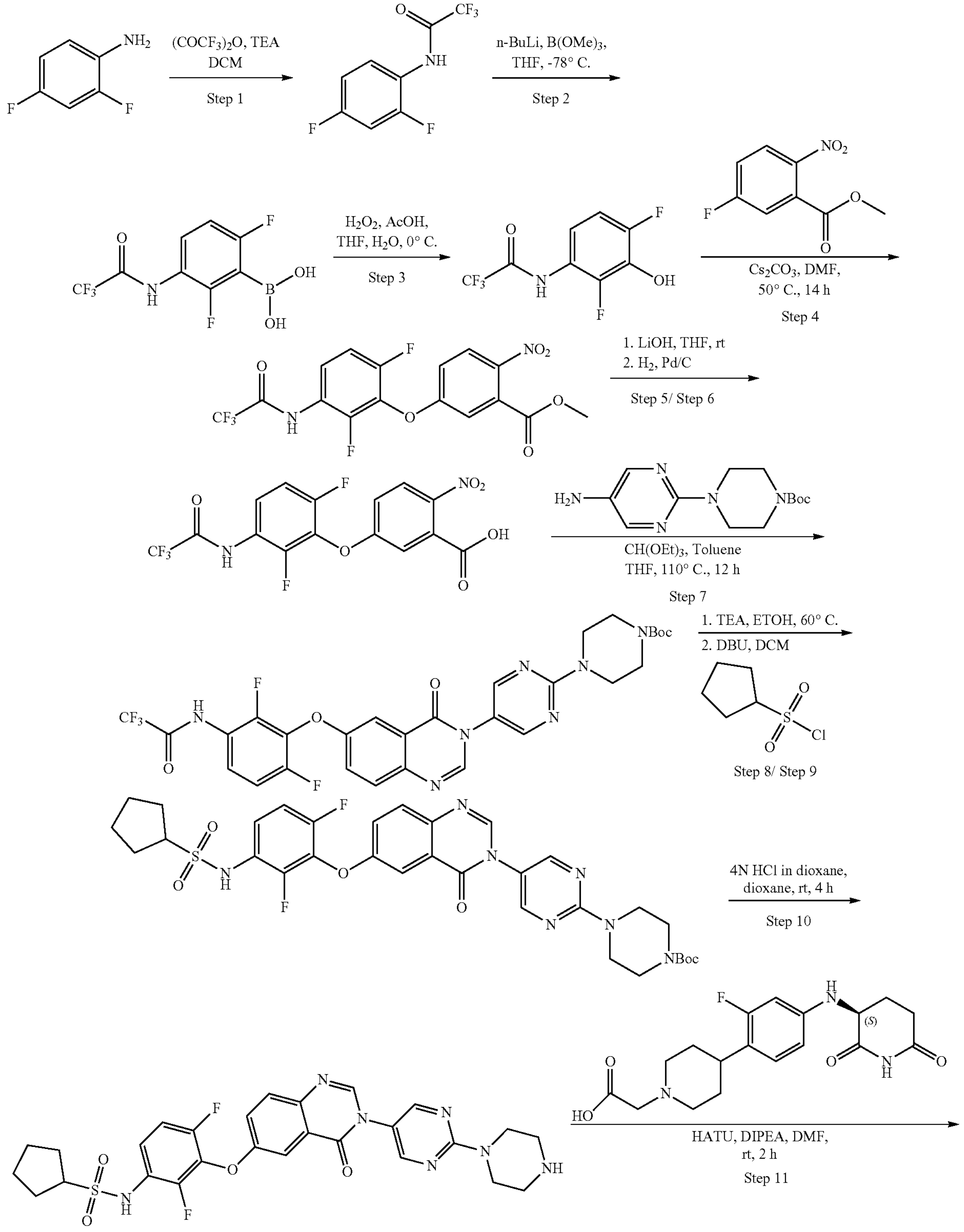

-continued

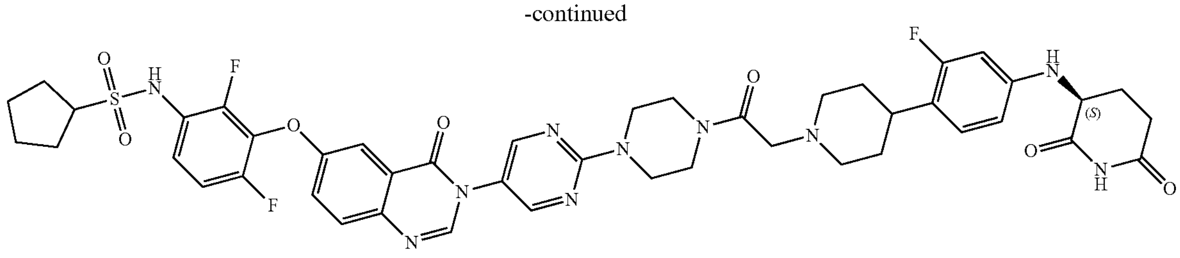

Step 1: To a cooled 0° C. solution of 2,4-difluoroaniline (5.0 g, 38.73 mmol, 3.94 mL) in dichloromethane (40 mL) were added trifluoro acetic anhydride (9.76 g, 46.47 mmol, 6.56 mL) followed by triethylamine (11.76 g, 116.18 mmol, 16.19 mL) and stirred at room temperature for 14 h. The reaction mixture was diluted water (40 mL), extracted with dichloromethane (100 mL). The organic layer was washed with sodium bicarbonate solution (30 mL), brine (30 mL), dried over sodium sulfate and concentrated under reduced pressure to afford crude, which was purified by silica gel column chromatography eluted with 10% ethyl acetate in petroleum ether to afford N-(2,4-difluorophenyl)-2,2,2-trifluoro-acetamide (7.0 g, 30.97 mmol, 80% yield) as a brown solid. LCMS m/z (ESI): 224.1 $[M-H]^-$ Step 2: A solution of N-(2,4-difluorophenyl)-2,2,2-trifluoro-acetamide (7.0 g, 31.10 mmol) was taken in dry tetrahydrofuran (60 mL) and added n-butyl lithium (1.6 M, 48.59 mL) at −78° C. and stirred the reaction mixture for 15 minutes. Trimethyl borate (4.85 g, 46.64 mmol, 5.30 mL) was added to the reaction mixture at the same temperature and stirred for 3 h. The reaction mixture was quenched in 1.5N HCl (5 mL) extracted with ethyl acetate (60 mL). The organic layer was washed with sodium bicarbonate solution (20 mL), brine (20 mL), dried over sodium sulfate and concentrated under reduced pressure to afford crude. The crude compound was purified by silica gel column chromatography eluted with 20% ethyl acetate in petroleum ether to afford [2,6-difluoro-3-[(2,2,2-trifluoroacetyl)amino]phenyl] boronic acid (5.1 g, 18.36 mmol, 59% yield) as brown solid. LCMS m/z (ESI): 268.1 $[M-H]^-$ Step 3: To a stirred solution of [2,6-difluoro-3-[(2,2,2-trifluoroacetyl)amino]phenyl]boronic acid (5.1 g, 18.96 mmol) in tetrahydrofuran (40 mL), acetic acid (4 mL) was added hydrogen peroxide (1.84 g, 18.96 mmol, 1.68 mL, 35%) at 0° C. and stirred the reaction mixture at room temperature for 14 h. The reaction mixture was diluted with ethyl acetate (30 mL), washed with water (10 mL), brine (10 mL), dried over sodium sulfate and concentrated under reduced pressure to afford crude. The resulting crude was purified by silica gel column chromatography eluted with 25% ethyl acetate in petroleum ether to afford N-(2,4-difluoro-3-hydroxy-phenyl)-2,2,2-trifluoro-acetamide (3.5 g, 14.18 mmol, 75% yield) as a brown solid. LCMS m/z (ESI): 240.0, $[M-H]^-$ Step 4: To a solution of N-(2,4-difluoro-3-hydroxy-phenyl)-2,2,2-trifluoro-acetamide (3.4 g, 14.10 mmol) in N,N-dimethylformamide (20 mL) were added cesium carbonate (4.59 g, 14.10 mmol) followed by addition of methyl 5-hydroxy-2-nitro-benzoate (2.78 g, 14.10 mmol) at room temperature and the reaction mixture was heated at 50° C. for 5 h. The reaction mixture was dilute with ethyl acetate (120 mL), washed with water (40 mL), brine (40 mL), dried over sodium sulfate and concentrated under reduced pressure to afford crude. The resulting crude was purified by silica gel column chromatography eluted with 30% ethyl acetate in petroleum ether to afford methyl 5-[2,6-difluoro-3-[(2,2,2-trifluoroacetyl)amino]phenoxy]-2-nitro-benzoate (4.1 g, 9.09 mmol, 64% yield) as a light brown solid. LCMS m/z (ESI): 419.0 $[M-H]^-$ Step 5: A solution of methyl 5-[2,6-difluoro-3-[(2,2,2-trifluoroacetyl)amino]phenoxy]-2-nitro-benzoate (4.1 g, 9.76 mmol) in water was added lithium hydroxide monohydrate (695.99 mg, 16.59 mmol, 460.92 μL) at 0-5° C. The resulted reaction mixture was stirred at room temperature for 3 h. After completion, reaction solvent was removed under reduced pressure to afford the crude compound. Crude compound was diluted with water and acidified with 1.5 N HCl and extracted with ethyl acetate (20 mL). The organic layer was dried over sodium sulfate and concentrated under reduced pressure to afford 5-[2,6-difluoro-3-[(2,2,2-trifluoroacetyl)amino]phenoxy]-2-nitro-benzoic acid (3.8 g, 8.53 mmol, 87% yield) as a light brown solid. LCMS m/z (ESI): 405.1 [M−H]−

Step 6: A solution of 5-[2,6-difluoro-3-[(2,2,2-trifluoroacetyl)amino]phenoxy]-2-nitro-benzoic acid (680 mg, 1.67 mmol) in ethyl acetate (20 mL) was degassed with nitrogen for 5 minutes, 10% palladium on carbon (150 mg, 1.41 mmol) was added to the reaction mixture and stirred under $H_2$ balloon pressure for 4 h. The reaction mixture was filtered through celite and the filtrate was concentrated under reduced pressure to afford 2-amino-5-[2,6-difluoro-3-[(2,2,2-trifluoroacetyl)amino]phenoxy]benzoic acid (510 mg, 1.24 mmol, 74% yield) as an off-white solid. LCMS m/z (ESI): 377.1 $[M+H]^+$ Step 7: To a solution of tert-butyl 4-(5-aminopyrimidin-2-yl)piperazine-1-carboxylate (890.95 mg, 3.19 mmol), 2-amino-5-[2,6-difluoro-3-[(2,2,2-trifluoroacetyl)amino]phenoxy]benzoic acid (1.2 g, 3.19 mmol) in toluene (7.98 mL) and tetrahydrofuran (3.99 mL) was added triethyl orthoformate (945.37 mg, 6.38 mmol, 1.06 mL) and acetic acid (19.15 mg, 318.95 μmol, 18.26 μL) at room temperature. The resulting reaction mixture was heated to 110° C. for 16 h. The reaction mixture was diluted with water (10 mL), was extracted with ethyl acetate (2×50 mL). The combined organic layer was washed with brine (5 mL), dried over sodium sulfate, and concentrated under reduced pressure to afford the crude. The crude product was purified by silica gel column chromatography eluted with 0-30% ethyl acetate in petroleum ether as eluent to afford tert-butyl 4-[5-[6-[2,6-difluoro-3-[(2,2,2-trifluoroacetyl)amino]phenoxy]-4-oxo-quinazolin-3-yl]pyrimidin-2-yl]piperazine-1-carboxylate (1.0 g, 1.50 mmol, 47% yield) as an off-white solid. LCMS m/z (ESI): 648.6 $[M+H]^+$ Step 8: To a solution of tert-butyl 4-[5-[6-[2,6-difluoro-3-[(2,2,2-trifluoroacetyl)amino]phenoxy]-4-oxo-quinazolin-3-yl]pyrimidin-2-yl]piperazine-1-carboxylate (950 mg, 1.47 mmol) in ethanol (15 mL) was added triethylamine (2.23 g, 22.01 mmol, 3.07 mL) at room temperature. The resulting reaction mixture was heated to 80° C. for 16 h. The reaction mixture was concentrated under reduced pressure to afford crude and the crude product was washed with petroleum ether to afford tert-butyl 4-[5-[6-(3-amino-2,6-difluoro-phenoxy)-4-oxo-quinazolin-3-yl]pyrimidin-2-yl]piperazine-1-carboxylate (0.8 g, 1.45 mmol, 99% yield) as a brownish viscous liquid. LCMS m/z (ESI): 552.2 $[M+H]^+$ Step 9: To a cooled 0° C. solution of tert-butyl 4-[5-[6-(3-amino-2,6-difluoro-phenoxy)-4-oxo-quinazolin-3-yl]pyrimidin-2-yl]piperazine-1-carboxylate (400 mg, 725.24 μmol) in dichloromethane (7.89 mL) was added 1,8-diazabicyclo[5.4.0]undec-7-ene (110.41 mg, 725.24 μmol, 108.24 μL) and stirred for 10 minutes. Cyclopentane sulfonyl chloride (122.31 mg, 725.24 μmol, 92.28 μL) was added to the reaction mixture and stirred at room temperature for 4 h. The reaction mixture was diluted with dichloromethane (80 mL), washed with water (30 mL), brine (30 mL), dried over sodium sulfate and concentrated under reduced pressure to afford crude. The resulting crude was purified by silica gel column chromatography eluted with 60% ethyl acetate in petroleum ether to afford tert-butyl 4-[5-[6-[3-(cyclopentylsulfonylamino)-2,6-difluoro-phenoxy]-4-oxo-quinazolin-3-yl]pyrimidin-2-yl]piperazine-1-carboxylate (230 mg, 303.70 μmol, 42% yield) as a light brown solid. LCMS m/z (ESI): 684.2 $[M+H]^+$ Step 10: To a stirred solution of tert-butyl 4-[5-[6-[3-(cyclopentylsulfonylamino)-2,6-difluoro-phenoxy]-4-oxo-quinazolin-3-yl]pyrimidin-2-yl]piperazine-1-carboxylate (230 mg, 336.39 μmol) in 1,4 dioxane (2 mL) was added 4M hydrogen chloride in 1,4-dioxane (4 M, 3 mL) at 0° C. and the resulting reaction mixture was stirred at room temperature for 4 h. The reaction mixture was concentrated under reduced pressure to afford crude which was triturated with diethyl ether to afford N-[2,4-difluoro-3-[4-oxo-3-(2-piperazin-1-ylpyrimidin-5-yl)quinazolin-6-yl]oxy-phenyl]cyclopentanesulfonamide (210 mg, 327.16 μmol, 97% yield) as a light brown solid. LCMS m/z (ESI): 584.6, $[M+H]^+$ Step 11: Target compound was prepared via HATU mediated acid-amine coupling reaction (Procedure A-E). Amide coupling was carried out using N-[2,4-difluoro-3-[4-oxo-3-(2-piperazin-1-ylpyrimidin-5-yl)quinazolin-6-yl]oxy-phenyl]cyclopentanesulfonamide (100 mg, 161.27 μmol), 2-[4-[2-fluoro-4-[[(3S)-2,6-dioxo-3-piperidyl]amino]phenyl]-1-piperidyl]acetic acid (58.60 mg, 146.57 μmol), HATU (61.32 mg, 161.27 μmol) and N,N-diisopropylethylamine (83.37 mg, 645.09 μmol, 112.36 μL). The resulting crude was purified by reverse phase column chromatography by using 30 g snap eluted with 50% acetonitrile in 0.1% formic acid in water to afford N-[2,4-difluoro-3-[3-[2-[4-[2-[4-[2-fluoro-4-[[(3S)-2,6-dioxo-3-piperidyl]amino]phenyl]-1-piperidyl]acetyl]piperazin-1-yl]pyrimidin-5-yl]-4-oxo-quinazolin-6-yl]oxy-phenyl]cyclopentanesulfonamide (15 mg, 14.68 μmol, 9% yield) as an off-white solid. LCMS m/z (ESI): 929.0 $[M+H]^+$; $^1$HNMR (400 MHz, DMSO-$d_6$): δ=10.80 (s, 1H), 9.83 (s, 1H), 8.56 (s, 2H), 8.32 (s, 1H), 7.84 (d, J=8.80 Hz, 1H), 7.73 (dd, J=2.80, 8.80 Hz, 1H), 7.49-7.34 (m, 3H), 7.00 (s, 1H), 6.49-6.44 (m, 2H), 6.06 (d, J=5.60 Hz, 1H), 4.36-4.27 (m, 1H), 3.96-3.81 (m, 4H), 3.68-3.54 (m, 5H), 2.74-2.69 (m, 1H), 2.61-2.57 (m, 2H), 2.57-2.51 (m, 4H), 2.15-2.04 (m, 1H), 1.94-1.51 (m, 13H).

Example 139

3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorophenoxy]-4-oxoquinazoline

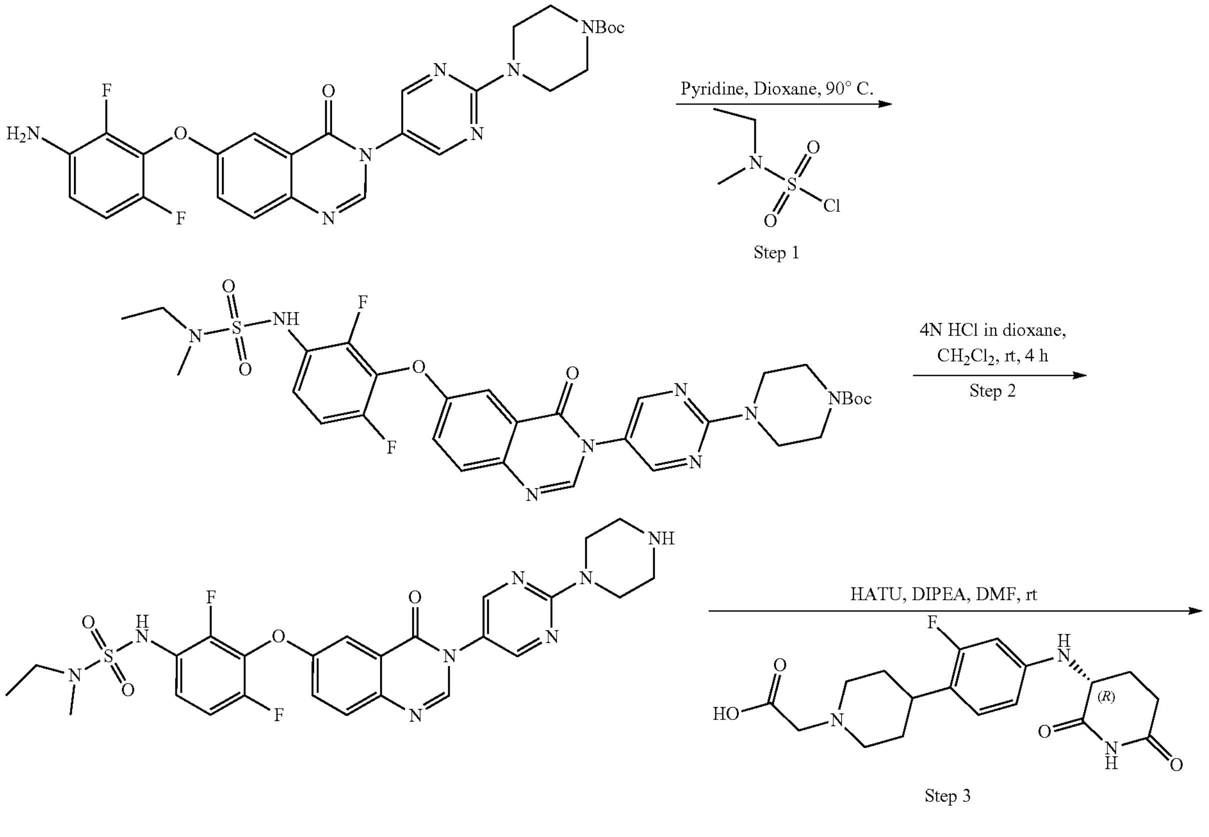

-continued

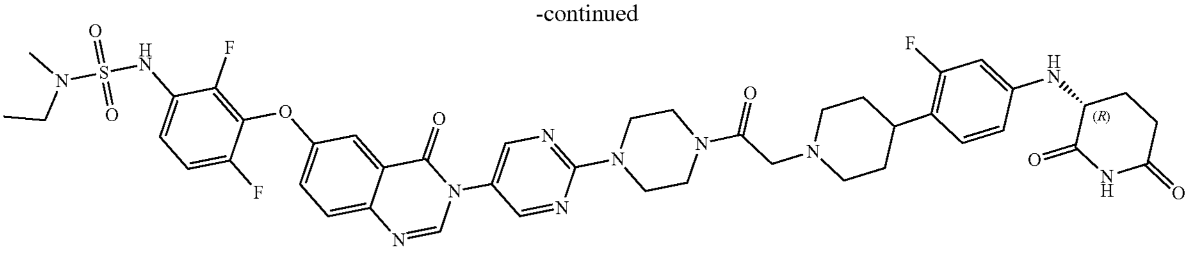

Step 1: To a stirred solution of N-ethyl-N-methyl-sulfamoyl chloride (342.93 mg, 2.18 mmol, 268.27 μL), tert-butyl 4-[5-[6-(3-amino-2,6-difluoro-phenoxy)-4-oxo-quinazolin-3-yl]pyrimidin-2-yl]piperazine-1-carboxylate (0.2 g, 362.62 μmol) in dioxane (2 mL) were added pyridine (286.83 mg, 3.63 mmol, 293.28 μL) at room temperature. The resulting mixture was heated to 90° C. for 16 h. After completion, the reaction mixture was diluted with water (10 mL) and obtained solid was filtered off to afford tert-butyl 4-[5-[6-[3-[[ethyl(methyl)sulfamoyl]amino]-2,6-difluoro-phenoxy]-4-oxo-quinazolin-3-yl]pyrimidin-2-yl]piperazine-1-carboxylate (0.15 g, 180.17 μmol, 50% yield) as a brown solid. LCMS, m/z: 617.2 $[M-{}^tBu+H]^+$.

Step 2: Requisite amine was synthesized by 4M HCl in dioxane mediated N-Boc deprotection (Procedure A-D). N-Boc deprotection was done on tert-butyl 4-[5-[6-[3-[[ethyl(methyl)sulfamoyl]amino]-2,6-difluoro-phenoxy]-4-oxo-quinazolin-3-yl]pyrimidin-2-yl]piperazine-1-carboxylate (0.15 g, 222.98 μmol) using hydrogen chloride solution 4.0 M in dioxane (2 mL) to afford crude 6-[3-[[ethyl(methyl)sulfamoyl]amino]-2,6-difluoro-phenoxy]-4-oxo-3-(2-piperazin-1-ylpyrimidin-5-yl)quinazoline (0.13 g, 169.09 μmol, 76% yield) as a brown solid. LCMS m/z: 573.6 $[M+H]^+$.

Step 3: Target compound was prepared via HATU mediated acid-amine coupling reaction (Procedure A-E). Amide coupling was carried out using 6-[3-[[ethyl(methyl)sulfamoyl]amino]-2,6-difluoro-phenoxy]-4-oxo-3-(2-piperazin-1-ylpyrimidin-5-yl)quinazoline (65 mg, 113.52 μmol), 2-[4-[4-[[(3R)-2,6-dioxo-3-piperidyl]amino]-2-fluoro-phenyl]-1-piperidyl]acetic acid (41.25 mg, 113.52 μmol), N,N-diisopropylethylamine (73.36 mg, 567.60 μmol, 98.87 μL) and HATU (43.16 mg, 113.52 μmol). The crude compound was purified by reverse phase column chromatography eluted with 40% acetonitrile in 0.1% ammonium bicarbonate in water to afford 6-[3-[[ethyl(methyl)sulfamoyl]amino]-2,6-difluoro-phenoxy]-3-[2-[4-[2-[4-[2-fluoro-4-[[(3R)-2,6-dioxo-3-piperidyl]amino]phenyl]-1-piperidyl]acetyl]piperazin-1-yl]pyrimidin-5-yl]-4-oxo-quinazoline (17 mg, 18.20 μmol, 16% yield) as an off-white solid. LCMS m/z (ESI+): 918.0 $[M+H]^+$. $^1$HNMR (400 MHz, DMSO-$d_6$): δ=10.78 (s, 1H), 9.80 (s, 1H), 8.55 (s, 2H), 8.32 (s, 1H), 7.84 (d, J=8.80 Hz, 1H), 7.73 (dd, J=3.20, 9.00 Hz, 1H), 7.45-7.35 (m, 3H), 7.00 (t, J=8.40 Hz, 1H), 6.46-6.42 (m, 2H), 6.00 (d, J=7.60 Hz, 1H), 4.33-4.27 (m, 1H), 3.95-3.78 (m, 4H), 3.75-3.65 (m, 2H), 3.62-3.53 (m, 2H), 3.28-3.18 (m, 3H), 3.09 (q, J=36.00 Hz, 2H), 3.02-2.93 (m, 2H), 2.82-2.67 (m, 5H), 2.04-2.22 (m, 3H), 1.92-1.80 (m, 1H), 1.73-1.58 (m, 4H), 0.99 (t, J=7.20 Hz, 3H).

Example 140

3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorophenoxy]-4-oxoquinazoline

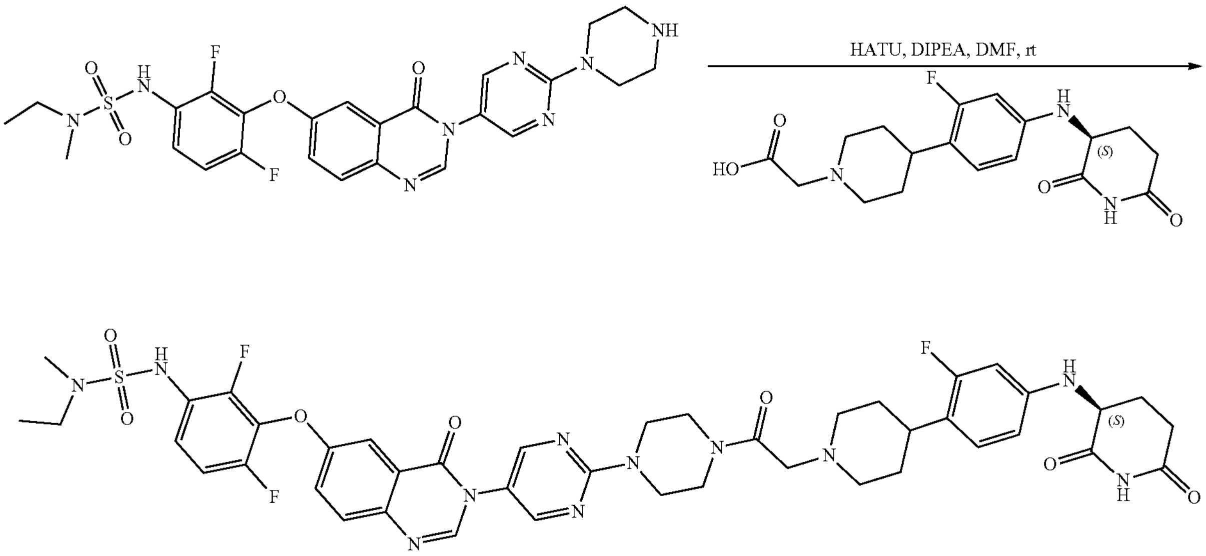

Target compound was prepared via HATU mediated acid-amine coupling reaction (Procedure A-E). Amide coupling was carried out using 2-[4-[2-fluoro-4-[[(3S)-2,6-dioxo-3-piperidyl]amino]phenyl]-1-piperidyl]acetic acid (42.67 mg, 106.72 μmol), 6-[3-[[ethyl(methyl)sulfamoyl]amino]-2,6-difluoro-phenoxy]-4-oxo-3-(2-piperazin-1-ylpyrimidin-5-yl)quinazoline (65 mg, 106.72 μmol), N,N-diisopropylethylamine (68.97 mg, 533.62 μmol, 92.95 μL) and HATU (40.58 mg, 106.72 μmol). The crude compound was purified by reverse phase column chromatography eluted with 40% acetonitrile in 0.1% ammonium bicarbonate in water to afford 6-[3-[[ethyl(methyl)sulfamoyl]amino]-2,6-difluoro-phenoxy]-3-[2-[4-[2-[4-[2-fluoro-4-[[(3S)-2,6-dioxo-3-piperidyl]amino]phenyl]-1-piperidyl]acetyl]piperazin-1-yl]pyrimidin-5-yl]-4-oxo-quinazoline (9 mg, 9.21 μmol, 9% yield) as an off-white solid. LCMS m/z (ESI+): 918.0 $[M+H]^+$. $^1$HNMR (400 MHz, DMSO-$d_6$): δ=10.78 (s, 1H), 8.56 (s, 2H), 8.31 (s, 1H), 7.83 (d, J=9.20 Hz, 1H), 7.72 (dd, J=2.80, 8.80 Hz, 1H), 7.40-7.36 (m, 2H), 7.30 (t, J=40.00 Hz, 1H), 7.00 (t, J=8.40 Hz, 1H), 6.47-6.42 (m, 2H), 6.01 (d, J=7.60 Hz, 1H), −19.20-4.34 (m, 1H), 3.95-3.86 (m, 2H), 3.84-3.77 (m, 2H), 3.75-3.68 (m, 2H), 3.63-3.54 (m, 2H), 3.28-3.20 (m, 2H), 3.06 (q, J=24.00 Hz, 2H), 2.98 (d, J=36.00 Hz, 2H), 2.84-2.73 (m, 1H), 2.67 (s, 3H), 2.64-2.58 (m, 2H), 2.18-2.05 (m, 3H), 1.94-1.82 (m, 1H), 1.72-1.60 (m, 4H), 0.99 (t, J=7.20 Hz, 3H).

Example 141

3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-6-[3-[[ethyl(methyl)sulfamoyl]amino]-2,6-difluorobenzoyl]-4-oxoquinazoline

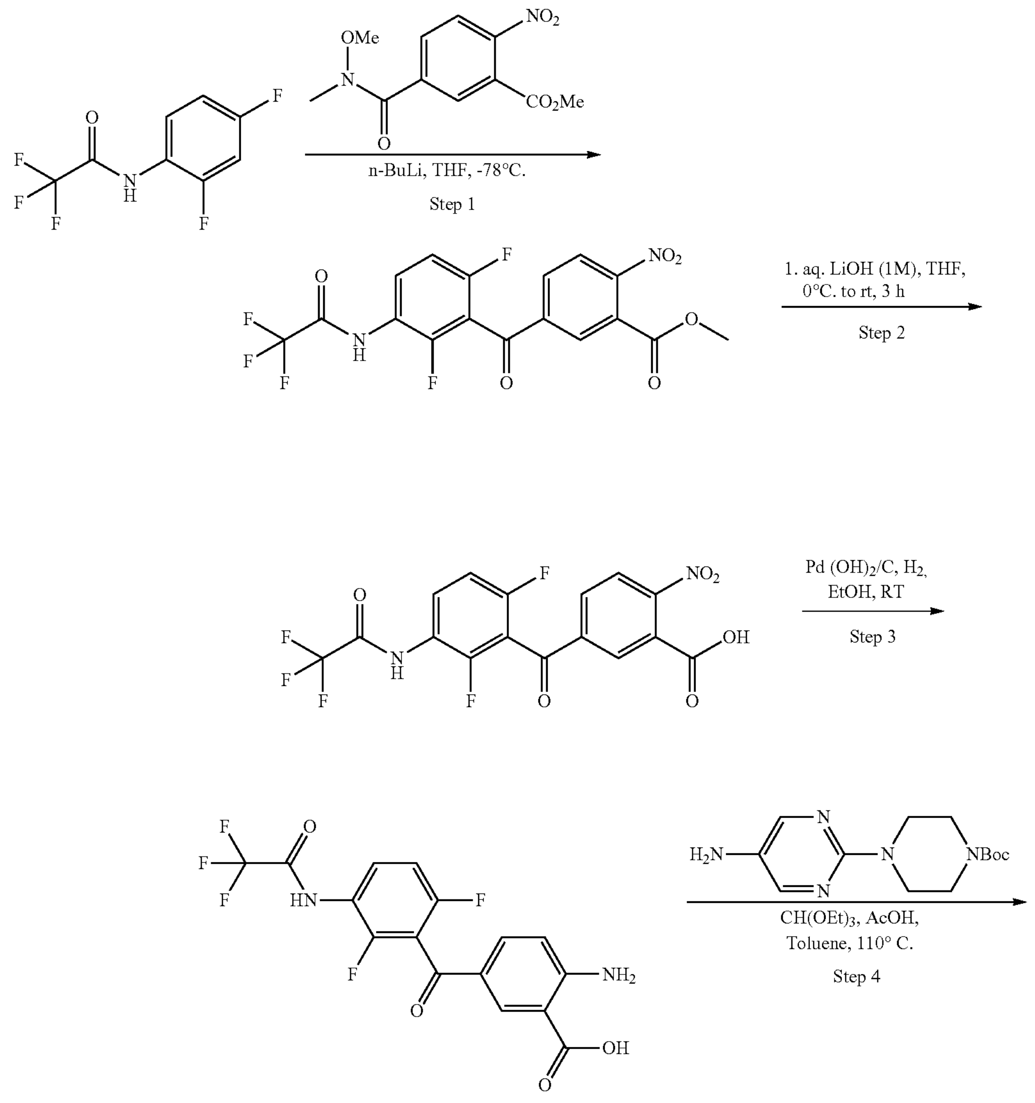

-continued
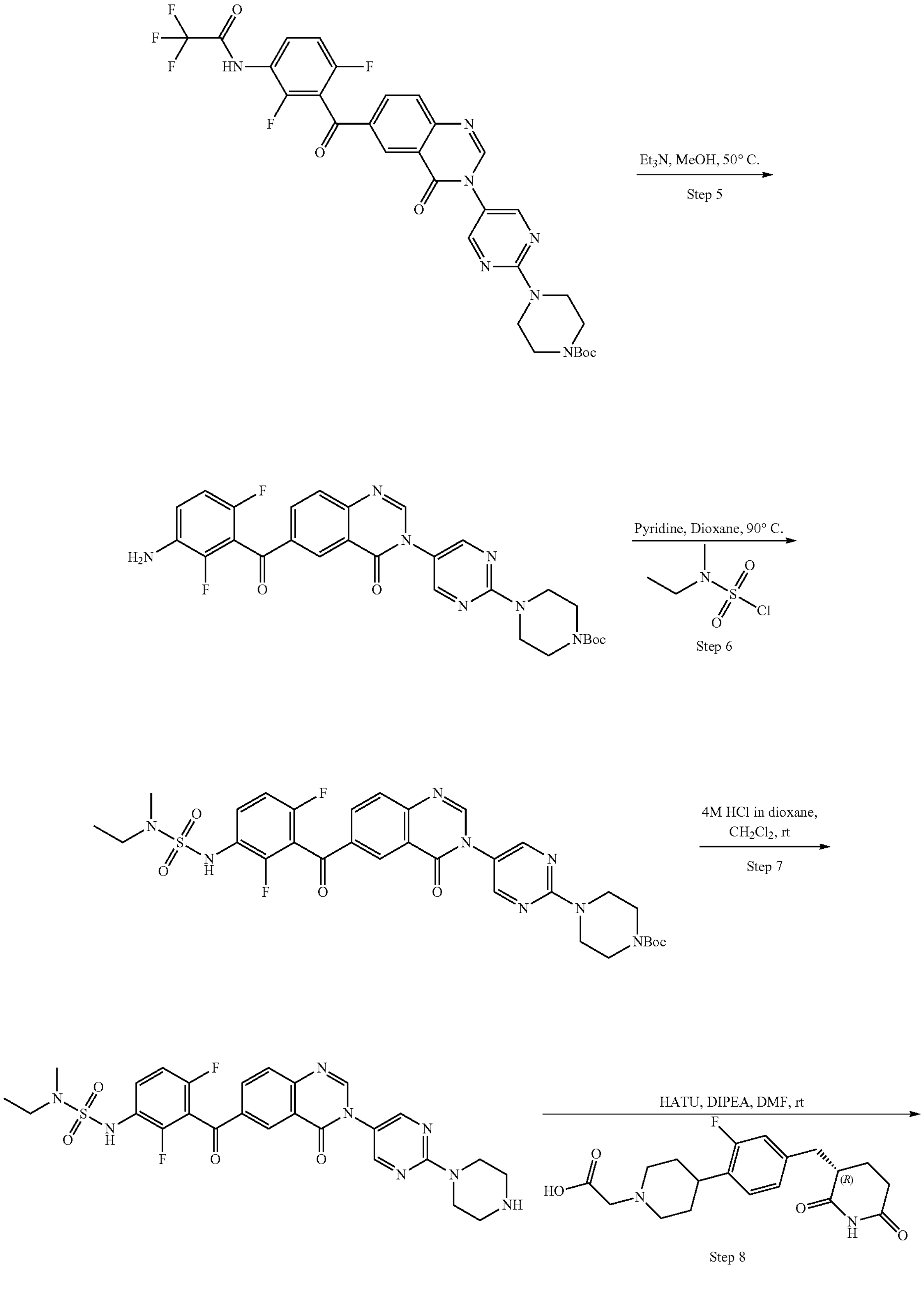

-continued

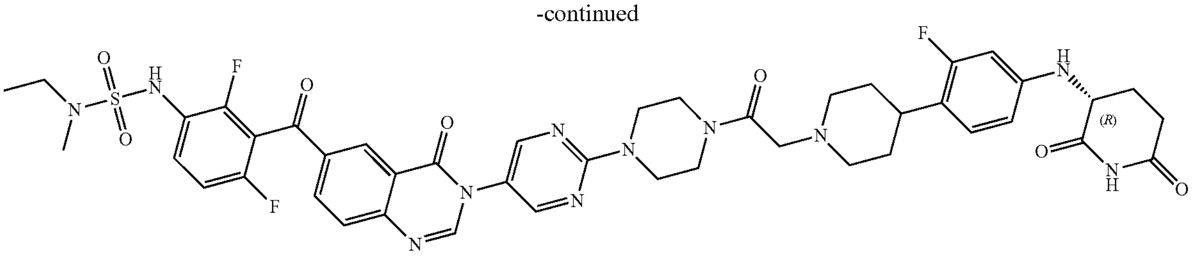

Step 1: To a stirred solution of N-(2,4-difluorophenyl)-2,2,2-trifluoro-acetamide (3.01 g, 13.39 mmol) in THF (30 mL) was added n-butyllithium, 2.2M in hexane, packaged under Argon in resealable ChemSeal bottles (1.6 M, 17.57 mL) at −78° C. and stirred for 1 h at the same temperature. The solution of methyl 5-[methoxy(methyl)carbamoyl]-2-nitro-benzoate (3.77 g, 14.06 mmol) in THF (10 mL) was added to the reaction mixture dropwise at −78° C. and further stirred for 2 h at the same temperature. After completion of reaction, the reaction mixture was quenched with ice cold water and extracted using ethyl acetate (2×100 mL). The organic layer was dried and concentrated to afford crude. The crude product was purified by flash silica gel column chromatography eluting with ethyl acetate in petroleum ether to afford methyl 5-[2,6-difluoro-3-[(2,2,2-trifluoroacetyl)amino]benzoyl]-2-nitro-benzoate (2.6 g, 5.47 mmol, 41% yield) as a pale yellow oil. LCMS m/z ($ES^+$): 430.8 $[M-H]^-$.

Step 2: To a stirred solution of methyl 5-[2,6-difluoro-3-[(2,2,2-trifluoroacetyl)amino]benzoyl]-2-nitro-benzoate (2.6 g, 6.01 mmol) in THF (20 mL) was added lithium hydroxide monohydrate, 98% (1.0 M, 6.01 mL) at room temperature. The contents were stirred at room temperature for 3.5 h. After completion, mixture was acidified with 1.5 N HCl and extracted with ethyl acetate, dried over sodium sulfate and concentrated under vacuum to afford 5-[2,6-difluoro-3-[(2,2,2-trifluoroacetyl)amino]benzoyl]-2-nitro-benzoic acid (2.2 g, 4.26 mmol, 71% yield) as an off-white viscous solid. LCMS m/z (ES): 417.3$[M-H]^-$.

Step 3: To a stirred solution of 5-[2,6-difluoro-3-[(2,2,2-trifluoroacetyl)amino]benzoyl]-2-nitro-benzoic acid (750 mg, 1.79 mmol) in dry ethanol (20 mL) was added palladium, 10% on carbon (375.00 mg, 3.52 mmol) under nitrogen at ambient temperature. The contents were stirred at 25° C. for 16 h under bladder hydrogen pressure. After completion of the reaction, the mixture was filtered through a pad of celite under nitrogen using 10% methanol in dichloromethane. Filtrate was concentrated under reduced pressure to afford 2-amino-5-[2,6-difluoro-3-[(2,2,2-trifluoroacetyl)amino]benzoyl]benzoic acid (400 mg, 813.92 μmol, 45% yield) as an off-white solid. LCMS m/z ($ES^+$): 389.4 $[M+H]^+$.

Step 4: Quinazolinone intermediate was synthesized by following general procedure for cyclization (Procedure A-A) using 2-amino-5-[2,6-difluoro-3-[(2,2,2-trifluoroacetyl)amino]benzoyl]benzoic acid (404.13 mg, 1.04 mmol), tert-butyl 4-(5-aminopyrimidin-2-yl)piperazine-1-carboxylate (290.76 mg, 1.04 mmol), triethyl orthoformate (308.52 mg, 2.08 mmol, 346.27 μL) and acetic acid (12.50 mg, 208.18 μmol, 11.92 μL). The desired compound was purified from crude by silica gel chromatography using 80% ethyl acetate in petroleum ether as eluent to afford tert-butyl 4-[5-[6-[2,6-difluoro-3-[(2,2,2-trifluoroacetyl)amino]benzoyl]-4-oxo-quinazolin-3-yl]pyrimidin-2-yl]piperazine-1-carboxylate (90 mg, 88.23 μmol, 8% yield) as a light yellow solid. LCMS m/z (ESI+): 658.0 $[M-H]^-$.

Step 5: To a solution of tert-butyl 4-[5-[6-[2,6-difluoro-3-[(2,2,2-trifluoroacetyl)amino]benzoyl]-4-oxo-quinazolin-3-yl]pyrimidin-2-yl]piperazine-1-carboxylate (80 mg, 121.29 μmol) in ethanol (1 mL) was added triethylamine (61.37 mg, 606.46 μmol, 84.53 μL) and the reaction mixture was stirred at 80° C. for 16 h. After completion of reaction, mixture was concentrated and diluted with ethyl acetate and washed with water. The organic layer was dried and concentrated to afford product tert-butyl 4-[5-[6-(3-amino-2,6-difluoro-benzoyl)-4-oxo-quinazolin-3-yl]pyrimidin-2-yl]piperazine-1-carboxylate (60 mg, 58.52 μmol, 48% yield). LCMS m/z ($ES^+$): 508.2 $[M-{}^tBu+H]^+$.

Step 6: To a solution of tert-butyl 4-[5-[6-(3-amino-2,6-difluoro-benzoyl)-4-oxo-quinazolin-3-yl]pyrimidin-2-yl]piperazine-1-carboxylate (55 mg, 97.59 μmol), in 1,4-dioxane (1.01 mL) was added pyridine (38.60 mg, 487.97 μmol, 39.47 μL) and N-ethyl-N-methyl-sulfamoyl chloride (15.38 mg, 97.59 μmol, 12.03 μL) at room temperature under nitrogen atmosphere. The reaction mixture was heated at 60° C. for 16 h. After completion, the reaction mixture was diluted with cold water (10 mL) and extracted to ethyl acetate (20 mL). The organic layer was dried over sodium sulfate and concentrated under reduced pressure to afford crude, which was triturated with petroleum ether to afford tert-butyl 4-[5-[6-[3-[[ethyl(methyl)sulfamoyl]amino]-2,6-difluoro-benzoyl]-4-oxo-quinazolin-3-yl]pyrimidin-2-yl]piperazine-1-carboxylate (60 mg, 76.85 μmol, 79% yield) as a brown solid. LCMS m/z (ES): 683.0 $[M-H]^-$.

Step 7: Requisite amine was synthesized by 4 M HCl in dioxane mediated N-Boc deprotection (Procedure A-D). N-Boc deprotection was done on tert-butyl 4-[5-[6-[3-[[ethyl(methyl)sulfamoyl]amino]-2,6-difluoro-benzoyl]-4-oxo-quinazolin-3-yl]pyrimidin-2-yl]piperazine-1-carboxylate (60 mg, 87.63 μmol) using hydrogen chloride, 4 M in 1,4-dioxane (4 M, 328.61 μL) to afford 6-[3-[[ethyl(methyl)sulfamoyl]amino]-2,6-difluoro-benzoyl]-4-oxo-3-(2-piperazin-1-ylpyrimidin-5-yl)quinazoline (45 mg, 61.61 μmol, 70% yield) as an off-white solid. LCMS m/z (ES): 585.2 $[M+H]^+$.

Step 8: Target compound was prepared via HATU mediated acid-amine coupling reaction (Procedure A-E). Amide coupling was carried out using 6-[3-[[ethyl(methyl)sulfamoyl]amino]-2,6-difluoro-benzoyl]-4-oxo-3-(2-piperazin-1-ylpyrimidin-5-yl)quinazoline (20 mg, 32.20 μmol), 2-[4-[2-fluoro-4-[[(3R)-2,6-dioxo-3-piperidyl]amino]phenyl]-1-piperidyl]acetic acid (11.70 mg, 29.27 μmol), N,N-diisopropylethylamine (12.49 mg, 96.61 μmol, 16.83 μL) and HATU (18.37 mg, 48.30 μmol). The crude compound was purified by reverse phase column chromatography eluted with 50% acetonitrile in 0.1% formic acid in water to afford product 6-[3-[[ethyl(methyl)sulfamoyl]amino]-2,6-difluoro-benzoyl]-3-[2-[4-[2-[4-[2-fluoro-4-[[(3R)-2,6-di-oxo-3-piperidyl]amino]phenyl]-1-piperidyl]acetyl]piperazin-1-yl]pyrimidin-5-yl]-4-oxo-quinazoline (3 mg, 3.00 μmol, 9% yield) as an off-white solid. LCMS m/z (ESI): 930.3 $[M+H]^+$. $^1$HNMR (400 MHz, DMSO-$d_6$): δ=10.80 (s, 1H), 9.80 (s, 1H), 8.57 (d, J=14.40 Hz, 1H), 8.44 (d, J=20.00 Hz, 1H), 8.36 (dd, J=2.40, 8.60 Hz, 1H), 7.95 (d, J=8.40 Hz, 1H), 7.73-7.67 (m, 1H), 7.36 (t, J=1.60 Hz, 1H), 7.00 (t, J=8.40 Hz, 1H), 6.45 (d, J=12.00 Hz, 2H), 6.05 (s, 1H), 4.30-4.40 (m, 1H), 3.87 (d, J=28.40 Hz, 4H), 3.66-3.62 (m, 3H), 3.39-3.34 (m, 2H), 2.74-2.73 (m, 3H), 2.60-2.53 (m, 8H), 2.08-2.07 (m, 2H), 1.71 (s, 2H), 1.24 (s, 4H), 1.01 (t, J=7.20 Hz, 3H).
Examples 142 and 143
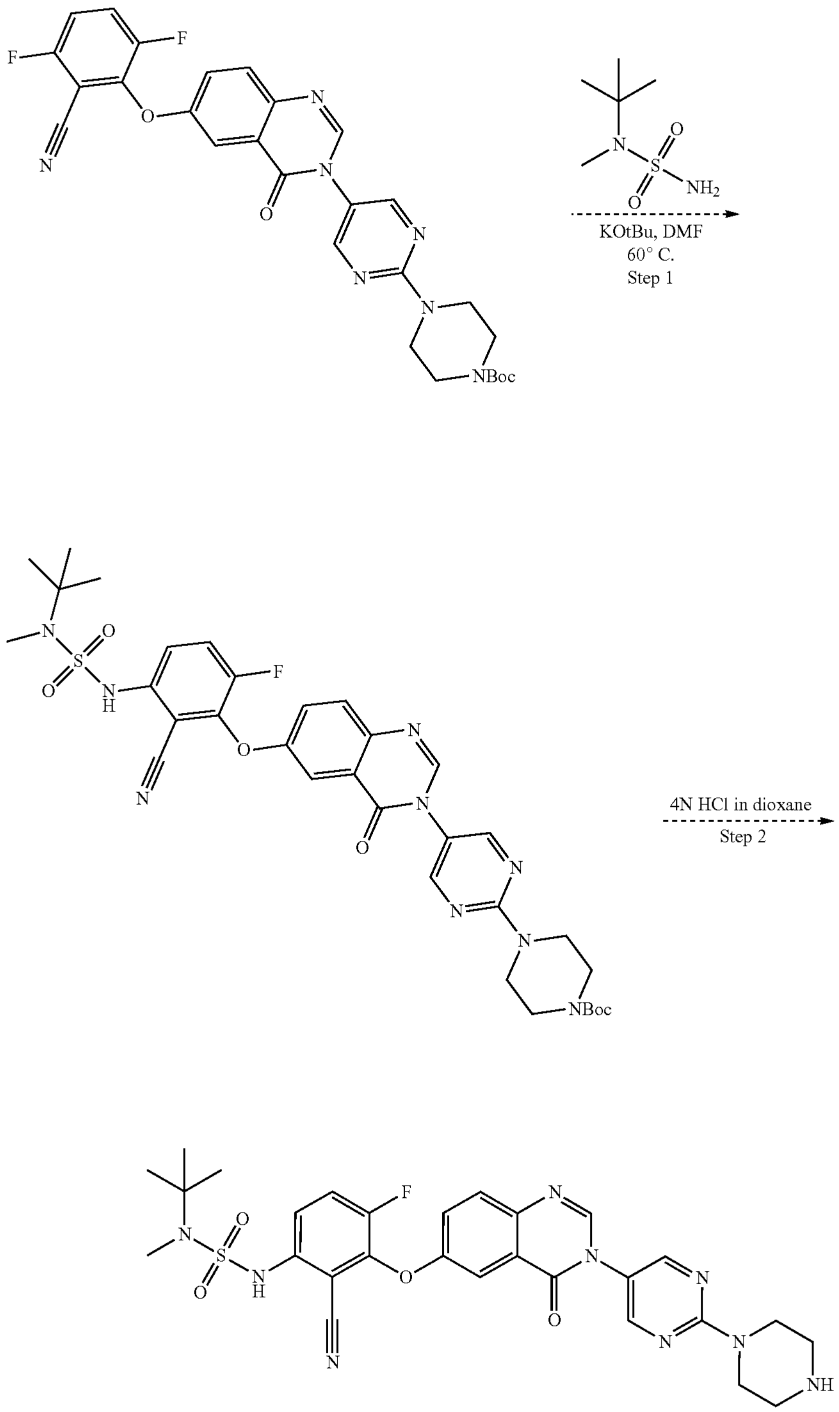

Step 1: Starting compound is synthesized following the procedures in Example 84. To a solution of tert-butyl 4-[5-[6-(2-cyano-3,6-difluoro-phenoxy)-4-oxo-quinazolin-3-yl]pyrimidin-2-yl]piperazine-1-carboxylate (1 eq.) in N,N-dimethylformamide is added potassium tert-butoxide (2.5 eq.) and 2-methyl-2-[methyl(sulfamoyl)amino]propane (2 eq.) at room temperature. The resulting reaction mixture is stirred at 60° C. for 16 hours. After completion of the reaction as confirmed by LC-MS, a workup is performed and the crude compound is purified by column chromatography to afford tert-butyl 4-[5-[6-[3-[[tert-butyl(methyl)sulfamoyl]amino]-2-cyano-6-fluoro-phenoxy]-4-oxo-quinazolin-3-yl]pyrimidin-2-yl]piperazine-1-carboxylate.

Step 2: A solution of tert-butyl 4-[5-[6-[3-[[tert-butyl(methyl)sulfamoyl]amino]-2-cyano-6-fluoro-phenoxy]-4-oxo-quinazolin-3-yl]pyrimidin-2-yl]piperazine-1-carboxylate (1 equiv.) in dichloromethane is added 4 N HCl in dioxane (10 equiv.) at 0° C. The resulted reaction mixture is stirred at room temperature for 2 hours. After completion, the reaction solvent is removed under reduced pressure and the crude compound is triturated with methyl t-butyl ether (MTBE) to afford the product 6-[3-[[tert-butyl(methyl)sulfamoyl]amino]-2-cyano-6-fluoro-phenoxy]-4-oxo-3-(2-piperazin-1-ylpyrimidin-5-yl)quinazoline.

Example 142

6-[3-[[tert-butyl(methyl)sulfamoyl]amino]-2-cyano-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline

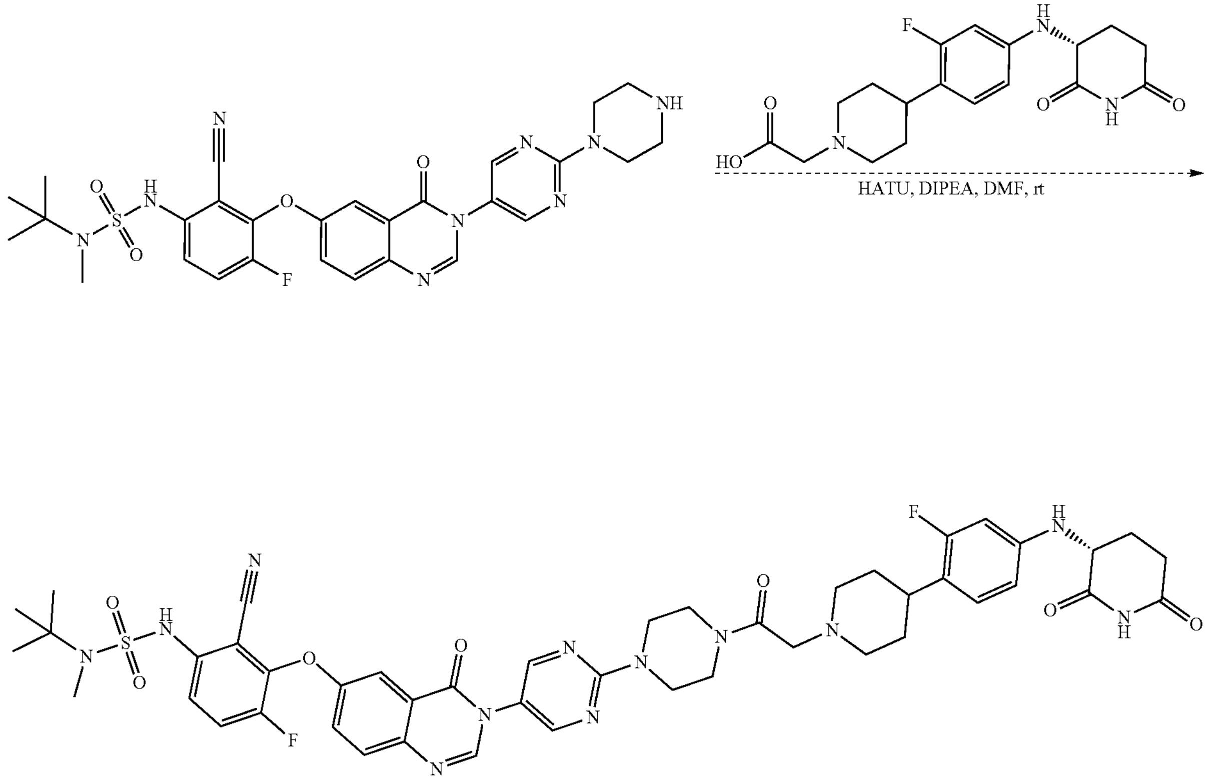

To a solution of 2-[4-[4-[[(3R)-2,6-dioxo-3-piperidyl]amino]-2-fluoro-phenyl]-1-piperidyl]acetic acid (1 equiv.) and 6-[3-[[tert-butyl(methyl)sulfamoyl]amino]-2-cyano-6-fluoro-phenoxy]-4-oxo-3-(2-piperazin-1-ylpyrimidin-5-yl)quinazoline (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, a workup is performed, and the crude product is purified by reverse phase HPLC to afford the target compound 6-[3-[[tert-butyl(methyl)sulfamoyl]amino]-2-cyano-6-fluorophenoxy]-3-[2-[4-[2-[4-[4-[[(3R)-2,6-dioxopiperidin-3-yl]amino]-2-fluorophenyl]piperidin-1-yl]acetyl]piperazin-1-yl]pyrimidin-5-yl]-4-oxoquinazoline.

Example 143

6-[3-[[tert-butyl(methyl)sulfamoyl]amino]-2-cyano-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline

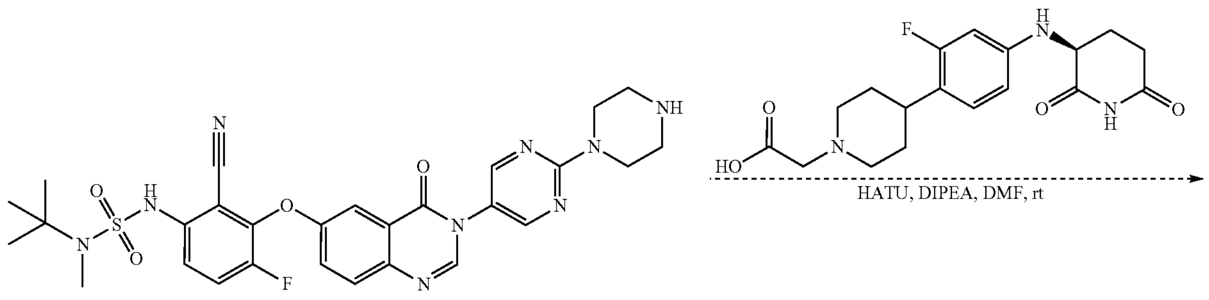

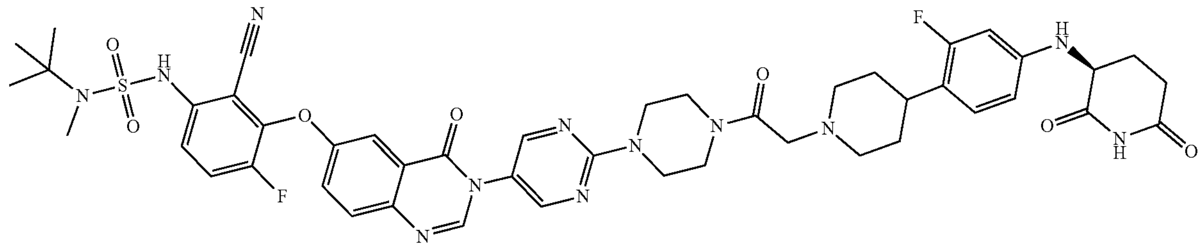

To a solution of 2-[4-[4-[[(3S)-2,6-dioxo-3-piperidyl]amino]-2-fluoro-phenyl]-1-piperidyl]acetic acid (1 equiv.) and 6-[3-[[tert-butyl(methyl)sulfamoyl]amino]-2-cyano-6-fluoro-phenoxy]-4-oxo-3-(2-piperazin-1-ylpyrimidin-5-yl)quinazoline (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, a workup is performed, and the crude product is purified by reverse phase HPLC to afford the target compound 6-[3-[[tert-butyl(methyl)sulfamoyl]amino]-2-cyano-6-fluorophenoxy]-3-[2-[4-[2-[4-[4-[[(3S)-2,6-dioxopiperidin-3-yl]amino]-2-fluorophenyl]piperidin-1-yl]acetyl]piperazin-1-yl]pyrimidin-5-yl]-4-oxoquinazoline.

Examples A1-A3

Intermediate 1

6-[2-cyano-3-[[ethyl(methyl)sulfamoyl]amino]-6-fluoro-phenoxy]-4-oxo-3-[2-(4-piperidyl)ethyl]quinazoline hydrochloride

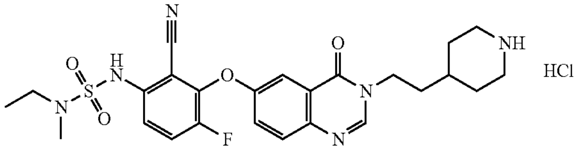 [SMILES: CCN(C)S(=O)(=O)Nc1ccc(F)c(Oc2ccc3ncn(CCC4CCNCC4)c(=O)c3c2)c1C#N ; Cl]

tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate (386 mg, 614 μmol) was dissolved in 1,4-dioxane (2.4 ml). 4 M HCl in 1,4-dioxane (3.07 mL, 12.3 mmol, Eq: 20) was added, and the reaction was stirred at rt for 3 h. The reaction mixture was concentrated in vacuo and dried under high vacuum to give the title compound as a colourless solid (386 mg, 90% purity, 100% yield). m/z 529.4 [M+H]+, ESI pos.

Intermediate 2

2-[4-[2-[6-[2-cyano-3-[[ethyl(methyl)sulfamoyl]amino]-6-fluoro-phenoxy]-4-oxo-quinazolin-3-yl]ethyl]-1-piperidyl]acetic acid, 2,2,2-trifluoroacetic acid salt

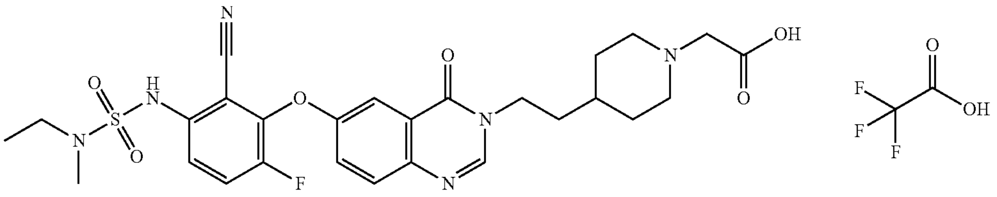 [SMILES: CCN(C)S(=O)(=O)Nc1ccc(F)c(Oc2ccc3ncn(CCC4CCN(CC(=O)O)CC4)c(=O)c3c2)c1C#N ; O=C(O)C(F)(F)F]

A mixture of Intermediate 1 (100 mg, 142 μmol, Eq: 1), tert-butyl 2-bromoacetate (55.2 mg, 283 μmol, Eq: 2) and DIPEA (110 mg, 148 μl, 849 μmol, Eq: 6) in DMF (1 ml) was stirred at rt for 2 h. The reaction mixture was poured into water and extracted with AcOEt (2×). The organic layers were combined, washed 3× with water, dried over $Na_2SO_4$ and concentrated in vacuo to give 90 mg of a light yellow waxy solid. The residue was dissolved in DCM (1 ml) and TFA (444 mg, 300 μl, 3.89 mmol, Eq: 27.8) was added. The reaction mixture was stirred at rt overnight, then concentrated in vacuo and dried under high vacuum to give the title compound as a yellow solid (125 mg, 80% purity, 100% yield).

Intermediate 3

N-[2-cyano-4-fluoro-3-[4-oxo-3-[2-(4-piperidyl)ethyl]quinazolin-6-yl]oxy-phenyl]cyclopentanesulfonamide hydrochloride

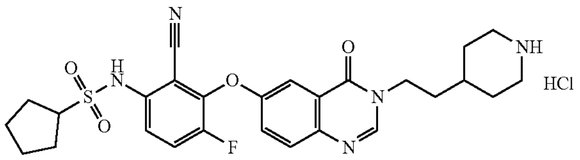 [SMILES: N#Cc1c(NS(=O)(=O)C2CCCC2)ccc(F)c1Oc1ccc2ncn(CCC3CCNCC3)c(=O)c2c1 ; Cl]

tert-butyl 4-(2-(6-(2-cyano-3-(cyclopentanesulfonamido)-6-fluorophenoxy)-4-oxoquinazolin-3(4H)-yl)ethyl)piperidine-1-carboxylate (380 mg, 595 μmol, Eq: 1) was dissolved in 1,4-dioxane (2.3 ml). 4 M HCl in 1,4-dioxane (2.97 ml, 11.9 mmol, Eq: 20) was added. The reaction mixture was stirred at rt for 3 h, then concentrated in vacuo and dried under high vacuum to give the title compound as a yellow solid (370 mg, 90% purity, 97% yield). m/z 538.5 [M−H]−, ESI neg.

General Procedure for Examples A1-A3

A solution of amine intermediate (or salt thereof) (1 eq), carboxylic acid intermediate (1.2 eq), HATU (1.5 eq) and DIPEA (3-5 eq) in DMF (0.1 M) was stirred at rt. The reaction was monitored by LCMS, and further reactants, HATU and/or DIPEA were added if necessary. The crude reaction mixture was purified by preparative reverse-phase HPLC.

Example A1

6-[2-cyano-3-[[ethyl(methyl)sulfamoyl]amino]-6-fluoro-phenoxy]-3-[2-[1-[2-[4-[4-[(2,6-dioxo-3-piperidyl)amino]phenyl]-1-piperidyl]acetyl]-4-piperidyl]ethyl]-4-oxo-quinazoline

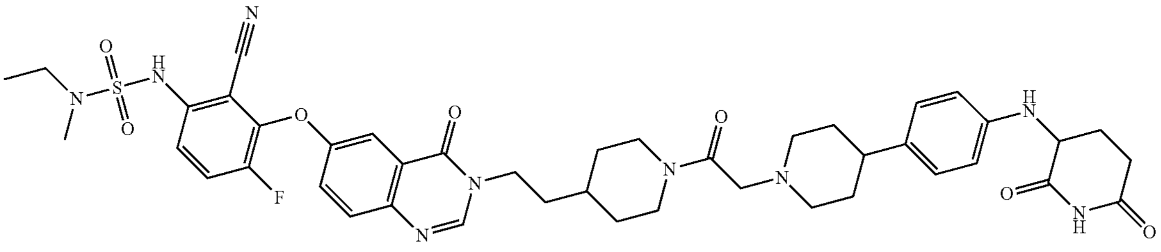 [SMILES: CCN(C)S(=O)(=O)Nc1ccc(F)c(Oc2ccc3ncn(CCC4CCN(C(=O)CN5CCC(c6ccc(NC7CCC(=O)NC7=O)cc6)CC5)CC4)c(=O)c3c2)c1C#N]

According to the general procedure for examples A1-A3, 2-(4-(4-((2,6-dioxopiperidin-3-yl)amino)phenyl)piperidin-1-yl)acetic acid hydrochloride (30 mg, 53 μmol) and Intermediate 1 (30 mg, 69 μmol) gave the title compound as a light grey solid (33 mg, 73%). LCMS ($ES^+$): m/z 856.7 $[M+H]^+$.

Example A2

6-[2-cyano-3-[[ethyl(methyl)sulfamoyl]amino]-6-fluoro-phenoxy]-3-[2-[1-[2-[4-[4-[(2,6-dioxo-3-piperidyl)amino]phenyl]-1-piperidyl]-2-oxo-ethyl]-4-piperidyl]ethyl]-4-oxo-quinazoline, 2,2,2-trifluoroacetic acid salt

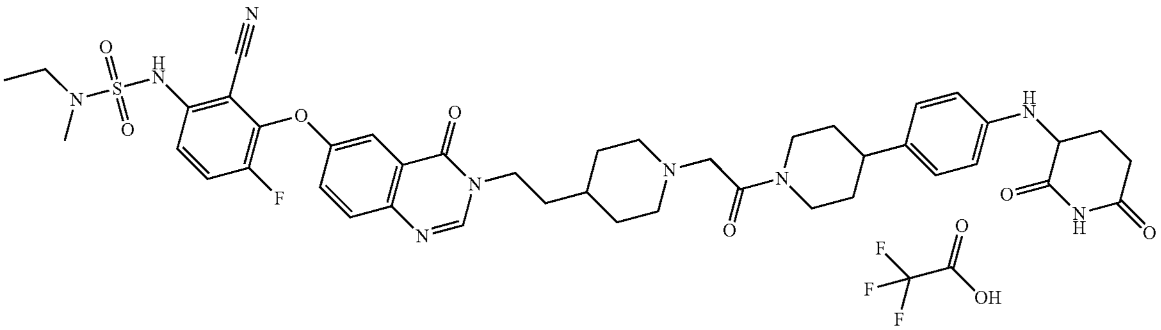

According to the general procedure for examples A1-A3, 3-((4-(piperidin-4-yl)phenyl)amino)piperidine-2,6-dione hydrochloride (14 mg, 43 μmol) and Intermediate 2 (30 mg, 43 μmol) gave the title compound as a light grey solid (14 mg, 33%). LCMS ($ES^+$): m/z 856.4 $[M+H]^+$.

Example A3

N-[2-cyano-3-[3-[2-[1-[2-[4-[4-[(2,6-dioxo-3-piperidyl)amino]phenyl]-1-piperidyl]acetyl]-4-piperidyl]ethyl]-4-oxo-quinazolin-6-yl]oxy-4-fluoro-phenyl]cyclopentanesulfonamide 2,2,2-trifluoroacetic acid salt

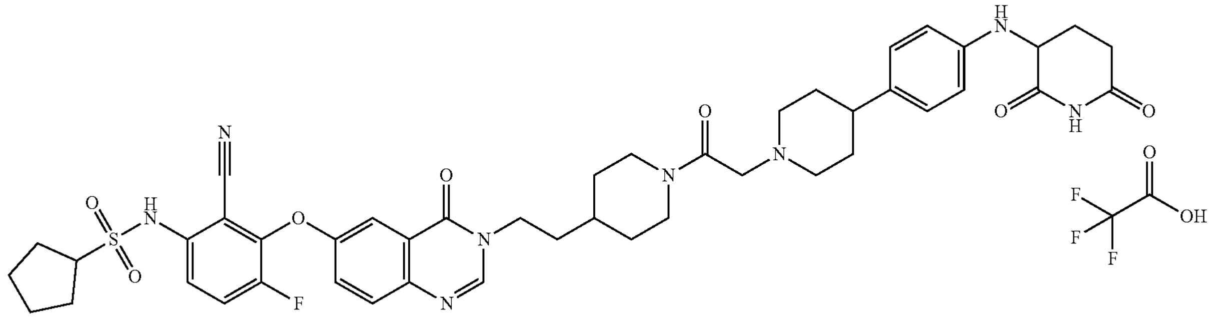

According to the general procedure for examples A1-A3, 2-(4-(4-((2,6-dioxopiperidin-3-yl)amino)phenyl)piperidin-1-yl)acetic acid hydrochloride (38 mg, 62 μmol followed by a further 15 mg, 33 μmol) and Intermediate 1 (33 mg, 52 μmol) gave the title compound as a light green solid (18 mg, 34% yield). LCMS ($ES^+$): m/z 867.6 $[M+H]^+$.

General scheme for Scaffold B

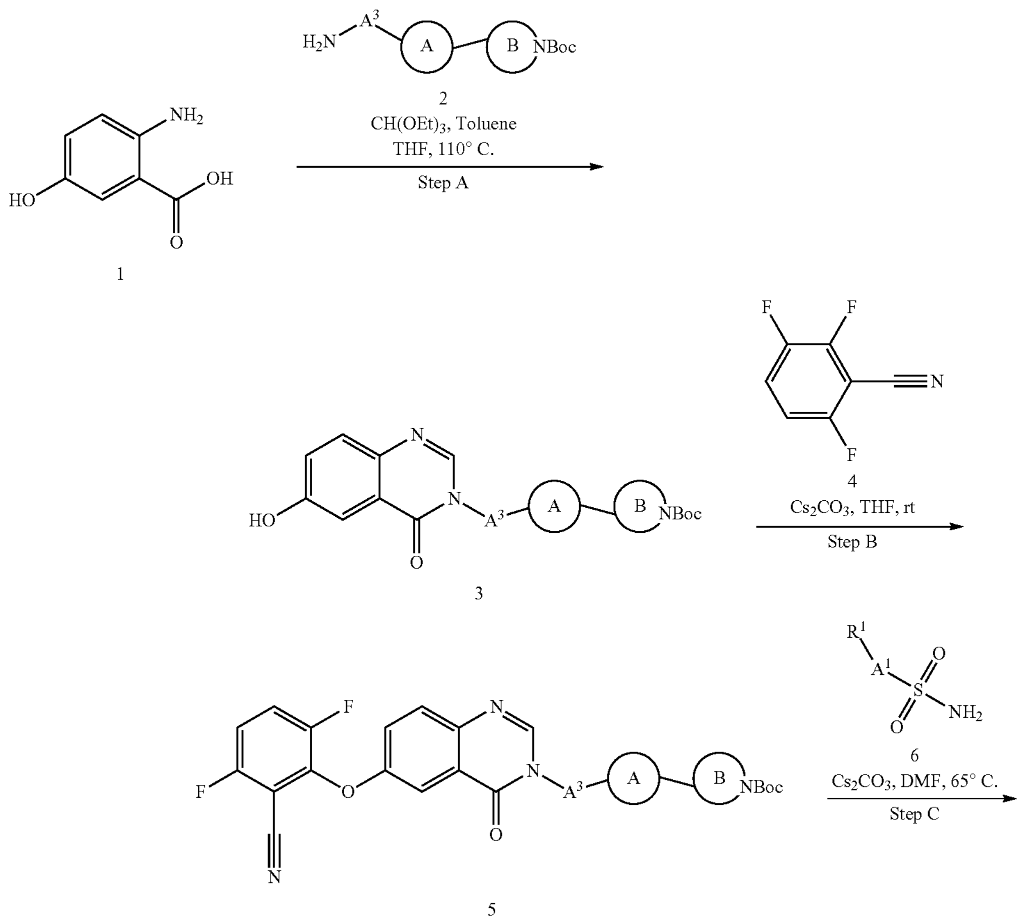

-continued

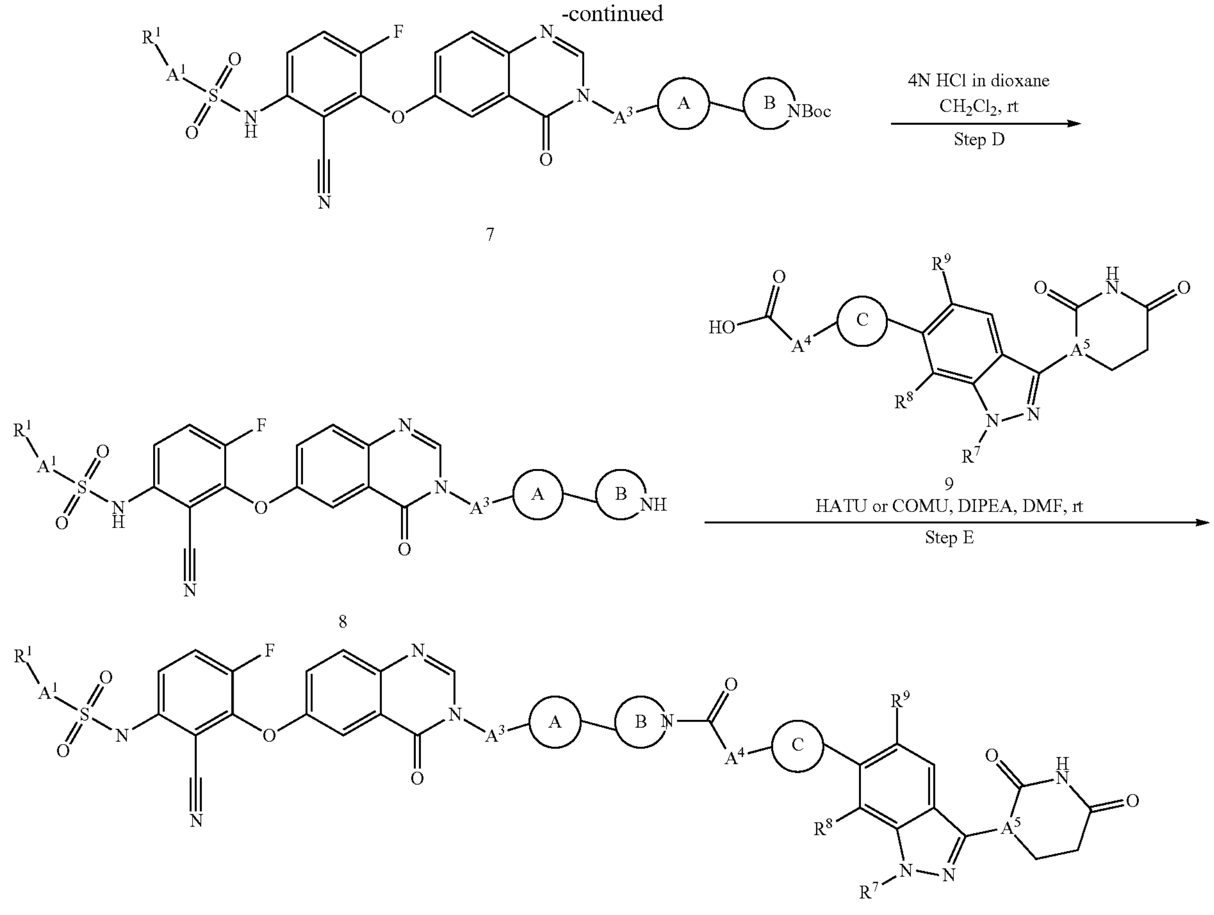

Step A—General procedure for cyclization (Procedure B-A): To a stirred solution of 2-amino-5-hydroxy-benzoic acid (1, 1 eq.) in Toluene:Tetrahydrofuran (5:1) was added anhydrous triethyl orthoformate (2 eq.) at room temperature followed by amine (commercially available or as described herein) (2, 1 eq.) was added and the resulting reaction mixture was heated at 110° C. for 18 h in sealed tube. For cyclization with amine salts (HCl, TFA etc.,), catalytic acetic acid (0.1 eq.) addition gave better conversions. After completion, the reaction mixture was cooled to room temperature. To the reaction mixture was added aqueous sodium bicarbonate solution and the aqueous layers were extracted with ethyl acetate. The combined organic layers were washed with brine, dried over anhydrous sodium sulfate, filtered and filtrate was evaporated under reduced pressure to afford the desired crude product. The crude material was purified by silica gel flash column chromatography using 5% methanol-dichloromethane as eluent to afford quinazolinone intermediate (3).

Step B—General procedure for O-arylation (Procedure B—B): To a stirred solution of quinazolinone intermediate (3, 1 eq.) in N,N-Dimethylformamide/THF (10 mL) was added cesium carbonate/potassium tert-butoxide (1.1 eq.) and commercially available 2,3,6-trifluorobenzonitrile (4, 1.1 eq.) at room temperature. The resulting reaction mixture was stirred at room temperature for 16 h. After completion, the reaction mixture was quenched with water and extracted with ethyl acetate. Combined organic layers were washed with brine, dried over sodium sulfate, and concentrated under vacuum to yield crude. Crude compound was purified by silica gel flash column chromatography using 50% ethyl acetate in petroleum ether as eluent to yield intermediate (5).

Step C—General procedure for Sulfomoylation (Procedure B—C): To a solution of intermediate 5 (1 eq.) in N,N-Dimethylformamide was added cesium carbonate (2.5 eq.) and sulfamoyl derivative (commercially available or as described herein in methods I and II; 2 eq.) at room temperature. The resulting reaction mixture was stirred at 60° C. for 16 h. After completion of the reaction, the reaction mixture was cooled to room temperature, diluted with water and extracted with ethyl acetate. The combined organic layers were washed with brine solution, dried over sodium sulfate, filtered, and concentrated under reduced pressure to afford the crude. The crude compound was purified by silica gel flash column chromatography with 20 to 50% ethyl acetate in petroleum ether as eluent to afford sulfonamide intermediate (7).

Note: For majority of reactions, after addition of water, precipitation of solids was observed. These solids were filtered through filter paper. Filtrate was extracted by ethyl acetate. Combined organic layers were washed with brine, dried over sodium sulfate, and concentrated under vacuum to yield sulfonamide intermediate (7) with decent purity.

Step D—General procedure for N-Boc deprotection (Procedure B-D): A solution of sulfonamide intermediate (7, 1 eq.) was taken in dichloromethane and added TFA (5 eq.) or 4N HCl in dioxane (10 eq.) at 0° C. The resulted reaction mixture was stirred at room temperature for 2 h. After completion, reaction solvent was removed under reduced pressure get crude product. Crude compound was triturated with methyl tert-butyl ether (MTBE) to afford targeting ligand (8).

Step E—General procedure for Acid-Amine coupling (Procedure B-E): To a stirred solution of intermediate acid (9, 1 eq.) and amine (8, 1 eq.) in N,N-Dimethylformamide (4 mL/mmol) was added N,N-diisopropylethylamine (4 eq.) at room temperature under nitrogen, followed by the addition of HATU (1.1 eq.) at same temperature. The reaction mixture was stirred at room temperature for 12 h. After completion, the reaction mixture was diluted with water and extracted with 10% isopropanol in dichloromethane. Combined organic layers were dried over sodium sulfate, filtered and concentrated under reduced pressure to afford crude compound. The crude compound was purified by reverse phase purification and fractions were lyophilized to afford the target compound (10).

Step E—Alternative general procedure for Acid-Amine coupling (Procedure B—F): To a stirred solution of acid (9, 1 eq.) and amine (8, 1 eq.) in N,N-Dimethylformamide, was added N,N-diisopropylethylamine (4 eq.) and COMU (1.1 eq.) at room temperature under nitrogen atmosphere. The reaction mixture was stirred at room temperature for 6 h. After completion, the reaction mixture was diluted with water (10 mL) and extracted with 10% isopropanol in dichloromethane (3×20 mL). Combined organic layers were dried over sodium sulfate, filtered, and concentrated under reduced pressure to afford crude. The desired product was purified from crude by reverse phase purification and fractions were lyophilized to afford target compound (10).

Example 144

6-[2-cyano-3-[[ethyl(methyl)sulfamoyl]amino]-6-fluorophenoxy]-3-[2-[1-[2-[4-[3-(2,6-dioxopiperidin-3-yl)-1-methylindazol-6-yl]piperidin-1-yl]acetyl]piperidin-4-yl]ethyl]-4-oxoquinazoline

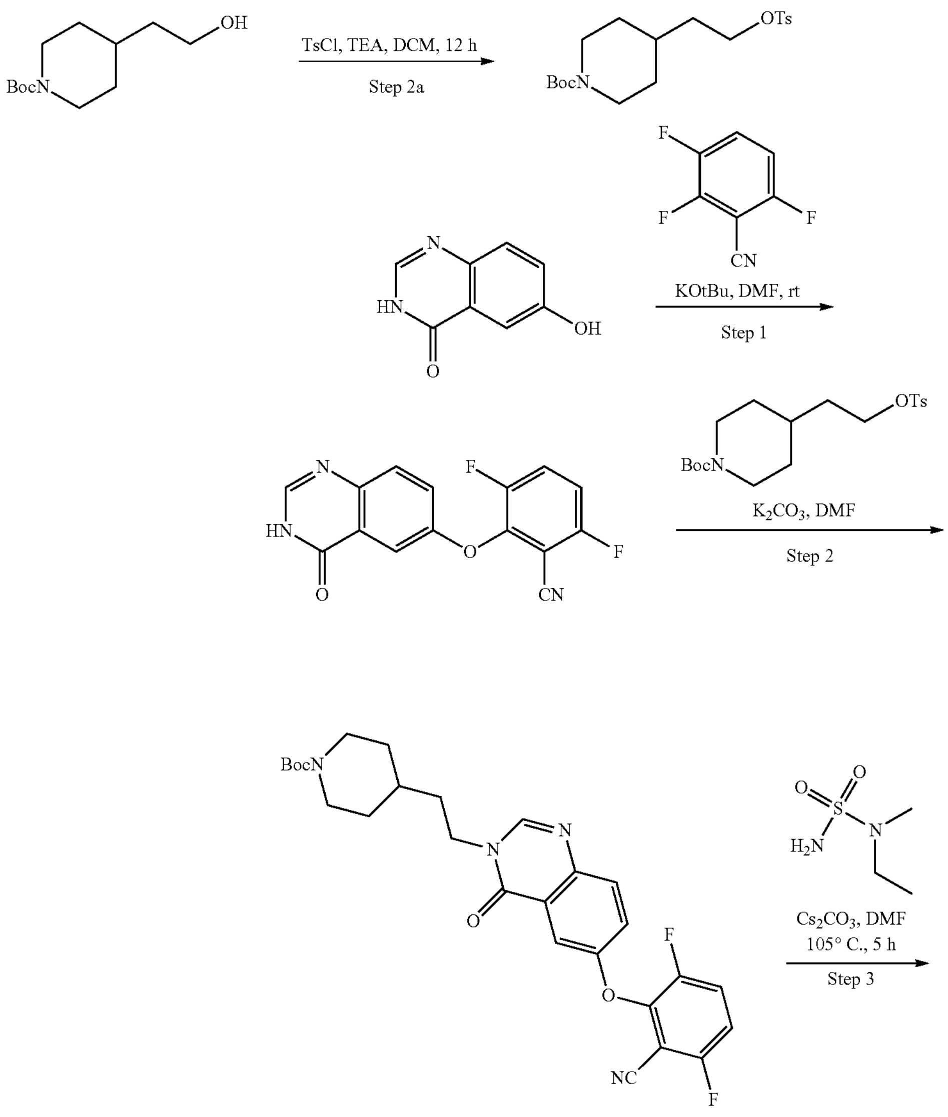

-continued

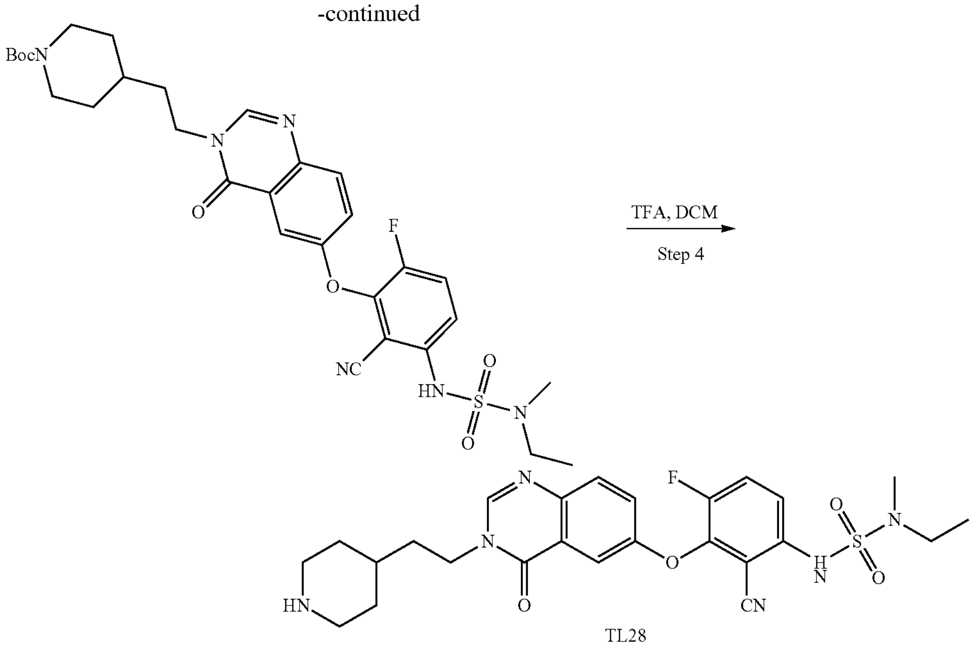

TL28

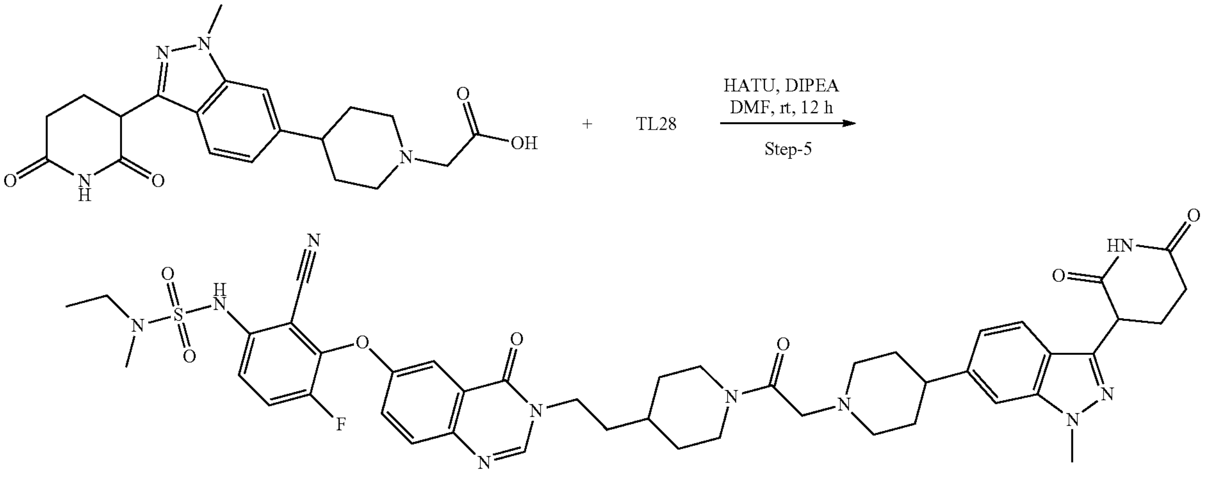

Step 1: O-arylated quinazolinone intermediate was synthesized by following general procedure for O-arylation (Procedure B—B) using 6-hydroxy-3H-quinazolin-4-one (5 g, 30.84 mmol), potassium tert-butoxide (3.81 g, 33.92 mmol) and 2,3,6-trifluorobenzonitrile (5.33 g, 33.92 mmol, 3.92 mL) to obtain compound 3,6-difluoro-2-[(4-oxo-3H-quinazolin-6-yl)oxy]benzonitrile (6.8 g, 22.21 mmol, 72% yield) as off-white solid. LCMS m/z (ESI): 300.20 $[M+H]^+$ Step 2a: To a stirred solution of tert-butyl 4-(2-hydroxyethyl)piperidine-1-carboxylate (2 g, 8.72 mmol, 1.92 mL) in dichloromethane (20 mL) was added Triethylamine (882.54 mg, 8.72 mmol, 1.22 mL) at 0° C. followed by p-Toluenesulfonyl chloride (1.83 g, 9.59 mmol) at the same temperature and the resulting reaction mixture was warmed to room temperature for 12 h. After completion, the reaction mixture was diluted with water (40 mL) and extracted with ethyl acetate (2×50 mL). The combined organic layers were dried over sodium sulfate, filtered and concentrated under reduced pressure afford tert-butyl 4-[2-(p-tolylsulfonyloxy)ethyl]piperidine-1-carboxylate (2.8 g, crude) as colorless liquid. LCMS m/z (ESI): 284.30 $[M+H-CO_2{}^tBu]^+$ Step 2: To a stirred solution of 3,6-difluoro-2-[(4-oxo-3H-quinazolin-6-yl)oxy]benzonitrile (1.5 g, 5.01 mmol) in N,N-Dimethylformamide (15 mL) was added potassium tert-butoxide (618.75 mg, 5.51 mmol) at room temperature followed by tert-butyl 4-[2-(p-tolylsulfonyloxy)ethyl]piperidine-1-carboxylate (1.92 g, 5.01 mmol) and the resulting reaction mixture was stirred for 12 h at room temperature. After completion of the reaction the reaction mixture was diluted with water (40 mL) and extracted with ethyl acetate (2×50 mL). The combined organic layers were dried over sodium sulfate, filtered and concentrated under reduced pressure to afford crude. The crude compound was purified by silica gel flash column chromatography with 5% methanol in dichloromethane as a eluent to afford tert-butyl 4-[2-[6-(2-cyano-3,6-difluoro-phenoxy)-4-oxo-quinazolin-3-yl]ethyl]piperidine-1-carboxylate (2.4 g, 3.93 mmol, 78% yield) as pale brown liquid. LCMS m/z (ESI): 509.3 $[M-H]^-$ Step 3: Sulfamoylated quinazolinone intermediate was synthesized by following Procedure B—C using tert-butyl 4-[2-[6-(2-cyano-3,6-difluoro-phenoxy)-4-oxo-quinazolin-3-yl]ethyl]piperidine-1-carboxylate (0.5 g, 979.37 μmol), cesium carbonate (797.75 mg, 2.45 mmol) and [methyl (sulfamoyl)amino]ethane (270.68 mg, 1.96 mmol). The crude compound was purified by silica gel flash column chromatography with 5% methanol in dichloromethane as a eluent to afford tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate (180 mg, 242.32 μmol, 25% yield) as pale brown solid. LCMS m/z (ESI): 529.3 $[M+H-CO_2{}^tBu]^+$ Step 4: The requisite amine was synthesized by following Procedure B-D using tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate (180 mg, 286.30 μmol) and TFA (592.00 mg, 5.19 mmol, 0.4 mL). The resulted crude compound was triturated with methyl t-butyl ether to afford 6-[2-cyano-3-[[ethyl(methyl)sulfamoyl]amino]-6-fluoro-phenoxy]-4-oxo-3-[2-(4-piperidyl)ethyl]quinazoline (200 mg, crude) as pale brown semisolid. LCMS m/z (ESI): 529.2 $[M+H]^+$ Step 5: Title compound was prepared via HATU mediated acid-amine coupling reaction (Procedure B-E). Amide coupling was carried out using 6-[2-cyano-3-[[ethyl(methyl)sulfamoyl]amino]-6-fluoro-phenoxy]-4-oxo-3-[2-(4-piperidyl)ethyl]quinazoline (20 mg, 37.84 μmol), HATU (17.26 mg, 45.40 μmol) and N,N-diisopropylethylamine (24.45 mg, 189.18 μmol, 32.95 μL) and 2-[4-[3-(2,6-dioxo-3-piperidyl)-1-methyl-indazol-6-yl]-1-piperidyl]acetic acid (14.55 mg, 37.84 μmol) to afford the title compound as crude product. Crude product was purified again by Prep HPLC purification (method: 10 mM ammonium acetate:acetonitrile; Column: BRIDGE C8(19×150)MM, 5MIC) and pure fractions were lyophilized to afford 6-[2-cyano-3-[[ethyl(methyl)sulfamoyl]amino]-6-fluoro-phenoxy]-3-[2-[1-[2-[4-[3-(2,6-dioxo-3-piperidyl)-1-methyl-indazol-6-yl]-1-piperidyl]acetyl]-4-piperidyl]ethyl]-4-oxo-quinazoline (6.93 mg, 7.65 μmol, 20% yield) as an off-white solid. LCMS m/z (ESI): 895.30 $[M+H]^+$; $^1$H NMR (400 MHz, DMSO-$d_6$): δ=10.90 (s, 1H), 8.39 (s, 1H), 7.76 (d, J=8.80 Hz, 1H), 7.65-7.64 (m, 2H), 7.43 (s, 1H), 7.34 (s, 2H), 7.05 (d, J=8.00 Hz, 1H), 4.36-4.32 (m, 2H), 4.32-3.98 (m, 6H), 3.10-2.90 (m, 6H), 2.67 (s, 3H), 2.67-2.60 (m, 6H), 2.25-2.10 (m, 2H), 2.05-1.85 (m, 4H), 1.84-1.70 (m, 3H), 1.70-1.45 (m, 5H), 1.25-1.10 (m, 1H), 1.03 (t, J=6.80 Hz, 3H).

Example 145

6-[2-cyano-3-[[ethyl(methyl)sulfamoyl]amino]-6-fluorophenoxy]-3-[3-[1-[2-[4-[3-(2,6-dioxopiperidin-3-yl)-1-methylindazol-6-yl]piperidin-1-yl]acetyl]piperidin-4-yl]propyl]-4-oxoquinazoline

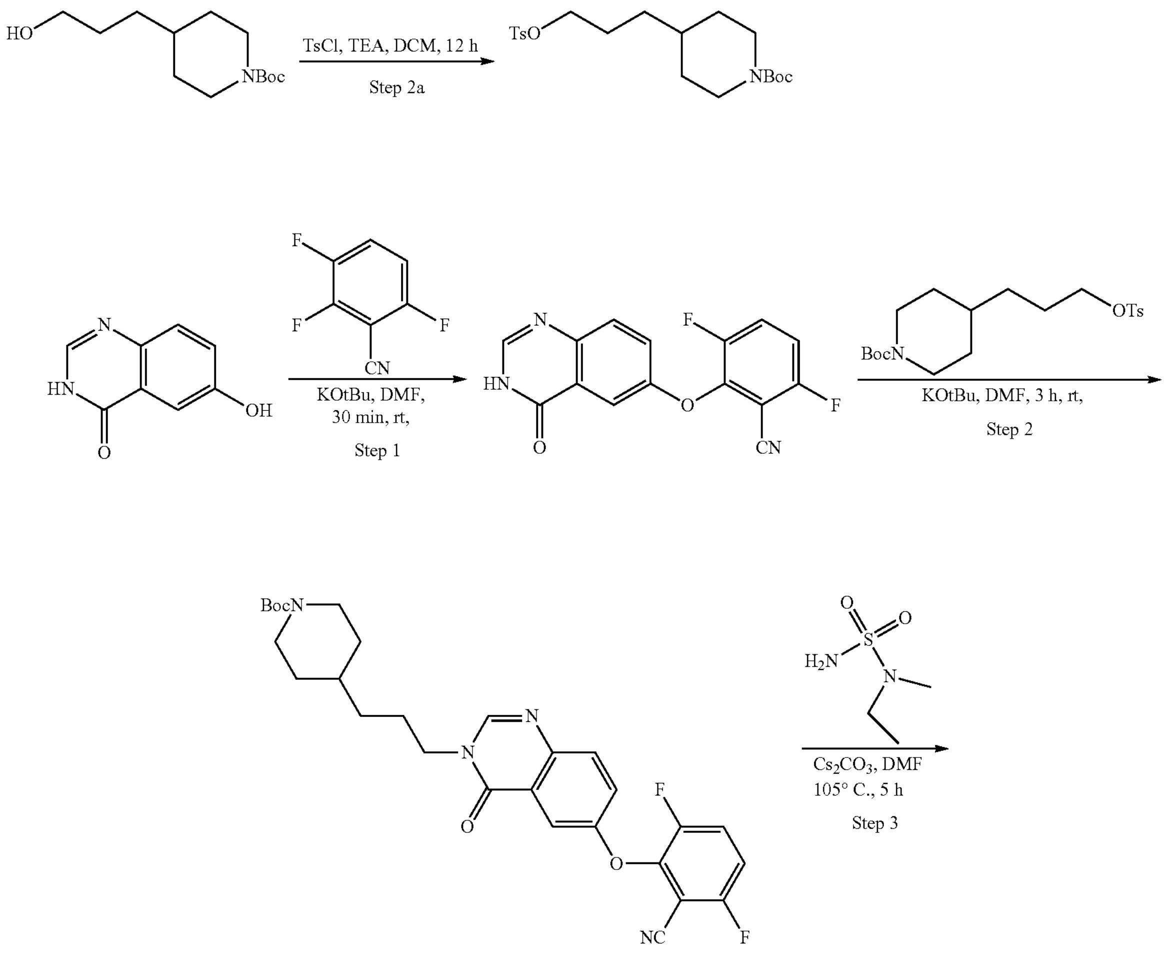

-continued

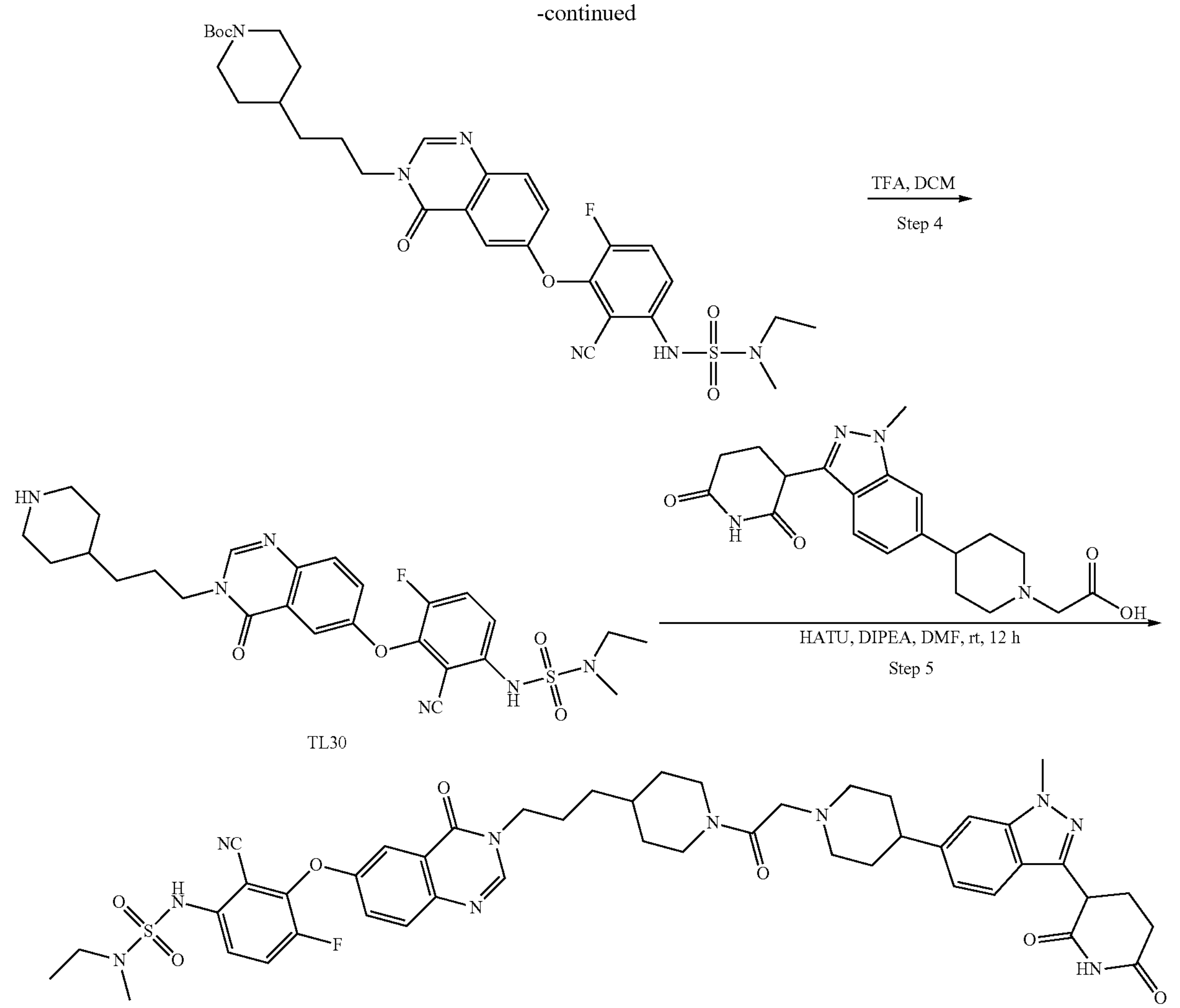

Step 1—O-arylated quinazolinone intermediate was synthesized by following Procedure B—B using 6-hydroxy-3H-quinazolin-4-one (5 g, 30.84 mmol), potassium tert-butoxide (3.81 g, 33.92 mmol) and 2,3,6-trifluorobenzonitrile (5.33 g, 33.92 mmol, 3.92 mL) to obtain compound 3,6-difluoro-2-[(4-oxo-3H-quinazolin-6-yl)oxy]benzonitrile (6.8 g, 22.21 mmol, 72% yield) as off-white solid. LCMS m/z (ESI): 300.2 $[M+H]^+$ Step 2a: To a stirred solution of 4-(3-hydroxypropyl) piperidine-1-carboxylate (2.5 g, 10.27 mmol) in dichloromethane (15 mL) was added Triethylamine (2.60 g, 25.68 mmol, 3.58 mL) at 0° C. followed by p-Toluene sulfonyl chloride (2.15 g, 11.30 mmol) at the same temperature and the resulting reaction mixture was warmed to room temperature for 12 h. After completion of the reaction the reaction mixture was diluted with water (50 mL) and extracted with ethyl acetate (2×70 mL). The combined organic layers were dried over sodium sulfate, filtered, and concentrated under reduced pressure to afford crude product. The crude compound was purified by silica gel flash column chromatography with 15% ethyl acetate in petroleum ether as eluent to afford tert-butyl 4-[3-(p-tolylsulfonyloxy)propyl]piperidine-1-carboxylate (2.2 g, 5.42 mmol, 53% yield) as an off-white solid. LCMS m/z (ESI): 298.30 $[M+H-CO_2{}^tBu]^+$ Step 2: To a stirred solution of 3,6-difluoro-2-[(4-oxo-3H-quinazolin-6-yl)oxy]benzonitrile (1.5 g, 5.01 mmol) in N,N-dimethylformamide (20 mL) was added potassium tert-butoxide (618.75 mg, 5.51 mmol) at room temperature followed by tert-butyl 4-[3-(p-tolylsulfonyloxy)propyl]piperidine-1-carboxylate (2.19 g, 5.51 mmol) and the resulting reaction mixture was stirred for 3 h at room temperature. After completion of the reaction the reaction mixture was diluted with water (50 mL) and extracted with ethyl acetate (2×100 mL). The combined organic layers were dried over sodium sulfate, filtered, and concentrated under reduced pressure to afford crude. The crude compound was purified by silica gel flash column chromatography with 5% methanol in dichloromethane as a eluent to afford tert-butyl 4-[3-[6-(2-cyano-3,6-difluoro-phenoxy)-4-oxo-quinazolin-3-yl]propyl]piperidine-1-carboxylate (2.4 g, 3.66 mmol, 73% yield) as pale brown liquid. LCMS m/z (ESI): 523.3 $[M-H]^-$ Step 3: Sulfamoylated quinazolinone intermediate was synthesized by following Procedure B—C using tert-butyl 4-[3-[6-(2-cyano-3,6-difluoro-phenoxy)-4-oxo-quinazolin-3-yl]propyl]piperidine-1-carboxylate (700 mg, 1.33 mmol), cesium carbonate (1.09 g, 3.34 mmol) and [methyl(sulfamoyl)amino]ethane (368.81 mg, 2.67 mmol). The crude compound was purified by silica gel flash column chromatography with 5% methanol in dichloromethane as a eluent to afford tert-butyl 4-[3-[6-[2-cyano-3-[[ethyl(methyl)sulfamoyl]amino]-6-fluoro-phenoxy]-4-oxo-quinazolin-3-yl]propyl]piperidine-1-carboxylate (260 mg, 355.98 μmol, 27% yield) as pale brown solid. LCMS m/z (ESI): 641.3 $[M-H]^-$ Step 4: The requisite amine was synthesized by following Procedure B-D using tert-butyl 4-[3-[6-[2-cyano-3-[[ethyl(methyl)sulfamoyl]amino]-6-fluoro-phenoxy]-4-oxo-quinazolin-3-yl]propyl]piperidine-1-carboxylate (260 mg, 404.52 μmol) and TFA (740.00 mg, 6.49 mmol, 0.5 mL). The resulted crude compound was triturated with methyl t-butyl ether to afford 6-[2-cyano-3-[[ethyl(methyl)sulfamoyl]amino]-6-fluoro-phenoxy]-4-oxo-3-[3-(4-piperidyl)propyl]quinazoline (280 mg, crude) as pale brown semi-solid. LCMS m/z (ESI): 543.3 $[M+H]^+$ Step 5: Target compound was prepared via HATU mediated acid-amine coupling reaction (Procedure B-E). Amide coupling was carried out using 6-[2-cyano-3-[[ethyl(methyl)sulfamoyl]amino]-6-fluoro-phenoxy]-4-oxo-3-[3-(4-piperidyl)propyl]quinazoline (20 mg, 30.46 μmol), 2-[4-[3-(2,6-dioxo-3-piperidyl)-1-methyl-indazol-6-yl]-1-piperidyl]acetic acid (13 mg, 30.89 μmol), N,N-diisopropylethylamine (371.00 mg, 2.87 mmol, 0.50 mL) and HATU (14 mg, 36.82 μmol) to afford the title compound as crude product. Crude product was purified by Prep HPLC purification method: 10 mM ammonium acetate:acetonitrile. Pure fractions were lyophilized to afford 6-[2-cyano-3-[[ethyl(methyl)sulfamoyl]amino]-6-fluoro-phenoxy]-3-[3-[1-[2-[4-[3-(2,6-dioxo-3-piperidyl)-1-methyl-indazol-6-yl]-1-piperidyl]acetyl]-4-piperidyl]propyl]-4-oxo-quinazoline (13.90 mg, 15.22 μmol, 50% yield) as an off-white solid. LCMS m/z (ESI): 909.20 $[M+H]^+$; $^1$H-NMR (400 MHz, DMSO-$d_6$): δ=10.90 (s, 1H), 9.73 (bs, 1H), 8.37 (s, 1H), 7.76 (d, J=8.92 Hz, 1H), 7.66-7.63 (m, 2H), 7.53 (t, J=9.76 Hz, 1H), 7.43 (s, 1H), 7.34 (dd, J=6.92, 8.00 Hz, 2H), 7.05 (d, J=8.44 Hz, 1H), 4.36-4.32 (m, 2H), 3.98-3.93 (m, 5H), 3.82-3.79 (m, 3H), 3.04 (q, J=7.20 Hz, 2H), 2.98-2.81 (m, 1H), 2.75-2.70 (m, 3H), 2.68-2.67 (m, 2H), 2.57 (s, 3H), 2.56-2.50 (m, 2H), 2.37-2.33 (m, 1H), 2.19-2.14 (m, 1H), 2.10-1.90 (m, 5H), 1.75-1.65 (m, 4H), 1.55-1.45 (m, 1H), 1.26-1.23 (m, 2H), 1.10-1.07 (m, 1H), 1.03 (t, J=7.16 Hz, 3H).

Example 146

6-[2-cyano-3-[[ethyl(methyl)sulfamoyl]amino]-6-fluorophenoxy]-3-[1-[1-[2-[4-[3-(2,6-dioxopiperidin-3-yl)-1-methylindazol-6-yl]piperidin-1-yl]acetyl]piperidin-4-yl]pyrazol-4-yl]-4-oxoquinazoline

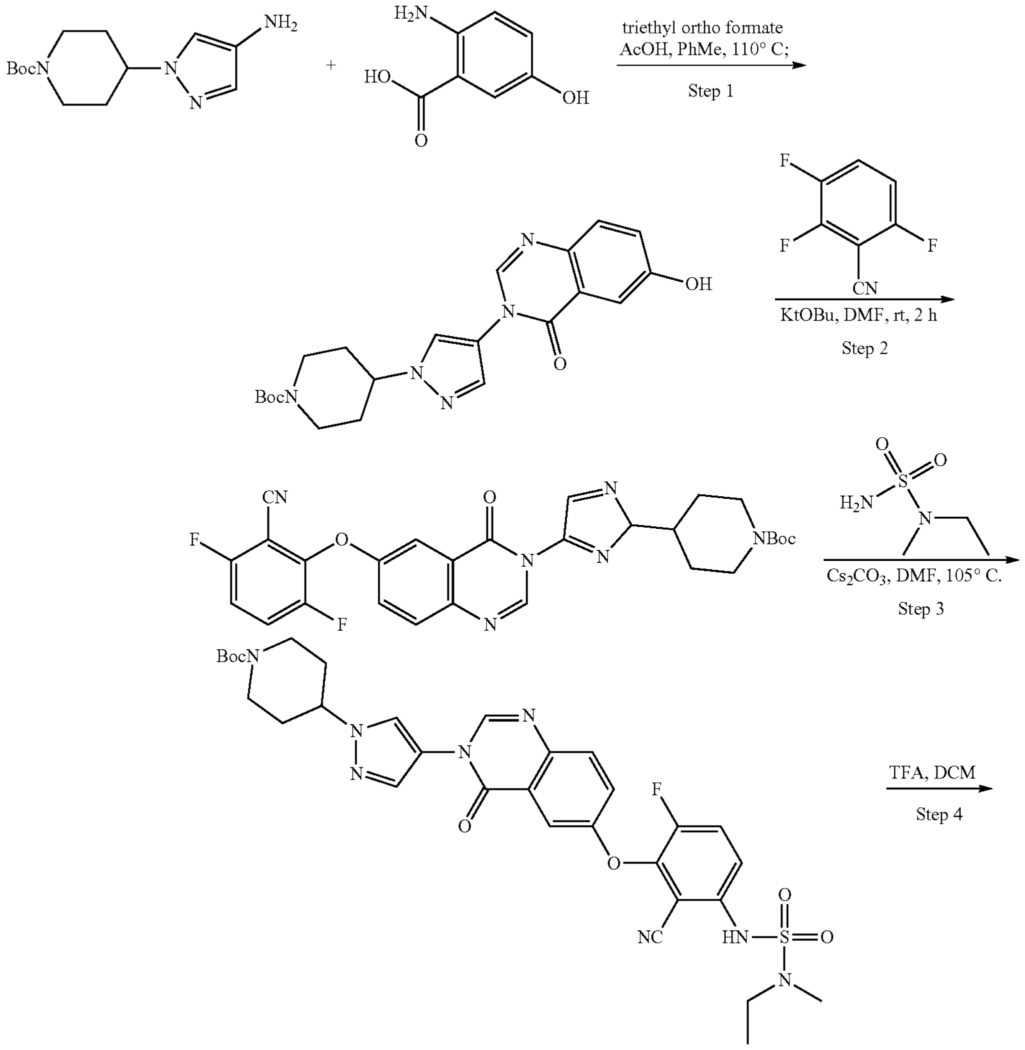

-continued

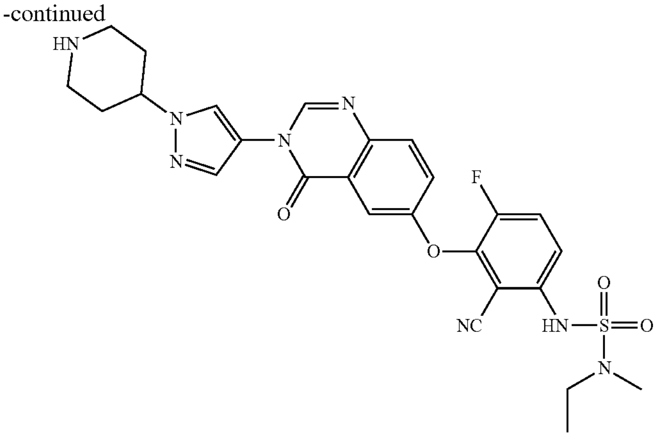

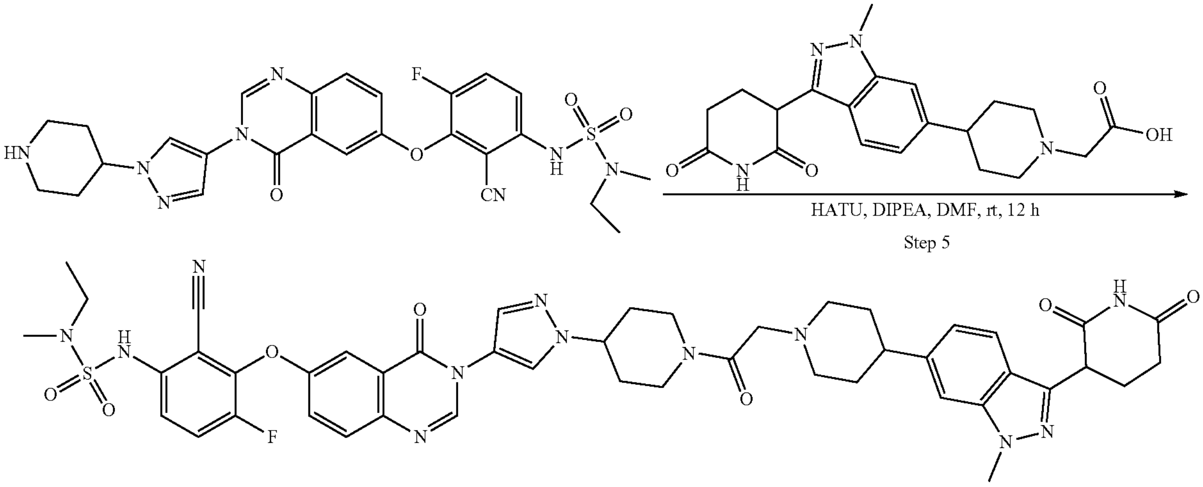

Step 1: The quinazolinone intermediate was synthesized by following general procedure for cyclization (Procedure B-A) using 2-amino-5-hydroxy-benzoic acid (1.5 g, 9.80 mmol), Triethyl orthoformate (2.18 g, 14.69 mmol, 2.44 mL) and tert-butyl 4-(4-aminopyrazol-1-yl)piperidine-1-carboxylate (2.61 g, 9.80 mmol). The desired compound was purified by silica gel flash column chromatography using 3% methanol in dichloromethane as eluent to afford tert-butyl 4-[4-(6-hydroxy-4-oxo-quinazolin-3-yl)pyrazol-1-yl]piperidine-1-carboxylate (1.2 g, 2.53 mmol, 26% yield) as a brown solid. LCMS m/z (ESI): 409.9 $[M+H]^+$ Step 2: The O-arylated quinazolinone intermediate was synthesized by following the general procedure (Procedure B—B) using tert-butyl 4-[4-(6-hydroxy-4-oxo-quinazolin-3-yl)pyrazol-1-yl]piperidine-1-carboxylate (700 mg, 1.70 mmol), potassium tert-butoxide (210.00 mg, 1.87 mmol) and 2,3,6-trifluorobenzonitrile (293.99 mg, 1.87 mmol, 216.17 μL) to obtain tert-butyl 4-[4-[6-(2-cyano-3,6-difluoro-phenoxy)-4-oxo-quinazolin-3-yl]pyrazol-1-yl]piperidine-1-carboxylate (0.8 g, crude) as an brown solid. LCMS m/z (ESI): 547.2 $[M+H]^+$ Step 3: Sulfamoylated quinazolinone intermediate was synthesized by following the general procedure (Procedure B—C) using tert-butyl 4-[4-[6-(2-cyano-3,6-difluoro-phenoxy)-4-oxo-quinazolin-3-yl]pyrazol-1-yl]piperidine-1-carboxylate (300 mg, 546.91 μmol), cesium carbonate (445.48 mg, 1.37 mmol) and [methyl(sulfamoyl)amino]ethane (151.15 mg, 1.09 mmol). Crude product purified by silica gel flash column chromatography using 5% methanol in dichloromethane as eluent to afford tert-butyl 4-[4-[6-[2-cyano-3-[[ethyl(methyl)sulfamoyl]amino]-6-fluoro-phenoxy]-4-oxo-quinazolin-3-yl]pyrazol-1-yl]piperidine-1-carboxylate (120 mg, 173.70 μmol, 32% yield) as a pale brown solid. LCMS m/z (ESI): 665.1 $[M-H]^+$ Step 4: The requisite amine was synthesized following general procedure (Procedure B-D) using tert-butyl 4-[4-[6-[2-cyano-3-[[ethyl(methyl)sulfamoyl]amino]-6-fluoro-phenoxy]-4-oxo-quinazolin-3-yl]pyrazol-1-yl]piperidine-1-carboxylate (120 mg, 179.99 μmol) and TFA (20.52 mg, 179.99 μmol, 13.87 μL). The resulted crude compound was triturated with methyl t-butyl ether to afford the TFA salt of 6-[2-cyano-3-[[ethyl(methyl)sulfamoyl]amino]-6-fluoro-phenoxy]-4-oxo-3-[1-(4-piperidyl)pyrazol-4-yl]quinazoline (150 mg, crude) as a pale brown semi-solid. LCMS m/z (ESI): $[M-H]^+$ 565.20

Step 5: The target compound was prepared via HATU mediated acid-amine coupling reaction (Procedure B-E). The amide coupling was carried out using 6-[2-cyano-3-[[ethyl(methyl)sulfamoyl]amino]-6-fluoro-phenoxy]-4-oxo-3-[1-(4-piperidyl)pyrazol-4-yl]quinazoline (20 mg, 35.30 μmol), 2-[4-[3-(2,6-dioxo-3-piperidyl)-1-methyl-indazol-6-yl]-1-piperidyl]acetic acid (13 mg, 30.89 μmol), N,N-diisopropylethylamine (371.00 mg, 2.87 mmol, 0.50 mL) and HATU (14 mg, 36.82 μmol) to afford the title compound as crude product. The crude material was purified by Prep HPLC purification method: 10 mM Ammonium acetate: acetonitrile. Pure fractions were lyophilized to afford product 6-[2-cyano-3-[[ethyl(methyl)sulfamoyl]amino]-6-fluoro-phenoxy]-3-[1-[1-[2-[4-[3-(2,6-dioxo-3-piperidyl)-1-methyl-indazol-6-yl]-1-piperidyl]acetyl]-4-piperidyl]pyrazol-4-yl]-4-oxo-quinazoline (9.60 mg, 10.24 μmol, 35% yield) as an off-white solid. LCMS m/z (ESI): 933.20[M+H]$^+$; $^1$H-NMR (400 MHz, DMSO-$d_6$): δ=10.90 (s, 1H), 9.89 (bs, 1H), 8.46 (s, 1H), 8.34 (s, 1H), 7.90 (s, 1H), 7.82 (d, J=8.80 Hz, 1H), 7.67 (dd, J=8.40, 13.00 Hz, 1H), 7.59 (t, J=10.00 Hz, 1H), 7.43 (d, J=3.20 Hz, 2H), 7.38-7.34 (m, 1H), 7.06 (d, J=8.80 Hz, 2H), 4.57-4.50 (m, 1H), 4.41 (d, J=43.60 Hz, 1H), 4.35-4.32 (m, 1H), 4.15-4.00 (m, 2H), 3.98 (s, 3H), 3.06 (q, J=7.20 Hz, 2H), 2.88-2.85 (m, 3H), 2.76-2.68 (m, 3H), 2.65 (s, 3H), 2.64-2.61 (m, 2H), 2.37-2.33 (m, 1H), 2.19-2.11 (m, 4H), 2.08-2.00 (m, 5H), 1.96-1.76 (m, 2H), 1.03 (t, J=7.20 Hz, 3H).

Example 147

6-[2-cyano-3-[[ethyl(methyl)sulfamoyl]amino]-6-fluorophenoxy]-3-[7-[2-[4-[3-(2,4-dioxo-1,3-diazinan-1-yl)-1-methylindazol-6-yl]piperidin-1-yl]acetyl]-7-azaspiro[3.5]nonan-2-yl]-4-oxoquinazoline

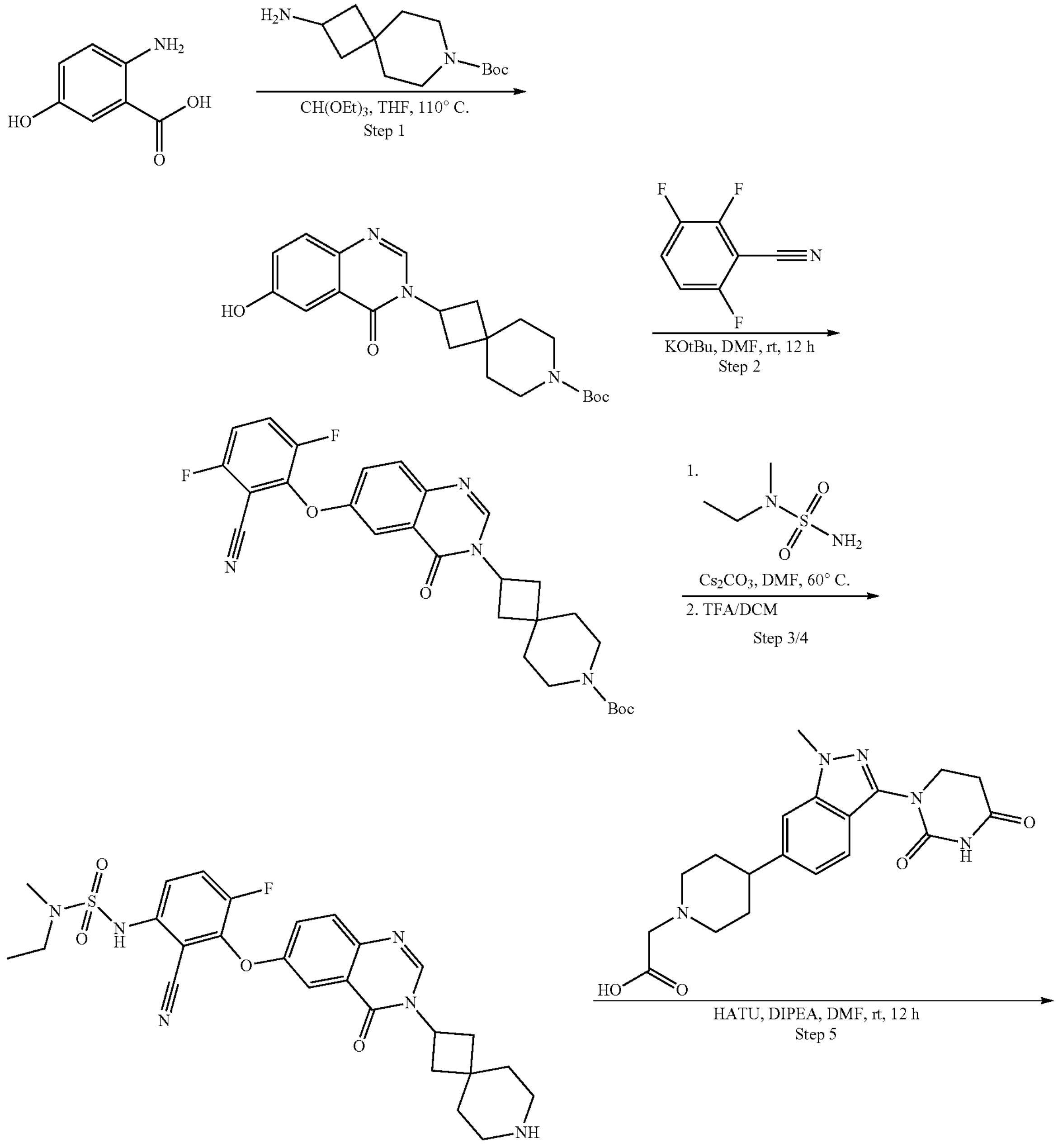

-continued

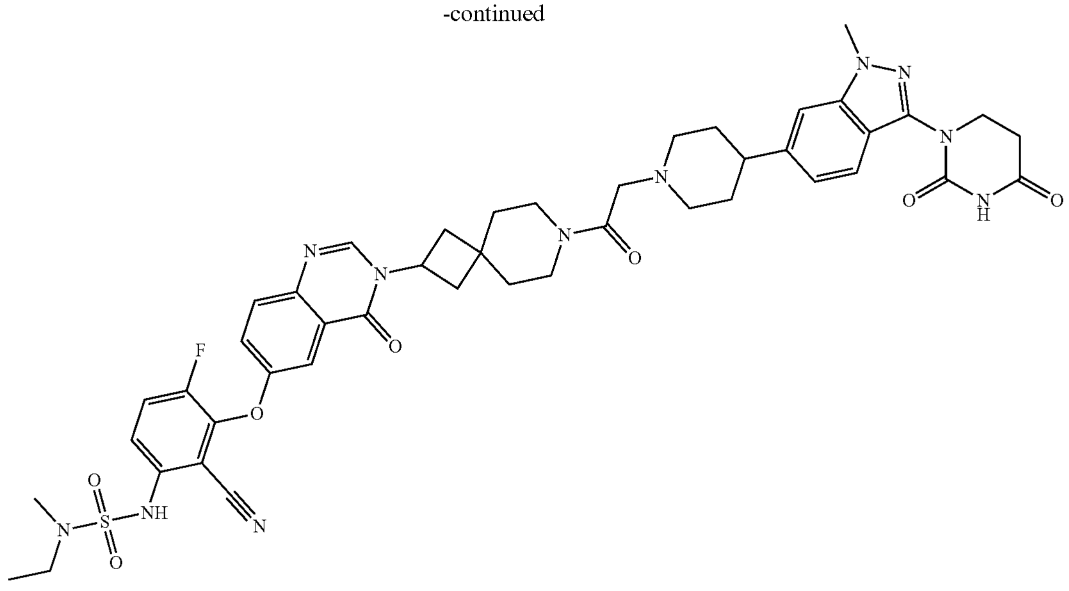

Step 1: Quinazolinone intermediate was synthesized by following general procedure for cyclization (Procedure B-A) using 2-amino-5-hydroxy-benzoic acid (3.50 g, 22.88 mmol), Triethyl orthoformate (3.70 g, 24.96 mmol, 4.15 mL) and tert-butyl 2-amino-7-azaspiro[3.5]nonane-7-carboxylate (5 g, 20.80 mmol). The desired compound was purified by silica gel flash column chromatography using 80% ethyl acetate in petroleum ether as eluent to afford tert-butyl 2-(6-hydroxy-4-oxo-quinazolin-3-yl)-7-azaspiro[3.5]nonane-7-carboxylate (4.5 g, 11.39 mmol, 55% yield) as an off-white solid. LCMS m/z (ESI): 386.0 $[M+H]^+$.

Step 2: O-arylated quinazolinone intermediate was synthesized by following general procedure for O-arylation (Procedure B—B) using tert-butyl 2-(6-hydroxy-4-oxo-quinazolin-3-yl)-7-azaspiro[3.5]nonane-7-carboxylate (4.5 g, 11.67 mmol), potassium tertiary butoxide (1.57 g, 14.01 mmol) and 2,3,6-trifluorobenzonitrile (2.02 g, 12.84 mmol, 1.48 mL). The desired compound was purified from crude by silica gel flash column chromatography using 80% ethyl acetate in petroleum ether as eluent to afford tert-butyl 2-[6-(2-cyano-3,6-difluoro-phenoxy)-4-oxo-quinazolin-3-yl]-7-azaspiro[3.5]nonane-7-carboxylate (6.0 g, 11.01 mmol, 94% yield) as a semisolid. LCMS m/z (ESI): 523.2 $[M+H]^+$.

Step 3: Sulfamoylated quinazolinone intermediate was synthesized by following Procedure B—C using tert-butyl 2-[6-(2-cyano-3,6-difluoro-phenoxy)-4-oxo-quinazolin-3-yl]-7-azaspiro[3.5]nonane-7-carboxylate (3.0 g, 5.74 mmol), cesium carbonate (5.61 g, 17.22 mmol) and [methyl(sulfamoyl)amino]ethane (1.59 g, 11.48 mmol). After completion, the reaction mixture was diluted with water (20 ml), and the resulting solid was filtered off. The filtrate was extracted with ethyl acetate (2×60 ml), and the separated organic layer was dried over sodium sulfate, filtered and concentrated under reduced pressure to afford tert-butyl 2-[6-[2-cyano-3-[[ethyl(methyl)sulfamoyl]amino]-6-fluoro-phenoxy]-4-oxo-quinazolin-3-yl]-7-azaspiro[3.5]nonane-7-carboxylate (2.2 g, 3.23 mmol, 56% yield) as an off-white solid. LCMS m/z (ESI): 641.2 $[M+H]^+$.

Step 4: The requisite amine was synthesized by Trifluoroacetic acid mediated N-Boc deprotection (Procedure B-D). N-Boc deprotection was done on tert-butyl 2-[6-[2-cyano-3-[[ethyl(methyl)sulfamoyl]amino]-6-fluoro-phenoxy]-4-oxo-quinazolin-3-yl]-7-azaspiro[3.5]nonane-7-carboxylate (2.2 g, 3.43 mmol) using Trifluoroacetic acid, 99% (3.92 g, 34.34 mmol, 2.65 mL) to afford 3-(7-azaspiro[3.5]nonan-2-yl)-6-[2-cyano-3-[[ethyl(methyl)sulfamoyl]amino]-6-fluoro-phenoxy]-4-oxo-quinazoline (2.1 g, 3.13 mmol, 91% yield) as a liquid gum. LCMS m/z (ESI): 539.0 $[M+H]^+$.

Step 5: Target compound was prepared via HATU mediated acid-amine coupling reaction (Procedure B-E). Amide coupling was carried out using 2-[4-[3-(2,4-dioxohexahydropyrimidin-1-yl)-1-methyl-indazol-6-yl]-1-piperidyl]acetic acid (161.11 mg, 381.89 μmol), 3-(7-azaspiro[3.5]nonan-2-yl)-6-[2-cyano-3-[[ethyl(methyl)sulfamoyl]amino]-6-fluoro-phenoxy]-4-oxo-quinazoline (0.25 g, 381.89 μmol), N,N-diisopropylethylamine (246.79 mg, 1.91 mmol, 332.60 μL) and HATU (217.81 mg, 572.84 μmol). The crude compound was purified by reverse phase column chromatography eluted with 45% acetonitrile in 0.1% formic acid to afford 6-[2-cyano-3-[[ethyl(methyl)sulfamoyl]amino]-6-fluoro-phenoxy]-3-[7-[2-[4-[3-(2,4-dioxohexahydropyrimidin-1-yl)-1-methyl-indazol-6-yl]-1-piperidyl]acetyl]-7-azaspiro[3.5]nonan-2-yl]-4-oxo-quinazoline (194 mg, 213.29 μmol, 56% yield) as an off-white solid. LCMS m/z (ESI): 908.3$[M+H]^+$. $^1$H-NMR (400 MHz, DMSO-$d_6$): δ=10.56 (s, 1H), 9.81 (bs, 1H), 8.41 (s, 1H), 7.78 (d, J=8.80 Hz, 1H), 7.66-7.63 (m, 3H), 7.45 (d, J=8.00 Hz, 1H), 7.35 (d, J=2.80 Hz, 2H), 7.06 (d, J=8.40 Hz, 1H), 4.98 (d, J=8.40 Hz, 1H), 3.99 (s, 3H), 3.92 (t, J=6.40 Hz, 3H), 3.53-3.43 (m, 5H), 3.05 (q, J=7.20 Hz, 2H), 2.76 (t, J=6.80 Hz, 5H), 2.67 (s, 3H), 2.35-2.33 (m, 5H), 1.96-1.77 (m, 5H), 1.77-1.61 (m, 4H), 1.04 (t, J=7.20 Hz, 3H).

Example 148
3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-1-methylindazol-6-yl]piperidin-1-yl]acetyl]-1-oxa-8-azaspiro[4.5]decane
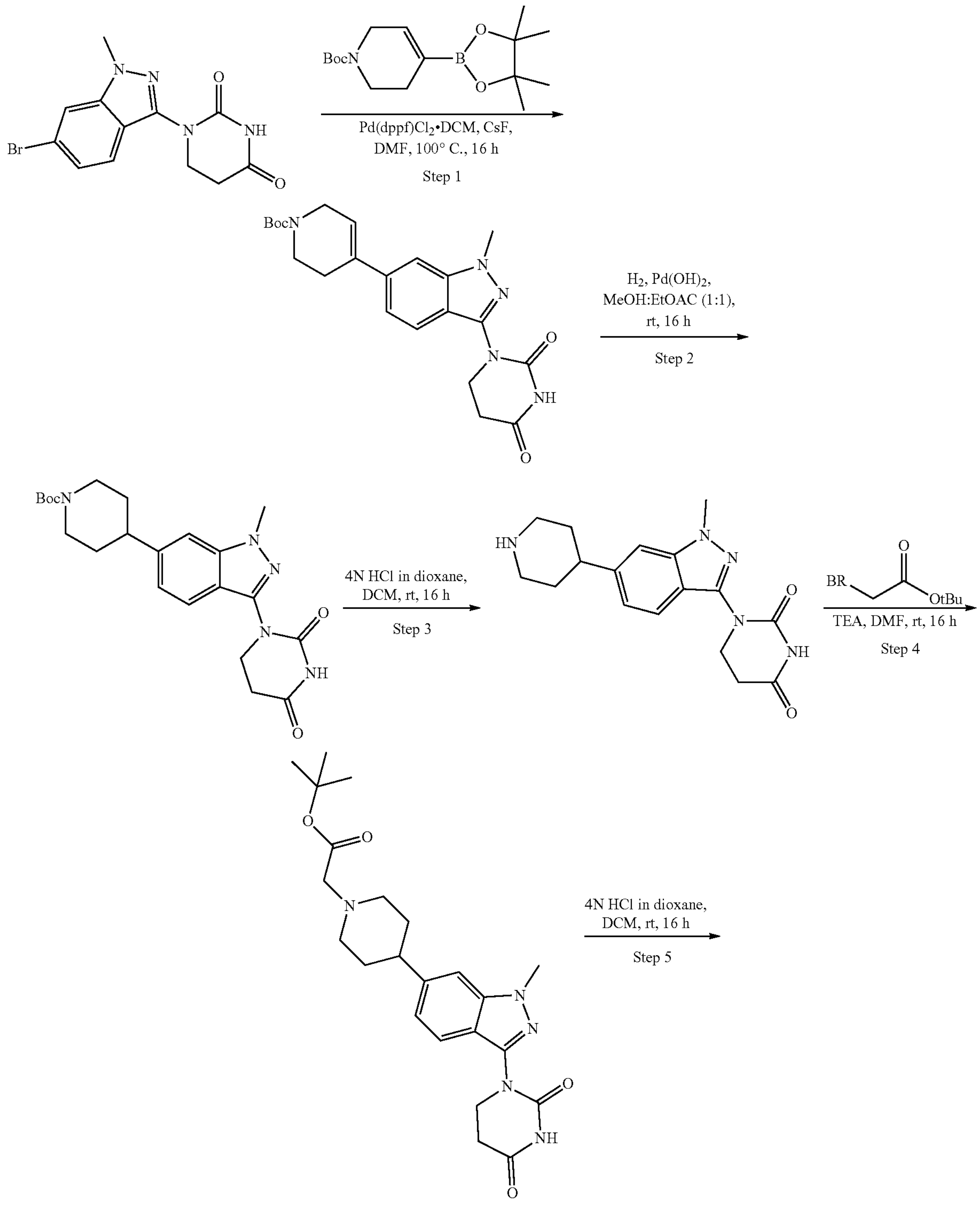

-continued

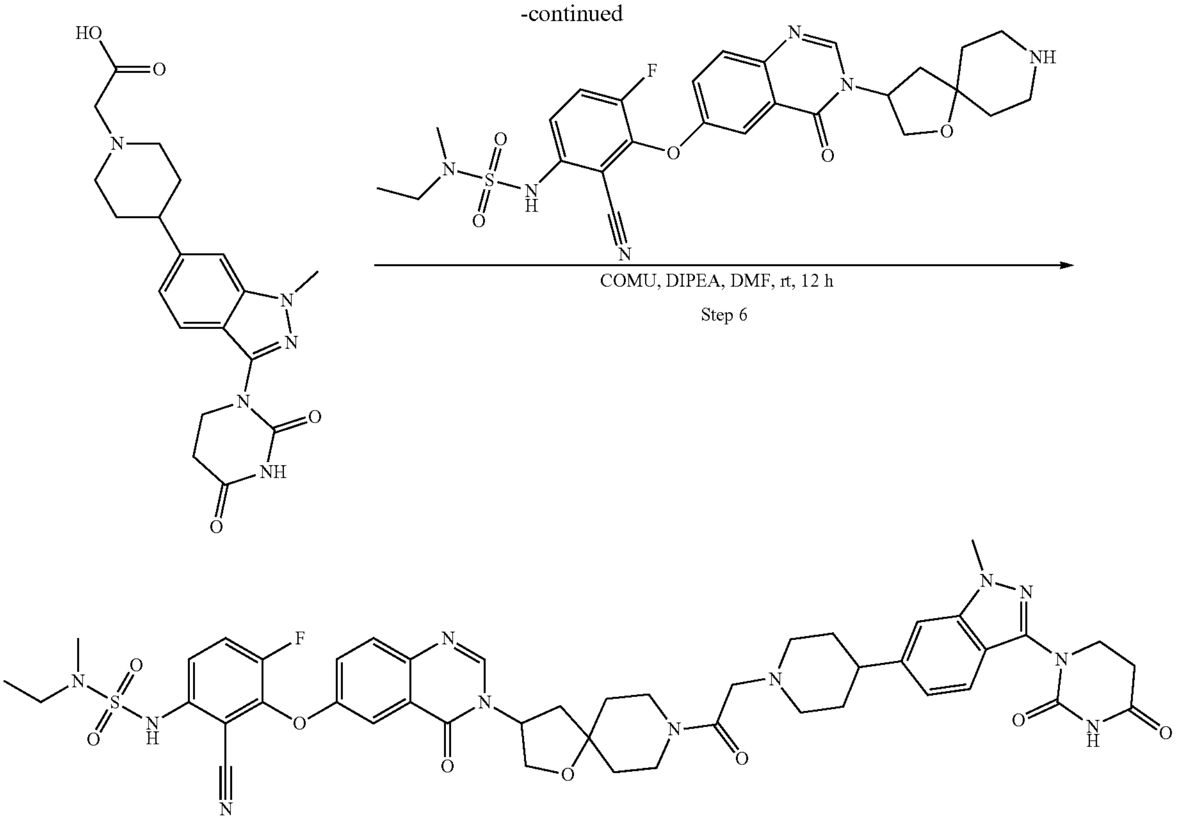

Step 1: To a solution of 1-(6-bromo-1-methyl-indazol-3-yl)hexahydropyri midine-2,4-dione (1.5 g, 4.64 mmol) in N,N-Dimethylformamide (20 mL) in a sealed tube, were added tert-butyl 4-(4,4,5,5-tetramethyl-1,3,2-dioxaborolan-2-yl)-3,6-dihydro-2H-pyridine-1l-carboxylate (2.87 g, 9.28 mmol) and cesium fluoride (1.41 g, 9.28 mmol, 342.28 μL). The reaction mixture was degassed with nitrogen gas for 10 mins and before adding [1,1'-Bis(diphenylphosphino)ferrocene]dichloropalladium (II), complex with dichloromethane (758.11 mg, 928.38 μmol). The reaction mixture was stirred at 100° C. for 16 h. After completion, the reaction mixture was diluted with water (70 mL) and extracted with ethyl acetate (3×100 mL). Combined organic layers were washed with cold water (3×70 mL), dried over sodium sulfate, filtered and concentrated. The crude mixture was purified by column chromatography (silica gel) using 70-80% ethyl acetate in pet ether as eluent to afford tert-butyl 4-[3-(2,4-dioxohexahydropyrimidin-1-yl)-1-methyl-indazol-6-yl]-3,6-dihydro-2H-pyridine-1-carboxylate (1.85 g, 3.24 mmol, 70% yield) as an off-white solid. LCMS m/z (ESI): 426.3 $[M+H]^+$.

Step 2: To a solution of tert-butyl 4-[3-(2,4-dioxohexahydropyrimidin-1-yl)-1-methyl-indazol-6-yl]-3,6-dihydro-2H-pyridine-1-carboxylate (1.85 g, 4.35 mmol) in methanol (20 mL) and ethyl acetate (20 mL), was added dihydroxypalladium (3.5 g, 24.92 mmol), saturated with hydrogen by bubbling hydrogen gas for 10 min. The contents were subjected to hydrogenation (1 atm) at room temperature for 16 h. After completion, the reaction mixture was filtered through a pad of celite and washed with methanol (200 mL). The filtrate was concentrated under reduced pressure to afford tert-butyl 4-[3-(2,4-dioxohexahydropyrimidin-1-yl)-1-methyl-indazol-6-yl]piperidine-1-carboxylate (1.5 g, 2.47 mmol, 57% yield) as an off-white solid. LCMS m/z (ESI): 321.8 $[M-Boc+H]^+$.

Step 3: To a solution of tert-butyl 4-[3-(2,4-dioxohexahydropyrimidin-1-yl)-1-methyl-indazol-6-yl]piperidine-1-carboxylate (1.5 g, 3.51 mmol) in dichloromethane (20 mL), was added hydrogen chloride solution (4.0 M in dioxane, 15 mL) at 0° C. The reaction mixture was stirred at room temperature for 16 h. After completion, the reaction mixture was concentrated under reduced pressure to afford 1-[1-methyl-6-(4-piperidyl) indazol-3-yl]hexahydropyrimidine-2,4-dione (1.45 g, 3.99 mmol) as an off-white solid, which was carried forward without further purification. $^1H$ NMR (400 MHz, DMSO-$d_6$): δ=10.57 (s, 1H), 8.77 (s, 1H), 7.61 (d, J=11.20 Hz, 1H), 7.40 (s, 1H), 7.03 (d, J=11.20 Hz, 1H), 3.98 (s, 3H), 3.91 (t, J=8.80 Hz, 2H), 3.03 (d, J=14.40 Hz, 3H), 2.76 (t, J=9.20 Hz, 2H), 2.44-2.32 (m, 3H), 1.98-1.87 (m, 3H).

Step 4: To a solution of 1-[1-methyl-6-(4-piperidyl)indazol-3-yl]hexahydropyrimidine-2,4-dione (1.45 g, 3.99 mmol) in N,N-Dimethylformamide (20 mL) and Triethylamine (2.02 g, 19.93 mmol, 2.78 mL), was added tert-butyl 2-bromoacetate (1.17 g, 5.98 mmol, 876.70 μL) at room temperature. The reaction mixture was stirred at room temperature for 16 h under nitrogen atmosphere. After completion, the reaction mixture was poured into ice cold water (50 mL) and extracted with ethyl acetate (3×70 mL). The organic layers were washed with cold water (3×30 mL), dried over sodium sulfate, filtered and concentrated under reduced pressure to afford tert-butyl 2-[4-[3-(2,4-dioxohexahydropyrimidin-1-yl)-1-methyl-indazol-6-yl]-1-piperidyl] acetate (1.35 g, 2.99 mmol, 75% yield) as light brown solid, which was used without further purification. LCMS m/z (ESI): 442.3 $[M+H]^+$.

Step 5: To a solution of tert-butyl 2-[4-[3-(2,4-dioxohexahydropyrimidin-1-yl)-1-methyl-indazol-6-yl]-1-piperidyl]

acetate (1.35 g, 3.06 mmol) in dichloromethane (15 mL), was added hydrogen chloride solution (4.0M in dioxane, 14 mL) at 5° C. under nitrogen atmosphere. The reaction mixture was stirred at room temperature for 16 h. After completion, the reaction mixture was concentrated under reduced pressure to afford 2-[4-[3-(2,4-dioxohexahydropyrimidin-1-yl)-1-methyl-indazol-6-yl]-1-piperidyl]acetic acid (1.45 g, 3.44 mmol) as an off-white solid. LCMS m/z (ESI): 386.2 $[M+H]^+$.

Step 6: The title compound was prepared via COMU mediated acid-amine coupling reaction (Procedure B—F). Amide coupling was carried out using 2-[4-[3-(2,4-dioxohexahydropyrimidin-1-yl)-1-methyl-indazol-6-yl]-1-piperidyl]acetic acid (195.62 mg, 463.69 μmol), 3-[6-[2-cyano-3-[[ethyl(methyl)sulfamoyl]amino]-6-fluoro-phenoxy]-4-oxo-quinazolin-3-yl]-1-oxa-8-azaspiro [4.5]decane (0.25 g, 421.54 μmol), N,N-diisopropylethylamine (272.40 mg, 2.11 mmol, 367.12 μL) and [[(Z)-(1-cyano-2-ethoxy-2-oxo-ethylidene)amino]oxy-morpholino-methylene]-dimethyl-ammonium; hexafluorophosphate (198.58 mg, 463.69 μmol). The crude compound was purified by reverse phase column chromatography, eluting with 50% acetonitrile in 0.1% ammonium acetate in water, to afford 3-[6-[2-cyano-3-[[ethyl(methyl)sulfamoyl]amino]-6-fluoro-phenoxy]-4-oxo-quinazolin-3-yl]-8-[2-[4-[3-(2,4-dioxohexahydropyrimidin-1-yl)-1-methyl-indazol-6-yl]-1-piperidyl]acetyl]-1-oxa-8-azaspiro[4.5]decane (182 mg, 195.61 μmol, 46% yield) as pink solid. LCMS m/z (ESI): 922.3 $[M-H]^-$; $^1$H NMR (400 MHz, DMSO-$d_6$): δ=10.57 (s, 1H), 9.76 (s, 1H), 8.35 (s, 1H), 7.78 (d, J=8.80 Hz, 1H), 7.67 (dd, J=3.20, 9.00 Hz, 1H), 7.60 (d, J=8.00 Hz, 2H), 7.44 (s, 1H), 7.35 (d, J=3.20 Hz, 2H), 7.06 (d, J=8.00 Hz, 1H), 5.32 (s, 1H), 4.20-4.13 (m, 2H), 3.98 (s, 1H), 3.91 (t, J=6.80 Hz, 3H), 3.80-3.74 (m, 1H), 3.50 (s, 2H), 3.06 (d, J=7.20 Hz, 2H), 2.78-2.70 (m, 6H), 2.66 (s, 4H), 2.49-2.38 (m, 4H), 2.14-2.07 (m, 1H), 2.05-1.89 (m, 4H), 1.83-1.50 (m, 5H), 1.04 (t, J=6.80 Hz, 3H).

Example 149

6-[2-cyano-3-[[ethyl(methyl)sulfamoyl]amino]-6-fluorophenoxy]-3-[7-[2-[4-[3-(2,6-dioxopiperidin-3-yl)-1-methylindazol-6-yl]piperidin-1-yl]acetyl]-7-azaspiro[3.5]nonan-2-yl]-4-oxoquinazoline

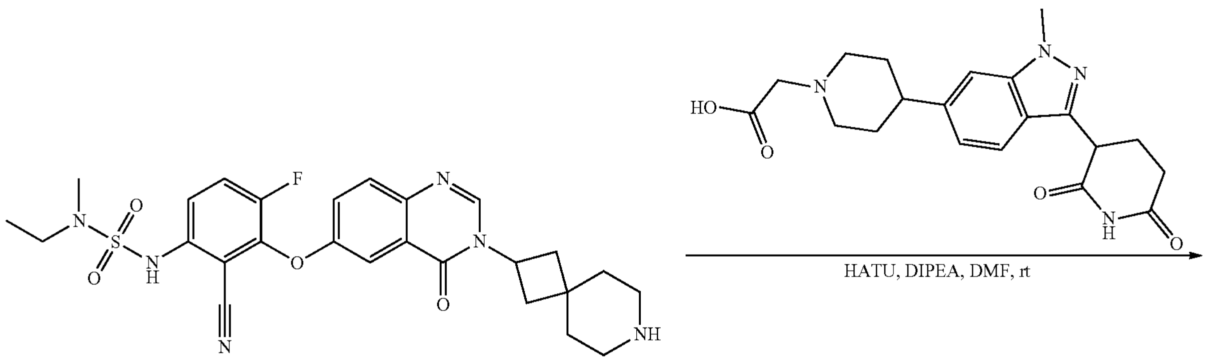

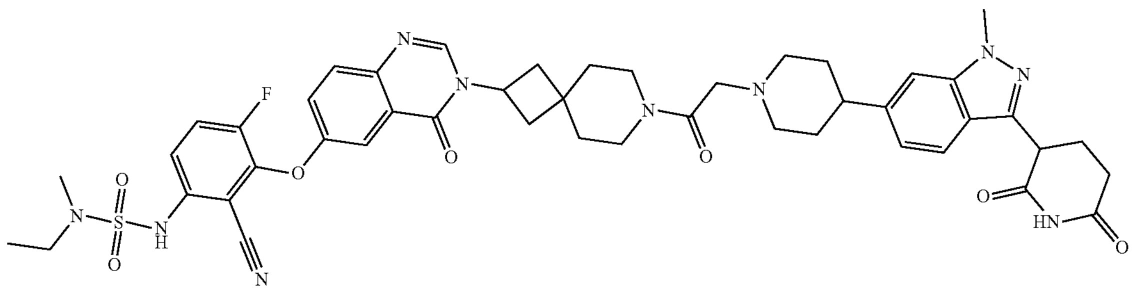

Target compound was prepared via HATU mediated acid-amine coupling reaction (Procedure B-E). Amide coupling was carried out using 3-(7-azaspiro[3.5]nonan-2-yl)-6-[2-cyano-3-[[ethyl(methyl)sulfamoyl]amino]-6-fluoro-phenoxy]-4-oxo-quinazoline (0.25 g, 433.22 μmol), 2-10 [4-[3-(2,6-dioxo-3-piperidyl)-1-methyl-indazol-6-yl]-1-piperidyl] acetic acid (182.34 mg, 433.22 μmol), HATU (215.28 mg, 563.19 μmol) and N,N-diisopropylethylamine (296.80 mg, 2.30 mmol, 0.4 mL). The resulting crude compound was purified by reverse phase column chromatography [Mobile-phase A: 0.100 Ammonium acetate in water, Mobile-phase B: acetonitrile; column: 100 g RediSep® Rf C18] to afford 6-[2-cyano-3-[[ethyl(methyl)sulfamoyl]amino]-6-fluoro-phenoxy]-3-[7-[2-[4-[3-(2,6-dioxo-3-piperidyl)-1-methyl-indazol-6-yl]-1-piperidyl]acetyl]-7-azaspiro[3.5]nonan-2-yl]-4-oxo-quinazoline (130 mg, 139.43 μmol, 32% yield) as off-white solid. LCMS m/z (ESI): 907.4 $[M+H]^+$; $^1H$ NMR (400 MHz, DMSO-$d_6$): δ=10.90 (s, 1H), 9.83 (bs, 1H), 8.41 (s, 1H), 7.77 (d, J=9.20 Hz, 1H), 7.65 (dd, J=6.00, 7.20 Hz, 2H), 7.51-7.60 (m, 1H), 7.44 (s, 1H), 7.34 (d, J=2.80 Hz, 2H), 7.06 (d, J=8.00 Hz, 1H), 4.91-5.01 (m, 1H), 4.34 (dd, J=5.20, 9.80 Hz, 1H), 3.99 (s, 3H), 3.41-3.55 (m, 4H), 3.3-3.21 (m, 1H), 3.01-3.06 (m, 2H), 2.75-2.91 (m, 1H), 2.61-2.71 (m, 6H), 2.52-2.58 (m, 2H), 2.25-2.45 (m, 5H), 2.13-2.21 (m, 2H), 1.90-2.05 (m, 4H), 1.55-1.79 (m, 5H), 1.04 (t, J=7.20 Hz, 3H).

Example 150

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]piperidin-1-yl]acetyl]-1-oxa-8-azaspiro[4.5]decane

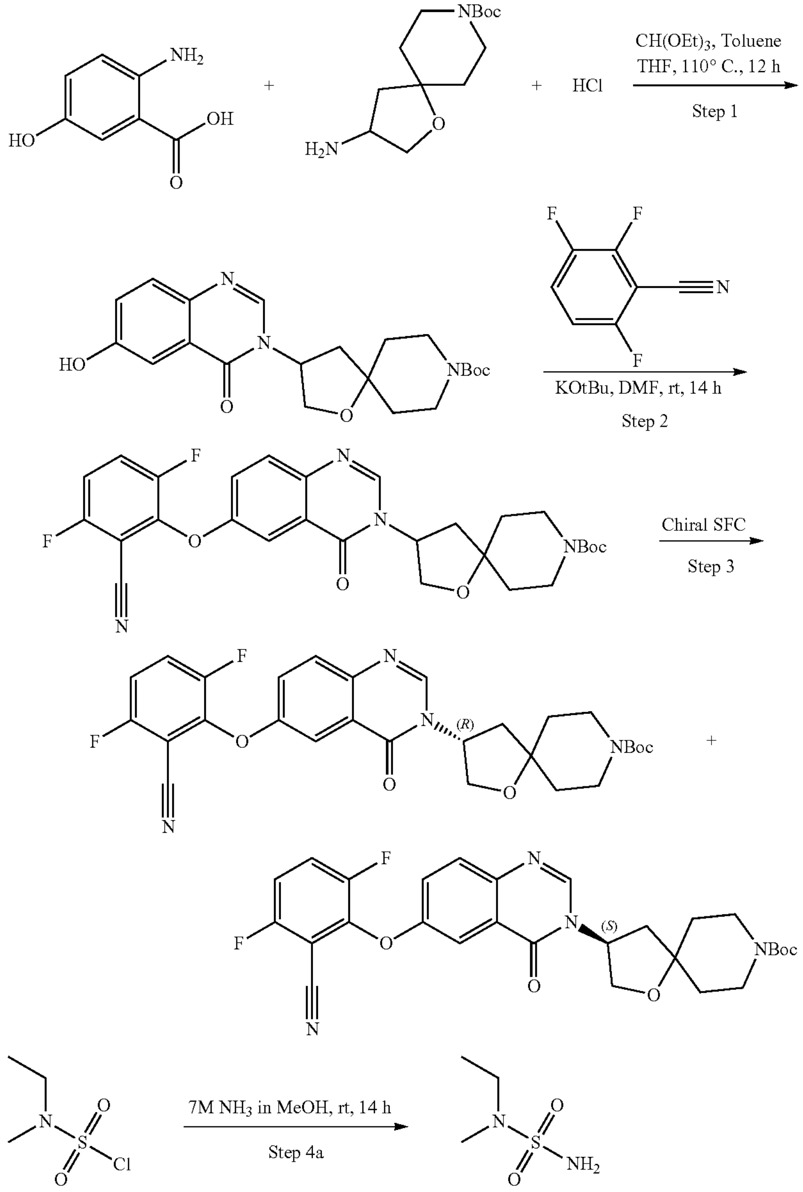

-continued

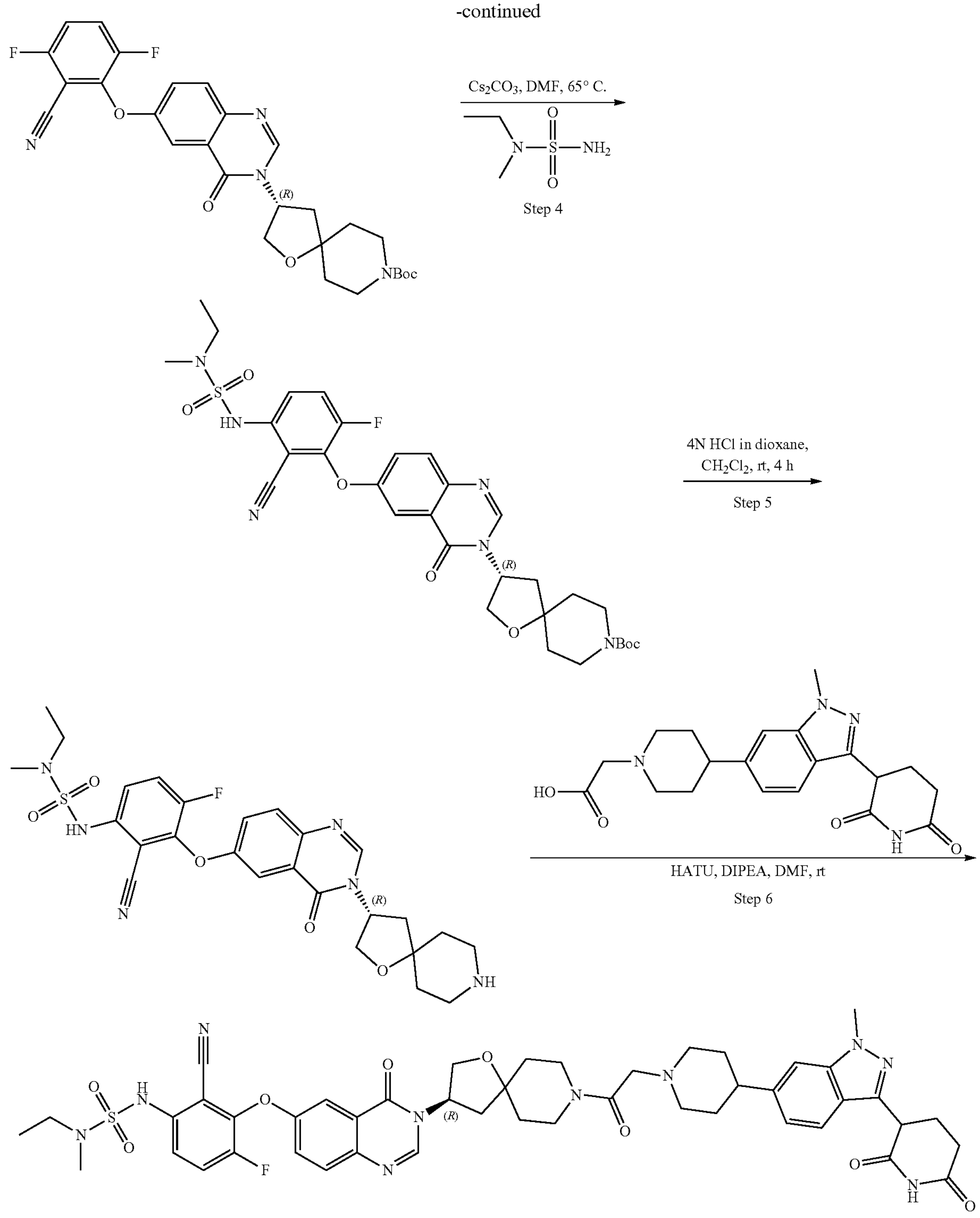

Step 1: The quinazolinone intermediate was synthesized by following the general procedure for cyclization (Procedure B-A) using tert-butyl 3-amino-1-oxa-8-azaspiro[4.5]decane-8-carboxylate·HCl (15 g, 51.23 mmol), 2-amino-5-hydroxy-benzoic acid (7.85 g, 51.23 mmol), Triethyl orthoformate (10.63 g, 71.72 mmol, 11.93 mL). The crude compound was triturated with 20% ethyl acetate in petroleum ether to afford tert-butyl 3-(6-hydroxy-4-oxo-quinazolin-3-yl)-1-oxa-8-azaspiro[4.5]decane-8-carboxylate (12.0 g, 25.29 mmol, 49% yield) as a brown solid. LCMS m/z (ESI): 402.20[M+H]$^+$ Step 2: The O-arylated quinazolinone intermediate was synthesized by following the general procedure for O-arylation (Procedure B—B) using tert-butyl 3-(6-hydroxy-4-oxo-quinazolin-3-yl)-1-oxa-8-azaspiro[4.5]decane-8-carboxylate (12.0 g, 25.11 mmol), cesium carbonate (24.54 g, 75.33 mmol) and 2,3,6-trifluorobenzonitrile (5.13 g, 32.64 mmol, 3.77 mL). The crude compound was purified by column chromatography on silica gel, eluting with 60% ethyl acetate in petroleum ether to afford tert-butyl 3-[6-(2-cyano-3,6-difluoro-phenoxy)-4-oxo-quinazolin-3-yl]-1-oxa-8-azaspiro[4.5]decane-8-carboxylate (9.0 g, 16.54 mmol, 66% yield) as off-white solid along with 1.8 g. LCMS m/z (ESI): 539.2[M+H]$^+$.

Step 3: Tert-butyl 3-[6-(2-cyano-3,6-difluoro-phenoxy)-4-oxo-quinazolin-3-yl]-1-oxa-8-azaspiro[4.5]decane-8-carboxylate (9.0 g, 16.54 mmol) was subjected for chiral SFC purification to resolute the enantiomers. The racemic intermediate was chirally resolved using chiral SFC method using Lux A1 column (250 mm×30 mm; 5 micron) eluting with 40% isopropyl alcohol/$CO_2$ with 0.5% iso-propylamine in methanol as co-solvent (Flow Rate: 4 ml/min; Outlet Pressure: 100 bar) to afford 3.5 g of first eluting isomer and 3.7 g of second eluting isomer.

The configuration of the two isomers is arbitrarily assigned as follows.

Enantiomer 1: First eluting isomer was arbitrarily assigned as tert-butyl (S)-3-(6-(2-cyano-3,6-difluoro-phenoxy)-4-oxoquinazolin-3(4H)-yl)-1-oxa-8-azaspiro[4.5]decane-8-carboxylate Enantiomer 2: Second eluting isomer was arbitrarily assigned as tert-butyl (R)-3-(6-(2-cyano-3,6-difluoro-phenoxy)-4-oxoquinazolin-3(4H)-yl)-1-oxa-8-azaspiro[4.5]decane-8-carboxylate.

Step 4a: To a solution of N-ethyl-N-methyl-sulfamoyl chloride (10 g, 63.44 mmol, 7.81 mL) in MeOH (20 mL) was added 7M ammonia in MeOH (7 M, 30 mL) at 0° C. and stirred the reaction mixture at room temperature for 14 h. The reaction mixture was concentrated under reduced pressure to afford crude product. The crude compound was diluted with water (150 mL), extracted with ethyl acetate (2×150 mL). The combined organic layers were washed with sodium bicarbonate solution (100 ml), brine (100 ml), dried over sodium sulfate and concentrated under reduced pressure to afford crude which was purified by column chromatography on silica gel, eluted with 40% ethyl acetate in petroleum ether to afford [methyl(sulfamoyl)amino]ethane (7.0 g, 48.12 mmol, 76% yield) as colorless liquid. $^1$HNMR (400 MHz, DMSO-$d_6$): δ=6.65 (s, 2H), 2.98 (q, J=7.20 Hz, 2H), 2.61 (s, 3H), 1.09 (t, J=7.20 Hz, 3H).

Step 4: The sulfamoylated quinazolinone intermediate was synthesized by following the general procedure (Procedure B—C) using tert-butyl (3R)-3-[6-(2-cyano-3,6-difluoro-phenoxy)-4-oxo-quinazolin-3-yl]-1-oxa-8-azaspiro[4.5]decane-8-carboxylate (3.7 g, 6.87 mmol), cesium carbonate (5.60 g, 17.18 mmol) and [methyl(sulfamoyl)amino]ethane (1.42 g, 10.31 mmol). The crude compound was triturated with 10% dichloromethane in petroleum ether to afford tert-butyl (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (2.8 g, 3.58 mmol, 52% yield) as off-white solid LCMS m/z (ESI): 601.0 [M+H−$^t$Bu]$^+$ Step 5: The requisite amine was synthesized by HCl mediated N-Boc deprotection (Procedure B-D). N-Boc deprotection was done on tert-butyl (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (2.7 g, 4.11 mmol) and 4M hydrogen chloride solution in 1,4-dioxane (4M, 36.68 mL). The reaction mixture was concentrated under reduced pressure to afford crude which was triturated with diethyl ether to afford the HCl salt of (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (2.7 g, 3.90 mmol, 95% yield) as a light brown solid. LCMS m/z (ESI): 557.0 [M+H]$^+$ Step 6: Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (300 mg, 404.67 μmol), 2-[4-[3-(2,6-dioxo-3-piperidyl)-1-methyl-indazol-6-yl]-1-piperidyl]acetic acid (155.57 mg, 404.67 μmol), N,N-diisopropylethylamine (209.21 mg, 1.62 mmol, 281.95 μL) and HATU (153.87 mg, 404.67 μmol). The crude compound was purified by reverse phase column chromatography, eluting with 50% acetonitrile in 0.1% ammonium acetate in water, to afford (3R)-3-[6-[2-cyano-3-[[ethyl(methyl)sulfamoyl]amino]-6-fluoro-phenoxy]-4-oxo-quinazolin-3-yl]-8-[2-[4-[3-(2,6-dioxo-3-piperidyl)-1-methyl-indazol-6-yl]-1-piperidyl]acetyl]-1-oxa-8-azaspiro[4.5]decane (102 mg, 107.04 μmol, 26% yield) as an off-white solid. LCMS m/z (ESI): 923.2 [M+H]$^+$; $^1$H NMR (400 MHz, DMSO-$d_6$): δ=10.89 (s, 1H), 9.86 (bs, 1H), 8.35 (s, 1H), 7.78 (d, J=8.80 Hz, 1H), 7.66 (dd, J=8.80, 3.20 Hz, 2H), 7.55 (s, 1H), 7.44 (bs, 1H), 7.35 (d, J=3.20 Hz, 1H), 7.06 (d, J=8.40 Hz, 1H), 5.34 (s, 1H), 4.35-4.32 (m, 1H), 4.18-4.13 (m, 2H), 3.98 (d, J=2.00 Hz, 3H), 3.81-3.72 (m, 2H), 3.51 (bs, 2H), 3.47-3.36 (m, 3H), 3.05 (d, J=7.60 Hz, 3H), 2.83-2.79 (m, 1H), 2.68-2.61 (m, 6H), 2.51-2.46 (m, 2H), 2.30-2.14 (m, 3H), 2.10-1.90 (m, 4H), 1.86-1.62 (m, 4H), 1.60-1.52 (m, 1H), 1.04 (t, J=7.20 Hz, 3H).

Example 151

(3R)-3-[6-[2-cyano-3-[[ethyl(methyl)sulfamoyl]amino]-6-fluorophenoxy]-4-oxoquinazolin-3-yl]-8-[2-[1-[3-(2,6-dioxopiperidin-3-yl)-1-methylindazol-6-yl]piperidin-4-yl]acetyl]-1-oxa-8-azaspiro[4.5]decane

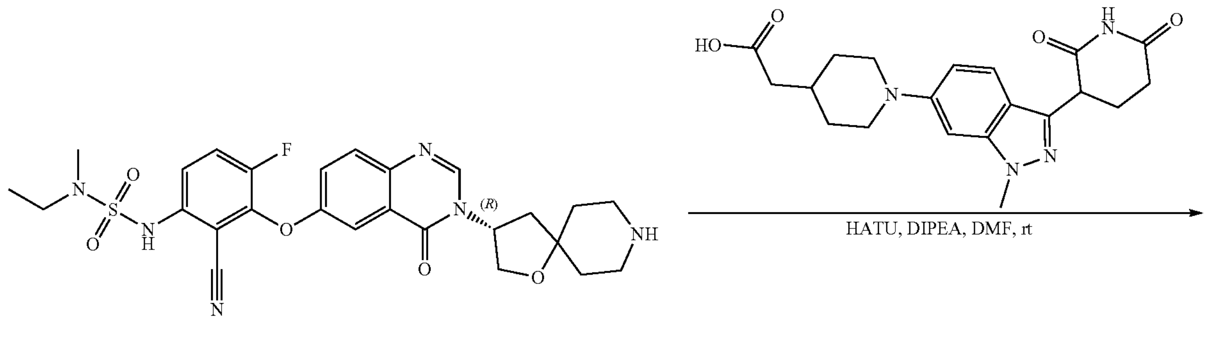

-continued

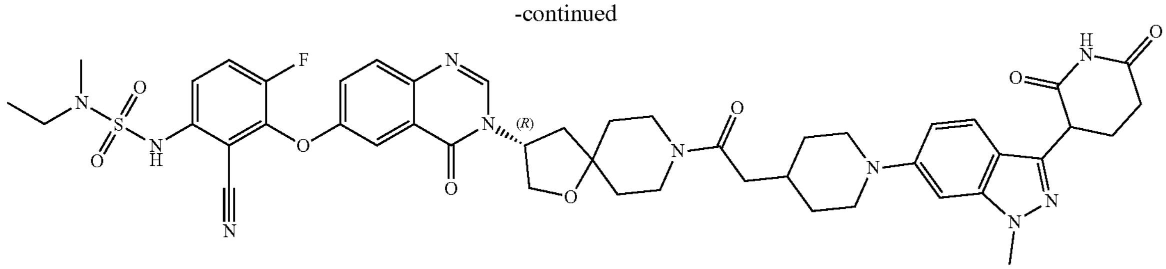

Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (170 mg, 286.64 μmol), 2-[1-[3-(2,6-dioxo-3-piperidyl)-1-methyl-indazol-6-yl]-4-piperidyl]acetic acid (120.65 mg, 286.64 μmol), N,N-diisopropylethylamine (148.18 mg, 1.15 mmol, 199.71 μL) and HATU (108.99 mg, 286.64 μmol). The crude compound was purified by reverse phase column chromatography, eluting with 50% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[1-[3-(2,6-dioxo-3-piperidyl)-1-methyl-indazol-6-yl]-4-piperidyl]acetyl]-1-oxa-8-azaspiro[4.5]decane (68 mg, 68.42 μmol, 24% yield) as off-white solid. LCMS m/z (ESI): 923.2 $[M+H]^+$; $^1$H NMR (400 MHz, DMSO-$d_6$): δ=10.86 (s, 1H), 10.20 (s, 1H), 8.36 (s, 1H), 7.92-7.81 (m, 1H), 7.80 (d, J=9.20 Hz, 1H), 7.70 (dd, J=9.00, 3.20 Hz, 1H), 7.47 (d, J=9.20 Hz, 2H), 7.36 (d, J=2.80 Hz, 1H), 6.90 (d, J=8.40 Hz, 1H), 6.83 (s, 1H), 5.35-5.29 (m, 1H), 4.25 (dd, J=9.40, 5.20 Hz, 1H), 4.17-4.10 (m, 2H), 3.88 (m, 3H), 3.79-3.70 (m, 3H), 3.51-3.49 (m, 1H), 3.35-3.40 (m, 2H), 3.18-3.13 (m, 2H), 2.78 (s, 3H), 2.73 (s, 1H), 2.70-2.51 (m, 2H), 2.60-2.54 (m, 1H), 2.34-2.28 (m, 3H), 2.18-2.15 (m, 1H), 2.08-2.05 (m, 1H), 1.89 (s, 1H), 1.80-1.64 (m, 7H), 1.35-1.24 (m, 2H), 1.05 (t, J=7.20 Hz, 3H).

Example 152

(3R)-3-[6-[2-cyano-3-[[ethyl(methyl)sulfamoyl]amino]-6-fluorophenoxy]-4-oxoquinazolin-3-yl]-8-[2-[1-[3-(2,6-dioxopiperidin-3-yl)-1-methylindazol-6-yl]-4-hydroxypiperidin-4-yl]acetyl]-1-oxa-8-azaspiro[4.5]decane

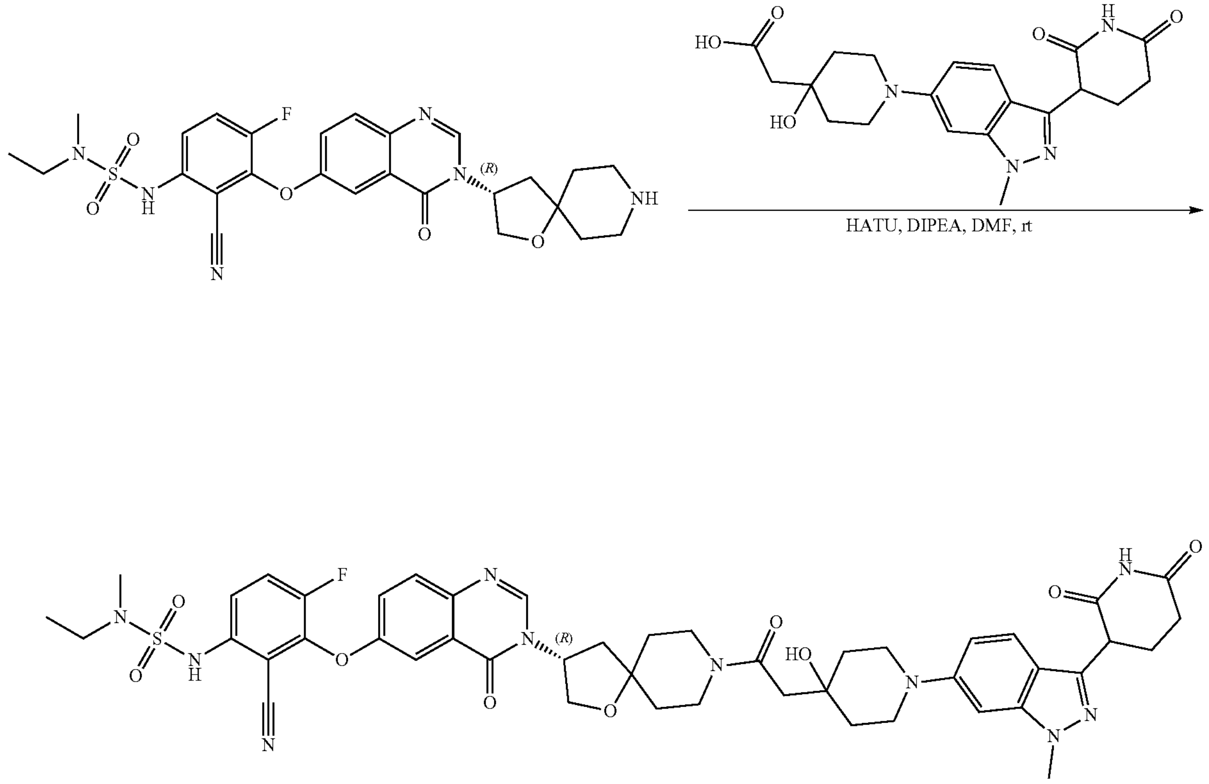

Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (180 mg, 292.88 μmol), 2-[1-[3-(2,6-dioxo-3-piperidyl)-1-methyl-indazol-6-yl]-4-hydroxy-4-piperidyl]acetic acid (127.96 mg, 292.88 μmol), N,N-diisopropylethylamine (151.41 mg, 1.17 mmol, 204.06 μL) and HATU (122.50 mg, 322.17 μmol). The crude compound was purified by reverse phase column chromatography, eluting with 43% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[1-[3-(2,6-dioxo-3-piperidyl)-1-methyl-indazol-6-yl]-4-hydroxy-4-piperidyl]acetyl]-1-oxa-8-azaspiro[4.5]decane (101 mg, 100.59 μmol, 34% yield) as an off-white solid. LCMS m/z (ESI): 939.2 $[M+H]^+$; $^1H$ NMR (400 MHz, DMSO-$d_6$): δ 20=10.85 (s, 1H), 10.19 (s, 1H), 8.36 (s, 1H), 7.87 (bs, 1H), 7.80 (d, J=8.80 Hz, 1H), 7.70 (dd, J=9.00, 2.80 Hz, 1H), 7.51 (d, J=3.60 Hz, 1H), 7.47 (d, J=9.20 Hz, 1H), 7.37 (d, J=3.20 Hz, 1H), 6.91 (d, J=9.20 Hz, 1H), 6.85 (s, 1H), 5.47-5.29 (m, 1H), 5.02 (s, 1H), 4.32-4.25 (m, 1H), 4.30-4.20 (m, 2H), 3.89 (s, 2H), 3.85-3.74 (m, 1H), 3.72-3.61 (m, 1H), 3.50 (d, J=11.60 Hz, 3H), 3.28-3.16 (m, 4H), 2.79 (s, 3H), 2.63-2.56 (m, 4H), 2.40-2.28 (m, 4H), 2.19-2.10 (m, 2H), 2.09-2.01 (m, 1H), 1.76-1.68 (m, 7H), 1.06 (t, J=7.20 Hz, 3H).

Example 153

6-[2-cyano-3-[[ethyl(methyl)sulfamoyl]amino]-6-fluorophenoxy]-3-[(3S)-8-[2-[4-[3-(2,6-dioxopiperidin-3-yl)-1-methylindazol-6-yl]piperidin-1-yl]acetyl]-8-azaspiro[4.5]decan-3-yl]-4-oxoquinazoline

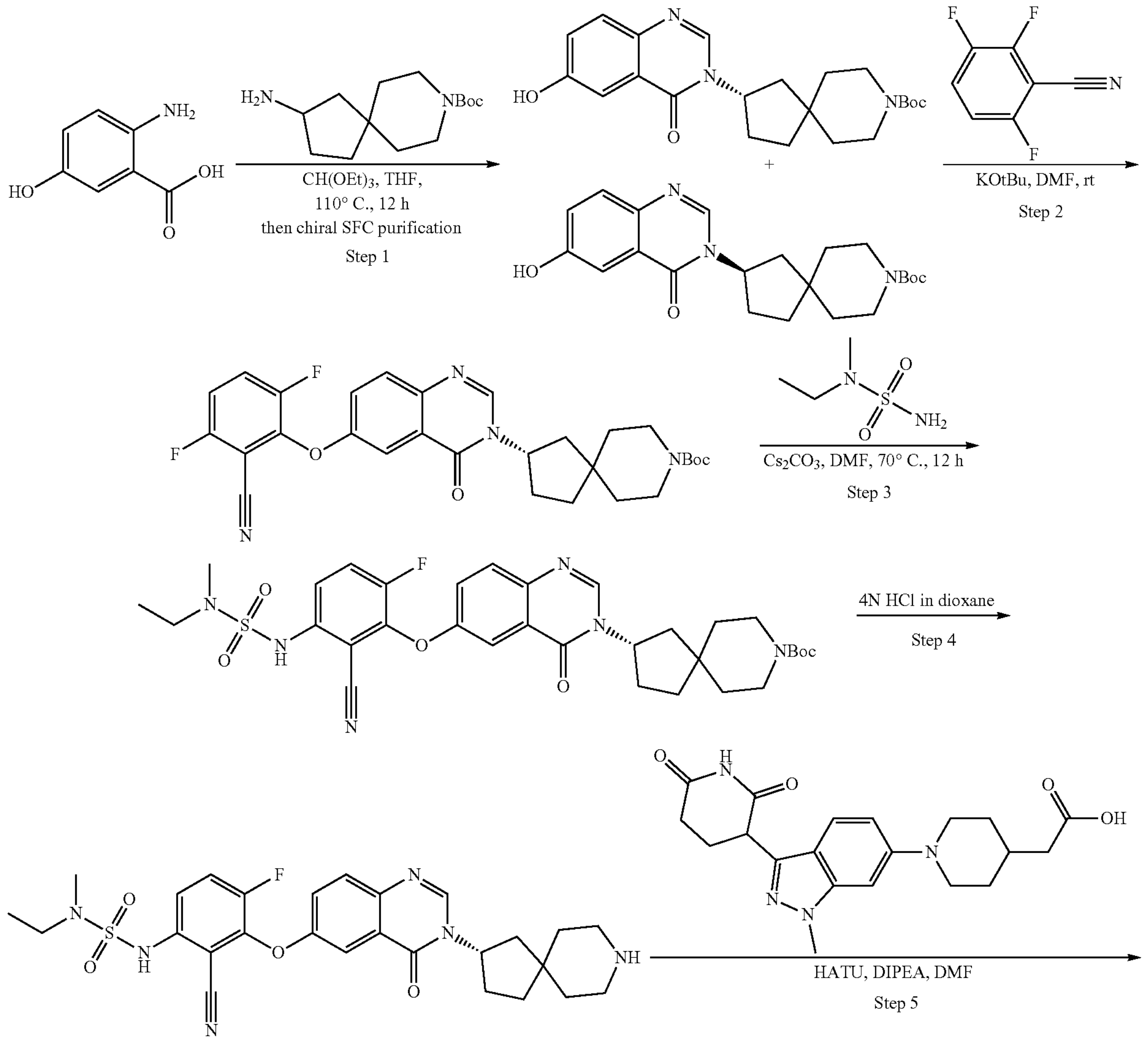

-continued

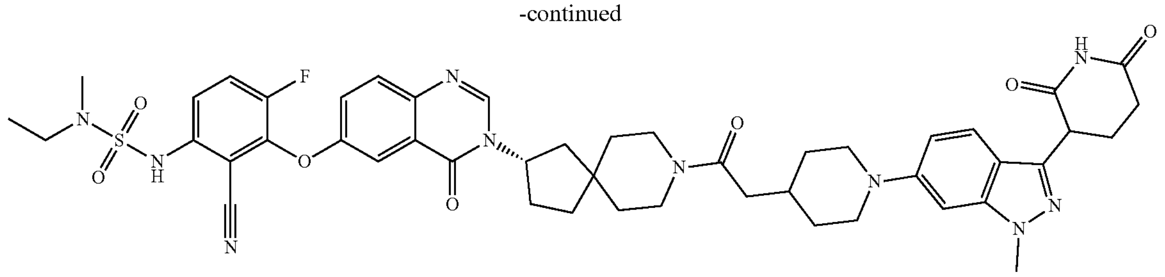

Step 1: Quinazolinone intermediate was synthesized by following general procedure for cyclization (Procedure B-A) using tert-butyl 3-amino-8-azaspiro[4.5]decane-8-carboxylate (5.0 g, 19.66 mmol), 2-amino-5-hydroxy-benzoic acid (3.01 g, 19.66 mmol), triethyl orthoformate (7.28 g, 49.14 mmol, 8.17 mL) and acetic acid (118.04 mg, 1.97 mmol, 112.42 μL). The crude compound was purified by silica gel flash column chromatography with ethyl acetate in petroleum ether to afford tert-butyl 3-(6-hydroxy-4-oxo-quinazolin-3-yl)-8-azaspiro[4.5]decane-8-carboxylate (5.6 g, 13.72 mmol, 70% yield) as a brown solid. The racemic cyclization compound was chirally resolved using chiral SFC purification. 3.0 g of racemic cyclized compound was submitted for SFC Purification using Chiralcel OX—H column (Flowrate: 3 ml/min, Co-Solvent: 30% methanol, Outlet Pressure: 100 bar, Temperature: 35° C.). After SFC purification, 1.3 g of first eluting isomer (Enantiomer 1) and 1.3 g of Second eluting isomer (Enantiomer 2) was obtained. Stereochemistry of the first eluting isomer was arbitrarily assigned as S-enantiomer and second eluting isomer was arbitrarily assigned as R-enantiomer. LCMS m/z (ESI): 400.2 $[M+H]^+$ The configuration of the two isomers is arbitrarily assigned as follows.

Enantiomer 1: First eluting isomer was arbitrarily assigned as tert-butyl 3-[(3S)-6-hydroxy-4-oxo-quinazolin-3-yl]-8-azaspiro[4.5]decane-8-carboxylate Enantiomer 2: Second eluting isomer was arbitrarily assigned as tert-butyl 3-[(3R)-6-hydroxy-4-oxo-quinazolin-3-yl]-8-azaspiro[4.5]decane-8-carboxylate Step 2: O-arylated quinazolinone intermediate was synthesized by following general procedure for O-arylation (Procedure B—B) using tert-butyl 3-[(3S)-6-hydroxy-4-oxo-quinazolin-3-yl]-8-azaspiro[4.5]decane-8-carboxylate (1.30 g, 3.25 mmol), potassium tert-butoxide (730.32 mg, 6.51 mmol) and 2,3,6-trifluorobenzonitrile (511.21 mg, 3.25 mmol, 375.89 μL). Crude compound was purified by silica gel flash column chromatography, eluting with 60% ethyl acetate in petroleum ether as eluent, to afford tert-butyl (3 S)-3-[6-(2-cyano-3,6-difluoro-phenoxy)-4-oxo-quinazolin-3-yl]-8-azaspiro[4.5]decane-8-carboxylate (1.2 g, 1.71 mmol, 53% yield) as an off-white solid. LCMS m/z (ESI): 481.1 $[M+H-{}^tBu]^+$ Step 3: Sulfamoylated quinazolinone intermediate was synthesized by following Procedure B—C using tert-butyl (3S)-3-[6-(2-cyano-3,6-difluoro-phenoxy)-4-oxo-quinazolin-3-yl]-8-azaspiro[4.5]decane-8-carboxylate (1.20 g, 2.24 mmol), cesium carbonate (1.82 g, 5.59 mmol) and [methyl (sulfamoyl)amino]ethane (618.10 mg, 4.47 mmol) to afford tert-butyl (3S)-3-[6-[2-cyano-3-[[ethyl(methyl)sulfamoyl] amino]-6-fluoro-phenoxy]-4-oxo-quinazolin-3-yl]-8-azaspiro[4.5]decane-8-carboxylate (960.0 mg, 1.01 mmol, 45% yield) as colorless liquid. LCMS m/z (ESI): 653.2 $[M-H]^-$ Step 4: The requisite amine was synthesized by HCl mediated N-Boc deprotection (Procedure B-D). N-Boc deprotection was done on tert-butyl (3S)-3-[6-[2-cyano-3-[[ethyl(methyl)sulfamoyl]amino]-6-fluoro-phenoxy]-4-oxo-quinazolin-3-yl]-8-azaspiro[4.5]decane-8-carboxylate (400.00 mg, 610.92 μmol) using hydrogen chloride solution in dioxane (4M, 3.0 mL). The residue obtained was triturated with diethyl ether (2×10 mL) and dried under reduced pressure to afford 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (360.0 mg, 542.20 μmol, 89% yield) as yellow solid. LCMS m/z (ESI): 555.2 $[M+H]^+$ Step 5: The title compound was prepared via HATU mediated acid-amine coupling reaction (Procedure B-E). Amide coupling was carried out using 3-[(3S)-8-azaspiro[4.5]decan-3-yl]-6-[2-cyano-3-[[ethyl(methyl)sulfamoyl] amino]-6-fluoro-phenoxy]-4-oxo-quinazoline (100 mg, 156.86 μmol), 2-[4-[3-(2,6-dioxo-3-piperidyl)-1-methyl-indazol-6-yl]-1-piperidyl]acetic acid (60.30 mg, 156.86 μmol), N,N-diisopropylethylamine (81.09 mg, 627.44 μmol, 109.29 μL) and HATU (59.64 mg, 156.86 μmol). The crude compound was purified by reverse phase column chromatography, eluting with 50% acetonitrile in 0.1% formic acid in water, to afford 6-[2-cyano-3-[[ethyl(methyl)sulfamoyl] amino]-6-fluoro-phenoxy]-3-[(3S)-8-[2-[4-[3-(2,6-dioxo-3-piperidyl)-1-methyl-indazol-6-yl]-1-piperidyl]acetyl]-8-azaspiro[4.5]decan-3-yl]-4-oxo-quinazoline (40 mg, 40.08 μmol, 26% yield) as ash solid. LCMS m/z (ESI): 921.2 $[M+H]^+$; $^1H$ NMR (400 MHz, DMSO-$d_6$): δ=10.89 (s, 1H), 9.89 (s, 1H), 8.44 (d, J=3.20 Hz, 1H), 7.78 (d, J=8.80 Hz, 1H), 7.66 (dd, J=9.00, 3.20 Hz, 1H), 7.44 (s, 1H), 7.40-7.38 (m, 1H), 7.36 (d, J=2.80 Hz, 1H), 7.07 (d, J=8.00 Hz, 1H), 5.12-5.01 (m, 1H), 4.35 (dd, J=5.20, 10.00 Hz, 1H), 3.99 (s, 4H), 3.69-3.55 (m, 1H), 3.44-3.32 (m, 5H), 3.10-3.08 (m, 3H), 2.93-2.80 (m, 2H), 2.71-2.52 (m, 6H), 2.43-2.31 (m, 2H), 2.16-1.99 (m, 9H), 1.86-1.83 (m, 3H), 1.66-1.57 (m, 3H), 1.51-1.43 (m, 1H), 1.07-1.03 (m, 3H).

Example 154

6-[2-cyano-3-[[ethyl(methyl)sulfamoyl]amino]-6-fluorophenoxy]-3-[(3S)-8-[2-[4-[3-(2,4-dioxo-1,3-diazinan-1-yl)-1-methylindazol-6-yl]piperidin-1-yl]acetyl]-8-azaspiro[4.5]decan-3-yl]-4-oxoquinazoline

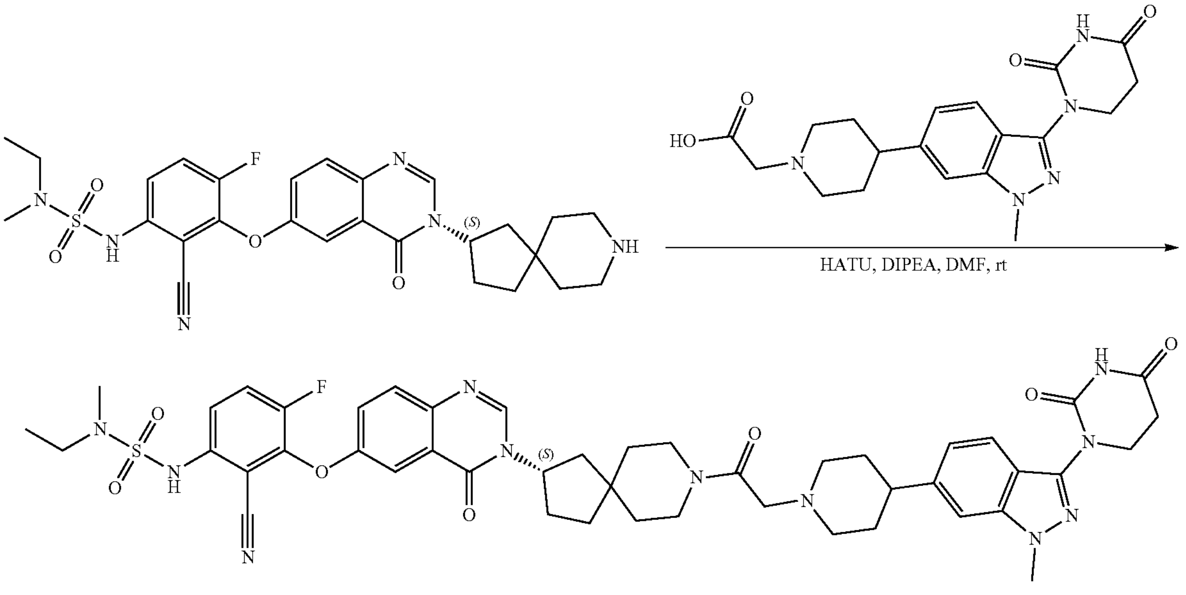

Target compound was prepared via HATU mediated acid-amine coupling reaction (Procedure B-E). Amide coupling was carried out using 2-[4-[3-(2,4-dioxohexahydropyrimidin-1-yl)-1-methyl-indazol-6-yl]-1-piperidyl]acetic acid (192.70 mg, 456.78 μmol), 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (0.27 g, 456.78 μmol), N,N-diisopropylethylamine (295.18 mg, 2.28 mmol, 397.81 μL) and HATU (260.52 mg, 685.17 μmol). The crude compound was purified by reverse phase column chromatography, eluting with 50% acetonitrile in 0.1% ammonium acetate in water, to afford 6-[2-cyano-3-[[ethyl(methyl)sulfamoyl]amino]-6-fluoro-phenoxy]-3-[(3S)-8-[2-[4-[3-(2,4-dioxohexahydropyrimidin-1-yl)-1-methyl-indazol-6-yl]-1-piperidyl]acetyl]-8-azaspiro[4.5]decan-3-yl]-4-oxo-quinazoline (18 mg, 18.52 μmol, 4% yield) as an off-white solid. LCMS m/z (ESI): 922.2 $[M+H]^+$. $^1H$ NMR (400 MHz, DMSO-$d_6$): δ=10.56 (s, 1H), 9.65 (bs, 1H), 8.44 (d, J=4.00 Hz, 1H), 7.77 (d, J=8.80 Hz, 1H), 7.66 (d, J=2.80 Hz, 1H), 7.64 (d, J=2.80 Hz, 1H), 7.60 (d, J=8.40 Hz, 1H), 7.44 (s, 1H), 7.35 (s, 2H), 7.06 (d, J=8.40 Hz, 1H), 5.04 (t, J=11.60 Hz, 1H), 3.98 (s, 3H), 3.92 (t, J=6.80 Hz, 2H), 3.59-3.51 (m, 1H), 3.49-3.34 (m, 3H), 3.15 (q, J=6.80 Hz, 2H), 2.96-2.81 (m, 2H), 2.76 (t, J=6.80 Hz, 2H), 2.68-2.67 (m, 2H), 2.65 (s, 3H), 2.12-2.09 (m, 4H), 1.98-1.96 (m, 4H), 1.85-1.65 (m, 3H), 1.64-1.47 (m, 6H), 1.03 (t, J=10.80 Hz, 3H).

Example 155

9-[6-[2-cyano-3-[[ethyl(methyl)sulfamoyl]amino]-6-fluorophenoxy]-4-oxoquinazolin-3-yl]-3-[2-[4-[3-(2,4-dioxo-1,3-diazinan-1-yl)-1-methylindazol-6-yl]piperidin-1-yl]acetyl]-3-azaspiro[5.5]undecane

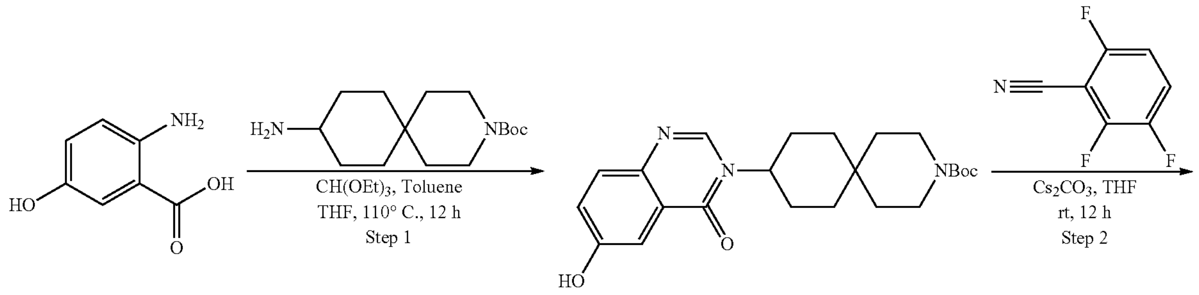

-continued

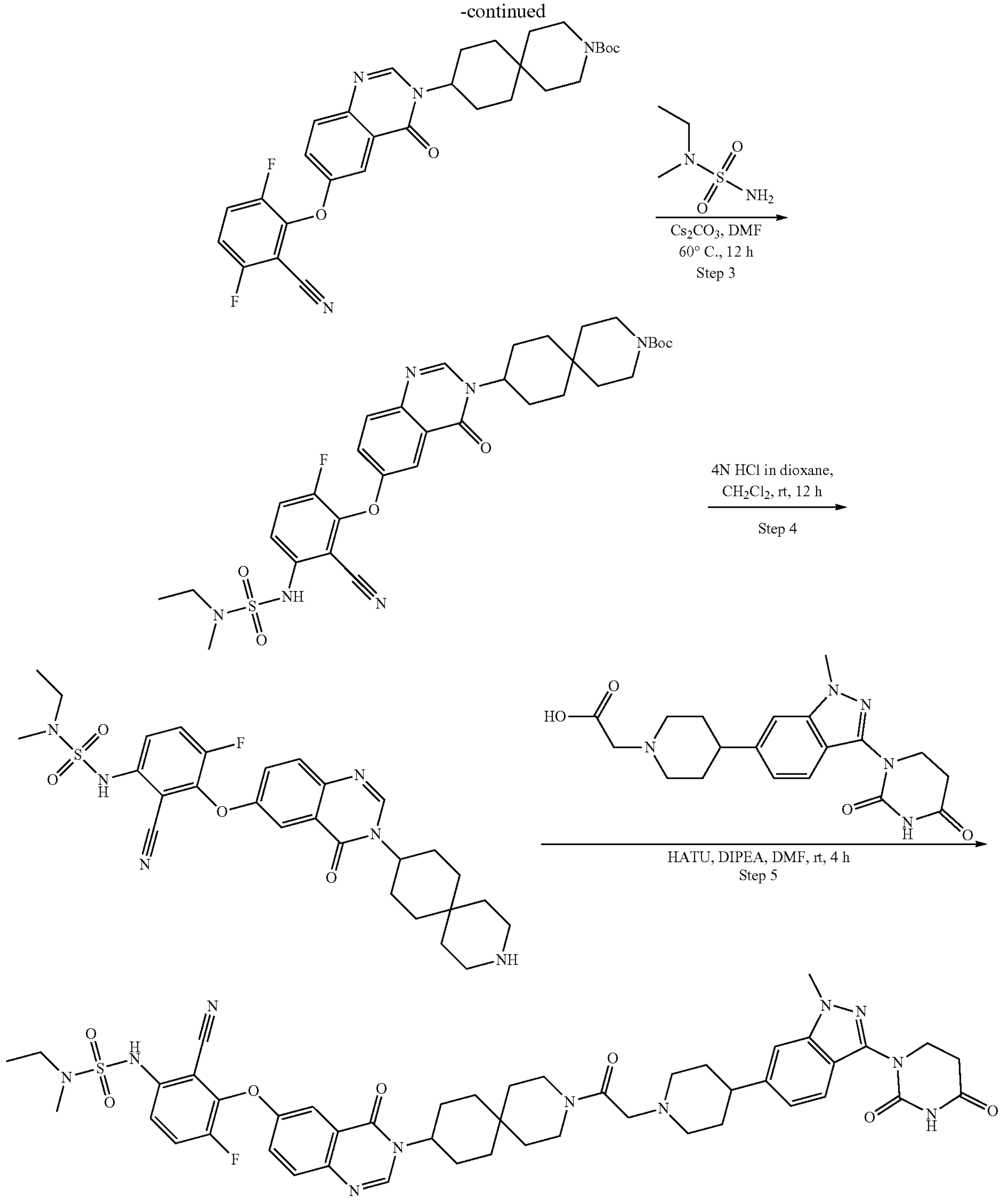

Step 1: Quinazolinone intermediate was synthesized by following general procedure for cyclization (Procedure B-A) using 2-amino-5-hydroxy-benzoic acid (3.14 g, 20.49 mmol), triethyl orthoformate (4.14 g, 27.94 mmol, 4.65 mL), and tert-butyl 9-amino-3-azaspiro[5.5]undecane-3-carboxylate (5 g, 18.63 mmol). The desired compound was purified by silica gel flash column chromatography using 50% ethyl acetate in petroleum ether as eluent to afford tert-butyl 9-(6-hydroxy-4-oxo-quinazolin-3-yl)-3-azaspiro[5.5]undecane-3-carboxylate (5.6 g, 10.78 mmol, 58% yield) as a brown solid. LCMS m/z (ESI): 414.2 $[M+H]^+$.

Step 2: O-arylated quinazolinone intermediate was synthesized by following general procedure for O-arylation (Procedure B—B) using tert-butyl 9-(6-hydroxy-4-oxo-quinazolin-3-yl)-3-azaspiro[5.5]undecane-3-carboxylate (5.5 g, 13.30 mmol), cesium carbonate (13.00 g, 39.90 mmol) and 2,3,6-trifluorobenzonitrile (4.18 g, 26.60 mmol, 3.07 mL). The desired compound was purified by silica gel flash column chromatography using 70-80% ethyl acetate in petroleum ether as eluent to afford tert-butyl 9-[6-(2-cyano-3,6-difluoro-phenoxy)-4-oxo-quinazolin-3-yl]-3-azaspiro[5.5]undecane-3-carboxylate (3.6 g, 6.05 mmol, 46% yield) as a light yellow solid. LCMS m/z (ESI): 551.2 $[M+H]^+$.

Step 3: Sulfamoylated quinazolinone intermediate was synthesized by following Procedure B—C using tert-butyl 9-[6-(2-cyano-3,6-difluoro-phenoxy)-4-oxo-quinazolin-3-yl]-3-azaspiro[5.5]undecane-3-carboxylate (3.6 g, 6.54 mmol), cesium carbonate (2.13 g, 6.54 mmol), and [methyl(sulfamoyl)amino]ethane (903.53 mg, 6.54 mmol). The reaction mixture was stirred at 60° C. for 12 h. After completion, the reaction mixture was diluted with water (100 mL). The reaction mixture was filtered through filter paper to remove the fluorescent impurity. The filtrate was extracted with ethyl acetate (3×150 mL). Combined organic layers were washed with cold water (3×50 mL), dried over sodium sulfate, filtered and concentrated under reduced pressure to afford tert-butyl 9-[6-[2-cyano-3-[[ethyl(methyl)sulfamoyl]amino]-6-fluoro-phenoxy]-4-oxo-quinazolin-3-yl]-3-azaspiro[5.5]undecane-3-carboxylate (1.8 g, 2.27 mmol, 35% yield) as a light yellow solid. LCMS m/z (ESI): 669.2 $[M+H]^+$.

Step 4: The requisite amine was synthesized by 4M HCl in Dioxane mediated N-Boc deprotection (Procedure B-D). N-Boc deprotection was done on tert-butyl 9-[6-[2-cyano-3-[[ethyl(methyl)sulfamoyl]amino]-6-fluoro-phenoxy]-4-oxo-quinazolin-3-yl]-3-azaspiro[5.5]undecane-3-carboxylate (1.8 g, 2.69 mmol) using hydrogen chloride in 1,4-dioxane, 99% (4 M, 20 mL) at 5° C. under nitrogen atmosphere. The reaction mixture was stirred at room temperature for 12 h. After completion, the reaction mixture was concentrated under reduced pressure to afford crude 9-[6-[2-cyano-3-[[ethyl(methyl)sulfamoyl]amino]-6-fluoro-phenoxy]-4-oxo-quinazolin-3-yl]-3-azaspiro[5.5]undecane (1.8 g, 2.41 mmol, 90% yield) as off-white solid. LCMS m/z (ESI): 569.2 $[M+H]^+$.

Step 5: Target compound was prepared via HATU mediated acid-amine coupling reaction (Procedure B-E). Amide coupling was carried out using 2-[4-[3-(2,4-dioxohexahydropyrimidin-1-yl)-1-methyl-indazol-6-yl]-1-piperidyl]acetic acid (76.69 mg, 181.78 μmol), 9-[6-[2-cyano-3-[[ethyl(methyl)sulfamoyl]amino]-6-fluoro-phenoxy]-4-oxo-quinazolin-3-yl]-3-azaspiro[5.5]undecane (0.1 g, 165.26 μmol), N,N-diisopropylethylamine (213.58 mg, 1.65 mmol, 287.85 μL) and HATU (69.12 mg, 181.78 μmol). The crude compound was purified by reverse phase column chromatography, eluting with 50% acetonitrile in 0.1% formic acid in water, to afford 9-[6-[2-cyano-3-[[ethyl(methyl)sulfamoyl]amino]-6-fluoro-phenoxy]-4-oxo-quinazolin-3-yl]-3-[2-[4-[3-(2,4-dioxohexahydropyrimidin-1-yl)-1-methyl-indazol-6-yl]-1-piperidyl]acetyl]-3-azaspiro[5.5]undecane (36.54 mg, 37.20 μmol, 23% yield) as an off-white solid. LCMS m/z (ESI): 935.9 $[M+H]^+$; $^1H$ NMR (400 MHz, DMSO-$d_6$): δ=10.56 (s, 1H), 9.86 (s, 1H), 8.53 (d, J=8.00 Hz, 1H), 7.83-7.81 (m, 1H), 7.79 (d, J=9.20 Hz, 1H), 7.69 (dd, J=3.20, 8.80 Hz, 1H), 7.63 (d, J=8.80 Hz, 1H), 7.50-7.46 (m, 1H), 7.44 (s, 1H), 7.38 (t, J=2.40 Hz, 1H), 7.19 (s, 1H), 4.51 (s, 1H), 4.29 (s, 2H), 4.00 (s, 3H), 3.92 (t, J=6.80 Hz, 3H), 3.55 (s, 4H), 3.19-3.13 (m, 6H), 2.78-2.75 (m, 5H), 2.21-2.01 (m, 6H), 1.93-1.65 (m, 6H), 1.50-1.29 (m, 4H), 1.08-1.04 (m, 3H).

Example 156

9-[6-[2-cyano-3-[[ethyl(methyl)sulfamoyl]amino]-6-fluorophenoxy]-4-oxoquinazolin-3-yl]-3-[2-[4-[3-(2,6-dioxopiperidin-3-yl)-1-methylindazol-6-yl]piperidin-1-yl]acetyl]-3-azaspiro[5.5]undecane

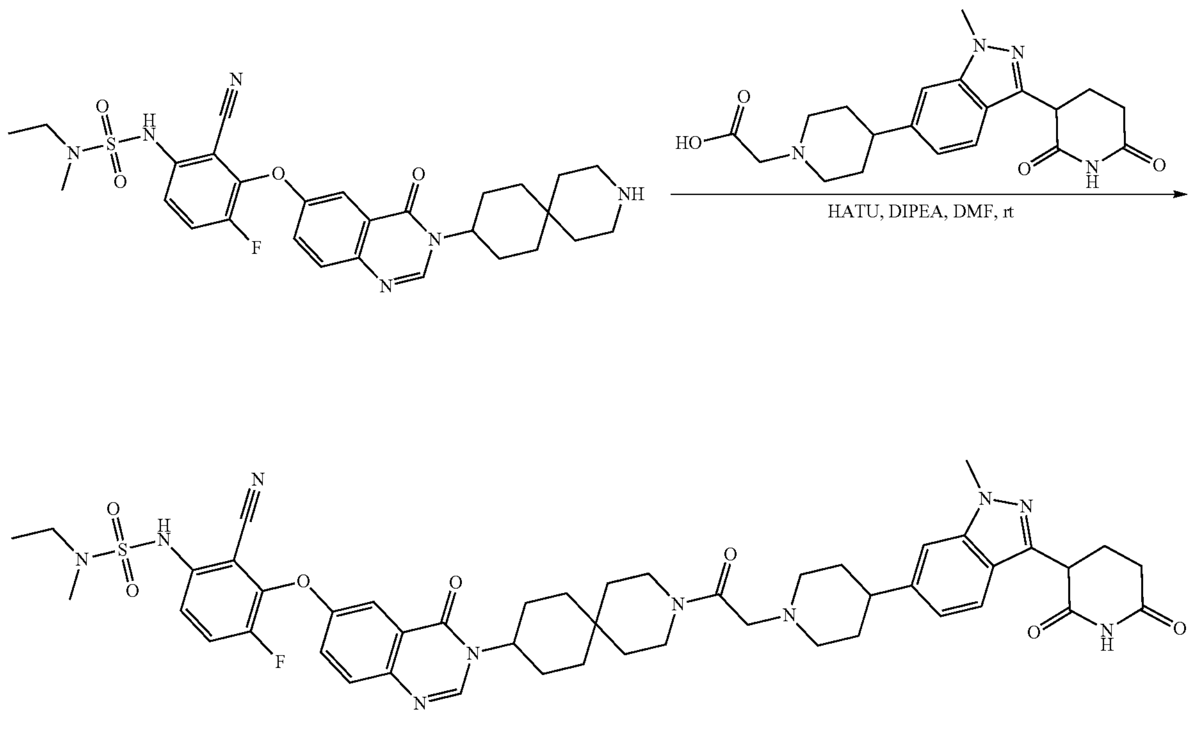

Target compound was prepared via HATU mediated acid-amine coupling reaction (Procedure B-E). Amide coupling was carried out using 9-[6-[2-cyano-3-[[ethyl(methyl)sulfamoyl]amino]-6-fluoro-phenoxy]-4-oxo-quinazolin-3-yl]-3-azaspiro[5.5]undecane (100 mg, 175.85 μmol), 2-[4-[3-(2,6-dioxo-3-piperidyl)-1-methyl-indazol-6-yl]-1-piperidyl] acetic acid (81.12 mg, 211.02 μmol), N,N-diisopropylethylamine (113.64 mg, 879.26 μmol, 153.15 μL) and HATU (73.55 mg, 193.44 μmol). The crude compound was purified by reverse phase column chromatography eluted with 40-45% formic acid buffer in acetonitrile to afford 9-[6-[2-cyano-3-[[ethyl(methyl)sulfamoyl]amino]-6-fluoro-phenoxy]-4-oxo-quinazolin-3-yl]-3-[2-[4-[3-(2,6-dioxo-3-piperidyl)-1-methyl-indazol-6-yl]-1-piperidyl]acetyl]-3-azaspiro[5.5]undecane (25 mg, 25.37 μmol, 14% yield) as off-white solid. LCMS m/z (ESI): 935.2 $[M+H]^+$. $^1$H NMR (400 MHz, DMSO-$d_6$): δ=10.91 (s, 1H), 10.20 (bs, 1H), 9.51 (bs, 1H), 8.54 (d, J=8.80 Hz, 1H), 7.81-7.90 (m, 1H), 7.80 (d, J=8.80 Hz, 1H), 7.69 (dd, J=2.80, 8.80 Hz, 2H), 7.48 (dd, J=4.40, 9.00 Hz, 1H), 7.44 (s, 1H), 7.37 (t, J=2.40 Hz, 1H), 7.07 (d, J=9.20 Hz, 1H), 4.56 (t, J=12.40 Hz, 1H), 4.35 (dd, J=5.20, 10.00 Hz, 2H), 4.21-4.51 (m, 1H), 3.99 (s, 3H), 3.51-3.62 (m, 3H), 3.24-3.45 (m, 2H), 2.92-3.21 (m, 4H), 2.79 (s, 3H), 2.31-2.71 (m, 4H), 1.98-2.21 (m, 8H), 1.80-1.91 (m, 2H), 1.65-1.80 (m, 4H), 1.25-1.45 (m, 4H), 1.06 (t, J=7.20 Hz, 3H).

Example 157

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

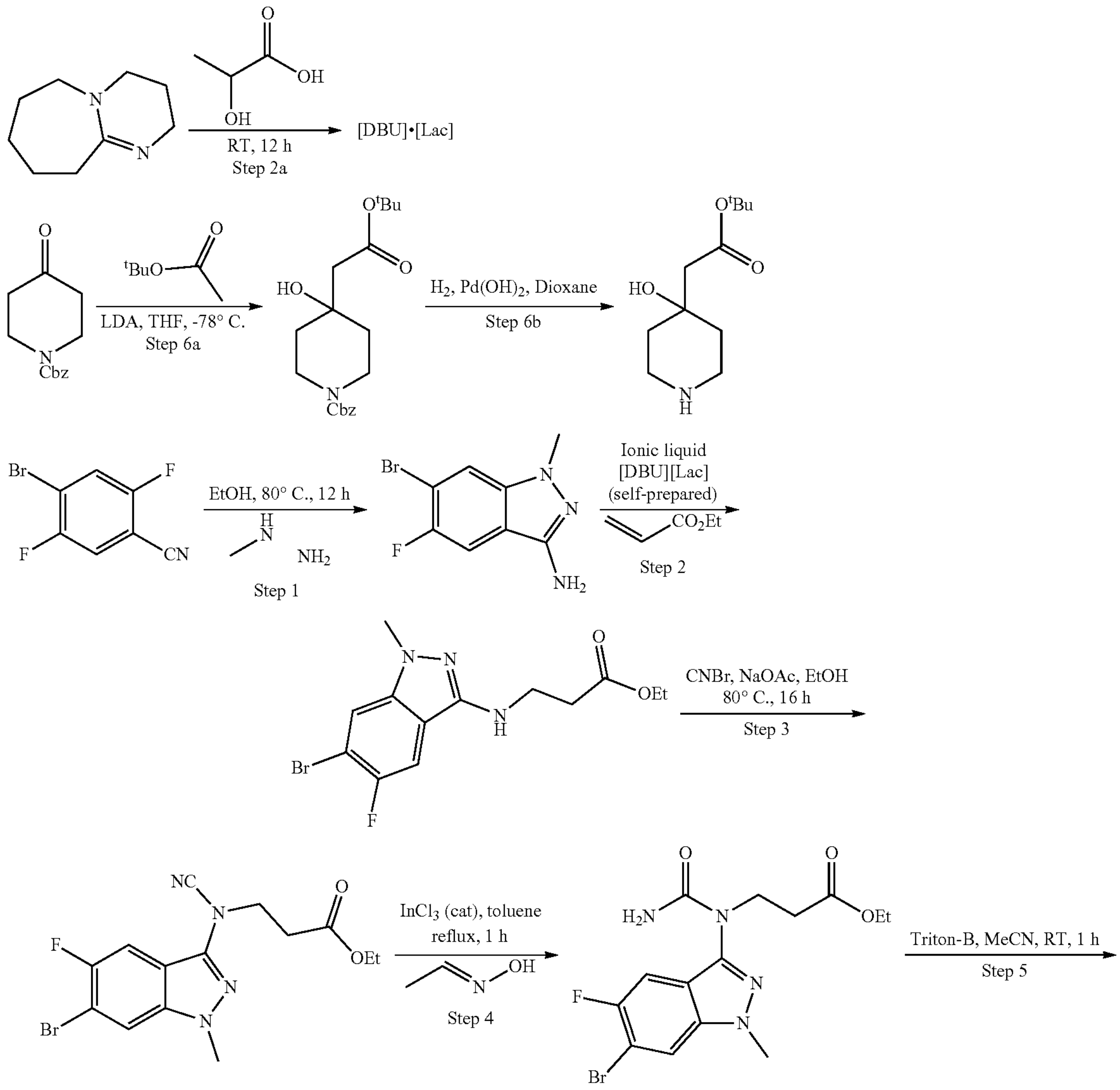

-continued

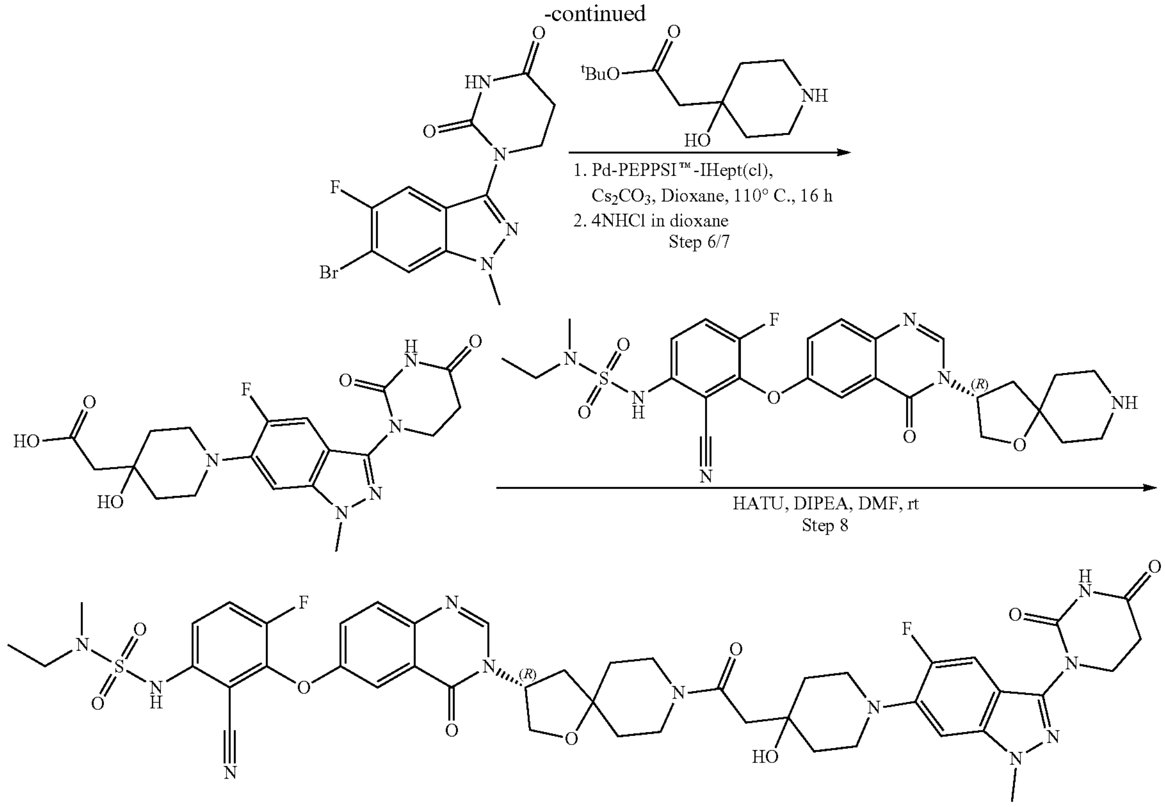

Step 1: To a stirred solution of 4-bromo-2,5-difluorobenzonitrile (25 g, 114.68 mmol) in ethanol (250 mL) was added methylhydrazine (85% aq. solution, 21.13 g, 458.72 mmol) at room temperature under nitrogen atmosphere. The resulting reaction mixture was heated to 80° C. for 12 h. After completion, the resulting solution was quenched with water (80 ml), and the obtained precipitate was filtered and dried to afford 6-bromo-5-fluoro-1-methyl-indazol-3-amine (17.5 g, 70.71 mmol, 62% yield) as off-white solid, which was carried forward without further purification. LCMS m/z (ESI): 246.0 $[M+H]^+$ Step 2a: A mixture of DBU (200 g, 1.31 mol, 1.00 eq) and lactic acid (118 g, 1.31 mol, 97.5 mL, 1.00 eq) in a flask (2.00 L) was degassed and purged with $N_2$ for 3 times. The resulting mixture was stirred at 25° C. for 12 h under nitrogen atmosphere to obtain [DBU]·[Lac]ionic liquid (316 g, crude) as a thick solution, which was carried forward without further purification.

Step 2: To a solution of 6-bromo-5-fluoro-1-methyl-indazol-3-amine (17.5 g, 71.70 mmol) in [DBU]·[Lac]ionic liquid (18 g) was added ethyl prop-2-enoate (50.25 g, 501.92 mmol, 54.38 mL) at room temperature under nitrogen atmosphere. The resulting solution was heated to 90° C. for 48 h. After completion, the resulting solution was quenched with water (100 ml) and extracted with ethyl acetate (2×100 mL). The combined organic layer was dried over sodium sulfate and concentrated under reduced pressure. The resulting crude product was purified by silica gel flash column chromatography using ethyl acetate-petroleum ether (0-60%) to afford ethyl 3-[(6-bromo-5-fluoro-1-methyl-indazol-3-yl)amino]propanoate (11.0 g, 30.97 mmol, 43% yield) as red semisolid. LCMS m/z (ESI): 344.4 $[M+H]^+$.

Step 3: A solution of ethyl 3-[(6-bromo-5-fluoro-1-methyl-indazol-3-yl)amino]propanoate (11 g, 31.96 mmol) in ethanol (110 mL) was added sodium acetate (15.73 g, 191.76 mmol, 10.28 mL) and cyanogen bromide (16.93 g, 159.80 mmol, 8.38 mL) at room temperature under nitrogen atmosphere. The reaction mixture was heated to 85° C. for 16 h. The reaction mixture was diluted with water (50 mL) and extracted with ethyl acetate (2×100 mL). The organic layer was washed with brine (30 mL), dried over sodium sulfate and concentrated under reduced pressure to afford ethyl 3-[(6-bromo-5-fluoro-1-methyl-indazol-3-yl)-cyano-amino]propanoate (12 g, 25.98 mmol, 81% yield) as yellow solid, which was carried forward without further purification. LCMS m/z (ESI): 371.0 $[M+H]^+$ Step 4: To a stirred solution of ethyl 3-[(6-bromo-5-fluoro-1-methyl-indazol-3-yl)-cyano-amino]propanoate (12 g, 32.50 mmol) in toluene (120 mL) was added indium (III) chloride (718.91 mg, 3.25 mmol) and acetaldoxime (5.76 g, 97.51 mmol) at room temperature under nitrogen atmosphere. The reaction mixture was heated to 110° C. for 1 h. After completion, the reaction mixture was filtered and concentrated under reduced pressure. The resulting crude product was purified by silica gel flash column chromatography using ethyl acetate-petroleum ether (0-80%) to afford ethyl 3-[(6-bromo-5-fluoro-1-methyl-indazol-3-yl)-carbamoyl-amino]propanoate (8.0 g, 20.33 mmol, 63% yield) as off-white solid. LCMS m/z (ESI): 387.0 $[M+H]^+$.

Step 5: To a stirred solution of ethyl 3-[(6-bromo-5-fluoro-1-methyl-indazol-3-yl)-carbamoyl-amino]propanoate (8.0 g, 20.66 mmol) in acetonitrile (80 mL) was added benzyl trimethylammonium hydroxide (25% solution in methanol, 4.15 g, 6.20 mmol, 25% purity) at room temperature under nitrogen atmosphere. The reaction mixture stirred at room temperature for 1 h. The reaction mixture was diluted with water (50 mL), extracted with ethyl acetate (3×80 mL). The combined organic layer were dried over sodium sulfate and concentrated under reduced pressure to afford 1-(6-bromo-5-fluoro-1-methyl-indazol-3-yl)hexahydropyrimidine-2,4-dione (5.2 g, 15.01 mmol, 73% yield) as off-white solid. LCMS m/z (ESI): 343.0 [M+H]$^+$.

Step 6a: To a well stirred solution of tert-butyl acetate (18.67 g, 160.76 mmol, 160.76 mL) in THF (200 mL) was added lithium di-isopropyl amide (2M in THF, 64.30 mL) at −78° C. and the reaction mixture was stirred at same temperature for 1 h. Then, to the reaction mixture was added the solution of benzyl 4-oxopiperidine-1-carboxylate (15 g, 64.31 mmol, 12.82 mL) slowly at −78° C. before stirred for 1 h. The reaction mixture was quenched with saturated ammonium chloride solution. The reaction mixture was diluted with ethyl acetate (200 mL), and washed with water (40 mL) and brine (40 mL). The organic layer was dried with sodium sulfate, filtered and concentrated under reduced pressure to afford benzyl 4-(2-tert-butoxy-2-oxo-ethyl)-4-hydroxy-piperidine-1-carboxylate (22.5 g, 64.02 mmol, 100% yield) as colorless oil. LCMS m/z (ESI)=294.2 [M+H−56]$^+$.

Step 6b: To a stirred solution of benzyl 4-(2-tert-butoxy-2-oxo-ethyl)-4-hydroxy-piperidine-1-carboxylate (23 g, 65.82 mmol) in 1,4-dioxane (200 mL) was added palladium (7.00 g, 65.82 mmol), which was saturated with hydrogen by bubbling hydrogen gas through for 10 minutes and then subjected to hydrogenation (1 atm) at room temperature for 20 h. After completion, the reaction mixture was purged with nitrogen and the reaction mixture was filtered through a pad of celite. The filtrate was concentrated under reduced pressure to afford tert-butyl 2-(4-hydroxy-4-piperidyl)acetate (14 g, 64.94 mmol, 99% yield) as off-white solid, which was carried forward without further purification. LCMS m/z (ESI): 216.3 [M+H]$^+$ Step 6: A solution of 1-(6-bromo-5-fluoro-1-methyl-indazol-3-yl)hexahydropyrimidine-2,4-dione (4.4 g, 12.90 mmol) in 1,4-dioxane (80 mL) was taken in a sealed tube and added cesium carbonate (10.51 g, 32.25 mmol) and tert-butyl 2-(4-hydroxy-4-piperidyl)acetate (5.55 g, 25.80 mmol) at room temperature under nitrogen atmosphere. The reaction mixture was degassed with nitrogen for 10 minutes, then added Pd-PEPPSI-IHept catalyst (626.85 mg, 644.39 μmol) at room temperature. The resulting reaction mixture was heated to 105° C. for 16 h. The reaction mixture was diluted with water (20 mL) and extracted with ethyl acetate (2×50 mL). The combined organic layers were dried over sodium sulfate and concentrated under reduced pressure. The resulting product was purified by silica gel flash column chromatography using ethyl acetate-petroleum ether (0-80%) to afford tert-butyl 2-[1-[3-(2,4-dioxohexahydropyrimidin-1-yl)-5-fluoro-1-methyl-indazol-6-yl]-4-hydroxy-4-piperidyl]acetate (4.0 g, 7.67 mmol, 59% yield) as off-white solid. LCMS m/z (ESI): 476.2 [M+H]$^+$.

Step 7: To a stirred solution of tert-butyl 2-[1-[3-(2,4-dioxohexahydropyrimidin-1-yl)-5-fluoro-1-methyl-indazol-6-yl]-4-hydroxy-4-piperidyl]acetate (0.5 g, 1.05 mmol) in dichloromethane (5 mL) was added hydrogen chloride solution in 1,4-dioxane (4.0 M, 10.51 mL) at 0° C. under nitrogen atmosphere. The resulting solution was stirred at room temperature for 24 h. The resulting solution was concentrated under reduced pressure to afford 2-[1-[3-(2,4-dioxohexahydropyrimidin-1-yl)-5-fluoro-1-methyl-indazol-6-yl]-4-hydroxy-4-piperidyl]acetic acid (0.48 g, 884.68 μmol, 84% yield) as a brownish semisolid, which was carried forward without further purification. LCMS m/z (ESI): 420.2 [M+H]$^+$.

Step 8: To a stirred solution of (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (650 mg, 1.17 mmol), 2-[1-[3-(2,4-dioxohexahydropyrimidin-1-yl)-5-fluoro-1-methyl-indazol-6-yl]-4-hydroxy-4-piperidyl] acetic acid (489.78 mg, 1.17 mmol) in N,N-dimethylformamide (8 mL) were added HATU (444.03 mg, 1.17 mmol) and N,N-diisopropylethylaminediisopropylethylamine (603.71 mg, 4.67 mmol, 813.63 μL) and stirred at room temperature for 4 h. After completion, the reaction mixture was concentrated under reduced pressure to half of its volume, and was directly purified by reverse phase column chromatography eluted with 50% acetonitrile in 0.1% ammonium acetate in water to afford (3R)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (310 mg, 320.23 μmol, 27% yield) as off-white solid. LCMS m/z (ESI): 958.2 [M+H]$^+$. $^1$H NMR (400 MHz, DMSO-$d_6$): δ=10.50 (s, 1H), 10.20 (s, 1H), 8.37 (s, 1H), 7.88 (t, J=10.00 Hz, 1H), 7.79-7.80 (m, 1H), 7.69-7.72 (m, 1H), 7.49-7.52 (m, 1H), 7.37 (d, J=2.40 Hz, 1H), 7.33 (d, J=13.20 Hz, 1H), 7.13 (d, J=6.40 Hz, 1H), 5.31 (s, 1H), 5.03 (s, 1H), 4.10-4.21 (m, 2H), 3.94 (s, 3H), 3.88-3.92 (m, 2H), 3.75-3.85 (m, 1H), 3.51-3.71 (m, 3H), 3.15-3.25 (m, 3H), 3.05-3.15 (m, 2H), 2.80 (s, 3H), 2.65-2.75 (m, 3H), 2.32-2.56 (m, 3H), 2.00-2.12 (m, 1H), 1.50-1.90 (m, 8H), 1.06 (t, J=−6.80 Hz, 3H).

Example 158

9-[6-[2-cyano-3-[[ethyl(methyl)sulfamoyl]amino]-6-fluorophenoxy]-4-oxoquinazolin-3-yl]-3-[2-[1-[3-(2,4-dioxo-1,3-diazinan-1-yl)-5-fluoro-1-methylindazol-6-yl]-4-hydroxypiperidin-4-yl]acetyl]-3-azaspiro[5.5]undecane

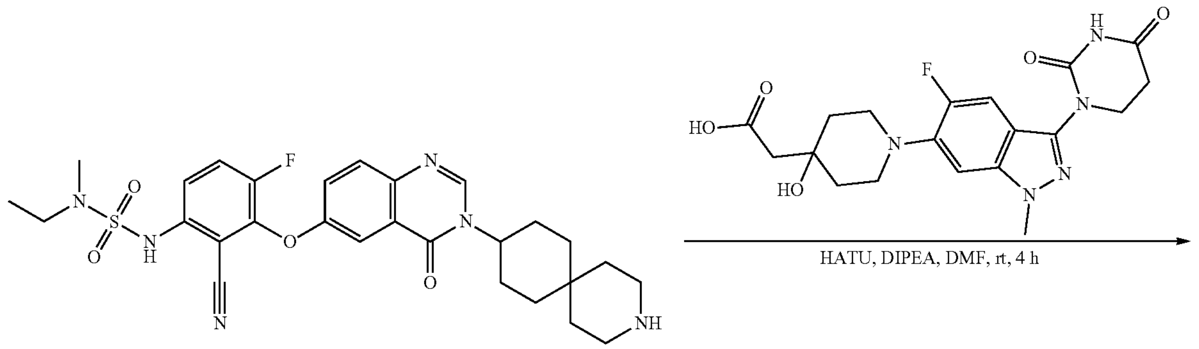

-continued

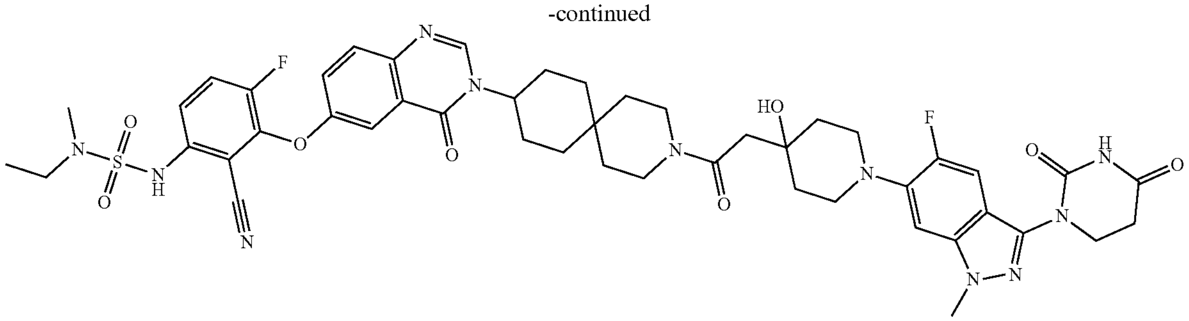

Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (0.05 g, 109.68 μmol), 9-[6-[2-cyano-3-[[ethyl(methyl)sulfamoyl]amino]-6-fluoro-phenoxy]-4-oxo-quinazolin-3-yl]-3-azaspiro[5.5]undecane (73.01 mg, 120.65 μmol), N,N-diisopropylethylamine (141.76 mg, 1.10 mmol, 191.04 μL) and HATU (45.87 mg, 120.65 μmol). The crude compound was purified by reverse phase column chromatography eluted with 50% acetonitrile in 0.1% formic acid in water to afford product 9-[6-[2-cyano-3-[[ethyl(methyl)sulfamoyl]amino]-6-fluoro-phenoxy]-4-oxo-quinazolin-3-yl]-3-[2-[1-[3-(2,4-dioxohexahydropyrimidin-1-yl)-5-fluoro-1-methyl-indazol-6-yl]-4-hydroxy-4-piperidyl]acetyl]-3-azaspiro[5.5]undecane (28.24 mg, 28.83 μmol, 26% yield) as off-white solid. LCMS m/z (ESI): 970.2 $[M+H]^+$; $^1H$ NMR (400 MHz, DMSO-$d_6$): δ=10.46 (s, 1H), 10.13 (s, 1H), 8.44 (s, 1H), 7.70 (d, J=-8.80 Hz, 1H), 7.59 (d, J=7.20 Hz, 1H), 7.33 (s, 1H), 7.26 (d, J=12.80 Hz, 2H), 7.06 (d, J=7.20 Hz, 1H), 5.04 (d, J=7.20 Hz, 1H), 4.48 (s, 1H), 3.87 (s, 3H), 3.82 (t, J=6.40 Hz, 2H), 3.45 (s, 4H), 3.09-3.00 (m, 6H), 2.69-2.61 (m, 6H), 2.51-2.49 (m, 2H), 1.79 (d, J=13.60 Hz, 2H), 1.66-1.50 (m, 10H), 1.30-1.17 (m, 4H), 0.97 (t, J=7.20 Hz, 3H).

Example 159

6-[2-cyano-3-[[ethyl(methyl)sulfamoyl]amino]-6-fluorophenoxy]-3-[(3S)-8-[2-[1-[3-(2,4-dioxo-1,3-diazinan-1-yl)-5-fluoro-1-methylindazol-6-yl]-4-hydroxypiperidin-4-yl]acetyl]-8-azaspiro [4.5] decan-3-yl]-4-oxoquinazoline

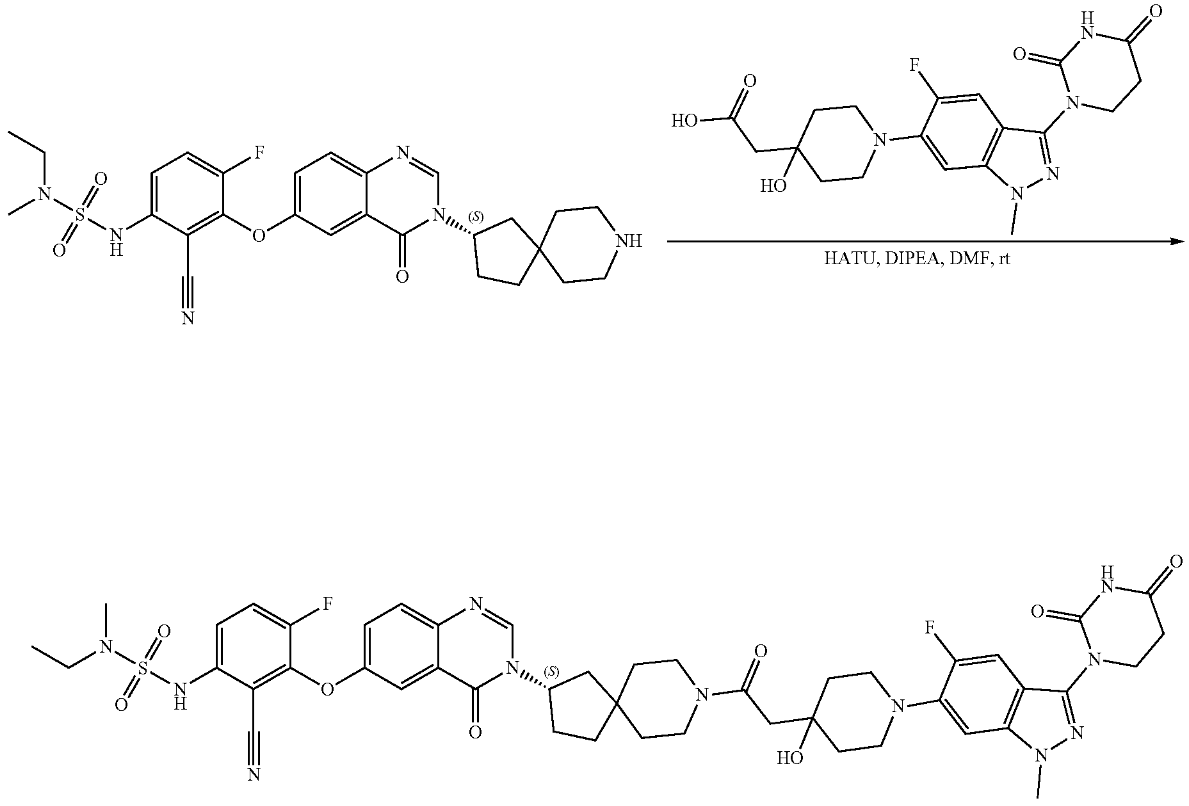

Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (42.57 mg, 93.39 μmol), 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (60 mg, 101.51 μmol), N,N-diisopropylethylamine (65.59 mg, 507.53 μmol, 88.40 μL) and HATU (57.89 mg, 152.26 μmol The crude compound was purified by reverse phase column chromatography, eluting with 35% acetonitrile in 0.1% formic acid in water, to afford product 6-[2-cyano-3-[[ethyl(methyl)sulfamoyl]amino]-6-fluoro-phenoxy]-3-[(3S)-8-[2-[1-[3-(2,4-dioxohexahydropyrimidin-1-yl)-5-fluoro-1-methyl-indazol-6-yl]-4-hydroxy-4-piperidyl]acetyl]-8-azaspiro[4.5]decan-3-yl]-4-oxo-quinazoline (38 mg, 38.36 μmol, 38% yield) as off-white solid. LCMS m/z (ESI): 956.2 $[M+H]^+$; $^1H$ NMR (400 MHz, DMSO-$d_6$): δ=10.53 (s, 1H), 10.19 (s, 1H), 8.45 (s, 1H), 7.74 (d, J=2.40 Hz, 1H), 7.70 (s, 1H), 7.67 (d, J=8.80 Hz, 1H), 7.42 (s, 1H), 7.35 (d, J=Hz, 1H), 7.31 (s, 1H), 7.13 (d, J=7.20 Hz, 1H), 5.08-5.04 (m, 2H), 3.94 (s, 3H), 3.89 (t, J=6.40 Hz, 2H), 3.60-3.58 (m, 2H), 3.45-3.41 (m, 2H), 3.18-3.10 (m, 6H), 2.75-2.67 (m, 4H), 2.56-2.51 (m, 2H), 2.10-2.05 (m, 3H), 1.73-1.52 (m, 12H), 1.05 (t, J=6.80 Hz, 3H).

Examples 160-161

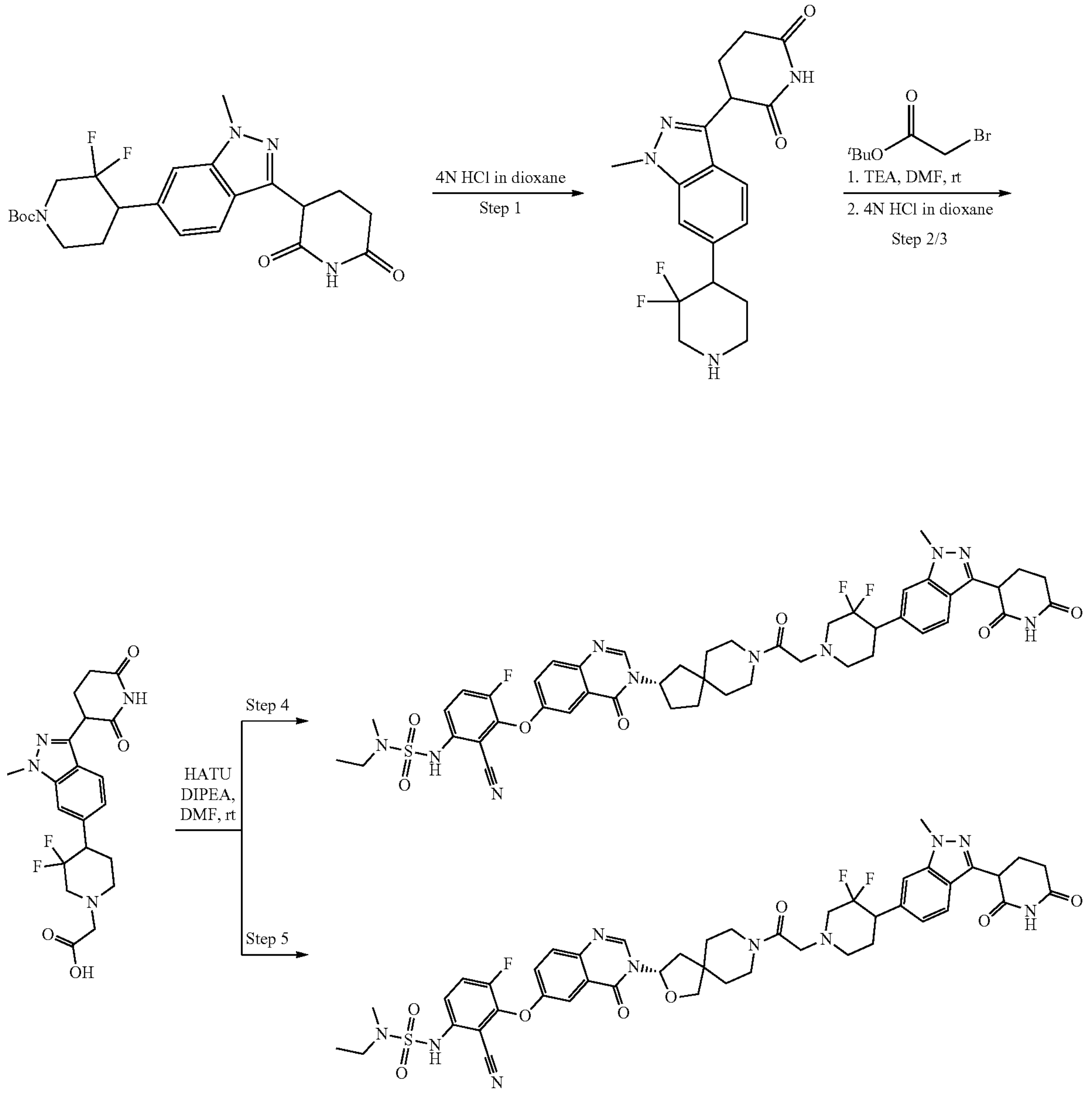

Step 1: To a stirred solution of tert-butyl 4-[3-(2,6-dioxo-3-piperidyl)-1-methyl-indazol-6-yl]-3,3-difluoro-piperidine-1-carboxylate (215 mg, 464.88 μmol) in 1,4-dioxane (2 mL) was added hydrogen chloride solution in 1,4-dioxane (4 M, 4 mL) at 5° C. under nitrogen atmosphere. The reaction mixture was stirred at room temperature for 2 h. After completion, the reaction mixture was concentrated under reduced pressure and washed with the petroleum ether to afford 3-[6-(3,3-difluoro-4-piperidyl)-1-methyl-indazol-3-yl]piperidine-2,6-di one (198 mg, 463.09 μmol, 100% yield), which was carried forward without further purification. LCMS m/z (ESI). 363.2 $[M+H]^+$.

Step 2: To a stirred solution of 3-[6-(3,3-difluoro-4-piperidyl)-1-methyl-indazol-3-yl]piperidine-2,6-dione (200 mg, 551.92 μmol) in N,N-dimethylformamide (3 mL) were added triethylamine (223.39 mg, 2.21 mmol, 307.71 μL) followed by tert-butyl 2-bromoacetate (107.65 mg, 551.92 μmol, 80.94 μL) at room temperature under nitrogen atmosphere. The reaction mixture was stirred at room temperature for 14 h. The reaction mixture was diluted with water (10 mL) and extracted with ethyl acetate (3×10 mL). The combined organic layer was washed with brine solution (30 mL), dried over sodium sulfate and concentrated under reduced pressure to afford tert-butyl 2-[4-[3-(2,6-dioxo-3-piperidyl)-1-methyl-indazol-6-yl]-3,3-difluoro-1-piperidyl] acetate (230 mg, 413.84 μmol, 75% yield) as a brown solid. LCMS m/z (ESI): 477.2 $[M+H]^+$.

Step 3: To a stirred solution of tert-butyl 2-[4-[3-(2,6-dioxo-3-piperidyl)-1-methyl-indazol-6-yl]-3,3-difluoro-1-piperidyl]acetate (230 mg, 482.67 μmol) in dichloromethane (2 mL) was added hydrogen chloride solution in 1,4-dioxane (4 M, 4 mL) at 0° C. under nitrogen atmosphere. The reaction mixture was stirred at room temperature for 4 h. The reaction mixture was concentrated under vacuum, and the crude material was triturated with the petroleum ether to afford 2-[4-[3-(2,6-dioxo-3-piperidyl)-1-methyl-indazol-6-yl]-3,3-difluoro-1-piperidyl]acetic acid (262 mg, 480.57 μmol, 100% yield) as a light brown solid. LCMS m/z (ESI): 421.2 $[M+H]^+$.

Example 160

6-[2-cyano-3-[[ethyl(methyl)sulfamoyl]amino]-6-fluorophenoxy]-3-[(3S)-8-[2-[4-[3-(2,6-dioxopiperidin-3-yl)-1-methylindazol-6-yl]-3,3-difluoropiperidin-1-yl]acetyl]-8-azaspiro[4.5]decan-3-yl]-4-oxoquinazoline Step 4: Target compound was prepared via HATU mediated acid-amine coupling reaction (Procedure B-E). Amide coupling was carried out using 3-[(3S)-8-azaspiro[4.5]decan-3-yl]-6-[2-cyano-3-[[ethyl(methyl)sulfamoyl]amino]-6-fluoro-phenoxy]-4-oxo-quinazoline (100 mg, 180.30 μmol), 2-[4-[3-(2,6-dioxo-3-piperidyl)-1-methyl-indazol-6-yl]-3,3-difluoro-1-piperidyl]acetic acid (90.96 mg, 216.36 μmol), N,N-diisopropylethylamine (116.51 mg, 901.49 μmol, 157.02 μL) and HATU (75.41 mg, 198.33 μmol). The crude compound was purified by reverse phase column chromatography, eluting with 40 to 50% acetonitrile in 0.1% formic acid in water, to afford to afford 6-[2-cyano-3-[[ethyl (methyl)sulfamoyl]amino]-6-fluoro-phenoxy]-3-[(3S)-8-[2-[4-[3-(2,6-dioxo-3-piperidyl)-1-methyl-indazol-6-yl]-3,3-difluoro-1-piperidyl]acetyl]-8-azaspiro[4.5]decan-3-yl]-4-oxo-quinazoline (16.44 mg, 15.76 μmol, 9% yield) as off-white solid. LCMS m/z (ESI): 957.2 $[M+H]^+$. $^1$H NMR (400 MHz, DMSO-$d_6$): δ=10.91 (s, 1H), 10.20 (s, 1H), 8.45 (s, 1H), 7.71-7.80 (m, 1H), 7.79 (d, J=8.80 Hz, 1H), 7.67 (t, J=8.40 Hz, 2H), 7.53 (s, 1H), 7.46 (s, 1H), 7.37 (s, 1H), 7.09 (d, J=8.00 Hz, 1H), 5.01-5.10 (m, 1H), 4.31-4.39 (m, 1H), 4.00 (s, 3H), 3.51-3.61 (m, 2H), 3.25-3.45 (m, 4H), 3.10-3.25 (m, 4H), 2.99 (d, J=9.60 Hz, 1H), 2.75 (s, 3H), 2.60-2.71 (m, 3H), 2.38-2.58 (m, 2H), 2.02-2.31 (m, 5H), 1.78-1.91 (m, 3H), 1.40-1.77 (m, 5H), 1.05 (t, J=7.20 Hz, 3H).

Example 161

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]-3,3-difluoropiperidin-1-yl]acetyl]-1-oxa-8-azaspiro[4.5]decane Step 5: Target compound was prepared via HATU mediated acid-amine coupling reaction (Procedure B-E). Amide coupling was carried out using (3R)-3-[6-[2-cyano-3-[[ethyl (methyl)sulfamoyl]amino]-6-fluoro-phenoxy]-4-oxo-quinazolin-3-yl]-1-oxa-8-azaspiro[4.5]decane (70 mg, 125.76 μmol), 2-[4-[3-(2,6-dioxo-3-piperidyl)-1-methyl-indazol-6-yl]-3,3-difluoro-1-piperidyl]acetic acid (63.45 mg, 150.91 μmol), N,N-diisopropylethylamine (81.27 mg, 628.81 μmol, 109.53 μL) and HATU (52.60 mg, 138.34 μmol). The crude compound was purified by reverse phase column chromatography, eluting with 40-50% acetonitrile in 0.1% formic acid in water, to afford (3R)-3-[6-[2-cyano-3-[[ethyl (methyl)sulfamoyl]amino]-6-fluoro-phenoxy]-4-oxo-quinazolin-3-yl]-8-[2-[4-[3-(2,6-dioxo-3-piperidyl)-1-methyl-indazol-6-yl]-3,3-difluoro-1-piperidyl]acetyl]-1-oxa-8-azaspiro[4.5]decane (13.03 mg, 12.40 μmol, 10% yield) as off-white solid. LCMS m/z (ESI): 959.2 $[M+H]^+$. $^1$H NMR (400 MHz, DMSO-$d_6$): δ=10.90 (s, 1H), 10.21 (s, 1H), 8.37 (s, 1H), 7.81-7.91 (m, 1H), 7.83 (d, J=11.60 Hz, 1H), 7.70 (dd, J=2.80, 9.00 Hz, 1H), 7.66 (dd, J=2.80, 8.60 Hz, 1H), 7.53 (s, 1H), 7.45-7.53 (m, 1H), 7.37 (d, J=2.40 Hz, 1H), 7.09 (d, J=8.00 Hz, 1H), 5.28-5.38 (m, 1H), 4.31-4.38 (m, 1H), 4.09-4.20 (m, 2H), 4.00 (d, J=4.00 Hz, 3H), 3.50-3.74 (m, 3H), 3.30-3.45 (m, 3H), 3.11-3.31 (m, 4H), 2.95-3.05 (m, 1H), 2.79 (s, 3H), 2.35-2.71 (m, 4H), 2.05-2.31 (m, 5H), 1.51-1.91 (m, 5H), 1.06 (t, J=7.20 Hz, 3H).

Example 162

6-[2-cyano-3-[[ethyl(methyl)sulfamoyl]amino]-6-fluorophenoxy]-3-[(3S)-8-[2-[4-[3-(2,4-dioxo-1,3-diazinan-1-yl)-5-fluoro-1-methylindazol-6-yl]piperazin-1-yl]acetyl]-8-azaspiro [4.5]decan-3-yl]-4-oxoquinazoline

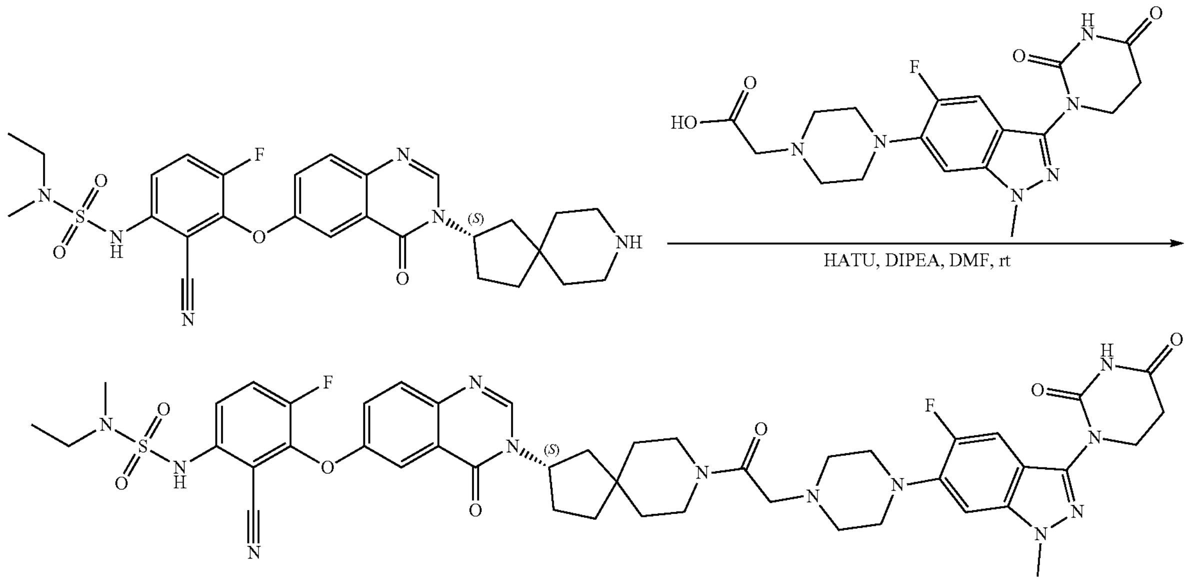

Target compound was prepared via HATU mediated acid-amine coupling reaction (Procedure B-E). Amide coupling was carried out using 2-[4-[3-(2,4-dioxohexahydropyrimidin-1-yl)-5-fluoro-1-methyl-indazol-6-yl]piperazin-1-yl] acetic acid (35.04 mg, 79.48 μmol), 3-[(3S)-8-azaspiro[4.5] decan-3-yl]-6-[2-cyano-3-(dimethylsulfamoylamino)-6-fluoro-phenoxy]-4-oxo-quinazoline (50 mg, 86.64 μmol), N,N-diisopropylethylamine (55.99 mg, 433.22 μmol, 75.46 μL) and HATU (49.42 mg, 129.97 μmol). The crude compound was purified by reverse phase column chromatography, eluting with 35% acetonitrile in 0.1% ammonium acetate in water, to afford 6-[2-cyano-3-[[ethyl(methyl)sulfamoyl]amino]-6-fluoro-phenoxy]-3-[(3S)-8-[2-[4-[3-(2,4-dioxohexahydropyrimidin-1-yl)-5-fluoro-1-methyl-indazol-6-yl]piperazin-1-yl]acetyl]-8-azaspiro[4.5]decan-3-yl]-4-oxo-quinazoline (16 mg, 16.65 μmol, 19% yield) as an off-white solid. LCMS m/z (ESI): 940.8 $[M+H]^+$; $^1$H NMR (400 MHz, DMSO-$d_6$): δ=10.54 (s, 1H), 10.16 (bs, 1H), 8.44 (s, 1H), 7.78 (d, J=8.80 Hz, 1H), 7.73 (s, 1H), 7.68 (d, J=2.80 Hz, 1H), 7.43 (d, J=5.60 Hz, 1H), 7.39 (s, 1H), 7.35 (s, 1H), 7.15 (d, J=6.80 Hz, 1H), 5.05 (t, J=9.20 Hz, 1H), 3.95 (s, 3H), 3.90 (t, J=6.80 Hz, 2H), 3.54-3.44 (m, 3H), 3.14-3.09 (m, 6H), 2.76-2.73 (m, 6H), 2.68 (s, 3H), 2.10-2.05 (m, 3H), 1.86-1.81 (m, 3H), 1.62-1.44 (m, 7H), 1.05 (t, J=7.20 Hz, 3H).

Example 163

9-[6-[2-cyano-3-[[ethyl(methyl)sulfamoyl]amino]-6-fluorophenoxy]-4-oxoquinazolin-3-yl]-3-[2-[4-[3-(2,4-dioxo-1,3-diazinan-1-yl)-5-fluoro-1-methylindazol-6-yl]piperazin-1-yl]acetyl]-3-azaspiro[5.5]undecane

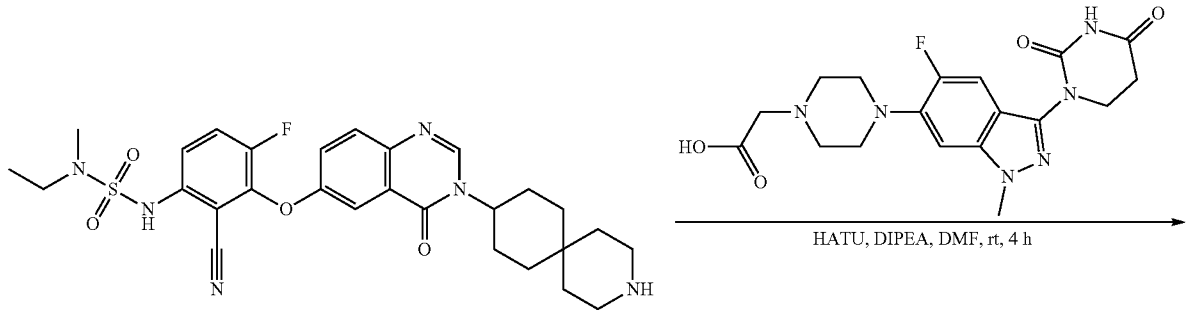

-continued

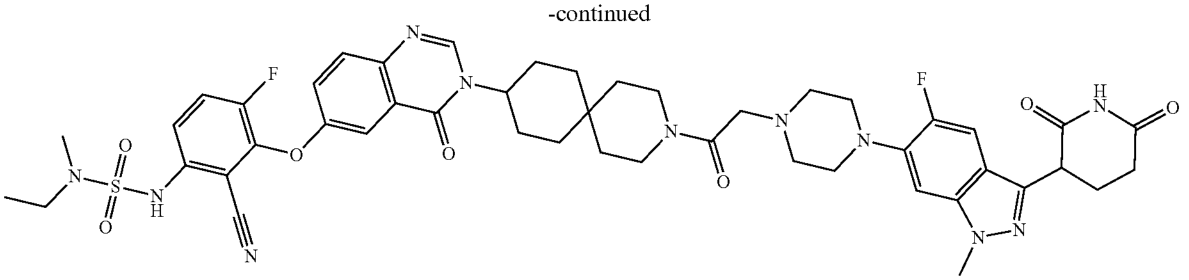

Target compound was prepared via HATU mediated acid-amine coupling reaction (Procedure B-E). Amide coupling was carried out using 2-[4-[3-(2,4-dioxohexahydropyrimidin-1-yl)-5-fluoro-1-methyl-indazol-6-yl]piperazin-1-yl] acetic acid (0.035 g, 79.39 μmol), 9-[6-[2-cyano-3-[[ethyl (methyl)sulfamoyl]amino]-6-fluoro-phenoxy]-4-oxo-quinazolin-3-yl]-3-azaspiro[5.5]undecane (49.66 mg, 82.07 μmol), N,N-diisopropylethylamine (102.61 mg, 793.91 μmol, 138.28 μL) and HATU (33.21 mg, 87.33 μmol). The crude compound was purified by reverse phase column chromatography, eluting with 46% acetonitrile in 0.1% formic acid in water, to afford 9-[6-[2-cyano-3-[[ethyl (methyl)sulfamoyl]amino]-6-fluoro-phenoxy]-4-oxo-quinazolin-3-yl]-3-[2-[4-[3-(2,4-dioxohexahydropyrimidin-1-yl)-5-fluoro-1-methyl-indazol-6-yl]piperazin-1-yl]acetyl]-3-azaspiro[5.5]undecane (4.83 mg, 4.95 μmol, 6% yield) as an off-white solid. LCMS m/z (ESI): 956.2 $[M+H]^+$; $^1H$ NMR (400 MHz, DMSO-$d_6$): δ=10.55 (s, 1H), 10.17 (s, 1H), 8.52 (s, 1H), 7.78 (dd, J=2.00, 8.80 Hz, 2H), 7.68 (d, J=9.60 Hz, 1H), 7.44 (d, J=3.60 Hz, 1H), 7.37 (d, J=14.40 Hz, 1H), 7.15 (d, J=7.20 Hz, 1H), 4.55 (s, 1H), 3.96 (s, 3H), 3.90 (t, J=6.80 Hz, 2H), 3.49 (s, 5H), 3.15-3.11 (m, 6H), 2.87 (s, 7H), 2.50-2.49 (m, 3H), 2.06 (d, J=11.20 Hz, 2H), 1.86 (d, J=12.00 Hz, 2H), 1.74-1.64 (m, 4H), 1.40-1.24 (m, 5H), 1.04 (t, J=7.20 Hz, 3H).

Example 164

(3R)-3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-5-fluoro-1-methylindazol-6-yl]piperazin-1-yl]acetyl]-1-oxa-8-azaspiro[4.5]decane

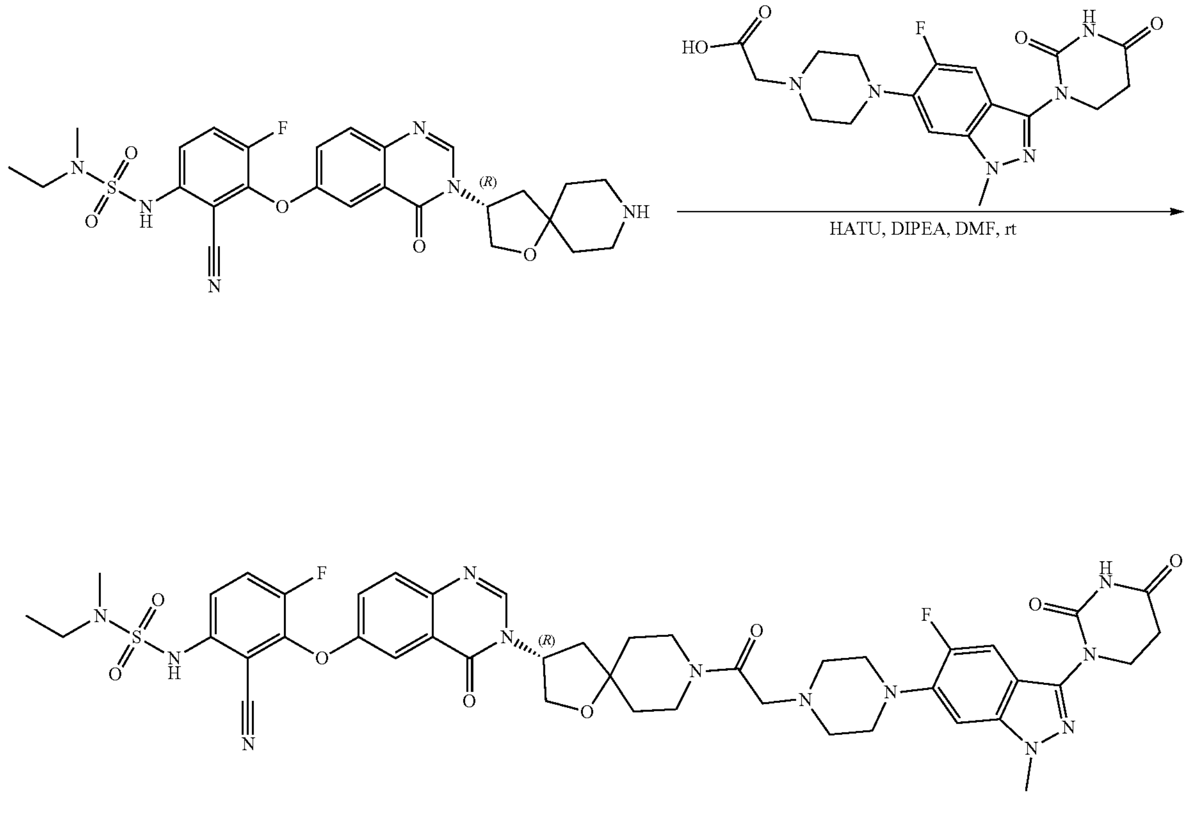

The title compound was prepared via HATU mediated acid-amine coupling reaction (Procedure B-E). Amide coupling was carried out using (3R)-3-[6-[2-cyano-3-[[ethyl (methyl)sulfamoyl]amino]-6-fluoro-phenoxy]-4-oxo-quinazolin-3-yl]-1-oxa-8-azaspiro[4.5]decane (55 mg, 74.19 μmol), 2-[4-[3-(2,4-dioxohexahydropyrimidin-1-yl)-5-fluoro-1-methyl-indazol-6-yl]piperazin-1-yl]acetic acid (34.89 mg, 68.05 μmol), N,N-diisopropylethylamine (38.35 mg, 296.76 μmol, 51.69 μL) and HATU (28.21 mg, 74.19 μmol). The crude compound was purified by reverse phase column chromatography, eluting with 40% acetonitrile in 0.1% formic acid in water, to afford (3R)-3-[6-[2-cyano-3-[[ethyl(methyl)sulfamoyl]amino]-6-fluoro-phenoxy]-4-oxo-quinazolin-3-yl]-8-[2-[4-[3-(2,4-dioxohexahydropyrimidin-1-yl)-5-fluoro-1-methyl-indazol-6-yl]piperazin-1-yl] acetyl]-1-oxa-8-azaspiro[4.5]decane (6 mg, 5.71 μmol, 8% yield) as off-white solid. LCMS m/z (ESI): 943.2 $[M+H]^+$; $^1H$ NMR (400 MHz, DMSO-$d_6$): δ=10.55 (s, 1H), 10.14 (s, 1H), 8.36 (s, 1H), 7.86 (t, J=10.00 Hz, 1H), 7.80 (d, J=8.80 Hz, 1H), 7.70 (d, J=8.80 Hz, 1H), 7.51-7.49 (m, 1H), 7.39 (d, J=17.60 Hz, 2H), 7.19 (s, 1H), 5.30 (s, 1H), 4.15 (d, J=15.20 Hz, 2H), 3.97 (s, 3H), 3.90 (t, J=6.40 Hz, 2H), 3.81-3.72 (m, 2H), 3.48-3.34 (m, 3H), 3.17-3.15 (m, 5H), 2.79 (s, 3H), 2.75 (t, J=6.40 Hz, 2H), 2.50-2.3.47 (m, 4H), 2.12-2.11 (m, 1H), 1.83-1.56 (m, 5H), 1.06 (t, J=7.20 Hz, 3H).

Example 165

(3R)—N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxo-quinazolin-6-yl]oxy-4-fluorophenyl]-3-fluoropyrrolidine-1-sulfonamide

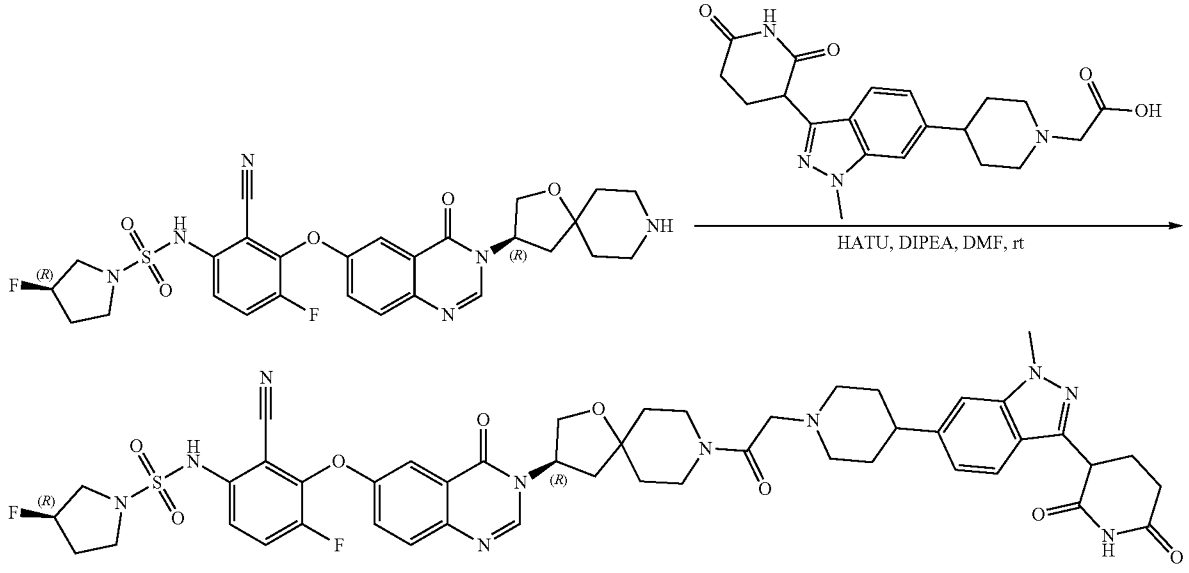

Target compound was prepared via HATU mediated acid-amine coupling reaction (Procedure B-E). Amide coupling was carried out using (3R)—N-[2-cyano-4-fluoro-3-[3-[(3R)-1-oxa-8-azaspiro[4.5]decan-3-yl]-4-oxo-quinazolin-6-yl]oxy-phenyl]-3-fluoro-pyrrolidine-1-sulfonamide (70 mg, 99.99 μmol), 2-[4-[3-(2,6-dioxo-3-piperidyl)-1-methyl-indazol-6-yl]-1-piperidyl]acetic acid (38.44 mg, 91.33 μmol), N,N-diisopropylethylamine (12.92 mg, 99.99 μmol, 17.42 μL) and HATU (38.02 mg, 99.99 μmol). The crude compound was purified by reverse phase column chromatography, eluting with 50% acetonitrile in 0.1% formic acid in water, to afford (3R)—N— [2-cyano-3-[3-[(3R)-8-[2-[4-[3-(2,6-dioxo-3-piperidyl)-1-methyl-indazol-6-yl]-1-piperidyl]acetyl]-1-oxa-8-azaspiro[4.5]decan-3-yl]-4-oxo-quinazolin-6-yl]oxy-4-fluoro-phenyl]-3-fluoro-pyrrolidine-1-sulfonamide (16 mg, 15.62 μmol, 16% yield) as an off-white solid. LCMS m/z (ESI): 953.2 $[M+H]^+$; $^1H$ NMR (400 MHz, DMSO-$d_6$): δ=10.91 (s, 1H), 9.59 (s, 1H), 8.36 (s, 1H), 7.79 (d, J=8.80 Hz, 2H), 7.68 (d, J=8.80 Hz, 2H), 7.46 (d, J=24.40 Hz, 1H), 7.39 (d, J=2.40 Hz, 2H), 7.06 (d, J=7.20 Hz, 1H), 5.39-5.26 (m, 2H), 4.37-4.33 (m, 2H), 4.18-4.14 (m, 2H), 4.00 (s, 3H), 3.82-3.79 (m, 1H), 3.58-3.34 (m, 7H), 3.11-2.97 (m, 4H), 2.68-2.38 (m, 4H), 2.15-1.85 (m, 9H), 1.77-1.58 (m, 5H).

Example 166
6-[2-chloro-3-[[ethyl(methyl)sulfamoyl]amino]-6-fluorophenoxy]-3-[(3S)-8-[2-[4-[3-(2,6-dioxopiperidin-3-yl)-1-methylindazol-6-yl]piperidin-1-yl]acetyl]-8-azaspiro[4.5]decan-3-yl]-4-oxoquinazoline
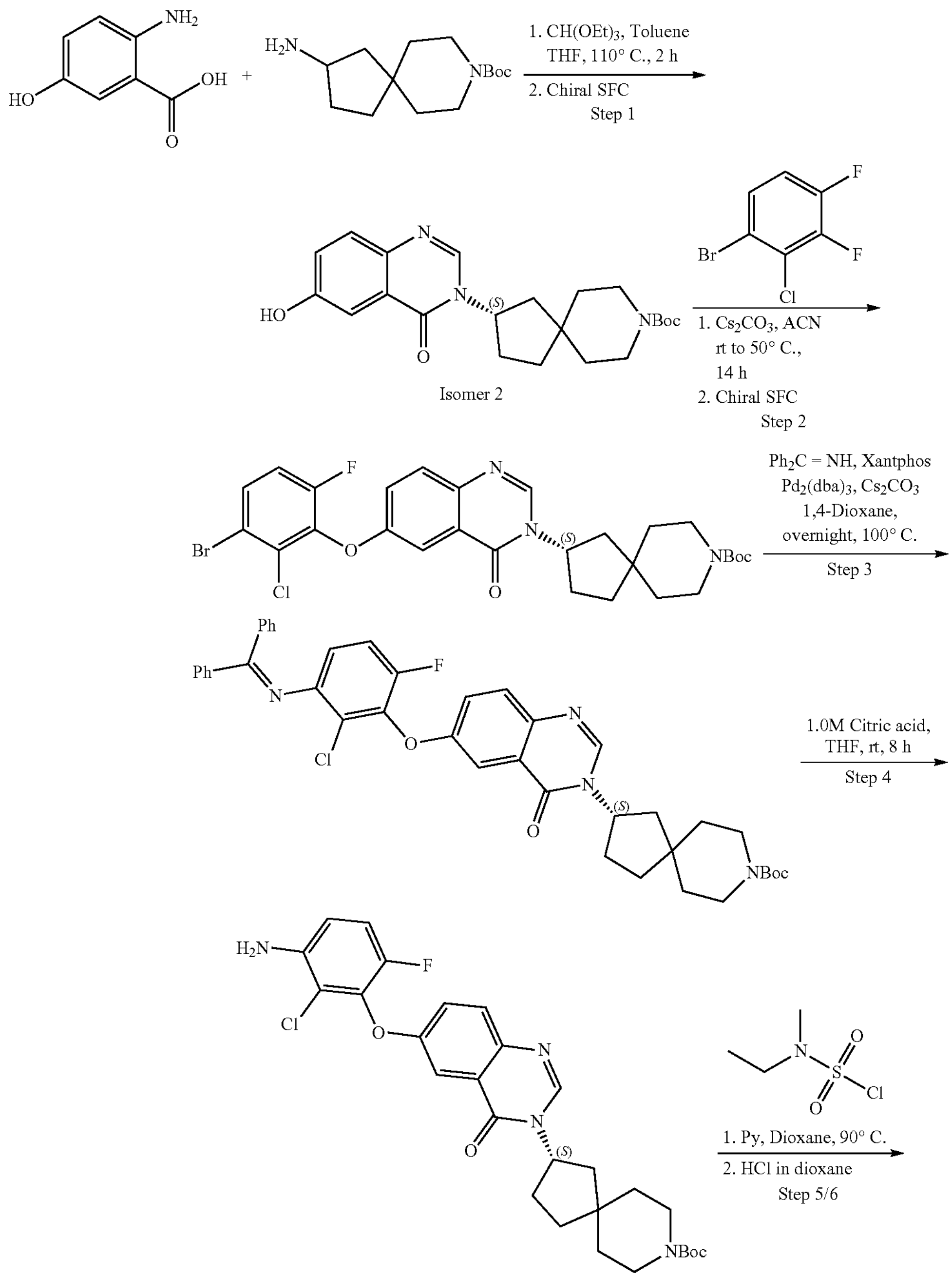

-continued

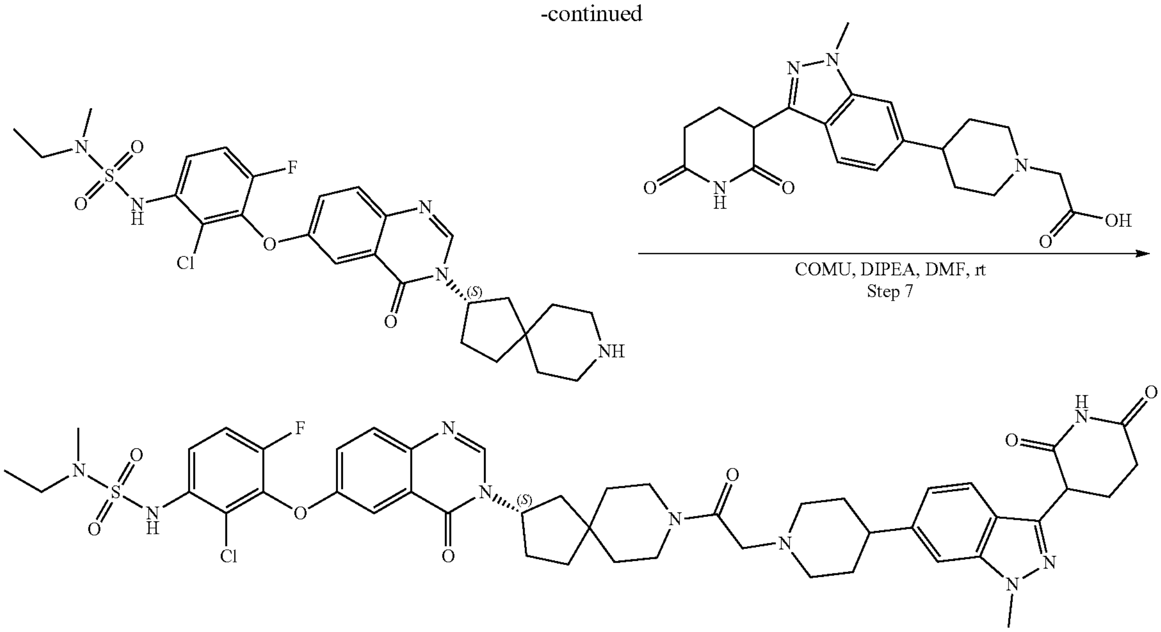

Step 1: Quinazolinone intermediate was synthesized by following general procedure for cyclization (Procedure B-A) using 2-amino-5-hydroxy-benzoic acid (3.31 g, 21.62 mmol), tert-butyl 3-amino-8-azaspiro[4.5]decane-8-carboxylate (5 g, 19.66 mmol), triethyl orthoformate (7.28 g, 49.14 mmol, 8.17 mL) and acetic acid (118.04 mg, 1.97 mmol, 112.42 μL). The desired compound was purified from crude by silica gel flash column chromatography using 0-80% ethyl acetate in petroleum ether as eluent to afford racemic tert-butyl 2-(6-hydroxy-4-oxoquinazolin-3(4H)-yl)-8-azaspiro[4.5]decane-8-carboxylate (4.4 g) as an off-white solid. 3.7 g of racemic mixture was submitted to chiral SFC purification and second eluting product tert-butyl (3S)-3-(6-hydroxy-4-oxo-quinazolin-3-yl)-8-azaspiro[4.5]decane-8-carboxylate (1.2 g, 3.00 mmol, 15% yield) as an off-white solid is the desired isomer. LCMS m/z (ESI): 400.3 $[M+H]^+$.

Step 2: To a solution of tert-butyl (3S)-3-(6-hydroxy-4-oxo-quinazolin-3-yl)-8-azaspiro[4.5]decane-8-carboxylate (0.8 g, 2.00 mmol) in N,N-DIMEHTYLFORMAMIDE (10 mL) was added cesium carbonate (1.63 g, 5.01 mmol) and 1-bromo-2-chloro-3,4-difluoro-benzene (683.19 mg, 3.00 mmol) at rt under nitrogen. The resulting solution was heated to 60° C. for 12 h. After completion, the resulting solution was diluted with water (15 ml), and extracted with ethyl acetate (2×30 ml). The separated organic layer was dried over sodium sulfate, filtered and concentrated under reduced pressure. The resulting crude product was purified by silica gel (50 g SNAP) column chromatography using ethyl acetate-petroleum ether (0-70%) to afford tert-butyl (3S)-3-[6-(3-bromo-2-chloro-6-fluoro-phenoxy)-4-oxo-quinazolin-3-yl]-8-azaspiro[4.5]decane-8-carboxylate (0.5 g, 720.78 μmol, 36% yield) as brown liquid. LCMS m/z (ESI): 607.8[$[M+H]^+$.

Step 3: To a stirred solution of diphenylmethanimine (223.96 mg, 1.24 mmol, 207.37 μL) and tert-butyl(3S)-3-[6-(3-bromo-2-chloro-6-fluoro-phenoxy)-4-oxo-quinazolin-3-yl]-8-azaspiro[4.5]decane-8-carboxylate (0.5 g, 823.85 μmol) in dioxane (5 mL) was added cesium carbonate (805.27 mg, 2.47 mmol) and the mixture was degassed with nitrogen for 5 minutes. Xantphos (95.34 mg, 164.77 μmol) and Tris(dibenzylideneacetone)dipalladium(0) (75.44 mg, 82.38 μmol) was added and the resulting mixture was stirred for 16 h at 100° C. After completion, the reaction was diluted with water (15 mL) and extracted with ethyl acetate (2×35 mL). Combined organic layers were dried over sodium sulfate and concentrated under reduced pressure to afford crude product. The resulting crude product was purified by silica gel (25 g SNAP) column chromatography using ethyl acetate-petroleum ether (0-60%) to afford tert-butyl (3S)-3-[6-[3-(benzhydrylideneamino)-2-chloro-6-fluoro-phenoxy]-4-oxo-quinazolin-3-yl]-8-azaspiro[4.5]decane-8-carboxylate (0.36 g, 331.22 μmol, 40% yield) as semi solid. LCMS m/z (ESI): 707.0 $[M+H]^+$ Step 4: To a stirred solution of tert-butyl (3S)-3-[6-[3-(benzhydrylideneamino)-2-chloro-6-fluoro-phenoxy]-4-oxo-quinazolin-3-yl]-8-azaspiro[4.5]decane-8-carboxylate (0.5 g, 706.98 μmol) in THF (5 mL) was added citric acid in water (1.0 M, 5 mL) and the resulting mixture was stirred for 16 h at room temperature. After completion, the reaction was diluted with water (10 mL) and ethyl acetate (20 mL). After separation, the aqueous layer was back extracted by ethyl acetate (20 mL). Combined organic layers were dried over sodium sulfate and concentrated under reduced pressure. The resulting crude product was purified by silica gel (25 g) column chromatography using ethyl acetate-petroleum ether (0-60%) to afford tert-butyl(3S)-3-[6-(3-amino-2-chloro-6-fluoro-phenoxy)-4-oxo-quinazolin-3-yl]-8-azaspiro[4.5]decane-8-carboxylate (0.23 g, 331.47 μmol, 47% yield) as brown viscous solid. LCMS m/z (ESI): 543.2 $[M+H]^+$.

Step 5: To a solution of tert-butyl (3S)-3-[6-(3-amino-2-chloro-6-fluoro-phenoxy)-4-oxo-quinazolin-3-yl]-8-azaspiro[4.5]decane-8-carboxylate (0.23 g, 423.55 μmol) in 1,4-dioxane (3 mL) were added pyridine (335.03 mg, 4.24 mmol, 342.56 μL) and N-ethyl-N-methyl-sulfamoyl chloride (400.56 mg, 2.54 mmol, 312.94 μL) at rt under nitrogen atmosphere. The resulting solution was heated at 90° C. for 12 hours. After completion, the reaction mixture was diluted with ethyl acetate (20 ml) and washed with water (5 ml). The organic layer was dried over sodium sulfate, filtered, and evaporated under reduced pressure. The crude compound was purified by silica gel flash column chromatography with 70% ethyl acetate in pet ether as a eluent to afford tert-butyl (3S)-3-[6-[2-chloro-3-[[ethyl(methyl)sulfamoyl]amino]-6-fluoro-phenoxy]-4-oxo-quinazolin-3-yl]-8-azaspiro[4.5]decane-8-carboxylate (0.11 g, 113.93 μmol, 27% yield) as a brown liquid. LCMS m/z (ESI): 607.8 $[M+H]^+$.

Step 6: To a solution of tert-butyl (3S)-3-[6-[2-chloro-3-[[ethyl(methyl)sulfamoyl]amino]-6-fluoro-phenoxy]-4-oxo-quinazolin-3-yl]-8-azaspiro[4.5]decane-8-carboxylate (0.11 g, 165.62 μmol) in dichloromethane (1 mL) was added hydrogen chloride solution in 1,4-dioxane (4.0 M, 1 mL) at 0° C. under nitrogen. The resulting solution was stirred at RT for 4 h. After completion, the resulting solution was concentrated under reduced pressure to afford 3-[(3S)-8-azaspiro[4.5]decan-3-yl]-6-[2-chloro-3-[[ethyl(methyl)sulfamoyl]amino]-6-fluoro-phenoxy]-4-oxo-quinazoline (0.1 g, 117.23 μmol, 71% yield) as a viscous solid. LCMS m/z (ESI): 564.0 $[M+H]^+$.

Step 7: Target compound was prepared via COMU mediated acid-amine coupling reaction (Procedure B—F). Amide coupling was carried out using 3-[(3S)-8-azaspiro[4.5]decan-3-yl]-6-[2-chloro-3-[[ethyl(methyl)sulfamoyl]amino]-6-fluoro-phenoxy]-4-oxo-quinazoline (50 mg, 83.26 μmol), 2-[4-[3-(2,6-dioxo-3-piperidyl)-1-methyl-indazol-6-yl]-1-piperidyl]acetic acid (32.01 mg, 76.05 μmol), N,N-diisopropylethylamine (53.80 mg, 416.30 μmol, 72.51 μL), and (1-Cyano-2-ethoxy-2-oxoethylidenaminooxy)dimethyl-amino-morpholino-carbenium hexafluorophosphate (53.49 mg, 124.89 μmol). The crude compound was purified by reverse phase column chromatography, eluting with 35% acetonitrile in 0.1% formic acid in water, to afford 6-[2-chloro-3-[[ethyl(methyl)sulfamoyl]amino]-6-fluoro-phenoxy]-3-[(3S)-8-[2-[4-[3-(2,6-dioxo-3-piperidyl)-1-methyl-indazol-6-yl]-1-piperidyl]acetyl]-8-azaspiro[4.5]decan-3-yl]-4-oxo-quinazoline (15 mg, 14.00 μmol, 17% yield) as off-white solid. LCMS m/z (ESI): 930.2 $[M+H]^+$. $^1H$ NMR (400 MHz, DMSO-$d_6$): δ=10.89 (s, 1H), 8.42 (bs, 1H), 8.16 (s, 1H), 7.77 (d, J=9.20 Hz, 1H), 7.63 (t, J=8.00 Hz, 2H), 7.53 (d, J=7.60 Hz, 2H), 7.43 (s, 1H), 7.21 (s, 1H), 7.04 (d, J=9.20 Hz, 1H), 5.03-5.02 (m, 1H), 4.33 (q, J=4.80 Hz, 1H), 3.97 (s, 3H), 3.55 (d, J=12.80 Hz, 3H), 3.11 (q, J=7.20 Hz, 2H), 3.02-3.00 (m, 2H), 2.75 (s, 3H), 2.68-2.56 (m, 4H), 2.30-2.06 (m, 7H), 1.83-1.68 (m, 7H), 1.61-1.57 (m, 4H), 1.43-1.25 (m, 2H), 1.02 (t, J=7.20 Hz, 3H).

Example 167

N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]cyclopentanesulfonamide

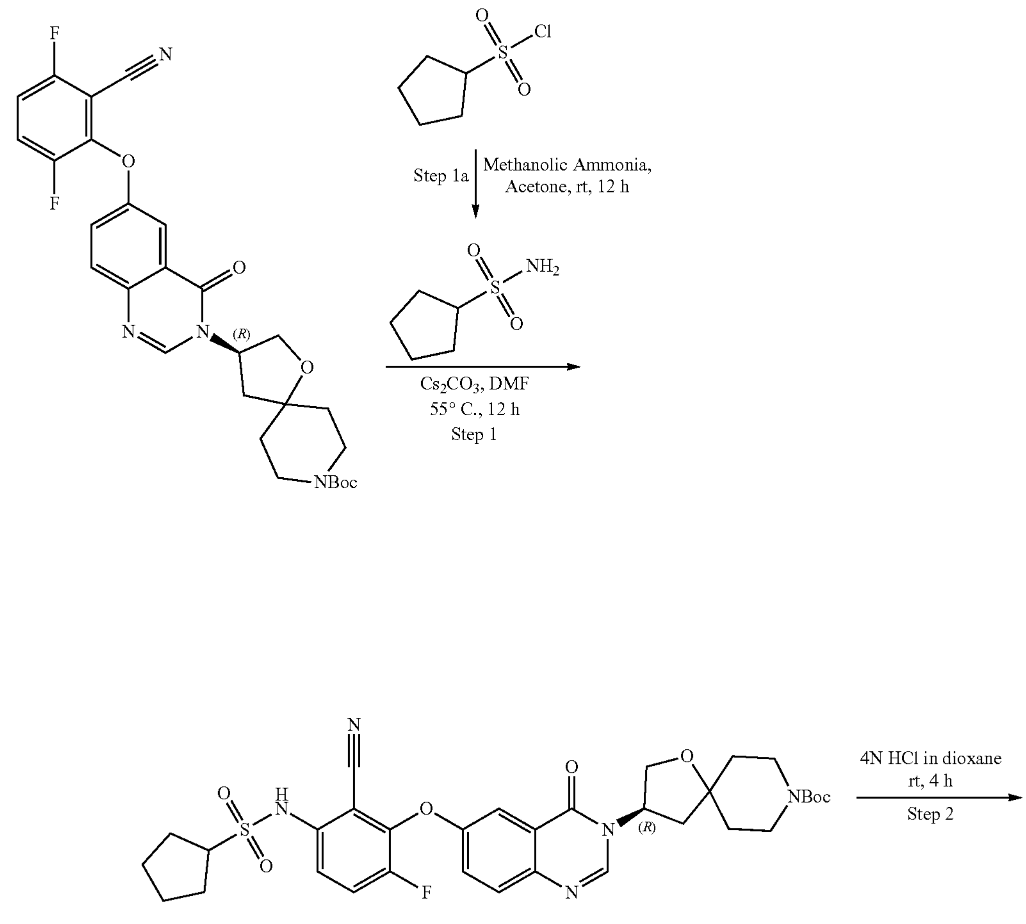

-continued

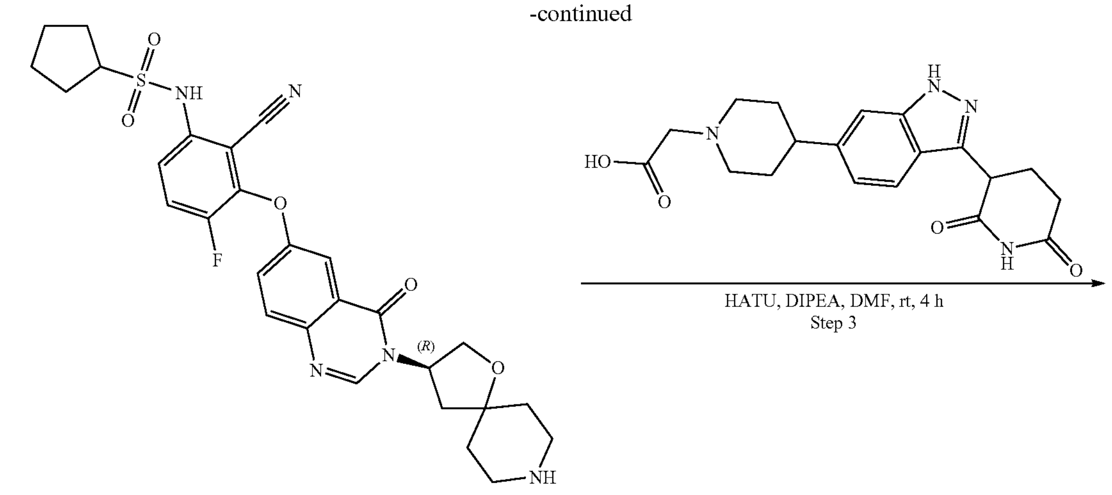

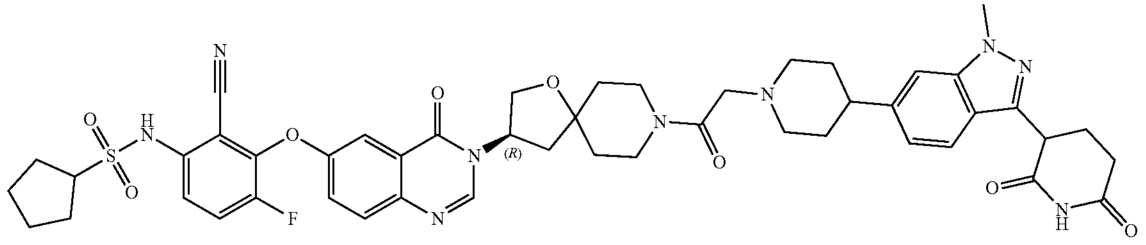

Step 1a: To a solution of cyclopentane sulfonyl chloride (2.00 g, 11.86 mmol, 1.50 mL) in acetone (10 mL) was added ammonia solution 25% (18.00 g, 513.55 mmol, 20 mL) slowly at 5° C. The reaction mixture was stirred at room temperature for 12 h under nitrogen atmosphere. After completion, the reaction mixture was concentrated under reduced pressure. The crude compound was purified by column chromatography (silica gel) using 40-50% ethyl acetate in pet ether as eluent to afford cyclopentane sulphonamide (0.74 g, 4.96 mmol, 42% yield) as a brown solid. $^1$H NMR (400 MHz, DMSO-$d_6$): δ=6.69 (s, 2H), 1.89-1.99 (m, 4H), 1.66-1.57 (m, 4H).

Step 1: Sulfamoylated quinazolinone intermediate was synthesized by following general (Procedure B—C) using tert-butyl (3R)-3-[6-(2-cyano-3,6-difluoro-phenoxy)-4-oxo-quinazolin-3-yl]-1-oxa-8-azaspiro[4.5]decane-8-carboxylate (0.22 g, 408.51 μmol), cesium carbonate (399.30 mg, 1.23 mmol) and cyclopentane sulphonamide (182.86 mg, 1.23 mmol). The reaction mixture was stirred at 55° C. for 12 h. After completion, the reaction mixture was diluted with water (20 mL), and precipitated solid was filtered off. The aqueous layer was extracted with ethyl acetate (3×50 mL). The combined organic layers were washed with cold water (3×30 mL), dried over sodium sulfate, filtered and concentrated under reduced pressure to afford tert-butyl (3R)-3-[6-[2-cyano-3-(cyclopentylsulfonylamino)-6-fluoro-phenoxy]-4-oxo-quinazolin-3-yl]-1-oxa-8-azaspiro[4.5]decane-8-carboxylate (0.25 g, 319.06 μmol, 78% yield) as light brown viscous solid. LCMS m/z (ESI): 666.0 [M−H]$^-$.

Step 2: The requisite amine was synthesized by 4M HCl in Dioxane mediated N-Boc deprotection (Procedure B-D). N-Boc deprotection was done on tert-butyl (3R)-3-[6-[2-cyano-3-(cyclopentylsulfonylamino)-6-fluoro-phenoxy]-4-oxo-quinazolin-3-yl]-1-oxa-8-azaspiro[4.5]decane-8-carboxylate (0.25 g, 374.39 μmol) using hydrogen chloride, 4M in 1,4-dioxane, 99% (3 mL) to afford N-[2-cyano-4-fluoro-3-[3-[(3R)-1-oxa-8-azaspiro[4.5]decan-3-yl]-4-oxo-quinazolin-6-yl]oxy-phenyl]cyclopentanesulfonamide (0.25 g, 374.16 μmol, 100% yield) as a light orange viscous solid. LCMS m/z (ESI): 568.2 [M+H]$^+$.

Step 3: Target compound was prepared via HATU mediated acid-amine coupling reaction (Procedure B-E). Amide coupling was carried out using 2-[4-[3-(2,6-dioxo-3-piperidyl)-1-methyl-indazol-6-yl]-1-piperidyl]acetic acid (48.77 mg, 115.88 μmol), N-[2-cyano-4-fluoro-3-[3-[(3R)-1-oxa-8-azaspiro[4.5]decan-3-yl]-4-oxo-quinazolin-6-yl]oxy-phenyl]cyclopentanesulfonamide (0.07 g, 115.88 μmol), N,N-diisopropylethylamine (149.76 mg, 1.16 mmol, 201.84 μL) and HATU (48.47 mg, 127.46 μmol). The crude compound was purified by reverse phase column chromatography, eluting with 43% acetonitrile in 0.1% formic acid in water, to afford N-[2-cyano-3-[3-[(3R)-8-[2-[4-[3-(2,6-dioxo-3-piperidyl)-1-methyl-indazol-6-yl]-1-piperidyl]acetyl]-1-oxa-8-azaspiro[4.5]decan-3-yl]-4-oxo-quinazolin-6-yl]oxy-4-fluoro-phenyl]cyclopentanesulfonamide (17.26 mg, 17.48 μmol, 15% yield) as an off-white solid. LCMS m/z (ESI): 935.2 [M+H]$^+$; $^1$H NMR (400 MHz, DMSO-$d_6$): δ=10.90 (s, 1H), 9.86 (s, 1H), 8.35 (s, 1H), 7.77 (d, J=9.20 Hz, 1H), 7.66 (dd, J=9.00, 3.20, Hz, 2H), 7.53 (s, 1H), 7.44 (s, 1H), 7.38 (d, J=2.80 Hz, 1H), 7.06 (d, J=7.60 Hz, 2H), 5.31 (s, 1H), 4.36-4.32 (m, 1H), 4.19-4.13 (m, 3H), 3.99 (s, 3H), 3.79-3.71 (m, 1H), 3.52-3.34 (m, 5H), 2.87-2.71 (m, 1H), 2.63-2.58 (m, 3H), 2.50-2.34 (m, 3H), 2.19-2.10 (m, 3H), 1.93-1.78 (m, 10H), 1.69-1.66 (m, 4H), 1.55-1.51 (m, 3H).

Example 168

N-[2-cyano-3-[3-[(3R)-8-[2-[4-[3-(2,6-dioxopiperidin-3-yl)-1-methylindazol-6-yl]piperidin-1-yl]acetyl]-1-oxa-8-azaspiro[4.5]decan-3-yl]-4-oxoquinazolin-6-yl]oxy-4-fluorophenyl]propane-2-sulfonamide

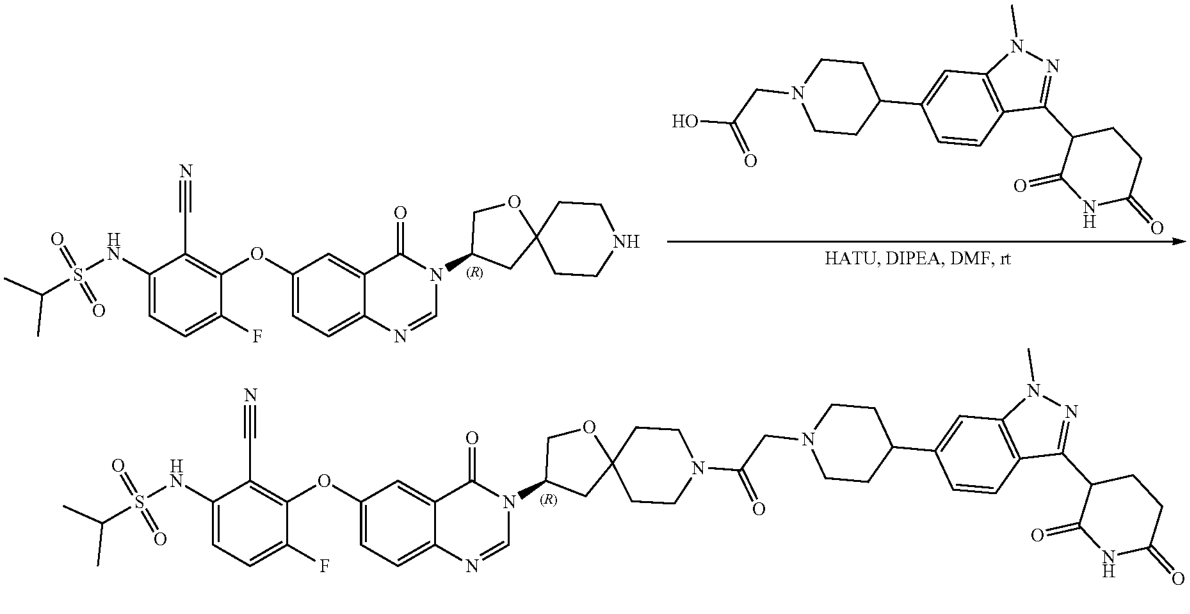

Target compound was prepared via HATU mediated acid-amine coupling reaction (Procedure B-E). Amide coupling was carried out using 2-[4-[3-(2,6-dioxo-3-piperidyl)-1-methyl-indazol-6-yl]-1-piperidyl]acetic acid (65 mg, 154.44 μmol), N-[2-cyano-4-fluoro-3-[3-[(3R)-1-oxa-8-azaspiro[4.5]decan-3-yl]-4-oxo-quinazolin-6-yl]oxy-phenyl]propane-2-sulfonamide (107.13 mg, 185.32 μmol), N,N-diisopropylethylamine (119.76 mg, 926.61 μmol, 161.40 μL) and HATU (70.46 mg, 185.32 μmol). The crude product was purified by C18-reverse phase column chromatography using Isolera (100 g RediSep® Rf C18, Method: 0.1% formic acid in water:acetonitrile) and pure fractions were lyophilized to afford N-[2-cyano-3-[3-[(3R)-8-[2-[4-[3-(2,6-dioxo-3-piperidyl)-1-methyl-indazol-6-yl]-1-piperidyl]acetyl]-1-oxa-8-azaspiro[4.5]decan-3-yl]-4-oxo-quinazolin-6-yl]oxy-4-fluoro-phenyl]propane-2-sulfonamide (23 mg, 23.81 μmol, 15% yield) as an off-white solid. LCMS m/z (ESI): 908.20 $[M+H]^+$; $^1H$ NMR (400 MHz, DMSO-$d_6$): δ=10.90 (s, 1H), 8.35 (s, 1H), 7.77 (d, J=8.80 Hz, 1H), 7.66 (d, J=8.40 Hz, 2H), 7.44-7.38 (m, 4H), 7.06 (s, 1H), 5.40-5.25 (m, 1H), 4.40-4.30 (m, 2H), 4.25-4.10 (m, 2H), 3.99 (s, 3H), 3.82-3.70 (m, 2H), 3.55-3.40 (m, 3H), 3.20-2.70 (m, 4H), 2.70-2.60 (m, 2H), 2.45-2.32 (m, 2H), 2.20-1.50 (m, 12H), 1.26 (d, J=6.00 Hz, 6H).

Example 169

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]cyclohexyl]acetyl]-1-oxa-8-azaspiro[4.5]decane

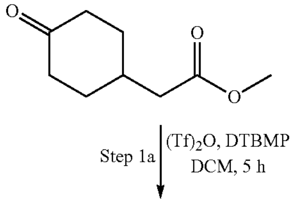

-continued
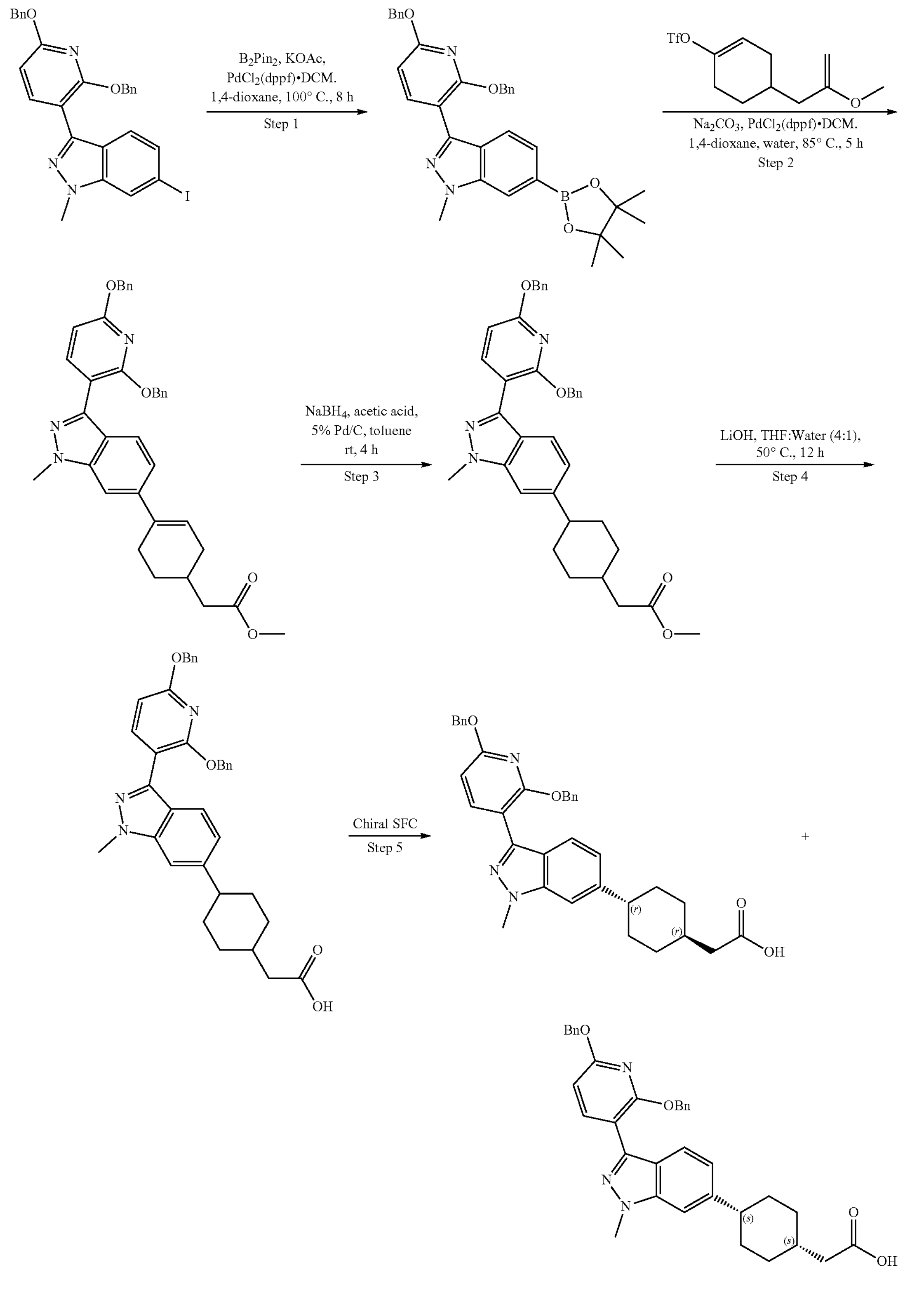

-continued

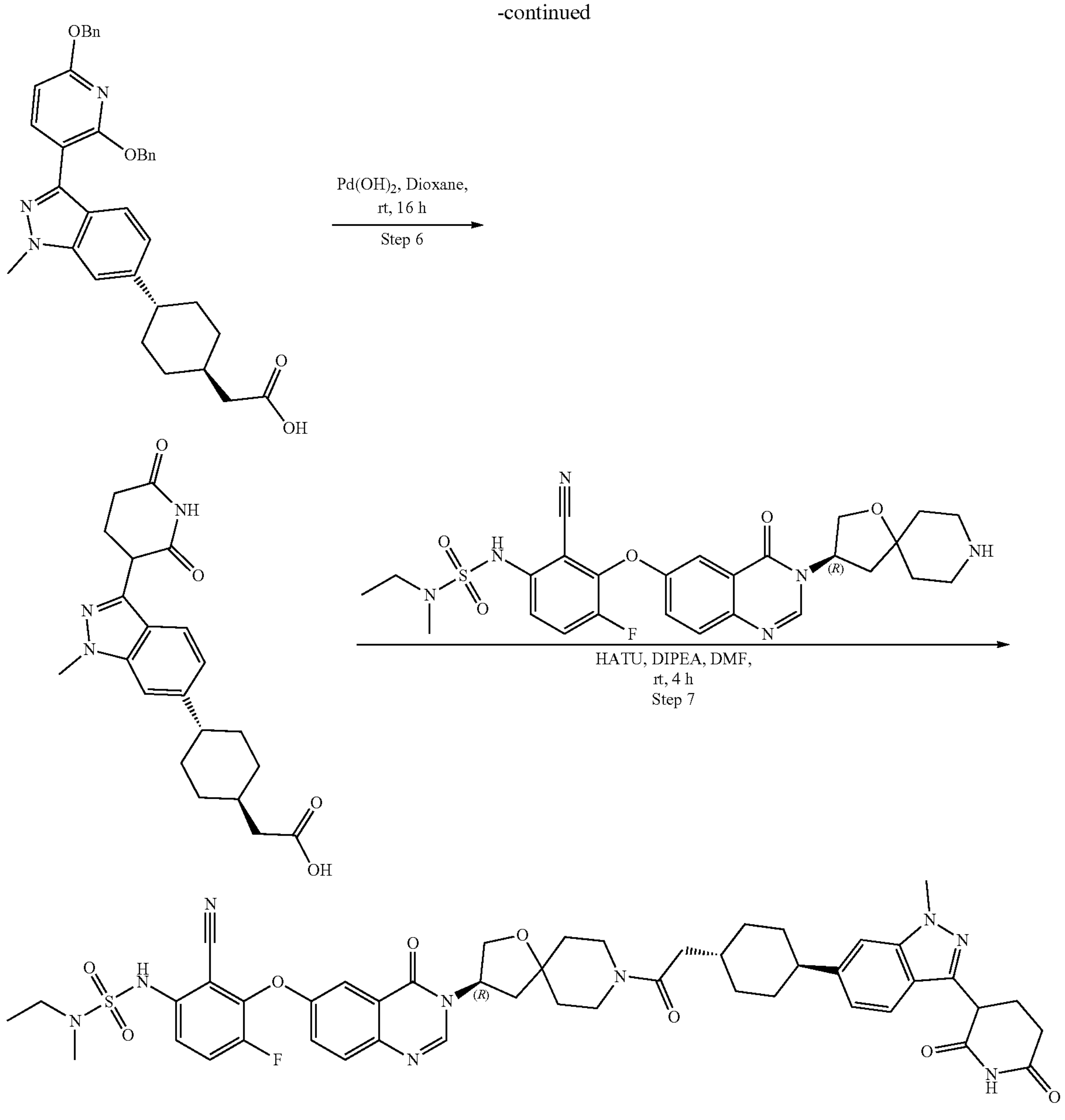

Step 1: A solution of 3-(2,6-dibenzyloxy-3-pyridyl)-6-iodo-1-methyl-indazole (1.9 g, 3.47 mmol) in 1,4-dioxane (30 mL) was taken in a sealed tube and added potassium acetate (1.02 g, 10.41 mmol, 650.92 μL) and 4,4,5,5-tetramethyl-2-(4,4,5,5-tetramethyl-1,3,2-dioxaborolan-2-yl)-1,3,2-dioxaborolane (1.32 g, 5.21 mmol). The reaction mixture was purged with nitrogen gas for 10 minutes, then added Pd(dppf)$Cl_2$·dichloromethane (283.46 mg, 347.10 μmol), again purged with nitrogen gas for 5 minutes and then stirred at 100° C. for 8 h. After completion, the reaction mixture was diluted with water (70 mL), extracted with ethyl acetate (3×150 mL). Combined organic layers dried over sodium sulfate, filtered, and concentrated to afford crude. Desired product was purified from crude by silica gel flash column chromatography by using 20-30% ethyl acetate in petroleum ether as eluent to afford 3-(2,6-dibenzyloxy-3-pyridyl)-1-methyl-6-(4,4,5,5-tetramethyl-1,3,2-dioxaborolan-2-yl)indazole (1.3 g, 1.87 mmol, 54% yield) as a light yellow viscous liquid. LCMS m/z (ESI): 548.2 [M+H]$^+$.

Step 1a: To a stirred solution of methyl 2-(4-oxocyclohexyl)acetate (2 g, 11.75 mmol) in dichloromethane (40 mL), was added 2,6-ditert-butyl-4-methyl-pyridine (2.90 g, 14.10 mmol). The reaction mixture was stirred at room temperature for 30 minutes under nitrogen atmosphere and then cooled the reaction mixture to 0° C. To the reaction mixture trifluoromethanesulfonic anhydride (3.48 g, 12.34 mmol, 2.07 mL) was added dropwise at 0° C. under nitrogen atmosphere. The reaction mixture was stirred at room temperature for 5 h. After completion, the reaction mixture was quenched with saturated sodium bicarbonate solution (70 mL) by dropwise at 0° C. and extracted with dichloromethane (3×100 mL). Combined organic layers dried over sodium sulfate, filtered and concentrated under reduced pressure to afford crude. Desired product was purified from crude by silica gel flash column chromatography by using 5-20% ethyl acetate in petroleum ether as eluent to afford methyl 2-[4-(trifluoromethylsulfonyloxy)cyclohex-3-en-1-yl]acetate (2.6 g, 8.60 mmol, 73% yield) as a colorless liquid. $^1$H-NMR (400 MHz, $CDCl_3$): δ=5.75 (d, J=2.00 Hz, 1H), 3.71 (s, 3H), 2.41-2.52 (m, 1H), 2.31-2.40 (m, 3H), 2.10-2.21 (m, 1H), 1.90-2.01 (m, 2H), 1.48-1.70 (m, 2H).

Step 2: To a stirred solution of 3-(2,6-dibenzyloxy-3-pyridyl)-1-methyl-6-(4,4,5,5-tetramethyl-1,3,2-dioxaborolan-2-yl)indazole (1.2 g, 2.19 mmol) in 1,4-dioxane (20 mL) and water (2 mL) in sealed tube, were added sodium carbonate (696.98 mg, 6.58 mmol, 275.49 μL) and methyl 2-[4-(trifluoromethylsulfonyloxy)cyclohex-3-en-1-yl]acetate (993.84 mg, 3.29 mmol). The reaction mixture was purged with nitrogen gas for 10 minutes, then added Pd(dppf)$Cl_2$·dichloromethane (179.01 mg, 219.20 μmol), again purged with nitrogen gas for 5 minutes and then stirred at 85° C. for 5 h. After completion, the reaction mixture was diluted with water (70 mL), extracted with ethyl acetate (3×150 mL). Combined organic layers dried over sodium sulfate, filtered, and concentrated to afford crude. Desired product was purified from crude by silica gel flash column chromatography by using 20-30% ethyl acetate in petroleum ether as eluent to afford methyl 2-[4-[3-(2,6-dibenzyloxy-3-pyridyl)-1-methyl-indazol-6-yl]cyclohex-3-en-1-yl]acetate (0.8 g, 1.24 mmol, 56% yield) as a light green viscous liquid. LCMS m/z (ESI): 574.2 $[M+H]^+$.

Step 3: To a stirred solution of methyl 2-[4-[3-(2,6-dibenzyloxy-3-pyridyl)-1-methyl-indazol-6-yl]cyclohex-3-en-1-yl]acetate (0.2 g, 348.63 μmol) in toluene (4 mL), was added glacial acetic acid (125.61 mg, 2.09 mmol) and 5% palladium on carbon (0.1 g, 939.67 μmol). The reaction mixture was stirred at room temperature for 5 minutes under nitrogen atmosphere and then sodium borohydride (80 mg) was added and stirred the reaction mixture for 5 minutes. Again, sodium borohydride (80 mg) was added and stirred the reaction mixture for 2 h under nitrogen atmosphere at room temperature. Again, cooled the reaction mixture to 5° C. and sodium borohydride (80 mg) was added. The reaction mixture was stirred at room temperature for 2 h under nitrogen atmosphere. After completion, the reaction mixture was filtered through celite bed and bed washed with THF: toluene mixture (200 mL:50 mL) and ethyl acetate (100 mL). Filtrate was concentrated under reduced pressure to afford crude. Desired product was purified from crude by silica gel flash column chromatography by using 20-30% ethyl acetate in petroleum ether as eluent to afford methyl 2-[4-[3-(2,6-dibenzyloxy-3-pyridyl)-1-methyl-indazol-6-yl]cyclohexyl]acetate (0.12 g, 203.69 μmol, 58% yield) as a light green viscous liquid. LCMS m/z (ESI): 576.2 $[M+H]^+$.

Step 4/Step 5: To a stirred solution of methyl 2-[4-[3-(2,6-dibenzyloxy-3-pyridyl)-1-methyl-indazol-6-yl]cyclohexyl]acetate (0.35 g, 607.96 μmol) in tetrahydrofuran (20 mL) and water (5 mL), was added lithium hydroxide hydrate (510.24 mg, 12.16 mmol, 337.91 μL) at room temperature under nitrogen atmosphere. The reaction mixture was stirred at 50° C. for 12 h. After completion, the reaction mixture was concentrated under reduced pressure, acidified by using 1.5N HCl solution (pH-2) at 0° C. Filtered the solids and washed with water (50 mL), vacuum dried for 4 h to afford Mixture (350 mg, 95% pure). Mixture was purified by chiral SFC purification using Chiralpak OX—H column to afford 2-((1R,4R)-4-(3-(2,6-bis(benzyloxy)pyridin-3-yl)-1-methyl-1H-indazol-6-yl)cyclohexyl)acetic acid (0.12 g, 208.93 μmol, 34% yield) and 2-((1S,4S)-4-(3-(2,6-bis(benzyloxy)pyridin-3-yl)-1-methyl-1H-indazol-6-yl)cyclohexyl) acetic acid (0.15 g, 267.06 μmol, 43.93% yield). LCMS m/z (ESI): 562.2 $[M+H]^+$.

Note: The absolute stereochemistry for the separated isomers was arbitrarily assigned as follows; first eluting peak ($F_1$-3.99 RT) arbitrarily assigned as trans compound (1r,4r) and second eluting peak ($F_2$-4.92 RT) as cis compound (1s, 4s).

Step 6: To a stirred solution of 2-((1R,4R)-4-(3-(2,6-bis(benzyloxy)pyridin-3-yl)-1-methyl-1H-indazol-6-yl)cyclohexyl)acetic acid (0.12 g, 213.65 μmol) in 1,4-dioxane (5 mL), was charged 20% $Pd(OH)_2$ (0.1 g, 712.08 μmol), saturated with hydrogen by bubbling hydrogen gas through for 10 minutes and then subjected to hydrogenation (1 atm) at room temperature for 16 h. After completion, the reaction mixture was purged with nitrogen, catalyst was removed by filtration through celite pad and washed with 1,4-dioxane (200 mL). The filtrate was concentrated under reduced pressure to afford crude 2-((1r,4r)-4-(3-(2,6-dioxopiperidin-3-yl)-1-methyl-1H-indazol-6-yl)cyclohexyl)acetic acid (0.08 g, 205.78 μmol, 96% yield) as an off-white solid. LCMS m/z (ESI): 384.2 $[M+H]^+$.

Step 7: Target compound was prepared via HATU mediated acid-amine coupling reaction (Procedure B-E). Amide coupling was carried out using 2-((1r,4r)-4-(3-(2,6-dioxopiperidin-3-yl)-1-methyl-1H-indazol-6-yl)cyclohexyl)acetic acid (54.52 mg, 129.83 μmol), N,N-diisopropylethylamine (152.55 mg, 1.18 mmol, 205.59 μL), HATU (49.37 mg, 129.83 μmol) and (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (0.07 g, 118.03 μmol). The desired product was purified from crude by reverse phase column chromatography (0.1% formic acid in water:acetonitrile) and fractions were lyophilized to afford (3R)-3-[6-[2-cyano-3-[[ethyl(methyl)sulfamoyl]amino]-6-fluoro-phenoxy]-4-oxo-quinazolin-3-yl]-8-[2-(1r,4r)-[4-[3-(2,6-dioxo-3-piperidyl)-1-methyl-indazol-6-yl]cyclohexyl]acetyl]-1-oxa-8-azaspiro[4.5]decane (27 mg, 27.30 μmol, 23% yield) as an off-white solid. LCMS m/z (ESI): 922.2 $[M+H]^+$. $^1$H-NMR (400 MHz, DMSO-$d_6$): δ=10.88 (s, 1H), 10.19 (s, 1H), 8.36 (s, 1H), 7.80 (s, 1H), 7.78 (s, 1H), 7.69 (dd, J=2.80, 9.00 Hz, 1H), 7.60 (d, J=8.40 Hz, 1H), 7.45 (s, 1H), 7.36 (d, J=3.20 Hz, 1H), 7.09 (d, J=8.40 Hz, 1H), 5.35-5.25 (m, 1H), 4.39-4.30 (m, 1H), 4.20-4.09 (m, 2H), 3.97 (s, 3H), 3.78-3.65 (m, 1H), 3.65-3.45 (m, 2H), 3.17 (q, J=7.20 Hz, 2H), 2.80 (s, 3H), 2.72-2.60 (m, 4H), 2.40-2.30 (m, 3H), 2.28-2.12 (m, 2H), 2.12-2.02 (m, 2H), 1.88-1.58 (m, 13H), 1.06 (t, J=6.80 Hz, 3H).

Example 170

(3R)-3-[6-[2-cyano-3-[[ethyl(methyl)sulfamoyl]amino]-6-fluorophenoxy]-4-oxoquinazolin-3-yl]-8-[2-[4-[3-(2,6-dioxopiperidin-3-yl)-1-methylindazol-6-yl]cyclohexyl]acetyl]-1-oxa-8-azaspiro[4.5]decane

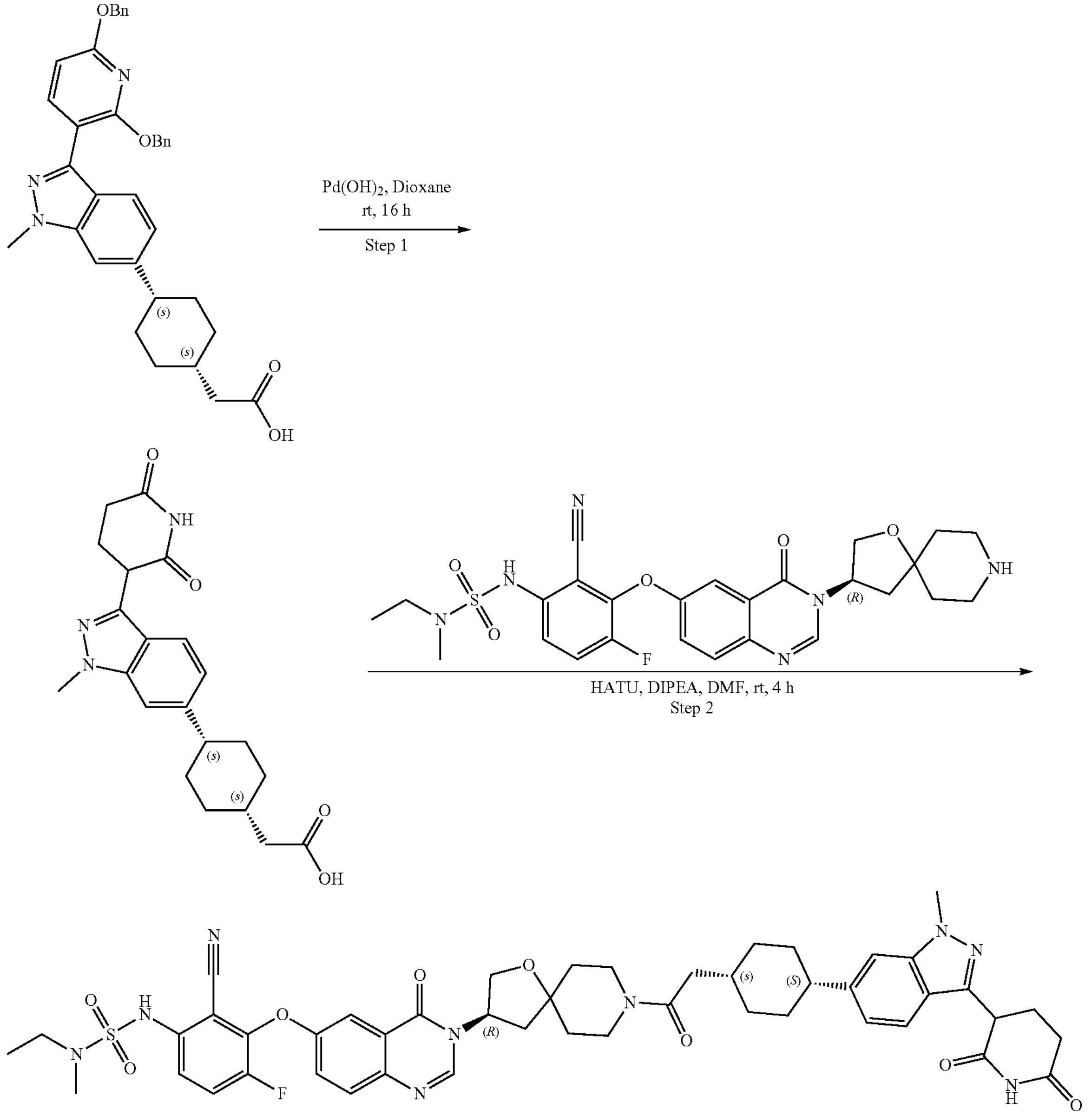

Step 1: To a stirred solution of 2-((1s,4s)-4-(3-(2,6-bis(benzyloxy)pyridin-3-yl)-1-methyl-1H-indazol-6-yl)cyclohexyl)acetic acid (0.15 g, 267.06 μmol) in 1,4-dioxane (5 mL), was charged 20% $Pd(OH)_2/C$ (0.12 g, 854.49 μmol), saturated with hydrogen by bubbling hydrogen gas through for 10 min and then subjected to hydrogenation (1 atm) at room temperature for 16 h. After completion, the reaction mixture was purged with nitrogen, catalyst was removed by filtration through celite pad and washed with 1,4-dioxane (200 mL). The filtrate was concentrated under reduced pressure to afford crude 2-((1s,4s)-4-(3-(2,6-dioxopiperidin-3-yl)-1-methyl-1H-indazol-6-yl)cyclohexyl)acetic acid (0.11 g, 246.71 μmol, 92% yield) as an off-white solid. LCMS m/z (ESI): 384.2 $[M+H]^+$.

Step 2: Target compound was prepared via HATU mediated acid-amine coupling reaction (Procedure B-E). Amide coupling was carried out using 2-((1s,4s)-4-(3-(2,6-dioxopiperidin-3-yl)-1-methyl-1H-indazol-6-yl)cyclohexyl)acetic acid (45.26 mg, 118.03 μmol), N,N-diisopropylethylamine (91.53 mg, 708.18 μmol, 123.35 μL) and HATU (44.88 mg, 118.03 μmol) and (3R)-3-[6-[2-cyano-3-[[ethyl(methyl)sulfamoyl]amino]-6-fluoro-phenoxy]-4-oxo-quinazolin-3-yl]-

1-oxa-8-azaspiro[4.5]decane (0.07 g, 118.03 μmol). The desired product was purified from crude by reverse phase column chromatography (10 mM ammonium acetate in water:acetonitrile) and fractions were lyophilized to afford (3R)-3-[6-[2-cyano-3-[[ethyl(methyl)sulfamoyl]amino]-6-fluoro-phenoxy]-4-oxo-quinazolin-3-yl]-8-[2-(1S,4S)-[4-[3-(2,6-dioxo-3-piperidyl)-1-methyl-indazol-6-yl]cyclo-hexyl]acetyl]-1-oxa-8-azaspiro[4.5]decane (34 mg, 35.53 μmol, 30% yield) as an off-white solid. LCMS m/z (ESI): 922.2 $[M+H]^+$ and $^1$H-NMR (400 MHz, DMSO-$d_6$): δ=10.87 (s, 1H), 10.18 (s, 1H), 8.37 (d, J=5.20 Hz, 1H), 7.82-7.84 (m, 1H), 7.80 (d, J=8.80 Hz, 1H), 7.70 (dd, J=2.40, 8.80 Hz, 1H), 7.59 (d, J=8.40 Hz, 1H), 7.47 (dd, J=26.40, 20.60 Hz, 1H), 7.36 (d, J=10.80 Hz, 1H), 7.38 (s, 1H), 7.03 (d, J=8.40 Hz, 1H), 5.31 (s, 1H), 4.32 (q, J=4.80 Hz, 1H), 4.16-4.12 (m, 2H), 3.97 (s, 2H), 3.76-3.64 (m, 1H), 3.55-3.42 (m, 2H), 3.23 (q, J=7.20 Hz, 2H), 2.79 (s, 3H), 2.68-2.56 (m, 4H), 2.37-2.33 (m, 5H), 2.28-2.27 (m, 2H), 1.87-1.56 (m, 12H), 1.22-1.10 (m, 2H), 1.06 (t, J=7.20 Hz, 3H).

Example 171

(3R)-3-[6-[2-cyano-3-[[ethyl(methyl)sulfamoyl]amino]-6-fluorophenoxy]-4-oxoquinazolin-3-yl]-8-[2-[3-[3-(2,6-dioxopiperidin-3-yl)-1-methylindazol-6-yl]azetidin-1-yl]acetyl]-1-oxa-8-azaspiro[4.5]decane

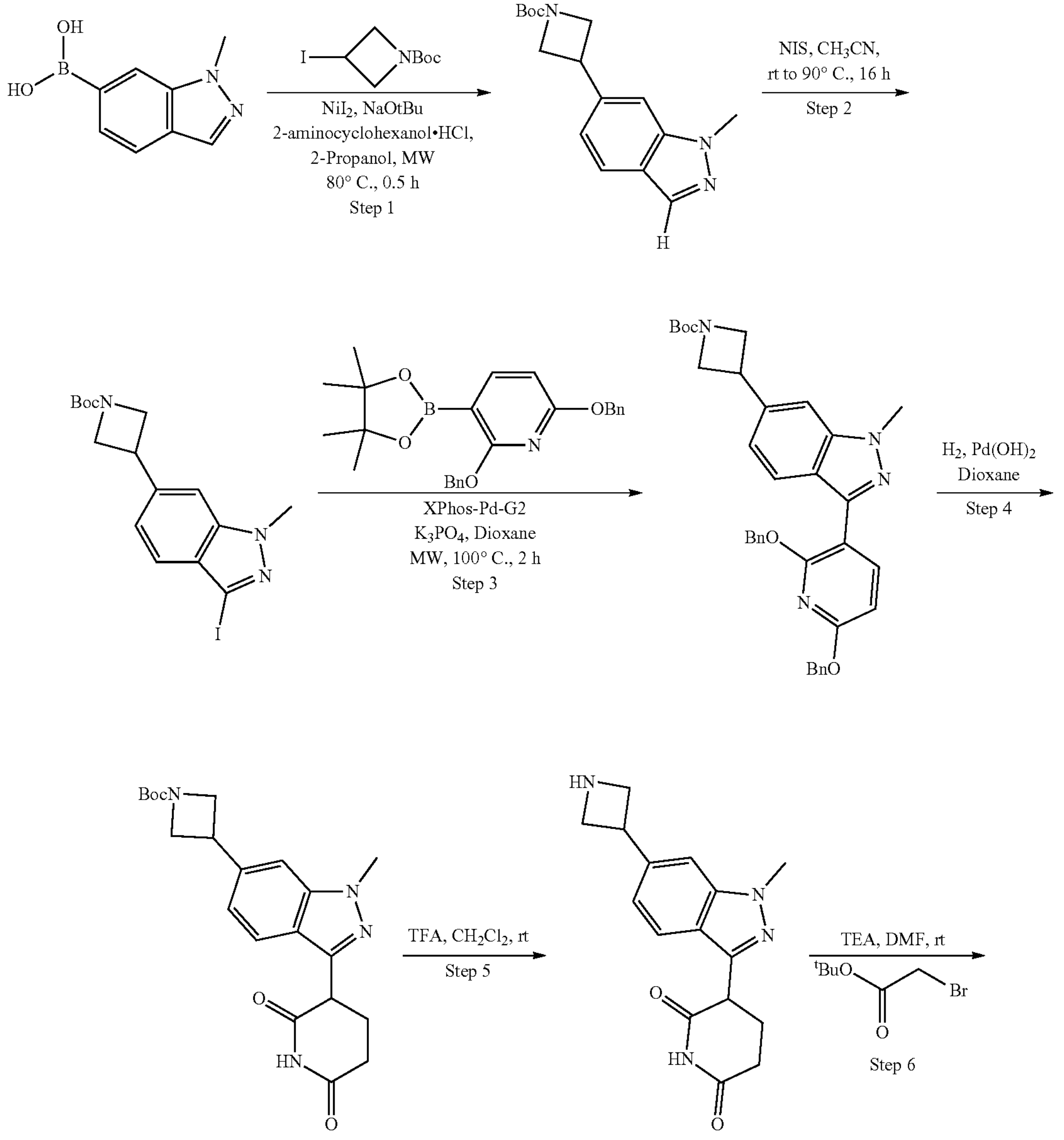

-continued

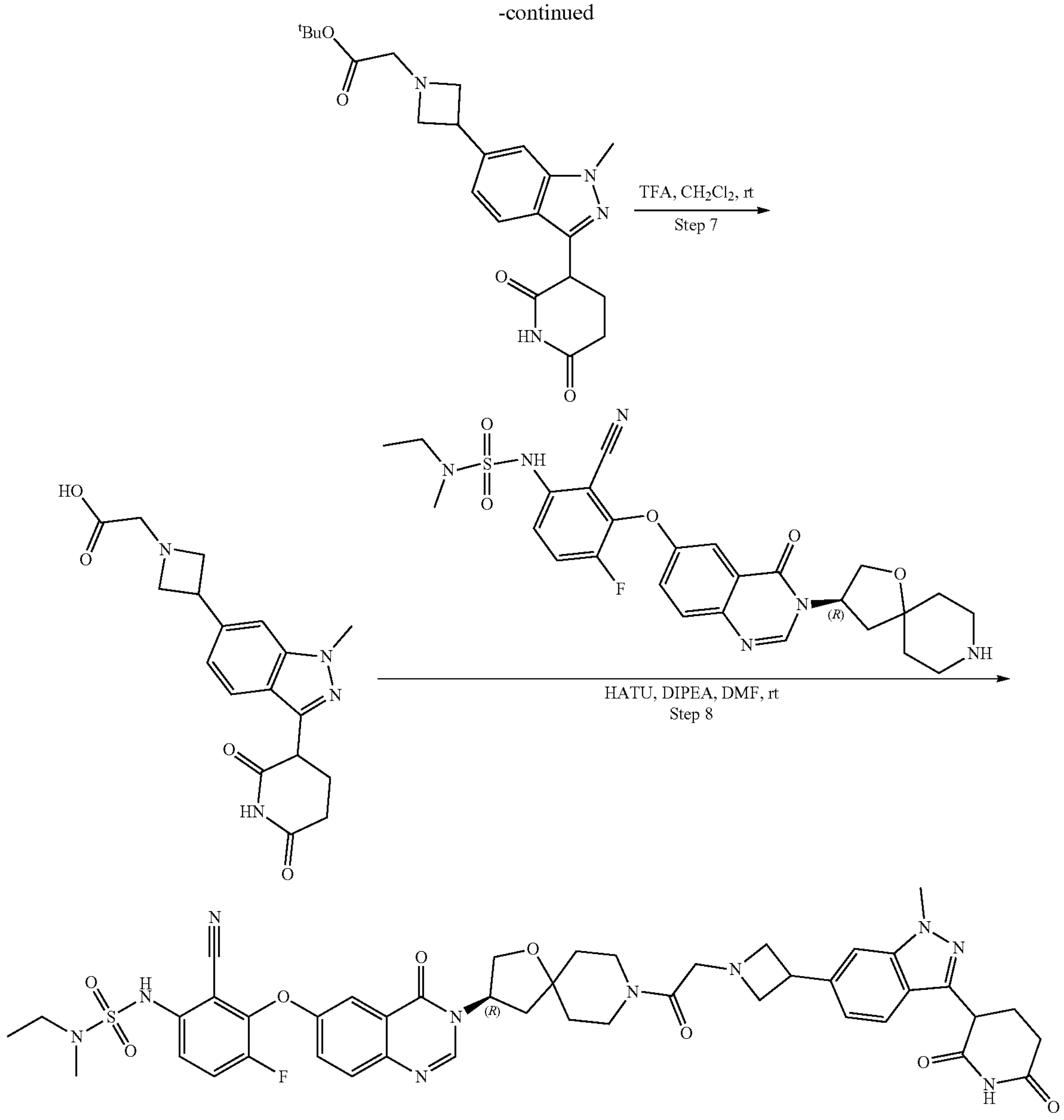

Step 1: To a stirred solution of (1-methylindazol-6-yl) boronic acid (621.60 mg, 3.53 mmol) in Isopropyl alcohol (2.5 mL) in a microwave vial was added trans-2-Aminocyclohexanol hydrochloride (16.07 mg, 105.97 μmol), diiodo nickel (33.11 mg, 105.97 μmol) and sodium tert-butoxide (1 M, 3.53 mL) at room temperature under nitrogen. After 5 minutes stirring, a solution of tert-butyl 3-iodoazetidine-1-carboxylate (500 mg, 1.77 mmol) in Isopropyl alcohol (2.5 mL) was added at same temperature. Resulting reaction mixture was irradiated under microwave at 80° C. for 30 minutes. After completion of the reaction, reaction mixture was quenched with water (50 mL) and extracted by ethyl acetate (2×30 mL). The combined organic layers were washed with brine solution, dried over anhydrous sodium sulfate, filtered and concentrated under reduced pressure to afford crude product, which was purified by column chromatography using silica gel and 60-70% ethyl acetate in petroleum ether as eluents to afford tert-butyl 3-(1-methylindazol-6-yl)azetidine-1-carboxylate (350 mg, 1.13 mmol, 64% yield) as a pale yellow oil. LCMS m/z (ESI): 288.20 $[M+H]^+$.

Step 2: To a stirred solution of tert-butyl 3-(1-methylindazol-6-yl) azetidine-1-carboxylate (200 mg, 696.00 μmol) in acetonitrile (5 mL) in sealed tube was added N-iodosuccinimide (469.77 mg, 2.09 mmol, 29.49 μL) at room temperature. The resulting reaction mixture was stirred at 90° C. for 16 h in closed seal tube. After completion of the reaction, reaction mixture was diluted with water (50 mL) and extracted by ethyl acetate (2×30 mL). The combined organic layers were washed with 10% sodium thiosulfate solution followed by brine solution, dried over anhydrous sodium sulfate, filtered and concentrated under reduced pressure to afford tert-butyl 3-(3-iodo-1-methyl-indazol-6-yl)azetidine-1-carboxylate (260 mg, 548.62 μmol, 79% yield) as a pale brown oil. LCMS m/z (ESI): 414.0 $[M+H]^+$ Step 3: To a stirred solution of tert-butyl 3-(3-iodo-1-methyl-indazol-6-yl)azetidine-1-carboxylate (300 mg, 725.95 μmol) and (2,6-dibenzyloxy-3-pyridyl)boronic acid (218.98 mg, 653.35 μmol) in 1,4-dioxane (10 mL) and water (2 mL) was added potassium phosphate tribasic (385.24 mg, 1.81 mmol) at room temperature under nitrogen atmosphere. The reaction mixture was purged with nitrogen for 15 min followed by the addition of XPhos Pd G2 (57.12 mg, 72.59 μmol). The reaction mixture was stirred at 100° C. for 16 h in microwave. After completion of the reaction, the reaction mixture was cooled to room temperature, filtered through celite and celite bed was washed with ethyl acetate (2×50 mL). The combined filtrate was concentrated under reduced pressure to afford crude. The crude compound was purified by silica gel flash column chromatography with 80-90% ethyl acetate in petroleum ether as a eluent to afford tert-butyl 3-[3-(2,6-dibenzyloxy-3-pyridyl)-1-methyl-indazol-6-yl]azetidine-1-carboxylate (320 mg, 439.76 μmol, 61% yield) as a pale yellow oil. LCMS m/z (ESI): 577.50 $[M+H]^+$.

Step 4: To a stirred solution of tert-butyl 3-[3-(2,6-dibenzyloxy-3-pyridyl)-1-methyl-indazol-6-yl]azetidine-1-carboxylate (320 mg, 554.90 μmol) in 1,4-dioxane (10 mL) was added Palladium hydroxide (100 mg, 142.41 μmol) under nitrogen atmosphere at room temperature. The reaction mixture stirred under $H_2$ pressure for 16 h. After completion of the reaction, the catalyst was removed by filtration through celite bed. The celite bed was washed with ethyl acetate (2×30 mL) and filtrate was concentrated under reduced pressure to afford crude product, which was purified by silica gel flash column chromatography with 90-100% ethyl acetate in petroleum ether as an eluent to afford tert-butyl 3-[3-(2,6-dioxo-3-piperidyl)-1-methyl-indazol-6-yl]azetidine-1-carboxylate (150 mg, 358.95 μmol, 65% yield) as a pale brown solid. LCMS m/z (ESI): 399.0 $[M+H]^+$ Step 5: To a stirred solution of tert-butyl 3-[3-(2,6-dioxo-3-piperidyl)-1-methyl-indazol-6-yl]azetidine-1-carboxylate (150 mg, 376.45 μmol) in dichloromethane (1 mL) was added trifluoroacetic acid (740.00 mg, 6.49 mmol, 0.5 mL) at 0° C. The resulted reaction mixture stirred at room temperature for 2 h. After completion of the reaction, the reaction mixture was concentration under reduced pressure and triturated with methyl t-butyl ether to afford crude 3-[6-(azetidin-3-yl)-1-methyl-indazol-3-yl]piperidine-2,6-dione (150 mg, 358.48 μmol, 95% yield) as a brown solid. LCMS m/z (ESI): 299.10 $[M+H]^+$ Step 6: To a stirred solution of 33-[6-(azetidin-3-yl)-1-methyl-indazol-3-yl]piperidine-2,6-dione (150 mg, 363.76 μmol) in N,N-dimethylformamide (3 mL) were added triethylamine (92.02 mg, 909.40 μmol, 126.75 μL) followed by tert-butyl bromoacetate (85.14 mg, 436.51 μmol, 64.02 μL) at room temperature under nitrogen atmosphere. The reaction mixture was stirred at room temperature for 12 h. After completion of the reaction, the reaction mixture was diluted with water (10 mL) and extracted with ethyl acetate (3×10 mL). The organic layer was washed with brine solution (30 mL), dried over sodium sulfate, filtered and concentrated under reduced pressure to afford crude. The crude product was purified by silica gel flash column chromatography with 5-10% methanol in dichloromethane as a eluent to afford tert-butyl 2-[3-[3-(2,6-dioxo-3-piperidyl)-1-methyl-indazol-6-yl]azetidin-1-yl]acetate (60 mg, 125.56 μmol, 35% yield) as a pale yellow oil. LCMS m/z (ESI): 431.20 $[M+H]^+$ Step 7: The requisite amine was synthesized by following Procedure B-D using of tert-butyl 2-[3-[3-(2,6-dioxo-3-piperidyl)-1-methyl-indazol-6-yl]azetidin-1-yl]acetate (60 mg, 145.46 μmol) and added trifluoroacetic acid (444.00 mg, 3.89 mmol, 0.3 mL). The resulted crude compound was triturated with methyl t-butyl ether to afford crude 2-[3-[3-(2,6-dioxo-3-piperidyl)-1-methyl-indazol-6-yl]azetidin-1-yl]acetic acid TFA salt (65 mg, 129.06 μmol, 89% yield) as a pale brown oil. LCMS m/z (ESI): 357.20 $[M+H]^+$.

Step 8: Target compound was prepared via HATU mediated acid-amine coupling reaction (Procedure B-E). Amide coupling was carried out using 2-[3-[3-(2,6-dioxo-3-piperidyl)-1-methyl-indazol-6-yl]azetidin-1-yl]acetic acid (65 mg, 138.18 μmol), (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (73.76 mg, 124.36 μmol), N,N-diisopropylethylamine (107.15 mg, 829.09 μmol, 144.41 μL) and HATU (57.79 mg, 152.00 μmol) to afford crude product. The crude compound was purified by reverse phase column chromatography eluted with 46% acetonitrile in 0.1% formic acid in water to afford product (3R)-3-[6-[2-cyano-3-[[ethyl(methyl)sulfamoyl]amino]-6-fluoro-phenoxy]-4-oxo-quinazolin-3-yl]-8-[2-[3-[3-(2,6-dioxo-3-piperidyl)-1-methyl-indazol-6-yl]azetidin-1-yl]acetyl]-1-oxa-8-azaspiro[4.5]decane (13.5 mg, 14.29 μmol, 10% yield) as an off-white solid. LCMS m/z (ESI): 894.8 $[M+H]^+$; $^1$H-NMR (400 MHz, DMSO-$d_6$): δ=10.90 (s, 1H), 10.38 (s, 1H), 8.34 (s, 1H), 7.77 (d, J=8.80 Hz, 1H), 7.72 (d, J=8.40 Hz, 1H), 7.66 (d, J=2.80 Hz, 1H), 7.64 (s, 1H), 7.47 (s, 1H), 7.35-7.32 (m, 2H), 7.18 (d, J=8.40 Hz, 1H), 5.31 (s, 1H), 4.39-4.33 (m, 5H), 4.21-4.10 (m, 5H), 4.01 (s, 3H), 3.73 (t, J=4.40 Hz, 1H), 3.50-3.42 (m, 3H), 3.03 (q, J=7.20 Hz, 2H), 2.53 (s, 3H), 2.51-2.50 (m, 1H), 2.36-2.33 (m, 2H), 2.20-2.09 (m, 2H), 2.08-1.69 (m, 4H), 1.61-1.50 (m, 1H), 1.03 (t, J=7.20 Hz, 3H).

Example 172

6-[2-cyano-3-[[ethyl(methyl)sulfamoyl]amino]-6-fluorophenoxy]-3-[(3S)-8-[2-[1-[3-(2,4-dioxo-1,3-diazinan-1-yl)-7-fluoro-1-methylindazol-6-yl]-4-hydroxypiperidin-4-yl]acetyl]-8-azaspiro[4.5]decan-3-yl]-4-oxoquinazoline

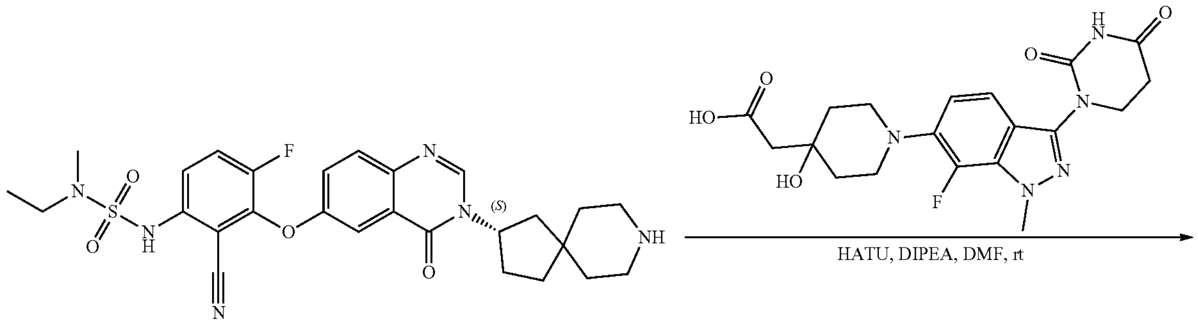

-continued

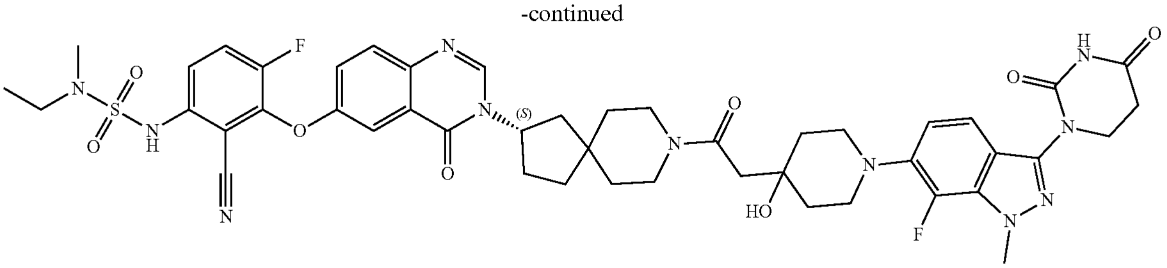

Target compound was prepared via HATU mediated acid-amine coupling reaction (Procedure B-E). Amide coupling was carried out using 2-[1-[3-(2,4-dioxohexahydropyrimidin-1-yl)-7-fluoro-1-methyl-indazol-6-yl]-4-hydroxy-4-piperidyl]acetic acid HCl salt (75 mg, 164.52 μmol), 3-[(3S)-8-azaspiro[4.5]decan-3-yl]-6-[2-cyano-3-[[ethyl(methyl)sulfamoyl]amino]-6-fluoro-phenoxy]-4-oxo-quinazoline HCl salt (97.25 mg, 164.52 μmol), N,N-diisopropylethylamine (127.58 mg, 987.13 μmol, 171.94 μL) and HATU (75.07 mg, 197.43 μmol) to afford crude product. The crude compound was purified by reverse phase column chromatography eluted with 50% acetonitrile in 0.1% formic acid in water to afford product 6-[2-cyano-3-[[ethyl(methyl)sulfamoyl]amino]-6-fluoro-phenoxy]-3-[(3S)-8-[2-[1-[3-(2,4-dioxohexahydropyrimidin-1-yl)-7-fluoro-1-methyl-indazol-6-yl]-4-hydroxy-4-piperidyl]acetyl]-8-azaspiro[4.5]decan-3-yl]-4-oxo-quinazoline (24.1 mg, 25.13 μmol, 15% yield) as an off-white solid. LCMS m/z (ESI): 955.8 $[M+H]^+$; $^1$H-NMR (400 MHz, DMSO-$d_6$): δ=10.57 (s, 1H), 10.18 (s, 1H), 8.45 (s, 1H), 7.87 (t, J=9.60 Hz, 1H), 7.80 (d, J=8.80 Hz, 1H), 7.69 (dd, J=3.20, 9.00 Hz, 1H), 7.50 (dd, J=4.00, 9.20 Hz, 1H), 7.37 (d, J=2.80 Hz, 1H), 7.34 (d, J=8.80 Hz, 1H), 6.95 (t, J=8.80 Hz, 1H), 5.06-5.04 (m, 2H), 4.06 (s, 3H), 3.90 (t, J=6.40 Hz, 2H), 3.62-3.53 (m, 2H), 3.49-3.38 (m, 2H), 3.20-3.15 (m, 6H), 2.80 (s, 3H), 2.74 (t, J=12.00 Hz, 2H), 2.59-2.52 (m, 2H), 2.12-2.06 (m, 3H), 1.83-1.71 (m, 4H), 1.68-1.45 (m, 7H), 1.06 (t, J=6.80 Hz, 3H).

Example 173

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-7-fluoro-1-methylindazol-6-yl]-4-hydroxypiperidin-4-yl]acetyl]-1-oxa-8-azaspiro[4.5]decane

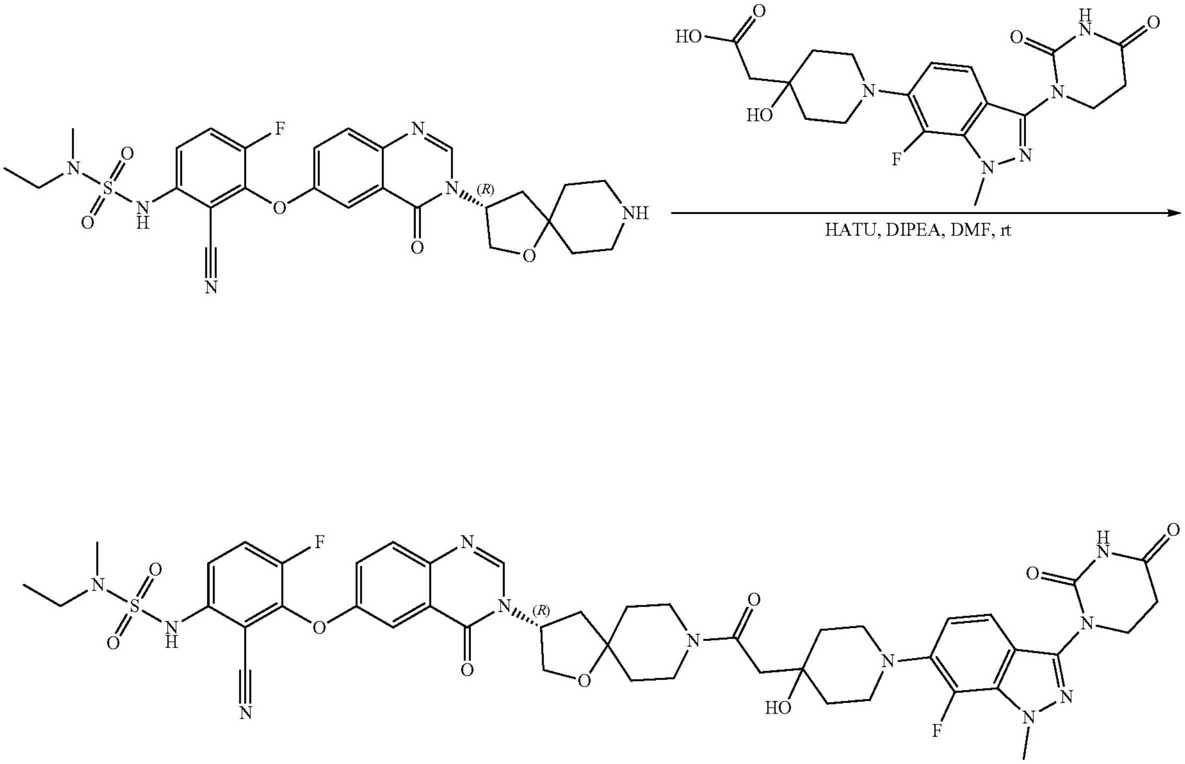

Target compound was prepared via HATU mediated acid-amine coupling reaction (Procedure B-E). Amide coupling was carried out using 2-[1-[3-(2,4-dioxohexahydropyrimidin-1-yl)-7-fluoro-1-methyl-indazol-6-yl]-4-hydroxy-4-piperidyl]acetic acid (40 mg, 87.74 μmol), (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane HCl salt (52.04 mg, 87.74 μmol), N,N-diisopropylethylamine (68.04 mg, 526.47 μmol, 91.70 μL) and HATU (40.04 mg, 105.29 μmol) to afford crude product. The crude compound was purified by reverse phase column chromatography eluted with 50% acetonitrile in 0.1% ammonium acetate in water to afford product (3R)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-7-fluoro-1-methyl-indazol-6-yl]-4-hydroxy-4-piperidyl]acetyl]-1-oxa-8-azaspiro[4.5]decane (25 mg, 25.10 μmol, 29% yield) as an off-white solid. LCMS m/z (ESI): 958.00 $[M+H]^+$; $^1$H-NMR (400 MHz, DMSO-$d_6$): δ=10.58 (s, 1H), 10.19 (s, 1H), 8.36 (s, 1H), 7.86 (s, 1H), 7.80 (d, J=8.80 Hz, 1H), 7.70 (dd, J=3.20, 9.00 Hz, 1H), 7.50 (dd, J=4.00, 9.20 Hz, 1H), 7.37 (d, J=2.80 Hz, 1H), 7.33 (d, J=8.80 Hz, 1H), 6.95 (t, J=8.00 Hz, 1H), 5.32-5.29 (m, 1H), 5.01 (s, 1H), 4.15-4.11 (m, 2H), 4.05 (s, 3H), 3.90 (t, J=6.40 Hz, 2H), 3.82-3.71 (m, 1H), 3.70-3.60 (m, 1H), 3.51-3.48 (m, 1H), 3.16-3.14 (m, 6H), 2.79 (s, 3H), 2.76 (t, J=6.80 Hz, 2H), 2.52-2.51 (m, 2H), 2.37-2.33 (m, 1H), 2.10-2.06 (m, 1H), 1.90-1.51 (m, 9H), 1.06 (t, J=7.20 Hz, 3H).

Example 174

(3R)-3-[6-[2-cyano-3-[[ethyl(methyl)sulfamoyl]amino]-6-fluorophenoxy]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

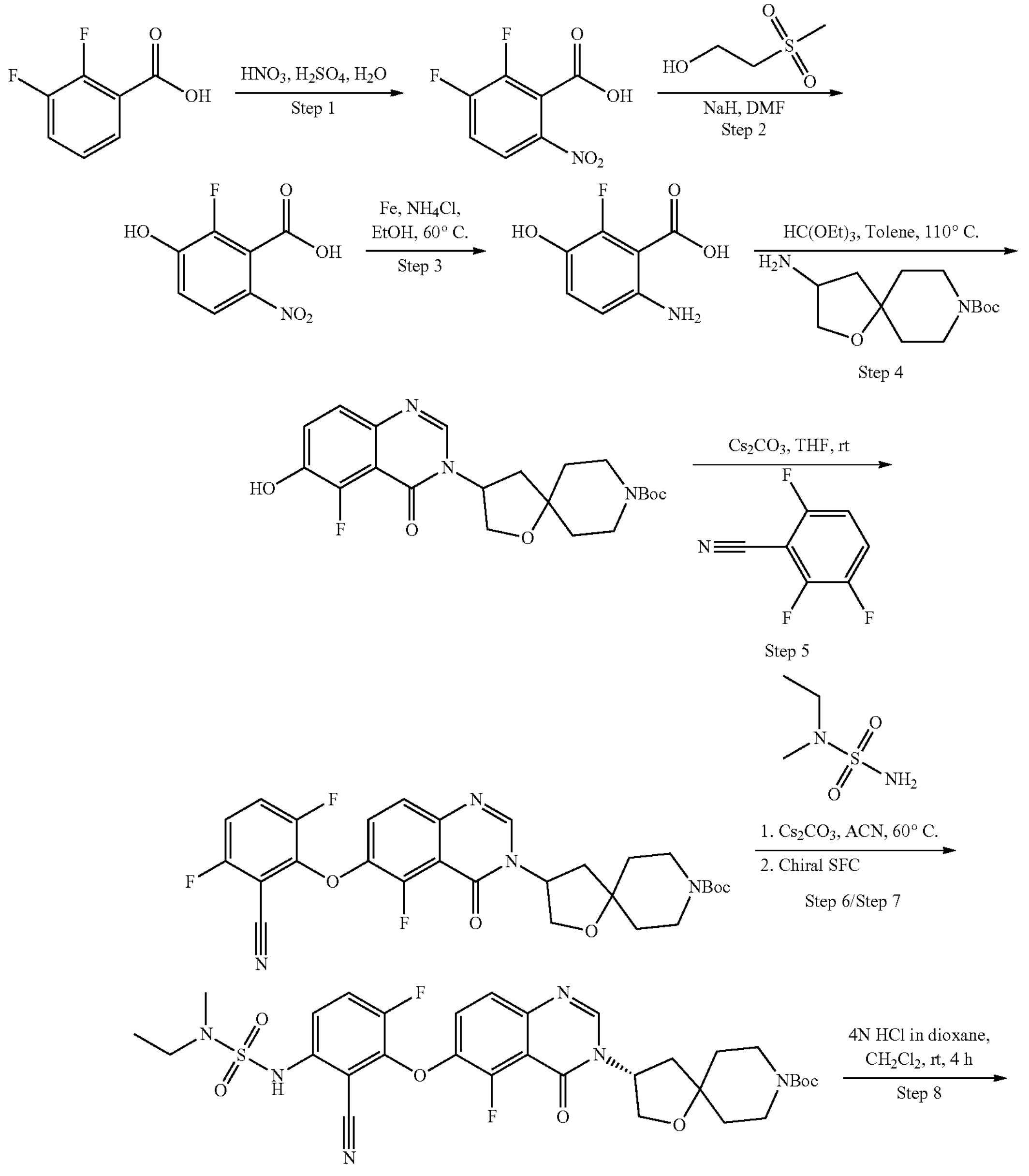

-continued

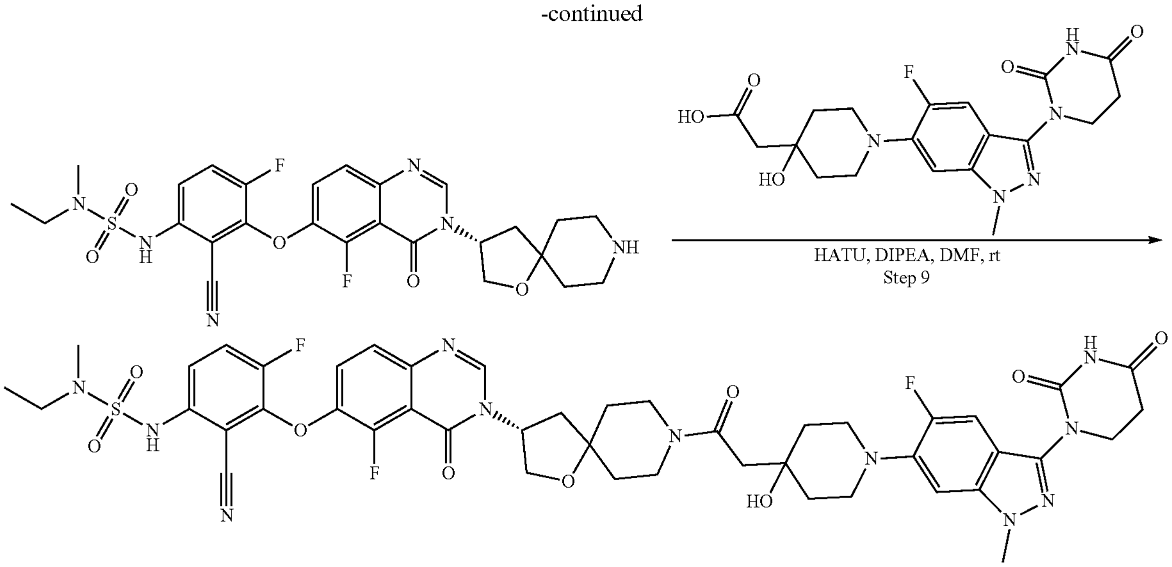

Step 1: To a stirred solution of 2,3-difluorobenzoic acid (10 g, 63.25 mmol) in sulfuric acid (80.52 g, 820.99 mmol, 44.00 mL) was added nitric Acid (4.78 g, 75.90 mmol, 3.17 mL) dropwise at 0° C. under inert condition. The reaction mixture was stirred at 0-5° C. for 2 h. After completion, the reaction mixture was diluted with water (200 mL) and extracted with ethyl acetate (3×100 mL). Combined organic layers washed dried over sodium sulfate, filtered and concentrated under reduced pressure to afford 2,3-difluoro-6-nitro-benzoic acid (9.2 g, 44.39 mmol, 70% yield) as a yellow solid, which was carried forward without further purification. LCMS m/z (ESI): 202.2 $[M-H]^-$.

Step 2: To a stirred solution of 2,3-difluoro-6-nitro-benzoic acid (2.7 g, 13.29 mmol) in N,N-dimethylformamide (40 mL) was added sodium hydride (60% dispersion in mineral oil, 2.55 g, 63.68 mmol) The reaction mixture was stirred at 0° C. and stirred for 1 h. After completion, the reaction mixture was quenched dropwise with saturated ammonium chloride solution (50 mL) at 0° C. and extracted with ethyl acetate (3×200 mL). The combined organic layers were washed with cold water (3×100 mL), dried over sodium sulfate, filtered and concentrated under reduced pressure. The crude product was purified by silica gel flash column chromatography using 10-20% ethyl acetate in petroleum ether as eluent to afford 2-fluoro-3-hydroxy-6-nitro-benzoic acid (2.7 g, 10.91 mmol, 82% yield) as a yellow solid. LCMS m/z (ESI): 200.2 $[M-H]^-$ Step 3: To a stirred solution of 2-fluoro-3-hydroxy-6-nitro-benzoic acid (2.7 g, 13.43 mmol) in 1,4-dioxane (30 mL) was added palladium hydroxide on carbon, 20 wt. % (1.89 g, 13.43 mmol) water at room temperature under nitrogen atmosphere. The resulting suspension was stirred at room temperature under hydrogen atmosphere bladder for 16 h. After completion, the reaction mixture was filtered through a pad of celite, washing with methanol (100 mL). The combined filtrate was concentrated under reduced pressure to afford 6-amino-2-fluoro-3-hydroxy-benzoic acid (2.7 g, 7.99 mmol, 60% yield) as a brown viscous solid, which was carried forward without further purification. LCMS m/z (ESI): 170.10 $[M-H]^-$ Step 4: To a stirred solution of 6-amino-2-fluoro-3-hydroxy-benzoic acid (1.2 g, 7.01 mmol) in Toluene (18 mL) and Tetrahydrofuran (3 mL) were added tert-butyl 3-amino-1-oxa-8-azaspiro[4.5]decane-8-carboxylate (1.80 g, 7.01 mmol) and diethoxy methoxy ethane (1.25 g, 8.41 mmol, 1.40 mL) at room temperature under nitrogen atmosphere. The reaction mixture was stirred at 110° C. for 12 h. After completion, the reaction mixture was diluted with water (150 mL) and extracted with ethyl acetate (3×200 mL). The combined organic layers were washed with 10% sodium bicarbonate solution (3×100 mL), dried over sodium sulfate, filtered, and concentrated under reduced pressure. The product was purified by silica gel flash column chromatography by using 70-90% ethyl acetate in petroleum ether as eluent to afford tert-butyl 3-(5-fluoro-6-hydroxy-4-oxo-quinazolin-3-yl)-1-oxa-8-azaspiro[4.5]decane-8-carboxylate (0.460 g, 931.09 μmol, 13% yield). LCMS m/z (ESI): 420.2 $[M+H]^+$ Step 5: O-arylated quinazolinone intermediate was synthesized by following Procedure B—B using tert-butyl 3-(5-fluoro-6-hydroxy-4-oxo-quinazolin-3-yl)-1-oxa-8-azaspiro[4.5]decane-8-carboxylate (0.440 g, 1.05 mmol), cesium carbonate (1.03 g, 3.15 mmol) and 2,3,6-trifluorobenzonitrile (197.75 mg, 1.26 mmol, 145.40 μL). The crude compound was purified by silica gel flash column chromatography with 80-90% ethyl acetate in petroleum ether as a eluent to afford tert-butyl 3-[6-(2-cyano-3,6-difluoro-phenoxy)-5-fluoro-4-oxo-quinazolin-3-yl]-1-oxa-8-azaspiro[4.5]decane-8-carboxylate (0.450 g, 749.43 μmol, 71% yield) as light brown liquid. LCMS m/z (ESI): 501.20 $[M+H-{}^tBu]^+$ Step 6/Step 7: To a stirred solution of tert-butyl 3-[6-(2-cyano-3,6-difluoro-phenoxy)-5-fluoro-4-oxo-quinazolin-3-yl]-1-oxa-8-azaspiro[4.5]decane-8-carboxylate (700 mg, 1.26 mmol) in N,N-Dimethylformamide (5 mL) were added cesium carbonate (1.02 g, 3.14 mmol) and [methyl(sulfamoyl)amino]ethane (260.72 mg, 1.89 mmol) at room temperature. The reaction mixture was stirred at 55° C. for 16 h. After completion, the reaction mixture was diluted with water (3 mL), obtained solid was filtered through filter paper. The aqueous layer was extracted with ethyl acetate (3x30 mL). Combined organic layers washed with cold water (3x15 mL), dried over sodium sulfate, filtered and concentrated under reduced pressure to afford crude tert-butyl 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane-8-carboxylate (0.25 g, 364.65 μmol, 29% yield) as a brown solid. This racemic product was subjected for chiral SFC purification using Lux A1 column to afford tert-butyl (S)-3-(6-(2-cyano-3-((N-ethyl-N-methyl-sulfamoyl)amino)-6-fluorophenoxy)-5-fluoro-4-oxoquinazolin-3(4H)-yl)-1-oxa-8-azaspiro[4.5]decane-8-carboxylate (100 mg, 100% pure, first eluting isomer, arbitrarily assigned as S-isomer) and tert-butyl (R)-3-(6-(2-cyano-3-((N-ethyl-N— methylsulfamoyl)amino)-6-fluorophenoxy)-5-fluoro-4-oxoquinazolin-3(4H)-yl)-1-oxa-8-azaspiro[4.5]decane-8-carboxylate (90 mg, 100% pure, second eluting isomer, arbitrarily assigned as R-isomer) as a light brown solid. LCMS m/z (ESI): 619.2[M+H−56]$^+$.

Note: First eluting peak was arbitrarily assigned as S-isomer and second eluting peak was arbitrarily assigned as R-isomer.

Step 8: The requisite amine was synthesized by HCl mediated N-Boc deprotection (Procedure B-D). N-Boc deprotection was done on tert-butyl 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane-8-carboxylate (100 mg, 148.21 μmol) using 4M hydrogen chloride solution in dioxane (4 M, 37.05 μL) to afford crude 3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane (100 mg, 129.35 μmol, 87% yield) as an off-white solid. LCMS m/z (ESI): 575.0 [M+H]$^+$ Step 9: Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (72.99 mg, 174.03 μmol), N,N-diisopropylethylamine (112.46 mg, 870.17 μmol, 151.57 μL), HATU (72.79 mg, 191.44 μmol) and (3R)-3-[6-[2-cyano-3-[[ethyl(methyl)sulfamoyl]amino]-6-fluoro-phenoxy]-5-fluoro-4-oxo-quinazolin-3-yl]-1-oxa-8-azaspiro[4.5]decane (0.100 g, 174.03 μmol). The desired product was purified by reverse phase column chromatography (ammonium acetate in water:acetonitrile) and fractions were lyophilized to afford (3R)-3-[6-[2-cyano-3-[[ethyl(methyl)sulfamoyl]amino]-6-fluoro-phenoxy]-5-fluoro-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (47.81 mg, 48.81 μmol, 28% yield) as an off-white solid. LCMS m/z (ESI): 976.2 [M+H]$^+$; $^1$H-NMR (400 MHz, DMSO-$d_6$): δ=10.53 (s, 1H), 10.18 (s, 1H), 8.35 (s, 1H), 7.50-7.75 (m, 2H), 7.51 (d, J=8.80 Hz, 1H), 7.29-7.40 (m, 1H), 7.33 (d, J=12.80 Hz, 1H), 7.13 (d, J=7.20 Hz, 1H), 5.28-5.38 (m, 1H), 5.03 (d, J=1.60 Hz, 1H), 4.11-4.19 (m, 2H), 3.95 (s, 3H), 3.89 (t, J=6.40 Hz, 2H), 3.71-3.81 (m, 1H), 3.61-3.70 (m, 1H), 3.48-3.60 (m, 1H), 3.25-3.45 (m, 1H), 3.02-3.21 (m, 6H), 2.60-2.77 (m, 3H), 2.58 (s, 3H), 2.35-2.60 (m, 2H), 2.05-2.15 (m, 1H), 1.55-1.88 (m, 8H), 1.05 (t, J=7.20 Hz, 3H).

Example 175

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide

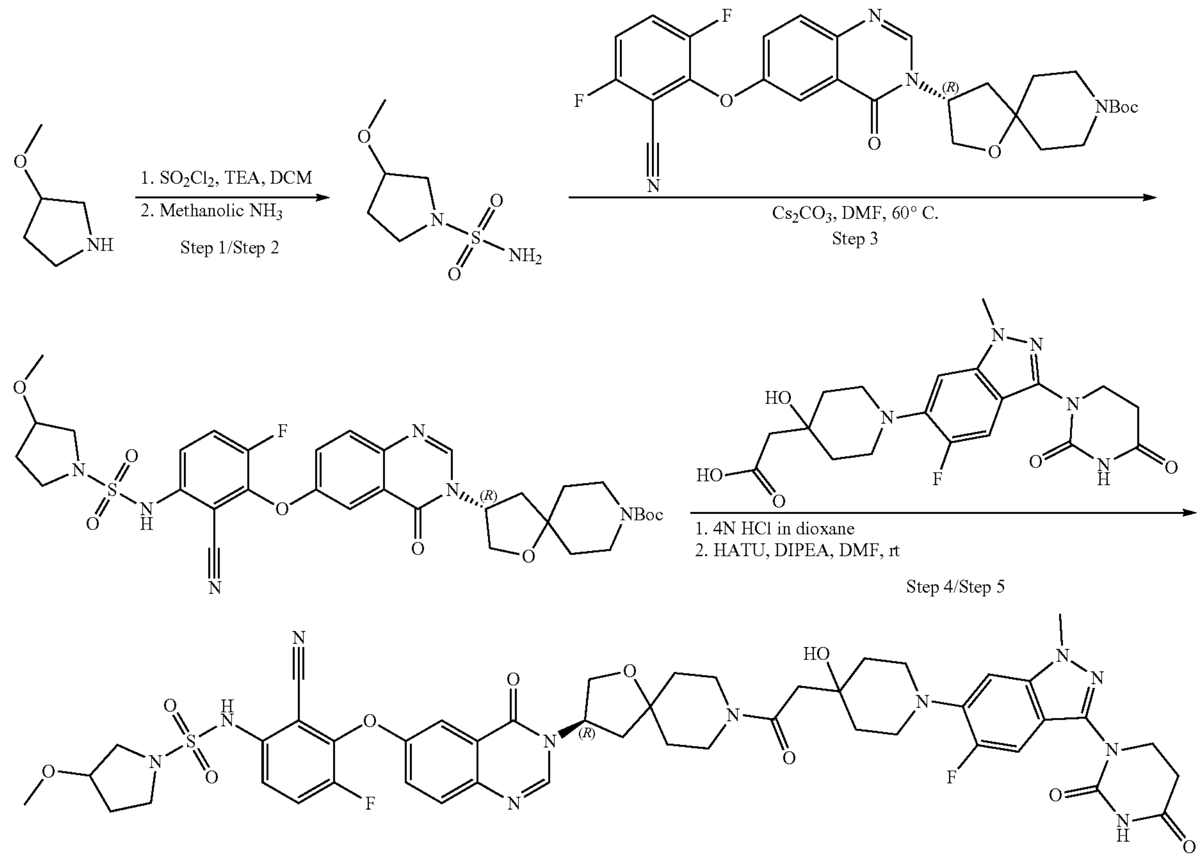

Step 1/Step 2: To a stirred −30° C. solution of 3-methoxypyrrolidine (0.500 g, 4.94 mmol) in dichloromethane (5 mL) was added N,N-diisopropylethylamine (958.31 mg, 7.41 mmol, 1.29 mL) and sulfuryl chloride (1.67 g, 12.36 mmol). The resultant reaction mixture was stirred at −30° C. for 2 h. The reaction mixture was quenched by dropwise addition of with water (60 mL), then extracted with ethyl acetate (2×100 mL). The combined organic layers were washed with 1.5N HCl solution (2×50 mL). The organic phase was dried over sodium sulfate, filtered, and concentrated under reduced pressure to afford crude 3-methoxypyrrolidine-1-sulfonyl chloride.

To a solution of crude 3-methoxypyrrolidine-1-sulfonyl chloride (0.6 g, 3.01 mmol) in methanol (8 mL) was added 7M ammonia in MeOH (7 M, 429.31 μL) at 0° C. and stirred at room temperature for 14 h. The reaction mixture was concentrated under reduced pressure to provide crude material, which was diluted with water (30 mL), extracted with ethyl acetate (50 mL). The organic layer was washed with sodium bicarbonate solution (20 ml), brine (20 ml), dried over sodium sulfate and concentrated under reduced pressure. The resulting crude residue was purified by silica gel flash column chromatography, eluting with 40% ethyl acetate in petroleum ether, to afford 3-methoxypyrrolidine-1-sulfonamide (0.230 g, 738.72 μmol, 25% yield) as a light brown solid. LCMS m/z (ESI): 181.2 $[M+H]^+$.

Step 3: Sulfamoylated quinazolinone intermediate was synthesized by following general Procedure B—C using 3-methoxypyrrolidine-1-sulfonamide (50.20 mg, 278.53 μmol), cesium carbonate (226.88 mg, 696.33 μmol) and tert-butyl 3-[(3R)-6-(2-cyano-3,6-difluoro-phenoxy)-4-oxo-quinazolin-3-yl]-1-oxa-8-azaspiro[4.5]decane-8-carboxylate (0.15 g, 278.53 μmol) to afford crude tert-butyl 3-[(3R)-6-[2-cyano-6-fluoro-3-[(3-methoxypyrrolidin-1-yl) sulfonylamino]phenoxy]-4-oxo-quinazolin-3-yl]-1-oxa-8-azaspiro[4.5]decane-8-carboxylate (135 mg, 168.77 μmol, 61% yield) as a brown viscous liquid. LCMS m/z (ESI): 697.0 $[M+H]^+$.

Step 4: The requisite amine was synthesized by HCl mediated N-Boc deprotection (Procedure B-D). N-Boc deprotection was done on tert-butyl 3-[(3R)-6-[2-cyano-6-fluoro-3-[(3-methoxypyrrolidin-1-yl)sulfonylamino]phenoxy]-4-oxo-quinazolin-3-yl]-1-oxa-8-azaspiro[4.5]decane-8-carboxylate (0.135 g, 193.20 μmol) using 4M hydrogen chloride solution (4 M, 48.30 μL) to afford N-[2-cyano-4-fluoro-3-[(3R)-3-(1-oxa-8-azaspiro[4.5]decan-3-yl)-4-oxo-quinazolin-6-yl]oxy-phenyl]-3-methoxy-pyrrolidine-1-sulfonamide hydrochloride salt (125 mg, 189.54 μmol, 98% yield) as a light brown solid. LCMS m/z (ESI): 599.2 $[M+H]^+$.

Step 5: Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (77.07 mg, 183.75 μmol), N,N-diisopropylethylamine (118.74 mg, 918.74 μmol, 160.03 μL), HATU (76.85 mg, 202.12 μmol) and N-[2-cyano-4-fluoro-3-[3-[(3R)-1-oxa-8-azaspiro[4.5]decan-3-yl]-4-oxo-quinazolin-6-yl]oxy-phenyl]-3-methoxy-pyrrolidine-1-sulfonamide (0.11 g, 183.75 μmol). The desired product was purified from the crude residue by reverse phase column chromatography (ammonium acetate in water:acetonitrile), and fractions were lyophilized to afford N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-methoxy-pyrrolidine-1-sulfonamide (51.52 mg, 49.44 μmol, 27% yield) as an off-white solid. LCMS m/z (ESI): 1000.2 $[M+H]^+$; $^1$H-NMR (400 MHz, DMSO-$d_6$): δ=10.51 (s, 1H), 10.21 (s, 1H), 8.36 (s, 1H), 7.75-7.90 (m, 1H), 7.80 (d, J=8.80 Hz, 1H), 7.69 (dd, J=3.20, 8.80 Hz, 1H), 7.52 (d, J=5.20 Hz, 1H), 7.39 (d, J=2.80 Hz, 1H), 7.33 (d, J=12.80 Hz, 1H), 7.12 (d, J=7.20 Hz, 1H), 5.25-5.35 (m, 1H), 5.02 (d, J=1.60 Hz, 1H), 4.10-4.20 (m, 2H), 3.92-4.01 (m, 1H), 3.95 (s, 3H), 3.90 (t, J=6.80 Hz, 2H), 3.73-3.84 (m, 1H), 3.58-3.68 (m, 1H), 3.48-3.59 (m, 1H), 3.23-3.41 (m, 4H), 3.37 (s, 3H), 3.14-3.21 (m, 2H), 3.02-3.12 (m, 2H), 2.74 (t, J=6.80 Hz, 2H), 2.35-2.61 (m, 4H), 2.03-2.12 (m, 1H).

Example 176

(3S)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide

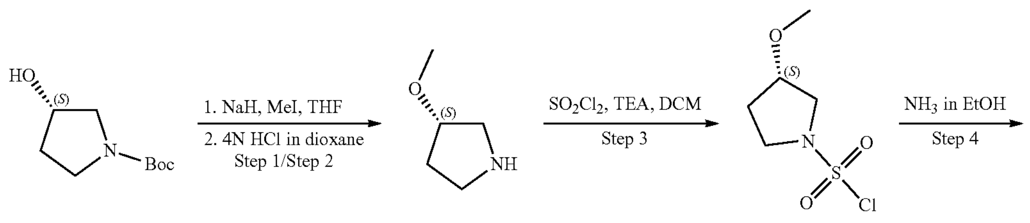

-continued

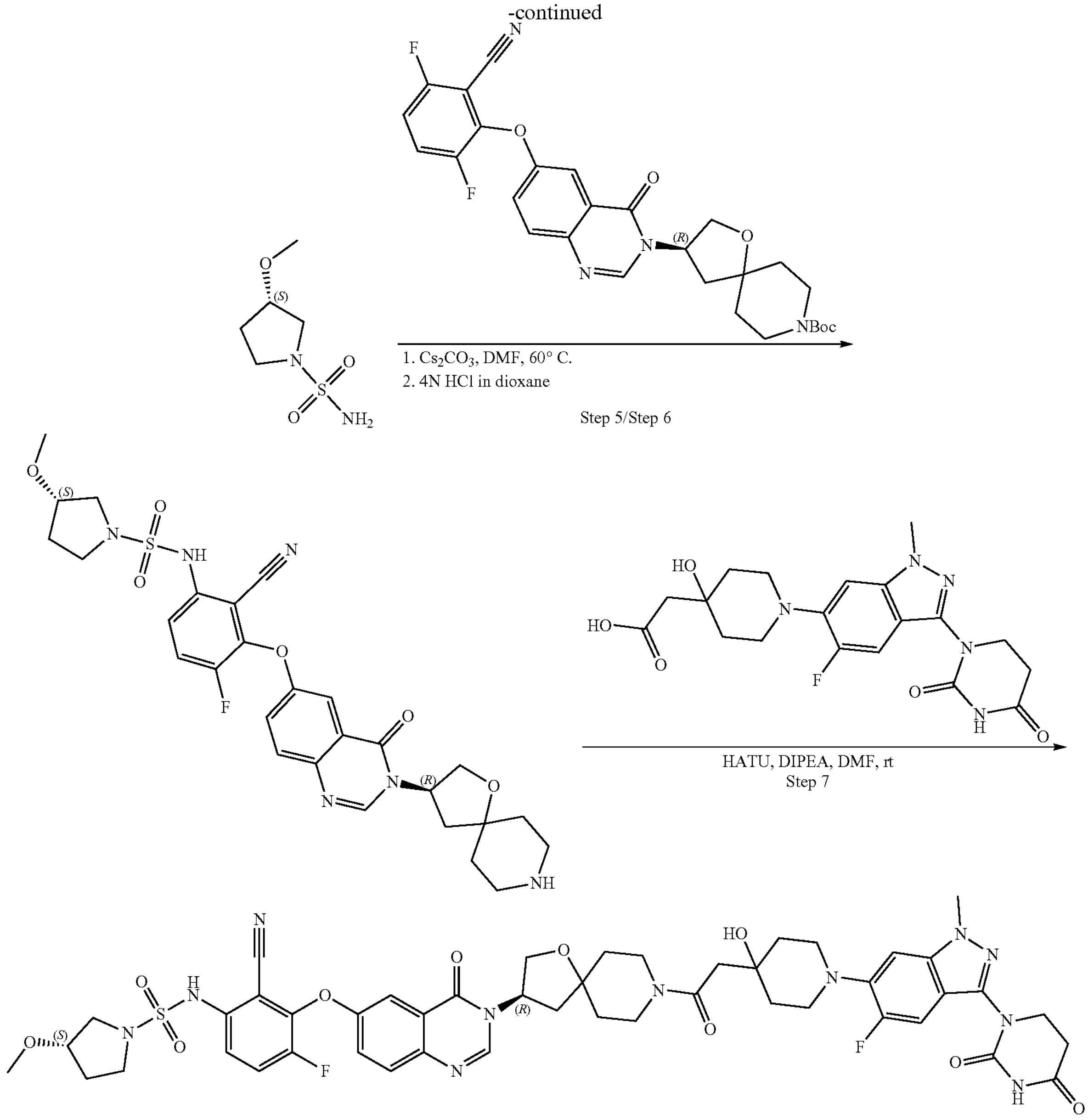

Step 1: To a stirred 0° C. solution of tert-butyl (3S)-3-hydroxypyrrolidine-1-carboxylate (5 g, 26.70 mmol) dissolved in tetrahydrofuran (50 mL) was added sodium hydride (2.32 g, 53.41 mmol, 60% dispersion in mineral oil). Stirring at 0° C. was continued for 1 h. Iodomethane (5.69 g, 40.06 mmol, 2.49 mL) was subsequently added, and the resultant reaction mixture was stirred at room temperature for 4 h. The reaction mixture was quenched by dropwise addition of ammonium chloride solution at 0° C. The phases were separated, and the aqueous layer further extracted with ethyl acetate (3×100 mL). The combined organic layers were dried over sodium sulfate and concentrated to afford crude material. The desired product was purified from crude by silica gel flash column chromatography eluting with 40-50% ethyl acetate in petroleum ether as eluent to afford tert-butyl (3S)-3-methoxypyrrolidine-1-carboxylate (5.5 g, 24.20 mmol, 91% yield) as a light brown viscous liquid. LCMS m/z (ESI): 102.0 $[M+H-100]^+$.

Step 2: To a stirred solution of tert-butyl (3S)-3-methoxypyrrolidine-1-carboxylate (5.5 g, 27.33 mmol) in dichloromethane (15 mL), was added 4M hydrogen chloride solution in dioxane (20 mL) at 5° C. under nitrogen atmosphere. The reaction mixture was stirred at room temperature for 3 h. The reaction mixture was concentrated under reduced pressure to afford crude (3S)-3-methoxypyrrolidine (4.5 g, 32.70 mmol) as a light brown solid. $^1$H-NMR (400 MHz, DMSO-$d_6$): δ=9.51 (s, 1H), 9.21 (s, 1H), 4.07 (q, J=2.40 Hz, 1H), 3.76 (s, 1H), 3.24 (s, 3H), 3.09-3.23 (m, 3H), 2.00-2.07 (m, 1H), 1.82-1.92 (m, 1H).

Step 3/Step 4: To a −30° C. stirred solution of (3S)-3-methoxypyrrolidine (4.5 g, 32.70 mmol) in dichloromethane (20 mL) were added N,N-diisopropylethylamine (6.34 g, 49.05 mmol, 8.54 mL) and sulfuryl chloride (11.03 g, 81.75 mmol). Stirring at −30° C. was continued for 2 h. The reaction mixture was quenched by dropwise addition of water (60 mL), extracted with dichloromethane (2×100 mL).

The combined organic layers were dried over sodium sulfate, filtered and concentrated under reduced pressure to afford crude (3S)-3-methoxypyrrolidine-1-sulfonyl chloride (3.1 g, 15.53 mmol, 47% yield), which was used in next step without further purification. To a stirred 0° C. solution of (3S)-3-methoxypyrrolidine-1-sulfonyl chloride (3.1 g, 15.53 mmol) in methanol (10 mL) was added 7M ammonia in methanol (7 M, 10 mL). The reaction mixture was warmed to room temperature and stirred for 16 h. After completion, the reaction mixture was concentrated under reduced pressure, diluted with water (100 mL) and extracted with ethyl acetate (3×100 mL). The organic layer was washed with sodium bicarbonate solution (70 ml), dried over sodium sulfate, and concentrated under reduced pressure to afford crude material. The desired product was purified from crude by silica gel flash column chromatography eluting with 30-40% ethyl acetate in petroleum ether as eluent to afford (3S)-3-methoxypyrrolidine-1-sulfonamide (0.470, 2.55 mmol, 16% yield) as off-white solid. LCMS m/z (ESI): 181.2 $[M+H]^+$.

Step 5: Sulfamoylated quinazolinone intermediate was synthesized by following Procedure B—C using tert-butyl (3R)-3-[6-(2-cyano-3,6-difluoro-phenoxy)-4-oxo-quinazolin-3-yl]-1-oxa-8-azaspiro[4.5]decane-8-carboxylate (100.00 mg, 185.69 μmol), cesium carbonate (181.50 mg, 557.06 μmol) and (3S)-3-methoxypyrrolidine-1-sulfonamide (83.66 mg, 464.22 μmol) to afford tert-butyl (3R)-3-[6-[2-cyano-6-fluoro-3-[[(3S)-3-methoxypyrrolidin-1-yl]sulfonylamino]phenoxy]-4-oxo-quinazolin-3-yl]-1-oxa-8-azaspiro[4.5]decane-8-carboxylate (130 mg, 142.21 μmol, 77% yield) as brown viscous liquid. LCMS m/z (ESI): 697.0 $[M-H]^-$.

Step 6: The requisite amine was synthesized by HCl mediated N-Boc deprotection (Procedure B-D). N-Boc deprotection was done on tert-butyl (3R)-3-[6-[2-cyano-6-fluoro-3-[[(3S)-3-methoxypyrrolidin-1-yl]sulfonylamino]phenoxy]-4-oxo-quinazolin-3-yl]-1-oxa-8-azaspiro[4.5]decane-8-carboxylate (130.00 mg, 186.04 μmol) using 4M hydrogen chloride solution in dioxane (4 M, 46.51 μL) to afford (3S)—N-[2-cyano-4-fluoro-3-[3-[(3R)-1-oxa-8-azaspiro[4.5]decan-3-yl]-4-oxo-quinazolin-6-yl]oxy-phenyl]-3-methoxy-pyrrolidine-1-sulfonamide (130 mg, 168.28 μmol, 90% yield) as light brown solid. LCMS m/z (ESI): 599.2 $[M+H]^+$.

Step 7: Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (91.08 mg, 217.16 μmol), N,N-diisopropylethylamine (140.33 mg, 1.09 mmol, 189.12 μL), HATU (82.57 mg, 217.16 μmol) and (3S)—N-[2-cyano-4-fluoro-3-[3-[(3R)-1-oxa-8-azaspiro[4.5]decan-3-yl]-4-oxo-quinazolin-6-yl]oxy-phenyl]-3-methoxy-pyrrolidine-1-sulfonamide (130.00 mg, 217.16 μmol). The crude residue was purified by reverse phase column chromatography (0.1% formic acid in water:acetonitrile) to afford (3S)—N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-methoxy-pyrrolidine-1-sulfonamide (32.06 mg, 31.24 μmol, 14% yield) as off-white solid. LCMS m/z (ESI): 1000.0 $[M+H]^+$; $^1H$-NMR (400 MHz, DMSO-$d_6$): δ=10.54 (s, 1H), 10.24 (s, 1H), 8.36 (s, 1H), 7.75-7.90 (m, 1H), 7.79 (d, J=8.80 Hz, 1H), 7.68 (dd, J=2.80, 8.80 Hz, 1H), 7.41-7.51 (m, 1H), 7.37 (d, J=2.80 Hz, 1H), 7.33 (d, J=12.80 Hz, 1H), 7.13 (d, J=7.20 Hz, 1H), 5.25-5.35 (m, 1H), 5.03 (d, J=2.40 Hz, 1H), 4.10-4.20 (m, 2H), 3.92-4.01 (m, 1H), 3.94 (s, 3H), 3.89 (t, J=6.40 Hz, 2H), 3.73-3.84 (m, 1H), 3.58-3.68 (m, 1H), 3.48-3.59 (m, 1H), 3.23-3.41 (m, 4H), 3.34 (s, 3H), 3.14-3.21 (m, 2H), 3.06 (t, J=10.80 Hz, 2H), 2.74 (t, J=6.40 Hz, 2H), 2.35-2.61 (m, 4H), 2.03-2.12 (m, 1H).

Example 177

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxypyrrolidine-1-sulfonamide

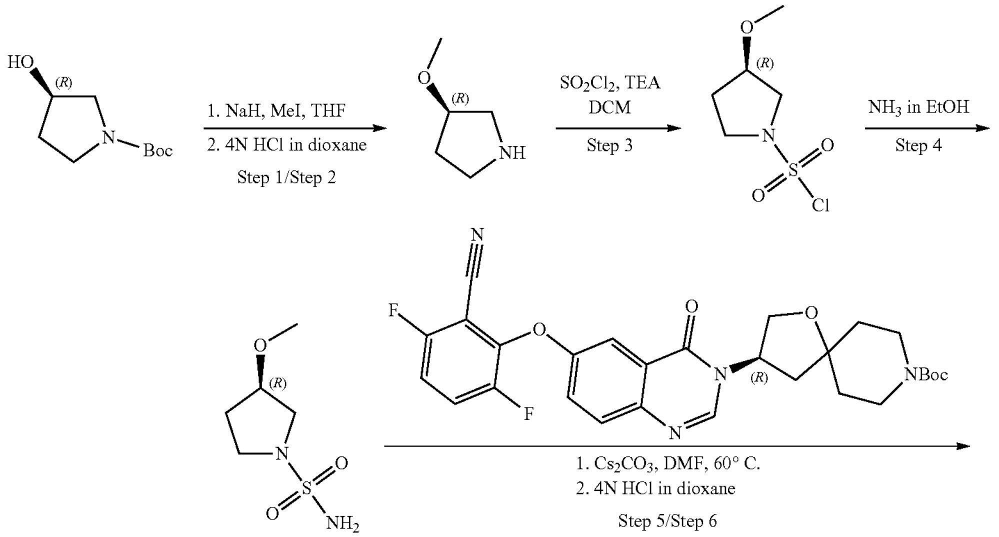

-continued

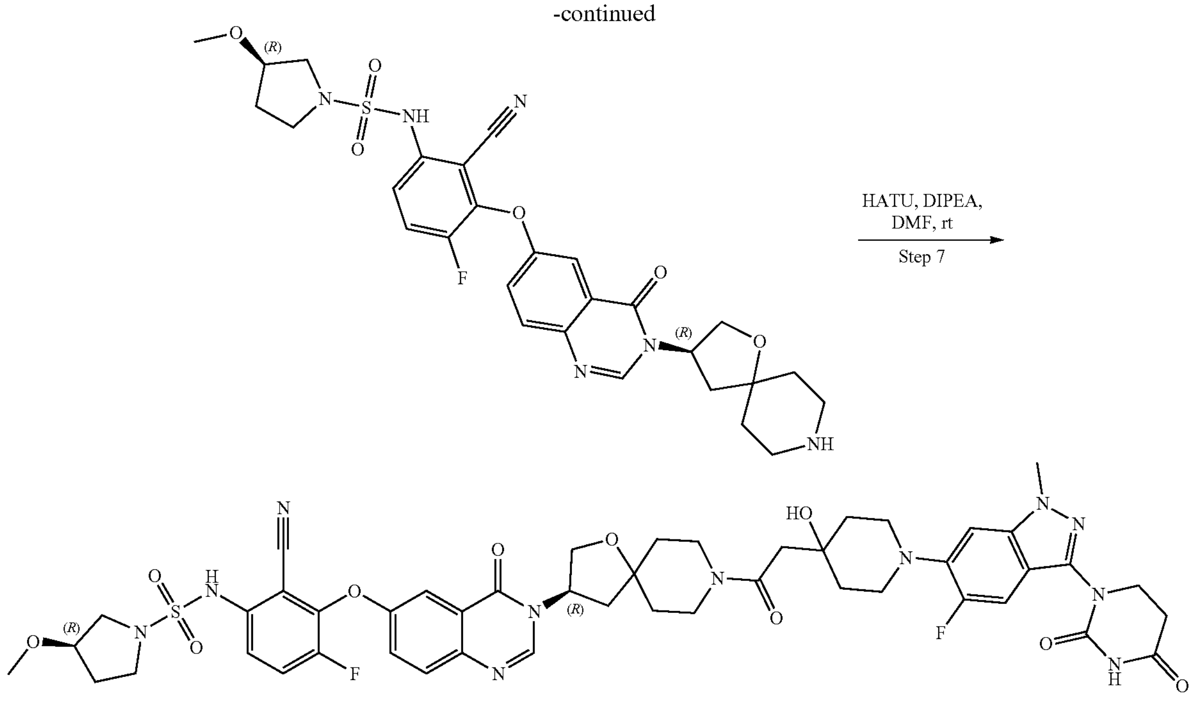

Step 1: To a stirred 0° C. solution tert-butyl (3R)-3-hydroxypyrrolidine-1-carboxylate (4 g, 21.36 mmol) in tetrahydrofuran (30 mL) was added sodium hydride (60% dispersion in mineral oil, 1.64 g, 42.73 mmol). Stirring at 0° C. was continued for 1 h and methyl iodide (4.55 g, 32.05 mmol, 1.99 mL) was added at the same temperature. The reaction mixture was allowed to warm to room temperature and stir for 2 h. The reaction mixture was quenched by dropwise addition of saturated ammonium chloride solution (30 mL) at 0° C. and extracted with ethyl acetate (3×70 mL). The combined organic layers washed with cold water (3×50 mL), dried over sodium sulfate, filtered, and concentrated under reduced pressure to afford crude material. The desired product was purified from the crude residue by silica gel flash column chromatography using 10-20% ethyl acetate in petroleum ether as eluent to afford tert-butyl (3R)-3-methoxypyrrolidine-1-carboxylate (4 g, 19.81 mmol, 93% yield) as a colorless liquid. GCMS m/z (ESI): 201.1 $[M+H]^+$.

Step 2: To a stirred solution of tert-butyl (3R)-3-methoxypyrrolidine-1-carboxylate (4 g, 19.87 mmol) in dioxane (3 mL) was added 4M hydrogen chloride solution in dioxane (4 M, 4.97 mL) at 5° C. under nitrogen atmosphere. The reaction mixture was stirred at room temperature for 2 h. After completion, the reaction mixture was concentrated under reduced pressure to afford crude (3R)-3-methoxypyrrolidine (3.3 g, 17.99 mmol, 91% yield) as light brown solid. $^1$H-NMR (400 MHz, DMSO-$d_6$): δ=9.60 (s, 1H), 9.29 (s, 1H), 4.07 (q, J=2.40 Hz, 1H), 3.65 (s, 1H), 3.25 (s, 3H), 3.09-3.25 m, 3H), 2.00-2.07 (m, 1H), 1.82-1.92 (m, 1H).

Step 3/Step 4: To a stirred −30° C. solution of (3R)-3-methoxypyrrolidine (3.5 g, 34.60 mmol) in dichloromethane (5 mL) were added N,N-diisopropylethylamine (6.71 g, 51.90 mmol, 9.04 mL), sulfuryl chloride (11.68 g, 86.51 mmol). Stirring at −30° C. was continued for 2 h. The reaction mixture was quenched by dropwise addition of water (60 mL). The layers were separated, and the aqueous further extracted with ethyl acetate (2×100 mL). The combined organic layers washed with 1.5N HCl solution (2×50 mL), dried over sodium sulfate, filtered, and concentrated under reduced pressure to afford crude (3R)-3-methoxypyrrolidine-1-sulfonyl chloride (3.3 g, 12.40 mmol, 35.82% yield). To a solution of (3R)-3-methoxypyrrolidine-1-sulfonyl chloride (3.3 g, 16.53 mmol) in methanol (8 mL) was added 7M ammonia in methanol (7 M, 2.36 mL) at 0° C. and stirred at room temperature for 14 h. The reaction mixture was concentrated under reduced pressure to afford a crude residue, which was partitioned between water (30 mL) and ethyl acetate (50 mL). The organic layer was washed with sodium bicarbonate solution (20 ml), brine (20 ml), dried over sodium sulfate, and concentrated under reduced pressure. The crude product was purified by silica gel flash column chromatography, eluting with 40% ethyl acetate in petroleum ether to afford (3R)-3-methoxypyrrolidine-1-sulfonamide (1.2 g, 6.66 mmol, 40% yield) as light brown solid. LCMS m/z (ESI): 181.2 $[M+H]^+$.

Step 5: Sulfamoylated quinazolinone intermediate was synthesized by following Procedure B—C using (3R)-3-methoxypyrrolidine-1-sulfonamide (150 mg, 832.29 μmol), cesium carbonate (325.41 mg, 998.75 μmol) and tert-butyl (3R)-3-[6-(2-cyano-3,6-difluoro-phenoxy)-4-oxo-quinazolin-3-yl]-1-oxa-8-azaspiro[4.5]decane-8-carboxylate (179.29 mg, 332.92 μmol) to afford crude tert-butyl (3R)-3-[6-[2-cyano-6-fluoro-3-[[(3R)-3-methoxypyrrolidin-1-yl]sulfonylamino]phenoxy]-4-oxo-quinazolin-3-yl]-1-oxa-8-azaspiro[4.5]decane-8-carboxylate (190 mg, 239.42 μmol, 72% yield) as brown viscous liquid. LCMS m/z (ESI): 700.0 $[M+H]^+$.

Step 6: The requisite amine was synthesized by hydrogen chloride mediated N-Boc deprotection (Procedure B-D). N-Boc deprotection was done on tert-butyl (3R)-3-[6-[2-cyano-6-fluoro-3-[[(3R)-3-methoxypyrrolidin-1-yl]sulfonylamino]phenoxy]-4-oxo-quinazolin-3-yl]-1-oxa-8-azaspiro[4.5]decane-8-carboxylate (190.00 mg, 271.91 μmol) using 4M hydrogen chloride solution in dioxane (4 M, 67.98 μL) to afford crude (3R)—N-[2-cyano-4-fluoro-3-[3-

[(3R)-1-oxa-8-azaspiro[4.5]decan-3-yl]-4-oxo-quinazolin-6-yl]oxy-phenyl]-3-methoxy-pyrrolidine-1-sulfonamide (170 mg, 243.74 μmol, 90% yield) as light brown solid. LCMS m/z (ESI): 599.2 $[M+H]^+$.

Step 7: Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (84.07 mg, 200.45 μmol), N,N-diisopropylethylamine (129.54 mg, 1.00 mmol, 174.58 μL) and HATU (83.84 mg, 220.50 μmol) and (3R)—N-[2-cyano-4-fluoro-3-[3-[(3R)-1-oxa-8-azaspiro[4.5]decan-3-yl]-4-oxo-quinazolin-6-yl]oxy-phenyl]-3-methoxy-pyrrolidine-1-sulfonamide (120.00 mg, 200.45 μmol). The desired product was purified from crude material by reverse phase column chromatography (0.1% formic acid in water:acetonitrile) and fractions were lyophilized to afford (3R)—N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-methoxy-pyrrolidine-1-sulfonamide (40.51 mg, 39.70 μmol, 20% yield) as off-white solid. LCMS m/z (ESI): 1000$[M+H]^+$; $^1$H-NMR (400 MHz, DMSO-$d_6$): δ=10.52 (s, 1H), 10.22 (s, 1H), 8.36 (s, 1H), 7.75-7.90 (m, 1H), 7.80 (d, J=8.80 Hz, 1H), 7.69 (dd, J=2.80, 8.80 Hz, 1H), 7.45-7.55 (m, 1H), 7.38 (d, J=2.80 Hz, 1H), 7.33 (d, J=12.80 Hz, 1H), 7.12 (d, J=7.20 Hz, 1H), 5.25-5.35 (m, 1H), 5.02 (s, 1H), 4.10-4.20 (m, 2H), 3.92-4.01 (m, 1H), 3.95 (s, 3H), 3.89 (t, J=6.80 Hz, 2H), 3.73-3.84 (m, 1H), 3.58-3.68 (m, 1H), 3.48-3.59 (m, 1H), 3.23-3.41 (m, 4H), 3.19 (s, 3H), 3.14-3.21 (m, 2H), 3.02-3.11 (m, 2H), 2.74 (t, J=6.80 Hz, 2H), 2.35-2.61 (m, 4H), 2.03-2.12 (m, 1H).

Example 178

(3R)-3-[6-[2-cyano-3-[[ethyl(methyl)sulfamoyl]amino]-6-fluoroanilino]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

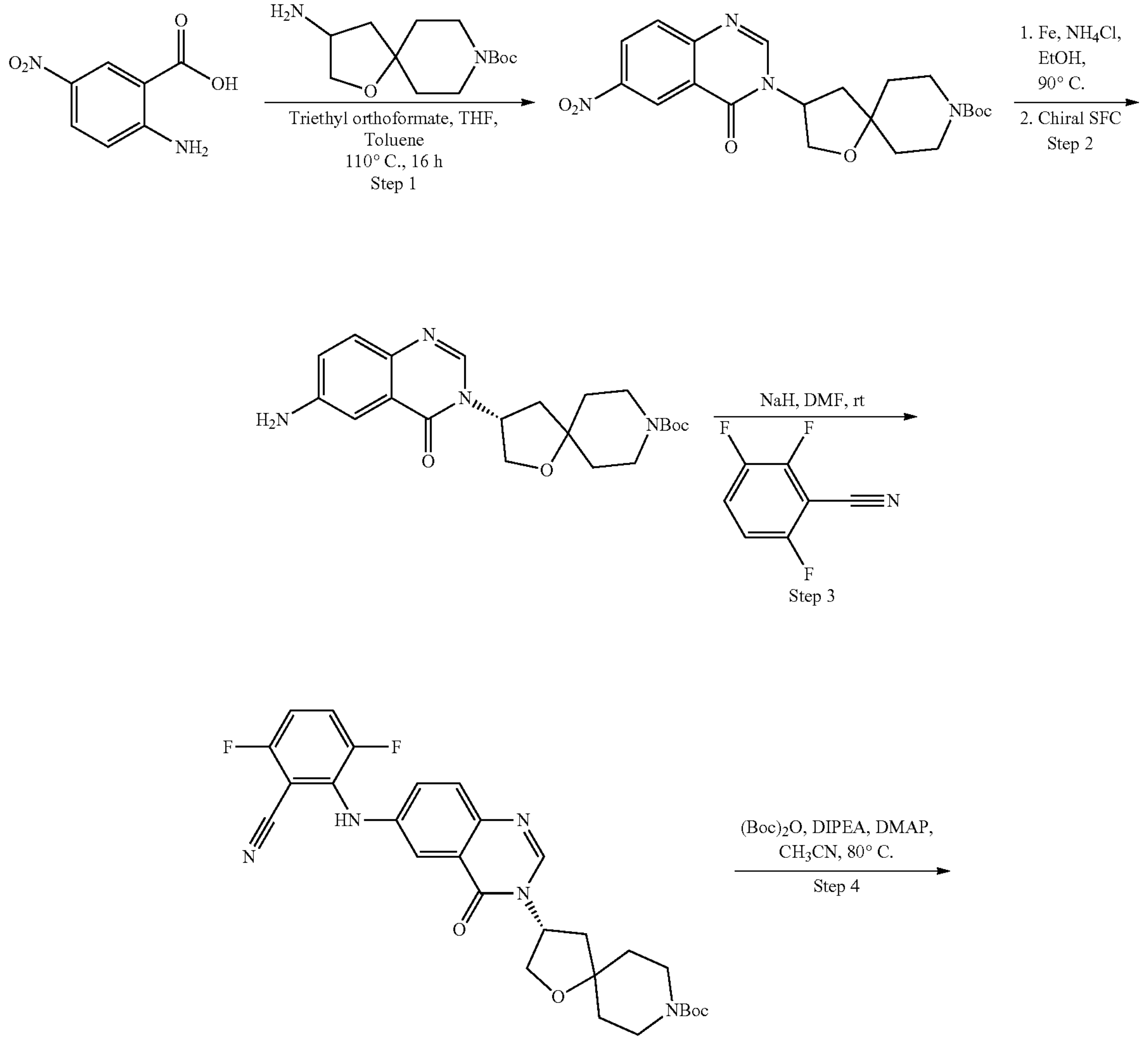

-continued

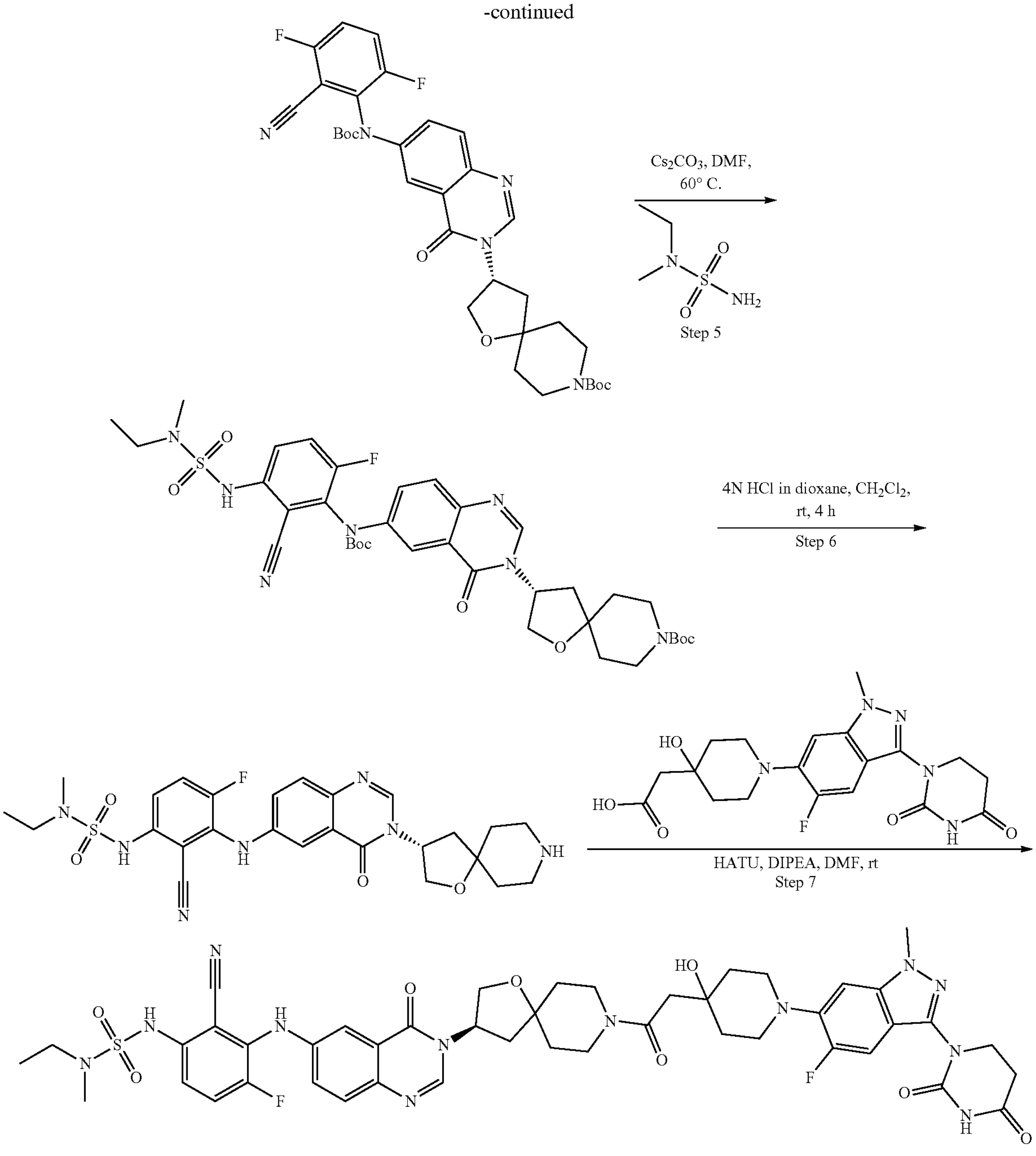

Step 1: Quinazolinone intermediate was synthesized by following general procedure for cyclization (Procedure B-A) using tert-butyl 3-amino-1-oxa-8-azaspiro[4.5]decane-8-carboxylate (2 g, 7.80 mmol), 2-amino-5-nitro-benzoic acid (1.42 g, 7.80 mmol), triethyl orthoformate (3.47 g, 23.41 mmol, 3.89 mL). After reaction completion, the reaction mixture was diluted water (50 mL) and extracted with ethyl acetate (3×50 mL). The organic layer was washed with sodium bicarbonate solution (2×50 mL) and brine (50 mL), dried over sodium sulfate and concentrated under reduced pressure to provide a crude residue, which was triturated with 10% ethyl acetate in petroleum ether to afford tert-butyl 3-(6-nitro-4-oxo-quinazolin-3-yl)-1-oxa-8-azaspiro[4.5]decane-8-carboxylate (3 g, 5.44 mmol, 70% yield) as a brown solid. LCMS m/z (ESI): 375.2 $[M-CO_2{}^tBu+H]^+$ Step 2: To a stirred solution of tert-butyl 3-(6-nitro-4-oxo-quinazolin-3-yl)-1-oxa-8-azaspiro[4.5]decane-8-carboxylate (3 g, 6.97 mmol) in water (5 mL)/ethanol (25 mL) were added iron powder (1.95 g, 34.85 mmol, 247.59 μL) and ammonium chloride (1.86 g, 34.85 mmol, 1.22 mL) at room temperature. The reaction mixture was stirred at 85° C. for 3 h. After completion, the reaction mixture was filtered and concentrated under reduced pressure to provide crude material. The crude was dissolved in water (50 mL) and extracted with ethyl acetate (3×50 mL). The combined organic phases were dried over anhydrous sodium sulfate, filtered, and the filtrate was evaporated under reduced pressure to afford crude product. The crude material was purified by silica gel chromatography using 70-80% ethyl acetate in petroleum ether as eluent to afford tert-butyl 3-(6-amino-4-oxo-quinazolin-3-yl)-1-oxa-8-azaspiro[4.5]decane-8-carboxylate (1.8 g, 4.45 mmol, 63.85% yield) as a brown solid. The racemic compound was chirally resolved by chiral SFC (column Lux-A1 [250*30 mm, 5 micron]; Mobile phase: 50% IPA-$CO_2$+0.5% isopropyl amine in methanol; Flow rate: 120 mL/min; cycle time: 7.6 min; back pressure: 100 bar; UV: 210 nm) to afford peak 1 (first-eluted, arbitrarily assigned as S-isomer) tert-butyl (S)-3-(6-amino-4-oxoquinazolin-3(4H)-yl)-1-oxa-8-azaspiro[4.5]decane-8-carboxylate (610 mg) as off-white solid and the desired peak 2 (second eluted, arbitrarily assigned as R-isomer) tert-butyl (R)-3-(6-amino-4-oxoquinazolin-3(4H)-yl)-1-oxa-8-azaspiro[4.5]decane-8-carboxylate (600 mg, 2.93 mmol, 10% yield) as off-white solid. LCMS m/z (ESI): 401.2 $[M+H]^+$ Step 3: To a stirred solution of sodium hydride (60% dispersion in mineral oil, 172.22 mg, 4.49 mmol) in N,N-dimethylformamide (10 mL) was added tert-butyl (3R)-3-(6-amino-4-oxo-quinazolin-3-yl)-1-oxa-8-azaspiro[4.5]decane-8-carboxylate (600 mg, 1.50 mmol) dissolved in N,N-dimethylformamide (5 mL) at 0° C. The reaction mixture was stirred at room temperature for 2 h. Next, 2,3,6-trifluorobenzonitrile (470.73 mg, 3.00 mmol, 346.12 μL) was added to the reaction mixture at room temperature and stirred for 16 h. After completion, the reaction mixture was quenched with cold water (50 mL) and extracted with ethyl acetate (2×50 mL). The combined organic layer was dried with anhydrous sodium sulfate and concentrated under reduced pressure to afford crude. The crude compound was purified by silica gel flash column chromatography with 70-80% ethyl acetate in pet ether as a eluent to afford tert-butyl (3R)-3-[6-(2-cyano-3,6-difluoro-anilino)-4-oxo-quinazolin-3-yl]-1-oxa-8-azaspiro[4.5]decane-8-carboxylate (720 mg, 688.1 μmol, 46% yield) as a brown solid. LCMS m/z (ESI): 538.8 $[M+H]^+$ Step 4: To a solution of tert-butyl(3R)-3-[6-(2-cyano-3,6-difluoro-anilino)-4-oxo-quinazolin-3-yl]-1-oxa-8-azaspiro[4.5]decane-8-carboxylate (700 mg, 1.30 mmol) in anhydrous acetonitrile (8 mL) were added DMAP (79.54 mg, 651.09 μmol) and triethylamine (395.31 mg, 3.91 mmol, 544.50 μL) at room temperature. Di-tert-butyl pyro carbonate (568.40 mg, 2.60 mmol, 597.68 μL) was added dropwise at 0° C., and the contents were allowed to stir at room temperature for 16 h. After completion, the reaction mixture was quenched with water (50 mL), extracted with ethyl acetate (60 mL), dried over sodium sulfate, and filtered. The solvent was evaporated. The crude material was purified by silica gel flash column chromatography with 70-80% ethyl acetate in petroleum ether as a eluent to afford tert-butyl (3R)-3-[6-(N-tert-butoxycarbonyl-2-cyano-3,6-difluoro-anilino)-4-oxo-quinazolin-3-yl]-1-oxa-8-azaspiro[4.5]decane-8-carboxylate (600 mg, 412.59 μmol, 32% yield) as an off-white solid. LCMS m/z (ESI): 638.4 $[M+H]^+$ Step 5: Sulfamoylated quinazolinone intermediate was synthesized by following Procedure B—C using of tert-butyl (3R)-3-[6-(N-tert-butoxycarbonyl-2-cyano-3,6-difluoro-anilino)-4-oxo-quinazolin-3-yl]-1-oxa-8-azaspiro[4.5]decane-8-carboxylate (600 mg, 940.92 μmol), cesium carbonate (919.71 mg, 2.82 mmol) and [methyl(sulfamoyl)amino]ethane (370.77 mg, 2.35 mmol). The crude compound was purified using reverse phase prep HPLC (Column: X— select C18 (150*19) mm 5 micron Prep method: 0.1% ammonium acetate in water/acetonitrile) to afford tert-butyl (3R)-3-[6-[N-tert-butoxycarbonyl-2-cyano-3-[[ethyl(methyl)sulfamoyl]amino]-6-fluoro-anilino]-4-oxo-quinazolin-3-yl]-1-oxa-8-azaspiro[4.5]decane-8-carboxylate (160 mg, 185.75 μmol, 20% yield) as an off-white solid. LCMS m/z (ESI): 754.1 $[M-H]^-$ Step 6: The requisite amine was synthesized by following Procedure B-D using tert-butyl (3R)-3-[6-[N-tert-butoxycarbonyl-2-cyano-3-[[ethyl(methyl)sulfamoyl]amino]-6-fluoro-anilino]-4-oxo-quinazolin-3-yl]-1-oxa-8-azaspiro[4.5]decane-8-carboxylate (160 mg, 211.68 μmol) and hydrogen chloride solution (4.0M in dioxane, 3 mL). The resulted crude compound was triturated with methyl t-butyl ether to afford (3R)-3-[6-[2-cyano-3-[[ethyl(methyl)sulfamoyl]amino]-6-fluoro-anilino]-4-oxo-quinazolin-3-yl]-1-oxa-8-azaspiro[4.5]decane (140 mg, 204.18 μmol, 96% yield) as an off-white solid. LCMS m/z (ESI): 556.7 $[M+H]^+$ Step 7: Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-anilino]-4-oxo-quinazolin-3-yl]-1-oxa-8-azaspiro[4.5]decane (70 mg, 102.09 μmol), 2-[1-[3-(2,4-dioxohexahydropyrimidin-1-yl)-5-fluoro-1-methyl-indazol-6-yl]-4-hydroxy-4-piperidyl]acetic acid (51.38 mg, 112.71 μmol), N,N-diisopropylethylamine (131.94 mg, 1.02 mmol, 177.82 μL) and HATU (58.23 mg, 153.13 μmol). The crude compound was purified by reverse phase column chromatography eluted with 45% acetonitrile in 0.1% ammonium acetate in water to afford product (3R)-3-[6-[2-cyano-3-[[ethyl(methyl)sulfamoyl]amino]-6-fluoro-anilino]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (21 mg, 20.74 μmol, 20% yield) as an off-white solid. LCMS m/z (ESI): 957.0 $[M+H]^+$; $^1$HNMR (400 MHz, DMSO-$d_6$): δ=10.53 (s, 1H), 9.98 (s, 1H), 9.01 (bs, 1H), 8.24 (s, 1H), 7.66-7.59 (m, 2H), 7.35-7.27 (m, 4H), 7.13 (d, J=7.20 Hz, 1H), 5.36-5.33 (m, 1H), 5.04-5.03 (m, 1H), 4.14-4.13 (m, 2H), 3.95 (s, 3H), 3.91-3.89 (m, 2H), 3.88-3.79 (m, 1H), 3.79-3.64 (m, 1H), 3.64-3.51 (m, 1H), 3.19-3.17 (m, 4H), 3.16-3.06 (m, 2H), 2.79-2.72 (m, 5H), 2.52 (s, 3H), 2.42-2.39 (m, 1H), 2.08-2.03 (m, 1H), 1.82-1.68 (m, 8H), 1.06 (t, J=7.20 Hz, 3H).

Example 179
3-[6-[2-cyano-3-[[ethyl(methyl)sulfamoyl]amino]-6-fluorophenoxy]-5-(dimethylamino)-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane
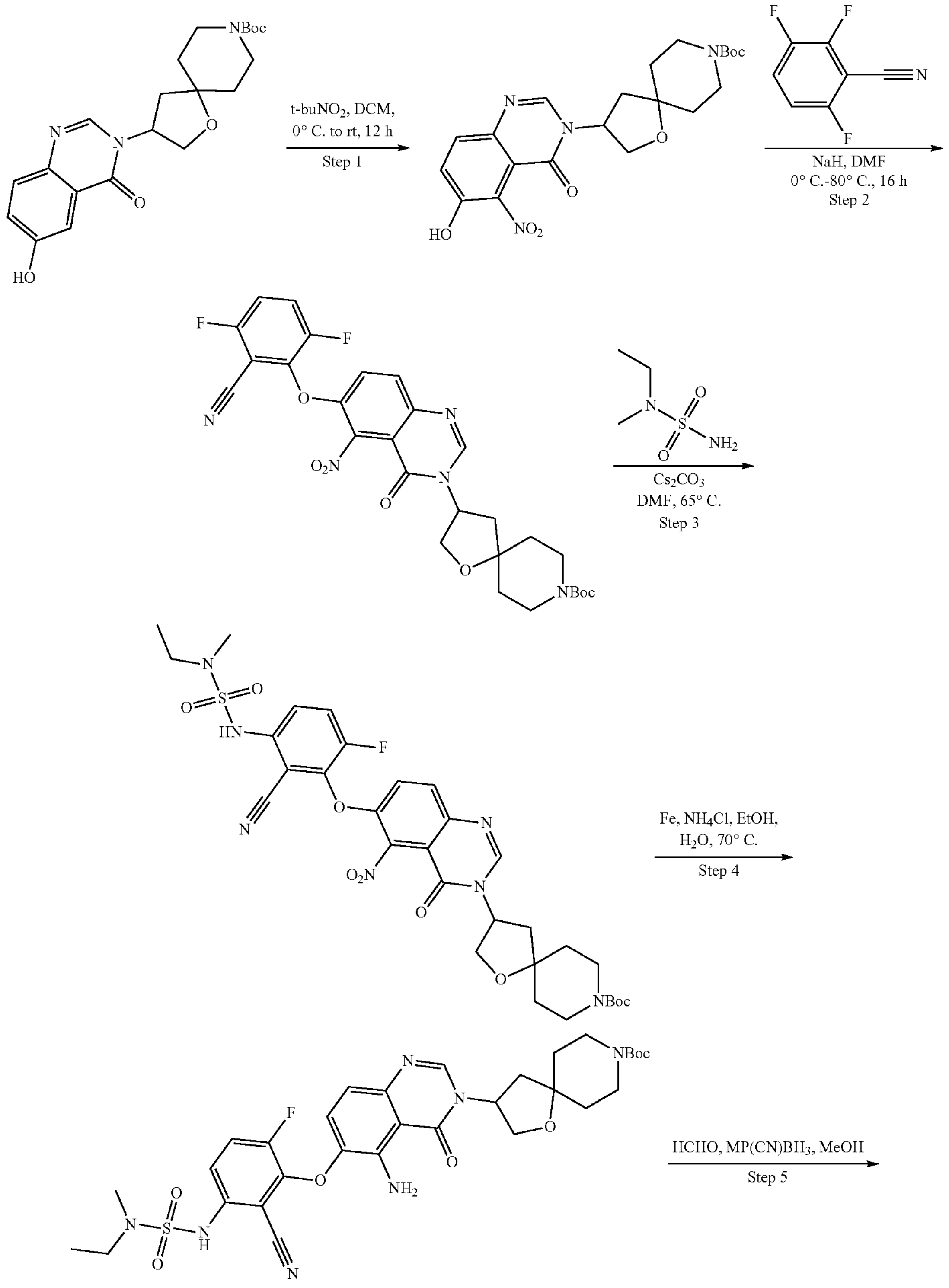

-continued

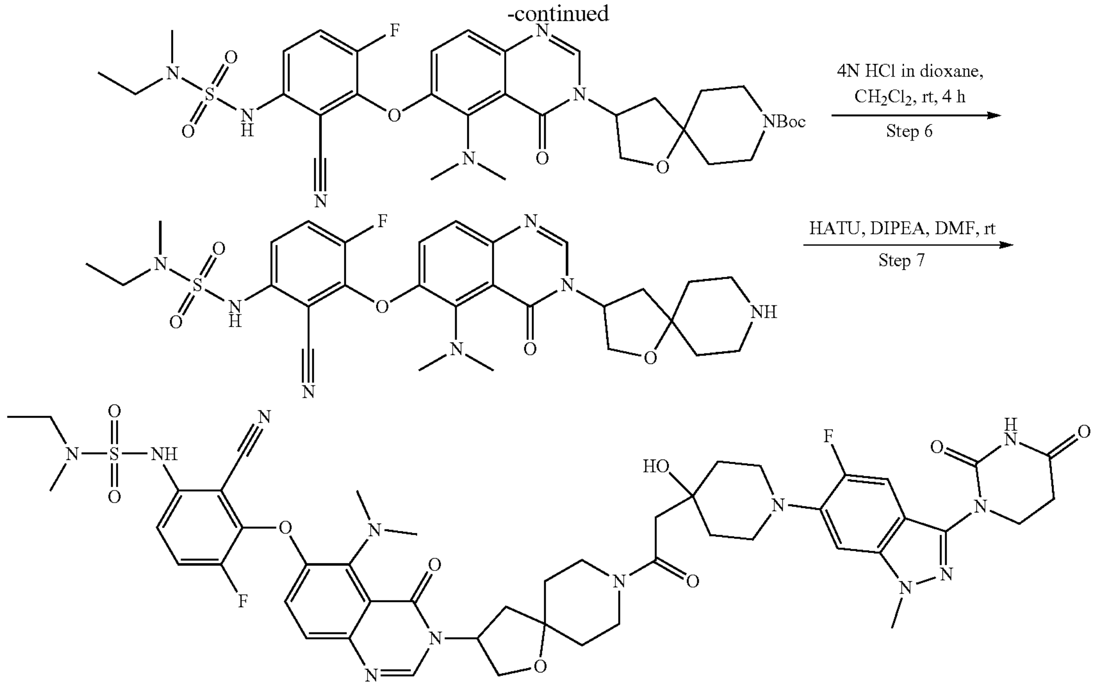

Step 1: To a stirred solution of tert-butyl 3-(6-hydroxy-4-oxo-quinazolin-3-yl)-1-oxa-8-azaspiro[4.5]decane-8-carboxylate (400 mg, 996.38 μmol) in dichloromethane (10 mL) was added tert-butyl nitrite (308.24 mg, 2.99 mmol, 355.52 μL) at 0° C. and the reaction mixture was stirred at room temperature for 12 h under nitrogen atmosphere. After completion of the reaction, the reaction mixture was diluted with water (20 mL) and extracted with dichloromethane (3×30 mL). The combined organic layers were washed with brine solution (50 mL), dried over sodium sulfate, filtered, and concentrated under reduced pressure to afford the crude. The crude compound was purified by silica gel flash column chromatography with 80-85% ethyl acetate in petroleum ether as a eluent to afford tert-butyl 3-(6-hydroxy-5-nitro-4-oxo-quinazolin-3-yl)-1-oxa-8-azaspiro[4.5]decane-8-carboxylate (210 mg, 437.45 μmol, 44% yield) as a brown solid. LCMS m/z (ESI): 445.6 $[M-H]^-$ Step 2: To a stirred solution of sodium hydride (60% dispersion in mineral oil, 33.47 mg, 1.46 mmol) in N,N-Dimethylformamide (2 mL) was added solution of tert-butyl 3-(6-hydroxy-5-nitro-4-oxo-quinazolin-3-yl)-1-oxa-8-azaspiro[4.5]decane-8-carboxylate (130 mg, 291.18 μmol) in N,N-Dimethylformamide (2 mL) at 0° C., and the reaction mixture was stirred at room temperature for 2 h. Then 2,3,6-trifluorobenzonitrile (137.23 mg, 873.55 μmol, 100.90 μL) was added to the reaction mixture and was stirred at 80° C. for 16 h. After completion of the reaction, the reaction mixture was quenched with cold water (10 mL) and extracted with ethyl acetate (2×10 mL). The combined organic layer was dried with anhydrous sodium sulfate and concentrated under reduced pressure to afford crude. The crude compound was purified by silica gel flash column chromatography with 60-70% ethyl acetate in petroleum ether as a eluent to afford tert-butyl 3-[6-(2-cyano-3,6-difluoro-phenoxy)-5-nitro-4-oxo-quinazolin-3-yl]-1-oxa-8-azaspiro[4.5]decane-8-carboxylate (60 mg, 90.48 μmol, 31% yield) as a brown solid. LCMS m/z (ESI): 484.0 $[M+H-CO2tBu]^+$ Step 3: Sulfamoylated quinazolinone intermediate was synthesized by following Procedure B—C using tert-butyl 3-[6-(2-cyano-3,6-difluoro-phenoxy)-5-nitro-4-oxo-quinazolin-3-yl]-1-oxa-8-azaspiro[4.5]decane-8-carboxylate (40 mg, 68.55 μmol), cesium carbonate (67.00 mg, 205.64 μmol) and [methyl(sulfamoyl)amino]ethane 28.42 mg, 205.64 μmol). The crude compound was purified by silica gel flash column chromatography with 70-80% ethyl acetate in petroleum ether as a eluent to afford tert-butyl 3-[6-[2-cyano-3-[[ethyl(methyl)sulfamoyl]amino]-6-fluoro-phenoxy]-5-nitro-4-oxo-quinazolin-3-yl]-1-oxa-8-azaspiro[4.5]decane-8-carboxylate (25 mg, 27.79 μmol, 41% yield) as a brown viscous. LCMS m/z (ESI): 700.0 $[M-H]^-$.

Step 4: To a stirred solution of tert-butyl 3-[6-[2-cyano-3-[[ethyl(methyl)sulfamoyl]amino]-6-fluoro-phenoxy]-5-nitro-4-oxo-quinazolin-3-yl]-1-oxa-8-azaspiro[4.5]decane-8-carboxylate (25 mg, 35.63 μmol) in water (1 mL)/ethanol (3 mL) were added iron powder (9.95 mg, 178.13 μmol) and ammonium chloride (9.53 mg, 178.13 μmol) at room temperature. The reaction mixture was stirred at 80° C. for 3 h. After completion of the reaction, the reaction mixture was filtered and concentrated under vacuum to afford crude. This crude was dissolved in water (5 mL), extracted with ethyl acetate (2×10 mL). The combined organic phases were dried with anhydrous sodium sulfate, filtered and the filtrate was evaporated under reduced pressure to afford crude product, which was purified by silica gel flash column chromatography using 80-90% ethyl acetate in petroleum ether as eluent to afford tert-butyl 3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (20 mg, 21.44 μmol, 60% yield) as a brown viscous. LCMS m/z (ESI): 672.20 $[M+H]^+$ Step 5: To a stirred solution of tert-butyl 3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (150 mg, 223.30 μmol) and paraformaldehyde (67.05 mg, 2.23 mmol, 62.08 μL) in methanol (4 mL) was added acetic acid (134.10 mg, 2.23 mmol, 127.71 μL) at room temperature. The reaction mixture was stirred at 60° C. for 2 h. MP-Cyanoborohydride(2.04 mmol/g) (264.20 mg, 538.98 μmol) was added and the reaction mixture was further stirred at 60° C. for 16 h. After completion, the reaction mixture was filtered and concentrated under vacuum to afford crude. The crude was purified by C18-reverse phase column chromatography (15 g RediSep® Rf C18, Method: 10 mM ammonium acetate in water:acetonitrile) and pure fractions were lyophilized to afford tert-butyl 3-[6-[2-cyano-3-[[ethyl(methyl)sulfamoyl]amino]-6-fluoro-phenoxy]-5-(dimethylamino)-4-oxo-quinazolin-3-yl]-1-oxa-8-azaspiro[4.5]decane-8-carboxylate (50 mg, 44.30 μmol, 20% yield) as an off-white solid. LCMS m/z (ESI): 700.20 $[M+H]^+$.

Step 6: The requisite amine was synthesized by following Procedure B-D using tert-butyl 3-[6-[2-cyano-3-[[ethyl (methyl)sulfamoyl]amino]-6-fluoro-phenoxy]-5-(dimethylamino)-4-oxo-quinazolin-3-yl]-1-oxa-8-azaspiro[4.5]decane-8-carboxylate (25 mg, 35.72 μmol) in dichloromethane (2 mL) and hydrogen chloride solution 4.0 M in dioxane (1 mL). The resulted crude compound was triturated with methyl t-butyl ether to afford 3-[6-[2-cyano-3-[[ethyl (methyl)sulfamoyl]amino]-6-fluoro-phenoxy]-5-(dimethylamino)-4-oxo-quinazolin-3-yl]-1-oxa-8-azaspiro[4.5]decane (25 mg, 24.76 μmol, 69% yield) as an off-white solid. LCMS m/z (ESI): 600.20 $[M+H]^+$.

Step 7: Target compound was prepared via HATU mediated acid-amine coupling reaction (Procedure B-E). Amide coupling was carried out using 3-[6-[2-cyano-3-[[ethyl (methyl)sulLfamoyl]amino]-6-fluoro-phenoxy]-5-(dimethylamino)-4-oxo-quinazolin-3-yl]-1-oxa-8-azaspiro[4.5]decane (25 mg, 39.30 μmol), 2-[1-[3-(2,4-dioxohexahydropyrimidin-1-yl)-5-fluoro-1-methyl-indazol-6-yl]-4-hydroxy-4-piperidyl]acetic acid (26.87 mg, 58.95 μmol), N,N-diisopropylethylamine (74.20 mg, 574.11 μmol, 0.1 mL) and HATU (17.93 mg, 47.16 μmol) to afford crude product. The crude compound was purified by reverse phase column chromatography eluting with 43% acetonitrile in 0.1% formic acid in water to afford product 3-[6-[2-cyano-3-[[ethyl(methyl)sμLfamoyl]amino]-6-fluoro-phenoxy]-5-(dimethylamino)-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (5.5 mg, 5.05 μmol, 13% yield) as an off-white solid. LCMS m/z (ESI): 1001.20 $[M+H]^+$; $^1$HNMR (400 MHz, DMSO-$d_6$): δ=10.53 (s, 1H), 8.23 (s, 2H), 7.45-7.05 (m, 6H), 6.65-6.50 (m, 1H), 5.40-5.30 (m, 1H), 5.05-5.04 (m, 1H), 4.18-4.10 (m, 2H), 3.95 (s, 3H), 3.93 (t, J=7.20 Hz, 2H), 3.85-3.75 (m, 1H), 3.70-3.60 (m, 1H), 3.60-3.50 (m, 2H), 3.25-3.15 (m, 3H), 3.10-3.00 (m, 2H), 2.95 (q, J=7.20 Hz, 2H), 2.83 (s, 6H), 2.80-2.70 (m, 2H), 2.68 (s, 3H), 2.45-2.35 (m, 1H), 2.05-1.95 (m, 1H), 1.85-1.60 (m, 7H), 1.01 (t, J=7.20 Hz, 3H).

Example 180

(3R)-3-[6-[2-cyano-3-[[ethyl(methyl)sulfamoyl] amino]-6-fluorophenoxy]-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane

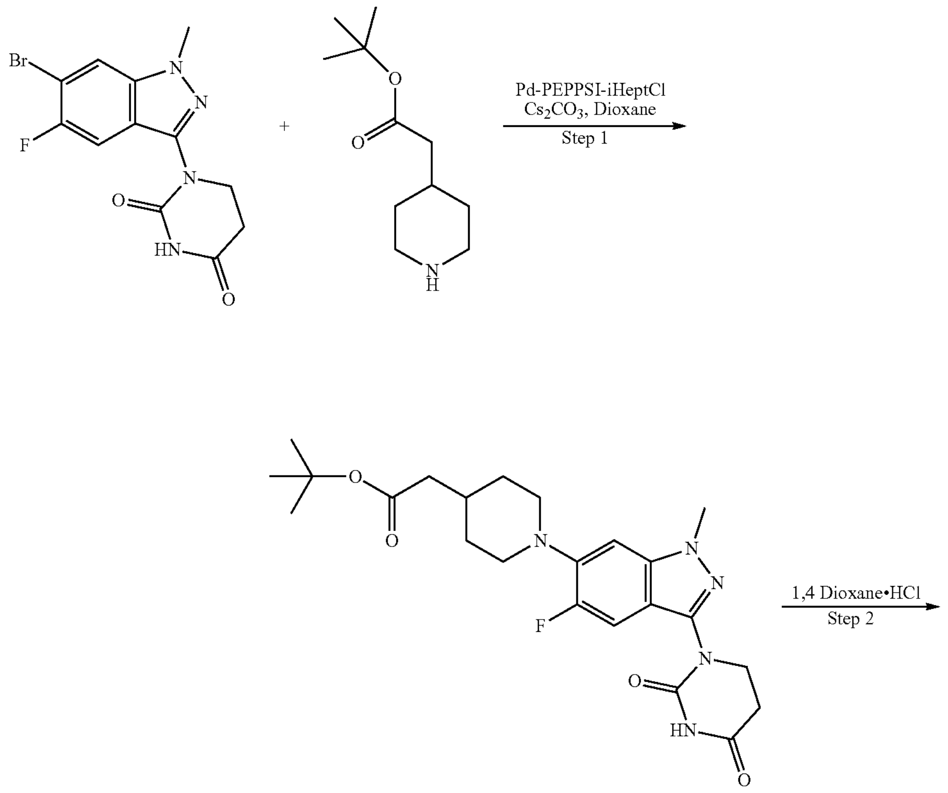

-continued

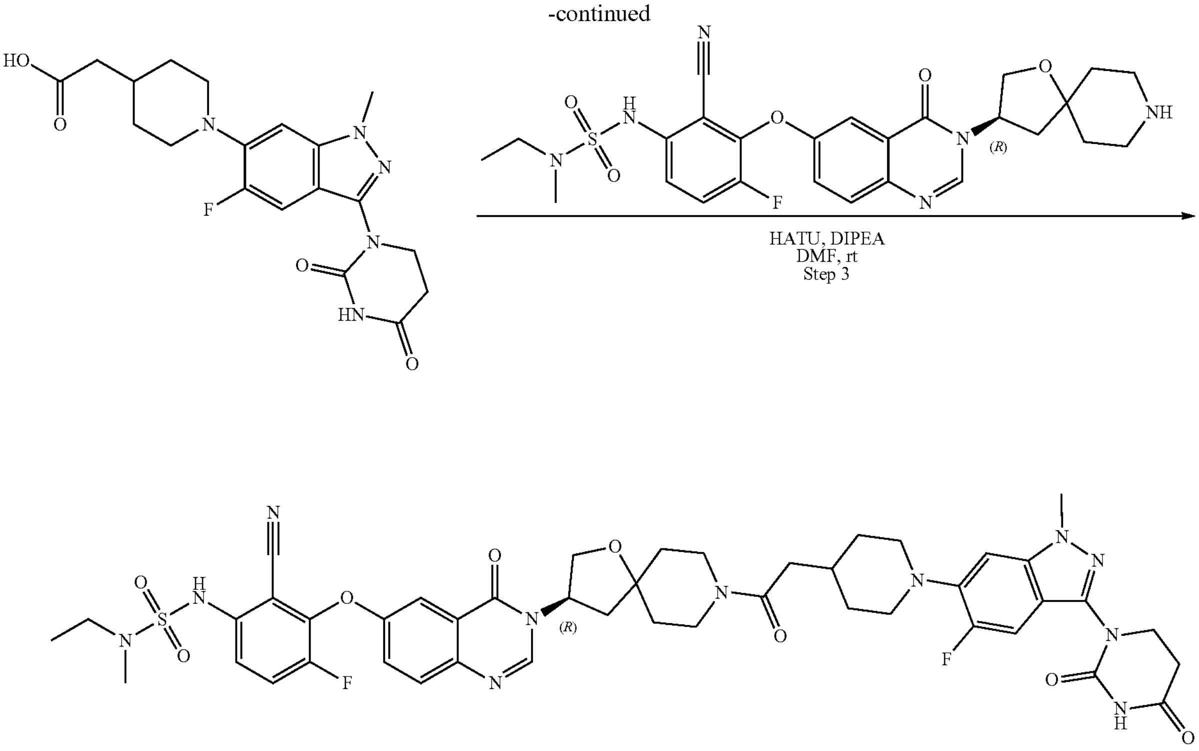

Step 1: A mixture of 1-(6-bromo-5-fluoro-1-methyl-indazol-3-yl)hexahydropyrimidine-2,4-dione (300 mg, 879.42 μmol), tert-butyl 2-(4-piperidyl)acetate (175.26 mg, 879.42 μmol) and cesium carbonate (573.06 mg, 1.76 mmol) in 1,4-dioxane (4 mL) was combined in sealed tube and degassed with $N_2$ for 10 minutes. Pd-PEPPSI-$^i$HeptCl (42.82 mg, 43.97 μmol) was added to the reaction mixture, and the resultant reaction mixture was sealed and heated at 100° C. for 14 h. The reaction mixture was diluted with water (60 mL) and extracted with ethyl acetate (120 mL). The organic layer was washed with water (50 mL), brine (50 mL), dried over sodium sulfate, and concentrated under reduced pressure. The crude material thus obtained was purified by silica gel flash column chromatography eluting with 70% ethyl acetate in petroleum ether to afford tert-butyl 2-[1-[3-(2,4-dioxohexahydropyrimidin-1-yl)-5-fluoro-1-methyl-indazol-6-yl]-4-piperidyl]acetate (160 mg, 311.95 μmol, 35% yield) as off-white solid. LCMS m/z (ESI): 460.2 $[M+H]^+$)

Step 2: To a 0° C. solution of tert-butyl 2-[1-[3-(2,4-dioxohexahydropyrimidin-1-yl)-5-fluoro-1-methyl-indazol-6-yl]-4-piperidyl]acetate (130 mg, 282.91 μmol) in dichloromethane (2 mL) was added 4M hydrogen chloride in 1,4-dioxane (4 M, 3 mL). The resultant reaction mixture was stirred at room temperature for 4 h. The reaction mixture was concentrated under reduced pressure to furnish crude, which was triturated with diethyl ether to afford 2-[1-[3-(2,4-dioxohexahydropyrimidin-1-yl)-5-fluoro-1-methyl-indazol-6-yl]-4-piperidyl]acetic acid (115 mg, 242.36 μmol, 86% yield) as light brown solid. LCMS m/z (ESI): 404.5 $[M+H]^+$)

Step 3: The target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane HCl salt (110 mg, 185.48 μmol), 2-[1-[3-(2,4-dioxohexahydropyrimidin-1-yl)-5-fluoro-1-methyl-indazol-6-yl]-4-piperidyl] acetic acid (74.82 mg, 185.48 μmol), N,N-diisopropylethylamine (95.89 mg, 741.90 μmol, 129.23 μL) and HATU (70.52 mg, 185.48 μmol) to afford (3R)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-piperidyl]acetyl]-1-oxa-8-azaspiro[4.5]decane (32 mg, 33.87 μmol, 18% yield) as off-white solid. LCMS m/z (ESI): 942.0 $[M+H]^+$; $^1$H-NMR (400 MHz, DMSO-$d_6$): δ=10.54 (s, 1H), 10.20 (s, 1H), 8.36 (s, 1H), 7.86 (bs, 1H), 7.80 (d, J=8.80 Hz, 1H), 7.70 (dd, J=3.20, 9.00 Hz, 1H), 7.49 (dd, J=3.60, 9.00 Hz, 1H), 7.36 (dd, J=2.80, 6.80 Hz, 1H), 7.32 (s, 1H), 7.09 (d, J=6.80 Hz, 1H), 5.33-5.26 (m, 1H), 4.12 (t, J=3.60 Hz, 1H), 4.31-4.30 (m, 2H), 3.94 (s, 3H), 3.89 (t, J=6.80 Hz, 2H), 3.76-3.68 (m, 1H), 3.53-3.38 (m, 4H), 3.16 (q, J=7.20 Hz, 2H), 2.79 (s, 3H), 2.74 (t, J=6.80 Hz, 2H), 2.68-2.67 (m, 2H), 2.39-2.34 (m, 3H), 2.08-2.07 (m, 1H), 1.83-1.64 (m, 7H), 1.42-1.39 (m, 2H), 1.05 (t, J=6.80 Hz, 3H).

Example 181
(3R)-3-[6-[2-cyano-3-[[ethyl(methyl)sulfamoyl]amino]-6-fluorophenoxy]-5-methoxy-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane
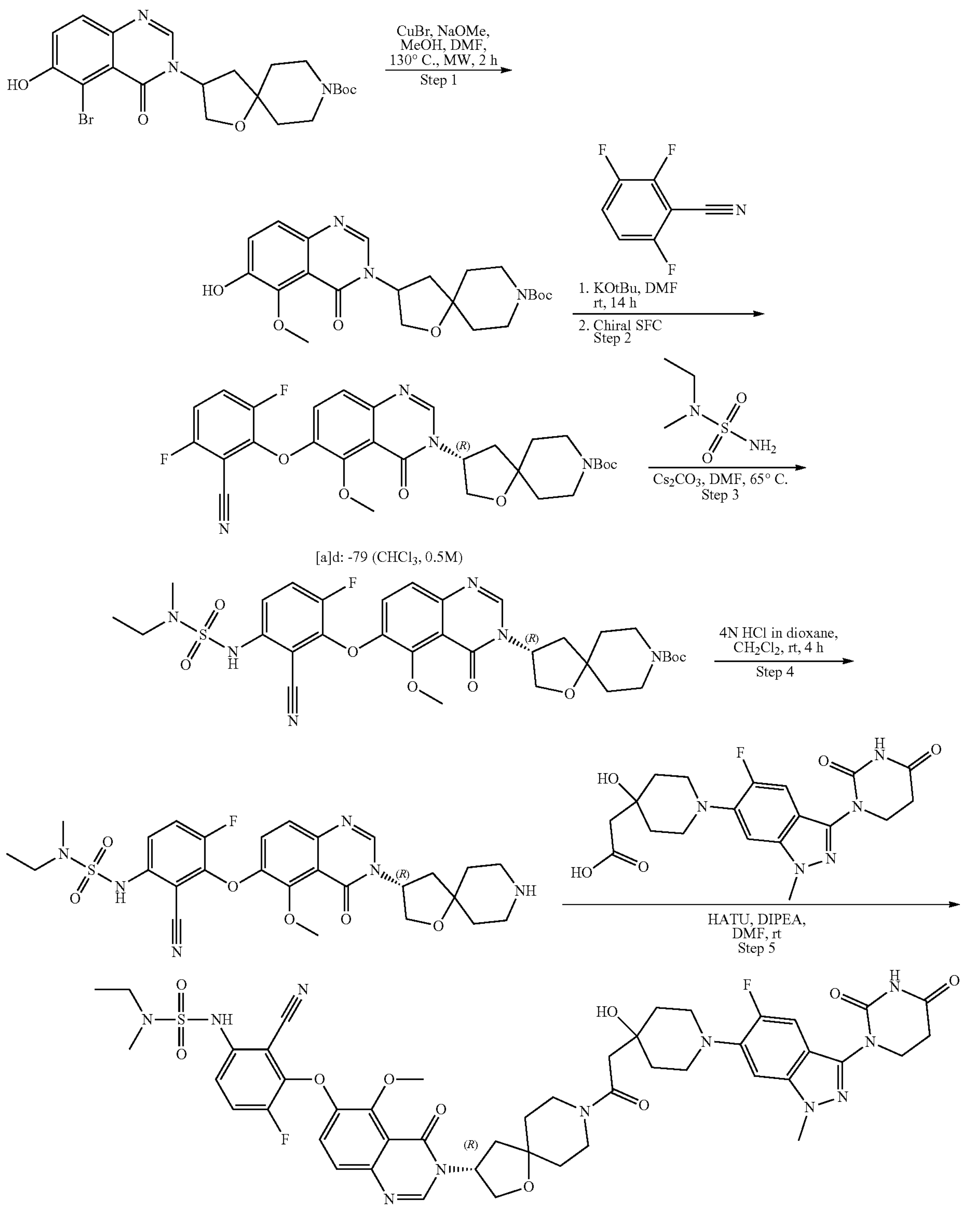

Step 1: To a stirred solution of tert-butyl 3-(5-bromo-6-hydroxy-4-oxo-quinazolin-3-yl)-1-oxa-8-azaspiro[4.5]decane-8-carboxylate (1.1 g, 2.29 mmol) and sodium methoxide (742.28 mg, 13.74 mmol, 766.03 μL) in anhydrous N,N-dimethylformamide (6 mL) and methanol (3 mL) was added copper (I) bromide (164.25 mg, 1.14 mmol, 34.87 μL) at room temperature under nitrogen atmosphere. The reaction mixture was stirred at 130° C. for 2 h in a microwave reactor. The reaction mixture was quenched with saturated aqueous ammonium chloride solution (30 mL) and extracted with ethyl acetate (2×50 mL). The combined organic phases were dried with anhydrous sodium sulfate, filtered and the filtrate was evaporated under reduced pressure to provide crude product, which was purified by silica gel flash column chromatography using 80-90% ethyl acetate in petroleum ether as eluent to afford tert-butyl 3-(6-hydroxy-5-methoxy-4-oxo-quinazolin-3-yl)-1-oxa-8-azaspiro[4.5]decane-8-carboxylate (400 mg, 880.69 μmol, 38% yield) as a brown solid. LCMS m/z (ESI): 432.20 $[M+H]^+$ Step 2: O-arylated quinazolinone intermediate was synthesized by following Procedure B—B using tert-butyl 3-(6-hydroxy-5-methoxy-4-oxo-quinazolin-3-yl)-1-oxa-8-azaspiro[4.5]decane-8-carboxylate (400 mg, 927.04 μmol), potassium tert-butoxide (312.07 mg, 2.78 mmol) and 2,3,6-trifluorobenzonitrile (436.89 mg, 2.78 mmol, 321.24 μL). The crude compound was purified by silica gel flash column chromatography with 60-70% ethyl acetate in petroleum ether as an eluent to afford pure product. This product was chirally resolved by SFC (Column Name: Lux A1) to afford tert-butyl (3R)-3-[6-(2-cyano-3,6-difluoro-phenoxy)-5-methoxy-4-oxo-quinazolin-3-yl]-1-oxa-8-azaspiro[4.5]decane-8-carboxylate (110 mg, 192.69 μmol, 21% yield) (SOR:[α]D: −79.27, assigned as R-isomer, Second eluted) as an off-white solid. LCMS m/z (ESI): 513.20 $[M+H-CO_2{}^tBu]$+ and tert-butyl (3S)-3-[6-(2-cyano-3,6-difluoro-phenoxy)-5-methoxy-4-oxo-quinazolin-3-yl]-1-oxa-8-azaspiro[4.5]decane-8-carboxylate (100 mg, 170.41 μmol, 18% yield, First eluted) as an off-white solid. LCMS m/z (ESI): 513.20 $[M+H-CO2tBu]^+$ Step 3: Sulfamoylated quinazolinone intermediate was synthesized by following general Procedure B—C using tert-butyl (3R)-3-[6-(2-cyano-3,6-difluoro-phenoxy)-5-methoxy-4-oxo-quinazolin-3-yl]-1-oxa-8-azaspiro[4.5]decane-8-carboxylate (110 mg, 193.47 μmol), cesium carbonate (189.11 mg, 580.41 μmol) and [methyl(sulfamoyl)amino]ethane (133.68 mg, 967.34 μmol). The crude was purified by C18-reverse phase column chromatography using Isolera (15 g RediSep® Rf C18, Method: 10 mM ammonium acetate in water:acetonitrile) and pure fractions were lyophilized to afford tert-butyl (3R)-3-[6-[2-cyano-3-[[ethyl(methyl)sulfamoyl]amino]-6-fluoro-phenoxy]-5-methoxy-4-oxo-quinazolin-3-yl]-1-oxa-8-azaspiro[4.5]decane-8-carboxylate (60 mg, 85.93 μmol, 44% yield) as an off-white solid. LCMS m/z (ESI): 685.00 $[M-H]^-$ Step 4: The requisite amine was synthesized by following general Procedure B-D using tert-butyl (3R)-3-[6-[2-cyano-3-[[ethyl(methyl)sulfamoyl]amino]-6-fluoro-phenoxy]-5-methoxy-4-oxo-quinazolin-3-yl]-1-oxa-8-azaspiro[4.5]decane-8-carboxylate (60.00 mg, 87.37 μmol) and hydrogen chloride solution 4.0 M in dioxane (2 mL). The resulted crude compound was triturated with methyl t-butyl ether to afford (3R)-3-[6-[2-cyano-3-[[ethyl(methyl)sulfamoyl]amino]-6-fluoro-phenoxy]-5-methoxy-4-oxo-quinazolin-3-yl]-1-oxa-8-azaspiro[4.5]decane (50 mg, 74.39 μmol, 85% yield) as an off-white solid. LCMS m/z (ESI): 587.20 $[M+H]^+$ Step 5: Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-5-methoxy-4-oxo-quinazolin-3-yl]-1-oxa-8-azaspiro[4.5]decane (50 mg, 85.23 μmol), 2-[1-[3-(2,4-dioxohexahydropyrimidin-1-yl)-5-fluoro-1-methyl-indazol-6-yl]-4-hydroxy-4-piperidyl]acetic acid (58.28 mg, 127.85 μmol) and N,N-diisopropylethylamine (236.43 mg, 1.83 mmol, 318.64 μL) and HATU (38.89 mg, 102.28 μmol). The crude compound was purified by reverse phase column chromatography eluting with 50% acetonitrile in 0.1% formic acid in water to afford (3R)-3-[6-[2-cyano-3-[[ethyl(methyl)sulfamoyl]amino]-6-fluoro-phenoxy]-5-methoxy-4-oxo-quinazolin-3-yl]-8-[2-[l-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (22 mg, 21.60 μmol, 25% yield) as an off-white solid. LCMS m/z (ESI): 988.00 $[M+H]^+$; $^1$H-NMR (400 MHz, DMSO-$d_6$): δ=10.54 (s, 1H), 10.10 (s, 1H), 8.32 (s, 1H), 7.68-7.65 (m, 1H), 7.52 (s, 1H), 7.46 (d, J=9.20 Hz, 1H), 7.33 (d, J=12.00 Hz, 2H), 7.13 (s, 1H), 5.42-5.30 (m, 1H), 5.04 (s, 1H), 4.15 (d, J=5.20 Hz, 2H), 3.94 (s, 3H), 3.89 (t, J=6.40 Hz, 2H), 3.80 (s, 3H), 3.69-3.51 (m, 2H), 3.19-3.02 (m, 5H), 2.76-2.69 (m, 4H), 2.58-2.51 (m, 4H), 2.42-2.40 (m, 3H), 2.12-2.01 (m, 1H), 1.82-1.43 (m, 8H), 1.06 (t, J=7.20 Hz, 3H).

Example 182

(3R)-3-[5-amino-6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

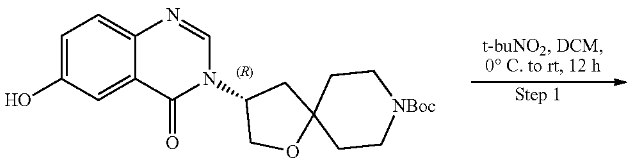

-continued

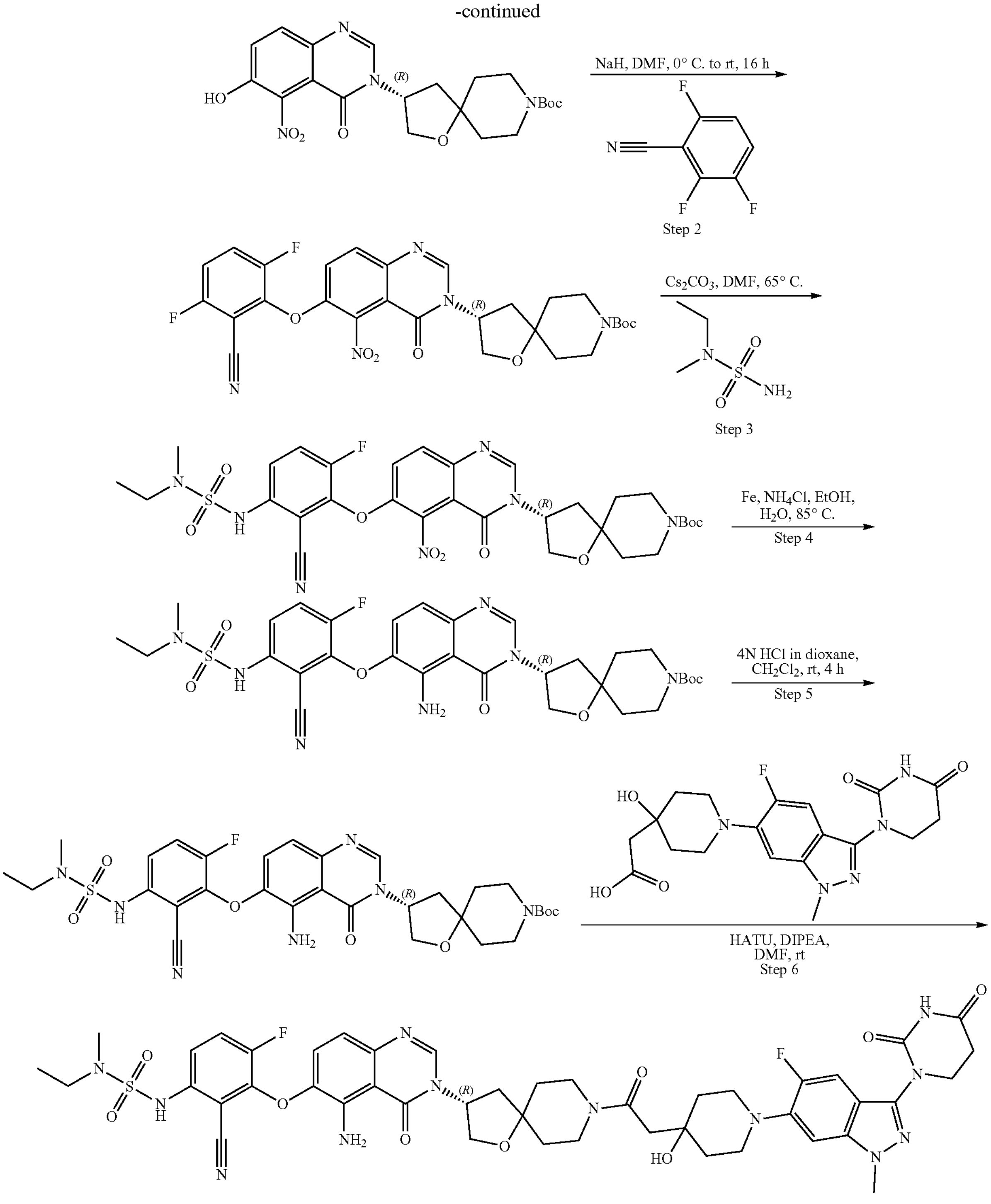

Step 1: To a stirred solution of tert-butyl 3-[(3R)-6-hydroxy-4-oxo-quinazolin-3-yl]-1-oxa-8-azaspiro[4.5]decane-8-carboxylate (1.50 g, 3.74 mmol) in dichloromethane (20 mL) was added tert-butyl nitrite (1.54 g, 14.95 mmol, 1.78 mL) at 0° C., and the reaction mixture was stirred at room temperature for 12 h. The reaction mixture was diluted with water (20 mL) and extracted with dichloromethane (3x30 mL). The combined organic layers were washed with aqueous brine solution (50 mL), dried over sodium sulfate, filtered, and concentrated under reduced pressure. The crude material was purified by silica gel flash column chromatography with 85-90% ethyl acetate in petroleum ether as a eluent to afford tert-butyl (3R)-3-(6-hydroxy-5-nitro-4-oxo-quinazolin-3-yl)-1-oxa-8-azaspiro[4.5]decane-8-carboxylate (1 g, 1.93 mmol, 52% yield) as a brown solid. LCMS m/z (ESI): 445.2 $[M-H]^-$.

Step 2: To a stirred 0° C. solution of sodium hydride (60% dispersion in mineral oil, 343.30 mg, 8.96 mmol) in N,N-dimethylformamide (20 mL) was added solution of tert-butyl (3R)-3-(6-hydroxy-5-nitro-4-oxo-quinazolin-3-yl)-1-oxa-8-azaspiro[4.5]decane-8-carboxylate (1.00 g, 2.24 mmol) in N,N-dimethylformamide (5 mL). The reaction mixture was stirred at room temperature for 2 h. 2,3,6-Trifluorobenzonitrile (703.74 mg, 4.48 mmol, 517.45 μL) was added, and the resultant reaction mixture was stirred at 80° C. for 16 h. The reaction mixture was quenched with cold water (50 mL) and extracted with ethyl acetate (2×50 mL). The combined organic layer was dried with anhydrous sodium sulfate and concentrated under reduced pressure. The crude material was purified by silica gel flash column chromatography with 70-80% ethyl acetate in petroleum ether as a eluent to afford tert-butyl (3R)-3-[6-(2-cyano-3,6-difluoro-phenoxy)-5-nitro-4-oxo-quinazolin-3-yl]-1-oxa-8-azaspiro[4.5]decane-8-carboxylate (800 mg, 1.17 mmol, 52% yield) as a pale brown solid. LCMS m/z (ESI): 484.00 $[M-CO_2{}^tBu+H]^+$.

Step 3: Sulfamoylated quinazolinone intermediate was synthesized by following general Procedure B—C using tert-butyl (3R)-3-[6-(2-cyano-3,6-difluoro-phenoxy)-5-nitro-4-oxo-quinazolin-3-yl]-1-oxa-8-azaspiro[4.5]decane-8-carboxylate (800 mg, 1.37 mmol), cesium carbonate (1.34 g, 4.11 mmol) and [methyl(sulfamoyl)amino]ethane (947.24 mg, 6.85 mmol). The crude compound was purified by silica gel flash column chromatography with 80-85% ethyl acetate in petroleum ether as a eluent to afford tert-butyl (3R)-3-[6-[2-cyano-3-[[ethyl(methyl)sulfamoyl]amino]-6-fluoro-phenoxy]-5-nitro-4-oxo-quinazolin-3-yl]-1-oxa-8-azaspiro[4.5]decane-8-carboxylate (600 mg, 589.98 μmol, 43% yield) as a brown viscous liquid. LCMS m/z (ESI): 700.80 $[M-H]^-$.

Step 4: To a stirred solution of tert-butyl (3R)-3-[6-[2-cyano-3-[[ethyl(methyl)sulfamoyl]amino]-6-fluoro-phenoxy]-5-nitro-4-oxo-quinazolin-3-yl]-1-oxa-8-azaspiro[4.5]decane-8-carboxylate (600 mg, 855.04 μmol) in water (5 mL) and ethanol (7 mL) were added iron powder (477.50 mg, 8.55 mmol, 60.75 μL) and ammonium chloride (457.37 mg, 8.55 mmol, 298.94 μL) at room temperature. The reaction mixture was stirred at 85° C. for 6 h. The reaction mixture was filtered and concentrated under reduced pressure. This crude residue was dissolved in water (50 mL), extracted with ethyl acetate (2×50 mL). The combined organic phases were dried with anhydrous sodium sulfate, filtered and evaporated under reduced pressure. The crude material was purified by silica gel flash column chromatography using 80-90% ethyl acetate in petroleum ether as eluent to afford tert-butyl (3R)-3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (400 mg, 434.69 μmol, 51% yield) as a brown solid. LCMS m/z (ESI): 670.20 $[M-H]^-$.

Step 5: The requisite amine was synthesized by following general Procedure B-D using tert-butyl (3R)-3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane-8-carboxylate (100 mg, 148.87 μmol) and 4.0 M hydrogen chloride solution in dioxane (4 mL). The crude compound was triturated with methyl t-butyl ether to afford (3R)-3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane (100 mg, 110.18 μmol, 74% yield) as an off-white solid. LCMS m/z (ESI): 570.20 $[M-H]^-$ Step 6: The target compound was prepared via HATU mediated acid-amine coupling reaction (Procedure B-E). Amide coupling was carried out using (3R)-3-[5-amino-6-[2-cyano-3-[[ethyl(methyl)sulfamoyl]amino]-6-fluoro-phenoxy]-4-oxo-quinazolin-3-yl]-1-oxa-8-azaspiro[4.5]decane (100 mg, 164.45 μmol), 2-[1-[3-(2,4-dioxohexahydropyrimidin-1-yl)-5-fluoro-1-methyl-indazol-6-yl]-4-hydroxy-4-piperidyl]acetic acid (112.45 mg, 246.68 μmol), N,N-diisopropylethylamine (371.00 mg, 2.87 mmol, 0.5 mL) and HATU (75.04 mg, 197.34 μmol) to afford crude product. The crude compound was purified by reverse phase column chromatography eluted with 43% acetonitrile in 0.1% formic acid in water to afford product (3R)-3-[5-amino-6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (34 mg, 33.83 μmol, 21% yield) as an off-white solid. LCMS m/z (ESI): 973.20 $[M+H]^+$; $^1$H-NMR (400 MHz, DMSO-$d_6$): δ=10.54 (s, 1H), 10.12 (bs, 1H), 8.18 (s, 1H), 7.62 (bs, 1H), 7.33 (dd, J=1.20, 12.80 Hz, 2H), 7.23 (s, 1H), 7.13 (d, J=7.20 Hz, 2H), 6.97 (d, J=8.80 Hz, 1H), 6.66 (d, J=8.40 Hz, 1H), 5.35-5.31 (m, 1H), 5.04-5.04 (m, 1H), 4.15-4.14 (m, 1H), 3.95 (s, 3H), 3.89 (t, J=6.80 Hz, 2H), 3.85-3.75 (m, 1H), 3.70-3.60 (m, 1H), 3.60-3.45 (m, 1H), 3.20-3.00 (m, 5H), 2.78-2.70 (m, 5H), 2.59 (s, 3H), 2.45-2.35 (m, 2H), 2.08-2.00 (m, 1H), 1.90-1.55 (m, 9H), 1.05 (t, J=7.20 Hz, 3H).

Example 183

(3R)-3-[6-[2-cyano-3-[[ethyl(methyl)sulfamoyl]amino]-6-fluorophenoxy]-4-oxoquinazolin-3-yl]-8-[2-[4-[3-(2,4-dioxo-1,3-diazinan-1-yl)-5-fluoro-1-methylindazol-6-yl]piperidin-1-yl]acetyl]-1-oxa-8-azaspiro[4.5]decane

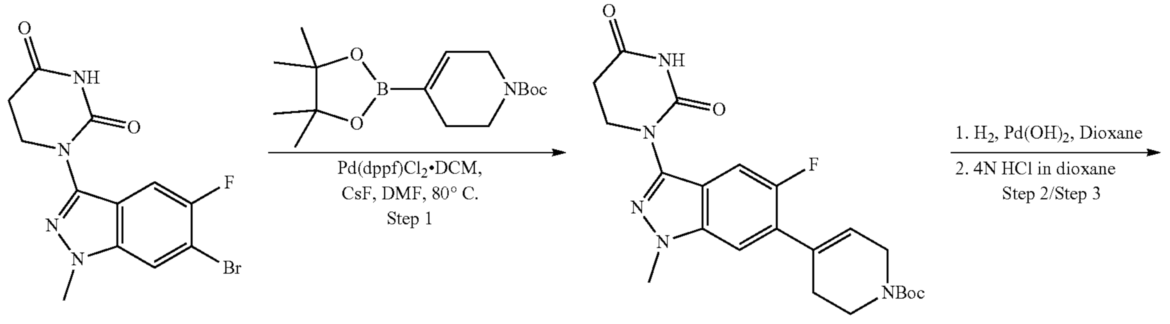

-continued

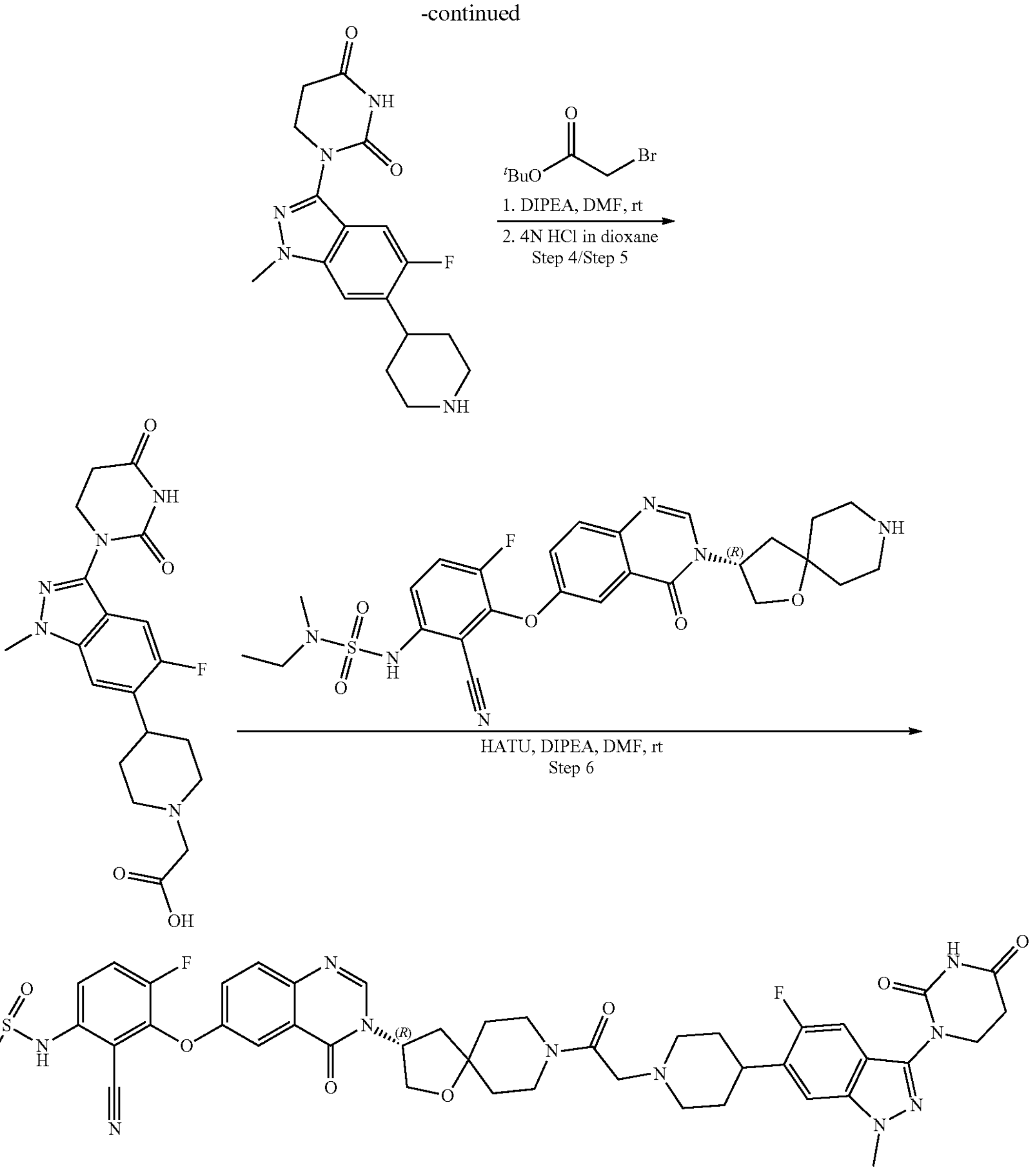

Step 1: A solution of tert-butyl 4-(4,4,5,5-tetramethyl-1,3,2-dioxaborolan-2-yl)-3,6-dihydro-2H-pyridine-1-carboxylate (906.41 mg, 2.93 mmol) in N,N-dimethylformamide (5 mL) was combined in a sealed tube at room temperature. 1-(6-Bromo-5-fluoro-1-methyl-indazol-3-yl)hexahydropyrimidine-2,4-dione (0.5 g, 1.47 mmol) and cesium fluoride (667.93 mg, 4.40 mmol, 162.12 µL) were added. The resulting mixture was degassed with nitrogen for 20 minutes, and 1,1-bis(diphenylphosphino)ferrocene-palladium(II)dichloride dichloromethane complex (179.54 mg, 219.85 µmol) was added. The resultant reaction mixture was sealed and stirred at 80° C. for 16 h. The reaction mixture was diluted with ethyl acetate (50 mL), filtered through celite bed, and washed with ethyl acetate (50 mL). The organic layer was washed with water (20 mL) and the separated organic layer was evaporated under reduced pressure. The crude product was purified by column chromatography (230-400 silica gel) using 90% ethyl acetate in petroleum ether as eluent to afford tert-butyl 4-[3-(2,4-dioxohexahydropyrimidin-1-yl)-5-fluoro-1-methyl-indazol-6-yl]-3,6-dihydro-2H-pyridine-1-carboxylate (0.42 g, 843.37 µmol, 58% yield) as off-white solid. LCMS m/z (ESI): 388.2 $[M+H-56]^+$ Step 2: Into a 50 mL single-necked round-bottomed flask containing a well stirred solution of tert-butyl 4-[3-(2,4-dioxohexahydropyrimidin-1-yl)-5-fluoro-1-methyl-indazol-6-yl]-3,6-dihydro-2H-pyridine-1-carboxylate (0.41 g, 924.53 µmol) in dioxane (4 mL) was added palladium hydroxide on carbon (0.2 g, 924.53 µmol) under nitrogen atmosphere at ambient temperature. The reaction mixture was subjected for hydrogenation with hydrogen bladder (1 atm pressure) for 16 h at room temperature. The reaction mixture was filtered through celite bed, rinsing with 10% methanol in dichloromethane (40 ml). The solvent was removed under reduced pressure to furnish tert-butyl 4-[3-(2,4-dioxohexahydropyrimidin-1-yl)-5-fluoro-1-methyl-indazol-6-yl]piperidine-1-carboxylate (0.4 g, 884.25 µmol, 96% yield) as brown solid. LCMS m/z=390.5 $[M+H-56]^+$ Step 3: To a solution of tert-butyl 4-[3-(2,4-dioxohexahydropyrimidin-1-yl)-5-fluoro-1-methyl-indazol-6-yl]piperidine-1-carboxylate (0.41 g, 920.34 μmol) in dichloromethane (2 mL) was added 4M hydrogen chloride solution in dioxane (4 mL) at 0° C. under nitrogen atmosphere. The resulting solution was stirred at room temperature for 3 h. The resulting solution was concentrated under reduced pressure to provide crude 1-[5-fluoro-1-methyl-6-(4-piperidyl)indazol-3-yl]hexahydropyrimidine-2,4-dione (0.35 g, 916.63 μmol, 100% yield) as a brown solid. LCMS m/z=346.5[M+H]$^+$ Step 4: To a stirred solution of 1-[5-fluoro-1-methyl-6-(4-piperidyl)indazol-3-yl]hexahydropyrimidine-2,4-dione (0.35 g, 1.01 mmol) in N,N-dimethylformamide (5 mL) were added N,N-diisopropylethylamine (327.44 mg, 2.53 mmol, 441.29 μL) and tert-butyl bromoacetate (197.67 mg, 1.01 mmol, 148.62 μL) at room temperature. The resulting mixture was stirred at room temperature for 12 h. After completion, the reaction mixture was diluted water (10 ml) and extracted with ethyl acetate (2×30 mL). The combined organic layer was evaporated under reduced pressure. The crude product thus obtained was purified by column chromatography (230-400 silica gel) using 90% ethyl acetate in petroleum ether as eluent to afford tert-butyl 2-[4-[3-(2,4-dioxohexahydropyrimidin-1-yl)-5-fluoro-1-methyl-indazol-6-yl]-1-piperidyl]acetate (0.31 g, 649.3 μmol, 64% yield) as off-white solid. LCMS m/z (ESI): 460.2 [M+H]$^+$ Step 5: To a solution of tert-butyl 2-[4-[3-(2,4-dioxohexahydropyrimidin-1-yl)-5-fluoro-1-methyl-indazol-6-yl]-1-piperidyl]acetate (0.31 g, 674.63 μmol) in dichloromethane (3 mL) was added 4M hydrogen chloride solution in dioxane (4.0 M, 2.53 mL) at 0° C. under nitrogen atmosphere. The resulting solution was stirred at petroleum ether for 16 h. The resulting solution was concentrated under reduced pressure to provide crude 2-[4-[3-(2,4-dioxohexahydropyrimidin-1-yl)-5-fluoro-1-methyl-indazol-6-yl]-1-piperidyl]acetic acid (0.27 g, 568.03 μmol, 84% yield) as a brownish solid. LCMS m/z (ESI): 404.2 [M+H]$^+$ Step 6: Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (0.1 g, 168.61 μmol), 2-[4-[3-(2,4-dioxohexahydropyrimidin-1-yl)-5-fluoro-1-methyl-indazol-6-yl]-1-piperidyl]acetic acid (74.17 mg, 168.61 μmol), HATU (64.11 mg, 168.61 μmol) and N,N-diisopropylethylamine (108.96 mg, 843.07 μmol, 146.85 μL). The crude material was purified by reverse phase column chromatography by using 30 g snap eluted with 35% acetonitrile in 0.1% formic acid in water to afford (3R)-3-[6-[2-cyano-3-[[ethyl(methyl)sulfamoyl]amino]-6-fluoro-phenoxy]-4-oxo-quinazolin-3-yl]-8-[2-[4-[3-(2,4-dioxohexahydropyrimidin-1-yl)-5-fluoro-1-methyl-indazol-6-yl]-1-piperidyl]acetyl]-1-oxa-8-azaspiro[4.5]decane (45 mg, 43.46 μmol, 26% yield) as off-white solid. LCMS m/z (ESI): 942.2 [M+H]$^+$; $^1$H-NMR (400 MHz, DMSO-$d_6$): δ=10.57 (s, 1H), 9.91 (s, 1H), 8.36 (d, J=1.20 Hz, 1H), 7.80 (d, J=8.80 Hz, 1H), 7.69 (dd, J=2.80, 8.80 Hz, 1H), 7.68-7.81 (m, 1H), 7.53 (d, J=5.20 Hz, 1H), 7.42-7.51 (m, 1H), 7.42 (d, J=10.80 Hz, 1H), 7.37 (d, J=2.80 Hz, 1H), 5.31-5.39 (m, 1H), 4.10-4.22 (m, 2H), 4.02 (s, 3H), 3.91 (t, J=6.80 Hz, 2H), 3.71-3.80 (m, 1H), 3.25-3.60 (m, 5H), 3.19-3.20 (m, 3H), 2.81-3.11 (m, 2H), 2.71-2.78 (m, 2H), 2.75 (s, 3H), 2.35-2.56 (m, 3H), 1.91-2.21 (m, 5H), 1.51-1.91 (m, 5H), 1.05 (t, J=7.20 Hz, 3H).

Example 184

(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

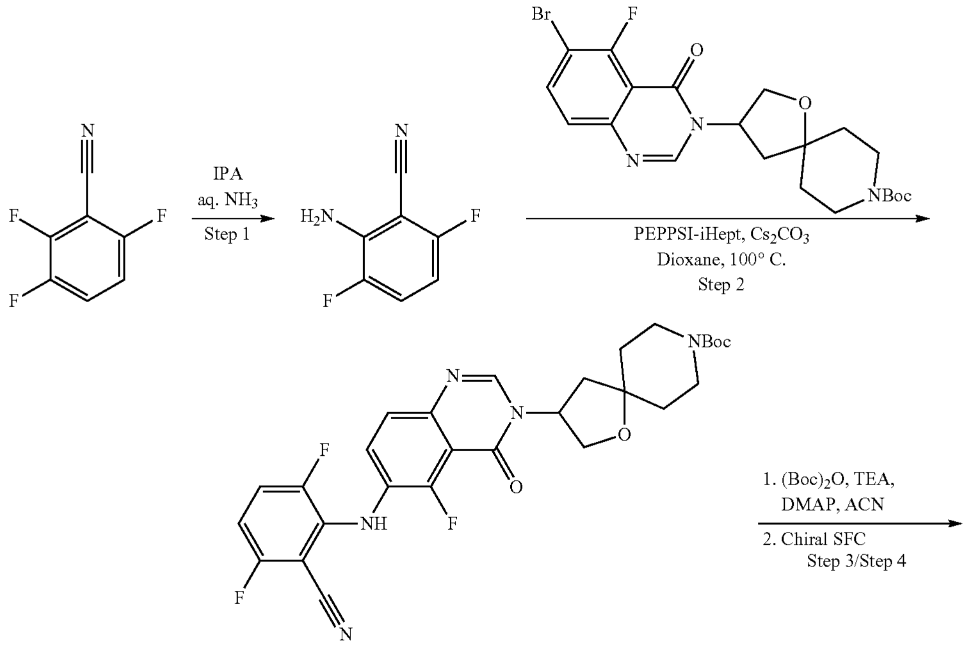

-continued

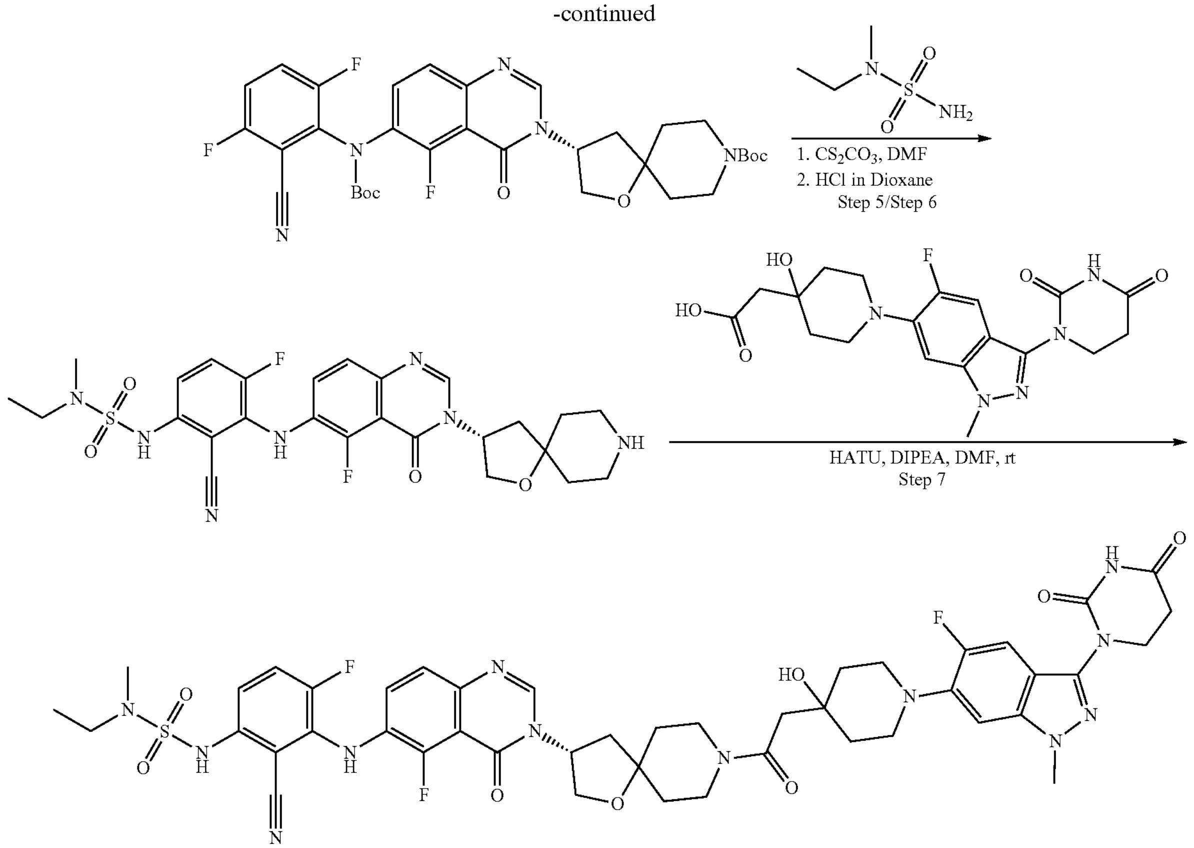

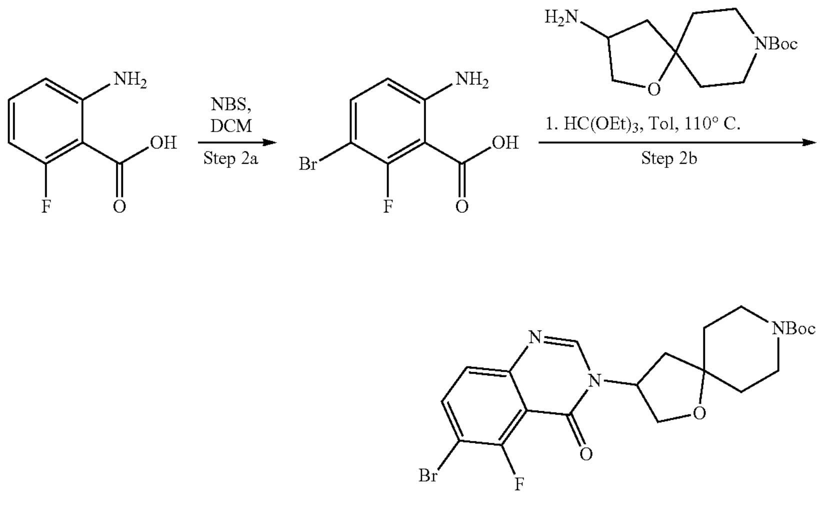 [SMILES: Nc1cccc(F)c1C(=O)O ; Nc1ccc(Br)c(F)c1C(=O)O ; CC(C)(C)OC(=O)N1CCC2(CC1)CC(N)CO2 ; CC(C)(C)OC(=O)N1CCC2(CC1)CC(n1cnc3ccc(Br)c(F)c3c1=O)CO2]

Step 1: To a stirred solution of 2,3,6-trifluorobenzonitrile (3 g, 19.10 mmol, 2.21 mL) in isopropanol (8 mL) was added ammonium hydroxide (8.03 g, 229.16 mmol, 8.92 mL) in tiny clave at 80° C. for 16 h. The reaction mixture was diluted with water (50 mL) and extracted with ethyl acetate(100 mL). The organic layer was washed with sodium bicarbonate solution (20 mL), brine (20 mL), dried over sodium sulfate, and concentrated under reduced pressure. The crude material thus obtained was purified by silica gel flash column chromatography eluting with 50-70% ethyl acetate in petroleum ether to afford 2-amino-3,6-difluoro-benzonitrile (0.9 g, 5.84 mmol, 31% yield) as white solid. GCMS m/z (ESI): 154 $[M-H]^-$.

Step 2a: A solution of 2-amino-6-fluoro-benzoic acid (5 g, 32.23 mmol) in dichloromethane (50 mL) was added N-bromosuccinimide (5.74 g, 32.23 mmol, 2.73 mL) at −10° C. under nitrogen atmosphere. The reaction mixture was stirred at room temperature for 2 h. The reaction mixture was diluted with water (70 mL) and extracted with ethyl acetate (2×100 mL). The organic layer was dried over sodium sulfate and concentrated under reduced pressure. The resulting crude product was purified by silica gel flash column chromatography using 0-70% of ethyl acetate in petroleum ether to provide 6-amino-3-bromo-2-fluoro-benzoic acid (4 g, 16.61 mmol, 52% yield) as a light yellow solid. LCMS m/z (ESI): 232.0 $[M-H]^-$.

Step 2b: Quinazolinone intermediate was synthesized by following general procedure for cyclization (Procedure B-A) using 6-amino-3-bromo-2-fluoro-benzoic acid (608.62 mg, 2.60 mmol), tert-butyl 3-amino-1-oxa-8-azaspiro[4.5] decane-8-carboxylate (1 g, 3.90 mmol) and triethyl orthoformate (1.16 g, 7.80 mmol, 1.30 mL). The crude residue was purified by silica gel flash column chromatography eluting with 60-80% ethyl acetate in petroleum ether as eluent to afford tert-butyl 3-(6-bromo-5-fluoro-4-oxo-quinazolin-3-yl)-1-oxa-8-azaspiro[4.5]decane-8-carboxylate (1.2 g, 2.30 mmol, 89% yield) as yellow solid. LCMS m/z (ESI): 426.0 $[M+H-56]^+$.

Step 2: A mixture of tert-butyl 3-(6-bromo-5-fluoro-4-oxo-quinazolin-3-yl)-1-oxa-8-azaspiro[4.5]decane-8-carboxylate (600 mg, 1.24 mmol, 21.78 μL) and 2-amino-3,6-difluoro-benzonitrile (191.71 mg, 1.24 mmol) in 1,4-dioxane (6 mL) in sealed tube was degassed with nitrogen for 10 minutes. cesium carbonate (1.01 g, 3.11 mmol) and Pd-PEPPSI-$^i$HeptCl (60.50 mg, 62.20 μmol) were added, and the reaction mixture was further, degassed with nitrogen for 5 minutes before being heated at 110° C. in for 12 h. The reaction mixture was diluted with water (20 mL) and extracted with ethyl acetate (30 mL). The organic layer was washed with water (10 mL), brine (10 mL), dried over sodium sulfate and concentrated under reduced pressure. The crude mixture was purified by silica gel flash column chromatography eluting with 0-70% of ethyl acetate in petroleum ether as eluent to afford tert-butyl 3-[6-(2-cyano-3,6-difluoro-anilino)-5-fluoro-4-oxo-quinazolin-3-yl]-1-oxa-8-azaspiro[4.5]decane-8-carboxylate (0.3 g, 516.09 μmol, 41% yield) as light brown solid. LCMS m/z (ESI): 556.7 $[M+H]^+$.

Step 3/Step 4: To a stirred solution of tert-butyl 3-[6-(2-cyano-3,6-difluoro-anilino)-5-fluoro-4-oxo-quinazolin-3-yl]-1-oxa-8-azaspiro[4.5]decane-8-carboxylate (300 mg, 540.01 μmol) in acetonitrile (5 mL) were added di-tert-butyl dicarbonate (235.71 mg, 1.08 mmol, 247.86 μL), DMAP (32.99 mg, 270.00 μmol) and triethylamine (163.93 mg, 1.62 mmol, 225.80 μL) at room temperature. The reaction mixture was stirred at room temperature for 16 h. The reaction mixture was diluted with water (10 mL) and extracted with ethyl acetate (3×30 mL). The combined organic layers were washed with cold water (3×15 mL), dried over sodium sulfate, filtered, and concentrated under reduced pressure. The crude material thus obtained was triturated with acetone and petroleum ether to afford product tert-butyl (3R)-3-[6-(N-tert-butoxycarbonyl-2-cyano-3,6-difluoro-anilino)-5-fluoro-4-oxo-quinazolin-3-yl]-1-oxa-8-azaspiro[4.5]decane-8-carboxylate (200 mg) as light brown solid. This racemic product was chirally resolved by chiral SFC purification using Lux-A1 column to afford tert-butyl (3R)-3-[6-(N-tert-butoxycarbonyl-2-cyano-3,6-difluoro-anilino)-5-fluoro-4-oxo-quinazolin-3-yl]-1-oxa-8-azaspiro[4.5] decane-8-carboxylate, fraction-1 (75 mg, 95.7% pure, arbitrarily assigned as R-isomer) and tert-butyl (3S)-3-[6-(N-tert-butoxycarbonyl-2-cyano-3,6-difluoro-anilino)-5-fluoro-4-oxo-quinazolin-3-yl]-1-oxa-8-azaspiro[4.5]decane-8-carboxylate (55 mg, 91% pure, arbitrarily assigned as S-isomer) as light brown solid. LCMS m/z (ESI): 671.2 $[M+H]^+$.

Note: First eluting peak was arbitrarily assigned as R-isomer and second eluting peak was arbitrarily assigned as S-isomer. This assignment is based on SOR data. The negative SOR value was considered as R-isomer and positive SOR value was considered as S-isomer.

Step 5: Sulfamoylated quinazolinone intermediate was synthesized by following Procedure B—C using tert-butyl (3R)-3-[6-(N-tert-butoxycarbonyl-2-cyano-3,6-difluoro-anilino)-5-fluoro-4-oxo-quinazolin-3-yl]-1-oxa-8-azaspiro[4.5]decane-8-carboxylate (75.00 mg, 114.39 μmol), cesium carbonate (111.81 mg, 343.16 μmol) and [methyl(sulfamoyl) amino]ethane (39.52 mg, 285.97 μmol) to afford tert-butyl (3R)-3-[6-[N-tert-butoxycarbonyl-2-cyano-3-[[ethyl (methyl)sulfamoyl]amino]-6-fluoro-anilino]-5-fluoro-4-oxo-quinazolin-3-yl]-1-oxa-8-azaspiro[4.5]decane-8-carboxylate (65 mg, 72.93 μmol, 64% yield) as brown viscous liquid. LCMS m/z (ESI): 772.2 $[M-H]^-$ Step 6: The requisite amine was synthesized by hydrogen chloride-mediated N-Boc deprotection (Procedure B-D). N-Boc deprotection of tert-butyl (3R)-3-[6-[N-tert-butoxycarbonyl-2-cyano-3-[[ethyl(methyl)sulfamoyl]amino]-6-fluoro-anilino]-5-fluoro-4-oxo-quinazolin-3-yl]-1-oxa-8-azaspiro[4.5]decane-8-carboxylate (100.00 mg, 129.22 μmol) using 4M hydrogen chloride solution in dioxane (35 μL) afforded crude(3R)-3-[6-[2-cyano-3-[[ethyl(methyl)sulfamoyl]amino]-6-fluoro-anilino]-5-fluoro-4-oxo-quinazolin-3-yl]-1-oxa-8-azaspiro[4.5]decane (80 mg, 117.31 μmol, 91% yield) as light brown solid. LCMS m/z (ESI): 574.7 $[M+H]^+$.

Step 7: Target compound was prepared via HATU mediated acid-amine coupling reaction (Procedure B-E). Amide coupling was carried out using (3R)-3-[6-[2-cyano-3-[[ethyl (methyl)sulfamoyl]amino]-6-fluoro-anilino]-5-fluoro-4-oxo-quinazolin-3-yl]-1-oxa-8-azaspiro[4.5]decane (70 mg, 122.03 μmol), N,N-diisopropylethylamine (78.86 mg, 610.17 μmol, 106.28 μL), 2-[1-[3-(2,4-dioxohexahydropyrimidin-1-yl)-5-fluoro-1-methyl-indazol-6-yl]-4-hydroxy-4-piperidyl]acetic acid (51.18 mg, 122.03 μmol) and HATU (51.04 mg, 134.24 μmol). The crude residue was purified by reverse phase column chromatography (0.1% ammonium bicarbonate in water:acetonitrile) to afford (3R)-3-[6-[2-cyano-3-[[ethyl(methyl)sulfamoyl]amino]-6-fluoro-anilino]-5-fluoro-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5] decane (14 mg, 14.13 μmol, 12% yield) as off-white solid. LCMS m/z (ESI): 975.0 $[M+H]^+$. $^1$H-NMR (400 MHz, DMSO-$d_6$): δ=10.53 (s, 1H), 9.89 (s, 1H), 8.77 (s, 1H), 8.25 (s, 1H), 7.42-7.61 (m, 1H), 7.41 (d, J=7.60 Hz, 2H), 7.33 (d, J=12.00 Hz, 1H), 7.18 (dd, J=4.00, 9.00 Hz, 1H), 7.13 (d, J=6.80 Hz, 1H), 5.34 (t, J=7.20 Hz, 1H), 5.03 (d, J=2.40 Hz, 1H), 4.14 (d, J=5.20 Hz, 2H), 3.95 (s, 3H), 3.89 (t, J=6.80 Hz, 2H), 3.72-3.82 (m, 1H), 3.60-3.70 (m, 1H), 3.45-3.60 (m, 1H), 3.22-3.40 (m, 1H), 3.02-3.20 (m, 6H), 2.65-2.81 (m, 3H), 2.58 (s, 3H), 2.38-2.61 (m, 2H), 2.01-2.10 (m, 1H), 1.51-1.88 (m, 8H), 1.04 (t, J=7.20 Hz, 3H).

Example 185
(3R)-3-[5-chloro-6-[2-cyano-3-[[ethyl(methyl)sulfamoyl]amino]-6-fluoroanilino]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane
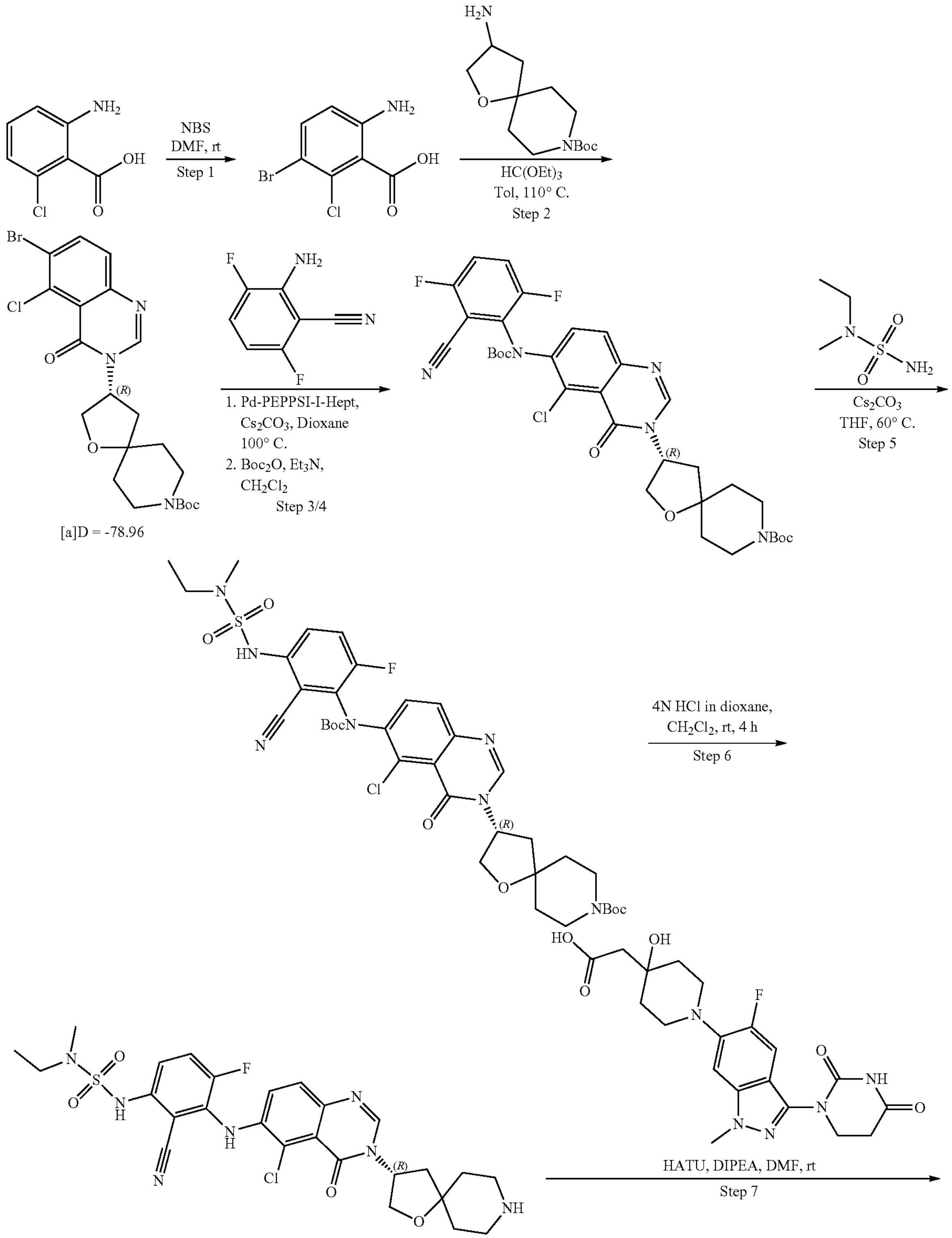

-continued

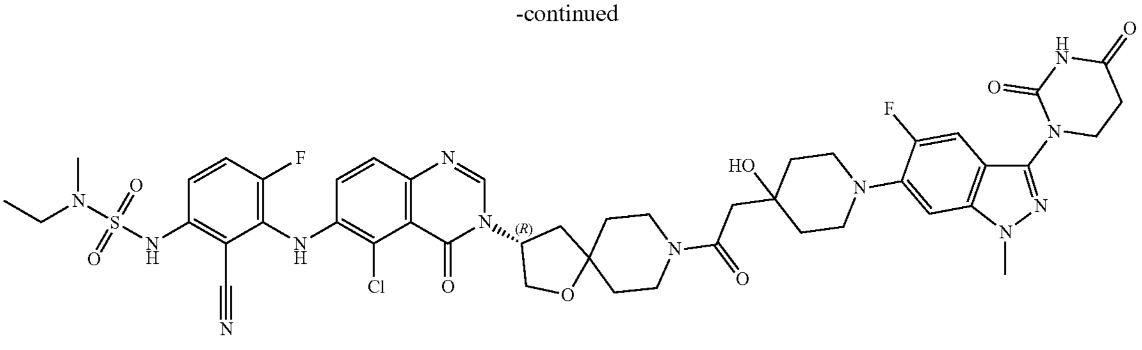

Step 1: To a stirred solution of 2-amino-6-chloro-benzoic acid (5 g, 29.14 mmol) in N,N-dimethylformamide (50 mL) was added N-bromosuccinimide (6.22 g, 34.97 mmol, 2.96 mL) at 10° C. portion-wise. The reaction was stirred at 0° C. for 16 h. The reaction mixture was poured into ice water (400 mL), and product was collected by filtration and dried to afford 6-amino-3-bromo-2-chloro-benzoic acid (5.7 g, 18.21 mmol, 62% yield) as a pale brown solid. LCMS (ESI+). 548.0 [M+H; Bromo isotope pattern].

Step 2: Quinazolinone intermediate was synthesized by following general procedure for cyclization (Procedure B-A) using 6-amino-3-bromo-2-chloro-benzoic acid (2.35 g, 9.36 mmol), tert-butyl 3-amino-1-oxa-8-azaspiro[4.5]decane-8-carboxylate (2 g, 7.80 mmol), diethoxymethoxyethane (3.47 g, 23.41 mmol, 3.89 mL) and acetic acid (93.71 mg, 1.56 mmol, 89.24 μL). The desired compound was purified from crude material by silica gel flash column chromatography using 50% ethyl acetate in petroleum ether as eluent to afford racemic compound. Chiral separation was conducted by SFC using Lux $C_2$ column to afford fraction-1 tert-butyl (3S)-3-(6-bromo-5-chloro-4-oxo-quinazolin-3-yl)-1-oxa-8-azaspiro[4.5]decane-8-carboxylate (380 mg, 758.18 μmol, 9.72% yield) assigned as S-isomer and fraction-2 tert-butyl (3R)-3-(6-bromo-5-chloro-4-oxo-quinazolin-3-yl)-1-oxa-8-azaspiro[4.5]decane-8-carboxylate (320 mg, 640.71 μmol, 8% yield) assigned as R-isomer, as a white solid.

Step 3: To a stirred solution of tert-butyl (3R)-3-(6-bromo-5-chloro-4-oxo-quinazolin-3-yl)-1-oxa-8-azaspiro[4.5]decane-8-carboxylate (300 mg, 601.45 μmol) and 2-amino-3,6-difluoro-benzonitrile (111.23 mg, 721.74 μmol) in 1,4-dioxane (5 mL) in a sealed tube was added cesium carbonate (391.93 mg, 1.20 mmol) and the mixture was degassed with nitrogen for 5 minutes. Pd-PEPPSI-$^{i}$Hept-Cl (29.25 mg, 30.07 μmol) was added, and the resulting reaction mixture was stirred at 100° C. for 16 h in a closed sealed tube. After completion of the reaction, the mixture was cooled to room temperature and diluted with ethyl acetate (20 mL) and water (20 mL). The organic layer was separated, dried over anhydrous sodium sulfate, filtered, and concentrated under reduced pressure. The crude residue was purified by silica gel flash column chromatography eluting with 0-50% ethyl acetate in petroleum ether to obtain tert-butyl (3R)-3-[5-chloro-6-(2-cyano-3,6-difluoro-anilino)-4-oxo-quinazolin-3-yl]-1-oxa-8-azaspiro[4.5]decane-8-carboxylate (160 mg, 268.53 μmol, 45% yield) as a yellow solid. LCMS (ESI+): 516.5 [M+H−$^{t}$Bu]$^{+}$.

Step 4: To a stirred solution of tert-butyl (3R)-3-[5-chloro-6-(2-cyano-3,6-difluoro-anilino)-4-oxo-quinazolin-3-yl]-1-oxa-8-azaspiro[4.5]decane-8-carboxylate (160 mg, 279.72 μmol) in acetonitrile (3 mL) was added triethylamine (84.91 mg, 839.16 μmol, 116.96 μL) and DMAP (17.09 mg, 139.86 μmol) at ambient temperature under nitrogen atmosphere. To the resulting reaction mixture was added di-tert-butyl dicarbonate (122.10 mg, 559.44 μmol, 128.39 μL). The resulting reaction mixture was allowed to warm to room temperature and stir 16 h. To the reaction mixture was added ice-cold water (10 mL), and the aqueous mixture was extracted using ethyl acetate (2×10 mL). The combined organic layers were dried over anhydrous sodium sulfate, filtered and concentrated under reduced pressure. The crude compound thus obtained was purified by column chromatography eluting from 40-100% ethyl acetate in petroleum ether to provide tert-butyl (3R)-3-[6-(N-tert-butoxycarbonyl-2-cyano-3,6-difluoro-anilino)-5-chloro-4-oxo-quinazolin-3-yl]-1-oxa-8-azaspiro[4.5]decane-8-carboxylate (130 mg, 164.41 μmol, 59% yield) as off-white solid. LCMS (ESI+): 672.3 [M+H]$^{+}$.

Step 5: Sulfamoylated quinazolinone intermediate was synthesized by following Procedure B—C using tert-butyl (3R)-3-[6-(N-tert-butoxycarbonyl-2-cyano-3,6-difluoro-anilino)-5-chloro-4-oxo-quinazolin-3-yl]-1-oxa-8-azaspiro[4.5]decane-8-carboxylate (130 mg, 193.42 μmol), cesium carbonate (189.06 mg, 580.26 μmol) and [methyl(sulfamoyl)amino]ethane (66.82 mg, 483.55 μmol). The crude compound was purified by column chromatography using 230-400 silica gel and 0-80% ethyl acetate in petroleum ether as eluent to afford tert-butyl (3R)-3-[6-[N-tert-butoxycarbonyl-2-cyano-3-[[ethyl(methyl)sulfamoyl]amino]-6-fluoro-anilino]-5-chloro-4-oxo-quinazolin-3-yl]-1-oxa-8-azaspiro[4.5]decane-8-carboxylate (75 mg, 51.25 μmol, 27% yield) as brown viscous solid. LCMS (ESI+): 788.3[M+H]$^{+}$.

Step 6: The requisite amine was synthesized according to Procedure B-D. N-Boc deprotection was performed on tert-butyl (3R)-3-[6-[N-tert-butoxycarbonyl-2-cyano-3-[[ethyl(methyl)sulfamoyl]amino]-6-fluoro-anilino]-5-chloro-4-oxo-quinazolin-3-yl]-1-oxa-8-azaspiro[4.5]decane-8-carboxylate (70 mg, 88.57 μmol) using 4M hydrogen chloride solution in 1,4-dioxane, (400 μL) at 0° C. The reaction mixture was concentrated under vacuum and washed with diethyl ether to provide (3R)-3-[5-chloro-6-[2-cyano-3-[[ethyl(methyl)sulfamoyl]amino]-6-fluoro-anilino]-4-oxo-quinazolin-3-yl]-1-oxa-8-azaspiro[4.5]decane (58 mg, 38.88 μmol, 44% yield) as off-white solid. LCMS: m/z 590.3[M−H]$^{-}$.

Step 7: The target compound was prepared via HATU mediated acid-amine coupling reaction (Procedure B-E). Amide coupling was carried out using (3R)-3-[5-chloro-6-[2-cyano-3-[[ethyl(methyl)sulfamoyl]amino]-6-fluoro-anilino]-4-oxo-quinazolin-3-yl]-1-oxa-8-azaspiro[4.5]decane (50 mg, 79.80 μmol), and 2-[1-[3-(2,4-dioxohexahydropyrimidin-1-yl)-5-fluoro-1-methyl-indazol-6-yl]-4-hydroxy-4-piperidyl]acetic acid (36.82 mg, 80.76 μmol), N,N-diisopropylethylamine (30.94 mg, 239.41 μmol, 41.70 μL) and HATU (45.52 mg, 119.71 μmol). The crude compound was purified by prep HPLC (X select C18 (10×150 mm) 5.0μ with Solvent A: 0.1% $NH_4HCO_3$ in water; Solvent B; acetonitrile, collected the pure fraction and lyophilized to afford (3R)-3-[5-chloro-6-[2-cyano-3-[[ethyl(methyl)sulfamoyl]amino]-6-fluoro-anilino]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (2.2 mg, 2.20 μmol, 3% yield) as an off-white solid. LCMS (ESI+): m/z 991.2[M+H]$^+$; $^1$H-NMR (400 MHz, DMSO-$d_6$): δ=10.53 (s, 1H), 9.96 (s, 1H), 8.35 (s, 1H), 8.27 (s, 1H), 7.61 (s, 1H), 7.51 (d, J=9.20 Hz, 1H), 7.35-7.30 (m, 2H), 7.13 (d, J=7.20 Hz, 2H), 5.33 (s, 1H), 5.04 (s, 1H), 4.15 (d, J=5.20 Hz, 2H), 3.95 (s, 3H), 3.91 (q, J=6.80 Hz, 2H), 3.90-3.40 (m, 3H), 3.19-3.04 (m, 6H), 2.79-2.70 (m, 5H), 2.58-2.38 (m, 4H), 2.08-2.06 (m, 1H), 1.82-1.24 (m, 8H), 1.05 (t, J=7.20 Hz, 3H).

Example 186

(3R)-3-[6-[2-cyano-3-[[ethyl(methyl)sulfamoyl]amino]-6-fluorophenoxy]-5-hydroxy-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

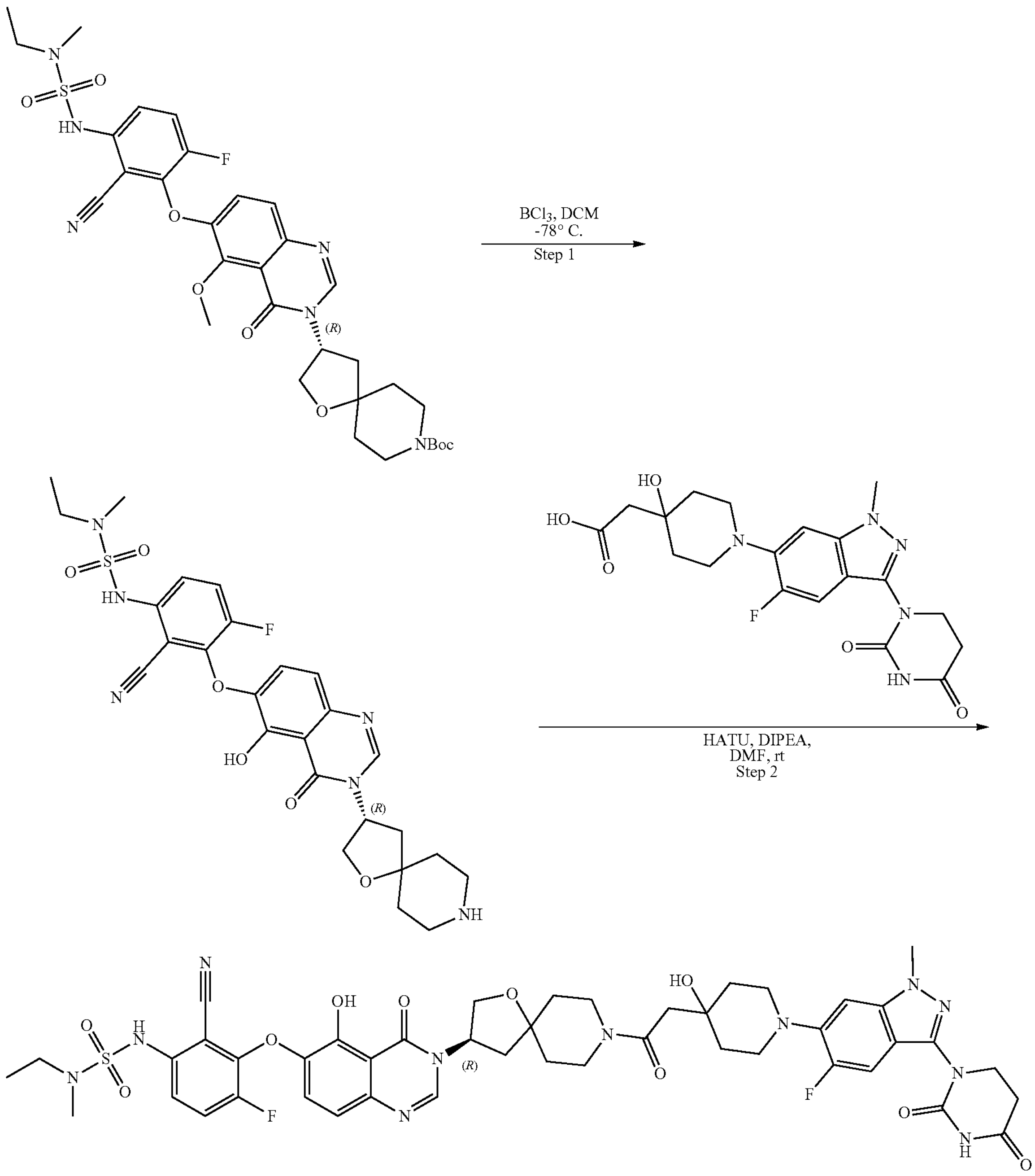

Step 1: To a stirred solution of tert-butyl (3R)-3-[6-[2-cyano-3-[[ethyl(methyl)sulfamoyl]amino]-6-fluoro-phenoxy]-5-methoxy-4-oxo-quinazolin-3-yl]-1-oxa-8-azaspiro[4.5]decane-8-carboxylate (40 mg, 58.25 μmol) in dichloromethane (3 mL) was added boron trichloride solution 1.0 M in methylene chloride (407.72 μmol, 0.4 mL) at −50° C. The reaction mixture was stirred at room temperature for 2 h. The reaction mixture was concentrated under reduced pressure, and the crude residue was triturated with methyl tert-butyl ether (3×10 mL) to provide (3R)-3-[6-[2-cyano-3-[[ethyl(methyl)sulfamoyl]amino]-6-fluoro-phenoxy]-5-hydroxy-4-oxo-quinazolin-3-yl]-1-oxa-8-azaspiro[4.5]decane (35 mg, 37.35 μmol, 64% yield) as an off-white solid. LCMS (ESI+): m/z 573.20 $[M+H]^+$.

Step 2: The target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-5-hydroxy-4-oxo-quinazolin-3-yl]-1-oxa-8-azaspiro[4.5]decane (35.00 mg, 37.35 μmol), 2-[1-[3-(2,4-dioxohexahydropyrimidin-1-yl)-5-fluoro-1-methyl-indazol-6-yl]-4-hydroxy-4-piperidyl]acetic acid (20.43 mg, 44.82 μmol), N,N-diisopropylethylamine (148.40 mg, 1.15 mmol, 0.2 mL) and HATU (17.04 mg, 44.82 μmol). The crude compound was purified Prep HPLC (Method: 0.1% formic acid in water:acetonitrile and Column: BRIDGE C8(19×150)MM, 5MIC) to afford (3R)-3-[6-[2-cyano-3-[[ethyl(methyl)sulfamoyl]amino]-6-fluoro-phenoxy]-5-hydroxy-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (3.5 mg, 3.57 μmol, 10% yield) as an off-white solid. LCMS m/z (ESI): 974.20 $[M+H]^+$; $^1$H-NMR (400 MHz, DMSO-$d_6$): δ=12.02 (s, 1H), 10.53 (s, 1H), 10.09 (s, 1H), 8.33 (s, 1H), 7.45-7.35 (m, 2H), 7.33 (d, J=12.80 Hz, 1H), 7.24 (s, 1H), 7.16-7.12 (m, 2H), 5.40-5.30 (m, 1H), 5.03 (s, 1H), 4.23-4.15 (m, 2H), 3.95-3.88 (m, 4H), 3.80-3.78 (m, 1H), 3.70-3.60 (m, 1H), 3.51-3.49 (m, 2H), 3.43-3.42 (m, 1H), 3.20-3.10 (m, 3H), 3.09-3.06 (m, 3H), 2.73 (q, J=6.40 Hz, 2H), 2.68 (s, 3H), 2.60-2.55 (m, 2H), 2.45-2.35 (m, 1H), 2.15-2.12 (m, 1H), 1.91-1.56 (m, 8H), 1.03 (t, J=6.80 Hz, 3H).

Example 187-191 Described Below are Representative Examples for the Deep Pocket Modifications

Example 187

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]piperidine-1-sulfonamide

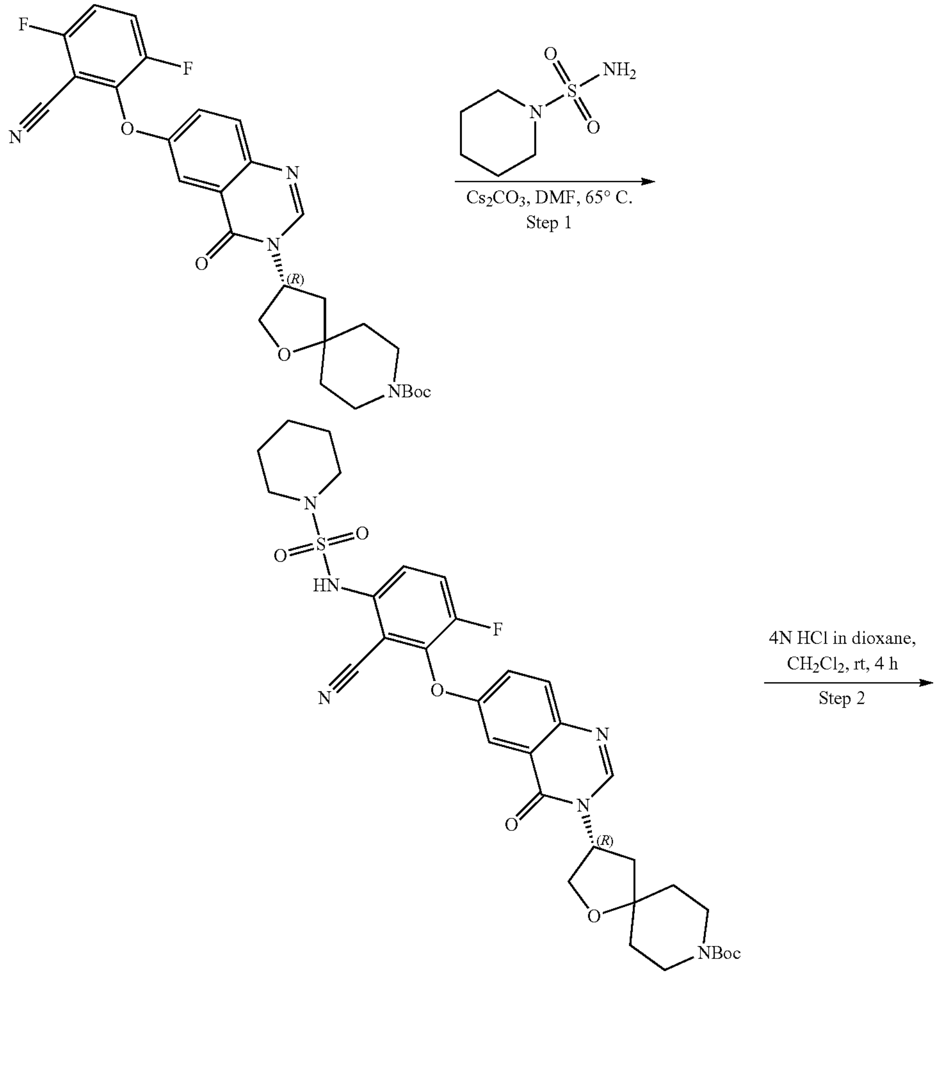

-continued

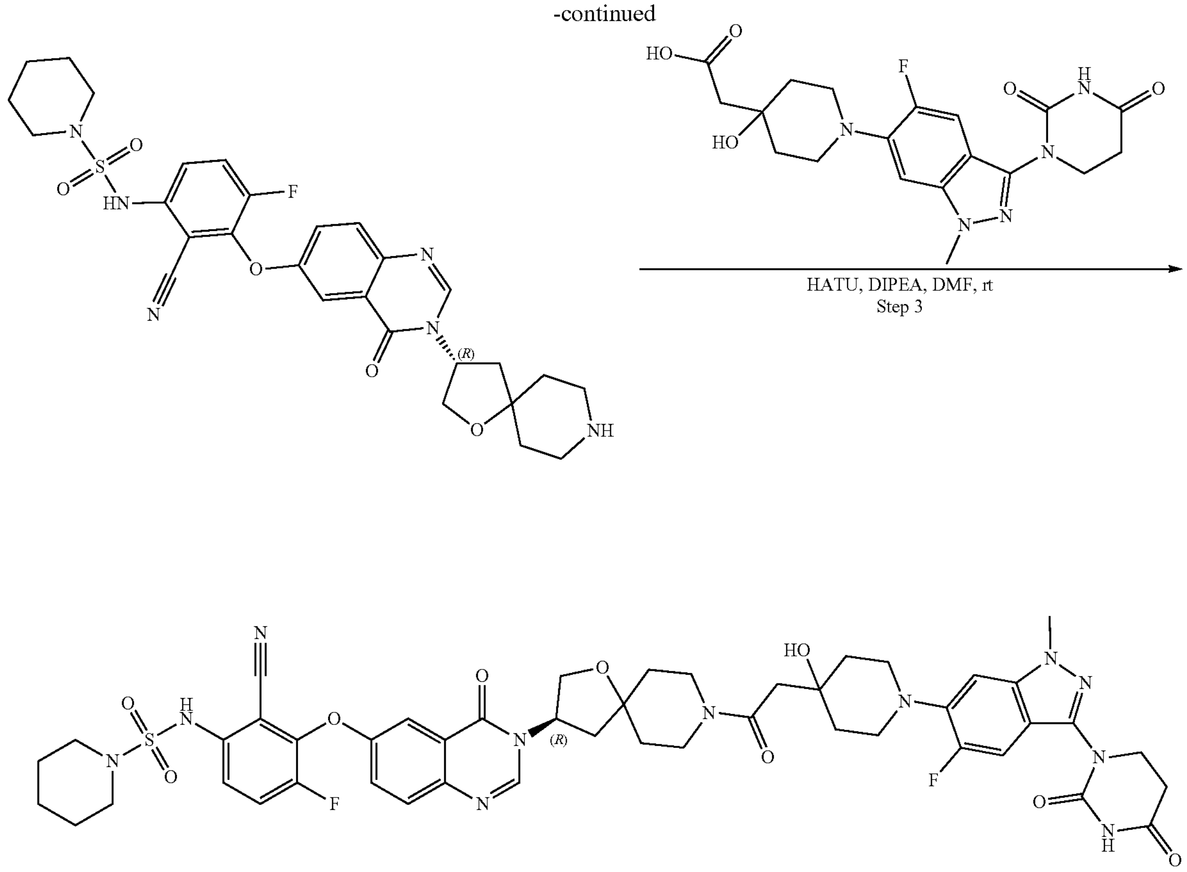

Step 1: Sulfamoylated quinazolinone intermediate was synthesized by following Procedure B—C using tert-butyl (3R)-3-[6-(2-cyano-3,6-difluoro-phenoxy)-4-oxo-quinazolin-3-yl]-1-oxa-8-azaspiro[4.5]decane-8-carboxylate (250 mg, 464.22 μmol), cesium carbonate (529.38 mg, 1.62 mmol) and piperidine-1-sulfonamide (190.59 mg, 1.16 mmol) to afford crude product. The crude compound was purified by silica gel flash column chromatography with 80-85% ethyl acetate in petroleum ether as a eluent to afford tert-butyl (3R)-3-[6-[2-cyano-6-fluoro-3-(1-piperidylsulfonylamino)phenoxy]-4-oxo-quinazolin-3-yl]-1-oxa-8-azaspiro[4.5]decane-8-carboxylate (180 mg, 238.91 μmol, 51% yield) as a brown solid. LCMS m/z (ESI): 681.4 $[M-H]^-$.

Step 2: The requisite amine was synthesized by following Procedure B-D using tert-butyl (3R)-3-[6-[2-cyano-6-fluoro-3-(1-piperidylsulfonylamino)phenoxy]-4-oxo-quinazolin-3-yl]-1-oxa-8-azaspiro[4.5]decane-8-carboxylate (180 mg, 263.64 μmol) and hydrogen chloride (4.0M in 1,4-dioxane) (4 M, 65.91 L). The resulting crude compound was triturated with methyl t-butyl ether to afford N-[2-cyano-4-fluoro-3-[3-[(3R)-1-oxa-8-azaspiro[4.5]decan-3-yl]-4-oxo-quinazolin-6-yl]oxy-phenyl]piperidine-1-sulfonamide (160 mg, 205.77 μmol, 78% yield) as an off-white solid. LCMS m/z (ESI): 581.2 $[M-H]^-$.

Step 3: The target compound was prepared via HATU mediated acid-amine coupling reaction (Procedure B-E). Amide coupling was carried out using 2-[4-[4-[(2,6-dioxo-3-piperidyl)amino]-2-fluoro-phenyl]-1-piperidyl]acetic acid (83.77 mg, 230.52 μmol), N-[2-cyano-4-fluoro-3-[3-[(3R)-1-oxa-8-azaspiro[4.5]decan-3-yl]-4-oxo-quinazolin-6-yl]oxy-phenyl]piperidine-1-sulfonamide (250 mg, 403.81 μmol), N,N-diisopropylethylamine (371.00 mg, 2.87 mmol, 0.5 mL) and HATU (191.92 mg, 504.76 μmol) to afford crude product. The crude compound was purified by reverse phase column chromatography eluted (acetonitrile: 0.1% formic acid in water) to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]piperidine-1-sulfonamide (80 mg, 79.25 μmol, 24% yield) as off-white solid. LCMS m/z (ESI): 984.2 $[M+H]^+$; $^1$H-NMR (400 MHz, DMSO-$d_6$): δ=10.53 (s, 1H), 10.27 (s, 1H), 8.36 (s, 1H), 7.86 (s, 1H), 7.81 (s, 1H), 7.71 (dd, J=3.20, 9.00 Hz, 1H), 7.53 (dd, J=4.00, 9.00 Hz, 1H), 7.33 (d, J=12.80 Hz, 1H), 7.36 (s, 1H), 7.12 (d, J=7.20 Hz, 1H), 5.40-5.30 (m, 1H), 5.02 (s, 1H), 4.16-4.11 (m, 2H), 4.12 (s, 3H), 3.89 (t, J=6.40 Hz, 2H), 3.80-3.70 (m, 1H), 3.70-3.60 (m, 1H), 3.60-3.50 (m, 1H), 3.16 (m, 6H), 3.09-3.04 (m, 2H), 2.71 (t, J=1.60 Hz, 2H), 2.67 (s, 2H), 2.50-2.33 (m, 2H), 2.10-2.07 (m, 1H), 1.82-1.67 (m, 8H), 1.53-1.47 (m, 6H).

Example 188
N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclohexanesulfonamide
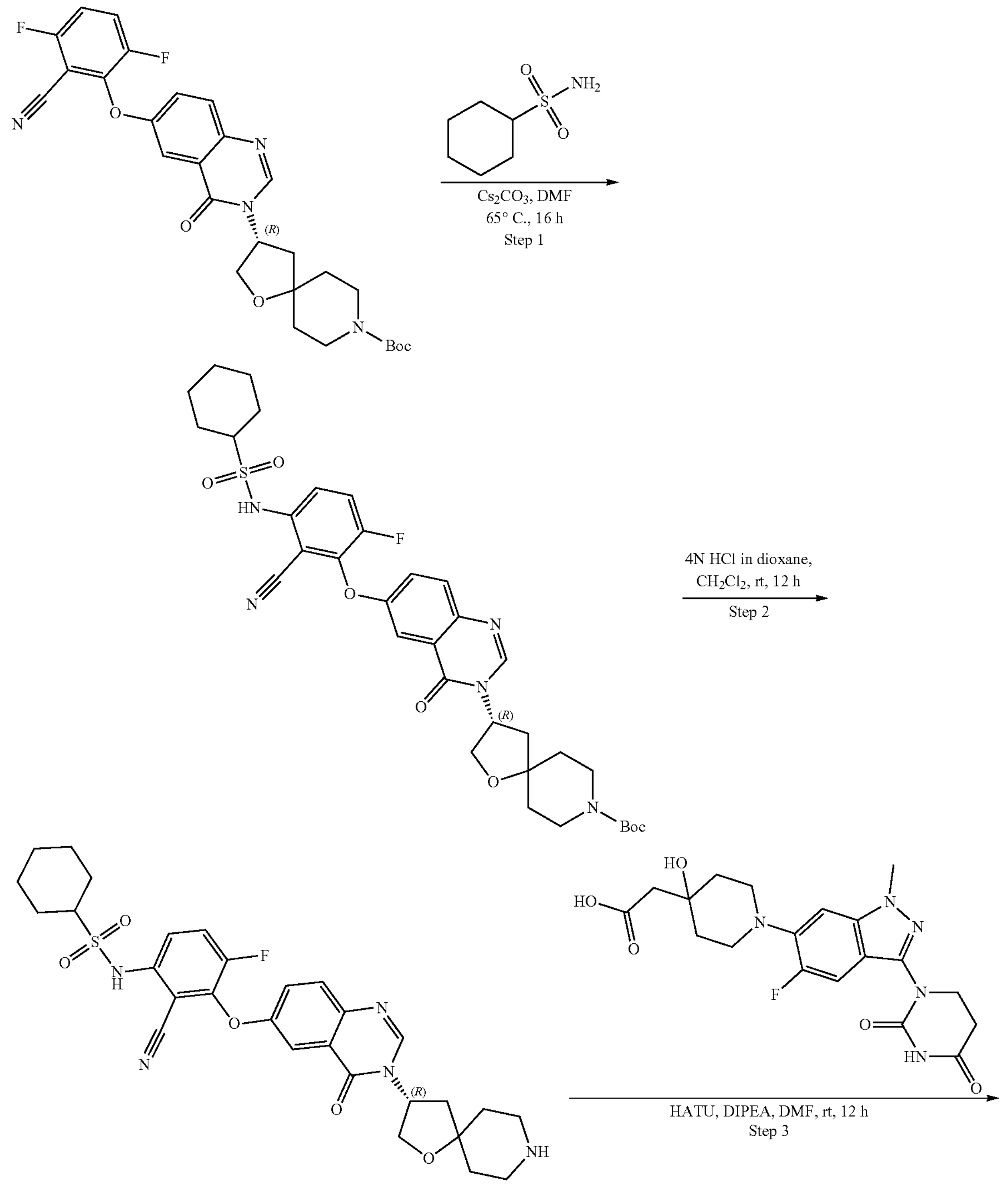

-continued

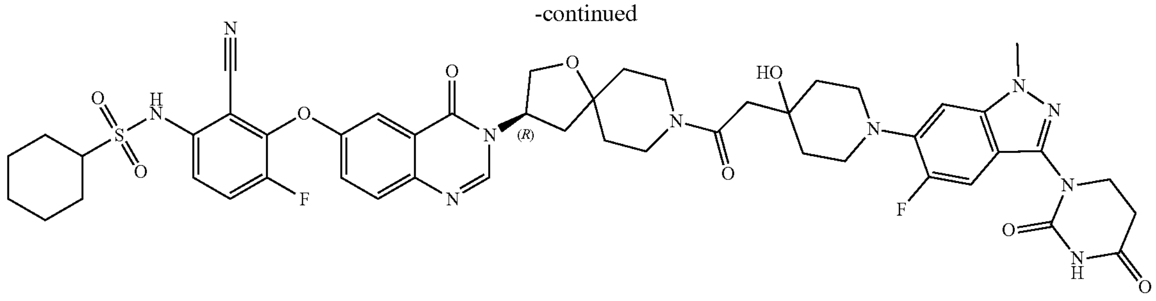

Step 1: Sulfamoylated quinazolinone intermediate was synthesized by following Procedure B—C using tert-butyl (3R)-3-[6-(2-cyano-3,6-difluoro-phenoxy)-4-oxo-quinazolin-3-yl]-1-oxa-8-azaspiro[4.5]decane-8-carboxylate (0.25 g, 464.22 μmol), cesium carbonate (453.75 mg, 1.39 mmol) and cyclohexane sulfonamide (189.44 mg, 1.16 mmol) to afford crude tert-butyl (3R)-3-[6-[2-cyano-3-(cyclohexylsulfonylamino)-6-fluoro-phenoxy]-4-oxo-quinazolin-3-yl]-1-oxa-8-azaspiro[4.5]decane-8-carboxylate (0.22 g, 290.16 μmol, 63% yield) as off-white solid. LCMS m/z (ESI): 682.4 $[M+H]^+$.

Step 2: The requisite amine was synthesized by HCl mediated N-Boc deprotection (Procedure B-D). N-Boc deprotection was done on tert-butyl (3R)-3-[6-[2-cyano-3-(cyclohexylsulfonylamino)-6-fluoro-phenoxy]-4-oxo-quinazolin-3-yl]-1-oxa-8-azaspiro[4.5]decane-8-carboxylate (0.22 g, 322.69 μmol) using hydrogen chloride (4M in dioxane) (4 M, 2 mL) to afford crude N-[2-cyano-4-fluoro-3-[3-[(3R)-1-oxa-8-azaspiro[4.5]decan-3-yl]-4-oxo-quinazolin-6-yl]oxy-phenyl]cyclohexanesulfonamide (0.22 g, 290.00 μmol, 90% yield) as a light brown solid. LCMS m/z (ESI): 582.2 $[M+H]^+$ Step 3: Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (156.06 mg, 342.34 μmol), N,N-diisopropylethylamine (480.91 mg, 3.72 mmol, 648.13 μL), HATU (155.63 mg, 409.31 μmol) and N-[2-cyano-4-fluoro-3-[3-[(3R)-1-oxa-8-azaspiro[4.5]decan-3-yl]-4-oxo-quinazolin-6-yl]oxy-phenyl]cyclohexanesulfonamide (0.23 g, 372.10 μmol). The desired product was purified from crude by reverse phase column chromatography (0.1% formic acid in water:acetonitrile) and fractions were lyophilized to afford N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]cyclohexanesulfonamide (116 mg, 110.21 μmol, 30% yield) as off-white solid. LCMS m/z (ESI): 983.0 $[M+H]^+$ and $^1H$ NMR (400 MHz, DMSO-$d_6$): δ=10.52 (s, 1H), 10.30 (s, 1H), 8.36 (s, 1H), 8.31 (s, 1H), 7.80 (d, J=9.20 Hz, 2H), 7.70 (d, J=3.20 Hz, 1H), 7.15-7.48 (m, 1H), 7.40 (d, J=2.80 Hz, 1H), 7.33 (d, J=12.80 Hz, 1H), 7.12 (d, J=7.20 Hz, 1H), 5.31 (s, 1H), 5.03 (d, J=1.60 Hz, 1H), 4.16-4.13 (m, 2H), 3.94 (s, 3H), 3.89 (t, J=6.80 Hz, 2H), 3.86-3.75 (m, 1H), 3.70-3.62 (m, 1H), 3.55-3.45 (m, 1H), 3.19-3.06 (m, 5H), 2.74 (t, J=6.80 Hz, 2H), 2.68 (t, J=1.60 Hz, 3H), 2.50-2.33 (m, 1H), 2.16-2.08 (m, 3H), 1.82-1.61 (m, 10H), 1.42-1.31 (m, 5H), 1.30-1.27 (m, 1H).

Example 189

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]propane-2-sulfonamide

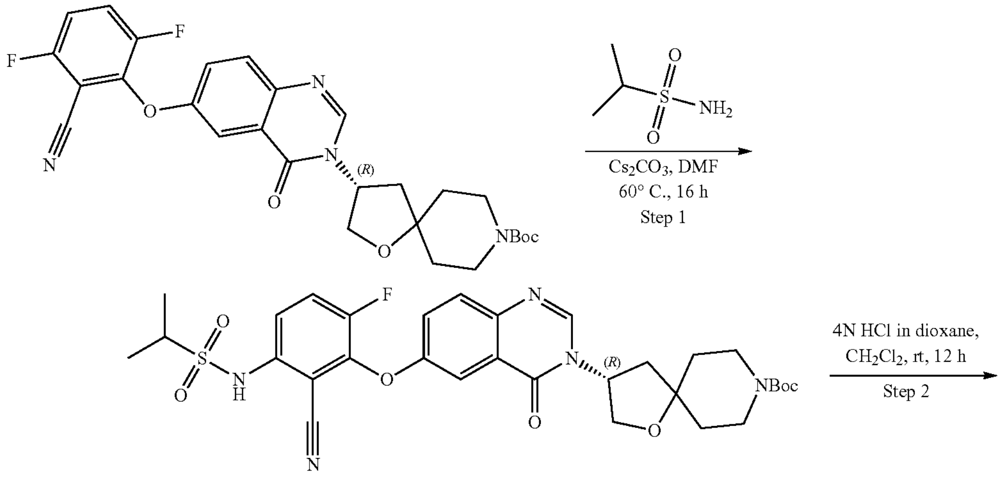

-continued

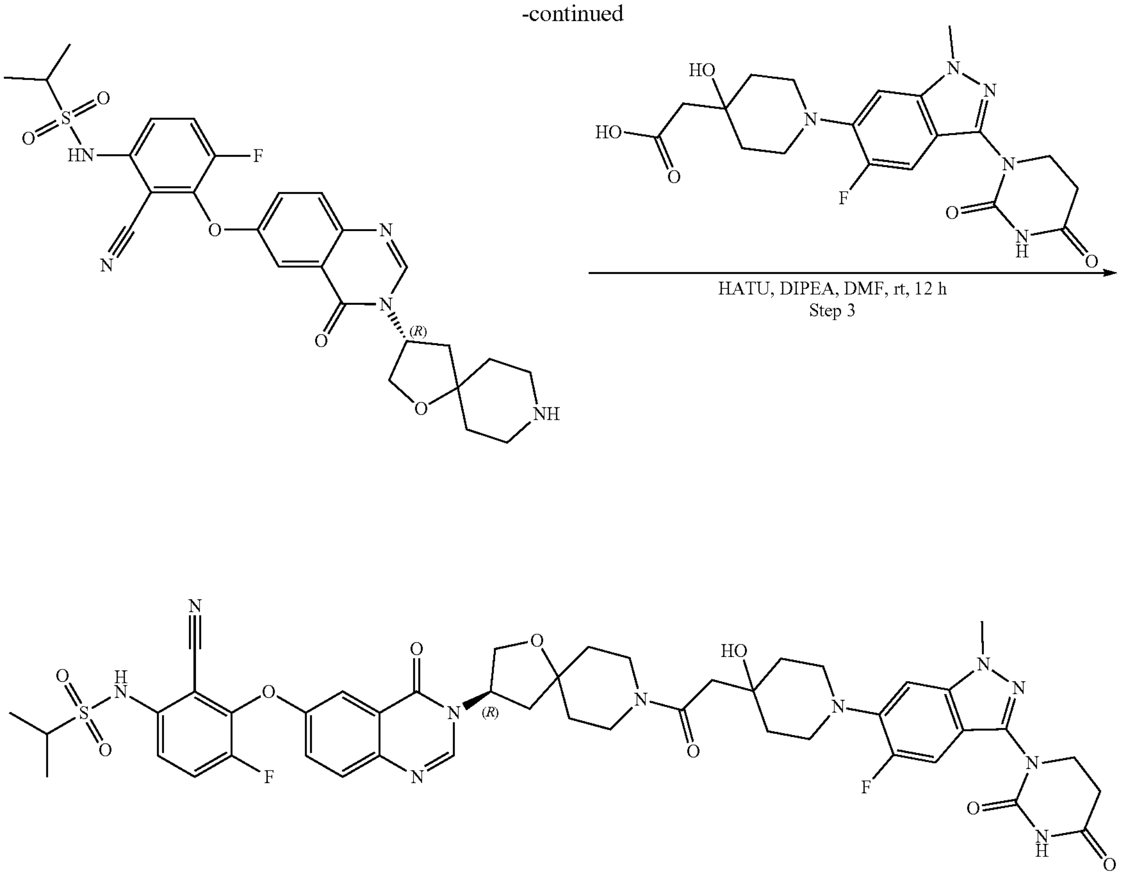

Step 1: Sulfamoylated quinazolinone intermediate was synthesized by following Procedure B—C using tert-butyl (3R)-3-[6-(2-cyano-3,6-difluoro-phenoxy)-4-oxo-quinazolin-3-yl]-1-oxa-8-azaspiro[4.5]decane-8-carboxylate (0.25 g, 464.22 μmol), cesium carbonate (453.75 mg, 1.39 mmol) and propane-2-sulfonamide (142.95 mg, 1.16 mmol) to afford crude tert-butyl (3R)-3-[6-[2-cyano-6-fluoro-3-(isopropylsulfonylamino)phenoxy]-4-oxo-quinazolin-3-yl]-1-oxa-8-azaspiro[4.5]decane-8-carboxylate (0.21 g, 286.08 μmol, 62% yield) as a brown viscous liquid. LCMS m/z (ESI): 586.0 $[M+H-56]^+$.

Step 2: The requisite amine was synthesized by HCl mediated N-Boc deprotection (Procedure B-D). N-Boc deprotection was done on tert-butyl (3R)-3-[6-[2-cyano-6-fluoro-3-(isopropylsulfonylamino)phenoxy]-4-oxo-quinazolin-3-yl]-1-oxa-8-azaspiro[4.5]decane-8-carboxylate (0.21 g, 327.25 μmol) using hydrogen chloride (4M in dioxane) (4 M, 2 mL) to afford crude N-[2-cyano-4-fluoro-3-[3-[(3R)-1-oxa-8-azaspiro[4.5]decan-3-yl]-4-oxo-quinazolin-6-yl]oxy-phenyl]propane-2-sulfonamide (0.21 g, 326.52 μmol, 100% yield) as an off-white solid. LCMS m/z (ESI): 542.2 $[M+H]^+$.

Step 3: Target compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (159.62 mg, 350.15 μmol), N,N-diisopropylethylamine (491.88 mg, 3.81 mmol, 662.91 μL), HATU (159.18 mg, 418.65 μmol) and N-[2-cyano-4-fluoro-3-[3-[(3R)-1-oxa-8-azaspiro[4.5]decan-3-yl]-4-oxo-quinazolin-6-yl]oxy-phenyl]propane-2-sulfonamide (0.22 g, 380.59 μmol). The desired product was purified from the crude by reverse phase column chromatography (0.1% formic acid in water:acetonitrile) and fractions were lyophilized to afford N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]propane-2-sulfonamide (109 mg, 108.25 μmol, 28% yield) as an off-white solid. LCMS m/z (ESI): 943.0 $[M+H]^+$ and $^1H$ NMR (400 MHz, DMSO-$d_6$): δ=10.54 (s, 1H), 10.33 (s, 1H), 8.37 (s, 1H), 7.80 (d, J=9.20 Hz, 2H), 7.71-7.68 (m, 1H), 7.51-7.50 (m, 1H), 7.41 (d, J=3.20 Hz, 1H), 5.34 (d, J=1612.80 Hz, 1H), 7.13 (d, J=7.60 Hz, 1H), 5.31 (m, 1H), 5.03 (s, 1H), 4.15-4.13 (m, 2H), 3.95 (s, 3H), 3.90 (t, J=6.80 Hz, 2H), 3.79 (m, 1H), 3.64 (m, 1H), 3.55-3.51 (m, 1H), 3.17 (d, J=9.60 Hz, 2H), 3.08 (d, J=11.20 Hz, 2H), 2.74 (t, J=6.80 Hz, 2H), 2.68 (t, J=1.60 Hz, 3H), 2.11-2.07 (m, 1H), 1.82-1.71 (m, 8H), 1.33 (d, J=6.40 Hz, 6H).

Example 190

(3R)—N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-fluoropyrrolidine-1-sulfonamide

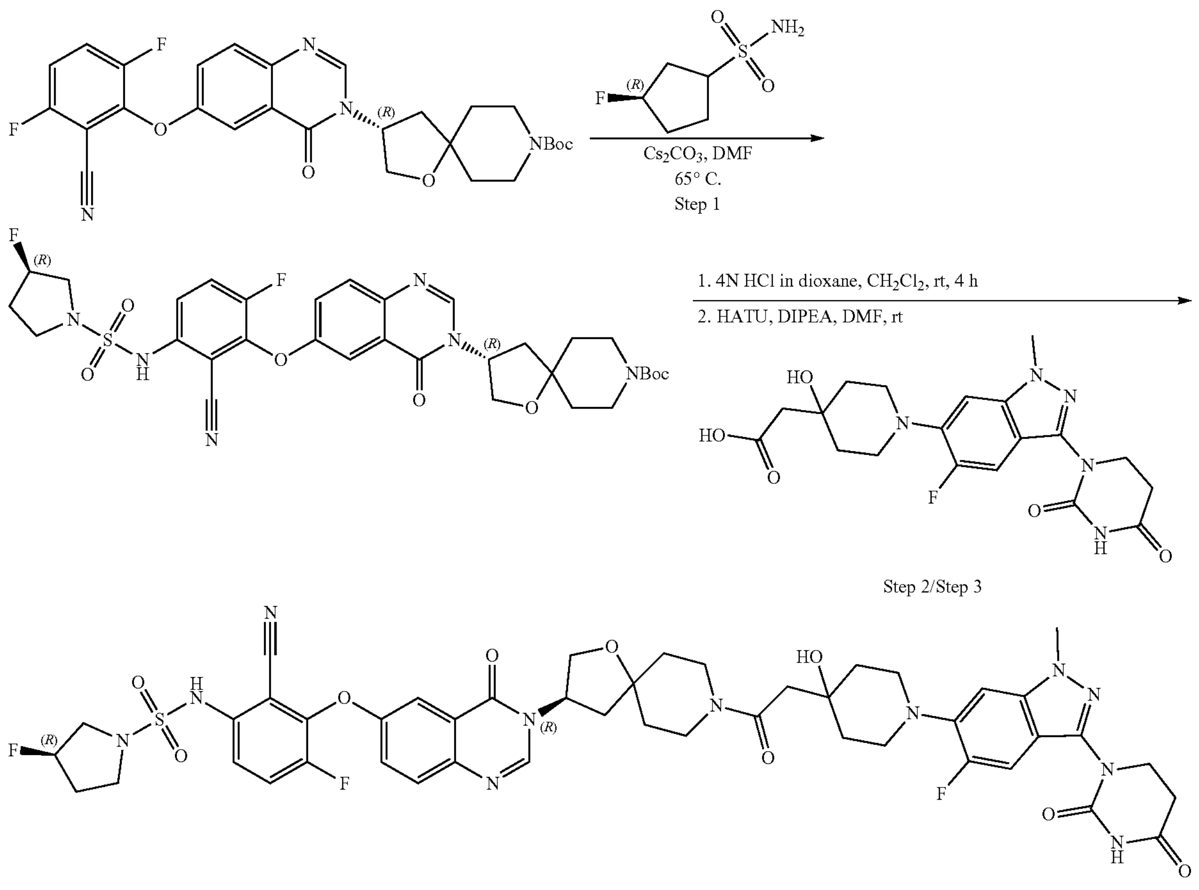

Step 1: Sulfamoylated quinazolinone intermediate was synthesized by following Procedure B—C using tert-butyl (3R)-3-[6-(2-cyano-3,6-difluoro-phenoxy)-4-oxo-quinazolin-3-yl]-1-oxa-8-azaspiro[4.5]decane-8-carboxylate (250.00 mg, 464.22 μmol), cesium carbonate (605.00 mg, 1.86 mmol) and (3R)-3-fluoropyrrolidine-1-sulfonamide (234.23 mg, 1.39 mmol) to afford crude tert-butyl (3R)-3-[6-[2-cyano-6-fluoro-3-[[(3R)-3-fluoropyrrolidin-1-yl]sulfamoylamino]phenoxy]-4-oxo-quinazolin-3-yl]-1-oxa-8-azaspiro[4.5]decane-8-carboxylate (210 mg, 260.35 μmol, 56% yield) as yellow solid. LCMS m/z (ESI): 685.2 $[M-H]^-$ Step 2: The requisite amine was synthesized by TFA mediated N-Boc deprotection (Procedure B-D). N-Boc deprotection was done on tert-butyl (3R)-3-[6-[2-cyano-6-fluoro-3-[[(3R)-3-fluoropyrrolidin-1-yl]sulfamoylamino]phenoxy]-4-oxo-quinazolin-3-yl]-1-oxa-8-azaspiro[4.5]decane-8-carboxylate (210 mg, 299.26 μmol) using hydrogen chloride (4M in dioxane) (4 M, 1.96 mL) to afford crude 3-fluoro-2-[4-oxo-3-[(3R)-1-oxa-8-azaspiro[4.5]decan-3-yl]quinazolin-6-yl]oxy-6-[[(3R)-3-fluoropyrrolidin-1-yl]sulfamoylamino]benzonitrile (200 mg, 285.23 μmol, 95% yield) as a light brown solid. LCMS m/z (ESI): 587.3 $[M+H]^+$ Step 3: Target compound was prepared via HATU mediated acid-amine coupling reaction (Procedure B-E). Amide coupling was carried out using (3R)—N-[2-cyano-4-fluoro-3-[3-[(3R)-1-oxa-8-azaspiro[4.5]decan-3-yl]-4-oxo-quinazolin-6-yl]oxy-phenyl]-3-fluoro-pyrrolidine-1-sulfonamide (185 mg, 315.37 μmol), 2-[1-[3-(2,4-dioxohexahydropyrimidin-1-yl)-5-fluoro-1-methyl-indazol-6-yl]-4-hydroxy-4-piperidyl]acetic acid (132.27 mg, 315.37 μmol), N,N-diisopropylethylamine (203.80 mg, 1.58 mmol, 274.66 μL) and HATU (131.91 mg, 346.91 μmol). The crude compound was purified by reverse phase column chromatography (0.1% formic acid in water:acetonitrile) to afford (3R)—N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-fluoro-pyrrolidine-1-sulfonamide (55.98 mg, 56.48 μmol, 18% yield) as an off-white solid. LCMS m/z (ESI): 988.0 $[M+H]^+$; 1H-NMR (400 MHz, DMSO-$d_6$): δ=10.52 (s, 1H), 10.34 (s, 1H), 8.36 (s, 1H), 7.87 (s, 1H), 7.80 (d, J=8.80 Hz, 2H), 7.69 (dd, J=2.80, 9.00 Hz, 1H), 7.53 (d, J=6.00 Hz, 1H), 7.39 (d, J=2.80 Hz, 1H), 7.33 (d, J=12.80 Hz, 1H), 7.12

(d, J=7.20 Hz, 1H), 5.41-5.25 (m, 2H), 5.02 (s, 1H), 4.21-4.09 (m, 2H), 3.94 (s, 3H), 3.89 (t, J=6.80 Hz, 2H), 3.82-3.73 (m, 1H), 3.67-3.59 (m, 1H), 3.54-3.46 (m, 4H), 3.21-3.12 (m, 2H), 3.12-3.01 (m, 2H), 2.74 (t, J=6.80 Hz, 2H), 2.62-2.56 (m, 2H), 2.37-2.33 (m, 2H), 2.16-2.07 (m, 4H), 1.82-1.68 (m, 8H).
Example 191
N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopentanesulfonamide
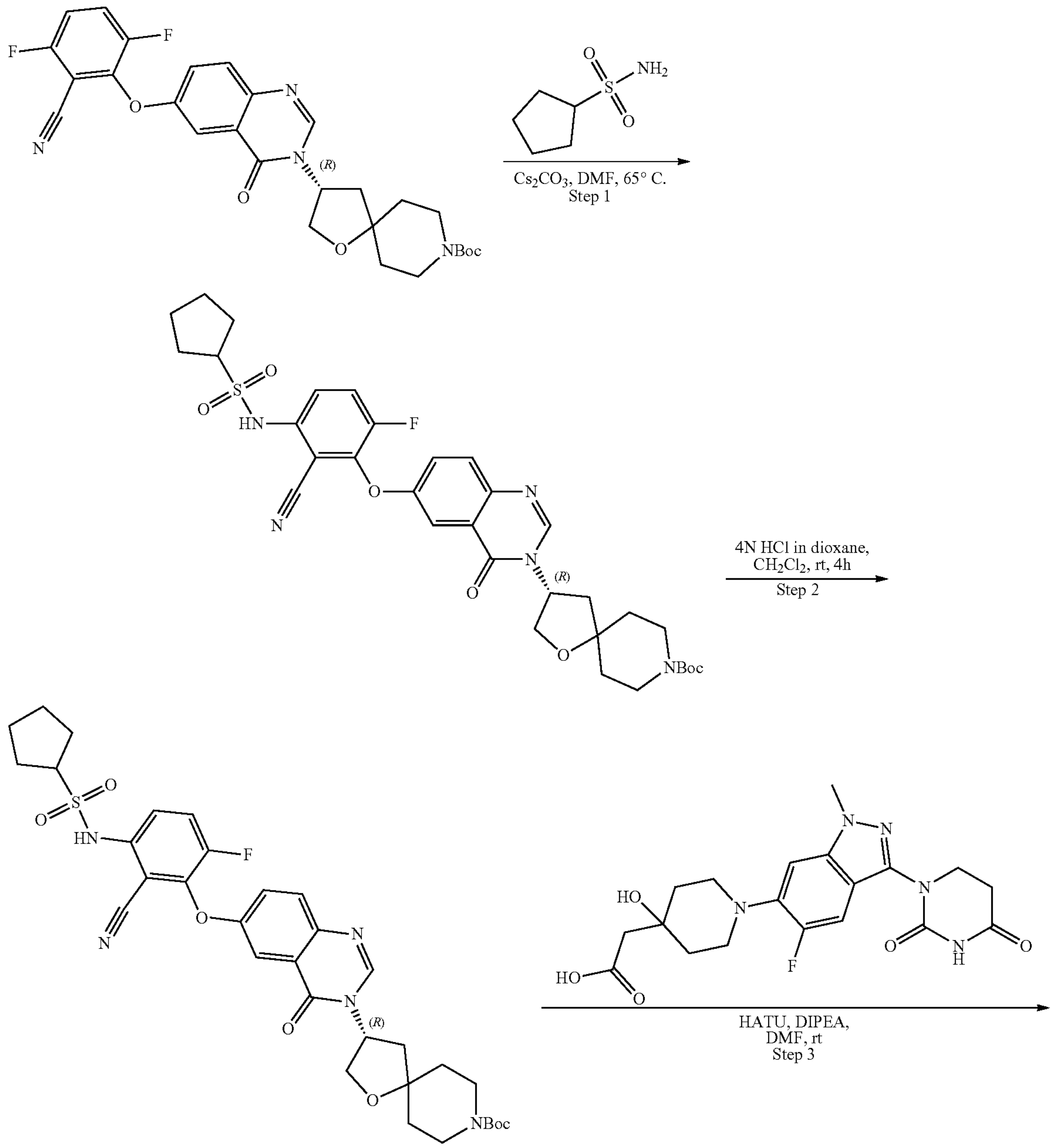

-continued

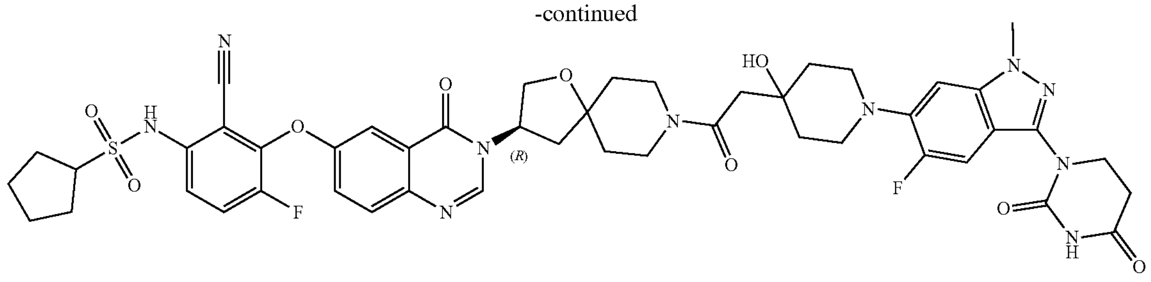

Step 1: Sulfamoylated quinazolinone intermediate was synthesized by following Procedure B—C using tert-butyl (3R)-3-[6-(2-cyano-3,6-difluoro-phenoxy)-4-oxo-quinazolin-3-yl]-1-oxa-8-azaspiro[4.5]decane-8-carboxylate (1.5 g, 2.79 mmol), cesium carbonate (2.27 g, 6.96 mmol) and cyclopentanesulfonamide (706.52 mg, 4.74 mmol) to afford tert-butyl (3R)-3-[6-[2-cyano-3-(cyclopentylsulfonylamino)-6-fluoro-phenoxy]-4-oxo-quinazolin-3-yl]-1-oxa-8-azaspiro[4.5]decane-8-carboxylate (1.35 g, 1.82 mmol, 65% yield) as an off-white solid. LCMS m/z (ESI): 612.4 $[M+H-{}^tBu]^+$.

Step 2: The requisite amine was synthesized by HCl mediated N-Boc deprotection (Procedure B-D). N-Boc deprotection was done on tert-butyl (3R)-3-[6-[2-cyano-3-(cyclopentylsulfonylamino)-6-fluoro-phenoxy]-4-oxo-quinazolin-3-yl]-1-oxa-8-azaspiro[4.5]decane-8-carboxylate (1.35 g, 2.02 mmol) using hydrogen chloride (4M in 1,4-dioxane, 20 mL) to afford N-[2-cyano-4-fluoro-3-[3-[(3R)-1-oxa-8-azaspiro[4.5]decan-3-yl]-4-oxo-quinazolin-6-yl]oxy-phenyl]cyclopentanesulfonamide (1.21 g, 1.82 mmol, 90% yield) as light brown solid. LCMS m/z (ESI): 568.5 $[M+H]^+$ Step 3: Target compound was prepared via HATU mediated acid-amine coupling reaction (Procedure B-E). Amide coupling was carried out using N-[2-cyano-4-fluoro-3-[3-[(3R)-1-oxa-8-azaspiro[4.5]decan-3-yl]-4-oxo-quinazolin-6-yl]oxy-phenyl]cyclopentanesulfonamide (1.2 g, 2.11 mmol), 2-[1-[3-(2,4-dioxohexahydropyrimidin-1-yl)-5-fluoro-1-methyl-indazol-6-yl]-4-hydroxy-4-piperidyl]acetic acid (886.65 mg, 2.11 mmol), N,N-diisopropylethylamine (1.09 g, 8.46 mmol, 1.47 mL) and HATU (803.83 mg, 2.11 mmol) to afford N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl] cyclopentanesulfonamide (600 mg, 615.28 μmol, 29% yield) as an off-white solid. LCMS m/z (ESI): 967.2 $[M-H]^-$; $^1$H-NMR (400 MHz, DMSO-$d_6$): δ=10.53 (s, 1H), 10.30 (s, 1H), 8.36 (bs, 1H), 7.80 (s, 1H), 7.80 (d, J=8.80 Hz, 1H), 7.70 (dd, J=2.80, 9.00 Hz, 1H), 7.49 (dd, J=4.40, 8.80 Hz, 1H), 7.41 (d, J=2.80 Hz, 1H), 7.33 (d, J=12.40 Hz, 1H), 7.12 (d, J=7.20 Hz, 1H), 5.25-5.35 (m, 1H), 5.03 (s, 1H), 4.10-4.23 (m, 2H), 3.95 (s, 3H), 3.89 (t, J=6.80 Hz, 2H), 3.75-3.85 (m, 1H), 3.60-3.72 (m, 2H), 3.44-3.57 (m, 1H), 3.17 (d, J=11.20 Hz, 2H), 3.06 (t, J=10.40 Hz, 2H), 2.74 (t, J=6.80 Hz, 2H), 2.58 (s, 2H), 2.32-2.45 (m, 2H), 2.05-2.15 (m, 1H), 1.85-2.04 (m, 4H), 1.50-1.90 (m, 12H).

Example 192-197 were synthesized using corresponding sulfonamides in the same manner as Examples 187-191 using Method I and II above and the General Procedures B-C to B-E

Example 192

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclopropanesulfonamide

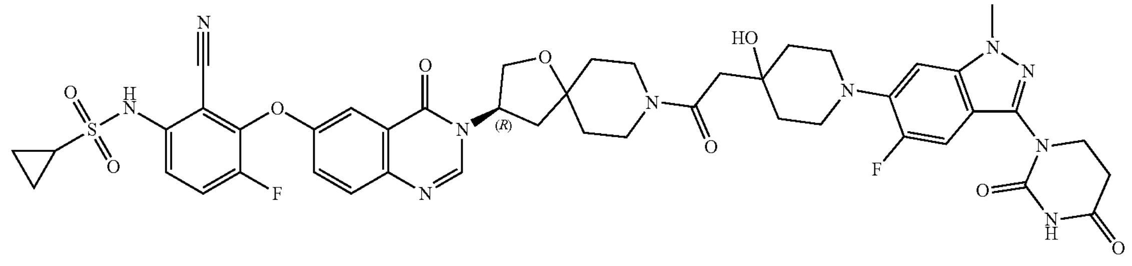

The title compound was purified by reverse phase preparatory HPLC (Column: Xbridge C-18 20×150 m mobile phase: A: 0.1% ammonium bicarbonate in water, B: acetonitrile) to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]cyclopropanesulfonamide (160 mg, 162.39 μmol, 59% yield) as an off-white solid. LCMS m/z (ESI): 941.2 $[M+H]^+$; $^1$H-NMR (400 MHz, DMSO-$d_6$): δ=10.53 (s, 1H), 10.27 (bs, 1H), 8.36 (s, 1H), 7.81 (s, 1H), 7.78 (s, 1H), 7.70 (dd, J=2.80, 9.00 Hz, 1H), 7.50-7.48 (m, 1H), 7.40 (d, J=2.80 Hz, 1H), 7.33 (d, J=12.80, Hz, 1H), 7.13 (d, J=7.20 Hz, 1H), 5.37-5.32 (m, 1H), 5.03 (d, J=2.40 Hz, 1H), 4.16-3.94 (m, 2H), 3.94 (s, 3H), 3.89 (t, J=6.40 Hz, 2H), 3.84-3.76 (m, 1H), 3.68-3.56 (m, 1H), 3.52-3.49 (m, 1H), 3.34-3.30 (m, 2H), 3.16-3.06 (m, 2H), 2.76-2.67 (m, 2H), 2.58-2.51 (m, 3H), 2.39-2.33 (m, 2H), 2.11-2.08 (m, 1H), 1.79-1.67 (m, 8H), 0.99-0.90 (m, 4H).

Example 193

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-methoxyazetidine-1-sulfonamide

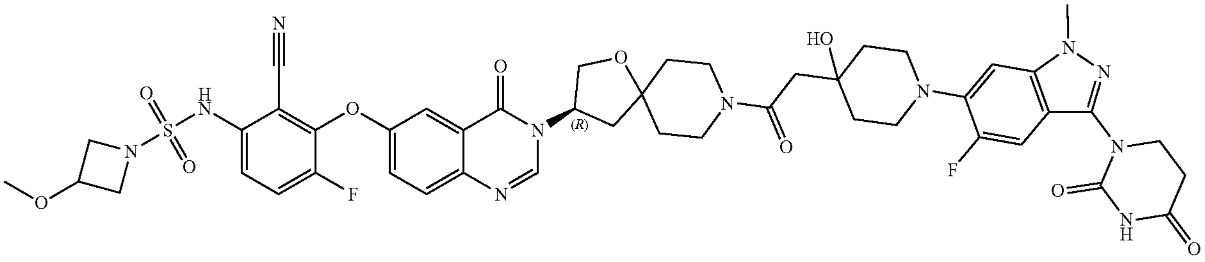

The title compound was purified by reverse phase column chromatography eluted with 50% acetonitrile with 0.1% formic acid in water to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-methoxy-azetidine-1-sulfonamide (53.8 mg, 54.54 μmol, 15% yield) as an off-white solid. LCMS m/z (ESI): 986.2 $[M+H]^+$; $^1$H-NMR (400 MHz, DMSO-$d_6$): δ=10.56 (s, 1H), 8.37 (s, 2H), 7.88 (t, J=9.60 Hz, 1H), 7.80 (d, J=9.20 Hz, 1H), 7.71 (dd, J=2.80, 9.00 Hz, 1H), 7.55 (dd, J=4.40, 9.20 Hz, 1H), 7.41 (d, J=2.80 Hz, 1H), 7.35 (s, 1H), 7.32 (s, 1H), 7.13 (d, J=7.20 Hz, 1H), 5.30 (m, 1H), 5.00 (s, 1H), 4.15 (q, J=7.20 Hz, 3H), 4.03 (t, J=6.80 Hz, 2H), 3.95 (s, 3H), 3.89 (t, J=6.80 Hz, 2H), 3.76 (q, J=4.80 Hz, 3H), 3.65 (m, 1H), 3.50 (m, 1H), 3.17 (d, J=14.80 Hz, 5H), 3.07 (d, J=10.80 Hz, 2H), 2.74 (t, J=6.80 Hz, 2H), 2.58-2.53 (m, 2H), 2.50-2.33 (m, 1H), 2.09-2.07 (m, 1H), 1.82-1.67 (m, 8H).

Example 194

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]-3-azabicyclo[3.1.0]hexane-3-sulfonamide

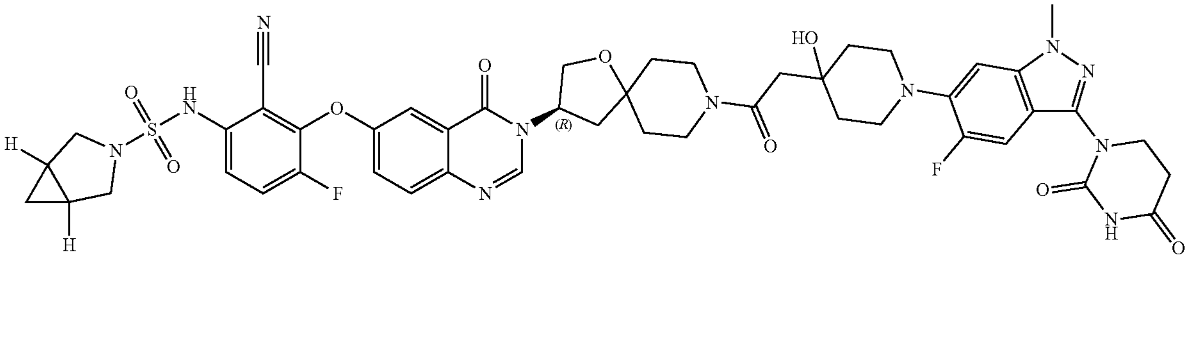

The title compound was purified by reverse phase column chromatography eluted with 40% acetonitrile in 0.1% ammonium bicarbonate in water to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]-3-azabicyclo[3.1.0]hexane-3-sulfonamide (63.3 mg, 62.29 μmol, 19% yield) as an off-white solid. LCMS m/z (ESI): 982.0 $[M+H]^+$; $^1$H-NMR (400 MHz, DMSO-$d_6$): δ=10.53 (s, 1H), 10.36 (s, 1H), 8.36 (s, 1H), 7.84 (s, 1H), 7.80 (d, J=8.80 Hz, 1H), 7.70 (dd, J=3.20, 9.00 Hz, 1H), 7.49 (s, 1H), 7.38 (d, J=3.20 Hz, 1H), 7.33 (d, J=12.80 Hz, 1H), 7.13 (d, J=7.20 Hz, 1H), 5.26-5.25 (m, 1H), 5.03 (s, 1H), 4.26-4.06 (m, 2H), 3.94 (s, 3H), 3.89 (t, J=6.40 Hz, 2H), 3.79-3.71 (m, 1H), 3.68-3.59 (m, 1H), 3.56-3.48 (m, 1H), 3.17 (t, J=4.40 Hz, 3H), 3.10-3.01 (m, 2H), 2.74 (t, J=6.40 Hz, 2H), 2.58-2.53 (m, 4H), 2.45-2.36 (m, 2H), 2.10-2.01 (m, 1H), 1.90-1.50 (m, 11H), 0.64-0.55 (m, 1H), 0.31 (s, 1H).

Example 195

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]pyrrolidine-1-sulfonamide

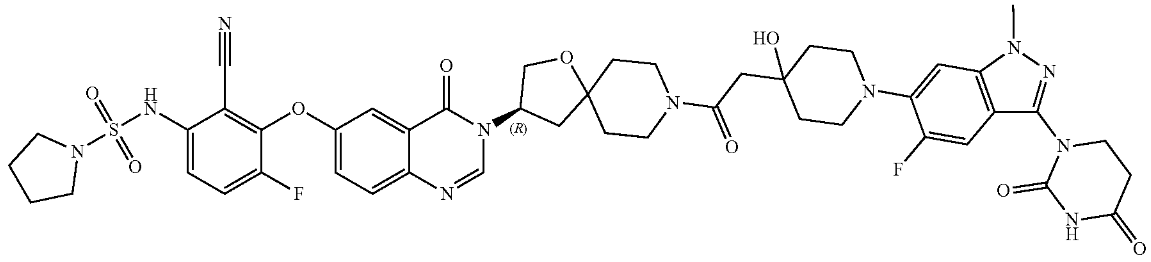

The title compound was purified by reverse phase column chromatography eluted with 45% acetonitrile in 0.1% ammonium bicarbonate in water to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]pyrrolidine-1-sulfonamide (62.17 mg, 63.46 μmol, 14% yield) as an off-white solid. LCMS m/z (ESI): 970.02 $[M+H]^+$; $^1$H-NMR (400 MHz, DMSO-$d_6$): δ=10.52 (s, 1H), 10.20 (s, 1H), 8.36 (s, 1H), 7.79 (d, J=9.20 Hz, 2H), 7.69 (dd, J=2.80, 9.00 Hz, 1H), 7.50 (d, J=4.80 Hz, 1H), 7.35 (dd, J=12.80, 14.00 Hz, 2H), 7.12 (d, J=7.20 Hz, 1H), 5.31 (s, 1H), 5.02 (d, J=2.00 Hz, 1H), 4.16-4.12 (m, 2H), 3.95 (s, 3H), 3.89 (t, J=6.80 Hz, 2H), 3.78-3.77 (m, 1H), 3.63 (s, 1H), 3.63 (m, 1H), 3.27 (d, J=43.60 Hz, 6H), 3.07 (t, J=10.40 Hz, 2H), 2.74 (t, J=6.80 Hz, 2H), 2.58 (s, 3H), 2.40-2.39 (m, 1H), 2.10-2.07 (m, 1H), 1.84-1.79 (m, 7H), 1.73-1.68 (m, 5H).

Example 196

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]azetidine-1-sulfonamide

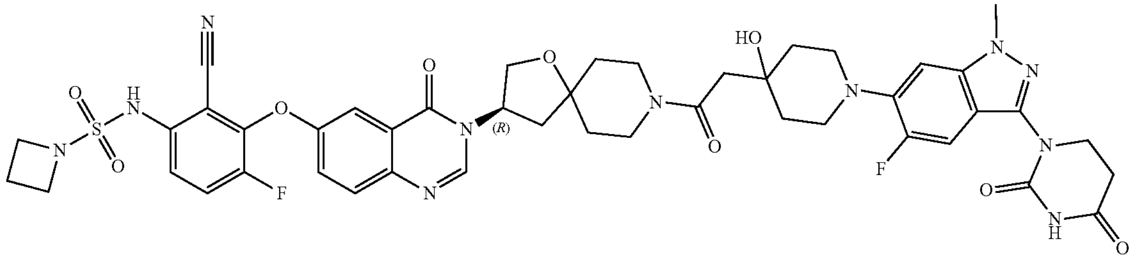

The title compound was purified by reverse phase column chromatography eluted with 43% acetonitrile in 0.1% formic acid in water to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl]azetidine-1-sulfonamide (51.25 mg, 49.79 μmol, 28% yield) as an off-white solid compound. LCMS m/z (ESI): 956.2 $[M+H]^+$; $^1$H-NMR (400 MHz, DMSO-$d_6$): δ=10.53 (s, 1H), 8.43 (s, 1H), 8.33 (s, 1H), 7.75 (d, J=8.80 Hz, 1H), 7.61 (q, J=2.80 Hz, 1H), 7.35-7.27 (m, 4H), 7.12 (d, J=7.20 Hz, 1H), 5.39-5.25 (m, 1H), 5.03 (d, J=3.60 Hz, 1H), 4.20-4.11 (m, 2H), 3.94 (s, 3H), 3.89 (t, J=6.40 Hz, 2H), 3.79-3.63 (m, 1H), 3.63-3.57 (m, 1H), 3.53 (t, J=9.20 Hz, 4H), 3.19-3.16 (m, 2H), 3.15-3.06 (m, 2H), 2.74 (t, J=6.80 Hz, 2H), 2.57-2.33 (m, 4H), 2.15-2.05 (m, 1H), 2.05-1.91 (m, 2H), 1.85-1.50 (m, 9H).

Example 197

(3R)-3-[6-[2-cyano-3-[[cyclopropyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

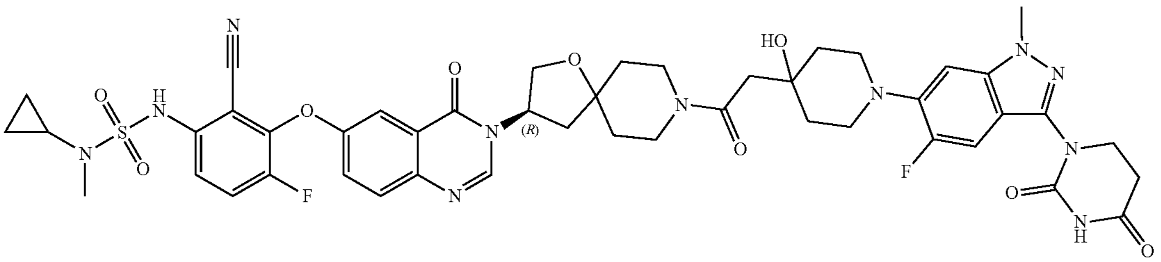

The title compound was purified by reverse phase column chromatography eluted with 40% acetonitrile in 0.1% formic acid in water to afford product (3R)-3-[6-[2-cyano-3-[[cyclopropyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (85 mg, 86.39 μmol, 27% yield) as an off-white solid. LCMS m/z (ESI): 970.2 $[M+H]^+$; $^1$H-NMR (400 MHz, DMSO-$d_6$): δ=10.99 (s, 1H), 9.99 (s, 1H), 8.58 (s, 2H), 8.32 (s, 1H), 7.86 (d, J=9.20 Hz, 1H), 7.76-7.73 (m, 2H), 7.47-7.46 (m, 1H), 7.39 (t, J=2.80 Hz, 1H), 6.99 (m, 1H), 6.52-6.50 (m, 1H), 6.47-6.46 (m, 1H), 6.11 (d, J=7.60 Hz, 1H), 4.33-4.31 (m, 2H), 3.95-3.92 (m, 2H), 3.90-3.86 (m, 2H), 3.69-3.65 (m, 2H), 3.59-3.55 (m, 2H), 3.52-3.49 (m, 2H), 3.15-2.98 (m, 2H), 2.95-2.85 (m, 2H), 2.78 (s, 3H), 2.75-2.73 (m, 1H), 2.68-2.67 (m, 1H), 2.61-2.60 (m, 1H), 2.09-2.01 (m, 3H), 2.09-2.01 (m, 3H).

Example 198

N-[2-cyano-3-[3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decan-3-yl]-4-oxoquinazolin-6-yl]oxy-4-fluorophenyl]cyclobutanesulfonamide

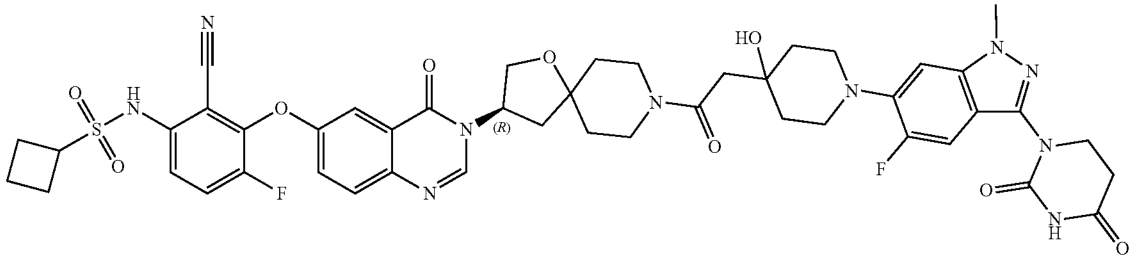

The title compound was purified by reverse phase column chromatography eluted with 45% acetonitrile in 0.1% ammonium bicarbonate in water to afford product N-[2-cyano-3-[3-[(3R)-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decan-3-yl]-4-oxo-quinazolin-6-yl]oxy-4-fluoro-phenyl] cyclobutanesulfonamide (65 mg, 67.55 μmol, 19% yield) as an off-white solid. LCMS m/z (ESI): 956.2 $[M+H]^+$; $^1$H-NMR (400 MHz, DMSO-$d_6$): δ=10.52 (s, 1H), 10.27 (s, 1H), 8.36 (s, 1H), 7.79 (d, J=9.20 Hz, 2H), 7.70 (dd, J=2.80, Hz, 1H), 7.44 (dd, J=4.00, 9.20 Hz, 1H), 7.41 (d, J=3.20 Hz, 1H), 7.33 (d, J=12.80 Hz, 1H), 7.12 (d, J=7.20 Hz, 1H), 5.31 (s, 1H), 5.03 (s, 1H), 4.16-4.14 (m, 2H), 4.13-3.94 (m, 1H), 3.91 (s, 3H), 3.88 (d, J=6.80 Hz, 2H), 3.85-3.72 (m, 1H), 3.61-3.60 (m, 1H), 3.68-3.48 (m, 1H), 3.33-3.18 (m, 2H), 3.16 (m, 1H), 3.05 (d, J=10.00 Hz, 1H), 2.74 (t, J=6.80 Hz, 2H), 2.51 (s, 2H), 2.37-2.30 (m, 3H), 2.27 (d, J=8.40 Hz, 2H), 2.10 (d, J=6.40 Hz, 1H), 1.95-1.91 (m, 2H), 1.89-1.78 (m, 4H), 1.73-1.67 (m, 4H).

Example 199

6-[2-cyano-3-[[ethyl(methyl)sulfamoyl]amino]-6-fluorophenoxy]-3-[2-[4-[2-[1-[3-(2,4-dioxo-1,3-diazinan-1-yl)-5-fluoro-1-methylindazol-6-yl]-4-hydroxypiperidin-4-yl]acetyl]piperazin-1-yl]pyrimidin-5-yl]-4-oxoquinazoline

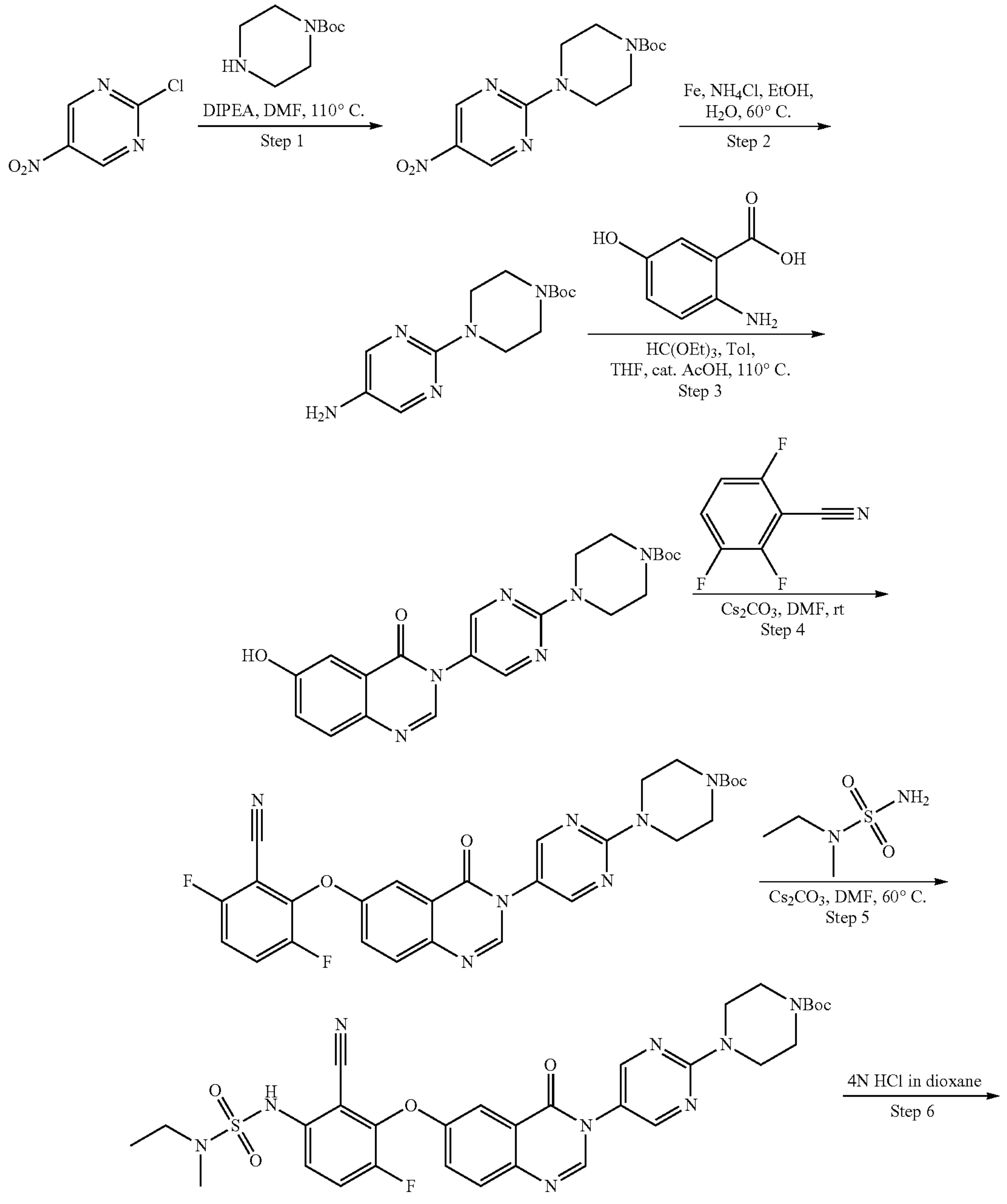

-continued

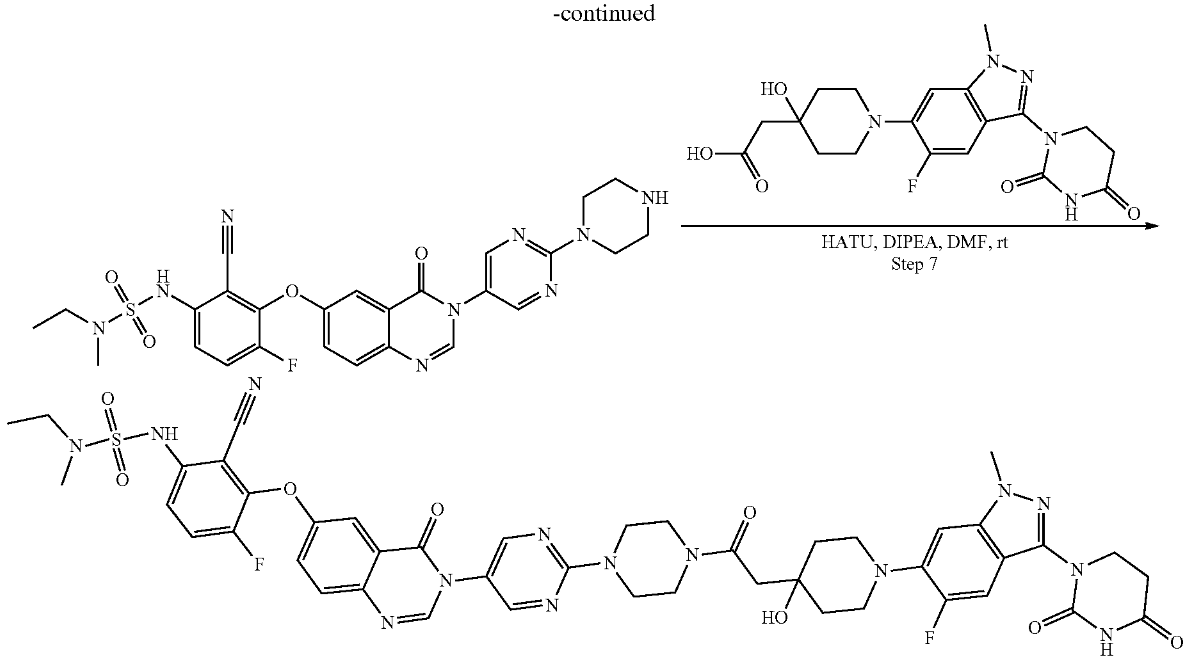

Step 1: To a solution of 2-chloro-5-nitro-pyrimidine (5 g, 31.34 mmol) in N,N-dimethylformamide (20 mL) in a sealed tube was added tert-butyl piperazine-1-carboxylate (5.84 g, 31.34 mmol) and N,N-diisopropylethylamine (16.20 g, 125.37 mmol, 21.84 mL) at room temperature under Nitrogen atmosphere. The reaction mixture was stirred at 110° C. for 12 h. After completion of the reaction, the reaction mixture was poured into ice cold water. Obtained solids were filtered through Buchner funnel and dried under reduced pressure to afford tert-butyl 4-(5-nitropyrimidin-2-yl)piperazine-1-carboxylate (3.78 g, 12.15 mmol, 39% yield) as light brown solid crude. LCMS m/z (ESI): 254 $[M+H-^tBu]^+$ Step 2: To a solution of tert-butyl 4-(5-nitropyrimidin-2-yl)piperazine-1-carboxylate (3.78 g, 12.22 mmol) in ethanol (32 mL) and water (4 mL) were added iron powder (3.41 g, 61.10 mmol, 434.13 μL) and Ammonium chloride (1.96 g, 36.66 mmol, 1.28 mL) at room temperature under inert atmosphere. The resulting reaction mixture was stirred at 70° C. for 6 h. After completion of the reaction, the reaction mixture was filtered through celite and washed with ethyl acetate (200 mL). The filtrate was washed with water (80 mL), saturated sodium bicarbonate solution (60 mL) and brine (60 mL). The organic layer was dried over sodium sulfate and concentrated under reduced pressure to afford the crude, which was purified by column chromatography on silica gel eluted with 70% ethyl acetate in petroleum ether to afford tert-butyl 4-(5-aminopyrimidin-2-yl)piperazine-1-carboxylate (1.67 g, 4.18 mmol, 34% yield) as a brown solid. LCMS m/z (ESI): 280.2 $[M+H]^+$ Step 3: Quinazolinone intermediate was synthesized by following the general procedure for cyclization (Procedure B-A) using tert-butyl 4-(5-aminopyrimidin-2-yl)piperazine-1-carboxylate (1.4 g, 5.01 mmol), 2-amino-5-hydroxy-benzoic acid (767.49 mg, 5.01 mmol), Triethyl orthoformate (1.49 g, 10.02 mmol, 1.67 mL) and acetic acid (3.01 mg, 50.12 μmol, 2.87 μL). The crude compound was purified by silica gel flash column chromatography with 70% ethyl acetate in petroleum ether as a eluent to afford tert-butyl 4-[5-(6-hydroxy-4-oxo-quinazolin-3-yl)pyrimidin-2-yl]piperazine-1-carboxylate (260 mg, 569.68 μmol, 11% yield) as a light yellow solid LCMS m/z (ESI): 425.2 $[M+H]^+$ Step 4: O-arylated quinazolinone intermediate was synthesized by following the general procedure for O-arylation (Procedure B—B) using tert-butyl 4-[5-(6-hydroxy-4-oxo-quinazolin-3-yl)pyrimidin-2-yl]piperazine-1-carboxylate (280 mg, 659.67 μmol), cesium carbonate (537.34 mg, 1.65 mmol) and 2,3,6-Trifluorobenzonitrile (155.45 mg, 989.51 μmol, 114.30 μL). The resulting crude was purified by silica gel flash column chromatography eluted with 60% ethyl acetate in petroleum ether to afford tert-butyl 4-[5-[6-(2-cyano-3,6-difluoro-phenoxy)-4-oxo-quinazolin-3-yl]pyrimidin-2-yl]piperazine-1-carboxylate (250 mg, 431.85 μmol, 65% yield) as an off-white solid. LCMS m/z (ESI): 562.2 $[M+H]^+$ Step 5: Sulfamoylated quinazolinone intermediate was synthesized by following Procedure B—C using tert-butyl 4-[5-[6-(2-cyano-3,6-difluoro-phenoxy)-4-oxo-quinazolin-3-yl]pyrimidin-2-yl]piperazine-1-carboxylate (220 mg, 391.78 μmol), [methyl(sulfamoyl)amino]ethane (108.28 mg, 783.56 μmol) and cesium carbonate (319.12 mg, 979.4 μmol). The crude compound was purified with 75% ethyl acetate in petroleum ether to afford tert-butyl 4-[5-[6-[2-cyano-3-[[ethyl(methyl)sulfamoyl]amino]-6-fluoro-phenoxy]-4-oxo-quinazolin-3-yl]pyrimidin-2-yl]piperazine-1-carboxylate (120 mg, 155.36 μmol, 40% yield) as an off-white solid. LCMS m/z (ESI): 624.2 $[M+H-^tBu]^+$ Step 6: The requisite amine was synthesized by HCl mediated N-Boc deprotection (Procedure B-D). N-Boc deprotection was done on tert-butyl 4-(5-(6-(2-cyano-3-((N-ethyl-N— methylsulfamoyl)amino)-6-fluorophenoxy)-4-oxoquinazolin-3(4H)-yl)pyrimidin-2-yl)piperazine-1-carboxylate (60 mg, 88.27 μmol), hydrogen chloride solution (4.0M in dioxane, 20 μL) to afford (6-[2-cyano-3-[[ethyl(methyl)sulfamoyl]amino]-6-fluoro-phenoxy]-4-oxo-3-(2-piperazin-1-ylpyrimidin-5-yl)quinazoline (53 mg, 75.71 μmol, 86% yield) as a light brown solid. LCMS m/z (ESI): 580.2 $[M+H]^+$ Step 7: Target compound was prepared via HATU mediated acid-amine coupling reaction (Procedure B-E). Amide coupling was carried out using 6-[2-cyano-3-[[ethyl(methyl)sulfamoyl]amino]-6-fluoro-phenoxy]-4-oxo-3-(2-piperazin-1-ylpyrimidin-5-yl)quinazoline (80 mg, 129.86 μmol), 2-[1-[3-(2,4-dioxohexahydropyrimidin-1-yl)-5-fluoro-1-methyl-indazol-6-yl]-4-hydroxy-4-piperidyl]acetic acid (59.91 mg, 142.84 μmol), N,N-diisopropylethylamine (83.91 mg, 649.28 μmol, 113.09 μL) and HATU (59.25 mg, 155.83 μmol). The crude compound was purified by reverse phase column chromatography eluted with 45% acetonitrile in 0.1% ammonium acetate in water to afford product 6-[2-cyano-3-[[ethyl(methyl)sulfamoyl]amino]-6-fluoro-phenoxy]-3-[2-[4-[2-[1-[3-(2,4-dioxohexahydropyrimidin-1-yl)-5-fluoro-1-methyl-indazol-6-yl]-4-hydroxy-4-piperidyl]acetyl]piperazin-1-yl]pyrimidin-5-yl]-4-oxo-quinazoline (36.25 mg, 36.69 μmol, 28% yield) as an off-white solid. LCMS m/z (ESI): 981.00 $[M+H]^+$; $^1$HNMR (400 MHz, DMSO-$d_6$): δ=10.53 (s, 1H), 10.19 (s, 1H), 8.57 (s, 2H), 8.34 (s, 1H), 7.84 (d, J=14.80 Hz, 2H), 7.75 (dd, J=3.20, 8.80 Hz, 1H), 7.48 (s, 1H), 7.40 (d, J=2.80 Hz, 1H), 7.34 (d, J=12.80 Hz, 1H), 7.13 (d, J=7.20 Hz, 1H), 4.95 (s, 1H), 3.95 (s, 3H), 3.91-3.83 (m, 6H), 3.66-3.65 (m, 4H), 3.20-3.06 (m, 6H), 2.77-2.73 (m, 4H), 2.67 (s, 3H), 1.89-1.84 (m, 2H), 1.78-1.75 (m, 2H), 1.04 (t, J=7.20 Hz, 3H).

Example 200

6-[2-cyano-3-[[ethyl(methyl)sulfamoyl]amino]-6-fluorophenoxy]-3-[(3R)-8-[4-[3-(2,4-dioxo-1,3-diazinan-1-yl)-5-fluoro-1-methylindazol-6-yl]piperidin-1-yl]-1-oxaspiro[4.5]decan-3-yl]-4-oxoquinazoline

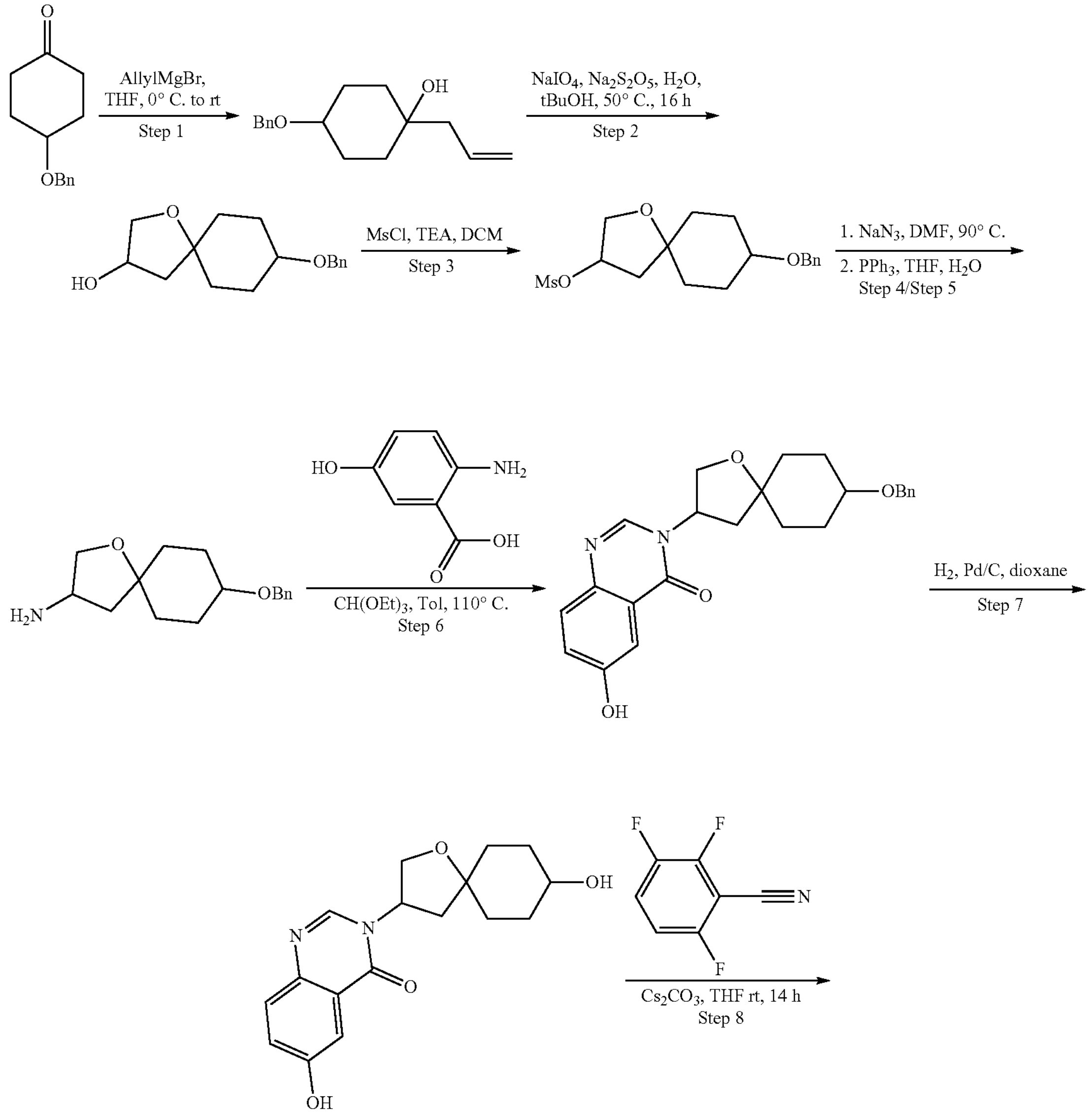

-continued

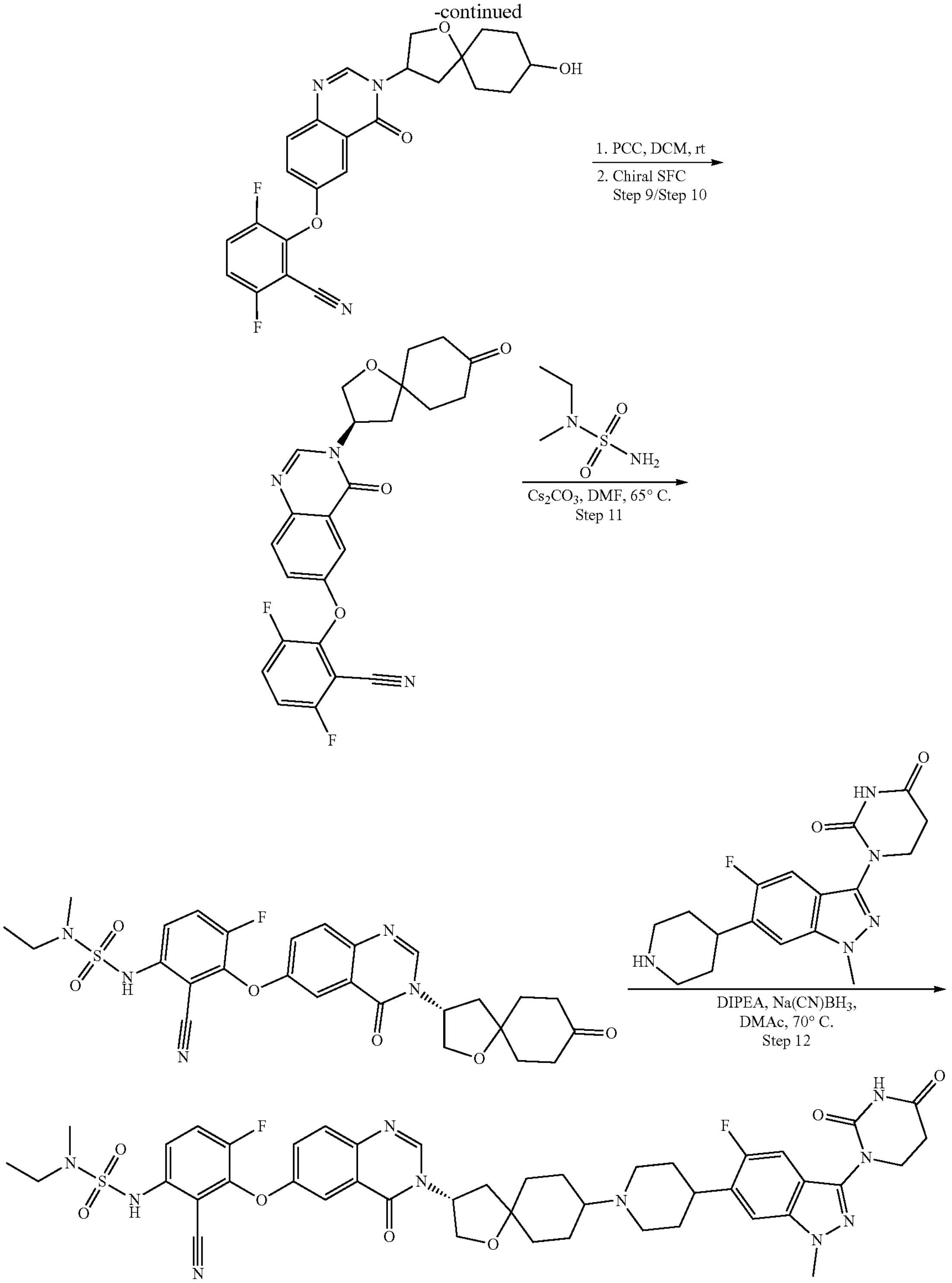

Step 1: Into a 500 mL two necked round bottomed flask containing a well-stirred solution of 4-benzyloxycyclohexanone (10 g, 48.96 mmol) in anhydrous tetrahydrofuran (150 mL) was added allyl magnesium bromide (1 M, 122.39 mL) at 0-5° C. under nitrogen atmosphere. The resulting mixture was stirred at ambient temperature for 6 h. After completion of the reaction as indicated by TLC, saturated ammonium chloride (100 mL) was added to the reaction mixture and extracted with ethyl acetate (3×100 mL). The combined organic layers were dried over anhydrous sodium sulfate, filtered and the filtrate was concentrated under reduced pressure to afford crude residue. The crude compound was purified by flash silica-gel column chromatography eluting at 40-50% of ethyl acetate in petroleum ether to afford 1-allyl-4-benzyloxy-cyclohexanol (3.7 g, 12.85 mmol, 26% yield) as a colourless viscous liquid. $^1$H-NMR (400 MHz, DMSO-$d_6$): δ=7.26-7.31 (m, 5H), 5.82-5.91 (m, 1H), 4.96-5.02 (m, 1H), 4.48 (s, 1H), 4.43 (d, J=8.80 Hz, 1H), 4.11 (s, 1H), 3.20-3.35 (m, 1H), 2.55-2.30 (m, 2H), 2.10 (d, J=9.60 Hz, 1H), 1.45-1.81 (m, 6H), 1.15-1.41 (m, 2H).

Step 2: Into a 250 mL single necked round bottomed flask containing a well-stirred solution of 1-allyl-4-benzyloxy-cyclohexanol (3.70 g, 15.02 mmol, 000) in a mixture of tert-butanol (40 mL) and water (20 mL) was added sodium metaperiodate (3.60 g, 16.83 mmol) at 0-5° C. To this reaction mixture, sodium metabisulfite (3.20 g, 16.83 mmol, 2.16 mL) in water (10 mL) was added at the same temperature. The resulting mixture was heated to 50° C. for 16 h. After completion of the reaction, the reaction mixture was cooled to room temperature and poured into water (100 mL) and extracted with ethyl acetate (3×100 mL). The combined organic phases were dried over anhydrous sodium sulfate, filtered and the filtrate was concentrated under reduced pressure to afford a crude residue. The crude product purified by flash silica-gel column chromatography eluting with 70-80% of ethyl acetate in petroleum ether to afford 8-benzyloxy-1-oxaspiro[4.5]decan-3-ol (1.10 g, 4.15 mmol, 28% yield) as a brownish viscous liquid. LCMS m/z (ESI): 263.4[M+H]$^+$.

Step 3: Into a 50 mL single necked round bottomed flask containing a well-stirred solution of 8-benzyloxy-1-oxaspiro[4.5]decan-3-ol (1.10 g, 4.19 mmol) in anhydrous dichloromethane (15 mL) was added triethylamine (1.45 g, 14.35 mmol, 2.0 mL) at 0-5° C., followed by the addition of methane sulfonyl chloride (740.00 mg, 6.46 mmol, 0.500 mL) at same temperature. The resulting mixture was stirred at ambient temperature for 16 h. After completion of the reaction, water (50 mL) was added to the reaction mixture and extracted with dichloromethane (2×100 mL). The combined organic layers were dried over anhydrous sodium sulfate, filtered and the filtrate was concentrated under reduced pressure to afford crude residue. The crude compound was purified by flash silica-gel column chromatography eluting with 40-50% ethyl acetate in petroleum ether to afford (8-benzyloxy-1-oxaspiro[4.5]decan-3-yl) methane sulfonate (1.0 g, 2.35 mmol, 56% yield) as yellowish viscous liquid. LCMS m/z (ESI): 341.4[M+H]$^+$.

Step 4: Into a 50 mL single-necked round-bottomed flask containing a well-stirred solution of (8-benzyloxy-1-oxaspiro[4.5]decan-3-yl) methane sulfonate (1.0 g, 2.94 mmol) in anhydrous N,N-dimethylformamide (10 mL) was added sodium azide (300 mg, 4.61 mmol, 162.16 μL) at ambient temperature under nitrogen atmosphere. The resulting mixture was heated to 80° C. for 16 h. After completion of the reaction, water (50 ml) was added to the reaction mixture and extracted with ethyl acetate (2×100 mL). The combined organic layers were dried over sodium sulfate, filtered, and concentrated under reduced pressure to afford crude residue. The crude residue was purified by flash silica-gel column chromatography eluted with 70-80% of ethyl acetate in petroleum ether to afford 3-azido-8-benzyloxy-1-oxaspiro[4.5]decane (780 mg, 2.23 mmol, 75.77% yield, 82% purity) as a brownish viscous liquid. LCMS m/z (ESI): 288.4[M+H]$^+$.

Step 5: Into a 50 mL single-necked round-bottomed flask containing a well-stirred solution of 3-azido-8-benzyloxy-1-oxaspiro[4.5]decane (780 mg, 2.71 mmol) in a mixture of tetrahydrofuran (10 mL) and water (1.0 mL) was added triphenyl phosphine (1.10 g, 4.19 mmol) at ambient temperature. The resulting mixture was heated to 80° C. for 3 h. After completion of the reaction water (50 ml) was added to the reaction mixture and extracted with ethyl acetate (3×100 mL). The combined organic layers were dried over sodium sulfate, filtered, and concentrated under reduced pressure to afford crude residue. The crude residue was purified by flash silica-gel column chromatography eluted with 0-20% methanol in dichloromethane to afford 8-benzyloxy-1-oxaspiro[4.5]decan-3-amine (510 mg, 1.85 mmol, 68% yield) as a brownish viscous liquid. LCMS m/z (ESI): 262.4[M+H]$^+$.

Step 6: Into a 50 mL sealed-tube containing a well-stirred solution of 8-benzyloxy-1-oxaspiro[4.5]decan-3-amine (510 mg, 1.95 mmol) in a mixture of toluene (10.0 mL) and tetrahydrofuran (3.0 mL) were added 2-amino-5-hydroxy-benzoic acid (370 mg, 2.42 mmol) and triethyl orthoformate (801.90 mg, 5.41 mmol, 0.900 mL) at ambient temperature under nitrogen atmosphere. The resulting mixture was heated to 110° C. for 16 h. After completion, the reaction mixture was cooled to room temperature and poured into water (50 mL) and extracted with ethyl acetate (2×100 mL). The combined organic phases were dried over anhydrous sodium sulfate, filtered and the filtrate was concentrated under reduced pressure. The crude residue was purified by flash silica-gel column chromatography eluting with 5-10% of methanol in dichloromethane to afford 3-(8-benzyloxy-1-oxaspiro[4.5]decan-3-yl)-6-hydroxy-quinazolin-4-one (560 mg, 1.30 mmol, 66% yield) as a pale brown solid. LCMS m/z (ESI): 407.7 [M+H]$^+$.

Step 7: Into a 50 mL single-necked round-bottomed flask containing a well-stirred solution of 3-(8-benzyloxy-1-oxaspiro[4.5]decan-3-yl)-6-hydroxy-quinazolin-4-one (560 mg, 1.38 mmol) in anhydrous 1,4-dioxane (10 mL) was added acetic acid (104.90 mg, 1.75 mmol, 0.100 mL) and charged 10% palladium on carbon(150 mg, 140.95 μmol, 10% purity), saturated with hydrogen by bubbling hydrogen gas through for 10 minutes and subjected to hydrogenation (1 atm) at ambient temperature for 16 h. After completion, the reaction mixture was purged with nitrogen, catalyst was removed by filtration through celite pad. The filtrate was concentrated under reduced pressure. The crude product was purified by flash silica-gel column chromatography eluting with 10-15% of methanol in dichloromethane to afford 6-hydroxy-3-(8-hydroxy-1-oxaspiro[4.5]decan-3-yl)quinazolin-4-one (340 mg, 913.54 μmol, 66% yield) as a pale yellow solid. LCMS m/z (ESI): 317.2 [M+H]$^+$.

Step 8: Into a 25 mL sealed tube containing a well-stirred solution of 6-hydroxy-3-(8-hydroxy-1-oxaspiro[4.5]decan-3-yl)quinazolin-4-one (340 mg, 1.07 mmol) in anhydrous tetrahydrofuran (10 mL) were added 2,3,6-trifluorobenzonitrile (260 mg, 1.66 mmol, 191.18 L) and cesium carbonate (1.10 g, 3.38 mmol) at ambient temperature under nitrogen atmosphere. The resulting mixture was stirred at ambient temperature for 16 h. After completion of the reaction, water (50 ml) was added to the reaction mixture and extracted with ethyl acetate (2×100 mL). The combined organic layers were dried over sodium sulfate, filtered, and concentrated under reduced pressure to afford crude residue. The crude residue was purified by flash silica-gel column chromatography eluting with 80-90% ethyl acetate in petroleum ether to afford 3,6-difluoro-2-[3-(8-hydroxy-1-oxaspiro[4.5]decan-3-yl)-4-oxo-quinazolin-6-yl]oxy-benzonitrile (380 mg, 687.20 μmol, 64% yield) as yellowish viscous liquid. LCMS m/z (ESI): 454.1 [M+H]$^+$.

Step 9/Step 10: Into a 50 mL single-necked round-bottomed flask containing a well-stirred solution of 3,6-difluoro-2-[3-(8-hydroxy-1-oxaspiro[4.5]decan-3-yl)-4-oxo-quinazolin-6-yl]oxy-benzonitrile (380 mg, 838.04 μmol) in anhydrous dichloromethane (10 mL) was added pyridinium chlorochromate (460 mg, 2.13 mmol) at ambient temperature under nitrogen atmosphere. The resulting mixture was stirred at ambient temperature for 16 h. After completion, the reaction mixture was filtered through celite and filtrate was concentrated under reduced pressure to afford crude residue. The crude residue was purified by flash silica-gel column chromatography eluting with 90-95% ethyl acetate in dichloromethane to afford 320 mg of racemic compound (95% pure). This compound was purified by chiral SFC purification (column: Chiralpak ASH [(250*30) mm, 5μ]; mobile Phase: $CO_2$:isopropyl alcohol (70:30); total flow: 70 g/min; wavelength: 220 nm; cycle time: 8.2 min; back pressure: 100 bar) to afford 3,6-difluoro-2-[4-oxo-3-[(3S)-8-oxo-1-oxaspiro[4.5]decan-3-yl]quinazolin-6-yl]oxy-benzonitrile (first eluting peak, 130 mg, 259.18 μmol, 31% yield) as a brownish viscous liquid and 3,6-difluoro-2-[4-oxo-3-[(3R)-8-oxo-1-oxaspiro[4.5]decan-3-yl]quinazolin-6-yl]oxy-benzonitrile (second eluting peak, 110 mg, 233.93 μmol, 28% yield) as an off-white solid. LCMS m/z (ESI): 452.2 $[M+H]^+$. SOR analysis: F1 $[\alpha]_d$: 64.4 ($CHCl_3$, 0.5M); F2 $[\alpha]_d$: −73.04 ($CHCl_3$, 0.5M)

Step 11: Into a 10 mL sealed tube containing a well-stirred solution of 3,6-difluoro-2-[4-oxo-3-[(3R)-8-oxo-1-oxaspiro[4.5]decan-3-yl]quinazolin-6-yl]oxy-benzonitrile (110 mg, 243.67 μmol) in anhydrous N,N-dimethylformamide (3.0 mL) were added [methyl(sulfamoyl)amino]ethane (60 mg, 434.19 μmol) and cesium carbonate (250 mg, 767.30 μmol) at ambient temperature under nitrogen atmosphere. The resulting mixture was heated to 65° C. for 16 h. After completion of the reaction, water (30 ml) was added to the reaction mixture and extracted with ethyl acetate (3×50 mL). The combined organic layers were dried over sodium sulfate, filtered, and concentrated under reduced pressure to afford crude residue. The crude residue was purified by flash silica-gel column chromatography eluted with 5-10% of methanol in dichloromethane to afford 6-[2-cyano-3-[[ethyl(methyl)sulfamoyl]amino]-6-fluoro-phenoxy]-4-oxo-3-[(3R)-8-oxo-1-oxaspiro[4.5]decan-3-yl]quinazoline (85 mg, 110.43 μmol, 45% yield) as a brownish viscous liquid. LCMS m/z (ESI): 570.2$[M+H]^+$ Step 12: Into a 10 mL sealed-tube containing a well-stirred solution of 6-[2-cyano-3-[[ethyl(methyl)sulfamoyl]amino]-6-fluoro-phenoxy]-4-oxo-3-[(3R)-8-oxo-1-oxaspiro[4.5]decan-3-yl]quinazoline (85 mg, 149.23 μmol) and 1-[5-fluoro-1-methyl-6-(4-piperidyl)indazol-3-yl]hexahydropyrimidine-2,4-dione hydrochloric acid salt (115 mg, 301.18 μmol) in anhydrous N,N-dimethylacetamide (5.0 mL) were added N,N-diisopropylethylamine (742.00 mg, 5.74 mmol, 1.0 mL) and sodium cyanoborohydride (100 mg, 1.59 mmol) at ambient temperature under nitrogen atmosphere. The resulting mixture was heated to 70° C. for 16 h.

After completion, the reaction mixture was filtered through celite and filtrate was concentrated under reduced pressure. The crude compound was purified by reverse phase column chromatography using A 50 g snap (high performance RediSep Gold® Rf C18) with acetonitrile in 0.1% ammonium bicarbonate in water to afford 6-[2-cyano-3-[[ethyl(methyl)sulfamoyl]amino]-6-fluoro-phenoxy]-3-[(3R)-8-[4-[3-(2,4-dioxohexahydropyrimidin-1-yl)-5-fluoro-1-methyl-indazol-6-yl]-1-piperidyl]-1-oxaspiro[4.5]decan-3-yl]-4-oxo-quinazoline (6.0 mg, 6.30 μmol, 4% yield) as an off-white solid. LCMS m/z (ESI): 899.0 $[M+H]^+$; $^1$H-NMR (400 MHz, DMSO-$d_6$): δ=10.57 (s, 1H), 9.40 (s, 1H), 8.32 (s, 1H), 7.76 (d, J=8.80 Hz, 1H), 7.63 (dd, J=2.80, 9.20 Hz, 1H), 7.58-7.45 (m, 1H), 7.43-7.34 (m, 3H), 7.27-7.26 (m, 1H), 5.32-5.22 (m, 1H), 4.16-4.05 (m, 2H), 4.01 (s, 3H), 3.91 (t, J=6.80 Hz, 2H), 3.20-2.99 (m, 5H), 2.76 (t, J=6.40 Hz, 3H), 2.60-2.50 (m, 4H), 1.95-1.44 (m, 15H), 1.03 (t, J=7.20 Hz, 3H).

Example 201

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-fluoropiperidin-4-yl]acetyl]-1-oxa-8-azaspiro[4.5]decane

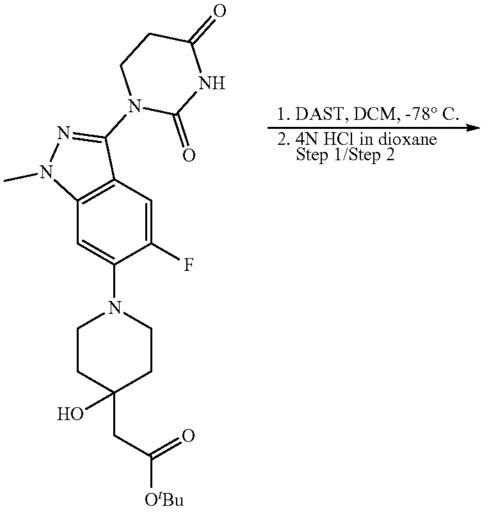

-continued

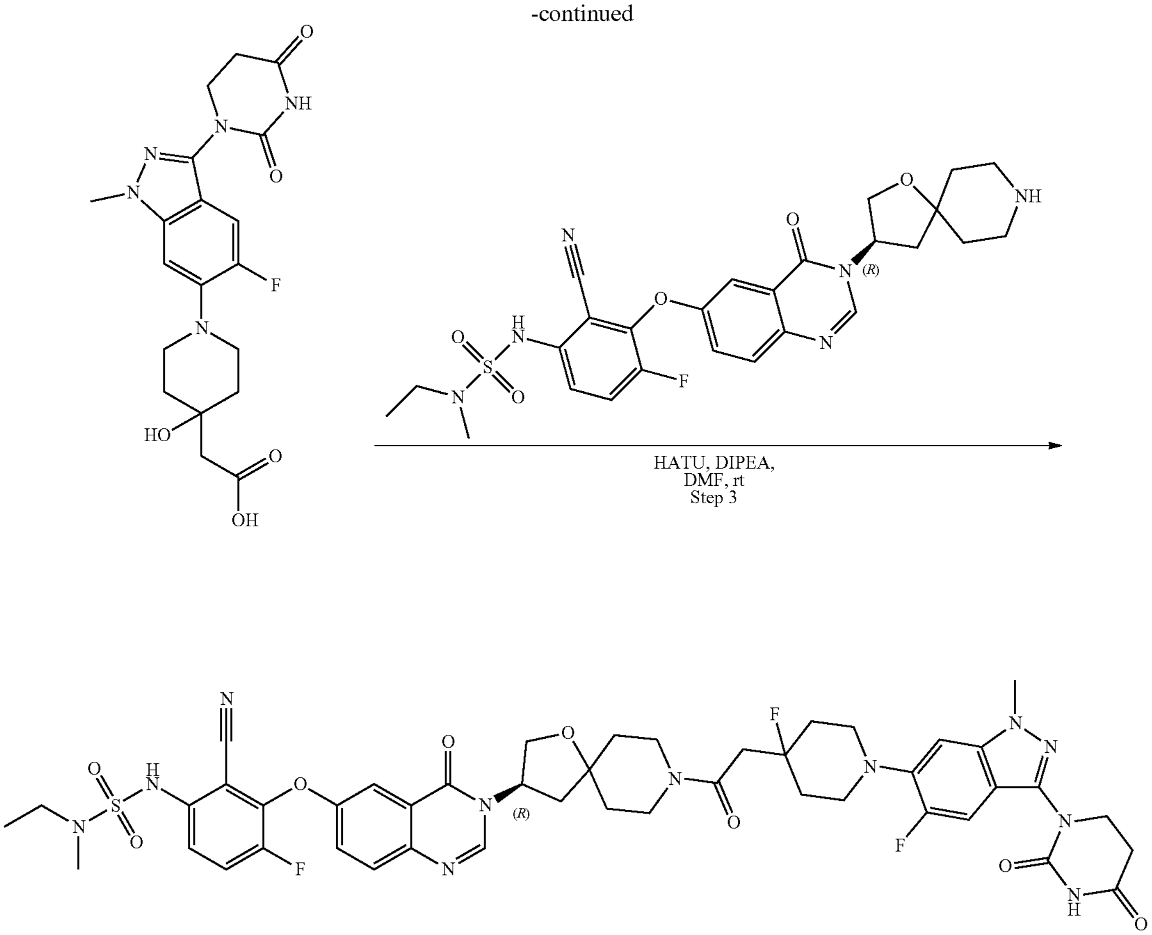

Step 1: To a solution of tert-butyl 2-[1-[3-(2,4-dioxohexahydropyrimidin-1-yl)-5-fluoro-1-methyl-indazol-6-yl]-4-hydroxy-4-piperidyl]acetate (200 mg, 420.60 μmol) in dichloromethane (3 mL) was added bis-(2-methoxyethyl) aminosulfur trifluoride (139.58 mg, 630.90 μmol) at −30° C. The reaction mixture was stirred at 0° C. for 1 h. The reaction mixture was quenched with water and extracted with dichloromethane (60 mL). The organic layer was washed with water(20 mL), brine (20 mL), dried under sodium sulfate and concentrated under reduced pressure to afford crude which was purified by silica gel column chromatography eluted with 60% ethyl acetate in petroleum ether to afford tert-butyl 2-[1-[3-(2,4-dioxohexahydropyrimidin-1-yl)-5-fluoro-1-methyl-indazol-6-yl]-4-fluoro-4-piperidyl]acetate (140 mg, 210.22 μmol, 50% yield) as a light brown solid. LCMS m/z (ESI): 478.2 $[M+H]^+$.

Step 2: To a cooled 0° C. solution of tert-butyl 2-[1-[3-(2,4-dioxohexahydropyrimidin-1-yl)-5-fluoro-1-methyl-indazol-6-yl]-4-fluoro-4-piperidyl]acetate (140 mg, 293.19 μmol) in dichloromethane (2 mL) was added 4M hydrogen chloride in 1,4-dioxane (4M, 3 mL) and the resulting reaction mixture was stirred at room temperature for 4 h. The reaction mixture was concentrated under reduced pressure to get crude which was triturated with diethyl ether to afford 2-[1-[3-(2,4-dioxohexahydropyrimidin-1-yl)-5-fluoro-1-methyl-indazol-6-yl]-4-fluoro-4-piperidyl]acetic acid (130 mg, 214.37 μmol, 73% yield) as a light brown solid. LCMS m/z (ESI): 422.2, $[M+H]^+$ Step 3: Target compound was prepared via HATU mediated acid-amine coupling reaction (Procedure B-E). Amide coupling was carried out using (3R)-3-[6-[2-cyano-3-[[ethyl (methyl)sulfamoyl]amino]-6-fluoro-phenoxy]-4-oxo-quinazolin-3-yl]-1-oxa-8-azaspiro[4.5]decane (80 mg, 143.73 μmol), 2-[1-[3-(2,4-dioxohexahydropyrimidin-1-yl)-5-fluoro-1-methyl-indazol-6-yl]-4-fluoro-4-piperidyl]acetic acid (60.57 mg, 143.73 μmol), HATU (54.65 mg, 143.73 μmol) and N,N-diisopropylethylamine (74.30 mg, 574.91 μmol, 100.14 μL). The crude compound was purified by reverse phase column chromatography by using 30 g snap eluted with 50% acetonitrile in 0.1% HCOOH in water to afford (3R)-3-[6-[2-cyano-3-[[ethyl(methyl)sulfamoyl] amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-fluoro-4-piperidyl]acetyl]-1-oxa-8-azaspiro[4.5]decane (14 mg, 14.45 μmol, 10.05% yield, 99.06% purity) as off-white solid. LCMS m/z (ESI): 960.2 $[M+H]^+$; $^1$H-NMR (400 MHz, DMSO-$d_6$): δ=10.54 (s, 1H), 10.21 (s, 1H), 8.35 (s, 1H), 7.79 (d, J=8.80 Hz, 1H), 7.64-7.75 (m, 1H), 7.68 (dd, J=2.80, 8.80 Hz, 1H), 7.38-7.46 (m, 1H), 7.35-7.38 (m, 2H), 7.17 (d, J=6.80 Hz, 1H), 5.23-5.33 (m, 1H), 4.11-4.21 (m, 2H), 3.95 (s, 3H), 3.90 (t, J=6.80 Hz, 2H), 3.71-3.81 (m, 1H), 3.55-3.65 (m, 1H), 3.44-3.55 (m, 1H), 3.25-3.35 (m, 4H), 3.08-3.18 (m, 2H), 2.88-2.98 (m, 2H), 2.78-2.88 (m, 2H), 2.62-2.70 (m, 5H), 2.54-2.60 (m, 2H), 2.31-2.41 (m, 1H), 1.98-2.18 (m, 5H), 1.50-1.81 (m, 4H).

Example 202
(3R)-3-[6-[2-cyano-3-[[ethyl(methyl)sulfamoyl]amino]-6-fluoroanilino]-5-fluoro-4-oxoquinazolin-3-yl]-8-[2-[1-[3-(2,4-dioxo-1,3-diazinan-1-yl)-5-fluoro-1-methylindazol-6-yl]piperidin-4-yl]acetyl]-1-oxa-8-azaspiro[4.5]decane
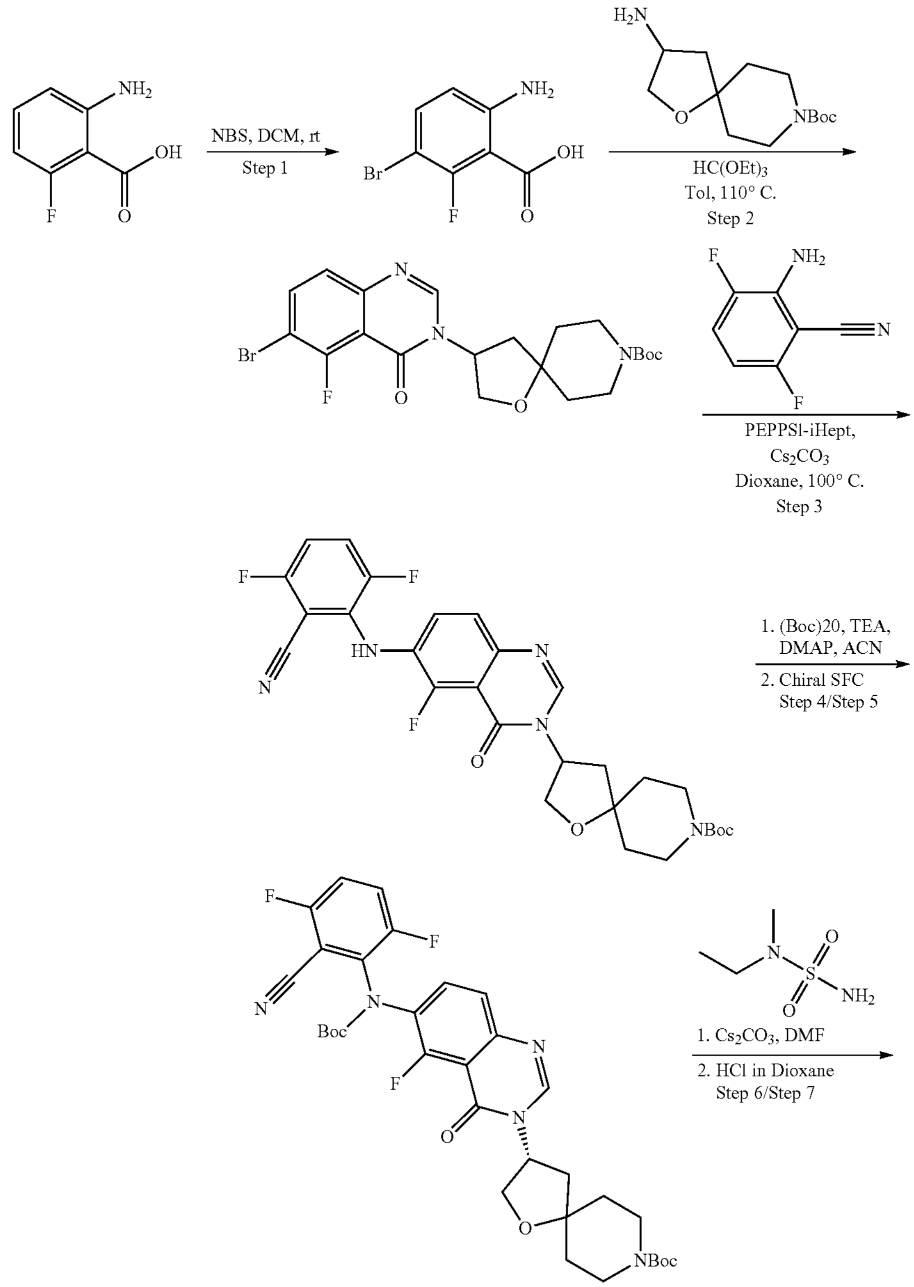

-continued

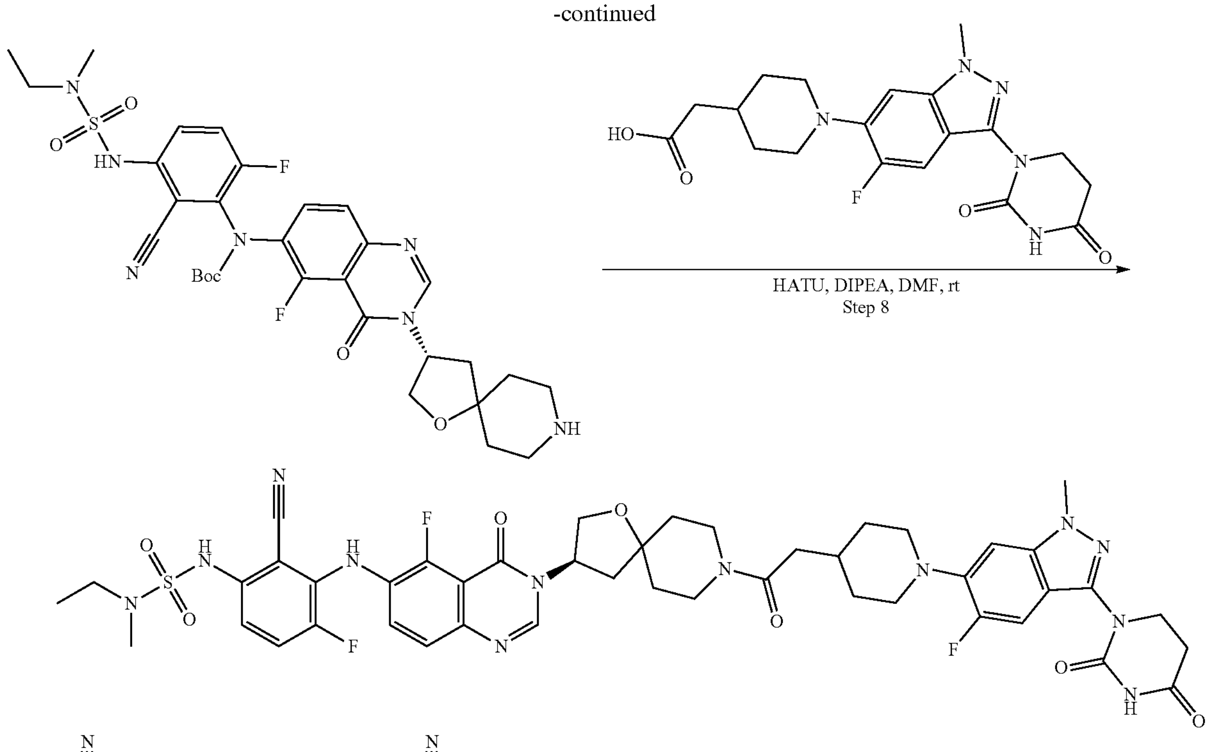

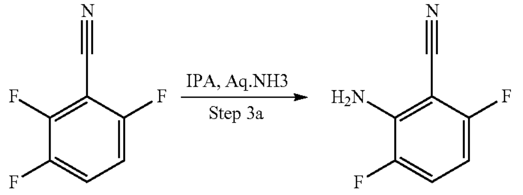 [SMILES: N#Cc1c(F)ccc(F)c1F ; N#Cc1c(F)ccc(F)c1N]

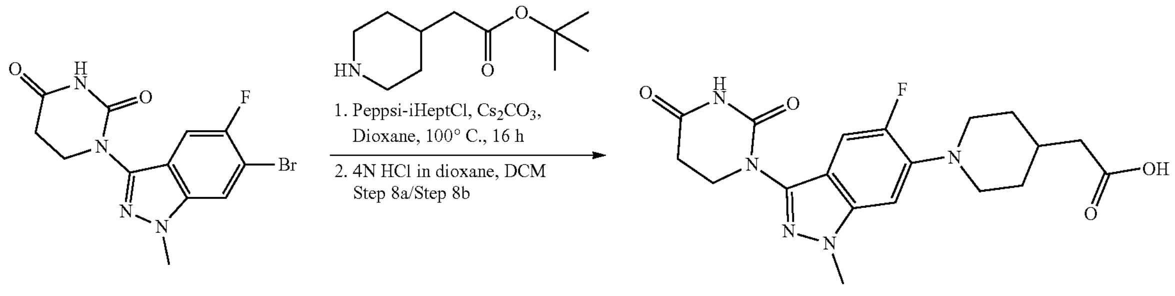 [SMILES: Cn1nc(N2CCC(=O)NC2=O)c2cc(F)c(Br)cc21 ; CC(C)(C)OC(=O)CC1CCNCC1 ; Cn1nc(N2CCC(=O)NC2=O)c2cc(F)c(N3CCC(CC(=O)O)CC3)cc21]

Step 1: To a stirred solution of 2-amino-6-fluoro-benzoic acid (2.0 g, 12.89 mmol) in dichloromethane (20 mL) was added N-bromosuccinimide (2.29 g, 12.89 mmol) at −10° C. under nitrogen atmosphere. Reaction mixture was stirred at room temperature for 2 h. The reaction mixture was diluted with water (30 mL), extracted with ethyl acetate (2×50 mL). The combined organic layers were dried over anhydrous sodium sulfate and concentrated under reduced pressure. The resulting crude product was purified by silica gel column chromatography using 0-80% ethyl acetate in petroleum ether to afford 6-amino-3-bromo-2-fluoro-benzoic acid (1.6 g, 6.23 mmol, 48% yield) as an off-white solid. LCMS m/z (ESI): 234.0 $[M+H]^+$ Step 2: A solution of 6-amino-3-bromo-2-fluoro-benzoic acid (1.7 g, 7.26 mmol), tert-butyl 3-amino-1-oxa-8-azaspiro[4.5]decane-8-carboxylate (1.86 g, 7.26 mmol) in toluene (24.55 mL) and tetrahydrofuran (4.09 mL) was added triethyl orthoformate (3.23 g, 21.79 mmol, 3.62 mL) at room temperature. The resulting reaction mixture was heated to 110° C. for 16 h. The reaction mixture was diluted with ethyl acetate (50 ml) and washed with water (10 mL). The organic layer was dried over sodium sulfate and concentrated under reduced pressure. The resulting crude product was purified by silica gel column chromatography using 0-90% of ethyl acetate in petroleum ether to afford tert-butyl 3-(6-bromo-5-fluoro-4-oxo-quinazolin-3-yl)-1-oxa-8-azaspiro[4.5]decane-8-carboxylate (1.58 g, 2.87 mmol, 39% yield) as a brownish solid. LCMS m/z (ESI): 484.4$[M+H]^+$ Step 3a: A solution of 2,3,6-trifluorobenzonitrile (3 g, 19.10 mmol, 2.21 mL) in isopropanol (15 mL) was taken in a tiny clave and added ammonium hydroxide (8.03 g, 229.16 mmol, 8.92 mL) at room temperature. The resulting reaction mixture was heated at 80° C. for 16 h. After completion, the reaction mixture was diluted with water (50 mL), extracted with ethyl acetate (100 mL). The organic layer was washed with sodium bicarbonate solution (20 mL), brine (20 mL), dried over sodium sulfate and concentrated under reduced pressure to afford crude which was purified by silica gel column chromatography eluted with 50-70% of ethyl acetate in petroleum ether to afford 2-amino-3,6-difluoro-benzonitrile (750 mg, 4.28 mmol, 22% yield) as a white solid. GC-MS m/z: 154 $[M-H]^-$.

Step 3: A solution of tert-butyl 3-(6-bromo-5-fluoro-4-oxo-quinazolin-3-yl)-1-oxa-8-azaspiro[4.5]decane-8-carboxylate (1.56 g, 3.24 mmol), 2-amino-3,6-difluoro-benzonitrile (0.5 g, 3.24 mmol) in 1,4-dioxane (5 mL) was added cesium carbonate (477.55 mg, 1.47 mmol). Reaction mixture was degassed with nitrogen atmosphere for 10 minutes and added Pd-PEPPSI-IHept-Cl 3-chloropyridine (28.49 mg, 29.29 μmol) at room temperature and heated to 110° C. for 16 h. The reaction mixture was diluted with water (5 mL), extracted with ethyl acetate (2×30 mL). The combined organic layer was dried over sodium sulfate and concentrated under reduced pressure. The crude product was purified by silica gel column chromatography using 60% ethyl acetate in petroleum ether as eluent to afford tert-butyl 3-[6-(2-cyano-3,6-difluoro-anilino)-5-fluoro-4-oxo-quinazolin-3-yl]-1-oxa-8-azaspiro[4.5]decane-8-carboxylate (0.6 g, 904.62 μmol, 28% yield) as an off-white solid. LCMS m/z (ESI): 556.4 $[M+H]^+$.

Step 4/Step 5: To a stirred solution of tert-butyl 3-[6-(2-cyano-3,6-difluoro-anilino)-5-fluoro-4-oxo-quinazolin-3-yl]-1-oxa-8-azaspiro[4.5]decane-8-carboxylate (0.8 g, 1.44 mmol) in acetonitrile (8 mL) were added di-tert-butyl dicarbonate (628.56 mg, 2.88 mmol, 660.95 L), DMAP (87.96 mg, 720.01 μmol) and triethylamine (437.15 mg, 4.32 mmol, 602.13 μL) at room temperature. The reaction mixture was stirred at room temperature for 16 h. After completion, the reaction mixture was diluted with water (10 mL) and extracted with ethyl acetate (3×30 mL). Combined organic layers were washed with cold water (3×15 mL), dried over sodium sulfate, filtered and concentrated under reduced pressure to afford crude which was purified by reverse phase column chromatography using 30 g C18 column eluted with 40% acetonitrile in water with 0.1% ammonium bicarbonate to afford racemic compound. The resulting product was purified by chiral SFC purification (column: Lux Cellulose-2 [(250*30) mm, 5μ]; mobile phase: $CO_2$:Methanol (60:40); total flow: 100 g/min; back pressure: 100 bar; wavelength: 220 nm; cycle time: 22.5 min) to afford tert-butyl (3R)-3-[6-(N-tert-butoxycarbonyl-2-cyano-3,6-difluoro-anilino)-5-fluoro-4-oxo-quinazolin-3-yl]-1-oxa-8-azaspiro[4.5]decane-8-carboxylate(fraction-1, arbitrarily assigned as R-isomer (0.16 g, 100%,) and tert-butyl (3R)-3-[6-(N-tert-butoxycarbonyl-2-cyano-3,6-difluoro-anilino)-5-fluoro-4-oxo-quinazolin-3-yl]-1-oxa-8-azaspiro[4.5]decane-8-carboxylate (fraction-2, arbitrarily assigned as S-isomer, 0.19 g, 99.7%) as light brown solids. LCMS m/z (ESI): 600.2 $[M+H-56]^+$ Step 6: To a solution of [methyl(sulfamoyl)amino]ethane (84.30 mg, 610.07 μmol), tert-butyl (3R)-3-[6-(N-tert-butoxycarbonyl-2-cyano-3,6-difluoro-anilino)-5-fluoro-4-oxo-quinazolin-3-yl]-1-oxa-8-azaspiro[4.5]decane-8-carboxylate (0.16 g, 244.03 μmol) in N,N-dimethylformamide (2 mL) was added cesium carbonate (238.53 mg, 732.08 μmol) at room temperature. The resulting reaction mixture was heated to 60° C. for 16 h. The reaction mixture was diluted with water (10 mL), was extracted with ethyl acetate (2×30 mL). The combined organic layer was washed with brine (5 mL), dried over sodium sulfate and concentrated under reduced pressure. Crude compound was purified by reverse phase column chromatography by using 30 g C18 column eluted with 40% acetonitrile in 0.1% ammonium bicarbonate in water to afford tert-butyl (3R)-3-[6-[N-tert-butoxycarbonyl-2-cyano-3-[[ethyl(methyl)sulfamoyl]amino]-6-fluoro-anilino]-5-fluoro-4-oxo-quinazolin-3-yl]-1-oxa-8-azaspiro[4.5]decane-8-carboxylate (80 mg, 103.38 μmol, 42% yield) as an off-white solid. LCMS m/z (ESI): 774.9$[M+H]^+$ Step 7: To a solution of tert-butyl (3R)-3-[6-[N-tert-butoxycarbonyl-2-cyano-3-[[ethyl(methyl)sulfamoyl]amino]-6-fluoro-anilino]-5-fluoro-4-oxo-quinazolin-3-yl]-1-oxa-8-azaspiro[4.5]decane-8-carboxylate (80 mg, 103.38 μmol) in dichloromethane (1 mL) was added 4M HCl in dioxane (4.0 M, 258.45 L) at 0° C. under nitrogen atmosphere. The resulting solution was stirred at room temperature for 2 h. The reaction mixture was concentrated under reduced pressure to afford (3R)-3-[6-[2-cyano-3-[[ethyl(methyl)sulfamoyl]amino]-6-fluoro-anilino]-5-fluoro-4-oxo-quinazolin-3-yl]-1-oxa-8-azaspiro[4.5]decane hydrochloric acid salt (63 mg, 100.04 μmol, 97% yield) as a brownish solid. LCMS m/z (ESI): 574.7 $[M+H]^+$.

Step 8a: A solution of tert-butyl 2-(4-piperidyl)acetate (154.04 mg, 772.93 μmol) in 1,4-dioxane (4 mL) was added cesium carbonate (419.72 mg, 1.29 mmol) and 1-(5-fluoro-6-iodo-1-methyl-indazol-3-yl)hexahydropyrimidine-2,4-dione (0.2 g, 515.28 μmol) at room temperature under nitrogen atmosphere. Reaction mixture was degassed with nitrogen gas for 10 minutes, then added Pd-PEPPSI-IHeptCl 3-chloropyridine (25.04 mg, 25.74 μmol) at room temperature and heated to 80° C. for 16 h. The reaction mixture was diluted with water (5 mL), extracted with ethyl acetate (2×20 mL). The combined organic layer was dried over sodium sulfate and concentrated under reduced pressure. The crude product was purified by silica gel column chromatography using 60% ethyl acetate in petroleum ether as eluent to afford tert-butyl 2-[1-[3-(2,4-dioxohexahydropyrimidin-1-yl)-5-fluoro-1-methyl-indazol-6-yl]-4-piperidyl]acetate (80 mg, 163.74 μmol, 32% yield) as an off-white solid. LCMS m/z (ESI): 460.3 $[M+H]^+$.

Step 8b: To a solution of tert-butyl 2-[1-[3-(2,4-dioxohexahydropyrimidin-1-yl)-5-fluoro-1-methyl-indazol-6-yl]-4-piperidyl]acetate (80 mg, 174.10 μmol) in dichloromethane (1 mL) was added 4M hydrogen chloride solution in dioxane (4.0 M, 435.24 μL) at 0° C. under nitrogen atmosphere. The resulting solution was stirred at room temperature for 12 h. The reaction mixture was concentrated under reduced pressure to afford crude2-[1-[3-(2,4-dioxohexahydropyrimidin-1-yl)-5-fluoro-1-methyl-indazol-6-yl]-4-piperidyl]acetic acid (76 mg, 157.83 μmol, 91% yield) as a brownish solid. LCMS m/z (ESI): 404.5$[M+H]^+$.

Step 8: The title compound was prepared via HATU mediated acid-amine coupling reaction (Procedure B-E). Amide coupling was carried out using 2-[1-[3-(2,4-dioxohexahydropyrimidin-1-yl)-5-fluoro-1-methyl-indazol-6-yl]-4-piperidyl]acetic acid (41.66 mg, 94.71 μmol), (3R)-3-[6-[2-cyano-3-[[ethyl(methyl)sulfamoyl]amino]-6-fluoro-anilino]-5-fluoro-4-oxo-quinazolin-3-yl]-1-oxa-8-azaspiro[4.5]decane (63 mg, 103.27 μmol), HATU (39.26 mg, 103.27 μmol) and N,N-diisopropylethylamine (66.73 mg, 516.33 μmol, 89.94 L). The crude compound was purified by reverse phase column chromatography by using 30 g snap eluted with 40% acetonitrile in 0.1% ammonium bicarbonate in water to afford (3R)-3-[6-[2-cyano-3-[[ethyl(methyl)sulfamoyl]amino]-6-fluoro-anilino]-5-fluoro-4-oxo-quinazolin-3-yl]-8-[2-[1-[3-(2,4-dioxohexahydropyrimidin-1-yl)-5-fluoro-1-methyl-indazol-6-yl]-4-piperidyl]acetyl]-1-oxa-8-azaspiro[4.5]decane (43 mg, 43.00 μmol, 42% yield) as an off-white solid. LCMS m/z (ESI): 959.2 $[M+H]^+$; $^1$H-NMR (400 MHz, DMSO-$d_6$): δ=10.53 (s, 1H), 9.88 (s, 1H), 8.74 (s, 1H), 8.25 (s, 1H), 7.50-7.60 (m, 1H), 7.42 (d, J=8.80 Hz, 1H), 7.32-7.43 (m, 1H), 7.34 (d, J=12.40 Hz, 1H), 7.18 (dd, J=4.00, 9.00 Hz, 1H), 7.09 (d, J=6.80 Hz, 1H), 5.30-5.36 (m, 1H), 4.14 (d, J=4.40 Hz, 2H), 3.94 (s, 3H), 3.89 (t, J=6.40 Hz, 2H), 3.69-3.78 (m, 1H), 3.32-3.61 (m, 4H), 3.11-3.18 (m, 2H), 2.65-2.81 (m, 6H), 2.35-2.58 (m, 4H), 2.01-2.10 (m, 1H), 1.60-1.91 (m, 8H), 1.35-1.51 (m, 2H), 1.04 (t, J=6.80 Hz, 3H).
Example 203
(3R)-3-[6-[2-cyano-3-[[ethyl(methyl)sulfamoyl]amino]-6-fluorophenoxy]-4-oxoquinazolin-3-yl]-8-[2-[(4R)-4-[3-(2,4-dioxo-1,3-diazinan-1-yl)-5-fluoro-1-methylindazol-6-yl]-3,3-difluoropiperidin-1-yl]acetyl]-1-oxa-8-azaspiro[4.5]decane
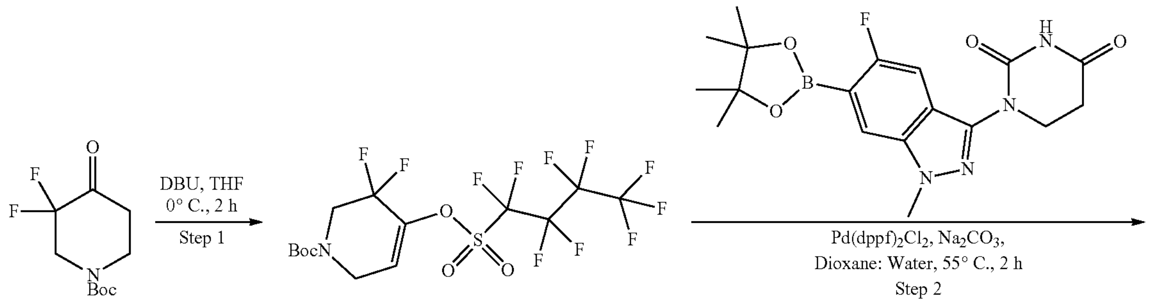
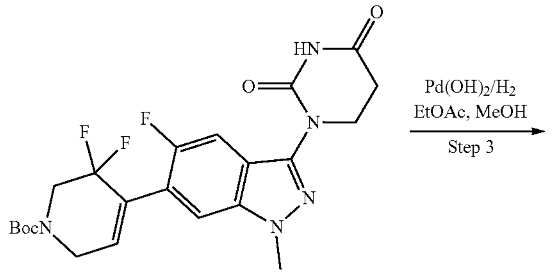
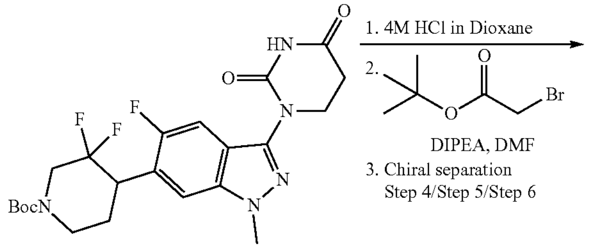

-continued

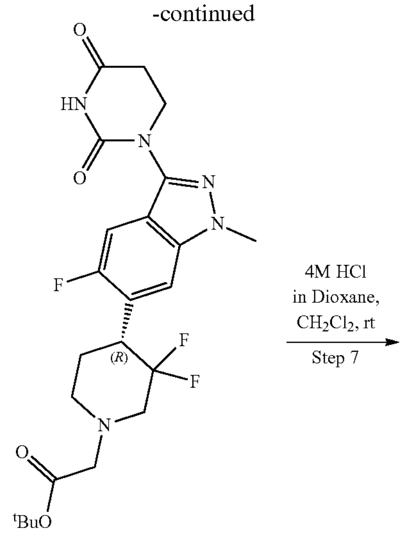

First eluted isomer

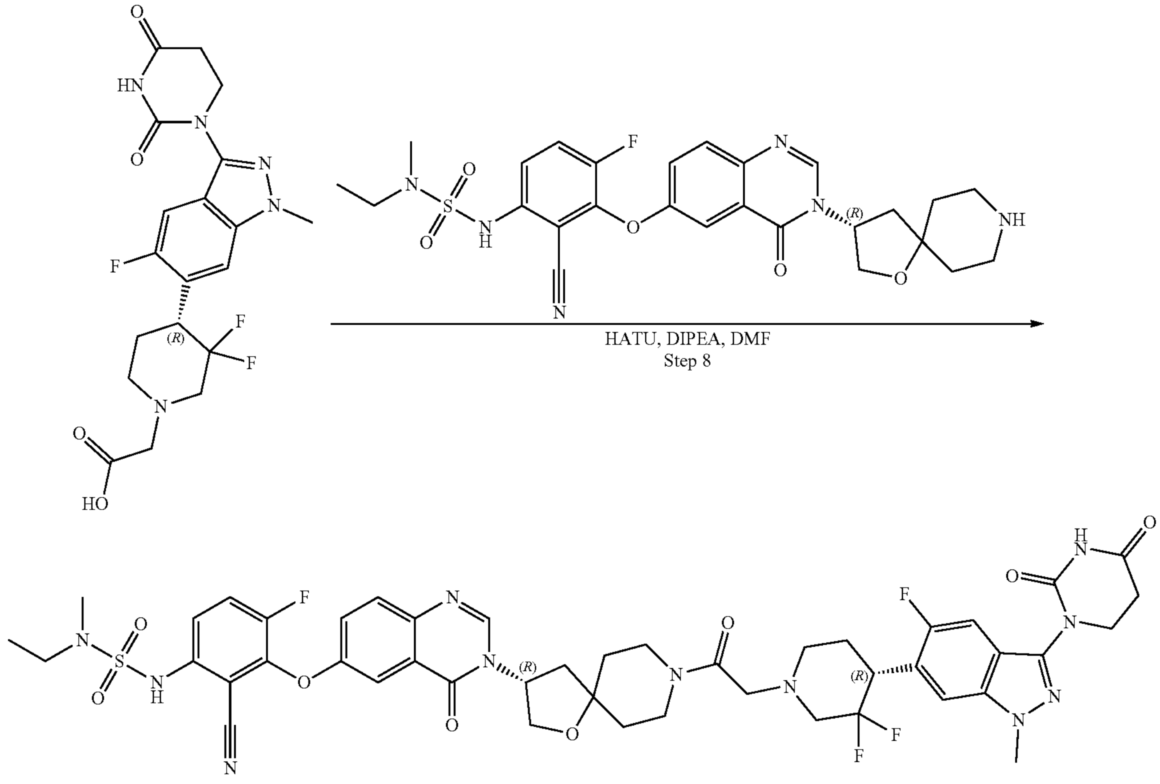

Step 1: To stirred a solution of tert-butyl 3,3-difluoro-4-oxo-piperidine-1-carboxylate (3 g, 12.75 mmol) in THF (50 mL) at −10° C. was added 1,8-diazabicyclo[5.4.0]undec-7-ene (5.82 g, 38.26 mmol, 5.71 mL) followed by a slow addition of a solution of 1,1,2,2,3,3,4,4,4-nonafluorobutane-1-sulfonyl fluoride (7.71 g, 25.51 mmol, 4.40 mL) in THF (40 mL). The reaction mixture was stirred at RT for 1 h. After completion, the reaction mixture was added with water (50 ml) and extracted with ethyl acetate (2×100 mL). The combined organic layers were washed with brine solution, dried over anhydrous sodium sulfate, filtered and concentrated under reduced pressure to afford crude product. Crude mixture was purified by silica gel column chromatography using 0-40% ethyl acetate in petroleum ether as eluents to afford tert-butyl 3,3-difluoro-4-(1,1,2,2,3,3,4,4,4-nonafluorobutylsulfonyloxy)-2,6-dihydropyridine-1-carboxylate (1.5 g, 2.87 mmol, 23% yield) as a colourless oil. $^1$H-NMR (400 MHz, DMSO-$d_6$): δ=6.60 (s, 1H), 4.29 (d, J=4.00 Hz, 2H), 4.05 (t, J=11.20 Hz, 2H), 1.51 (s, 9H).

Step 2: To a stirred solution of 1-[5-fluoro-1-methyl-6-(4,4,5,5-tetramethyl-1,3,2-dioxaborolan-2-yl)indazol-3-yl]hexahydropyrimidine-2,4-dione (500 mg, 1.29 mmol) and tert-butyl 3,3-difluoro-4-(1,1,2,2,3,3,4,4,4-nonafluorobutylsulfonyloxy)-2,6-dihydropyridine-1-carboxylate (732.92 mg, 1.42 mmol) in dioxane (8 ml) was added sodium carbonate (409.54 mg, 3.86 mmol, 161.75 μL) in water (2 ml). The resulting reaction mixture was degassed with nitrogen for 10 minutes, and [1,1'-bis(diphenylphosphino)

ferrocene]dichloropalladium (II), complex with dichloromethane (105.10 mg, 128.80 μmol) was added. The reaction mixture was heated to 60° C. for 2 h. After completion, the reaction mixture was cooled to room temperature and diluted with water (30 mL) and then extracted with ethyl acetate (2×50 mL). The combined organic layers were dried over anhydrous sodium sulfate and concentrated under reduced pressure to afford crude. The crude mixture was purified by silica gel column chromatography eluting from 0-100% ethyl acetate in petroleum ether to afford tert-butyl 4-[3-(2,4-dioxohexahydropyrimidin-1-yl)-5-fluoro-1-methyl-indazol-6-yl]-3,3-difluoro-2,6-dihydropyridine-1-carboxylate (180 mg, 302.97 μmol, 24% yield) as a yellow solid. LCMS m/z (ESI+): 480.6 $[M+H]^+$.

Step 3: To a solution of tert-butyl 4-[3-(2,4-dioxohexahydropyrimidin-1-yl)-5-fluoro-1-methyl-indazol-6-yl]-3,3-difluoro-2,6-dihydropyridine-1-carboxylate (180 mg, 375.43 μmol) in mixture of ethanol/ethyl acetate (1:2) in a 100 mL of tiny clave glass vessel was added palladium hydroxide on carbon, 20 wt. % (60 mg, 427.24 μmol) under nitrogen. The mixture was stirred under pressure of 5 $kg/cm^3$ at room temperature for 16 h. After completion of the reaction, the reaction mixture was filtered through celite bed and washed with 10% methanol in dichloromethane (100 mL), and the filtrate was concentrated under reduced pressure to afford tert-butyl 4-[3-(2,4-dioxohexahydropyrimidin-1-yl)-5-fluoro-1-methyl-indazol-6-yl]-3,3-difluoro-piperidine-1-carboxylate (170 mg, 340.62 μmol, 91% yield) as an off-white solid. LCMS m/z (ESI): 426.2 $[M-^tBu+H]^+$.

Step 4: To a stirred solution of tert-butyl 4-[3-(2,4-dioxohexahydropyrimidin-1-yl)-5-fluoro-1-methyl-indazol-6-yl]-3,3-difluoro-piperidine-1-carboxylate (70 mg, 145.39 μmol) in DCM (10 mL) was added hydrogen chloride, 4M in 1,4-dioxane (1 mL) at 0° C., the resulting reaction mixture was stirred at room temperature for 4 h. After completion of the reaction, the reaction mixture was concentrated under vacuum and washed with diethyl ether to give product 1-[6-(3,3-difluoro-4-piperidyl)-5-fluoro-1-methyl-indazol-3-yl]hexahydropyrimidine-2,4-dione (60 mg, 119.77 μmol, 82% yield) as an off-white solid. LCMS m/z (ESI+): 382.2 $[M+H]^+$.

Step 5: To a stirred solution of 1-[6-(3,3-difluoro-4-piperidyl)-5-fluoro-1-methyl-indazol-3-yl]hexahydropyrimidine-2,4-dione (60 mg, 157.34 μmol) in N,N-dimethylformamide (2 mL) was added N,N-diisopropylethylamine (61.00 mg, 472.01 μmol, 82.21 L) followed by tert-butyl bromoacetate (33.76 mg, 173.07 μmol, 25.38 μL) at 0° C. under nitrogen atmosphere. The reaction mixture was allowed to stir at room temperature for 16 h. After completion, the reaction mixture was added ice-cold water (5 mL) and extracted using ethyl acetate (2×20 mL). The combined organic layers were concentrated under reduced pressure. The obtained crude product was purified using reverse phase HPLC while eluting with 0-50% acetonitrile in 0.1% formic acid in water to afford tert-butyl 2-[4-[3-(2,4-dioxohexahydropyrimidin-1-yl)-5-fluoro-1-methyl-indazol-6-yl]-3,3-difluoro-1-piperidyl]acetate (40 mg, 80.49 μmol, 51% yield) as an off-white solid. LCMS m/z (ESI+): 496.2 $[M+H]^+$.

Step 6: The racemic compound tert-butyl 2-[4-[3-(2,4-dioxohexahydropyrimidin-1-yl)-5-fluoro-1-methyl-indazol-6-yl]-3,3-difluoro-1-piperidyl]acetate (40 mg, 80.73 μmol) was chirally resoluted by chiral SFC (column: YMC Cellulose-SC; mobile phase: $CO_2$:IPA (40:60); flow rate: 5 ml/min; back pressure: 100 bar; wavelength: 210 nm) to afford peak 1 (first eluted) tert-butyl 2-[(4R)-4-[3-(2,4-dioxohexahydropyrimidin-1-yl)-5-fluoro-1-methyl-indazol-6-yl]-3,3-difluoro-1-piperidyl]acetate (14 mg, 27.49 μmol, 34% yield, 100% ee, arbitrarily assigned as R-enantiomer) as an off-white solid and peak 2 (second eluted) tert-butyl 2-[(4S)-4-[3-(2,4-dioxohexahydropyrimidin-1-yl)-5-fluoro-1-methyl-indazol-6-yl]-3,3-difluoro-1-piperidyl]acetate (13 mg, 25.83 μmol, 32% yield, 100% ee, arbitrarily assigned S-enantiomer) as an off-white solid.

Step 7: To a stirred solution of tert-butyl 2-[(4R)-4-[3-(2,4-dioxohexahydropyrimidin-1-yl)-5-fluoro-1-methyl-indazol-6-yl]-3,3-difluoro-1-piperidyl]acetate (14 mg, 28.25 μmol) in dichloromethane (2 mL) was added hydrogen chloride solution 4.0M in dioxane (4 M, 105.95 μL) dropwise at 0° C. and the reaction mixture was further stirred at rt for 16 h. After completion of the reaction, the reaction mixture was concentrated and co-distilled with 10 ml of dichloromethane under reduced pressure to give 2-[(4R)-4-[3-(2,4-dioxohexahydropyrimidin-1-yl)-5-fluoro-1-methyl-indazol-6-yl]-3,3-difluoro-1-piperidyl]acetic acid (12 mg, 26.63 μmol, 94% yield) as an off-white solid. LCMS m/z (ESI+): 438.1 $[M-H]^-$.

Step 8: Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (15.21 mg, 27.32 μmol) and 2-[(4R)-4-[3-(2,4-dioxohexahydropyrimidin-1-yl)-5-fluoro-1-methyl-indazol-6-yl]-3,3-difluoro-1-piperidyl]acetic acid (13.00 mg, 27.32 μmol), N,N-diisopropylethylamine (10.59 mg, 81.96 μmol, 14.28 μL) and HATU (15.58 mg, 40.98 μmol). The crude compound was purified by reverse phase column chromatography eluted with 50% acetonitrile in 0.1% formic acid in water to afford (3R)-3-[6-[2-cyano-3-[[ethyl(methyl)sulfamoyl]amino]-6-fluoro-phenoxy]-4-oxo-quinazolin-3-yl]-8-[2-[(4R)-4-[3-(2,4-dioxohexahydropyrimidin-1-yl)-5-fluoro-1-methyl-indazol-6-yl]-3,3-difluoro-1-piperidyl]acetyl]-1-oxa-8-azaspiro[4.5]decane (7 mg, 7.05 μmol, 26% yield) as an off-white solid. LCMS m/z (ESI): 978.2 $[M+H]^+$. $^1H$-NMR (400 MHz, DMSO-$d_6$): δ=10.59 (s, 1H), 10.10 (s, 1H), 8.36 (d, J=4.80 Hz, 1H), 7.79 (d, J=8.80 Hz, 1H), 7.68 (t, J=2.40 Hz, 2H), 7.43 (d, J=10.40 Hz, 2H), 7.36 (s, 1H), 5.31 (s, 1H), 4.20-4.10 (m, 2H), 4.03 (d, J=7.20 Hz, 3H), 3.92 (t, J=6.80 Hz, 2H), 3.69-3.34 (m, 6H), 3.40-3.20 (m, 4H), 3.10 (d, J=6.80 Hz, 2H), 3.01 (d, J=9.60 Hz, 1H), 2.80-2.60 (m, 4H), 2.40 (m, 4H), 2.40-2.00 (m, 1H), 1.90-1.80 (m, 2H), 1.68 (d, J=9.20 Hz, 3H), 1.06 (t, J=Hz, 3H).

Example 204
(3R)-3-[6-[2-cyano-3-[[ethyl(methyl)sulfamoyl]amino]-6-fluorophenoxy]-4-oxoquinazolin-3-yl]-8-[2-[(4S)-4-[3-(2,4-dioxo-1,3-diazinan-1-yl)-5-fluoro-1-methylindazol-6-yl]-3,3-difluoropiperidin-1-yl]acetyl]-1-oxa-8-azaspiro[4.5]decane
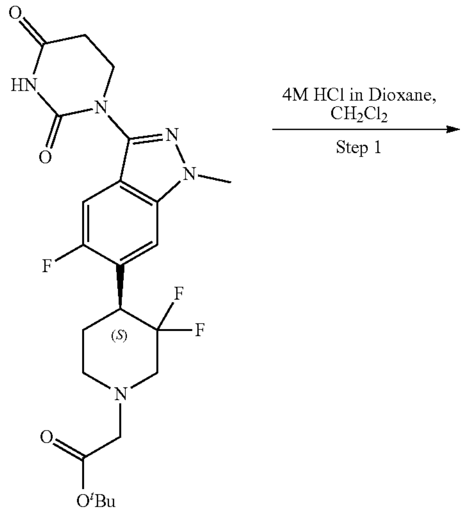
Second Eluted Isomer
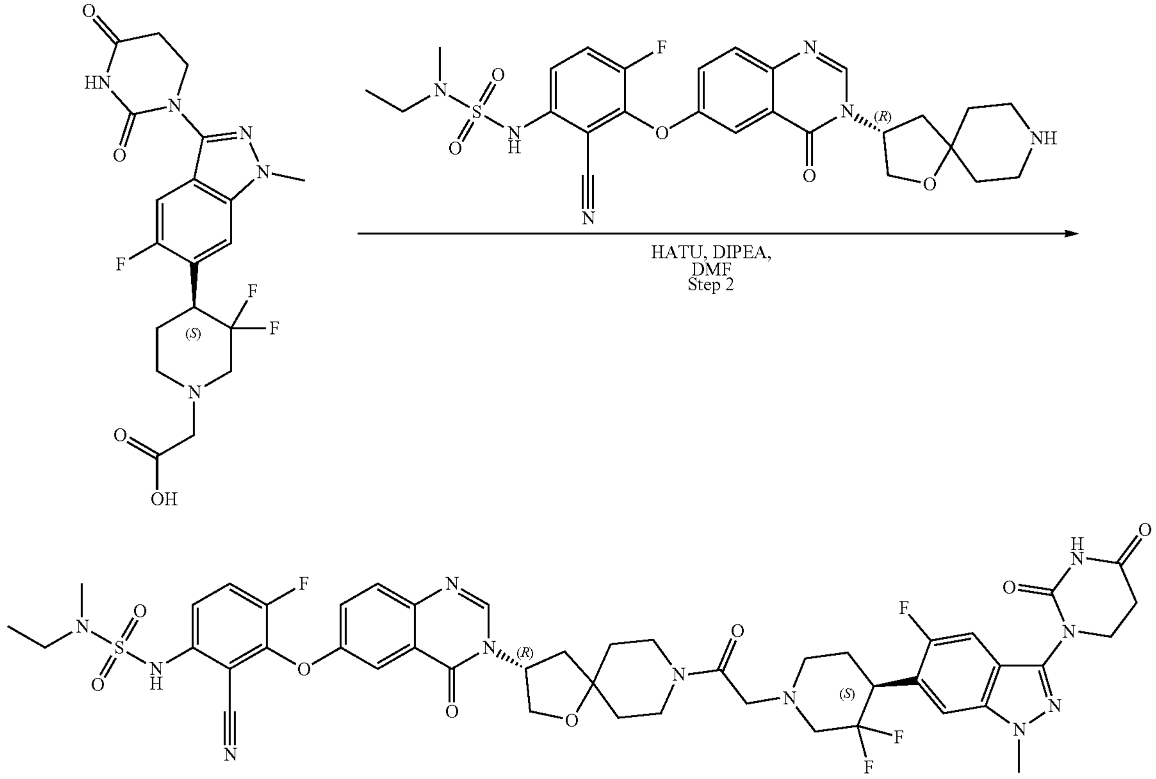

Step 1: To a stirred solution of tert-butyl 2-[(4S)-4-[3-(2,4-dioxohexahydropyrimidin-1-yl)-5-fluoro-1-methyl-indazol-6-yl]-3,3-difluoro-1-piperidyl]acetate (12 mg, 24.22 μmol, 000) in dichloromethane (2 mL) was added hydrogen chloride solution 4.0M in dioxane (4 M, 90.82 μL) dropwise at 0° C. and the reaction was further stirred at rt for 16 h. After completion of the reaction, reaction mixture was concentrated and co-distilled with 10 ml of dichloromethane under reduced pressure to give 2-[(4S)-4-[3-(2,4-dioxohexahydropyrimidin-1-yl)-5-fluoro-1-methyl-indazol-6-yl]-3,3-difluoro-1-piperidyl]acetic acid (11 mg, 21.82 μmol, 90% yield) as an off-white solid. LCMS m/z (ESI+): 438.2 $[M-H]^-$.

Step 2: Target compound was prepared via HATU mediated acid-amine coupling reaction (Procedure B-E). Amide coupling was carried out using (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (12.87 mg, 23.12 μmol) and 2-[(4S)-4-[3-(2,4-dioxohexahydropyrimidin-1-yl)-5-fluoro-1-methyl-indazol-6-yl]-3,3-difluoro-1-piperidyl]acetic acid (11 mg, 23.12 μmol), N,N-diisopropylethylamine (8.96 mg, 69.35 μmol, 12.08 μL) and HATU (13.18 mg, 34.67 μmol). The crude compound was purified by reverse phase column chromatography eluted with 50% acetonitrile in 0.1% formic acid in water to afford (3R)-3-[6-[2-cyano-3-[[ethyl(methyl)sulfamoyl]amino]-6-fluoro-phenoxy]-4-oxo-quinazolin-3-yl]-8-[2-[(4S)-4-[3-(2,4-dioxohexahydropyrimidin-1-yl)-5-fluoro-1-methyl-indazol-6-yl]-3,3-difluoro-1-piperidyl]acetyl]-1-oxa-8-azaspiro[4.5]decane (7 mg, 6.86 μmol, 30% yield) as an off-white solid. LCMS m/z (ESI): 978.2 $[M+H]^+$. $^1$H-NMR (400 MHz, DMSO-$d_6$): δ=10.59 (s, 1H), 10.21 (s, 1H), 8.36 (d, J=6.40 Hz, 1H), 7.79 (d, J=9.20 Hz, 1H), 7.68 (t, J=−7.60 Hz, 2H), 7.43 (d, J=10.40 Hz, 2H), 7.36 (s, 1H), 5.32 (s, 1H), 4.20-4.10 (m, 2H), 4.03 (d, J=6.40 Hz, 3H), 3.92 (t, J=6.40 Hz, 2H), 3.69-3.34 (m, 6H), 3.40-3.20 (m, 4H), 3.45 (d, J=361.20 Hz, 1H), 3.01 (d, J=9.60 Hz, 1H), 2.80-2.60 (m, 6H), 2.40 (m, 4H), 2.10-2.06 (m, 1H), 1.80-1.60 (m, 4H), 1.05 (t, J=7.20 Hz, 3H).

Example 205

(3R)-8-[2-[1-[5-chloro-3-(2,4-dioxohexahydropyrimidin-1-yl)-1-methyl-indazol-6-yl]-4-hydroxy-4-piperidyl]acetyl]-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane

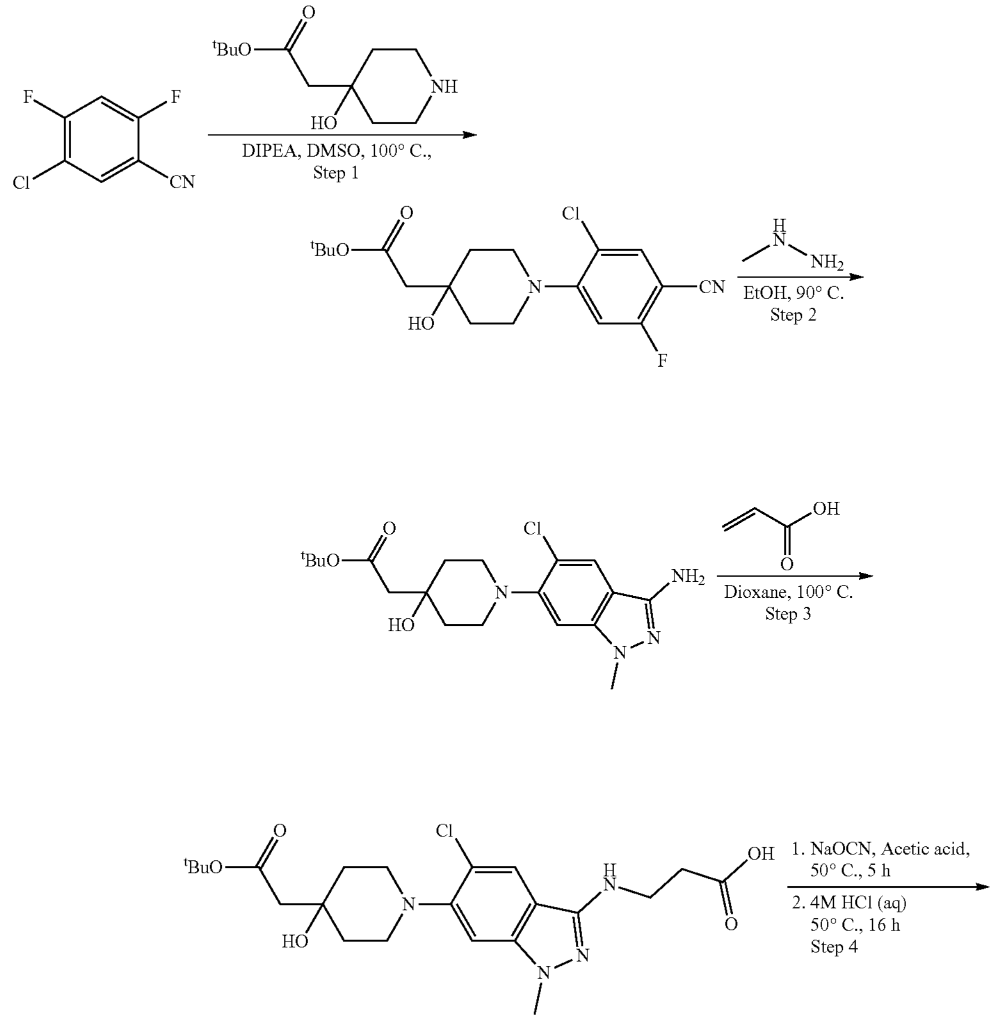

-continued

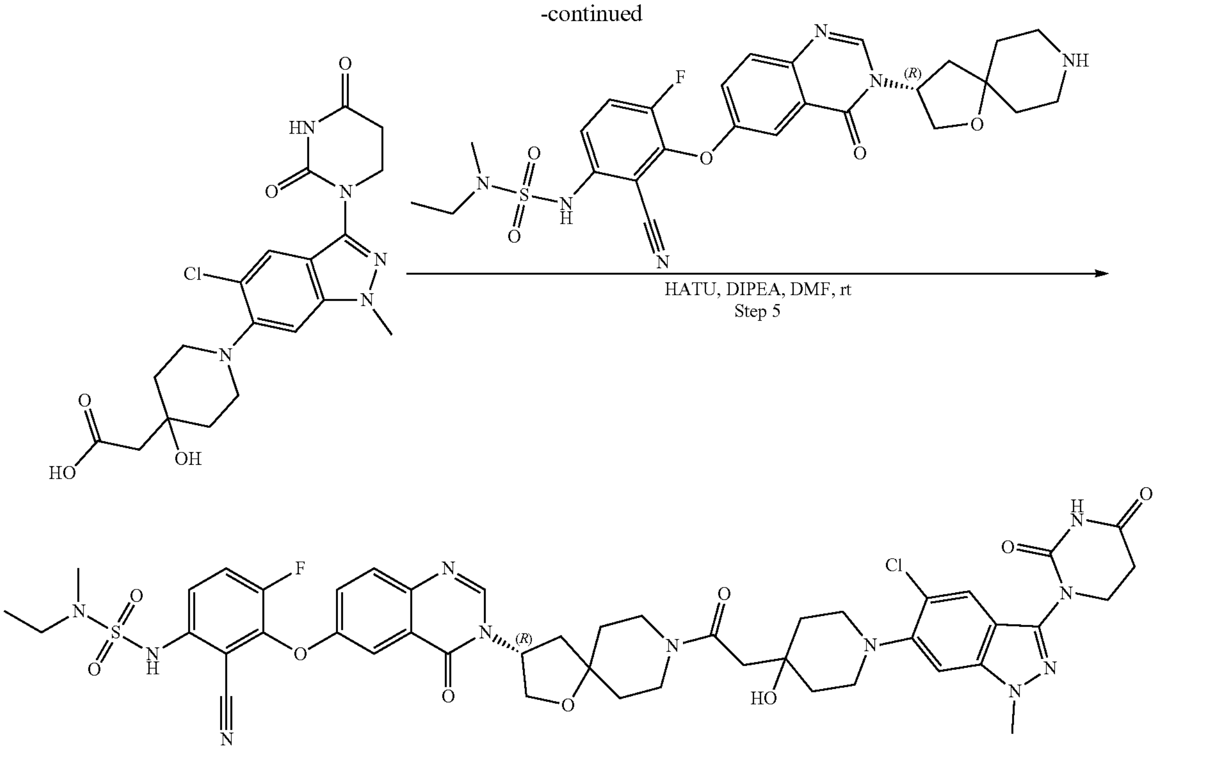

Step 1: To stirred a solution of tert-butyl 2-(4-hydroxy-4-piperidyl)acetate (1.24 g, 5.76 mmol) in dimethyl sulfoxide (10 mL) were added N,N-diisopropylethylamine (2.23 g, 17.29 mmol, 3.01 mL) and 5-chloro-2,4-difluoro-benzonitrile (1 g, 5.76 mmol) at room temperature. The reaction mixture was stirred at 100° C. for 2 hours. After completion, the reaction mixture was diluted with water and extracted with ethyl acetate (2×50 mL). The organic phase was dried over sodium sulfate, filtered and concentrated under reduced pressure to get crude which was purified by silica gel column chromatography using 0-20% ethyl acetate in petroleum ether as eluents to afford tert-butyl 2-[1-(2-chloro-4-cyano-5-fluoro-phenyl)-4-hydroxy-4-piperidyl]acetate (1.1 g, 2.93 mmol, 51% yield) as a white solid. LCMS: m/z 369.2 $[M+H]^+$.

Step 2: To a stirred solution of tert-butyl 2-[1-(2-chloro-4-cyano-5-fluoro-phenyl)-4-hydroxy-4-piperidyl]acetate (1 g, 2.71 mmol) in ethanol (10 mL) was added methyl hydrazine (374.73 mg, 8.13 mmol) at room temperature. The resulting reaction mixture was stirred at 90° C. for 24 h. After completion, the reaction solvent was removed by concentration under reduced pressure to get crude product, which was purified by silica gel flash column chromatography using 0-80% ethyl acetate in petroleum ether as eluents to afford tert-butyl 2-[1-(3-amino-5-chloro-1-methyl-indazol-6-yl)-4-hydroxy-4-piperidyl]acetate (580 mg, 1.39 mmol, 51% yield) as a pale yellow solid. LCMS ($ES^+$): m/z 395.2 $[M+H]^+$.

Step 3: To a solution of tert-butyl 2-[1-(3-amino-5-chloro-1-methyl-indazol-6-yl)-4-hydroxy-4-piperidyl]acetate (520 mg, 1.32 mmol) in 1,4-dioxane (6 mL) were added acrylic acid (189.78 mg, 2.63 mmol, 180.57 μL) at room temperature. The resulting mixture was stirred at 100° C. for 36 h. After 36 h, reaction mixture was basified with aq. sodium bicarbonate and extracted with ethyl acetate. The aqueous layer was further acidified with aq. 1.5N HCl and compound was extracted using ethyl acetate. The organic layer was dried over anhydrous sodium sulfate, filtered and concentrated under reduced pressure to afford 3-[[6-[4-(2-tert-butoxy-2-oxo-ethyl)-4-hydroxy-1-piperidyl]-5-chloro-1-methyl-indazol-3-yl]amino]propanoic acid (300 mg, 501.12 μmol, 38% yield) as an off-white solid. LCMS: m/z 467.3 $[M+H]^+$.

Step 4: To a stirred solution of 3-[[6-[4-(2-tert-butoxy-2-oxo-ethyl)-4-hydroxy-1-piperidyl]-5-chloro-1-methyl-indazol-3-yl]amino]propanoic acid (300 mg, 424.02 μmol) in acetic acid (4.05 mL) was added sodium cyanate (137.82 mg, 2.12 mmol, 72.92 μL) at room temperature and under nitrogen atmosphere. The resulting mixture was stirred at 50° C. for 5 h in a sealed tube. After completion, the crude mixture was concentrated and aqueous HCl (4M) solution was added and continued heating at 50° C. for 12 h. The crude reaction mixture was then concentrated and purified using reverse phase column chromatography using 48% acetonitrile in 0.1% formic acid in water to afford 2-[1-[5-chloro-3-(2,4-dioxohexahydropyrimidin-1-yl)-1-methyl-indazol-6-yl]-4-hydroxy-4-piperidyl]acetic acid (170 mg, 331.13 μmol, 78% yield) as an off-white solid. LCMS (ESI): m/z 436.10 $[M+H]^+$.

Step 5: Target compound was prepared via HATU mediated acid-amine coupling reaction (Procedure B-E). Amide coupling was carried out using 2-[1-[5-chloro-3-(2,4-dioxohexahydropyrimidin-1-yl)-1-methyl-indazol-6-yl]-4-hydroxy-4-piperidyl]acetic acid (80 mg, 166.01 μmol) and (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (98.46 mg, 166.01 μmol), N,N-diisopropylethylamine (107.28 mg, 830.07 μmol, 144.58 μL) and HATU (82.06 mg, 215.82 μmol). The crude compound was purified by reverse phase column chromatography eluted with 50% acetonitrile in 0.1% formic acid in water to afford (3R)-8-[2-[1-[5-chloro-3-(2,4-dioxohexahydropyrimidin-1-yl)-1-methyl-indazol-6-yl]-4-hydroxy-4-piperidyl]acetyl]-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (11 mg, 10.73 μmol, 6% yield) as an off-white solid. LCMS (ESI+): m/z 974.0. $[M+H]^+$. $^1$H-NMR (400 MHz, DMSO-$d_6$): δ=10.54 (s, 1H), 8.35 (s, 1H), 7.77 (d, J=8.80 Hz, 1H), 7.72 (s, 1H), 7.65 (dd, J=3.20, 8.60 Hz, 2H), 7.36 (d, J=2.80 Hz, 2H), 5.41-5.31 (m, 1H), 5.06 (d, J=2.40 Hz, 1H), 4.21-4.11 (m, 2H), 3.96 (s, 3H), 3.92-3.89 (m, 2H), 3.81-3.72 (m, 1H), 3.68-3.50 (m, 2H), 3.12-3.01 (m, 7H), 3.79-3.70 (m, 2H), 2.65-2.50 (m, 4H), 2.49-2.34 (m, 2H), 2.11-2.01 (m, 1H), 1.90-1.50 (m, 9H), 1.04 (t, J=7.20 Hz, 3H).

Example 206

(3R)-3-[6-[2-cyano-3-[[ethyl(methyl)sulfamoyl]amino]-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1,1-dioxo-1lambda6-thia-8-azaspiro[4.5]decane

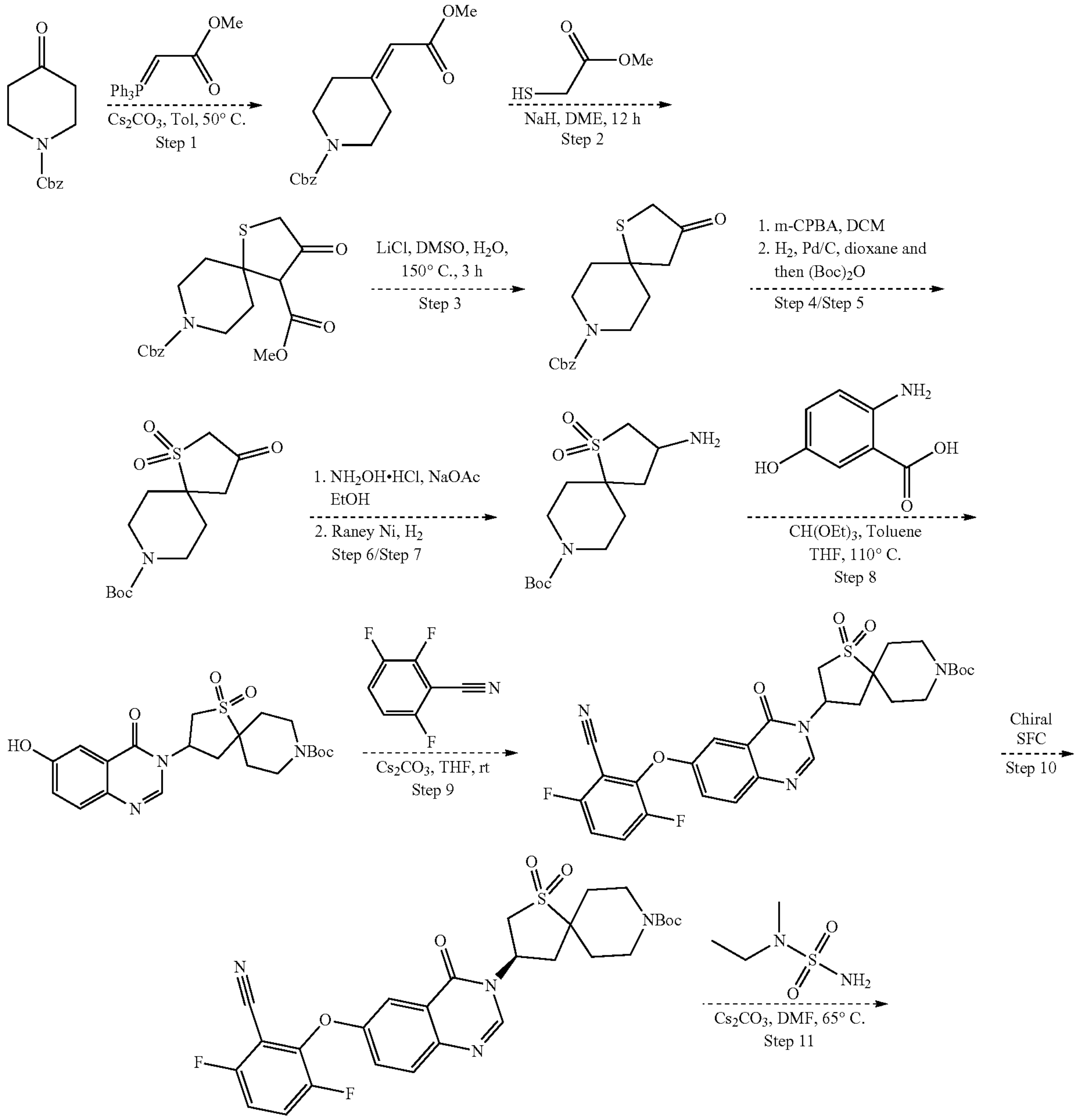

-continued

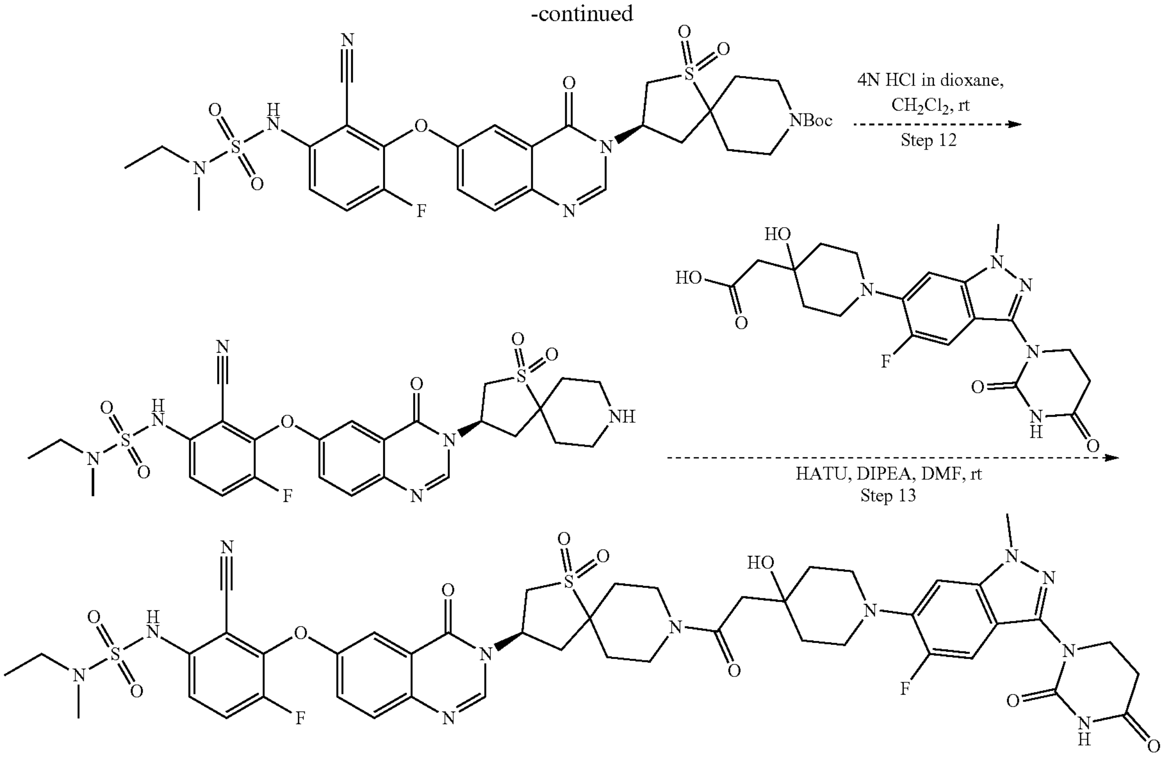

Step 1: To a solution of benzyl 4-oxopiperidine-1-carboxylate (1 equiv.) in toluene is added cesium carbonate (2 equiv.) and methyl 2-(triphenyl-phosphanylidene)acetate (1 equiv.) at room temperature under nitrogen atmosphere. The reaction mixture is stirred at 60° C. for 10 hours. Upon completion of the reaction as confirmed by LC-MS, a workup is performed and the crude product is purified by column chromatography to afford benzyl 4-(2-methoxy-2-oxo-ethylidene)piperidine-1-carboxylate.

Step 2: To a solution of benzyl 4-(2-methoxy-2-oxo-ethylidene)piperidine-1-carboxylate (500 mg, 1.73 mmol) in DME (21.58 mL) is added sodium hydride (60% dispersion in mineral oil) (1 equiv.) at room temperature. This is followed by the addition of methyl 2-sulfanylacetate (1.5 equiv.) at −10° C. under nitrogen atmosphere. The reaction mixture is stirred at 60° C. for 12 hours while monitoring by LC-MS. Upon completion of the reaction, a workup is performed and the crude product is purified by column chromatography to afford 08-benzyl 04-methyl 3-oxo-1-thia-8-azaspiro[4.5]decane-4,8-dicarboxylate.

Step 3: A solution of 08-benzyl 04-methyl 3-oxo-1-thia-8-azaspiro[4.5]decane-4,8-dicarboxylate (1 equiv.) in DMSO is added lithium chloride (3 equiv.) in water. The reaction mixture is heated at 150° C. for 3 hours while monitoring by LC-MS. After the reaction is complete, a workup is performed and the crude product is purified by column chromatography to afford benzyl 3-oxo-1-thia-8-azaspiro[4.5]decane-8-carboxylate.

Step 4: To a solution of benzyl 3-oxo-1-thia-8-azaspiro[4.5]decane-8-carboxylate (1 equiv.) in DCM is added 3-chlorobenzenecarboperoxoic acid (3 equiv.) at 0° C. under nitrogen atmosphere. The reaction mixture is stirred at room temperature for 12 hours. After completion of the reaction as confirmed by LC-MS, the reaction mixture is quenched with ammonium chloride solution and extracted with ethyl acetate. The organic layer is washed with brine, dried over anhydrous sodium sulfate, and concentrated in vacuo. The crude product is purified by column chromatography to afford benzyl 1,1,3-trioxo-1thia-8-azaspiro[4.5]decane-8-carboxylate.

Step 5: To a solution of benzyl 1,1,3-trioxo-1thia-8-azaspiro[4.5]decane-8-carboxylate (1 equiv.) in dioxane is added di-tert-butyl decarbonate (1 equiv.). The solution is purged with argon before the addition of 10% palladium on carbon (2.5 equiv.). The reaction mixture is then stirred under hydrogen atmosphere at room temperature overnight. After completion of the reaction as confirmed by LC-MS, the reaction mixture is filtered through a pad of celite, washed with ethyl acetate and concentrated in vacuo. The residue is purified by silica gel column chromatography to afford tert-butyl 1,1,3-trioxo-1thia-8-azaspiro[4.5]decane-8-carboxylate.

Step 6: To a solution of tert-butyl 1,1,3-trioxo-1thia-8-azaspiro[4.5]decane-8-carboxylate (1 equiv.) in ethanol are added hydroxylamine; hydrochloride (1.5 equiv.) and sodium acetate (3 equiv.). The reaction mixture is heated at 65° C. for 6 hours. After completion of the reaction as confirmed by LC-MS, the reaction mixture is cooled to room temperature and concentrated in vacuo. Water is then added to the residue and the resulting solid is filtered and dried under vacuum to afford tert-butyl (3Z)-3-hydroxyimino-1,1-dioxo-1thia-8-azaspiro[4.5]decane-8-carboxylate.

Step 7: A solution of tert-butyl (3Z)-3-hydroxyimino-1,1-dioxo-1thia-8-azaspiro[4.5]decane-8-carboxylate (1 equiv.) and Raney Nickel (6 equiv.) in ethanol is stirred under hydrogen atmosphere for 16 hours at room temperature. Upon completion of the reaction as confirmed by LC-MS, the reaction mixture is filtered through a pad of celite, which is washed with ethanol. The combined organic layer is then concentrated in vacuo to afford tert-butyl 3-amino-1,1-dioxo-1thia-8-azaspiro[4.5]decane-8-carboxylate.

Step 8: To a solution of 2-amino-5-hydroxy-benzoic acid (1 equiv.) in toluene:tetrahydrofuran (5:1) is added anhydrous triethyl orthoformate (2 equiv.) at room temperature followed by tert-butyl 3-amino-1,1-dioxo-1thia-8-azaspiro [4.5]decane-8-carboxylate (1 equiv.). The resulting reaction mixture is heated at 110° C. for 18 hours in a sealed tube. After completion of the reaction as confirmed by LC-MS, the reaction mixture is cooled to room temperature and a workup is performed. The crude product is purified by silica gel column chromatography to afford tert-butyl 3-(6-hydroxy-4-oxo-quinazolin-3-yl)-1,1-dioxo-1thia-8-azaspiro [4.5]decane-8-carboxylate.

Step 9: To a stirred solution of tert-butyl 3-(6-hydroxy-4-oxo-quinazolin-3-yl)-1,1-dioxo-1thia-8-azaspiro[4.5]decane-8-carboxylate (1 equiv.) in THF is added cesium carbonate (1.1 equiv.) and 2,3,6-trifluorobenzonitrile (1.1 equiv.) at room temperature. The resulting reaction mixture is stirred at room temperature for 16 hours. After completion of the reaction as confirmed by LC-MS, a workup is performed and the crude product is purified by silica gel column chromatography to afford tert-butyl 3-[6-(2-cyano-3,6-difluoro-phenoxy)-4-oxo-quinazolin-3-yl]-1,1-dioxo-1thia-8-azaspiro[4.5]decane-8-carboxylate.

Step 10: The racemic compound tert-butyl 3-[6-(2-cyano-3,6-difluoro-phenoxy)-4-oxo-quinazolin-3-yl]-1,1-dioxo-1thia-8-azaspiro[4.5]decane-8-carboxylate is resolved by chiral SFC purification to afford tert-butyl (3R)-3-[6-(2-cyano-3,6-difluoro-phenoxy)-4-oxo-quinazolin-3-yl]-1,1-dioxo-1thia-8-azaspiro[4.5]decane-8-carboxylate.

Step 11: A solution of tert-butyl (3R)-3-[6-(2-cyano-3,6-difluoro-phenoxy)-4-oxo-quinazolin-3-yl]-1,1-dioxo-1thia-8-azaspiro[4.5]decane-8-carboxylate (1 equiv.) in N,N-dimethylformamide is added cesium carbonate (2.5 equiv.) and [methyl(sulfamoyl)amino]ethane (2 equiv.) at room temperature. The resulting reaction mixture is stirred at 65° C. for 16 hours. After completion of the reaction as confirmed by LC-MS, a workup is performed, and the crude product is purified by silica gel column chromatography to afford tert-butyl (3R)-3-[6-[2-cyano-3-[[ethyl(methyl)sulfamoyl]amino]-6-fluoro-phenoxy]-4-oxo-quinazolin-3-yl]-1,1-dioxo-1thia-8-azaspiro[4.5]decane-8-carboxylate.

Step 12: A solution of tert-butyl (3R)-3-[6-[2-cyano-3-[[ethyl(methyl)sulfamoyl]amino]-6-fluoro-phenoxy]-4-oxo-quinazolin-3-yl]-1,1-dioxo-1thia-8-azaspiro[4.5]decane-8-carboxylate (1 equiv.) in dichloromethane is added 4 N HCl in dioxane (10 equiv.) at 0° C. The resulting reaction mixture is stirred at room temperature for 2 hours. Upon completion of the reaction as confirmed by LC-MS, the reaction is concentrated in vacuo and purified by silica gel column chromatography to afford (3R)-3-[6-[2-cyano-3-[[ethyl (methyl)sulfamoyl]amino]-6-fluoro-phenoxy]-4-oxo-quinazolin-3-yl]-1,1-dioxo-1thia-8-azaspiro[4.5]decane.

Step 13: To a solution of 2-[1-[3-(2,4-dioxohexahydropyrimidin-1-yl)-5-fluoro-1-methyl-indazol-6-yl]-4-hydroxy-4-piperidyl]acetic acid (1 equiv.) and (3R)-3-[6-[2-cyano-3-[[ethyl(methyl)sulfamoyl]amino]-6-fluoro-phenoxy]-4-oxo-quinazolin-3-yl]-1,1-dioxo-1thia-8-azaspiro[4.5]decane (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, the crude mixture is purified by reverse phase HPLC to afford the target compound (3R)-3-[6-[2-cyano-3-[[ethyl(methyl)sulfamoyl]amino]-6-fluorophenoxy]-4-oxo-quinazolin-3-yl]-8-[2-[1-[3-(2,4-dioxo-1,3-diazinan-1-yl)-5-fluoro-1-methylindazol-6-yl]-4-hydroxypiperidin-4-yl] acetyl]-1,1-dioxo-1lambda6-thia-8-azaspiro[4.5]decane.

Example 207

6-[2-cyano-3-[[ethyl(methyl)sulfamoyl]amino]-6-fluoro-phenoxy]-3-[(3R)-8-[[1-[3-(2,4-dioxohexahydropyrimidin-1-yl)-5-fluoro-1-methyl-indazol-6-yl]-4-hydroxy-4-piperidyl]methylsulfonyl]-1-oxaspiro [4.5]decan-3-yl]-4-oxo-quinazoline

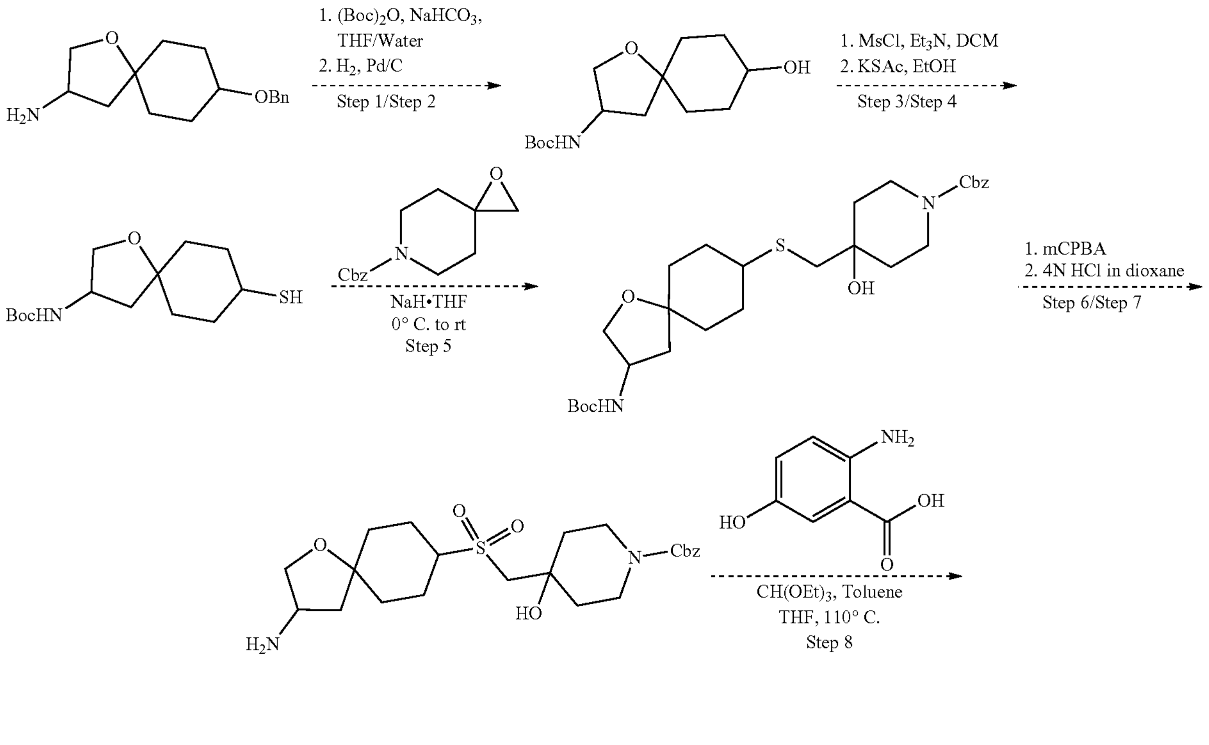

-continued
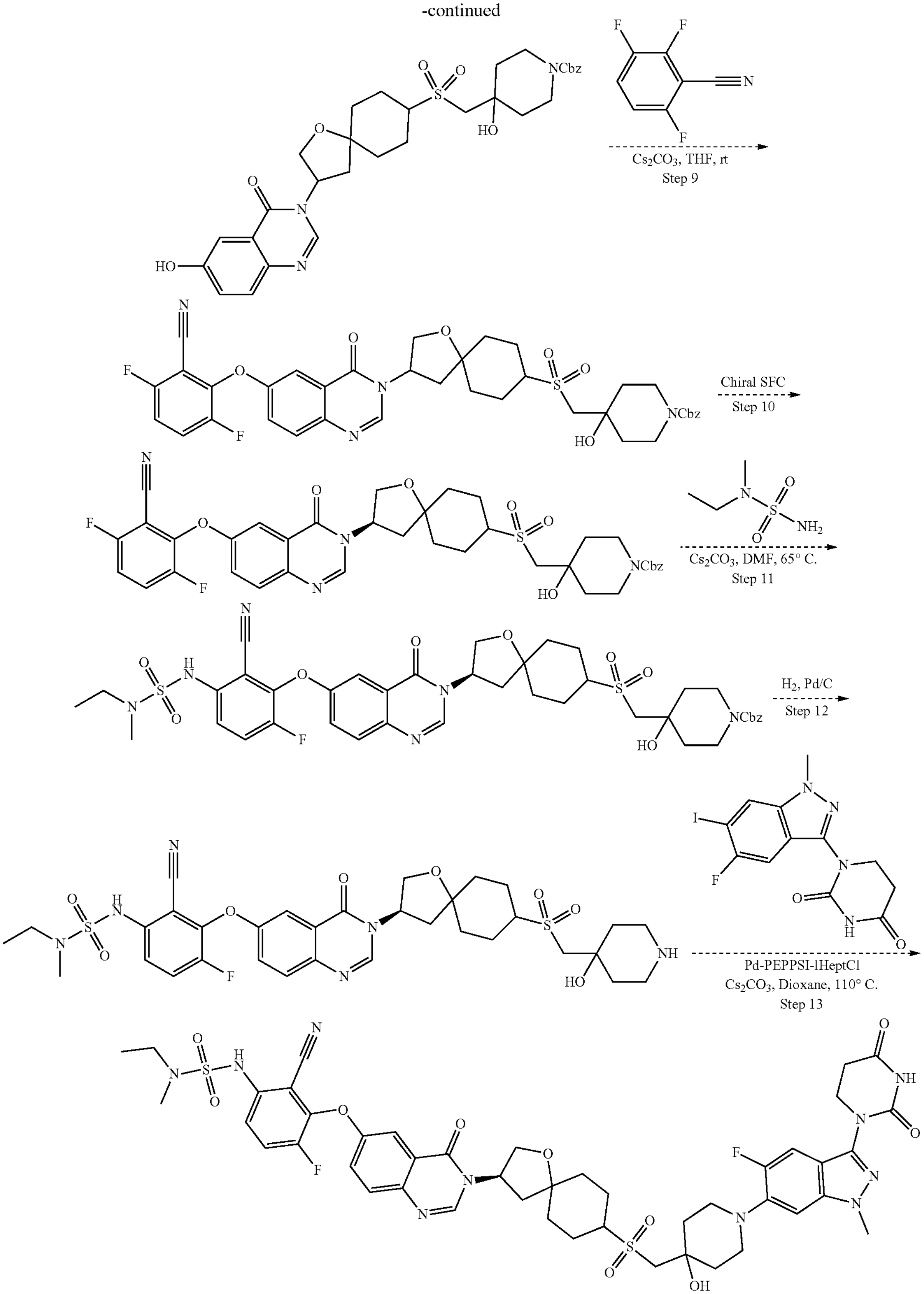

Step 1: A solution of 8-benzyloxy-1-oxaspiro[4.5]decan-3-amine (1 equiv.) in THF is added sodium bicarbonate (3 equiv.) in water and tert-butyl carbonate (1.5 equiv.) tert- at room temperature. The reaction mixture is stirred at room temperature for 4 hours. After completion of the reaction as confirmed by LC-MS, a workup is performed and the product tert-butyl N-(8-benzyloxy-1-oxaspiro[4.5]decan-3-yl)carbamate is directly used in the next step without purification.

Step 2: A solution of tert-butyl N-(8-benzyloxy-1-oxaspiro[4.5]decan-3-yl)carbamate (1 equiv.) is added 10% palladium on carbon (0.12 equiv.). The reaction mixture is then degassed with $N_2$ and stirred under hydrogen atmosphere at room temperature for 16 hours. After completion of the reaction as confirmed by LC-MS, the reaction mixture is filtered through a pad of celite, which is washed with ethyl acetate. The filtrate is then concentrated in vacuo to afford tert-butyl N-(8-hydroxy-1-oxaspiro[4.5]decan-3-yl)carbamate.

Step 3: A solution of tert-butyl N-(8-hydroxy-1-oxaspiro [4.5]decan-3-yl)carbamate (1 equiv.) in anhydrous DCM is added triethylamine (2.5 equiv.) and followed by mesyl chloride (1.5 equiv.) at 0° C. under nitrogen atmosphere. The resulting suspension is stirred at ambient temperature for 16 h. After completion of the reaction as confirmed by LC-MS, a workup is performed and the crude product is purified by column chromatography to afford [3-(tert-butoxycarbonylamino)-1-oxaspiro[4.5]decan-8-yl]methanesulfonate.

Step 4: A solution of [3-(tert-butoxycarbonylamino)-1-oxaspiro[4.5]decan-8-yl]methanesulfonate (1 equiv.) in anhydrous DMF is added potassium thioacetate (2.5 equiv.) at ambient temperature under nitrogen atmosphere. The reaction mixture is then stirred at 70° C. for 16 hours and monitored by LC-MS. Upon completion of the reaction, a workup is performed and the crude product is purified by column chromatography to afford tert-butyl N-(8-sulfanyl-1-oxaspiro[4.5]decan-3-yl)carbamate.

Step 5: A suspension of NaH (1.2 equiv.) in THF is cooled to 0° C., followed by the dropwise addition of tert-butyl N-(8-sulfanyl-1-oxaspiro[4.5]decan-3-yl)carbamate (1 equiv.). The reaction is stirred for 30 minutes before benzyl 1-oxa-6-azaspiro[2.5]octane-6-carboxylate (1.2 equiv.) is added and the reaction is allowed to warm to temperature and stirred at this temperature for 4 hours. After the reaction is complete as confirmed by LC-MS, the reaction mixture is carefully quenched with MeOH at 0° C. and a workup is performed. The crude product is purified by column chromatography to afford benzyl 4-[[3-(tert-butoxycarbonylamino)-1-oxaspiro[4.5]decan-8-yl]sulfanylmethyl]-4-hydroxy-piperidine-1-carboxylate.

Step 6: To a solution of benzyl 4-[[3-(tert-butoxycarbonylamino)-1-oxaspiro[4.5]decan-8-yl]sulfanylmethyl]-4-hydroxy-piperidine-1-carboxylate (1 equiv.) in DCM is added 3-chlorobenzenecarboperoxoic acid (3 equiv.) at 0° C. under nitrogen atmosphere. The reaction mixture is stirred at room temperature for 12 hours. After completion of the reaction as confirmed by LC-MS, the reaction mixture is quenched with ammonium chloride solution and extracted with ethyl acetate. The organic layer is washed with brine, dried over anhydrous sodium sulfate, and concentrated in vacuo. The crude product is purified by column chromatography to afford benzyl 4-[[3-(tert-butoxycarbonylamino)-1-oxaspiro[4.5]decan-8-yl]sulfonylmethyl]-4-hydroxy-piperidine-1-carboxylate.

Step 7: A solution of benzyl 4-[[3-(tert-butoxycarbonylamino)-1-oxaspiro[4.5]decan-8-yl]sulfonylmethyl]-4-hydroxy-piperidine-1-carboxylate (1 equiv.) in dichloromethane is added 4 N HCl in dioxane (10 equiv.) at 0° C. The resulting reaction mixture is stirred at room temperature for 2 hours. Upon completion of the reaction as confirmed by LC-MS, the reaction is concentrated in vacuo and purified by column chromatography to afford benzyl 4-[(3-amino-1-oxaspiro[4.5]decan-8-yl)sulfonylmethyl]-4-hydroxy-piperidine-1-carboxylate.

Step 8: To a stirred solution of 2-amino-5-hydroxy-benzoic acid (1 equiv.) in toluene:tetrahydrofuran (5:1) is added anhydrous triethyl orthoformate (2 equiv.) at room temperature followed by benzyl 4-[(3-amino-1-oxaspiro[4.5]decan-8-yl)sulfonylmethyl]-4-hydroxy-piperidine-1-carboxylate (1 equiv.). The resulting reaction mixture is heated at 110° C. for 18 hours in a sealed tube. After completion of the reaction as confirmed by LC-MS, the reaction mixture is cooled to room temperature and a workup is performed. The crude product is purified by column chromatography to afford benzyl 4-hydroxy-4-[[3-(6-hydroxy-4-oxo-quinazolin-3-yl)-1-oxaspiro[4.5]decan-8-yl]sulfonylmethyl]piperidine-1-carboxylate.

Step 9: To a stirred solution of benzyl 4-hydroxy-4-[[3-(6-hydroxy-4-oxo-quinazolin-3-yl)-1-oxaspiro[4.5]decan-8-yl]sulfonylmethyl]piperidine-1-carboxylate (1 equiv.) in THF is added cesium carbonate (1.1 equiv.) and 2,3,6-trifluorobenzonitrile (1.1 equiv.) at room temperature. The resulting reaction mixture is stirred at room temperature for 16 hours. After completion of the reaction as confirmed by LC-MS, a workup is performed and the crude product is purified by column chromatography to afford benzyl 4-[[3-[6-(2-cyano-3,6-difluoro-phenoxy)-4-oxo-quinazolin-3-yl]-1-oxaspiro[4.5]decan-8-yl]sulfonylmethyl]-4-hydroxy-piperidine-1-carboxylate.

Step 10: The racemic compound benzyl 4-[[3-[6-(2-cyano-3,6-difluoro-phenoxy)-4-oxo-quinazolin-3-yl]-1-oxaspiro[4.5]decan-8-yl]sulfonylmethyl]-4-hydroxy-piperidine-1-carboxylate is resolved by chiral SFC purification to afford benzyl 4-[[(3R)-3-[6-[2-cyano-3-[[ethyl(methyl)sulfamoyl]amino]-6-fluoro-phenoxy]-4-oxo-quinazolin-3-yl]-1-oxaspiro[4.5]decan-8-yl]sulfonylmethyl]-4-hydroxy-piperidine-1-carboxylate.

Step 11: A solution of benzyl 4-[[(3R)-3-[6-[2-cyano-3-[[ethyl(methyl)sulfamoyl]amino]-6-fluoro-phenoxy]-4-oxo-quinazolin-3-yl]-1-oxaspiro[4.5]decan-8-yl]sulfonylmethyl]-4-hydroxy-piperidine-1-carboxylate (1 equiv.) in N,N-dimethylformamide is added cesium carbonate (2.5 equiv.) and [methyl(sulfamoyl)amino]ethane (2 equiv.) at room temperature. The resulting reaction mixture is stirred at 65° C. for 16 hours. After completion of the reaction as confirmed by LC-MS, a workup is performed, and the crude product is purified by column chromatography to afford benzyl 4-[[(3R)-3-[6-[2-cyano-3-[[ethyl(methyl)sulfamoyl]amino]-6-fluoro-phenoxy]-4-oxo-quinazolin-3-yl]-1-oxaspiro[4.5]decan-8-yl]sulfonylmethyl]-4-hydroxy-piperidine-1-carboxylate.

Step 12: A solution of benzyl 4-[[(3R)-3-[6-[2-cyano-3-[[ethyl(methyl)sulfamoyl]amino]-6-fluoro-phenoxy]-4-oxo-quinazolin-3-yl]-1-oxaspiro[4.5]decan-8-yl]sulfonylmethyl]-4-hydroxy-piperidine-1-carboxylate (1 equiv.) in methanol is added 10% palladium on carbon (0.1 equiv.) at room temperature. The solution is degassed and stirred at hydrogen atmosphere for 16 hours or until completion of the reaction as confirmed by LC-MS. The reaction mixture is filtered through a pad of celite, and a workup is performed. The crude product is then purified by column chromatograph to afford 6-[2-cyano-3-[[ethyl(methyl)sulfamoyl]amino]-6-fluoro-phenoxy]-3-[(3R)-8-[(4-hydroxy-4-piperidyl)methylsulfonyl]-1-oxaspiro[4.5]decan-3-yl]-4-oxo-quinazoline.

Step 13: A solution of 1-(5-fluoro-6-iodo-1-methyl-indazol-3-yl)hexahydropyrimidine-2,4-dione (1 equiv.) in dioxane is added cesium carbonate (2.5 equiv.) and 6-[2-cyano-3-[[ethyl(methyl)sulfamoyl]amino]-6-fluoro-phenoxy]-3-[(3R)-8-[(4-hydroxy-4-piperidyl)methylsulfonyl]-1-oxaspiro[4.5]decan-3-yl]-4-oxo-quinazoline (1 equiv.) at room temperature. The reaction mixture is degassed with $N_2$ for 10 minutes before Pd-PEPPSI-IHeptCl (0.05 equiv.) is added. The reaction is heated at 110° C. for 12 hours while monitoring by LC-MS.

Upon completion of the reaction, a workup is performed and purified by column chromatography.

The product is further purified by prep-HPLC to afford 6-[2-cyano-3-[[ethyl(methyl)sulfamoyl]amino]-6-fluoro-phenoxy]-3-[(3R)-8-[[1-[3-(2,4-dioxohexahydropyrimidin-1-yl)-5-fluoro-1-methyl-indazol-6-yl]-4-hydroxy-4-piperidyl]methylsulfonyl]-1-oxaspiro[4.5]decan-3-yl]-4-oxo-quinazoline.

Example 208

6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1,8-diazaspiro[4.5]decan-3-yl]-4-oxoquinazoline

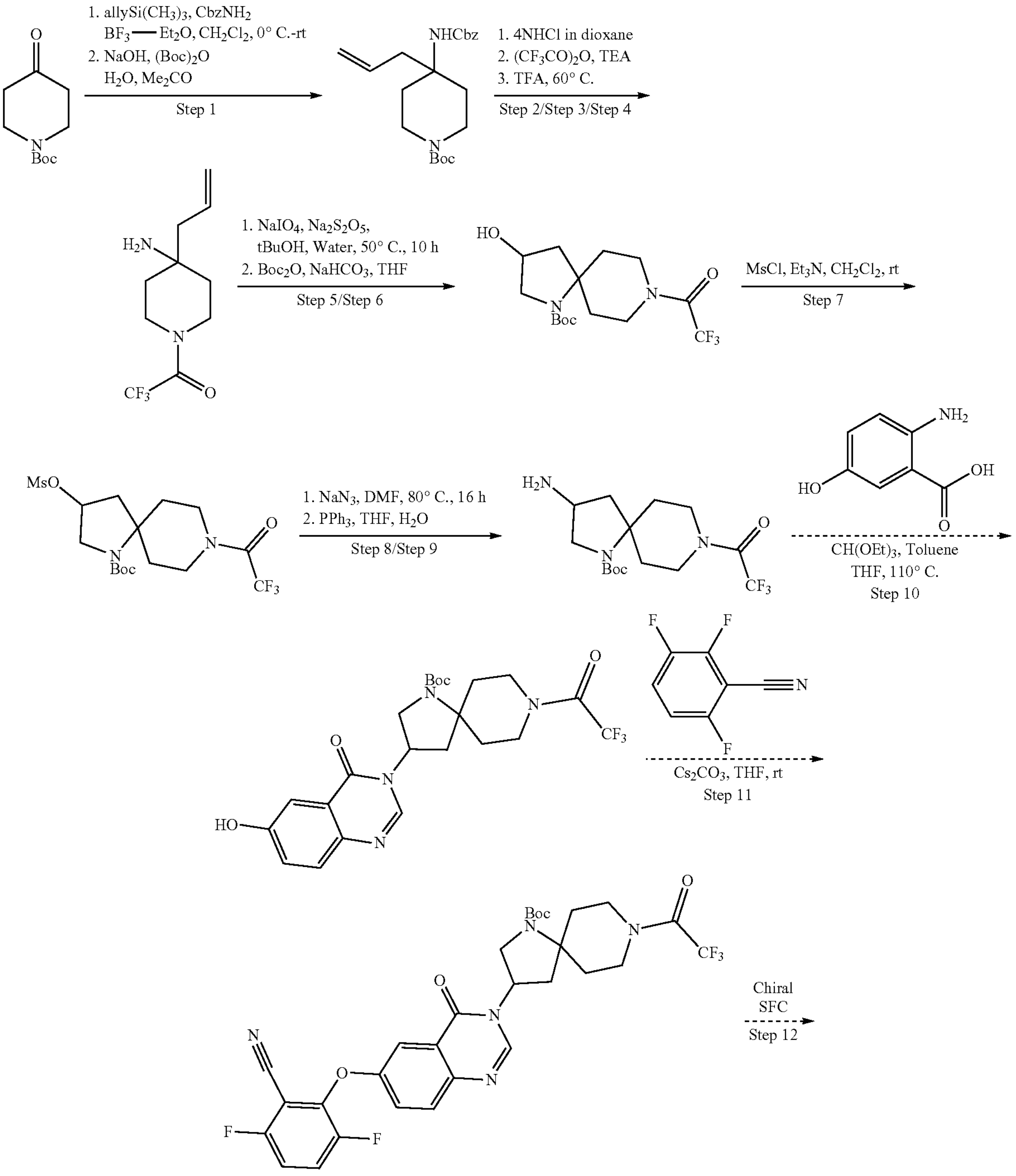

-continued
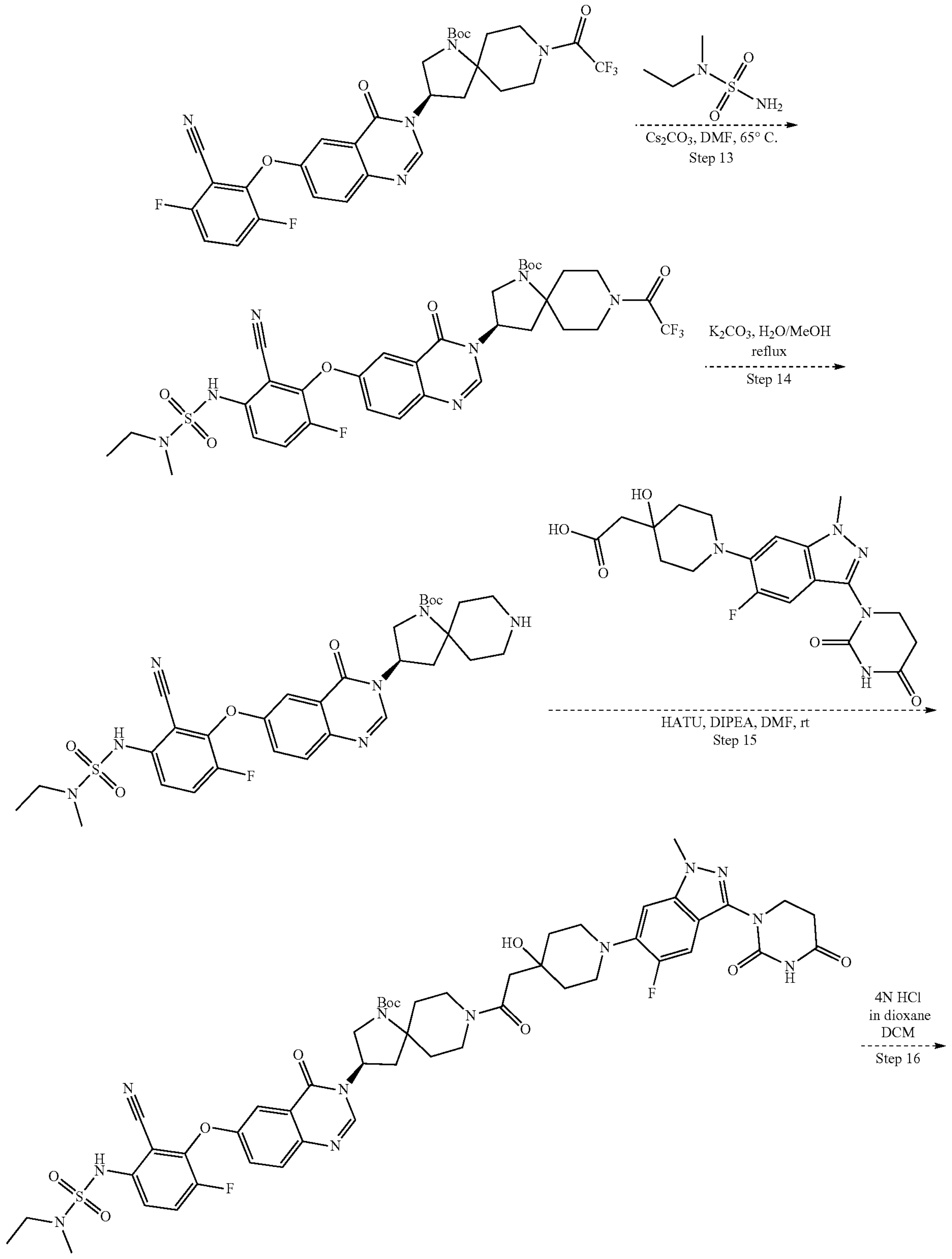

-continued

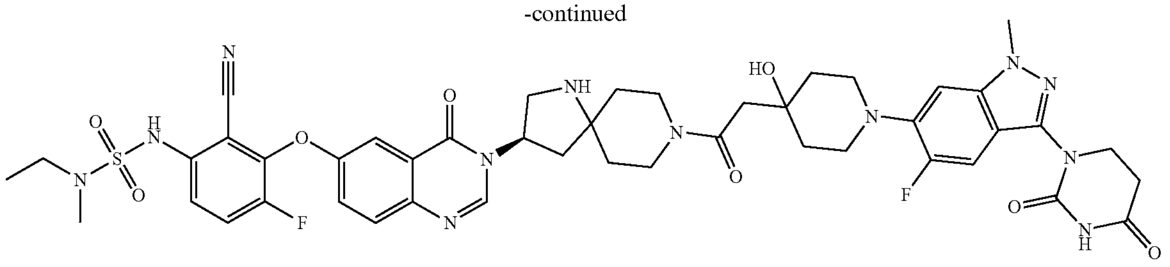

Step 1: To a stirred solution of tert-butyl 4-oxopiperidine-1-carboxylate (20 g, 100.38 mmol) in DCM (142.00 mL) was added benzyl carbamate (18.21 g, 120.45 mmol) and allyltrimethylsilane (17.20 g, 150.57 mmol, 23.99 mL) followed by the addition of boron trifluoride etherate (17.10 g, 120.45 mmol) dropwise at 0° C. The reaction mixture was stirred at 0° C. for 1 h, and then overnight in room temperature. The reaction mixture was concentrated under reduced pressure to get crude and taken into IM NaOH/acetone mixture, were added di-tert-butyl dicarbonate (21.91 g, 100.38 mmol, 23.04 mL) at room temperature for 5 h.

The reaction progress was monitored by TLC. After completion of the reaction, the reaction mixture was diluted with water and extracted with DCM. The combined organic layer was dried with anhydrous $Na_2SO_4$ and concentrated under reduced pressure to get crude. The crude was purified by silica gel (100-200 mesh) Biotage® Isolera column chromatography (product eluted in 29% to 32% EtOAc/Pet ether) to afford tert-butyl 4-allyl-4-(benzyloxycarbonylamino)piperidine-1-carboxylate (24.6 g, 61.09 mmol, 60.86% yield) as a colorless liquid. LC-MS ($ES^+$): m/z 275.2 $[M+H-CO_2{}^tBu]^+$.

Step 2: To a 1 L single neck round bottom flask containing a solution of tert-butyl 4-allyl-4-(benzyloxycarbonylamino)piperidine-1-carboxylate (24 g, 64.09 mmol) in DCM (200 mL) was added hydrochloric acid 4M in 1,4-dioxane (4 M, 96.14 mL) at 0° C., the resulting reaction mixture was stirred at room temperature for 2 hours. The progress of reaction was monitored by TLC and UPLC. After completion of the reaction, the reaction mixture was concentrated under vacuum and washed with diethyl ether and dried to get the desired product benzyl N-(4-allyl-4-piperidyl)carbamate (16.9 g, 61.52 mmol, 96.00% yield) as off white solid. LCMS ($ES^+$): m/z 275.2 $[M+H]^+$.

Step 3: To a stirred solution of benzyl N-(4-allyl-4-piperidyl)carbamate (16.5 g, 60.14 mmol) in DCM (20 mL) was added triethylamine (24.34 g, 240.56 mmol, 33.53 mL) and trifluoroacetic anhydride (25.26 g, 120.28 mmol, 16.99 mL) dropwise at 0° C. under nitrogen atmosphere. The reaction mixture was stirred at room temperature for 12 hours. The progress of the reaction was monitored by TLC. After completion of the reaction, the reaction mixture was diluted with water and extracted with DCM. The combined organic layer were washed with brine, dried over anhydrous $Na_2SO_4$ and organic layer concentrated under reduced pressure to get crude. The crude was purified by silica gel (100-200 mesh) Biotage® Isolera column chromatography (product eluted in 55% to 58% EtOAc/Pet ether) to afford benzyl N-[4-allyl-1-(2,2,2-trifluoroacetyl)-4-piperidyl]carbamate (8 g, 20.95 mmol, 34.84% yield) as a brown liquid. $^1H$ NMR (400 MHz, DMSO-$d_6$): δ=7.43 (s, 5H), 5.79-5.72 (m, 1H), 5.28 (s, 2H), 5.05 (ddd, J=10.6, 2.0 Hz, 2H), 3.77-3.62 (m, 2H), 3.45-3.39 (m, 2H), 2.70 (d, J=7.2 Hz, 2H), 2.53 (s, 1H), 2.25-2.20 (m, 2H), 2.10-2.05 (m, 2H) ppm.

Step 4: To a 100 mL single neck round bottom flask, benzyl N-[4-allyl-1-(2,2,2-trifluoroacetyl)-4-piperidyl]carbamate (4 g, 10.80 mmol) was added trifluoroacetic acid (12.31 g, 108.00 mmol, 8.32 mL) at 0° C., the resulting reaction mixture was stirred at room temperature for 12 hours at 60° C. The progress of reaction was monitored by TLC and UPLC. After completion of the reaction, the reaction mixture was concentrated under vacuum and purified using Biotage® Isolera column chromatography (100% ethyl acetate in pet ether) to afford product 1-(4-allyl-4-amino-1-piperidyl)-2,2,2-trifluoro-ethanone (2 g, 8.30 mmol, 76.82% yield) as an off-white solid. LC-MS (ESI+): m/z $[M+H]^+$.

Step 5: To a 100 mL sealed tube containing a well stirred solution of 1-(4-allyl-4-amino-1-piperidyl)-2,2,2-trifluoro-ethanone (1.3 g, 3.71 mmol, 061) in water (401.20 μL) and tert-butyl alcohol (1.20 mL) under nitrogen atmosphere was added sodium periodate (793.87 mg, 3.71 mmol) and sodium metabisulfite (705.59 mg, 3.71 mmol, 476.75 μL). The reaction mixture was stirred at 50° C. for 16 hours. After completion of the reaction as confirmed by UPLC, the crude product 2,2,2-trifluoro-1-(3-hydroxy-1,8-diazaspiro[4.5]decan-8-yl)ethanone (2.6 g, 2.37 mmol, 63.88% yield) was taken into the next step without purification. LCMS ($ES^+$): m/z 253.2 $[M+H]^+$.

Step 6: To a 100 mL sealed tube containing a well stirred solution of 2,2,2-trifluoro-1-(3-hydroxy-1,8-diazaspiro[4.5]decan-8-yl)ethanone (1.7 g, 6.74 mmol) in THF (9.99 mL) was added sodium bicarbonate (3.40 g, 40.44 mmol) and di-tert-butyl dicarbonate (2.21 g, 10.11 mmol, 2.32 mL) and the reaction mixture was stirred at room temperature for 16 hours. After completion of the reaction as confirmed by UPLC, the reaction mixture was concentrated and dissolved in ethyl acetate and washed with water. The organic layer was dried over $Na_2SO_4$ and concentrated in vacuo to afford crude tert-butyl 3-hydroxy-8-(2,2,2-trifluoroacetyl)-1,8-diazaspiro[4.5]decane-1-carboxylate (1.9 g, 4.31 mmol, 64.01% yield). LC-MS ($ES^+$): m/z 297.2 $[M-{}^tBu+H]^+$.

Step 7: To a 100 mL single neck round bottom flask containing a well-stirred solution of tert-butyl 3-hydroxy-8-(2,2,2-trifluoroacetyl)-1,8-diazaspiro[4.5]decane-1-carboxylate (1.9 g, 5.39 mmol) in DCM (20 mL) was added triethylamine (1.64 g, 16.18 mmol, 2.25 mL) and methanesulfonyl chloride (926.55 mg, 8.09 mmol, 627.32 μL) at room temperature under nitrogen atmosphere. The resulting solution was stirred at room temperature for 3 hours. After completion of the reaction as indicated by TLC, the reaction mixture was diluted with water (100 mL) and the product was extracted with DCM (2×100 mL). The organic layer was dried over anhydrous $Na_2SO_4$ and concentrated to get the crude compound tert-butyl 3-methylsulfonyloxy-8-(2,2,2-trifluoroacetyl)-1,8-diazaspiro[4.5]decane-1-carboxylate (1.6 g, 3.23 mmol, 59.96% yield). Crude only taken for next step. LC-MS (ESI): m/z 331.0 $[M+H-Boc]^+$.

Step 8: To a 100 mL single neck round bottom flask containing a well-stirred solution of tert-butyl 3-methylsulfonyloxy-8-(2,2,2-trifluoroacetyl)-1,8-diazaspiro[4.5]decane-1-carboxylate (2.8 g, 6.50 mmol) in DMF (30 mL) was added sodium azide (634.33 mg, 9.76 mmol) at room temperature. The resulting solution was stirred at 80° C. for 16 hours. After completion of the reaction as indicated by TLC, the reaction mixture was diluted with water (50 mL) and extracted with ethyl acetate (2×50 mL), the organic layer was dried over anhydrous $Na_2SO_4$ and concentrated to get a crude compound tert-butyl 3-azido-8-(2,2,2-trifluoroacetyl)-1,8-diazaspiro[4.5]decane-1-carboxylate (1.6 g, 4.07 mmol, 62.57% yield), which was used in the next step directly. LC-MS (ESI): m/z 278.2 $[M+H-Boc]^+$.

Step 9: To a 25 mL single neck round bottom flask containing a well-stirred solution of tert-butyl 3-azido-8-(2,2,2-trifluoroacetyl)-1,8-diazaspiro[4.5]decane-1-carboxylate (150 mg, 397.50 μmol) in water (0.5 mL) and THF (2 mL) was added triphenylphosphine (156.39 mg, 596.25 μmol). The resulting solution was stirred at 80° C. for 16 hours. After completion of the reaction as indicated by TLC, the reaction mixture was diluted with water (10 mL) and the product was extracted with ethyl acetate (2×10 mL). The organic layer was dried over anhydrous $Na_2SO_4$, concentrated and purified to afford tert-butyl 3-amino-8-(2,2,2-trifluoroacetyl)-1,8-diazaspiro[4.5]decane-1-carboxylate (60 mg, 111.00 μmol, 27.92% yield). LC-MS ($ES^+$): m/z 296.1 $[M+H-{}^tBu]^+$.

Step 10: To a stirred solution of 2-amino-5-hydroxybenzoic acid (1 equiv.) in toluene:tetrahydrofuran (5:1) is added anhydrous triethyl orthoformate (2 equiv.) at room temperature followed by tert-butyl 3-amino-8-(2,2,2-trifluoroacetyl)-1,8-diazaspiro[4.5]decane-1-carboxylate (1 equiv.). The resulting reaction mixture is heated at 110° C. for 18 hours in a sealed tube. After completion of the reaction as confirmed by LC-MS, the reaction mixture is cooled to room temperature and a workup is performed. The crude product is purified by column chromatography to afford tert-butyl 3-(6-hydroxy-4-oxo-quinazolin-3-yl)-8-(2,2,2-trifluoroacetyl)-1,8-diazaspiro[4.5]decane-1-carboxylate.

Step 11: To a stirred solution of tert-butyl 3-(6-hydroxy-4-oxo-quinazolin-3-yl)-8-(2,2,2-trifluoroacetyl)-1,8-diazaspiro[4.5]decane-1-carboxylate (1 equiv.) in THF is added cesium carbonate (1.1 equiv.) and 2,3,6-trifluorobenzonitrile (1.1 equiv.) at room temperature. The resulting reaction mixture is stirred at room temperature for 16 hours. After completion of the reaction as confirmed by LC-MS, a workup is performed and the crude product is purified by silica gel column chromatography to afford tert-butyl 3-[6-(2-cyano-3,6-difluoro-phenoxy)-4-oxo-quinazolin-3-yl]-8-(2,2,2-trifluoroacetyl)-1,8-diazaspiro[4.5]decane-1-carboxylate.

Step 12: The racemic compound tert-butyl 3-[6-(2-cyano-3,6-difluoro-phenoxy)-4-oxo-quinazolin-3-yl]-8-(2,2,2-trifluoroacetyl)-1,8-diazaspiro[4.5]decane-1-carboxylate is resolved by chiral SFC purification to afford tert-butyl (3R)-3-[6-(2-cyano-3,6-difluoro-phenoxy)-4-oxo-quinazolin-3-yl]-8-(2,2,2-trifluoroacetyl)-1,8-diazaspiro[4.5]decane-1-carboxylate.

Step 13: A solution of tert-butyl (3R)-3-[6-(2-cyano-3,6-difluoro-phenoxy)-4-oxo-quinazolin-3-yl]-8-(2,2,2-trifluoroacetyl)-1,8-diazaspiro[4.5]decane-1-carboxylate (1 equiv.) in N,N-dimethylformamide is added cesium carbonate (2.5 equiv.) and [methyl(sulfamoyl)amino]ethane (2 equiv.) at room temperature. The resulting reaction mixture is stirred at 65° C. for 16 hours. After completion of the reaction as confirmed by LC-MS, a workup is performed, and the crude product is purified by silica gel column chromatography to afford tert-butyl (3R)-3-[6-[2-cyano-3-[[ethyl(methyl)sulfamoyl]amino]-6-fluoro-phenoxy]-4-oxo-quinazolin-3-yl]-8-(2,2,2-trifluoroacetyl)-1,8-diazaspiro[4.5]decane-1-carboxylate.

Step 14: A solution of tert-butyl (3R)-3-[6-[2-cyano-3-[[ethyl(methyl)sulfamoyl]amino]-6-fluoro-phenoxy]-4-oxo-quinazolin-3-yl]-8-(2,2,2-trifluoroacetyl)-1,8-diazaspiro[4.5]decane-1-carboxylate (1 equiv.) in methanol and water is added anhydrous potassium carbonate (5 equiv.) at room temperature. The resulting mixture is heated to 50° C. for 16 hours and monitored by LC-MS. Upon completion, a workup is performed and the crude product is purified by silica gel column chromatography to afford tert-butyl (3R)-3-[6-[2-cyano-3-[[ethyl(methyl)sulfamoyl]amino]-6-fluoro-phenoxy]-4-oxo-quinazolin-3-yl]-1,8-diazaspiro[4.5]decane-1-carboxylate.

Step 15: To a solution of 2-[1-[3-(2,4-dioxohexahydropyrimidin-1-yl)-5-fluoro-1-methyl-indazol-6-yl]-4-hydroxy-4-piperidyl]acetic acid (1 equiv.) and tert-butyl (3R)-3-[6-[2-cyano-3-[[ethyl(methyl)sulfamoyl]amino]-6-fluoro-phenoxy]-4-oxo-quinazolin-3-yl]-1,8-diazaspiro[4.5]decane-1-carboxylate (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, the crude mixture is purified by column chromatography to afford the target compound tert-butyl (3R)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1,8-diazaspiro[4.5]decane-1-carboxylate.

Step 16: A solution of tert-butyl (3R)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1,8-diazaspiro[4.5]decane-1-carboxylate (1 equiv.) in dichloromethane is added 4 N HCl in dioxane (10 equiv.) at 0° C. The resulting reaction mixture is stirred at room temperature for 2 hours. Upon completion of the reaction as confirmed by LC-MS, the reaction is concentrated in vacuo and purified by reverse phase prep-HPLC to afford 6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1,8-diazaspiro[4.5]decan-3-yl]-4-oxoquinazoline.

Example 209
6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-methyl-1,8-diazaspiro[4.5]decan-3-yl]-4-oxoquinazoline
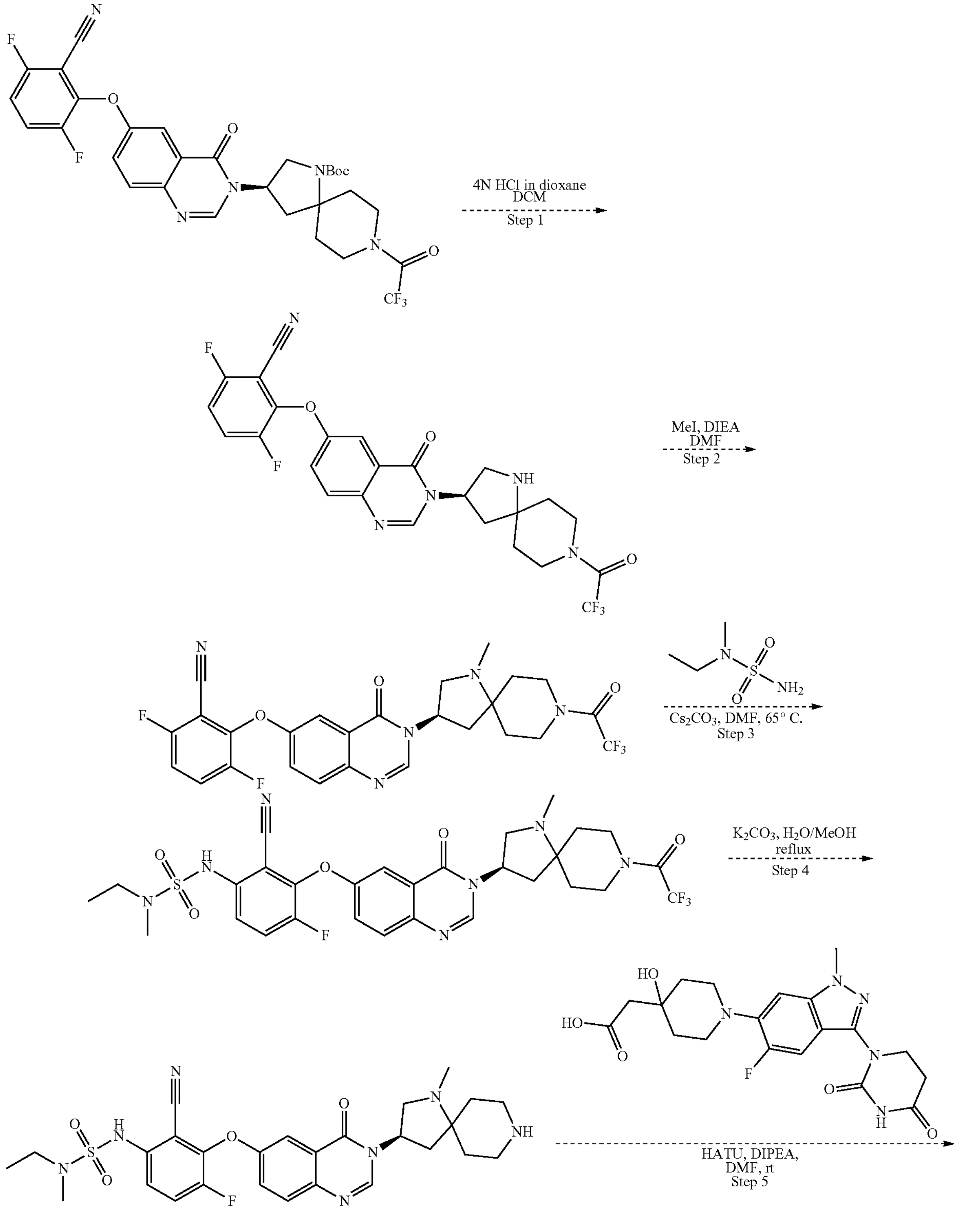

-continued

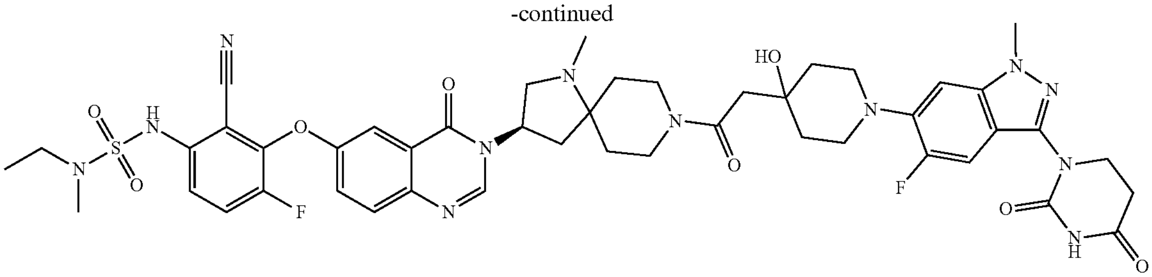

Step 1: A solution of tert-butyl (3R)-3-[6-(2-cyano-3,6-difluoro-phenoxy)-4-oxo-quinazolin-3-yl]-8-(2,2,2-trifluoroacetyl)-1,8-diazaspiro[4.5]decane-1-carboxylate (1 equiv.) in dichloromethane is added 4 N HCl in dioxane (10 equiv.) at 0° C. The resulting reaction mixture is stirred at room temperature for 2 hours. Upon completion of the reaction as confirmed by LC-MS, the reaction is concentrated in vacuo to afford 3,6-difluoro-2-[4-oxo-3-[(3R)-8-(2,2,2-trifluoroacetyl)-1,8-diazaspiro[4.5]decan-3-yl]quinazolin-6-yl]oxy-benzonitrile.

Step 2: A solution of 3,6-difluoro-2-[4-oxo-3-[(3R)-8-(2,2,2-trifluoroacetyl)-1,8-diazaspiro[4.5]decan-3-yl]quinazolin-6-yl]oxy-benzonitrile (1 equiv.), methyl iodide (2 equiv.) in DMF is added DIPEA (3 equiv.) and the reaction mixture is stirred at room temperature for 16 hours. After completion of the reaction as confirmed by LC-MS, a workup is performed and the crude product is purified by silica gel column chromatography to afford 3,6-difluoro-2-[3-[(3R)-1-methyl-8-(2,2,2-trifluoroacetyl)-1,8-diazaspiro[4.5]decan-3-yl]-4-oxo-quinazolin-6-yl]oxy-benzonitrile.

Step 3: A solution of 3,6-difluoro-2-[3-[(3R)-1-methyl-8-(2,2,2-trifluoroacetyl)-1,8-diazaspiro[4.5]decan-3-yl]-4-oxo-quinazolin-6-yl]oxy-benzonitrile (1 equiv.) in N,N-dimethylformamide is added cesium carbonate (2.5 equiv.) and [methyl(sulfamoyl)amino]ethane (2 equiv.) at room temperature. The resulting reaction mixture is stirred at 65° C. for 16 hours. After completion of the reaction as confirmed by LC-MS, a workup is performed, and the crude product is purified by silica gel column chromatography to afford 6-[2-cyano-3-[[ethyl(methyl)sulfamoyl]amino]-6-fluoro-phenoxy]-3-[(3R)-1-methyl-8-(2,2,2-trifluoroacetyl)-1,8-diazaspiro[4.5]decan-3-yl]-4-oxo-quinazoline.

Step 4: A solution of 6-[2-cyano-3-[[ethyl(methyl)sulfamoyl]amino]-6-fluoro-phenoxy]-3-[(3R)-1-methyl-8-(2,2,2-trifluoroacetyl)-1,8-diazaspiro[4.5]decan-3-yl]-4-oxo-quinazoline (1 equiv.) in methanol and water is added anhydrous potassium carbonate (5 equiv.) at room temperature. The resulting mixture is refluxed for 16 hours and monitored by LC-MS. Upon completion, a workup is performed and the crude product is purified by silica gel column chromatography to afford 6-[2-cyano-3-[[ethyl(methyl)sulfamoyl]amino]-6-fluoro-phenoxy]-3-[(3R)-1-methyl-1,8-diazaspiro[4.5]decan-3-yl]-4-oxo-quinazoline.

Step 5: To a solution of 2-[1-[3-(2,4-dioxohexahydropyrimidin-1-yl)-5-fluoro-1-methyl-indazol-6-yl]-4-hydroxy-4-piperidyl]acetic acid (1 equiv.) and 6-[2-cyano-3-[[ethyl(methyl)sulfamoyl]amino]-6-fluoro-phenoxy]-3-[(3R)-1-methyl-1,8-diazaspiro[4.5]decan-3-yl]-4-oxo-quinazoline (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, the crude mixture is purified by reverse phase prep-HPLC to afford the target compound 6-[2-cyano-3-[[ethyl(methyl)sulfamoyl]amino]-6-fluorophenoxy]-3-[(3R)-8-[2-[1-[3-(2,4-dioxo-1,3-diazinan-1-yl)-5-fluoro-1-methylindazol-6-yl]-4-hydroxypiperidin-4-yl]acetyl]-1-methyl-1,8-diazaspiro[4.5]decan-3-yl]-4-oxoquinazoline.

Example 210

(3R)-8-[2-[1-[3-(2,4-dioxohexahydropyrimidin-1-yl)-5-fluoro-1-methyl-indazol-6-yl]-4-hydroxy-4-piperidyl]acetyl]-3-[6-[3-[[ethyl(methyl)sulfamoyl]amino]-2,6-difluoro-benzoyl]-4-oxo-quinazolin-3-yl]-1-oxa-8-azaspiro[4.5]decane

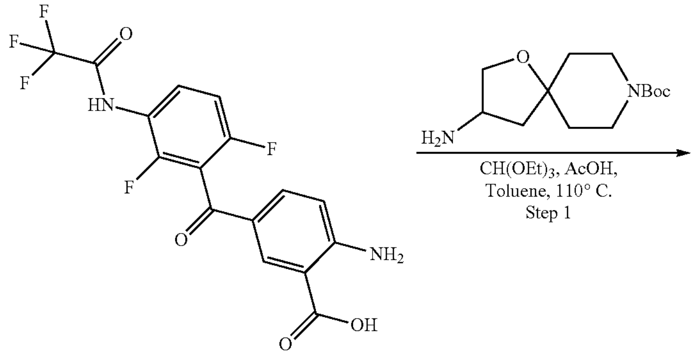

-continued

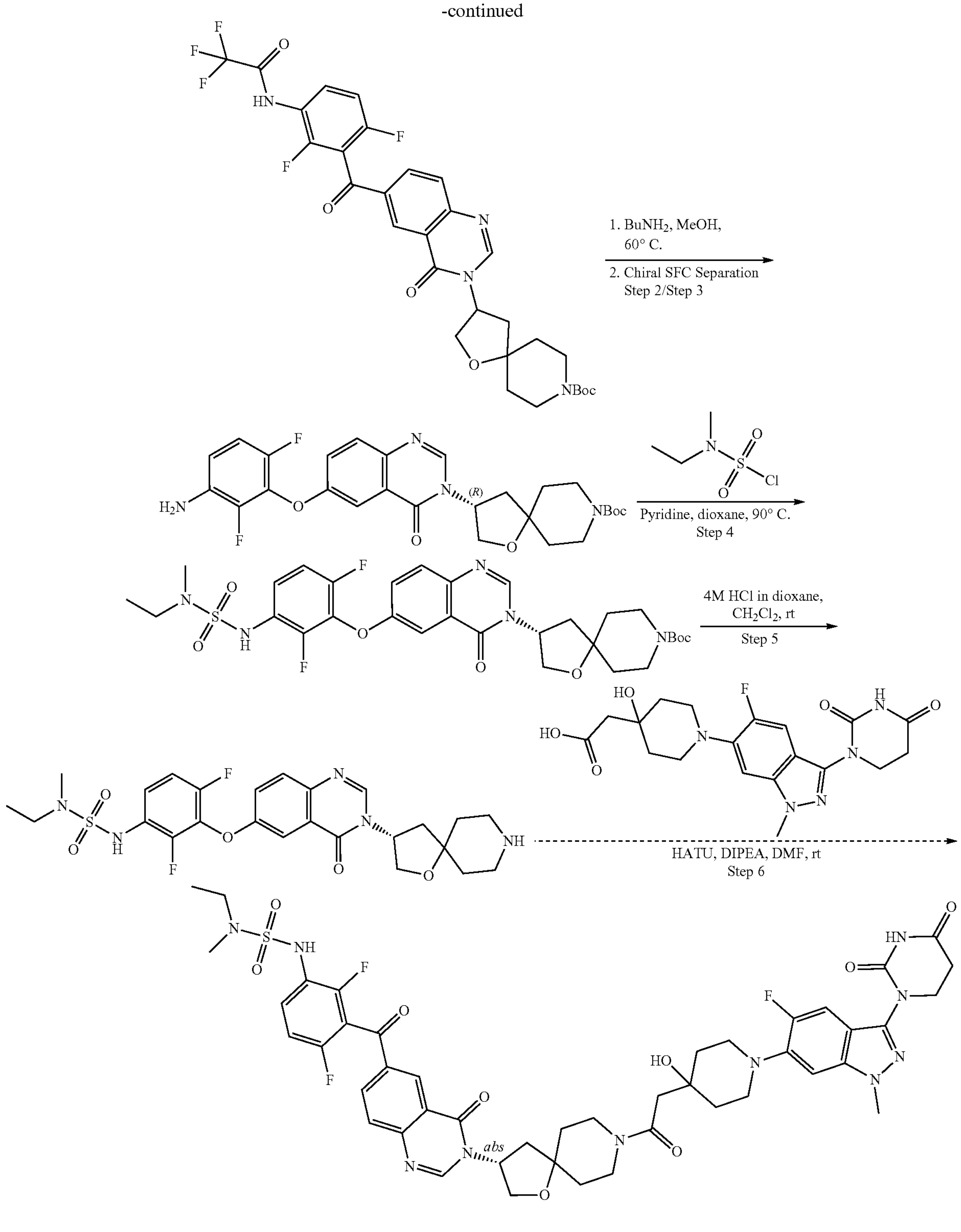

Step 1: To a stirred solution of 2-amino-5-[2,6-difluoro-3-[(2,2,2-trifluoroacetyl)amino]benzoyl]benzoic acid (1.09 g, 2.81 mmol) and tert-butyl 3-amino-1-oxa-8-azaspiro[4.5]decane-8-carboxylate (600 mg, 2.34 mmol) in toluene (10 mL) and THF (3 mL) was added diethoxymethoxyethane (693.76 mg, 4.68 mmol, 778.63 μL) followed by acetic acid (28.11 mg, 468.13 μmol, 26.77 μL) at ambient temperature. The resulting mixture was stirred at 110° C. for 16 h in a closed seal tube. After completion, the reaction mixture was diluted with water (10 mL), extracted with ethyl acetate (2×10 mL). The combined organic layers were washed with 10% sodium bicarbonate solution (10 mL) followed by brine solution, dried over anhydrous sodium sulfate, filtered and concentrated under reduced pressure to get crude product which was purified by silica gel column chromatography using 0-50% ethyl acetate in petroleum ether as eluents to afford tert-butyl 3-[6-[2,6-difluoro-3-[(2,2,2 trifluoroacetyl) amino]benzoyl]-4-oxo-quinazolin-3-yl]-1-oxa-8-azaspiro [4.5]decane-8-carboxylate (531 mg, 734.06 μmol, 31% yield) as a brown solid. LCMS (ESI+): m/z 637.7 $[M+H]^+$ and 581.1 $[M-{}^tBu+H]^+$.

Step 2: To a stirred solution of tert-butyl 3-[6-[2,6-difluoro-3-[(2,2,2-trifluoroacetyl)amino]benzoyl]-4-oxo-quinazolin-3-yl]-1-oxa-8-azaspiro[4.5]decane-8-carboxylate (360 mg, 565.54 μmol) in methanol (6 mL) was added n-butyl amine (206.82 mg, 2.83 mmol, 280.24 μL) at 0° C. and the resulting reaction mixture was warmed to 60° C. for 16 h. After completion, the reaction mixture was concentrated to get crude which was purified by flash silica gel column chromatography using 10% methanol in dichloromethane to afford tert-butyl 3-[6-(3-amino-2,6-difluoro-benzoyl)-4-oxo-quinazolin-3-yl]-1-oxa-8-azaspiro[4.5]decane-8-carboxylate (170 mg, 279.90 μmol, 49% yield) as an yellow solid. LCMS (ESI+): m/z 485.0 $[M-{}^tBu+H]^+$.

Step 3: The racemic compound tert-butyl 3-[6-(3-amino-2,6-difluoro-benzoyl)-4-oxo-quinazolin-3-yl]-1-oxa-8-azaspiro[4.5]decane-8-carboxylate (240 mg, 443.99 μmol) was chirally resolved by chiral SFC (column: YMC Amylose-SA [250*30 mm, 5 micron]; mobile phase: 40% (0.5% isopropyl amine in methanol) and 60% $CO_2$]; flow rate: 70 g/min; cycle time: 8 min; back pressure: 100 bar; UV: 220 nm) to afford peak 1 (first eluted) tert-butyl (3S)-3-[6-(3-amino-2,6-difluoro-benzoyl)-4-oxo-quinazolin-3-yl]-1-oxa-8-azaspiro[4.5]decane-8-carboxylate (110 mg, 203.49 μmol, 46% yield, 100% ee, SOR: +81.20) as an off-white solid and peak 2 (second eluted) tert-butyl (3R)-3-[6-(3-amino-2,6-difluoro-benzoyl)-4-oxo-quinazolin-3-yl]-1-oxa-8-azaspiro [4.5]decane-8-carboxylate (98 mg, 177.96 μmol, 40% yield, 96.2% ee, SOR: −79.12) as an off-white solids.

Step 4: Into a 10 mL sealed tube containing a well stirred solution of tert-butyl (3R)-3-[6-(3-amino-2,6-difluoro-benzoyl)-4-oxo-quinazolin-3-yl]-1-oxa-8-azaspiro[4.5]decane-8-carboxylate (80 mg, 148.00 μmol) in dioxane (2 mL) were added pyridine (117.06 mg, 1.48 mmol, 119.70 L) and N-ethyl-N-methyl-sulfamoyl chloride (139.96 mg, 887.97 μmol, 109.49 μL) at room temperature. The reaction mixture was stirred at 90° C. for 12 h. The reaction mixture was diluted with water and extracted with ethyl acetate (2×25 mL). The combined organic layer was washed with cold water, dried over sodium sulfate, filtered and concentrated under reduced pressure to afford crude, which was purified by silica gel column chromatography using 0-10% methanol in dichloromethane to afford tert-butyl (3R)-3-[6-[3-[[ethyl (methyl)sulfamoyl]amino]-2,6-difluoro-benzoyl]-4-oxo-quinazolin-3-yl]-1-oxa-8-azaspiro[4.5]decane-8-carboxylate (13 mg, 19.06 μmol, 13% yield) as a brown solid. LCMS (ESI+): 660.3 $[M-H]^-$.

Step 5: To a stirred solution of tert-butyl (3R)-3-[6-[3-[[ethyl(methyl)sulfamoyl]amino]-2,6-difluoro-benzoyl]-4-oxo-quinazolin-3-yl]-1-oxa-8-azaspiro[4.5]decane-8-carboxylate (13 mg, 19.65 μmol) in dichloromethane (0.2 mL) was added hydrogen chloride solution 4.0 M in dioxane (17.91 μL) at 0° C., the resulting reaction mixture was stirred at room temperature for 2 h. After completion of the reaction, the reaction mixture was concentrated under vacuum and washed with diethyl ether to afford (3R)-3-[6-[3-[[ethyl(methyl)sulfamoyl]amino]-2,6-difluoro-benzoyl]-4-oxo-quinazolin-3-yl]-1-oxa-8-azaspiro[4.5]decane (12 mg, 17.66 μmol, 90% yield) as an off-white solid. LCMS (ESI+): 562.3 $[M+H]^+$.

Step 6: To a solution of (3R)-3-[6-[3-[[ethyl(methyl) sulfamoyl]amino]-2,6-difluoro-benzoyl]-4-oxo-quinazolin-3-yl]-1-oxa-8-azaspiro[4.5]decane (1 equiv.) and 2-[1-[3-(2,4-dioxohexahydropyrimidin-1-yl)-5-fluoro-1-methyl-indazol-6-yl]-4-hydroxy-4-piperidyl]acetic acid (1 equiv.) in DMF are added N,N-diisopropylethylamine (3 equiv.) and HATU (1.5 equiv.) under nitrogen atmosphere. The reaction mixture is stirred at room temperature and monitored by LC-MS. Upon completion, the crude mixture is purified by reverse phase prep-HPLC to afford the target compound (3R)-8-[2-[1-[3-(2,4-dioxohexahydropyrimidin-1-yl)-5-fluoro-1-methyl-indazol-6-yl]-4-hydroxy-4-piperidyl] acetyl]-3-[6-[3-[[ethyl(methyl)sulfamoyl]amino]-2,6-difluoro-benzoyl]-4-oxo-quinazolin-3-yl]-1-oxa-8-azaspiro [4.5]decane.

Example 211

(3R)-3-[6-[3-[[tert-butyl(methyl)sulfamoyl]amino]-2-cyano-6-fluorophenoxy]-4-oxoquinazolin-3-yl]-8-[2-[1-[3-(2,4-dioxo-1,3-diazinan-1-yl)-5-fluoro-1-methylindazol-6-yl]-4-hydroxypiperidin-4-yl] acetyl]-1-oxa-8-azaspiro[4.5]decane

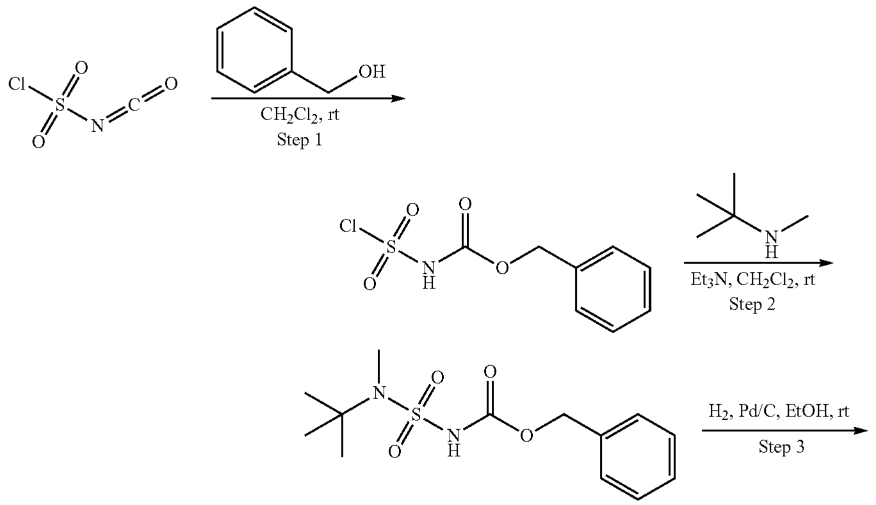

-continued

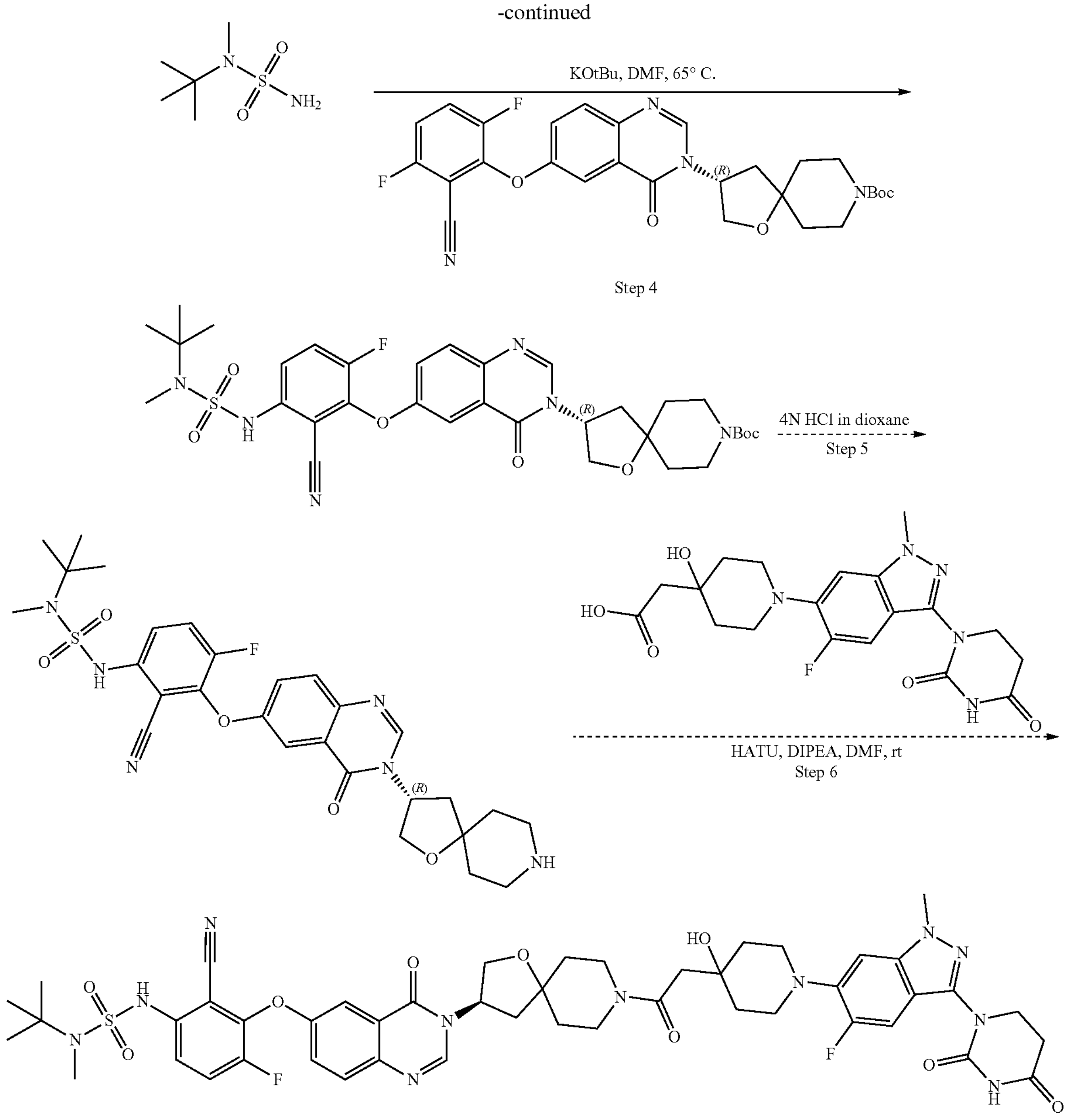

Step 1: To stirred a solution of N-(oxomethylene)sulfamoyl chloride (5 g, 35.33 mmol, 3.08 mL) in dichloromethane (50 mL) at 0° C. was added a solution of phenyl methanol (3.82 g, 35.33 mmol, 3.66 mL) in dichloromethane (50 mL). The resulting reaction mixture was stirred at room temperature for 1 h. After completion of the reaction, the reaction mixture was concentrated under reduced pressure to afford benzyl N-chlorosulfonylcarbamate (8 g, 30.44 mmol, 86% yield) as yellow solid. $^1$H-NMR (400 MHz, DMSO-$d_6$): δ=12.43 (s, 1H), 7.42-7.33 (m, 5H), 5.23 (s, 1H), 4.97 (s, 1H).

Step 2: To a stirred solution of benzyl N-chlorosulfonylcarbamate (3 g, 12.02 mmol) and N,2-dimethylpropan-2-amine (1.05 g, 12.02 mmol, 1.44 mL) in dichloromethane (30 mL) was added triethylamine (3.65 g, 36.05 mmol, 5.02 mL). The resulting reaction mixture was stirred at room temperature for 16 hours. After completion of the reaction, reaction mixture was concentrated under reduced pressure and purified using flash silica gel column chromatography eluting with 50% of ethyl acetate in petroleum ether to afford benzyl N-[tert-butyl(methyl)sulfamoyl]carbamate (1.5 g, 4.04 mmol, 34% yield). LCMS (ESI+): m/z 299.2 [M+H]$^+$.

Step 3: To a stirred solution of benzyl N-[tert-butyl (methyl)sulfamoyl]carbamate (1.5 g, 4.99 mmol) in ethanol (20 mL) was added palladium, 10% on carbon (797.16 mg, 7.49 mmol) under nitrogen. The suspension was degassed with nitrogen under vacuum. The mixture was stirred under hydrogen bladder at room temperature for 16 hours. After completion of the reaction, the reaction mixture was filtered through cellite bed and washed with 10% methanol in dichloromethane (300 mL), and the filtrate was concentrated under reduced pressure to afford 2-methyl-2-[methyl(sulfamoyl)amino]propane (900 mg, 4.60 mmol, 92% yield) as an off-white solid. $^1$H-NMR (400 MHz, DMSO-$d_6$): δ=6.63 (s, 2H), 2.67 (s, 3H), 1.30 (s, 9H).

Step 4: To a stirred solution of tert-butyl (3R)-3-[6-(2-cyano-3,6-difluoro-phenoxy)-4-oxo-quinazolin-3-yl]-1-oxa-8-azaspiro[4.5]decane-8-carboxylate (50 mg, 92.84 μmol) in N,N-dimethylformamide (2 mL) was added potassium tert-butoxide (31.25 mg, 278.53 μmol), and 2-methyl-2-[methyl(sulfamoyl)amino]propane (26.24 mg, 157.83 μmol) and the reaction mixture was heated at 50° C. for 16 hours. The reaction mixture was diluted with cold water (10 mL) and filtered. The filtrate was extracted ethyl acetate (20 mL). The organic layer was dried over sodium sulfate and concentrated under reduced pressure to get crude, which was triturated with 10% dichloromethane in petroleum ether to afford tert-butyl (3R)-3-[6-[3-[[tert-butyl(methyl)sulfamoyl]amino]-2-cyano-6-fluoro-phenoxy]-4-oxo-quinazolin-3-yl]-1-oxa-8-azaspiro[4.5]decane-8-carboxylate as an off-white solid. LCMS (ESI): m/z: 683.2 [M−H]$^-$.

Step 5: A solution of tert-butyl (3R)-3-[6-[3-[[tert-butyl(methyl)sulfamoyl]amino]-2-cyano-6-fluoro-phenoxy]-4-oxo-quinazolin-3-yl]-1-oxa-8-azaspiro[4.5]decane-8-carboxylate (1 equiv.) in dichloromethane is added 4 N HCl in dioxane (10 equiv.) at 0° C. The resulted reaction mixture is stirred at room temperature for 2 hours. Upon completion of the reaction as confirmed by LC-MS, the reaction is concentrated in vacuo and purified by column chromatography to afford (3R)-3-[6-[3-[[tert-butyl(methyl)sulfamoyl]amino]-2-cyano-6-fluoro-phenoxy]-4-oxo-quinazolin-3-yl]-1-oxa-8-azaspiro[4.5]decane.

Step 6: To a solution of 2-[1-[3-(2,4-dioxohexahydropyrimidin-1-yl)-5-fluoro-1-methyl-indazol-6-yl]-4-hydroxy-4-piperidyl]acetic acid (1 equiv.) and (3R)-3-[6-[3-[[tert-butyl(methyl)sulfamoyl]amino]-2-cyano-6-fluoro-phenoxy]-4-oxo-quinazolin-3-yl]-1-oxa-8-azaspiro[4.5]decane (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, the crude mixture is purified by reverse phase HPLC to afford the target compound (3R)-3-[6-[3-[[tert-butyl(methyl)sulfamoyl]amino]-2-cyano-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane.

Examples 212-213

(3R)-3-[6-[2-cyano-3-[[ethyl(methyl)sulfamoyl]amino]-6-fluoro-phenoxy]-4-oxo-quinazolin-3-yl]-8-[4-[3-(2,4-dioxohexahydropyrimidin-1-yl)-5-fluoro-1-methyl-indazol-6-yl]cyclohexyl]-1-oxa-8-azaspiro[4.5]decane cis-isomer and (3R)-3-[6-[2-cyano-3-[[ethyl(methyl)sulfamoyl]amino]-6-fluoro-phenoxy]-4-oxo-quinazolin-3-yl]-8-[4-[3-(2,4-dioxohexahydropyrimidin-1-yl)-5-fluoro-1-methyl-indazol-6-yl]cyclohexyl]-1-oxa-8-azaspiro[4.5]decane trans-isomer

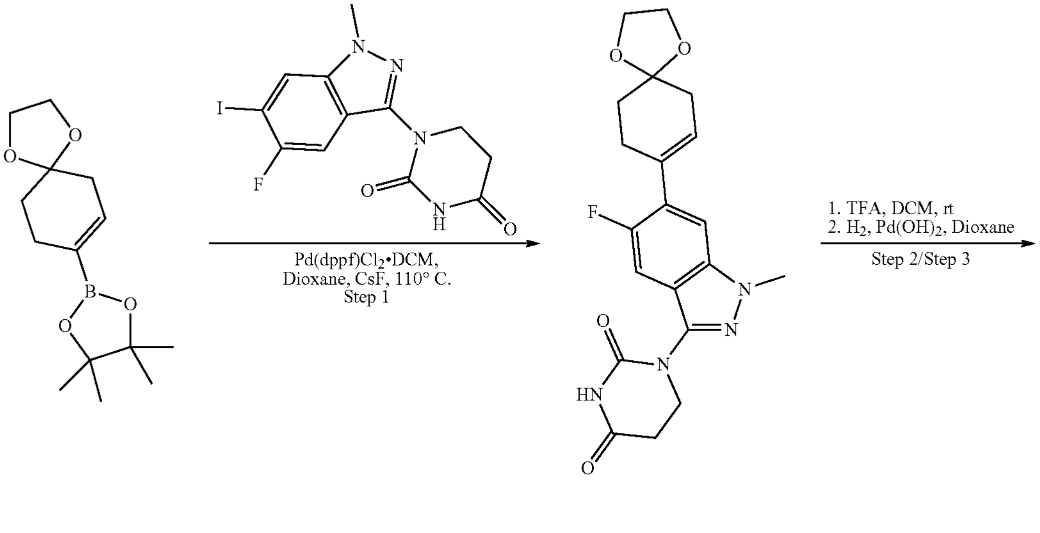

-continued

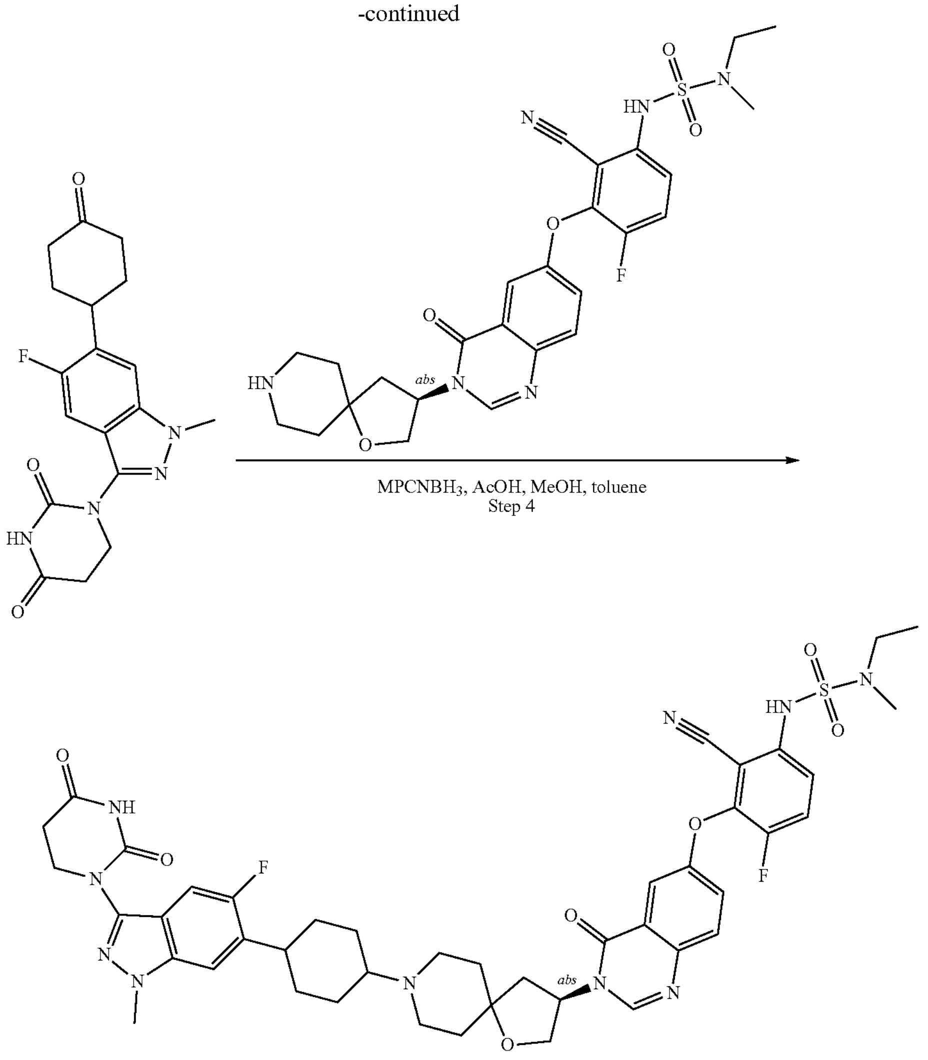

Step 1: To a stirred solution of 1-(5-fluoro-6-iodo-1-methyl-indazol-3-yl)hexahydropyrimidine-2,4-dione (2 g, 5.15 mmol) in dioxane (10 mL) in a sealed tube were added 2-(1,4-dioxaspiro[4.5]dec-7-en-8-yl)-4,4,5,5-tetramethyl-1,3,2-dioxaborolane (2.06 g, 7.73 mmol) and cesium fluoride (2.35 g, 15.46 mmol) at room temperature. The reaction mixture was purged with nitrogen gas for 10 minutes before Pd(dppf)$Cl_2$ dichloromethane (420.80 mg, 515.28 mol) was added. The reaction mixture was purged again with nitrogen gas for 5 minutes and then heated at 100° C. for 12 hours. After completion, the reaction mixture was diluted with water (100 mL), extracted with ethyl acetate (3×150 mL). The combined organic layers were washed with cold water (3×70 mL), dried over sodium sulfate, filtered, and concentrated to afford the crude. The crude was washed with methyl tert-butyl ether to afford 1-[6-(1,4-dioxaspiro[4.5]dec-7-en-8-yl)-5-fluoro-1-methyl-indazol-3-yl]hexahydropyrimidine-2,4-dione (1.5 g, 3.09 mmol, 60% yield) as a light brown solid. LCMS (ESI)=m/z 401.4 $[M+H]^+$.

Step 2: To a stirred solution of 1-[6-(1,4-dioxaspiro[4.5]dec-7-en-8-yl)-5-fluoro-1-methyl-indazol-3-yl]hexahydropyrimidine-2,4-dione (700 mg, 1.75 mmol) in dichloromethane (4.90 mL) was added trifluoroacetic acid (199.33 mg, 1.75 mmol, 134.69 μL) at 5° C. under nitrogen atmosphere. The reaction mixture was stirred at room temperature for 2 hours. After completion, the reaction mixture was concentrated under vacuum to afford crude. The desired product was purified by reverse phase column chromatography (0.1% formic acid in water:acetonitrile) to afford 1-[5-fluoro-1-methyl-6-(4-oxocyclohexen-1-yl)indazol-3-yl]hexahydropyrimidine-2,4-dione (270 mg, 633.57 μmol, 36% yield) as an off-white solid. LCMS (ESI)=m/z 357.2 $[M+H]^+$.

Step 3: To a stirred solution of 1-[5-fluoro-1-methyl-6-(4-oxocyclohexen-1-yl)indazol-3-yl]hexahydropyrimidine-2,4-dione (700 mg, 1.96 mmol) in 1,4-dioxane (10 mL) was charged palladium hydroxide on carbon, 20 wt. % 50% water (551.75 mg, 3.93 mmol). The reaction mixture was bubbled with hydrogen gas for 10 minutes and then subjected to hydrogenation (1 atm) at room temperature for 16 hours. After completion, the reaction mixture was purged with nitrogen, catalyst was removed by filtration through celite pad. The filtrate was concentrated under reduced pressure to afford crude which was purified by silica gel column chromatography using 100% of ethyl acetate as eluent to afford 1-[5-fluoro-1-methyl-6-(4-oxocyclohexyl)indazol-3-yl]hexahydropyrimidine-2,4-dione (300 mg, 734.25 μmol, 37% yield) as an off-white solid. LCMS (ESI)=m/z 359.4 $[M+H]^+$.

Step 4: To the stirred solution of amberlsyt basified amine (3R)-3-[6-[2-cyano-3-[[ethyl(methyl)sulfamoyl]amino]-6-fluoro-phenoxy]-4-oxo-quinazolin-3-yl]-1-oxa-8-azaspiro [4.5]decane (174.03 mg, 259.51 μmol) in methanol (2 mL) and 1-[5-fluoro-1-methyl-6-(4-oxocyclohexyl)indazol-3-yl] hexahydropyrimidine-2,4-dione (200 mg, 519.02 μmol) was added acetic acid (15.58 mg, 259.51 μmol, 14.86 μL) and the reaction mixture was heated at 75° C. for 4 h. Then MP-Cyanoborohydride (100 mg, 259.51 μmol) was added and the reaction was stirred for another 2 h at 75° C. After completion of the reaction, the reaction mixture was filtered through celite and concentrated under reduced pressure to yield the crude product, which was purified by reverse phase column chromatography (0.1% ammonium bicarbonate in water:ACN).

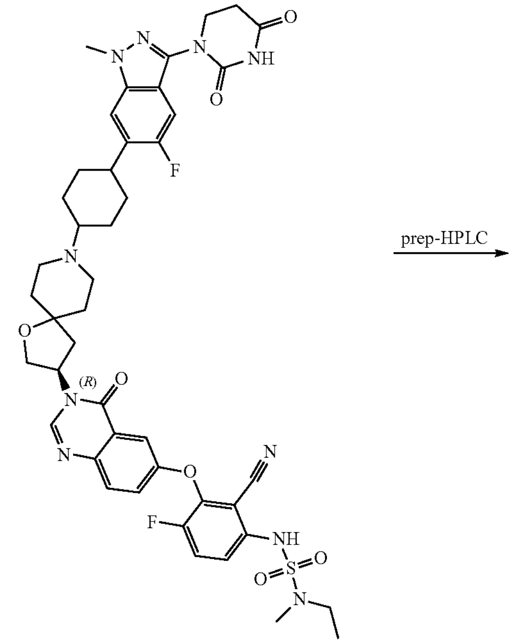

-continued

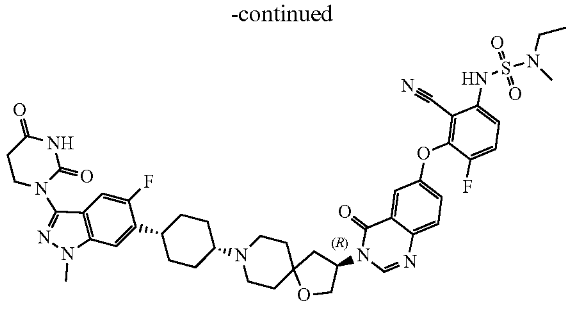

Example 212
cis-isomer

+

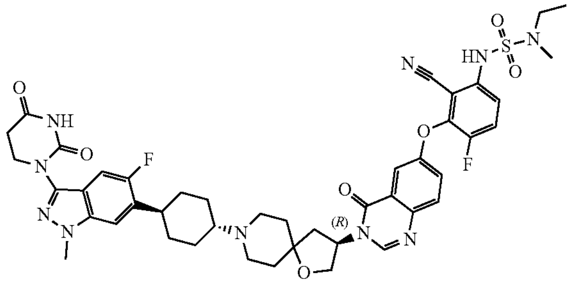

Example 213
trans-isomer

The product was further purified by prep-HPLC, and the separated diastereomers (fraction 1 and 2) were lyophilized to afford the trans-isomer (3R)-3-[6-[2-cyano-3-[[ethyl (methyl)sulfamoyl]amino]-6-fluoro-phenoxy]-4-oxo-quinazolin-3-yl]-8-[4-[3-(2,4-dioxohexahydropyrimidin-1-yl)-5-fluoro-1-methyl-indazol-6-yl]cyclohexyl]-1-oxa-8-azaspiro[4.5]decane (12.84 mg, 13.89 μmol, 5.35% yield) and the cis-isomer (3R)-3-[6-[2-cyano-3-[[ethyl(methyl)sulfamoyl]amino]-6-fluoro-phenoxy]-4-oxo-quinazolin-3-yl]-8-[4-[3-(2,4-dioxohexahydropyrimidin-1-yl)-5-fluoro-1-methyl-indazol-6-yl]cyclohexyl]-1-oxa-8-azaspiro[4.5] decane (11.1 mg, 11.70 μmol, 4.51% yield) as off white solids.

Example 212: LCMS (ESI): m/z 899.2 $[M+H]^+$. $^1$HNMR (400 MHz, DMSO-$d_6$): δ=10.56 (s, 1H), 8.70 (s, 1H), 8.33 (s, 1H), 7.76 (d, J=8.80 Hz, 1H), 7.65 (dd, J=3.20, 9.00 Hz, 1H), 7.25-7.55 (m, 2H), 7.49 (d, J=5.60 Hz, 1H), 7.39 (d, J=11.20 Hz, 1H), 7.34 (d, J=2.80 Hz, 1H), 5.26-5.32 (m, 1H), 3.96-4.22 (m, 2H), 4.03 (s, 3H), 3.91 (t, J=6.40 Hz, 2H), 2.95-3.21 (m, 4H), 3.40-3.61 (m, 1H), 2.75 (t, J=10.80 Hz, 2H), 2.38-2.65 (m, 6H), 1.52-2.21 (m, 14H), 1.03 (t, J=7.20 Hz, 3H) ppm.

Example 213: LCMS (ESI): m/z 899.3 $[M+H]^+$. $^1$HNMR (400 MHz, DMSO-$d_6$): δ=10.56 (s, 1H), 9.05 (s, 1H), 8.32 (s, 1H), 7.77 (d, J=8.80 Hz, 1H), 7.65 (dd, J=2.80, 8.80 Hz, 1H), 7.54 (d, J=6.00 Hz, 1H), 7.21-7.42 (m, 2H), 7.39 (d, J=10.80 Hz, 1H), 7.34 (d, J=2.80 Hz, 1H), 5.24-5.35 (m, 1H), 4.11-4.28 (m, 2H), 4.00 (s, 3H), 3.91 (t, J=6.80 Hz, 2H), 2.82-3.21 (m, 6H), 2.71-2.81 (m, 2H), 2.38-2.68 (m, 5H), 1.60-2.25 (m, 14H), 1.03 (t, J=7.20 Hz, 3H) ppm.

Example 214
(3R)-3-[6-[2-cyano-3-[[ethyl(methyl)sulfamoyl] amino]-6-fluoro-phenoxy]-4-oxo-quinazolin-3-yl]-8-[2-[1-[3-(2,4-dioxohexahydropyrimidin-1-yl)-5-fluoro-1-isopropyl-indazol-6-yl]-4-hydroxy-4-piperidyl]acetyl]-1-oxa-8-azaspiro[4.5]decane
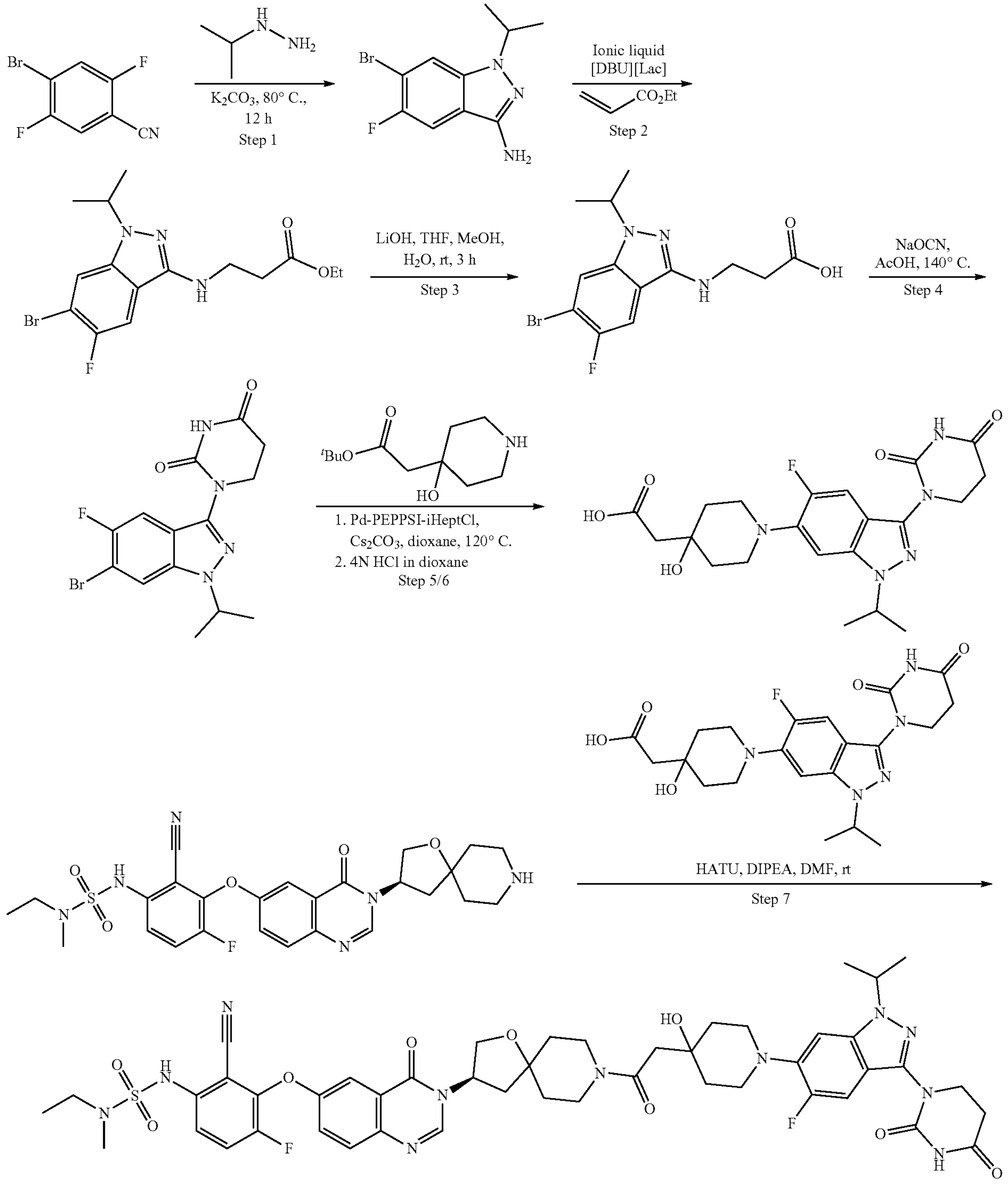
Step 1: To a solution of 4-bromo-2,5-difluoro-benzonitrile (10 g, 45.87 mmol) in DMF (100 mL) was added isopropyihydrazine hydrochloride (5.07 g, 45.87 mmol) and potassium carbonate, anhydrous, 99% (15.85 g, 114.68 mmol) at room temperature. The resulting solution was heated to 80° C. for 12 hours and monitored by LC-MS and TLC. After completion, the reaction mixture was quenched with water (30 ml) and extracted with ethyl acetate (2×60 mL). The organic layer was washed with brine (15 mL), dried over sodium sulfate and concentrated under reduced pressure. The crude product was purified by column chromatography using 60-120 mesh silica gel and 0-40% ethyl acetate in pet ether as eluent to afford 6-bromo-5-fluoro-1-isopropyl-indazol-3-amine (3.0 g, 10.65 mmol, 23.23% yield) as a brownish solid. LCMS (ESI)=m/z 272.1 $[M+H]^+$.

Step 2: To prepare [DBU][LAC]ionic liquid was prepared; 1 equiv. of lactic acid was added to 1 equiv. of DBU in a 10 ml single neck round bottom flask at room temperature under nitrogen-atmosphere. The resulting solution was stirred at this temperature for 12 hours. The obtained thicky solution was directly used for in the following Michael addition.

To a solution of 6-bromo-5-fluoro-1-isopropyl-indazol-3-amine (1.0 g, 3.67 mmol) in [DBU][LAC] ionic liquid (1.0 g, 3.67 mmol) was added ethyl acrylate (2.58 g, 25.72 mmol, 2.79 mL) at room temperature under nitrogen atmosphere. The resulting solution was heated to 97° C. for 72 hours and monitored by LC-MS/TLC. After completion, the resulting solution was quenched with water (10 ml) and extracted with ethyl acetate (2×20 mL). The organic layer was dried over sodium sulfate and concentrated under reduced pressure. The crude product was purified by silica gel (25 g SNAP) column chromatography using ethyl acetate-petroleum ether (0-60%) as eluent to afford ethyl 3-[(6-bromo-5-fluoro-1-isopropyl-indazol-3-yl)amino]propanoate (0.5 g, 1.21 mmol, 32.95% yield) as a brownish solid. LCMS (ESI)=m/z 372.4 $[M+H]^+$ Step 3: A solution of ethyl 3-[(6-bromo-5-fluoro-1-isopropyl-indazol-3-yl)amino]propanoate (0.2 g, 537.30 μmol) in THF (2 mL), methanol (0.5 mL) and water (0.5 mL) was added lithium hydroxide monohydrate, 98% (33.82 mg, 805.95 μmol, 22.40 μL) at 28° C. The resulted mixture was stirred at room temperature for 3 hours and monitored by TLC/LC-MS. After completion, the reaction solvent was removed under reduced pressure. The resulting residue was diluted with water and acidified with acetic acid to pH=5 to get a solid, which was filtered and dried to afford 3-[(6-bromo-5-fluoro-1-isopropyl-indazol-3-yl)amino]propanoic acid (0.14 g, 376.71 μmol, 70.11% yield) as a light brown solid. LCMS (ESI)=m/z 344.1 $[M+H]^+$ Step 4: To a stirred solution of 3-[(6-bromo-5-fluoro-1-isopropyl-indazol-3-yl)amino]propanoic acid (50 mg, 145.27 μmol) in acetic acid (1 mL) was added sodium cyanate (18.89 mg, 290.55 μmol) at room temperature. The reaction mixture was stirred at 140° C. for 16 hours. The progress of the reaction was monitored by TLC. After completion of the reaction, the reaction mixture was concentrated in vacuo to afford 1-(6-bromo-5-fluoro-1-isopropyl-indazol-3-yl)hexahydropyrimidine-2,4-dione (70 mg, 42.87 μmol, 29.51% yield) as a brown liquid. LCMS (ESI): m/z 371.2 $[M+H]^+$ Step 5: A solution of 1-(6-bromo-5-fluoro-1-isopropyl-indazol-3-yl)hexahydropyrimidine-2,4-dione (90 mg, 243.78 μmol) in dioxane (2 mL) was added cesium carbonate (198.57 mg, 609.44 μmol) and tert-butyl 2-(4-hydroxy-4-piperidyl)acetate (62.98 mg, 292.53 μmol) at room temperature under nitrogen atmosphere. The reaction mixture was degassed with $N_2$ for 10 min before Pd-PEPPSI-IHeptCl 3-chloropyridine (11.86 mg, 12.19 μmol) was added at room temperature. The reaction was then heated at 110° C. for 16 h. After completion of the reaction, the reaction mixture was diluted with water (5 mL) and extracted with ethyl acetate (2×30 mL). The organic layer was dried over sodium sulfate and concentrated under reduced pressure to yield the crude product, which was purified by column chromatography (230-400 mesh silica gel) using 60% ethyl acetate in pet ether as eluent to afford tert-butyl 2-[1-[3-(2,4-dioxohexahydropyrimidin-1-yl)-5-fluoro-1-isopropyl-indazol-6-yl]-4-hydroxy-4-piperidyl]acetate (40 mg, 78.54 μmol, 32.22% yield) as an off-white solid. UPLC-MS (ESI): m/z 504.7 $[M+H]^+$.

Step 6: To a solution of tert-butyl 2-[1-[3-(2,4-dioxohexahydropyrimidin-1-yl)-5-fluoro-1-isopropyl-indazol-6-yl]-4-hydroxy-4-piperidyl]acetate (40 mg, 79.43 μmol) in DCM (1 mL) was added 4.0M hydrogen chloride solution in dioxane (57.92 mg, 1.59 mmol, 72.41 μL) at 0° C. under nitrogen atmosphere. The resulting mixture was stirred at RT for 12 h. After completion of the reaction, the reaction mixture was concentrated under reduced pressure to give 2-[1-[3-(2,4-dioxohexahydropyrimidin-1-yl)-5-fluoro-1-isopropyl-indazol-6-yl]-4-hydroxy-4-piperidyl]acetic acid (38 mg, 72.29 μmol, 91.01% yield, HCl salt) as a brown semisolid. LC-MS (ESI): m/z 448.2 $[M+H]^+$.

Step 7: To a stirred solution of (3R)-3-[6-[2-cyano-3-[[ethyl(methyl)sulfamoyl]amino]-6-fluoro-phenoxy]-4-oxo-quinazolin-3-yl]-1-oxa-8-azaspiro[4.5]decane (50 mg, 84.31 μmol, HCl salt), 2-[1-[3-(2,4-dioxohexahydropyrimidin-1-yl)-5-fluoro-1-isopropyl-indazol-6-yl]-4-hydroxy-4-piperidyl]acetic acid (37.72 mg, 77.96 μmol, HCl salt) in DMF (1 mL) were added HATU (32.06 mg, 84.31 μmol) followed by DIPEA (54.48 mg, 421.54 μmol, 73.42 μL) at room temperature. The reaction mixture was stirred at this temperature for 4 h. After completion of reaction, the reaction mixture was diluted with water (4 mL) and extracted with 10% isopropanol/dichloromethane (2×4 mL). The combined organic layers were dried over sodium sulfate, filtered and concentrated under vacuum to give the crude product, which was purified by reverse phase column chromatography (ammonium bicarbonate buffer in CAN) to afford (3R)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-isopropyl-indazol-6-yl]-4-hydroxy-4-piperidyl]acetyl]-1-oxa-8-azaspiro[4.5]decane (25 mg, 24.67 μmol, 29.26% yield) as an off-white solid. LCMS (ESI): m/z 986.2 $[M+H]^+$. $^1H$-NMR (400 MHz, DMSO-$d_6$): δ=10.69 (s, 1H), 10.20 (s, 1H), 8.36 (s, 1H), 7.78-7.80 (m, 2H), 7.69 (dd, J=2.40, 9.00 Hz, 1H), 7.44 (d, J=12.40 Hz, 2H), 7.36 (d, J=2.80 Hz, 1H), 7.08 (d, J=7.20 Hz, 1H), 5.38-5.22 (m, 1H), 5.01 (s, 1H), 4.70-4.72 (m, 1H), 4.12-4.15 (m, 3H), 3.90 (m, 1H), 3.76-3.72 (m, 1H), 3.64-3.69 (m, 2H), 3.12-3.18 (m, 5H), 2.99 (t, J=10.40 Hz, 2H), 2.86 (t, J=6.80 Hz, 3H), 2.75 (s, 3H), 2.38-2.40 (m, 1H) 2.08 (m, 1H), 1.68-1.79 (m, 9H), 1.42-1.46 (m, 6H), 1.05 (t, J=7.20 Hz, 3H) ppm.

General scheme for Scaffold C
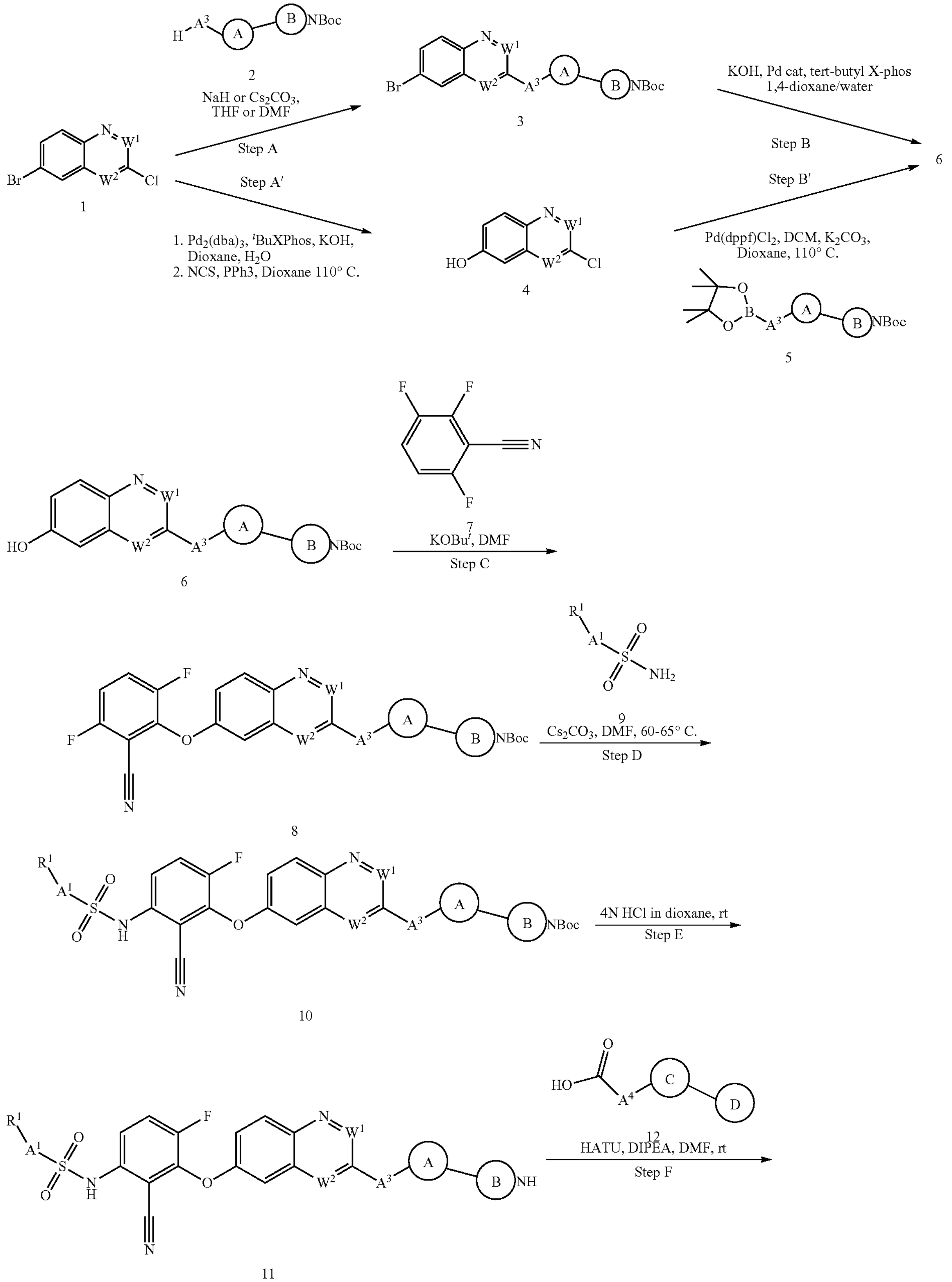

-continued

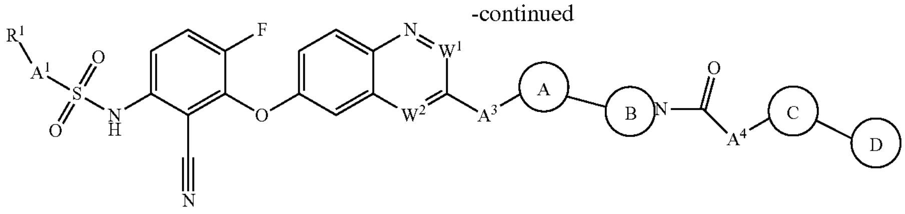

13

Step A—General Procedure for $S_NAr$ Substitution (Procedure C-A): To a stirred solution of amine (2) (1 eq) in THF was added sodium hydride (60% dispersion in mineral oil, 1.5 eq.) portion wise at 0° C. under inert atmosphere. Alternatively, $Cs_2CO_3$ and DMF could be used instead of sodium hydride and THF. After 30 minutes, 7-bromo-2-chloro-quinoxaline or a suitable derivative thereof (1) (1 eq.) was added to the reaction mixture at 0° C. and the reaction stirred at room temperature for 4 h. After completion, the reaction was quenched dropwise with water and extracted with ethyl acetate. The combined organic layers were washed with brine solution, dried over anhydrous sodium sulfate, and concentrated under reduced pressure to afford intermediate (3).

Step B—General Procedure for Hydroxylation (Procedure C—B): To a stirred solution of intermediate (3) (1 eq.) in 1,4-dioxane were added KOH (1 eq.) dissolved in water, and the ligand di-tert-butyl Xphos or $Me_4{}^t$ButylXphos (0.01-0.05 eq.). The resulting reaction mixture was degassed with nitrogen for 10 minutes. Then $Pd_2(dba)_3$ (0.01-0.05 eq.) was added and the reaction was heated to around 100° C. for 16 h. After completion, the reaction mixture was cooled to room temperature and filtered through celite, washing with ethyl acetate. The combined filtrate was concentrated under vacuum to yield quinoxaline intermediate (6).

Step A'—General Procedure for Hydroxylation (Procedure C-A'):

Step A'-1: A stirred solution of KOH (2.5 eq.) and 7-bromo-2-chloro-quinoxaline or a suitable derivative thereof (1) (1 eq.) in mixture of water and 1,4-dioxane in a sealed tube was degassed with nitrogen for 5 minutes. $Pd_2dba_3$ (0.1 eq.) and tBuXPhos (0.1 eq.) were added to the reaction mixture and the resulting mixture was stirred at 100° C. for 16 h in a closed sealed tube. After completion, the reaction mixture was diluted with 1M KOH solution and ethyl acetate. The layers were separated, and the aqueous layer was acidified to pH ~3 with 1.5N HCl solution. The obtained solid was filtered and dried to afford the intermediate quinoxaline-2,7-diol or a derivative thereof. Step A'—2: To a stirred solution of triphenylphosphine (2.5 eq.) in 1,4-dioxane was added N-Chlorosuccinimide (NCS) (2.5 eq.) at room temperature. The resulting reaction mixture was stirred at room temperature for 0.5 h. To this, quinoxaline-2,7-diol intermediate (1 eq.) was added and stirred at 110° C. for 4 h. After completion, the reaction mixture was diluted with water and extracted with ethyl acetate. The combined organic layer was washed with brine solution, dried over anhydrous sodium sulfate, filtered and concentrated under reduced pressure. The crude compound was purified by silica gel flash column chromatography while eluting with 0-30% ethyl acetate in petroleum ether as eluent to afford the intermediate 3-chloroquinoxalin-6-ol or a derivative thereof (4).

Step B'—General Procedure for Cross Coupling (Procedure C—B'): To a stirred solution of boronic ester (5) (2 eq.) and 3-chloroquinoxalin-6-ol intermediate (4) (1 eq.) in 1,4-dioxane and water was added potassium carbonate (2.5 eq.) at room temperature under nitrogen atmosphere. The reaction mixture was degassed with nitrogen for 15 min. $Pd(dppf)Cl_2{\cdot}CH_2Cl_2$ (0.1 eq.) was added and the reaction mixture was stirred at 100° C. for 16 h. After completion, the reaction mixture was cooled to room temperature, filtered through celite and washed with ethyl acetate. The combined filtrate was concentrated under reduced pressure to afford crude, which was purified by silica gel flash column chromatography with 45-50% ethyl acetate in petroleum ether as a eluent to afford quinoxaline intermediate (6).

Step C—General Procedure for O-Arylation (Procedure C-C): To a stirred solution of quinoxaline intermediate (6, 1 eq.) in N,N-Dimethylformamide/THF was added cesium carbonate/potassium tert-butoxide (1.1 eq.) and commercially available 2,3,6-trifluorobenzonitrile (7, 1.1 eq.) at room temperature. The resulting reaction mixture was stirred at room temperature for 16 h. After completion, the reaction mixture was quenched with water and extracted with ethyl acetate. Combined organic layers were washed with brine, dried over sodium sulfate, and concentrated under vacuum to yield crude. Crude compound was purified by silica gel flash column chromatography using 50% ethyl acetate in petroleum ether as eluent to yield intermediate (8).

Step D—General Procedure for Sulfomoylation (Procedure C-D): To a solution of intermediate (8) (1 eq.) in N,N-Dimethylformamide was added cesium carbonate (2.5 eq.) and sulfamoyl derivative (9) (commercially available or as described herein in methods I and II; 2 eq.) at room temperature. The resulting reaction mixture was stirred at 60° C. for 16 h. After completion of the reaction, the reaction mixture was cooled to room temperature, diluted with water and extracted with ethyl acetate. The combined organic layers were washed with brine solution, dried over sodium sulfate, filtered, and concentrated under reduced pressure to afford the crude. The crude compound was purified by silica gel flash column chromatography with 20 to 50% ethyl acetate in petroleum ether as eluent to afford sulfonamide intermediate (10).

Note: For majority of reactions, after addition of water, precipitation of solids was observed. These solids were filtered through filter paper. Filtrate was extracted by ethyl acetate. Combined organic layers were washed with brine, dried over sodium sulfate, and concentrated under vacuum to yield sulfonamide intermediate 10 with decent purity.

Step E—General Procedure for N-Boc Deprotection (Procedure C-E): A solution of sulfonamide intermediate (10, 1 eq.) was taken in dichloromethane and added TFA (5 eq.) or 4N HCl in dioxane (10 eq.) at 0° C. The resulted reaction mixture was stirred at room temperature for 2 h. After completion, reaction solvent was removed under reduced pressure get crude product. Crude compound was triturated with methyl t-butyl ether (MTBE) to afford targeting ligand (11).

Step F—General Procedure for Acid-Amine Coupling (Procedure C—F): To a stirred solution of acid (12, 1 eq.) and amine (11, 1 eq.) in N,N-Dimethylformamide (4 mL/mmol) was added N,N-diisopropylethylamine (4 eq.) at room temperature under nitrogen, followed by the addition of HATU (1.1 eq.) at same temperature. The reaction mixture was stirred at room temperature for 12 h. After completion, the reaction mixture was diluted with water and extracted with 10% isopropanol in dichloromethane. Combined organic layers were dried over sodium sulfate, filtered and concentrated under reduced pressure to afford crude compound. The crude compound was purified by reverse phase purification and fractions were lyophilized to afford the target compound (13).

Example 215

7-[2-cyano-3-[[ethyl(methyl)sulfamoyl]amino]-6-fluorophenoxy]-2-[4-[4-[2-[4-[4-[(2,6-dioxopiperidin-3-yl)amino]-2-fluorophenyl]piperidin-1-yl]acetyl]-1,4-diazepan-1-yl]pyrazol-1-yl]quinoxaline

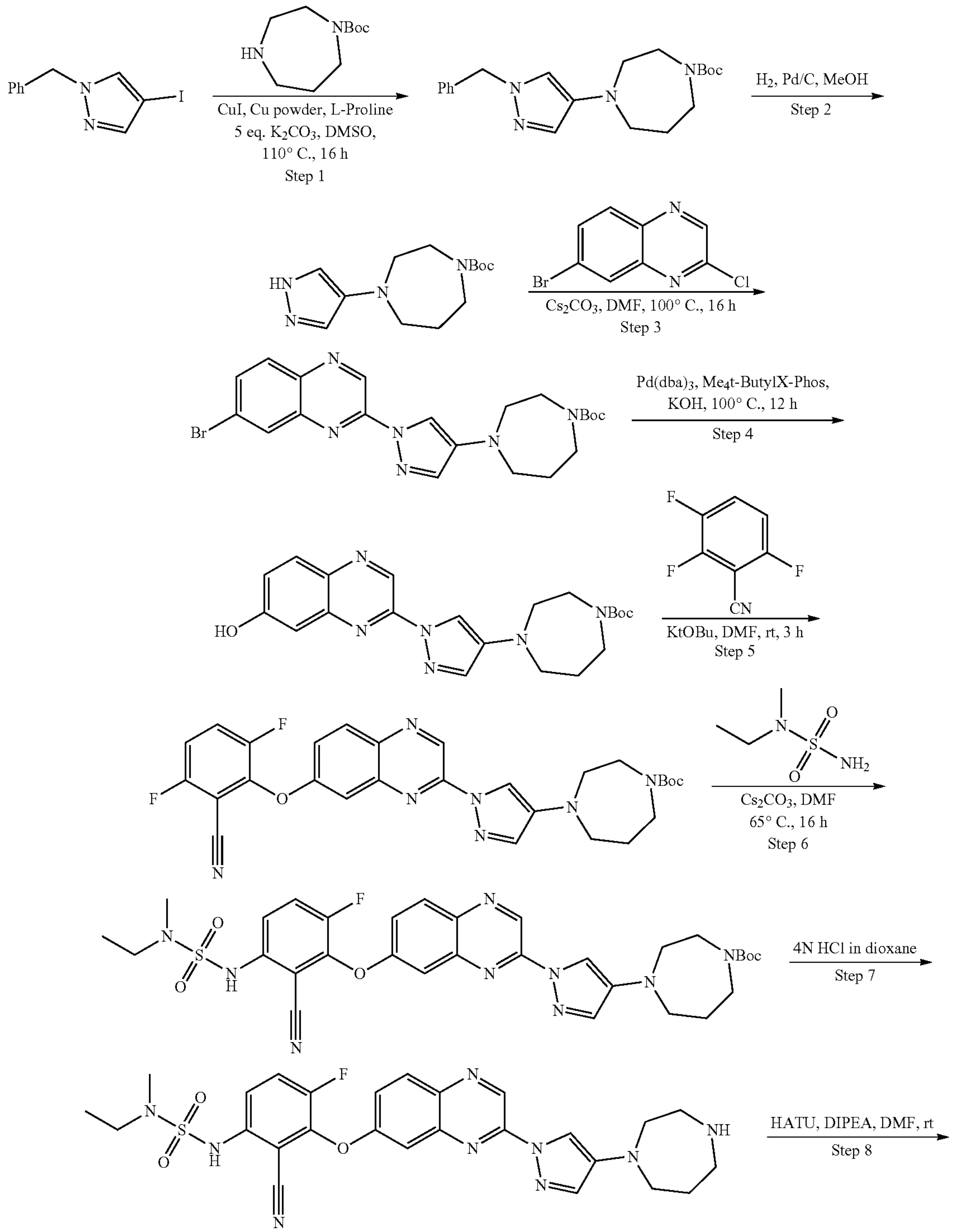

-continued

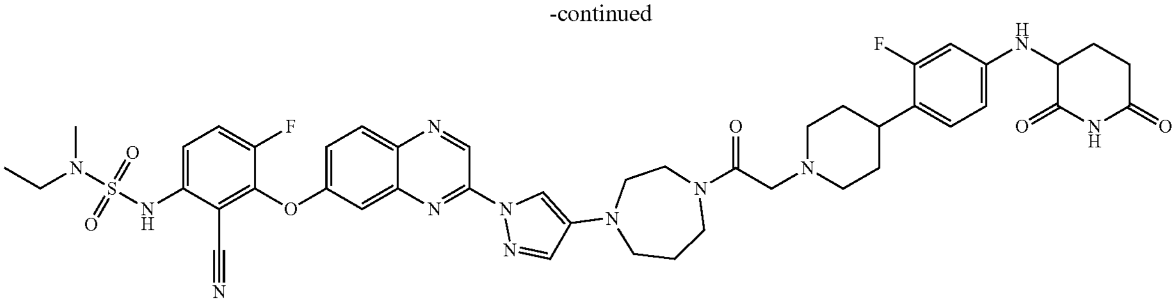

Step 1: A solution of 1-benzyl-4-iodo-pyrazole (2 g, 7.04 mmol) in dimethyl sulfoxide (20 mL) was added to a seal tube followed by anhydrous potassium carbonate (2.92 g, 21.12 mmol) at room temperature. The reaction mixture was degassed with nitrogen for 10 minutes then added Copper (I) iodide (134.07 mg, 703.99 μmol, 23.86 μL), Copper powder (44.70 mg, 703.99 μmol) and L-Proline (162.10 mg, 1.41 mmol, 119.19 μL) at room temperature. The resulting reaction mixture was stirred at 110° C. for 16 h after the tube was sealed. After completion, the reaction mixture was cooled to room temperature, diluted with water (500 mL) and extracted with ethyl acetate (3×300 mL). The combined organic layers were washed with brine solution (200 mL), dried over sodium sulfate, filtered, and concentrated under reduced pressure to afford the crude material. The crude compound was purified by silica gel flash column chromatography with 40-50% ethyl acetate in petroleum ether as eluent to afford tert-butyl 4-(1-benzylpyrazol-4-yl)-1,4-diazepane-1-carboxylate (800 mg, 1.99 mmol, 29% yield) as a brown viscous compound. LCMS m/z (ESI): 357.0 $[M+H]^+$ Step 2: To a stirred solution of tert-butyl 4-(1-benzylpyrazol-4-yl)-1,4-diazepane-1-carboxylate (800 mg, 2.24 mmol) in methanol (20 mL) was added 10% Palladium on carbon (300 mg, 2.82 mmol). The solution was saturated with hydrogen by bubbling hydrogen gas through for 10 minutes and then stirred under a hydrogen (1 atm) at 60° C. for 10 h. After completion, the reaction mixture was purged with nitrogen, catalyst was removed by filtration through celite pad. The filtrate was concentrated under reduced pressure. The crude compound was purified by silica gel flash column chromatography with 30-40% ethyl acetate in petroleum ether as the eluent to afford to afford the tert-butyl 4-(1H-pyrazol-4-yl)-1,4-diazepane-1-carboxylate (350 mg, 1.25 mmol, 56% yield) as a brown solid. LCMS m/z (ESI): 267.2 $[M+H]^+$ Step 3: A solution of tert-butyl 4-(1H-pyrazol-4-yl)-1,4-diazepane-1-carboxylate (300 mg, 1.13 mmol) in N,N-Dimethylformamide (6 mL) was taken in a sealed tube and cesium carbonate (440.40 mg, 1.35 mmol) was added followed by 7-bromo-2-chloro-quinoxaline (274.26 mg, 1.13 mmol) at room temperature under a nitrogen atmosphere. The resulting reaction mixture was stirred at 100° C. for 16 h. After completion, the reaction mixture was cooled to room temperature, diluted with water (100 mL) and extracted with ethyl acetate (3×70 mL). The combined organic layers were washed with brine solution (100 mL), dried over sodium sulfate, filtered, and concentrated under reduced pressure to afford the crude. The crude compound was purified by silica gel flash column chromatography with 20 to 30% ethyl acetate in petroleum ether as a eluent to afford tert-butyl 4-[1-(7-bromoquinoxalin-2-yl)pyrazol-4-yl]-1,4-diazepane-1-carboxylate (250 mg, 332.72 μmol, 30% yield) as a yellow solid. LCMS m/z (ESI): 416.8 $[M+H-{}^tBu]^+$ Step 4: A solution of tert-butyl 4-[1-(7-bromoquinoxalin-2-yl)pyrazol-4-yl]-1,4-diazepane-1-carboxylate (200 mg, 422.51 μmol) in Dioxane (4 mL) and water (1 mL) was added to a sealed tube followed by potassium Hydroxide (59.26 mg, 1.06 mmol, 29.05 μL) at room temperature under nitrogen atmosphere. The reaction mixture was degassed with nitrogen for 10 minutes, then dibenzylideneacetone palladium(0) (7.74 mg, 8.45 μmol) was added followed by di-tert-butyl-[2,3,4,5-tetramethyl-6-[2,4,6-tri(propan-2-yl) phenyl]phenyl]phosphane (10.16 mg, 21.13 μmol) at the same temperature. The resulting reaction mixture was heated to 100° C. for 16 h. After completion, the reaction mixture was cooled to room temperature, diluted with water (50 mL) and extracted with ethyl acetate (3×70 mL). The combined organic layers were washed with brine solution (100 mL), dried over sodium sulfate, filtered and concentrated under reduced pressure to afford the crude material. The crude compound was purified by silica gel flash column chromatography with 20-30% ethyl acetate in petroleum ether as the eluent to afford tert-butyl 4-[1-(7-hydroxyquinoxalin-2-yl)pyrazol-4-yl]-1,4-diazepane-1-carboxylate (100 mg, 236.32 μmol, 56% yield) as a yellow solid. LCMS m/z (ESI): 411.1 $[M+H]^+$ Step 5: To a stirred solution of tert-butyl 4-[1-(7-hydroxyquinoxalin-2-yl)pyrazol-4-yl]-1,4-diazepane-1-carboxylate (100 mg, 243.62 μmol) in N,N-Dimethylformamide (5 mL) was added potassium tert-butoxide (30.07 mg, 267.99 μmol) followed by 2,3,6-trifluorobenzonitrile (42.10 mg, 267.99 μmol, 30.95 μL) at 0° C. under an inert atmosphere. The reaction was stirred at room temperature for 3 h. After completion, the reaction mixture was diluted with cold water (50 mL) and extracted with ethyl acetate (3×60 ml). The combined organic layers were washed with cold water (2×100 mL), dried over anhydrous sodium sulfate and concentrated under reduced pressure to afford tert-butyl 4-[1-[7-(2-cyano-3,6-difluoro-phenoxy)quinoxalin-2-yl] pyrazol-4-yl]-1,4-diazepane-1-carboxylate (130 mg, 170.94 μmol, 70% yield) as a yellow solid. LCMS m/z (ESI): 492.1 $[M+H]^+$ Step 6: To a stirred solution of compound tert-butyl 4-[1-[7-(2-cyano-3,6-difluoro-phenoxy)quinoxalin-2-yl] pyrazol-4-yl]-1,4-diazepane-1-carboxylate (130 mg, 237.42 μmol) in N,N-Dimethylformamide (7 mL) was added cesium carbonate (193.39 mg, 593.55 μmol) and [methyl (sulfamoyl)amino]ethane (72.18 mg, 522.32 μmol) at room temperature. The reaction was then stirred at 65° C. for 16 h. After completion, the reaction mixture was cooled to room temperature and extracted with water (50 mL) and ethyl acetate (3×50 mL). The combined organic layers were dried over anhydrous sodium sulfate and concentrated under reduced pressure to afford tert-butyl 4-[1-[7-[2-cyano-3-[[ethyl(methyl)sulfamoyl]amino]-6-fluoro-phenoxy]quinoxalin-2-yl]pyrazol-4-yl]-1,4-diazepane-1-carboxylate (130 mg, 161.29 μmol, 68% yield) as a yellow solid. LCMS m/z (ESI): 664.2 $[M-H]^-$ Step 7: To a stirred solution of tert-butyl 4-[1-[7-[2-cyano-3-[[ethyl(methyl)sulfamoyl]amino]-6-fluoro-phenoxy]quinoxalin-2-yl]pyrazol-4-yl]-1,4-diazepane-1-carboxylate (130 mg, 195.27 μmol) in dichloromethane (10 mL) was added 4M hydrogen chloride solution in dioxane (71.20 mg, 1.95 mmol, 89.00 μL) at 0-5° C. The reaction mixture was stirred at room temperature for 2 h. After completion, the reaction mixture was concentrated under reduced pressure to afford the HCl salt of 7-[2-cyano-3-[[ethyl(methyl)sulfamoyl]amino]-6-fluoro-phenoxy]-2-[4-(1,4-diazepan-1-yl)pyrazol-1-yl]quinoxaline (100 mg, 157.79 μmol, 81% yield) as a yellow solid. LCMS m/z (ESI): 566.1 $[M+H]^+$ Step 8: The target compound was prepared via HATU mediated acid-amine coupling reaction (Procedure C-E). The amide coupling was carried out using 7-[2-cyano-3-[[ethyl(methyl)sulfamoyl]amino]-6-fluoro-phenoxy]-2-[4-(1,4-diazepan-1-yl)pyrazol-1-yl]quinoxaline (100 mg, 166.09 μmol), N,N-diisopropylethylamine (107.33 mg, 830.45 μmol, 144.65 μL), 2-[4-[4-[(2,6-dioxo-3-piperidyl)amino]-2-fluoro-phenyl]-1-piperidyl]acetic acid as its HCl salt (73.05 mg, 182.70 μmol) and HATU (63.15 mg, 166.09 μmol). The crude compound was purified by reverse phase purification, eluted with 25 to 30% acetonitrile in 0.1% FORMIC ACID in water to afford 7-[2-cyano-3-[[ethyl(methyl)sulfamoyl]amino]-6-fluoro-phenoxy]-2-[4-[4-[2-[4-[4-[(2,6-dioxo-3-piperidyl)amino]-2-fluoro-phenyl]-1-piperidyl]acetyl]-1,4-diazepan-1-yl]pyrazol-1-yl]quinoxaline (32.29 mg, 33.07 μmol, 20% yield) as a yellow solid. LCMS m/z (ESI): 911.3 $[M+H]^+$ $^1$HNMR (400 MHz, DMSO-$d_6$): δ=10.80 (s, 1H), 9.42 (s, 1H), 8.13-8.17 (m, 2H), 7.88 (d, J=17.20 Hz, 1H), 7.70-7.80 (m, 1H), 7.67 (ddd, J=1.20, 2.80, 9.00 Hz, 1H), 7.49-7.42 (m, 1H), 7.09 (s, 1H), 6.75-6.85 (m, 1H), 6.41-6.46 (m, 2H), 6.09 (d, J=7.60 Hz, 1H), 4.30-4.34 (m, 1H), 4.16-4.30 (m, 1H), 3.74 (s, 1H), 3.60 (s, 2H), 3.42-3.55 (m, 6H), 3.35-3.24 (m, 1H), 3.14 (q, J=6.80 Hz, 2H), 2.95-3.05 (m, 2H), 2.60-2.81 (m, 2H), 2.75 (s, 3H), 2.47-2.62 (m, 2H), 2.06-2.09 (m, 1H), 1.80-2.01 (m, 5H), 1.63-1.78 (m, 2H), 1.08 (t, J=7.20 Hz, 3H).

Example 216

7-[2-cyano-3-[[ethyl(methyl)sulfamoyl]amino]-6-fluorophenoxy]-2-[[1-[2-[4-[4-[(2,6-dioxopiperidin-3-yl)amino]-2-fluorophenyl]piperidin-1-yl]acetyl]piperidin-4-yl]methoxy]quinoxaline

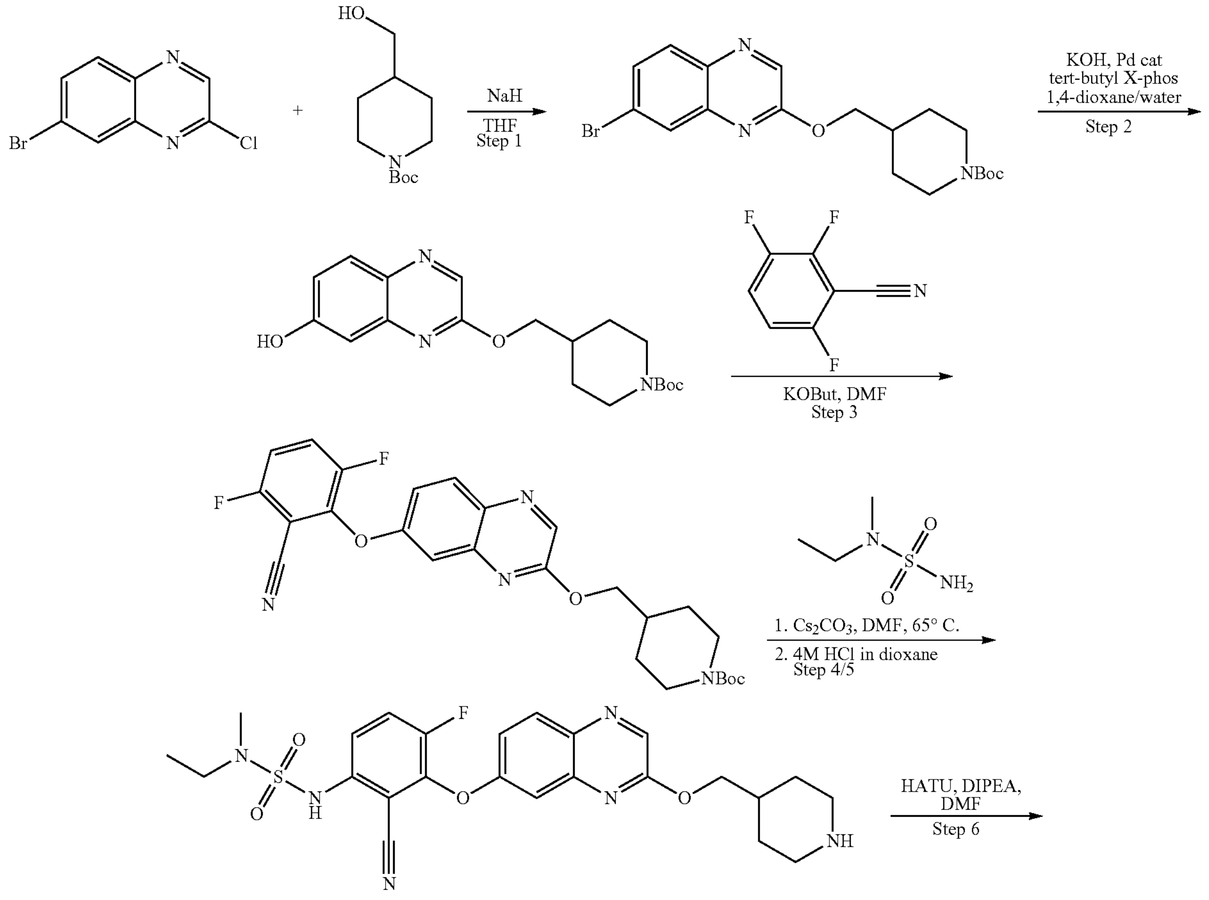

-continued

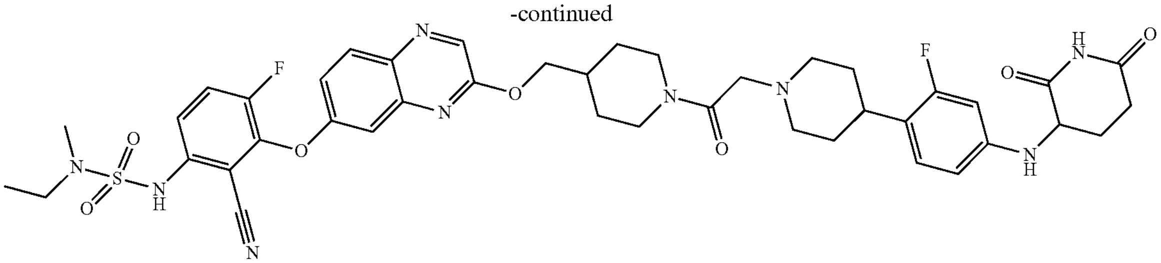

Step 1: To a stirred solution of tert-butyl 4-(hydroxymethyl)piperidine-1-carboxylate (200 mg, 928.98 μmol) in THF (5 mL) was added sodium hydride (60% dispersion in mineral oil, 32.04 mg, 1.39 mmol) portion wise at 0° C. under inert atmosphere. After 30 minutes, 7-bromo-2-chloro-quinoxaline (226.20 mg, 928.98 μmol) was added to the reaction mixture at 0° C. and the reaction stirred at room temperature for 4 h. After completion, the reaction was quenched dropwise with water and extracted with ethyl acetate (2×10 mL). The combined organic layers were washed with brine solution (15 mL), dried over anhydrous sodium sulfate, and concentrated under reduced pressure to afford tert-butyl 4-[(7-bromoquinoxalin-2-yl)oxymethyl]piperidine-1-carboxylate (250 mg, 562.38 μmol, 61% yield). LCMS m/z (ESI): 366.0 $[M+H-^tBu]^+$ Step 2: To a stirred solution of tert-butyl 4-[(7-bromoquinoxalin-2-yl)oxymethyl]piperidine-1-carboxylate (0.1 g, 236.79 μmol) in 1,4-dioxane (1 mL) were added KOH (13.29 mg, 236.79 μmol, 6.51 μL) dissolved in water (1 mL), and di-tert-butyl Xphos (5.03 mg, 11.84 μmol). The resulting reaction mixture was degassed with nitrogen for 10 minutes. Then $Pd_2(dba)_3$ (2.17 mg, 2.37 μmol) was added and the reaction was heated to 100° C. for 16 h. After completion, the reaction mixture was cooled to room temperature and filtered through celite, washing with ethyl acetate (5 mL). The combined filtrate was concentrated under vacuum to yield tert-butyl 4-[(7-hydroxyquinoxalin-2-yl)oxymethyl]piperidine-1-carboxylate (0.1 g, 250.40 μmol, 100% yield) as a white solid. LCMS m/z (ESI): 358.2 $[M-H]^-$ Step 3: To a stirred solution of tert-butyl 4-[(7-hydroxyquinoxalin-2-yl)oxymethyl]piperidine-1-carboxylate (0.1 g, 278.23 μmol) in N,N-dimethylformamide (2 mL) were added potassium tert-butoxide (62.44 mg, 556.45 μmol) and 2,3,6-trifluorobenzonitrile (43.71 mg, 278.23 μmol, 32.14 μL) at room temperature under inert atmosphere. The resulting reaction mixture was stirred at room temperature for 3 h. After completion, the reaction mixture was quenched with water (5 ml) and extracted with ethyl acetate (2×10 ml). The combined organic layer was washed with brine (10 ml), dried over sodium sulfate and concentrated under vacuum. Crude compound was purified by column purification using 50% ethyl acetate in petroleum ether as a eluent to afford tert-butyl 4-[[7-(2-cyano-3,6-difluoro-phenoxy)quinoxalin-2-yl]oxymethyl]piperidine-1-carboxylate (0.09 g, 181.03 μmol, 65% yield) as a colorless liquid. LCMS m/z (ESI): 441.0 $[M+H-^tBu]^+$ Step 4: To a stirred solution of tert-butyl 4-[[7-(2-cyano-3,6-difluoro-phenoxy)quinoxalin-2-yl]oxymethyl]piperidine-1-carboxylate (0.09 g, 181.27 μmol) in N,N-Dimethylformamide (2 mL) was taken in a sealed tube and added [methyl(sulfamoyl)amino]ethane (50.10 mg, 362.53 μmol) and cesium carbonate (147.65 mg, 453.17 μmol) under nitrogen atmosphere. Then the reaction mixture was stirred at 65° C. for 16 h. After completion, the reaction mixture was quenched with water (10 mL) and extracted with ethyl acetate (2×10 mL). The combined organic layers were washed with brine (10 mL), dried over sodium sulfate and concentrated under vacuum. The crude compound was purified by silica gel flash column chromatography by using 50-100% ethyl acetate in petroleum ether to afford methyl-tert-butyl 4-[[7-[2-cyano-3-[[ethyl(methyl)sulfamoyl]amino]-6-fluoro-phenoxy]quinoxalin-2-yl]oxymethyl]piperidine-1-carboxylate (70 mg, 101.81 μmol, 56% yield) as a brown liquid. LCMS m/z (ESI): 613.2 $[M-H]^-$ Step 5: To a stirred solution of tert-butyl 4-[[7-(2-cyano-3,6-difluoro-phenoxy)quinoxalin-2-yl]oxymethyl]piperidine-1-carboxylate (0.07 g, 140.99 μmol) in dichloromethane (2 mL) was added HCl in 1,4-dioxane (4.0 M, 0.7 mL) at 0° C. Then the reaction mixture was stirred at room temperature for 3 h. The reaction mixture was concentrated under vacuum and washed with petroleum ether (5 mL) to yield 3,6-difluoro-2-[3-(4-piperidylmethoxy)quinoxalin-6-yl]oxy-benzonitrile hydrochloride (0.07 g, 154.09 μmol, 100% yield) as a yellow solid. LCMS m/z (ESI): 515.2 $[M+H]^+$ Step 6: Target compound was prepared via HATU mediated acid-amine coupling reaction (Procedure C-E). Amide coupling was carried out using 7-[2-cyano-3-[[ethyl(methyl)sulfamoyl]amino]-6-fluoro-phenoxy]-2-(4-piperidylmethoxy)quinoxaline (70 mg, 127.03 μmol), 2-[4-[4-[(2,6-dioxo-3-piperidyl)amino]-2-fluoro-phenyl]-1-piperidyl]acetic acid (46.16 mg, 127.03 μmol), HATU (241.51 mg, 635.17 μmol) and N,N-diisopropylethylamine (16.42 mg, 127.03 μmol, 22.13 μL). Crude compound was purified by prep HPLC using 0.1% formic acid in water:acetonitrile as a eluent to afford 7-[2-cyano-3-[[ethyl(methyl)sulfamoyl]amino]-6-fluoro-phenoxy]-2-[[1-[2-[4-[4-[(2,6-dioxo-3-piperidyl)amino]-2-fluoro-phenyl]-1-piperidyl]acetyl]-4-piperidyl]methoxy]quinoxaline (10 mg, 10.57 μmol, 8% yield) as off-white solid. LCMS m/z (ESI): 860.3 $[M+H]^+$. $^1H$ NMR (400 MHz, DMSO-$d_6$): δ=10.80 (s, 1H), 8.51 (s, 1H), 8.06 (d, J=9.20 Hz, 1H), 7.51-7.60 (m, 1H), 7.49 (dd, J=2.80, 9.20 Hz, 1H), 7.31-7.39 (m, 1H), 6.95-7.02 (m, 1H), 6.97 (s, 1H), 6.48 (d, J=5.60 Hz, 1H), 6.46 (d, J=11.60 Hz, 1H), 6.07 (d, J=6.80 Hz, 1H), 4.42-4.39 (m, 1H), 4.33-4.35 (m, 4H), 3.80-3.97 (m, 2H), 3.01-3.12 (m, 3H), 2.60-2.82 (m, 3H), 2.65 (s, 3H), 2.46-2.51 (m, 2H), 2.05-2.20 (m, 3H), 1.70-1.96 (m, 8H), 1.15-1.40 (m, 3H), 1.04 (t, J=7.20 Hz, 3H).

Example 217
7-[2-cyano-3-[[ethyl(methyl)sulfamoyl]amino]-6-fluorophenoxy]-2-[[(1R,5S)-3-[2-[4-[4-[(2,6-di-oxopiperidin-3-yl)amino]-2-fluorophenyl]piperidin-1-yl]acetyl]-3-azabicyclo[3.1.0]hexan-6-yl]methoxy] quinoxaline
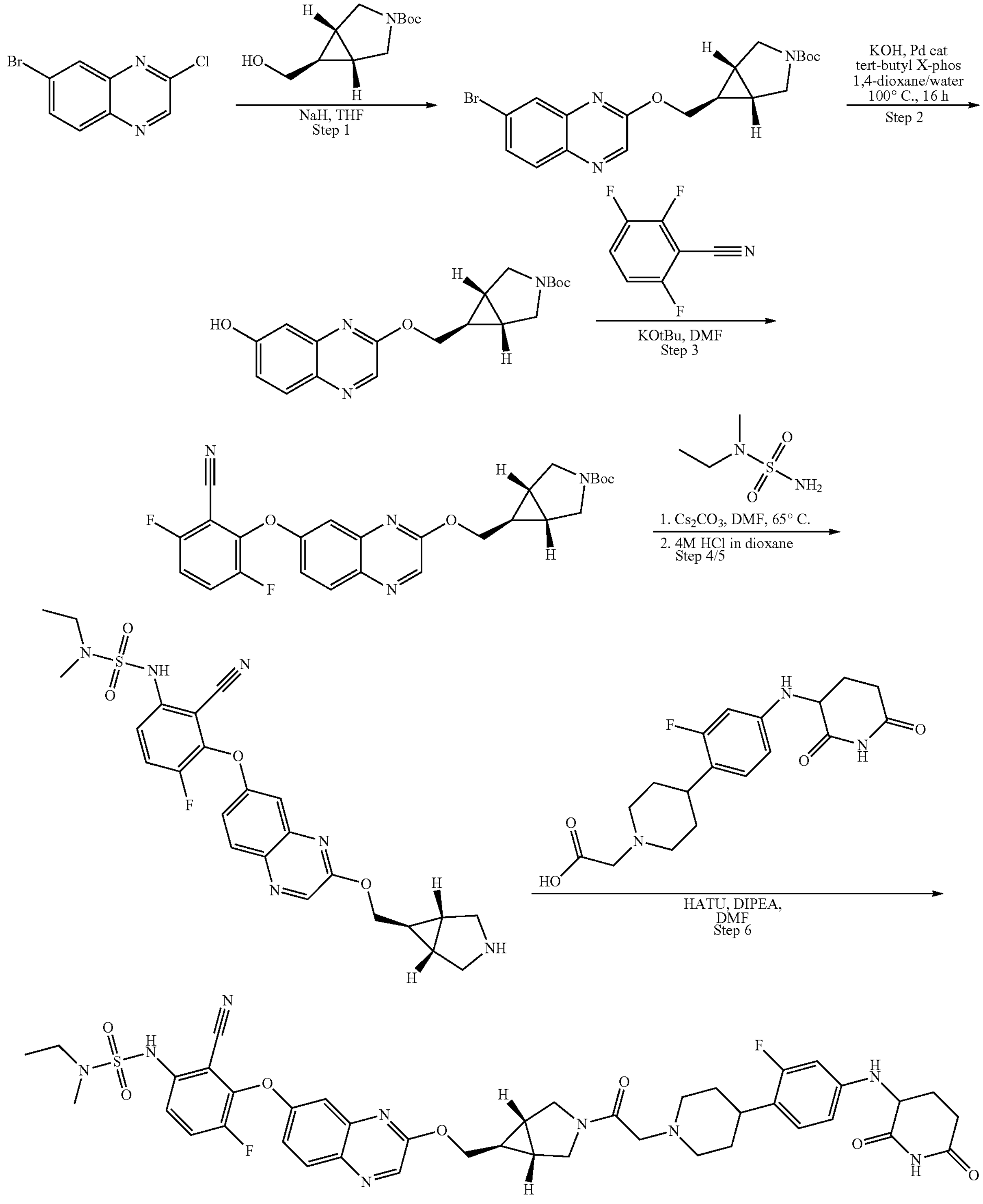

Step 1: To a stirred suspension of sodium hydride (60% dispersion in mineral oil, 330 mg, 8.25 mmol) in THF (20 mL) was added tert-butyl (1R,5S)-6-(hydroxymethyl)-3-azabicyclo[3.1.0]hexane-3-carboxylate (900 mg, 4.22 mmol) solution in THF (20 mL) at 0-5° C. under nitrogen atmosphere. The reaction mixture was stirred at room temperature for 30 minutes. The reaction mixture was again cooled to 0-5° C., then 7-bromo-2-chloro-quinoxaline (1.0 g, 4.11 mmol) solution in THF (20 mL) was added at the same temperature. The reaction mixture was stirred at room temperature for 3 h. After completion, the reaction mixture was cooled to 0-5° C., then added saturated ammonium chloride solution (100 mL) and extracted with ethyl acetate (2×200 mL). The combined organic layers were dried over sodium sulfate, filtered and concentrated under reduced pressure. This crude compound was purified by silica gel flash column chromatography with 30% ethyl acetate in petroleum ether as eluent to afford tert-butyl (1R,5S)-6-[(7-bromoquinoxalin-2-yl)oxymethyl]-3-azabicyclo[3.1.0]hexane-3-carboxylate (1.50 g, 3.35 mmol, 82% yield) as off-white solid. LCMS m/z (ESI): 364.0 $[M+H-^tBu]^+$ Step 2: A solution of tert-butyl (1R,5S)-6-[(7-bromoquinoxalin-2-yl)oxymethyl]-3-azabicyclo[3.1.0]hexane-3-carboxylate (1.40 g, 3.33 mmol) in 1,4-dioxane (20 mL) and water (10 mL) mixture was taken in a sealed tube and added potassium hydroxide (290 mg, 5.17 mmol, 142.16 μL) at room temperature. The reaction mixture was degassed with nitrogen for 15 minutes, then added tert-Butyl XPhos (71 mg, 167.20 μmol). The reaction mixture was again degassed with nitrogen for 10 minutes and added Tris(dibenzylideneacetone)dipalladium(0) (61 mg, 66.61 μmol) at the same temperature. The reaction mixture was heated to 100° C. for 16 h. After completion, saturated Ammonium chloride solution (100 mL) was added to the reaction mixture and extracted with ethyl acetate (3×100 mL). The combined organic layers were dried over sodium sulfate, filtered and concentrated under reduced pressure. This crude compound was purified by silica gel flash column chromatography with 90% ethyl acetate in petroleum ether as eluent to afford tert-butyl (1R,5S)-6-[(7-hydroxyquinoxalin-2-yl)oxymethyl]-3-azabicyclo[3.1.0]hexane-3-carboxylate (1.10 g, 2.95 mmol, 89% yield) as off-white solid. LCMS m/z (ESI): 356.1 $[M-H]^-$ Step 3: To a stirred solution of tert-butyl (1S,5R)-6-[(7-hydroxyquinoxalin-2-yl)oxymethyl]bicyclo[3.1.0]hexane-3-carboxylate (1.0 g, 2.81 mmol) in N,N-dimethylformamide (20 mL) was added potassium tert-butoxide (350 mg, 3.12 mmol) at room temperature under nitrogen atmosphere. The reaction mixture was stirred at room temperature for 30 minutes, then 2,3,6-trifluorobenzonitrile (490 mg, 3.12 mmol, 360.29 μL) solution in N,N-dimethylformamide (20 mL) was added at the same temperature. The reaction mixture was stirred at room temperature for 16 h. After completion, water was added to the reaction mixture (50 mL) and extracted with ethyl acetate (2×100 mL). The combined organic layers were dried over sodium sulfate, filtered and concentrated under reduced pressure. The crude compound was purified by silica gel flash column chromatography with 30% ethyl acetate in petroleum ether as eluent to afford tert-butyl (1S,5R)-6-[[7-(2-cyano-3,6-difluoro-phenoxy)quinoxalin-2-yl]oxymethyl]-3-azabicyclo[3.1.0]hexane-3-carboxylate (1.0 g, 1.96 mmol, 70% yield) as off-white solid. LCMS m/z (ESI): 439.0 $[M+H-^tBu]^+$ Step 4: A solution of tert-butyl (1S,5R)-6-[[7-(2-cyano-3,6-difluoro-phenoxy)quinoxalin-2-yl]oxymethyl]-3-azabicyclo[3.1.0]hexane-3-carboxylate (900 mg, 1.82 mmol) in N,N-dimethylformamide (10 mL) was taken in a sealed tube and cesium carbonate (1.50 g, 4.60 mmol) was added at room temperature under nitrogen atmosphere. The reaction mixture was heated to 60° C. for 16 h. After completion, water (50 mL) was added and the reaction mixture was extracted with ethyl acetate (2×100 mL). The combined organic layers were dried over sodium sulfate, filtered and concentrated under reduced pressure. The crude compound was purified by silica gel flash column chromatography with 60% ethyl acetate in petroleum ether as eluent to afford tert-butyl (1S,5R)-6-[[7-[2-cyano-3-[[ethyl(methyl)sulfamoyl]amino]-6-fluoro-phenoxy]quinoxalin-2-yl]oxymethyl]-3-azabicyclo[3.1.0]hexane-3-carboxylate (480 mg, 548.42 μmol, 30% yield) as a pale yellow solid. LCMS m/z (ESI): 611.2 $[M-H]^-$ Step 5: To a stirred solution of tert-butyl (1S,5R)-6-[[7-[2-cyano-3-[[ethyl(methyl)sulfamoyl]amino]-6-fluoro-phenoxy]quinoxalin-2-yl]oxymethyl]-3-azabicyclo[3.1.0]hexane-3-carboxylate (480 mg, 783.45 μmol) in dichloromethane (5.0 mL) was added hydrogen chloride solution in 1,4-dioxane (4.0 M, 4.0 mL) at 0-5° C. under nitrogen atmosphere. The reaction mixture was stirred at room temperature for 4 h. After completion, the reaction mixture was concentrated under reduced pressure and triturated with diethyl ether (2×50 mL) to afford 2-[[(1S,5R)-3-azabicyclo[3.1.0]hexan-6-yl]methoxy]-7-[2-cyano-3-[[ethyl(methyl)sulfamoyl]amino]-6-fluoro-phenoxy]quinoxaline (420 mg, 512.55 μmol, 65% yield) as a brown solid. LCMS m/z (ESI): 513.2 $[M+H]^+$ Step 6: Target compound was prepared via HATU mediated acid-amine coupling reaction (Procedure C-E). Amide coupling was carried out using 2-[[(1S,5R)-3-azabicyclo[3.1.0]hexan-6-yl]methoxy]-7-[2-cyano-3-[[ethyl(methyl)sulfamoyl]amino]-6-fluoro-phenoxy]quinoxaline (400 mg, 728.58 μmol), 2-[4-[4-[(2,6-dioxo-3-piperidyl)amino]-2-fluoro-phenyl]-1-piperidyl]acetic acid (300 mg, 750.29 μmol), N,N-diisopropylethylamine (2.23 g, 17.22 mmol, 3.0 mL) and HATU (310 mg, 815.30 μmol). The crude compound was purified by reverse phase column chromatography by using 150 g snap, eluting with 50% acetonitrile in 0.1% Ammonium acetate in water, to afford 7-[2-cyano-3-[[ethyl(methyl)sulfamoyl]amino]-6-fluoro-phenoxy]-2-[[(1S,5R)-3-[2-[4-[4-[(2,6-dioxo-3-piperidyl)amino]-2-fluoro-phenyl]-1-piperidyl]acetyl]-3-azabicyclo[3.1.0]hexan-6-yl]methoxy]quinoxaline (110 mg, 126.79 μmol, 17% yield) as a yellow solid. LCMS m/z (ESI): 856.2 $[M-H]^-$; $^1H$ NMR (400 MHz, DMSO-$d_6$): δ=10.81 (s, 1H), 9.79 (bs, 1H), 8.52 (s, 1H), 8.05 (d, J=8.80 Hz, 1H), 7.46-7.52 (m, 1H), 7.33 (dd, J=4.40, 9.40 Hz, 1H), 6.94-6.99 (m, 2H), 6.48 (d, J=6.80 Hz, 1H), 6.46 (d, J=12.00 Hz, 1H), 6.07 (d, J=7.60 Hz, 1H), 7.33 (dd, J=4.40, 9.40 Hz, 1H), 4.35-4.45 (m, 1H), 4.25-4.36 (m, 2H), 3.61-3.91 (m, 4H), 3.52-3.59 (m, 1H), 3.22-3.41 (m, 3H), 3.05 (q, J=7.20 Hz, 2H), 2.55-2.81 (m, 4H), 2.64 (s, 3H), 2.03-2.12 (m, 1H), 1.81-1.92 (m, 4H), 1.71-1.81 (m, 4H), 1.05-1.15 (m, 1H), 1.04 (t, J=7.20 Hz, 3H).

Example 218
3-[6-[2-cyano-3-[[ethyl(methyl)sulfamoyl]amino]-6-fluorophenoxy]quinolin-3-yl]-8-[2-[4-[4-[(2,6-di-oxopiperidin-3-yl)amino]-2-fluorophenyl]piperidin-1-yl]acetyl]-1-oxa-8-azaspiro[4.5]decane
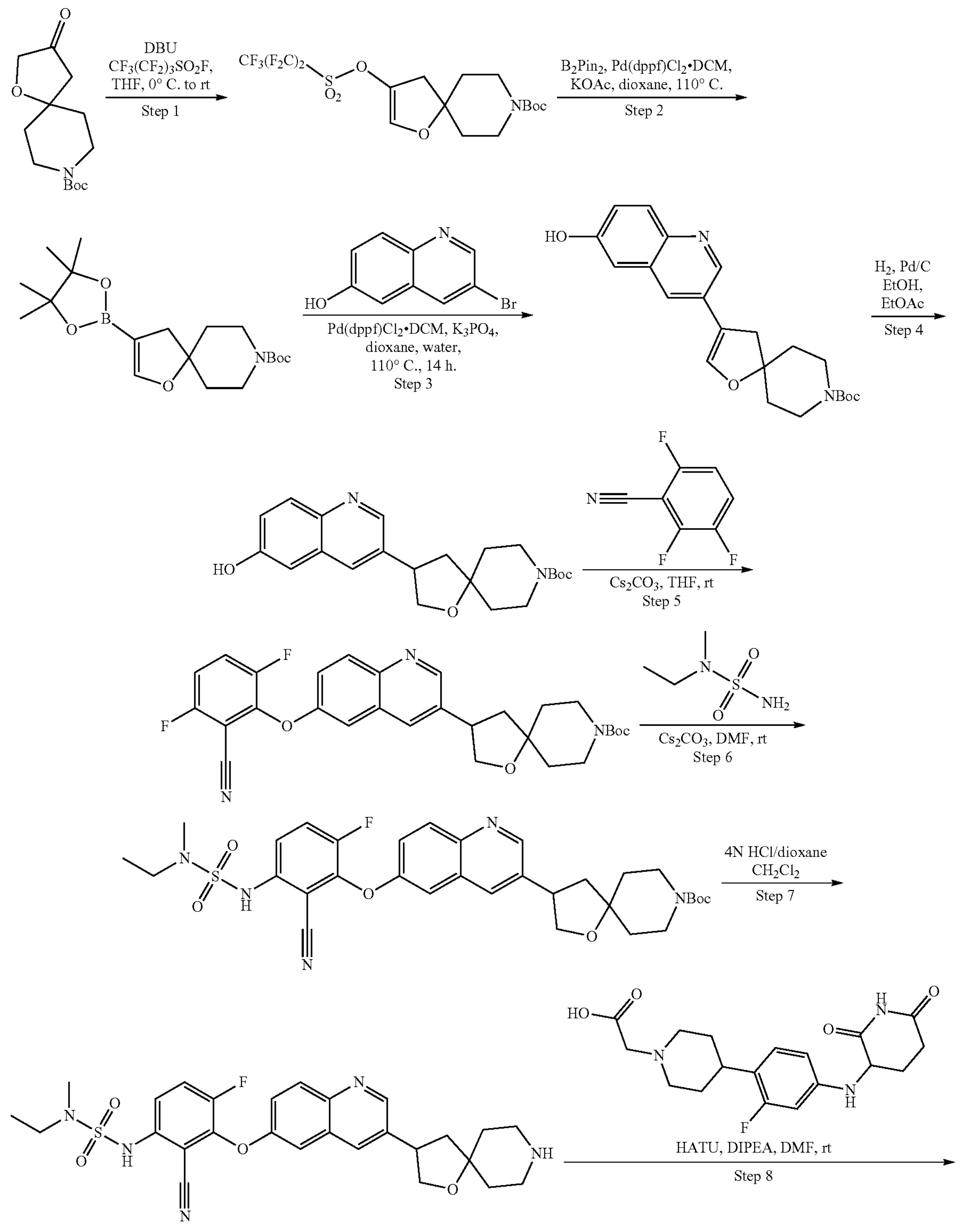

-continued

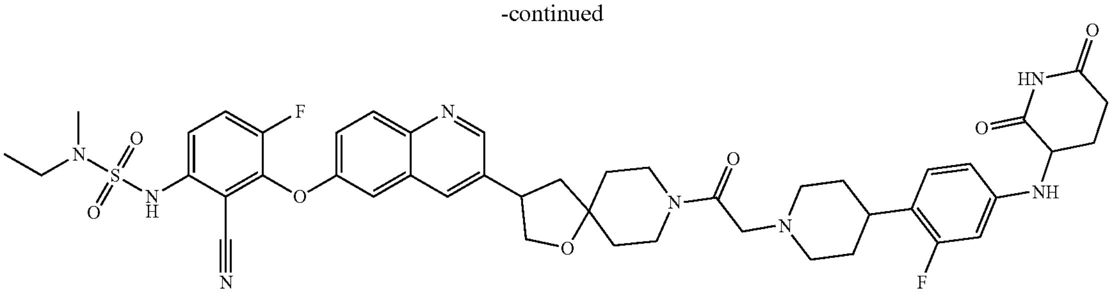

Step 1: To a solution of tert-butyl 3-oxo-1-oxa-8-azaspiro [4.5]decane-8-carboxylate (2.0 g, 7.83 mmol) in THF (20 mL) was added DBU (5.92 g, 23.50 mmol) at 0° C. under nitrogen. Reaction mixture was stirred at 0° C. for 0.5 h. To the reaction solution was added 1,1,2,2,3,3,4,4,4-nonafluorobutane-1-sulfonyl fluoride (7.10 g, 23.50 mmol, 4.06 mL) dropwise for 10 mins at 0° C. The resulting solution was slowly warmed to rt for 1 h. After completion, the reaction mixture was diluted with water (20 mL) and extracted with ethyl acetate (2×50 mL). The separated organic layer was dried over sodium sulfate, filtered and concentrated under reduced pressure. The resulting crude product was purified by silica gel (50 g SNAP) column chromatography using ethyl acetate-petroleum ether (0-40%) to afford tert-butyl 3-(1,1,2,2,3,3,4,4,4-nonafluorobutylsulfonyloxy)-1-oxa-8-azaspiro[4.5]dec-2-ene-8-carboxylate (3.0 g, 5.57 mmol, 71% yield) as a liquid. LCMS m/z (ESI): 438.0[M+H]$^+$.

Step 2: To a solution of tert-butyl 3-(1,1,2,2,3,3,4,4,4-nonafluorobutylsulfonyloxy)-1-oxa-8-azaspiro[4.5]dec-2-ene-8-carboxylate (1.5 g, 2.79 mmol) in 1,4-dioxane (25 mL) was added potassium acetate (821.82 mg, 8.37 mmol, 523.45 µL), Bis(pinacolato)diborane (1.06 g, 4.19 mmol) at rt. The resulting solution was degassed with nitrogen gas and heated at 100° C. for 12 h. After completion, the reaction mixture was cooled to rt, filtered through a celite bed and washed with ethyl acetate (60 ml). The collected filtrates were concentrated under reduced pressure to afford tert-butyl 3-(4,4,5,5-tetramethyl-1,3,2-dioxaborolan-2-yl)-1-oxa-8-azaspiro[4.5]dec-2-ene-8-carboxylate (1.65 g, 2.75 mmol, 99% yield) as a dark brown liquid, which was carried forward without further purification. LCMS m/z (ESI): 266.2[M+H]$^+$.

Step 3: To a solution of tert-butyl 3-(4,4,5,5-tetramethyl-1,3,2-dioxaborolan-2-yl)-1-oxa-8-azaspiro[4.5]dec-2-ene-8-carboxylate (1.22 g, 3.35 mmol) in 1,4-dioxane (10 mL) and water (2 mL) was added potassium carbonate, anhydrous, 99% (925.26 mg, 6.69 mmol, 404.05 µL) at rt under nitrogen. The reaction mixture was degassed with nitrogen for 10 min, and then [1,1'-Bis(diphenylphosphino)ferrocene]dichloropalladium(II), complex with dichloromethane (182.24 mg, 223.16 µmol) was added at the same temperature. The resulting solution was heated at 100° C. for 12 h. After completion, the resulting solution was cooled to rt, filtered through a celite bed and washed with ethyl acetate (50 ml). The collected filtrates were concentrated under reduced pressure. The crude compound was purified by silica gel flash column chromatography with 70% ethyl acetate in pet ether as a eluent to afford tert-butyl 3-(6-hydroxy-3-quinolyl)-1-oxa-8-azaspiro[4.5]dec-2-ene-8-carboxylate (0.6 g, 1.43 mmol, 64% yield) as a red solid. LCMS m/z (ESI): 383.2[M+H]$^+$.

Step 4: To a solution of tert-butyl 3-(6-hydroxy-3-quinolyl)-1-oxa-8-azaspiro[4.5]dec-2-ene-8-carboxylate (0.1 g, 261.47 µmol) in 1,4-dioxane (1 mL) was added palladium hydroxide on activated charcoal (18.63 mg, 130.74 µmol) and the reaction stirred for 12 h under hydrogen bladder pressure. After completion, the reaction mixture was filtered through a pad of Celite and washed with 10% methanol in dichloromethane (20 mL). The filtrate was concentrated under reduced pressure to afford tert-butyl 3-(6-hydroxy-3-quinolyl)-1-oxa-8-azaspiro [4.5]decane-8-carboxylate (90 mg, 223.18 µmol, 85% yield) as a brown solid. LCMS m/z (ESI): 385.6[M+H]$^+$.

Step 5: To a solution of 2,3,6-trifluorobenzonitrile (245.16 mg, 1.56 mmol, 180.26 µL), tert-butyl 3-(6-hydroxy-3-quinolyl)-1-oxa-8-azaspiro[4.5]decane-8-carboxylate (500 mg, 1.30 mmol) in THF (5 mL) was added cesium carbonate (1.06 g, 3.25 mmol) at rt under nitrogen. The reaction mixture was stirred at rt for 12 h. After completion, the reaction mixture was diluted with water (5 mL) and extracted with ethyl acetate (2×20 mL). The organic layer was dried over sodium sulfate and concentrated under reduced pressure. The resulting crude product was purified by silica gel (25 g SNAP) column chromatography using ethyl acetate-petroleum ether (0-70%) to afford tert-butyl 3-[6-(2-cyano-3,6-difluoro-phenoxy)-3-quinolyl]-1-oxa-8-azaspiro[4.5]decane-8-carboxylate (0.57 g, 1.07 mmol, 83% yield) as an off-white solid. LCMS m/z (ESI): 522.2[M+H]$^+$.

Step 6: To a solution of tert-butyl 3-[6-(2-cyano-3,6-difluoro-phenoxy)-3-quinolyl]-1-oxa-8-azaspiro[4.5]decane-8-carboxylate (0.57 g, 1.09 mmol) in N,N-DIMEHTYLFORMAMIDE (6 mL) was added cesium carbonate (890.21 mg, 2.73 mmol) and [methyl(sulfamoyl) amino]ethane (302.05 mg, 2.19 mmol) at rt under nitrogen. The reaction mixture was heated to 70° C. for 12 h. After completion, the reaction mixture was diluted with water (10 mL) and the resulting solid was filtered off. The filtrate was extracted with ethyl acetate (2×25 mL). The organic layer was washed with brine (10 mL), dried over sodium sulfate and concentrated under reduced pressure to afford tert-butyl 3-[6-[2-cyano-3-[[ethyl(methyl)sulfamoyl]amino]-6-fluoro-phenoxy]-3-quinolyl]-1-oxa-8-azaspiro[4.5]decane-8-carboxylate (0.43 g, 576.84 µmol, 53% yield) as a liquid, which was carried forward without further purification. LCMS m/z (ESI): 640.2[M+H]$^+$.

Step 7: To a solution of tert-butyl 3-[6-[2-cyano-3-[[ethyl (methyl)sulfamoyl]amino]-6-fluoro-phenoxy]-3-quinolyl]-1-oxa-8-azaspiro[4.5]decane-8-carboxylate (0.43 g, 672.15 µmol) in dichloromethane (5 mL) was added hydrogen chloride solution in 1,4-dioxane (4.0 M, 3.36 mL) at 0° C. under nitrogen. The resulting solution was stirred at RT for 3 h. After completion, the solution was concentrated under reduced pressure to afford 33-[6-[2-cyano-3-[[ethyl(methyl) sulfamoyl]amino]-6-fluoro-phenoxy]-3-quinolyl]-1-oxa-8-azaspiro[4.5]decane (0.42 g, 515.96 µmol, 77% yield) as a semisolid, which was carried forward without further purification. LCMS m/z (ESI): 540.2[M+H]$^+$.

Step 8: Target compound was prepared via HATU mediated acid-amine coupling reaction (Procedure C-E). Amide coupling was carried out using 2-[4-[4-[(2,6-dioxo-3-piperidyl)amino]-2-fluoro-phenyl]-1-piperidyl]acetic acid (80.81 mg, 222.38 μmol), 3-[6-[2-cyano-3-[[ethyl(methyl)sulfamoyl]amino]-6-fluoro-phenoxy]-3-quinolyl]-1-oxa-8-azaspiro[4.5]decane (0.12 g, 222.38 μmol), N,N-diisopropylethylamine (143.70 mg, 1.11 mmol, 193.67 μL) and HATU (127.50 mg, 333.57 μmol). The crude compound was purified by reverse phase column chromatography, eluting with 38% acetonitrile in 0.1% formic acid in water, to afford 3-[6-[2-cyano-3-[[ethyl(methyl)sulfamoyl]amino]-6-fluoro-phenoxy]-3-quinolyl]-8-[2-[4-[4-[(2,6-dioxo-3-piperidyl)amino]-2-fluoro-phenyl]-1-piperidyl]acetyl]-1-oxa-8-azaspiro[4.5]decane (24 mg, 24.64 μmol, 11% yield) as an off-white solid. LCMS m/z (ESI): 885.2[M+H]$^+$; $^1$H NMR (400 MHz, DMSO-$d_6$): δ=10.82 (s, 1H), 9.86 (bs, 1H), 8.82 (s, 1H), 8.24 (s, 1H), 8.06 (d, J=9.20 Hz, 1H), 7.76-7.70 (m, 1H), 7.61 (dd, J=2.80, 9.20 Hz, 1H), 7.44-7.41 (m, 1H), 7.26 (s, 1H), 6.97-6.91 (m, 1H), 6.48 (t, J=13.20 Hz, 2H), 6.12 (d, J=8.00 Hz, 1H), 4.30-4.23 (m, 4H), 3.82-3.78 (m, 3H), 3.44-3.34 (m, 4H), 3.15-3.05 (m, 3H), 2.71 (s, 3H), 2.51-2.40 (m, 2H), 2.33-2.31 (m, 2H), 1.89-1.59 (m, 13H), 1.06 (t, J=7.20 Hz, 3H).

Example 219

7-[2-cyano-3-[[ethyl(methyl)sulfamoyl]amino]-6-fluorophenoxy]-2-[8-[2-[4-[4-[(2,6-dioxopiperidin-3-yl)amino]-2-fluorophenyl]piperidin-1-yl]acetyl]-2,8-diazaspiro[4.5]decan-2-yl]quinoxaline

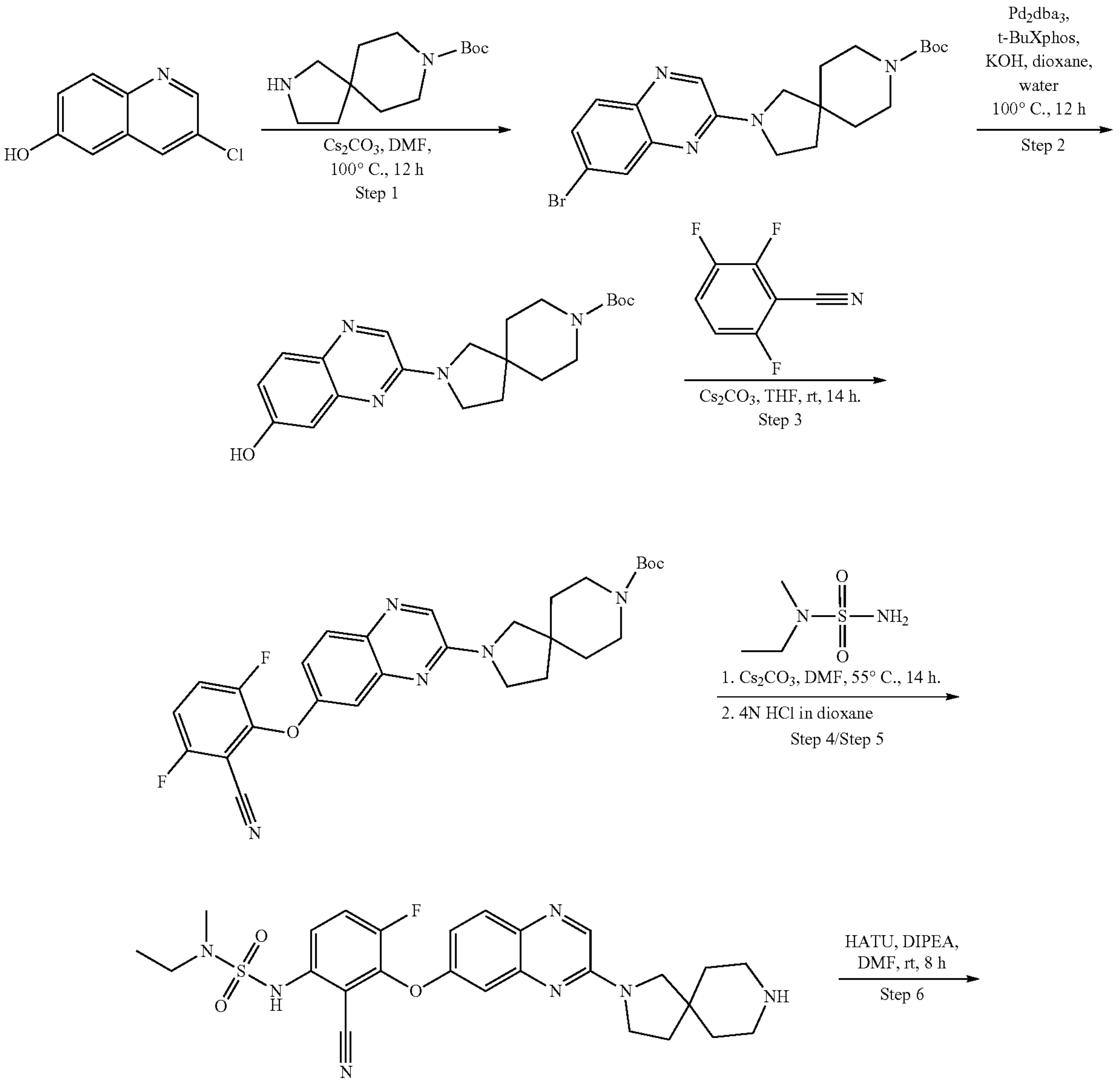

-continued

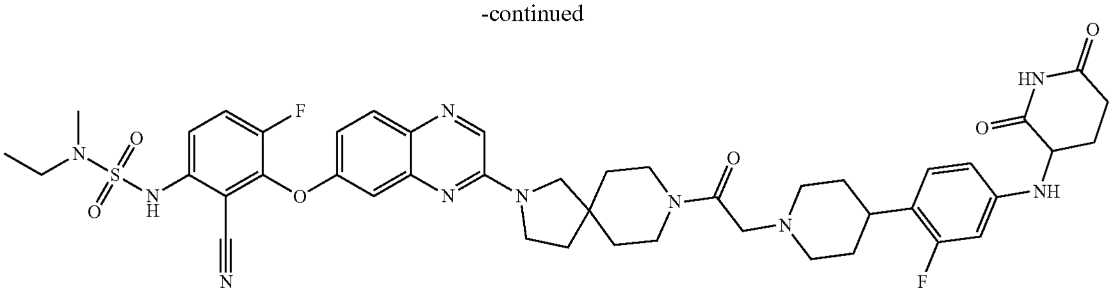

Step 1: Into a stirred solution of tert-butyl 2,8-diazaspiro[4.5]decane-8-carboxylate (1 g, 4.16 mmol) in tetrahydrofuran (15 mL) were added 7-bromo-2-chloroquinoxaline (1.01 g, 4.16 mmol) and cesium carbonate (3.39 g, 10.40 mmol) at room temperature under nitrogen atmosphere. The reaction mixture stirred at 100° C. for 12 h. The reaction mixture was cooled to room temperature and diluted with water (15 mL). The solution was extracted with ethyl acetate (3×20 mL), washed with brine (15 mL), dried over sodium sulfate and concentrated under reduced pressure to afford tert-butyl 2-(7-bromoquinoxalin-2-yl)-2,8-diazaspiro[4.5]decane-8-carboxylate (1.15 g, 2.52 mmol, 61% yield). LCMS m/z (ESI): 447.0 $[M+H]^+$.

Step 2: Into a stirred solution of tert-butyl 2-(7-bromoquinoxalin-2-yl)-2,8-diazaspiro[4.5]decane-8-carboxylate (900 mg, 2.01 mmol) in tetrahydrofuran (12 mL) were added potassium hydroxide (282.18 mg, 5.03 mmol, 138.32 μL) and water (1 mL) at room temperature under nitrogen atmosphere. The mixture was degassed with nitrogen for 10 minutes, added $Pd_2(dba)_3$ (184.22 mg, 201.18 μmol) and $Me_4{}^tButylXphos$ (96.71 mg, 201.18 μmol). The resulting mixture was stirred at 100° C. for 16 h. The reaction mixture was diluted with water (5 mL) and extracted ethyl acetate (3×15 mL). The combined organic layers were washed with brine (15 mL), dried over sodium sulfate, filtered, and evaporated under reduced pressure. The crude product was purified by column chromatography using 230-400 silica gel by eluting with 50-60% ethyl acetate in petroleum ether to afford tert-butyl 2-(7-hydroxyquinoxalin-2-yl)-2,8-diazaspiro[4.5]decane-8-carboxylate (450 mg, 1.12 mmol, 56% yield) as pale brown solid. LCMS: m/z (ESI): 385.2$[M+H]^+$.

Step 3: Into a stirred solution of tert-butyl 2-(7-hydroxyquinoxalin-2-yl)-2,8-diazaspiro[4.5]decane-8-carboxylate (450 mg, 1.17 mmol) in tetrahydrofuran (6 mL) were added 2,3,6-trifluorobenzonitrile (183.87 mg, 1.17 mmol, 135.20 μL) and cesium carbonate (1.14 g, 3.51 mmol) at room temperature under nitrogen atmosphere. The resulting mixture was stirred at room temperature for 16 h. The reaction mixture was diluted with water (3 mL) and extracted with ethyl acetate (3×20 mL). The combined organic layers were washed with brine (20 mL), dried over sodium sulfate, filtered, and concentrated under reduced pressure. The crude was purified by column chromatography using 230-400 silica gel by eluting with 70-80% ethyl acetate in petroleum ether to afford tert-butyl 2-[7-(2-cyano-3,6-difluoro-phenoxy)quinoxalin-2-yl]-2,8-diazaspiro[4.5]decane-8-carboxylate (550 mg, 1.05 mmol, 90% yield) as pale brown solid. LCMS m/z (ESI): 522.2 $[M+H]^+$.

Step 4: Into a stirred solution of tert-butyl 2-[7-(2-cyano-3,6-difluoro-phenoxy)quinoxalin-2-yl]-2,8-diazaspiro[4.5]decane-8-carboxylate (550 mg, 1.05 mmol) in N,N-dimethylformamide (5 mL) were added [methyl(sulfamoyl)amino]ethane (291.45 mg, 2.11 mmol) and cesium carbonate (1.03 g, 3.16 mmol) at room temperature under nitrogen atmosphere and the resulting mixture was heated at 70° C. for 16 h. The reaction mixture was diluted with cold water (5 mL), and the resulting solid was filtered off. The filtrate was extracted with ethyl acetate (3×50 mL), washed with brine (20 mL), and dried over sodium sulfate. The organic layer was evaporated under reduced pressure to afford tert-butyl 2-[7-[2-cyano-3-[[ethyl(methyl)sulfamoyl]amino]-6-fluoro-phenoxy]quinoxalin-2-yl]-2,8-diazaspiro[4.5]decane-8-carboxylate (150 mg, 178.15 μmol, 17% yield) as brown solid. LCMS m/z (ESI): 640.2$[M+H]^+$.

Step 5: Into a stirred solution of tert-butyl 2-[7-[2-cyano-3-[[ethyl(methyl)sulfamoyl]amino]-6-fluoro-phenoxy]quinoxalin-2-yl]-2,8-diazaspiro[4.5]decane-8-carboxylate (150 mg, 234.47 μmol) in dichloromethane (2 mL) was added hydrogen chloride in 1,4-dioxane (4 M, 1.47 mL) dropwise at 0° C. temperature under nitrogen atmosphere and resulting mixture was stirred at room temperature for 4 h. The reaction mixture was directly concentrated under reduced pressure to afford 7-[2-cyano-3-[[ethyl(methyl)sulfamoyl]amino]-6-fluoro-phenoxy]-2-(2,8-diazaspiro[4.5]decan-2-yl)quinoxaline (135 mg, 163.21 μmol, 70% yield) as off-white solid. LCMS m/z (ESI): 540.2 $[M+H]^+$.

Step 6: Target compound was prepared via HATU mediated acid-amine coupling reaction (Procedure C-E). Amide coupling was carried out using 7-[2-cyano-3-[[ethyl(methyl)sulfamoyl]amino]-6-fluoro-phenoxy]-2-(2,8-diazaspiro[4.5]decan-2-yl)quinoxaline (130 mg, 240.91 μmol), 2-[4-[4-[(2,6-dioxo-3-piperidyl)amino]-2-fluoro-phenyl]-1-piperidyl]acetic acid (87.54 mg, 240.91 μmol), N,N-diisopropylethylamine (155.68 mg, 1.20 mmol, 209.81 μL) and HATU (137.40 mg, 361.36 μmol). The crude compound was purified by reverse phase column chromatography by using 150 g snap, eluting with 50% acetonitrile in 0.1% formic acid in water, to afford 7-[2-cyano-3-[[ethyl(methyl)sulfamoyl]amino]-6-fluorophenoxy]-2-[8-[2-[4-[4-[(2,6-dioxopiperidin-3-yl)amino]-2-fluorophenyl]piperidin-1-yl]acetyl]-2,8-diazaspiro[4.5]decan-2-yl]quinoxaline (8 mg, 7.54 μmol, 6% yield) as yellow solid. LCMS m/z (ESI): 885.2 $[M+H]^+$; $^1H$ NMR (400 MHz, DMSO-$d_6$): δ=10.81 (s, 1H), 10.15 (bs, 1H), 9.51 (bs, 1H), 8.44 (s, 1H), 7.88 (d, J=9.20 Hz, 1H), 7.85-7.89 (m, 1H), 7.48 (dd, J=4.00, 9.20 Hz, 1H), 7.19 (dd, J=3.20, 9.00 Hz, 1H), 6.95-7.01 (m, 1H), 6.74 (d, J=2.80 Hz, 1H), 6.51 (d, J=7.60 Hz, 1H), 6.48 (d, J=12.40 Hz, 1H), 6.12 (d, J=8.00 Hz, 1H), 4.22-4.41 (m, 4H), 3.61-3.80 (m, 3H), 3.31-3.61 (m, 5H), 3.17 (q, J=6.80 Hz, 2H), 3.01-3.12 (m, 1H), 2.85-2.95 (m, 1H), 2.80 (s, 3H), 2.68-2.81 (m, 1H), 2.51-2.61 (m, 2H), 2.55 (s, 2H), 1.82-2.12 (m, 6H), 1.52-1.71 (m, 4H), 1.07 (t, J=6.80 Hz, 3H).

Example 220
7-[2-cyano-3-[[ethyl(methyl)sulfamoyl]amino]-6-fluorophenoxy]-2-[8-[2-[4-[4-[(2,6-dioxopiperidin-3-yl)amino]-2-fluorophenyl]piperidin-1-yl]acetyl]-8-azaspiro[4.5]decan-3-yl]quinoxaline
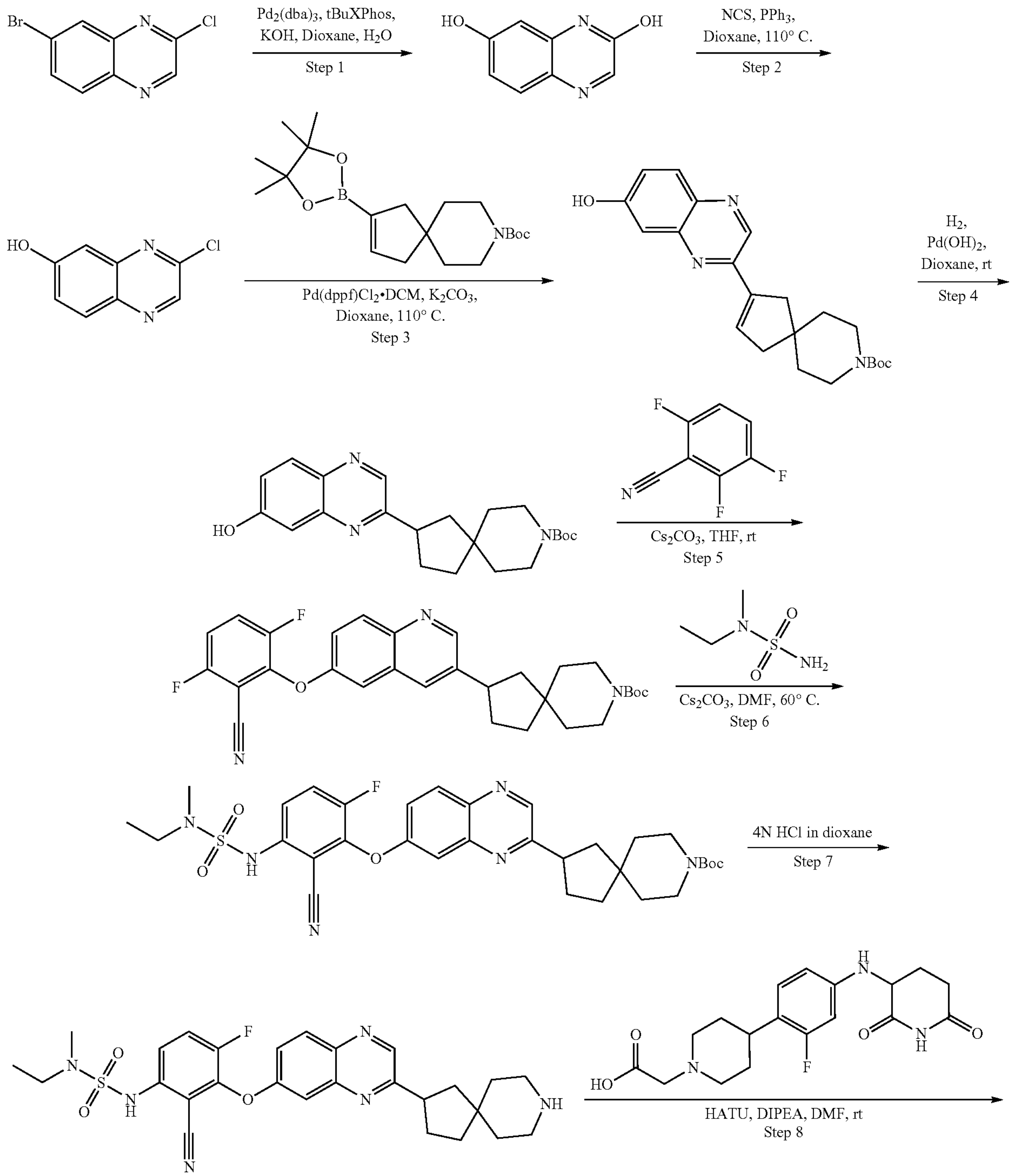

-continued

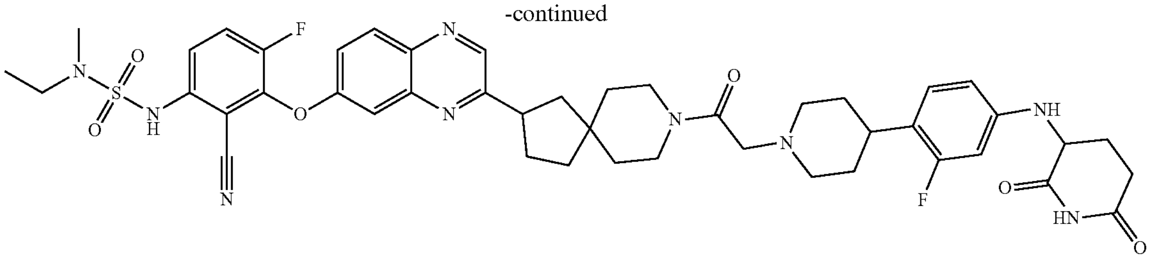

Step 1: A stirred solution of KOH (4.61 g, 82.14 mmol, 2.26 mL) and 7-bromo-2-chloro-quinoxaline (8 g, 32.86 mmol) in mixture of water (12 mL) and 1,4-dioxane (48 mL) in a sealed tube was degassed with nitrogen for 5 minutes. $Pd_2dba_3$ (3.01 g, 3.29 mmol) and $^t$BuXPhos (1.40 g, 3.29 mmol) were added to the reaction mixture and the resulting mixture was stirred at 100° C. for 16 h in a closed sealed tube. After completion, the reaction mixture was diluted with 1M KOH solution (100 mL) and ethyl acetate (200 mL). The layers were separated, and the aqueous layer was acidified to pH ~3 with 1.5N HCl solution. The obtained solid was filtered and dried to afford Quinoxaline-2,7-diol (3.8 g, 20.43 mmol, 62% yield) as a brown solid. LCMS m/z (ESI): 163.20 $[M+H]^+$.

Step 2: To a stirred solution of triphenylphosphine (7.28 g, 27.75 mmol) in 1,4-dioxane (100 mL) was added N-Chlorosuccinimide (3.71 g, 27.75 mmol, 2.25 mL) at room temperature. The resulting reaction mixture was stirred at room temperature for 0.5 h. To this, quinoxaline-2,7-diol (1.8 g, 11.10 mmol) was added and stirred at 110° C. for 4 h. After completion, the reaction mixture was diluted with water (100 mL) and extracted with ethyl acetate (2×100 mL). The combined organic layer was washed with brine solution, dried over anhydrous sodium sulfate, filtered and concentrated under reduced pressure. The crude compound was purified by silica gel flash column chromatography while eluting with 0-30% ethyl acetate in Pet ether as eluent to afford 3-chloroquinoxalin-6-ol (350 mg, 1.64 mmol, 15% yield) as a pale yellow solid. LCMS m/z (ESI): 179.20 $[M-H]^-$.

Step 3: To a stirred solution of tert-butyl 3-(4,4,5,5-tetramethyl-1,3,2-dioxaborolan-2-yl)-8-azaspiro[4.5]dec-2-ene-8-carboxylate (402.34 mg, 1.11 mmol) and 3-chloro-quinoxalin-6-ol (100 mg, 553.74 μmol) in 1,4-dioxane (5 mL) and water (1 mL) was added potassium carbonate (191.33 mg, 1.38 mmol) at room temperature under nitrogen atmosphere. The reaction mixture was degassed with nitrogen for 15 min. $Pd(dppf)Cl_2 \cdot CH_2Cl_2$ (45.22 mg, 55.37 μmol) was added and the reaction mixture was stirred at 100° C. for 16 h. After completion, the reaction mixture was cooled to room temperature, and filtered through celite, washing with ethyl acetate (2×50 mL). The combined filtrate was concentrated under reduced pressure to afford crude, which was purified by silica gel flash column chromatography with 45-50% ethyl acetate in petroleum ether as a eluent to afford tert-butyl 3-(7-hydroxyquinoxalin-2-yl)-8-azaspiro[4.5]dec-2-ene-8-carboxylate (150 mg, 374.70 μmol, 68% yield) as a brown semi solid. LCMS m/z (ESI): 382.20 $[M+H]^+$ Step 4: To a stirred solution of tert-butyl 3-(7-hydroxy-quinoxalin-2-yl)-8-azaspiro[4.5]dec-2-ene-8-carboxylate (270 mg, 707.79 μmol) in 1,4-dioxane (10 mL) was added palladium hydroxide (100 mg, 142.41 μmol) under nitrogen atmosphere at room temperature. The reaction mixture stirred under $H_2$ pressure (bladder) for 12 h. After completion of the reaction, the catalyst was removed by filtration through celite bed. The celite bed was washed with ethyl acetate (3×30 mL) and the filtrate was concentrated under reduced pressure. The crude compound was purified by silica gel flash column chromatography with 50-60% ethyl acetate in petroleum ether as a eluent to afford tert-butyl 3-(7-hydroxyquinoxalin-2-yl)-8-azaspiro[4.5]decane-8-carboxylate (120 mg, 294.93 μmol, 42% yield) as a brown viscous solid. LCMS m/z (ESI): 384.20 $[M+H]^+$.

Step 5: O-arylated quinoxaline intermediate was synthesized by following Procedure C-C using tert-butyl 3-(7-hydroxyquinoxalin-2-yl)-8-azaspiro[4.5]decane-8-carboxylate (120 mg, 312.92 μmol), cesium carbonate (254.89 mg, 782.30 μmol) and 2,3,6-trifluorobenzonitrile (54.07 mg, 344.21 μmol, 39.76 μL). The crude compound was purified by silica gel flash column chromatography with 50-60% ethyl acetate in petroleum ether as a eluent to afford tert-butyl 3-[7-(2-cyano-3,6-difluoro-phenoxy)quinoxalin-2-yl]-8-azaspiro[4.5]decane-8-carboxylate (80 mg, 136.47 μmol, 44% yield) as a pale yellow oil. LCMS m/z (ESI): 465.20 $[M+H-tBu]^+$ Step 6: Sulfamoylated quinoxaline intermediate was synthesized by following Procedure C-D using tert-butyl 3-[7-(2-cyano-3,6-difluoro-phenoxy)quinoxalin-2-yl]-8-azaspiro[4.5]decane-8-carboxylate (80 mg, 153.68 μmol), cesium carbonate (125.18 mg, 384.19 μmol) and [methyl(sulfamoyl)amino]ethane (31.85 mg, 230.52 μmol). The crude compound was purified by silica gel flash column chromatography with 90-100% ethyl acetate in petroleum ether as a eluent to afford tert-butyl 3-[7-[2-cyano-3-[[ethyl(methyl)sulfamoyl]amino]-6-fluoro-phenoxy]quinoxalin-2-yl]-8-azaspiro[4.5]decane-8-carboxylate (50 mg, 58.90 μmol, 38% yield) as a pale yellow oil. LCMS m/z (ESI): 637.20 $[M-H]^-$.

Step 7: The requisite amine was synthesized by following Procedure C-E using tert-butyl 3-[7-[2-cyano-3-[[ethyl(methyl)sulfamoyl]amino]-6-fluoro-phenoxy]quinoxalin-2-yl]-8-azaspiro[4.5]decane-8-carboxylate (50 mg, 78.28 μmol) and hydrogen chloride solution 4.0 M in 1,4-dioxane (1 mL). The resulted crude compound was triturated with methyl t-butyl ether to afford 2-(8-azaspiro[4.5]decan-3-yl)-7-[2-cyano-3-[[ethyl(methyl)sulfamoyl]amino]-6-fluoro-phenoxy]quinoxaline (40 mg, 39.99 μmol, 51% yield) as a yellow solid. LCMS m/z (ESI): 537.0 $[M-H]^-$ Step 8: Target compound was prepared via HATU mediated acid-amine coupling reaction (Procedure C—F). Amide coupling was carried out using 2-[4-[4-[(2,6-dioxo-3-piperidyl)amino]-2-fluoro-phenyl]-1-piperidyl]acetic acid (25 mg, 62.52 μmol), N,N-diisopropylethylamine (48.49 mg, 375.15 μmol, 65.34 μL), 2-(8-azaspiro[4.5]decan-3-yl)-7-[2-cyano-3-[[ethyl(methyl)sulfamoyl]amino]-6-fluoro-phenoxy]quinoxaline (39.55 mg, 68.78 μmol) and HATU (26.15 mg, 68.78 μmol). The crude compound was purified by reverse phase column chromatography, eluting with 50% acetonitrile in 0.1% ammonium acetate in water, to afford 7-[2-cyano-3-[[ethyl(methyl)sulfamoyl]amino]-6-fluoro-phenoxy]-2-[8-[2-[4-[4-[(2,6-dioxo-3-piperidyl)amino]-2-fluoro-phenyl]-1-piperidyl]acetyl]-8-azaspiro[4.5]decan-3-yl]quinoxaline (18 mg, 20.27 μmol, 32% yield) as a pale yellow solid. LCMS m/z (ESI): 884.20 $[M+H]^+$; $^1H$ NMR (400 MHz, DMSO-$d_6$): δ=10.80 (s, 1H), 9.71 (s, 1H), 8.85 (d, J=2.00 Hz, 1H), 8.12 (d, J=9.20 Hz, 1H), 7.68 (dd, J=9.20, 2.80, Hz, 1H), 7.52 (s, 1H), 7.36-7.34 (m, 1H), 7.10 (s, 1H), 6.99 (s, 1H), 6.50-6.45 (m, 2H), 6.08 (d, J=7.60 Hz, 1H), 4.40-4.25 (m, 1H), 4.00-3.75 (m, 2H), 3.70-3.35 (m, 4H), 3.04 (q, J=6.80 Hz, 2H), 2.90-2.55 (m, 7H), 2.12-2.07 (m, 5H), 1.92-1.51 (m, 15H), 1.04 (t, J=7.20 Hz, 3H).

Example 221

3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane

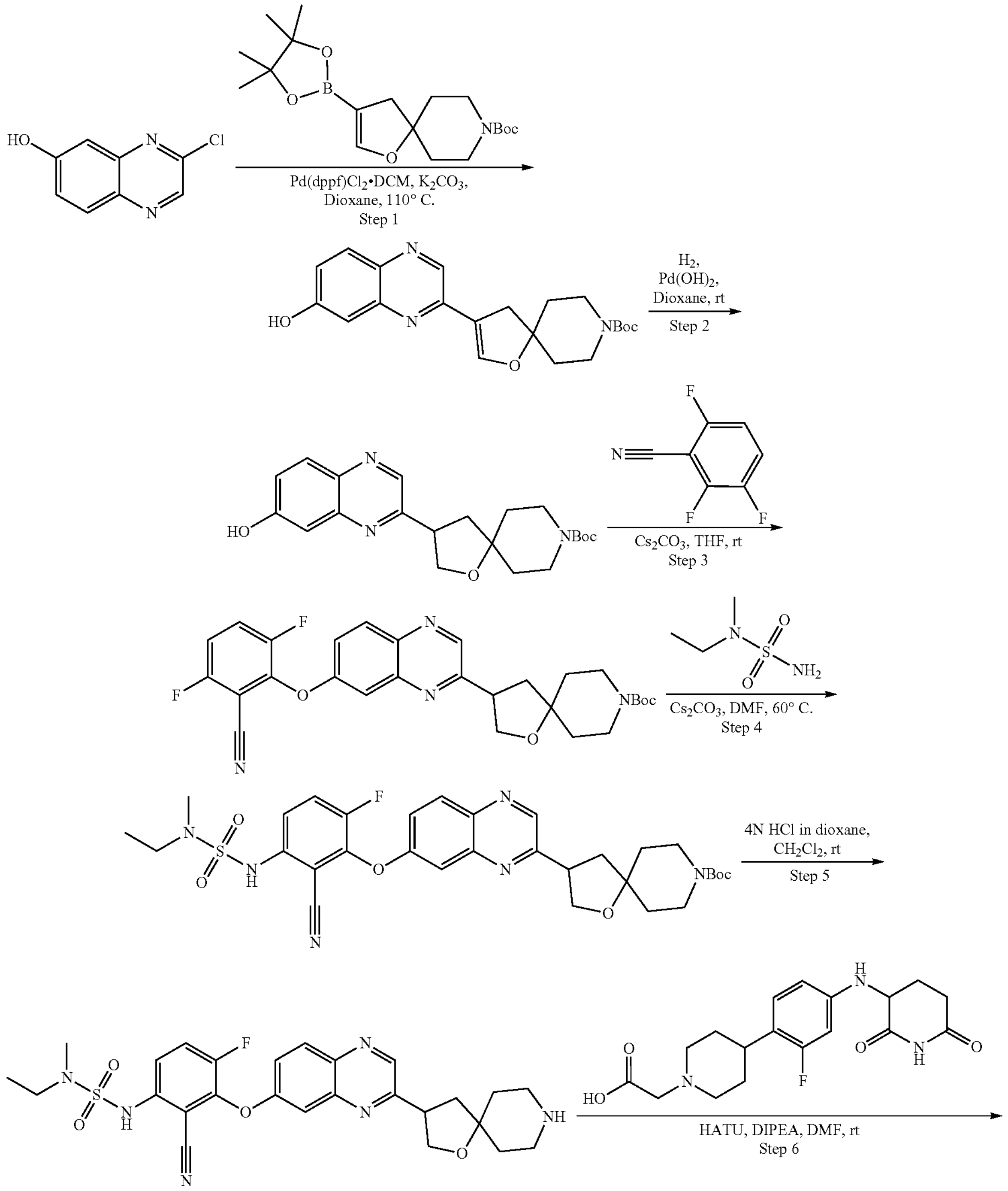

-continued

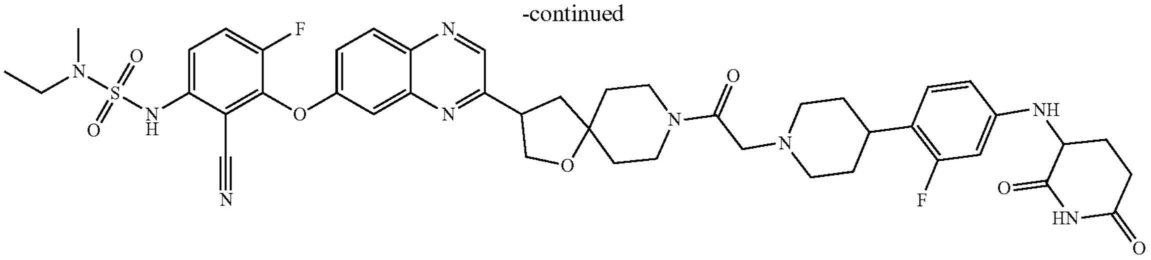

Step 1: To a stirred solution of 3-chloroquinoxalin-6-ol (0.2 g, 1.11 mmol) and tert-butyl 3-(4,4,5,5-tetramethyl-1,3,2-dioxaborolan-2-yl)-1-oxa-8-azaspiro[4.5]dec-2-ene-8-carboxylate (809.06 mg, 2.21 mmol) in 1,4-dioxane (8 mL) and water (2 mL) was added potassium carbonate (382.66 mg, 2.77 mmol) at room temperature under nitrogen atmosphere. The reaction mixture was purged with nitrogen for 15 min followed by the addition of $Pd(dppf)Cl_2 \cdot CH_2Cl_2$ (90.44 mg, 110.75 μmol). The reaction mixture was stirred at 100° C. for 16 h. After completion, the reaction mixture was cooled to room temperature, and filtered through celite, washing with ethyl acetate (2×50 mL). The combined filtrate was concentrated under reduced pressure and the crude product was purified by silica gel flash column chromatography with 70-80% ethyl acetate in petroleum ether as a eluent to afford tert-butyl 3-(7-hydroxyquinoxalin-2-yl)-1-oxa-8-azaspiro[4.5]dec-2-ene-8-carboxylate (0.2 g, 323.39 μmol, 29% yield) as a brown semi solid. LCMS m/z (ESI): 328.0 $[M+H-{}^tBu]^+$.

Step 2: To a stirred solution of tert-butyl 3-(7-hydroxyquinoxalin-2-yl)-1-oxa-8-azaspiro[4.5]dec-2-ene-8-carboxylate (0.2 g, 521.59 μmol) in 1,4-dioxane (5 mL) was added palladium hydroxide (109.87 mg, 782.39 μmol) under nitrogen atmosphere at room temperature. The reaction mixture stirred under $H_2$ pressure for 12 h. After completion, the catalyst was removed by filtration through celite bed, washing with ethyl acetate (3×10 mL). The filtrate was concentrated under reduced pressure, and the crude compound was purified by silica gel flash column chromatography with 80-90% ethyl acetate in petroleum ether as a eluent to afford tert-butyl 3-(7-hydroxyquinoxalin-2-yl)-1-oxa-8-azaspiro[4.5]decane-8-carboxylate (0.1 g, 210.95 μmol, 40% yield) as a brown solid. LCMS m/z (ESI): 330.20 $[M+H-{}^tBu]^+$.

Step 3: O-arylated quinoxaline intermediate was synthesized by following Procedure C-C using tert-butyl 3-(7-hydroxyquinoxalin-2-yl)-1-oxa-8-azaspiro[4.5]decane-8-carboxylate (0.1 g, 259.43 μmol), cesium carbonate (211.32 mg, 648.58 μmol) and 2,3,6-trifluorobenzonitrile (48.91 mg, 311.32 μmol, 35.96 μL). The crude compound was purified by silica gel flash column chromatography with 60-70% ethyl acetate in petroleum ether as a eluent to afford tert-butyl 3-[7-(2-cyano-3,6-difluoro-phenoxy)quinoxalin-2-yl]-1-oxa-8-azaspiro[4.5]decane-8-carboxylate (0.1 g, 186.30 μmol, 72% yield) as an off-white solid. LCMS m/z (ESI): 467.20 $[M+H-{}^tBu]^+$.

Step 4: Sulfamoylated quinoxaline intermediate was synthesized by following Procedure C-D using tert-butyl 3-[7-(2-cyano-3,6-difluoro-phenoxy)quinoxalin-2-yl]-1-oxa-8-azaspiro[4.5]decane-8-carboxylate (100 mg, 191.37 μmol), cesium carbonate (155.88 mg, 478.43 μmol) and [methyl(sulfamoyl)amino]ethane (39.67 mg, 287.06 μmol). The crude compound was purified by silica gel flash column chromatography with 60-70% acetone in petroleum ether as a eluent to afford tert-butyl 3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (20 mg, 21.21 μmol, 11% yield) as a pale yellow oil. LCMS m/z (ESI): 639.0 $[M-H]^-$ Step 5: The requisite amine was synthesized by following Procedure C-E using tert-butyl 3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (20 mg, 31.21 μmol) and hydrogen chloride solution in 1,4-dioxane (4.0 M, 0.2 mL). The resulting crude compound was triturated with methyl t-butyl ether to afford 3-[7-[2-cyano-3-[[ethyl(methyl)sulfamoyl]amino]-6-fluoro-phenoxy]quinoxalin-2-yl]-1-oxa-8-azaspiro[4.5]decane (17 mg, 20.08 μmol, 64% yield) as a yellow solid. LCMS m/z (ESI): 541.4 $[M+H]^+$ Step 6: Target compound was prepared via HATU mediated acid-amine coupling reaction (Procedure C—F). Amide coupling was carried out using 2-[4-[4-[(2,6-dioxo-3-piperidyl)amino]-2-fluoro-phenyl]-1-piperidyl]acetic acid (15 mg, 37.51 μmol), N,N-diisopropylethylamine (4.85 mg, 37.51 μmol, 6.53 μL), 3-[7-[2-cyano-3-[[ethyl(methyl)sulfamoyl]amino]-6-fluoro-phenoxy]quinoxalin-2-yl]-1-oxa-8-azaspiro[4.5]decane (17.32 mg, 30.01 μmol) and HATU (14.26 mg, 37.51 μmol). The crude compound was purified by reverse phase column chromatography, eluting with 46% acetonitrile in 0.1% ammonium acetate in water, to afford 3-[7-[2-cyano-3-[[ethyl(methyl)sulfamoyl]amino]-6-fluoro-phenoxy]quinoxalin-2-yl]-8-[2-[4-[4-[(2,6-dioxo-3-piperidyl)amino]-2-fluoro-phenyl]-1-piperidyl]acetyl]-1-oxa-8-azaspiro[4.5]decane (10.7 mg, 11.52 μmol, 31% yield) as an off-white solid. LCMS m/z (ESI): 886.20 $[M+H]^+$; $^1H$ NMR (400 MHz, DMSO-$d_6$): δ=10.79 (s, 1H), 9.66 (s, 1H), 8.88 (s, 1H), 8.15 (d, J=8.80 Hz, 1H), 7.71 (dd, J=2.80, 9.20 Hz, 1H), 7.64-7.56 (m, 1H), 7.35 (m, 1H), 7.13 (s, 1H), 6.98 (s, 1H), 6.50-6.45 (m, 2H), 6.07 (d, J=7.20 Hz, 1H), 4.33-4.28 (m, 2H), 4.03-3.98 (m, 2H), 3.90-3.70 (m, 1H), 3.48-3.46 (m, 2H), 3.06-3.05 (m, 2H), 2.80-2.60 (m, 6H), 2.40-2.13 (m, 2H), 2.11-2.07 (m, 2H), 2.00-1.60 (m, 13H), 1.24 (s, 2H), 1.04 (t, J=7.20 Hz, 3H).

Example 222
(3S)-3-[7-[2-cyano-3-[[ethyl(methyl)sulfamoyl]amino]-6-fluorophenoxy]quinoxalin-2-yl]-8-[2-[1-[3-(2,4-dioxo-1,3-diazinan-1-yl)-5-fluoro-1-methyl-indazol-6-yl]-4-hydroxypiperidin-4-yl]acetyl]-1-oxa-8-azaspiro[4.5]decane
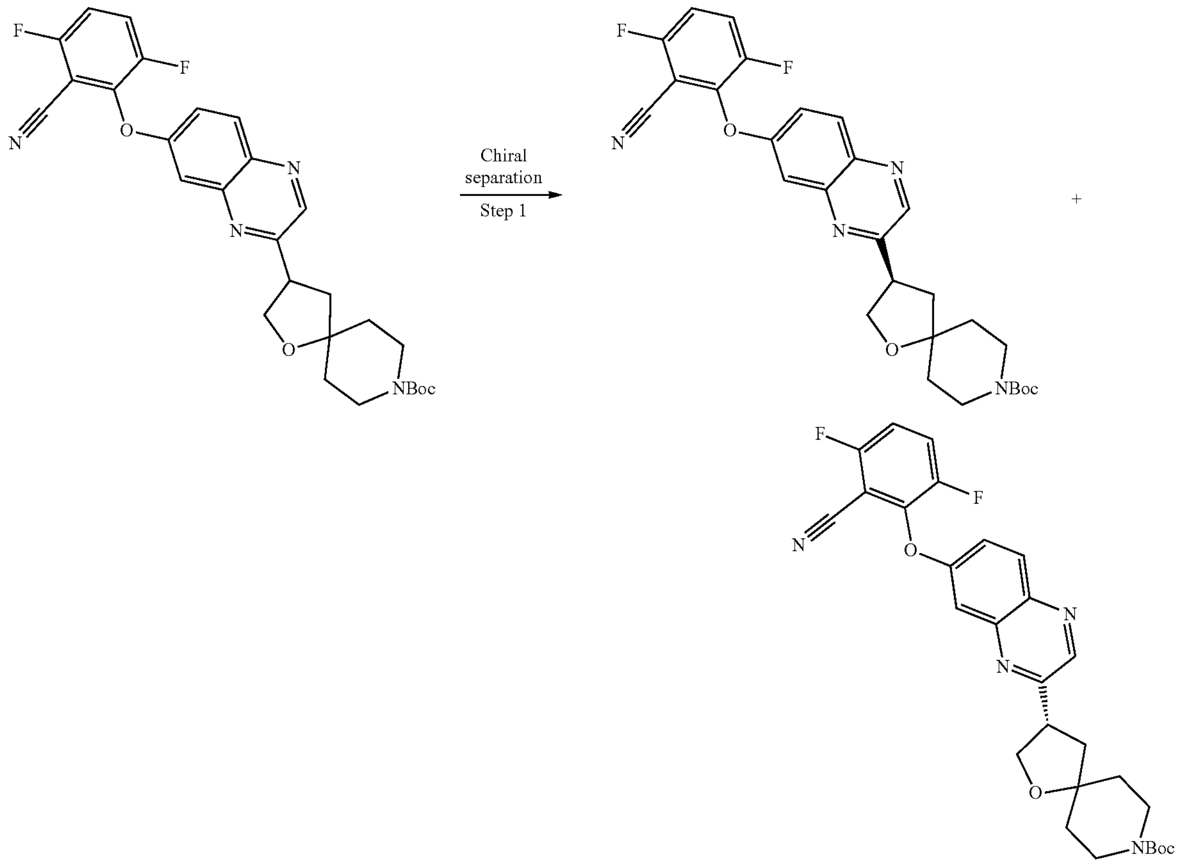
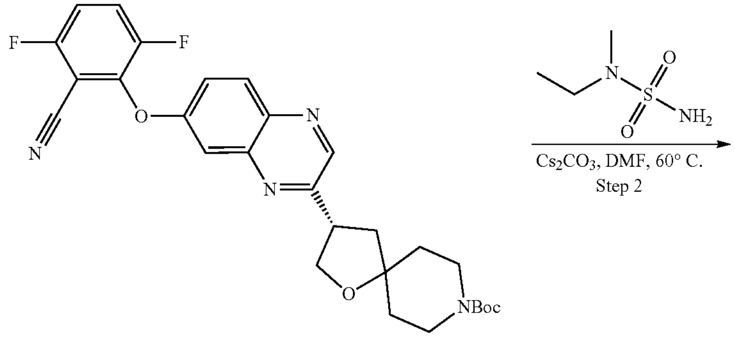

-continued

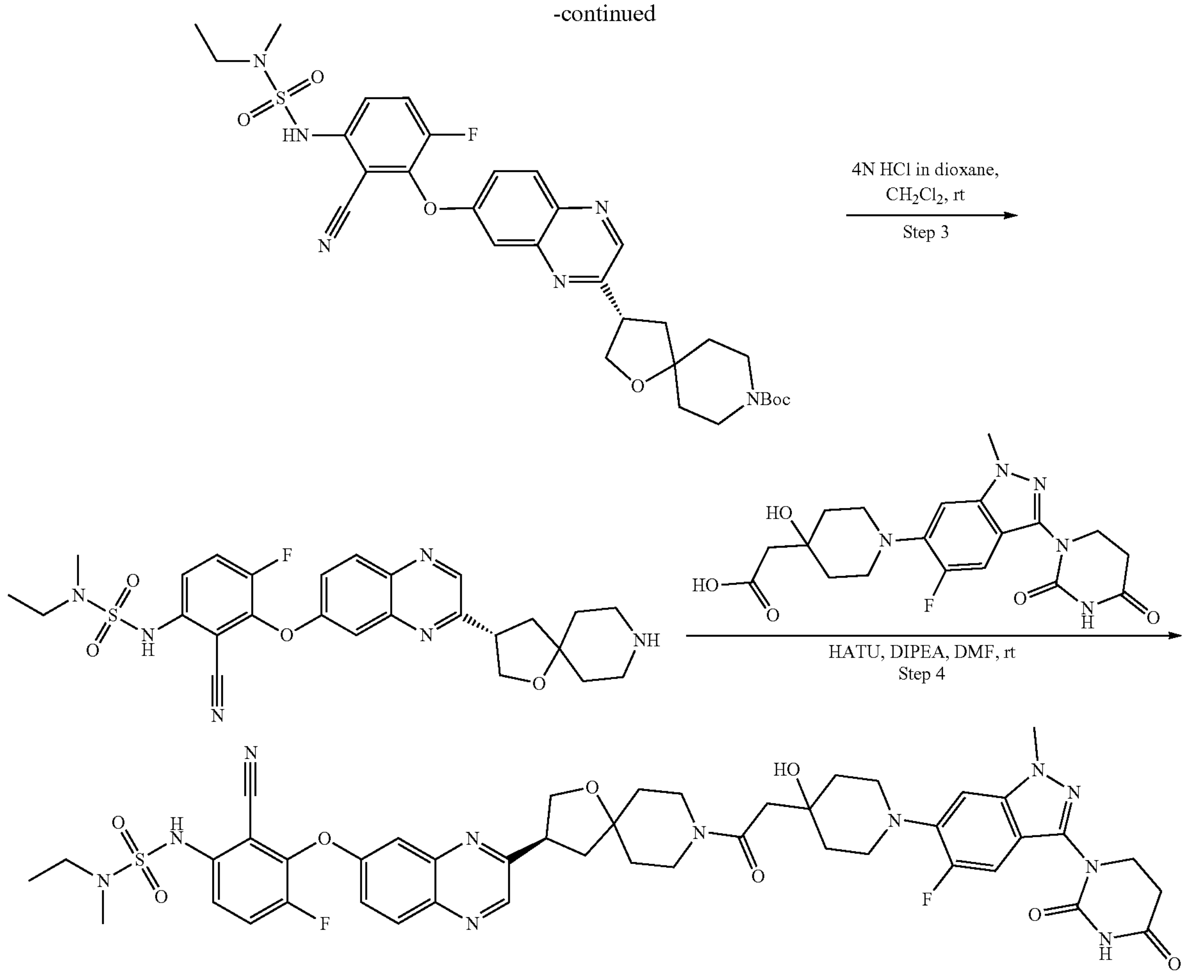

Step 1: tert-butyl 3-[7-(2-cyano-3,6-difluoro-phenoxy) quinoxalin-2-yl]-1-oxa-8-azaspiro[4.5]decane-8-carboxylate (0.4 g, 745.20 μmol) was chirally resolved to afford the corresponding pure enantiomers tert-butyl (3R)-3-[7-(2-cyano-3,6-difluoro-phenoxy)quinoxalin-2-yl]-1-oxa-8-azaspiro[4.5]decane-8-carboxylate (first eluting, 90 mg, 172.23 μmol) and tert-butyl (3S)-3-[7-(2-cyano-3,6-difluoro-phenoxy)quinoxalin-2-yl]-1-oxa-8-azaspiro[4.5]decane-8-carboxylate (second eluting, 90 mg, 172.23 μmol).

Note: After the SFC chiral purification. first eluting isomer (RT-3.0, (Separated in Lux A1 column)) arbitrarily assigned as R-isomer and second eluting isomer (RT-3.78) arbitrarily assigned as S-isomer. second eluting isomer (s-isomer [α]D=+42.4 conc: 0.5M). LCMS(ES$^+$): m/z 467.0 $[M+H-56]^+$ Step 2: To a solution of tert-butyl (3S)-3-[7-(2-cyano-3,6-difluoro-phenoxy)quinoxalin-2-yl]-1-oxa-8-azaspiro[4.5]decane-8-carboxylate (90 mg, 172.23 μmol) in N,N-dimethylformamide (2 mL) was added cesium carbonate (140.29 mg, 430.59 μmol) and [methyl(sulfamoyl)amino]ethane (47.60 mg, 344.47 μmol) at room temperature. Reaction mixture was heated to 65° C. for 16 h. The reaction mixture was diluted with water (20 mL), and the resulting solid was filtered off. The filtrate was extracted with ethyl acetate (2×25 mL), and the organic layer was washed with brine (10 mL), dried over sodium sulfate and concentrated under reduced pressure to afford tert-butyl (3S)-3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (80 mg, 103.30 μmol, 60% yield) as a brown liquid. LCMS m/z (ESI): 641.4 $[M+H]^+$.

Step 3: To a solution of tert-butyl (3S)-3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (80 mg, 124.86 μmol) in dichloromethane (1 mL) was added 4M hydrogen chloride solution in 1,4-dioxane (1 mL) at 0° C. under nitrogen atmosphere. The resulting solution was stirred at room temperature for 2 h. The resulting solution was concentrated under reduced pressure to afford (3S)-3-[7-[2-cyano-3-[[ethyl(methyl)sulfamoyl]amino]-6-fluoro-phenoxy]quinoxalin-2-yl]-1-oxa-8-azaspiro[4.5]decane (70 mg, 86.82 μmol, 70% yield) as a brown solid, which was carried forward without further purification. LCMS m/z (ESI): 541.6$[M+H]^+$ Step 4: Target compound was prepared via HATU mediated acid-amine coupling reaction (Procedure C-E). Amide coupling was carried out using 2-[1-[3-(2,4-dioxohexahydropyrimidin-1-yl)-5-fluoro-1-methyl-indazol-6-yl]-4-hydroxy-4-piperidyl]acetic acid (54.31 mg, 129.48 μmol), (3S)-3-[7-[2-cyano-3-[[ethyl(methyl)sulfamoyl]amino]-6-fluoro-phenoxy]quinoxalin-2-yl]-1-oxa-8-azaspiro[4.5]decane (70 mg, 129.48 μmol), HATU (49.23 mg, 129.48 μmol) and N,N-diisopropylethylamine (83.67 mg, 647.42 μmol, 112.77 μL). Crude compound was purified by reverse phase column chromatography by using 30 g snap, eluting with 35% acetonitrile in 0.1% formic acid in water, to afford (3S)-3-[7-[2-cyano-3-[[ethyl(methyl)sulfamoyl]amino]-6-fluoro-phenoxy]quinoxalin-2-yl]-8-[2-[1-[3-(2,4-dioxo-hexahydropyrimidin-1-yl)-5-fluoro-1-methyl-indazol-6-yl]-4-hydroxy-4-piperidyl]acetyl]-1-oxa-8-azaspiro[4.5]decane (43 mg, 43.38 μmol, 34% yield) as off-white solid. LCMS m/z (ESI): 942.0[M+H]$^+$; $^1$H NMR (400 MHz, DMSO-$d_6$): δ=10.54 (s, 1H), 10.19 (s, 1H), 8.91 (s, 1H), 8.18 (d, J=9.20 Hz, 1H), 7.89 (t, J=9.60 Hz, 1H), 7.74 (d, J=9.20 Hz, 1H), 7.52 (dd, J=4.00, 9.20 Hz, 1H), 7.33 (d, J=12.80 Hz, 1H), 7.23 (s, 1H), 7.13 (d, J=7.20 Hz, 1H), 5.04 (s, 1H), 4.28 (s, 1H), 4.07-3.99 (m, 2H), 3.96 (s, 3H), 3.91 (t, J=28.00 Hz, 3H), 3.72-3.62 (m, 1H), 3.57-3.45 (m, 1H), 3.23-3.12 (m, 4H), 3.12-3.03 (m, 2H), 2.81 (s, 3H), 2.75 (t, J=28.00 Hz, 2H), 2.68 (s, 1H), 2.58 (d, J=Hz, 2H), 2.42-2.33 (m, 2H), 2.17-2.12 (m, 1H), 1.82-1.80 (m, 3H), 1.74-1.67 (m, 5H), 1.62-1.53 (m, 1H), 1.07 (t, J=7.20 Hz, 3H).

Example 223

(3R)-3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane

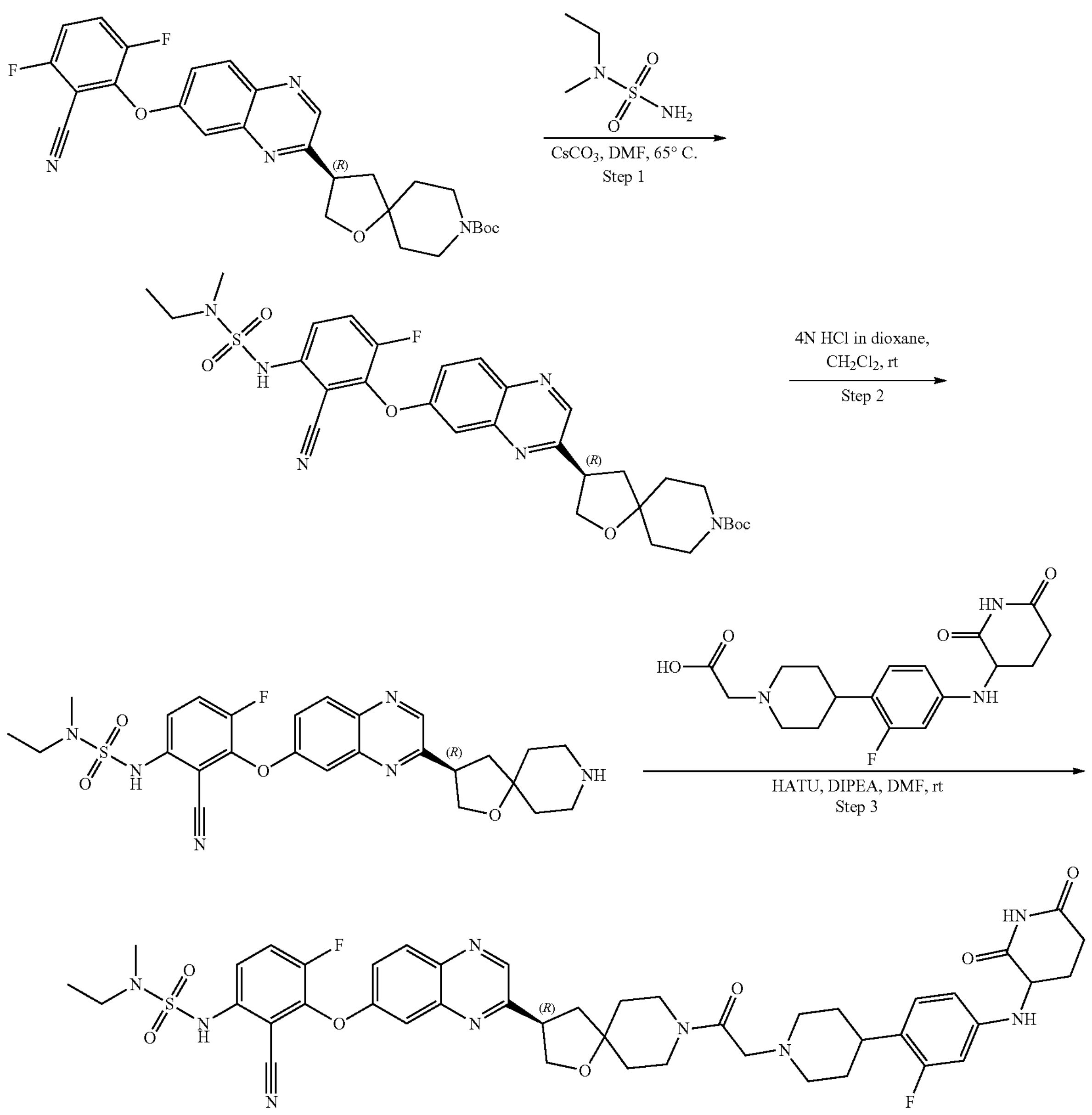

Step 1: Sulfamoylated quinoxaline intermediate was synthesized by following Procedure C-D using tert-butyl (3R)-3-[7-(2-cyano-3,6-difluoro-phenoxy)quinoxalin-2-yl]-1-oxa-8-azaspiro[4.5]decane-8-carboxylate (100 mg, 191.37 μmol), cesium carbonate (155.88 mg, 478.43 μmol) and [methyl(sulfamoyl)amino]ethane (39.67 mg, 287.06 μmol) to afford tert-butyl (3R)-3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (60 mg, 33.71 μmol, 18% yield) as pale yellow oil, which was carried forward without further purification. LCMS m/z (ESI): 639.20 $[M-H]^-$ Step 2: The requisite amine was synthesized by following Procedure C-E using tert-butyl (3R)-3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (60 mg, 93.64 μmol) and hydrogen chloride solution 4.0 M in dioxane (2 mL). The resulting crude compound was triturated with methyl t-butyl ether to afford (3R)-3-[7-[2-cyano-3-[[ethyl(methyl)sulfamoyl]amino]-6-fluoro-phenoxy]quinoxalin-2-yl]-1-oxa-8-azaspiro[4.5]decane (55 mg, 37.28 μmol, 40% yield) as a pale brown oil. LCMS m/z (ESI): 541.40 $[M+H]^+$ Step 3: Target compound was prepared via HATU mediated acid-amine coupling reaction (Procedure C—F). Amide coupling was carried out using (3R)-3-[7-[2-cyano-3-[[ethyl(methyl)sulfamoyl]amino]-6-fluoro-phenoxy]quinoxalin-2-yl]-1-oxa-8-azaspiro[4.5]decane (51.96 mg, 90.04 μmol), 2-[4-[4-[(2,6-dioxo-3-piperidyl)amino]-2-fluoro-phenyl]-1-piperidyl]acetic acid (40 mg, 100.04 μmol) N,N-diisopropylethylamine (77.58 mg, 600.23 μmol, 104.55 μL) and HATU (41.84 mg, 110.04 μmol). The crude compound was purified by reverse phase column chromatography, eluting with 50% acetonitrile in 0.1% ammonium acetate in water, to afford (3R)-3-[7-[2-cyano-3-[[ethyl(methyl)sulfamoyl]amino]-6-fluoro-phenoxy]quinoxalin-2-yl]-8-[2-[4-[4-[(2,6-dioxo-3-piperidyl)amino]-2-fluoro-phenyl]-1-piperidyl]acetyl]-1-oxa-8-azaspiro[4.5]decane (14.8 mg, 15.93 μmol, 16% yield) as pale yellow solid. LCMS m/z (ESI): 886.20 $[M+H]^+$; $^1$H NMR (400 MHz, DMSO-$d_6$): δ=10.78 (s, 1H), 9.65 (s, 1H), 8.87 (s, 1H), 8.14 (d, J=9.20 Hz, 1H), 7.70 (dd, J=2.40, 8.80 Hz, 1H), 7.34 (s, 1H), 7.12 (s, 1H), 6.99 (s, 1H), 6.47 (t, J=12.40 Hz, 2H), 6.04 (d, J=7.20 Hz, 1H), 4.37-4.23 (m, 2H), 4.23-3.92 (m, 2H), 3.84-3.42 (m, 3H), 3.11-2.90 (m, 3H), 2.79-2.71 (m, 2H), 2.63-2.50 (m, 5H), 2.42-2.33 (m, 4H), 2.20-2.10 (m, 3H), 1.90-1.50 (m, 11H), 1.04 (t, J=7.20 Hz, 3H).

Example 224

(3S)-3-[7-[2-cyano-3-[[ethyl(methyl)sulfamoyl]amino]-6-fluorophenoxy]quinoxalin-2-yl]-8-[2-[4-[4-[(2,6-dioxopiperidin-3-yl)amino]-2-fluorophenyl]piperidin-1-yl]acetyl]-1-oxa-8-azaspiro[4.5]decane

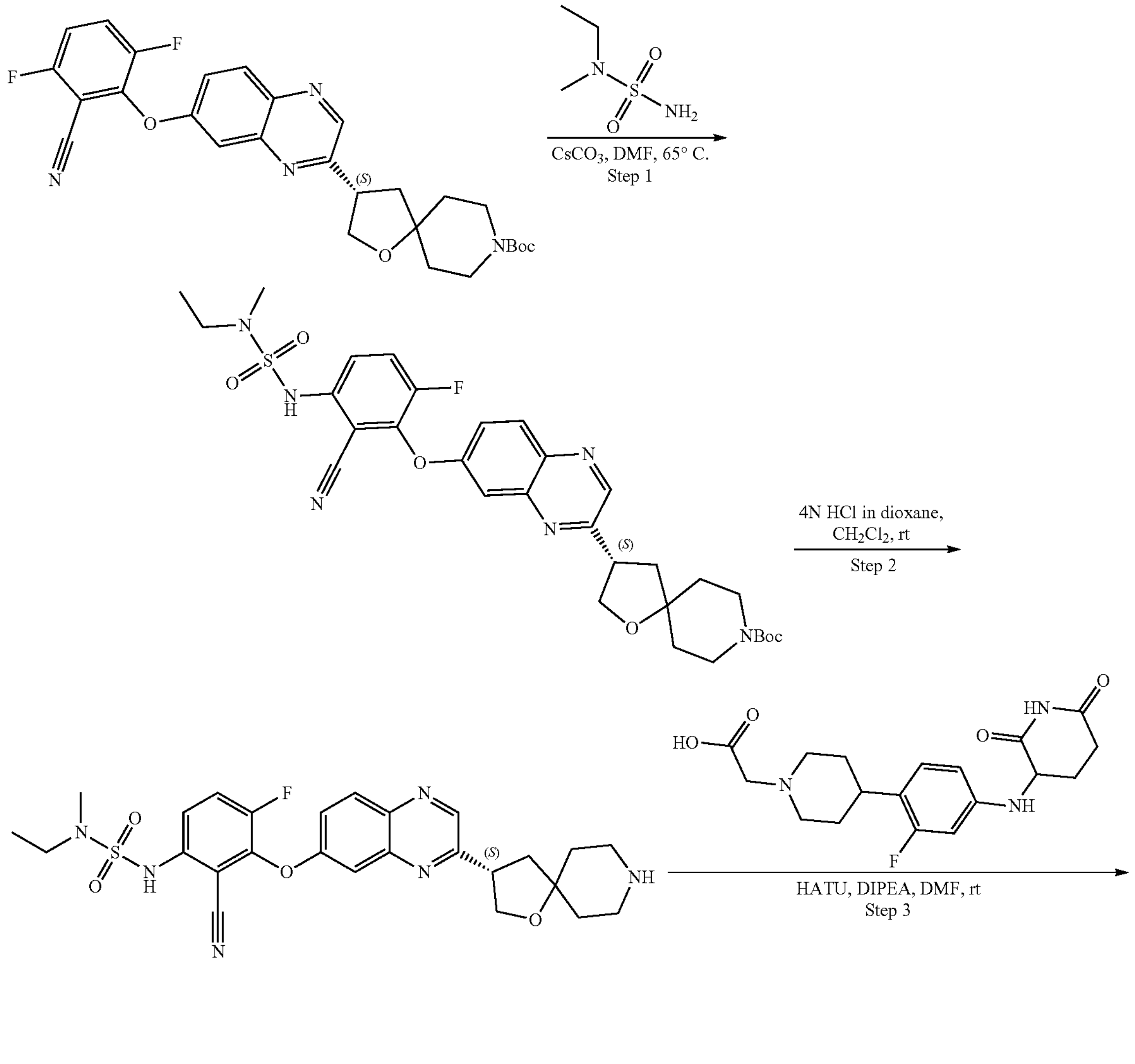

-continued

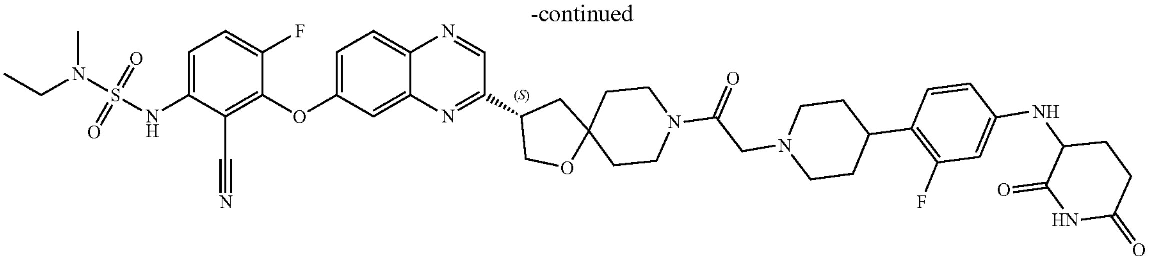

Step 1: Sulfamoylated quinoxaline intermediate was synthesized by following Procedure C-D using tert-butyl (3S)-3-[7-(2-cyano-3,6-difluoro-phenoxy)quinoxalin-2-yl]-1-oxa-8-azaspiro[4.5]decane-8-carboxylate (100.00 mg, 191.37 μmol), cesium carbonate (155.88 mg, 478.43 μmol) and [methyl(sulfamoyl)amino]ethane (39.67 mg, 287.06 μmol) to afford tert-butyl (3S)-3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (60 mg, 33.99 μmol, 18% yield) as a pale yellow oil, which was carried forward without further purification. LCMS m/z (ESI): 639.20 $[M-H]^-$ Step 2: The requisite amine was synthesized by following Procedure C-E using tert-butyl (3S)-3-[7-[2-cyano-3-[[ethyl(methyl)sulfamoyl]amino]-6-fluoro-phenoxy]quinoxalin-2-yl]-1-oxa-8-azaspiro[4.5]decane-8-carboxylate (60 mg, 93.64 μmol) and hydrogen chloride solution (4.0 M in 1,4-dioxane, 2 mL). The resulting crude compound was triturated with methyl t-butyl ether to afford (3S)-3-[7-[2-cyano-3-[[ethyl(methyl)sulfamoyl]amino]-6-fluoro-phenoxy]quinoxalin-2-yl]-1-oxa-8-azaspiro[4.5]decane (55 mg, 38.79 μmol, 41% yield) as a pale brown oil. LCMS m/z (ESI): 541.40 $[M+H]^+$ Step 3: Target compound was prepared via HATU mediated acid-amine coupling reaction (Procedure C—F). Amide coupling was carried out using (3S)-3-[7-[2-cyano-3-[[ethyl(methyl)sulfamoyl]amino]-6-fluoro-phenoxy]quinoxalin-2-yl]-1-oxa-8-azaspiro[4.5]decane (51.96 mg, 90.04 μmol), 2-[4-[4-[(2,6-dioxo-3-piperidyl)amino]-2-fluoro-phenyl]-1-piperidyl]acetic acid (40 mg, 100.04 μmol), N,N-diisopropylethylamine (77.58 mg, 600.23 μmol, 104.55 μL) and HATU (45.65 mg, 120.05 μmol). The crude compound was purified by reverse phase column chromatography, eluting with 46% acetonitrile in 0.1% ammonium acetate in water to afford (3S)-3-[7-[2-cyano-3-[[ethyl(methyl)sulfamoyl]amino]-6-fluoro-phenoxy]quinoxalin-2-yl]-8-[2-[4-[4-[(2,6-dioxo-3-piperidyl)amino]-2-fluoro-phenyl]-1-piperidyl]acetyl]-1-oxa-8-azaspiro[4.5]decane (17 mg, 18.36 μmol, 18% yield) as an off-white solid. LCMS m/z (ESI): 886.20 $[M+H]^+$; $^1H$ NMR (400 MHz, DMSO-$d_6$): δ=10.80 (s, 1H), 9.65 (s, 1H), 8.87 (s, 1H), 8.14 (d, J=9.20 Hz, 1H), 7.71 (dd, J=2.40, 8.80 Hz, 1H), 7.50 (s, 1H), 7.35 (s, 1H), 7.12 (s, 1H), 6.98 (s, 1H), 6.49-6.45 (m, 2H), 6.07 (d, J=8.00 Hz, 1H), 4.32-4.28 (m, 2H), 4.03-3.98 (m, 2H), 3.84-3.72 (m, 1H), 3.53-3.42 (m, 2H), 3.29-3.16 (m, 2H), 3.04 (d, J=6.80 Hz, 2H), 2.79-2.70 (m, 2H), 2.68-2.60 (m, 5H), 2.34-2.33 (m, 1H), 2.23-2.15 (m, 2H), 2.11-2.06 (m, 2H), 1.92-1.58 (m, 11H), 1.04 (t, J=7.20 Hz, 3H).

Example 225

(3S)-3-[6-[2-cyano-3-[[ethyl(methyl)sulfamoyl]amino]-6-fluorophenoxy]-4-methoxyquinolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane

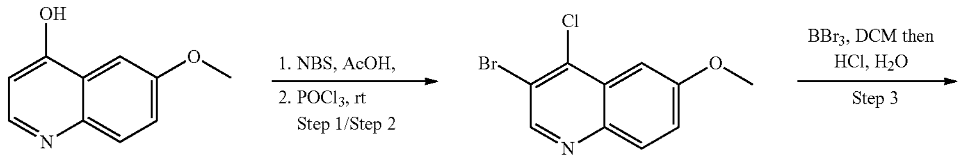

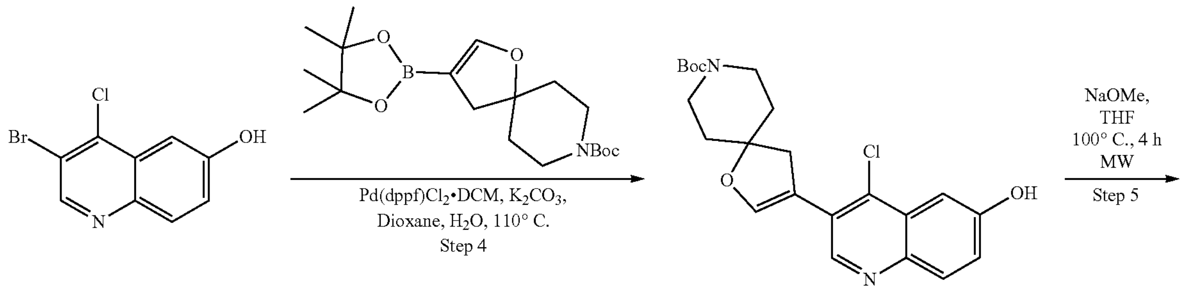

-continued

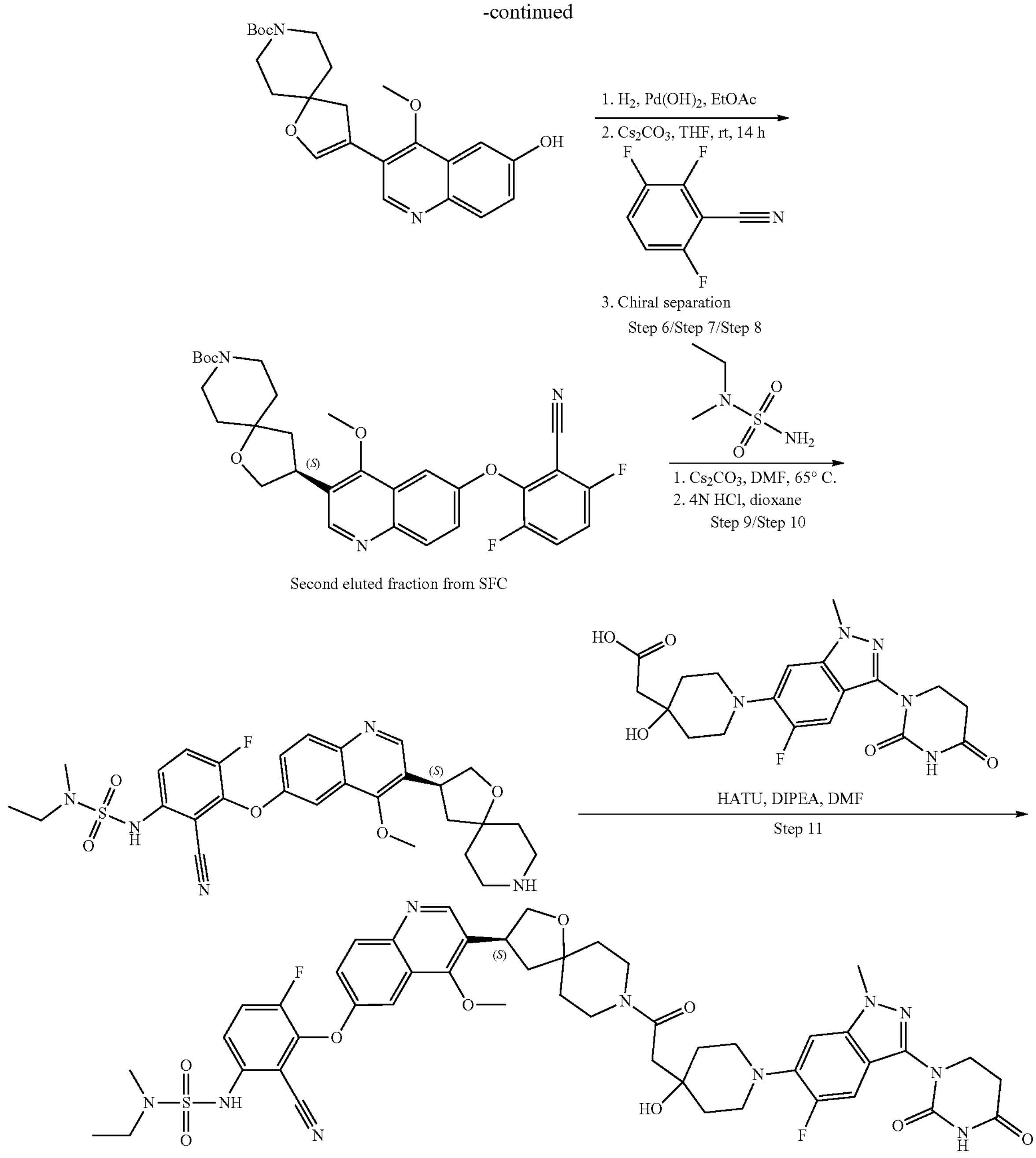

Step 1: To a stirred solution of 6-methoxyquinolin-4-ol (4.0 g, 22.83 mmol) in acetic acid (60 ml) under nitrogen atmosphere was added N-bromosuccinimide (4.10 g, 23.06 mmol, 1.95 mL) at 0° C. The reaction mixture was stirred at 0° C. for 30 min. After completion, the reaction mixture was quenched with water (60 ml) and extracted with ethyl acetate (2×50 ml). The organic phases were combined and washed with brine, dried over anhydrous sodium sulfate, filtered and concentrated under reduced pressure to afford product 3-bromo-6-methoxy-quinolin-4-ol (5.30 g, 20.44 mmol, 90% yield). LCMS m/z (ESI+): 254.2 $[M+H]^+$, 255.2 (Br-isotope pattern).

Step 2: To 3-bromo-6-methoxy-quinolin-4-ol (5 g, 19.68 mmol) was added phosphorus oxychloride (6.03 g, 39.36 mmol, 15 mL) at 0° C. under nitrogen atmosphere. The reaction mixture was warmed to rt and stirred at 90° C. for 2 h. After completion, the reaction mixture was added ice cold water and extracted with ethyl acetate (50 mL). The combined organic layer was washed with brine, dried over anhydrous sodium sulfate and organic layer was concentrated under reduced pressure to afford 3-bromo-4-chloro-6-methoxy-quinoline (5.2 g, 18.51 mmol, 94% yield) as a pale-yellow oil. LCMS m/z (ESI): 272.0$[M+H]^+$.

Step 3: To a stirred solution of 3-bromo-4-chloro-6-methoxy-quinoline (5.20 g, 19.08 mmol) in dichloromethane (20 mL) was added boron tribromide in dichloromethane (1 N, 19.08 mmol) at 0° C. under nitrogen atmosphere. The reaction was stirred at room temperature for 16 h. The reaction mixture was poured in to 200 mL of ice-cold water, organic phases were separated. The aqueous layer was acidified with 1 N HCl to pH 4 and desired compound was extracted using ethyl acetate (250 mL×2). The organic layer was washed with brine, dried over anhydrous sodium sulfate and concentrated under reduced pressure to afford 3-bromo-4-chloro-quinolin-6-ol (3.7 g, 13.17 mmol, 69% yield) as a grey color solid. LCMS m/z (ESI): 260.0 $[M+H]^+$.

Step 4: To a solution of tert-butyl 3-(4,4,5,5-tetramethyl-1,3,2-dioxaborolan-2-yl)-1-oxa-8-azaspiro[4.5]dec-2-ene-8-carboxylate (890.22 mg, 2.44 mmol) and 3-bromo-4-chloro-quinolin-6-ol (0.7 g, 2.71 mmol) in 1,4-dioxane (165.51 μL) and water (1.66 mL) was added potassium carbonate (935.66 mg, 6.77 mmol) at rt under nitrogen. The reaction mixture was degassed with nitrogen for 10 min, then added [1,1'-bis(diphenylphosphino)ferrocene]dichloropalladium(II), complex with dichloromethane (221 mg, 0.271 mmol) at same temperature. The resulting solution was heated to 100° C. for 12 h. After completion, the resulting solution was filtered through a celite bed and washed with ethyl acetate (10 ml). The collected filtrates were concentrated under reduced pressure. The crude compound was purified by silica gel column chromatography with 70% ethyl acetate in petroleum ether as a eluent to afford tert-butyl 3-(4-chloro-6-hydroxy-3-quinolyl)-1-oxa-8-azaspiro[4.5]dec-2-ene-8-carboxylate (600 mg, 1.30 mmol, 48% yield) as a brownish solid. LCMS m/z (ESI): 417.2$[M+H]^+$.

Step 5: To a stirred solution of tert-butyl 3-(4-chloro-6-hydroxy-3-quinolyl)-1-oxa-8-azaspiro[4.5]dec-2-ene-8-carboxylate (350 mg, 839.54 μmol) in anhydrous THF (5 mL) was added sodium methoxide, 25% in methanol (90.71 mg, 1.68 mmol, 93.61 μL) at room temperature under nitrogen atmosphere. The reaction mixture was stirred at 100° C. for 6 h under microwave condition. After completion of the reaction, the reaction mass was diluted with water and extracted using ethyl Acetate (2×10 mL). The separated organic layers were dried over anhydrous sodium sulfate, filtered and concentrated under reduced pressure to afford the crude compound. The crude product was purified by reverse phase column chromatography by using 120 g snap eluted with 40% acetonitrile in 0.1% formic acid in water to afford tert-butyl 3-(6-hydroxy-4-methoxy-3-quinolyl)-1-oxa-8-azaspiro[4.5]dec-2-ene-8-carboxylate (270 mg, 353.47 μmol, 42% yield) as a brown solid. LCMS m/z (ESI): 413.5$[M+H]^+$.

Step 6: To a stirred solution of tert-butyl 3-(6-hydroxy-4-methoxy-3-quinolyl)-1-oxa-8-azaspiro[4.5]dec-2-ene-8-carboxylate (270 mg, 654.58 μmol) in 1,4-dioxane (3.5 mL) was added palladium hydroxide on carbon, 20 wt. % 50% water (91.93 mg, 654.58 μmol) under inert atmosphere at room temperature. The reaction mixture was hydrogenated with hydrogen bladder pressure for 32 h at room temperature. After completion, the reaction mixture was filtered through a pad of celite using 10% methanol in dichloromethane (200 mL). Filtrate was concentrated under reduced pressure was purified by silica gel column chromatography with 70% ethyl acetate in petroleum ether as a eluent to afford tert-butyl 3-(6-hydroxy-4-methoxy-3-quinolyl)-1-oxa-8-azaspiro[4.5]decane-8-carboxylate (270 mg, 547.17 μmol, 84% yield) as a brown color solid. LCMS m/z (ESI): 415.6$[M+H]^+$.

Step 7/8: To a solution of tert-butyl 3-(6-hydroxy-4-methoxy-3-quinolyl)-1-oxa-8-azaspiro[4.5]decane-8-carboxylate (271.32 mg, 654.58 μmol) and 2,3,6-trifluorobenzonitrile (133.68 mg, 850.96 μmol, 98.29 μL) in THF (4 mL) was added cesium carbonate (639.82 mg, 1.96 mmol). The reaction was stirred at room temperature for 16 h. After completion of the reaction, the reaction mixture was diluted with water (30 mL) and extracted using ethyl acetate (2×50 mL). The combined organic layers were dried over anhydrous sodium sulfate, filtered and concentrated under reduced pressure to afford the crude compound. The obtained crude product was purified by flash silica gel column chromatography eluting with 0-100% ethyl acetate in petroleum ether to obtain a racemic compound as an off-white solid. The racemic compound was chirally resolved by chiral SFC (column: Lux Amylose-1 (250*30) mm, 5μ; mobile phase: $CO_2$: 0.5% isopropyl amine in methanol (60:40); flow rate: 70 g/min; back pressure: 100 bar; wavelength: 220; cycle time: 8 min) to afford peak 1 (first eluted) tert-butyl (3R)-3-[6-(2-cyano-3,6-difluoro-phenoxy)-4-methoxy-3-quinolyl]-1-oxa-8-azaspiro[4.5]decane-8-carboxylate (71 mg, 127.43 μmol, 19% yield, 99.36% ee, arbitrarily assigned as R enantiomer, SOR=+28.80) as an off-white solid and peak 2 (second eluted) tert-butyl (3S)-3-[6-(2-cyano-3,6-difluoro-phenoxy)-4-methoxy-3-quinolyl]-1-oxa-8-azaspiro[4.5]decane-8-carboxylate (65 mg, 116.66 μmol, 18% yield, 97.2% ee, arbitrarily assigned as S enantiomer, SOR=−18.00) as an off-white solid.

Step 9: Sulfamoylated intermediate was synthesized by following Procedure C-D using tert-butyl (3S)-3-[6-(2-cyano-3,6-difluoro-phenoxy)-4-methoxy-3-quinolyl]-1-oxa-8-azaspiro[4.5]decane-8-carboxylate (60.00 mg, 108.78 μmol), cesium carbonate (106.33 mg, 326.34 μmol) and [methyl(sulfamoyl)amino]ethane (25.55 mg, 184.92 μmol). After completion, the reaction mass was diluted with water (10 mL) and extracted using 10% methanol in dichloromethane (2×30 mL). The separated organic layers were dried over anhydrous sodium sulfate, filtered and concentrated under reduced pressure to afford the crude compound tert-butyl (3S)-3-[6-[2-cyano-3-[[ethyl(methyl)sulfamoyl]amino]-6-fluoro-phenoxy]-4-methoxy-3-quinolyl]-1-oxa-8-azaspiro[4.5]decane-8-carboxylate (48 mg, 52.32 μmol, 48% yield) as an off-white solid and proceeded to further step without purification. LCMS m/z (ESI): 670.5.$[M+H]^+$.

Step 10: Requisite amine was synthesized by 4 M HCl in dioxane mediated N-Boc deprotection Procedure C-E. N-Boc deprotection was done on tert-butyl (3S)-3-[6-[2-cyano-3-[[ethyl(methyl)sulfamoyl]amino]-6-fluoro-phenoxy]-4-methoxy-3-quinolyl]-1-oxa-8-azaspiro[4.5]decane-8-carboxylate (48.00 mg, 71.67 μmol) using hydrogen chloride, 4 M in 1,4-dioxane (1.5 mL) to afford (3S)-3-[6-[2-cyano-3-[[ethyl(methyl)sulfamoyl]amino]-6-fluoro-phenoxy]-4-methoxy-3-quinolyl]-1-oxa-8-azaspiro[4.5]decane (40 mg, 46.86 μmol, 65% yield) as an off-white solid. LCMS m/z ($ES^+$): 570.3$[M+H]^+$.

Step 11: Target compound was prepared via HATU mediated acid-amine coupling reaction (Procedure C—F). Amide coupling was carried out using (3S)-3-[6-[2-cyano-3-[[ethyl(methyl)sulfamoyl]amino]-6-fluoro-phenoxy]-4-methoxy-3-quinolyl]-1-oxa-8-azaspiro[4.5]decane (48 mg, 79.19 μmol), 2-[1-[3-(2,4-dioxohexahydropyrimidin-1-yl)-5-fluoro-1-methyl-indazol-6-yl]-4-hydroxy-4-piperidyl]acetic acid (33.21 mg, 72.86 μmol), N,N-diisopropylethylamine (51.18 mg, 395.97 μmol, 68.97 μL), and HATU (39.15 mg, 102.95 μmol). The crude compound was purified by reverse phase column chromatography eluted with 40% acetonitrile in 0.1% ammonium acetate in water to afford product (3S)-3-[6-[2-cyano-3-[[ethyl(methyl)sulfamoyl]amino]-6-fluoro-phenoxy]-4-methoxy-3-quinolyl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (15 mg, 14.41 μmol, 18% yield) as an off-white solid. LCMS m/z (ESI): 972.2 $[M+H]^+$; $^1$HNMR (400 MHz, DMSO-$d_6$): δ=10.54 (s, 1H), 10.20 (s, 1H), 8.91 (d, J=3.20

Hz, 1H), 8.11 (d, J=9.20 Hz, 1H), 7.88 (s, 1H), 7.60 (dd, J=2.80, 9.00 Hz, 1H), 7.50 (d, J=6.40 Hz, 1H), 7.33 (d, J=12.80 Hz, 1H), 7.28 (d, J=2.40 Hz, 1H), 7.13 (d, J=7.20 Hz, 1H), 5.06 (s, 1H), 4.20 (d, J=7.20 Hz, 1H), 3.95 (s, 3H), 3.89 (t, J=6.80 Hz, 4H), 3.86 (s, 3H), 3.74-3.62 (m, 1H), 3.61-3.50 (m, 1H), 3.21-3.10 (m, 4H), 2.80 (s, 3H), 2.75 (t, J=8.00 Hz, 2H), 2.59-2.52 (m, 4H), 2.50-2.34 (m, 2H), 1.97-1.71 (m, 10H), 1.06 (t, J=7.20 Hz, 3H).

Example 226

(3R)-3-[6-[2-cyano-3-[[ethyl(methyl)sulfamoyl]amino]-6-fluorophenoxy]-4-methoxyquinolin-3-yl]-8-[2-[1-[3-(2,4-dioxo-1,3-diazinan-1-yl)-5-fluoro-1-methylindazol-6-yl]-4-hydroxypiperidin-4-yl]acetyl]-1-oxa-8-azaspiro[4.5]decane Step 2: Requisite amine was synthesized by 4 M HCl in dioxane mediated N-Boc deprotection Procedure C-E. N-Boc deprotection was done on tert-butyl (3R)-3-[6-[2-cyano-3-[[ethyl(methyl)sulfamoyl]amino]-6-fluoro-phenoxy]-4-methoxy-3-quinolyl]-1-oxa-8-azaspiro[4.5]decane-8-carboxylate (40.00 mg, 59.72 μmol) using hydrogen chloride, 4 M in 1,4-dioxane (1.5 mL) to afford (3R)-3-[6-[2-cyano-3-[[ethyl(methyl)sulfamoyl]amino]-6-fluoro-phenoxy]-4-methoxy-3-quinolyl]-1-oxa-8-azaspiro[4.5]decane (32 mg, 31.68 μmol, 53% yield) as an off-white solid. LCMS m/z ($ES^+$): 570.4 $[M+H]^+$.

Step 3: Target compound was prepared via HATU mediated acid-amine coupling reaction (Procedure C—F). Amide coupling was carried out using (3R)-3-[6-[2-cyano-3-[[ethyl(methyl)sulfamoyl]amino]-6-fluoro-phenoxy]-4-methoxy-3-quinolyl]-1-oxa-8-azaspiro[4.5]decane (32 mg, 52.80 μmol), 2-[1-[3-(2,4-dioxohexahydropyrimidin-1-yl)-5-

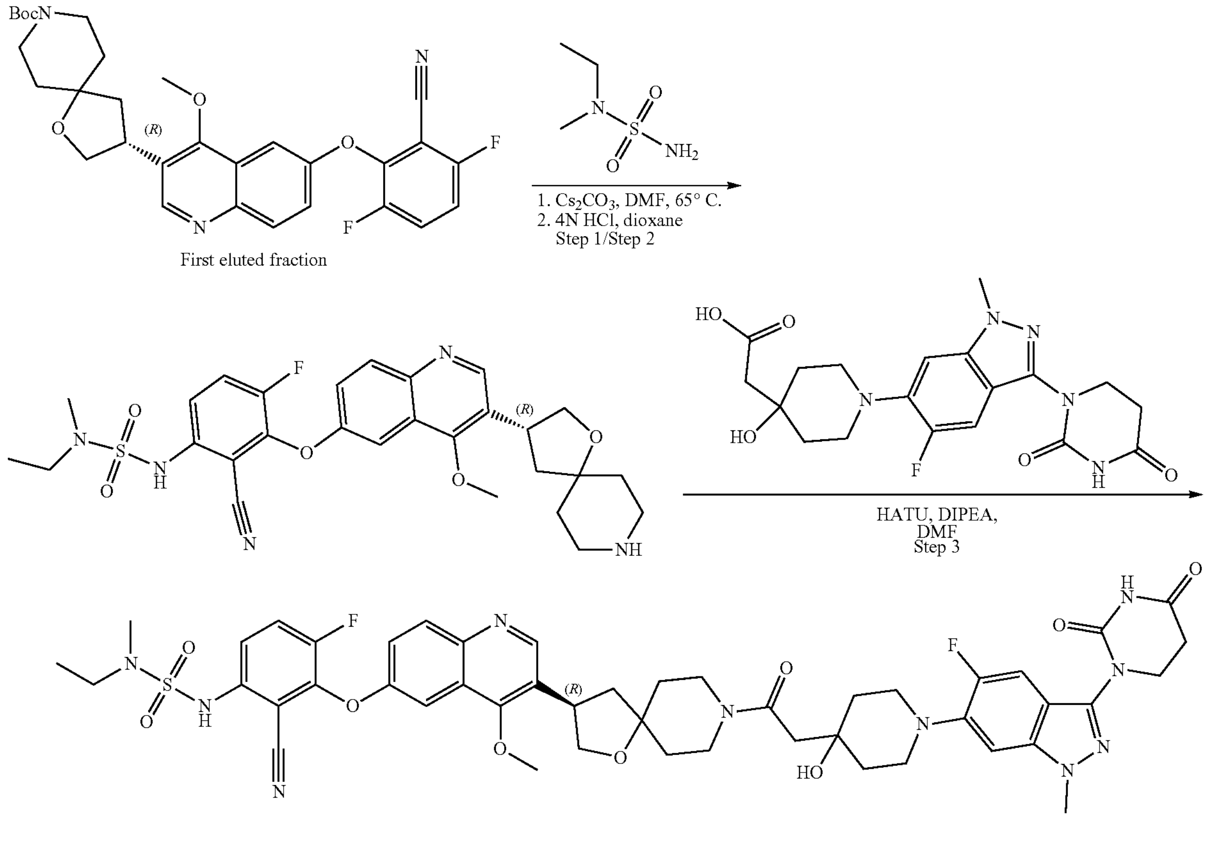

fluoro-1-methyl-indazol-6-yl]-4-hydroxy-4-piperidyl]acetic acid (24.36 mg, 53.43 μmol), N,N-diisopropylethylamine (34.12 mg, 263.98 μmol, 45.98 μL) and HATU (26.10 mg, 68.63 μmol). The crude compound was purified by reverse phase column chromatography eluted with 40% acetonitrile in 0.1% ammonium acetate in water to afford product (3R)-3-[6-[2-cyano-3-[[ethyl(methyl)sulfamoyl]amino]-6-fluoro-phenoxy]-4-methoxy-3-quinolyl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (6 mg, 5.94 μmol, 11% yield) as an off-white solid. LCMS m/z (ESI): 972.2 $[M+H]^+$. $^1$HNMR (400 MHz, DMSO-$d_6$): δ=10.54 (s, 1H), 10.19 (s, 1H), 8.90 (d, J=2.80 Hz, 1H), 8.10 (d, J=9.20 Hz, 1H), 7.83 (s, 1H), 7.59 (dd, J=2.80, 9.20 Hz, 1H), 7.47 (s, 1H), 7.33 (s, 1H), 7.27 (d, Step 1: Sulfamoylated intermediate was synthesized by following Procedure C-D using tert-butyl (3R)-3-[6-(2-cyano-3,6-difluoro-phenoxy)-4-methoxy-3-quinolyl]-1-oxa-8-azaspiro[4.5]decane-8-carboxylate (71.00 mg, 128.72 μmol), cesium carbonate (125.82 mg, 386.16 μmol) and [methyl(sulfamoyl)amino]ethane (30.24 mg, 218.83 μmol). After completion, the reaction mass was diluted with water (10 mL) and extracted using 10% methanol in dichloromethane (2×30 mL). The separated organic layers were dried over anhydrous sodium sulfate, filtered and concentrated under reduced pressure to afford the crude tert-butyl (3R)-3-[6-[2-cyano-3-[[ethyl(methyl)sulfamoyl]amino]-6-fluoro-phenoxy]-4-methoxy-3-quinolyl]-1-oxa-8-azaspiro[4.5]decane-8-carboxylate (42 mg, 47.66 μmol, 37% yield) as an off-white solid and proceeded to further step without purification. LCMS m/z (ESI): 670.5 $[M+H]^+$.

J=2.40 Hz, 1H), 7.13 (d, J=7.20 Hz, 1H), 5.06 (s, 1H), 4.22 (t, J=6.80 Hz, 1H), 3.95 (s, 1H), 3.89 (t, J=6.80 Hz, 4H), 3.86 (s, 3H), 3.73-3.62 (m, 1H), 3.60-3.49 (m, 1H), 3.29-3.04 (m, 7H), 2.76-2.72 (m, 4H), 2.59-2.51 (m, 4H), 2.40-2.37 (m, 1H), 2.01-1.98 (m, 2H), 1.82-1.71 (m, 9H), 1.05 (t, J=7.20 Hz, 3H).
Example 227
(3S)-3-[6-[2-cyano-3-[[ethyl(methyl)sulfamoyl]amino]-6-fluoro-phenoxy]cinnolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane
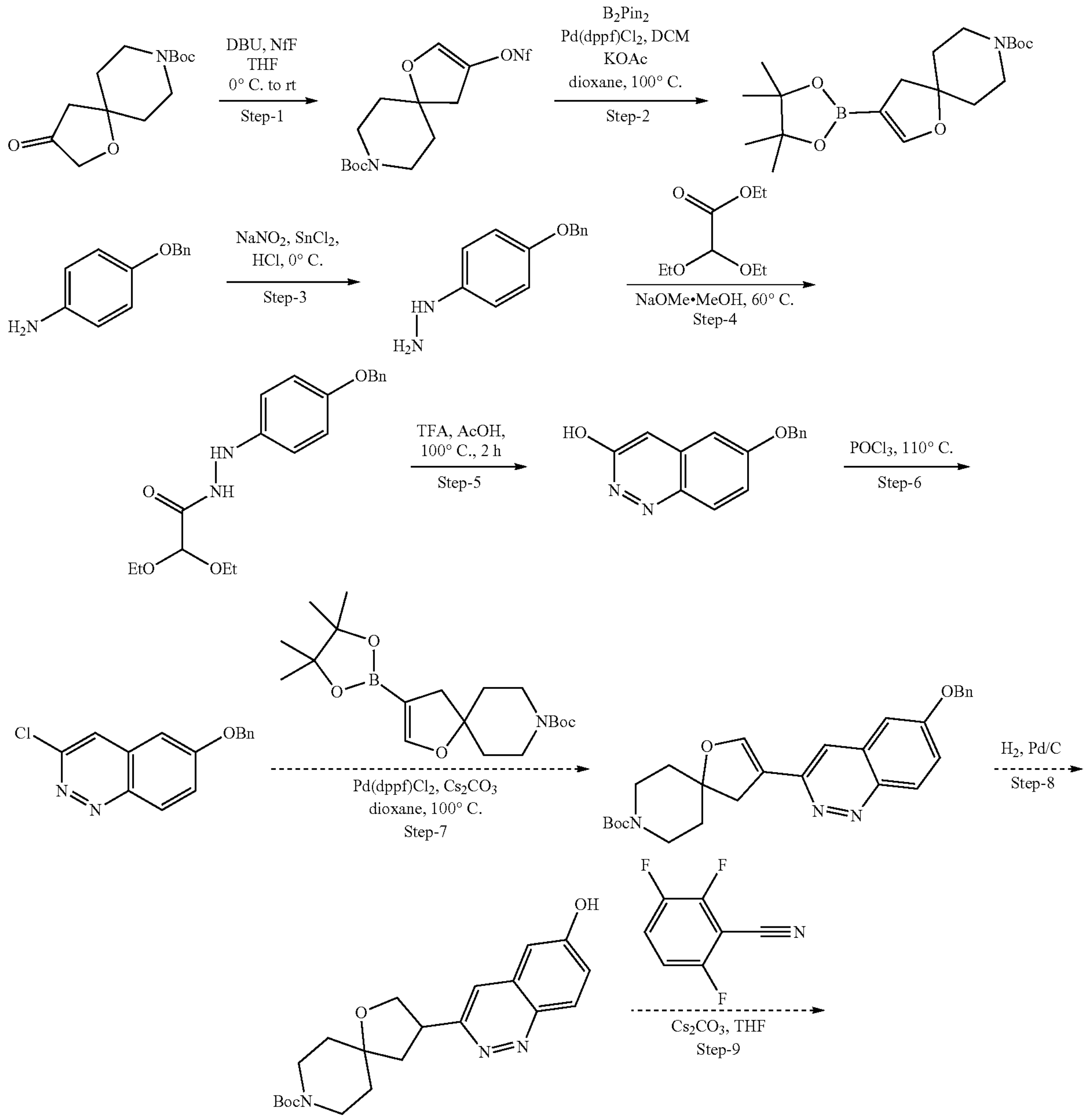

-continued
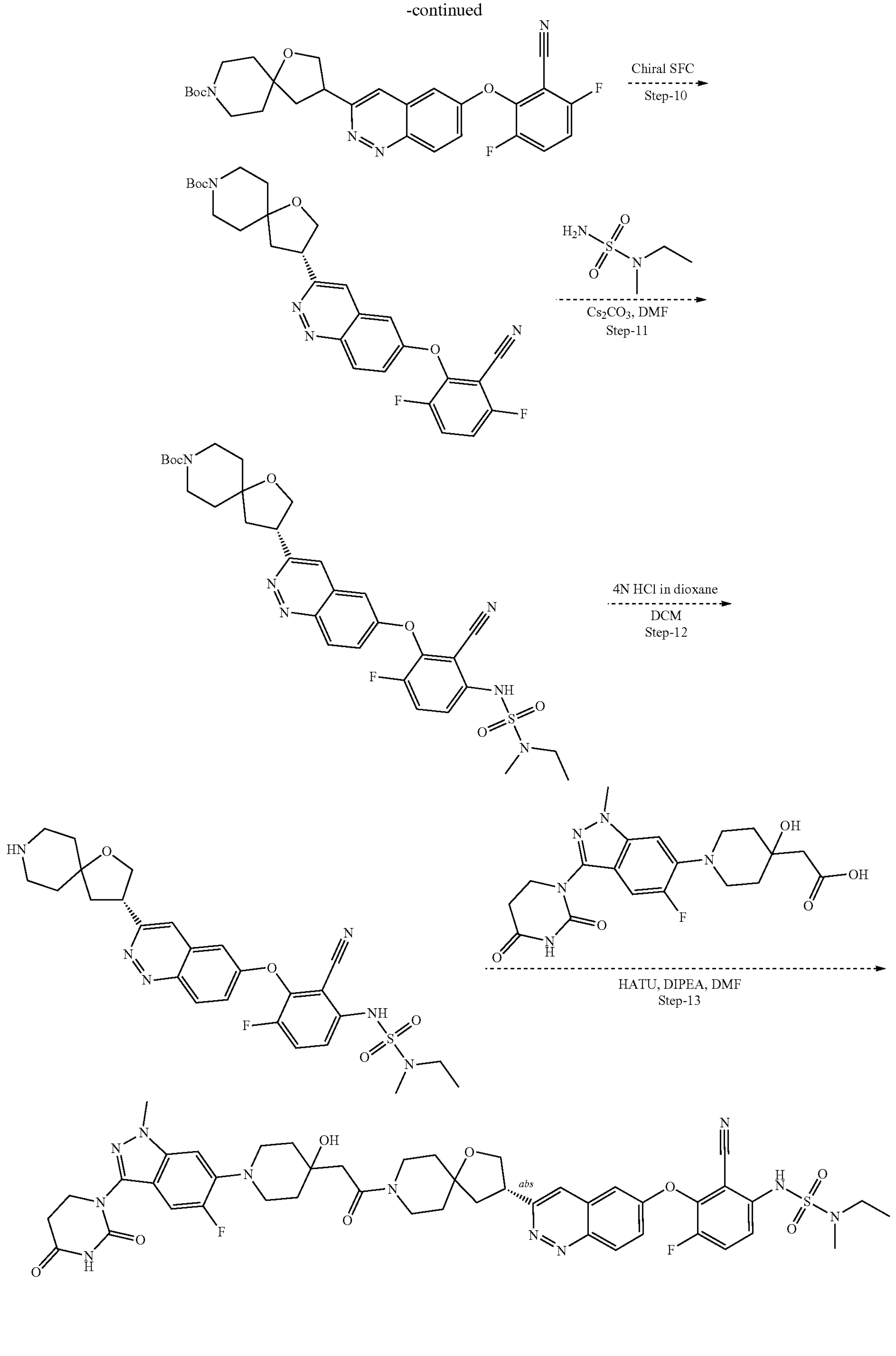

Step 1: To a 250 mL round bottom flask containing a well stirred solution of tert-butyl 3-oxo-1-oxa-8-azaspiro[4.5] decane-8-carboxylate (3.0 g, 11.75 mmol) in THF (30 mL) was added 1,8-diazabicyclo[5.4.0]undec-7-ene (8.94 g, 58.75 mmol, 8.77 mL) at 0° C. The resulting reaction mixture was slowly brought to ambient temperature and stirred for 1 hour. This was followed by the addition of 1,1,2,2,3,3,4,4,4-nonafluorobutane-1-sulfonyl fluoride (10.65 g, 35.25 mmol, 6.09 mL) at 0° C. The reaction mixture was then stirred at room temperature for 6 hours. After completion of the reaction as shown by TLC, the reaction mixture was diluted with water (50 mL) and extracted by ethyl acetate (3×60 mL). The combined organic layers were washed with brine solution, dried over anhydrous $Na_2SO_4$, filtered and concentrated under reduced pressure. The crude product was purified by column chromatography using 60-120 silica gel and 0-15% ethyl acetate in pet ether as eluent to afford tert-butyl 3-(1,1,2,2,3,3,4,4,4-nonafluorobutylsulfonyloxy)-1-oxa-8-azaspiro[4.5]dec-2-ene-8-carboxylate (4.5 g, 8.37 mmol, 71.23% yield) as a white gummy solid. LC-MS ($ES^+$): m/z 438.0 $[M+H-100]^+$.

Step 2: A solution of tert-butyl 3-(1,1,2,2,3,3,4,4,4-nonafluorobutylsulfonyloxy)-1-oxa-8-azaspiro[4.5]dec-2-ene-8-carboxylate (1.4 g, 2.61 mmol) in 1,4-dioxane (39.75 mL) was added potassium acetate (767.03 mg, 7.82 mmol) and bis(pinacolato)diboron (1.32 g, 5.21 mmol) at room temperature. The resulting solution was degassed with nitrogen gas for 5 minutes and added (1,1'-Bis(diphenylphosphino) ferrocene)palladium(II) dichloride (2.13 g, 2.61 mmol) at this temperature. The resulting solution was heated to 100° C. for 12 hours. The progress of the reaction was monitored by LCMS/TLC. The resulting solution was cooled to room temperature, filtered through a celite bed, and washed with ethyl acetate (60 ml). The collected filtrates were concentrated under reduced pressure to get the crude product, which was purified by column chromatography (230-400 mesh silica gel) using 40% ethyl acetate in pet ether as eluent to afford tert-butyl 3-(4,4,5,5-tetramethyl-1,3,2-dioxaborolan-2-yl)-1-oxa-8-azaspiro[4.5]dec-2-ene-8-carboxylate (750 mg, 1.50 mmol, 57.54% yield) as a liquid. LC-MS ($ES^+$): m/z 266.0 $[M-Boc+H]^+$.

Step 3: To a 50 mL single neck round bottom flask containing a well stirred solution of 4-benzyloxyaniline (700.00 mg, 3.51 mmol) in HCl (6 mL) was added sodium nitrite (218.16 mg, 3.16 mmol) in water (2 mL) at 0° C. The reaction mixture was stirred at 0° C. for 30 minutes and then added tin(II) chloride (1.73 g, 9.13 mmol) in HCl (6 mL) at this temperature. The reaction mixture was then stirred at ambient temperature for 2 hours. After completion of the reaction as confirmed by UPLC, the reaction mixture was filtered, washed with cold water and dried under high vacuum to afford the product (4-benzyloxyphenyl)hydrazine (700 mg, 3.27 mmol, 92.99% yield) as a light brown solid. LC-MS ($ES^+$): m/z 215.0 $[M+H]^+$.

Step 4: To a 100 mL single neck round bottom flask containing a well stirred solution of (4-benzyloxyphenyl) hydrazine (1.0 g, 4.67 mmol) in ethanol (15 mL) was added sodium methoxide (756.41 mg, 14.00 mmol) and ethyl 2,2-diethoxyacetate (1.23 g, 7.00 mmol) at ambient temperature under nitrogen atmosphere. The reaction mixture was stirred at 60° C. for 16 hours. After completion of the reaction as shown by TLC, the reaction mixture was quenched with water and extracted with ethyl acetate (2×20 mL). The organic phases were combined and washed with brine, dried over anhydrous $Na_2SO_4$, filtered and concentrated under reduced pressure. The crude product was purified by silica gel (230-400 mesh) column chromatography (40% EtOAc in Pet-ether) to afford N'-(4-benzyloxyphenyl)-2,2-diethoxy-acetohydrazide (570 mg, 1.56 mmol, 33.46% yield) as a yellow solid. LC-MS ($ES^+$): m/z 345.2 $[M+H]^+$ Step 5: To a solution of N'-(4-benzyloxyphenyl)-2,2-diethoxy-acetohydrazide (0.2 g, 580.71 μmol) in acetic acid (2 mL) was added trifluoroacetic acid (1.48 g, 12.98 mmol, 1 mL) at room temperature. The resulting solution was heated to 100° C. for 2 hours. The reaction was monitored by LCMS/TLC. After completion, the resulting solution was concentrated under reduced pressure to give a residue. The residue was dissolved in ethyl acetate (20 ml) and washed with 10% sodium bicarbonate solution (10 ml). The organic phase was dried (anhydrous $Na_2SO_4$), filtered and concentrated under reduced pressure to afford 6-benzyloxycinnolin-3-ol (80 mg, 317.12 μmol, 54.61% yield) as a brownish solid. LC-MS ($ES^+$): m/z 253.3 $[M+H]^+$ Step 6: A solution of 6-benzyloxycinnolin-3-ol (15 mg, 59.46 μmol) in phosphoryl trichloride (45.59 mg, 297.30 μmol) was heated to 110° C. for 4 hours. The reaction was monitored by LCMS/TLC. After completion, the resulting solution was concentrated under reduced pressure to afford 6-benzyloxy-3-chloro-cinnoline (10 mg, 23.26 μmol, 39.13% yield) as a brownish solid. LC-MS ($ES^+$): m/z 271.1 $[M+H]^+$.

Step 7: A solution of 6-(benzyloxy)-3-chlorocinnoline (1 equiv.) and tert-butyl 3-(4,4,5,5-tetramethyl-1,3,2-dioxaborolan-2-yl)-1-oxa-8-azaspiro[4.5]dec-2-ene-8-carboxylate (1.2 equiv.) in 1,4-dioxane is added cesium carbonate (3 equiv.) in water at room temperature under nitrogen atmosphere. The reaction mixture is degassed with $N_2$ for 10 minutes before 1,1'-bis(diphenylphosphino)ferrocene dichloropalladium (II) complex with dichloromethane (0.1 equiv.) is added and the reaction heated at 100° C. After completion of the reaction as confirmed by LC-MS, a workup is performed, and the crude product is purified by column chromatography to afford tert-butyl 3-(6-(benzyloxy)cinnolin-3-yl)-1-oxa-8-azaspiro[4.5]dec-2-ene-8-carboxylate.

Step 8: A solution of tert-butyl 3-(6-(benzyloxy)cinnolin-3-yl)-1-oxa-8-azaspiro[4.5]dec-2-ene-8-carboxylate (1 equiv.) in methanol is added 10% palladium on carbon (0.1 equiv.) at room temperature. The solution is degassed and stirred at hydrogen atmosphere for 16 hours or until completion of the reaction as confirmed by LC-MS. The reaction mixture is filtered through a pad of celite, and a workup is performed. The crude product is then purified by column chromatograph to afford tert-butyl 3-(6-hydroxycinnolin-3-yl)-1-oxa-8-azaspiro[4.5]decane-8-carboxylate.

Step 9: A solution of tert-butyl 3-(6-hydroxycinnolin-3-yl)-1-oxa-8-azaspiro[4.5]decane-8-carboxylate (1 equiv.) in THF is added cesium carbonate (1.1 equiv.) and 2,3,6-trifluorobenzonitrile (1.1 equiv.) at room temperature. The resulting reaction mixture is stirred at room temperature for 16 hours. After completion of the reaction as confirmed by LC-MS, a workup is performed, and the crude product is purified by column chromatography to afford tert-butyl 3-(6-(2-cyano-3,6-difluorophenoxy)cinnolin-3-yl)-1-oxa-8-azaspiro[4.5]decane-8-carboxylate.

Step 10: The racemic compound tert-butyl 3-(6-(2-cyano-3,6-difluorophenoxy)cinnolin-3-yl)-1-oxa-8-azaspiro[4.5] decane-8-carboxylate is resolved by chiral SFC purification to afford tert-butyl (S)-3-(6-(2-cyano-3,6-difluorophenoxy) cinnolin-3-yl)-1-oxa-8-azaspiro[4.5]decane-8-carboxylate.

Step 11: A solution of tert-butyl (S)-3-(6-(2-cyano-3,6-difluorophenoxy)cinnolin-3-yl)-1-oxa-8-azaspiro[4.5]decane-8-carboxylate (1 equiv.) in N,N-dimethylformamide is added cesium carbonate (2.5 equiv.) and [methyl(sulfamoyl)

amino]ethane (2 equiv.) at room temperature. The resulting reaction mixture is stirred at 60° C. for 16 hours. After completion of the reaction as confirmed by LC-MS, a workup is performed, and the crude product is purified by column chromatography to afford tert-butyl (S)-3-(6-(2-cyano-3-((N-ethyl-N-methylsulfamoyl)amino)-6-fluorophenoxy)cinnolin-3-yl)-1-oxa-8-azaspiro[4.5]decane-8-carboxylate.

Step 12: A solution of tert-butyl (S)-3-(6-(2-cyano-3-((N-ethyl-N-methylsulfamoyl)amino)-6-fluorophenoxy)cinnolin-3-yl)-1-oxa-8-azaspiro[4.5]decane-8-carboxylate (1 equiv.) in dichloromethane is added 4 N HCl in dioxane (10 equiv.) at 0° C. The resulted reaction mixture is stirred at room temperature for 2 hours. After completion, the reaction solvent is removed under reduced pressure and the crude compound is triturated with methyl t-butyl ether (MTBE) to afford the final product (3S)-3-[6-[2-cyano-3-[[ethyl(methyl)sulfamoyl]amino]-6-fluoro-phenoxy]cinnolin-3-yl]-1-oxa-8-azaspiro[4.5]decane.

Step 13: To a solution of 2-(1-(3-(2,4-dioxotetrahydropyrimidin-1(2H)-yl)-5-fluoro-1-methyl-1H-indazol-6-yl)-4-hydroxypiperidin-4-yl)acetic acid (1 equiv.) and (3S)-3-[6-[2-cyano-3-[[ethyl(methyl)sulfamoyl]amino]-6-fluoro-phenoxy]cinnolin-3-yl]-1-oxa-8-azaspiro[4.5]decane (1 equiv.) in N,N-dimethylformamide (4 mL/mmol) is added N,N-diisopropylethylamine (4 equiv.) at room temperature under nitrogen atmosphere. This is followed by the addition of HATU (1.1 equiv.) at the same temperature. The reaction mixture is stirred at room temperature for 12 hours. After completion, a workup is performed, and the crude product is purified by reverse phase HPLC to afford the target compound (3S)-3-[6-[2-cyano-3-[[ethyl(methyl)sulfamoyl]amino]-6-fluoro-phenoxy]cinnolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane.

Example 228

(3S)-3-[6-[2-cyano-3-[[ethyl(methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl]acetyl]-1-oxa-8-azaspiro[4.5]decane (Example 228)

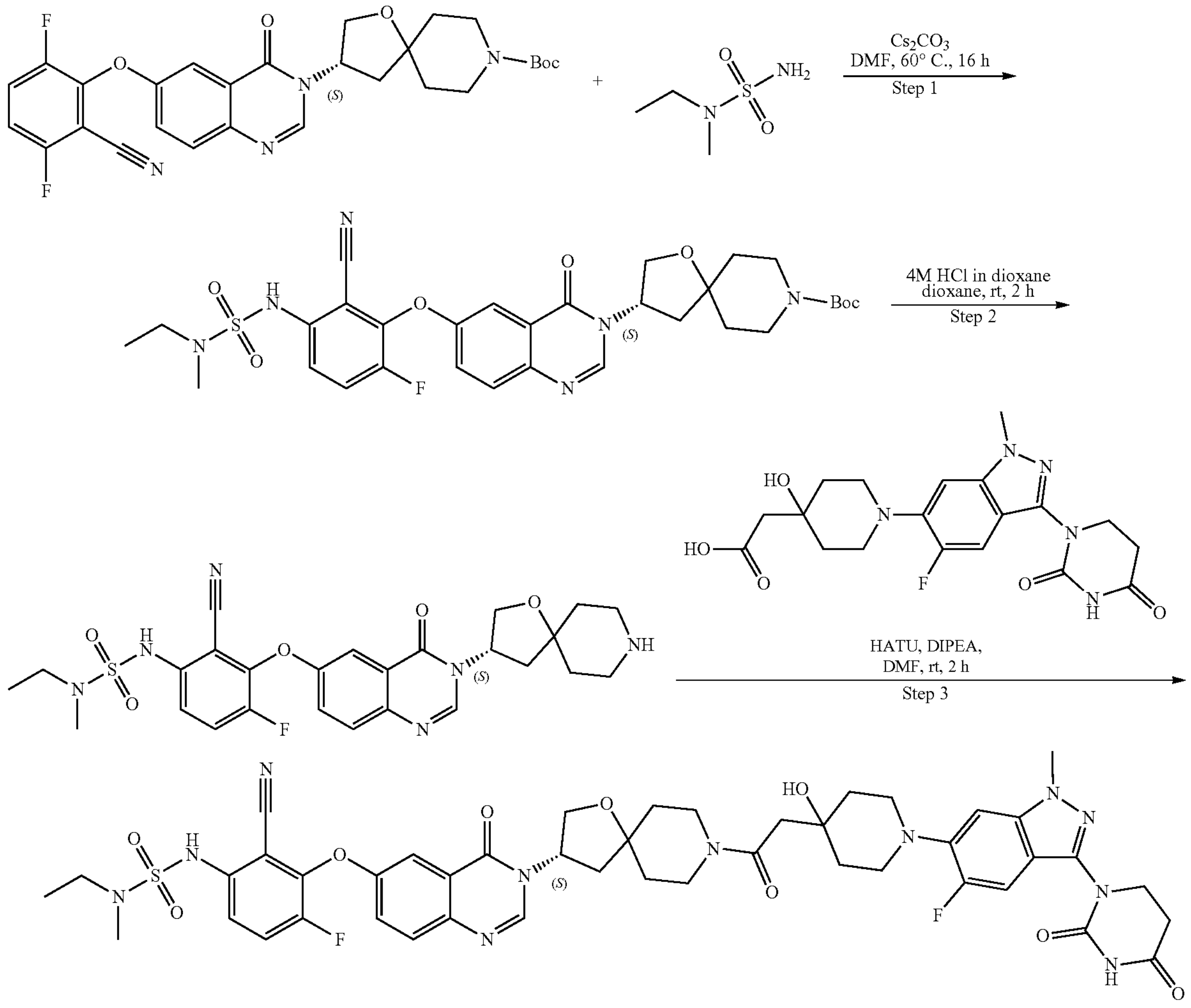

Step 1 and Step 2:

The procedures were identical to those of Step 4 and Step 5 in Example 150. Compound (3S)-3-[6-[2-cyano-3-[[ethyl (methyl)sulfamoyl]amino]-6-fluoro-phenoxy]-4-oxo-quinazolin-3-yl]-1-oxa-8-azaspiro[4.5]decane was obtained as a light brown solid. LCMS (ESI): m/z 557.3 $[M+H]^+$.

Step-3:

The procedure was identical to that of Step 8 in Example 157. The crude compound was purified by reverse phase column chromatography (40-45% ammonium bicarbonate buffer in acetonitrile) to yield (3S)-3-[6-[2-cyano-3-[[ethyl (methyl)sulfamoyl]amino]-6-fluoro-phenoxy]-4-oxo-quinazolin-3-yl]-8-[2-[1-[3-(2,4-dioxohexahydropyrimidin-1-yl)-5-fluoro-1-methyl-indazol-6-yl]-4-hydroxy-4-piperidyl] acetyl]-1-oxa-8-azaspiro[4.5]decane (69.16 mg, 70.93 μmol, 16.80% yield) as an off-white solid.

LCMS (ESI): m/z 958.2 $[M+H]^+$.

$^1$H-NMR (400 MHz, DMSO-$d_6$): δ 8.36 (s, 1H), 7.78 (s, 1H), 7.81 (s, 1H), 7.69 (dd, J=3.20, 9.00 Hz, 1H), 7.52-7.45 (m, 1H), 7.37 (d, J=2.80 Hz, 1H), 7.33 (d, J=12.80 Hz, 1H), 7.12 (d, J=6.80 Hz, 1H), 5.31 (m, 1H), 5.02 (d, J=2.00 Hz, 1H), 4.16-4.13 (m, 2H), 3.94-3.88 (m, 6H), 3.89-3.72 (m, 1H), 3.71-3.61 (m, 1H), 3.60-3.48 (m, 1H), 3.42-3.32 (m, 1H), 3.19-3.06 (m, 6H), 2.76-2.67 (m, 5H), 2.58-2.38 (m, 3H), 2.34-2.33 (m, 1H), 2.12-2.01 (m, 1H), 1.82-1.67 (m, 8H), 1.05 (t, J=7.20 Hz, 3H).

Example 229 Cellular HiBiT Assays

Materials

A375 (harboring BRAF homozygous V600E mutation) cell line was purchased from ATCC (Manassas, VA, USA). RPMI 1640 Medium (without phenol red), fetal bovine serum (FBS), and Sodium Pyruvate (100 mM) were purchased from Gibco (Grand Island, NY, USA). DMEM Medium (without phenol red and supplemented with L-glutamine) was purchased from Corning (Corning, NY, USA). Nano-Glo® HiBiT Lytic Assay System was purchased from Promega (Madison, WI, USA). A375.10 (HiBiT-$BRAF^{V600E}$) cell line, endogenously expressing $BRAF^{V600E}$ with HiBiT fusion tag via CRISPR, was made internally. HEK293T.114 (HiBiT-GSPT1) cell line, endogenously expressing GSPT1 with HiBiT fusion tag via CRISPR, was made internally. KELLY.2 (SALL4-HiBiT) cell line, endogenously expressing SALL4 with HiBiT fusion tag via CRISPR, was made internally from the KELLY cell line (ACC-No. 355) purchased from Leibniz-Institute DSMZ (Braunschweig, Germany). Cell culture flasks and 384-well microplates were acquired from VWR (Radnor, PA, USA) or Corning (Corning, NY, USA).

$BRAF^{V600E}$ Degradation Analysis $BRAF^{V600E}$ degradation was determined based on quantification of luminescent signal using Nano-Glo® HiBiT Lytic Assay kit. Test compounds were added to the 384-well plate from a top concentration of 10 μM with 11 points, half log titration in duplicates. A375.10 cells were added into 384-well plates at a cell density of 7500 cells per well. The plates were kept at 37° C. with 5% $CO_2$ for 24 hours. The cells treated in the absence of the test compound were the negative control and the cells without Nano-Glo® HiBiT Lytic reagent were the positive control. After 24-hour incubation, Nano-Glo® HiBiT Lytic Assay reagents were added to the cells. Luminescence was acquired on EnVision™ Multilabel Reader (PerkinElmer, Santa Clara, CA, USA). The resulting data for Compound 157 is shown in FIG. 1.

GSPT1 Degradation Analysis

GSPT1 degradation was determined based on quantification of luminescent signal using Nano-Glo® HiBiT Lytic Assay kit. Test compounds were added to the 384-well plate from a top concentration of 10 μM with 11 points, half log titration in duplicates. HEK293T.114 cells were added into 384-well plates at a cell density of 6000 cells per well. The plates were kept at 37° C. with 5% $CO_2$ for 6 hours. The cells treated in the absence of the test compound were the negative control and the cells without Nano-Glo® HiBiT Lytic reagent were the positive control. After 6-hour incubation, Nano-Glo® HiBiT Lytic Assay reagents were added to the cells. Luminescence was acquired on EnVision™ Multilabel Reader (PerkinElmer, Santa Clara, CA, USA). The resulting data for Compound 157 is shown in FIG. 2.

SALL4 Degradation Analysis

SALL4 degradation was determined based on quantification of luminescent signal using Nano-Glo® HiBiT Lytic Assay kit. Test compounds were added to the 384-well plate from a top concentration of 10 μM with 11 points, half log titration in duplicates. KELLY.2 cells were added into 384-well plates at a cell density of 6000 cells per well. The plates were kept at 37° C. with 5% $CO_2$ for 6 hours. The cells treated in the absence of the test compound were the negative control and the cells without Nano-Glo® HiBiT Lytic reagent were the positive control. After 6-hour incubation, Nano-Glo® HiBiT Lytic Assay reagents were added to the cells. Luminescence was acquired on EnVision™ Multilabel Reader (PerkinElmer, Santa Clara, CA, USA). The resulting data for Compound 157 is shown in FIG. 3.

Example 230 HTRF ERK Inhibition Assay

Materials

A375 (harboring BRAF homozygous V600E mutation) cell line was purchased from ATCC (CRL-1619). DMEM Medium without phenol red and supplemented with L-glutamine was purchased from Corning (Corning, NY, USA). Advanced phospho-ERK (Thr202/Tyr204) HTRF assay kits were purchased from Cisbio (Bedford, MA, USA). Cell culture flasks and 384-well microplates were acquired from VWR (Radnor, PA, USA) or Corning (Corning, NY, USA).

Phospho-ERK (T202/Y204) Inhibition Analysis

Inhibition of activated phospho-ERK (T202/Y204) protein was determined based on quantification of FRET signal using the Advanced phospho-ERK (T202/Y204) HTRF assay kit. Test compounds were added to the 384-well plate from a top concentration of 10 μM with 11 points, half log titration in duplicates. A375 cells were added into 384-well plates at a cell density of 8000 cells per well. The plates were kept at 37° C. with 5% $CO_2$ for 24 hours. Cells treated in the absence of the test compound were the negative control. Positive control was set by wells containing all reagents but no cells. FRET signal was acquired on EnVision™ Multilabel Reader (PerkinElmer, Santa Clara, CA, USA). The resulting data for Compound 157 is shown in FIG. 1.

Example 231 Western Blot Analysis

Methods: Western blot was used to determine BRAF V600E degradation characteristics and mechanism of action for Compound 157. A375 (ATCC, CRL-1619) cells cultured with DMEM media supplemented with 10% heat-inactivated FBS were plated in a 6-well dish at 500,000 cells/well and allowed to adhere for 16 hours. Cells were pre-treated for 1 hour with 10 μM of a compound targeting BRAF V600E without a function CRBN side, an IMiD targeting CRBN, MLN4924, or 1 μM bortezomib. After the pre-incubation, the cells were treated with or without 100 nM of Compound 157 for 24 hours, at which point the cells were rinsed with PBS and flash frozen. Cell pellets were lysed in lysis buffer [RIPA (Thermo, Ref 89901), 1× Halt Protease and Phosphatase inhibitor cocktail (Thermo, Pro #1361281), benzonase (Sigma, E1014-5JU)] for 10 minutes on ice. Insoluble proteins were cleared form the lysates by centrifugation (21.2×g, 10 minutes).

Compound $157^{NMe}$

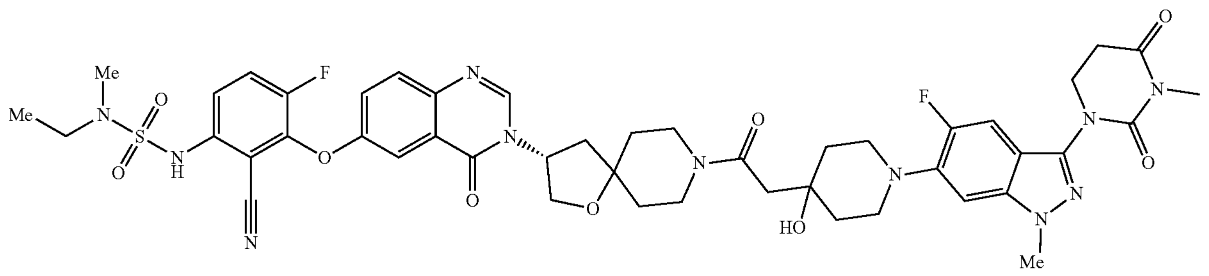

Protein concentrations were measured using the BCA Protein Assay Kit (Thermo, 23228). Protein standard curve, prepared with BSA, and samples protein concentrations were read using the Envision Multilabel Reader (PerkinElmer). Lysate concentrations were normalized with lysis buffer and Laemmli 6X, SDS-Sample Buffer, Reducing (Boston BioProducts, Inc. Part #BP-111R-50 ml). Normalized samples and Chameleon® Duo Pre-stained Protein Ladder (LI-COR, 928-60000) were loaded onto 4-15% Criterion™ Tris-HCl Protein Gel (Bio-Rad, #3450028). Gels ran at 120 V for 1.5 hours. Protein transfer was completed with the Trans-Blot Turbo Transfer System (Bio-Rad, 1704150EDU) at 25 V for 7 minutes using the Trans-Blot Turbo RTA Midi 0.2 μm Nitrocellulose Transfer Kit (Bio-Rad, catalog #1704271) following manufacturer recommendations.

Membranes were blocked while rocking for one hour in Intercept® Blocking Buffer (TBS) (LI-COR, catalog #927-50000). Primary antibodies BRAF (1:1000; Cell Signaling, D9T6S) and Vinculin (1:10,000; EMD, 05-386) were diluted in Intercept® T20 (TBS) Protein-Free Antibody Diluent (LI-COR, catalog #927-85001) and incubated while rocking at 4° C. overnight. Membranes were washed 3 times for 5 minutes in TBS-T while rocking. Secondary antibodies IR Dye 800 CW goat anti-rabbit (1:5000; LiCor, 926-32211/C91030-13) and IR Dye 680 RD goat anti-mouse (1:5000; LiCor, 926-68072/C90910-21) were diluted in Intercept® T20 (TBS) Protein-Free Antibody Diluent (LI-COR, catalog #927-85001) and incubated on membranes for 1 hour while rocking at room temperature. Membranes were washed as previously described and imaged on the Odyssey CLx. The results of this assay for Compound 157 are shown in FIG. 4.

This procedure was also used to determine BRAF V600E degradation characteristics of Compound 157 and Compound $157^{NMe}$. A375 (ATCC, CRL-1619) cells cultured with DMEM media supplemented with 10% heat-inactivated FBS were plated in a 6-well dish at 500,000 cells/well and allowed to adhere for 16 hours. Cells were treated with Compound 157 or Compound $157^{NMe}$ compounds serially diluted in DMSO for 24 hours. Samples were probed with the following primary antibodies: BRAF (1:1000; Cell Signaling, D9T6S), Vinculin (1:10,000; EMD, 05-386), ERK (1:1000; Cell Signaling, 4696S), and pERK T202/Y204 (1:1000; Cell Signaling, 9101S). The resulting data is shown in FIG. 9.

This procedure was also used to determine WT BRAF degradation characteristics of Compound 157. HCT-116 (ATCC, CCL-247) cells cultured with McCoy's 5a Medium Modified (ATCC, 30-2007) supplemented with 10% heat-inactivated FBS were plated in a 6-well dish at 500,000 cells/well and allowed to adhere for 16 hours. Cells were treated with Compound 157 compound serially diluted in DMSO for 24 hours. Samples were probed with the following primary antibodies: BRAF (1:1000; Cell Signaling, D9T6S), Vinculin (1:10,000; EMD, 05-386), ERK (1:1000; Cell Signaling, 4696S), and pERK T202/Y204 (1:1000; Cell Signaling, 9101S). The resulting data is shown in FIG. 12.

This procedure was also used to study a BRAF V600E and $NRAS^{Q61K}$ double mutant resistance model in response to a BRAF degrader or inhibitor in combination with trametinib. A375 (ATCC, CRL-1619) cells cultured with DMEM media supplemented with 10% heat-inactivated FBS were engineered using CRISPR to stably express $NRAS^{Q61K}$ as a model of resistance seen in patients. Cells were plated in a 6-well dish at 500,000 cells/well and allowed to adhere for 16 hours. Cells were treated with Compound 157 or encorafenib compounds serially diluted in DMSO for 24 hours. They were also treated in combination with 1 nM trametinib. Samples were probed with the following primary antibodies: BRAF (1:1000; Cell Signaling, D9T6S), Vinculin (1:10,000; EMD, 05-386), ERK (1:1000; Cell Signaling, 4696S), and pERK T202/Y204 (1:1000; Cell Signaling, 9101S). The resulting data is shown in FIG. 20.

This procedure was also used to determine BRAF degradation characteristics of Compound 157. HEK-293T (ATCC, CRL-3216) cells cultured with DMEM media supplemented with 10% heat-inactivated FBS were engineered to express HA tagged forms of BRAF V600E, WT, the p61 splice variant, Class II mutant G469A and Class III mutant G466V. Cells were plated in a 6-well dish at 500,000 cells/well and allowed to adhere for 16 hours. Cells were treated with Compound 157 compound serially diluted in DMSO for 24 hours. Samples were probed with the following primary antibodies: HA (1:1000; Cell Signaling, 3924) and Vinculin (1:10,000; EMD, 05-386). The resulting data is shown in FIG. 23.

This procedure was also used to determine BRAF degradation characteristics of Compound 157. H1666 (ATCC, CRL-5885) cells endogenously expressing the Class III mutation G466V were cultured with RPMI-1640 media supplemented with 5% heat-inactivated FBS. The cells were plated in a 6-well dish at 500,000 cells/well and allowed to adhere for 16 hours. Cells were treated with Compound 157 compound serially diluted in DMSO for 24 hours. The samples were processed for Western blot analysis in the same method described above in FIG. 2B. Samples were probed with the following primary antibodies: BRAF (1:1000; Cell Signaling, D9T6S), Vinculin (1:10,000; EMD, 05-386), ERK (1:1000; Cell Signaling, 4696S), and pERK T202/Y204 (1:1000; Cell Signaling, 9101S). The resulting data is shown in FIG. 24.

Example 232 Ternary Complex Formation Assay

Formation of the ternary complex between BRAF V600E, test compound and CRBN was quantified using AlphaLISA® assay. GST-tagged BRAF V600E and His-tagged CRBN were labeled with a donor/acceptor AlphaLISA® pair, and complex formation was monitored via a change in the Alpha-signal. Signal from the control wells was used as a normalization control. Concentration dependence of the ternary complex formation for Compound 157 had a characteristic bell-shaped curve, and no complex formation was observed for inactive version of the compound (Compound $157^{NMe}$)

Methods

Characterization of the ternary complex formation between GST-BRAF V600E, Compound 157 and his-CRBN was carried out using an AlphaLISA® assay. Compounds were dispensed from serially diluted DMSO stock in low dead volume plates into gray 384-well AlphaPlates using acoustic technology to 1% of total reaction volume. Compounds were arranged vertically in rows A through P. Concentration series were horizontal: columns 1-11, and then duplicates in columns 12-22. Columns 23 and 24 were reserved for 0% (no test compound, hence only background signal) and 100% controls (1 nM double-tagged MBP protein yielding signal corresponding to 10 nM of the complex), respectively.

Excitation of the donor beads results in generation of singlet oxygen molecules. If the ternary complex between BRAF V600E and CRBN is formed, it brings donor/acceptor beads in a close proximity and the donor-released singlet oxygen will stimulate light emission from the acceptor bead. In the absence of the ternary complex the average donor-acceptor distance is too large to stimulate acceptor emission.

A 10 μL mixture containing 16 nM of BRAF V600E and 64 nM of CRBN in 50 mM HEPES (pH 7.4), 200 mM NaCl, 1 mM TCEP, 0.05% Pluronic Acid, 0.1% BSA was added to the wells containing test compounds (columns 1-22) and the negative control wells (column 23). Positive control wells (column 24) contained 10 uL of double-tagged MBP at 20 nM. The plate was centrifuged for 30s, shaken for 30s at 2000 RPM and incubated for 1 h at room temperature. After incubation was complete, 10 uL of the mix containing donor and acceptor beads, 40 μg/ml of each, were added to all wells. Plates were again centrifuged for 30s, agitated for 30s at 2000 RPM and incubated for 1 h at room temperature. Plates were then read on an Envision plate reader with an appropriate AlphaLISA® filter set. The resulting data for Compound 157 is shown in FIG. 5.

Example 233 Kinome Profiling

Compound 157 was tested against many protein kinases to determine how selective it is for BRAF. The circles shown in FIGS. 6 and 7 demonstrate how much of the protein activity is left after being incubated with Compound 157.

Methods

The kinome scan profiling was performed at Eurofins DiscoverX Corporation. Kinase-tagged T7 phage strains were grown in parallel in 24-well blocks in an *E. coli* host derived from the BL21 strain. *E. coli* were grown to log-phase and infected with T7 phage from a frozen stock multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. The resulting data is shown in FIG. 6 and FIG. 7.

Example 234 Global Proteomics Profiling A375 and JURKAT Cell Lines

For A375 cells, a total of 8,760 proteins were identified with a protein false discovery rate of 2.65%. The results of this experiment demonstrate that, compared to 300 nM dabrafenib treatment, $BRAF^{V600E}$ is selectively degraded to 27% protein remaining while ARAF and RAF1 (a.k.a CRAF) remain largely unchanged. The only other protein found to be decreased was LOXL4 (sp|Q96JB6|LOXL4_HUMAN; Lysyl oxidase homolog 4) however, it was also observed to be decreased on the dabrafenib treated samples, to a lesser extent, and is therefore not considered to a true off-target of Compound 157 but rather a result of loss of $BRAF^{V600E}$ activity. In the experiment performed in JURKAT cells (ATCC, TIB-152), containing wild type BRAF, a total of 8,415 proteins were identified at protein false discovery rate of 2.8%. Data analysis shows that BRAF, ARAF, and RAF1 (a.k.a CRAF) are unchanged upon treatment with 300 nM Compound 157 for 24 hours indicating that Compound 157 is highly specific for $BRAF^{V600E}$ compared to wild type BRAF and the closely related proteins ARAF and RAF1 (a.k.a CRAF).

Experimental Methods for Global Proteomics Experiments for Compound 157 in A375 and JURKAT Cell Lines.

Each cell line was treated in duplicate with either DMSO or Compound 157 (final concentration 300 nM) for 24 hours in an incubator at 37° C. with 5% $CO_2$. After the 24-hour incubation, cells were harvested, washed twice with PBS, and snap frozen in liquid nitrogen. Samples were re-suspended in lysis buffer [8 M urea, 50 mM HEPES (pH 8.5), 50 mM NaCl, 1× protease inhibitor cocktail] and lysed by sonication at 4° C. with 85% amplitude in a pulse setting with 30 seconds on and 30 seconds off for a total sonication time of 5 minutes. Lysates were centrifuged at maximum speed for 10 minutes at 4° C. and the supernatant collected, reduced for 1 hour at room temperature with 5 mM TCEP, and the cysteine residues were then alkylated with 15 mM iodoacetamide (room temperature, in dark, 30 minutes). Protein content was extracted by methanol-chloroform precipitation and subsequent ice-cold acetone washes. Protein pellets were resuspended in 8 M urea, 50 mM HEPES (pH 8.5) buffer and protein concentrations were measured by BCA assay. Samples were then diluted to 4 M urea with 50 mM HEPES (pH 8.5) and digested at 37° C. for 1 hour with endoproteinase Lys-C, at a 1/250 enzyme/protein ratio. The mixtures were then diluted to 1 M urea with 50 mM HEPES (pH 8.5) and trypsin was added at a 1/150 enzyme/protein ratio. The reaction was incubated overnight at 37° C. and stopped by acidification with formic acid to a final concentration of 5% (v/v). Peptides were purified using C18 SepPak solid-phase extraction cartridges and dried to completion using a SpeedVac system.

For peptide tandem mass tag (TMT) labeling, 100 μg of peptides per sample was prepared at 1 μg/l concentration in 200 mM HEPES (pH 8.5), 30% acetonitrile (ACN) and each the specific TMT reagent. After 1 hour incubation at room temperature, reactions were quenched with 0.3% hydroxylamine for 15 minutes and mixed equally based on protein amount. The mixed sample was desalted using C18 SepPak solid-phase extraction cartridges, dried to completion in a SpeedVac and then resuspended in 5% ACN, 10 mM $NH_4HCO_3$ pH 8 for fractionation using basic pH reversed phase chromatography with a HPLC equipped with a 3.5 μm XBridge Peptide BEH C18 column. 96 fractions were collected, consolidated into 12 samples, desalted using SepPAK C18 cartridges, and then dried via vacuum centrifugation. Samples were then reconstituted in 16 μL of 5% formic for LC-MS/MS/MS analysis. 6 μL of each sample was separated by reversed phase chromatography using an EASY-Spray C18 column (2 μm particle size, 500 mm length×75 μm ID) mounted in an EASY-nLC 1200 LC pump coupled to an Orbitrap Fusion Lumos Tribid mass spectrometer. Peptides were separated using a 450 min gradient divided into 3 sections (5 to 25% ACN for 300 minutes, 25-40% ACN for 120 minutes, and 95% ACN for 30 minutes) at a flow rate of 300 nL/min. Peptides were collected in a data dependent acquisition method using CID for MS2 fragmentation and HCD for synchronous precursor selection based MS3 (SPS-MS3) fragmentation for TMT reporter ion release. All data files obtained from the mass spectrometer were processed using SEQUEST-based software developed by Professor Steve Gygi's laboratory at Harvard Medical School. Briefly, mass spectra were searched against the human non-redundant Uniprot protein database concatenated with a database composed of all protein sequences in the reversed order as well as known contaminants. In all SEQUEST searches, precursor ion tolerance was set at 25 ppm, including methionine oxidation (+15.9949 Da) and cysteine carbamidomethylation (+57.0215 Da) as variable modifications. TMT tag (+229.1629 Da) on lysine residues and peptide N-termini were set as static modifications. Peptide-spectrum matches (PSMs) were performed using a linear discriminant analysis and adjusted to a 2% false discovery rate (FDR). TMT reporter ion intensities were quantified by extracting the signal-to-noise ratio for each. Peptides were next collapsed into protein groups using a 4% protein FDR target. The resulting data is shown in FIG. 8.

Example 235 A375 Cell Growth Rate

A375 (ATCC, CRL-1619) cells cultured with DMEM media supplemented with 10% heat-inactivated FBS were plated in a 96-well dish at 3,000 cells/well. Compounds were serially diluted in DMSO and added to the culture media upon plating. The plate was sealed with a gas-permeable membrane Breathe-Easy sealing membrane (Sigma, Z380059) and cells were allowed to settle for 8 hours prior to initial imaging. Confluence was measured by imaging in a temperature- and humidity-controlled incubator (37° C., 5% CO2) over a 7-day period at 6-hour intervals by the IncuCyte (S3, Sartorius). Analysis was performed using the Incucyte software. The growth rate of A375 cells with Compound 157 is shown in FIG. 10 and FIG. 11. The experiment was also conducted with A375 cells that were engineered with CRISPR to have a $NRAS^{Q61K}$ mutation (ATCC, CRL-1619IG-2). This data is shown in FIG. 21.

Example 236 HCT-116 Cell Confluence

HCT-116 (ATCC, CCL-247) cells cultured with McCoy's 5a Medium Modified (ATCC, 30-2007) media supplemented with 10% heat-inactivated FBS were plated in a 96-well dish at 3,000 cells/well. Compounds were serially diluted in DMSO and added to the culture media upon plating. The plate was sealed with a gas-permeable membrane Breathe-Easy sealing membrane (Sigma, Z380059) and cells were allowed to settle for 8 hours prior to initial imaging. Confluence was measured by imaging in a temperature- and humidity-controlled incubator (37° C., 5% CO2) over a 7-day period at 6-hour intervals by the IncuCyte (S3, Sartorius). Analysis was performed using the Incucyte software. This data is shown in FIG. 13.

Example 237 HTRF ERK Inhibition Assay

Materials

A375 (harboring BRAF homozygous V600E mutation) were purchased from ATCC. DMEM Medium without phenol red and supplemented with L-glutamine was purchased from Corning (Corning, NY, USA). Advanced phospho-ERK (Thr202/Tyr204) HTRF assay kits were purchased from Cisbio (Bedford, MA, USA). Cell culture flasks and 384-well microplates were acquired from VWR (Radnor, PA, USA) or Corning (Corning, NY, USA).

Phospho-ERK (T202/Y204) Inhibition Analysis

Degradation of activated phospho-ERK (T202/Y204) protein was determined based on quantification of FRET signal using the Advanced phospho-ERK (T202/Y204) HTRF assay kit. Test compounds were added to the 384-well plate from a top concentration of 10 μM with 11 points, half log titration in duplicates. A375 cells were added into 384-well plates at a cell density of 8000 cells per well, respectively. The plates were kept at 37° C. with 5% CO2 for 24 hours. Cells treated in the absence of the test compound were the negative control. Positive control was set by wells containing all reagents but no cells. FRET signal was acquired on EnVision™ Multilabel Reader (PerkinElmer, Santa Clara, CA, USA).

Cell Growth Inhibition Analysis

A375 cell viability was determined based on quantification of ATP using CellTiter-Glo® 2.0 luminescent Assay kit, which signals the presence of metabolically-active cells. Briefly, test compound was added to 384-well plates at a top concentration of 10 μM with 14 points, half log titration in duplicates. A375 cells were seeded into the 384-well plates in DMEM medium containing 10% FBS at a cell density of 250 cells per well. Cells treated in the absence of the test compound were the negative control, normalized to 100% viability, and cells treated in the absence of CellTiter-Glo® 2.0 were the positive control, normalized to 0% viability. A375 cells were incubated at 37° C. with 5% CO2 for 72 hr. CellTiter-Glo reagent was then added to the cells and Luminescence was acquired on EnVision™ Multilabel Reader (PerkinElmer, Santa Clara, CA, USA). The resulting data is shown in Table 10.

TABLE 10

| | A375 cells | |
|---|---|---|
| | pERK $IC_{50}$ (nM) | $GI_{50}$ (nM) |
| Compound 157 | 3.2 | 9.3 |
| Compound $157^{NMe}$ | 13.5 | 22.5 |
| encorafenib | 2.1 | 8.0 |

All data in table represent the mean response of at least n = 3 assay results
All pERK data in table were collected at 24 hrs

Example 238 In Vivo Efficacy and Body Weight Change of Compound 157 in A375 Xenograft Tumors The efficacy study was conducted in female BALB/c nude mice bearing A375 tumors. Female BALB/c nude mice were inoculated subcutaneously in the right flank with A375 tumor cells ($5\times10^6$) in 0.2 mL of PBS supplemented with Matrigel (at a 1:1 ratio) for tumor development. Tumor volume was measured twice weekly in two dimensions using calipers, and volume ($mm^3$) was calculated using the formula: $V=0.5\ a\times b^2$ where a and b are the long and short diameters of the tumor in mm, respectively. Once the tumors reached an average tumor volume of 246 $mm^3$ (16 days after implantation), the animals were divided randomly into groups of 6, stratified to result in about equal average tumor sizes in each treatment group and treatment began on Day 0.

All agents were administered to mice bearing A375 tumors orally (PO), daily (QD; encorafenib), twice a day (BID) or three times a day (TID) for Compound 157, for 21 or 35 days. encorafenib was dosed at 35 mg/kg and Compound 157 at 0.1, 0.3, 1, 3 or 10 mg/kg twice a day or 2 mg/kg three times a day. Compound 157 was formulated in 20% PEG400+80% (25% SBECD). Body weight and MTV were measured on a 2× weekly schedule and reported as Mean±SEM.

Compound 157 efficacy in A375 xenograft tumors was evaluated at six different concentrations: 0.1-10 mg/kg. Compound 157 was administered BID (twice a day) or TID (three times a day) orally (PO). The efficacy of Compound 157 was compared to encorafenib (administered orally, once a day (QD) at 35 mg/kg). The results are shown in FIG. 4. Treatment with Compound 157 at 1 mg/kg PO BID, 2 mg/kg PO TID or 3 mg/kg PO BID results in potent tumor growth inhibition compared to vehicle-treated tumors, and treatment with 10 mg/kg PO BID results in robust tumor growth regression. All doses were well-tolerated as no group showed more than mean 3.5% body weight loss throughout the study. The resulting data is shown in FIGS. 14 and 15.

Example 239 In Vivo Pharmacokinetic Activity of Compound 157 in Plasma and A375 Xenograft Tumors Female nude mice were inoculated subcutaneously in the right flank with A375 tumor cells ($5\times10^6$) in 0.2 mL of PBS supplemented with Matrigel (at a 1:1 ratio) for tumor development. Tumor volume was measured twice weekly in two dimensions using calipers, and volume ($mm^3$) was calculated using the formula: $V=0.5\ a\times b^2$ where a and b are the long and short diameters of the tumor in mm, respectively. Once the tumors reached an average tumor volume of 313 $mm^3$, the animals were divided randomly into groups of 3, and administered a single oral dose of Compound 157 at 0.3, 1, 3, or 10 mg/kg. Compound 157 was formulated in 20% PEG400+80% (25% SBECD). Mice were sacrificed, and plasma and tumors were collected at 1-, 4-, 10-, 24- and 36-hours post single dose. 3 tumors and plasma samples were collected per each time point sampled. Plasma and tumor samples were injected into LC/MS/MS system for quantitative analysis. Data is represented as Mean±SEM. The resulting data is shown in FIGS. 16 and 17.

Additional samples were worked up and the results shown in FIGS. 18 and 19 as follows. Mice were sacrificed, and plasma and tumors were collected at 1-, 4-, 10-, 24- and 36-hours post single dose. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for B-RAF (CST, 14814) or Phospho-ERK (CST, 4370) expression. The intensity of individual bands was measured for data analysis using Image Studio software. Protein expression was quantitated in relation to the reference protein, GAPDH, to control for total protein concentration. The data was then normalized to the amount of target in the Compound 157 treated samples in comparison to the vehicle control samples. Data is represented as percent of target present in the vehicle control and normalized for total protein. Error bars represent ±SEM values.

Example 240 HTRF ERK Inhibition Assay

Materials

A375-$NRAS^{Q61K}$ cells (harboring BRAF homozygous V600E mutation and NRAS homozygous Q61K mutation) were purchased from ATCC. DMEM Medium without phenol red and supplemented with L-glutamine was purchased from Corning (Corning, NY, USA). Advanced phospho-ERK (Thr202/Tyr204) HTRF assay kits were purchased from Cisbio (Bedford, MA, USA). Cell culture flasks and 384-well microplates were acquired from VWR (Radnor, PA, USA) or Corning (Corning, NY, USA).

Phospho-ERK (T202/Y204) Degradation Analysis

Degradation of activated phospho-ERK (T202/Y204) protein was determined based on quantification of FRET signal using the Advanced phospho-ERK (T202/Y204) HTRF assay kit. Test compounds were added to the 384-well plate from a top concentration of 10 μM with 11 points, half log titration in duplicates. A375-$NRAS^{Q61K}$ cells were added into 384-well plates at a cell density of 2000 cells per well. The plates were kept at 37° C. with 5% CO2 for 24 hours. Cells treated in the absence of the test compound were the negative control. Positive control was set by wells containing all reagents but no cells. FRET signal was acquired on EnVision™ Multilabel Reader (PerkinElmer, Santa Clara, CA, USA).

Method for CellTiter-Glo Growth Inhibition Assay

Materials

A375-NRAS$^{Q61K}$ cells (harboring BRAF homozygous V600E mutation and NRAS homozygous Q61K mutation) were purchased from ATCC. DMEM Medium (without phenol red and supplemented with L-glutamine) was purchased from Corning (Corning, NY, USA). CellTiter-Glo® 2.0 Assay was purchased from Promega (Madison, WI, USA). Cell culture flasks and 384-well microplates were acquired from VWR (Radnor, PA, USA) or Corning (Corning, NY, USA).

Cell Growth Inhibition Analysis

A375-NRAS$^{Q61K}$ cell viability was determined based on quantification of ATP using CellTiter-Glo® 2.0 luminescent Assay kit, which signals the presence of metabolically-active cells. Briefly, test compound was added to 384-well plates at a top concentration of 10 μM with 14 points, half log titration in duplicates. A375-NRAS$^{Q61K}$ cells were seeded into the 384-well plates in DMEM medium containing 10% FBS at a cell density of 250 cells per well. Cells treated in the absence of the test compound were the negative control, normalized to 100% viability, and cells treated in the absence of CellTiter-Glo® 2.0 were the positive control, normalized to 0% viability. A375 cells were incubated at 37° C. with 5% CO2 for 96 hr. CellTiter-Glo reagent was then added to the cells and Luminescence was acquired on EnVision™ Multilabel Reader (PerkinElmer, Santa Clara, CA, USA).

TABLE 9

| | A375-NRAS$^{Q61K}$ cells | |
|---|---|---|
| | pERK $IC_{50}$ (nM) | $GI_{50}$ (nM) |
| Compound 157 | 7.8 | 55 |
| Compound 157$^{NMe}$ | 36.8 | 794 |
| encorafenib | 31.0 | 911 |

All data in table represent the mean response of at least n = 3 assay results
All pERK data in table were collected at 24 hrs Example 241 NRAS$^{Q61K}$ Tumor Volume Assay The A375 NRAS$^{Q61K}$ tumor V600E double mutant cells described in Example 240 were maintained in vitro in DMEM medium supplemented with 10% fetal bovine serum and 1% Penicillin-Streptomycin at 37° C. in an atmosphere of 5% CO2 in air. The tumor cells were routinely subcultured twice weekly. The cells growing in an exponential growth phase were harvested and counted for tumor inoculation.

The efficacy study was conducted in female BALB/c nude mice bearing A375 NRAS$^{Q61K}$ tumors. Female nude mice were inoculated subcutaneously in the right flank with A375 NRAS$^{Q61K}$ tumor cells ($10\times10^6$) in 0.2 mL of PBS supplemented with Matrigel (at a 1:1 ratio) for tumor development. Tumor volume was measured twice weekly in two dimensions using calipers, and volume ($mm^3$) was calculated using the formula: $V=0.5\ axb^2$ where a and b are the long and short diameters of the tumor in mm, respectively. Once the tumors reached an average tumor volume of 139 $mm^3$ (40 days after implantation), the animals were divided randomly into groups of 8, stratified to result in about equal average tumor sizes in each treatment group and treatment began on Day 1.

All agents were administered to mice bearing A375 NRAS$^{Q61K}$ tumors orally (PO), daily (QD) for encorafenib at 35 mg/kg or twice a day (BID) for trametinib at 0.1 mg/kg and Compound 157 at 3, 10, or 30 mg/kg as a single agent or 1, 3, 10, 30 mg/kg combined with trametinib. Doses were administered for 21 days. Compound 157 was formulated in 20% PEG400+80% (25% SBECD). Body weight and MTV were measured on a 2× weekly schedule and reported as Mean±SEM. The resulting data is shown in FIG. 22.

Example 242 H1666 Cell Confluence

H1666 (ATCC, CRL-5885) cells cultured with RPMI-1640 media supplemented with 5% heat-inactivated FBS plated in a 96-well dish at 3,000 cells/well. Compounds were serially diluted in DMSO and added to the culture media upon plating. The plate was sealed with a gas-permeable membrane Breathe-Easy sealing membrane (Sigma, Z380059) and cells were allowed to settle for 8 hours prior to initial imaging. Confluence was measured by imaging in a temperature- and humidity-controlled incubator (37° C., 5% CO2) over a 7-day period at 6-hour intervals by the IncuCyte (S3, Sartorius). Analysis was performed using the Incucyte software. The resulting data is shown in FIG. 25.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teaching of this invention that certain changes and modifications may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

We claim:

1. A compound of structure:

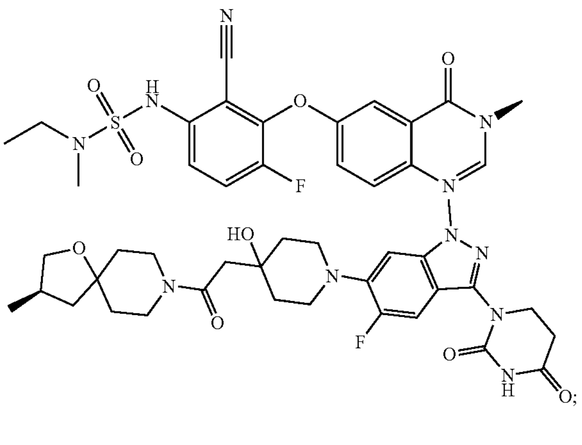

or a pharmaceutically acceptable salt thereof.

2. A compound of structure:
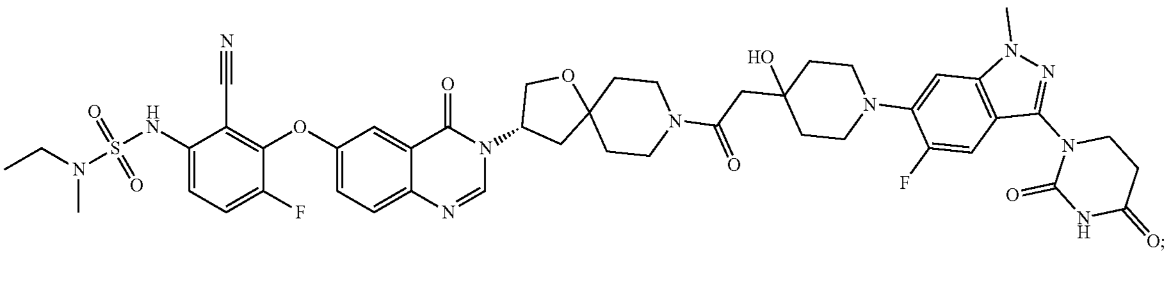 [SMILES: CCN(C)S(=O)(=O)Nc1ccc(F)c(Oc2ccc3ncn(C4COC5(CCN(C(=O)CC6(O)CCN(c7cc8c(cc7F)c(N7CCC(=O)NC7=O)nn8C)CC6)CC5)C4)c(=O)c3c2)c1C#N]
or a pharmaceutically acceptable salt thereof.
3. A compound of structure:
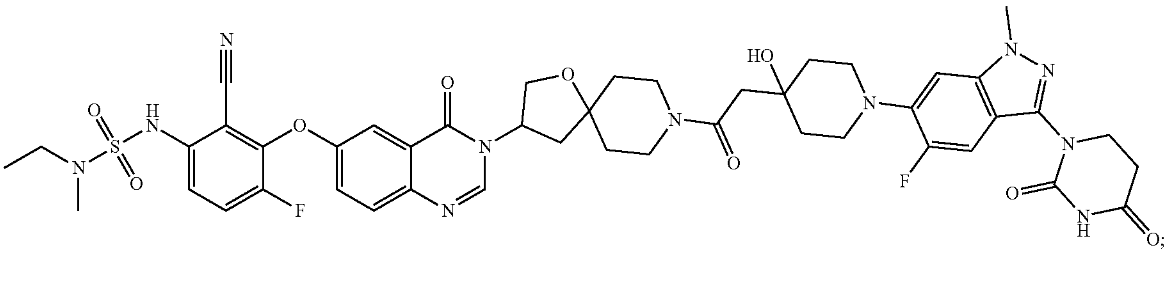
or a pharmaceutically acceptable salt thereof.
4. A compound of structure:
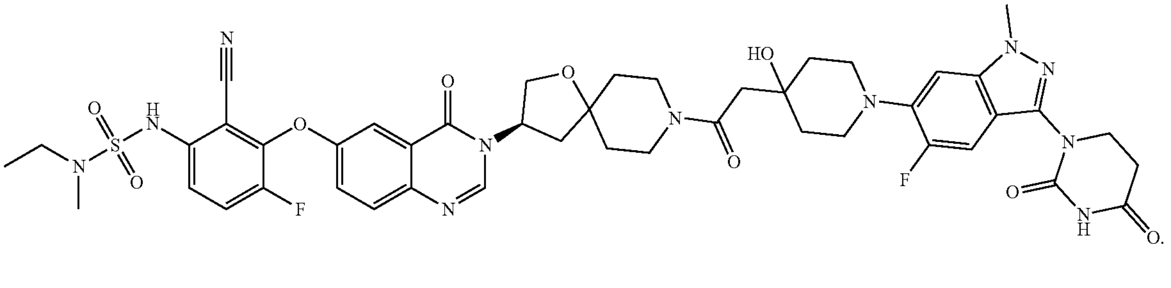 [SMILES: CCN(C)S(=O)(=O)Nc1ccc(F)c(Oc2ccc3ncn([C@H]4COC5(CCN(C(=O)CC6(O)CCN(c7cc8c(cc7F)c(N7CCC(=O)NC7=O)nn8C)CC6)CC5)C4)c(=O)c3c2)c1C#N]
* * * * *